US011547673B1

(12) United States Patent
Sahin et al.

(10) Patent No.: US 11,547,673 B1
(45) **Date of Patent: *Jan. 10, 2023**

(54) CORONAVIRUS VACCINE

(71) Applicant: BioNTech SE, Mainz (DE)

(72) Inventors: Ugur Sahin, Mainz (DE); Alptekin Güler, Mainz (DE); Andreas Kuhn, Mainz (DE); Alexander Muik, Seeheim-Jugenheim (DE); Annette Vogel, Mainz (DE); Kerstin Walzer, Seeheim-Jugenheim (DE); Sonja Witzel, Bad Vilbel (DE); Stephanie Hein, Rüsselsheim (DE); Özlem Türeci, Mainz (DE)

(73) Assignee: BioNTech SE, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/233,396

(22) Filed: Apr. 16, 2021

(30) Foreign Application Priority Data

| | | |
|---|---|---|
| Apr. 22, 2020 | (WO) | PCT/EP2020/061239 |
| Jun. 18, 2020 | (WO) | PCT/EP2020/066968 |
| Jun. 26, 2020 | (WO) | PCT/EP2020/068174 |
| Jul. 13, 2020 | (WO) | PCT/EP2020/069805 |
| Jul. 31, 2020 | (WO) | PCT/EP2020/071733 |
| Aug. 3, 2020 | (WO) | PCT/EP2020/071839 |
| Aug. 24, 2020 | (WO) | PCT/EP2020/073668 |
| Nov. 9, 2020 | (WO) | PCT/EP2020/081544 |
| Nov. 12, 2020 | (WO) | PCT/EP2020/081981 |
| Nov. 18, 2020 | (WO) | PCT/EP2020/082601 |
| Nov. 20, 2020 | (WO) | PCT/EP2020/082989 |
| Nov. 25, 2020 | (WO) | PCT/EP2020/083435 |
| Dec. 2, 2020 | (WO) | PCT/EP2020/084342 |
| Dec. 8, 2020 | (WO) | PCT/EP2020/085145 |
| Dec. 10, 2020 | (WO) | PCT/EP2020/085653 |
| Dec. 23, 2020 | (WO) | PCT/EP2020/087844 |
| Jan. 4, 2021 | (WO) | PCT/EP2021/050027 |
| Jan. 15, 2021 | (WO) | PCT/EP2021/050874 |
| Jan. 15, 2021 | (WO) | PCT/EP2021/050875 |
| Jan. 26, 2021 | (WO) | PCT/EP2021/051772 |
| Feb. 3, 2021 | (WO) | PCT/EP2021/052572 |
| Feb. 4, 2021 | (WO) | PCT/EP2021/052716 |
| Feb. 24, 2021 | (WO) | PCT/EP2021/054622 |

(51) Int. Cl.

| | |
|---|---|
| ***A61K 39/215*** | (2006.01) |
| ***A61P 31/14*** | (2006.01) |
| ***A61K 9/51*** | (2006.01) |
| ***C12N 7/00*** | (2006.01) |
| ***A61K 9/00*** | (2006.01) |
| *A61K 39/00* | (2006.01) |

(52) U.S. Cl.
CPC .......... *A61K 9/5123* (2013.01); *A61K 9/0019* (2013.01); *A61K 39/215* (2013.01); *A61P 31/14* (2018.01); *C12N 7/00* (2013.01); *A61K 2039/53* (2013.01); *A61K 2039/54* (2013.01); *A61K 2039/545* (2013.01); *C12N 2770/18022* (2013.01); *C12N 2770/18034* (2013.01); *C12N 2770/18071* (2013.01)

(58) Field of Classification Search
None
See application file for complete search history.

(56) References Cited

U.S. PATENT DOCUMENTS

| | | | |
|---|---|---|---|
| 4,898,278 | A | 2/1990 | Leoncavallo et al. |
| 6,381,981 | B1 | 5/2002 | Yaddgo et al. |
| 7,736,850 | B2 | 6/2010 | Van Der Werf et al. |
| 7,901,708 | B2 | 3/2011 | MacLachlan et al. |
| 8,058,069 | B2 | 11/2011 | Yaworski et al. |
| 8,329,070 | B2 | 12/2012 | MacLachlan et al. |
| 8,710,200 | B2 | 4/2014 | Schrum et al. |
| 8,754,062 | B2 | 6/2014 | de Fougerolles et al. |
| 8,822,663 | B2 | 9/2014 | Schrum et al. |
| 8,999,380 | B2 | 4/2015 | Bancel et al. |
| 9,220,755 | B2 | 12/2015 | Chakraborty et al. |
| 9,221,891 | B2 | 12/2015 | Bancel et al. |
| 9,283,287 | B2 | 3/2016 | Chakraborty et al. |
| 9,295,717 | B2 | 3/2016 | Sahin et al. |
| 9,303,079 | B2 | 4/2016 | Chakraborty et al. |

(Continued)

FOREIGN PATENT DOCUMENTS

| | | | |
|---|---|---|---|
| AU | 2015210364 | A1 | 8/2015 |
| AU | 2016253972 | B2 | 1/2020 |

(Continued)

OTHER PUBLICATIONS

Lan et al. (Nature. Published online Mar. 30, 2020; 581: 215-220).*
Tang et al. ("On the origin and continuing evolution of SARS-CoV-2." National Science Review 7.6 (2020): 1012-1023).*
Boon et al. "Temporal-Geographical Dispersion of SARS-CoV-2 Spike Glycoprotein Variant Lineages and Their Functional Prediction Using in Silico Approach." Mbio 12.5 (Oct. 26, 2021): e02687-21).*
SEQ ID No. 7 alignments with SEQ ID 84 and 86 in U.S. Appl. No. 10/953,089, filed Jan. 27, 2020 earliest priority.*

(Continued)

*Primary Examiner* — Shanon A. Foley
(74) *Attorney, Agent, or Firm* — Choate, Hall & Stewart LLP; Brenda Herschbach Jarrell; Janet M. Tse

(57) ABSTRACT

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses. Specifically, in one embodiment, the present disclosure relates to methods comprising administering to a subject RNA encoding a peptide or protein comprising an epitope of SARS-CoV-2 spike protein (S protein) for inducing an immune response against coronavirus S protein, in particular S protein of SARS-CoV-2, in the subject, i.e., vaccine RNA encoding vaccine antigen.

45 Claims, 155 Drawing Sheets

Specification includes a Sequence Listing.

(56) References Cited

U.S. PATENT DOCUMENTS 9,334,328 B2 5/2016 Schrum et al.
9,364,435 B2 6/2016 Yaworski et al.
9,428,535 B2 8/2016 de Fougerolles et al.
9,464,124 B2 10/2016 Bancel et al.
9,476,055 B2 10/2016 Sahin et al.
9,492,386 B2 11/2016 MacLachlan et al.
9,504,651 B2 11/2016 MacLachlan et al.
9,512,456 B2 12/2016 Wang et al.
9,533,047 B2 1/2017 de Fougerolles et al.
9,597,380 B2 3/2017 Chakraborty et al.
9,657,295 B2 5/2017 Schrum et al.
9,669,089 B2 6/2017 Thess et al.
9,737,619 B2 8/2017 Ansell et al.
9,850,269 B2 12/2017 DeRosa et al.
9,868,691 B2 1/2018 Benenato
9,868,692 B2 1/2018 Benenato
9,872,900 B2 1/2018 Ciaramella et al.
9,957,499 B2 5/2018 Heartlein et al.
9,970,047 B2 5/2018 Heartlein et al.
10,022,435 B2 7/2018 Ciaramella et al.
10,064,934 B2 9/2018 Ciaramella et al.
10,064,935 B2 9/2018 Ciaramella et al.
10,064,959 B2 9/2018 Schrum et al.
10,106,490 B2 10/2018 Du
10,106,800 B2 10/2018 Sahin et al.
10,124,055 B2 11/2018 Ciaramella et al.
10,166,298 B2 1/2019 Ansell et al.
10,207,010 B2 2/2019 Besin et al.
10,232,055 B2 3/2019 Kariko et al.
10,238,754 B2 3/2019 Guild et al.
10,266,485 B2 4/2019 Benenato
10,272,150 B2 4/2019 Ciaramella et al.
10,273,269 B2 4/2019 Ciaramella
10,286,086 B2 5/2019 Roy et al.
10,350,303 B1 7/2019 Guild et al.
10,385,088 B2 8/2019 Fraley et al.
10,413,618 B2 9/2019 Guild et al.
10,442,756 B2 10/2019 Benenato et al.
10,449,244 B2 10/2019 Ciaramella et al.
10,465,190 B1 11/2019 Chen et al.
10,493,143 B2 12/2019 Ciaramella et al.
10,493,167 B2 12/2019 de Fougerolles et al.
10,519,189 B2 12/2019 Hogrefe et al.
10,526,629 B2 1/2020 Rabideau et al.
10,543,269 B2 1/2020 Ciaramella et al.
10,577,403 B2 3/2020 De Fougerolles et al.
10,583,203 B2 3/2020 De Fougerolles et al.
10,648,017 B2 5/2020 Wochner
10,653,712 B2 5/2020 Hoge et al.
10,653,767 B2 5/2020 Ciaramella et al.
10,695,419 B2 6/2020 Ciaramella et al.
10,702,599 B2 7/2020 Ciaramella et al.
10,702,600 B1 7/2020 Ciaramella et al.
10,703,789 B2 7/2020 De Fougerolles et al.
10,709,779 B2 7/2020 Ciaramella et al.
10,717,982 B2 7/2020 Eberle et al.
10,723,692 B2 7/2020 Ansell et al.
10,738,306 B2 8/2020 Thess
10,760,070 B2 9/2020 Funkner et al.
10,772,975 B2 9/2020 Bancel et al.
10,808,242 B2 10/2020 Kariko et al.
10,857,105 B2 12/2020 Benenato et al.
10,858,647 B2 12/2020 Issa et al.
10,906,944 B2 2/2021 He et al.
10,912,826 B2 2/2021 Thess et al.
10,913,768 B2 2/2021 Hogrefe et al.
10,925,935 B2 2/2021 Chakraborty et al.
10,925,958 B2 2/2021 Ciaramella
10,960,070 B2 3/2021 Graham et al.
10,973,909 B1 4/2021 Csiszovszki et al.
11,040,112 B2 6/2021 Ansell et al.
11,045,540 B2 6/2021 Ciaramella
11,213,482 B1 1/2022 Gambotto et al.
11,241,493 B2 2/2022 Rauch et al.
2005/0002953 A1 1/2005 Herold
2005/0095582 A1 5/2005 Gillim-Ross et al.
2005/0112554 A1 5/2005 Zhao et al.
2005/0178142 A1 8/2005 Perry et al.
2005/0249742 A1 11/2005 Ruprecht et al.
2006/0121580 A1 6/2006 ter Meulen et al.
2006/0196193 A1 9/2006 Byrne
2007/0128217 A1 6/2007 ter Meulen et al.
2007/0270361 A1 11/2007 Lu et al.
2010/0017904 A1 1/2010 Abad et al.
2011/0300205 A1 12/2011 Geall et al.
2012/0082693 A1 4/2012 Van Der Werf et al.
2012/0101148 A1 4/2012 Aking et al.
2013/0102034 A1 4/2013 Schrum
2013/0236974 A1 9/2013 de Fougerolles
2013/0245103 A1 9/2013 de Fougerolles et al.
2013/0259923 A1 10/2013 Bancel et al.
2013/0266640 A1 10/2013 de Fougerolles et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0308304 A1 10/2014 Manoharan et al.
2014/0378538 A1 12/2014 Bancel
2015/0051268 A1 2/2015 Bancel et al.
2015/0056253 A1 2/2015 Bancel et al.
2015/0141499 A1 5/2015 Bancel et al.
2015/0265698 A1 9/2015 Pushko et al.
2015/0307542 A1 10/2015 Roy et al.
2015/0315541 A1 11/2015 Bancel et al.
2015/0376115 A1 12/2015 Ansell et al.
2016/0022580 A1 1/2016 Ramsay et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0235864 A1 8/2016 Schlake et al.
2016/0243221 A1 8/2016 Hoge et al.
2016/0317647 A1 11/2016 Ciaramella et al.
2017/0043037 A1 2/2017 Kariko et al.
2017/0056528 A1 3/2017 De Fougerolles et al.
2017/0130255 A1 5/2017 Wang et al.
2017/0166905 A1 6/2017 Eberle et al.
2017/0202979 A1 7/2017 Chakraborty et al.
2017/0204152 A1 7/2017 Nelson et al.
2017/0362627 A1 12/2017 Reynders, III et al.
2018/0000953 A1 1/2018 Almarsson et al.
2018/0002393 A1 1/2018 Bancel et al.
2018/0086816 A1 3/2018 Hoge et al.
2018/0112221 A1 4/2018 Schrum et al.
2018/0161422 A1 6/2018 Thess et al.
2018/0237766 A1 8/2018 Heartlein et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0256750 A1 9/2018 Butora et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0291425 A1 10/2018 Heartlein et al.
2018/0303925 A1 10/2018 Weissman et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0318446 A1 11/2018 Bancel et al.
2018/0353618 A1 12/2018 Burkhardt et al.
2018/0369374 A1 12/2018 Frederick et al.
2018/0369419 A1 12/2018 Benenato et al.
2018/0371047 A1 12/2018 Ticho et al.
2019/0000959 A1 1/2019 Ciaramella et al.
2019/0002890 A1 1/2019 Martini et al.
2019/0008938 A1 1/2019 Ciaramella et al.
2019/0008948 A1 1/2019 Ciaramella et al.
2019/0015501 A1 1/2019 Ciaramella et al.
2019/0030129 A1 1/2019 Schrum et al.
2019/0060458 A1 2/2019 De Fougerolles et al.
2019/0062762 A1 2/2019 Sahin et al.

(56) References Cited

U.S. PATENT DOCUMENTS

2019/0071682 A1 3/2019 Orlandini Von Niessen et al.
2019/0078087 A1 3/2019 Butora et al.
2019/0085368 A1 3/2019 Bancel et al.
2019/0100748 A1 4/2019 Issa et al.
2019/0144480 A1 5/2019 DeRosa et al.
2019/0153428 A1* 5/2019 Kariko ................. C12N 15/102
2019/0160185 A1 5/2019 Schrum et al.
2019/0167811 A1 6/2019 Benenato et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0211368 A1 7/2019 Butora et al.
2019/0216951 A1 7/2019 Baumhof
2019/0218546 A1 7/2019 Butora et al.
2019/0225644 A1 7/2019 Butora et al.
2019/0240317 A1 8/2019 Ciaramella et al.
2019/0241633 A1 8/2019 Fotin-Mleczek et al.
2019/0247417 A1 8/2019 Hoge et al.
2019/0255194 A1 8/2019 Roy et al.
2019/0275170 A1 9/2019 Benenato et al.
2019/0298657 A1 10/2019 Martini et al.
2019/0298658 A1 10/2019 Benenato et al.
2019/0300906 A1 10/2019 Martini et al.
2019/0314291 A1 10/2019 Besin et al.
2019/0314292 A1 10/2019 Benenato et al.
2019/0314524 A1 10/2019 Ansell et al.
2019/0336452 A1 11/2019 Brader
2019/0336595 A1 11/2019 Ciaramella
2019/0351040 A1 11/2019 Valiante et al.
2019/0351048 A1 11/2019 Rauch
2019/0382774 A1 12/2019 Hoge et al.
2019/0390181 A1 12/2019 Benenato et al.
2020/0010528 A1 1/2020 Seidel, III et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0060971 A1 2/2020 Eber et al.
2020/0061185 A1 2/2020 Graham et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.
2020/0109420 A1 4/2020 Brito et al.
2020/0113832 A1 4/2020 Yaworski et al.
2020/0123100 A1 4/2020 Benenato et al.
2020/0129445 A1 4/2020 Patel et al.
2020/0129608 A1 4/2020 Ciaramella et al.
2020/0129615 A1 4/2020 Ciaramella et al.
2020/0147176 A1 5/2020 Gieseke et al.
2020/0155706 A1 5/2020 De Fougerolles et al.
2020/0163878 A1 5/2020 Baumhof et al.
2020/0164038 A1 5/2020 De Fougerolles et al.
2020/0206362 A1 7/2020 Besin et al.
2020/0208145 A1 7/2020 Moore et al.
2020/0216878 A1 7/2020 Wochner
2020/0239869 A1 7/2020 Issa et al.
2020/0247861 A1 8/2020 De Fougerolles et al.
2020/0254086 A1 8/2020 Hoge et al.
2020/0268664 A1 8/2020 MacLachlan et al.
2020/0282046 A1 9/2020 Ciaramella et al.
2020/0282047 A1 9/2020 Ciaramella et al.
2020/0332293 A1 10/2020 Thess
2020/0338214 A1 10/2020 Guild et al.
2020/0354423 A1 11/2020 De Fougerolles et al.
2020/0383922 A1 12/2020 Ketterer et al.
2020/0392518 A1 12/2020 Eberle et al.
2020/0399629 A1 12/2020 Kariko et al.
2020/0405844 A1 12/2020 Ciaramella et al.
2021/0023199 A1 1/2021 Kallen et al.
2021/0030683 A1 2/2021 Eber et al.
2021/0030866 A1 2/2021 Kallen et al.
2021/0040473 A1 2/2021 Funkner et al.
2021/0046173 A1 2/2021 Ciaramella et al.
2021/0060175 A1 3/2021 Fotin-Mleczek et al.
2021/0077634 A1 3/2021 De Fougerolles et al.
2021/0107861 A1 4/2021 Ansell et al.
2021/0128716 A1 5/2021 Thess et al.
2021/0139543 A1 5/2021 He et al.
2021/0163919 A1 6/2021 Issa et al.
2021/0187097 A1 6/2021 Ciaramella et al.
2021/0217484 A1 7/2021 Giessel et al.
2021/0228707 A1 7/2021 Metkar et al.
2021/0228708 A1 7/2021 Smith et al.
2021/0230578 A1 7/2021 Issa et al.
2021/0246170 A1 8/2021 Langedijk et al.
2021/0251898 A1 8/2021 Baumhof et al.
2021/0275664 A1 9/2021 Graham et al.
2021/0299244 A1 9/2021 Mosharraf et al.
2021/0299251 A1 9/2021 Mosharraf et al.
2021/0308257 A1 10/2021 Kuo et al.
2021/0322541 A1 10/2021 Akahata et al.
2021/0332085 A1 10/2021 Chen
2021/0346493 A1 11/2021 Zhou et al.
2021/0355170 A1 11/2021 Whitehead et al.
2021/0379181 A1 12/2021 Rauch et al.
2021/0388032 A1 12/2021 Langedijk et al.
2022/0016234 A1 1/2022 Rice et al.
2022/0040292 A1 2/2022 Tang et al.
2022/0072155 A1 3/2022 Ansell et al.
2022/0105201 A1 4/2022 Guild et al.
2022/0193226 A1 6/2022 Rauch et al.
2022/0202930 A1 6/2022 Roth et al.
2022/0211838 A1 7/2022 Oostvogels et al.
2022/0211841 A1 7/2022 Oostvogels et al.
2022/0218815 A1 7/2022 Rauch et al.
2022/0218816 A1 7/2022 Ying
2022/0249704 A1 8/2022 Sahin et al.
2022/0273820 A1 9/2022 Sahin et al.

FOREIGN PATENT DOCUMENTS

AU 2015280499 B2 3/2020
CN 107033250 A 8/2017
CN 110167587 A 8/2019
CN 106795096 B 5/2020
CN 111088283 B 6/2020
CN 111303254 A 6/2020
CN 110951756 B 8/2020
CN 110974950 B 8/2020
CN 111518175 A 8/2020
CN 111592602 A 8/2020
CN 111139241 B 9/2020
CN 111218459 B 9/2020
CN 111363858 B 9/2020
CN 111748557 A 10/2020
CN 111778254 A 10/2020
CN 111848753 A 10/2020
CN 111218458 B 11/2020
CN 111876419 A 11/2020
CN 111939250 A 11/2020
CN 111978377 A 11/2020
CN 112023035 A 12/2020
CN 112028976 A 12/2020
CN 112043825 A 12/2020
CN 112048005 A 12/2020
CN 112094327 A 12/2020
CN 112220920 A 1/2021
CN 112226445 A 1/2021
CN 112266411 A 1/2021
CN 112321688 A 2/2021
CN 112358533 A 2/2021
CN 112480217 A 3/2021
CN 112626089 A 4/2021
CN 112794884 A 5/2021
CN 113186203 A 7/2021
EP 1291300 A2 3/2003
EP 1392341 B1 3/2005
EP 1857122 B1 12/2010
EP 2691101 A2 2/2014
EP 2791160 A1 10/2014
EP 2833892 A2 2/2015

(56) References Cited

FOREIGN PATENT DOCUMENTS

| | | | |
|---|---|---|---|
| EP | 2833894 | A1 | 2/2015 |
| EP | 1685844 | B1 | 3/2015 |
| EP | 3134131 | A1 | 3/2017 |
| EP | 3160938 | A1 | 5/2017 |
| EP | 3169693 | A1 | 5/2017 |
| EP | 3190361 | A1 | 7/2017 |
| EP | 2958588 | B1 | 8/2017 |
| EP | 3218508 | A1 | 9/2017 |
| EP | 2506857 | B1 | 2/2018 |
| EP | 3289083 | A1 | 3/2018 |
| EP | 2971102 | B1 | 6/2018 |
| EP | 3334828 | A1 | 6/2018 |
| EP | 3350157 | A2 | 7/2018 |
| EP | 3350333 | A2 | 7/2018 |
| EP | 3362460 | A1 | 8/2018 |
| EP | 3362461 | A1 | 8/2018 |
| EP | 3364949 | A1 | 8/2018 |
| EP | 3364983 | A2 | 8/2018 |
| EP | 3036330 | B1 | 9/2018 |
| EP | 3368507 | A1 | 9/2018 |
| EP | 3386484 | A1 | 10/2018 |
| EP | 3394030 | A1 | 10/2018 |
| EP | 2970955 | B1 | 11/2018 |
| EP | 2763701 | B1 | 12/2018 |
| EP | 3090060 | B1 | 2/2019 |
| EP | 3452101 | A2 | 3/2019 |
| EP | 3318248 | B1 | 4/2019 |
| EP | 3468537 | A1 | 4/2019 |
| EP | 2717893 | B1 | 5/2019 |
| EP | 3260541 | B1 | 5/2019 |
| EP | 3292873 | B1 | 5/2019 |
| EP | 3501550 | A1 | 6/2019 |
| EP | 1797886 | B1 | 7/2019 |
| EP | 3505176 | A1 | 7/2019 |
| EP | 3512944 | A1 | 7/2019 |
| EP | 3134506 | B1 | 8/2019 |
| EP | 3520820 | A1 | 8/2019 |
| EP | 3520821 | A1 | 8/2019 |
| EP | 3532070 | A1 | 9/2019 |
| EP | 3538067 | A1 | 9/2019 |
| EP | 3540060 | A1 | 9/2019 |
| EP | 3577221 | A1 | 12/2019 |
| EP | 3578200 | A1 | 12/2019 |
| EP | 3578205 | A1 | 12/2019 |
| EP | 3578659 | A1 | 12/2019 |
| EP | 3586861 | A1 | 1/2020 |
| EP | 3590949 | A1 | 1/2020 |
| EP | 3595676 | A1 | 1/2020 |
| EP | 3595727 | A1 | 1/2020 |
| EP | 3596041 | A1 | 1/2020 |
| EP | 3596042 | A1 | 1/2020 |
| EP | 3607074 | A1 | 2/2020 |
| EP | 3492109 | B1 | 3/2020 |
| EP | 3625345 | A1 | 3/2020 |
| EP | 3638215 | A1 | 4/2020 |
| EP | 3062798 | B1 | 5/2020 |
| EP | 3668522 | A2 | 6/2020 |
| EP | 3294885 | B1 | 7/2020 |
| EP | 3682905 | A1 | 7/2020 |
| EP | 3886897 | A1 | 10/2021 |
| EP | 3718565 | B1 | 4/2022 |
| JP | H10-113117 | A | 5/1998 |
| JP | 6594421 | B2 | 10/2019 |
| RU | 2731342 | C1 | 9/2020 |
| RU | 2731356 | C1 | 9/2020 |
| RU | 2733834 | C1 | 10/2020 |
| WO | WO-1998/051278 | A2 | 11/1998 |
| WO | WO-02/098443 | A2 | 12/2002 |
| WO | WO-2004/002453 | A1 | 1/2004 |
| WO | WO-2004/004743 | A1 | 1/2004 |
| WO | WO-2004/096842 | A2 | 11/2004 |
| WO | WO-2004/110081 | A1 | 12/2004 |
| WO | WO-2005/027963 | A2 | 3/2005 |
| WO | WO-2006/138380 | A2 | 12/2006 |
| WO | WO-2007/024708 | A2 | 3/2007 |
| WO | WO-2007/036366 | A2 | 4/2007 |
| WO | WO-2008/027942 | A2 | 3/2008 |
| WO | WO-2008/157688 | A2 | 12/2008 |
| WO | WO-2009/127060 | A1 | 10/2009 |
| WO | WO-2011/068810 | A1 | 6/2011 |
| WO | WO-2012/045075 | A1 | 4/2012 |
| WO | WO-2012/135805 | A2 | 10/2012 |
| WO | WO-2012/170930 | A1 | 12/2012 |
| WO | WO-2013/052523 | A1 | 4/2013 |
| WO | WO-2013/090648 | A1 | 6/2013 |
| WO | WO-2013/143699 | A1 | 10/2013 |
| WO | WO-2013/151668 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2014/089239 | A1 | 6/2014 |
| WO | WO-2014/127917 | A1 | 8/2014 |
| WO | WO-2014/144711 | A1 | 9/2014 |
| WO | WO-2014/152659 | A1 | 9/2014 |
| WO | WO-2014/152966 | A1 | 9/2014 |
| WO | WO-2014/159813 | A1 | 10/2014 |
| WO | WO-2014/164253 | A1 | 10/2014 |
| WO | WO-2015/005253 | A1 | 1/2015 |
| WO | WO-2015/024667 | A1 | 2/2015 |
| WO | WO-2015/062738 | A1 | 5/2015 |
| WO | WO-2015/101416 | A1 | 7/2015 |
| WO | WO-2015/164674 | A1 | 10/2015 |
| WO | WO-2015/164773 | A1 | 10/2015 |
| WO | WO-2015/199952 | A1 | 12/2015 |
| WO | WO-2016/005004 | A1 | 1/2016 |
| WO | WO-2016/005324 | A1 | 1/2016 |
| WO | WO-2016/011226 | A1 | 1/2016 |
| WO | WO-2016/045732 | A1 | 3/2016 |
| WO | WO-2016/077123 | A1 | 5/2016 |
| WO | WO-2016/164762 | A1 | 10/2016 |
| WO | WO-2016/165831 | A1 | 10/2016 |
| WO | WO-2016/176330 | A1 | 11/2016 |
| WO | WO-2016/180430 | A1 | 11/2016 |
| WO | WO-2016/184575 | A1 | 11/2016 |
| WO | WO-2016/184576 | A2 | 11/2016 |
| WO | WO-2016/193206 | A1 | 12/2016 |
| WO | WO-2016/201377 | A1 | 12/2016 |
| WO | WO-2017/015457 | A1 | 1/2017 |
| WO | WO-2017/025447 | A1 | 2/2017 |
| WO | WO-2017/036889 | A1 | 3/2017 |
| WO | WO-2017/049245 | A2 | 3/2017 |
| WO | WO-2017/049275 | A2 | 3/2017 |
| WO | WO-2017053297 | A1 | 3/2017 |
| WO | WO-2017/059902 | A1 | 4/2017 |
| WO | WO-2017/066781 | A1 | 4/2017 |
| WO | WO-2017/066789 | A1 | 4/2017 |
| WO | WO-2017/066793 | A1 | 4/2017 |
| WO | WO-2017/070601 | A1 | 4/2017 |
| WO | WO-2017/070618 | A1 | 4/2017 |
| WO | WO-2017/070626 | A2 | 4/2017 |
| WO | WO-2017060314 | A2 | 4/2017 |
| WO | WO-2017/075531 | A1 | 5/2017 |
| WO | WO-2017/099823 | A1 | 6/2017 |
| WO | WO-2017/112865 | A1 | 6/2017 |
| WO | WO-2017/127750 | A1 | 7/2017 |
| WO | WO-2017/191274 | A2 | 11/2017 |
| WO | WO-2017/201333 | A1 | 11/2017 |
| WO | WO-2017/218704 | A1 | 12/2017 |
| WO | WO-2017/220954 | A1 | 12/2017 |
| WO | WO-2018/053209 | A1 | 3/2018 |
| WO | WO-2018/081459 | A1 | 5/2018 |
| WO | WO-2018/081462 | A1 | 5/2018 |
| WO | WO-2018/089540 | A1 | 5/2018 |
| WO | WO-2018/089851 | A2 | 5/2018 |
| WO | WO-2018078053 | A1 | 5/2018 |
| WO | WO-2018081318 | A1 | 5/2018 |
| WO | WO-2018081480 | A1 | 5/2018 |
| WO | WO-2018/115527 | A2 | 6/2018 |
| WO | WO-2018/144778 | A1 | 8/2018 |
| WO | WO-2018/157009 | A1 | 8/2018 |
| WO | WO-2018/170245 | A1 | 9/2018 |
| WO | WO-2018/170306 | A1 | 9/2018 |
| WO | WO-2018/170322 | A1 | 9/2018 |
| WO | WO-2018/170336 | A1 | 9/2018 |

(56) References Cited

FOREIGN PATENT DOCUMENTS

| | | | |
|---|---|---|---|
| WO | WO-2018/170347 | A1 | 9/2018 |
| WO | WO-2018/187590 | A1 | 10/2018 |
| WO | WO-2018/213789 | A1 | 11/2018 |
| WO | WO-2018/232355 | A1 | 12/2018 |
| WO | WO-2018/232357 | A1 | 12/2018 |
| WO | WO-2019/035998 | A1 | 2/2019 |
| WO | WO-2019/036670 | A2 | 2/2019 |
| WO | WO-2019/036683 | A1 | 2/2019 |
| WO | WO-2019/036685 | A1 | 2/2019 |
| WO | WO-2019/092002 | A1 | 5/2019 |
| WO | WO-2019/092437 | A1 | 5/2019 |
| WO | WO-2019/148101 | A1 | 8/2019 |
| WO | WO-2019/209914 | A2 | 10/2019 |
| WO | WO-2019/232097 | A1 | 12/2019 |
| WO | WO-2020/006242 | A1 | 1/2020 |
| WO | WO-2020/025576 | A1 | 2/2020 |
| WO | WO-2020/056370 | A1 | 3/2020 |
| WO | WO-2020/061284 | A1 | 3/2020 |
| WO | WO-2020/061295 | A1 | 3/2020 |
| WO | WO-2020/061367 | A1 | 3/2020 |
| WO | WO-2020/072605 | A1 | 4/2020 |
| WO | WO-2020/097291 | A1 | 5/2020 |
| WO | WO-2020/150152 | A1 | 7/2020 |
| WO | WO-2020/0160397 | A1 | 8/2020 |
| WO | WO-2020/172239 | A1 | 8/2020 |
| WO | WO-2020/185811 | A1 | 9/2020 |
| WO | WO-2020/190750 | A1 | 9/2020 |
| WO | WO-2020/198337 | A1 | 10/2020 |
| WO | WO-2020/243561 | A1 | 12/2020 |
| WO | WO-2021/000968 | A2 | 1/2021 |
| WO | WO-2021/000969 | A2 | 1/2021 |
| WO | WO-2021/030533 | A1 | 2/2021 |
| WO | WO-2021/050864 | A1 | 3/2021 |
| WO | WO-2021/055811 | A1 | 3/2021 |
| WO | WO-2021/084282 | A1 | 5/2021 |
| WO | WO-2021/138447 | A1 | 7/2021 |
| WO | WO-2021/147025 | A1 | 7/2021 |
| WO | WO-2021/154763 | A1 | 8/2021 |
| WO | WO-2021/154812 | A1 | 8/2021 |
| WO | WO-2021/155243 | A1 | 8/2021 |
| WO | WO-2021/155323 | A1 | 8/2021 |
| WO | WO-2021/155733 | A1 | 8/2021 |
| WO | WO-2021/156267 | A1 | 8/2021 |
| WO | WO-2021/159040 | A2 | 8/2021 |
| WO | WO-2021/159118 | A2 | 8/2021 |
| WO | WO-2021/159130 | A2 | 8/2021 |
| WO | WO-2021/159648 | A1 | 8/2021 |
| WO | WO-2021/159985 | A1 | 8/2021 |
| WO | WO-2021/160346 | A1 | 8/2021 |
| WO | WO-2021/160850 | A1 | 8/2021 |
| WO | WO-2021/163365 | A1 | 8/2021 |
| WO | WO-2021/163371 | A1 | 8/2021 |
| WO | WO-2021/163398 | A1 | 8/2021 |
| WO | WO-2021/163427 | A1 | 8/2021 |
| WO | WO-2021/163456 | A1 | 8/2021 |
| WO | WO-2021/165667 | A1 | 8/2021 |
| WO | WO-2021/181100 | A1 | 9/2021 |
| WO | WO-2021/188969 | A2 | 9/2021 |
| WO | WO-2021/191630 | A1 | 9/2021 |
| WO | WO-2021/194826 | A2 | 9/2021 |
| WO | WO-2021/198705 | A1 | 10/2021 |
| WO | WO-2021/198706 | A2 | 10/2021 |
| WO | WO-2021/200800 | A1 | 10/2021 |
| WO | WO-2021/201612 | A1 | 10/2021 |
| WO | WO-2021/202599 | A2 | 10/2021 |
| WO | WO-2021/202772 | A1 | 10/2021 |
| WO | WO-2021/203017 | A2 | 10/2021 |
| WO | WO-2021/203018 | A1 | 10/2021 |
| WO | WO-2021/203044 | A2 | 10/2021 |
| WO | WO-2021/204179 | A1 | 10/2021 |
| WO | WO-2021/205455 | A1 | 10/2021 |
| WO | WO-2021/206581 | A1 | 10/2021 |
| WO | WO-2021/209824 | A1 | 10/2021 |
| WO | WO-2021/210686 | A1 | 10/2021 |
| WO | WO-2021/211279 | A1 | 10/2021 |
| WO | WO-2021/211688 | A1 | 10/2021 |
| WO | WO-2021/211748 | A1 | 10/2021 |
| WO | WO-2021/211749 | A1 | 10/2021 |
| WO | WO-2021/211760 | A1 | 10/2021 |
| WO | WO-2021/212568 | A1 | 10/2021 |
| WO | WO-2021/213924 | A1 | 10/2021 |
| WO | WO-2021/213945 | A1 | 10/2021 |
| WO | WO-2021/214204 | A1 | 10/2021 |
| WO | WO-2021/216729 | A1 | 10/2021 |
| WO | WO-2021/216738 | A2 | 10/2021 |
| WO | WO-2021/216743 | A2 | 10/2021 |
| WO | WO-2021/203017 | A3 | 11/2021 |
| WO | WO-2021/220319 | A1 | 11/2021 |
| WO | WO-2021/221486 | A1 | 11/2021 |
| WO | WO-2021/222304 | A1 | 11/2021 |
| WO | WO-2021/223647 | A1 | 11/2021 |
| WO | WO-2021/224946 | A1 | 11/2021 |
| WO | WO-2021/226436 | A1 | 11/2021 |
| WO | WO-2021/227401 | A1 | 11/2021 |
| WO | WO-2021/231560 | A1 | 11/2021 |
| WO | WO-2021/231929 | A1 | 11/2021 |
| WO | WO-2021/231963 | A1 | 11/2021 |
| WO | WO-2021/214081 | A3 | 12/2021 |
| WO | WO-2021/239880 | A1 | 12/2021 |
| WO | WO-2021/253172 | A1 | 12/2021 |
| WO | WO-2022/003119 | A1 | 1/2022 |
| WO | WO-2022/005503 | A1 | 1/2022 |
| WO | WO-2022/009121 | A1 | 1/2022 |
| WO | WO-2022/011092 | A1 | 1/2022 |
| WO | WO-2022/011332 | A2 | 1/2022 |
| WO | WO-2022/101469 | A1 | 5/2022 |

OTHER PUBLICATIONS

Anderson, E.J. et al., Safety and Immunogenicity of SARS-CoV-2 mRNA-1273 Vaccine in Older Adults, N. Engl. J. Med., 383(25):2427-2438 (2020).

Boone, L. et al., Selection and interpretation of clinical pathology indicators of hepatic injury in preclinical studies, Vet Clin Pathol., 34(3):182-8 (2005).

Brooks, M. et al., Non-Lethal Endotoxin Injection: A Rat Model of Hypercoagulability, PLoS One, 12(1):e0169976 (2017).

Cai, Y. et al., Distinct conformational states of SARS-CoV-2 spike protein, Science, 369(6511):1586-1592 (2020).

Chan, J. F. et al., A familial cluster of pneumonia associated with the 2019 novel coronavirus indicating person-to-person transmission a study of a family cluster, Lancet, 395(10223):514-523 (2020).

Corbett, K. S. et al., SARS-CoV-2 mRNA Vaccine Development Enabled by Prototype Pathogen Preparedness, posted on bioRxiv (Jun. 2020), 39 pages.

Corbett, K.S. et al., Evaluation of mRNA-1273 against SARS-CoV-2 B.1.351 Infection in Nonhuman Primates, posted on bioRxiv (May 2021), 33 pages.

Corbett, K.S. et al., Evaluation of the mRNA-1273 Vaccine against SARS-CoV-2 in Nonhuman Primates, N. Engl. J. Med., 383(16):1544-1555 (2020).

Corbett, K.S. et al., Immune Correlates of Protection by mRNA-1273 Immunization against SARS-CoV-2 Infection in Nonhuman Primates, posted on bioRxiv (Apr. 2021), 33 pages.

Corbett, K.S. et al., SARS-CoV-2mRNA vaccine design enabled by prototype pathogen preparedness, Nature, 586:567-571 (2020).

Ennulat, D. et al., Diagnostic performance of traditional hepatobiliary biomarkers of drug-induced liver injury in the rat, Toxicol Sci., 116(2):397-412 (2010).

Garrido, C. et al., SARS-CoV-2 vaccines elicit durable immune responses in infant rhesus macaques, Sci. Immunol., 23 pages (2021).

Hassett, K. et al., Optimization of Lipid Nanoparticles for Intra-muscular Administration of mRNA Vaccines, Mol Ther Nucleic Acids, 15:1-11 (2019).

Ivens, I. et al., PEGylated Biopharmaceuticals: Current Experience and Considerations for Nonclinical Development, Toxicol Pathol., 43(7):959-83 (2015).

Jackson, L.A. et al., An mRNA Vaccine against SARS-CoV-2—Preliminary Report, N. Engl. J. Med., 383:1920-1931 (2020).

(56) References Cited

OTHER PUBLICATIONS

Jiang, S. et al., Neutralizing Antibodies against SARS-CoV-2 and Other Human Coronaviruses, Trends in Immunology, 41(5):355-359 (2020).
Ke, Z. et al., Structures, conformations and distributions of SARs-CoV-2 spike protein trimers on intact virions, bioRxiv (2020).
Kim, A. et al., A mouse model of anemia of inflammation: complex pathogenesis with partial dependence on hepcidinm, Blood, 123(8):1129-36 (2014).
Kim, A. et al., Isocitrate treatment of acute anemia of inflammation in a mouse model. Blood Cells Mol Dis., 56(1):31-6 (2016).
Kim, J. et al., Viral Load Kinetics of SARS-CoV-2 Infection in First Two Patients in Korea, J Korean Med Sci., 35(7):e86 (2020).
Kirchdoerfer, R. N. et al., Stabilized coronavirus spikes are resistant to conformational changes induced by receptor recognition or proteolysis, Sci. Repo., 8(15701):1-11 (2018).
Kozauer, N. et al., Cross-Discipline Team Leader Review, Center for Drug Evaluation and Research 210922, 485 pages (2020).
Muik, A. et al., Neutralization of SARS-CoV-2 lineage B.1.1.7 pseudovirus by BNT162b2 vaccine-elicited human sera, Sci., 371:1152-1153 (2021).
Munster, et al., Respiratory disease and virus shedding in rhesus macaques inoculated with SARS-CoV-2, bioRxiv (2020).
Pallesen, J. et al., Immunogenicity and structures of a rationally designed prefusion MERS-CoV spike antigen, Proc Natl Acad Sci USA, 114(35):E7348-E7357 (2017).
Pardi, N. et al., Nucleoside-modified mRNA immunization elicits influenza virus hemagglutinin stalk-specific antibodies, Nat Commun., 22;9(1):3361 (2018).
Pardi, N. et al., Zika virus protection by a single low-dose nucleoside-modified mRNA vaccination, Nature, 543(7644):248-251 (2017).
Pegu, A. et al., Durability of mRNA-1273-induced antibodies against SARS-CoV-2 variants, posted on bioRxiv (May 2021), 39 pages.
Polack, F. P. et al., Safety and Efficacy of the BNT162b2 mRNA Covid-19 Vaccine, N. Engl. J. Med., 383(27):2603-2615 (2020).
Sahin, U. et al., mRNA-based therapeutics—developing a new class of drugs, Nat Rev Drug Discov., 13(10):759-80 (2014).
Sellers, R. et al., Scientific and Regulatory Policy Committee Points to Consider*: Approaches to the Conduct and Interpretation of Vaccine Safety Studies for Clinical and Anatomic Pathologists, Toxicol Pathol., 48(2):257-276 (2020).
Singh, D. et al., SARS-CoV-2 infection leads to acute infection with dynamic cellular and inflammatory flux in the lung that varies across nonhuman primate species, bioRxiv (2020).
Vogel, A. B. et al., A prefusion SARS-CoV-2 spike RNA vaccine is highly immunogenic and prevents lung infection in non-human primates, posted on bioRxiv (Sep. 2020), 38 pages.
Vogel, A. B. et al., BNT162b vaccines are immunogenic and protect non-human primates against SARS-CoV-2, posted on bioRxiv (Dec. 2020), 71 pages.
Vogel, A.B. et al., BNT162b vaccines protect rhesus macaques from SARS-CoV-2, Nature, 592:283-289 (Feb. 2021).
Walsh, E. E. et al., Safety and Immunogenicity of Two RNA-Based Covid-19 Vaccine Candidates, N. Engl. J. Med., 383:2439-2450 (2020).
World Health Organization—WHO guidelines on nonclinical evaluation of vaccines, Annex 1 in World Health Organization, WHO technical report series, No. 927, Geneva, Switzerland; World Health Organization; 31-63 (2005).
World Health Organization, Annex 2, Guidelines on nonclinical evaluation of vaccine adjuvants and adjuvanted vaccines, in WHO technical report series No. 987, Geneva, Switzerland; World Health Organization; 59-100 (2014).
Wrapp, D. et al., Cryo-EM structure of the 2019-nCoV spike in the prefusion conformation, Science, 367(6483):1260-1263 (2020).
Wu, K. et al., mRNA-1273 vaccine induces neutralizing antibodies against spike mutants from global SARS-CoV-2 variants, posted on bioRxiv (Jan. 2021), 20 pages.
Wu, K. et al., Variant SARS-CoV-2 mRNA vaccines confer broad neutralization as primary or booster series in mice, posted on bioRxiv (Apr. 2021), 28 pages.
Yong, C. et al., Recent Advances in the Vaccine Development Against Middle East Respiratory Syndrome—Coronavirus, Front Microbiol., 10:1781 (2019).
Zakhartchouk, A. et al., Immunogenicity of a receptor-binding domain of SARS coronavirus spike protein in mice: implications for a subunit vaccine, Vaccine, 25(1):136-43 (2007).
Zhou, M. et al., Coronavirus disease 2019 (COVID-19): a clinical update, Front Med., 14(2):126-135 (2020).
Zost, S. et al.,Rapid isolation and profiling of a diverse panel of human monoclonal antibodies targeting the SARS-CoV-2 spike protein, Nat Med., 26(9):1422-1427 (2020).
Zou, L. et al., SARS-CoV-2 Viral Load in Upper Respiratory Specimens of Infected Patients, N Engl J Med., 382(12):1177-1179 (2020).
U.S. Appl. No. 17/233,395, filed Apr. 16, 2021.
U.S. Appl. No. 17/233,399, filed Apr. 16, 2021.
[No Author Listed], 10 Million Doses of mRNA-based COVID-19 Vaccine to be supplied to Taiwan Region, 2 pages (Jul. 12, 2021).
[No Author Listed], An In Vitro Study Shows Pfizer-BioNTech COVID-19 Vaccine Elicits Antibodies that Neutralize SARS-CoV-2 with a Mutation Associated with Rapid Transmission, 3 pages (Jan. 8, 2021).
[No Author Listed], BioNTech and Fosun Pharma Announce Start of Clinical Trial of mRNA-based COVID-19 Vaccine Candidate in China, 2 pages (Aug. 5, 2020).
[No Author Listed], BioNTech and Fosun Pharma Announce the Start of a Phase 2 Clinical Trial of Lead mRNA COVID-19 Vaccine BNT162b2 in China, 2 pages (Nov. 25, 2020).
[No Author Listed], BioNTech and Fosun Pharma form COVID-19 vaccine strategic alliance in China, 2 pages (Mar. 16, 2020).
[No Author Listed], BioNTech and Fosun Pharma Receive Authorization for Emergency Use in Hong Kong for COVID-19 Vaccine, 2 pages (Jan. 25, 2021).
[No Author Listed], BioNTech and Fosun Pharma Receive Special Import Authorization in Macau for COVID-19 Vaccine, 2 pages (Feb. 25, 2021).
[No Author Listed], BioNTech and Fosun Pharma to Potentially Supply 10 Million Doses of BioNTech's NT162 mRNA-based Vaccine Candidate Against SARS-CoV-2 to Hong Kong SAR and Macao SAR, 2 pages (Aug. 27, 2020).
[No Author Listed], BioNTech and Fosun Pharma to Supply China with mRNA-based COVID-19 Vaccine, 2 pages (Dec. 16, 2020).
[No Author Listed], BioNTech and Pfizer announce completion of dosing for first cohort of Phase 1/2 trial of COVID-19 vaccine candidates in Germany, 2 pages (Apr. 29, 2020).
[No Author Listed], BioNTech and Pfizer Announce Nature Publication of German Phase 1/2 Study Data from mRNA-based Vaccine Candidate BNT162b1 Against SARS-CoV-2, 3 pages (Sep. 30, 2020).
[No Author Listed], BioNTech and Pfizer announce regulatory approval from German authority Paul-Ehrlich-Institut to commence first clinical trial of COVID-19 vaccine candidates, 3 pages (Apr. 22, 2020).
[No Author Listed], BioNTech and Pfizer Initiate Rolling Submission to European Medicines Agency for SARS-CoV-2 Vaccine Candidate BNT162b2, 3 pages (Oct. 6, 2020).
[No Author Listed], BioNTech and Pfizer Receive Regulatory Approval From Paul-Ehrlich-Institut to commence German Part of Global Phase 2/3 Trial for COVID-19 Vaccine Candidate BNT162b2, 3 pages (Sep. 7, 2020).
[No Author Listed], BioNTech Recognizes Employees and Partners for Their Support in Developing Historic Vaccine, 2 pages (Dec. 31, 2020).
[No Author Listed], BioNTech reports rapid progress on COVID-19 vaccine program to address global public health threat, 2 pages (Mar. 16, 2020).
[No Author Listed], BioNTech to Acquire GMP Manufacturing Site to Expand COVID-19 Vaccine Production Capacity in First Half 2021, 2 pages (Sep. 17, 2020).

(56) References Cited

OTHER PUBLICATIONS

[No Author Listed], BioNTech to Hold Press Conference to Provide an Update on COVID-19 Vaccine Development Program, 1 page (Dec. 2, 2020).
[No Author Listed], BioNTech to Hold Press Conference to Provide an Update on COVID-19 Vaccine Development Program, 1 page (Dec. 21, 2020).
[No Author Listed], BioNTech to Hold Webcast to Present Early Positive Data from Ongoing Phase 1/2 Study of mRNA-based Vaccine Candidate Against SARS-CoV-2, 1 page (Jul. 1, 2020).
[No Author Listed], BioNTech to Receive up to €375M in Funding from German Federal Ministry of Education and Research to Support COVID-19 Vaccine Program BNT162, 2 pages (Sep. 15, 2020).
[No Author Listed], Canada Exercises Increased Option for 20 Million Doses of mRNA Vaccine Against COVID-19 (mRNA-1273), Moderna Press Release, 2 pages (Sep. 22, 2020).
[No Author Listed], EMA Approves New Storage Option for Pfizer-BioNTech Vaccine, Easing Distribution and Storage of Doses Across European Union, 3 pages (Mar. 26, 2021).
[No Author Listed], Experimental COVID-19 Vaccine Protects Upper and Lower Airways in Nonhuman Primates, NIH News Release, 2 pages (Jul. 28, 2020).
[No Author Listed], Experimental COVID-19 Vaccine Safe, Generates Immune Response, NIH News Release, 2 pages (Jul. 14, 2020).
[No Author Listed], In Vitro Studies Demonstrate Pfizer and BioNTech COVID-19 Vaccine Elicits Antibodies that Neutralize SARS-CoV-2 with Key Mutations Present in U.K. and South African Variants, 3 pages (Jan. 27, 2021).
[No Author Listed], In Vitro Study Published in the New England Journal of Medicine Demonstrates Sera from Individuals Immunized with the Pfizer-BioNTech COVID-19 Vaccine Neutralize SARS-CoV-2 with South African Variant Spike Mutations, 3 pages (Feb. 17, 2021).
[No Author Listed], Investment Plan for Europe: European Investment Bank to provide BioNTech with up to €100 million in debt financing for COVID-19 vaccine development and manufacturing, 2 pages (Jun. 11, 2020).
[No Author Listed], Moderna Advances Late-Stage Development of its Vaccine (mRNA-1273) Against COVID-19, Moderna Press Release, 3 pages (Jun. 11, 2020).
[No Author Listed], Moderna and Lonza Announce Worldwide Strategic Collaboration to Manufacture Moderna's Vaccine (mRNA-1273) Against Novel Coronavirus, Moderna Press Release, 3 pages (May 1, 2020).
[No Author Listed], Moderna Announces Award from U.S. Government Agency BARDA for up to $483 Million to Accelerate Development of mRNA Vaccine (mRNA-1273) Against Novel Coronavirus, Moderna Press Release, 3 pages (Apr. 16, 2020).
[No Author Listed], Moderna Announces Expansion of BARDA Agreement to Support Larger Phase 3 Program forVaccine (mRNA-1273) Against COVID-19, Moderna Press Release, 3 pages (Jul. 26, 2020).
[No Author Listed], Moderna Announces First Participant Dosed in NIH-led Phase 1 Study of mRNA Vaccine (mRNA-1273) Against Novel Coronavirus, Moderna Press Release, 2 pages (Mar. 16, 2020).
[No Author Listed], Moderna Announces First Participants in Each Age Cohort Dosed in Phase 2 Study of mRNA Vaccine (mRNA-1273) Against Novel Coronavirus, Moderna Press Release, 2 pages (May 29, 2020).
[No Author Listed], Moderna Announces IND Submitted to U.S. FDA for Phase 2 Study of mRNA Vaccine (mRNA-1273) Against Novel Coronavirus, Moderna Press Release, 3 pages (Apr. 27, 2020).
[No Author Listed], Moderna Announces Phase 3 COVE Study of mRNA Vaccine Against COVID-19 (mRNA-1273) Begins, Moderna Press Release, 3 pages (Jul. 27, 2020).
[No Author Listed], Moderna Announces Positive Interim Phase 1 Data for its mRNA Vaccine (mRNA-1273) Against Novel Coronavirus, Moderna Press Release, 3 pages (May 18, 2020).
[No Author Listed], Moderna Announces Progress Across Broad Portfolio and all Three Clinical Stage Therapeutic Areas at 2020 R&D Day, Moderna Press Release, 4 pages (Sep. 17, 2020).
[No Author Listed], Moderna Announces Publication in the New England Journal of Medicine of Interim Results From Phase 1 Study of Its mRNA Vaccine Against COVID-19 (mRNA-1273), Moderna Press Release, 5 pages (Jul. 14, 2020).
[No Author Listed], Moderna Announces Publication in the New England Journal of Medicine of Non-Human Primate Preclinical Viral Challenge Study of its mRNA Vaccine Against COVID-19 (mRNA-1273), Moderna Press Release, 3 pages (Jul. 28, 2020).
[No Author Listed], Moderna Announces Supply Agreement with U.S. Government for Initial 100 Million Doses of mRNA Vaccine Against COVID-19 (mRNA-1273), Moderna Press Release, 3 pages (Aug. 11, 2020).
[No Author Listed], Moderna Completes Enrollment of Phase 2 Study of its mRNA Vaccine Against COVID-19 (mRNA-1273), Moderna Press Release, 2 pages (Jul. 8, 2020).
[No Author Listed], Moderna Confirms Advanced Discussions with European Commission to Supply Europe with 80 Million Doses of mRNA Vaccine Against COVID-19 mRNA-1273), Moderna Press Release, 3 pages (Aug. 24, 2020).
[No Author Listed], Moderna Confirms Discussions with the Ministry of Health, Labour and Welfare to Supply Japan with 40 Million Doses of mRNA Vaccine Against COVID-19 (mRNA-1273), Moderna Press Release, 2 pages (Aug. 28, 2020).
[No Author Listed], Moderna Receives FDA Fast Track Designation for mRNA Vaccine (mRNA-1273) Against Novel Coronavirus, Moderna Press Release, 2 pages (May 12, 2020).
[No Author Listed], Moderna Ships mRNA Vaccine Against Novel Coronavirus (mRNA-1273) for Phase 1 Study, Moderna Press Release, 2 pages (Feb. 24, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 6 pages (Feb. 11, 2021).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 8 pages (Apr. 30, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 8 pages (May 28, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), First Posted: Feb. 25, 2020, 18 pages, <https://clinicaltrials.gov/ct2/show/NCT04283461>.
[No Author Listed], NIH Clinical Trial NCT04283461, Safety and Immunogenicity Study of 2019-nCoV Vaccine (mRNA-1273) to Treat Novel Coronavirus, 6 pages (Feb. 21, 2020).
[No Author Listed], NIH Clinical Trial of Investigational Vaccine for COVID-19 begins, NIH News Release, 3 pages (Mar. 16, 2020).
[No Author Listed], NIH-Moderna Investigational COVID-19 Vaccine Shows Promise in Mouse Studies, NIH News Release, 2 pages (Aug. 5, 2020).
[No Author Listed], Pfizer and BioNTech Achieve First Authorization in the World for a Vaccine to Combat COVID-19, 3 pages (Dec. 2, 2020).
[No Author Listed], Pfizer and BioNTech Achieve Health Canada Authorization for Their Vaccine to Combat COVID-19, 2 pages (Dec. 9, 2020).
[No Author Listed], Pfizer and BioNTech Announce Agreement with the United Kingdom for 30 Million Doses of mRNA-based Vaccine Candidate Against SARS-CoV-2, 3 pages (Jul. 20, 2020).
[No Author Listed], Pfizer and BioNTech Announce an Agreement with U. S. Government for up to 600 Million Doses of mRNA-based Vaccine Candidate Against SARS-CoV-2, 3 pages (Jul. 22, 2020).

(56) References Cited

OTHER PUBLICATIONS

[No Author Listed], Pfizer and BioNTech Announce Collaboration with Biovac to Manufacture and Distribute COVID-19 Vaccine Doses within Africa, 4 pages (Jul. 21, 2021).
[No Author Listed], Pfizer and BioNTech Announce Data From Preclinical Studies of mRNA-Based Vaccine Candidate Against COVID-19, 3 pages (Sep. 9, 2020).
[No Author Listed], Pfizer and BioNTech Announce Early Positive Data from an Ongoing Phase 1/2 Study of mRNA-based Vaccine Candidate Against SARS-CoV-2, 3 pages (Jul. 1, 2020).
[No Author Listed], Pfizer and BioNTech Announce Early Positive Update from German Phase 1/2 COVID-19 Vaccine Study, Including First T Cell Response Data, 3 pages (Jul. 20, 2020).
[No Author Listed], Pfizer and BioNTech Announce Further Details on Collaboration to Accelerate Global COVID-19 Vaccine Development, 2 pages (Apr. 9, 2020).
[No Author Listed], Pfizer and BioNTech Announce New England Journal of Medicine Publication of Phase 1 Data on Lead mRNA Vaccine Candidate BNT162b2 Against COVID-19, 2 pages (Oct. 14, 2020).
[No Author Listed], Pfizer and BioNTech Announce Publication of Peer-Reviewed Data from Ongoing Phase 1/2 study of mRNA-based Vaccine Candidate, BNT162b1, Against SARS-CoV-2 in Nature, 4 pages (Aug. 12, 2020).
[No Author Listed], Pfizer and BioNTech Announce Publication of Results from Landmark Phase 3 Trial of BNT162b2 COVID-19 Vaccine Candidate in the New England Journal of Medicine, 3 pages (Dec. 10, 2020).
[No Author Listed], Pfizer and BioNTech Announce Vaccine Candidate Against COVID-19 Achieved Success in First Interim Analysis from Phase 3 Study, 3 pages (Nov. 9, 2020).
[No Author Listed], Pfizer and BioNTech Choose Lead mRNA Vaccine Candidate Against COVID-19 and Commence Pivotal Phase 2/3 Global Study, 3 pages (Jul. 27, 2020).
[No Author Listed], Pfizer and BioNTech Commence Global Clinical Trial to Evaluate COVID-19 Vaccine in Pregnant Women, 3 pages (Feb. 18, 2021).
[No Author Listed], Pfizer and BioNTech Confirm High Efficacy and No Serious Safety Concerns Through Up to Six Months Following Second Dose in Updated Topline Analysis of Landmark COVID-19 Vaccine Study, 4 pages (Apr. 1, 2021).
[No Author Listed], Pfizer and BioNTech Dose First Participants in the U.S. as Part of Global COVID-19 mRNA Vaccine Development Program, 2 pages (May 5, 2020).
[No Author Listed], Pfizer and BioNTech Granted FDA Fast Track Designation for Two Investigational mRNA-based Vaccine Candidates Against SARS-CoV-2, 2 pages (Jul. 13, 2020).
[No Author Listed], Pfizer and BioNTech Initiate a Study as Part of Broad Development Plan to Evaluate COVID-19 Booster and New Vaccine Variants, 3 pages (Feb. 25, 2021).
[No Author Listed], Pfizer and BioNTech Initiate Rolling Submission of Biologies License Application for U.S. FDA Approval of their COVID-19 Vaccine, 3 pages (May 7, 2021).
[No Author Listed], Pfizer and BioNTech Propose Expansion of Pivotal COVID-19 Vaccine Trial, 2 pages (Sep. 12, 2020).
[No Author Listed], Pfizer and BioNTech Provide Data from German Phase 1/2 Study Further Characterizing Immune Response Following Immunization with Lead COVID-19 Vaccine Candidate BNT162b2, 3 pages (Dec. 14, 2020).
[No Author Listed], Pfizer and BioNTech Publish Data from In Vitro Studies in Nature Medicine Demonstrating COVID-19 Vaccine Elicits Antibodies that Neutralize SARS-CoV-2 with Key Mutations Present in U.K. and South African Variants, 3 pages (Feb. 8, 2021).
[No Author Listed], Pfizer and BioNTech Publish Data on COVID-19 Vaccine-Induced Antibodies' Ability to Neutralize SARS-CoV-2 U.K. Strain Pseudovirus in Cell Culture in Science, 3 pages (Jan. 29, 2021).
[No Author Listed], Pfizer and BioNTech Publish Preclinical Data from Investigational COVID-19 Vaccine Program in Nature, 3 pages (Feb. 1, 2021).
[No Author Listed], Pfizer and BioNTech Publish Results of Study Showing COVID-19 Vaccine Elicits Antibodies that Neutralize Pseudovirus Bearing the SARS-CoV-2 U.K. Strain Spike Protein in Cell Culture, 3 pages (Jan. 20, 2021).
[No Author Listed], Pfizer and BioNTech Reach Agreement with COVAX for Advance Purchase of Vaccine to Help Combat COVID-19, 3 pages (Jan. 22, 2021).
[No Author Listed], Pfizer and BioNTech Reach an Agreement to Supply the EU with 200 Million Doses of Their BNT162b2 mRNA-based Vaccine Candidate against COVID-19, 3 pages (Nov. 11, 2020).
[No Author Listed], Pfizer and BioNTech Receive Authorization in the European Union for COVID-19 Vaccine, 4 pages (Dec. 21, 2020).
[No Author Listed], Pfizer and BioNTech Receive CHMP Positive Opinion for their COVID-19 Vaccine, 3 pages (Dec. 21, 2020).
[No Author Listed], Pfizer and BioNTech Receive Conditional Marketing Authorization by Swissmedic for COVID-19 Vaccine, 3 pages (Dec. 19, 2020).
[No Author Listed], Pfizer and BioNTech Receive FDA Advisory Committee Vote Supporting Potential First Emergency Use Authorization for Vaccine to Combat COVID-19 in the U.S., 3 pages (Dec. 10, 2020).
[No Author Listed], Pfizer and BioNTech Receive First Authorization in European Union for COVID-19 Vaccine in Adolescents, 3 pages (May 28, 2021).
[No Author Listed], Pfizer and BioNTech Receive First U.S. Authorization for Emergency Use of COVID-19 Vaccine in Adolescents, 4 pages (May 11, 2021).
[No Author Listed], Pfizer and BioNTech Receive Health Canada Authorization of COVID-19 Vaccine in Adolescents, 2 pages (May 5, 2021).
[No Author Listed], Pfizer and BioNTech Request Regulatory Agencies Expand Emergency Use of Their COVID-19 Vaccine to Adolescents, 3 pages (Apr. 9, 2021).
[No Author Listed], Pfizer and BioNTech Share Positive Early Data on Lead mRNA Vaccine Candidate BNT162b2 Against COVID-19, 3 pages (Aug. 20, 2020).
[No Author Listed], Pfizer and BioNTech Sign Agreement for Additional Supply to Turkey of 60 Million Doses of their COVID-19 Vaccine, 3 pages (May 20, 2021).
[No Author Listed], Pfizer and BioNTech Submit COVID-19 Vaccine Stability Data at Standard Freezer Temperature to the U.S. FDA, 3 pages (Feb. 19, 2021).
[No Author Listed], Pfizer and BioNTech Submitted Application for Conditional Marketing Authorization for COVID-19 Vaccine to the EMA, 3 pages (Dec. 1, 2020).
[No Author Listed], Pfizer and BioNTech to Co-develop Potential COVID-19 Vaccine, 2 pages (Mar. 17, 2020).
[No Author Listed], Pfizer and BioNTech to Potentially Supply the EU with 200 Million Doses of mRNA-based Vaccine Candidate Against SARS-CoV-2, 3 pages (Sep. 9, 2020).
[No Author Listed], Pfizer and BioNTech to Provide 500 Million Doses of COVID-19 Vaccine to U.S. Government for Donation to Poorest Nations, 4 pages (Jun. 10, 2021).
[No Author Listed], Pfizer and BioNTech to Provide COVID-19 Vaccine Doses for Olympic Athletes at the 2020 Tokyo Games, 4 pages (May 6, 2021).
[No Author Listed], Pfizer and BioNTech to Supply Canada with their BNT162 mRNA-Based Vaccine Candidate, 3 pages (Aug. 5, 2020).
[No Author Listed], Pfizer and BioNTech to Supply Japan with 120 Million Doses of Their BNT162 mRNA-Based Vaccine Candidate, 3 pages (Jul. 31, 2020).
[No Author Listed], Pfizer and BioNTech to Supply the U.S. with 100 Million Additional Doses of COVID-19 Vaccine, 3 pages (Dec. 23, 2020).
[No Author Listed], Pfizer and BioNTech to Supply the United States with 100 Million Additional Doses of COVID-19 Vaccine, 3 pages (Feb. 12, 2021).

(56) References Cited

OTHER PUBLICATIONS

[No Author Listed], Pfizer and BioNTech to Supply U.S. Government with an Additional 200 Million Doses of COVID-19 Vaccine to Help Meet Continued Need for Vaccine Supply in the U.S., 3 pages (Jul. 23, 2021).
[No Author Listed], Pfizer Canada and BioNTech Initiate Rolling Submission to Health Canada for SARS-CoV-2 Vaccine Candidate BNT162b2, 2 pages (Oct. 9, 2020).
[No Author Listed], Pfizer-BioNTech Announce Positive Topline Results of Pivotal COVID-19 Vaccine Study in Adolescents, 3 pages (Mar. 31, 2021).
[No Author Listed], Pfizer-BioNTech's COVID-19 Vaccine Arrives in Rwanda, 3 pages (Mar. 3, 2021).
[No Author Listed], Phase 3 Clinical Trial of Investigational Vaccine for COVID-19 Begins, NIH News Release, 3 pages (Jul. 27, 2020).
[No Author Listed], Real-World Evidence Confirms High Effectiveness of Pfizer-BioNTech COVID-19 Vaccine and Profound Public Health Impact of Vaccination One Year After Pandemic Declared, 4 pages (Mar. 11, 2021).
[No Author Listed], Severe acute respiratory syndrome coronavirus 2 isolate Wuhan-Hu-1, complete genome, Gen Bank: Accession No. 045512, 16 pages (published on Jan. 2020).
[No Author Listed], Severe acute respiratory syndrome coronavirus 2 isolate Wuhan-Hu-1, complete genome, Genbank Accession No. MN908947.3, 11 pages (Mar. 18, 2020).
[No Author Listed], Statement on Voluntary COVID-19 Vaccination for BioNTech Employees and Suppliers to Ensure Undisrupted Manufacturing and Distribution of COVID-19 Vaccine Doses, 1 page (Jan. 11, 2021).
[No Author Listed], U.S. CDC Committee of Independent Health Experts Recommends Vaccination with Pfizer and BioNTech COVID-19 Vaccine for Persons Ages 16 Years and Older, 3 pages (Dec. 12, 2020).
[No Author Listed], U.S. FDA Grants Priority Review for the Biologies License Application for Pfizer-BioNTech COVID-19 Vaccine, 3 pages (Jul. 16, 2021).
[No Author Listed], Update on vaccine production at BioNTech's manufacturing site in Marburg, 2 pages (Feb. 10, 2021).
Abu-Raddad, L. J. et al., Effectiveness of the BNT162b2 Covid-19 Vaccine against the B.1.1.7 and B.1.351 Variants, N. Engl. J. Med., 3 pages (2021).
Adams, P. et al., PHENIX: a comprehensive Python-based system for macromolecular structure solution, Acta Crystallogr D Biol Crystallogr, 66(Pt 2):213-21 (2010).
Adney, D. et al., Efficacy of an Adjuvanted Middle East Respiratory Syndrome Coronavirus Spike Protein Vaccine in Dromedary Camels and Alpacas, Viruses, 11(3):212 (2019).
Agnihothram, S. et al., Development of a Broadly Accessible Venezuelan Equine Encephalitis Virus Replicon Particle Vaccine Platform, J Virol, 92(11):e00027-18 (2018).
Al Kahlout, R. et al., Comparative Serological Study for the Prevalence of Anti-MERS Coronavirus Antibodies in High- and Low-Risk Groups in Qatar, J Immunol Res, 2019:1386740, 8 pages (2019).
Al-Amri, S. et al., Immunogenicity of Candidate MERS-CoV DNA Vaccines Based on the Spike Protein, Sci Rep, 7:44875, 8 pages (2017).
Andries, O. et al., N(I)-methylpseudouridine-incorporated mRNA outperforms pseudouridineincorporated mRNA by providing enhanced protein expression and reduced immunogenicity in mammalian cell lines and mice, J Control Release, 217:337-44 (2015).
Bao, L. et al., Reinfection could not occur in SARS-CoV-2 infected rhesus macaques, bioRXiv, 20 pages (2020).
Bao, L. et al., The Pathogenicity of SARS-CoV-2 in hACE2 Transgenic Mice, bioRxiv, 24 pages (2020).
Berger Rentsch, M. and Zimmer, G., A vesicular stomatitis virus replicon-based bioassay for the rapid and sensitive determination of multi-species type I interferon, PLoS One,6(10):e25858, 8 pages (2011).

Bergtold, A. et al., Cell Surface Recycling of Internalized Antigen Permits Dendritic Cell Priming of B Cells, Immunity, 23:503-514 (2005).
Berkhout, B. and Van Hemert, F., On the biased nucleotide composition of the human coronavirus RNA genome, Virus Research, 202:41-47 (2015).
Bouloy, M. et al., Both the 7-methyl and the 2'-0-methyl groups in the CAP of mRNA strongly influence its ability to act as primer for influenza virus RNA transcription, Proceedings of the National Academy of Sciences of the USA, 77(7):3952-3956 (1980).
Braathen, R. et al., The Magnitude and IgG Subclass of Antibodies Elicited by Targeted DNA Vaccines Are Influenced by Specificity for APC Surface Molecules, ImmunoHorizons, 2(1):21pgs (2018).
Brown, E. L. and Essigmann, H. T., Original Antigenic Sin: the Downside of Immunological Memory and Implications for COVID-19, Amer. Soc. Microbio., 6(2):e00056-21, 6 pages (2021).
Bruun, T. et al., Engineering a Rugged Nanoscaffold to Enhance Plug-and-Display Vaccination, ACS Nano, 12(9):8855-8866 (2018).
Chan, J. et al., Genomic characterization of the 2019 novel human-pathogenic coronavirus isolated from a patient with a ypical pneumonia after visiting Wuhan, Emerg Microbes Infect, 9(1):221-236 (2020).
Chan, J. et al., NCBI GenBank: MN938384.1, Severe acute respiratory syndrome coronavirus 2 isolate 2019_nCOV_HKU_SZ_002a_2020, complete genome, NCBI GenBank (Feb. 11, 2020).
Chandrashekar, A. et al., SARS-CoV-2 infection protects against rechallenge in rhesus macaques, Sci. Mag., 12 pages (2020).
Chi, X. et al., A neutralizing human antibody binds to the N-terminal domain of the Spike protein of SARS-CoV-2, Science, 369(6504):650-655 (2020).
Cohen, Jon, Scientists are moving at record speed to create new coronavirus vaccines but they may come too late, Science; AAAS, retrieved from the Internet: https://www.sciencemag.org/news/2020/01/scientists-are-moving-record-speed-create-new-coronavirus-vaccines-they-may-come-too, 6 pages (May 25, 2021).
Cossarizza, A. et al., SARS-CoV-2, the Virus that Causes COVID-19: Cytometry and the New Challenge for Global Health, Cytometry Part A, 4 pages (2020).
Cullis, P. and Hope, M., Lipid Nanoparticle Systems for Enabling Gene Therapies, Mol Ther, 25(7):1467-1475 (2017).
Database EMBL [Online] EBI; Jan. 15, 2020 (Jan. 15, 2020), Zhang Y. et al: "Wuhan seafood market pneumonia virus isolate Wuhan-Hu-1, complete genome.", XP055796635, Database accession No. MN908947 the whole document.
Database UniParc, Database accession No. UPI00131F240A, retrieved from UniProt, 4 pages Aug. 23, 2021.
Database UniParc, Database accession No. UPI0013753F0, retrieved from UniProt, one page (Sep. 2, 2021).
De Wit, E. et al., SARS and MERS: recent insights into emerging coronaviruses, Nat Rev Microbiol., 14(8):523-34 (2016).
Diao, B. et al., Human kidney is a target for novel severe acute respiratory syndrome coronavirus 2 infection, Nat Commun., 12(1):2506, 9 pages (2021).
Du, L. et al., Recombinant adeno-associated virus expressing the receptor-binding domain of severe acute respiratory syndrome coronavirus S protein elicits neutralizing antibodies: Implication for developing SARS vaccines, Virology, 353(1):6-16 (2006).
Emsley, P. et al., Features and development of Coot, Acta Crystallogr D Biol Crystallogr, 66(Pt 4):486-501 (2010).
Fan, X. et al., Cryo-EM analysis of the post-fusion structure of the SARS-CoV spike glycoprotein, Nat Commun., 11(1):3618, 10 pages (2020).
Faria, N. et al., Genomic characterisation of an emergent SARS-CoV-2 lineage in Manaus: preliminary findings—SARS-CoV-2 coronavirus / nCoV-2019 Genomic Epidemiology—Virological, retrieved from the Internet: https//virological.org/t/genomic-characterisation-of-an-emergent-sars-cov-2-lineage-in-manaus-preliminary-findings/586, 6 pages (May 31, 2021).
Farooq, F. et al., Circulating follicular T helper cells and cytokine profile in humans following vaccination with the rVSV-ZEBOV Ebola vaccine, Scientific Reports, 6(27944):1-9 (2016).
Feldstein, L. R. et al., Multisystem Inflammatory Syndrome in U.S. Children and Adolescents, N. Engl. Med., 383(4):334-346 (2020).

(56) References Cited

OTHER PUBLICATIONS

Fierz, W. and Walz, B., Antibody Dependent Enhancement Due to Original Antigenic Sin and the Development of SARS, Front. Immun., 11(1120):1-5 (2020).
Folegatti, P. et al., Safety and immunogenicity of the ChAdOx1 nCoV-19 vaccine against SARS-CoV-2: a preliminary report of a phase 1/2, single-blind, randomised controlled trial, Lancet, 396(10249):467-478 (2020).
Follis, K. et al., Furin cleavage of the SARS coronavirus spike glycoprotein enhances cell-cell fusion but does not affect virion entry, Virology, 350(2):358-69 (2006).
Funk, C. et al., A Snapshot of the Global Race for Vaccines Targeting SARS-CoV-2 and the COVID-19 Pandemic, Front Pharmacol., 11:937, 17 pages (2020).
Furuichi, Y. and Shatkin, A., Viral and cellular mRNA capping: past and prospects, Adv Virus Res, 55:135-84 (2000).
Furuichi, Yasuhiro, Caps on Eukaryotic mRNAs, John Wiley & Sons, pp. 1-12 (Jul. 2014).
Gallie, Daniel R., The cap and poly(A) tail function synergistically to regulate mRNA translational efficiency, Genes Dev, 5(11):2108-16 (1991).
Garcia-Doval, C. and Van Raaij, M. J., Structure of the receptor-binding carboxy-terminal domain of bacteriophage T7 tail fibers, PNAS, 109(24):9390-9395 (2012).
Gautam, U. et al., In vivo inhibition of tryptophan catabolism reorganizes the tuberculoma and augments immune-mediated control of *Mycobacterium tuberculosis*, Proc Natl Acad Sci USA, 115(1):E62-E71 (2018).
Gebre, M. S. et al., Optimization of Non-Coding Regions Improves Protective Efficacy of an mRNA SARS-CoV-2 Vaccine in Nonhuman Primates, bioRxiv, 36 pages (2021).
GenBank MN975262.1 "Wuhan seafood market pneumonia virus isolate 2019-nCoV_HKU-SZ-005b_2020, complete genome" (Jan. 24, 2020) [retrieved on Jun. 2, 2021, https://www.ncbi.nlm.nih.gov/nuccore/1800242661 ?sat=48&satkey=350763] whole doc.
GenBank QHN73810.1 "surface glycoprotein [Wuhan seafood market pneumonia virus]" (Jan. 24, 2020) [retrieved on Jun. 2, 2021, https://www.ncbi.nlm.nih.gov/protein/QHN73810.1/] whole doc.
Gomes, A. C. et al., Type of RNA Packed in VLPs Impacts IgG Class Switching-Implications for an Influenza Vaccine Design, MDPI, 7(47):1-13 (2019).
Graham, Barney S., Rapid COVID-19 vaccine development, Science, 368(6494):945-946 (2020).
Habjan, M. et al., Sequestration by IFIT1 impairs translation of 2'0-unmethylated capped RNA, PLOS Pathogens, 9(10):e1003663 (2013).
Hait, S. H. et al., Early T Follicular Helper Cell Responses and Germinal Center Reactions Are Associated with Viremia Control in Immunized Rhesus Macaques, Journal of Virology, 93(4):1-22 (2019).
He, Y. et al., Receptor-binding domain of SARS-CoV spike protein induces highly potent neutralizing antibodies: implication for developing subunit vaccine, Biochem Biophys Res Commun, 324(2):773-81 (2004).
Henderson, R. et al., Controlling the SARS-CoV-2 spike glycoprotein conformation, Nat Struct Mol Biol., 27(10):925-933 (2020).
Hodgson, J., The pandemic pipeline, Nature Biotechnology, 38(5):523-532 (2020).
Hodgson, J., The pandemic pipeline, Nature Biotechnology, Gale Group Inc, New York, 38(5):523-532 (2020).
Hoffman, M. et al., SARS-CoV-2 variants B.1.351 and B.1.1.248: Escape from the therapeutic antibodies and antibodies induced by infection and vaccination, bioRxiv, retrieved from the Internet: https//www.biorxiv.org/content/10.1101/2021.02.11.430787v1.full.pdf (Aug. 23, 2021).
Hoffmann, M. et al., SARS-CoV-2 Cell Entry Depends on ACE2 and TMPRSS2 and Is Blocked by a Clinically Proven Protease Inhibitor, Cell, 181(2):271-280 (2020).
Holdsworth, S. R. et al., Th1 and Th2 T helper cell subsets affect patterns of injury and outcomes in glomerulonephritis, Kidney International, 55:1198-1216 (1999).
Honda-Okubo, Y. et al., Severe Acute Respiratory Syndrome-Associated Coronavirus Vaccines Formulated with Delta Inulin Adjuvants Provide Enhanced Protection while Ameliorating Lung Eosinophilic Immunopathology, Journal of Virology, 89(6):2995-3007 (2015).
Hsieh, C. et al., Structure-based design of prefusion-stabilized SARS-CoV-2 spikes, Science, 369:1501-1505 (2020).
Hsieh, C. et al., Structure-based Design of Prefusion-stabilized SARS-CoV-2 Spikes, bioRxiv, retrieved from the Internet: https://www.ncbi.nlm.nih.gov/pmc/articles/PMC7302215/pdf/nihpp-2020.5.30.125484.pdf, 39 pages (May 30, 2020).
Huang, C. et al., Clinical features of patients infected with 2019 novel coronavirus in Wuhan, China, Lancet, 395(10223)497-506 (2020).
Huang, Q. et al., A single-dose mRNA vaccine provides a long-term protection for hACE2 transgenic mice from SARS-CoV-2, Nat. Comm., 12(776):1-10 (2021).
Huang, Y. et al., Structural and functional properties of SARS-CoV-2 spike protein: potential antivirus drug development for COVID-19, Acta Pharma. Sinica, 41:1141-1149 (2020).
Huber, V. C. et al., Distinct Contributions of Vaccine-Induced Immunoglobulin G1 (IgG1) and IgG2a Antibodies to Protective Immunity against Influenza, Clinical and Vaccine Immunology, 13(9):981-990 (2006).
Hulswit, R. et al., Coronavirus Spike Protein and Tropism Changes, Adv Virus Res., 96:29-57 (2016).
Hyde, J. L. et al., A viral RNA structural element alters host recognition of nonself RNA, Science, 343(6172):783-787 (2014).
International Search Report and Written Opinion for Application No. PCT/US2021/015145, 5 pages, dated May 3, 2021.
International Search Report for PCT/EP2021/059947, 6 pages (dated Aug. 5, 2021).
International Search Report for PCT/EP2021/060004, 7 pages (dated Sep. 8, 2021).
International Search Report for PCT/EP2021/060508, 7 pages (dated Aug. 5, 2021).
Jackson, N. A. C. et al., The promise of mRNA vaccines: a biotech and industrial perspective, NPJ Vaccines, 5(11):1-6 (2020).
Jafarzadeh, H. et al., Contribution of monocytes and macrophages to the local tissue inflammation and cytokine storm in COVID-19: Lessons from SARS and MERS, and potential therapeutic interventions, Life Sci., 257:118102, 16 pages (2020).
Jaimes, J. et al., Phylogenetic Analysis and Structural Modeling of SARS-CoV-2 Spike Protein Reveals an Evolutionary Distinct and Proteolytically Sensitive Activation Loop, J Mol Biol., 432(10):3309-3325 (2020).
Ji, R. et al., BNT162b2 Vaccine Encoding the SARS-CoV-2 P2 S Protects Transgenic hACE2 Mice against COVID-19, Vaccines, 9(324):1-7 (2021).
Kauffman, K. et al., Materials for non-viral intracellular delivery of messenger RNA Therapeutics, J Control Release, 240:227-234 (2016).
Kleine-Weber, H., et al., Functional analysis of potential cleavage sites in the MERS-coronavirus spike protein, Sci Rep., 8(1):16597 (2018).
Klimek, L. et al., Severe allergic reactions after COVID-19 vaccination with the Pfizer/BioNTech vaccine in Great Britain and USA, Allergo J. Int., 5 pages (2021).
Kozma, G. T. et al., Pseudo-anaphylaxis to Polyethylene Glycol (PEG)-Coated Liposomes: Roles of Anti-PEG IgM and Complement Activation in a Porcine Model of Human Infusion Reactions, ACS Nano, 13:9315-9324 (2019).
Kremsner, P. et al., Phase 1 Assessment of the Safety and Immunogenicity of an mRNALipid Nanoparticle Vaccine Candidate Against SARS-CoV-2 in Human Volunteers, medRxiv, pp. 1-38 (2020).
Kurimoto, S. et al., PEG-OligoRNA Hybridization of mRNA for Developing Sterically Stable Lipid Nanoparticles toward In Vivo Administration, Molecules, 24(7):1303, 16 pages (2019).

(56) References Cited

OTHER PUBLICATIONS

Laczkó, D. et al., A Single Immunization with Nucleoside-Modified mRNA Vaccines Elicits Strong Cellular and Humoral Immune Responses against SARS-CoV-2 in Mice, Immunity, 53(4):724-732 (2020).
Lambert, P. et al., Consensus summary report for CEPI/BC Mar. 12-13, 2020 meeting: Assessment of risk of disease enhancement with COVID-19 vaccines, Vaccine, 38(31):4783-4791 (2020).
Lee, Y. et al., Cross Protection against Influenza A Virus by Yeast-Expressed Heterologous Tandem Repeat M2 Extracellular Proteins, PLoS One, 10(9):e0137822 (15).
Lester, S. et al., Middle East respiratory coronavirus (MERS-CoV) spike (S) protein vesicular stomatitis virus pseudoparticle neutralization assays offer a reliable alternative to the conventional neutralization assay in human seroepidemiological studies, Access Microbiol., 1(9):e000057, 9 pages (2019).
Li, Fang, Structure, Function, and Evolution of Corona virus Spike Proteins, Annu Rev Viral, 3(1):237-261 (2016).
Liu, Y. et al., BNT162b2-Elicited Neutralization against New SARS-CoV-2 Spike Variants, N. Eng. J. Med., 2 pages (2021).
Liu, Y. et al., Neutralizing Activity of BNT162b2-Elicited Serum, N. Eng. J. Med., 384(15):1-3 (2021).
Lu, R. et al., Genomic characterisation and epidemiology of 2019 novel coronavirus: implications for virus origins and receptor binding, Lancet, 395(10224):565-574 (2020).
McCown, P. J. et al., Naturally occurring modified ribonucleosides, WIREs RNA, 11(e1595):1-71 (2020).
McKay, P. et al., Self-amplifying RN A SARS-Co V-2 lipid nanoparticle vaccine candidate induces high neutralizing antibody titers in mice, Nat Commun, 11(1):3523, 7 pages (2020).
Meier, S. et al., Foldon, The Natural Trimerization Domain of T4 Fibritin, Dissociates into a Monomeric A-state Form containing a Stable β-Hairpin: Atomic Details of Trimer Dissociation and Local β-Hairpin Stability from Residual Dipolar Couplings, J. Mol. Biol., 344(4):1051-1069 (2004).
Mishra, S. and Carnahan, R. et al., Coronavirus: A new type of vaccine using RNA could help defeat COVID-19, The Conversation, 4 pages (2020).
Mulligan, M. et al., Phase I/II study of COVID-19 RNA vaccine BNT162b1 in adults, Nature, 586(7830):589-593 (2020).
Mulligan, M. J. et al., Phase 1/2 Study to Describe the Safety and Immunogenicity of a COVID-19 RNA Vaccine Candidate (BNT162b1) in Adults 18 to 55 Years of Age: Interim Report, bioRxiv, 586:16pgs (2020).
Munoz-Fontela, C. et al., Animal models for COVID-19, Nature, 586:509-515 (2020).
Muruato, A. et al., A high-throughput neutralizing antibody assay for COVID-19 diagnosis and vaccine evaluation, Nat Commun., 11(1):4059 (2020).
Muthumani, K. et al., A synthetic consensus anti-spike protein DNA vaccine induces protective immunity against Middle East respiratory syndrome coronavirus in nonhuman primates, Science Translational Medicine, 7(301):1-14 (2015).
Nathan, A. et al., Structure-guided T cell vaccine design for SARS-CoV-2 variants and sarbecovriuses, Cell, 184:1-13 (2021).
No Author Listed, Messenger RNA encoding the full-length SARS-CoV-2 spike glycoprotein, WHO International Nonproprietary Names Progamme, 4 pages (Jun. 2021).
Nurieva, R. I. et al., Generation of T Follicular Helper Cells is Mediated by Interleukin-21 but Independent of T Helper 1,2, or 17 Cell Lineages, Immunity, 29:138-149 (2008).
Oany, A. et al., Design of an epitope-based peptide vaccine against spike protein of human coronavirus: an in silico approach, Drug Des Devel Ther., 8:1139-49 (2014).
Ogando, N. S. et al., SARS-coronavirus-2 replication in Vero E6 cells: replication kinetics, rapid adaptation and cytopathology, bioRxiv, 40 pages (2020).
Ou, X. et al., Characterization of spike glycoprotein of SARS-CoV-2 on virus entry and its immune cross-reactivity with SARS-CoV, Nat Commun., 11(1):1620, 12 pages (2020).
Pape, K. A. et al., The Humoral Immune Response is Initiated in Lymph Nodes by B Cells that Acquire Soluble Antigen Directly in the Follicles, Immunity, 26:491-502 (2007).
Pardi, N. et al., mRNA vaccines—a new era in vaccinology, Nat Rev Drug Discov, 17(4):261-279 (2018).
Pardi, Norbert, COVID-19 Symposium: Nucleoside-modified mRNA Vaccines Against SARS-CoV-2, Penn Medicine, 10 pages (2020).
Pardi, Norbert, Developement of nucleoside modified mRNA Vaccines against SARS-COV-2, Penn Medicine, 10 pages (2020).
Peng, Y. et al., Broad and strong memory $CD4^+$ and $CD8^+$ T cells induced by SARS-CoV-2 in UK convalescent individuals following COVID-19, Nat. Immun., 21:1336-1345 (2020).
Quinlan, B. D. et al., The SARS-CoV-2 receptor-binding domain elicits a potent neutralizing response without antibody-dependent enhancement, bioRxiv, 24 pages (2020).
Ralph, R. et al., 2019-nCoV (Wuhan virus), a novel Coronavirus: human-to-human transmission, travel-related cases, and vaccine readiness, J Infect Dev Ctries., 14(1):3-17 (2020).
Ramanathan, A. et al., mRNA capping: biological functions and applications, Nucleic Acids Research, 44(16) 7511-752:7511-7526 (2016).
Ramanathan, A. et al., mRNA capping: biological functions and applications, Nucleic Acids Research, 44(16) 7511-7526 (2016).
Rambaut, A. et al., A dynamic nomenclature proposal for SARS-CoV-2 lineages to assist genomic epidemiology, Nat Microbiol., 5(11):1403-1407 (2020).
Rambaut, A. et al., Preliminary genomic characterisation of an emergent SARS-CoV-2 lineage in the UK defined by a novel set of spike mutations—SARS-CoV-2 coronavirus / nCoV-2019 Genomic Epidemiology—Virological, retrieved from Internet: https://virological.org/t/preliminary-genomic-characterisation-of-an-emergent-sars-cov-2-lineage-in-the-uk-defined-by-a-novel-set-of-spike-mutations/563, 9 pages (May 7, 2021).
Rauch, S. et al., mRNA-based SARS-CoV-2 vaccine candidate CVnCoV induces high levels of virus-neutralising antibodies and mediates protection in rodents, NPJ, 57:1-9 (2021).
Rauch, S. et al., New Vaccine Technologies to Combat Outbreak Situations, Frontiers in Immunology, 9(1963):1-24 (2018).
Rohou, A. and Grigorieff, N., CTFFIND4: Fast and accurate defocus estimation from electron micrographs, J Struct Biol., 192(2):216-21 (2015).
Roth, N. et al., CV2COV, an enhanced mRNA based SARS-COV-2 vaccine candidate supports higher protein expression and improved immunogenicity in rats, bioRxiv, 12 pages (2021).
Sahin, U. et al., BNT162b2 vaccine induces neutralizing antibodies and poly-specific T cells in humans, Nat., 26 pages (2021).
Sahin, U. et al., Concurrent human antibody and TH1 type T-cell responses elicited by a COVID-19 RNA vaccine, medRXiv, 27 pages (2020).
Sahin, U. et al., COVID-19 vaccine BNT162b1 elicits human antibody and TH1 T cell responses, Nature, 586(7830):594-599 (2020).
Schlake, T. et al., Developing mRNA-vaccine technologies, RNA Biol, 9(11):1319-30 (2012).
Shang, J. et al., Structural basis of receptor recognition by SARS-CoV-2, Nature, 581 (7807):221-224 (2020).
Singh, D. et al., Responses to acute infection with SARS-CoV-2 in the lungs of rhesus macaques, baboons and marmosets, Nat Microbiol., 6(1):73-86 (2021).
Song, E. et al., Divergent and self-reactive immune responses in the CNS of COVID-19 patients with neurological symptoms, Cell Repo. Med., 2(100288):24 pages (2021).
Song, W. et al., Cryo-EM structure of the SARS coronavirus spike glycoprotein in complex with its host cell receptor ACE2, PLOS Pathogens, 1-19 (2018).
Song, Z. et al., From SARS to MERS, Thrusting Coronaviruses into the Spotlight, Viruses, 11(1):59, 28 pages (2019).
Stadler, K. et al., SARS Beginning to Understand a New Virus, Nature Reviews, 1:209-218 (2003).
Stertz, S. et al., The intracellular sites of early replication and budding of SARS-coronavirus, Virology, 361:304-315 (2007).

(56) References Cited

OTHER PUBLICATIONS

Tegunov, D. and Cramer, P., Real-time cryo-electron microscopy data preprocessing with Warp, Nat Methods, 16(11):1146-1152 (2019).
Thanh, Le, T. et al., The COVID-19 vaccine development landscape, Nat Rev Drug Discov., 19(5):305-306 (2020).
Tian, J. et al., SARS-CoV-2 spike glycoprotein vaccine candidate NVX-CoV2373 immunogenicity in baboons and protection in mice, Nat Commun, 12(1):372 (2021).
Tseng, C. et al., Immunization with SARS coronavirus vaccines leads to pulmonary immunopathology on challenge with the SARS virus, PLoS One, 7(4):e35421, 13 pages (2012).
Turner, J. S. et al., SARS-CoV-2 mRNA vaccines induce persistent human germinal centre responses, Nat., 25 pages (2021).
Van Doremalen, N. et al., ChAdOx1 nCoV-19 vaccine prevents SARS-CoV-2 pneumonia in rhesus macaques, Nature, 586(7830):578-582 (2020).
Viner, R. et al., Kawasaki-like disease: emerging complication during the COVID-19 pandemic, Lancet, 395(10239):1741-1743 (2020).
Vogel, A. B. et al., BNT162b vaccines protect rhesus macaques from SARS-CoV-2 (with supplementary materials), Nature, 44 pages (2021).
Vojdani, A. et al., Reaction of Human Monoclonal Antibodies to SARS-CoV-2 Proteins With Tissue Antigens: Implications for Autoimmune Diseases, Front. Immun., 11(617089):1-16 (2021).
Wang, F. et al., An Evidence Based Perspective on mRN A-SARS-Co V-2 Vaccine Development, Med Sci Monit, 26:e924701-e924700-8 (2020).
Wang, L. et al., Evaluation of candidate vaccine approaches for MERS-CoV, Nature Communications, 6(7712):1-11 (2015).
Wang, N. et al., Structural Definition of a Neutralization-sensitive Epitope on the MERS-CoV SI-NTD, Cell Rep, 28(13):3395-3405 (2019).
Wang, Z. et al., mRNA vaccine-elicited antibodies to SARS-CoV-2 and circulating variants, Nature, 592(7855):616-622 (2021).
Winkler, E. S. et al., SARS-CoV-2 infection of human ACE2-transgenic mice causes severe lung inflammation and impaired function, Nat. Immun., 21:1327-1335 (2020).
Wrapp D. et al., Prefusion 2019-nCoV spike glycoprotein with a single receptor-binding domain up, 78 pages, (Jan. 16, 2021), deposited on Feb. 10, 2020, Retrieved from the Internet: URL:https://www.rcsb.org/structure/6vsb [retrieved on May 21, 2021] the whole document.
Wrapp, D. et al., Cryo-EM structure of the 2019-nCoV spike in the prefusion conformation, Supplementary Materials, Science, 19 pages (2020).
Wrapp, D. et al., Prefusion 2019-nCoV spike glycoprotein with a single receptor-binding domain up, PDB: database, 4 pages (2020).
Written Opinion for PCT/EP2021/059947, 9 pages (dated Aug. 5, 2021).
Written Opinion for PCT/EP2021/060004, 14 pages (dated Sep. 8, 2021).
Written Opinion for PCT/EP2021/060508, 11 pages (dated Aug. 5, 2021).
Wu, F. et al., A new coronavirus associated with human respiratory disease in China, Nature, 579(7798):265-269 (2020).
Wu, J. et al., Nowcasting and forecasting the potential domestic and international spread of the 2019-nCoV outbreak originating in Wuhan, China: a modelling study, Lancet, 395(10225):689-697 (2020).
Wu, Y. et al., A noncompeting pair of human neutralizing antibodies block COVID-19 virus binding to its receptor ACE2, Science, 368(6496):1274-1278 (2020).
Xia, X., Detailed Dissection and Critical Evaluation of the Pfizer/BioNTech and Moderna mRNA Vaccines, Vaccines, 9(734):1-19 (2021).
Xie, X. et al., Neutralization of SARS-CoV-2 spike 69/70 deletion, E484K and N501Y variants by BNT162b2 vaccine-elicited sera, Nat. Med., 6 pages (2021).
Xu, J. et al., Antibodies and vaccines against Middle East respiratory syndrome coronavirus, Emerging Microbes and Infections, 8:841-856 (2019).
Yan, R. et al., Structural basis for the recognition of the SARS-CoV-2 by full-length human ACE2, Sci. Mag., 10 pages (2020).
Yang, D. et al., Attenuated Interferon and Proinflammatory Response in SARS-CoV-2-Infected Human Dendritic Cells Is Associated With Viral Antagonism of STAT1 Phosphorylation, J Infect Dis., 222(5):734-745 (2020).
Yang, X. et al., Highly Stable Timers Formed by Human Immunodeficiency Virus Type 1 Envelope Glycoproteins Fused with the Trimeric Motif of T4 Bacteriophage Fibritin, Journal of Virology, 76(9):4634-4642 (2002).
Yi, C. et al., Key residues of the receptor binding motif in the spike protein of SARS-CoV-2 that interact with ACE2 and neutralizing antibodies, Cell Mol Immunol., 17(6):621-630 (2020).
Yu, F. et al., Measures for diagnosing and treating infections by a novel coronavirus responsible for a pneumonia outbreak originating in Wuhan, China, Microbes Infect., 22(2):74-79 (2020).
Yu, J. et al., DNA vaccine protection against SARS-CoV-2 in rhesus macaques, Sci. Mag., 11 pages (2020).
Yuan, M. et al., A highly conserved cryptic epitope in the receptor binding domains of SARS-CoV-2 and SARS-CoV, Science, 368(6491):630-633 (2020).
Zeng, C. et al., Leveraging mRNAs sequences to express SARS-CoV-2 antigens in vivo, Biorxiv, 16 pages (2020), Retrieved from the Internet: URL:https://www.biorxiv.org/content/10.1101/2020.04.01.019877vl.full.pdf.
Zeng, C. et al., Leveraging mRNAs sequences to express SARS-CoV-2 antigens in vivo, Supplementary Information, bioRxiv, 13 pages (2020).
Zhang, N. et al., A Thermostable mRNA Vaccine against COVID-19, Cell, 182(5):1271-1283 (2020).
Zhang, Y. et al., Wuhan seafood market pneumonia virus isolate Wuhan-Hu-1, complete genome, Database EMBL, Database Accession No. MN908947 (Jan. 15, 2020).
Zhao, L. et al., Nanoparticle vaccines, Vaccine, 32(3):327-37 (2014).
Zhou, Y. et al., Enhancement versus neutralization by SARS-CoV-2 antibodies from a convalescent donor associates with distinct epitopes on the RBD, Cell Repo., 34(108699):1-23 (2021).
Zhu, F. et al., Safety, tolerability, and immunogenicity of a recombinant adenovirus type-5 vectored COVID-19 vaccine: a dose-escalation, open-label, non-randomised, first-in-human trial, Lancet, 395(10240):1845-1854 (2020).
Zhu, N. et al., A Novel Coronavirus from Patients with Pneumonia in China, 2019, N Engl J Med., 382(8):727-733 (2020).
Zhu, X. et al., Receptor-binding domain as a target for developing SARS vaccines, J Thorac Dis., 5 Suppl 2(Suppl 2):S142-8 (2013).
Zimmer, Katarina, A Guide to Emerging SARS-CoV-2 Variants, retrieved from the Internet: https://www.the-scientist.com/news-opinion/a-guide-to-emerging-sars-cov-2-variants-68387, 7 pages (May 31, 2021).
Zivanov, J. et al., New tools for automated high-resolution cryo-EM structure determination in RELION-3, Elife, 7:e42166, 22 pages (2018).
Moderna TX Clinical Trial, NCT04283461, Safety and Immunogenicity Study of 2019-nCoV Vaccine (mRNA-1273) for Prophjylaxis of SARS-CoV-2 Infection (COVID-19), 18 pages (2020).
Wang, F. et al., An Evidence Based Perspective on mRNA-SARS-CoV-2 Vaccine Development, Medical Science Monitor, 26, 8 pages (2020).
[No Author Listed] “CureVac Announces Positive Results in Low Dose—1 μg—Rabies Vaccine Clinical Phase 1 Study.” CureVac Press Release. Jan. 7, 2020.
Aldrich, C. et al., Proof-of-concept of a low-dose unmodified MRNA-based rabies vaccine formulated with lipid nanoparticles in human volunteers: A phase 1 trial, Vaccine, 39:1310-1318 (2021).
Leung, A. K.K. et al., Lipid Nanoparticles for Short Interfering RNA Delivery, Advances in Genetics 88:71-110 (2014).
Pardi, N. et al., Characterization of HIV-1 Nucleoside-Modified mRNA Vaccines in Rabbits and Rhesus Macaques, Molecular Therapy: Nucleic Acids, 15:36-47 (2019).

(56) References Cited

OTHER PUBLICATIONS

Chen, Y. et al., Emerging Coronaviruses: Genome structure, replication, and pathogenesis, J Med Virol., 92:418-423, (2020).
International Nonproprietary Names for Pharmaceutical Substances (INN), WHO Drug Information, vol. 33, No. 3, 139 pages, (2019).
Orlandini Von Niessen, A. G. et al., Improving mRNA-Based Therapeutic Gene Delivery by Expression—Augmenting 3' UTRs Identified by Cellular Library Screening, Molecular Therapy Original Article, 27(4):824-836 (2019).
Zhang, J. et al., Progress and Prospects on Vaccine Development against SARS-CoV-2, Vaccines, 8(153):1-12 (2020).
[No Author Listed], Assessment Report—Comirnaty, 140 pages Jan. 19, 2021.
Sequence Alignment for Seq ID No. 7, 3 pages (2022).
Sequence Alignment for Seq ID No. 9, 6 pages (2022).
Sinopeg Data Sheet, 10 pages (2022).

* cited by examiner

A

B

Geometric Mean and 95% CI: SARS-CoV-2 Anti-RBD Binding Antibody Levels – All-Available Immunogenicity Population – Stage 1, 2 Dose, 21 Days Apart – 65-85 Years of Age – BNT162b1

Note: Dot presents individual antibody levels.
Note: Number within each bar denotes geometric mean.

Geometric Mean and 95% CI: SARS-CoV-2 Serum Neutralizing Titer 50 –
All-Available Immunogenicity Population – Stage 1, 2 Dose, 21 Days Apart – 65-85 Years of Age – BNT162b1

Note: Dot presents individual antibody levels.
Note: Number within each bar denotes geometric mean.

Local Reactions, by Maximum Severity, Within 7 Days After Each Dose – Safety Population – Stage 1, 2 Dose, 21 Days Apart – 18-55 Years of Age – BNT162b2

Note: Number above each bar denotes percentage of participants reporting the event with any severity.

Note: Severity was not collected for use of antipyretic or pain medication.
Note: Number above each bar denotes percentage of participants reporting the event with any severity.

Note: Dot presents individual antibody levels.
Note: Number within each bar denotes geometric mean.

Abbreviations: GMC = geometric mean concentration; IgG = immunoglobulin G; RBD = receptor-binding domain.
Note: Dots present individual antibody levels.
Note: Number within each bar denotes geometric mean.

Abbreviations: GMC = geometric mean concentration; IgG = immunoglobulin G; RBD = receptor-binding domain.
Note: Dots present individual antibody levels.
Note: Number within each bar denotes geometric mean.

A

D

A

A

B

C

IHC-ISH, modRNA-V9, draining LN, 6h, T20-0148

CORONAVIRUS VACCINE

This application claims priority under 35 U.S.C. § 119 to each of the following applications, the disclosure of each of which is hereby incorporated by reference in its entirety: international application no. PCT/EP20/61239, filed Apr. 22, 2020; international application no. PCT/EP20/66968, filed Jun. 18, 2020; international application no. PCT/EP20/68174, filed Jun. 26, 2020; international application no. PCT/EP20/69805, filed Jul. 13, 2020; international application no. PCT/EP20/71733, filed Jul. 31, 2020; international application no. PCT/EP20/71839, filed Aug. 3, 2020; international application no. PCT/EP20/73668, filed Aug. 24, 2020; international application no. PCT/EP20/81544, filed Nov. 9, 2020; international application no. PCT/EP20/81981, filed Nov. 12, 2020; international application no. PCT/EP20/82601, filed Nov. 18, 2020; international application no. PCT/EP20/82989, filed Nov. 20, 2020; international application no. PCT/EP20/83435, filed Nov. 25, 2020; international application no. PCT/EP20/84342, filed Dec. 2, 2020; international application no. PCT/EP20/85145, filed Dec. 8, 2020; international application no. PCT/EP20/85653, filed Dec. 10, 2020; international application no. PCT/EP20/87844, filed Dec. 23, 2020; international application no. PCT/EP21/50027, filed Jan. 4, 2021; international application no. PCT/EP21/50874, filed Jan. 15, 2021; international application no. PCT/EP21/50875, filed Jan. 15, 2021; international application no. PCT/EP21/51772, filed Jan. 26, 2021; international application no. PCT/EP21/52572, filed Feb. 3, 2021; international application no. PCT/EP21/52716, filed Feb. 4, 2021; and international application no. PCT/EP21/54622, filed Feb. 24, 2021.

The instant application contains a Sequence Listing which has been submitted electronically in ASCII format and is hereby incorporated by reference in its entirety. Said ASCII copy, created on Apr. 16, 2021, is named 2013237-0165_SL.txt and is 172,032 bytes bytes in size.

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses. These methods and agents are, in particular, useful for the prevention or treatment of coronavirus infection. Administration of RNA disclosed herein to a subject can protect the subject against coronavirus infection. Specifically, in one embodiment, the present disclosure relates to methods comprising administering to a subject RNA encoding a peptide or protein comprising an epitope of SARS-CoV-2 spike protein (S protein) for inducing an immune response against coronavirus S protein, in particular S protein of SARS-CoV-2, in the subject, i.e., vaccine RNA encoding vaccine antigen. Administering to the subject RNA encoding vaccine antigen may provide (following expression of the RNA by appropriate target cells) vaccine antigen for inducing an immune response against vaccine antigen (and disease-associated antigen) in the subject.

In December 2019, a pneumonia outbreak of unknown cause occurred in Wuhan, China and it became clear that a novel coronavirus (severe acute respiratory syndrome coronavirus 2; SARS-CoV-2) was the underlying cause. The genetic sequence of SARS-CoV-2 became available to the WHO and public (MN908947.3) and the virus was categorized into the betacoronavirus subfamily. By sequence analysis, the phylogenetic tree revealed a closer relationship to severe acute respiratory syndrome (SARS) virus isolates than to another coronavirus infecting humans, namely the Middle East respiratory syndrome (MERS) virus. On February 2nd, a total of 14'557 cases were globally confirmed in 24 countries including Germany and a subsequent self-sustaining, human-to-human virus spread resulted in that SARS-CoV-2 became a global epidemic.

Coronaviruses are positive-sense, single-stranded RNA ((+)ssRNA) enveloped viruses that encode for a total of four structural proteins, spike protein (S), envelope protein (E), membrane protein (M) and nucleocapsid protein (N). The spike protein (S protein) is responsible for receptor-recognition, attachment to the cell, infection via the endosomal pathway, and the genomic release driven by fusion of viral and endosomal membranes. Though sequences between the different family members vary, there are conserved regions and motifs within the S protein making it possible to divide the S protein into two subdomains: S1 and S2. While the S2, with its transmembrane domain, is responsible for membrane fusion, the S1 domain recognizes the virus-specific receptor and binds to the target host cell. Within several coronavirus isolates, the receptor binding domain (RBD) was identified and a general structure of the S protein defined (FIG. 1).

Vaccine approaches and therapeutics against SARS-CoV-2 are currently not available, but urgently needed.

Due to the importance of the S protein in host cell recognition and entry, as well as in the induction of virus neutralising antibodies by the host immune system, we decided to target the viral S protein of SARS-CoV-2 and subdomains of the S protein such as S1 or RBD for vaccine development. Mutations within the regions important for conformation might be beneficial for inducing a stronger protective immune response. Therefore, we envision testing several constructs (FIG. 2). As the naïve S protein is a trimer and this trimeric structure has most likely an effect on the stability of the protein and the antigenicity, we included a strategy based on a stabilized construct introducing the T4 bacteriophage fibritin domain which is also in use in HIV for generating stable gp140 trimers and functional for SARS RBD-constructs.

SUMMARY

The present invention generally embraces the immunotherapeutic treatment of a subject comprising the administration of RNA, i.e., vaccine RNA, encoding an amino acid sequence, i.e., a vaccine antigen, comprising SARS-CoV-2 S protein, an immunogenic variant thereof, or an immunogenic fragment of the SARS-CoV-2 S protein or the immunogenic variant thereof, i.e., an antigenic peptide or protein. Thus, the vaccine antigen comprises an epitope of SARS-CoV-2 S protein for inducing an immune response against coronavirus S protein, in particular SARS-CoV-2 S protein, in the subject. RNA encoding vaccine antigen is administered to provide (following expression of the polynucleotide by appropriate target cells) antigen for induction, i.e., stimulation, priming and/or expansion, of an immune response, e.g., antibodies and/or immune effector cells, which is targeted to target antigen (coronavirus S protein, in particular SARS-CoV-2 S protein) or a procession product thereof. In one embodiment, the immune response which is to be induced according to the present disclosure is a B cell-mediated immune response, i.e., an antibody-mediated immune response. Additionally or alternatively, in one embodiment, the immune response which is to be induced according to the present disclosure is a T cell-mediated immune response. In one embodiment, the immune response is an anti-coronavirus, in particular anti-SARS-CoV-2 immune response.

The vaccine described herein comprises as the active principle single-stranded RNA that may be translated into the respective protein upon entering cells of a recipient. In addition to wildtype or codon-optimized sequences encoding the antigen sequence, the RNA may contain one or more structural elements optimized for maximal efficacy of the RNA with respect to stability and translational efficiency (5' cap, 5' UTR, 3' UTR, poly(A)-tail). In one embodiment, the RNA contains all of these elements. In one embodiment, beta-S-ARCA(D1) ($m_2^{7,2'-O}$ GppSpG) or $m_2^{7,3'-O}$Gppp ($m_1^{2'-O}$)ApG may be utilized as specific capping structure at the 5'-end of the RNA drug substances. As 5'-UTR sequence, the 5'-UTR sequence of the human alpha-globin mRNA, optionally with an optimized 'Kozak sequence' to increase translational efficiency may be used. As 3'-UTR sequence, a combination of two sequence elements (FI element) derived from the "amino terminal enhancer of split" (AES) mRNA (called F) and the mitochondrial encoded 12S ribosomal RNA (called I) placed between the coding sequence and the poly(A)-tail to assure higher maximum protein levels and prolonged persistence of the mRNA may be used. These were identified by an ex vivo selection process for sequences that confer RNA stability and augment total protein expression (see WO 2017/060314, herein incorporated by reference). Alternatively, the 3'-UTR may be two re-iterated 3'-UTRs of the human beta-globin mRNA. Furthermore, a poly(A)-tail measuring 110 nucleotides in length, consisting of a stretch of 30 adenosine residues, followed by a 10 nucleotide linker sequence (of random nucleotides) and another 70 adenosine residues may be used. This poly(A)-tail sequence was designed to enhance RNA stability and translational efficiency.

Furthermore, a secretory signal peptide (sec) may be fused to the antigen-encoding regions preferably in a way that the sec is translated as N terminal tag. In one embodiment, sec corresponds to the secreotory signal peptide of the S protein. Sequences coding for short linker peptides predominantly consisting of the amino acids glycine (G) and serine (S), as commonly used for fusion proteins may be used as GS/Linkers.

The vaccine RNA described herein may be complexed with proteins and/or lipids, preferably lipids, to generate RNA-particles for administration. If a combination of different RNAs is used, the RNAs may be complexed together or complexed separately with proteins and/or lipids to generate RNA-particles for administration.

In one aspect, the invention relates to a composition or medical preparation comprising RNA encoding an amino acid sequence comprising a SARS-CoV-2 S protein, an immunogenic variant thereof, or an immunogenic fragment of the SARS-CoV-2 S protein or the immunogenic variant thereof.

In one embodiment, an immunogenic fragment of the SARS-CoV-2 S protein comprises the S1 subunit of the SARS-CoV-2 S protein, or the receptor binding domain (RBD) of the S1 subunit of the SARS-CoV-2 S protein.

In one embodiment, the amino acid sequence comprising a SARS-CoV-2 S protein, an immunogenic variant thereof, or an immunogenic fragment of the SARS-CoV-2 S protein or the immunogenic variant thereof is able to form a multimeric complex, in particular a trimeric complex. To this end, the amino acid sequence comprising a SARS-CoV-2 S protein, an immunogenic variant thereof, or an immunogenic fragment of the SARS-CoV-2 S protein or the immunogenic variant thereof may comprise a domain allowing the formation of a multimeric complex, in particular a trimeric complex of the amino acid sequence comprising a SARS-CoV-2 S protein, an immunogenic variant thereof, or an immunogenic fragment of the SARS-CoV-2 S protein or the immunogenic variant thereof. In one embodiment, the domain allowing the formation of a multimeric complex comprises a trimerization domain, for example, a trimerization domain as described herein.

In one embodiment, the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

In one embodiment, the amino acid sequence comprising a SARS-CoV-2 S protein, an immunogenic variant thereof, or an immunogenic fragment of the SARS-CoV-2 S protein or the immunogenic variant thereof comprises a secretory signal peptide.

In one embodiment, the secretory signal peptide is fused, preferably N-terminally, to a SARS-CoV-2 S protein, an immunogenic variant thereof, or an immunogenic fragment of the SARS-CoV-2 S protein or the immunogenic variant thereof.

In one embodiment, (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

In one embodiment, the RNA is a modified RNA, in particular a stabilized mRNA. In one embodiment, the RNA comprises a modified nucleoside in place of at least one uridine. In one embodiment, the RNA comprises a modified nucleoside in place of each uridine. In one embodiment, the modified nucleoside is independently selected from pseudouridine (ψ), N1-methyl-pseudouridine (m1ψ), and 5-methyl-uridine (m5U).

In one embodiment, the RNA comprises a modified nucleoside in place of uridine.

In one embodiment, the modified nucleoside is selected from pseudouridine (ψ), N1-methyl-pseudouridine (m1ψ), and 5-methyl-uridine (m5U).

In one embodiment, the RNA comprises a 5' cap.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

In one embodiment, the poly-A sequence comprises at least 100 nucleotides.

In one embodiment, the poly-A sequence comprises or consists of the nucleotide sequence of SEQ ID NO: 14.

In one embodiment, the RNA is formulated or is to be formulated as a liquid, a solid, or a combination thereof.

In one embodiment, the RNA is formulated or is to be formulated for injection.

In one embodiment, the RNA is formulated or is to be formulated for intramuscular administration.

In one embodiment, the RNA is formulated or is to be formulated as particles.

In one embodiment, the particles are lipid nanoparticles (LNP) or lipoplex (LPX) particles.

In one embodiment, the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

In one embodiment, the RNA lipoplex particles are obtainable by mixing the RNA with liposomes. In one embodiment, the RNA lipoplex particles are obtainable by mixing the RNA with lipids.

In one embodiment, the RNA is formulated or is to be formulated as colloid. In one embodiment, the RNA is formulated or is to be formulated as particles, forming the dispersed phase of a colloid. In one embodiment, 50% or more, 75% or more, or 85% or more of the RNA are present in the dispersed phase. In one embodiment, the RNA is formulated or is to be formulated as particles comprising RNA and lipids. In one embodiment, the particles are formed by exposing RNA, dissolved in an aqueous phase, with lipids, dissolved in an organic phase. In one embodiment, the organic phase comprises ethanol. In one embodiment, the particles are formed by exposing RNA, dissolved in an aqueous phase, with lipids, dispersed in an aqueous phase. In one embodiment, the lipids dispersed in an aqueous phase form liposomes.

In one embodiment, the RNA is mRNA or saRNA.

In one embodiment, the composition or medical preparation is a pharmaceutical composition.

In one embodiment, the composition or medical preparation is a vaccine.

In one embodiment, the pharmaceutical composition further comprises one or more pharmaceutically acceptable carriers, diluents and/or excipients.

In one embodiment, the composition or medical preparation is a kit.

In one embodiment, the RNA and optionally the particle forming components are in separate vials.

In one embodiment, the kit further comprises instructions for use of the composition or medical preparation for inducing an immune response against coronavirus in a subject.

In one aspect, the invention relates to the composition or medical preparation described herein for pharmaceutical use.

In one embodiment, the pharmaceutical use comprises inducing an immune response against coronavirus in a subject.

In one embodiment, the pharmaceutical use comprises a therapeutic or prophylactic treatment of a coronavirus infection.

In one embodiment, the composition or medical preparation described herein is for administration to a human.

In one embodiment, the coronavirus is a betacoronavirus.

In one embodiment, the coronavirus is a sarbecovirus.

In one embodiment, the coronavirus is SARS-CoV-2.

In one aspect, the invention relates to a method of inducing an immune response against coronavirus in a subject comprising administering to the subject a composition comprising RNA encoding an amino acid sequence comprising a SARS-CoV-2 S protein, an immunogenic variant thereof, or an immunogenic fragment of the SARS-CoV-2 S protein or the immunogenic variant thereof.

In one embodiment, an immunogenic fragment of the SARS-CoV-2 S protein comprises the S1 subunit of the SARS-CoV-2 S protein, or the receptor binding domain (RBD) of the S1 subunit of the SARS-CoV-2 S protein.

In one embodiment, the amino acid sequence comprising a SARS-CoV-2 S protein, an immunogenic variant thereof, or an immunogenic fragment of the SARS-CoV-2 S protein or the immunogenic variant thereof is able to form a multimeric complex, in particular a trimeric complex. To this end, the amino acid sequence comprising a SARS-CoV-2 S protein, an immunogenic variant thereof, or an immunogenic fragment of the SARS-CoV-2 S protein or the immunogenic variant thereof may comprise a domain allowing the formation of a multimeric complex, in particular a trimeric complex of the amino acid sequence comprising a SARS-CoV-2 S protein, an immunogenic variant thereof, or an immunogenic fragment of the SARS-CoV-2 S protein or the immunogenic variant thereof. In one embodiment, the domain allowing the formation of a multimeric complex comprises a trimerization domain, for example, a trimerization domain as described herein.

In one embodiment, the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

In one embodiment, the amino acid sequence comprising a SARS-CoV-2 S protein, an immunogenic variant thereof, or an immunogenic fragment of the SARS-CoV-2 S protein or the immunogenic variant thereof comprises a secretory signal peptide.

In one embodiment, the secretory signal peptide is fused, preferably N-terminally, to a SARS-CoV-2 S protein, an immunogenic variant thereof, or an immunogenic fragment of the SARS-CoV-2 S protein or the immunogenic variant thereof.

In one embodiment, (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

In one embodiment, the RNA is a modified RNA, in particular a stabilized mRNA. In one embodiment, the RNA comprises a modified nucleoside in place of at least one uridine. In one embodiment, the RNA comprises a modified nucleoside in place of each uridine. In one embodiment, the modified nucleoside is independently selected from pseudouridine (i), N1-methyl-pseudouridine (m1ψ), and 5-methyl-uridine (m5U).

In one embodiment, the RNA comprises a modified nucleoside in place of uridine.

In one embodiment, the modified nucleoside is selected from pseudouridine (i), N1-methyl-pseudouridine (m1ψ), and 5-methyl-uridine (m5U).

In one embodiment, the RNA comprises a cap.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

In one embodiment, the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

In one embodiment, the poly-A sequence comprises at least 100 nucleotides.

In one embodiment, the poly-A sequence comprises or consists of the nucleotide sequence of SEQ ID NO: 14.

In one embodiment, the RNA is formulated as a liquid, a solid, or a combination thereof.

In one embodiment, the RNA is administered by injection.

In one embodiment, the RNA is administered by intramuscular administration.

In one embodiment, the RNA is formulated as particles.

In one embodiment, the particles are lipid nanoparticles (LNP) or lipoplex (LPX) particles.

In one embodiment, the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

In one embodiment, the RNA lipoplex particles are obtainable by mixing the RNA with liposomes. In one embodiment, the RNA lipoplex particles are obtainable by mixing the RNA with lipids.

In one embodiment, the RNA is formulated as colloid. In one embodiment, the RNA is formulated as particles, forming the dispersed phase of a colloid. In one embodiment, 50% or more, 75% or more, or 85% or more of the RNA are present in the dispersed phase. In one embodiment, the RNA is formulated as particles comprising RNA and lipids. In one embodiment, the particles are formed by exposing RNA, dissolved in an aqueous phase, with lipids, dissolved in an organic phase. In one embodiment, the organic phase comprises ethanol. In one embodiment, the particles are formed by exposing RNA, dissolved in an aqueous phase, with lipids, dispersed in an aqueous phase. In one embodiment, the lipids dispersed in an aqueous phase form liposomes.

In one embodiment, the RNA is mRNA or saRNA.

In one embodiment, the method is a method for vaccination against coronavirus.

In one embodiment, the method is a method for therapeutic or prophylactic treatment of a coronavirus infection.

In one embodiment, the subject is a human.

In one embodiment, the coronavirus is a betacoronavirus.

In one embodiment, the coronavirus is a sarbecovirus.

In one embodiment, the coronavirus is SARS-CoV-2.

In one embodiment of the method described herein, the composition is a composition described herein.

In one aspect, the invention relates to a composition or medical preparation described herein for use in a method described herein.

Among other things, the present disclosure demonstrates that a composition comprising a lipid nanoparticle encapsulated mRNA encoding at least a portion (e.g., that is or comprises an epitope) of a SARS-CoV-2-encoded polypeptide (e.g., of a SARS-CoV-2-encoded S protein) can achieve detectable antibody titer against the epitope in serum within 7 days after administration to a population of adult human subjects according to a regimen that includes administration of at least one dose of the vaccine composition. Moreover, the present disclosure demonstrates persistence of such antibody titer. In some embodiments, the present disclosure demonstrates increased such antibody titer when a modified mRNA is used, as compared with that achieved with a corresponding unmodified mRNA.

In some embodiments, a provided regimen includes at least one dose. In some embodiments, a provided regimen includes a first dose and at least one subsequent dose. In some embodiments, the first dose is the same amount as at least one subsequent dose. In some embodiments, the first dose is the same amount as all subsequent doses. In some embodiments, the first dose is a different amount as at least one subsequent dose. In some embodiments, the first dose is a different amount than all subsequent doses. In some embodiments, a provided regimen comprises two doses. In some embodiments, a provided regimen consists of two doses.

In particular embodiments, the immunogenic composition is formulated as a single-dose in a container, e.g., a vial. In some embodiments, the immunogenic composition is formulated as a multi-dose formulation in a vial. In some embodiments, the multi-dose formulation includes at least 2 doses per vial. In some embodiments, the multi-dose formulation includes a total of 2-20 doses per vial, such as, for example, 2, 3, 4, 5, 6, 7, 8, 9, 10, 11, or 12 doses per vial. In some embodiments, each dose in the vial is equal in volume. In some embodiments, a first dose is a different volume than a subsequent dose.

A "stable" multi-dose formulation exhibits no unacceptable levels of microbial growth, and substantially no or no breakdown or degradation of the active biological molecule component(s). As used herein, a "stable" immunogenic composition includes a formulation that remains capable of eliciting a desired immunologic response when administered to a subject.

In some embodiments, the multi-dose formulation remains stable for a specified time with multiple or repeated inoculations/insertions into the multi-dose container. For example, in some embodiments the multi-dose formulation may be stable for at least three days with up to ten usages, when contained within a multi-dose container. In some embodiments, the multi-dose formulations remain stable with 2-20 inoculations/insertions.

In some embodiments, administration of a composition comprising a lipid nanoparticle encapsulated mRNA encoding at least a portion (e.g., that is or comprises an epitope) of a SARS-CoV-2-encoded polypeptide (e.g., of a SARS-CoV-2-encoded S protein), e.g., according to a regimen as described herein, may result in lymphopenia in some subjects (e.g., in all subjects, in most subjects, in about 50% or fewer, in about 40% or fewer, in about 40% or fewer, in about 25% or fewer, in about 20% or fewer, in about 15% or fewer, in about 10% or fewer, in about 5% or fewer, etc). Among other things, the present disclosure demonstrates that such lymphopenia can resolve over time. For example, in some embodiments, lymphopenia resolves within about 14, about 10, about 9, about 8, about 7 days or less. In some embodiments, lymphopenia is Grade 3, Grade 2, or less.

Thus, among other things, the present disclosure provides compositions comprising a lipid nanoparticle encapsulated mRNA encoding at least a portion (e.g., that is or comprises an epitope) of a SARS-CoV-2-encoded polypeptide (e.g., of a SARS-CoV-2-encoded S protein) that are characterized, when administered to a relevant population of adults, to display certain characteristics (e.g., achieve certain effects) as described herein. In some embodiments, provided compositions may have been prepared, stored, transported, characterized, and/or used under conditions where temperature does not exceed a particular threshold. Alternatively or additionally, in some embodiments, provided compositions may have been protected from light (e.g., from certain wavelengths) during some or all of their preparation, storage, transport, characterization, and/or use. In some embodiments, one or more features of provided compositions (e.g., mRNA stability, as may be assessed, for example, by one or more of size, presence of particular moiety or modification, etc; lipid nanoparticle stability or aggregation, pH, etc) may be or have been assessed at one or more points during preparation, storage, transport, and/or use prior to administration.

Among other things, the present disclosure documents that certain provided compositions in which nucleotides within an mRNA are not modified (e.g., are naturally-occurring A, U, C, G), and/or provided methods relating to such compositions, are characterized (e.g., when administered to a relevant population, which may in some embodiments be or comprise an adult population), by an intrinsic adjuvant effect. In some embodiments, such composition and/or method can induce an antibody and/or a T cell response. In some embodiments, such a composition and/or method can induce a higher T cell response, as compared to conventional vaccines (e.g., non-mRNA vaccines such as protein vaccines).

Alternatively or additionally, the present disclosure documents that provided compositions (e.g., compositions comprising a lipid nanoparticle encapsulated mRNA encoding at least a portion (e.g., that is or comprises an epitope) of a SARS-CoV-2-encoded polypeptide (e.g., of a SARS-CoV-2-encoded S protein)) in which nucleotides within an mRNA are modified, and/or provided methods relating to such compositions, are characterized (e.g., when administered to a relevant population, which may in some embodiments be or comprise an adult population), by absence of an intrinsic adjuvant effect, or by a reduced intrinsic adjuvant effect as compared with an otherwise comparable composition (or method) with unmodified results. Alternatively or additionally, in some embodiments, such compositions (or methods) are characterized in that they (e.g., when administered to a relevant population, which may in some embodiments be or comprise an adult population) induce an antibody response and/or a CD4+ T cell response. Still further alternatively or additionally, in some embodiments, such compositions (or methods) are characterized in that they (e.g., when administered to a relevant population, which may in some embodiments be or comprise an adult population) induce a higher CD4+ T cell response than that observed with an alternative vaccine format (e.g., a peptide vaccine). In some embodiments involving modified nucleotides, such modified nucleotides may be present, for example, in a 3' UTR sequence, an antigen-encoding sequence, and/or a 5'UTR sequence. In some embodiments, modified nucleotides are or include one or more modified uracil residues and/or one or more modified cytosine residues. Among other things, the present disclosure documents that provided (e.g., compositions comprising a lipid nanoparticle encapsulated mRNA encoding at least a portion (e.g., that is or comprises an epitope) of a SARS-CoV-2-encoded polypeptide (e.g., of a SARS-CoV-2-encoded S protein)) and/or methods are characterized by (e.g., when administered to a relevant population, which may in some embodiments be or comprise an adult population) sustained expression of an encoded polypeptide (e.g., of a SARS-CoV-2-encoded protein [such as an S protein] or portion thereof, which portion, in some embodiments, may be or comprise an epitope thereof). For example, in some embodiments, such compositions and/or methods are characterized in that, when administered to a human, they achieve detectable polypeptide expression in a biological sample (e.g., serum) from such human and, in some embodiments, such expression persists for a period of time that is at least at least 36 hours or longer, including, e.g., at least 48 hours, at least 60 hours, at least 72 hours, at least 96 hours, at least 120 hours, at least 148 hours, or longer.

Those skilled in the art, reading the present disclosure, will appreciate that it describes various mRNA constructs encoding at least a portion (e.g., that is or comprises an epitope) of a SARS-CoV-2-encoded polypeptide (e.g., of a SARS-CoV-2-encoded S protein)). Such person of ordinary skill, reading the present disclosure, will particularly appreciate that it describes various mRNA constructs encoding at least a portion of a SARS-CoV-2 S protein, for example at least an RBD portion of a SARS-CoV-2 S protein. Still further, such a person of ordinary skill, reading the present disclosure, will appreciate that it describes particular characteristics and/or advantages of mRNA constructs encoding at least a portion (e.g., that is or comprises an epitope) of a SARS-CoV-2-encoded polypeptide (e.g., of a SARS-CoV-2-encoded S protein). Among other things, the present disclosure particularly documents surprising and useful characteristics and/or advantages of certain mRNA constructs encoding a SARS-CoV-2 RBD portion and, in some embodiments, not encoding a full length SARS-CoV-2 S protein. Without wishing to be bound by any particular theory, the present disclosure suggests that provided mRNA constructs that encode less than a full-length SARS-CoV-2 S protein, and particularly those that encode at least an RBD portion of such SARS-CoV-2 S protein may be particularly useful and/or effective for use as or in an immunogenic composition (e.g., a vaccine), and/or for achieving immunological effects as described herein (e.g., generation of SARS-CoV-2 neutralizing antibodies, and/or T cell responses (e.g., CD4+ and/or CD8+ T cell responses)). In some embodiments, the present disclosure provides an RNA (e.g., mRNA) comprising an open reading frame encoding a polypeptide that comprises a receptor-binding portion of a SARS-CoV-2 S protein, which RNA is suitable for intracellular expression of the polypeptide. In some embodiments, such an encoded polypeptide does not comprise the complete S protein. In some embodiments, the encoded polypeptide comprises the receptor binding domain (RBD), for example, as shown in SEQ ID NO: 5. In some embodiments, the encoded polypeptide comprises the peptide according to SEQ ID NO: 29 or 31. In some embodiments, such an RNA (e.g., mRNA) may be complexed by a (poly)cationic polymer, polyplex(es), protein(s) or peptide(s). In some embodiments, such an RNA may be formulated in a lipid nanoparticle (e.g., ones described herein). In some embodiments, such an RNA (e.g., mRNA) may be particularly useful and/or effective for use as or in an immunogenic composition (e.g., a vaccine), and/or for achieving immunological effects as described herein (e.g., generation of SARS-CoV-2 neutralizing antibodies, and/or T cell responses (e.g., CD4+ and/or CD8+ T cell responses)). In some embodiments, such an RNA (e.g., mRNA) may be useful for vaccinating humans (including, e.g., humans known to have been exposed and/or infected by SARS-CoV-2, and/or humans not known to have been exposed to SARS-CoV-2).

Those skilled in the art, reading the present disclosure, will further appreciate that it describes various mRNA constructs comprising a nucleic acid sequence that encodes a full-length SARS-CoV-2 Spike protein (e.g., including embodiments in which such encoded SARS-CoV-2 Spike protein may comprise at least one or more amino acid substitutions, e.g., proline substitutions as described herein, and/or embodiments in which the mRNA sequence is codon-optimized e.g., for mammalian, e.g., human, subjects). In some embodiments, such a full-length SARS-CoV-2 Spike protein may have an amino acid sequence that is or comprises that set forth in SEQ ID NO: 7. Still further, such a person of ordinary skill, reading the present disclosure, will appreciate, among other things, that it describes particular characteristics and/or advantages of certain mRNA constructs comprising a nucleic acid sequence that encodes a full-length SARS-CoV-2 Spike protein. Without wishing to be bound by any particular theory, the present disclosure suggests that provided mRNA constructs that encode a full-length SARS-CoV-2 S protein may be particularly useful and/or effective for use as or in an immunogenic composition (e.g., a vaccine) in particular subject population (e.g., particular age populations). For example, in some embodiments, such an mRNA composition may be particularly useful in younger (e.g., less than 25 years old, 20 years old, 18 years old, 15 years, 10 years old, or lower) subjects; alternatively or additionally, in some embodiments, such an mRNA composition may be particularly useful in elderly subjects (e.g., over 55 years old, 60 years old, 65 years old, 70 years old, 75 years old, 80 years old, 85 years old, or higher). In particular embodiments, an immunogenic composition comprising such an mRNA construct provided herein exhibits a minimal to modest increase (e.g., no more than 30% increase, no more than 20% increase, or no more than 10% increase, or lower) in dose level and/or dose number-dependent systemic reactogenicity (e.g., fever, fatigue, headache, chills, diarrhea, muscle pain, and/or joint pain, etc.) and/or local tolerability (e.g., pain, redness, and/or swelling, etc.), at least in some subjects (e.g., in some subject age groups); in some embodiments, such reactogenicity and/or local tolerability is observed particularly, in in younger age group (e.g., less than 25 years old, 20 years old, 18 years years old or lower) subjects, and/or in older (e.g., elderly) age group (e.g., 65-85 years old). In some embodiments, provided mRNA constructs that encode a full-length SARS-CoV-2 S protein may be particularly useful and/or effective for use as or in an immunogenic composition (e.g., a vaccine) for inducing SARS-CoV-2 neutralizing antibody response level in a population of subjects that are at high risk for severe diseases associated with SARS-CoV-2 infection (e.g., an elderly population, for example, 65-85 year-old group). In some embodiments, a person of ordinary skill, reading the present disclosure, will appreciate, among other things, that provided mRNA constructs that encode a full-length SARS-CoV-2 S protein, which exhibit a favorable reactogenicity profile (e.g., as described herein) in younger and elderly age populations, may be particularly useful and/or effective for use as or in an immunogenic composition (e.g., a vaccine) for achieving immunological effects as described herein (e.g., generation of SARS-CoV-2 neutralizing antibodies, and/or T cell responses (e.g., CD4+ and/or CD8+ T cell responses)). In some embodiments, the present disclosure also suggests that provided mRNA constructs that encode a full-length SARS-CoV-2 S protein may be particularly effective to protect against SARS-CoV-2 infection, as characterized by earlier clearance of SARS-CoV-2 viral RNA in non-human mammalian subjects (e.g., *Rhesus macaques*) that were immunized with immunogenic compositions comprising such mRNA constructs and subsequently challenged by SARS-CoV-2 strain. In some embodiments, such earlier clearance of SARS-CoV-2 viral RNA may be observed in the nose of non-human mammalian subjects (e.g., *Rhesus macaques*) that were immunized with immunogenic compositions comprising such mRNA constructs and subsequently challenged by SARS-CoV-2 strain.

In some embodiments, the present disclosure provides an RNA (e.g., mRNA) comprising an open reading frame encoding a full-length SARS-CoV-2 S protein (e.g., a full-length SARS-CoV-2 S protein with one or more amino acid substitutions), which RNA is suitable for intracellular expression of the polypeptide. In some embodiments, the encoded polypeptide comprises the amino acid sequence of SEQ ID NO:_7. In some embodiments, such an RNA (e.g., mRNA) may be complexed by a (poly)cationic polymer, polyplex(es), protein(s) or peptide(s). In some embodiments, such an RNA may be formulated in a lipid nanoparticle (e.g., ones described herein).

In some embodiments, an immunogenic composition provided herein may comprise a plurality of (e.g., at least two or more, including, e.g., at least three, at least four, at least five, at least six, at least seven, at least eight, at least nine, at least ten, etc.) immunoreactive epitopes of a SARS-CoV-2 polypeptide or variants thereof. In some such embodiments, such a plurality of immunoreactive epitopes may be encoded by a plurality of RNAs (e.g., mRNAs). In some such embodiments, such a plurality of immunoreactive epitopes may be encoded by a single RNA (e.g., mRNA). In some embodiments, nucleic acid sequences encoding a plurality of immunoreactive epitopes may be separated from each other in a single RNA (e.g., mRNA) by a linker (e.g., a peptide linker in some embodiments). Without wishing to be bound by any particular theory, in some embodiments, provided polyepitope immunogenic compositions (including, e.g., those that encode a full-length SARS-CoV-2 spike protein) may be particularly useful, when considering the genetic diversity of SARS-CoV-2 variants, to provide protection against numerous viral variants and/or may offer a greater opportunity for development of a diverse and/or otherwise robust (e.g., persistent, e.g., detectable about 5, 10, 15, 20, 25, 30, 35, 40, 45, 50, 55, 60 or more days after administration of one or more doses) neutralizing antibody and/or T cell response, and in particular a particularly robust $T_H1$-type T cell (e.g., CD4+ and/or CD8+ T cell) response.

In some embodiments, the present disclosure documents that provided compositions and/or methods are characterized by (e.g., when administered to a relevant population, which may in some embodiments be or comprise an adult population) in that they achieve one or more particular therapeutic outcomes (e.g., effective immune responses as described herein and/or detectable expression of encoded SARS-CoV-2 S protein or an immunogenic fragment thereof) with a single administration; in some such embodiments, an outcome may be assessed, for example, as compared to that observed in absence of mRNA vaccines described herein. In some embodiments, a particular outcome may be achieved at a lower dose than required for one or more alternative strategies.

In some embodiments, the present disclosure provides an immunogenic composition comprising an isolated messenger ribonucleic acid (mRNA) polynucleotide, wherein the isolated mRNA polynucleotide comprises an open reading frame encoding a polypeptide that comprises a receptor-binding portion of a SARs-CoV-2 S protein, and wherein the isolated mRNA polynucleotide is formulated in at least one lipid nanoparticle. For example, in some embodiments, such a lipid nanoparticle may comprise a molar ratio of 20-60% ionizable cationic lipid, 5-25% non-cationic lipid (e.g., neutral lipid), 25-55% sterol or steroid, and 0.5-15% polymer-conjugated lipid (e.g., PEG-modified lipid). In some embodiments, a sterol or steroid included in a lipid nanoparticle may be or comprise cholesterol. In some embodiments, a neutral lipid may be or comprise 1,2-distearoyl-sn-glycero-3-phosphocholine (DSPC). In some embodiments, a polymer-conjugated lipid may be or comprise PEG2000 DMG. In some embodiments, such an immunogenic composition may comprise a total lipid content of about 1 mg to 10 mg, or 3 mg to 8 mg, or 4 mg to 6 mg. In some embodiments, such an immunogenic composition may comprise a total lipid content of about 5 mg/mL-15 mg/mL or 7.5 mg/mL-12.5 mg/mL or 9-11 mg/mL. In some embodiments, such an isolated mRNA polynucleotide is provided in an effective amount to induce an immune response in a subject administered at least one dose of the immunogenic composition. In some embodiments, a polypeptide encoded by a provided isolated mRNA polynucleotide does not comprise the complete S protein. In some embodiments, such an isolated mRNA polynucleotide provided in an immunogenic composition is not self-replicating RNA.

In some embodiments, an immune response may comprise generation of a binding antibody titer against SARS-CoV-2 protein (including, e.g., a stabilized prefusion spike trimer in some embodiments) or a fragment thereof. In some embodiments, an immune response may comprise generation of a binding antibody titer against the receptor binding domain (RBD) of the SARS-CoV-2 spike protein. In some embodiments, a provided immunogenic composition has been established to achieve a detectable binding antibody titer after administration of a first dose, with seroconversion in at least 70% (including, e.g., at least 80%, at least 90%, at least 95% and up to 100%) of a population of subjects receiving such a provided immunogenic composition, for example, by about 2 weeks.

In some embodiments, an immune response may comprise generation of a neutralizing antibody titer against SARS-CoV-2 protein (including, e.g., a stabilized prefusion spike trimer in some embodiments) or a fragment thereof. In some embodiments, an immune response may comprise generation of a neutralizing antibody titer against the receptor binding domain (RBD) of the SARS-CoV-2 spike protein. In some embodiments, a provided immunogenic composition has been established to achieve a neutralizing antibody titer in an appropriate system (e.g., in a human infected with SARS-CoV-2 and/or a population thereof, and/or in a model system therefor). For example, in some embodiments, such neutralizing antibody titer may have been demonstrated in one or more of a population of humans, a non-human primate model (e.g., *Rhesus macaques*), and/or a mouse model.

In some embodiments, a neutralizing antibody titer is a titer that is (e.g., that has been established to be) sufficient to reduce viral infection of B cells relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more.

In some embodiments, a neutralizing antibody titer is a titer that is (e.g., that has been established to be) sufficient to reduce the rate of asymptomatic viral infection relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more. In some embodiments, such reduction can be characterized by assessment of SARS-CoV-2 N protein serology. Significant protection against asymptomatic infection was also confirmed by real life observations (see also: Dagan N. et al., N Engl J Med. 2021, doi: 10.1056/NEJMoa2101765. Epub ahead of print. PMID: 33626250) In some embodiments, a neutralizing antibody titer is a titer that is (e.g., that has been established to be) sufficient to reduce or block fusion of virus with epithelial cells and/or B cells of a vaccinated subject relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more.

In some embodiments, induction of a neutralizing antibody titer may be characterized by an elevation in the number of B cells, which in some embodiments may include plasma cells, class-switched IgG1- and IgG2-positive B cells, and/or germinal center B cells. In some embodiments, a provided immunogenic composition has been established to achieve such an elevation in the number of B cells in an appropriate system (e.g., in a human infected with SARS-CoV-2 and/or a population thereof, and/or in a model system therefor). For example, in some embodiments, such an elevation in the number of B cells may have been demonstrated in one or more of a population of humans, a non-human primate model (e.g., *rhesus macaques*), and/or a mouse model. In some embodiments, such an elevation in the number of B cells may have been demonstrated in draining lymph nodes and/or spleen of a mouse model after (e.g., at least 7 days, at least 8 days, at least 9 days, at least 10 days, at least 11 days, at least 12 days, at least 13 days, at least 14 days, after) immunization of such a mouse model with a provided immunogenic composition.

In some embodiments, induction of a neutralizing antibody titer may be characterized by a reduction in the number of circulating B cells in blood. In some embodiments, a provided immunogenic composition has been established to achieve such a reduction in the number of circulating B cells in blood of an appropriate system (e.g., in a human infected with SARS-CoV-2 and/or a population thereof, and/or in a model system therefor). For example, in some embodiments, such a reduction in the number of circulating B cells in blood may have been demonstrated in one or more of a population of humans, a non-human primate model (e.g., *Rhesus macaques*), and/or a mouse model. In some embodiments, such a reduction in the number of circulating B cells in blood may have been demonstrated in a mouse model after (e.g., at least 4 days, at least 5 days, at least 6 days, at least 7 days, at least 8 days, at least 9 days, at least 10 days, after) immunization of such a mouse model with a provided immunogenic composition. Without wishing to be bound by theory, a reduction in circulating B cells in blood may be due to B cell homing to lymphoid compartments.

In some embodiments, an immune response induced by a provided immunogenic composition may comprise an elevation in the number of T cells. In some embodiments, such an elevation in the number of T cells may include an elevation in the number of T follicular helper ($T_{FH}$) cells, which in some embodiments may comprise one or more subsets with ICOS upregulation. One of skilled in the art will understand that proliferation of $T_{FH}$ in germinal centres is integral for generation of an adaptive B-cell response, and also that in humans, $T_{FH}$ occurring in the circulation after vaccination is typically correlated with a high frequency of antigen-specific antibodies. In some embodiments, a provided immunogenic composition has been established to achieve such an elevation in the number of T cells (e.g., $T_{FH}$ cells) in an appropriate system (e.g., in a human infected with SARS-CoV-2 and/or a population thereof, and/or in a model system therefor). For example, in some embodiments, such an elevation in the number of T cells (e.g., $T_{FH}$ cells) may have been demonstrated in one or more of a population of humans, a non-human primate model (e.g., *Rhesus macaques*), and/or a mouse model. In some embodiments, such an elevation in the number of T cells (e.g., e.g., $T_{FH}$ cells) may have been demonstrated in draining lymph nodes, spleen, and/or blood of a mouse model after (e.g., at least 4 days, at least 5 days, at least 6 days, at least 7 days, at least 8 days, at least 9 days, at least 10 days, at least 11 days, at least 12 days, at least 13 days, at least 14 days, after) immunization of such a mouse model with a provided immunogenic composition. In some embodiments, a protective response against SARS-CoV-2 induced by a provided immunogenic composition has been established in an appropriate model system for SARS-CoV-2. For example, in some embodiments, such a protective response may have been demonstrated in an animal model, e.g., a non-human primate model (e.g., *Rhesus macaques*) and/or a mouse model. In some embodiments, a non-human primate (e.g., *Rhesus macaque*) or a population thereof that has/have received at least one immunization with a provided immunogenic composition is/are challenged with SARS-CoV-2, e.g., through intranasal and/or intratracheal route. In some embodiments, such a challenge may be performed several weeks (e.g., 5-10 weeks) after at least one immunization (including, e.g., at least two immunizations) with a provided immunogenic composition. In some embodiments, such a challenge may be performed when a detectable level of a SARS-CoV-2 neutralizing titer (e.g., antibody response to SARS-CoV-2 spike protein and/or a fragment thereof, including, e.g., but not limited to a stabilized prefusion spike trimer, S-2P, and/or antibody response to receptor-binding portion of SARS-CoV-2) is achieved in non-human primate(s) (e.g., *Rhesus macaque* (s)) that has received at least one immunization (including, e.g., at least two immunizations) with a provided immunogenic composition. In some embodiments, a protective response is characterized by absence of or reduction in detectable viral RNA in bronchoalveolar lavage (BAL) and/or nasal swabs of challenged non-human primate (s) (e.g., *Rhesus macaque* (s)). In some embodiments, immunogenic compositions described herein may have been characterized in that a larger percent of challenged animals, for example, non-human primates in a population (e.g., *Rhesus macaques*), that have received at least one immunization (including, e.g., at least two immunizations) with a provided immunogenic composition display absence of detectable RNA in their BAL and/or nasal swab, as compared to a population of non-immunized animals, for example, non-human primates (e.g., *rhesus macaques*). In some embodiments, immunogenic compositions described herein may have been characterized in that challenged animals, for example, non-human in a population (e.g., *Rhesus macaques*), that have received at least one immunization (including, e.g., at least two immunizations) with a provided immunogenic composition may show clearance of viral RNA in nasal swab no later than 10 days, including, e.g., no later than 8 days, no later than 6 days, no later than 4 days, etc., as compared to a population of non-immunized animals, for example, non-human primates (e.g., *Rhesus macaques*).

In some embodiments, immunogenic compositions described herein when administered to subjects in need thereof do not substantially increase the risk of vaccine-associated enhanced respiratory disease. In some embodiments, such vaccine-associated enhanced respiratory disease may be associated with antibody-dependent enhancement of replication and/or with vaccine antigens that induced antibodies with poor neutralizing activity and Th2-biased responses. In some embodiments, immunogenic compositions described herein when administered to subjects in need thereof do not substantially increase the risk of antibody-dependent enhancement of replication.

In some embodiments, a single dose of an mRNA composition (e.g., formulated in lipid nanoparticles) can induce a therapeutic antibody response in less than 10 days of vaccination.

In some embodiments, such a therapeutic antibody response may be characterized in that when such an mRNA vaccine can induce production of about 10-100 ug/mL IgG measured at 10 days after vaccination at a dose of 0.1 to 10 ug or 0.2-5 ug in an animal model. In some embodiments, such a therapeutic antibody response may be characterized in that such an mRNA vaccine induces about 100-1000 ug/mL IgG measured at 20 days of vaccination at a dose of 0.1 to 10 ug or 0.2-5 ug in an animal model. In some embodiments, a single dose may induce a pseudovirus-neutralization titer, as measured in an animal model, of 10-200 pVN50 titer 15 days after vaccination. In some embodiments, a single dose may induce a pseudovirus-neutralization titer, as measured in an animal model, of 50-500 pVN50 titer 15 days after vaccination.

In some embodiments, a single dose of an mRNA composition can expand antigen-specific CD8 and/or CD4 T cell response by at least at 50% or more (including, e.g., at least 60%, at least 70%, at least 80%, at least 90%, at least 95%, or more), as compared to that observed in absence of such an mRNA construct encoding a SARS-COV2 immunogenic protein or fragment thereof (e.g., spike protein and/or receptor binding domain). In some embodiments, a single dose of an mRNA composition can expand antigen-specific CD8 and/or CD4 T cell response by at least at 1.5-fold or more (including, e.g., at least 2-fold, at least 3-fold, at least 5-fold, at least 10-fold, at least 50-fold, at least 100-fold, at least 500-fold, at least 1000-fold, or more), as compared to that observed in absence of such an mRNA construct encoding a SARS-COV2 immunogenic protein or fragment thereof (e.g., spike protein and/or receptor binding domain).

In some embodiments, a regimen (e.g., a single dose of an mRNA composition) can expand T cells that exhibit a Th1 phenotype (e.g., as characterized by expression of IFN-gamma, IL-2, IL-4, and/or IL-5) by at least at 50% or more (including, e.g., at least 60%, at least 70%, at least 80%, at least 90%, at least 95%, or more), as compared to that observed in absence of such an mRNA construct encoding a SARS-COV2 immunogenic protein or fragment thereof (e.g., spike protein and/or receptor binding domain). In some embodiments, a regimen (e.g., a single dose of an mRNA composition) can expand T cells that exhibit a Th1 phenotype (e.g., as characterized by expression of IFN-gamma, IL-2, IL-4, and/or IL-5), for example by at least at 1.5-fold or more (including, e.g., at least 2-fold, at least 3-fold, at least 5-fold, at least 10-fold, at least 50-fold, at least 100-fold, at least 500-fold, at least 1000-fold, or more), as compared to that observed in absence of such an mRNA construct encoding a SARS-COV2 immunogenic protein or fragment thereof (e.g., spike protein and/or receptor binding domain). In some embodiments, a T-cell phenotype may be or comprise a Th1-dominant cytokine profile (e.g., as characterized by INF-gamma positive and/or IL-2 positive), and/or no by or biologically insignificant IL-4 secretion.

In some embodiments, a regimen as described herein (e.g., one or more doses of an mRNA composition) induces and/or achieves production of RBD-specific CD4+ T cells. Among other things, the present disclosure documents that mRNA compositions encoding an RBD-containing portion of a SARS-CoV-2 spike protein (e.g., and not encoding a full-length SARS-CoV-2 spike protein) may be particularly useful and/or effective in such induction and/or production of RBD-specific CD4+ T cells. In some embodiments, RBD-specific CD4+ T-cells induced by an mRNA composition described herein (e.g., by an mRNA composition that encodings an RBD-containing-portion of a SARS-CoV-2 spike protein and, in some embodiments not encoding a full-length SARS-CoV-2 spike protein) demonstrate a Th1-dominant cytokine profile (e.g., as characterized by INF-gamma positive and/or IL-2 positive), and/or by no or biologically insignificant IL-4 secretion.

In some embodiments, characterization of CD4+ and/or CD8+ T cell responses (e.g., described herein) in subjects receiving mRNA compositions (e.g., as described herein) may be performed using ex vivo assays using PBMCs collected from the subjects, e.g., assays as described in the Examples.

In some embodiments, immunogenicity of mRNA compositions described herein may be assessed by one of or more of the following serological immunongenicity assays: detection of IgG, IgM, and/or IgA to SARS-CoV-2 S protein present in blood samples of a subject receiving a provided mRNA composition, and/or neutralization assays using SARS-CoV-2 pseudovirus and/or a wild-type SARS-CoV-2 virus.

In some embodiments, an mRNA composition (e.g., as described herein) provide a relatively low adverse effect (e.g., Grade 1-Grade 2 pain, redness and/or swelling) within 7 days after vaccinations at a dose of 10 ug-100 ug or 1 ug-50 ug. In some embodiments, mRNA compositions (e.g., as described herein) provide a relatively low observation of systemic events (e.g., Grade 1-Grade 2 fever, fatigue, headache, chills, vomiting, diarrhea, muscle pain, joint pain, medication, and combinations thereof) within 7 days after vaccinations at a dose of 10 ug-100 ug.

In some embodiments, mRNA compositions are characterized in that when administered to subjects at 10-100 ug dose or 1 ug-50 ug, IgG directed to a SARS-CoV2 immunogenic protein or fragment thereof (e.g., spike protein and/or receptor binding domain) may be produced at a level of 100-100,000 U/mL or 500-50,000 U/mL 21 days after vaccination.

In some embodiments, an mRNA encodes a natively-folded trimeric receptor binding protein of SARS-CoV-2. In some embodiments, an mRNA encodes a variant of such receptor binding protein such that the encoded variant binds to ACE2 at a Kd of 10 pM or lower, including, e.g., at a Kd of 9 pM, 8 pM, 7 pM, 6 pM, 5 pM, 4 pM, or lower. In some embodiments, an mRNA encodes a variant of such receptor binding protein such that the encoded variant binds to ACE2 at a Kd of 5 pM. In some embodiments, an mRNA encodes a trimeric receptor binding portion of SARS-CoV-2 that comprises an ACE2 receptor binding site. In some embodiments, an mRNA comprises a coding sequence for a receptor-binding portion of SARS-CoV-2 and a trimerization domain (e.g., a natural trimerization domain (foldon) of T4 fibritin) such that the coding sequence directs expression of a trimeric protein that has an ACE2 receptor binding site and binds ACE2. In some embodiments, an mRNA encodes a trimeric receptor binding portion of SARS-CoV-2 or a variant thereof such that its Kd is smaller than that for a monomeric receptor-binding domain (RBD) of SARS-CoV-2. For example, in some embodiments, an mRNA encodes a trimeric receptor binding portion of SARS-CoV-2 or a variant thereof such that its Kd is at least 10-fold (including, e.g., at least 50-fold, at least 100-fold, at least 500-fold, at least 1000-fold, etc.) smaller than that for a RBD of SARS-CoV-2.

In some embodiments, a trimer receptor binding portion of SARS-CoV-2 encoded by an mRNA (e.g., as described herein) may be determined to have a size of about 3-4 angstroms when it is complexed with ACE2 and $B^0AT1$ neutral amino acid acid transporter in a closed conformation, as characterized by electron cryomicroscopy (cryoEM). In some embodiments, geometric mean SARS-CoV-2 neutralizing titer that characterizes and/or is achieved by an mRNA composition or method as described herein can reach at least 1.5-fold, including, at least 2-fold, at least 2.5-fold, at least 3-fold, or higher, that of a COVID-19 convalescent human panel (e.g., a panel of sera from COVID-19 convalescing humans obtained 20-40 days after the onset of symptoms and at least 14 days after the start of asymptomatic convalescence.

In some embodiments, mRNA compositions as provided herein may be characterized in that subjects who have been treated with such compositions (e.g., with at least one dose, at least two doses, etc) may show reduced and/or more transient presence of viral RNA in relevant site(s) (e.g., nose and/or lungs, etc, and/or any other tissue susceptible to infection) as compared with an appropriate control (e.g., an established expected level for a comparable subject or population not having been so treated and having been exposed to virus under reasonably comparable exposure conditions)

In some embodiments, the RBD antigen expressed by an mRNA construct (e.g., as described herein) can be modified by addition of a T4-fibritin-derived "foldon" trimerization domain, for example, to increase its immunogenicity.

In some embodiments, mRNA compositions and/or methods described herein are characterized in that certain local reactions (e.g., pain, redness, and/or swelling, etc.) and/or systemic events (e.g., fever, fatigue, headache, etc.) may appear and/or peak at Day 2 after vaccination. In some embodiments, mRNA compositions described herein are characterized in that certain local reactions (e.g., pain, redness, and/or swelling, etc.) and/or systemic events (e.g., fever, fatigue, headache, etc.) may resolve by Day 7 after vaccination.

In some embodiments, mRNA compositions and/or methods described herein are characterized in that no Grade 1 or greater change in routine clinical laboratory values or laboratory abnormalities are observed in subjects receiving mRNA compositions (e.g., as described herein). Examples of such clinical laboratory assays may include lymphocyte count, hematological changes, etc.

In some embodiments, mRNA compositions and/or methods described herein are characterized in that by 21 days after a first dose (e.g., 10-100 ug inclusive or 1 ug-50 ug inclusive), geometric mean concentrations (GMCs) of IgG directed to a SARS-CoV-2 S polypeptide or an immunogenic fragment thereof (e.g., RBD) may reach 200-3000 units/mL or 500-3000 units/mL or 500-2000 units/mL, compared to 602 units/mL for a panel of COVID-19 convalescent human sera. In some embodiments, mRNA compositions described herein are characterized in that by 7 days after a second dose (e.g., 10-30 ug inclusive; or 1 ug-50 ug inclusive), geometric mean concentrations (GMCs) of IgG directed to a SARS-CoV-2 spike polypeptide or an immunogenic fragment thereof (e.g., RBD) may increase by at least 8-fold or higher, including, e.g., at least 9-fold, at least 10-fold, at least 15-fold, at least 20-fold, at least 25-fold, at least 30-fold, at least 35-fold, at least 40-fold, or higher. In some embodiments, mRNA compositions described herein are characterized in that by 7 days after a second dose (e.g., 10-30 ug inclusive; or 1 ug-50 ug inclusive), geometric mean concentrations (GMCs) of IgG directed to a SARS-CoV-2 S polypeptide or an immunogenic fragment thereof (e.g., RBD) may increase to 1500 units/mL to 40,000 units/mL or 4000 units/mL to 40,000 units/mL. In some embodiments, antibody concentrations described herein can persist to at least 20 days or longer, including, e.g., at least 25 days, at least 30 days, at least 35 days, at least 40 days, at least 45 days, at least 50 days, after a first dose, or at least 10 days or longer, including, e.g., at least 15 days, at least 20 days, at least 25 days, or longer, after a second dose. In some embodiments, antibody concentrations can persist to 35 days after a first dose, or at least 14 days after a second dose.

In some embodiments, mRNA compositions described herein are characterized in that when measured at 7 days after a second dose (e.g., 1-50 ug inclusive), GMC of IgG directed to a SARS-CoV-2 S polypeptide or an immunogenic fragment thereof (e.g., RBD) is at least 30% higher (including, e.g., at least 40% higher, at least 50% higher, at least 60%, higher, at least 70% higher, at least 80% higher, at least 90% higher, at least 95% higher, as compared to antibody concentrations observed in a panel of COVID-19 convalescent human serum. In many embodiments, geometric mean concentration (GMC) of IgG described herein is GMCs of RBD-binding IgG.

In some embodiments, mRNA compositions described herein are characterized in that when measured at 7 days after a second dose (e.g., 10-50 ug inclusive), GMC of IgG directed to a SARS-CoV-2 S polypeptide or an immunogenic fragment thereof (e.g., RBD) is at least 1.1-fold higher (including, e.g., at least 1.5-fold, at least 2-fold, at least 3-fold, at least 4-fold, at least 5-fold, at least 6-fold higher, at least 7-fold higher, at least 8-fold higher, at least 9-fold higher, at least 10-fold higher, at least 15-fold higher, at least 20-fold higher, at least 25-fold higher, at least 30-fold higher), as compared to antibody concentrations observed in a panel ofCOVID-19 convalescent human serum. In many embodiments, geometric mean concentration (GMC) of IgG described herein is GMCs of RBD-binding IgG.

In some embodiments, mRNA compositions described herein are characterized in that when measured at 21 days after a second dose, GMC of IgG directed to a SARS-CoV-2 S polypeptide or an immunogenic fragment thereof (e.g., RBD) is at least 5-fold higher (including, e.g., at least 6-fold higher, at least 7-fold higher, at least 8-fold higher, at least 9-fold higher, at least 10-fold higher, at least 15-fold higher, at least 20-fold higher, at least 25-fold higher, at least 30-fold higher), as compared to antibody concentrations observed in a panel of COVID-19 convalescent human serum. In many embodiments, geometric mean concentration (GMC) of IgG described herein is GMCs of RBD-binding IgG.

In some embodiments, mRNA compositions and/or methods described herein are characterized in that an increase (e.g., at least 30%, at least 40%, at least 50%, or more) in SARS-CoV-2 neutralizing geometric mean titers (GMTs) is observed 21 days after a first dose. In some embodiments, mRNA compositions described herein are characterized in that a substantially greater serum neutralizing GMTs are achieved 7 days after subjects receive a second dose (e.g., 10 μg-30 μg inclusive), reaching 150-300, compared to 94 for a COVID-19 convalescent serum panel.

In some embodiments, mRNA compositions and/or methods described herein are characterized in that 7 days after administration of the second dose, the protective efficacy is at least 60%, e.g., at least 70%, at least 80%, at least 90, or at least 95%. In one embodiment, mRNA compositions and/or methods described herein are characterized in that 7 days after administration of the second dose, the protective efficacy is at least 70%. In one embodiment, mRNA compositions and/or methods described herein are characterized in that 7 days after administration of the second dose, the protective efficacy is at least 80%. In one embodiment, mRNA compositions and/or methods described herein are characterized in that 7 days after administration of the second dose, the protective efficacy is at least 90%. In one embodiment, mRNA compositions and/or methods described herein are characterized in that 7 days after administration of the second dose, the protective efficacy is at least 95%.

In some embodiments, an RNA composition provided herein is characterized in that it induces an immune response against SARS-CoV-2 after at least 7 days after a dose (e.g., after a second dose). In some embodiments, an RNA composition provided herein is characterized in that it induces an immune response against SARS-CoV-2 in less than 14 days after a dose (e.g., after a second dose). In some embodiments, an RNA composition provided herein is characterized in that it induces an immune response against SARS-CoV-2 after at least 7 days after a vaccination regimen. In some embodiments, a vaccination regimen comprises a first dose and a second dose. In some embodiments, a first dose and a second dose are administered by at least 21 days apart. In some such embodiments, an immune response against SARS-CoV-2 is induced at least after 28 days after a first dose.

In some embodiments, mRNA compositions and/or methods described herein are characterized in that geometric mean concentration (GMCs) of antibodies directed to a SARS-CoV-2 spike polypeptide or an immunogenic fragment thereof (e.g., RBD), as measured in serum from subjects receiving mRNA compositions of the present disclosure (e.g., at a dose of 10-30 ug inclusive), is substantially higher than in a convalescent serum panel (e.g., as described herein). In some embodiments where a subject may receive a second dose (e.g., 21 days after 1 first dose), geometric mean concentration (GMCs) of antibodies directed to a SARS-CoV-2 spike polypeptide or an immunogenic fragment thereof (e.g., RBD), as measured in serum from the subject, may be 8.0-fold to 50-fold higher than a convalescent serum panel GMC. In some embodiments where a subject may receive a second dose (e.g., 21 days after 1 first dose), geometric mean concentration (GMCs) of antibodies directed to a SARS-CoV-2 spike polypeptide or an immunogenic fragment thereof (e.g., RBD), as measured in serum from the subject, may be at least 8.0-fold or higher, including, e.g., at least 10-fold, at least 20-fold, at least 30-fold, at least 40-fold, at least 50-fold, at least 60-fold or higher, as compared to a convalescent serum panel GMC.

In some embodiments, mRNA compositions and/or methods described herein are characterized in that the SARS-CoV-2 neutralizing geometric mean titer, as measured at 28 days after a first dose or 7 days after a second dose, may be at least 1.5-fold or higher (including, e.g., at least 2-fold, at least 2.5-fold, at least 3-fold, at least 3.5-fold or higher), as compared to a neutralizing GMT of a convalescent serum panel.

In some embodiments, a regimen administered to a subject may be or comprise a single dose. In some embodiments, a regimen administered to a subject may comprise a plurality of doses (e.g., at least two doses, at least three doses, or more). In some embodiments, a regimen administered to a subject may comprise a first dose and a second dose, which are given at least 2 weeks apart, at least 3 weeks apart, at least 4 weeks apart, or more. In some embodiments, such doses may be at least 1 month, at least 2 months, at least 3 months, at least 4 months, at least 5 months, at least 6 months, at least 7 months, at least 8 months, at least 9 months, at least 10 months, at least 11 months, at least 12 months, or more apart. In some embodiments, doses may be administered days apart, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more days apart. In some embodiments, doses may be administered about 1 to about 3 weeks apart, or about 1 to about 4 weeks apart, or about 1 to about 5 weeks apart, or about 1 to about 6 weeks apart, or about 1 to more than 6 weeks apart. In some embodiments, doses may be separated by a period of about 7 to about 60 days, such as for example about 14 to about 48 days, etc. In some embodiments, a minimum number of days between doses may be about 1, 2, 3, 4, 5, 6, 7, 8, 9, 10, 11, 12, 13, 14, 15, 16, 17, 18, 19, 20, 21 or more. In some embodiments, a maximum number of days between doses may be about 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or fewer. In some embodiments, doses may be about 21 to about 28 days apart. In some embodiments, doses may be about 19 to about 42 days apart. In some embodiments, doses may be about 7 to about 28 days apart. In some embodiments, doses may be about 14 to about 24 days. In some embodiments, doses may be about 21 to about 42 days.

In some embodiments, particularly for compositions established to achieve elevated antibody and/or T-cell titres for a period of time longer than about 3 weeks—e.g., in some embodiments, a provided composition is established to achieve elevated antibody and/or T-cell titres (e.g., specific for a relevant portion of a SARS-CoV-2 spike protein) for a period of time longer than about 3 weeks; in some such embodiments, a dosing regimen may involve only a single dose, or may involve two or more doses, which may, in some embodiments, be separated from one another by a period of time that is longer than about 21 days or three weeks. For example, in some such embodiments, such period of time may be about 4 weeks, 5 weeks, 6 weeks 7 weeks, 8 weeks, 9 weeks, 10 weeks, 11 weeks, 12 weeks, 13 weeks, 14 weeks, 15 wees, 16 weeks, 17 weeks, 18 weeks, 19 weeks, 20 weeks or more, or about 1 month, 2 months, 3 months, 4 months, 5 months, 6 months, 7 months, 8 months, 9 months, 10, months, 11 months, 12 months or more, or in some embodiments about a year or more. In some embodiments, a first dose and a second dose (and/or other subsequent dose) may be administered by intramuscular injection. In some embodiments, a first dose and a second dose may be administered in the deltoid muscle. In some embodiments, a first dose and a second dose may be administered in the same arm. In some embodiments, an mRNA composition described herein is administered (e.g., by intramuscular injection) as a series of two doses (e.g., 0.3 mL each) 21 days part. In some embodiments, each dose is about 30 ug. In some embodiments, each dose may be higher than 30 ug, e.g., about 40 ug, about 50 ug, about 60 ug. In some embodiments, each dose may be lower than 30 ug, e.g., about 20 ug, about 10 ug, about 5 ug, etc. In some embodiments, each dose is about 3 ug or lower, e.g., about 1 ug. In some such embodiments, an mRNA composition described herein is administered to subjects of age 16 or older (including, e.g., 16-85 years). In some such embodiments, an mRNA composition described herein is administered to subjects of age 18-55. In some such embodiments, an mRNA composition escribed herein is administered to subjects of age 56-85. In some embodiments, an mRNA composition described herein is administered (e.g., by intramuscular injection) as a single dose.

In some embodiments, mRNA compositions and/or methods described herein are characterized in that RBD-specific IgG (e.g., polyclonal response) induced by such mRNA compositions and/or methods exhibit a higher binding affinity to RBD, as compared to a reference human monoclonal antibody with SARS-CoV-2 RBD-binding affinity (e.g., CR3022 as described in J. ter Meulen et al., PLOS Med. 3, e237 (2006).)

In some embodiments, mRNA compositions and/or methods described herein are characterized in that sera of vaccinated subjects display neutralizing activity across a panel (e.g., at least 10, at least 15, or more) of SARs-CoV-2 spike variants. In some embodiments, such SARs-CoV-2 spike variants include mutations in RBD (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1), and/or mutations in spike protein (e.g., but not limited to D614G, etc., as compared to SEQ ID NO: 1). Those skilled in the art are aware of various spike variants, and/or resources that document them (e.g., the Table of mutating sites in Spike maintained by the COVID-19 Viral Genome Analysis Pipeline and found at cov.lanl.gov/components/sequence/COV/int_sites_tbls.comp) (last accessed 24 Aug. 2020), and, reading the present specification, will appreciate that mRNA compositions and/or methods described herein can be characterized for there ability to induce sera in vaccinated subject that display neutralizing activity with respect to any or all of such variants and/or combinations thereof.

In particular embodiments, mRNA compositions encoding RBD of a SARS-CoV-2 spike protein are characterized in that sera of vaccinated subjects display neutralizing activity across a panel (e.g., at least 10, at least 15, or more) of SARs-CoV-2 spike variants including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1). In particular embodiments, mRNA compositions encoding a SARS-CoV-2 spike protein variant that includes two consecutive proline substitutions at amino acid positions 986 and 987, at the top of the central helix in the S2 subunit, are characterized in that sera of vaccinated subjects display neutralizing activity across a panel (e.g., at least 10, at least 15, or more) of SARs-CoV-2 spike variants including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1). For example, in some embodiments, the mRNA composition encoding SEQ ID NO: 7 (S P2) elicits an immune response against any one of a SARs-CoV-2 spike variant including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1).

In some embodiments, mRNA compositions and/or methods described herein are characterized in that sera of vaccinated subjects display neutralizing activity against one or more SARs-CoV-2 spike variants including a mutation at position 501 in spike protein as compared to SEQ ID NO: 1. In some embodiments, mRNA compositions and/or methods described herein are characterized in that sera of vaccinated subjects display neutralizing activity against one or more SARs-CoV-2 spike variants including a N501Y mutation in spike protein as compared to SEQ ID NO: 1.

Said one or more SARs-CoV-2 spike variants including a mutation at position 501 in spike protein as compared to SEQ ID NO: 1 or said one or more SARs-CoV-2 spike variants including a N501Y mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, E484K, A701V, L18F, R246I, K417N, L242/A243/L244 deletion etc., as compared to SEQ ID NO: 1).

In particular embodiments, mRNA compositions and/or methods described herein are characterized in that sera of vaccinated subjects display neutralizing activity against SARs-CoV-2 spike variant "Variant of Concern 202012/01" (VOC-202012/01; also known as lineage B.1.1.7). The variant had previously been named the first Variant Under Investigation in December 2020 (VUI-202012/01) by Public Health England, but was reclassified to a Variant of Concern (VOC-202012/01). VOC-202012/01 is a variant of SARS-CoV-2 which was first detected in October 2020 during the COVID-19 pandemic in the United Kingdom from a sample taken the previous month, and it quickly began to spread by mid-December. It is correlated with a significant increase in the rate of COVID-19 infection in United Kingdom; this increase is thought to be at least partly because of change N501Y inside the spike glycoprotein's receptor-binding domain, which is needed for binding to ACE2 in human cells. The VOC-202012/01 variant is defined by 23 mutations: 13 non-synonymous mutations, 4 deletions, and 6 synonymous mutations (i.e., there are 17 mutations that change proteins and six that do not). The spike protein changes in VOC 202012/01 include deletion 69-70, deletion 144, N501Y, A570D, D614G, P681H, T716I, S982A, and D1118H. One of the most important changes in VOC-202012/01 seems to be N501Y, a change from asparagine (N) to tyrosine (Y) at amino-acid site 501. This mutation alone or in combination with the deletion at positions 69/70 in the N terminal domain (NTD) may enhance the transmissibility of the virus.

In particular embodiments, mRNA compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, mRNA compositions and/or methods described herein are characterized in that sera of vaccinated subjects display neutralizing activity against SARs-CoV-2 spike variant "501.V2". This variant was first observed in samples from October 2020, and since then more than 300 cases with the 501.V2 variant have been confirmed by whole genome sequencing (WGS) in South Africa, where in December 2020 it was the dominant form of the virus. Preliminary results indicate that this variant may have an increased transmissibility. The 501.V2 variant is defined by multiple spike protein changes including: D80A, D215G, E484K, N501Y and A701V, and more recently collected viruses have additional changes: L18F, R246I, K417N, and deletion 242-244.

In particular embodiments, mRNA compositions and/or methods described herein are characterized in that sera of vaccinated subjects display neutralizing activity against SARs-CoV-2 spike variant including the following mutations: D80A, D215G, E484K, N501Y and A701V as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

In some embodiments, mRNA compositions and/or methods described herein are characterized in that sera of vaccinated subjects display neutralizing activity against one or more SARs-CoV-2 spike variants including a H69/V70 deletion in spike protein as compared to SEQ ID NO: 1.

In some embodiments, one or more SARs-CoV-2 spike variants including a H69/V70 deletion in spike protein as compared to SEQ ID NO: 1 may include one or more further mutations as compared to SEQ ID NO: 1 (e.g., but not limited to Y144 deletion, N501Y, A570D, D614G, P681H, T716I, S982A, D1118H, D80A, D215G, E484K, A701V, L18F, R246I, K417N, L242/A243/L244 deletion, Y453F, I692V, S1147L, M1229I etc., as compared to SEQ ID NO: 1), In particular embodiments, mRNA compositions and/or methods described herein are characterized in that sera of vaccinated subjects display neutralizing activity against SARs-CoV-2 spike variant "Variant of Concern 202012/01" (VOC-202012/01; also known as lineage B.1.1.7).

In particular embodiments, mRNA compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, mRNA compositions and/or methods described herein are characterized in that sera of vaccinated subjects display neutralizing activity against SARs-CoV-2 spike variant "Cluster 5", also referred to as ΔFVI-spike by the Danish State Serum Institute (SSI). It was discovered in North Jutland, Denmark, and is believed to have been spread from minks to humans via mink farms. In cluster 5, several different mutations in the spike protein of the virus have been confirmed. The specific mutations include 69-70deltaHV (a deletion of the histidine and valine residues at the 69th and 70th position in the protein), Y453F (a change from tyrosine to phenylalanine at position 453), I692V (isoleucine to valine at position 692), M1229I (methionine to isoleucine at position 1229), and optionally S1147L (serine to leucine at position 1147).

In particular embodiments, mRNA compositions and/or methods described herein are characterized in that sera of vaccinated subjects display neutralizing activity against SARs-CoV-2 spike variant including the following mutations: deletion 69-70, Y453F, I692V, M1229I, and optionally S1147L, as compared to SEQ ID NO: 1.

In some embodiments, mRNA compositions and/or methods described herein are characterized in that sera of vaccinated subjects display neutralizing activity against one or more SARs-CoV-2 spike variants including a mutation at position 614 in spike protein as compared to SEQ ID NO: 1. In some embodiments, mRNA compositions and/or methods described herein are characterized in that sera of vaccinated subjects display neutralizing activity against one or more SARs-CoV-2 spike variants including a D614G mutation in spike protein as compared to SEQ ID NO: 1.

In some embodiments, one or more SARs-CoV-2 spike variants including a mutation at position 614 in spike protein as compared to SEQ ID NO: 1 or said one or more SARs-CoV-2 spike variants including a D614G mutation in spike protein as compared to SEQ ID NO: 1 may include one or more further mutations as compared to SEQ ID NO: 1 (e.g., but not limited to H69/V70 deletion, Y144 deletion, N501Y, A570D, P681H, T716I, S982A, D1118H, D80A, D215G, E484K, A701V, L18F, R246I, K417N, L242/A243/

L244 deletion, Y453F, I692V, S1147L, M1229I etc., as compared to SEQ ID NO: 1).

In particular embodiments, mRNA compositions and/or methods described herein are characterized in that sera of vaccinated subjects display neutralizing activity against SARs-CoV-2 spike variant “Variant of Concern 202012/01” (VOC-202012/01; also known as lineage B.1.1.7).

In particular embodiments, mRNA compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, mRNA compositions and/or methods described herein are characterized in that sera of vaccinated subjects display neutralizing activity against one or more SARs-CoV-2 spike variants including a mutation at positions 501 and 614 in spike protein as compared to SEQ ID NO: 1. In some embodiments, mRNA compositions and/or methods described herein are characterized in that sera of vaccinated subjects display neutralizing activity against one or more SARs-CoV-2 spike variants including a N501Y mutation and a D614G mutation in spike protein as compared to SEQ ID NO: 1.

In some embodiments, one or more SARs-CoV-2 spike variants including a mutation at positions 501 and 614 in spike protein as compared to SEQ ID NO: 1 or said one or more SARs-CoV-2 spike variants including a N501Y mutation and a D614G mutation in spike protein as compared to SEQ ID NO: 1 may include one or more further mutations as compared to SEQ ID NO: 1 (e.g., but not limited to H69/V70 deletion, Y144 deletion, A570D, P681H, T716I, S982A, D1118H, D80A, D215G, E484K, A701V, L18F, R246I, K417N, L242/A243/L244 deletion, Y453F, I692V, S1147L, M1229I etc., as compared to SEQ ID NO: 1).

In particular embodiments, mRNA compositions and/or methods described herein are characterized in that sera of vaccinated subjects display neutralizing activity against SARs-CoV-2 spike variant “Variant of Concern 202012/01” (VOC-202012/01; also known as lineage B.1.1.7).

In particular embodiments, mRNA compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, mRNA compositions and/or methods described herein are characterized in that sera of vaccinated subjects display neutralizing activity against one or more SARs-CoV-2 spike variants including a mutation at position 484 in spike protein as compared to SEQ ID NO: 1. In some embodiments, mRNA compositions and/or methods described herein are characterized in that sera of vaccinated subjects display neutralizing activity against one or more SARs-CoV-2 spike variants including a E484K mutation in spike protein as compared to SEQ ID NO: 1.

In some embodiments, one or more SARs-CoV-2 spike variants including a mutation at position 484 in spike protein as compared to SEQ ID NO: 1 or said one or more SARs-CoV-2 spike variants including a E484K mutation in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1). In particular embodiments, mRNA compositions and/or methods described herein are characterized in that sera of vaccinated subjects display neutralizing activity against SARs-CoV-2 spike variant “501.V2”.

In particular embodiments, mRNA compositions and/or methods described herein are characterized in that sera of vaccinated subjects display neutralizing activity against SARs-CoV-2 spike variant including the following mutations: D80A, D215G, E484K, N501Y, and A701V, as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

Lineage B.1.1.248, known as the Brazil(ian) variant, is one of the variants of SARS-CoV-2 which has been named P.1 lineage and has 17 unique amino acid changes, 10 of which in its spike protein, including N501Y and E484K. B.1.1.248 originated from B.1.1.28. E484K is present in both B.1.1.28 and B.1.1.248. B.1.1.248 has a number of S-protein polymorphisms [L18F, T20N, P26S, D138Y, R190S, K417T, E484K, N501Y, H655Y, T1027I, V1176F] and is similar in certain key RBD positions (K417, E484, N501) to variant described from South Africa.

In particular embodiments, mRNA compositions and/or methods described herein are characterized in that sera of vaccinated subjects display neutralizing activity against SARs-CoV-2 spike variant “B.1.1.28”.

In particular embodiments, mRNA compositions and/or methods described herein are characterized in that sera of vaccinated subjects display neutralizing activity against SARs-CoV-2 spike variant “B.1.1.248”.

In particular embodiments, mRNA compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, mRNA compositions and/or methods described herein are characterized in that sera of vaccinated subjects display neutralizing activity against one or more SARs-CoV-2 spike variants including a mutation at positions 501 and 484 in spike protein as compared to SEQ ID NO: 1. In some embodiments, mRNA compositions and/or methods described herein are characterized in that sera of vaccinated subjects display neutralizing activity against one or more SARs-CoV-2 spike variants including a N501Y mutation and a E484K mutation in spike protein as compared to SEQ ID NO: 1.

In some embodiments, one or more SARs-CoV-2 spike variants including a mutation at positions 501 and 484 in spike protein as compared to SEQ ID NO: 1 or said one or more SARs-CoV-2 spike variants including a N501Y mutation and a E484K mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1).

In particular embodiments, mRNA compositions and/or methods described herein are characterized in that sera of vaccinated subjects display neutralizing activity against SARs-CoV-2 spike variant “501.V2”.

In particular embodiments, mRNA compositions and/or methods described herein are characterized in that sera of vaccinated subjects display neutralizing activity against SARs-CoV-2 spike variant including the following mutations: D80A, D215G, E484K, N501Y and A701V as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

In particular embodiments, mRNA compositions and/or methods described herein are characterized in that sera of vaccinated subjects display neutralizing activity against SARs-CoV-2 spike variant “B.1.1.248”.

In particular embodiments, mRNA compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, mRNA compositions and/or methods described herein are characterized in that sera of vaccinated subjects display neutralizing activity against one or more SARs-CoV-2 spike variants including a mutation at positions 501, 484 and 614 in spike protein as compared to SEQ ID NO: 1. In some embodiments, mRNA compositions and/or methods described herein are characterized in that sera of vaccinated subjects display neutralizing activity against one or more SARs-CoV-2 spike variants including a N501Y mutation, a E484K mutation and a D614G mutation in spike protein as compared to SEQ ID NO: 1.

In some embodiments, one or more SARs-CoV-2 spike variants including a mutation at positions 501, 484 and 614 in spike protein as compared to SEQ ID NO: 1 or said one or more SARs-CoV-2 spike variants including a N501Y mutation, a E484K mutation and a D614G mutation in spike protein as compared to SEQ ID NO: 1 may include one or more further mutations as compared to SEQ ID NO: 1 (e.g., but not limited to H69/V70 deletion, Y144 deletion, A570D, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1).

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, mRNA compositions and/or methods described herein are characterized in that sera of vaccinated subjects display neutralizing activity against one or more SARs-CoV-2 spike variants including a L242/A243/L244 deletion in spike protein as compared to SEQ ID NO: 1.

In some embodiments, one or more SARs-CoV-2 spike variants including a L242/A243/L244 deletion in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, E484K, A701V, L18F, R246I, K417N, Y453F, I692V, S1147L, M1229I, T20N, P26S, D138Y, R190S, K417T, H655Y, T1027I, V1176F etc., as compared to SEQ ID NO: 1).

In particular embodiments, mRNA compositions and/or methods described herein are characterized in that sera of vaccinated subjects display neutralizing activity against SARs-CoV-2 spike variant “501.V2”.

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V and deletion 242-244 as compared to SEQ ID NO: 1, and optionally: L18F, R246I, and K417N, as compared to SEQ ID NO: 1. Said SARs-CoV-2 spike variant may also include a D614G mutation as compared to SEQ ID NO: 1.

In some embodiments, mRNA compositions and/or methods described herein are characterized in that sera of vaccinated subjects display neutralizing activity against one or more SARs-CoV-2 spike variants including a mutation at position 417 in spike protein as compared to SEQ ID NO: 1. In some embodiments, mRNA compositions and/or methods described herein are characterized in that sera of vaccinated subjects display neutralizing activity against one or more SARs-CoV-2 spike variants including a K417N or K417T mutation in spike protein as compared to SEQ ID NO: 1.

In some embodiments, one or more SARs-CoV-2 spike variants including a mutation at position 417 in spike protein as compared to SEQ ID NO: 1 or said one or more SARs-CoV-2 spike variants including a K417N or K417T mutation in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, E484K, A701V, L18F, R246I, L242/A243/L244 deletion, Y453F, I692V, S1147L, M1229I, T20N, P26S, D138Y, R190S, H655Y, T1027I, V1176F etc., as compared to SEQ ID NO: 1).

In particular embodiments, mRNA compositions and/or methods described herein are characterized in that sera of vaccinated subjects display neutralizing activity against SARs-CoV-2 spike variant “501.V2”.

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V and K417N, as compared to SEQ ID NO: 1, and optionally: L18F, R246I, and deletion 242-244 as compared to SEQ ID NO: 1. Said SARs-CoV-2 spike variant may also include a D614G mutation as compared to SEQ ID NO: 1.

In particular embodiments, mRNA compositions and/or methods described herein are characterized in that sera of vaccinated subjects display neutralizing activity against SARs-CoV-2 spike variant “B.1.1.248”.

In particular embodiments, mRNA compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, mRNA compositions and/or methods described herein are characterized in that sera of vaccinated subjects display neutralizing activity against one or more SARs-CoV-2 spike variants including a mutation at positions 417 and 484 and/or 501 in spike protein as compared to SEQ ID NO: 1. In some embodiments, mRNA compositions and/or methods described herein are characterized in that sera of vaccinated subjects display neutralizing activity against one or more SARs-CoV-2 spike variants including a K417N or K417T mutation and a E484K and/or N501Y mutation in spike protein as compared to SEQ ID NO: 1.

In some embodiments, one or more SARs-CoV-2 spike variants including a mutation at positions 417 and 484 and/or 501 in spike protein as compared to SEQ ID NO: 1 or said one or more SARs-CoV-2 spike variants including a K417N or K417T mutation and a E484K and/or N501Y mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, A701V, L18F, R246I, L242/A243/L244 deletion, Y453F, I692V, S1147L, M1229I, T20N, P26S, D138Y, R190S, H655Y, T1027I, V1176F etc., as compared to SEQ ID NO: 1).

In particular embodiments, mRNA compositions and/or methods described herein are characterized in that sera of vaccinated subjects display neutralizing activity against SARs-CoV-2 spike variant “501.V2”.

In particular embodiments, mRNA compositions and/or methods described herein are characterized in that sera of vaccinated subjects display neutralizing activity against SARs-CoV-2 spike variant including the following mutations: D80A, D215G, E484K, N501Y, A701V and K417N, as compared to SEQ ID NO: 1, and optionally: L18F, R246I, and deletion 242-244 as compared to SEQ ID NO: 1. Said SARs-CoV-2 spike variant may also include a D614G mutation as compared to SEQ ID NO: 1.

In particular embodiments, mRNA compositions and/or methods described herein are characterized in that sera of vaccinated subjects display neutralizing activity against SARs-CoV-2 spike variant “B.1.1.248”.

In particular embodiments, mRNA compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

The SARs-CoV-2 spike variants described herein may or may not include a D614G mutation as compared to SEQ ID NO: 1.

In some embodiments, mRNA compositions and/or methods described herein can provide protection against SARS-CoV-2 and/or decrease severity of SARS-CoV-2 infection in at least 50% of subjects receiving such mRNA compositions and/or methods.

In some embodiments, populations to be treated with mRNA compositions described herein include subjects of age 18-55. In some embodiments, populations to be treated with mRNA compositions described herein include subjects of age 56-85. In some embodiments, populations to be treated with mRNA compositions described herein include older subjects (e.g., over age 60, 65, 70, 75, 80, 85, etc, for example subjects of age 65-85). In some embodiments, populations to be treated with mRNA compositions described herein include subjects of age 18-85. In some embodiments, populations to be treated with mRNA compositions described herein include subjects of age 18 or younger. In some embodiments, populations to be treated with mRNA compositions described herein include subjects of age 12 or younger. In some embodiments, populations to be treated with mRNA compositions described herein include subjects of age 10 or younger. In some embodiments, populations to be treated with mRNA compositions described herein may include adolescent populations (e.g., individuals approximately 12 to approximately 17 years of age). In some embodiments, populations to be treated with mRNA compositions described herein include infants (e.g., less than 1 year old). In some embodiments, populations to be treated with mRNA compositions described herein do not include infants (e.g., less than 1 year) whose mothers have received such mRNA compositions described herein during pregnancy. Without wishing to be bound by any particular theory, a rat study as shown in Example 31 has suggested that a SARS-CoV-2 neutralizing antibody response induced in female rats given such mRNA compositions during pregnancy can pass onto fetuses. In some embodiments, populations to be treated with mRNA compositions described herein include infants (e.g., less than 1 year) whose mothers did not receive such mRNA compositions described herein during pregnancy. In some embodiments, populations to be treated with mRNA compositions described herein may include pregnant women; in some embodiments, infants whose mothers were vaccinated during pregnancy (e.g., who received at least one dose, or alternatively only who received both doses), are not vaccinated during the first weeks, months, or even years (e.g., 1, 2, 3, 4, 5, 6, 7, 8 weeks or more, or 1, 2, 3, 4, 5, 6, 7, 8, 9, 10, 11, 12, 13, 14, 15, 16, 17, 18, 19, 20, 21, 22, 23, 24 moths or more, or 1, 2, 3, 4, 5 years or more) post-birth. Alternatively or additionally, in some embodiments, infants whose whose mothers were vaccinated during pregnancy (e.g., who received at least one dose, or alternatively only who received both doses), receive reduced vaccination (e.g., lower doses and/or smaller numbers of administrations—e.g., boosters—and/or lower total exposure over a given period of time) after birth, for example during the first weeks, months, or even years (e.g., 1, 2, 3, 4, 5, 6, 7, 8 weeks or more, or 1, 2, 3, 4, 5, 6, 7, 8, 9, 10, 11, 12, 13, 14, 15, 16, 17, 18, 19, 20, 21, 22, 23, 24 months or more, or 1, 2, 3, 4, 5 years or more) post-birthor may need reduced vaccination (e.g., lower doses and/or smaller numbers of administrations—e.g., boosters—over a given period of time), In some embodiments, compositions as provided herein are administered to populations that do not include pregnant women.

In some particular embodiments, compositions as provided herein are administered to pregnant women according to a regimen that includes a first dose administered after about 24 weeks of gestation (e.g., after about 22, 23, 24, 25, 26, 27, 28 or more weeks of gestation); in some embodiments, compositions as provided herein are administered to pregnant women according to a regimen that includes a first dose administered before about 34 weeks of gestation (e.g., before about 30, 31, 32, 33, 34, 35, 36, 37, 38 weeks of gestation). In some embodiments, compositions as provided herein are administered to pregnant women according to a regimen that includes a first dose administered after about 24 weeks (e.g., after about 27 weeks of gestation, e.g., between about 24 weeks and 34 weeks, or between about 27 weeks and 34 weeks) of gestation and a second dose administered about 21 days later; in some embodiments both doses are administered prior to delivery. Without wishing to be bound by any particular theory, it is proposed that such a regimen (e.g., involving administration of a first dose after about 24 weeks, or 27 weeks of gestation and optionally before about 34 weeks of gestation), and optionally a second dose within about 21 days, ideally before delivery, may have certain advantages in terms of safety (e.g., reduced risk of premature delivery or of fetal morbidity or mortality) and/or efficacy (e.g., carryover vaccination imparted to the infant) relative to alternative dosing regimens (e.g., dosing at any time during pregnancy, refraining from dosing during pregnancy, and/or dosing later in pregnancy for example so that only one dose is administered during gestation. In some embodiments, as noted herein (see also Example 34), infants born of mothers vaccinated during pregnancy, e.g, according to a particular regimen as described herein, may not need further vaccination, or may need reduced vaccination (e.g., lower doses and/or smaller numbers of administrations—e.g., boosters —, and/or lower overall exposure over a given period of time), for a period of time (e.g., as noted herein) after birth.

In some embodiments, compositions as provided herein are administered to populations in which women are advised against becoming pregnant for a period of time after receipt of the vaccine (e.g., after receipt of a first dose of the vaccine, after receipt of a final dose of the vaccine, etc.); in some such embodiments, the period of time may be at least 1 week, at least 2 weeks, at least 3 weeks, at least 4 weeks, at least 5 weeks, at least 6 weeks, at least 7 weeks, at least 8 weeks, at least 9 weeks, at least 10 weeks or more, or may be at least 1 month, at least 2 months, at least 3 months, at least 4 months, at least 5 months, at least 6 months, or more.

In some embodiments, populations to be treated with mRNA compositions described herein may include one or more populations with one or more particularly high risk conditions or history, e.g., as noted herein. For example, in some embodiments, populations to be treated with mRNA compositions described herein may include subjects whose profession and/or environmental exposure may dramatically increase their risk of getting SARS-CoV-2 infection (including, e.g., but not limited to mass transportation, prisoners, grocery store workers, residents in long-term care facilities, butchers or other meat processing workers, healthcare workers, and/or first responders, e.g., emergency responders). In particular embodiments, populations to be treated with mRNA compositions described herein may include healthcare workers and/or first responders, e.g., emergency responders. In some embodiments, populations to be treated with mRNA compositions described herein may include those with a history of smoking or vaping (e.g., within 6 months, 12 months or more, including a history of chronic smoking or vaping). In some embodiments, populations to be treated with mRNA compositions described herein may include certain ethnic groups that have been determined to be more susceptible to SARS-CoV-2 infection.

In some embodiments, populations to be treated with mRNA compositions described herein may include certain populations with a blood type that may have been determined to more susceptible to SARS-CoV-2 infection. In some embodiments, populations to be treated with mRNA compositions described herein may include immunocompromised subjects (e.g., those with HIV/AIDS; cancer and transplant patients who are taking certain immunosuppressive drugs; autoimmune diseases or other physiological conditions expected to warrant immunosuppressive therapy (e.g., within 3 months, within 6 months, or more); and those with inherited diseases that affect the immune system (e.g., congenital agammaglobulinemia, congenital IgA deficiency)). In some embodiments, populations to be treated with mRNA compositions described herein may include those with an infectious disease. For example, in some embodiments, populations to be treated with mRNA compositions described herein may include those infected with human immunodeficiency virus (HIV) and/or a hepatitis virus (e.g., HBV, HCV). In some embodiments, populations to be treated with mRNA compositions described herein may include those with underlying medical conditions. Examples of such underlying medical conditions may include, but are not limited to hypertension, cardiovascular disease, diabetes, chronic respiratory disease, e.g., chronic pulmonary disease, asthma, etc., cancer, and other chronic diseases such as, e.g., lupus, rheumatoid arthritis, chonic liver diseases, chronic kidney diseases (e.g., Stage 3 or worse such as in some embodiments as characterized by a glomerular filtration rate (GFR) of less than 60 mL/min/1.73 $m^2$). In some embodiments, populations to be treated with mRNA compositions described herein may include overweight or obese subjects, e.g., specifically including those with a body mass index (BMI) above about 30 $kg/m^2$. In some embodiments, populations to be treated with mRNA compositions described herein may include subjects who have prior diagnosis of COVID-19 or evidence of current or prior SARS-CoV-2 infection, e.g., based on serology or nasal swab. In some embodiments, populations to be treated include white and/or non-Hispanic/non-Latino.

In some embodiments, certain mRNA compositions described herein (e.g., BNT162b1) may be selected for administration to Asian populations (e.g., Chinese populations), or in particular embodiments to older Asian populations (e.g, 60 years old or over, e.g., 60-85 or 65-85 years old).

In some embodiments, an mRNA composition as provided herein is administered to and/or assessed in subject(s) who have been determined not to show evidence of prior infection, and/or of present infection, before administration; in some embodiments, evidence of prior infection and/or of present infection, may be or include evidence of intact virus, or any viral nucleic acid, protein, lipid etc. present in the subject (e.g., in a biological sample thereof, such as blood, cells, mucus, and/or tissue), and/or evidence of a subject's immune response to the same. In some embodiments, an mRNA composition as provided herein is administered to and/or assessed in subject(s) who have been determined to show evidence of prior infection, and/or of present infection, before administration; in some embodiments, evidence of prior infection and/or of present infection, may be or include evidence of intact virus, or any viral nucleic acid, protein, lipid etc. present in the subject (e.g., in a biological sample thereof, such as blood, cells, mucus, and/or tissue), and/or evidence of a subject's immune response to the same. In some embodiments, a subject is considered to have a prior infection based on having a positive N-binding antibody test result or positive nucleic acid amplification test (NAAT) result on the day of Dose 1.

In some embodiments, an RNA (e.g., mRNA) composition as provided herein is administered to a subject who has been informed of a risk of side effects that may include one or more of, for example: chills, fever, headache, injection site pain, muscle pain, tiredness; in some embodiments, an RNA (e.g., mRNA) composition is administered to a subject who has been invited to notify a healthcare provider if one or more such side effects occurs, is experienced as more than mild or moderate, persists for a period of more than a day or a few days, or if any serious or unexpected event is experienced that the subject reasonably considers may be associated with receipt of the composition. In some embodiments, an RNA (e.g., mRNA) composition as provided herein is administered to a subject who has been invited to notify a healthcare provider of particular medical conditions which may include, for example, one or more of allergies, bleeding disorder or taking a blood thinner medication, breastfeeding, fever, immunocompromised state or taking medication that affects the immune system, pregnancy or plan to become pregnant, etc. In some embodiments, an RNA (e.g., mRNA) composition as provided herein is administered to a subject who has been invited to notify a healthcare provider of having received another COVID-19 vaccine. In some embodiments, an RNA (e.g., mRNA) composition as provided herein is administered to a subject not having one of the following medical conditions: experiencing febrile illness, receiving immunosuppressant therapy, receiving anticoagulant therapy, suffering from a bleeding disorder (e.g., one that would contraindicate intramuscular injection), or pregnancy and/or breatfeeding/lactation. In some embodiments, an RNA (e.g., mRNA) composition as provided herein is administered to a subject not having received another COVID-19 vaccine. In some embodiments, an RNA (e.g., mRNA) composition as provided herein is administered to a subject who has not had an allergic reaction to any component of the RNA (e.g., mRNA) composition. Examples of such allergic reaction may include, but are not limited to difficulty breathing, swelling of fact and/or throat, fast hearbeat, rash, dizziness and/or weakness. In some embodiments, an RNA (e.g., mRNA) composition as provided herein is administered to a subject who received a first dose and did not have an allergic reaction (e.g., as described herein) to the first dose. In some embodiments where allergic reaction occurs in subject(s) after receiving a dose of an RNA (e.g., mRNA) composition as provided herein, such subject(s) may be administered one or more interventions such as treatment to manage and/or reduce symptom(s) of such allergic reactions, for example, fever-reducing and/or anti-inflammatory agents.

In some embodiments, a subject who has received at least one dose of an RNA (e.g., mRNA) composition as provided herein is informed of avoiding being exposed to a coronavirus (e.g., SARS-CoV-2) unless and until several days (e.g., at least 7 days, at least 8 days, 9 days, at least 10 days, at least 11 days, at least 12 days, at least 13 days, at least 14 days, etc.) have passed since administration of a second dose. For example, a subject who has received at at least one dose of an RNA (e.g., mRNA) composition as provided herein is informed of taking precautionary measures against SARS-CoV-2 infection (e.g., remaining socially distant, wearing masks, frequent hand-washing, etc.) unless and until several days (e.g., at least 7 days, at least 8 days, 9 days, at least 10 days, at least 11 days, at least 12 days, at least 13 days, at least 14 days, etc.) have passed since administration of a second dose. Accordingly, in some embodiments, methods of administering an RNA (e.g., mRNA) composition as provided herein comprise administering a second dose of such an RNA (e.g., mRNA) composition as provided herein to a subject who received a first dose and took precautionary measures to avoid being exposed to a coronavirus (e.g., SARS-CoV-2).

In some embodiments, mRNA compositions described herein may be delivered to a draining lymph node of a subject in need thereof, for example, for vaccine priming. In some embodiments, such delivery may be performed by intramuscular administration of a provided mRNA composition.

In some embodiments, different particular mRNA compositions may be administered to different subject population(s); alternatively or additionally, in some embodiments, different dosing regimens may be administered to different subject populations. For example, in some embodiments, mRNA compositions administered to particular subject population(s) may be characterized by one or more particular effects (e.g., incidence and/or degree of effect) in those subject populations. In some embodiments, such effect(s) may be or comprise, for example titer and/or persistence of neutralizing antibodies and/or T cells (e.g., $T_H1$-type T cells such as $CD4^+$ and/or $CD8^+$ T cells), protection against challenge (e.g., via injection and/or nasal exposure, etc), incidence, severity, and/or persistence of side effects (e.g., reactogenicity), etc.

In some embodiments, one or more mRNA compositions described herein may be administered according to a regimen established to reduce COVID-19 incidence per 1000 person-years, e.g., based on a laboratory test such as nucleic acid amplification test (NAAT). In some embodiments, one or more mRNA compositions described herein may be administered according to a regimen established to reduce COVID-19 incidence per 1000 person-years based on a laboratory test such as nucleic acid amplification test (NAAT) in subjects receiving at least one dose of a provided mRNA composition with no serological or virological evidence (e.g., up to 7 days after receipt of the last dose) of past SARS-CoV-2 infection. In some embodiments, one or more mRNA compositions described herein may be administered according to a regimen established to reduce confirmed severe COVID-19 incidence per 1000 person-years. In some embodiments, one or more mRNA compositions described herein may be administered according to a regimen established to reduce confirmed severe COVID-19 incidence per 1000 person-years in subjects receiving at least one dose of a provided mRNA composition with no serological or virological evidence of past SARS-CoV-2 infection.

In some embodiments, one or more mRNA compositions described herein may be administered according to a regimen established to produce neutralizing antibodies directed to a SARS-CoV-2 spike polypeptide and/or an immunogenic fragment thereof (e.g., RBD) as measured in serum from a subject that achieves or exceeds a reference level (e.g., a reference level determined based on human SARS-CoV-2 infection/COVID-19 convalescent sera) for a period of time and/or induction of cell-mediated immune response (e.g., a T cell response against SARS-CoV-2), including, e.g., in some embodiments induction of T cells that recognize at least one or more MHC-restricted (e.g., MHC class I-restricted) eptiopes within a SARS-CoV-2 spike polypeptide and/or an immunogenic fragment thereof (e.g., RBD) for a period of time. In some such embodiments, the period of time may be at least 2 months, 3 months, at least 4 months, at least 5 months, at least 6 months, at least 7 months, at least 8 months, at least 9 months, at least 10 months, at least 11 months, at least 12 months or longer. In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 40); HLA-A*0201 RLQSLQTYV (SEQ ID NO: 41); HLA-A*2402 QYIKWPWYI (SEQ ID NO: 42); HLA-A*2402 NYNYLYRLF (SEQ ID NO: 43); HLA-A*2402 KWPWYIWLGF (SEQ ID NO: 44); HLA-B*3501 QPTESIVRF (SEQ ID NO: 45); HLA-B*3501 IPFAMQMAY (SEQ ID NO: 46); or HLA-B*3501 LPFNDGVYF (SEQ ID NO: 47).

In some embodiments, efficacy is assessed as COVID-19 incidence per 1000 person-years in individuals without serological or virological ecidence of past SARS-CoV-2 infection before and during vaccination regimen; alternatively or additionally, in some embodiments, efficacy is assessed as COVID-19 incidence per 1000 person-years in subjects with and without evidence of past SARS-CoV-2 infection before and during vaccination regimen. In some such embodiments, such incidence is of COVID-19 cases confirmed within a specific time period after the final vaccination dose (e.g., a first dose in a single-dose regimen; a second dose in a two-dose regimen, etc); in some embodiments, such time period may be within (i.e., up to and including 7 days) a particular number of days (e.g., 3, 4, 5, 6, 7, 8, 9, 10, 11, 12, 13, 14, 15, 16, 17, 18, 19, 20, 21, 22, 23, 24, 25, 26, 27, 28, 29, 30 days or more). In some embodiments, such time period may be within 7 days or within 14 days or within 21 days or within 28 days. In some embodiments, such time period may be within 7 days. In some embodiments, such time period may be within 14 days.

In some embodiments (e.g., in some embodiments of assessing efficacy), a subject is determined to have experienced COVID-19 infection if one or more of the following is established: detection of SARS-CoV-2 nucleic acid in a sample from the subject, detection of antibodies that specifically recognize SARS-CoV-2 (e.g., a SARS-Co-V-2 spike protein), one or more symptoms of COVID-19 infection, and combinations thereof. In some such embodiments, detection of SARS-CoV-2 nucleic acid may involve, for example, NAAT testing on a mid-turbinatae swap sample. In some such embodiments, detection of relevant antibodies may involve serological testing of a blood sample or portion thereof. In some such embodiments, symptoms of COVID-19 infection may be or include: fever, new or increased cough, new or increased shortness of breath, chills, new or increased muscle pain, new loss of taste or smell, sore throat, diarrhea, vomiting and combinations thereof. In some such embodiments, symptoms of COVID-19 infection may be or include: fever, new or increased cough, new or increased shortness of breath, chills, new or increased muscle pain, new loss of taste or smell, sore throat, diarrhea, vomiting, fatigue, headache, nasal congestion or runny nose, nausea, and combinations thereof. In some such embodiments, a subject is determined to have experienced COVID-19 infection if such subject both has experienced one such symptom and also has received a positive test for SARS-CoV-2 nucleic acid or antibodies, or both. In some such embodiments, a subject is determined to have experienced COVID-19 infection if such subject both has experienced one such symptom and also has received a positive test for SARS-CoV-2 nucleic acid. In some such embodiments, a subject is determined to have experienced COVID-19 infection if such subject both has experienced one such symptom and also has received a positive test for SARS-CoV-2 antibodies.

In some embodiments (e.g., in some embodiments of assessing efficacy), a subject is determined to have experienced severe COVID-19 infection if such subject has experienced one or more of: clinical signs at rest indicative or severe systemic illness (e.g., one or more of respiratory rate at greater than or equal to 30 breaths per minute, heart rate at or above 125 beats per minute, $SpO_2$ less than or equal to 93% on room air at sea level or a $PaO_2/FiO_2$ below 300 m Hg), respiratory failure (e.g., one or more of needing high-flow oxygen, noninvasive ventilation, mechanical ventilation, ECMO), evidence of shock (systolic blood pressure below 90 mm Hg, diastolic blood pressure below 60 mm Hg, requiring vasopressors), significant acute renal, hepatic, or neurologic dystfunction, admission ot an intensive care unit, death, and combinations thereof.

In some embodiments, one or more mRNA compositions described herein may be administered according to a regimen established to reduce the percentage of subjects reporting at least one of the following: (i) one or more local reactions (e.g., as described herein) for up to 7 days following each dose; (ii) one or more systemic events for up to 7 days following each dose; (iii) adverse events (e.g., as described herein) from a first dose to 1 month after the last dose; and/or (iv) serious adverse events (e.g., as described herein) from a first dose to 6 months after the last dose.

In some embodiments, one or more subjects who have received an RNA (e.g., mRNA) composition as described herein may be monitored (e.g., for a period of at least 1, 2, 3, 4, 5, 6, 7, 8, 9, 10 days or more, including, for example, 1, 2, 3, 4, 5, 6, 7, 8, 9, 10, 11, 12 weeks or more, including for example 1, 2, 3, 4, 5, 6, 7, 8, 9, 10, 11, 12, 13, 14, 15, 16, 17, 18, 19, 20, 21, 22, 23, 24 months or more, including for example 1, 2, 3, 4, 5, 6, 7, 8, 9, 10 years or more) to assess, for example, presence of an immune response to component(s) of the administered composition, evidence of exposure to and/or immune response to SARS-CoV-2 or another coronavirus, evidence of any adverse event, etc. In some embodiments, monitoring may be via tele-visit. Alternatively or additionally, in some embodiments, monitoring may be in-person.

In some embodiments, a treatment effect conferred by one or more mRNA compositions described herein may be characterized by (i) a SARS-CoV-2 anti-S1 binding antibody level above a pre-determined threshold; (ii) a SARS-CoV-2 anti-RBD binding antibody level above a pre-determined threshold; and/or (iii) a SARS-CoV-2 serum neutralizing titer above a threshold level, e.g., at baseline, 1 month, 3 months, 6 months, 9 months, 12 months, 18 months, and/or 24 months after completion of vaccination. In some embodiments, anti-S1 binding antibody and/or anti-RBD binding antibody levels and/or serum neutralizing titers may be characterized by geometric mean concentration (GMC), geometric mean titer (GMT), or geometric mean fold-rise (GMFR).

In some embodiments, a treatment effect conferred by one or more mRNA compositions described herein may be characterized in that percentage of treated subjects showing a SARS-CoV-2 serum neutralizing titer above a pre-determined threshold, e.g., at baseline, 1 month, 3 months, 6 months, 9 months, 12 months, 18 months, and/or 24 months after completion of vaccination, is higher than the percentage of non-treated subjects showing a SARS-CoV-2 serum neutralizing titer above such a pre-determined threshold (e.g., as described herein). In some embodiments, a serum neutralizing titer may be characterized by geometric mean concentration (GMC), geometric mean titer (GMT), or geometric mean fold-rise (GMFR).

In some embodiments, a treatment effect conferred by one or more mRNA compositions described herein may be characterized by detection of SARS-CoV-2 NVA-specific binding antibody.

In some embodiments, a treatment effect conferred by one or more mRNA compositions described herein may be characterized by SARS-CoV-2 detection by nucleic acid amplification test.

In some embodiments, a treatment effect conferred by one or more mRNA compositions described herein may be characterized by induction of cell-mediated immune response (e.g., a T cell response against SARS-CoV-2), including, e.g., in some embodiments induction of T cells that recognize at least one or more MHC-restricted (e.g., MHC class I-restricted) eptiopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 40); HLA-A*0201 RLQSLQTYV (SEQ ID NO: 41); HLA-A*2402 QYIKWPWYI (SEQ ID NO: 42); HLA-A*2402 NYNYLYRLF (SEQ ID NO: 43); HLA-A*2402 KWPWYIWLGF (SEQ ID NO: 44); HLA-B*3501 QPTESIVRF (SEQ ID NO: 45); HLA-B*3501 IPFAMQMAY (SEQ ID NO: 46); or HLA-B*3501 LPFNDGVYF (SEQ ID NO: 47).

In some embodiments, primary vaccine efficacy (VE) of one or more mRNA compositions described herein may be established when there is sufficient evidence (posterior probability) that either primary VE1 or both primary VE1 and primary VE2 are >30% or higher (including, e.g., greater than 40%, greater than 50%, greater than 60%, greater than 70%, greater than 80%, greater than 90%, greater than 95%, greater than 96%, greater than 97%, greater than 98%, or higher), wherein primary VE is defined as primary VE=100×(1−IRR); and IRR is calculated as the ratio of COVID-19 illness rate in the vaccine group to the corresponding illness rate in the placebo group. Primary VE1 represents VE for prophylactic mRNA compositions described herein against confirmed COVID-19 in participants without evidence of infection before vaccination, and primary VE2 represents VE for prophylactic mRNA compositions described herein against confirmed COVID-19 in all participants after vaccination. In some embodiments, primary VE1 and VE2 can be evaluated sequentially to control the overall type I error of 2.5% (hierarchical testing). In some embodiments where one or more RNA (e.g., mRNA) compositions described herein are demonstrated to achieve primary VE endponts as discussed above, secondary VE endpoints (e.g., confirmed severe COVID-19 in participants without evidence of infection before vaccination and confirmed severe COVID-19 in all participants) can be evaluated sequentially, e.g., by the same method used forthe primary VE endpoint evaluation (hierarchical testing) as discussed above. In some embodiments, evaluation of primary and/or secondary VE endpoints may be based on at least 20,000 or more subjects (e.g., at least 25,000 or more subjects) randomized in a 1:1 ratio to the vaccine or placebo group, e.g., based on the following assumptions: (i) 1.0% illness rate per year in the placebo group, and (ii) 20% of the participants being non-evaluable or having serological evidence of prior infection with SARS-CoV-2, potentially making them immune to further infection.

In some embodiments, one or more mRNA compositions described herein may be administered according to a regimen established to achieve maintenance and/or continued enhancement of an immune response. For example, in some embodiments, an administration regimen may include a first dose optionally followed by one or more subsequent doses; in some embodiments, need for, timing of, and/or magnitude of any such subsequent dose(s) may be selected to maintain, enhance, and/or modify one or more immune responses or features thereof. In some embodiments, number, timing, and/or amount(s) of dose(s) have been established to be effective when administered to a relevant population. In some embodiments, number, timing and/or amount(s) of dose(s) may be adjusted for an individual subject; for example, in some embodiments, one or more features of an immune response in an individual subject may be assessed at least once (and optionally more than once, for example multiple times, typically spaced apart, often at pre-selected intervals) after receipt of a first dose. For example, presence of antibodies, B cells, and/or T cells (e.g., CD4+ and/or CD8+ T cells), and/or of cytokines secreted thereby and/or identity of and/or extent of responses to particular antigen(s) and/or epitope(s) may be assessed. In some embodiments, need for, timing of, and/or amount of a subsequent dose may be determined in light of such assessments.

As noted hereinabove, in some embodiments, one or more subjects who have received an RNA (e.g., mRNA) composition as described herein may be monitored (e.g., for a period of at least 1, 2, 3, 4, 5, 6, 7, 8, 9, 10 days or more, including, for example, 1, 2, 3, 4, 5, 6, 7, 8, 9, 10, 11, 12 weeks or more, including for example 1, 2, 3, 4, 5, 6, 7, 8, 9, 10, 11, 12, 13, 14, 15, 16, 17, 18, 19, 20, 21, 22, 23, 24 months or more, including for example 1, 2, 3, 4, 5, 6, 7, 8, 9, 10 years or more) from receipt of any particular dose to assess, for example, presence of an immune response to component(s) of the administered composition, evidence of exposure to and/or immune response to SARS-CoV-2 or another coronavirus, evidence of any adverse event, etc, including to perform assessment of one or more of presence of antibodies, B cells, and/or T cells (e.g., CD4+ and/or CD8+ T cells), and/or of cytokines secreted thereby and/or identity of and/or extent of responses to particular antigen(s) and/or epitope(s) may be assessed. Administration of a composition as described herein may be in accordance with a regimen that includes one or more such monitoring steps.

For example, in some embodiments, need for, timing of, and/or amount of a second dose relative to a first dose (and/or of a subsequent dose relative to a prior dose) is assessed, determined, and/or selected such that administration of such second (or subsequent) dose achieves amplification or modification of an immune response (e.g., as described herein) observed after the first (or other prior) dose. In some embodiments, such amplification of an immune response (e.g., ones described herein) may be at least 30%, at least 40%, at least 50%, at least 60%, at least 70%, at least 80%, at least 90%, at least 95%, or higher, as compared to the level of an immune response observed after the first dose. In some embodiments, such amplification of an immune response may be at least 1.5 fold, at least 2-fold, at least 3-fold, at least 4-fold, at least 5-fold, at least 6-fold, at least 7-fold, at least 8-fold, at least 9-fold, at least 10-fold, at least 20-fold, at least 30-fold, or higher, as compared to the level of an immune response observed after the first dose.

In some embodiments, need for, timing of, and/or amount of a second (or subsequent) dose relative to a first (or other prior) dose is assessed, determined, and/or selected such that administration of the later dose extends the durability of an immune response (e.g., as described herein) observed after the earlier dose; in some such embodiments, the durability may be extended by at least 1 week, at least 2 weeks, at least 3 weeks, at least 1 month, at least 2 months, at least 3 months, at least 4 months, at least 5 months, at least 6 months, at least 7 months, at least 8 months, at least 9 months, or longer. In some embodiments, an immune response observed after the first dose may be characterized by production of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 40); HLA-A*0201 RLQSLQTYV (SEQ ID NO: 41); HLA-A*2402 QYIKWPWYI (SEQ ID NO: 42); HLA-A*2402 NYNYLYRLF (SEQ ID NO: 43); HLA-A*2402 KWPWYIWLGF (SEQ ID NO: 44); HLA-B*3501 QPTESIVRF (SEQ ID NO: 45); HLA-B*3501 IPFAMQMAY (SEQ ID NO: 46); or HLA-B*3501 LPFNDGVYF (SEQ ID NO: 47).

In some embodiments, need for, timing of, and/or amount of a second dose relative to a first dose (or other subsequent dose relative to a prior dose) is assessed, determined and/or selected such that administration of such second (or subsequent) dose maintains or exceeds a reference level of an immune response; in some such embodiments, the reference level is determined based on human SARS-CoV-2 infection/COVID-19 convalescent sera and/ro PBMC samples drawn from subjects (e.g., at least a period of time such as at least 14 days or longer, including, e.g., 15 days, 16 days, 17 days, 18 days, 19 days, 20 days, 25 days, 30 days, 35 days, 40 days, 45 days, 50 days, 55 days, 60 days, or longer, after PCR-confirmed diagnosis when the subjects were asymptomatic. In some embodiments, an immune response may be characterized by production of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) eptiopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 40); HLA-A*0201 RLQSLQTYV (SEQ ID NO: 41); HLA-A*2402 QYIKWPWYI (SEQ ID NO: 42); HLA-A*2402 NYNYLYRLF (SEQ ID NO: 43); HLA-A*2402 KWPWYIWLGF (SEQID NO: 44); HLA-B*3501 QPTESIVRF (SEQ ID NO: 45); HLA-B*3501 IPFAMQMAY (SEQ ID NO: 46); or HLA-B*3501 LPFNDGVYF (SEQ ID NO: 47).

In some embodiments, determination of need for, timing of, and/or amount of a second (or subsequent) dose may include one or more steps of assessing, after (e.g., 7, 8, 9, 10, 11, 12, 13, 14, 15, 16, 17, 18, 19, 20, 21 days or longer after) a first (or other prior) dose, presence and/or expression levels of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 40); HLA-A*0201 RLQSLQTYV (SEQ ID NO: 41); HLA-A*2402 QYIKWPWYI (SEQ ID NO: 42); HLA-A*2402 NYNYLYRLF (SEQID NO: 43); HLA-A*2402 KWPWYIWLGF (SEQID NO: 44); HLA-B*3501 QPTESIVRF (SEQ ID NO: 45); HLA-B*3501 IPFAMQMAY (SEQ ID NO: 46); or HLA-B*3501 LPFNDGVYF (SEQ ID NO: 47).

In some embodiments, a kit as provided herein may comprise a real-time monitoring logging device, which, for example in some embodiments, is capable of providing shipment temperatures, shipment time and/or location.

In some embodiments, an RNA (e.g., mRNA) composition as described herein may be shipped, stored, and/or utilized, in a container (such as a vial or syringe), e.g., a glass container (such as a glass vial or syringe), which, in some embodiments, may be a single-dose container or a multi-dose container (e.g., may be arranged and constructed to hold, and/or in some embodiments may hold, a single dose, or multiple doses of a product for administration). In some embodiments, a multi-dose container (such as a multi-dose vial or syringe) may be arranged and constructed to hold, and/or may hold 2, 3, 4, 5, 6, 7, 8, 9, 10 or more doses; in some particular embodiments, it may be designed to hold and/or may hold 5 doses. In some embodiments, a single-dose or multi-dose container (such as a single-dose or multi-dose vial or syringe) may be arranged and constructed to hold and/or may hold a volume or amount greater than the indicated number of doses, e.g., in order to permit some loss in transfer and/or administration. In some embodiments, an RNA (e.g., mRNA) composition as described herein may be shipped, stored, and/or utilized, in a preservative-free glass container (e.g., a preservative-free glass vial or syringe, e.g., a single-dose or multi-dose preservative-free glass vial or syringe). In some embodiments, an RNA (e.g., mRNA) composition as described herein may be shipped, stored, and/or utilized, in a preservative-free glass container (e.g., a preservative-free glass vial or syringe, e.g., a single-dose or multi-dose preservative-free glass vial or syringe) that contains 0.45 ml of frozen liquid (e.g., including 5 doses). In some embodiments, an RNA (e.g., mRNA) composition as described herein and/or a container (e.g., a vial or syringe) in which it is disposed, is shipped, stored, and/or utilized may be maintained at a temperature below room temperature, at or below 4° C., at or below 0° C., at or below −20° C., at or below −60° C., at or below −70° C., at or below −80° C., at or below −90° C., etc. In some embodiments, an RNA (e.g., mRNA) composition as described herein and/or a container (e.g., a viral or syringe) in which it is disposed, is shipped, stored, and/or utilized may be maintained at a temperature between −80° C. and −60° C. and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about 25° C., and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about 5° C. (e.g., below about 4° C.), and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about −20° C., and in some embodiments protected from light. In some embodiments, an RNA (e.g., mRNA) composition as described herein and/or a container (e.g., a viral or syringe) in which it is disposed, is shipped, stored, and/or utilized may be maintained at a temperature above about −60° C. (e.g., in some embodiments at or above about −20° C., and in some embodiments at or above about 4-5° C., in either case optionally below about 25° C.), and in some embodiments protected from light, or otherwise without affirmative steps (e.g., cooling measures) taken to achieve a storage temperature materially below about −20° C.

In some embodiments, an RNA (e.g., mRNA) composition as described herein and/or a container (e.g., a vial or syringe) in which it is disposed is shipped, stored, and/or utilized together with and/or in the context of a thermally protective material or container and/or of a temperature adjusting material. For example, in some embodiments, an RNA (e.g., mRNA) composition as described herein and/or a container (e.g., a vial or syringe) in which it is disposed is shipped, stored, and/or utilized together with ice and/or dry ice and/or with an insulating material. In some particular embodiments, a container (e.g., a vial or syringe) in which an RNA (e.g., mRNA) composition is disposed is positioned in a tray or other retaining device and is further contacted with (or otherwise in the presence of) temperature adjusting (e.g., ice and/or dry ice) material and/or insulating material. In some embodiments, multiple containers (e.g., multiple vials or syringes such as single use or multi-use vials or syringes as described herein) in which a provided RNA (e.g., mRNA) composition is disposed are co-localized (e.g., in a common tray, rack, box, etc.) and packaged with (or otherwise in the presence of) temperature adjusting (e.g., ice and/or dry ice) material and/or insulating material. To give but one example, in some embodiments, multiple containers (e.g., multiple vials or syringes such as single use or multi-use vials or syringes as described herein) in which an RNA (e.g., mRNA) composition is disposed are positioned in a common tray or rack, and multiple such trays or racks are stacked in a carton that is surrounded by a temperature adjusting material (e.g., dry ice) in a thermal (e.g., insulated) shipper. In some embodiments, temperature adjusting material is replenished periodically (e.g., within 24 hours of arrival at a site, and/or every 2 hours, 4 hours, 6 hours, 8 hours, 10 hours, 12 hours, 14 hours, 16 hours, 18 hours, 20 hours, 22 hours, 1 day, 2 days, 3 days, 4 days, 5 days, 6 days, 7 days, 8 days, 9 days, 10 days, etc.). Preferably, re-entry into a thermal shipper should be infrequent, and desirably should not occur more than twice a day. In some embodiments, a thermal shipper is re-closed within 5, 4, 3, 2, or 1 minute, or less, of having been opened. In some embodiments, a provided RNA (e.g., mRNA) composition that has been stored within a thermal shipper for a period of time, optionally within a particular temperature range remains useful. For example, in some embodiments, if a thermal shipper as described herein containing a provided RNA (e.g., mRNA) composition is or has been maintained (e.g., stored) at a temperature within a range of about 15° C. to about 25° C., the RNA (e.g., mRNA) composition may be used for up to 10 days; that is, in some embodiments, a provided RNA (e.g., mRNA) composition that has been maintained within a thermal shipper, which thermal shipper is at a temperature within a range of about 15° C. to about 25° C., for a period of not more than 10 days is administered to a subject. Alternatively or additionally, in some embodiments, if a provided RNA (e.g., mRNA) composition is or has been maintained (e.g., stored) within a thermal shipper, which thermal shipper has been maintained (e.g., stored) at a temperature within a range of about 15° C. to about 25° C., it may be used for up to 10 days; that is, in some embodiments, a provided RNA (e.g., mRNA) composition that has been maintained within a thermal shipper, which thermal shipper has been maintained at a temperature within a range of about 15° C. to about 25° C. for a period of not more than 10 days is administered to a subject.

In some embodiments, a provided RNA (e.g., mRNA) composition is shipped and/or stored in a frozen state. In some embodiments, a provided RNA (e.g., mRNA composition is shipped and/or stored as a frozen suspension, which in some embodiments does not contain preservative. In some embodiments, a frozen RNA (e.g., mRNA) composition is thawed. In some embodiments, a thawed RNA (e.g., mRNA) composition (e.g., a suspension) may contain white to off-white opaque amorphous particles. In some embodiments, a thawed RNA (e.g., mRNA) composition may be used for up to a small number (e.g., 1, 2, 3, 4, 5, or 6) of days after thawing if maintained (e.g., stored) at a temperature at or below room temperature (e.g., below about 30° C., 25° C., 20° C., 15° C., 10° C., 8° C., 4° C., etc). In some embodiments, a thawed RNA (e.g., mRNA) composition may be used after being stored (e.g., for such small number of days) at a temperature between about 2° C. and about 8° C.; alternatively or additionally, a thawed RNA (e.g., mRNA) composition may be used within a small number (e.g., 1, 2, 3, 4, 5, 6) of hours after thawing at room temperature. Thus, in some embodiments, a provided RNA (e.g., mRNA) composition that has been thawed and maintained at a temperature at or below room temperature, and in some embodiments between about 2° C. and about 8° C., for not more than 6, 5, 4, 3, 2, or 1 days is administered to a subject. Alternatively or additionally, in some embodiments, a provided RNA (e.g., mRNA) composition that has been thawed and maintained at room temperature for not more than 6, 5, 4, 3, 2, or 1 hours is administered to a subject. In some embodiments, a provided RNA (e.g., mRNA) composition is shipped and/or stored in a concentrated state. In some embodiments, such a concentrated composition is diluted prior to administration. In some embodiments, a diluted composition is administered within a period of about 10, 9, 8, 7, 6, 5, 4, 3, 2, or 1 hour(s) post-dilution; in some embodiments, such administration is within 6 hours post-dilution. Thus, in some embodiments, diluted preparation of a provided RNA (e.g., mRNA) composition is administered to a subject within 6 hours post-dilution (e.g., as described herein after having been maintained at an appropriate temperature, e.g., at a temperature below room temperature, at or below 4° C., at or below 0° C., at or below −20° C., at or below −60° C., at or below −70° C., at or below −80° C., etc, and typically at or above about 2° C., for example between about 2° C. and about 8° C. or between about 2° C. and about 25° C.). In some embodiments, unusued composition is discarded within several hours (e.g., about 10, about 9, about 8, about 7, about 6, about 5 or fewer hours) after dilution; in some embodiments, unused composition is discarded within 6 hours of dilution.

In some embodiments, an RNA (e.g., mRNA) composition that is stored, shipped or utilized (e.g., a frozen composition, a liquid concentrated composition, a diluted liquid composition, etc.) may have been maintained at a temperature materially above −60° C. for a period of time of at least 1, 2, 3, 4, 5, 6, 7 days or more, or at least 1, 2, 3, 4, 5, 6, 7, 8, 9, 10 weeks or more, or at least 1, 2, 3, 4, 5, 6, 7, 8, 9, 10, 11, 12 months or more; in some such embodiments, such composition may have been maintained at a temperature at or above about −20° C. for such period of time, and/or at a temperature up to or about 4-5° C. for such period of time, and/or may have been maintained at a temperature above about 4-5° C., and optionally about 25° C. for a period of time up that is less than two (2) months and/or optionally up to about one (1) month. In some embodiments, such composition may not have been stored, shipped or utilized (or otherwise exposed to) a temperature materially above about 4-5° C., and in particular not at or near a temperature of about 25° C. for a period of time as long as about 2 weeks, or in some embodiments 1 week. In some embodiments, such composition may not have been stored, shipped or utilized (or otherwise exposed to) a temperature materially above about −20° C., and in particular not at or near a temperature of about 4-5° C. for a period of time as long as about 12 months, 11 months, 10 months, 9 months, 8 months, 7 months, 6 months, 5 months, 4 months, 3 months, 2 months, or, in some embodiments, for a period of time as long as about 8 weeks or 6 weeks or materially more than about 2 months or, in some embodiments, 3 months or, in some embodiments 4 months.

In some embodiments, an RNA (e.g., mRNA) composition that is stored, shipped or utilized (e.g., a frozen composition, a liquid concentrated composition, a diluted liquid composition, etc.) may be protected from light. In some embodiments, one or more steps may be taken to reduce or minimize exposure to light for such compositions (e.g., which may be disposed within a container such as a vial or a syringe). In some embodiments, exposure to direct sunlight and/or to ultraviolent light is avoided. In some embodiments, a diluted solution may be handled and/or utilized under normal room light conditions (e.g., without particular steps taken to minimize or reduce exposure to room light). It should be understood that strict adherence to aseptic techniques is desirable during handling (e.g., diluting and/or administration) of an RNA (e.g., mRNA) composition as described herein. In some embodiments, an RNA (e.g., mRNA) composition as described herein is not administered (e.g., is not injected) intravenously. In some embodiments, an RNA (e.g., mRNA) composition as described herein is not administered (e.g., is not injected) intradermally. In some embodiments, an RNA (e.g., mRNA) composition as described herein is not administered (e.g., is not injected) subcutaneously. In some embodiments, an RNA (e.g., mRNA) composition as described herein is not administered (e.g., is not injected) any of intravenously, intradermally, or subcutaneously. In some embodiments, an RNA (e.g., mRNA) composition as described herein is not administered to a subject with a known hypersensitivity to any ingredient thereof. In some embodiments, a subject to whom an RNA (e.g., mRNA) composition has been administered is monitored for one or more signs of anaphylaxis. In some embodiments, a subject to whom an RNA (e.g., mRNA) composition is administered had previously received at least one dose of a different vaccine for SARS-CoV-2; in some embodiments, a subject to whom an RNA (e.g., mRNA) composition is administered had not previously received a different vaccine for SARS-CoV-2. In some embodiments, a subject's temperature is taken promptly prior to administration of an RNA (e.g., mRNA) composition (e.g., shortly before or after thawing, dilution, and/or administration of such composition); in some embodiments, if such subject is determined to be febrile, administration is delayed or canceled. In some embodiments, an RNA (e.g., mRNA) composition as described herein is not administered to a subject who is receiving anticoagulant therapy or is suffering from or susceptible to a bleeding disorder or condition that would contraindicate intramuscular injection. In some embodiments, an RNA (e.g., mRNA) composition as described herein is administered by a healthcare professional who has communicated with the subject receiving the composition information relating to side effects and risks. In some embodiments, an RNA (e.g., mRNA) composition as described herein is administered by a healthcare professional who has agreed to submit an adverse event report for any serious adverse events, which may include for example one or more of death, development of a disability or congenital anomaly/birth defect (e.g., in a child of the subject), inpatient hospitalization (including prolongation of an existing hospitalization), a life-threatening event, a medical or surgical intervention to prevent death, a persistent or significant or substantial disruption of the ability to conduct normal life functions; or another important medical event that may jeopardize the individual and may require medical or surgical intervention (treatment) to prevent one of the other outcomes. In some embodiments, provided RNA compositions are administered to a population of individuals under 18 years of age, or under 17 years of age, or under 16 years of age, or under 15 years of age, or under 14 years of age, or under 13 years of age, for example according to a regimen established to have a rate of incidence for one or more of the local reaction events indicated below that does not exceed the rate of incidence indicated below:

pain at the injection site (75% after a first dose and/or a second dose, and/or a lower incidence after a second dose, e.g., 65% after a second dose);

redness at the injection site (less than 5% after a first dose and/or a second dose); and/or swelling at the injection site (less than 5% after a first dose and/or a second dose).

In some embodiments, provided RNA compositions are administered to a population of individuals under 18 years of age, or under 17 years of age, or under 16 years of age, or under 15 years of age, or under 14 years of age, or under 13 years of age, for example according to a regimen established to have a rate of incidence for one or more of the systemic reaction events indicated below that does not exceed the rate of incidence indicated below:

fatigue (55% after a first dose and/or a second dose);
headache (50% after a first dose and/or a second dose);
muscle pain (40% after a first dose and/or a second dose);
chills (40% after a first dose and/or a second dose);
joint pain (20% after a first dose and/or a second dose);
fever (25% after a first dose and/or a second dose);
vomiting (10% after a first dose and/or a second dose); and/or
diarrhea (10% after a first dose and/or a second dose).

In some embodiments, medication that alleviates one or more symptoms of one or more local reaction and/or systemic reaction events (e.g., described herein) are administered to individuals under 18 years of age, or under 17 years of age, or under 16 years of age, or under 15 years of age, or under 14 years of age, or under 13 years of age who have been administered with provided RNA compositions and have experienced one or more of the local and/or systemic reaction events (e.g., described herein). In some embodiments, antipyretic and/or pain medication can be administered to such individuals.

The sequence within the S1 subunit consists of the signal sequence (SS) and the receptor binding domain (RBD) which is the key subunit within the S protein which is relevant for binding to the human cellular receptor ACE2. The S2 subunit contains the S2 protease cleavage site (S2') followed by a fusion peptide (FP) for membrane fusion, heptad repeats (HR1 and HR2) with a central helix (CH) domain, the transmembrane domain (TM) and a cytoplasmic tail (CT).

Figure 1:
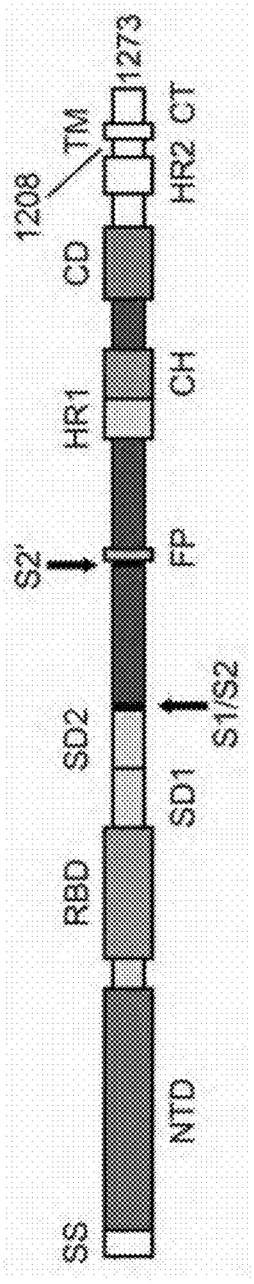
FIG. 1: Schematic overview of the S protein organization of the SARS-CoV-2 S protein.
Figure 2:
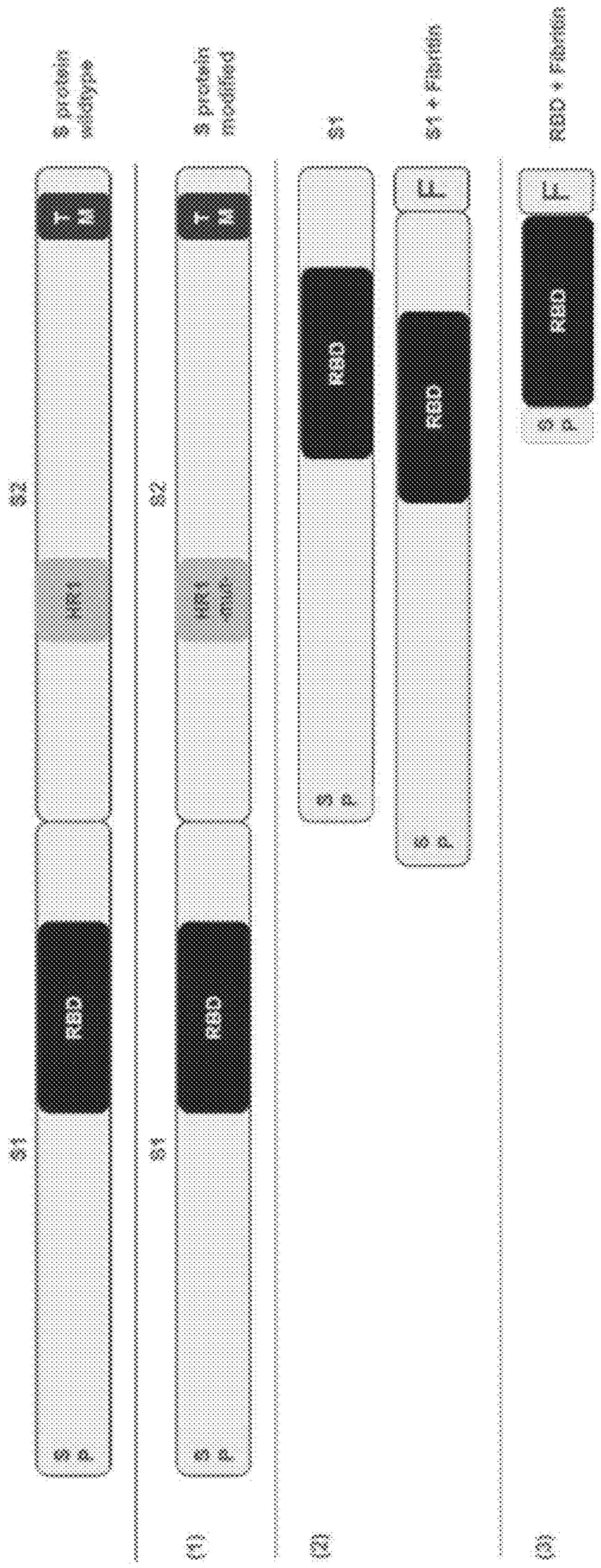

FIG. 2: Anticipated constructs for the development of a SARS-CoV-2 vaccine.

Based on the full and wildtype S protein, we have designed different construct encoding the (1) full protein with mutations in close distance to the first heptad repeat (HRP1) that include stabilizing mutations preserving neutralisation sensitive sites, the (2) S1 domain or the (3) RB domain (RBD) only. Furthermore, to stabilize the protein fragments a fibritin domain (F) was fused to the C-terminus. All constructs start with the signal peptide (SP) to ensure Golgi transport to the cell membrane.

Figure 3:
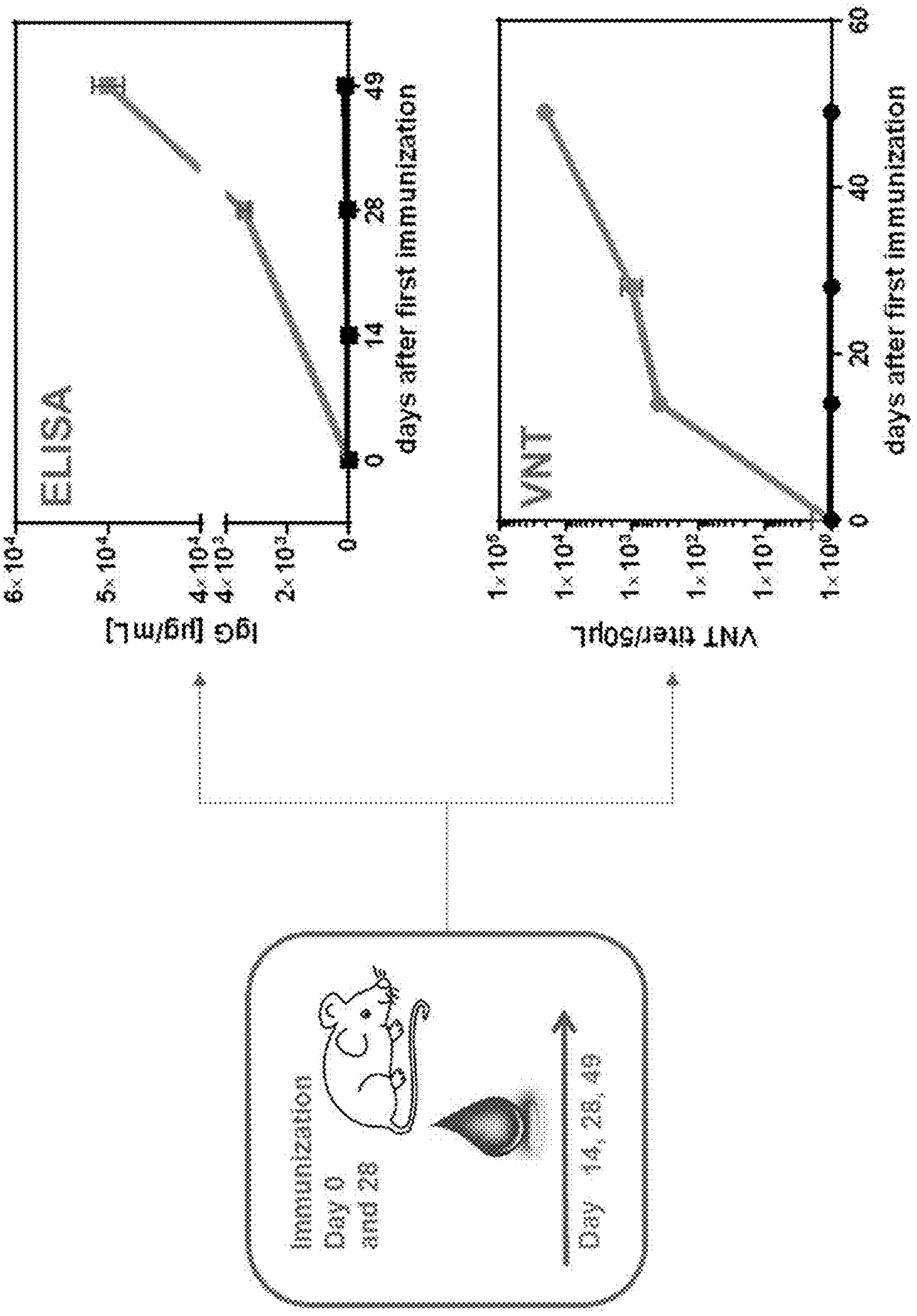

FIG. 3: Antibody immune response against Influenza HA using the LNP-formulated modRNA.

BALB/c mice were immunized twice with 1 μg of the vaccine candidate. Total amount of viral antigen specific immunoglobulin G (IgG) was measured via ELISA. The functionality of the antibodies was assessed via VNT.

Figure 4:
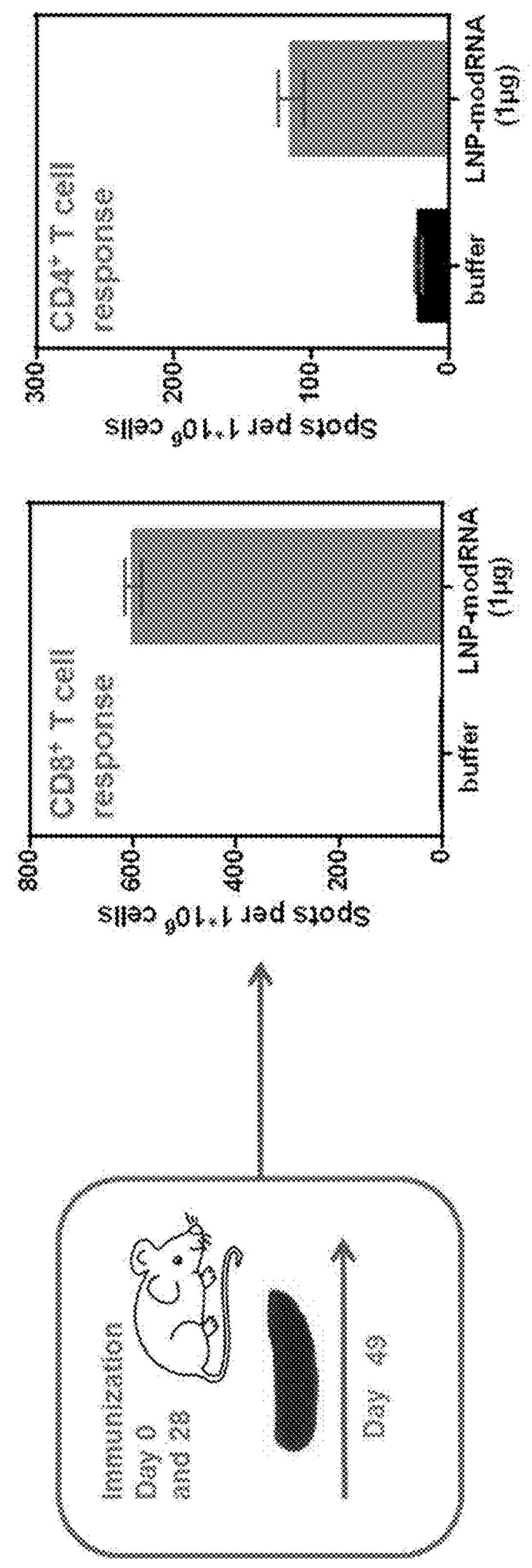

FIG. 4: T cell response against Influenza HA using the LNP-formulated modRNA platform.

BALB/c mice were immunized IM with 1 μg of the vaccine candidate, twice. The T cell response was analyzed using antigen specific peptides for T cell stimulation recovered from the spleen. IFNγ release was measured after peptide stimulation using an ELISpot assay.

Figure 5:
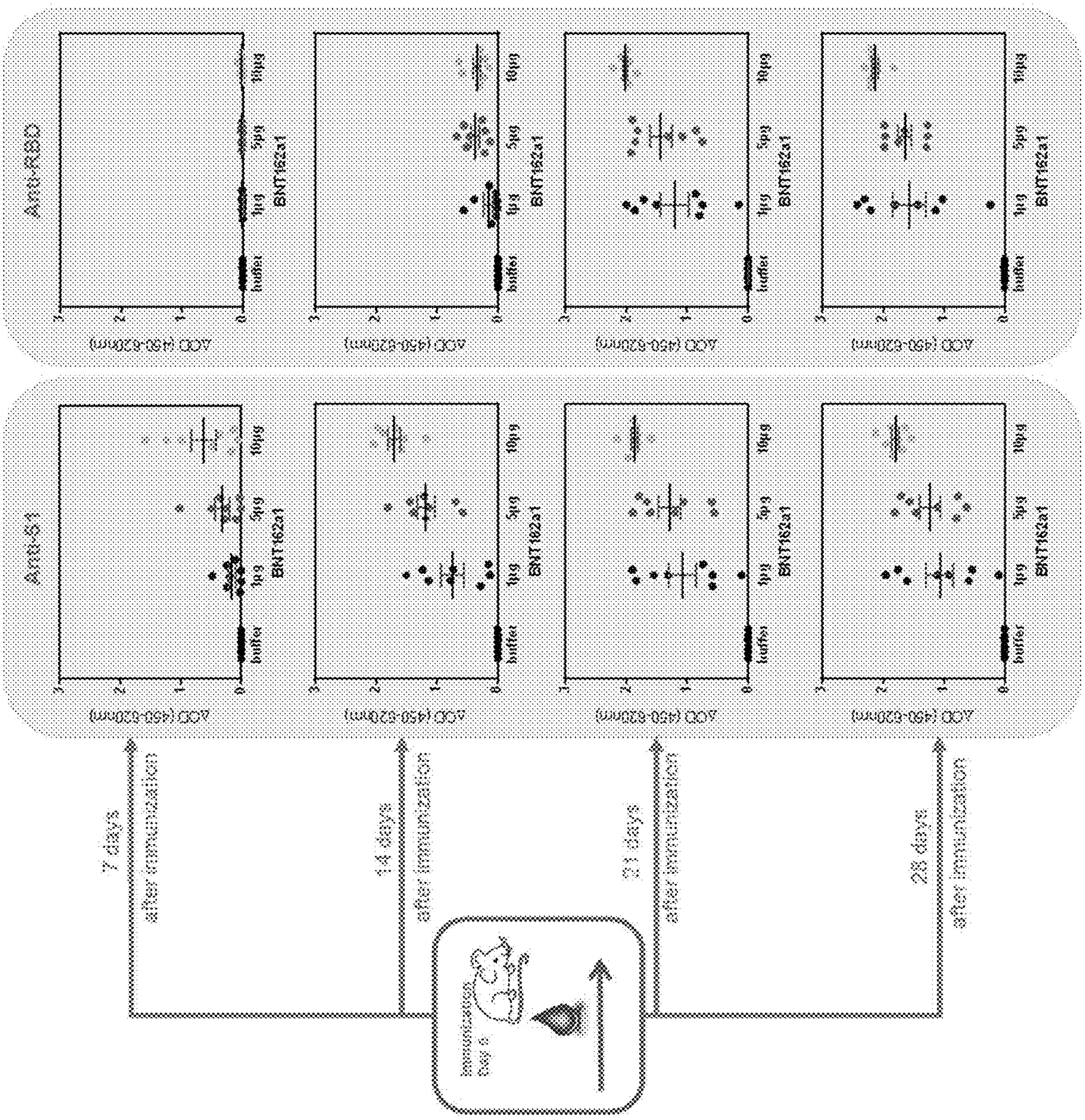

FIG. 5: Anti-S protein IgG response 7, 14, 21 and 28 d after immunization with BNT162a1.

BALB/c mice were immunized IM once with 1, 5 or 10 μg of LNP-formulated RBL063.3. On day 7, 14, 21 and 28 after immunization, animals were bled and the serum samples were analyzed for total amount of anti-S1 (left) and anti-RBD (right) antigen specific immunoglobulin G (IgG) measured via ELISA. For day 7, day 14, day 21 and day 28, values for a serum dilution of 1:100 were included in the graph. One point in the graph stands for one mouse, every mouse sample was measured in duplicates (group size n=8; mean+SEM is included for the groups).

Figure 6:
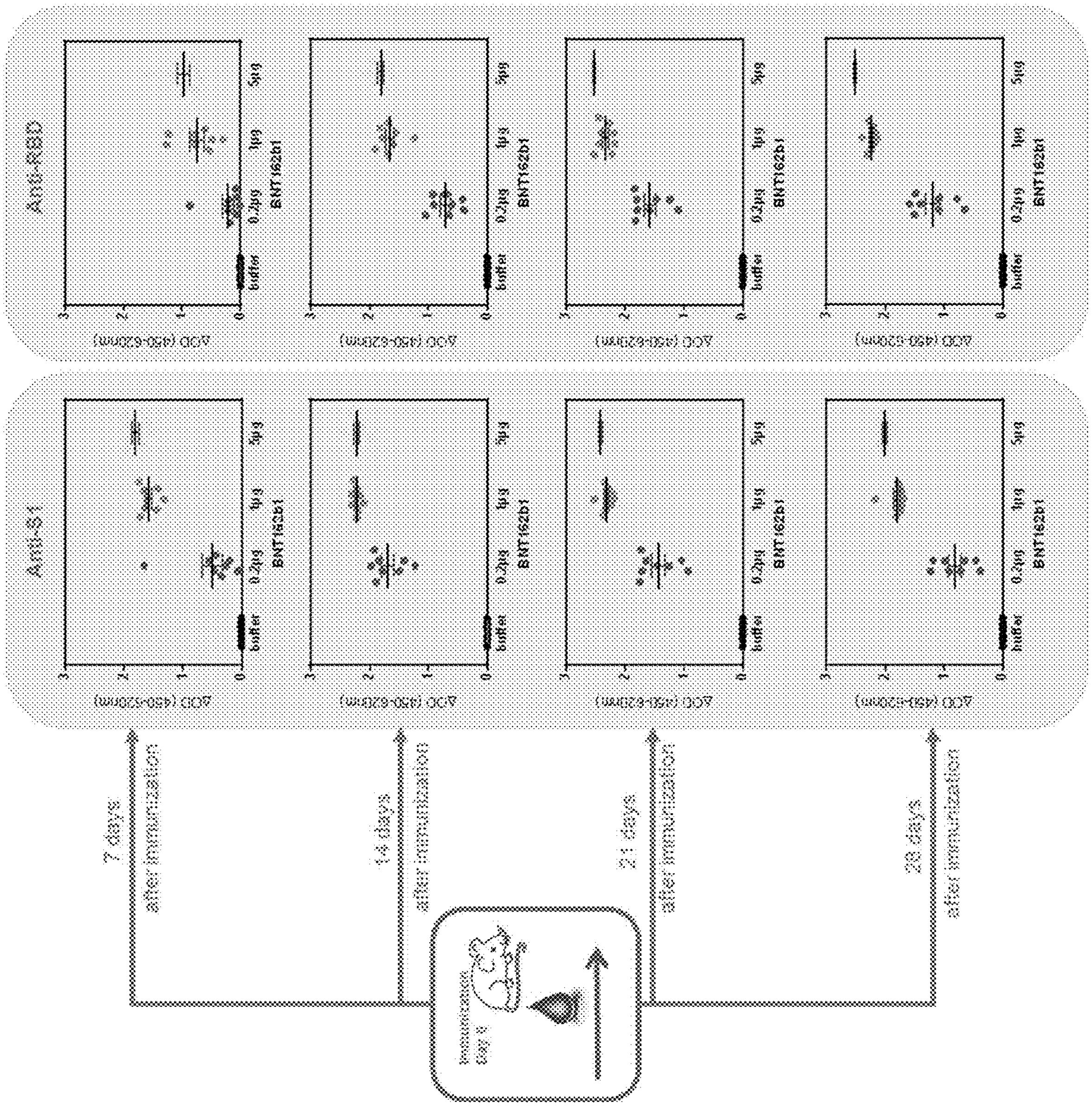

FIG. 6: Anti-S protein IgG response 7, 14, 21 and 28 d after immunization with BNT162b1.

BALB/c mice were immunized IM once with 0.2, 1 or 5 μg of LNP-formulated RBP020.3. On day 7, 14. 21 and 28 after immunization, animals were bled and the serum samples were analyzed for total amount of anti-S1 (left) and anti-RBD (right) antigen specific immunoglobulin G (IgG) measured via ELISA. For day 7 (1:100), day 14 (1:300), day 21 (1:900), and day 28 (1:2700) different serum dilution were included in the graph. One point in the graph stands for one mouse, every mouse sample was measured in duplicates (group size n=8; mean+SEM is included for the groups).

Figure 7:
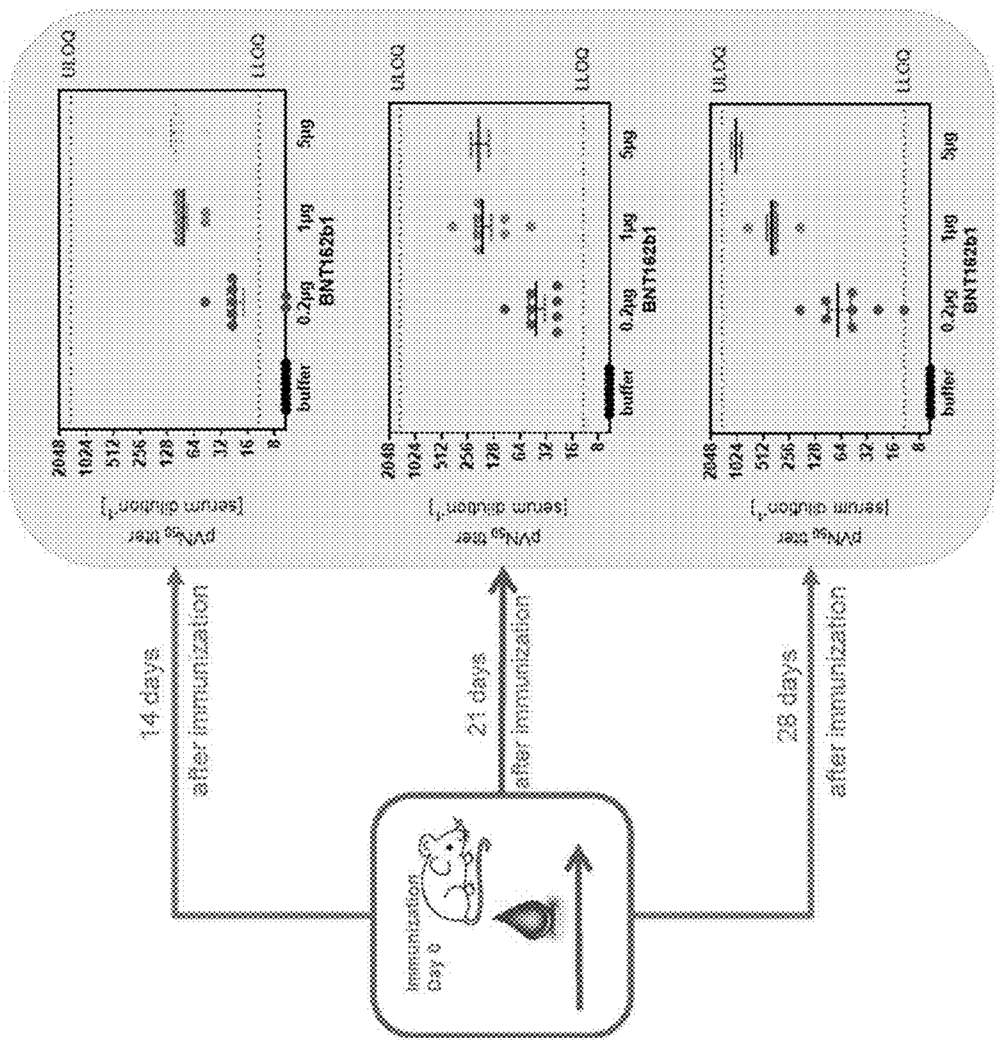

FIG. 7: Neutralization of SARS-CoV-2 pseudovirus 14, 21 and 28 d after immunization with BNT162b1.

BALB/c mice were immunized IM once with 0.2, 1 or 5 μg of LNP-formulated RBP020.3. On 14, 21 and 28 d after immunization, animals were bled, and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 8:
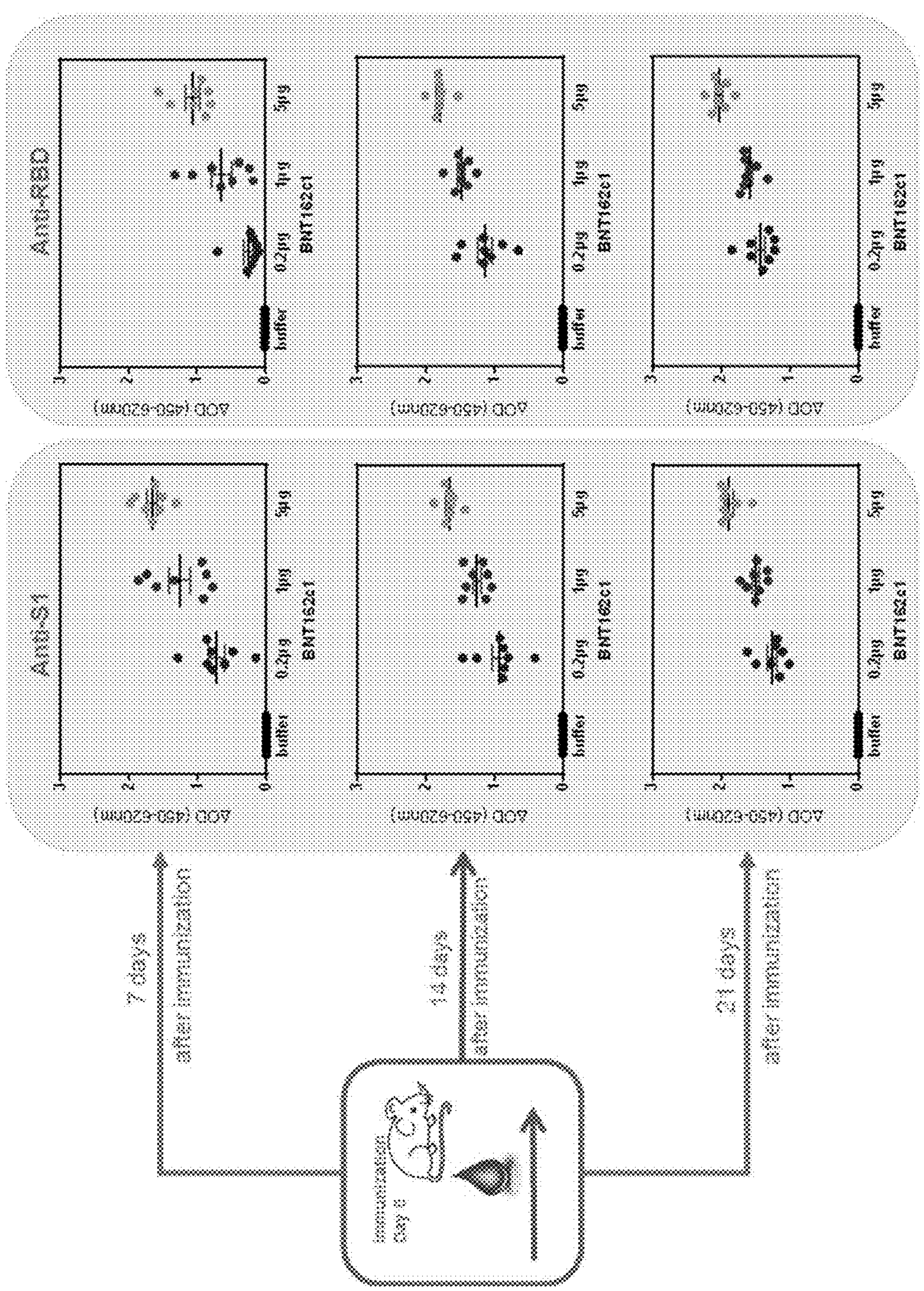

FIG. 8: Anti-S protein IgG response 7, 14 and 21 d after immunization with BNT162c1.

BALB/c mice were immunized IM once with 0.2, 1 or 5 μg of LNP-formulated RBS004.3. On day 7, 14 and 21 after immunization, animals were bled and the serum samples were analyzed for total amount of anti-S1 (left) and anti-RBD (right) antigen specific immunoglobulin G (IgG) measured via ELISA. For day 7 (1:100), day 14 (1:300), and day 21 (1:900) different serum dilution were included in the graph. One point in the graph stands for one mouse, every mouse sample was measured in duplicates (group size n=8; mean+SEM is included for the groups).

Figure 9:
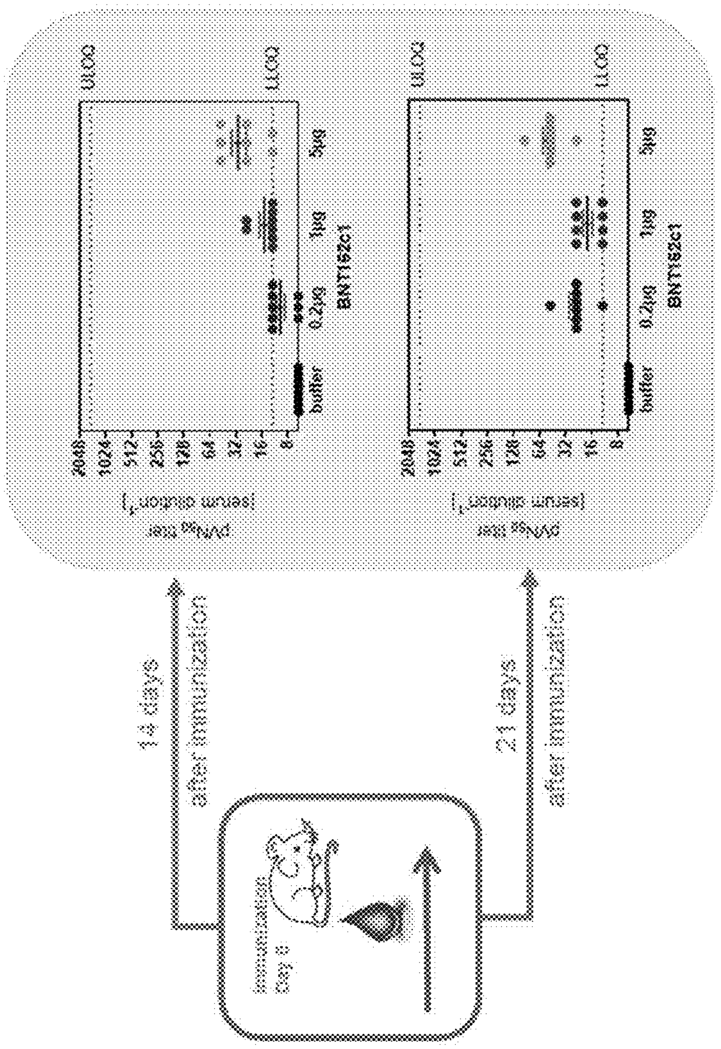

FIG. 9: Neutralization of SARS-CoV-2 pseudovirus 14 and 21 d after immunization with BNT162c1.

BALB/c mice were immunized IM once with 0.2, 1 or 5 μg of LNP-formulated RBS004.3. On 14 and 21 d after immunization, animals were bled and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 10:
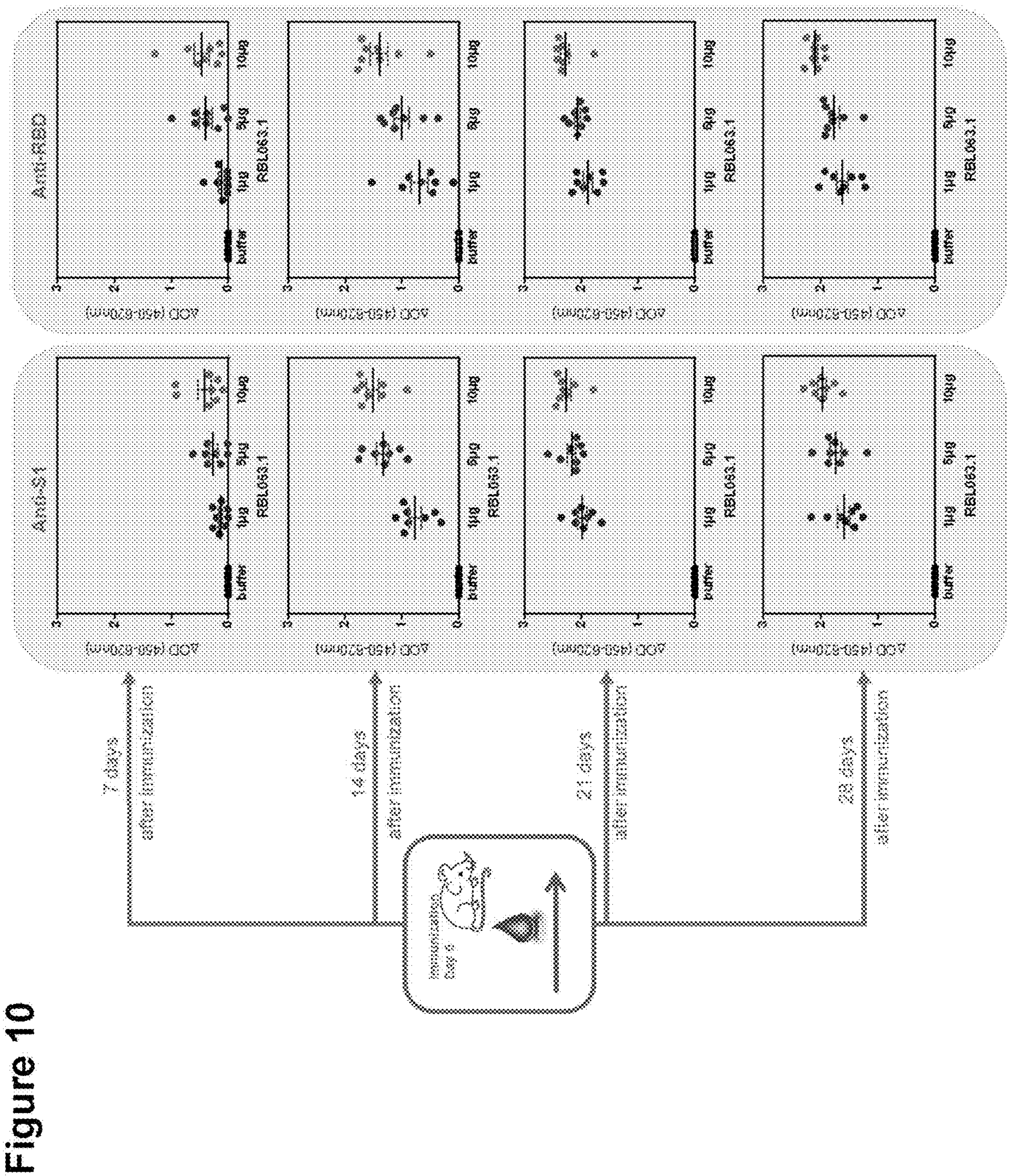

FIG. 10: Anti-S protein IgG response 7, 14, 21 and 28 d after immunization with LNP-formulated RBL063.1.

BALB/c mice were immunized IM once with 1, 5 or 10 μg of LNP-formulated RBL063.1. On day 7, 14, 21 and 28 after immunization, animals were bled and the serum samples were analyzed for total amount of anti-S1 (left) and anti-RBD (right) antigen specific immunoglobulin G (IgG) measured via ELISA. For day 7 (1:100), day 14 (1:100), day 21 (1:300) and day 28 (1:900) different serum dilution were included in the graph. One point in the graph stands for one mouse, every mouse sample was measured in duplicates (group size n=8; mean+SEM is included for the groups).

Figure 11:
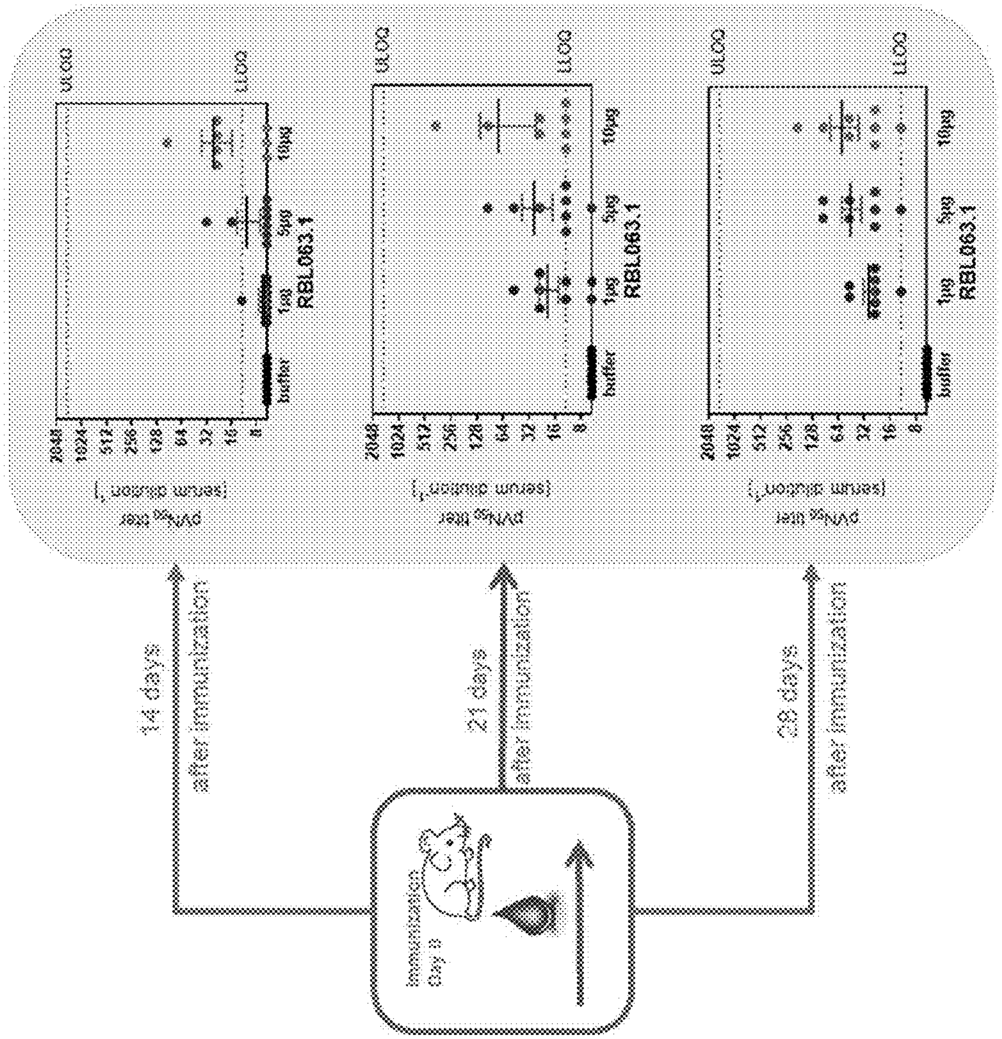

FIG. 11: Neutralization of SARS-CoV-2 pseudovirus 14, 21 and 28 d after immunization with LNP-formulated RBL063.1.

BALB/c mice were immunized IM once with 1, 5 or 10 μg of LNP-formulated RBL063.1. On 14, 21, and 28 d after immunization, animals were bled and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 12:
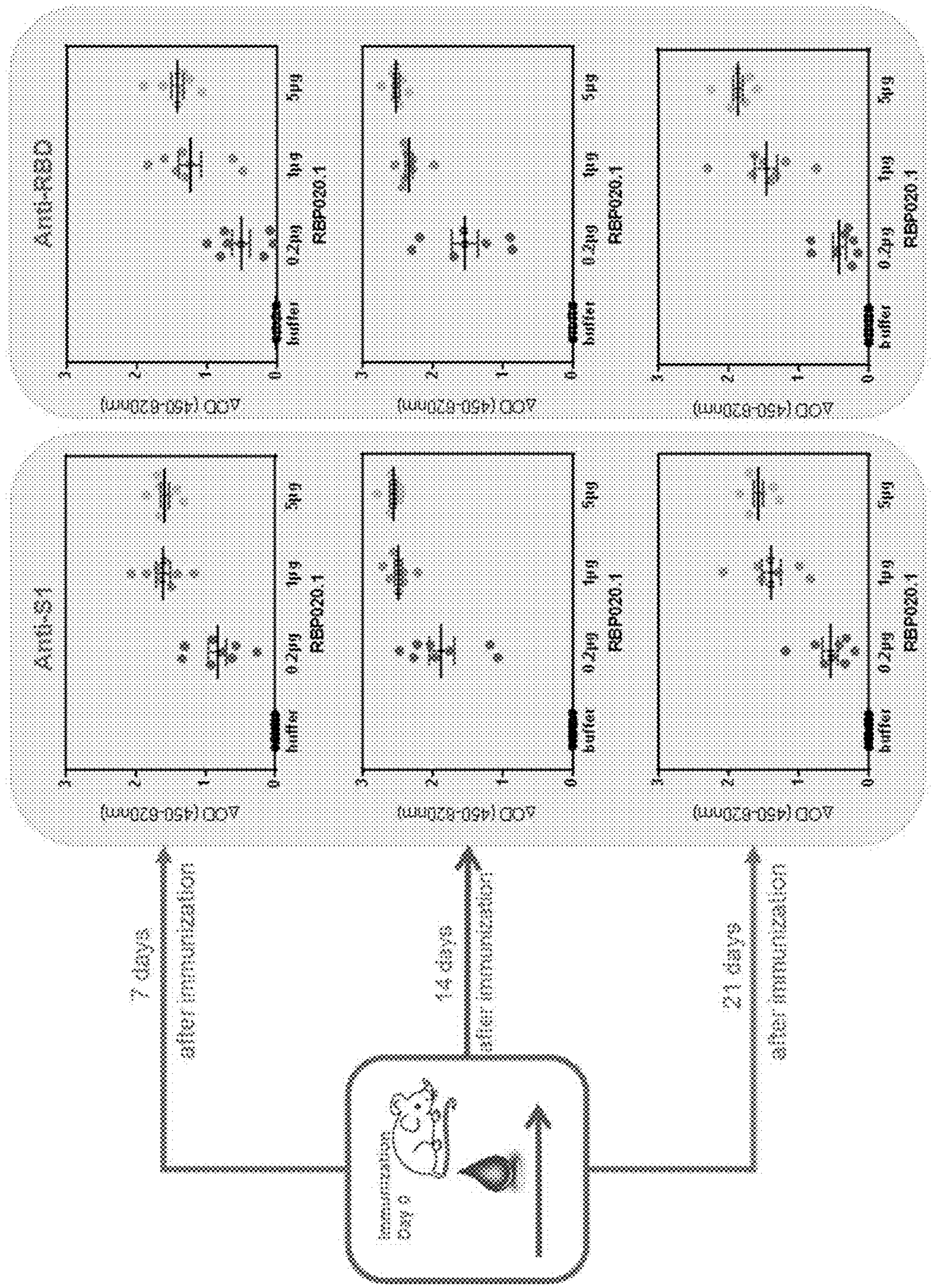

FIG. 12: Anti-S protein IgG response 7, 14 and 21 d after immunization with BNT162b2 (LNP-formulated RBP020.1).

BALB/c mice were immunized IM once with 0.2, 1 or 5 μg of LNP-formulatedRBP020.1. On day 7, 14, and 21 after immunization, animals were bled and the serum samples were analyzed for total amount of anti-S1 (left) and anti-RBD (right) antigen specific immunoglobulin G (IgG) measured via ELISA. For day 7 (1:100), day 14 (1:300), and day 21 (1:1100) different serum dilution were included in the graph. One point in the graph stands for one mouse, every mouse sample was measured in duplicates (group size n=8; mean+SEM is included for the groups).

Figure 13:
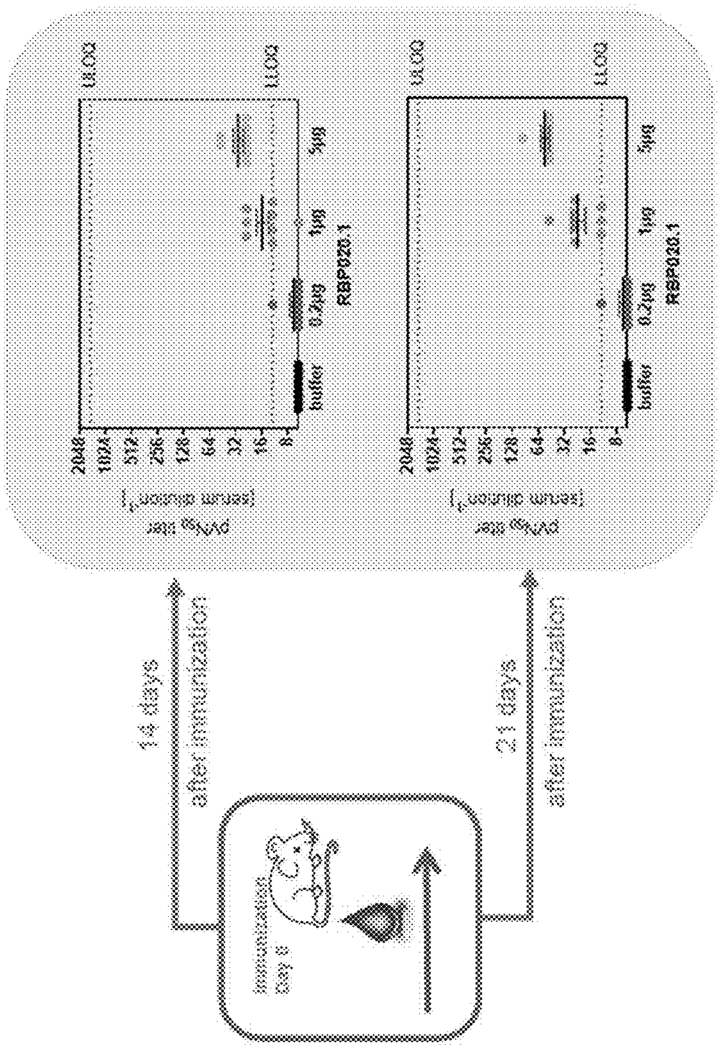

FIG. 13: Neutralization of SARS-CoV-2 pseudovirus 14 and 21 after immunization with BNT162b2 (LNP-formulated RBP020.1).

BALB/c mice were immunized IM once with 0.2, 1 or 5 μg of LNP-formulated RBP020.1. On day 14 and 21 after immunization, animals were bled and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 14:
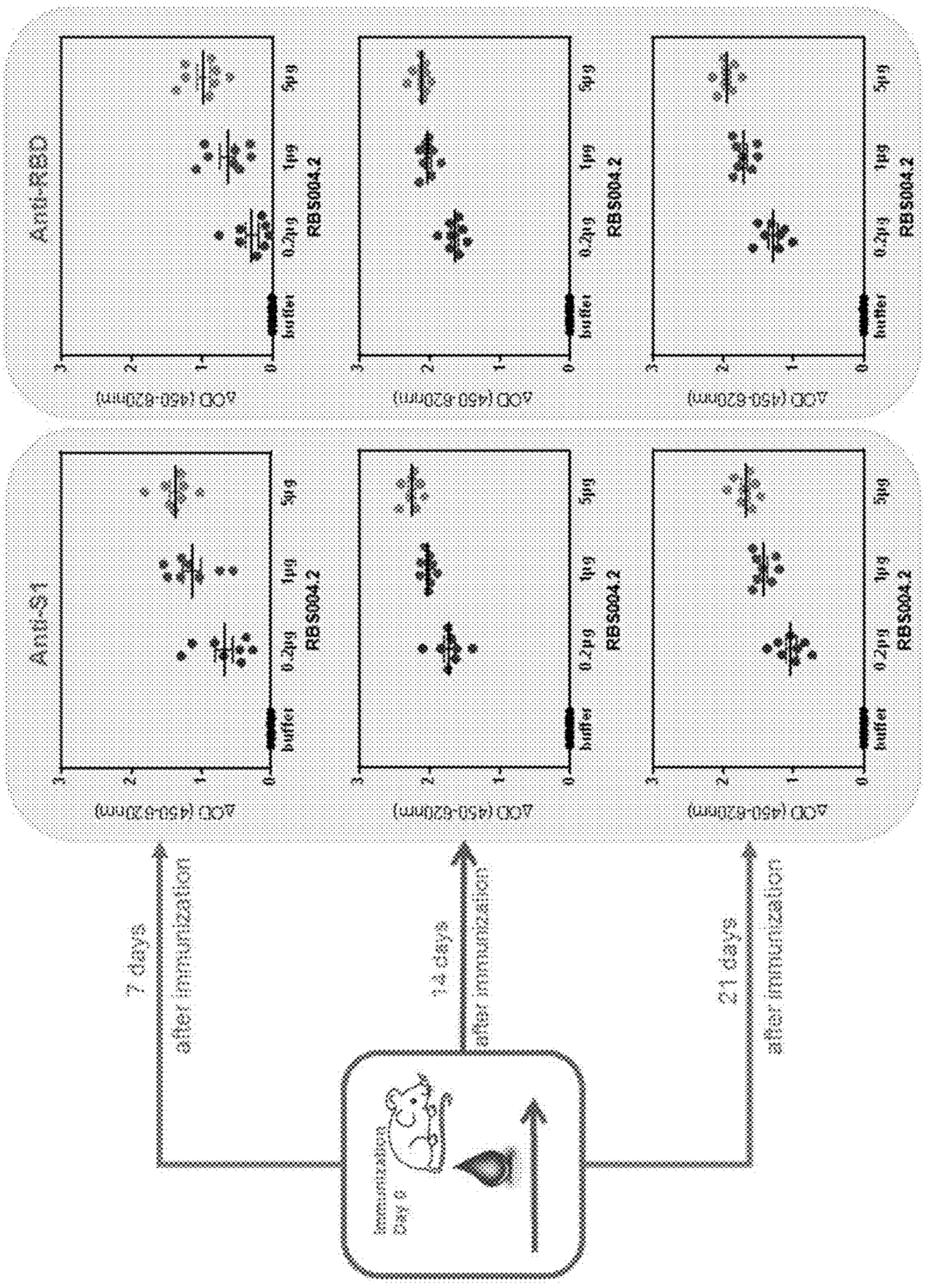

FIG. 14: Anti-S protein IgG response 7, 14 and 21 d after immunization with LNP-formulated RBS004.2.

BALB/c mice were immunized IM once with 0.2, 1 or 5 μg of LNP-formulated RBS004.2. On day 7, 14 and 21 after immunization, animals were bled and the serum samples were analyzed for total amount of anti-S1 (left) and anti-RBD (right) antigen specific immunoglobulin G (IgG) measured via ELISA. For day 7 (1:100), day 14 (1:300), and day 21 (1:900) different serum dilution were included in the graph. One point in the graph stands for one mouse, every mouse sample was measured in duplicates (group size n=8; mean+SEM is included for the groups).

Figure 15:
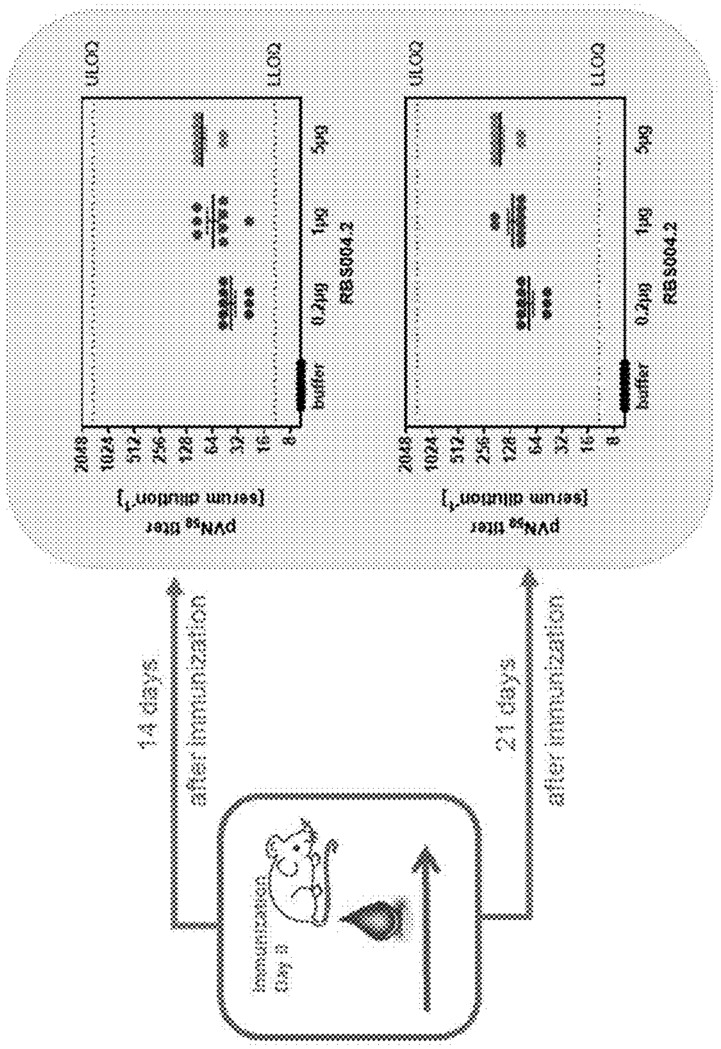

FIG. 15: Neutralization of SARS-CoV-2 pseudovirus 14 and 21 after immunization with LNP-formulated RBS004.2.

BALB/c mice were immunized IM once with 0.2, 1 or 5 μg of LNP-formulated RBS004.2. On 14, and 21 d after immunization, animals were bled, and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 16:
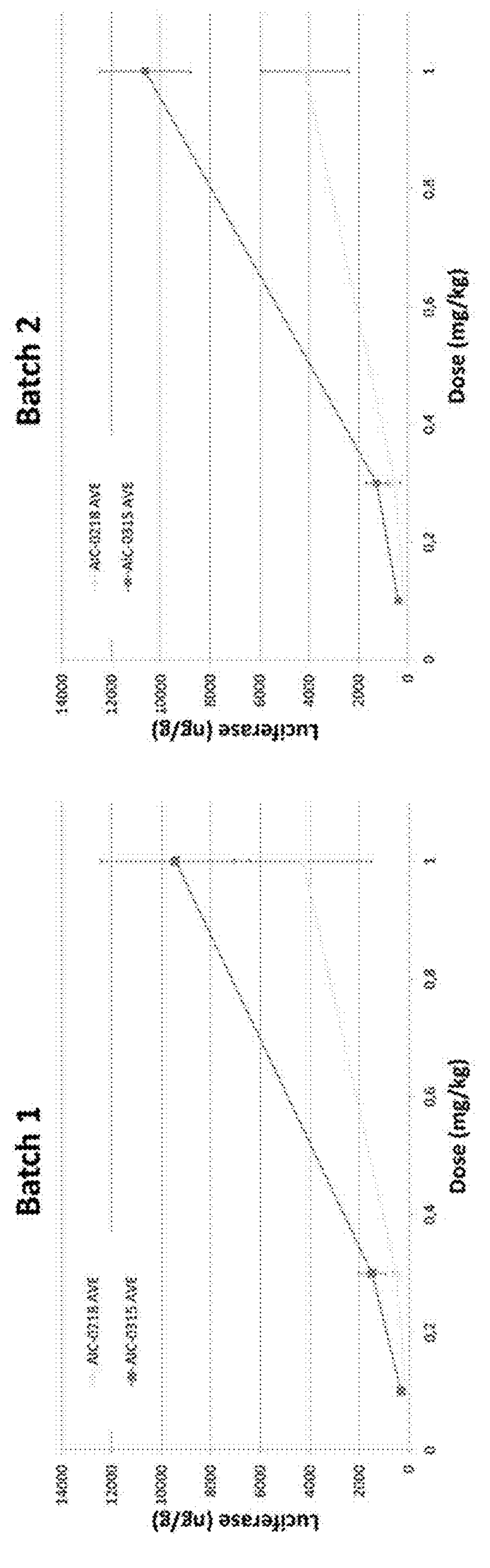

FIG. 16: ALC-0315 activity in the screening process.

Figure 17:
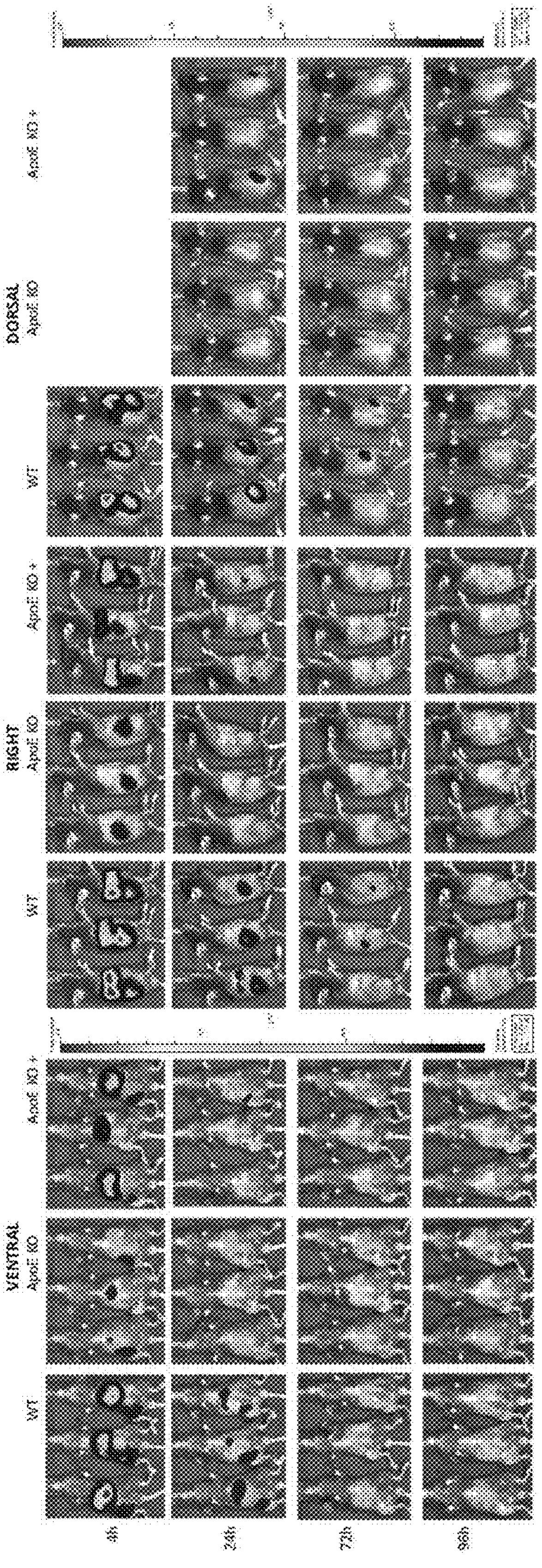

FIG. 17: Luciferase expression was monitored on the right (site of injection), dorsal (site of injection) and ventral (drainage to the liver) sides of the animal after intramuscular administration in wild-type (WT) or ApoE knockout C57Bl/6 mice in the presence or absence of ApoE3. Luciferase expression was detected using Xenolight D-Luciferin Rediject at 4, 24, 72 and 96 hours post administration.

Figure 18:
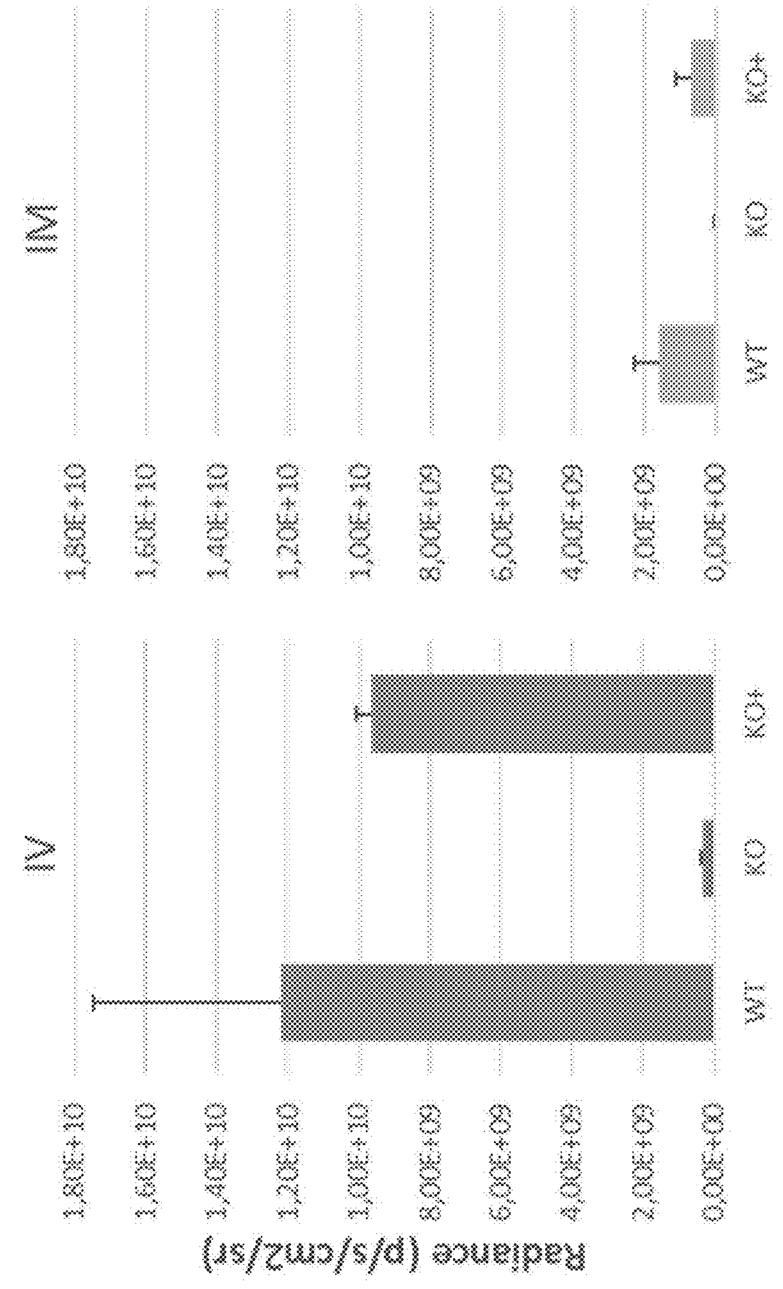

FIG. 18: Luciferase activity after intravenous (IV) and intramuscular (IM) administration in wild-type (WT) or ApoE knockout C57Bl/6 mice in the presence (KO+) or absence (KO) of ApoE3. Luciferase expression was detected using Xenolight D-Luciferin Rediject at 4 hours post administration.

Figure 19:
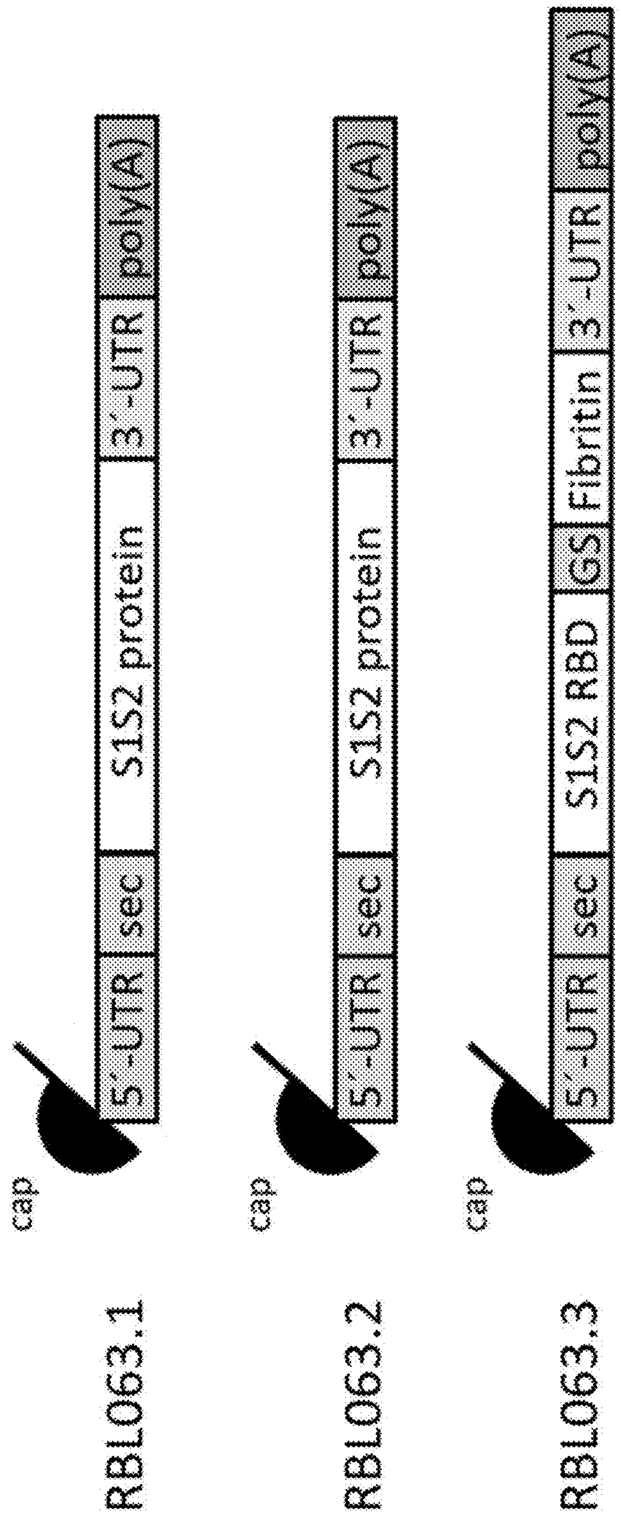

FIG. 19: General structure of the RNA.

Schematic illustration of the general structure of the RNA vaccines with 5'-cap, 5'- and 3'-untranslated regions, coding sequences with intrinsic secretory signal peptide as well as GS-linker, and poly(A)-tail. Please note that the individual elements are not drawn exactly true to scale compared to their respective sequence lengths.

UTR=Untranslated region; sec=Secretory signal peptide; RBD=Receptor Binding Domain; GS=Glycine-serine linker.

Figure 20:
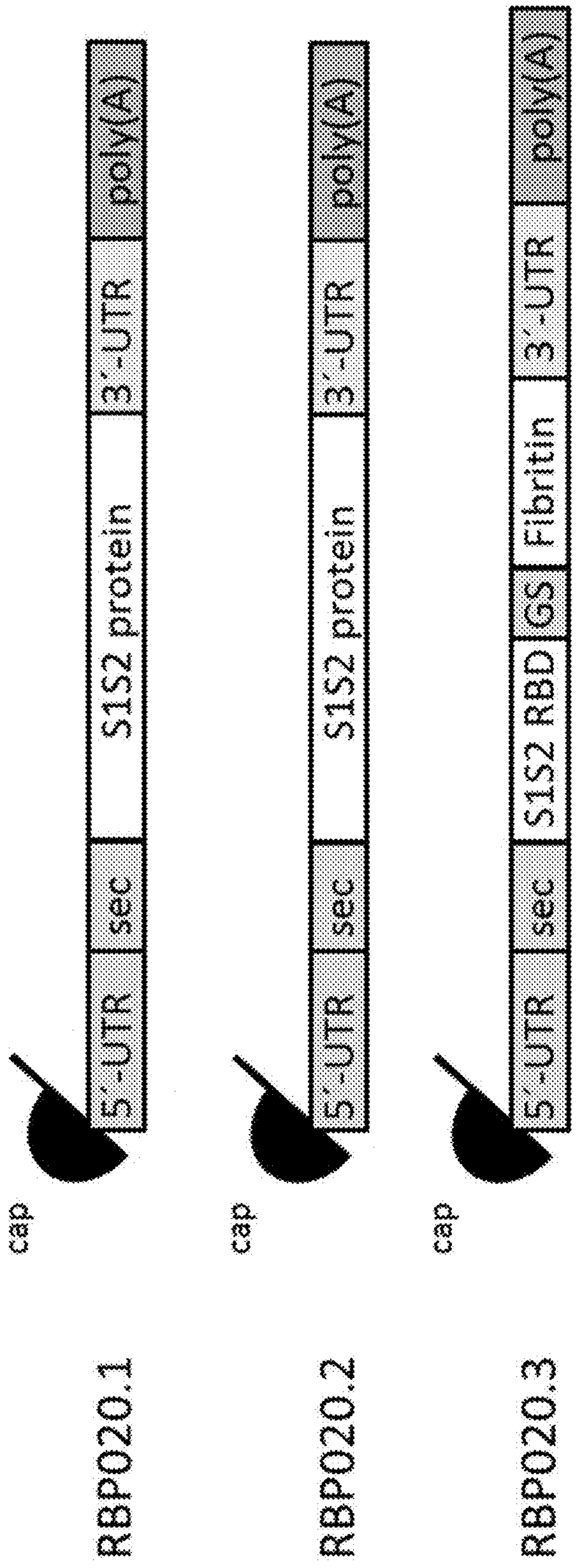

FIG. 20: General structure of the RNA.

Schematic illustration of the general structure of the RNA drug substances with 5'-cap, 5'- and 3'-untranslated regions, coding sequences with intrinsic secretory signal peptide as well as GS-linker, and poly(A)-tail. Please note that the individual elements are not drawn exactly true to scale compared to their respective sequence lengths.

GS=Glycine-serine linker; UTR=Untranslated region; Sec=Secretory signal peptide; RBD=Receptor Binding Domain.

Figure 21:
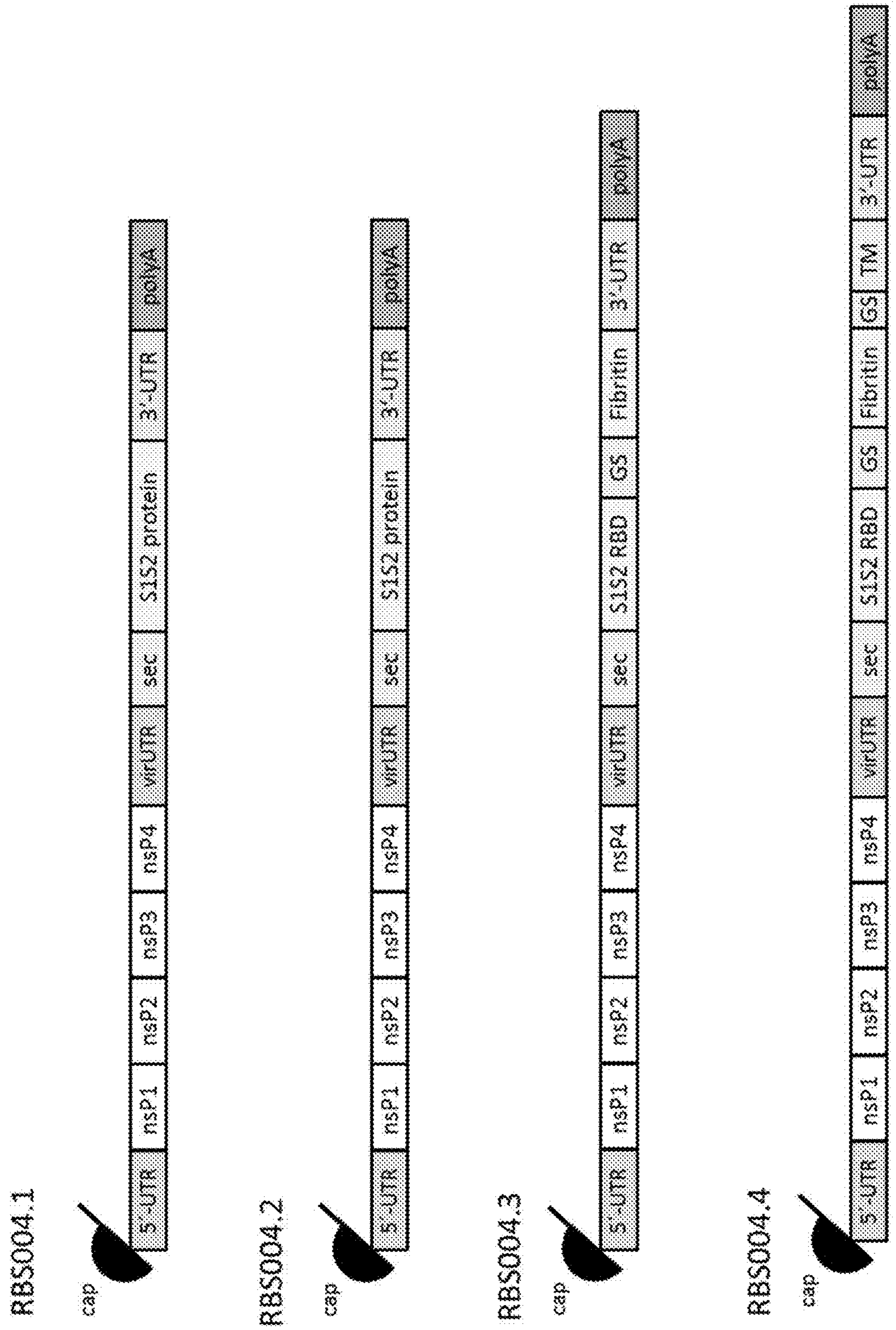

FIG. 21: General structure of the RNA.

Schematic illustration of the general structure of the RNA vaccines with 5'-cap, 5'- and 3'-untranslated regions, coding sequences of the Venezuelan equine encephalitis virus (VEEV) RNA-dependent RNA polymerase replicase and the SARS-CoV-2 antigen with intrinsic secretory signal peptide as well as GS-linker, and poly(A)-tail. Please note that the individual elements are not drawn exactly true to scale compared to their respective sequence lengths. UTR=Untranslated region; Sec=Secretory signal peptide; RBD=Receptor Binding Domain; GS=Glycine-serine linker.

Figure 22:
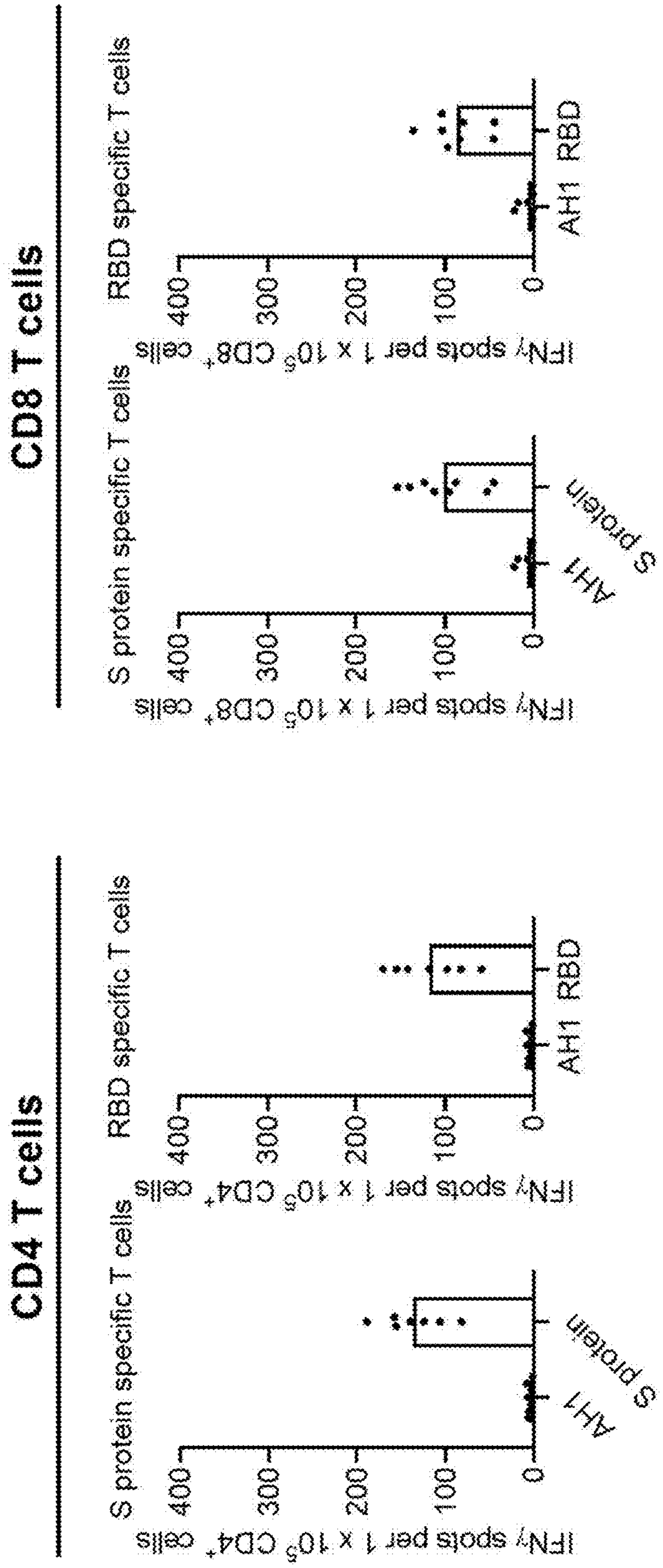

FIG. 22: ELISpot analysis 28 d after immunization with BNT162b1.

BALB/c mice were immunized IM once with 1 μg of LNP-formulated RBP020.3. On day 28 after immunization, mice were euthanized and splenocytes were prepared. ELISpot assay was performed using MACS-sorted CD4+ and CD8+ T cells. T cells were stimulated with an S protein- or RBD-specific overlapping peptide pool and IFN-γ secretion was measured to assess T-cell responses. One point in the graph stands for the individual spot count of one mouse, every mouse sample was measured in duplicates (group size n=8; mean is included for the groups).

Figure 23:
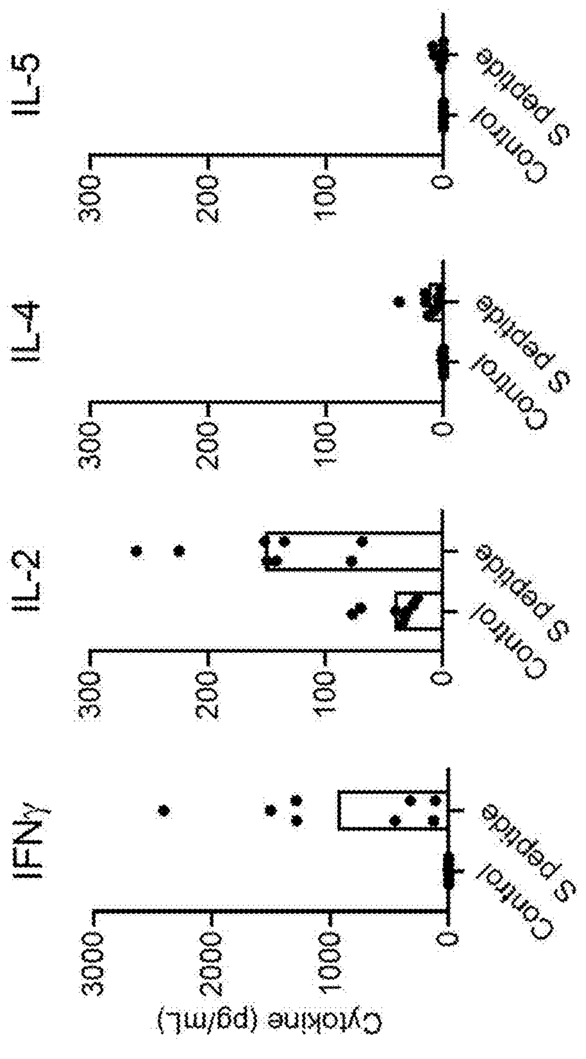

FIG. 23: Cytokine concentrations in supernatants of re-stimulated splenocytes 12 d after immunization with BNT162b1.

BALB/c mice were immunized IM once with 5 μg of LNP-formulated RBP020.3. On day 12 after immunization, mice were euthanized. Splenocytes were prepared and were stimulated with an S protein-specific overlapping peptide pool. After 48 h of stimulation, supernatant was collected and cytokine concentrations were determined. One point in the graph stands for the individual cytokine concentration of one mouse, every mouse sample was measured in duplicates (group size n=8; mean is included for the groups).

Figure 24:
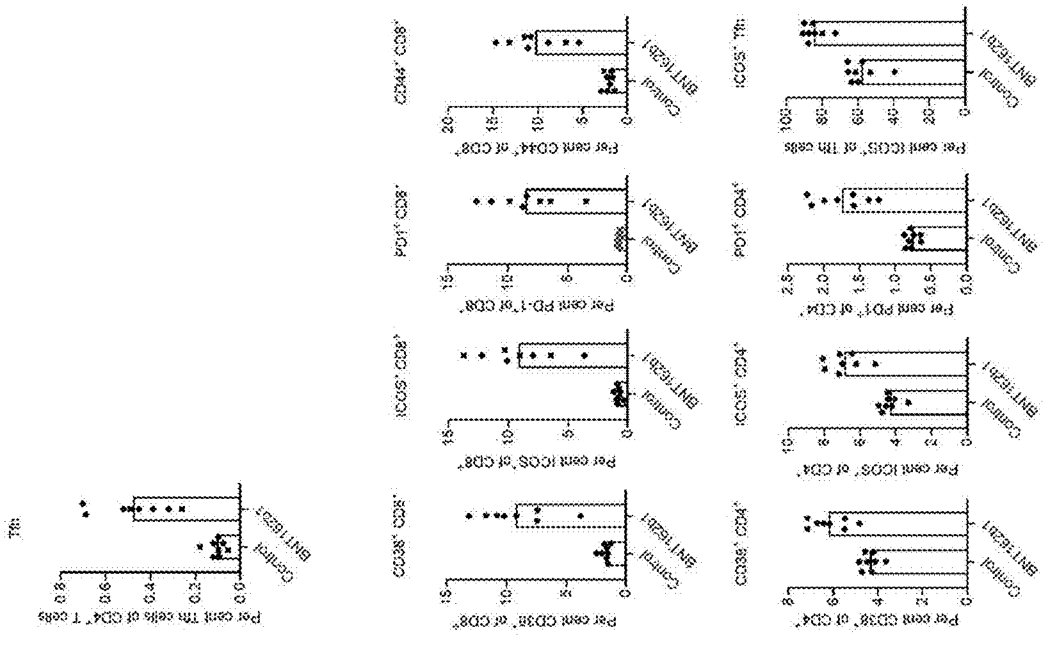

FIG. 24: T cell immunophenotyping in PBMCs 7 days after immunization with BNT162b1.

BALB/c mice were immunized IM once with 5 μg of LNP-formulated RBP020.3. On day 7 after immunization, mice were bled. Flow cytometry analysis of PBMCs was performed of T cells. T cells were defined as viable $CD3^+$ $CD4^+$ and $CD3^+CD8^+$ T cells. Additional phenotyping markers are included in the figures. Tfh cells were gated from CD4+ T cells and defined as $CD4^+T\text{-}bet^-GATA3^-$ $CD44^+CD62L^-PD\text{-}1^+CXCR5^+$ cells. One point in the graph stands for the individual cell fraction of one mouse (group size n=8; mean is included for the groups).

Figure 25:
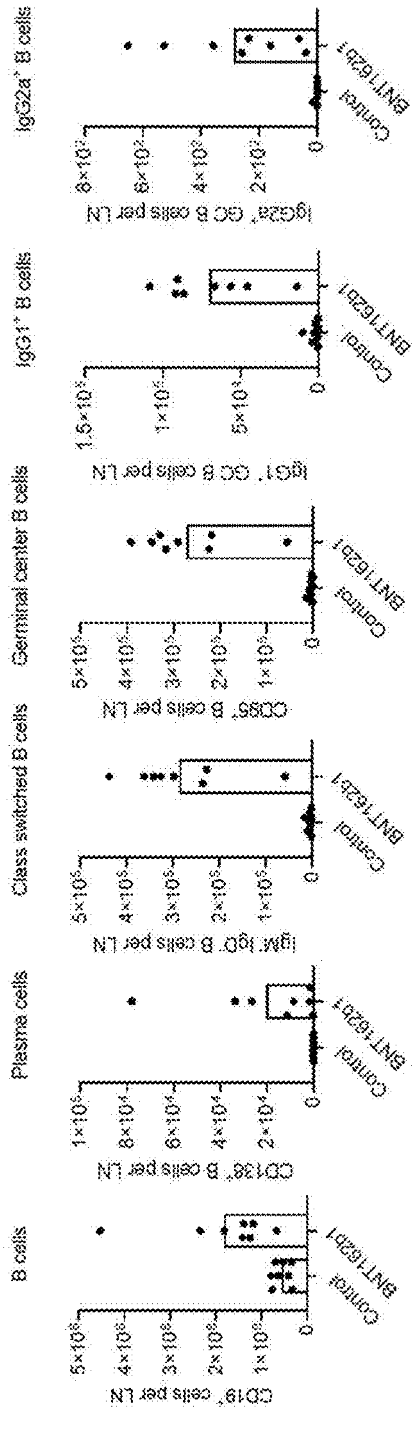

FIG. 25: B cell immunophenotyping in draining lymph nodes 12 days after immunization with BNT162b1.

BALB/c mice were immunized IM once with 5 μg of LNP-formulated RBP020.3. On day 12 after immunization, mice were euthanized. Flow cytometry analysis of lymphocytes was performed of B cells. Activated B cells were gated within single, viable lymphocytes and defined as IgD-Dump (CD4, CD8, F4/80, GR-1)$^-$ cells. Plasma cells were defined as $CD138^+B220^{low/-}$ cells. Switched B cells were gated from non-plasma cells and defined as $CD19^+CD138^-IgM^-$. Germinal center (GC) B cells were gated from switched B cells and defined as $CD19^+IgM^-CD38^-CD95^+$ cells and gated for IgG1 and IgG2a. One point in the graph stands for the individual cell fraction of one mouse (group size n=8; mean is included for the groups).

Figure 26:
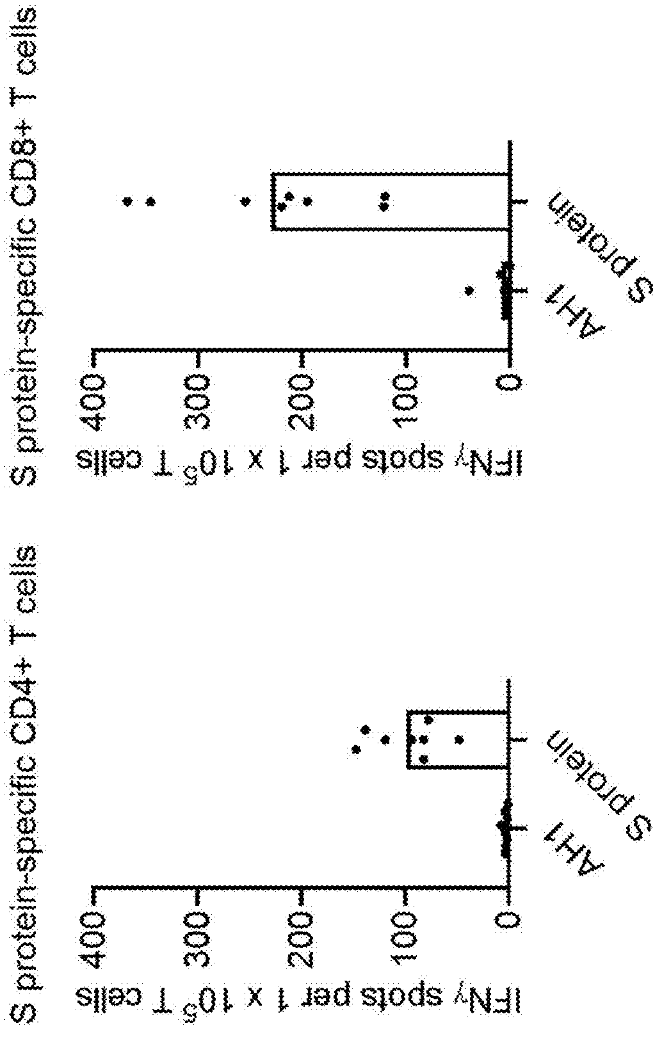

FIG. 26: ELISpot analysis 28 d after immunization with LNP-formulated modRNA RBP020.1.

BALB/c mice were immunized IM once with 5 μg of LNP-formulated RBP020.1. On day 28 after immunization, mice were euthanized and splenocytes were prepared. ELISpot assay was performed using MACS-sorted CD4+ and CD8+ T cells. T cells were stimulated with an S protein-specific overlapping peptide pool and IFN-γ secretion was measured to assess T-cell responses. One point in the graph stands for the individual spot count of one mouse, every mouse sample was measured in duplicates (group size n=8; mean is included for the groups).

Figure 27:
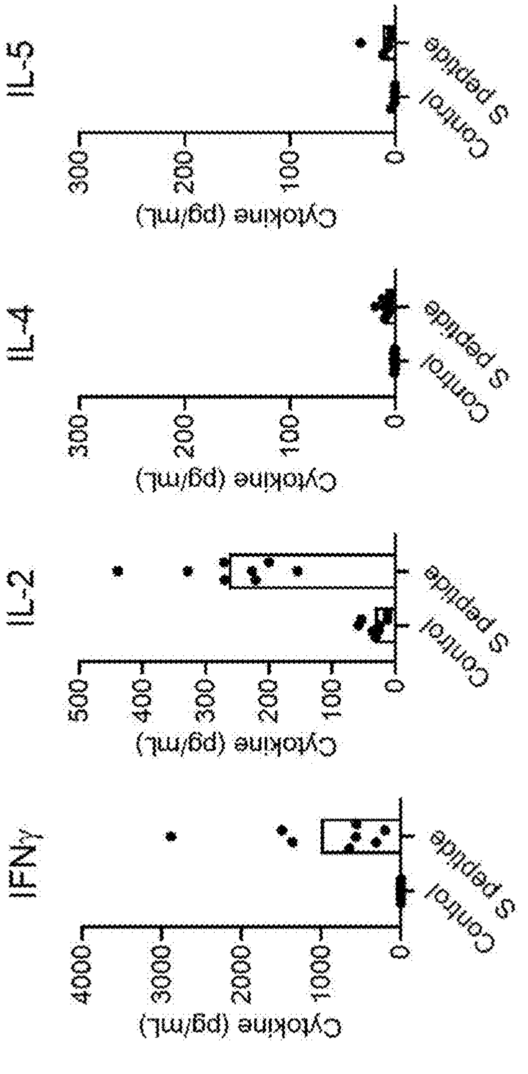

FIG. 27: Cytokine concentrations in supernatants of re-stimulated splenocytes 28 d after immunization with LNP-formulated modRNA RBP020.1.

BALB/c mice were immunized IM once with 5 μg of LNP-formulated RBP020.1. On day 28 after immunization, mice were euthanized. Splenocytes were prepared and were stimulated with an S protein-specific overlapping peptide pool. After 48 h of stimulation, supernatant was collected and cytokine concentrations were determined. One point in the graph stands for the individual cytokine concentration of one mouse, every mouse sample was measured in duplicates (group size n=8; mean is included for the groups).

Figure 28:
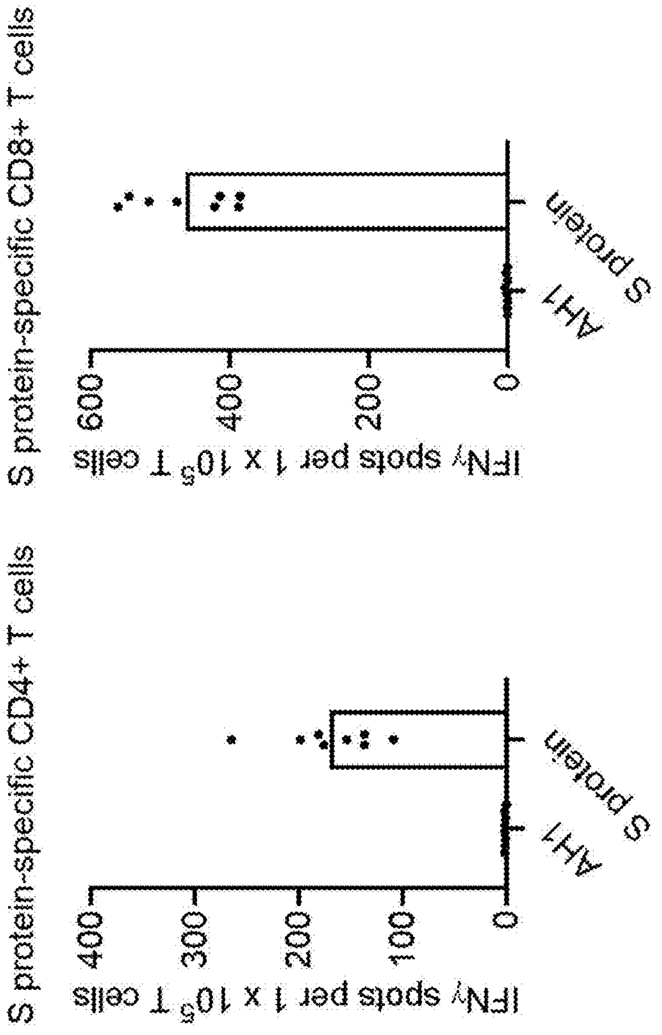

FIG. 28: ELISpot analysis 28 d after immunization with LNP-formulated saRNA RBS004.2. BALB/c mice were immunized IM once with 5 μg of LNP-formulated RBS004.2. On day 28 after immunization, mice were euthanized and splenocytes were prepared. ELISpot assay was performed using MACS-sorted CD4+ and CD8+ T cells. T cells were stimulated with an S protein-specific overlapping peptide pool and IFN-γ secretion was measured to assess T-cell responses. One point in the graph stands for the individual spot count of one mouse, every mouse sample was measured in duplicates (group size n=8; mean is included for the groups).

Figure 29:
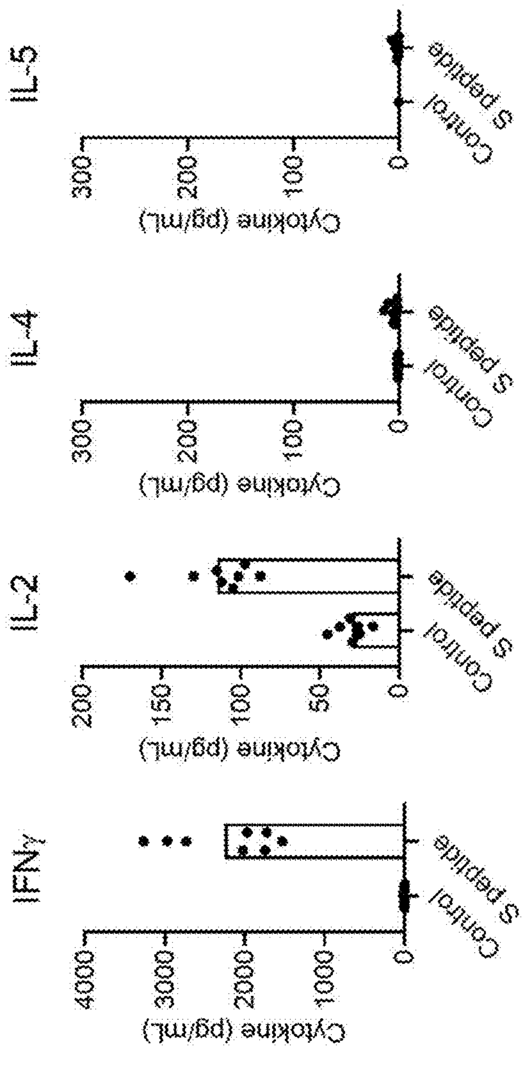

FIG. 29: Cytokine concentrations in supernatants of re-stimulated splenocytes 28 d after immunization with LNP-formulated saRNA RBS004.2.

BALB/c mice were immunized IM once with 1 μg of LNP-formulated RBS004.2. On day 28 after immunization, mice were euthanized. Splenocytes were prepared and were stimulated with an S protein-specific overlapping peptide pool. After 48 h of stimulation, supernatant was collected and cytokine concentrations were determined. One point in the graph stands for the individual cytokine concentration of one mouse, every mouse sample was measured in duplicates (group size n=8; mean is included for the groups).

Figure 30:
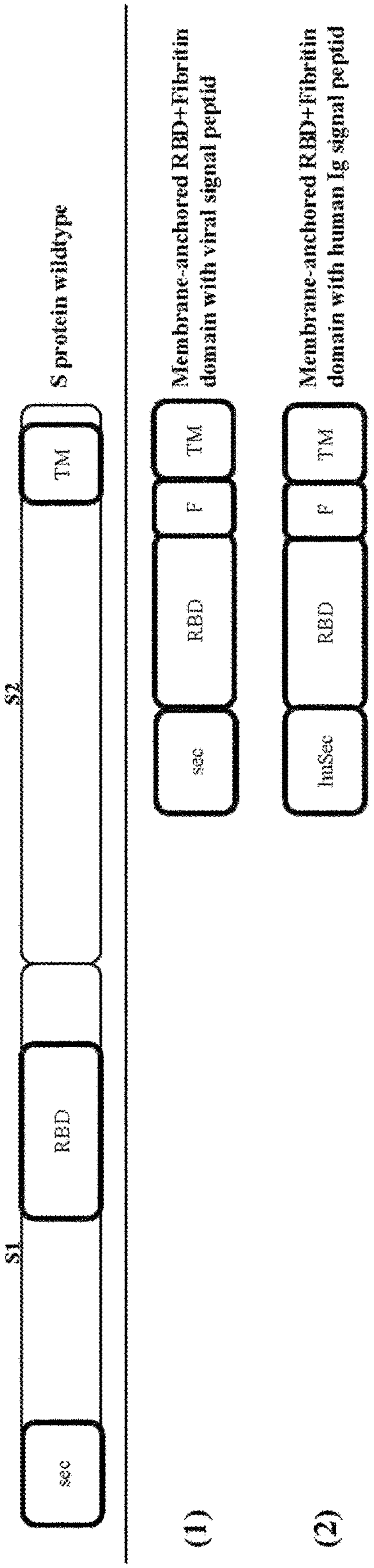

FIG. 30: Schematic overview of the S protein organization of the SARS-CoV-2 S protein and novel constructs for the development of a SARS-CoV-2 vaccine.

Based on the wildtype S protein, we have designed two different transmembrane-anchored RBD-based vaccine constructs encoding the RBD fragment fused to the T4 fibritin trimerization domain (F) and the autochthonus transmembrane domain (TM). Construct (1) starts with the SARS-CoV-2-S signal peptide (SP; AA 1-19 of the S protein) whereas construct (2) starts with the human Ig heavy chain signal peptide (huSec) to ensure Golgi transport to the cell membrane.

Figure 31:
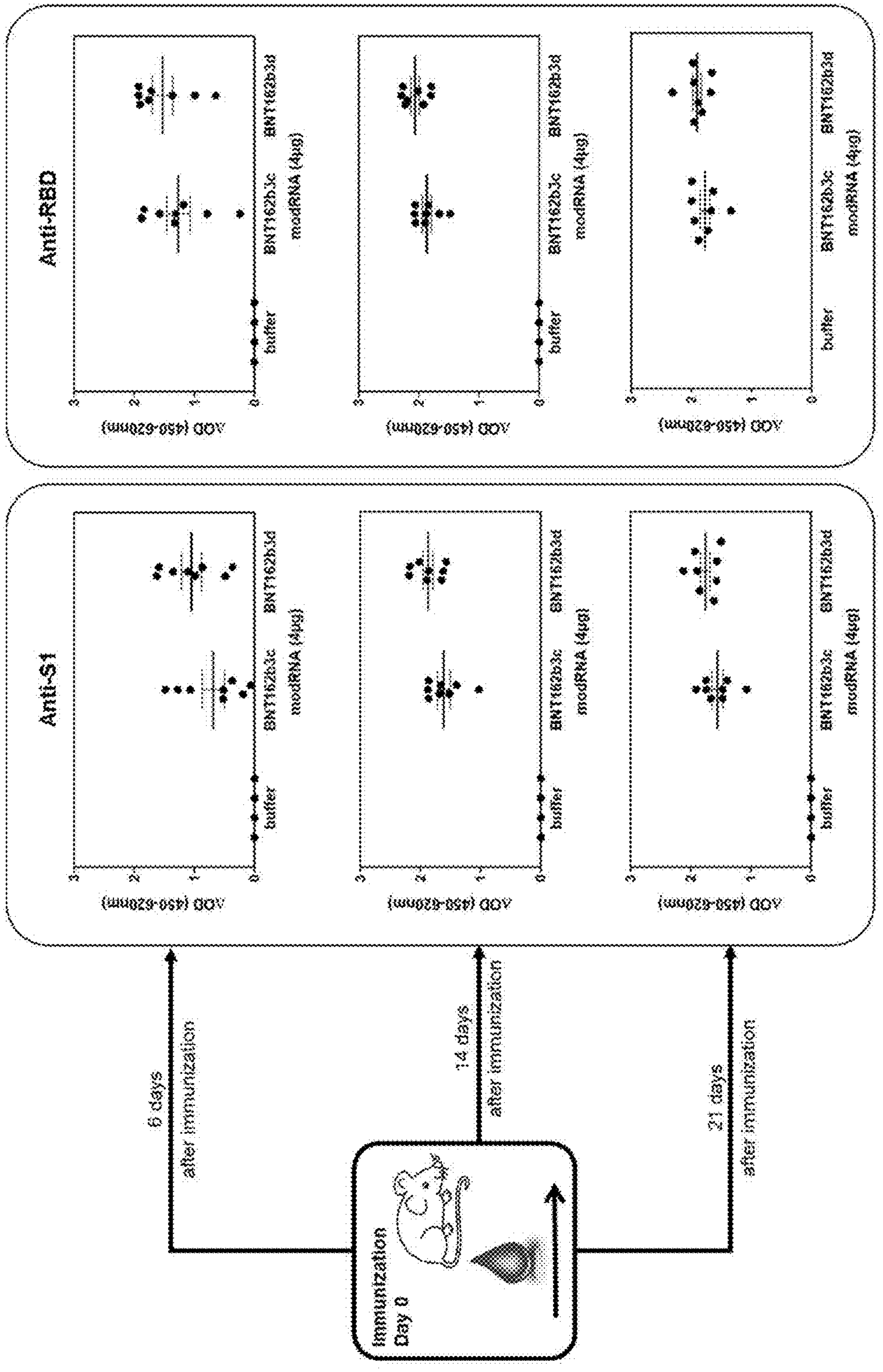

FIG. 31: Anti-S protein IgG response 6, 14 and 21 d after immunization with LNP-C12 formulated modRNA coding for transmembrane-anchored RBD-based vaccine constructs.

BALB/c mice were immunized IM once with 4 μg of LNP-C12-formulated transmembrane-anchored RBD-based vaccine constructs (surrogate to BNT162b3c/BNT162b3d). On day 6, 14 and 21 after immunization, animals were bled and the serum samples were analyzed for total amount of anti-S1 (left) and anti-RBD (right) antigen specific immunoglobulin G (IgG) measured via ELISA. For day 6 (1:50), day 14 (1:300) and day 21 (1:900) different serum dilution were included in the graph. One point in the graph stands for one mouse, every mouse sample was measured in duplicates (group size n=8; mean+SEM is included for the groups).

Figure 32:
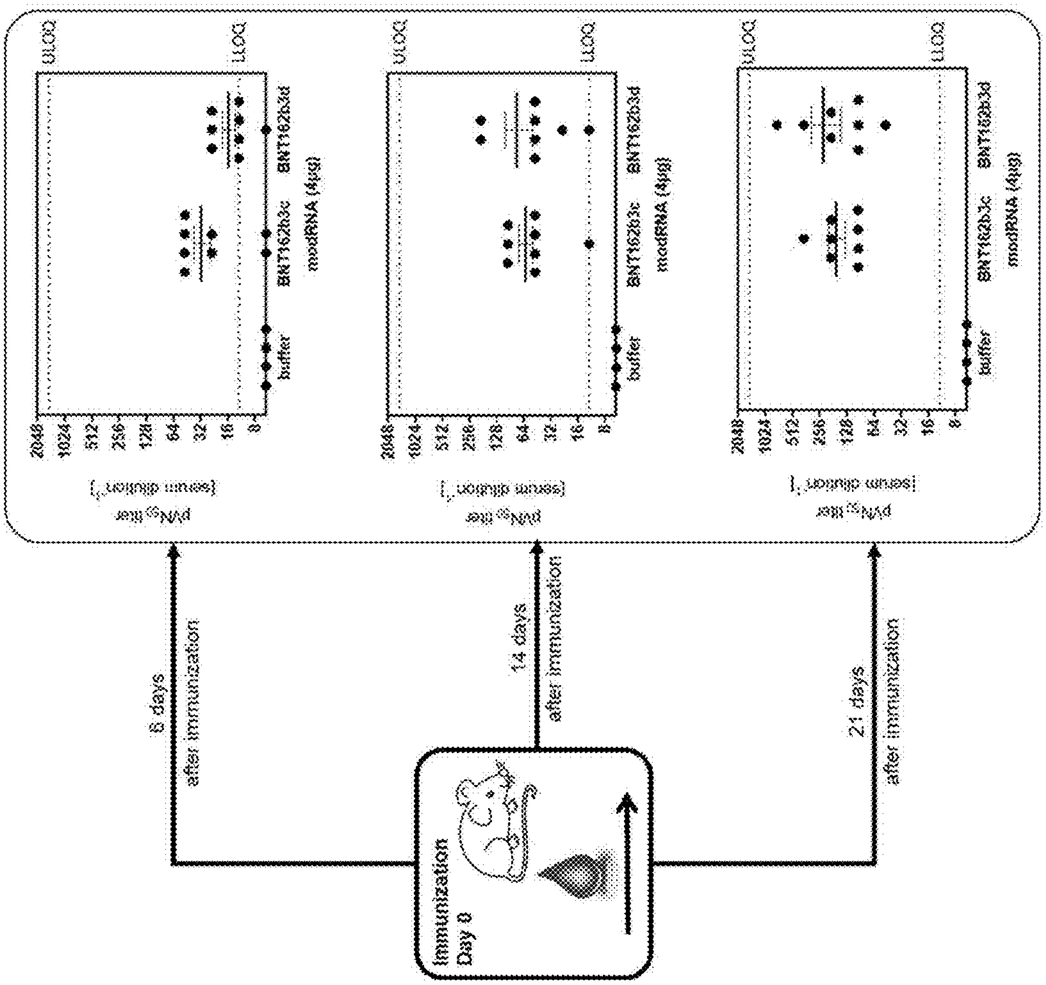

FIG. 32: Neutralization of SARS-CoV-2 pseudovirus 6, 14 and 21 d after immunization with LNP-C12 formulated modRNA coding for transmembrane-anchored RBD-based vaccine constructs.

BALB/c mice were immunized IM once with 4 μg of LNP-C12-formulated transmembrane-anchored RBD-based vaccine constructs (surrogate to BNT162b3c/BNT162b3d). On day 6, 14 and 21 after immunization, animals were bled and the sera were tested for SARS CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 33:
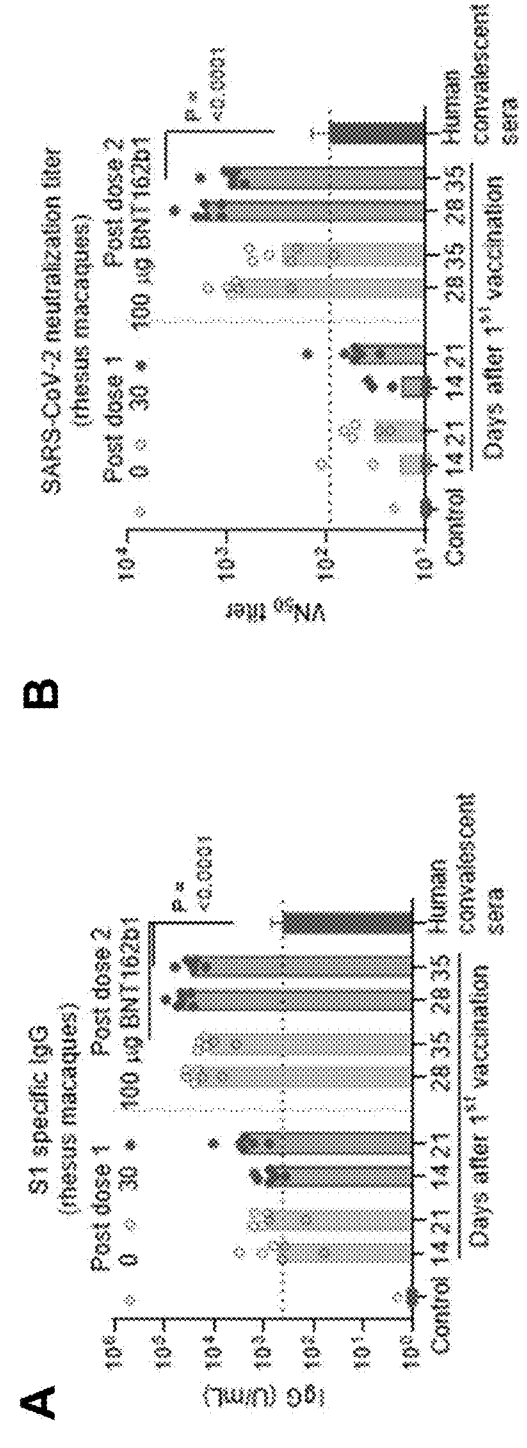

FIG. 33: Immunogenicity of BNT162b1 in *Rhesus macaques* and comparison to human convalescent sera.

*Rhesus macaques* were immunized IM on days 0 and 21 with 30 μg or 100 μg of BNT162b1 or with placebo (0.9% NaCl). Sera were obtained before immunization and 14, 21, 28, and 35 days after immunization; PBMCs were obtained before and 14 and 42 days after immunization. Sera from COVID-19 patients were obtained 20-40 days after the onset of symptoms and after at least 14 days of asymptomatic convalescence. (A) Geometric mean concentrations of IgG binding to a recombinant S1 protease fragment of SARS-CoV-2 S, in *Rhesus macaque* sera drawn at the indicated times after immunization (n=6 per group, all measurement time points of the placebo group depicted under 'Control') and in human convalescent sera (n=62). (B) SARS-CoV-2 geometric mean 50% neutralization titers of the *Rhesus macaque* sera (n=6 per group, all measurement time points of the placebo group depicted under 'Control') and human convalescent sera (n=38). P values were determined by a two-tailed one-way ANOVA and Dunnett's multiple comparisons test. (C) Flow cytometry analysis of $CD4^+$ T cells producing IFNγ, IL-2, TNF ($T_H1$), IL-21 or IL-4 ($T_H2$) cytokines in the *Rhesus macaque* PBMCs on day 42. P values were determined by a two-tailed Kruskal-Wallis test followed by Dunn's multiple comparisons test. Each data point corresponds to an individual animal.

Figure 34:
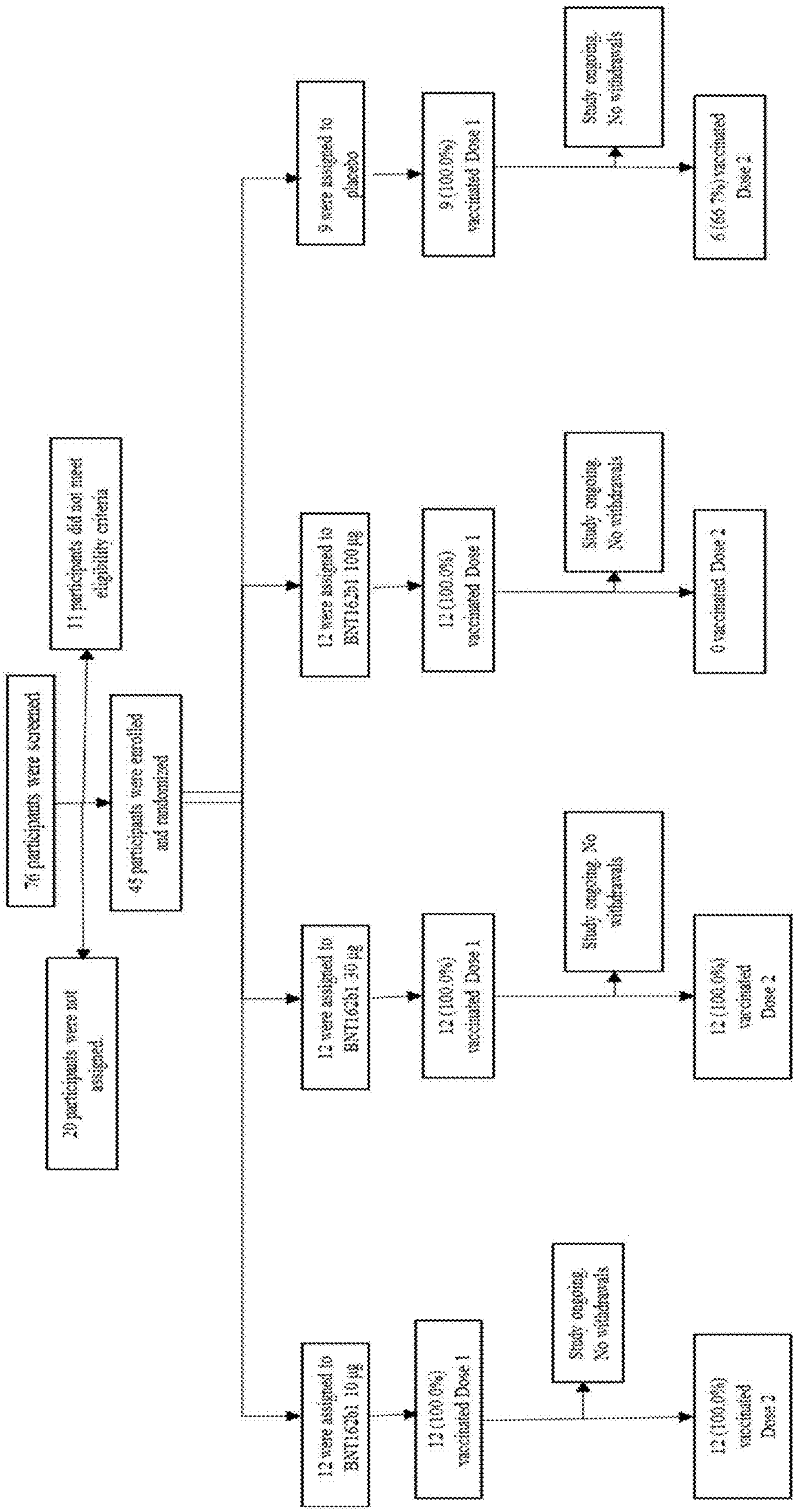

FIG. 34: Overview of study population

Figure 35:
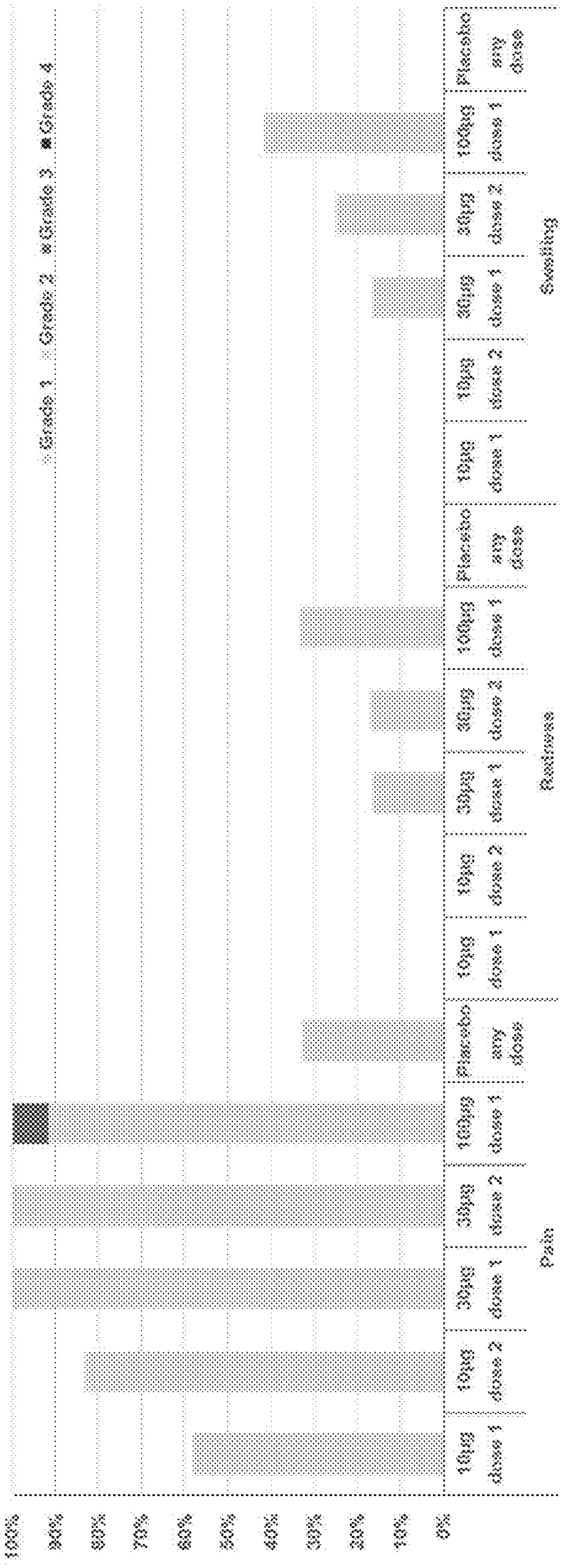

FIG. 35: Local Reactions Reported within 7 Days of Vaccination all Dose Levels Solicited injection-site (local) reactions were: pain at injection site (mild=does not interfere with activity; moderate=interferes with activity; severe=prevents daily activity; Grade 4=emergency room visit or hospitalization) and redness and swelling (mild=2.5 to 5.0 cm in diameter; moderate=5.5 to 10.0 cm in diameter; severe=>10.0 cm in diameter; Grade 4=necrosis or exfoliative dermatitis for redness, and necrosis for swelling). Data were collected with the use of electronic diaries for 14 days after each vaccination.

Figure 36:
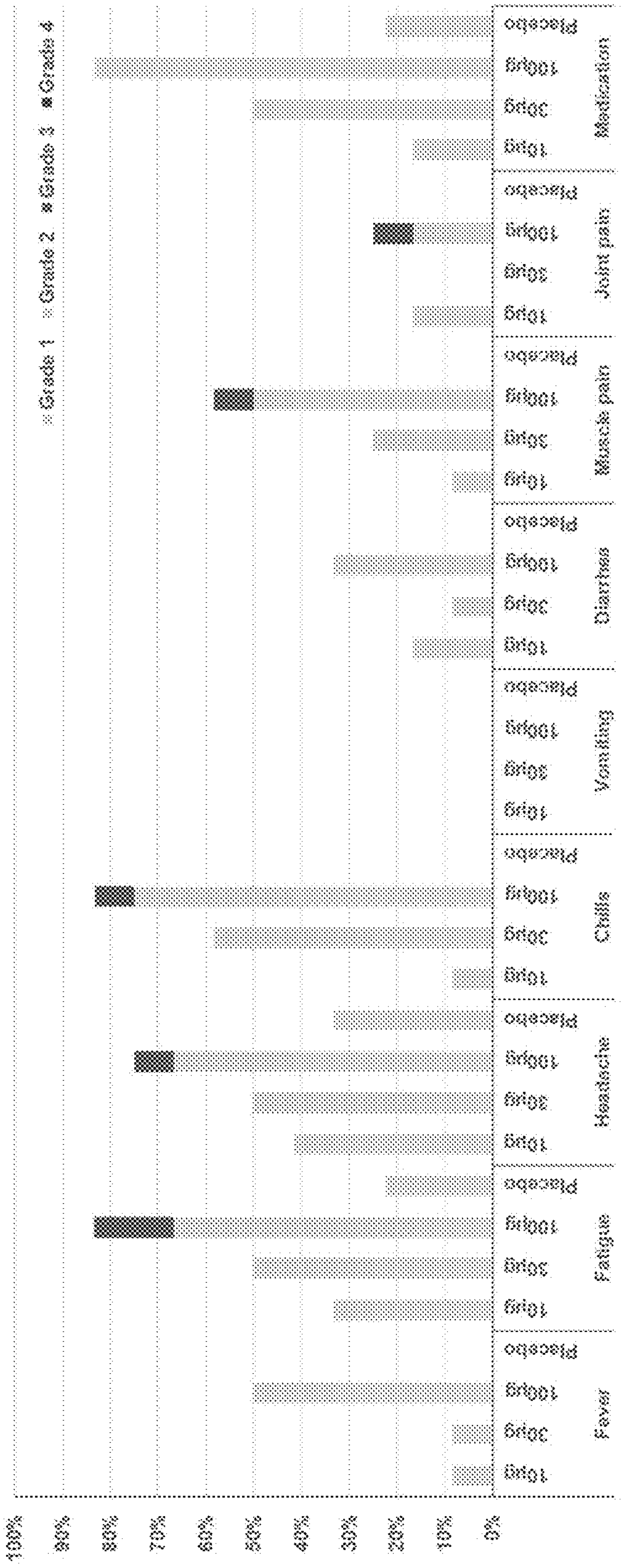
Figure 36:
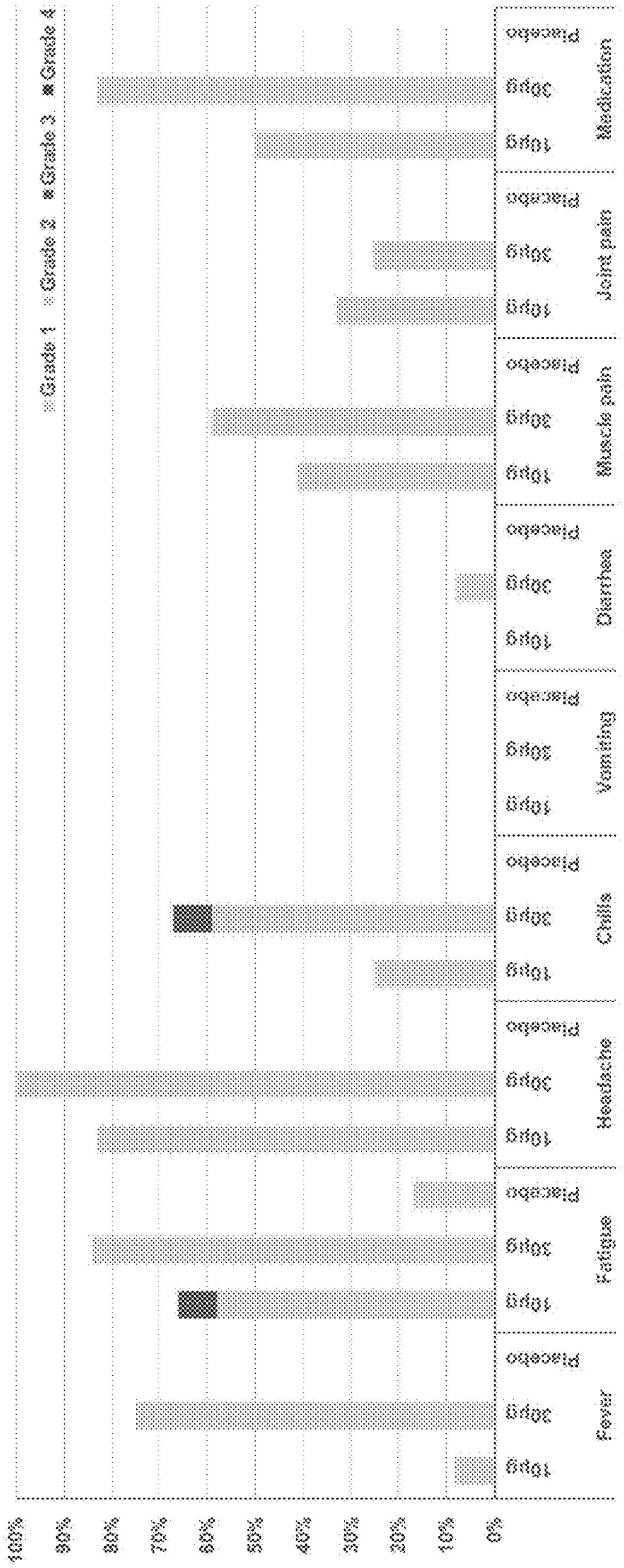

FIG. 36: (A) Systemic Events Reported within 7 days after Vaccination 1: All Dose Levels; (B) Systemic Events Reported within 7 days after Vaccination 2: 10 μg & 30 μg Dose Levels Solicited systemic events were: nausea/vomiting (mild=no interference with activity or 1 to 2 times in 24 hours; moderate=some interference with activity or >2 times in 24 hours; severe=prevents daily activity or requires intravenous hydration; Grade 4=emergency room visit or hospitalization for hypotensive shock), diarrhea (mild, 2 to 3 loose stools in 24 hours; moderate, 4 to 5 loose stools in 24 hours; severe, ≥6 loose stools in 24 hours; Grade 4=emergency room visit or hospitalization), headache (mild=no interference with activity; moderate=repeated use of non-narcotic pain reliever >24 hours or some interference with activity; severe=significant, any use of narcotic pain reliever or prevents daily activity; Grade 4=emergency room visit or hospitalization), fatigue/tiredness (mild=no interference with activity; moderate=some interference with activity; severe=significant; prevents daily activity; Grade 4=emergency room visit or hospitalization), muscle pain (pain that is occurring in areas other than the injection site; mild=no interference with activity; moderate=some interference with activity; severe=significant; prevents daily activity; Grade 4=emergency room visit or hospitalization), joint pain (mild=no interference with activity; moderate=some interference with activity; severe=significant; prevents daily activity; Grade 4=emergency room visit or hospitalization), and fever (mild=100.4° F. to 101.1° F. [38.0° C. to 38.4° C.]; moderate=101.2° F. to 102.0° F. [38.5° C. to 38.9° C.]; severe=102.1° F. to 104.0° F. [39.0° C. to 40.0° C.]; Grade 4=>104.0° F. [>40.0° C.]).

Figure 37:
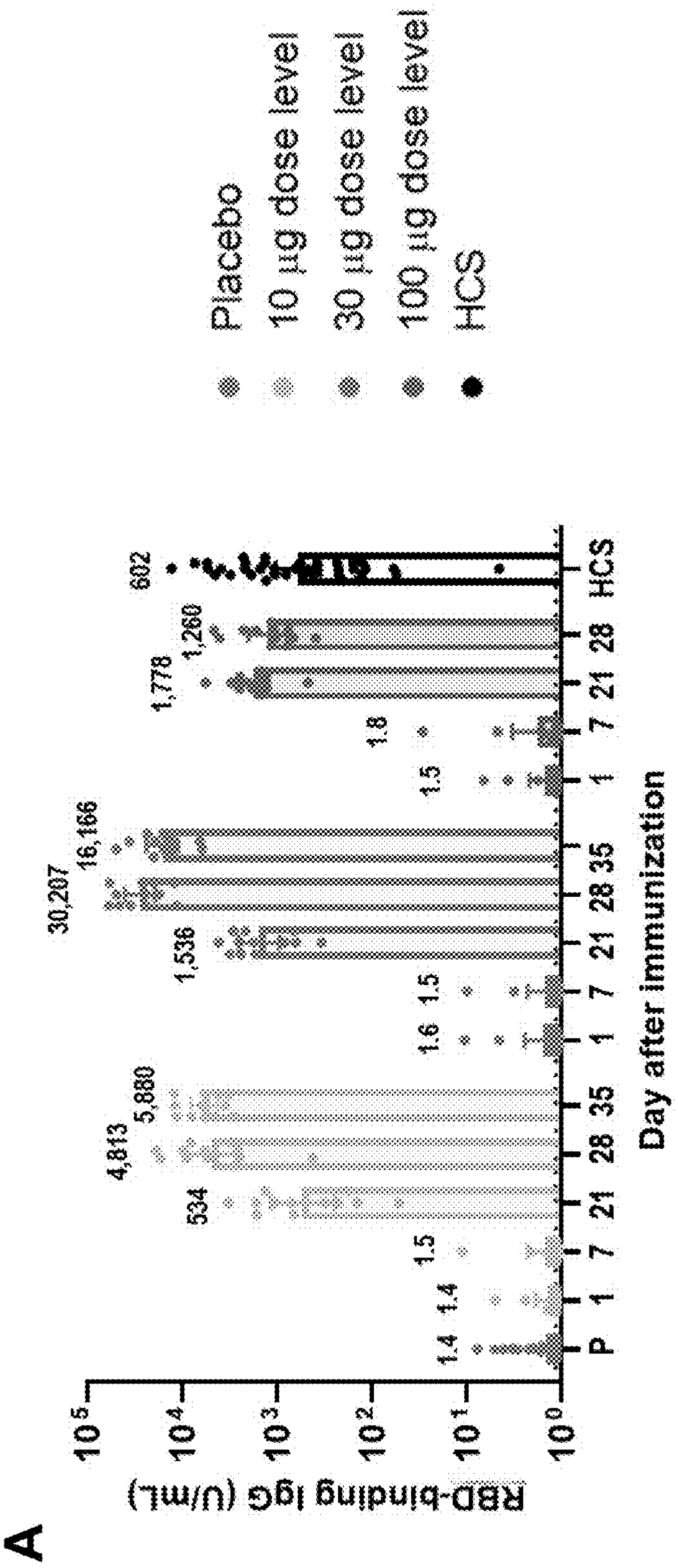
Figure 37:
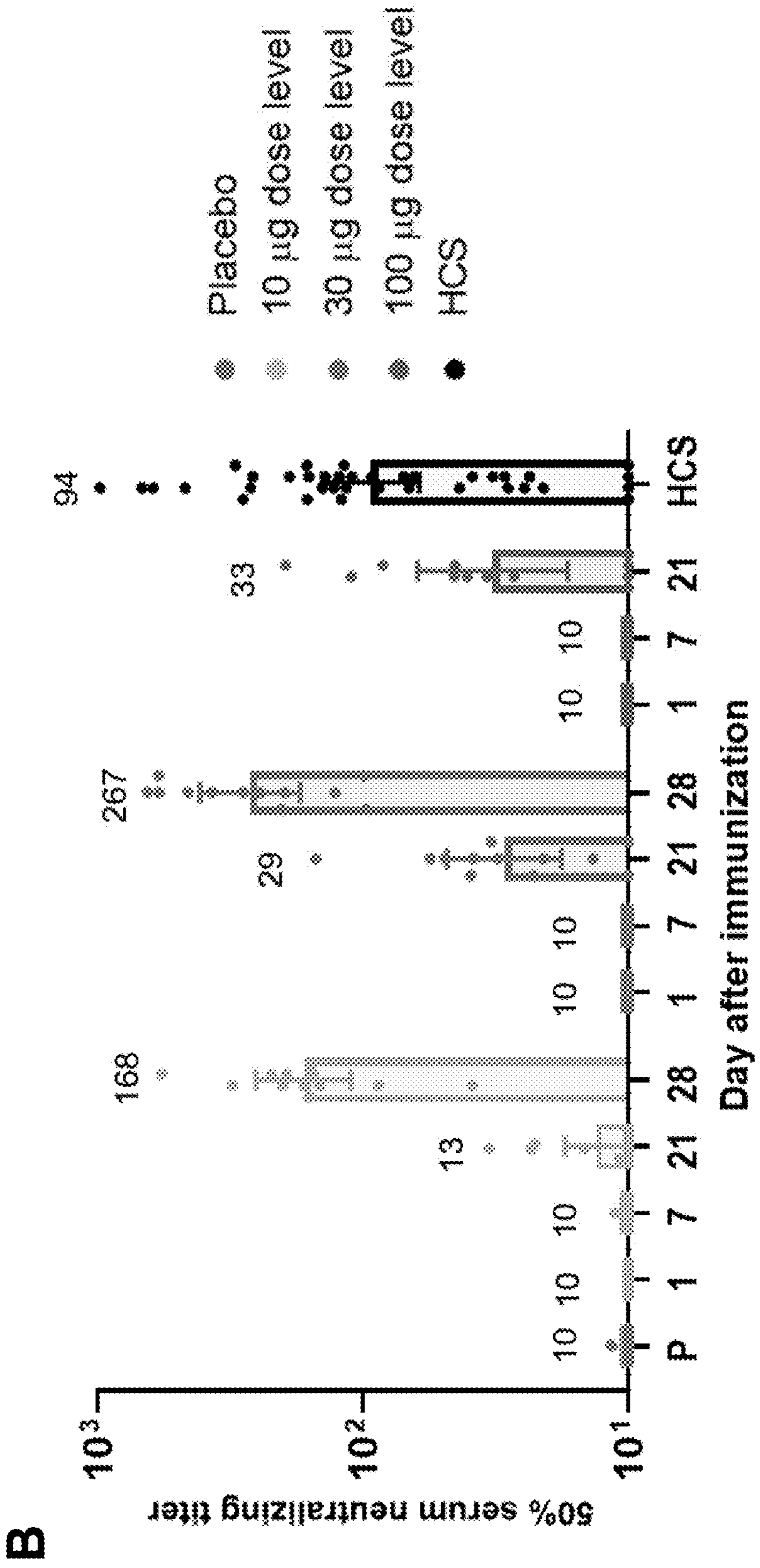

FIG. 37: Immunogenicity of BNT162b1—RBD-Binding IgG GMCs and SARS CoV2 50% Neutralizing Titers after 1 or 2 doses Subjects in groups of 15 were immunized with the indicated dose levels of BNT162b1 (n=12) or with placebo (P, n=3) on days 1 (all dose levels and placebo) and 21 (10 μg and 30 μg dose levels and placebo). Sera were obtained before immunization (Day 1) and 7, 21, and 28 days after the first immunization. Human COVID-19 convalescent sera (HCS) (n=38) were obtained 20-40 days after the onset of symptoms and after at least 14 days of asymptomatic convalescence. (A) GMCs of recombinant RBD-binding IgG. Lower limit of quantitation (LLOQ) 1.15 (dotted line). (B) 50% SARS-CoV-2 neutralizing GMTs. Each data point represents a serum sample, and each vertical bar represents a geometric mean with 95% confidence interval.

Figure 38:
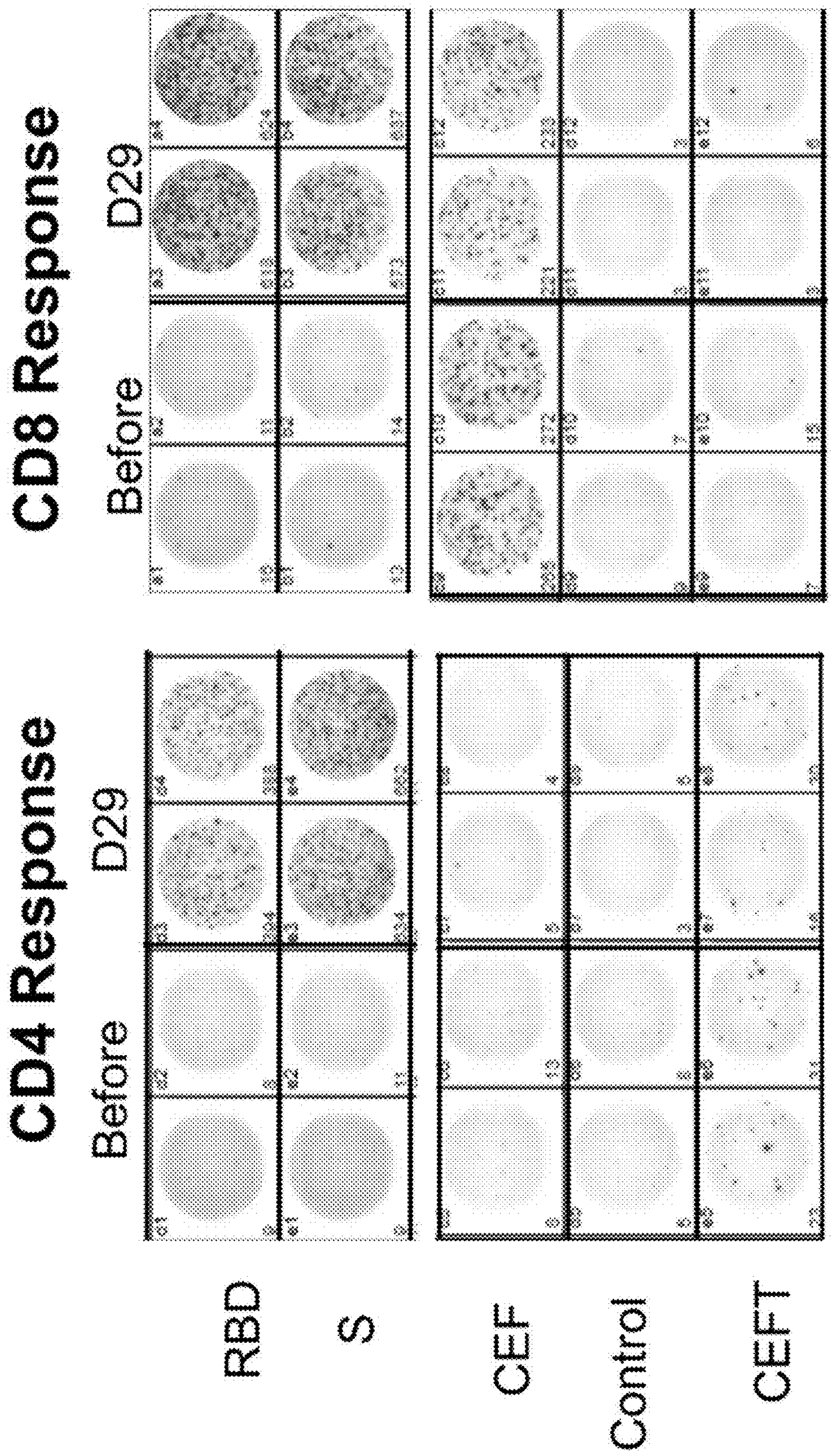

FIG. 38: BNT162b1 induces strong CD4 and CD8 T cell response in humans

BNT162 induced T cells: INFγ ELISpot ex vivo; T cell responses in 8 of 8 tested subjects. Here: subject vaccinated prime/boost with 10 μg BNT162b1; CEF: CMV, EBV, Influenza CD8 T cell epitope mix, CEFT: CMV, EBV, Influenza, Tetanus CD4 T cell epitope mix.

Figure 39:
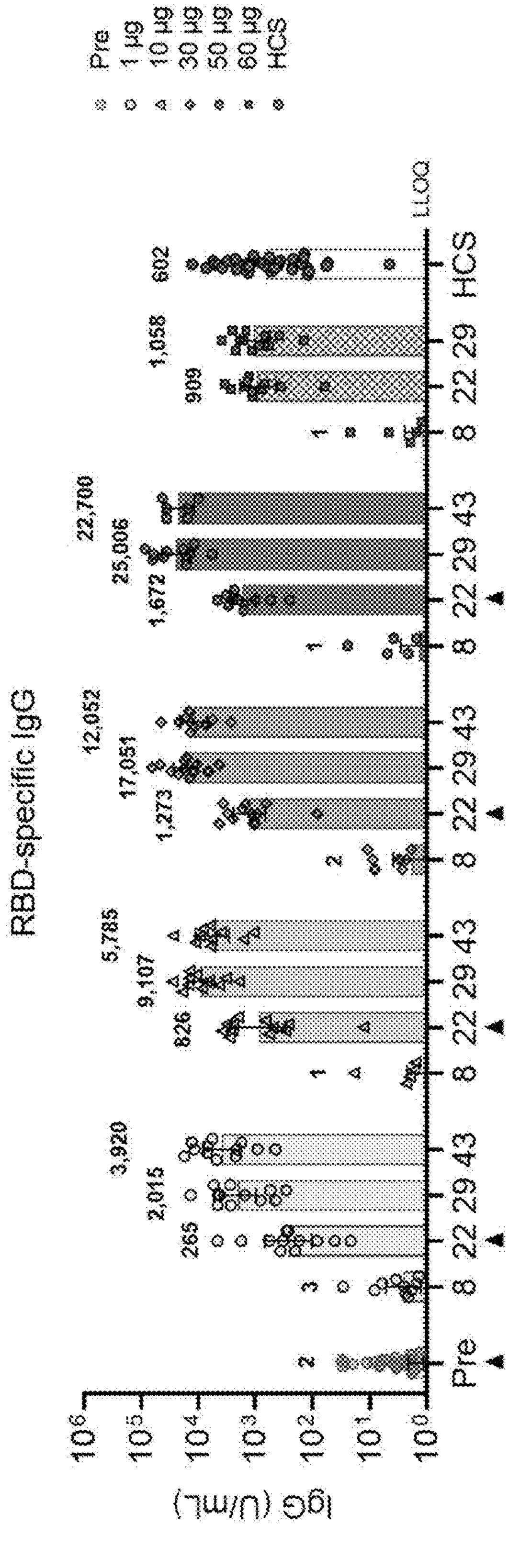

FIG. 39: BNT162b1-induced IgG concentrations

Subjects were immunised with BNT162b1 on days 1 (all dose levels) and 22 (all dose levels except 60 μg) (n=12 per group, from day 22 on n=11 for the 10 μg and 50 μg cohort). Sera were obtained on day 1 (Pre prime) and on day 8, 22 (pre boost), 29 and 43. Pre-dose responses across all dose levels were combined. Human COVID-19 convalescent sera (HCS, n=38) were obtained at least 14 days after PCR-confirmed diagnosis and at a time when the donors were no longer symptomatic. For RBD-binding IgG concentrations below the lower limit of quantification (LLOQ=1.15), LLOQ/2 values were plotted. Arrowheads indicate vaccination. Chequered bars indicate that no boost immunisation was performed. Values above bars are geometric means with 95% confidence intervals. At the time of submission, day 43 data were pending for five subjects of the 50 μg cohort and all subjects of the 60 μg cohort.

Figure 40:
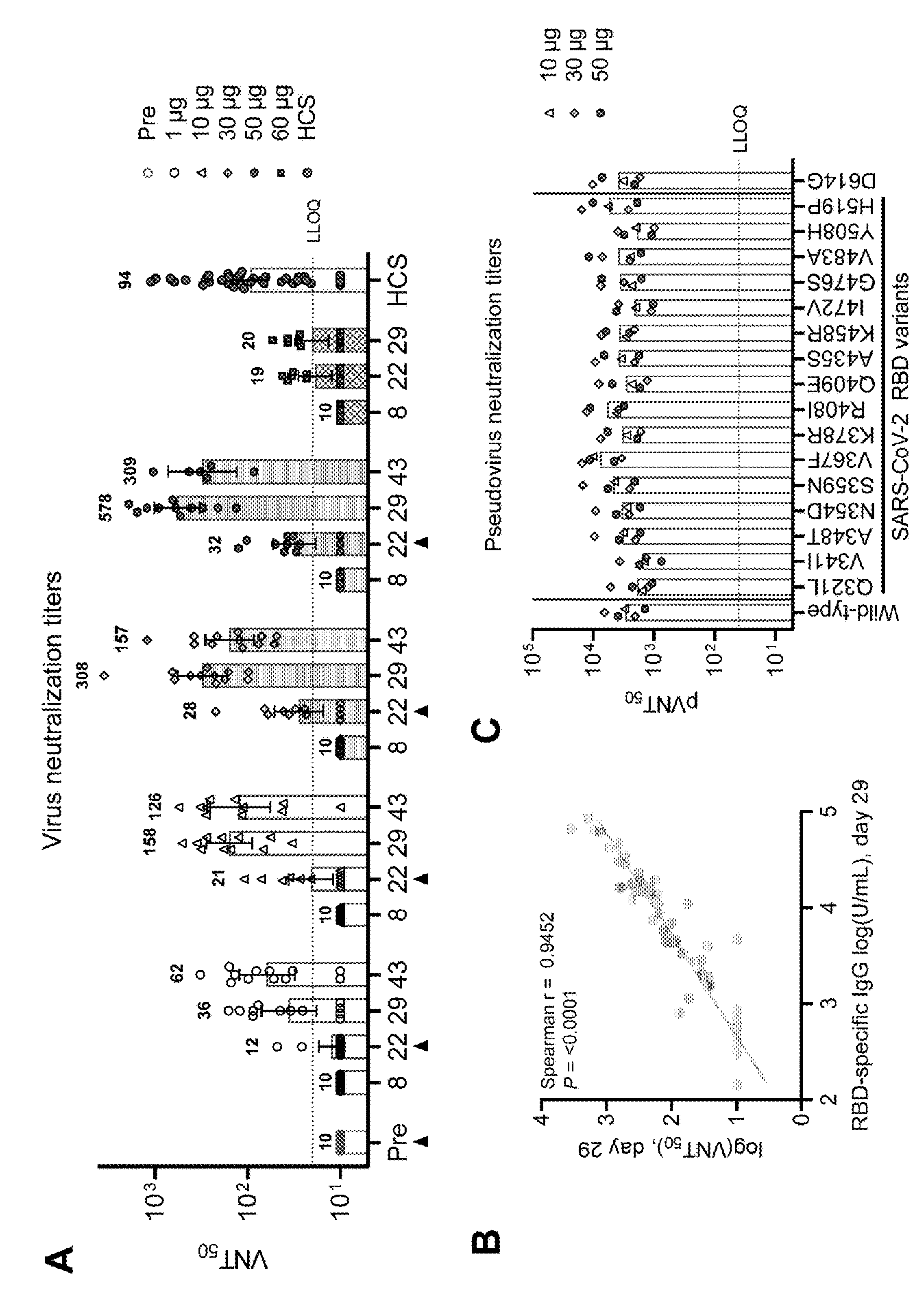

FIG. 40: BNT162b1-induced virus neutralisation titers

The vaccination schedule and serum sampling are the same as in FIG. 39. (A) SARS-CoV-2 50% neutralisation titers ($VNT_{50}$) in immunized subjects and COVID-19 convalescent patients (HCS). For values below the lower limit of quantification (LLOQ)=20, LLOQ/2 values were plotted. Arrowheads indicate days of immunisation. Chequered bars indicate that no boost immunisation was performed. Geometric mean (values above bars) with 95% confidence interval. At the time of submission, day 43 data were not yet available for five subjects of the 50 μg cohort and all subjects of the 60 μg cohort, (B) Correlation of RBD-binding IgG geometric mean concentrations (GMC) (as in FIG. 39) with $VNT_{50}$ on day 29 (all evaluable subject sera). Nonparametric Spearman correlation. (C) Pseudovirus 50% neutralisation titers ($pVNT_{50}$) across a pseudovirus panel displaying 17 SARS-CoV-2 spike protein variants including 16 RBD mutants and the dominant spike protein variant D614G (dose level 10, 30 and 50 μg, n=1-2 each; day 29). Lower limit of quantification (LLOQ)=40. Geometric mean.

Figure 41:
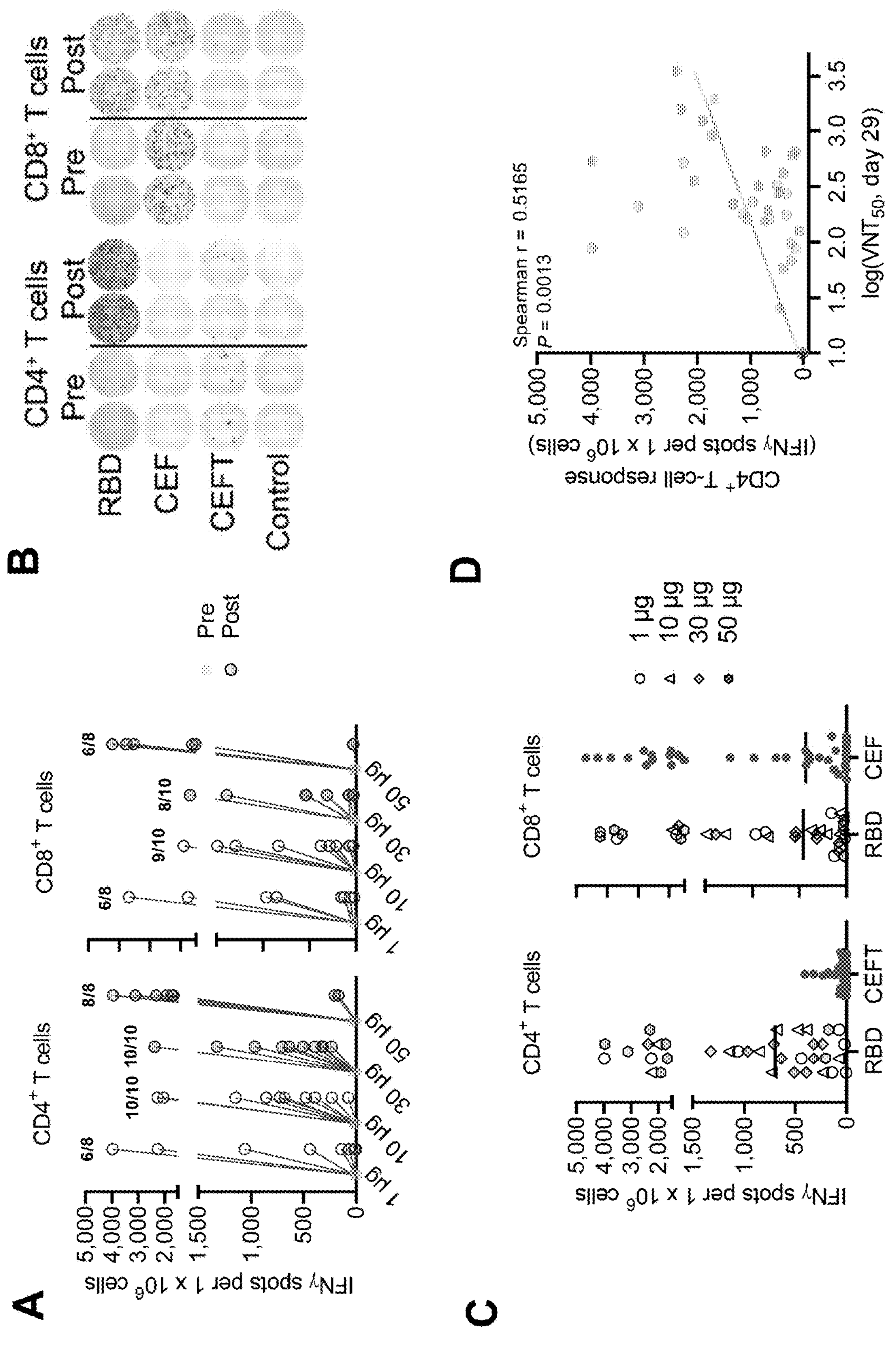

FIG. 41: Frequency and magnitude of BNT162b1-induced $CD4^+$ and $CD8^+$ T-cell responses The vaccination schedule is as in FIG. 39. PBMCs obtained on day 1 (Pre) and on day 29 (Post, 7 days after boost) (1 and 50 μg, n=8 each; 10 and 30 μg, n=10 each) were enriched for $CD4^+$ or $CD8^+$ T cell effectors and separately stimulated over night with an overlapping peptide pool representing the vaccine-encoded RBD for assessment in direct ex vivo IFNγ ELISpot. Common pathogen T-cell epitope pools CEF (CMV, EBV, influenza virus HLA class I epitopes) and CEFT (CMV, EBV, influenza virus, tetanus toxoid HLA class II epitopes) served to assess general T-cell reactivity, medium served as negative control. Each dot represents the normalized mean spot count from duplicate wells for one study subject, after subtraction of the medium-only control. (A) Ratios above post-vaccination data points are the number of subjects with detectable $CD4^+$ or $CD8^+$ T cell response within the total number of tested subjects per dose cohort. (B) Exemplary $CD4^+$ and $CD8^+$ ELISpot of a 10-μg cohort subject. (C) RBD-specific $CD4^+$ and $CD8^+$ T cell responses in all prime/boost vaccinated subjects and their baseline CEFT- and CEF-specific T-cell responses. (D) Correlation of $VNT_{50}$ (as in FIG. 40(A)) with $CD4^+$ T-cell responses (as in FIG. 41) of dose cohorts 10 to 50 μg (1 and 50 μg, n=8 each; 10 and 30 μg, n=10 each). Nonparametric Spearman correlation.

Figure 42:
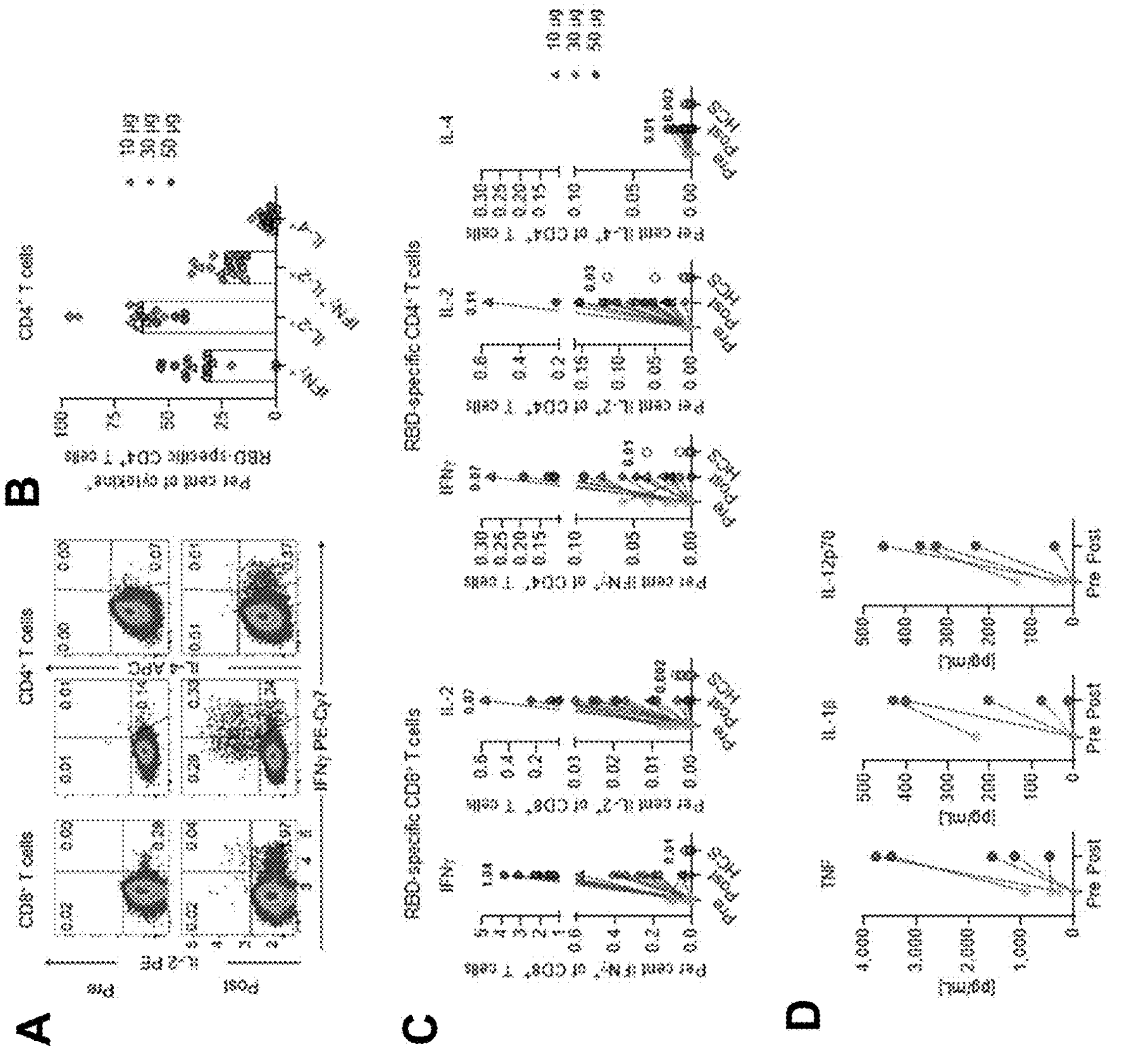

FIG. 42: Cytokine polarisation of BNT162b1-induced T cells

The vaccination schedule and PBMC sampling are as in FIG. 41. PBMCs of vaccines and COVID-19 recovered donors (HCS n=6; in (C)) were stimulated over night with an overlapping peptide pool representing the vaccine-encoded RBD and analysed by flow cytometry ((A)-(C)) and bead-based immunoassay (D). (A) Exemplary pseudo color flow cytometry plots of cytokine-producing $CD4^+$ and $CD8^+$ T cells of a 10-μg cohort subject. (B) RBD-specific $CD4^+$ T cells producing the indicated cytokine as fraction of total cytokine-producing RBD-specific $CD4^+$ T cells, and (C) RBD-specific $CD8^+$ (left) or $CD4^+$ (right) T cells producing the indicated cytokine as fraction of total circulating T cells of the same subset. One CD4 non-responder (<0.02% total cytokine producing T cells) and one CD8 non-responder (<0.01% total cytokine producing T cells) from the 30-μg cohort were excluded in (B). Values above data points are the mean fractions across all dose cohorts. (D) PBMCs from the 50-μg cohort. Each dot represents the mean from duplicate wells subtracted by the DMSO control for one study subject. Lower limits of quantification (LLOQ) were 6.3 pg/mL for TNF, 2.5 pg/mL for IL-1β, and 7.6 pg/mL for IL-12p70. Mean (B).

Figure 43:
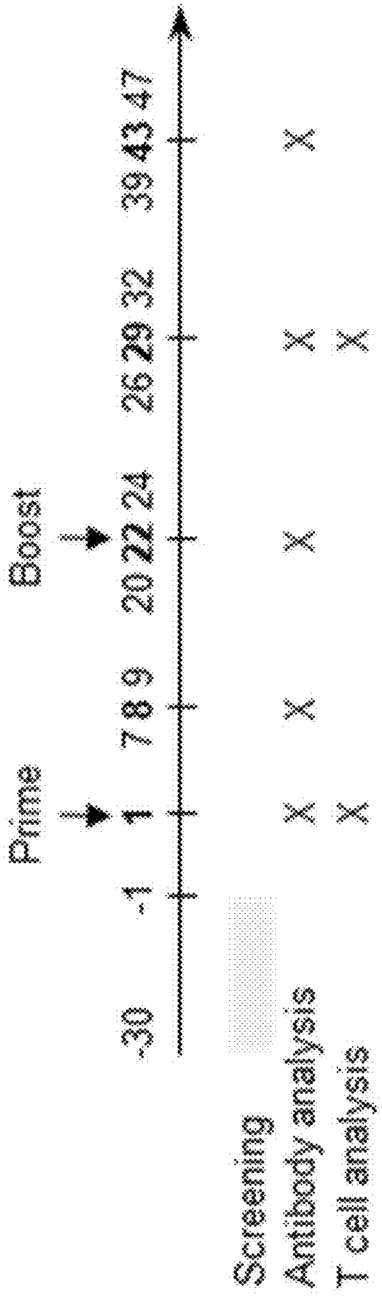

FIG. 43: Schedule of vaccination and assessment

Figure 44:
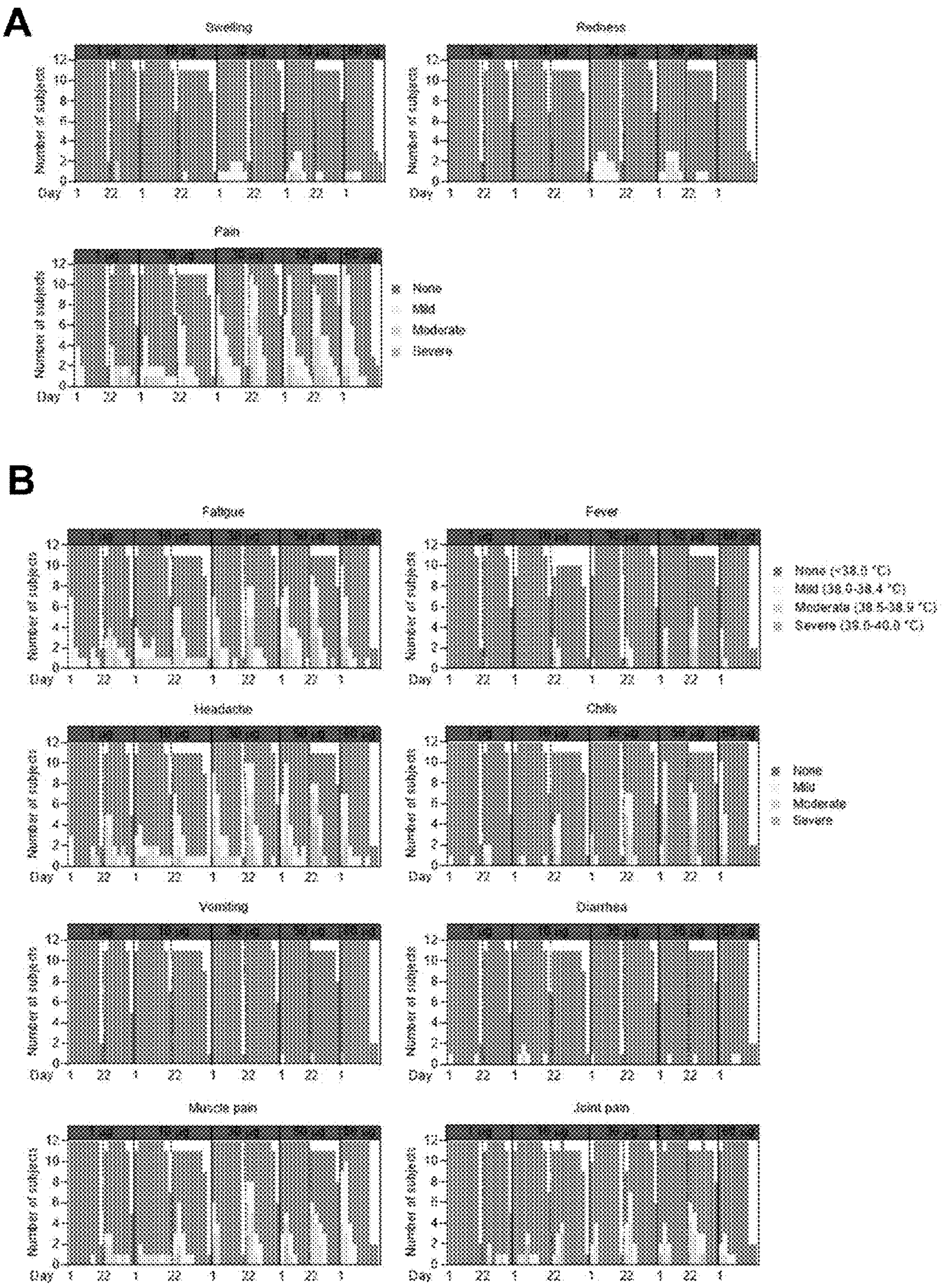

FIG. 44: Solicited adverse events

Subjects were immunized with the indicated dose levels of BNT162b1 on days 1 (all dose levels) and 22 (all dose levels except 60 μg) (n=12 per group, n=11 for 10 μg and 50 μg cohort from day 22 on). (A), (B) Number of subjects with local (A) or systemic reactions (B) by day (day 1-9, 22-30) and cohort. Grading of adverse events was performed according to FDA recommendations (U.S. Department of Health and Human Services, Administration, F. and D. & Research, C. for B. E. and. Toxicity grading scale for healthy adult and adolescent volunteers enrolled in preventive vaccine clinical trials. (2007). Available at: www.fda.gov/regulatory-information/search-fda-guidance-documents/toxicity-grading-scale-healthy-adult-and-adolescent- volunteers-enrolled-preventive-vaccine-clinical.).

Figure 45:
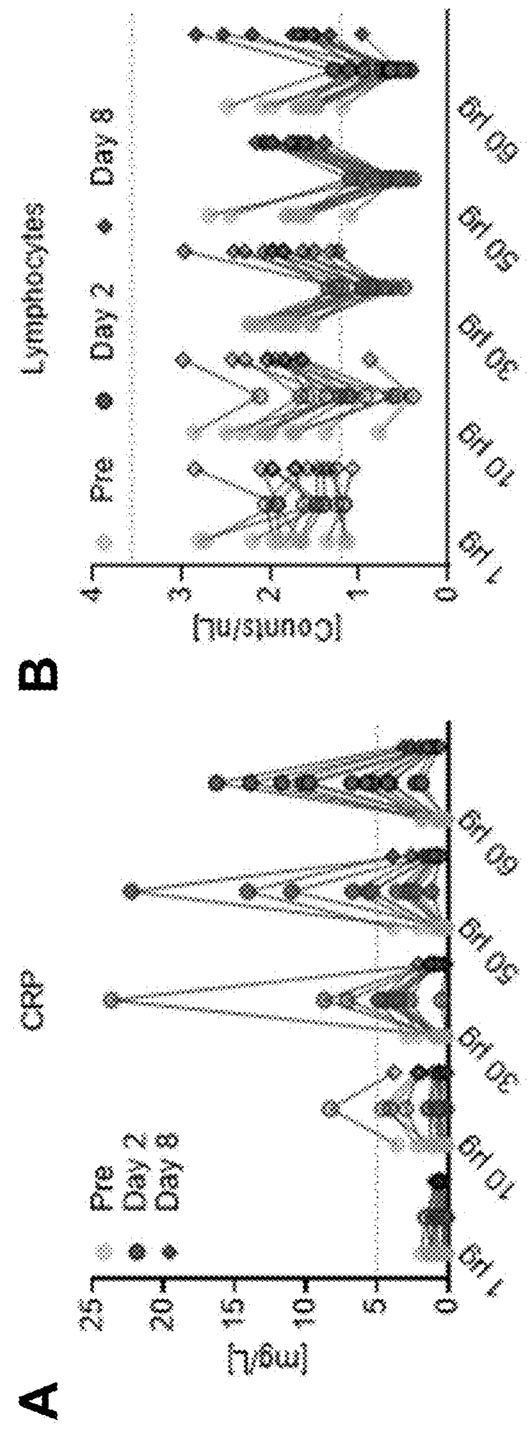

FIG. 45: Pharmacodynamic markers

Subjects were immunised with the indicated dose levels of BNT162b1 on days 1 (all dose levels) and 22 (all dose levels except 60 μg). (A) Kinetics of C-reactive protein (CRP) level and (B) Kinetics of lymphocyte counts. Dotted lines indicate upper and lower limit of reference range. For values below the lower limit of quantification (LLOQ=0.3), LLOQ/2 values were plotted (A).

Figure 46:
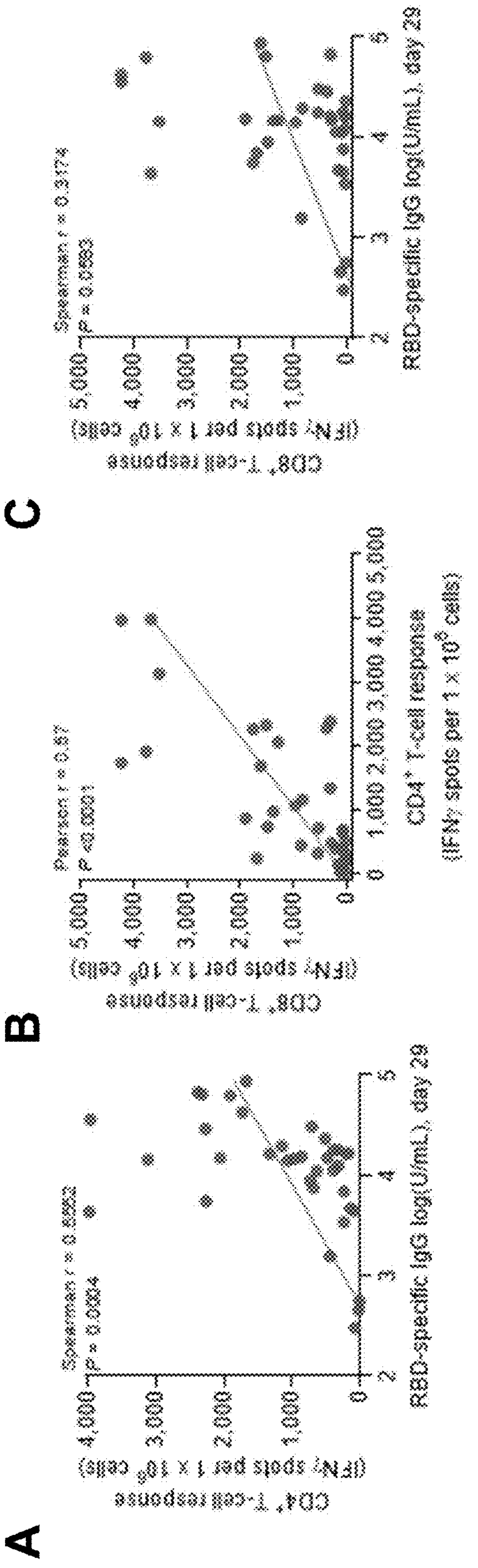

FIG. 46: Correlation of antibody and T-cell responses

Subjects were immunised with the indicated dose levels of BNT162b1 on days 1 (all dose levels) and 22 (all dose levels except 60 μg). (A) Correlation of RBD-specific IgG responses (from FIG. 39*a*) with $CD4^+$ T-cell responses on day 29 (1 and 50 μg, n=8 each; 10 and 30 μg, n=10 each). Nonparametric Spearman correlation. (B) Correlation of $CD4^+$ with $CD8^+$ T-cell responses (as in FIG. 41) from day 29 of dose cohorts 10 to 50 μg (1 and 50 μg, n=8 each; 10 and 30 μg, n=10 each). Parametric Pearson correlation. (C) Correlation of RBD-specific IgG responses (from FIG. 39*a*) with $CD8^+$ T-cell responses on day 29 (1 and 50 μg, n=8 each; 10 and 30 μg, n=10 each). Nonparametric Spearman correlation.

Figure 47:
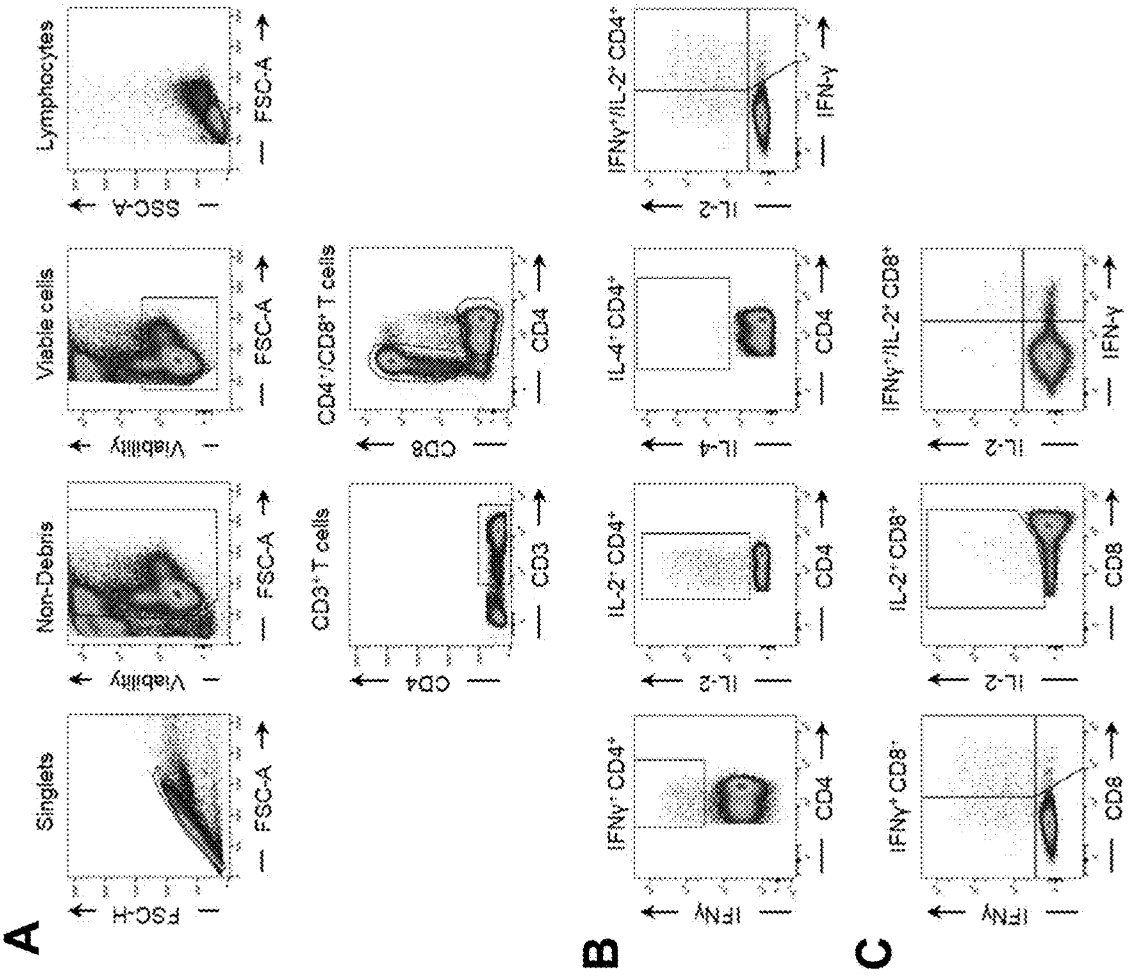

FIG. 47: Gating strategy for flow cytometry analysis of data shown in FIG. 42

Flow cytometry gating strategy for identification of IFNγ, IL-2 and IL-4 secreting T cells in study subject PBMC samples. (A) $CD4^+$ and $CD8^+$ T cells were gated within single, viable lymphocytes. (B), (C) Gating of IFNγ, IL-2 and IL-4 in $CD4^+$ T cells (B), and IFNγ and IL-2 in $CD8^+$ T cells (C).

Figure 48:
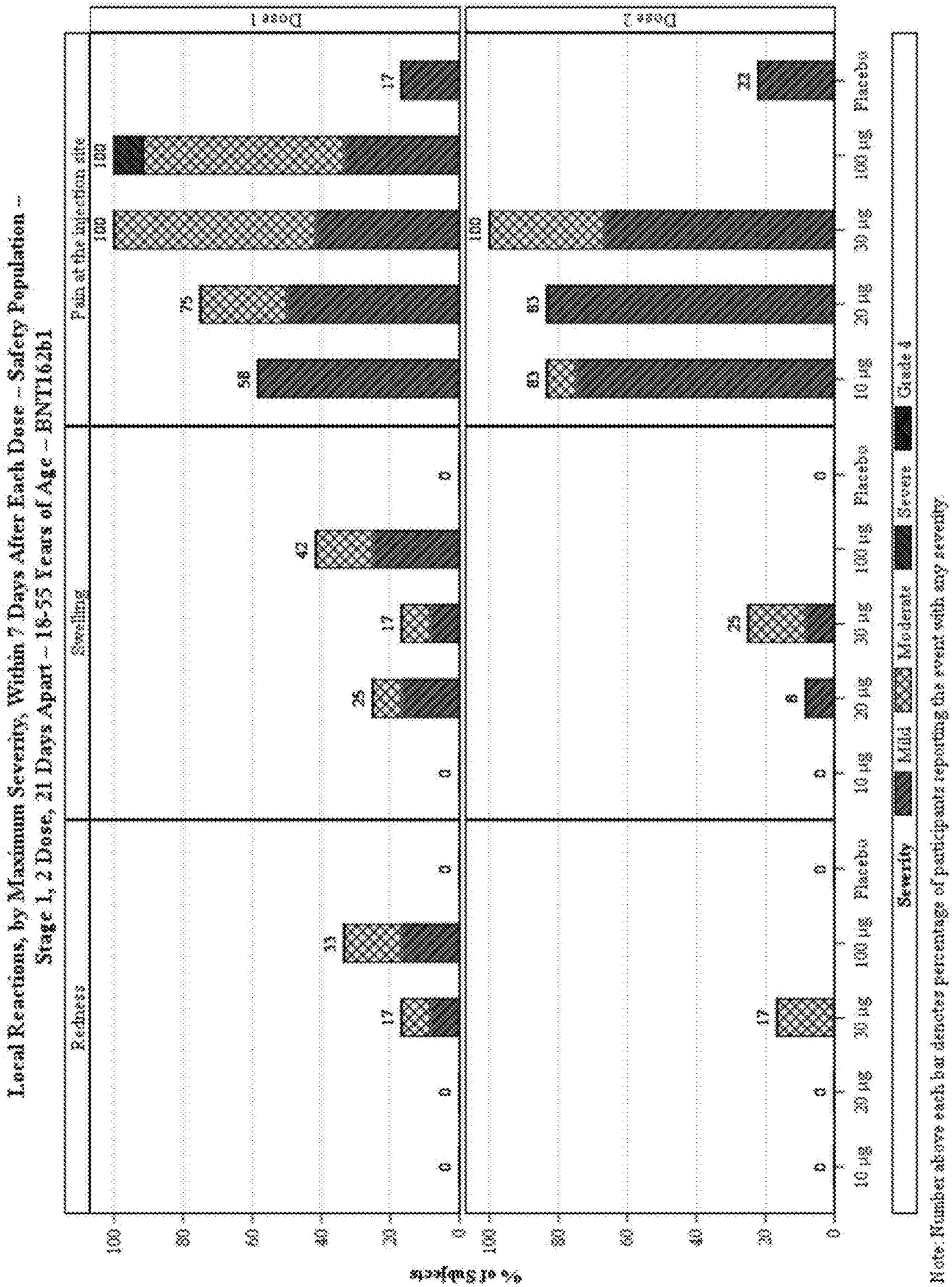

FIG. 48: BNT162b1 18-55 years of age: Local Reactions After Each Dose

Figure 49:
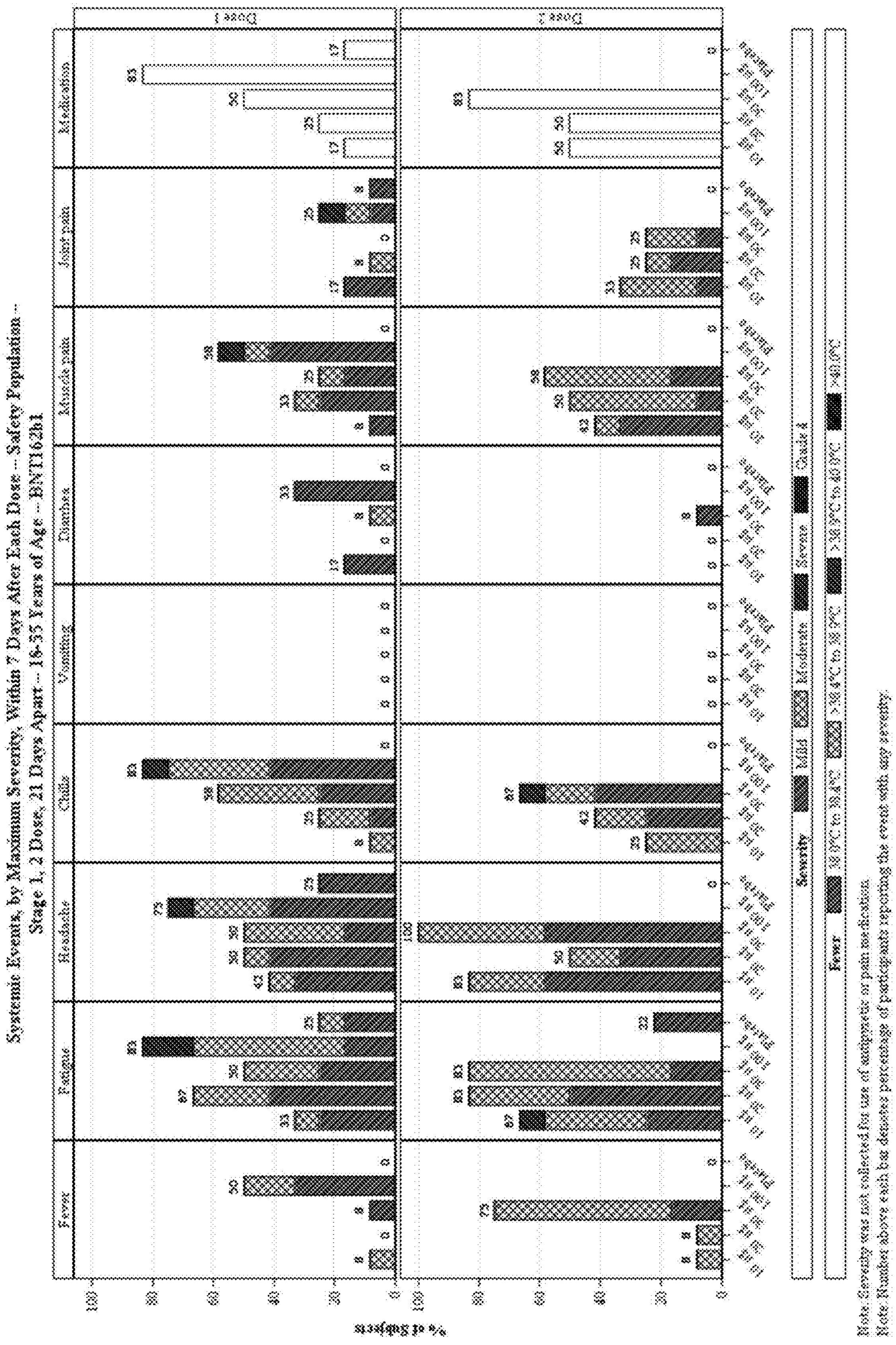

FIG. 49: BNT162b1 18-55 years of age: Systemic Events After Each Dose

Figure 50:
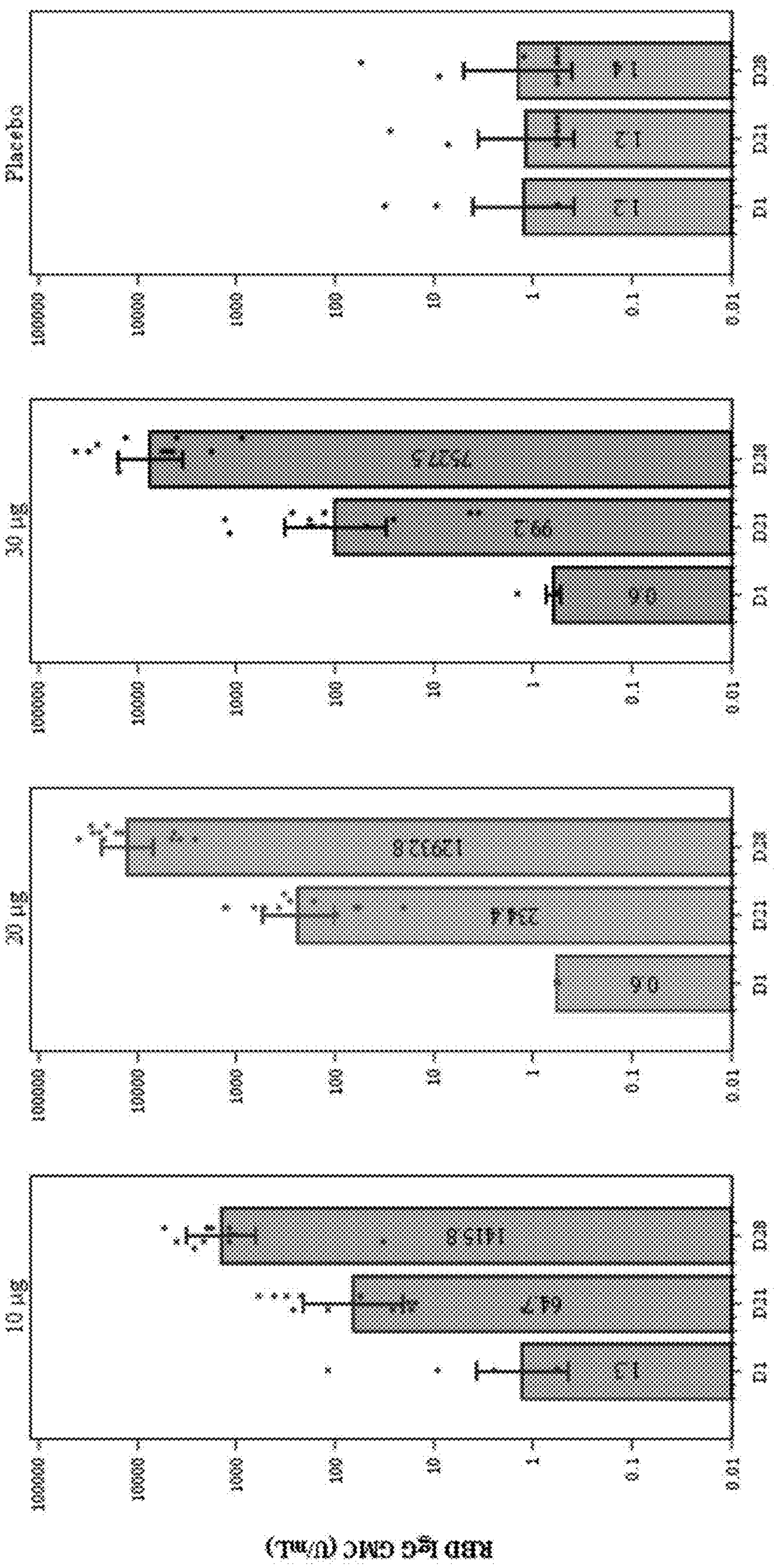

FIG. 50: BNT162b1 65-85 years of age: RBD-Binding IgG GMCs

Figure 51:
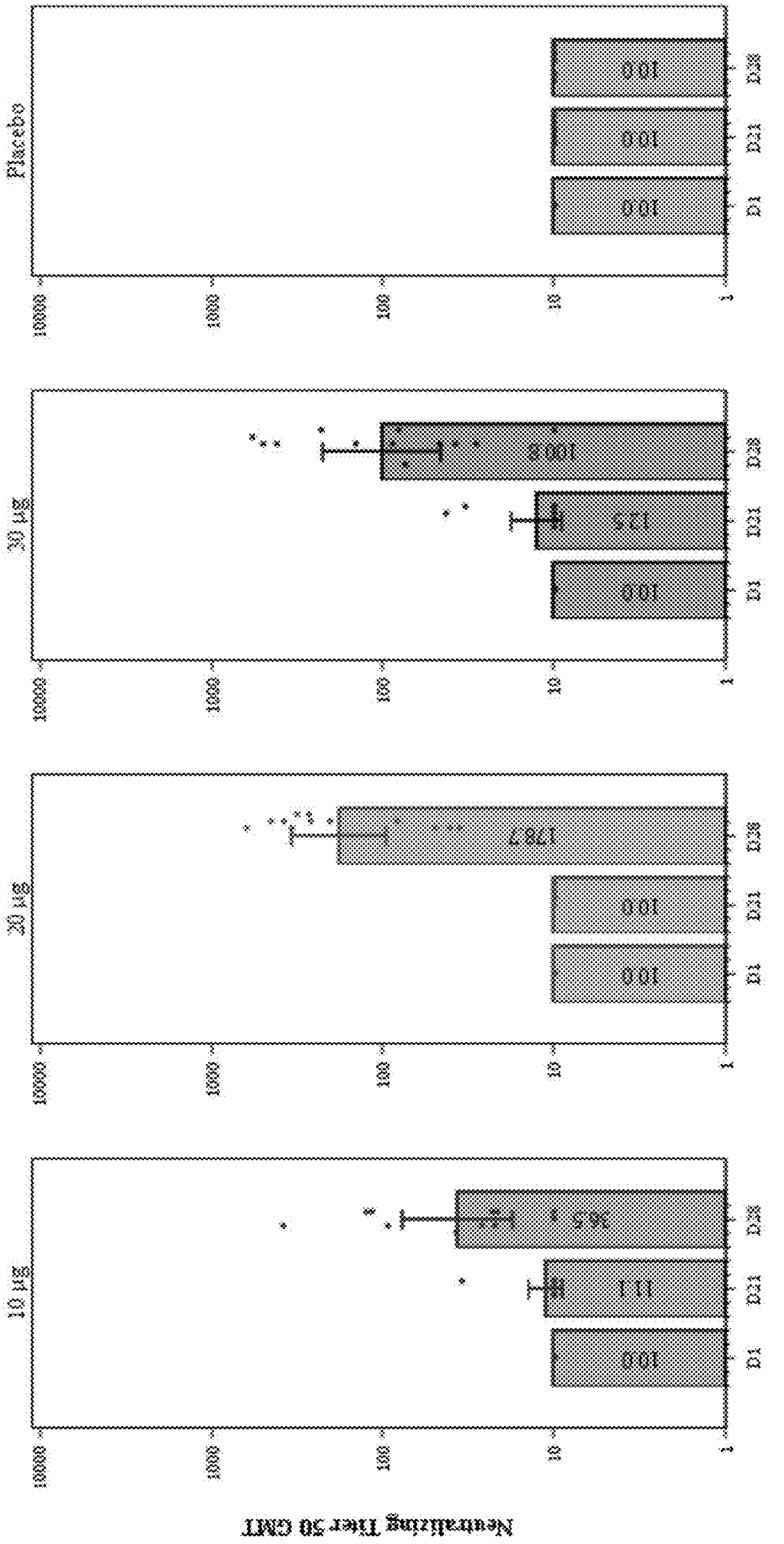

FIG. 51: BNT162b1 65-85 years of age: 50% SARS-CoV-2 Neutralizing GMTs

Figure 52:
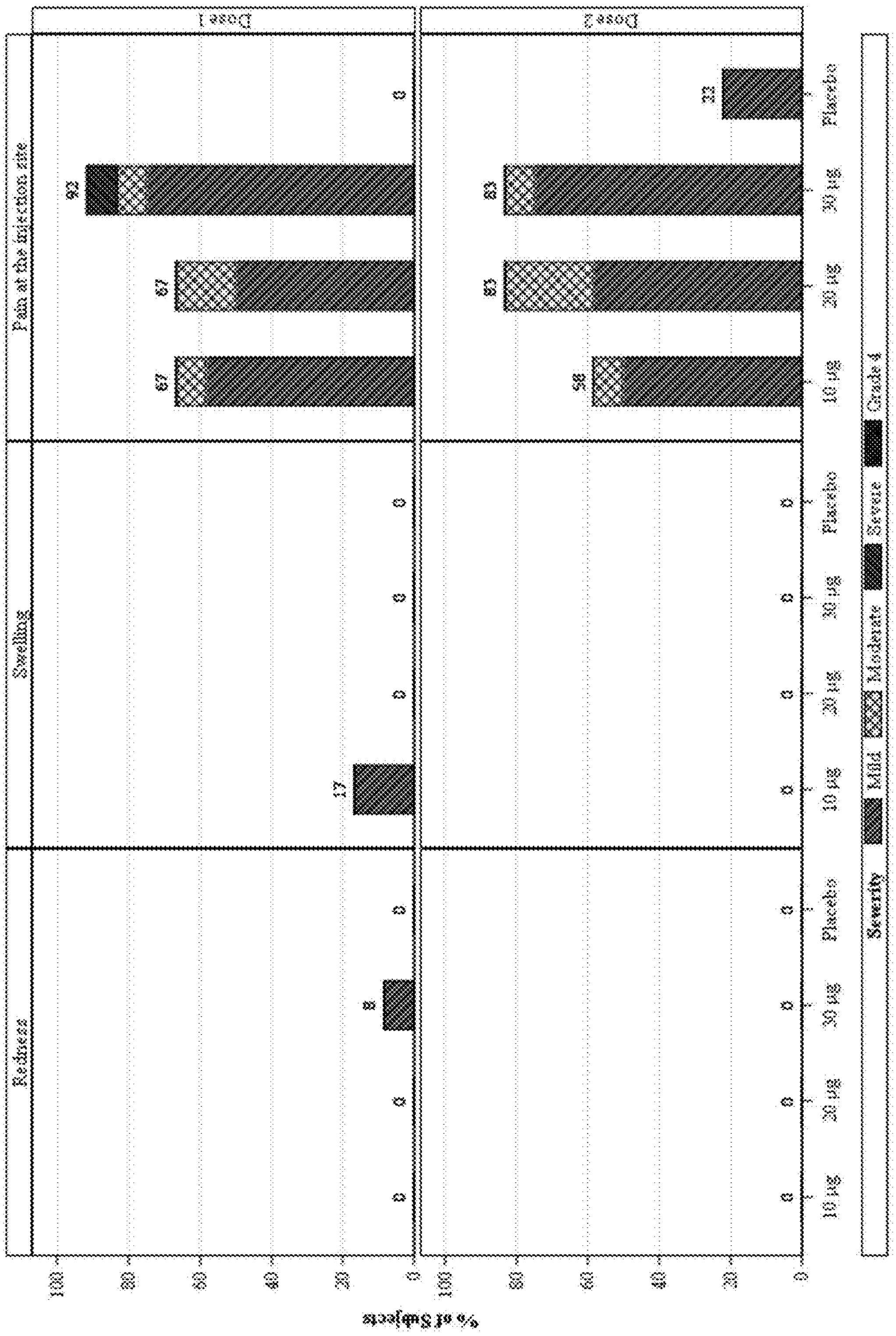

FIG. 52: BNT162b2 18-55 years of age: Local Reactions After Each Dose

Figure 53:
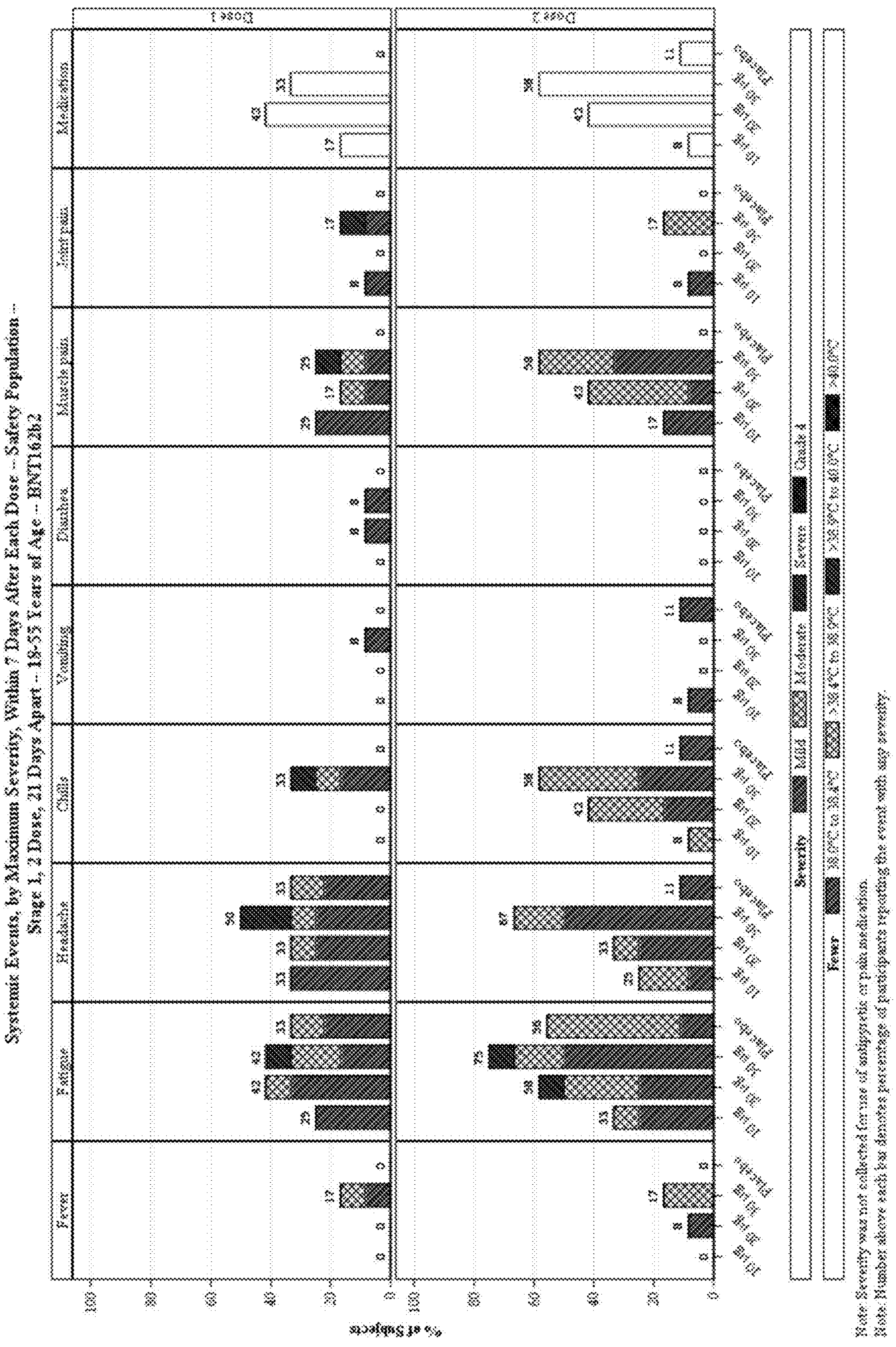

FIG. 53: BNT162b2 18-55 years of age: Systemic Events After Each Dose

Figure 54:
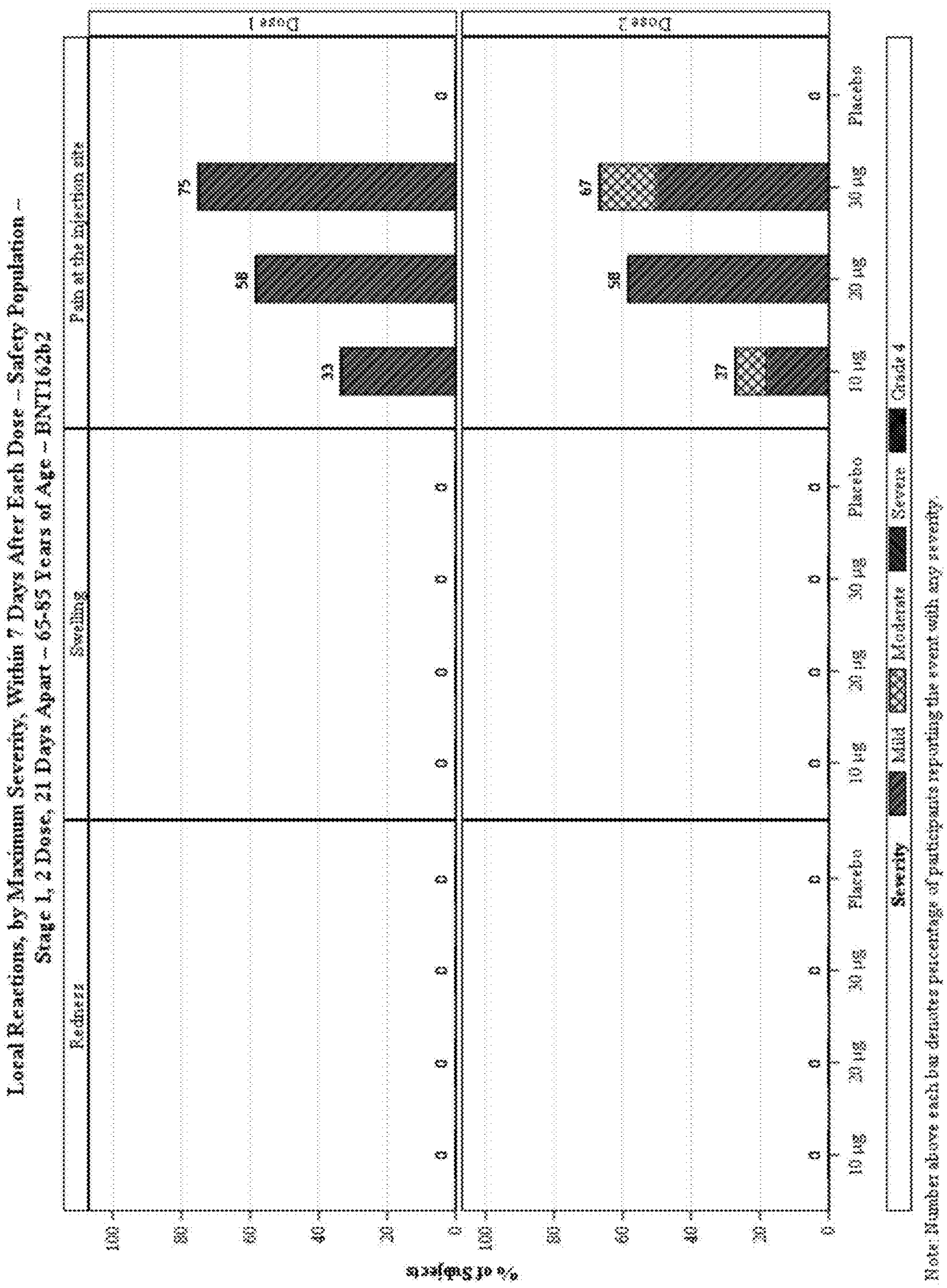

FIG. 54: BNT162b2 65-85 years of age: Local Reactions After Each Dose

Figure 55:
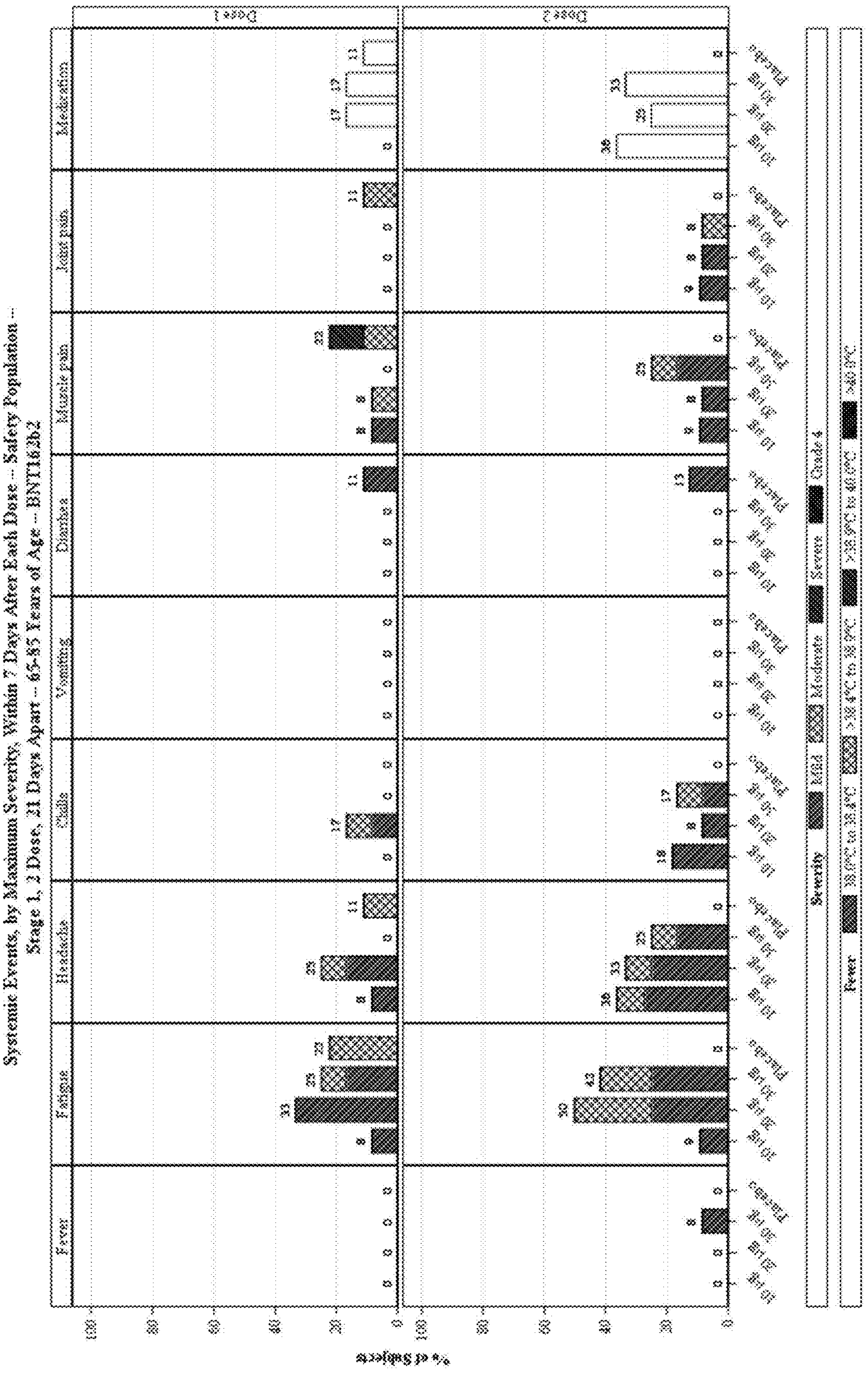

FIG. 55: BNT162b2 65-85 years of age: Systemic Events After Each Dose

Figure 56:
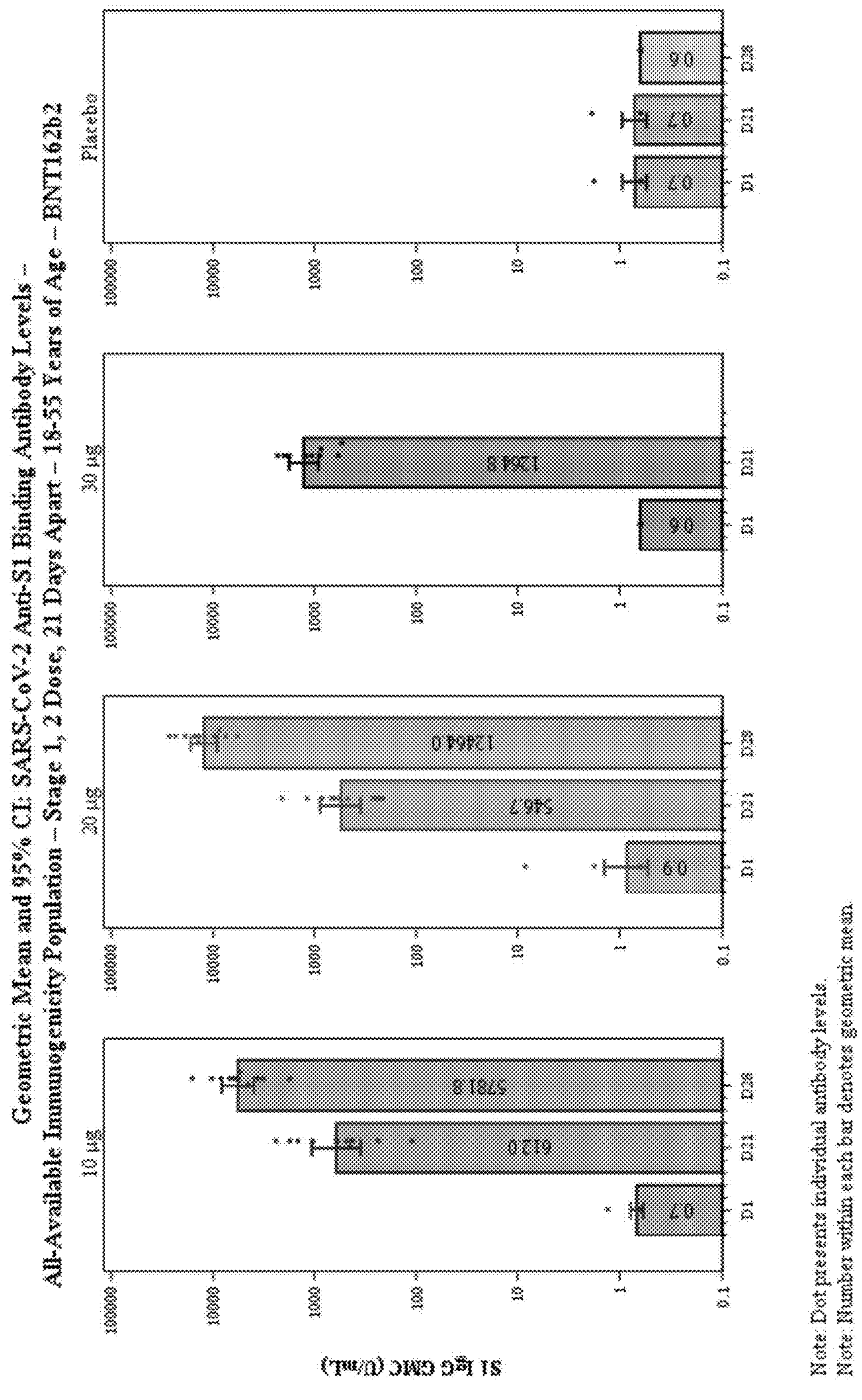

FIG. 56: BNT162b2 18-55 years of age: S1-Binding IgG GMCs

Figure 57:
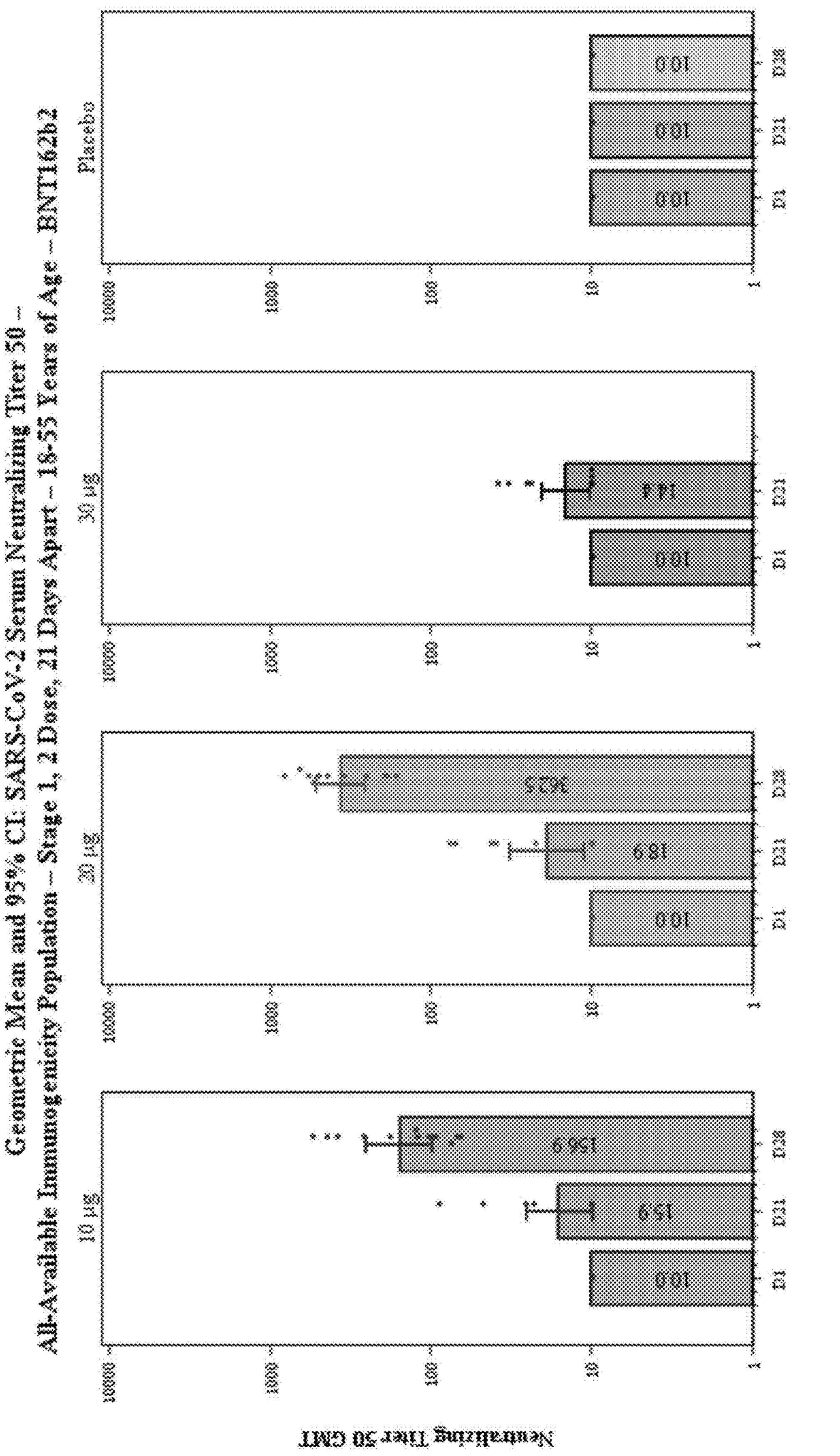

FIG. 57: BNT162b2 18-55 years of age: 50% SARS-CoV-2 Neutralizing GMTs

Figure 58:
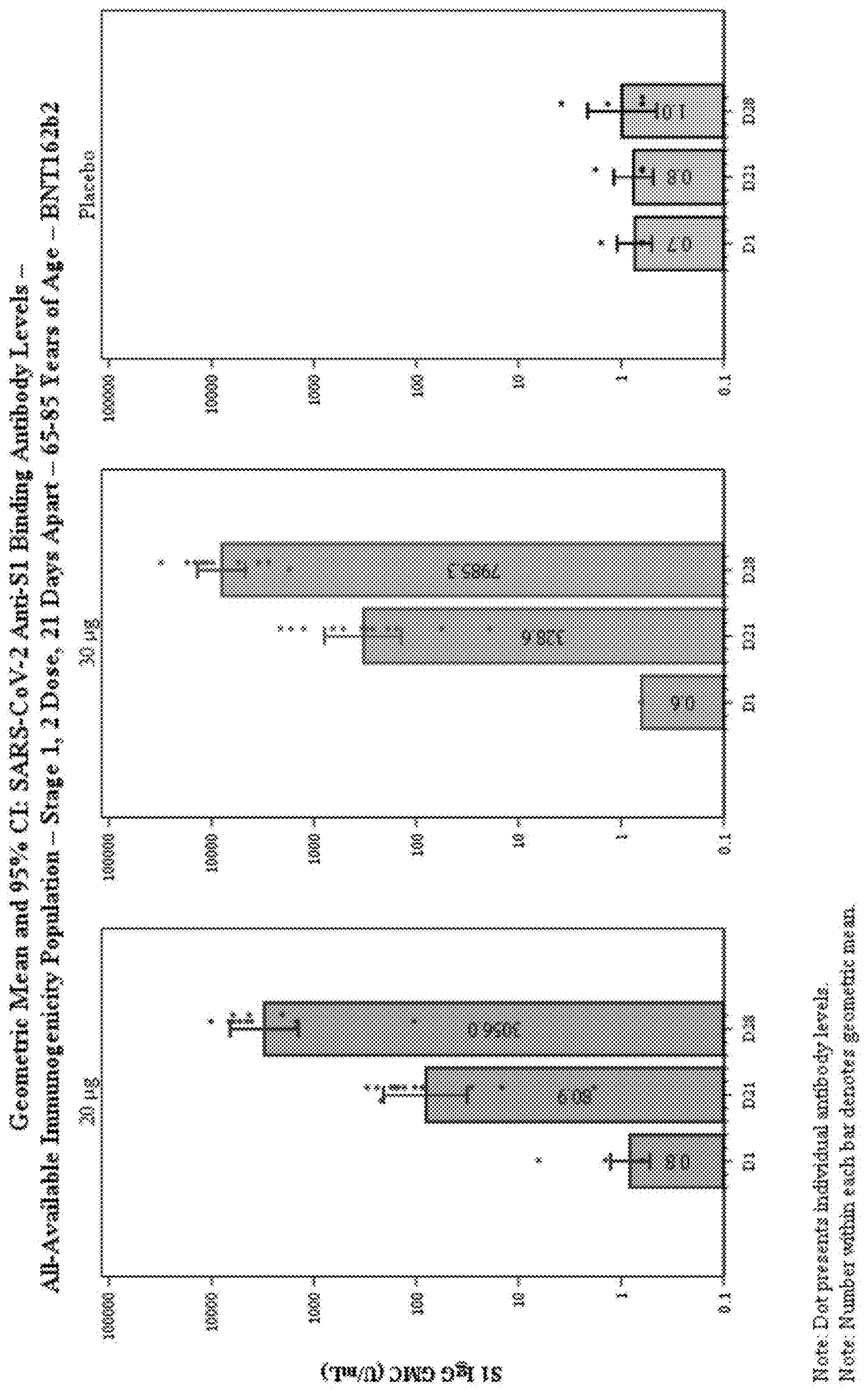

FIG. 58: BNT162b2 65-85 years of age: S1-Binding IgG GMCs

Figure 59:
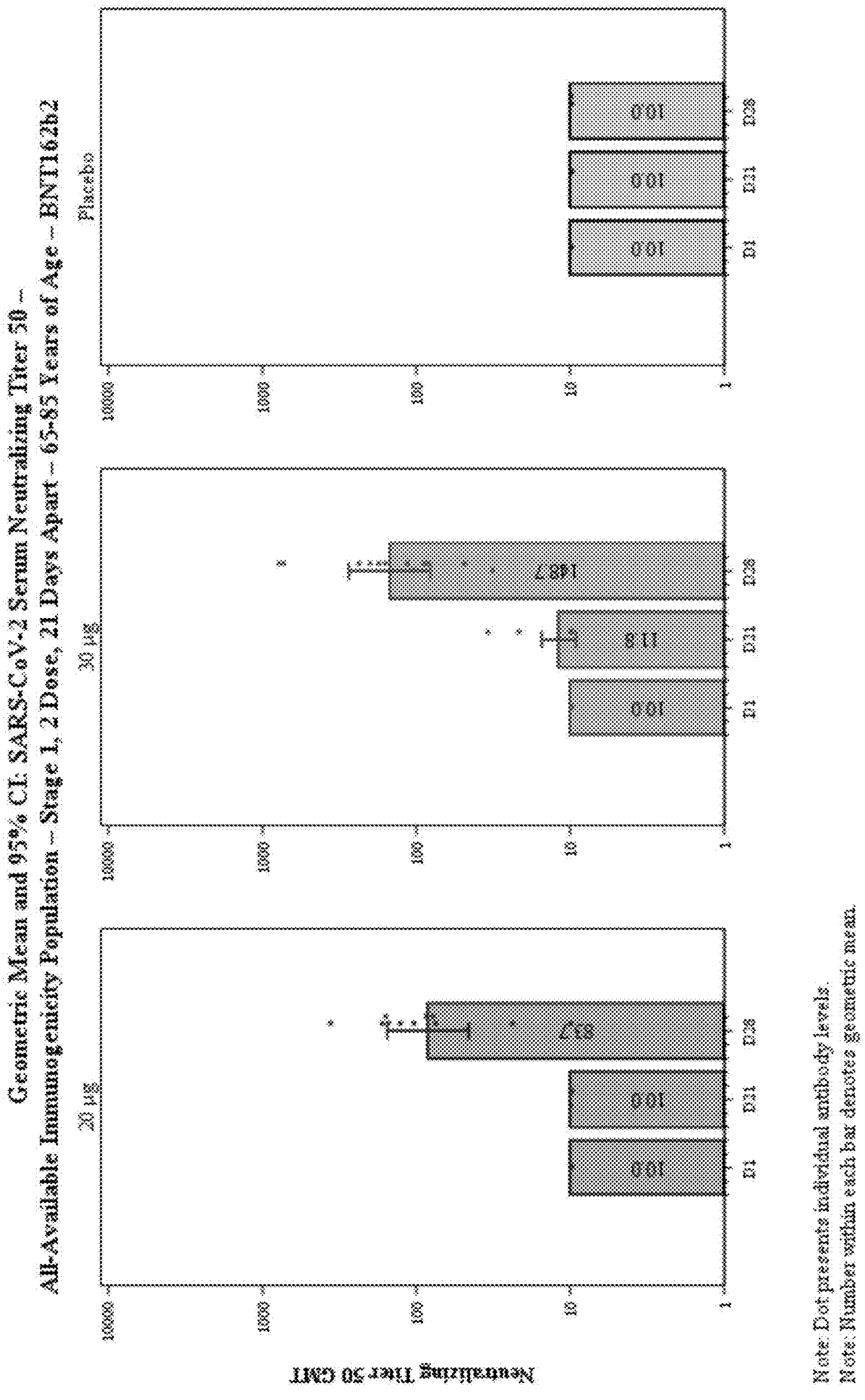

FIG. 59: BNT162b2 65-85 years of age: 50% SARS-CoV-2 Neutralizing GMTs

Figure 60:
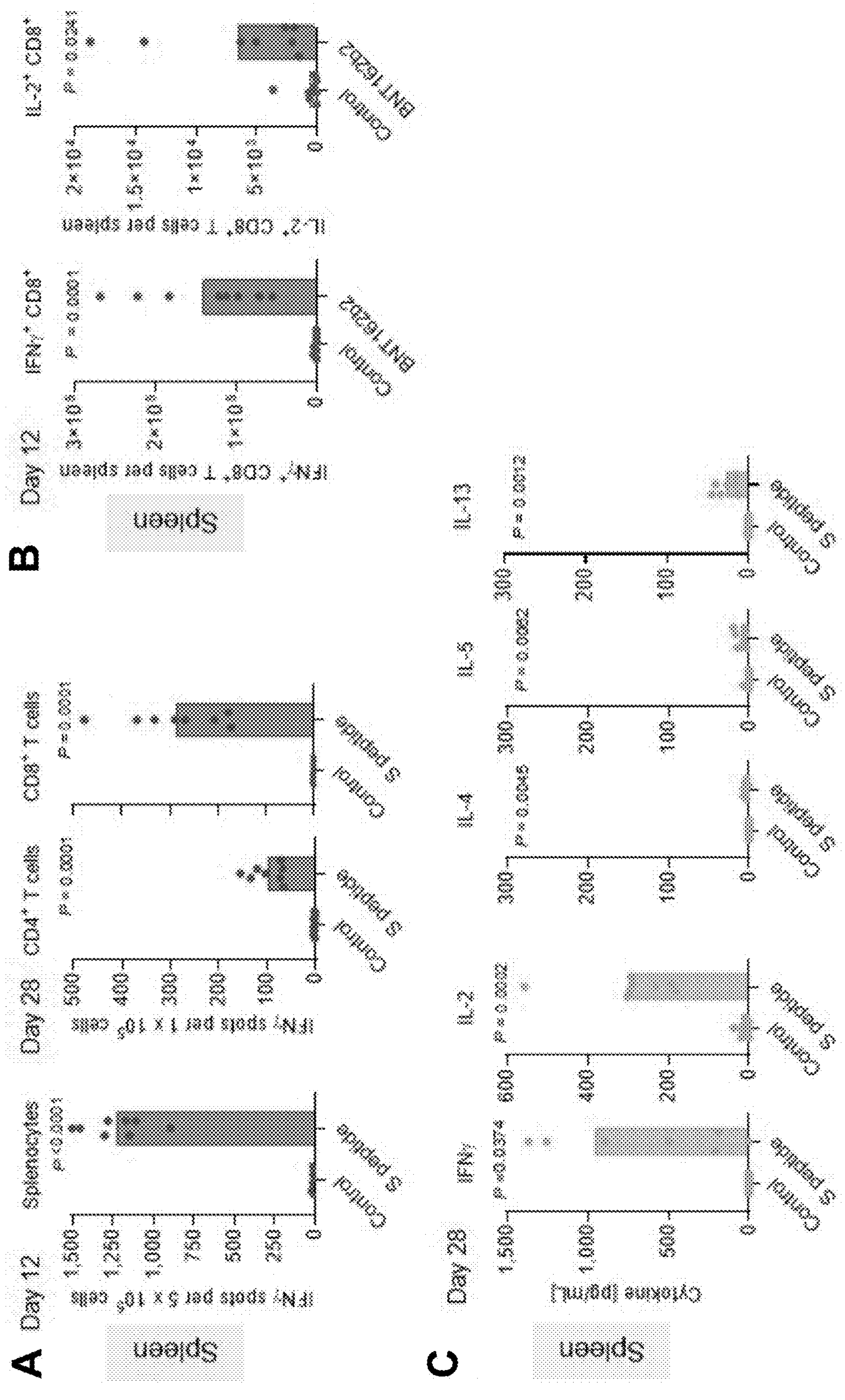

FIG. 60: BNT162b2-elicited T cell responses in mice

Splenocytes of BALB/c mice immunized IM with BNT162b2 or bufferwere ex vivo restimulated with full-length S peptide mix or negative controls (irrelevant peptide in (A), right); no peptide in ((A), left) and in (C)). P-values were determined by a two-tailed paired t-test. (A) IFNγ ELISpot of splenocytes collected 12 days after immunization of mice (n=8 per group) with 5 μg BNT162b2 (left). IFNγ ELISpot of isolated splenic $CD4^+$ T cells or $CD8^+$ T cells 28 days after immunization of mice (n=8 mice per group) with 1 μg BNT162b2 (middle and right). (B) CD8+ T-cell specific cytokine release by splenocytes of mice (n=8 per group) immunized with 5 μg BNT162b2 or buffer (control), determined by flow cytometry. S-peptide specific responses are corrected for background (no peptide). (C) Cytokine production by splenocytes obtained 28 days after immunization of mice (n=8 per group, n=7 for IL-4, IL-5, and IL-13, as one outlier was removed via routs test [Q=1%] forthe S peptide stimulated samples) with 1 μg BNT162b2, determined by bead-based multiplex analysis.

Figure 61:
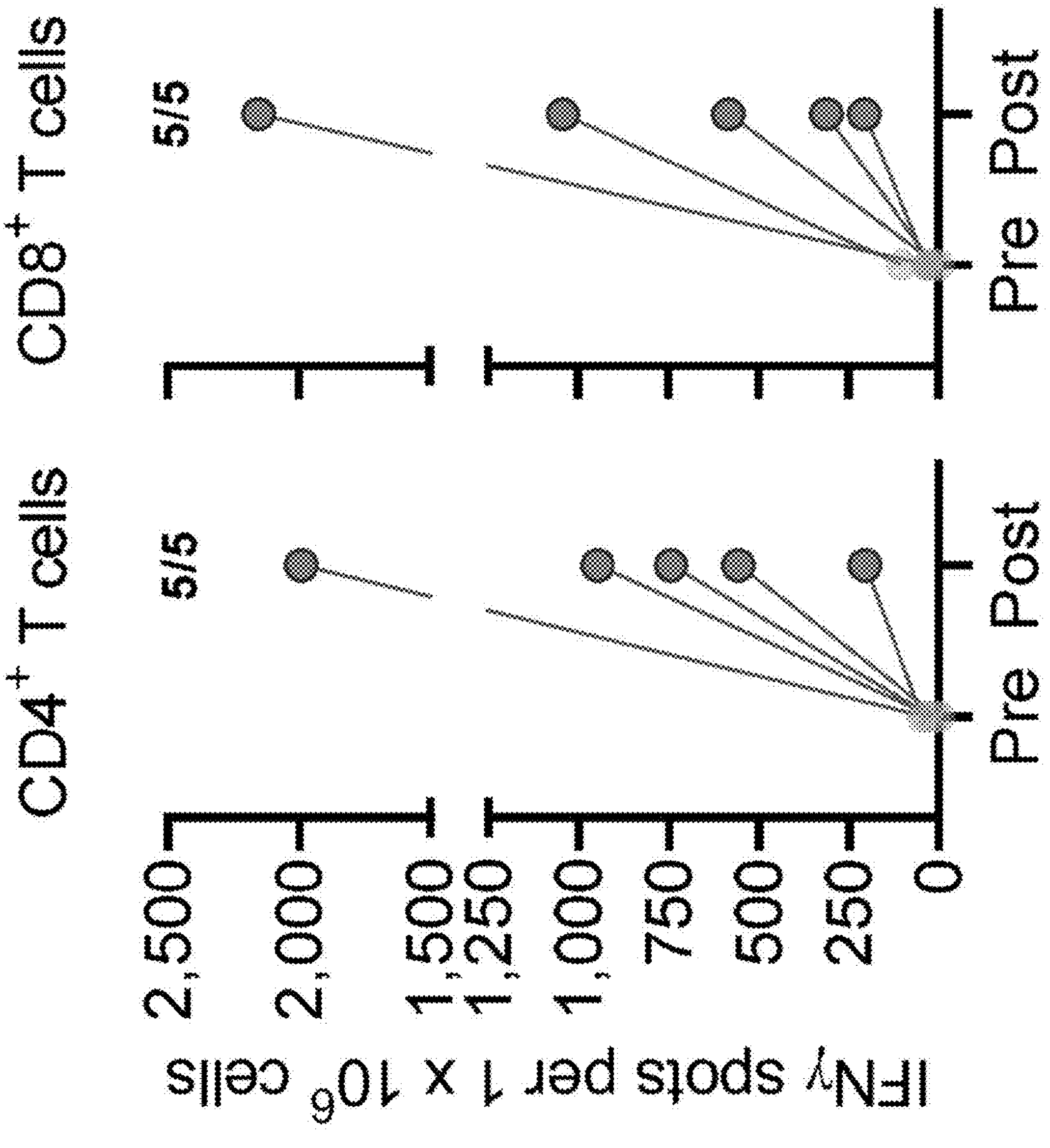

FIG. 61: IFNγ ELISpot data for 5 subjects vaccinated with 10 μg BNT162b2

Background-subtracted spot counts from duplicates prior to vaccination (Pre) and on day 29 (Post –7 days post boost) per $10^6$ cells. T cell response analysis was performed in a GCLP-compliant manner using a validated ex-vivo IFNγ ELISpot assay. All tests were performed in duplicate and included negative and positive controls (medium only and anti-CD3). In addition, peptide epitopes derived from cytomegalovirus (CMV), Epstein Barr virus (EBV), and influenza virus were used as positive controls. CD4- or CD8-depleted PBMCs were stimulated for 16-20 h in pre-coated ELISpot plates (Mabtech) with overlapping peptides covering the N-terminal portion and C-terminal portion of the spike glycoprotein. For analysis of ex vivo T-cell responses, bound IFNγ was visualized by an alkaline phosphatase-conjugated secondary antibody. Plates were scanned using a Robot ELISPOT Reader and analysed by ImmunoCapture V6.3 or AID ELISPOT 7.0 software. Spot counts were summarized as mean values for each duplicate. T cell counts were calculated as the sum of spot counts detected after stimulation with S pool 1 and S pool 2. T-cell responses stimulated by peptides were compared to effectors incubated with medium only as negative control using an ELISpot data analysis Tool (EDA), based on two statistical tests (distribution free resampling) according to Moodie et al. (Moodie Z. et al., J Immunol Methods 315, 2006, 121-32; Moodie Z. et al., Cancer Immunol Immunother 59, 2010, 1489-501) thus providing sensitivity while maintaining control over false positive rate. No significant changes were observed between the pre- and day 29 T cell responses against the positive control peptides from CMV, EBV, and influenza virus (not shown).

Figure 62:
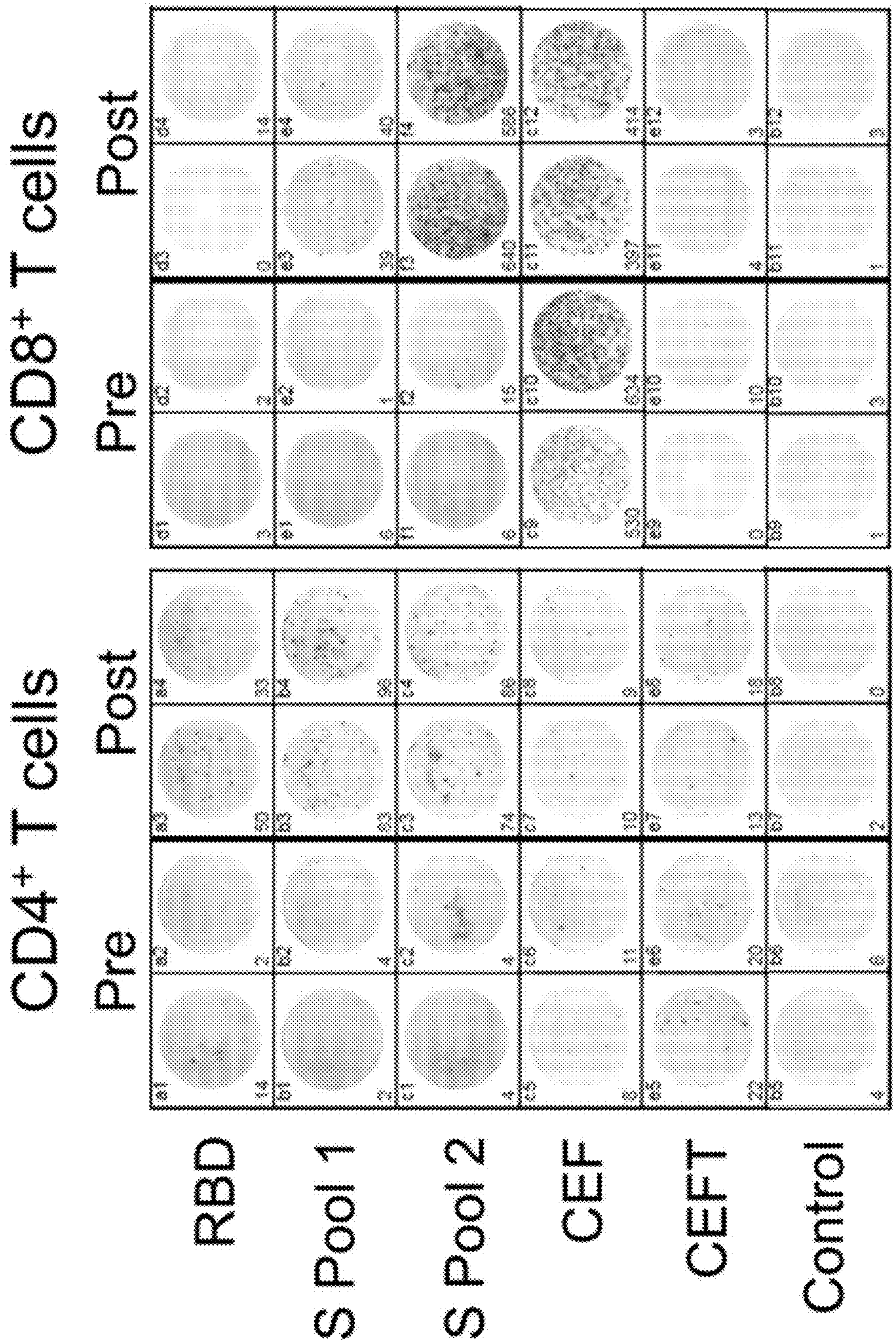

FIG. 62: Example of CD4+ and CD8+IFNγ ELISpot data

IFNγ ELISpot was performed as in FIG. 61 using PBMCs obtained from a subject prior to immunization and on day 29 after dose 1 of 10 μg BNT162b2 (7 days post dose 2). HLA class I and class II peptide pools CEF (cytomegalovirus [CMV], Epstein Barr virus [EBV] (7 days post dose 2), and influenza virus, HLA class I epitope mix) and CEFT (CMV, EBV, influenza virus, and tetanus toxoid HLA class II cell epitope mix) were used as benchmarking controls to assess CD8+ and CD4+ T cell reactivity.

Figure 63:
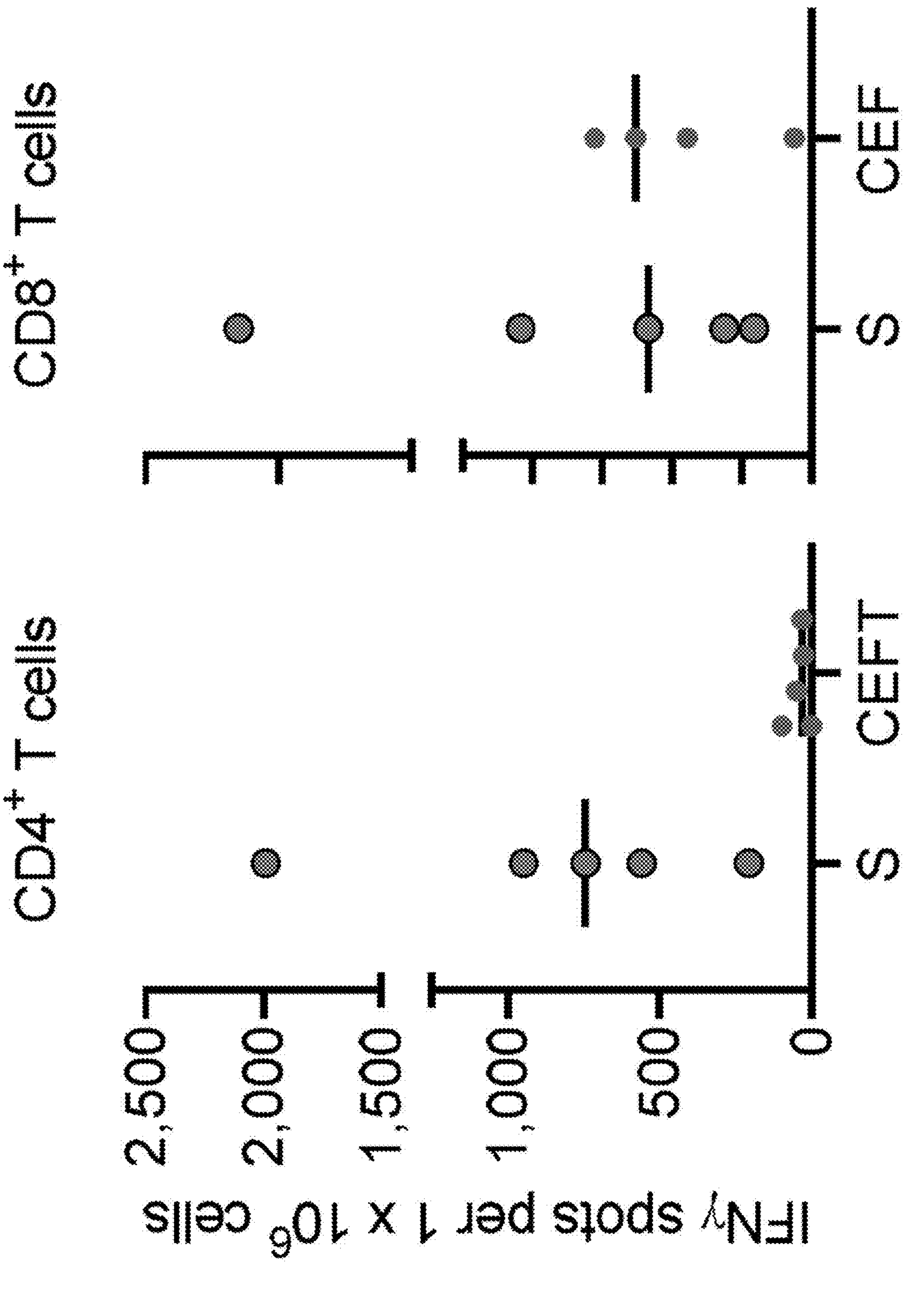

FIG. 63: Comparison of BNT162b2-elicited and benchmark INFγ ELISpot responses IFNγ spot counts from day 29 (7 day post dose 2) PBMC samples obtained from 5 subjects who were immunized with 10 μg of BNT162b2 on days 1 and 22. CEF (CMV, EBV, and influenza virus HLA class I epitope mix), and CEFT (CMV, EBV, influenza virus, and tetanus toxoid HLA class II cell epitope mix) were used as benchmarking controls to assess CD8+ and CD4+ T cell reactivity. Horizontal lines indicate median values.

Figure 64:
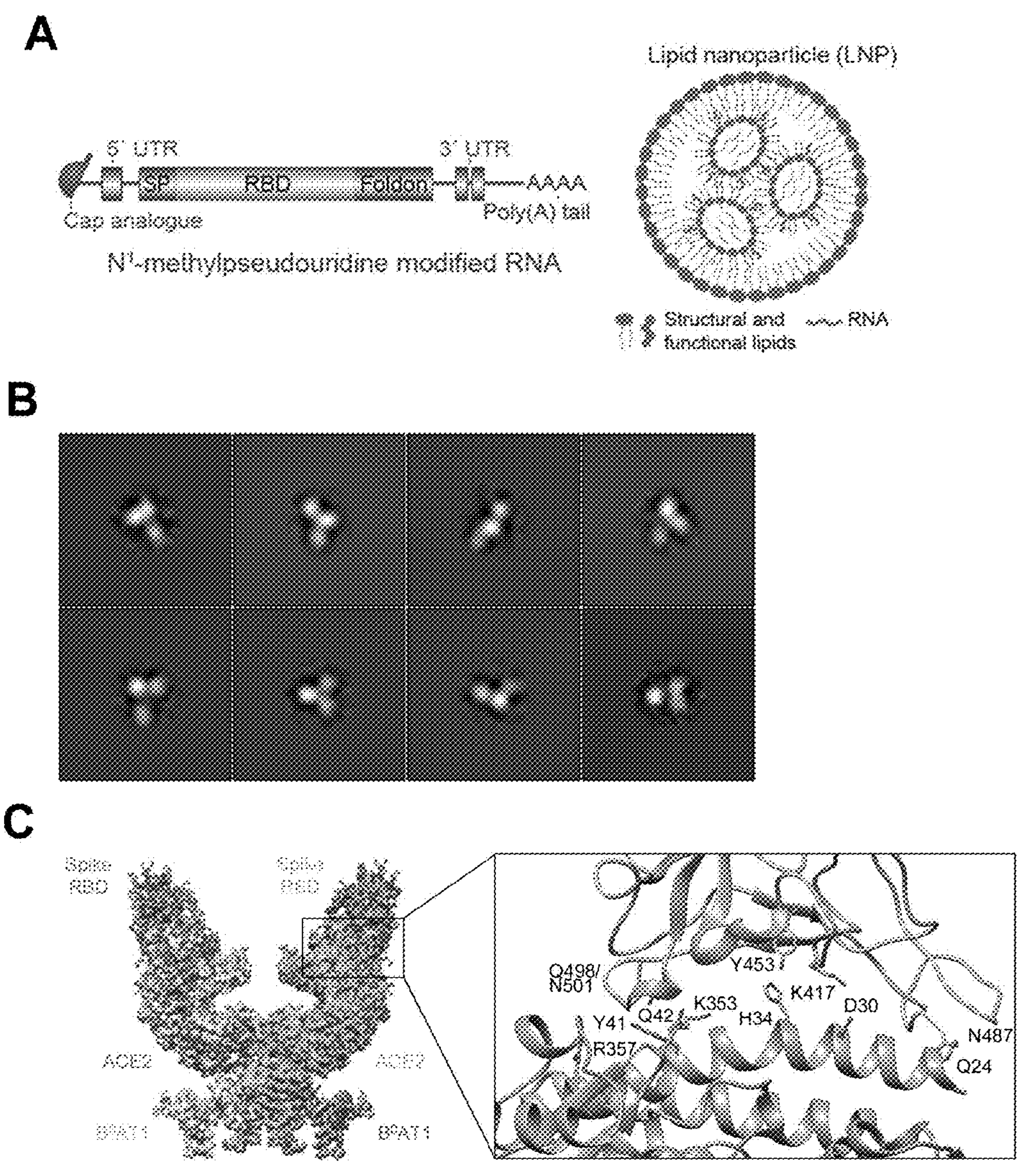

FIG. 64: Design and characterisation of the immunogen (A), Structure of BNT162b1. Linear diagram of RNA (left), and cartoon of LNP (right). UTR, untranslated region; SP, signal peptide. (B) Representative 2D class averages from electron microscopy of negatively stained RBD-foldon trimers. Box edge: 37 nm. (C) Density map of the ACE2/$B^0$AT1/RBD-foldon trimer complex at 3.24 Å after focused refinement of the ACE2 extracellular domain bound to an RBD monomer. Surface color-coding by subunit. A ribbon model refined to the density shows the RBD-ACE2 binding interface, with residues potentially mediating polar interactions labeled.

Figure 65:
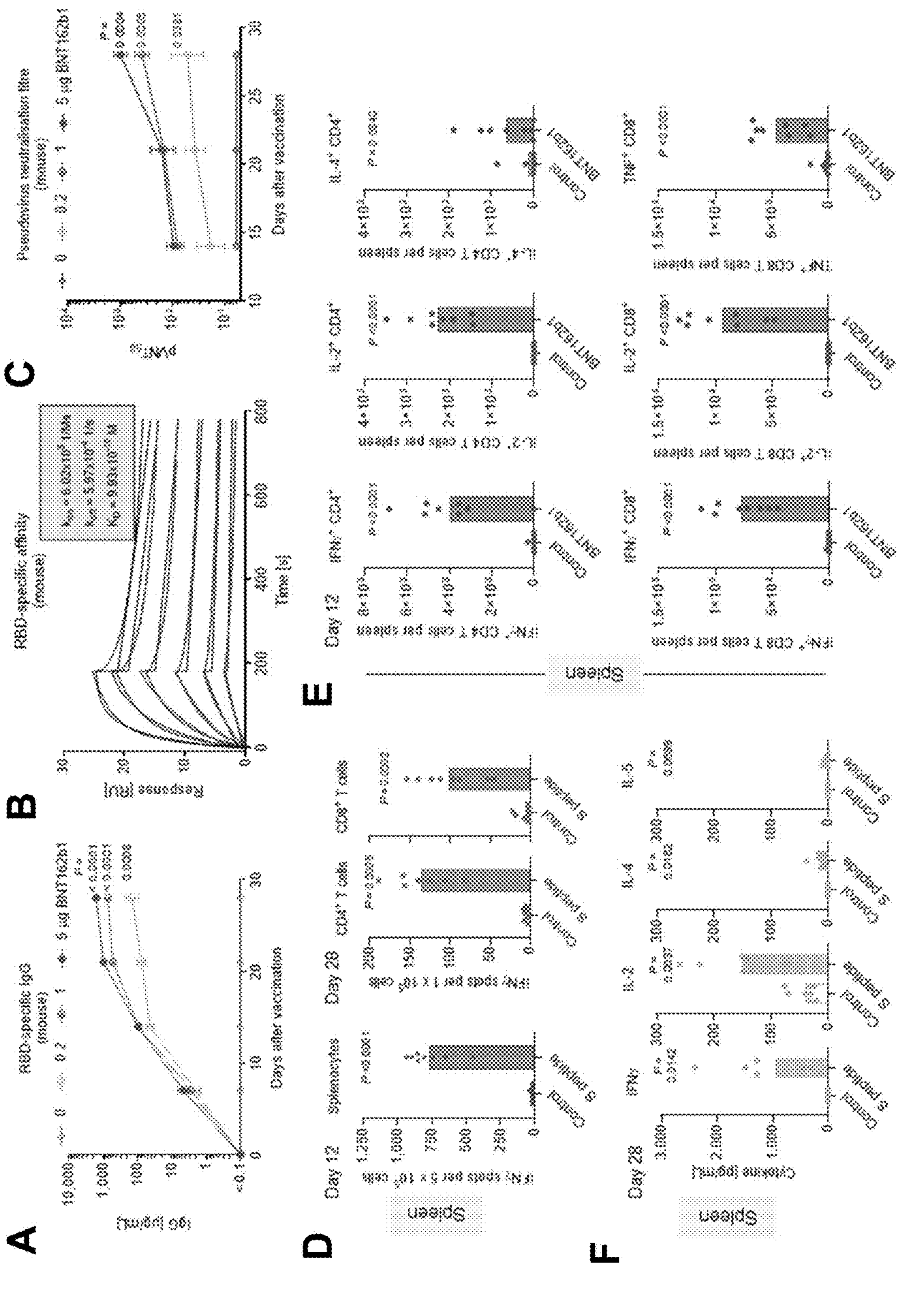

FIG. 65: Mouse immunogenicity (A)-(C), BALB/c mice (n=8 per group) were immunised intramuscularly (IM) with 0.2, 1 or 5 μg of BNT162b1 or buffer. Geometric mean of each group ±95% Cl, P-values compare day 28 to non-immunised (0 μg; n=8) baseline sera (multiple comparison of mixed-effect analysis using Dunnett's multiple comparisons test) ((A), (C)). (A) RBD-binding IgG responses in sera obtained 7, 14, 21 and 28 days after immunisation, determined by ELISA. For day 0, a pre-screening of randomised animals was performed (n=4). (B) Representative surface plasmon resonance sensorgram of the binding kinetics of His-tagged RBD to immobilised mouse IgG from serum 28 days after immunisation with 5 μg BNT162b1 (n=8). Actual binding (green) and the best fit of the data to a 1:1 binding model (black). (C) VSV-SARS-CoV-2 pseudovirus 50% serum neutralising titers ($pVNT_{50}$). (D)-(F), Splenocytes of BALB/c mice immunised IM with BNT162b1 or buffer (control) were ex vivo re-stimulated with full-length S peptide mix or negative controls (no peptide in ((D), left) and in ((E), (F)); irrelevant peptide in ((D), right)). P-values were determined by a two-tailed paired t-test. (D) IFNγ ELISpot of splenocytes collected 12 days after immunisation of mice (n=8 per group) with 5 μg BNT162b1 (left). IFNγ ELISpot of isolated splenic $CD4^+$ T cells (n=7, one outlier removed by Grubbs test, α=0.05) or $CD8^+$ T cells (n=8) 28 days after immunisation with 1 μg BNT162b1 (middle and right). (E) T-cell specific cytokine release by splenocytes of mice (n=8 per group) immunised with 5 μg BNT162b1, determined by flow cytometry. S-peptide specific responses are corrected for background (no peptide). (F) Cytokine production by splenocytes obtained 28 days after immunisation of mice (n=8 per group) with 0.2 μg BNT162b1, determined by bead-based multiplex analysis.

Figure 66:
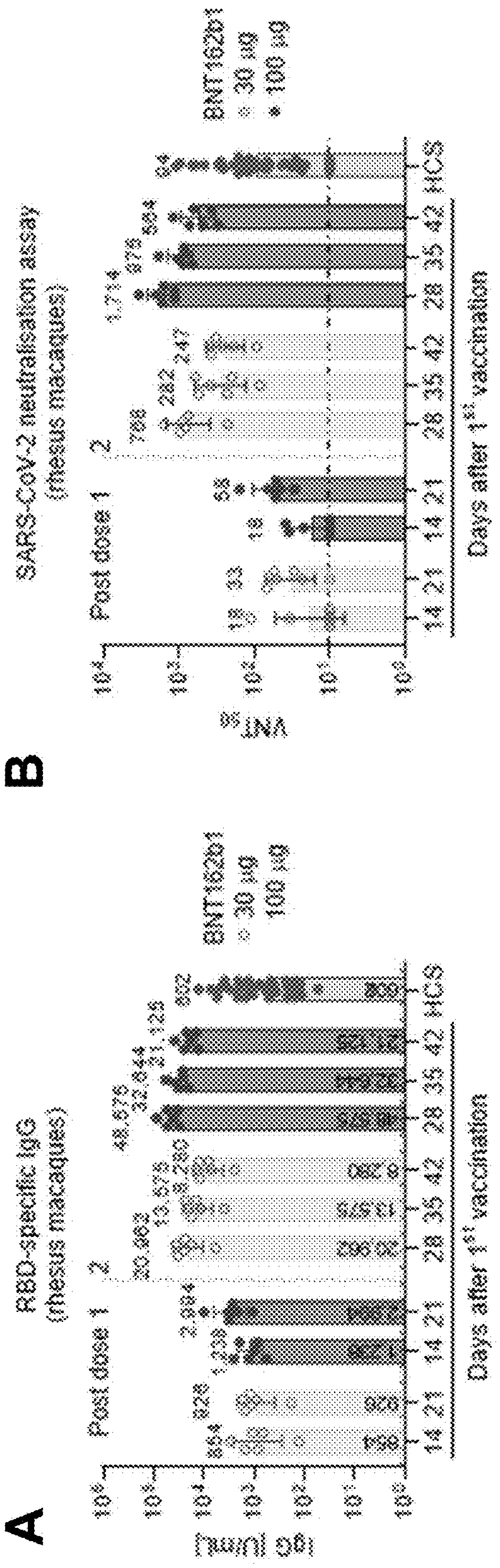

FIG. 66: Immunogenicity of BNT162b1 in *Rhesus macaques* and comparison to human convalescent sera (A), (B) Male *Rhesus macaques* 2-4 years of age (n=6 per group) were immunised IM on Days 0 and 21 with 30 μg or 100 μg of BNT162b1 or with buffer, and serum was obtained before and 14, 21, 28, 35 and 42 days after immunisation. Human convalescent sera (HCS) were obtained from SARS-CoV-2-infected patients at least 14 days after PCR-confirmed diagnosis and at a time when acute COVID-19 symptoms had resolved (n=38). Values above bars give the geometric means. (A) Geometric mean concentrations (GMCs) of IgG binding a recombinant SARS-CoV-2 RBD. Dashed line indicates geometric mean of sera from all time points for the placebo group (1.72 U/mL). Group IgG titers for every time point were analysed for statistical significance against HCS samples using one-way ANOVA with Dunnett's multiple comparison correction, and statistical significance was confirmed in the 30 μg dose-level group (Day 28, p<0.0001; Day 35, p=0.0016), and in the 100 μg dose-level group (Day 28, 35 and 42, all p<0.0001). (B) SARS-CoV-2 50% neutralisation titers ($VNT_{50}$). Dashed line indicates geometric mean of sera from all time points for the placebo group (10.31 U/mL). Group $VNT_{50}$ for every time point were analysed for statistical significance against HCS samples using one-way ANOVA with Dunnett's multiple comparison correction, and statistical significance was confirmed in the 30 μg dose-level group (Day 28, p<0.0001), and in the 100 μg dose-level group (Day 28 and 35, both p<0.0001; Day 42, p=0.007).

Figure 67:
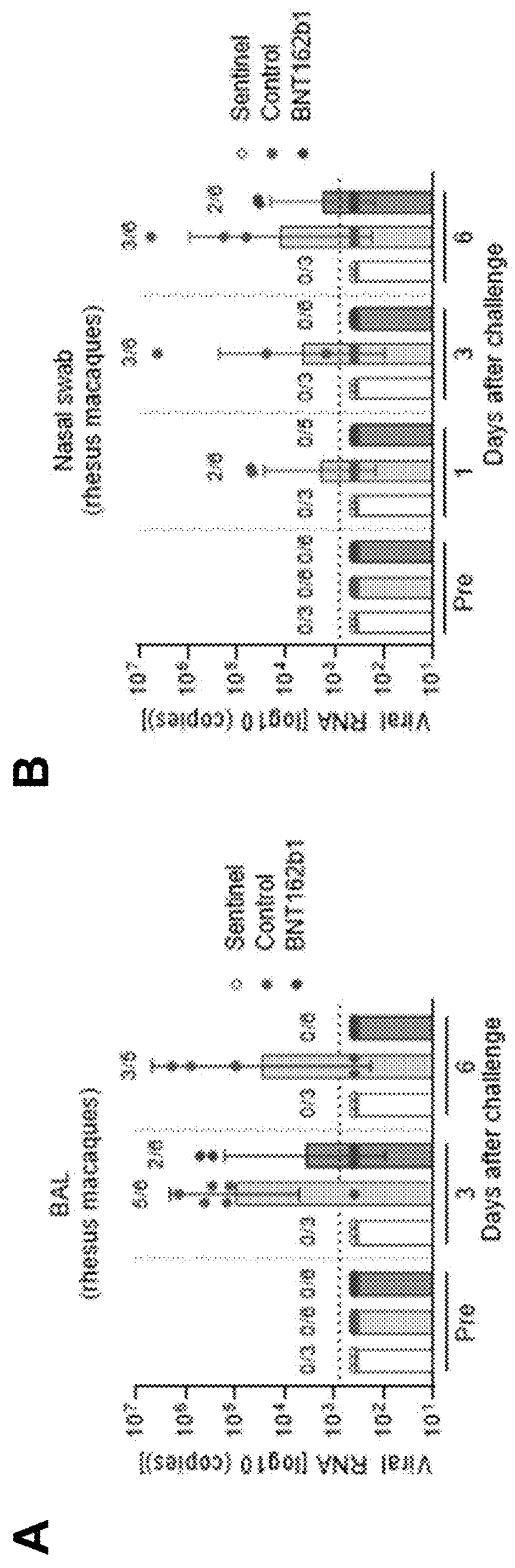

FIG. 67: Viral RNA in non-immunised and immunised *Rhesus macaques* after SARS-CoV-2 challenge

*Rhesus macaques* (n=6 per group) were immunised on Days 0 and 21 with 100 μg BNT162b1 or buffer (Control) as described in FIG. 66. Forty-one to 48 days after the second immunisation, the animals were challenged with $1\times10^6$ total pfu of SARS-CoV-2 split equally between the IN and IT routes. Three non-immunised age-matched male *Rhesus macaques* were challenged with cell culture medium (Sentinel). Viral RNA levels were detected by RT-qPCR. Ratios above data points are the number of viral RNA positive animals within all animals per group. (A) Viral RNA in bronchoalveolar lavage (BAL) fluid obtained before, and on Days 3 and 6 after challenge. At day 6, the viral load between the control and BNT162b1-immunized animals was statistically significant (p=0.0131). (B) Viral RNA in nasal swabs obtained before challenge and on day 1, 3, and 6 after challenge. At day 3, the viral load between the control and BNT162b1-immunized animals was statistically significant (p=0.0229). Dotted lines indicate the lower limits of detection (LLOD). Negative specimens were set to 2 the LLOD. P-values were determined by categorical analysis for binomial response (undetectable viral load after challenge as success, measurable viral load after challenge as failure).

Figure 68:
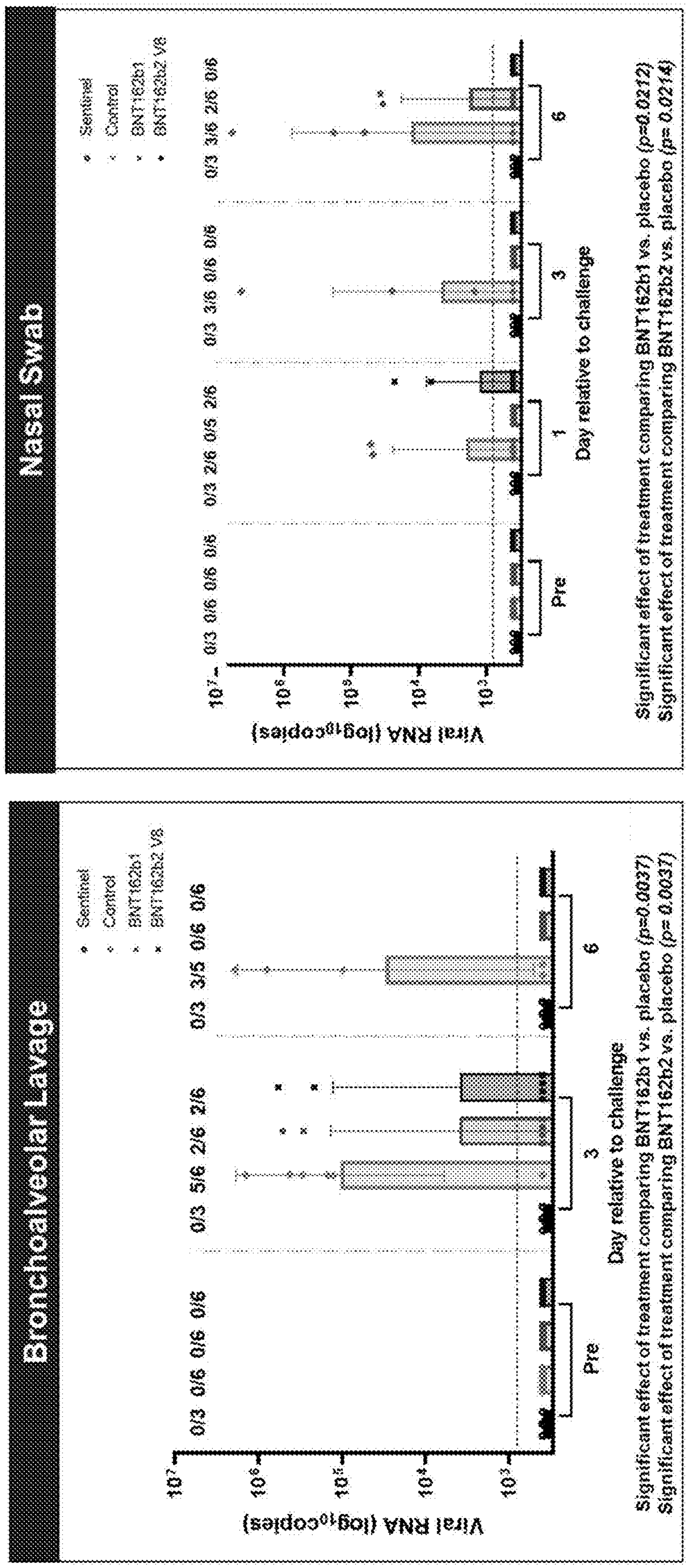
Figure 78:
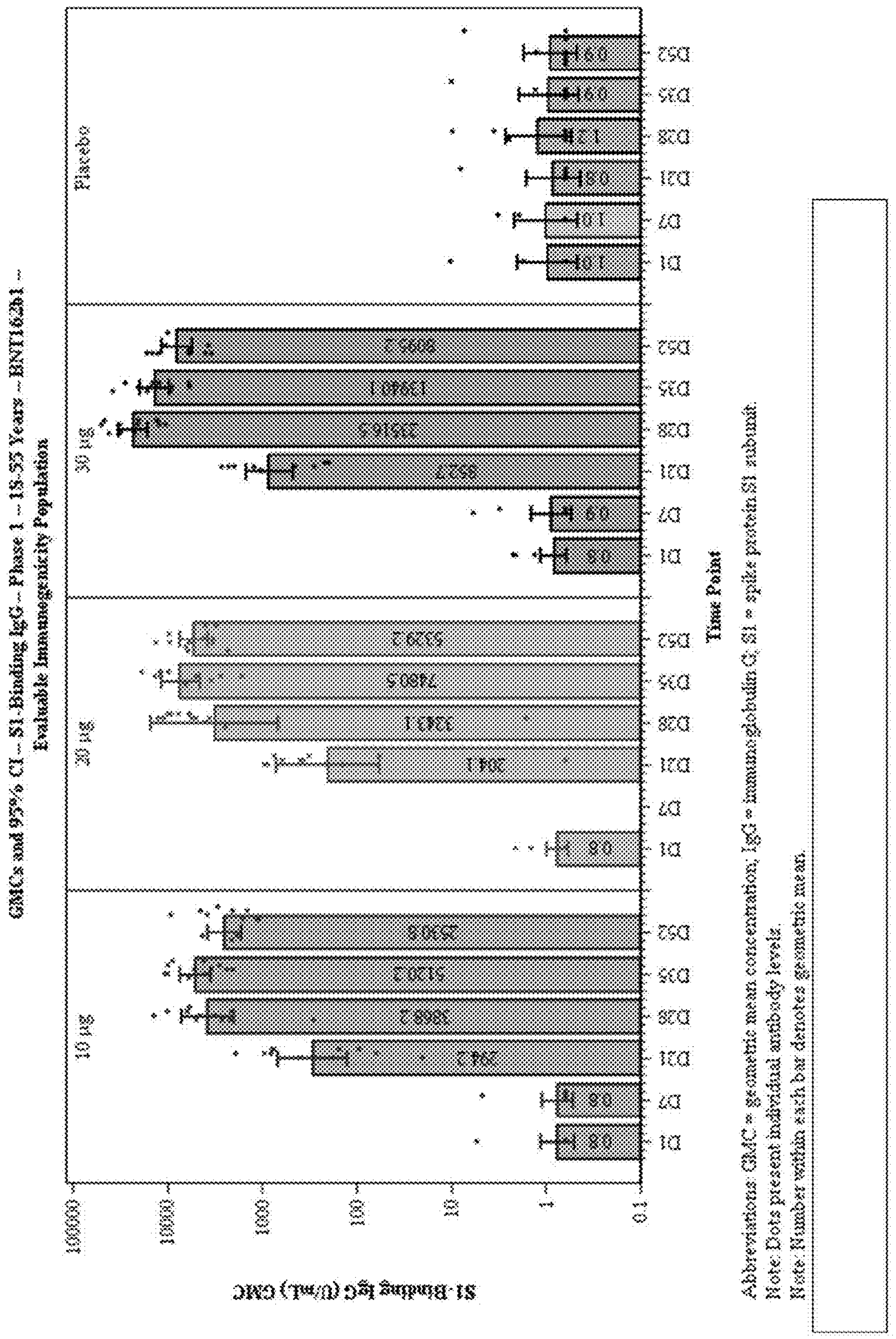
Figure 79:
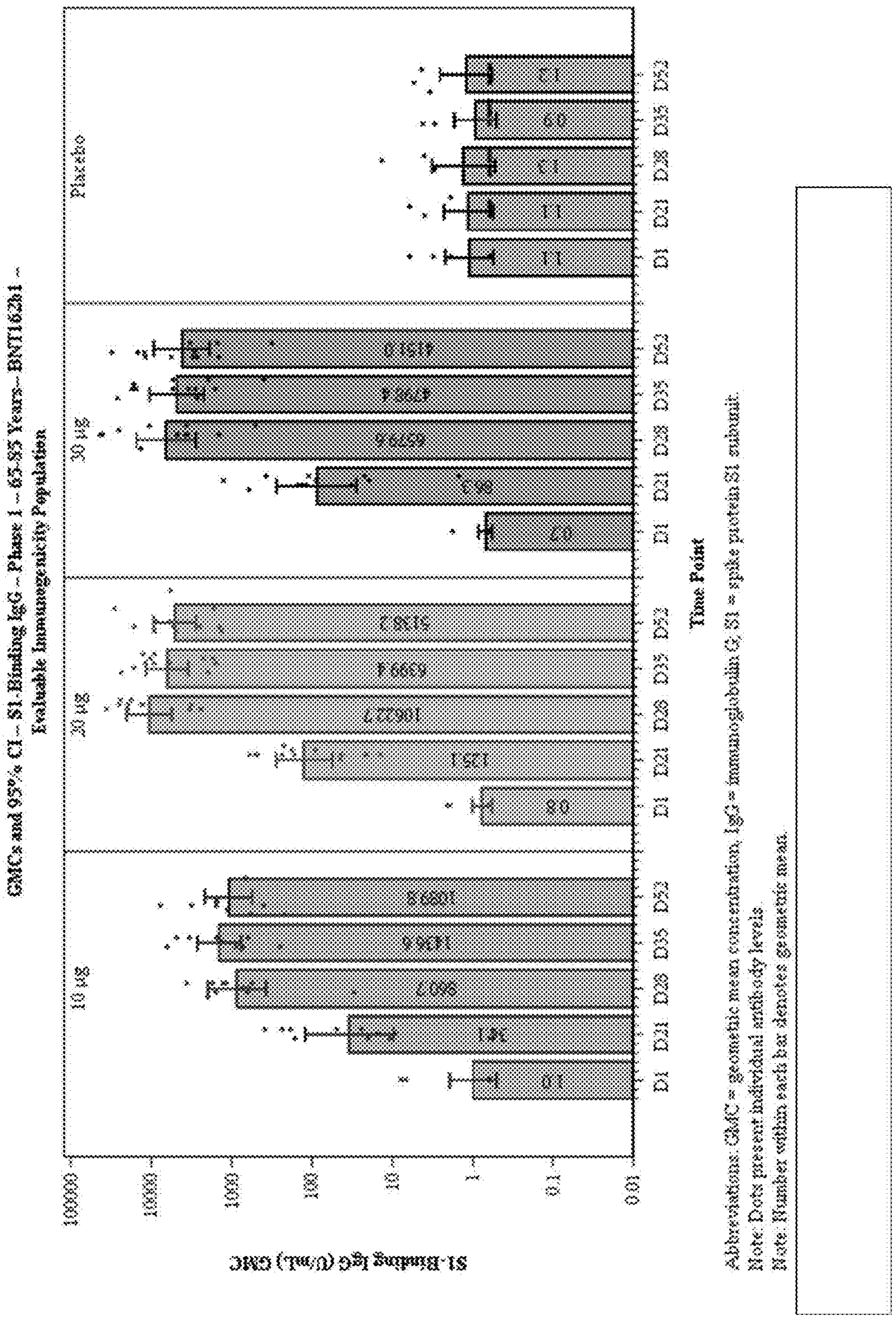
Figure 88:
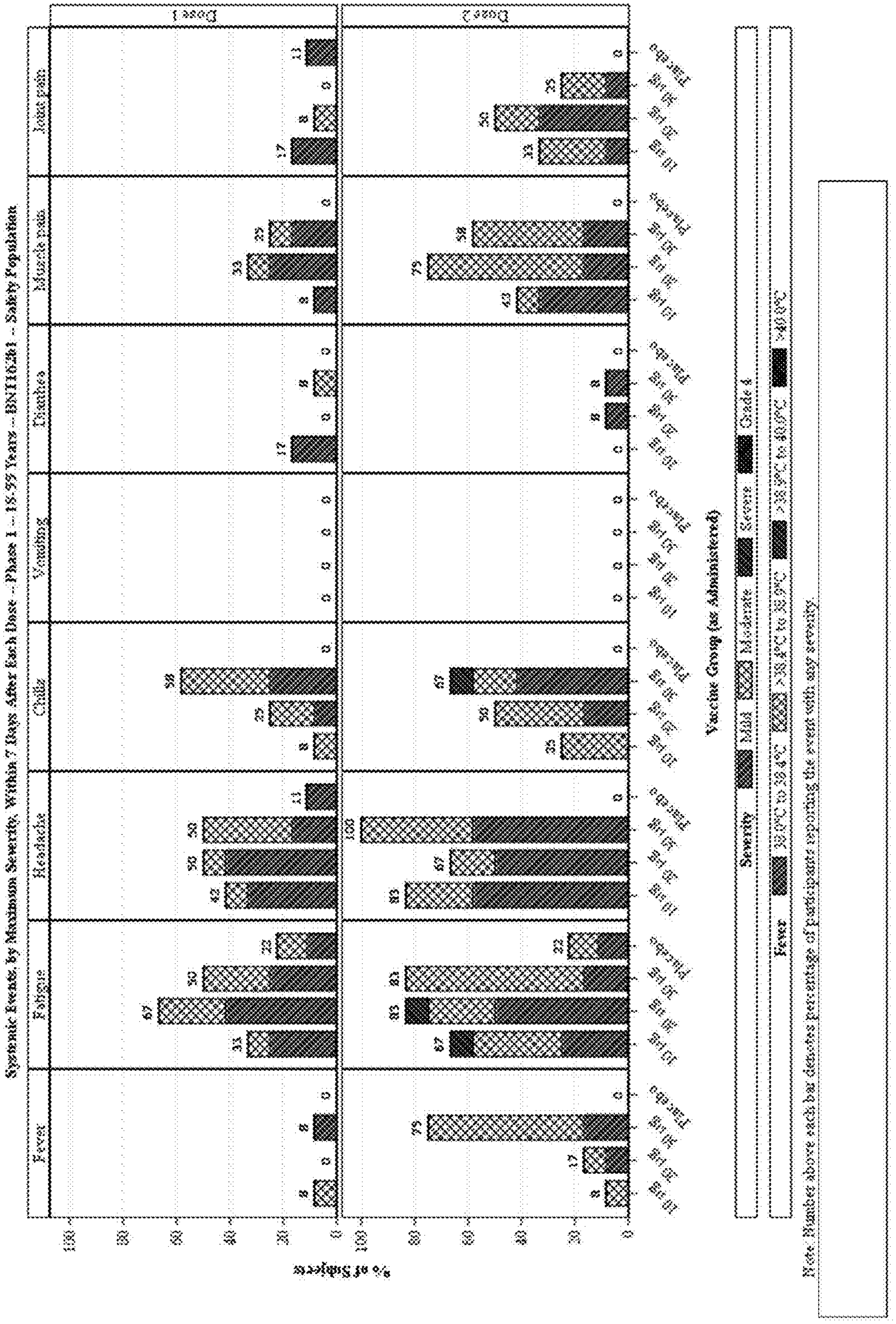
Figure 89:
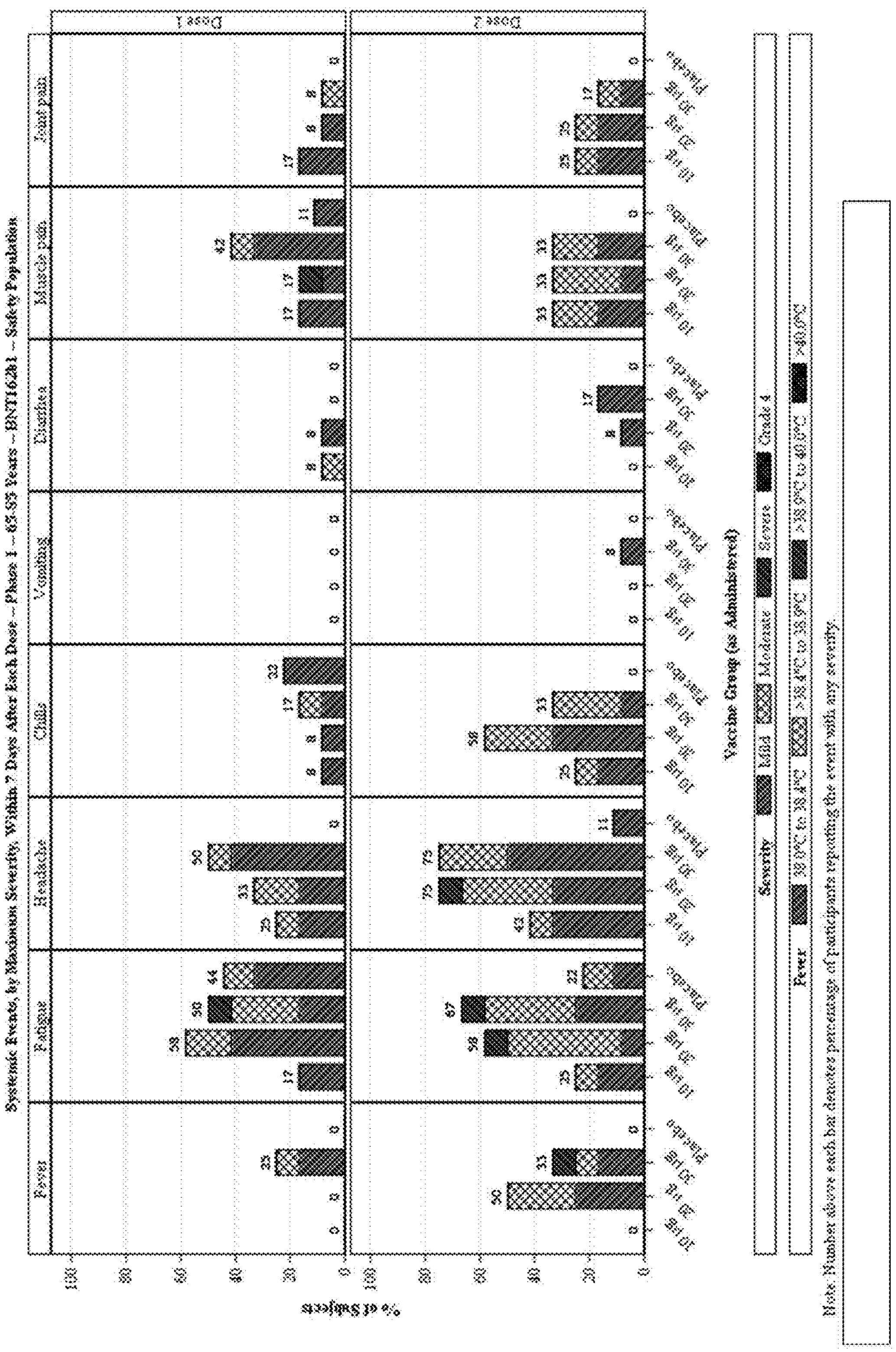
Figure 92:
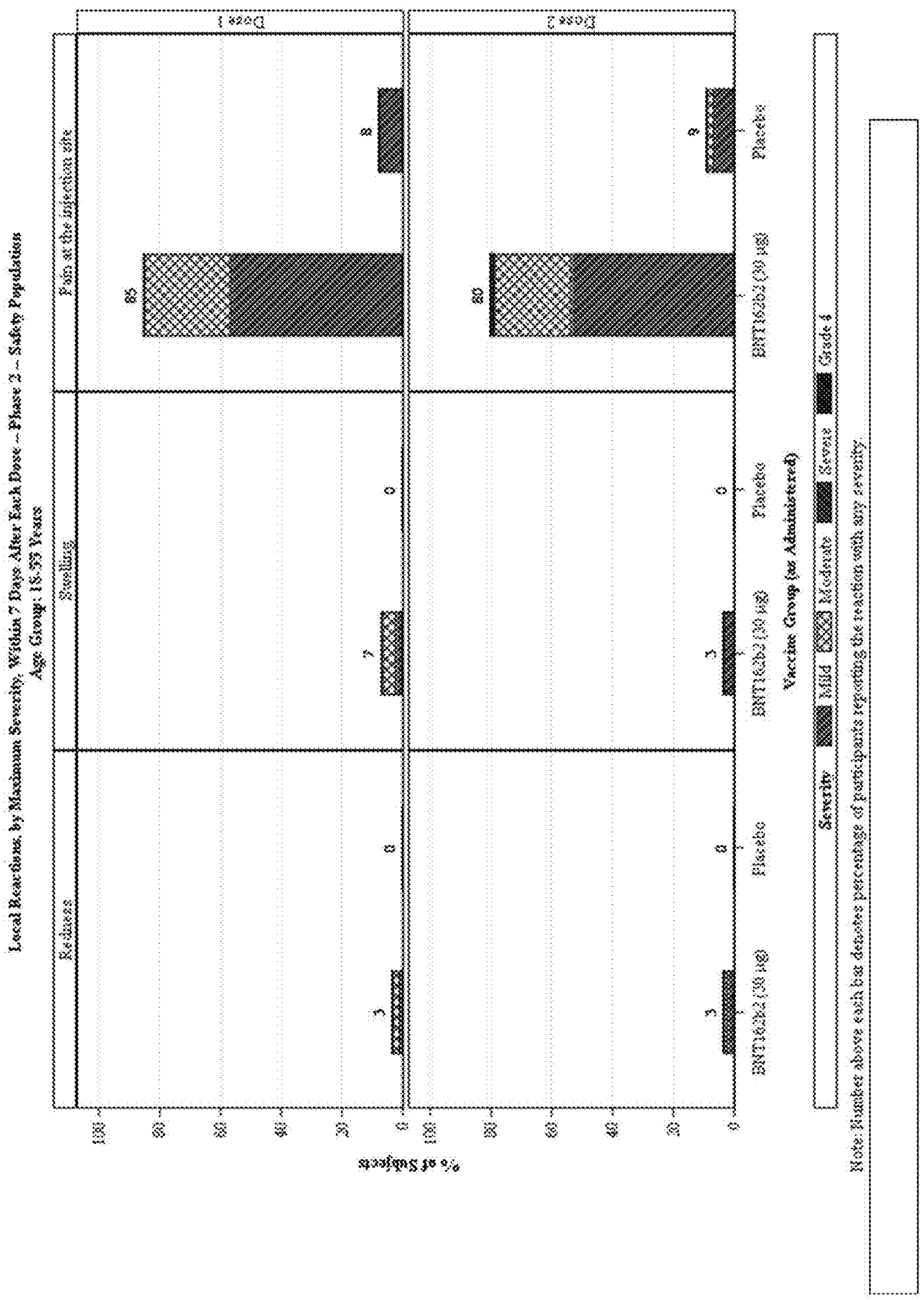
Figure 93:
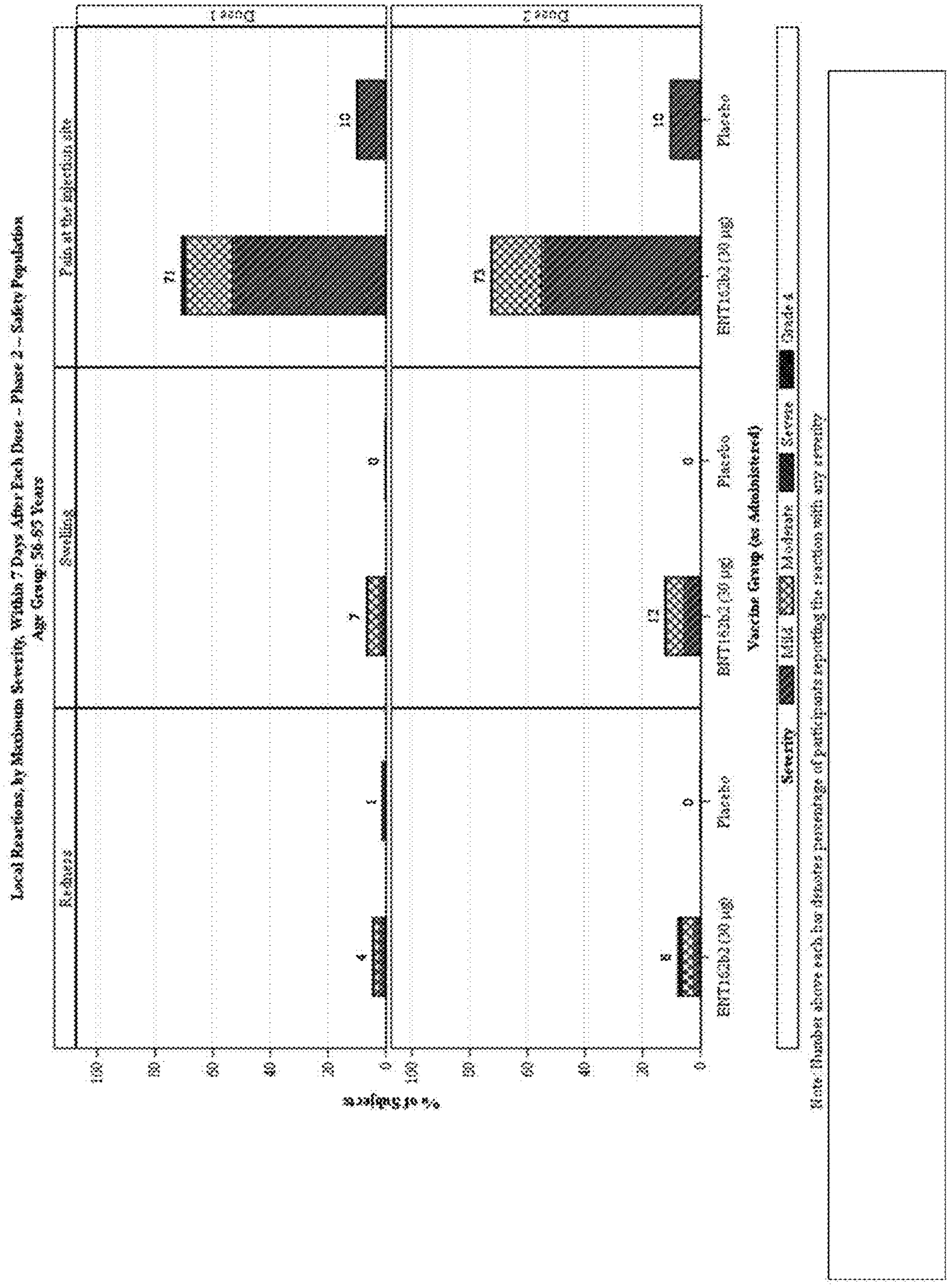
Figure 96:
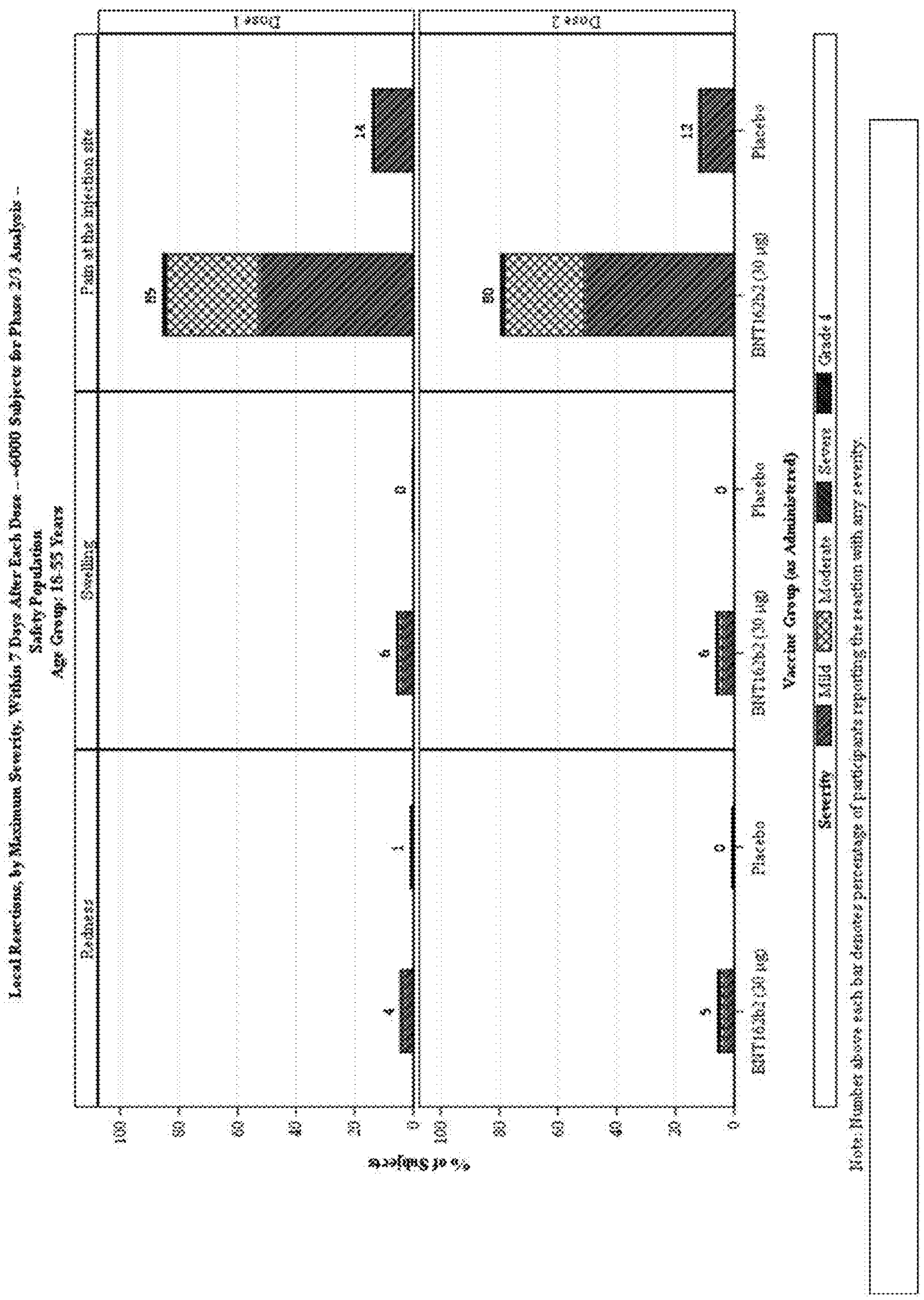
Figure 97:
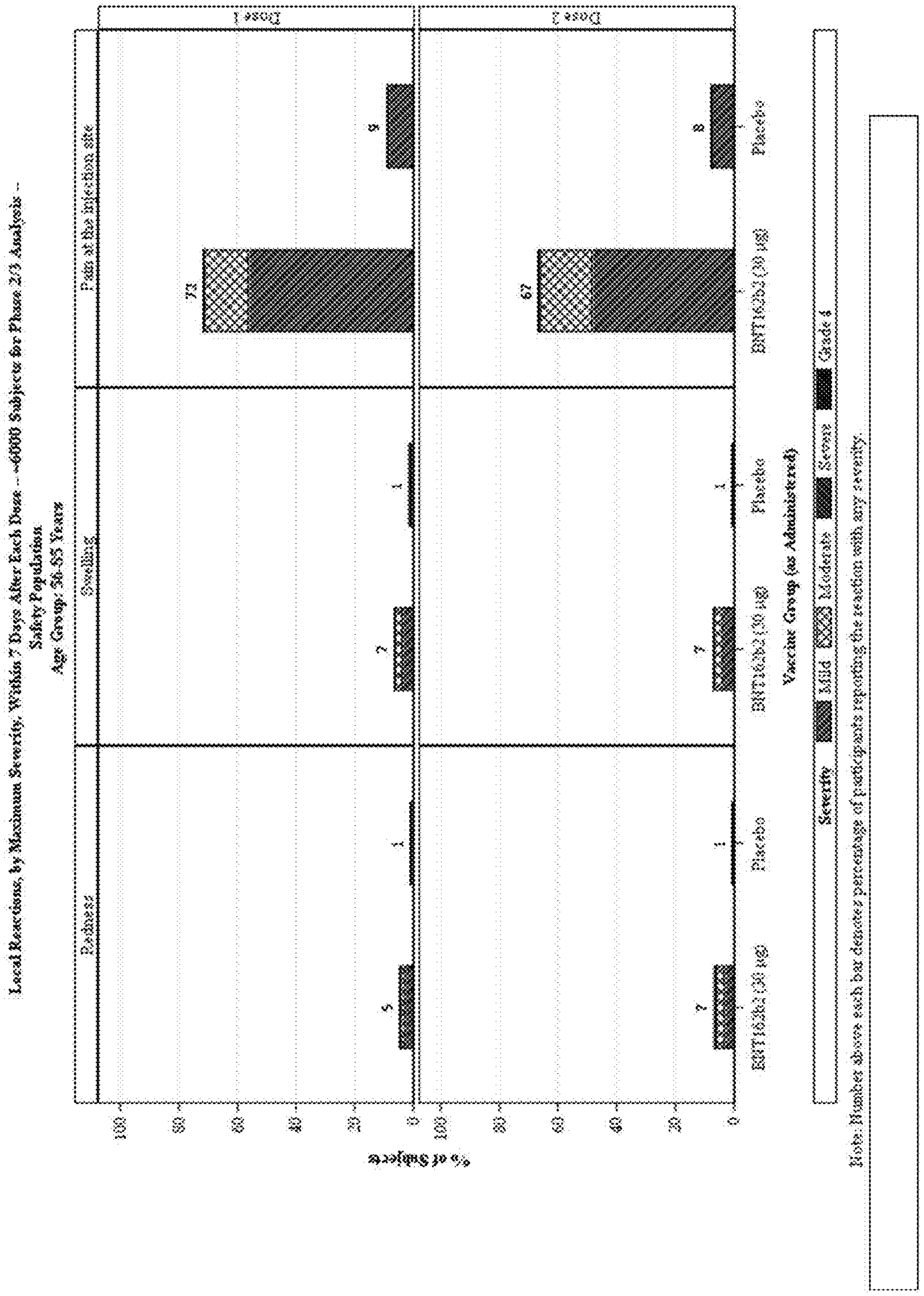

FIG. 68: BNT162b1 and b2 V8 immunization reduces viral RNA in *Rhesus macaques* after challenge with SARS-CoV-2; b2 shows earlier clearance in nose FIG. 69: Exemplary pandemic supply product packaging overview FIG. 70: Exemplary vaccine storage & handling at the point of vaccination FIG. 71: Exemplary multi-dose preparation FIG. 72. Geometric Mean Titers and 95% Cl: SARS-CoV-2 Neutralization Assay—NT50—Phase 1, 2 Doses, 21 Days Apart—18-55 Years of Age—BNT162b1—Evaluable Immunogenicity Population FIG. 73. Geometric Mean Titers and 95% CI: SARS-CoV-2 Neutralization Assay—NT50—Phase 1, 2 Doses, 21 Days Apart—65-85 Years of Age—BNT162b1—Evaluable Immunogenicity Population FIG. 74. Geometric Mean Titers and 95% Cl: SARS-CoV-2 Neutralization Assay—NT50—Phase 1, 2 Doses, 21 Days Apart—18-55 Years of Age—BNT162b2—Evaluable Immunogenicity Population FIG. 75. Geometric Mean Titers and 95% Cl: SARS-CoV-2 Neutralization Assay—NT50—Phase 1, 2 Doses, 21 Days Apart—65-85 Years of Age—BNT162b2—Evaluable Immunogenicity Population FIG. 76. Geometric Mean Concentrations and 95% Cl: SARS-CoV-2 RBD-binding IgG Level Assay—Phase 1, 2 Doses, 21 Days Apart—18-55 Years of Age—BNT162b1—Evaluable Immunogenicity Population FIG. 77. Geometric Mean Concentrations and 95% Cl: SARS-CoV-2 RBD-binding IgG Level Assay—Phase 1, 2 Doses, 21 Days Apart—65-85 Years of Age, BNT162b1—Evaluable Immunogenicity Population FIG. 78. Geometric Mean Concentrations and 95% Cl: SARS-CoV-2 S1-binding IgG Level Assay—Phase 1, 2 Doses, 21 Days Apart—18-55 Years of Age—BNT162b1—Evaluable Immunogenicity Population FIG. 79. Geometric Mean Concentrations and 95% CI: SARS-CoV-2 S1-binding IgG Level Assay—Phase 1, 2 Doses, 21 Days Apart—65-85 Years of Age—BNT162b1—Evaluable Immunogenicity Population FIG. 80. Geometric Mean Concentrations and 95% CI: SARS-CoV-2 S1-binding IgG Level Assay—Phase 1, 2 Doses, 21 Days Apart—18-55 Years of Age—BNT162b2—Evaluable Immunogenicity Population FIG. 81. Geometric Mean Concentrations and 95% CI: SARS-CoV-2 S1-binding IgG Level Assay—Phase 1, 2 Doses, 21 Days Apart—65-85 Years of Age—BNT162b2—Evaluable Immunogenicity Population FIG. 82. Geometric Mean Concentrations and 95% CI: SARS-CoV-2 RBD-binding IgG Level Assay—Phase 1, 2 Doses, 21 Days Apart—18-55 Years of Age—BNT162b2—Evaluable Immunogenicity Population FIG. 83. Geometric Mean Concentrations and 95% Cl: SARS-CoV-2 RBD-binding IgG Level Assay—Phase 1, 2 Doses, 21 Days Apart—65-85 Years of Age—BNT162b2—Evaluable Immunogenicity Population FIG. 84. Subjects Reporting Local Reactions, by Maximum Severity, Within 7 Days After Each Dose—Phase 1, 2 Doses, 21 Days Apart—18-55 Years of Age—BNT162b1—Safety Population FIG. 85. Subjects Reporting Local Reactions, by Maximum Severity, Within 7 Days After Each Dose—Phase 1, 2 Doses, 21 Days Apart—65-85 Years of Age—BNT162b1—Safety Population FIG. 86. Subjects Reporting Local Reactions, by Maximum Severity, Within 7 Days After Each Dose—Phase 1, 2 Doses, 21 Days Apart—18-55 Years of Age—BNT162b2—Safety Population FIG. 87. Subjects Reporting Local Reactions, by Maximum Severity, Within 7 Days After Each Dose—Phase 1, 2 Doses, 21 Days Apart—65-85 Years of Age—BNT162b2—Safety Population FIG. 88. Subjects Reporting Systemic Events, by Maximum Severity, Within 7 Days After Each Dose—Phase 1, 2 Doses, 21 Days Apart—18-55 Years of Age—BNT162b1—Safety Population FIG. 89. Subjects Reporting Systemic Events, by Maximum Severity, Within 7 Days After Each Dose—Phase 1, 2 Doses, 21 Days Apart—65-85 Years of Age—BNT162b1—Safety Population FIG. 90. Subjects Reporting Systemic Events, by Maximum Severity, Within 7 Days After Each Dose—Phase 1, 2 Doses, 21 Days Apart—18-55 Years of Age—BNT162b2—Safety Population FIG. 91. Subjects Reporting Systemic Events, by Maximum Severity, Within 7 Days After Each Dose—Phase 1, 2 Doses, 21 Days Apart—65-85 Years of Age—BNT162b2—Safety Population FIG. 92. Subjects Reporting Local Reactions, by Maximum Severity, Within 7 Days After Each Dose, Age Group 18 55 Years—Phase 2—Safety Population FIG. 93. Subjects Reporting Local Reactions, by Maximum Severity, Within 7 Days After Each Dose, Age Group 56 85 Years—Phase 2—Safety Population FIG. 94. Subjects Reporting Systemic Events, by Maximum Severity, Within 7 Days After Each Dose, Age Group 18 55 Years—Phase 2—Safety Population FIG. 95. Subjects Reporting Systemic Events, by Maximum Severity, Within 7 Days After Each Dose, Age Group 56 85 Years—Phase 2—Safety Population FIG. 96. Subjects Reporting Local Reactions, by Maximum Severity, Within 7 Days After Each Dose, Age Group 18 55 Years—~6000 Subjects for Phase 2/3—Safety Population FIG. 97. Subjects Reporting Local Reactions, by Maximum Severity, Within 7 Days After Each Dose, Age Group 56 85 Years—~6000 Subjects for Phase 2/3—Safety Population FIG. 98. Subjects Reporting Systemic Events, by Maximum Severity, Within 7 Days After Each Dose, Age Group 18-55 Years—~6000 Subjects for Phase 2/3—Safety Population FIG. 99. Subjects Reporting Systemic Events, by Maximum Severity, Within 7 Days After Each Dose, Age Group 56-85 Years—~6000 Subjects for Phase 2/3—Safety Population FIG. 100. Cumulative Incidence Curves for the First COVID-19 Occurrence After Dose 1—Dose 1 All-Available Efficacy Population FIG. 101. BNT162b2—Exemplary functional 50% SARS-CoV-2 neutralising antibody titers ($VN_{50}$). Younger adults (aged 18 to 55 years) and older adults (aged 56 to 85 years) were immunized with BNT162b2 on day 1 and day 22

(n=12 per group). Sera were obtained from younger adults on day 1 (baseline) and on day 8, 22 (pre boost), 29, 43, 50 and 85. Sera were obtained from older adults on day 1 (baseline) and on day 8, 22, and 29. Human COVID-19 convalescent sera (HSC, n=38) were obtained at least 14 days after a confirmed diagnosis and at a time when the donors were no longer symptomatic. SARS-CoV-2 50% neutralization titers ($VN_{50}$ titers) with 95% confidence intervals are shown for younger adults immunized with 1, 3, 10, 20, or 30 μg BNT162b2, and older adults immunized with 20 μg BNT162b2. Values smaller than the limit of detection (LOD) are plotted as 0.5*LOD. Arrowheads indicate baseline (pre-Dose 1, Day 1) and Dose 2 (Day 22). The dotted horizontal line represents the LOD. $VN_{50}$=50% SARS-CoV-2 neutralizing antibody titers; HCS=human COVID-19 convalescent serum.

Figure 102:
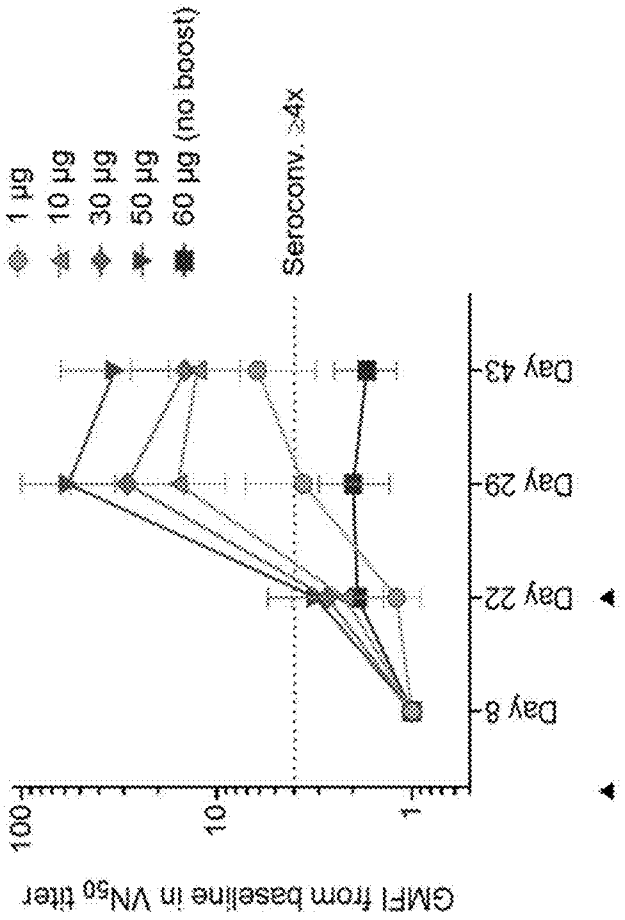

FIG. 102. BNT162b1—Exemplary fold increase from baseline in functional 50% SARS-CoV-2 neutralizing antibody titers ($VN_{50}$).

The vaccination schedule and serum sampling are the same as in FIG. 39 (n=12 per group). Geometric means fold increase (GMFI) from baseline in $VN_{50}$ titer with 95% confidence intervals are shown for younger participants (aged 18 to 55 yrs) immunized with 1, 10, 30, 50, or 60 μg BNT162b1. Arrowheads indicate baseline (pre-dose 1, Day 1) and dose 2 (Day 22). Dose 2 was not performed in the 60 μg dose group. The dotted horizontal line represents the threshold for seroconversion (fold increase ≥4). $VN_{50}$=50% SARS-CoV-2 neutralizing antibody titers.

Figure 103:
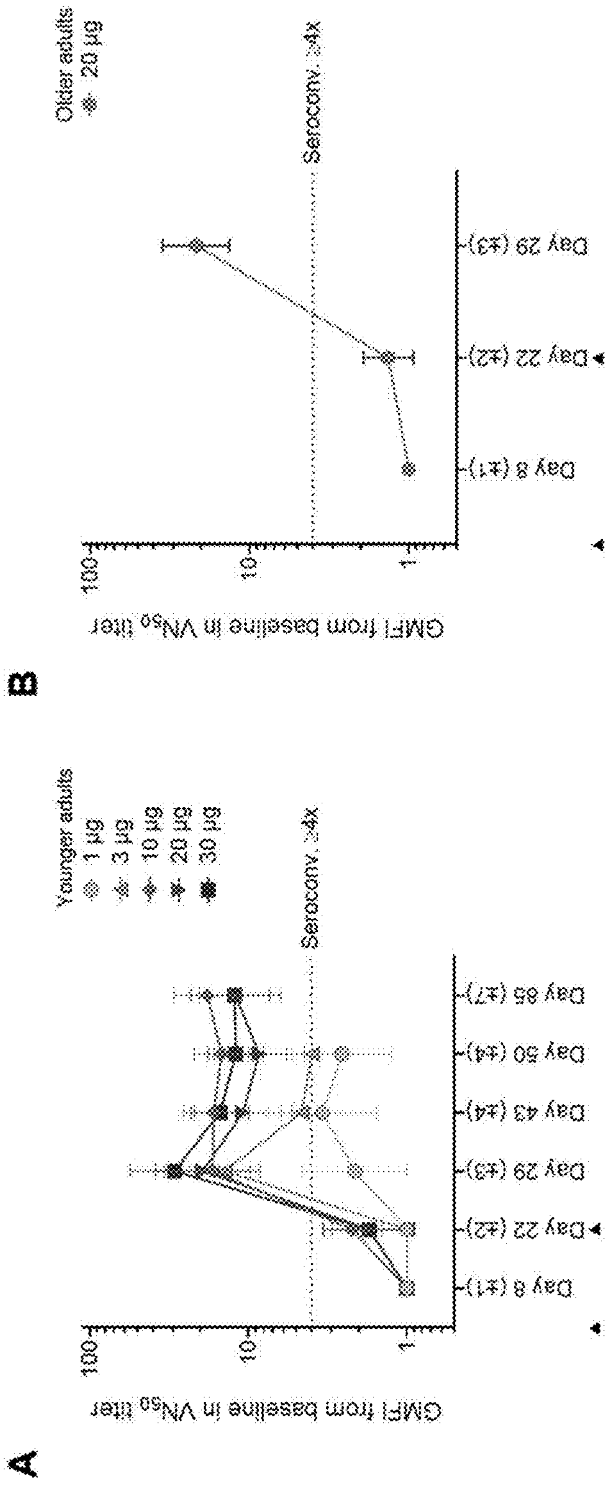

FIG. 103. BNT162b2—Exemplary fold increase from baseline in functional 50% SARS-CoV-2 neutralizing antibody titers ($VN_{50}$).

Figure 101:
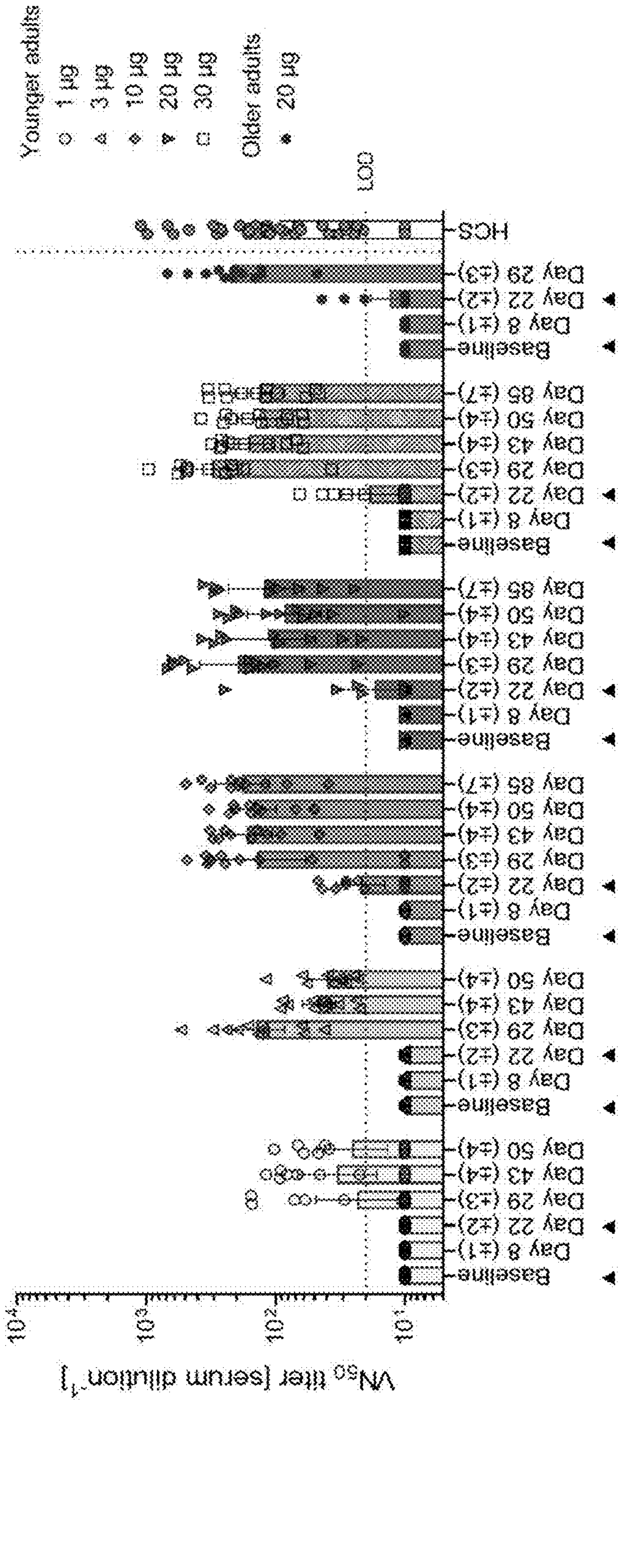

The vaccination schedule and serum sampling are the same as in FIG. 101. Geometric means fold increase (GMFI) from baseline in $VN_{50}$ titer with 95% confidence intervals are shown for (A) younger participants (aged 18 to 55 yrs) immunized with 1, 3, 10, 20, or 30 μg BNT162b2, and (B) older participants (aged 56 to 85 yrs) immunized with 20 μg BNT162b2. Arrowheads indicate baseline (pre-Dose 1, Day 1) and Dose 2 (Day 22). The dotted horizontal line represents the threshold for seroconversion (fold increase ≥4). $VN_{50}$=50% SARS-CoV-2 neutralizing antibody titers.

Figure 104:
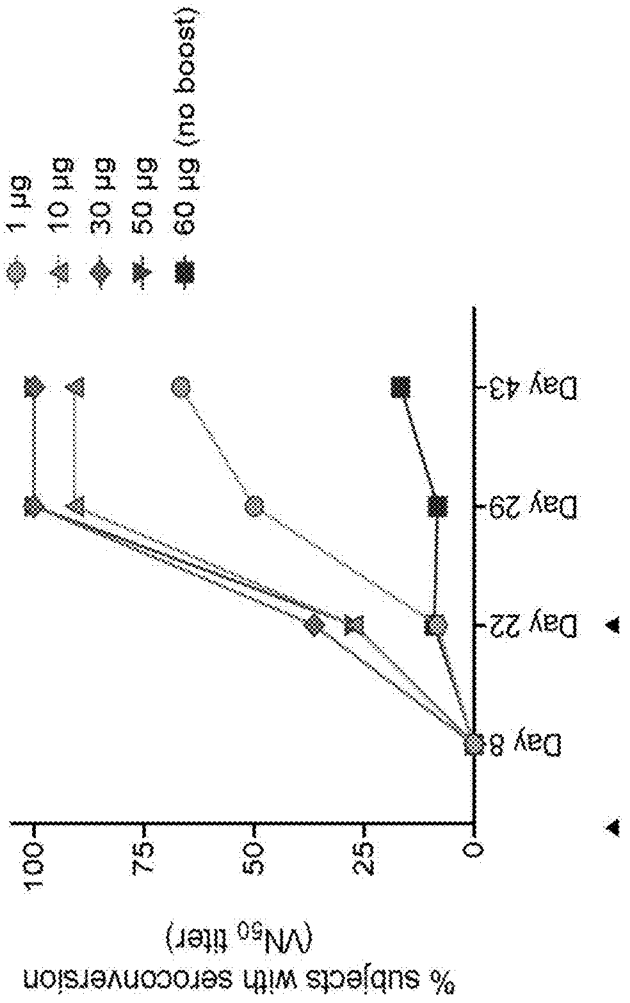

FIG. 104. Exemplary frequencies of participants with SARS-CoV-2 GMT seroconversion after immunization with BNT162b1.

The vaccination schedule and serum sampling are the same as in FIG. 39 (n=12 per group). Seroconversion with regard to 50% SARS-CoV-2 neutralizing antibody titers ($VN_{50}$) is shown for younger participants (aged 18 to 55 yrs) immunized with 1, 10, 30, 50, or 60 μg BNT162b1. Seroconversion is defined as a minimum of a 4-fold increase of functional antibody response as compared to baseline. Arrowheads indicate baseline (pre-Dose 1, Day 1) and Dose 2 (Day 22). Dose 2 was not performed in the 60 μg dose group. GMT=geometric mean titer.

Figure 105:
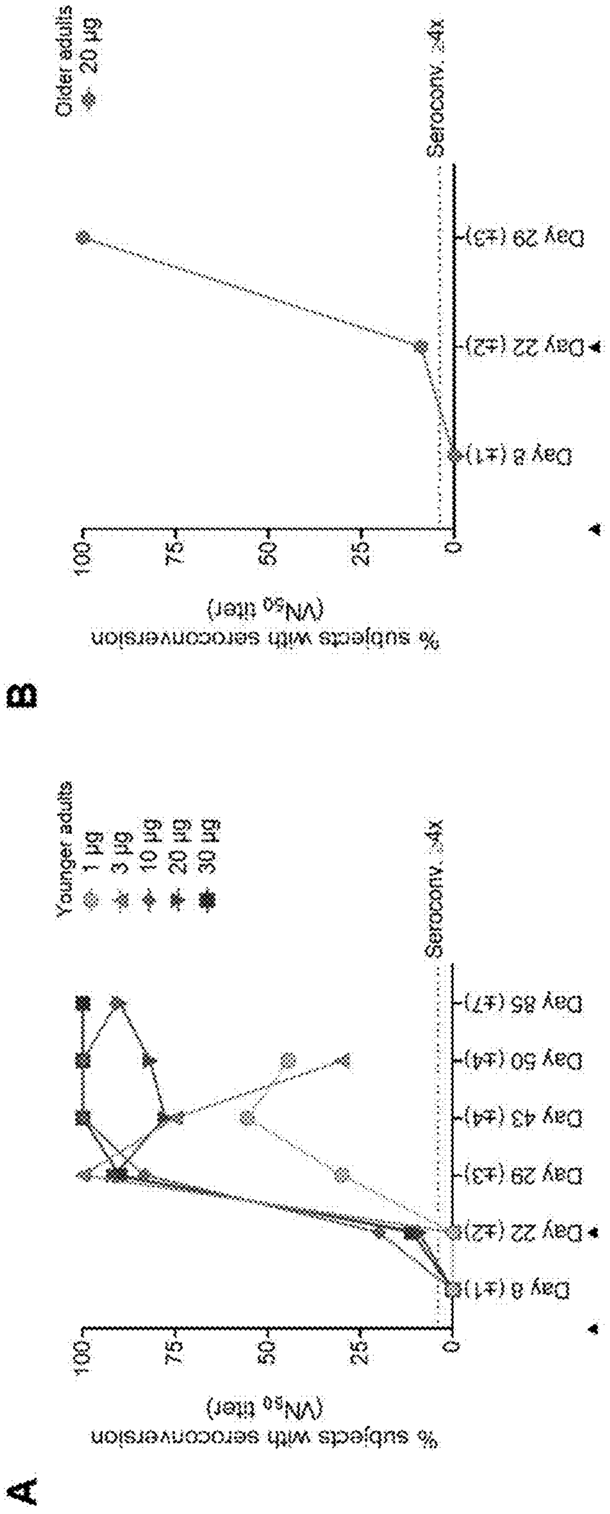

FIG. 105. Exemplary frequencies of participants with SARS-CoV-2 GMT seroconversion after immunization with BNT162b2.

The vaccination schedule and serum sampling are the same as in FIG. 101. Seroconversion with regard to 50% SARS-CoV-2 neutralizing antibody titers ($VN_{50}$) is shown for (A) younger participants (aged 18 to 55 yrs) dosed with 1, 3, 10, 20, or 30 μg BNT162b2, and (B) older participants (aged 56 to 85 yrs) dosed with 20 μg BNT162b2. Seroconversion is defined as a minimum of 4-fold increase of functional antibody response as compared to baseline. Arrowheads indicate baseline (pre-Dose 1, Day 1) and Dose 2 (Day 22). GMT=geometric mean titer.

Figure 106:
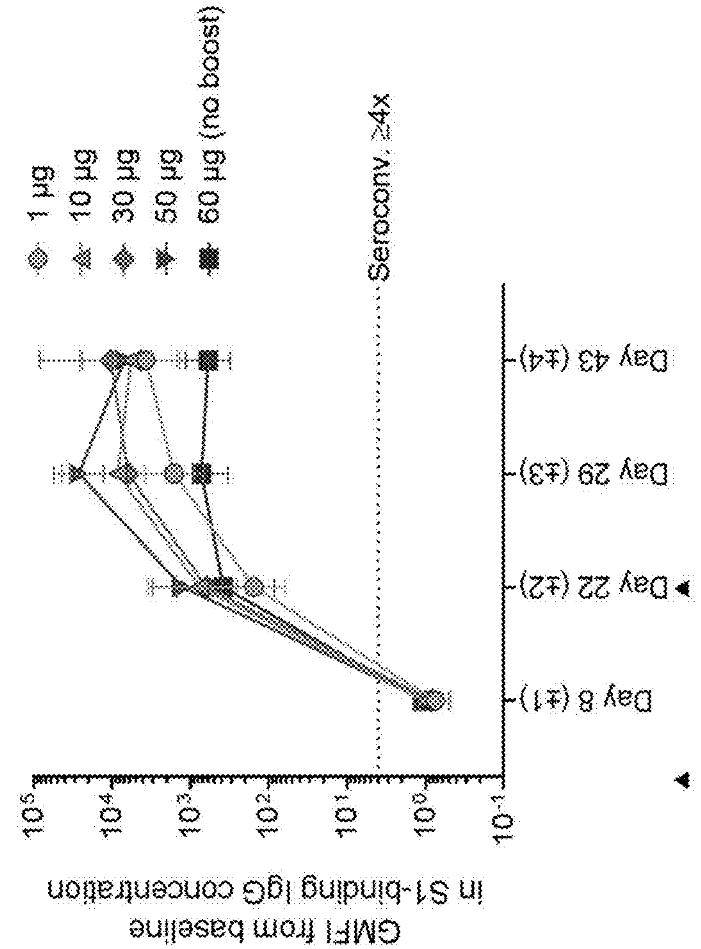

FIG. 106. Exemplary fold increase from baseline in S1-binding antibody concentrations after immunization with BNT162b1.

The vaccination schedule and serum sampling are the same as in FIG. 39 (n=12 per group). Geometric means fold increase (GMFI) from baseline in S1-binding antibody concentrations with 95% confidence intervals are shown for younger participants (aged 18 to 55 yrs) immunized with 1, 10, 30, 50, or 60 μg BNT162b1. Arrowheads indicate baseline (pre-Dose 1, Day 1) and Dose 2 (Day 22). Dose 2 was not performed in the 60 μg dose group. The dotted horizontal line represents the threshold for seroconversion (fold increase ≥4).

Figure 107:
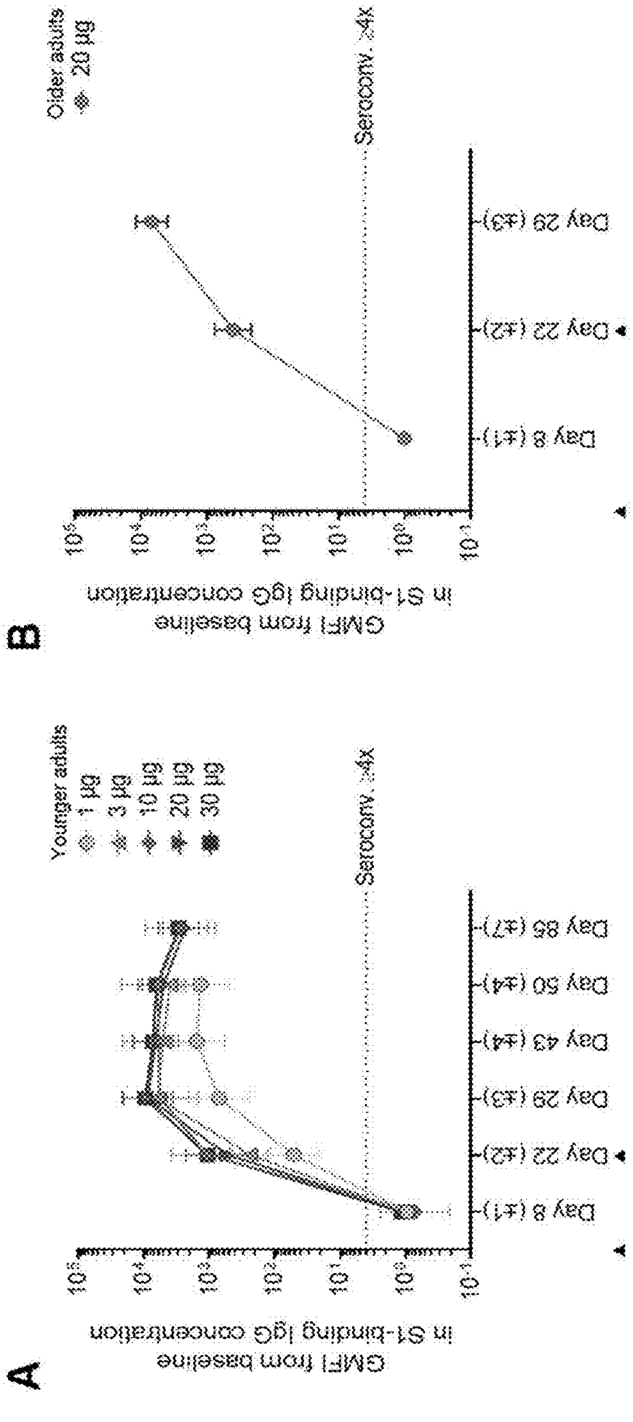

FIG. 107. Exemplary fold increase from baseline in S1-binding antibody concentration after immunization with BNT162b2.

The vaccination schedule and serum sampling are the same as in FIG. 101. Geometric means fold increase (GMFI) from baseline in S1-binding antibody concentrations with 95% confidence intervals are shown for (A) younger participants (aged 18 to 55 yrs) immunized with 1, 3, 10, 20, or 30 μg BNT162b2, and (B) older participants (aged 56 to 85 yrs) immunized with 20 μg BNT162b2. Arrowheads indicate baseline (pre-Dose 1, Day 1) and Dose 2 (Day 22). The dotted horizontal line represents the threshold for seroconversion (fold increase ≥4).

Figure 108:
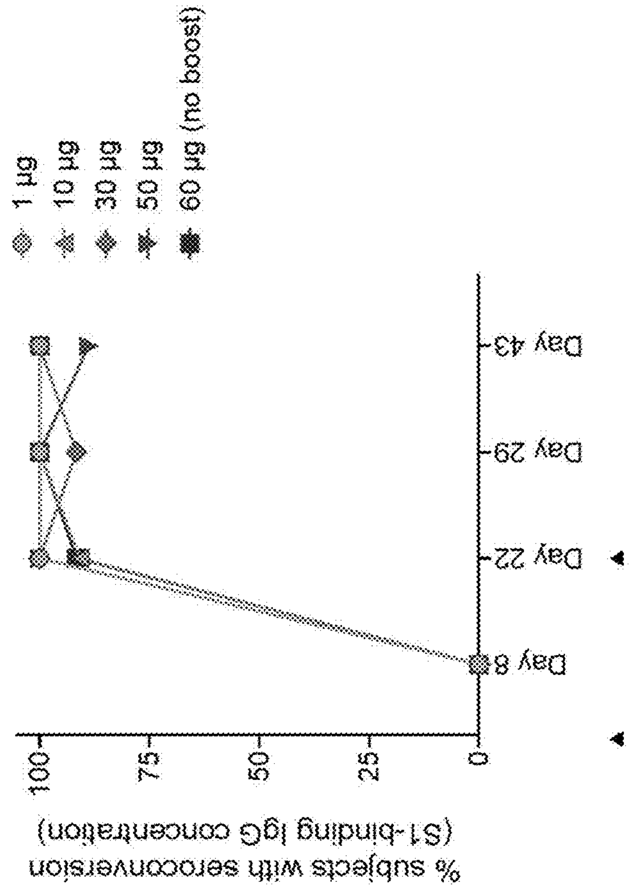

FIG. 108. Exemplary frequencies of participants with S1-binding IgG GMC seroconversion after immunization with BNT162b1.

The vaccination schedule and serum sampling are the same as in FIG. 39 (n=12 per group). Seroconversion with regard to S1-binding antibody GMC is shown for younger participants (aged 18 to 55 yrs) immunized with 1, 10, 30, 50, or 60 μg BNT162b1. Seroconversion is defined as at least a 4-fold increase of S1-binding IgG GMC response as compared to baseline. Arrowheads indicate baseline (pre-Dose 1, Day 1) and Dose 2 (Day 22). Dose 2 was not performed in the 60 μg dose group. GMC=geometric mean concentration.

Figure 109:
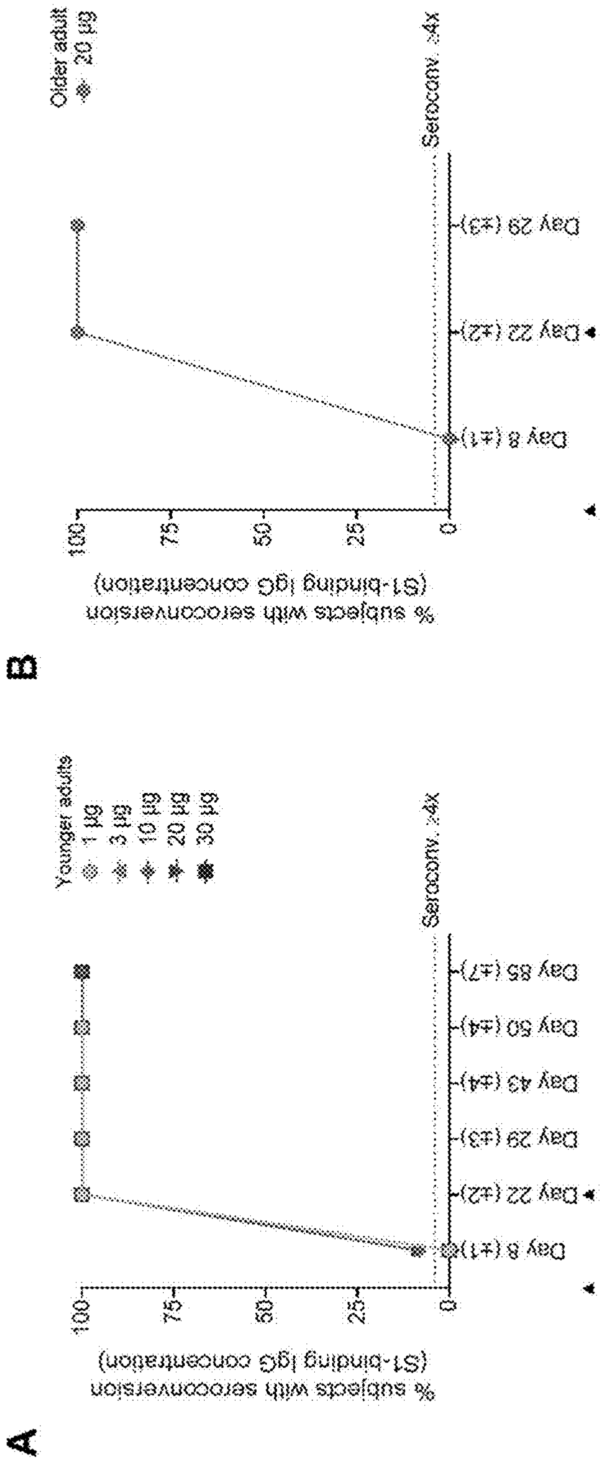

FIG. 109. Exemplary frequencies of participants with S1-binding IgG GMC seroconversion after immunization with BNT162b2.

The vaccination schedule and serum sampling are the same as in FIG. 101. Seroconversion with regard to S1-binding antibody GMC is shown for (A) younger participants (aged 18 to 55 yrs) immunized with 1, 3, 10, 20, or 30 μg BNT162b2, and (B) older participants (aged 56 to 85 yrs) dosed with 20 μg BNT162b2. Seroconversion is defined as at least a 4-fold increase of S1-binding IgG GMC response as compared to baseline. Arrowheads indicate baseline (pre-Dose 1, Day 1) and Dose 2 (Day 22). GMC=geometric mean concentration FIG. 110. Exemplary results of cytokine production produced from S-specific $CD4^+$ T cells from younger participants immunized with BNT162b2.

Peripheral blood mononuclear cell (PBMC) cell fractions isolated from blood of participants treated with varying doses of BNT162b2 were collected at baseline (pre-Dose one) and 29 days (±3 days) after Dose one and analyzed. Participants included younger participants (age 18-55 years) dosed at 1 μg (n=8), 3 μg (n=9), 10 μg (n=10), 20 μg (n=9), or 30 μg (n=10). Bar charts show arithmetic means with 95% confidence interval. Cytokine production was calculated by summing up the fractions of all $CD4^+$ T cells positive for either IFNγ, IL-2, or IL-4, setting this sum to 100% and calculating the fraction of each specific cytokine-producing subset thereof. Two participants from the 1 μg cohort, 1 participant from the 3 μg cohort, and 1 participant from the 10 μg cohort were excluded from this analysis (frequency of total cytokine-producing $CD4^+$ T cells <0.03%). IFN=interferon; IL=interleukin; younger participants=participants aged 18 to 55 yrs; S protein=SARS-CoV-2 spike protein.

Figure 111:
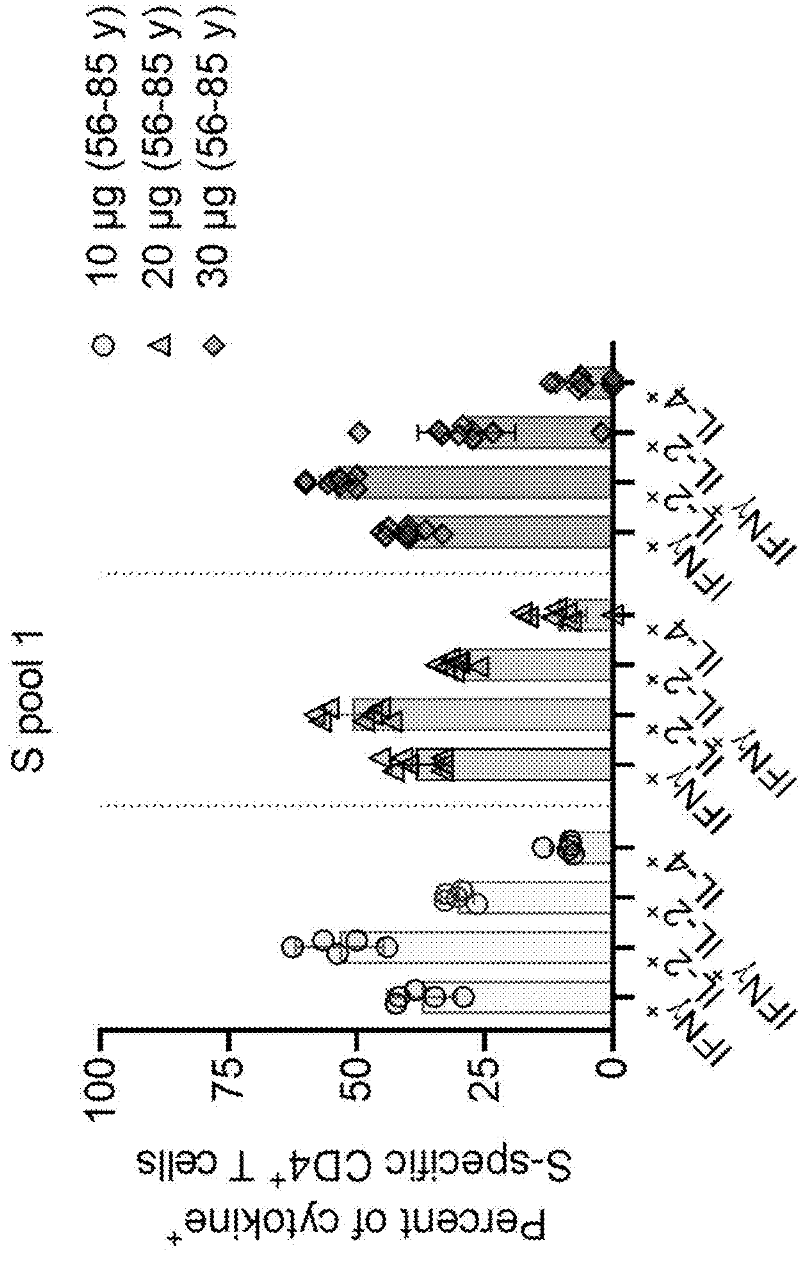

FIG. 111. Exemplary results of cytokine production produced from S-specific $CD4^+$ T cells from older participants immunized with BNT162b2.

Peripheral blood mononuclear cell (PBMC) cell fractions isolated from blood of participants treated with varying doses of BNT162b2 were collected at baseline (pre-Dose one) and 29 days (±3 days) after Dose one and analyzed. Participants included older participants (age 56-85 years) dosed at 10 μg (n=11), 20 μg (n=8), or 30 μg (n=9). Bar charts show arithmetic means with 95% Cl. Cytokine production was calculated by summing up the fractions of all CD4+ T cells positive for either IFNγ, IL-2, or IL-4, setting this sum to 100%, and calculating the fraction of each specific cytokine-producing subset thereof. Six participants from the 10 μg cohort and 1 participant from the 20 μg cohort were excluded from this analysis (frequency of total cytokine-producing $CD4^+$ T cells <0.03%). IFN=interferon; IL=interleukin; older participants=participants aged 56 to 85 yrs; S protein=SARS-CoV-2 spike protein.

Figure 112:
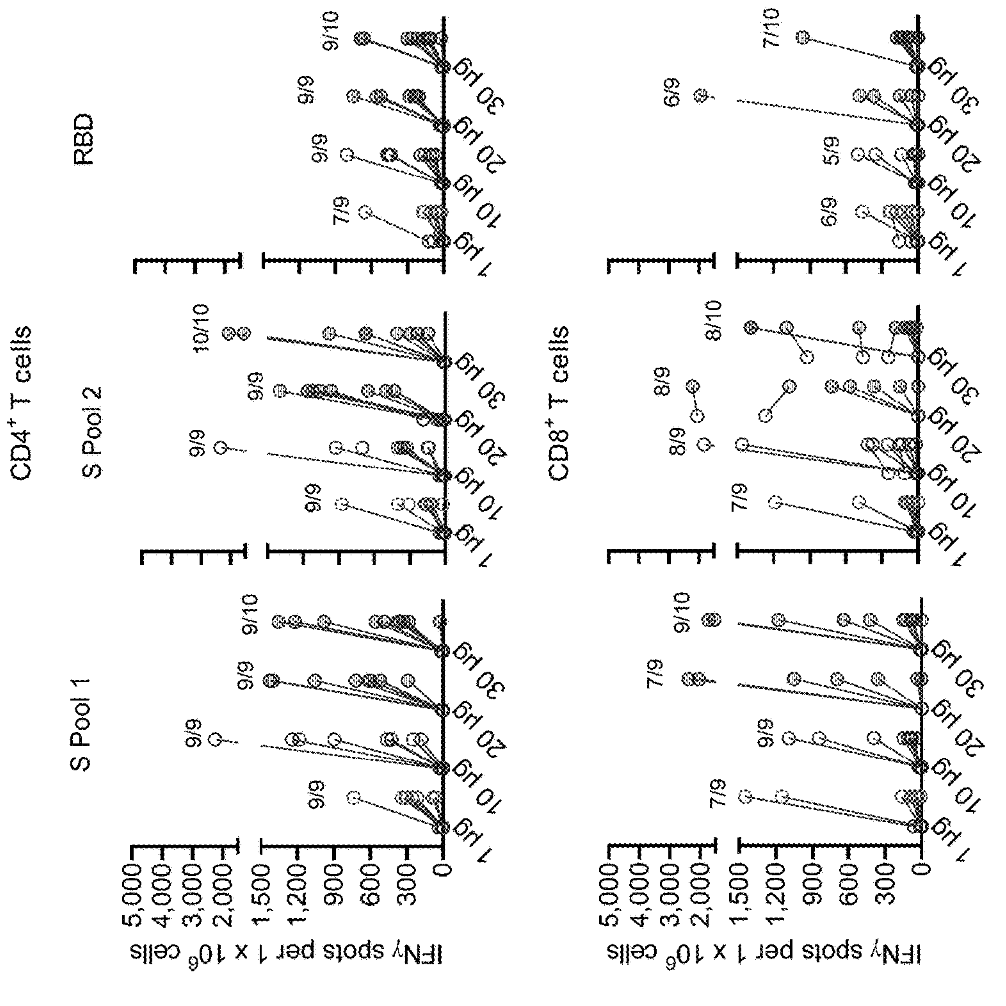
Figure 112:
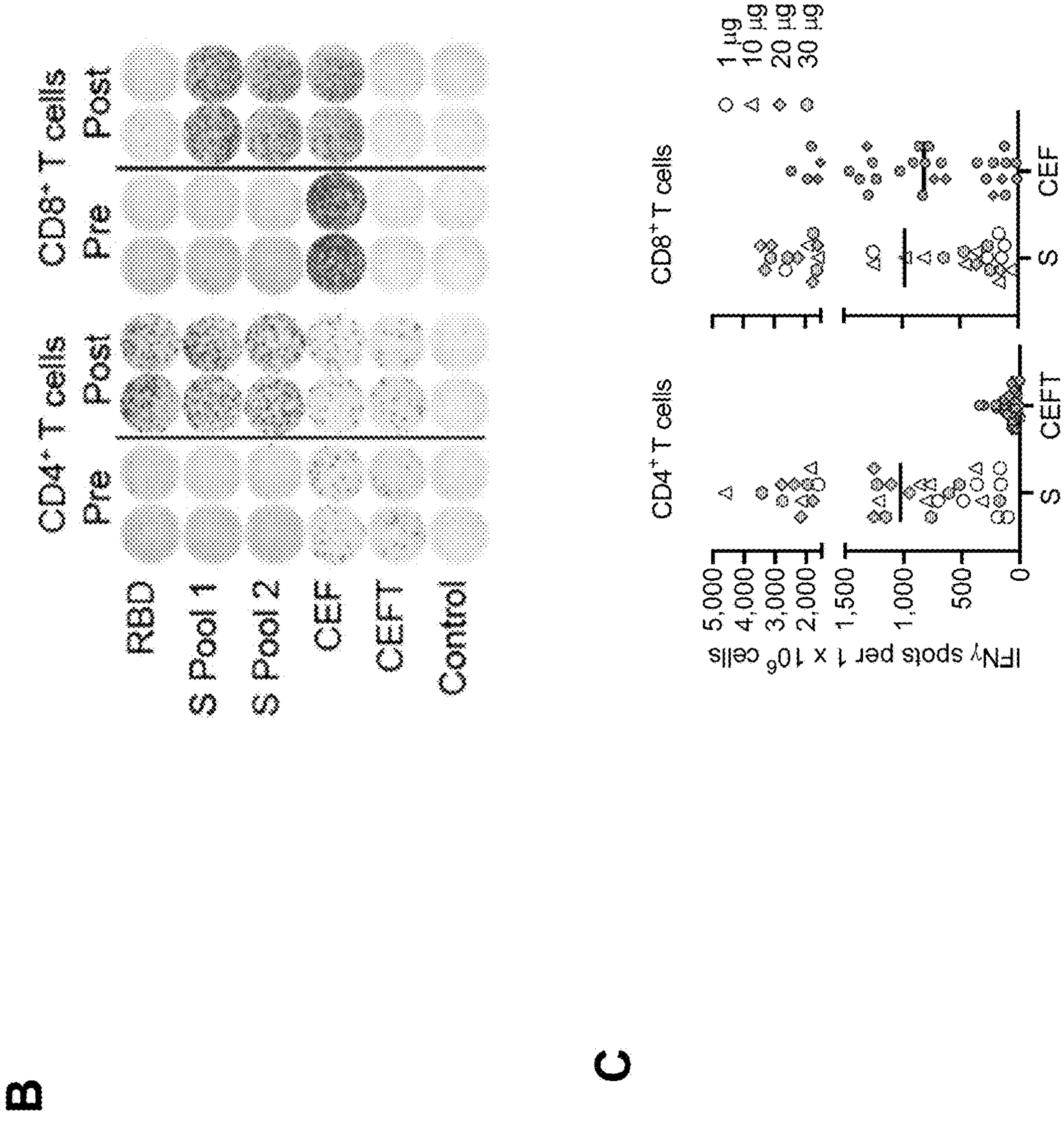

FIG. 112. Incidence and magnitude of BNT162b2-induced T-cell responses.

PBMCs obtained on day 1 (pre-prime) and day 29 (7 days post-boost) (dose cohorts 1, 10 and 20 μg, n=9 each; 30 μg, n=10) were enriched for $CD4^+$ or $CD8^+$ T cell effectors and separately stimulated over night with three overlapping peptide pools representing different portions of the wild-type sequence of SARS-CoV-2 S (N-terminal pools S pool 1 and RBD, and the C-terminal S pool 2), for assessment in direct ex vivo IFNγ ELISpot. Common pathogen T-cell epitope pools CEF (immune dominant HLA class I epitopes of CMV, EBV, influenza virus) and CEFT (immune dominant HLA class II epitopes CMV, EBV, influenza virus, tetanus toxoid) were used as controls. Cell culture medium served as negative control. Each dot represents the normalised mean spot count from duplicate wells for one study participant, after subtraction of the medium-only control ((A), (C)). (A) Antigen-specific $CD4^+$ and $CD8^+$ T-cell responses for each dose cohort. The number of participants with a detectable T-cell response on day 29 over the total number of tested participants per dose cohort is provided. Spot count data from two participants from the 20 μg dose cohort could not be normalised and are not plotted. (B) Example of $CD4^+$ and $CD8^+$ ELISpot for a 30 μg dose cohort participant. (C) S-specific T-cell responses in all participants who recognised either S peptide pool and their baseline CEFT- and CEF-specific T-cell responses. Horizontal bars indicate median values.

Figure 113:
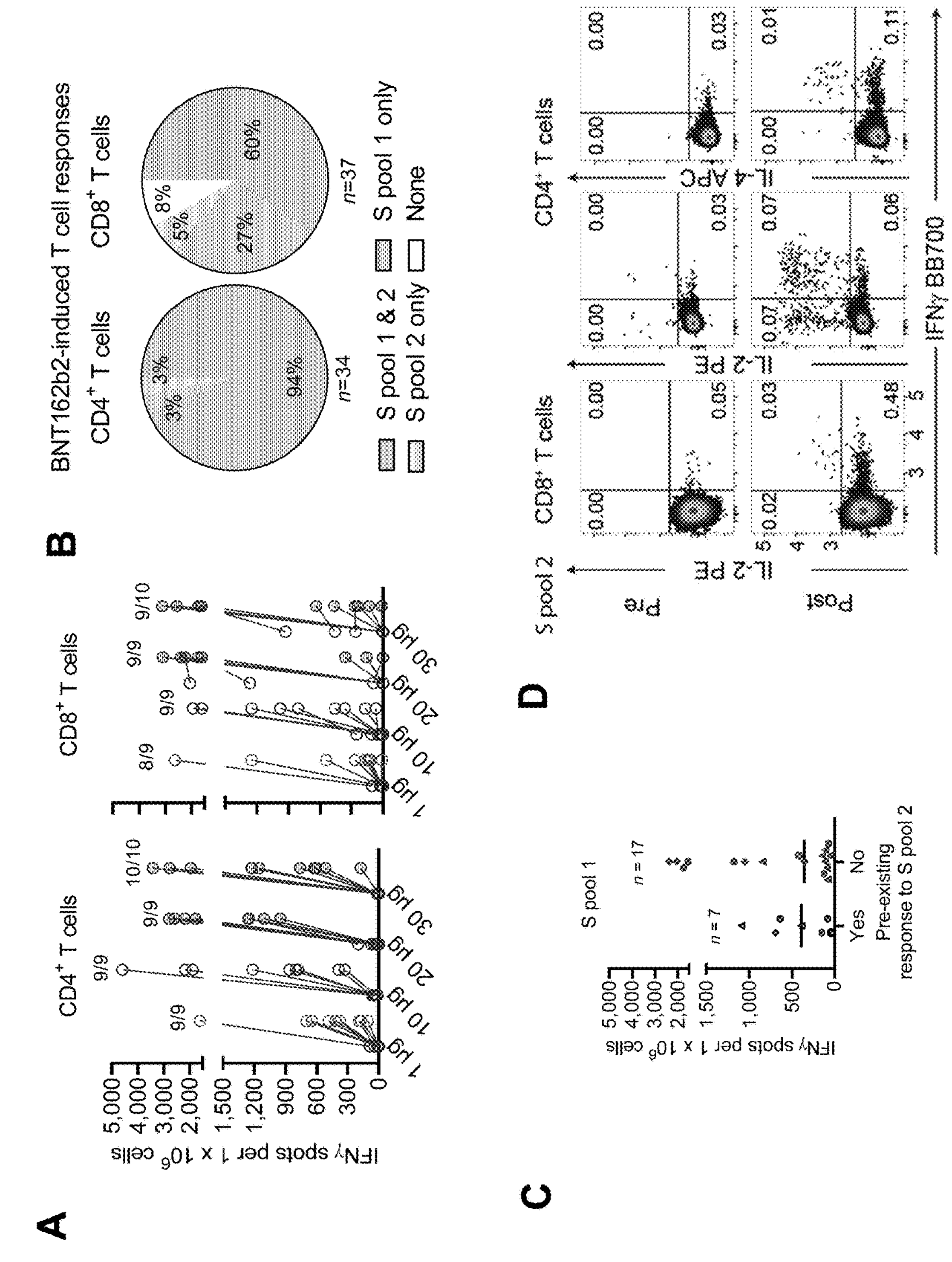
Figure 113:
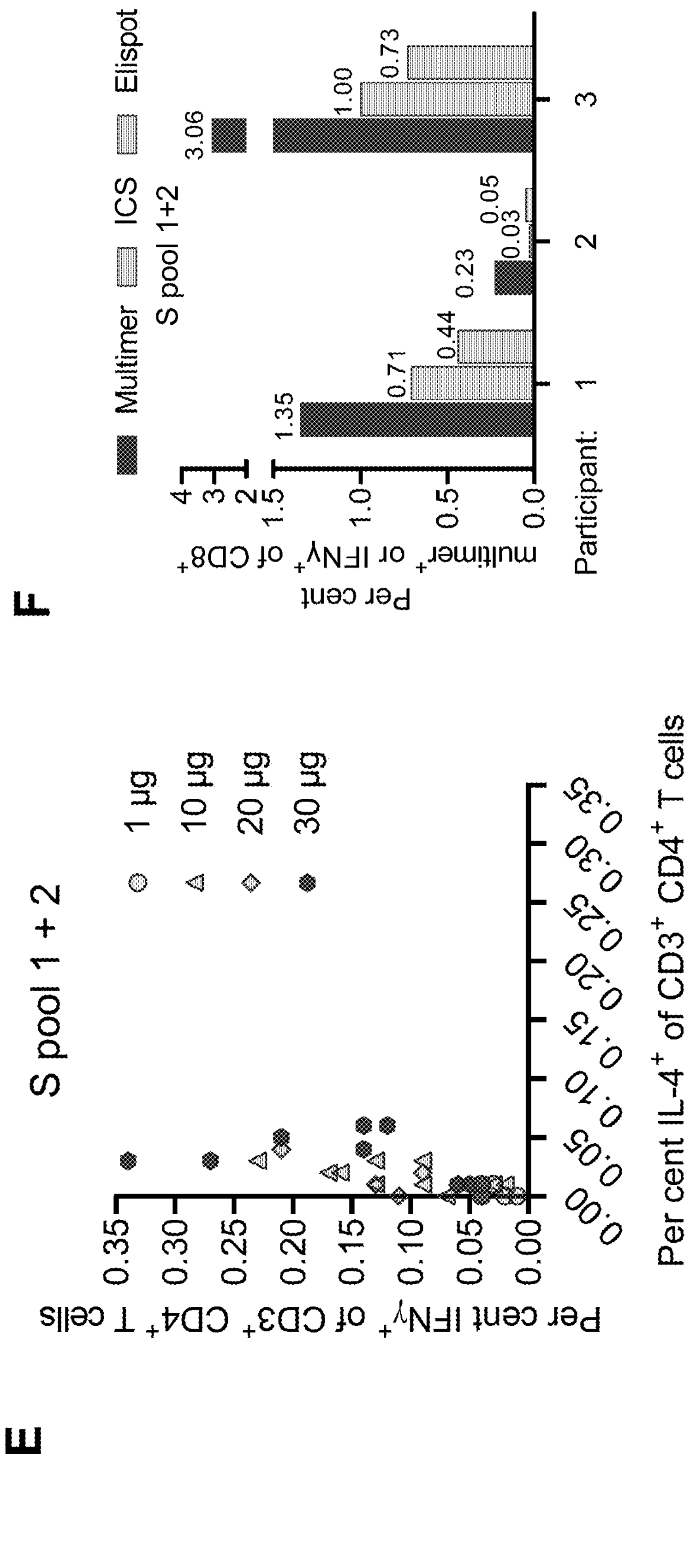

FIG. 113. BNT162b2-induced S-specific $CD8^+$ and $CD4^+$ T cells.

$CD4^+$ or $CD8^+$ T cell effector-enriched fractions of immunised participants derived from PBMCs obtained on day 1 (pre-prime) and day 29 (7 days post-boost) (1, 10 and 20 μg dose cohorts, n=9 each; 30 μg dose cohort, n=10) were stimulated overnight with two overlapping peptide pools covering the wild-type SARS-CoV-2 S (S pool 1 and S pool 2) for assessment in direct ex vivo IFNγ ELISpot ((A)-(C)). Each dot represents the normalised mean spot count from duplicate wells for one study participant, after subtraction of the medium-only control, T-cell responses against S pool 1 and S pool 2 per participant were combined. Spot count data from two participants from the 20 μg dose cohort could not be normalised and are not plotted. PBMCs from vaccinated participants on day 29 (7 days post-boost) (dose cohorts 1 μg, n=7; 10 and 30 μg, n=10; 20 μg, n=9) were stimulated as described above and analysed by flow cytometry ((D), (E)). (A) S-specific $CD4^+$ and $CD8^+$ T-cell responses for each dose cohort. Number of participants with detectable T-cell response on day 29 over the total number of tested participants per dose cohort is provided. (B) Mapping of vaccine-induced responses of participants with evaluable baseline data (n=34 for $CD4^+$ and n=37 for $CD8^+$ T cell responses) to different portions of S. De novo induced or amplified responses are classified as BNT162b2-induced response; no responses or pre-existing responses that were not amplified by the vaccinations are classified as no vaccine response (none). (C) Response strength to S pool 1 in individuals with or without a pre-existing response to S pool 2. Data from the 1 μg dose cohort are excluded, as no baseline response to S pool 2 was present in this dose cohort. Horizontal bars represent median of each group. (D) Examples of pseudocolor flow cytometry plots of cytokine-producing $CD4^+$ and $CD8^+$ T cells from a participant prime/boost vaccinated with 30 μg BNT162b2. (E) Frequency of vaccine-induced, S-specific IFNγ+CD4$^+$ T cells vs. IL4$^+$ CD4+ T cells. ICS stimulation was performed using a peptide mixture of S pool 1 and S pool 2. Each data point represents one study participant (1 μg dose cohort, n=8; 20 μg dose cohort, n=8; 10 and 30 μg, n=10 each). One participant from the 20 μg dose cohort with a strong pre-existing $CD4^+$ T cell response to S pool 2 was excluded. (F) Antigen-specific $CD8^+$ T cell frequencies determined by pMHC class I multimer staining (% multimer$^+$ of $CD8^+$), ICS and ELISpot (% IFNγ$^+$ of $CD8^+$) for the three participants analysed in FIG. 116. Signals for S pool 1 and S pool 2 were merged.

Figure 114:
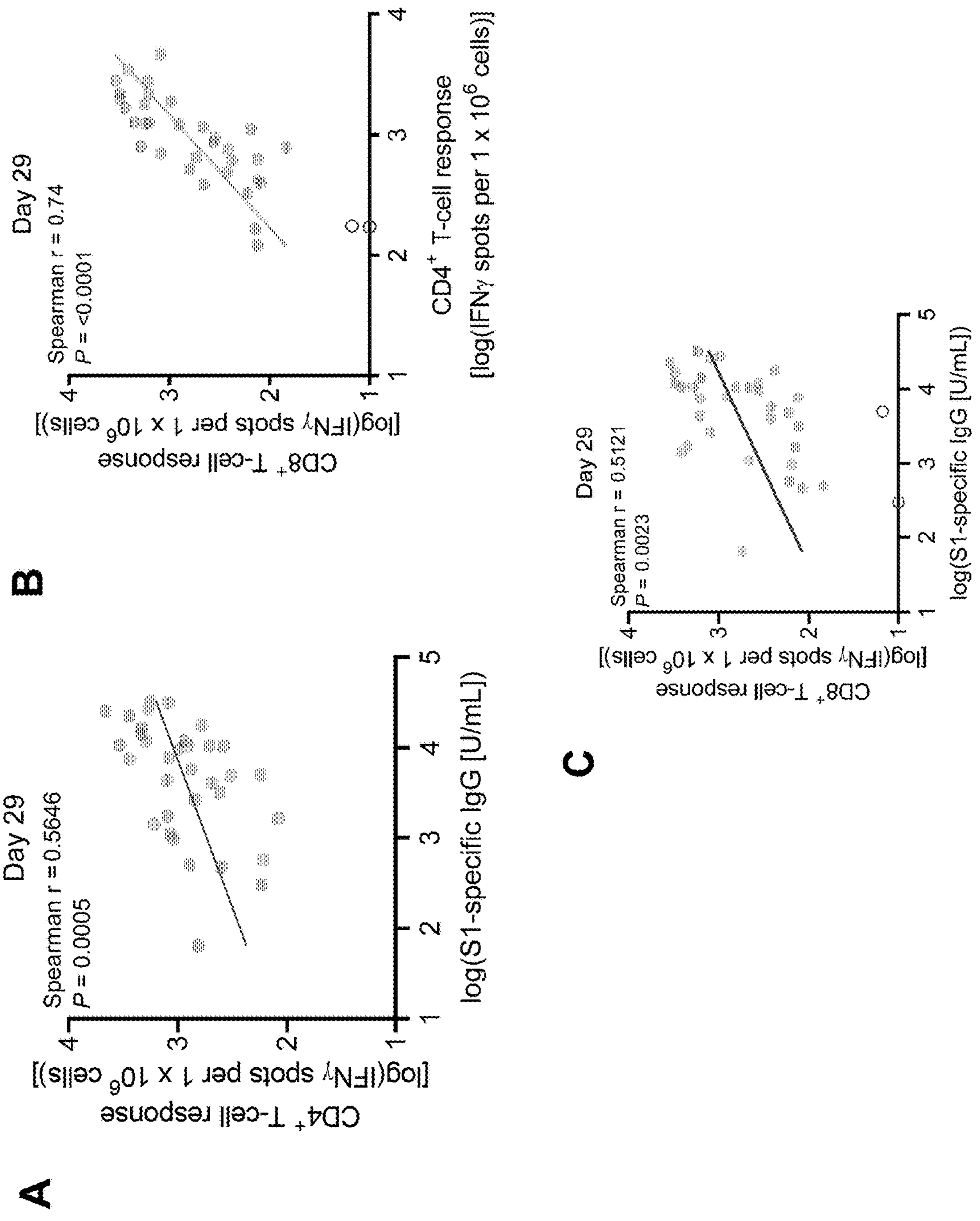

FIG. 114. Correlation of antibody and T-cell responses.

Data are plotted for all prime/boost vaccinated participants (dose cohorts 1, 10, 20 and 30 μg) from day 29, with data points for participants with no detectable T cell response (open circles; (B), (C)) excluded from correlation analysis. (A) Correlation of S1-specific IgG responses with S-specific $CD4^+$ T-cell responses. (B) Correlation of S-specific $CD4^+$ with $CD8^+$ T-cell responses. (C) Correlation of S1-specific IgG responses with S-specific $CD8^+$ T-cell responses.

Figure 115:
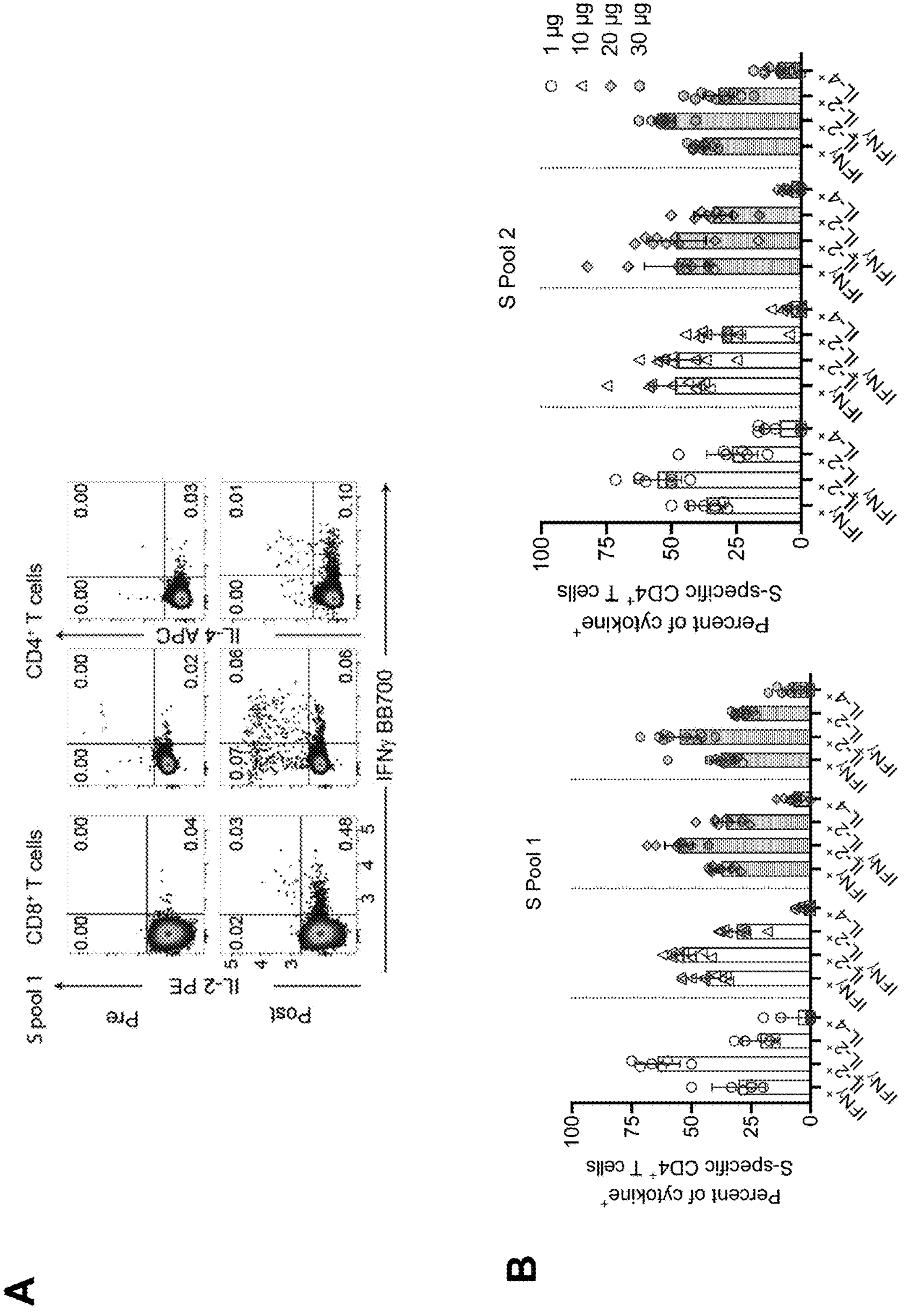
Figure 115:
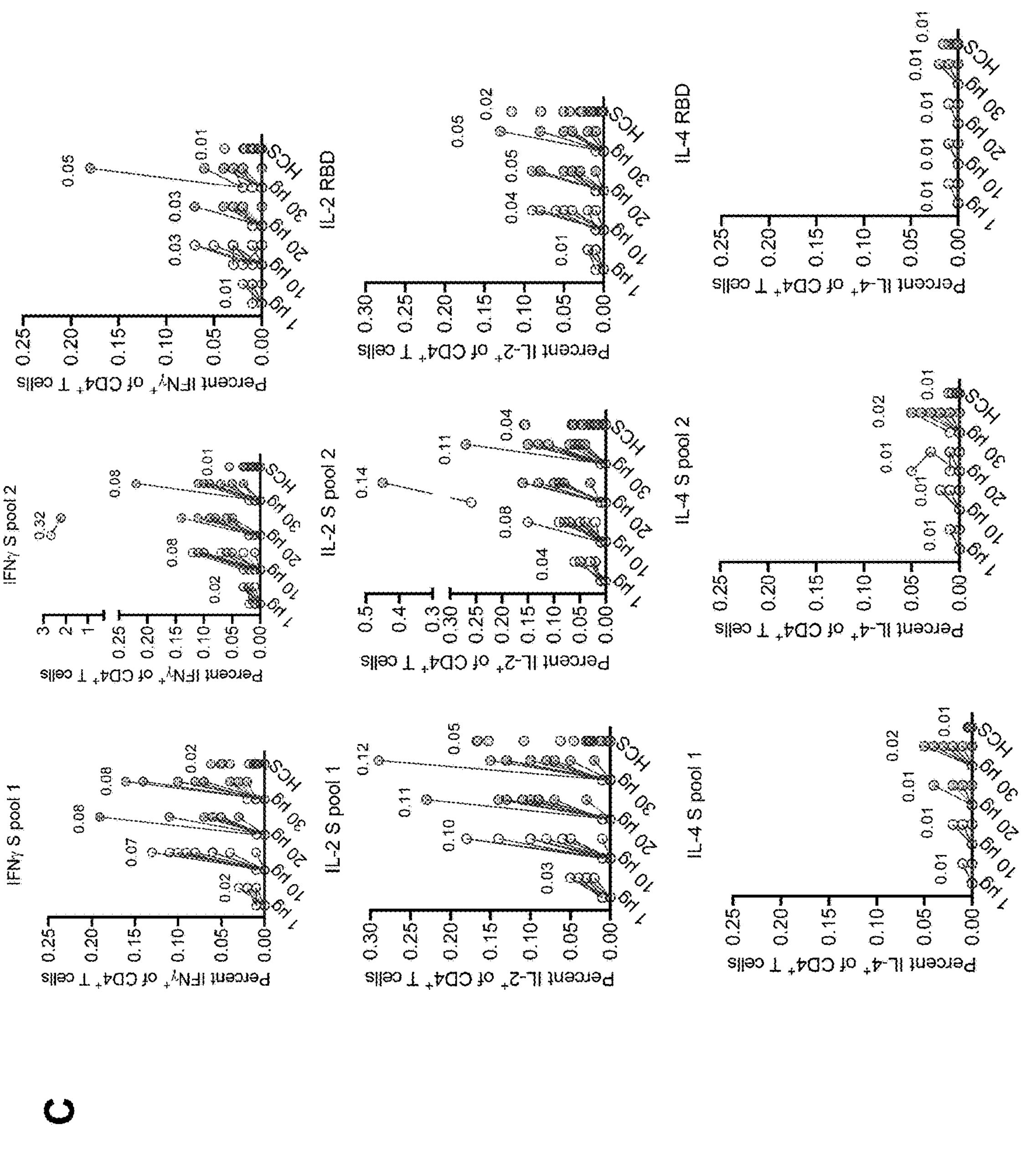
Figure 115:
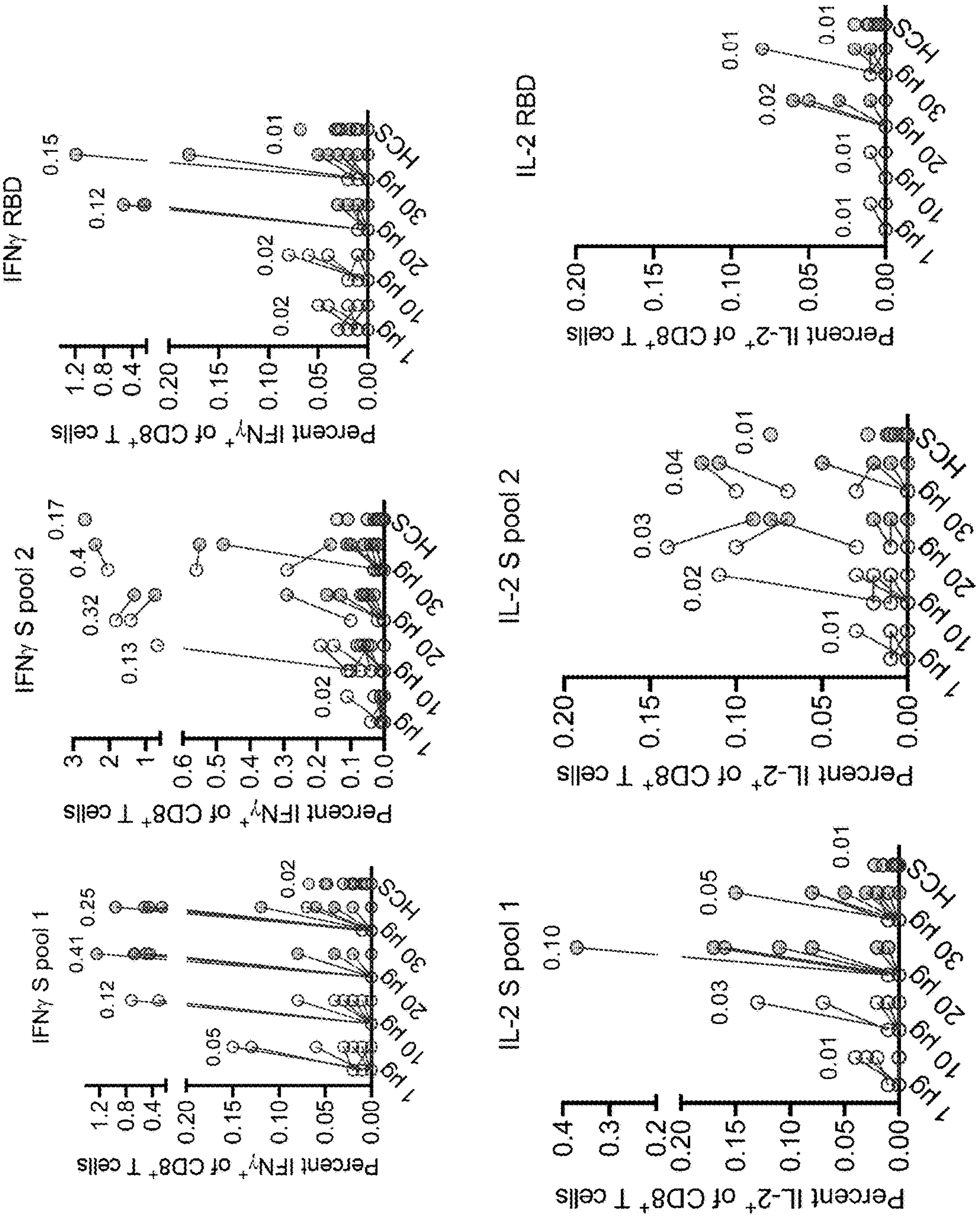

FIG. 115. Cytokine polarisation of BNT162b2-induced T cells.

PBMCs obtained on day 1 (pre-prime) and day 29 (7 days post-boost) (dose cohorts 1 μg, n=8; 10 and 30 μg, n=10 each; 20 μg, n=9) and COVID-19 recovered donors (HCS, n=18; (C), (D)) were stimulated over night with three overlapping peptide pools representing different portions of the wild-type sequence of SARS-CoV-2 S (N-terminal pools S pool 1 [aa 1-643] and RBD [aa1-16 fused to aa 327-528 of S], and the C-terminal S pool 2 [aa 633-1273]), and analysed by flow cytometry. (A) Example of pseudocolor flow cytometry plots of cytokine-producing $CD4^+$ and $CD8^+$ T cells from a 30 μg dose cohort participant in response to S pool 1. (B) S-specific $CD4^+$ T cells producing the indicated cytokine as a fraction of total cytokine-producing S-specific $CD4^+$ T cells in response to S pool 1 and S pool 2. CD4 non-responders (<0.03% total cytokine producing T cells: 1 μg, n=2 [S pool 1] and n=1 [S pool 2]; 10 μg, n=1) were excluded. Arithmetic mean with 95% confidence interval. (C) S-specific $CD4^+$ (S pool 1, S pool 2 and RBD) and (D) $CD8^+$ T cells (S pool 1, S pool 2 and RBD) producing the indicated cytokine as a fraction of total circulating T cells of the same subset. Values above data points indicate mean fractions per dose cohort. Participant PBMCs were tested as single instance ((B)-(D)).

Figure 116:
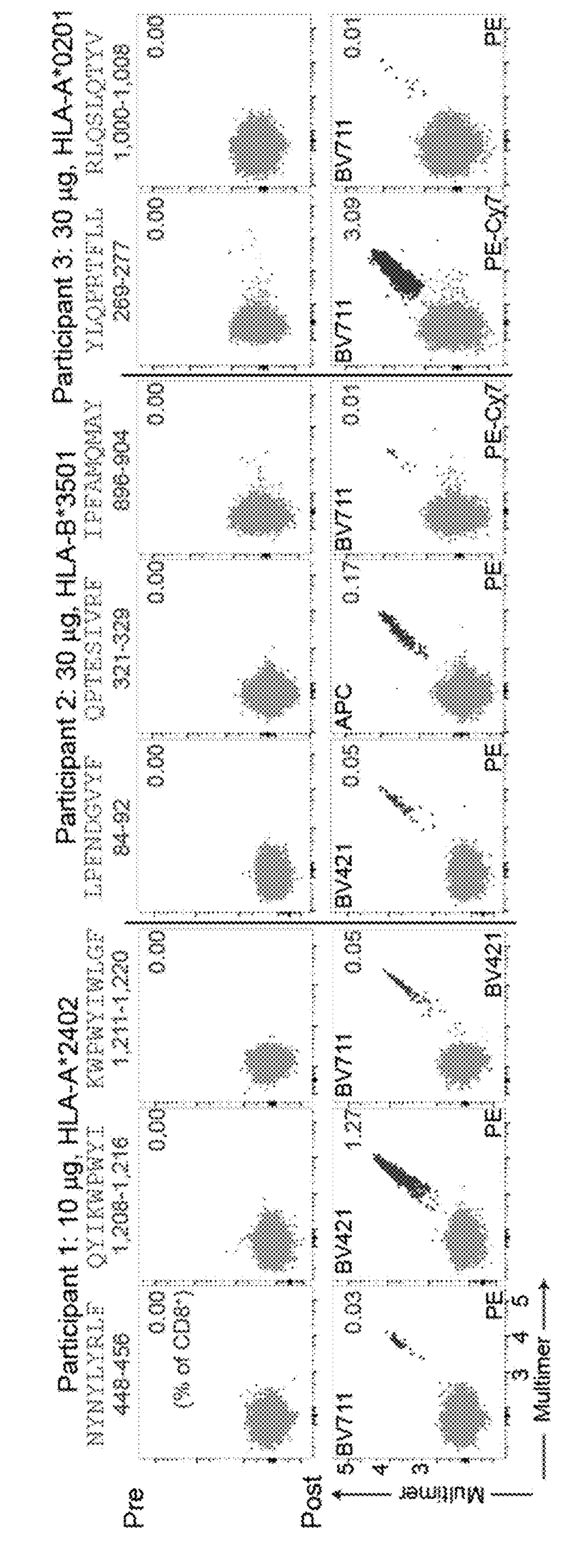
Figure 116:
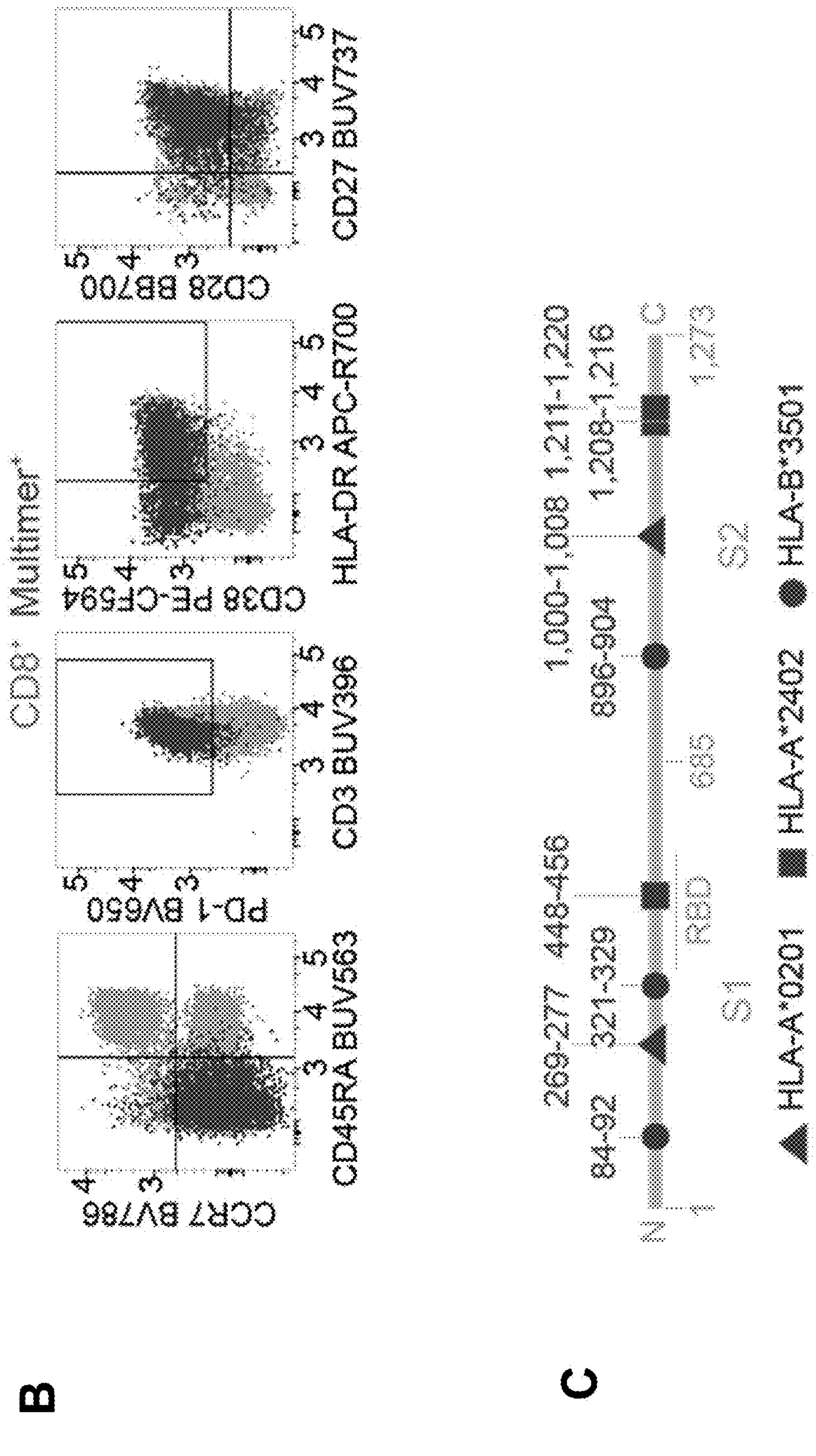

FIG. 116. Characterization of BNT162b2-induced T cells on the single epitope level.

PBMCs obtained on day 1 (pre-prime) and day 29 (7 days post-boost) of three vaccinated participants (dose cohorts 10 μg, n=1; 30 μg, n=2) were stained with individual pMHC class I multimer cocktails and analysed for T cell epitope specificity (A) and phenotype ((B); example from participant 3; YLQPRTFLL (SEQ ID NO: 40)) by flow cytometry. Peptide sequences above dot plots indicate pMHC class I multimer epitope specificity, numbers above dot plots indicate the amino acids corresponding to the epitope within S. (C) Localization of identified MHC class I-restricted epitopes within S.

Figure 117:
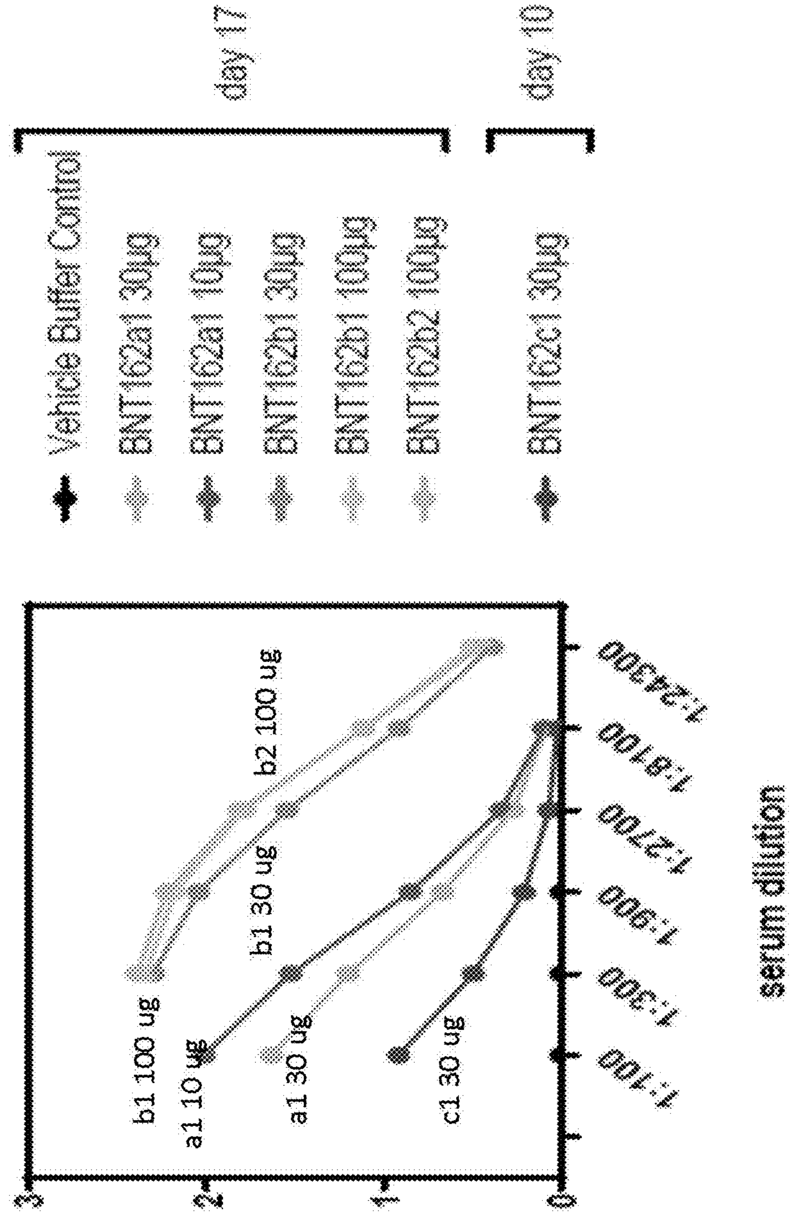

FIG. 117. ELISA screening analysis of exemplary cohort sera to detect antibody responses directed against the recombinant SARS-CoV-2 spike protein S1 domain.

ELISA was performed using serum samples collected on day 10 after two immunisations (prime/boost on days 1 and 8) with BNT162c1, or on day 17 after three administrations (prime/boost on days 1/8/15) of BNT162a1, BNT162b1, or BNT162b2 to analyse elicited antibody responses. The serum samples were tested against the S1 protein. Group mean AOD values of n=20 mice/group are shown by dots across serum dilutions ranging from 1:100 to 1:24,300.

Figure 118:
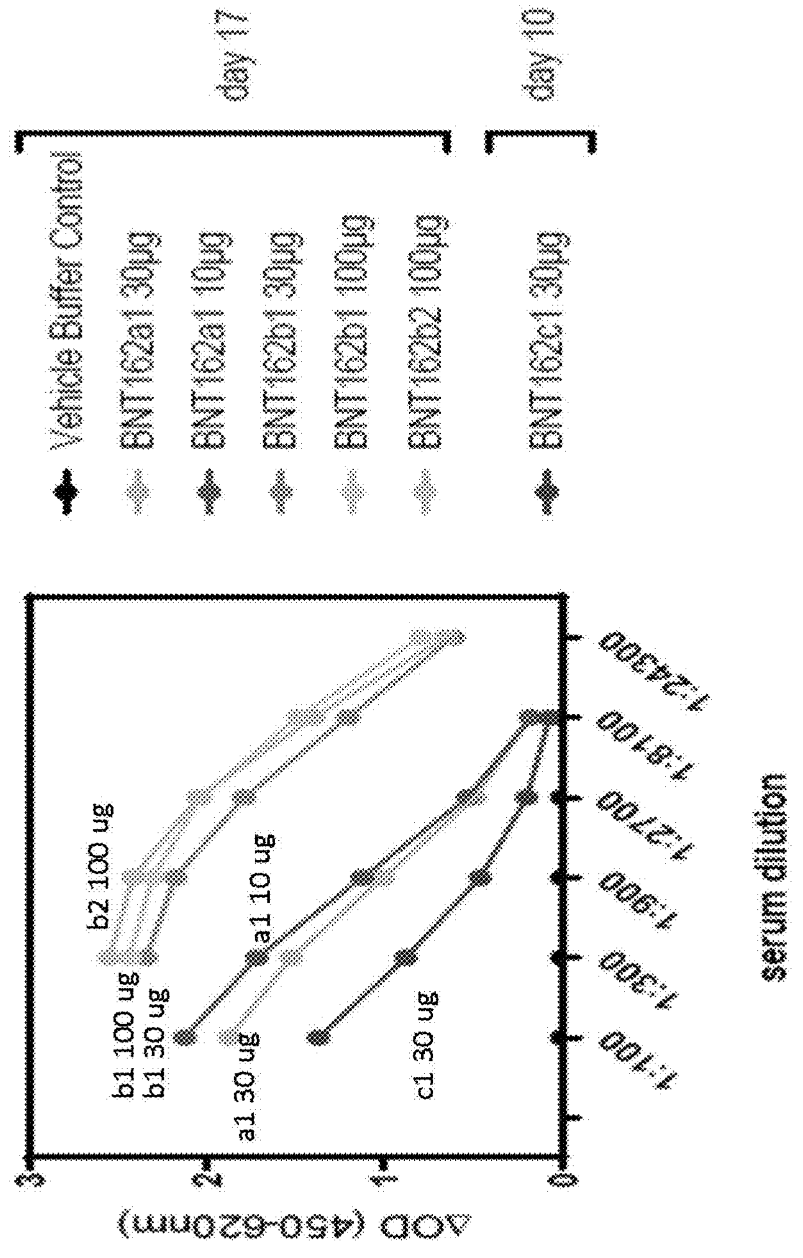

FIG. 118. ELISA screening analysis of exemplary cohort sera to detect antibody responses directed against the recombinant SARS-CoV-2 spike protein RBD domain.

ELISA was performed using serum samples collected on day 10 after two immunisations (prime/boost on days 1 and 8) with BNT162c1, or on day 17 after three administrations (prime/boost on days 1/8/15) of BNT162a1, BNT162b1, or BNT162b2 to analyse elicited antibody responses. The serum samples were tested against the RBD domain. Group mean AOD values of n=20 mice/group are shown by dots across serum dilutions ranging from 1:100 to 1:24,300.

Figure 119:
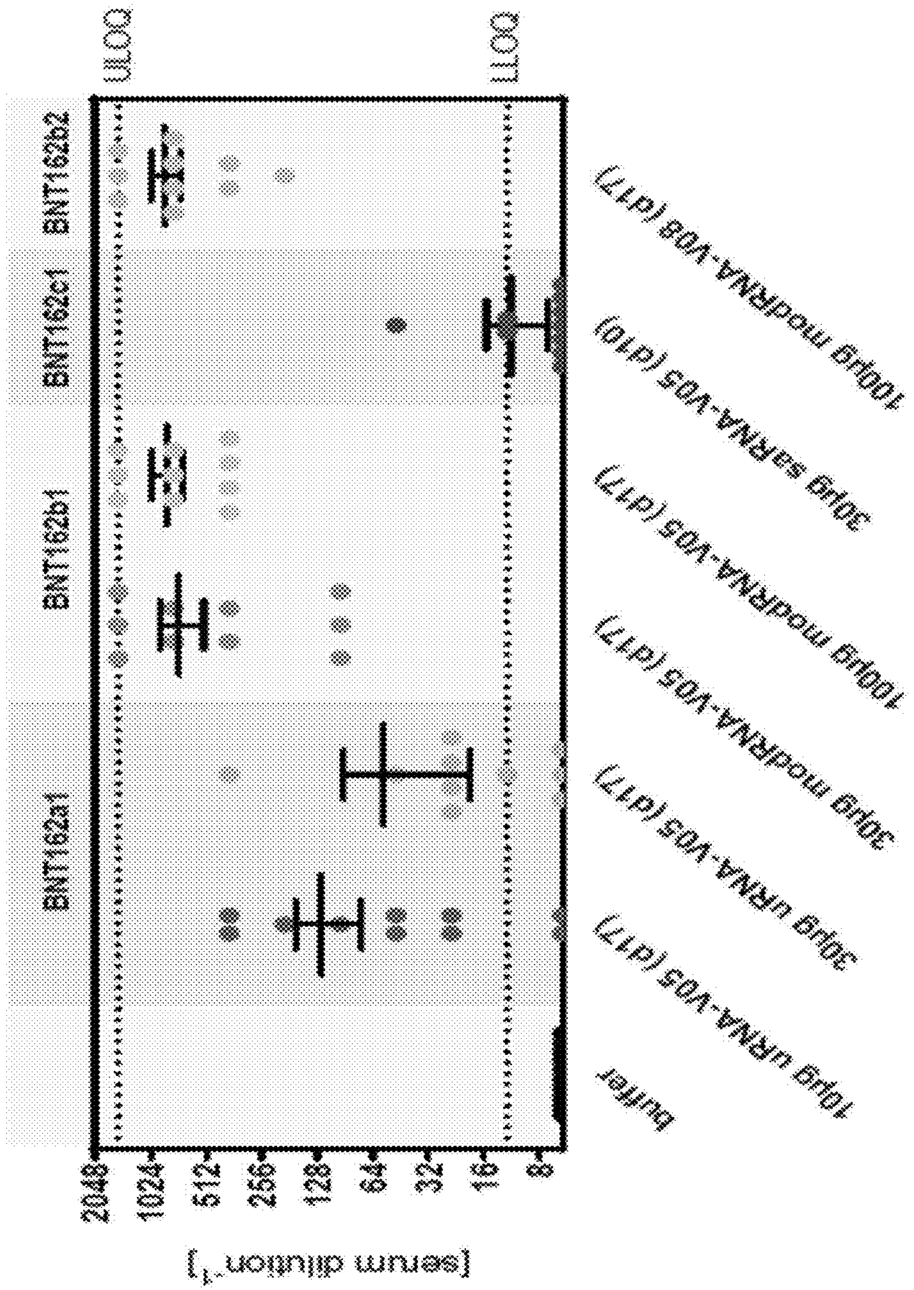

FIG. 119. Pseudovirus neturalisation activity of exemplary cohort sera plotted as $pVN_{50}$ titre.

Serum samples were collected on day 10 (BNT162c1, saRNA) or day 17 (all other cohorts) after first immunisation of the animals and titres of virus-neutralising antibodies were determined by pseudovirus-based neutralisation test (pVNT). Individual VNT titres resulting in 50% pseudovirus neutralisation ($pVN_{50}$) are shown by dots; group mean values are indicated by horizontal bars (±SEM, standard error of the mean).

Figure 120:
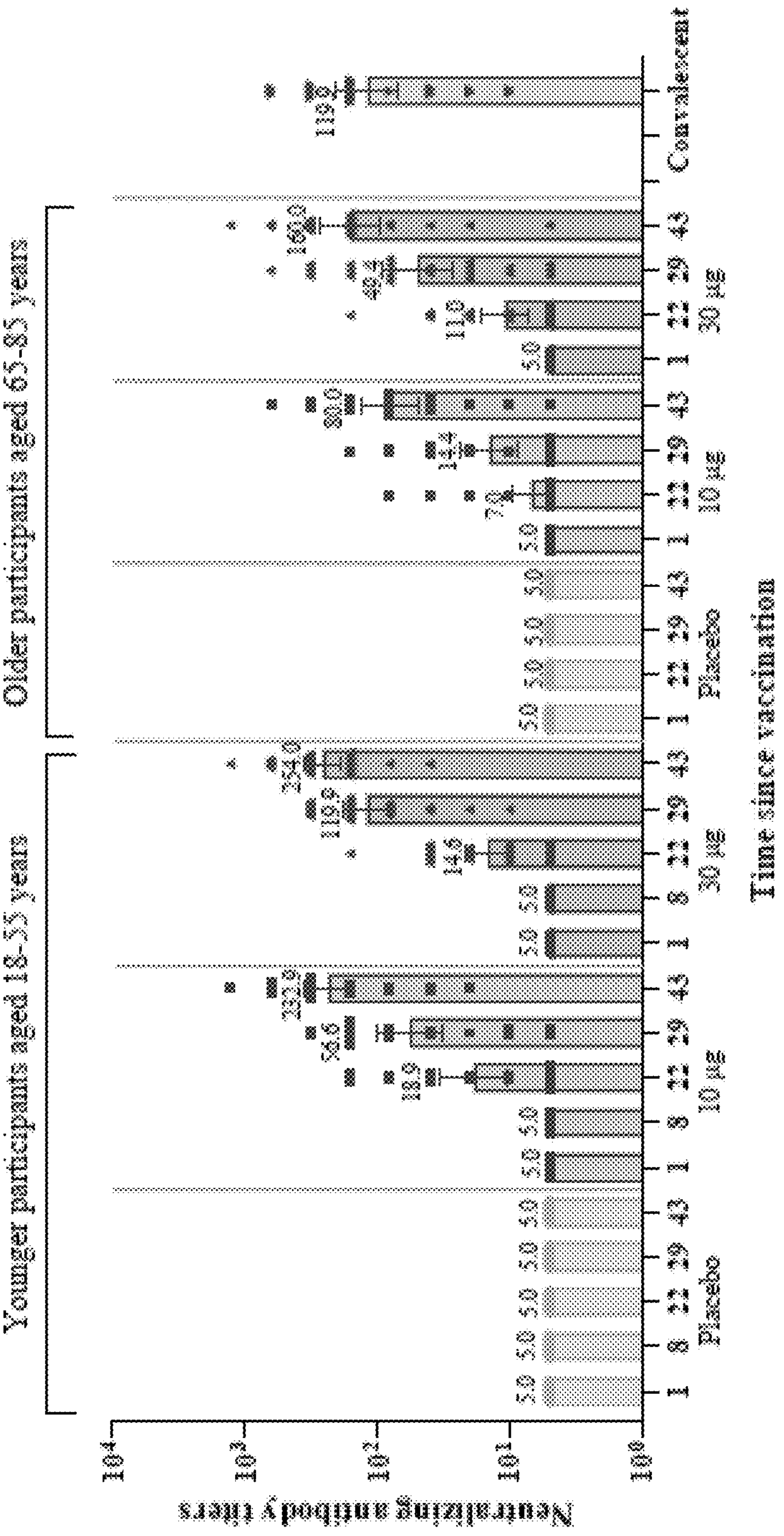
Figure 120:
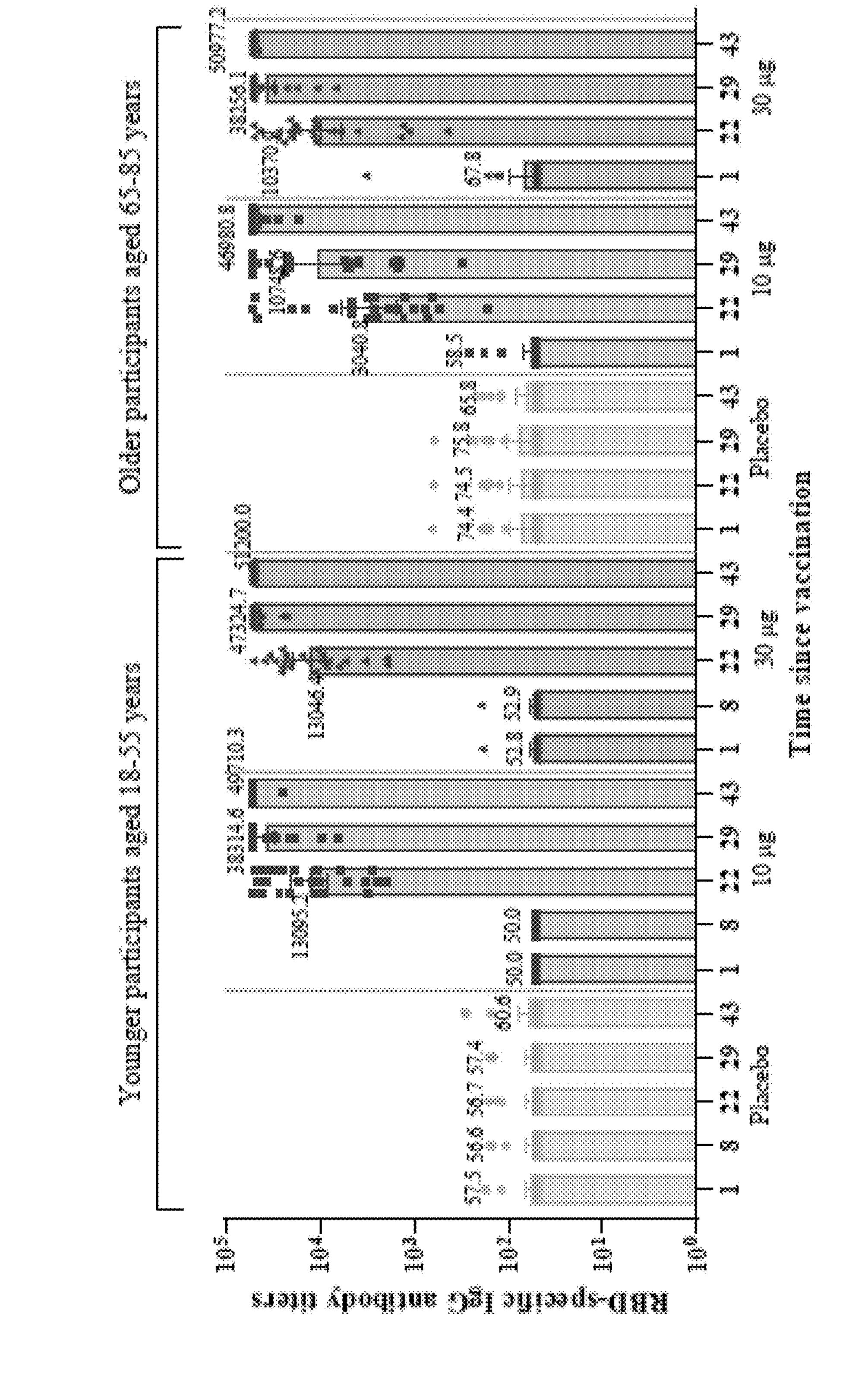
Figure 120:
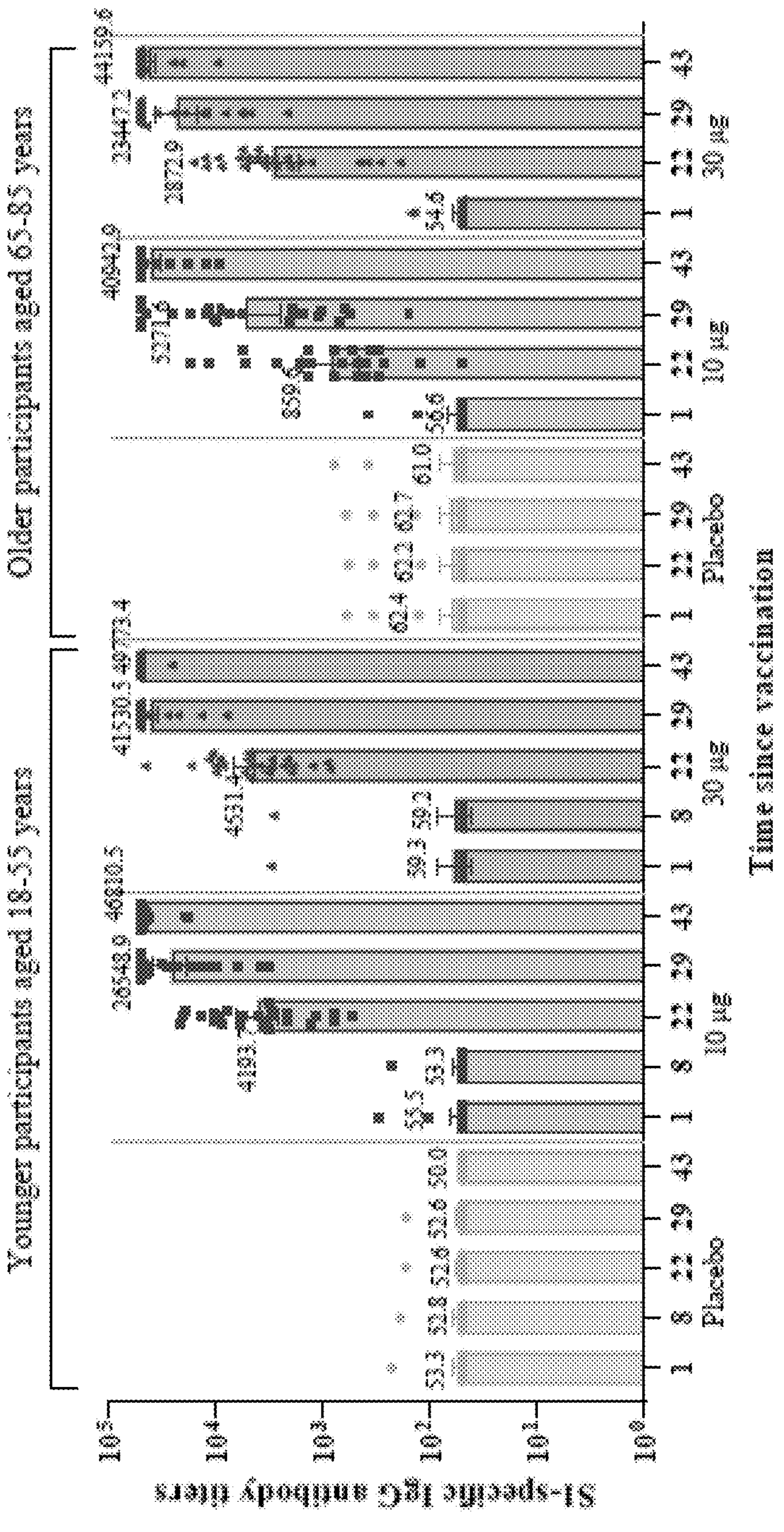

FIG. 120. The virus-neutralising antibodies and specific binding antibody responses to RBD and S1 in participants.

RBD=receptor binding domain. GMT=geometric mean titer. Serum samples were obtained before vaccination (day 1) and day 8, 22, 29, and 43 after the prime vaccination in younger adult group, and they were obtained before vaccination (day 1) and day 22, 29, and 43 days after the prime vaccination in older adult group. A panel of human COVID-19 convalescent serum (n=24) were obtained at least 14 days after PCR-confirmed diagnosis in COVID-19 patients. (A) GMTs of SARS-CoV-2 neutralizing antibodies. (B) GMTs of binding antibodies to RBD measured by ELISA. (C) GMTs of ELISA antibodies to S1. Each point represents a serum sample, and each vertical bar represents a geometric mean with 95% Cl.

Figure 121:
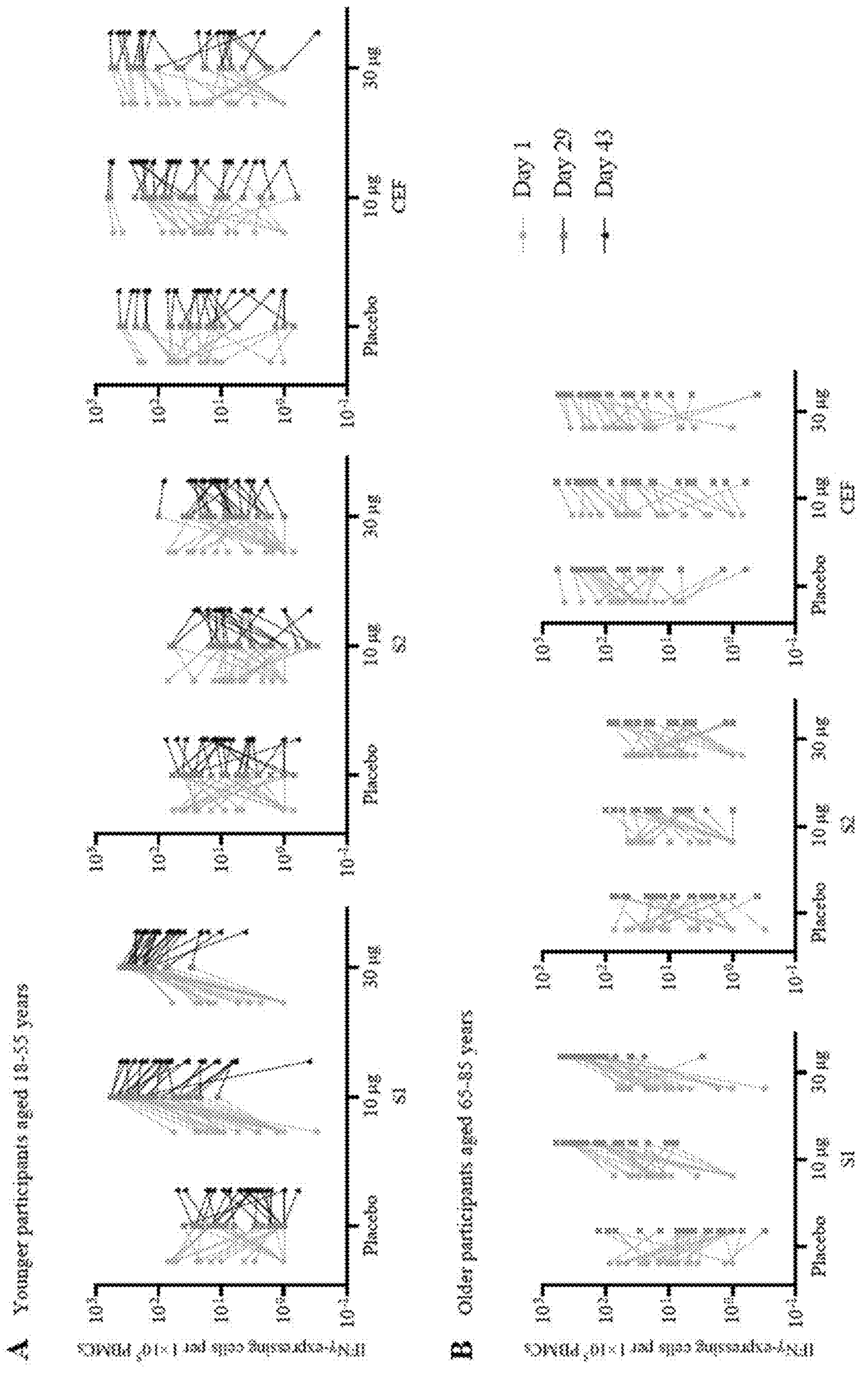

FIG. 121. T-cell response in participants before and after vaccination measured by IFN-γ ELISpot.

IFN=interferon. PBMC=peripheral blood mononuclear cells. The S1 peptide pool covers the N-terminal half of SARS-CoV-2 spike, including RBD. S2 peptide pool covers the C-terminal of SARS-CoV-2 spike, not including RBD. CEF peptide pool consists of 32 MHC class I restricted viral peptides from human cytomegalovirus, Epstein-Barr virus and influenza virus. Panel A shows the number of specific T cell with secretion of IFN-γ at day 1, 29, and 43 in the younger participants aged 18-55 years. Panel B shows the number of specific T cell with secretion of IFN-γ at day 1, 29, and 43 in the older participants aged 65-85 years.

Figure 122:
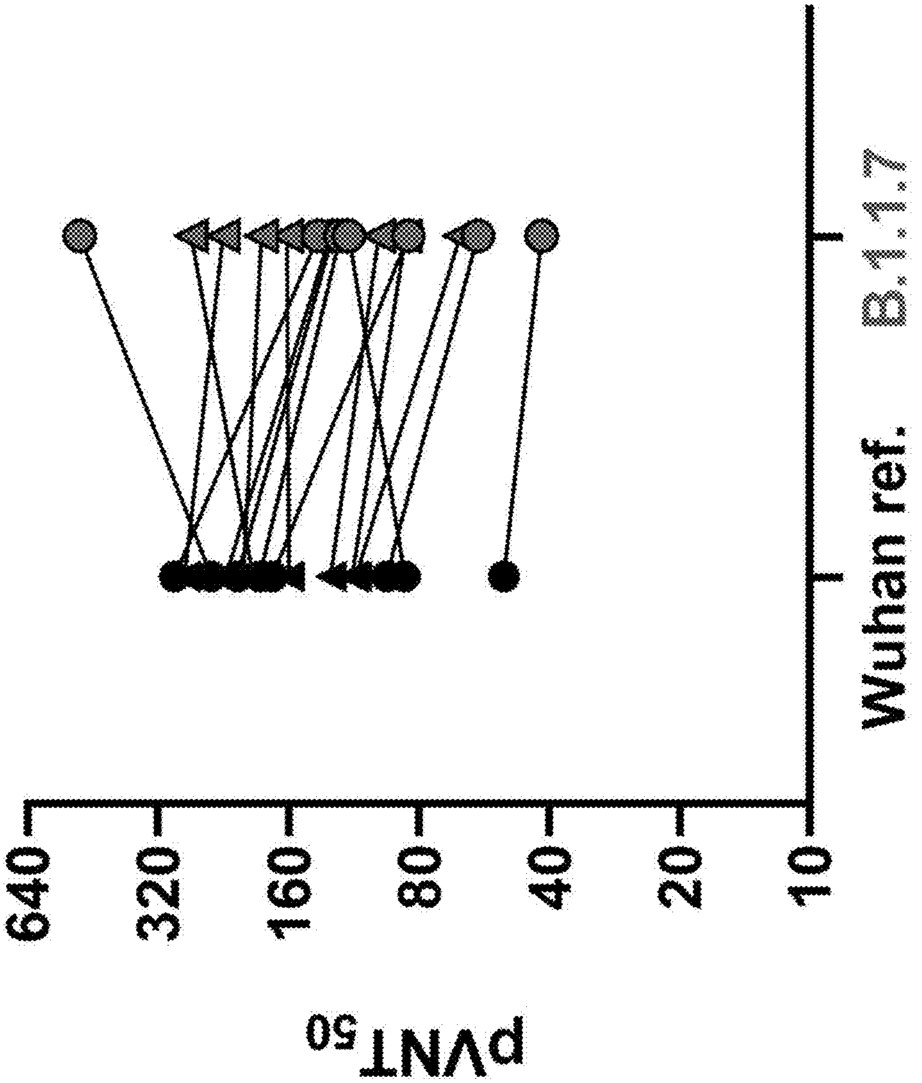

FIG. 122. 50% pseudovirus neutralization titers of 16 sera from BNT162b2 vaccine recipients against VSV-SARS-CoV-2-S pseudovirus bearing the Wuhan or lineage B.1.1.7 spike protein. N=8 representative sera each from younger adults (aged 18 to 55 yrs; indicated by triangles) and older adults (aged 56 to 85 yrs; indicated by circles) drawn at day 43 (21 days after dose 2) were tested.

Figure 123:
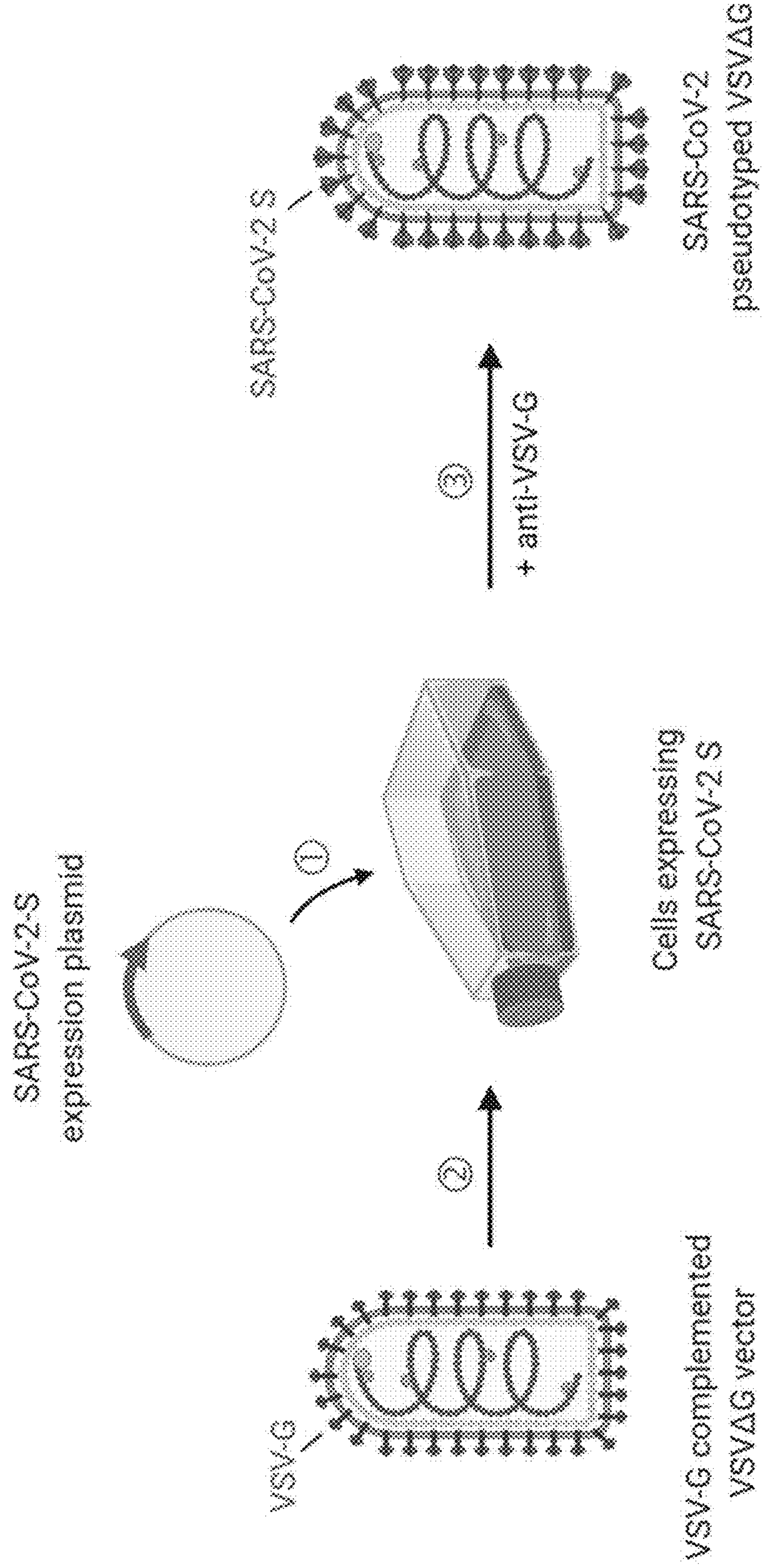

FIG. 123. Schematic illustration of the production of VSV pseudoviruses bearing SARS-CoV-2 S protein. (1) Transfection of SARS-CoV-2-S expression plasmid into HEK293/T17 cells. (2) Infection of SARS-CoV-2 S expressing cells with VSV-G complemented input virus lacking the VSV-G in its genome (VSVΔG) and encoding for reporter genes. (3) Neutralization of residual VSV-G complemented input virus by addition of anti-VSV-G antibody yields SARS-CoV-2 S pseudotyped VSVΔG as a surrogate for live SARS-CoV-2.

Figure 124:
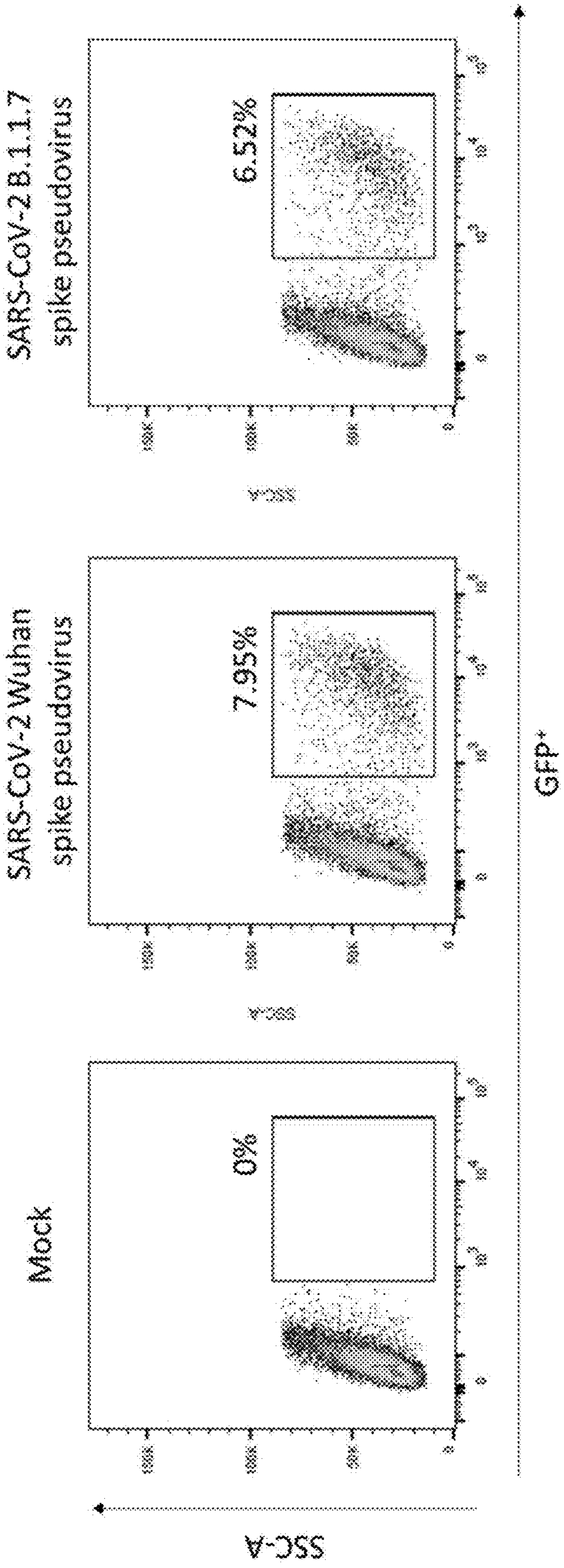

FIG. 124. Titration of SARS-CoV-2 Wuhan reference strain and lineage B.1.1.7 spike-pseudotyped VSV on Vero 76 cells using GFP-infected cells as read-out.

Figure 125:
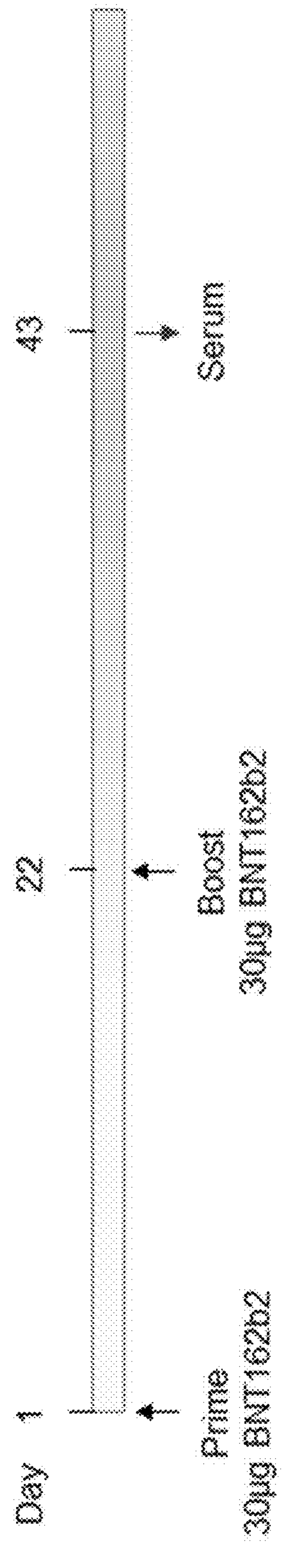

FIG. 125. Scheme of the BNT162b2 vaccination and serum sampling.

Figure 126:
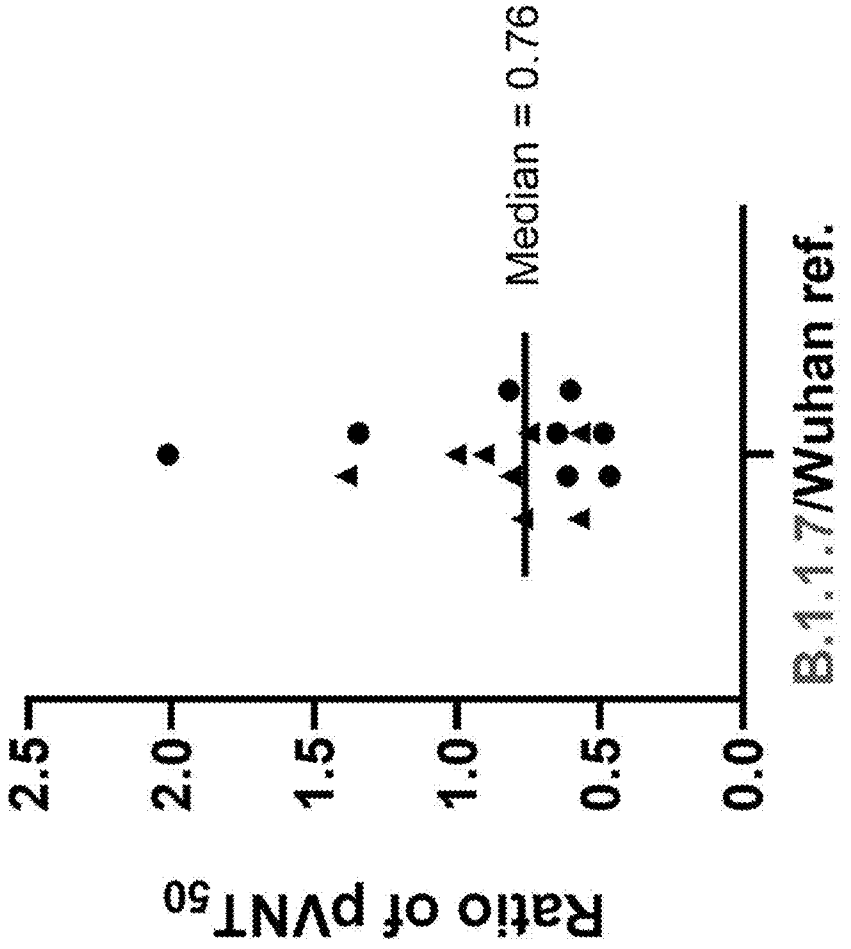

FIG. 126. Plot of the ratio of $pVNT_{50}$ between SARS-CoV-2 lineage B.1.1.7 and Wuhan reference strain spike-pseudotyped VSV. Triangles represent sera from younger adults (aged 18 to 55 yrs), and circles represent sera from older adults (aged 56 to 85 yrs). The sea were drawn on day 43 (21 days after dose 2).

Figure 127:
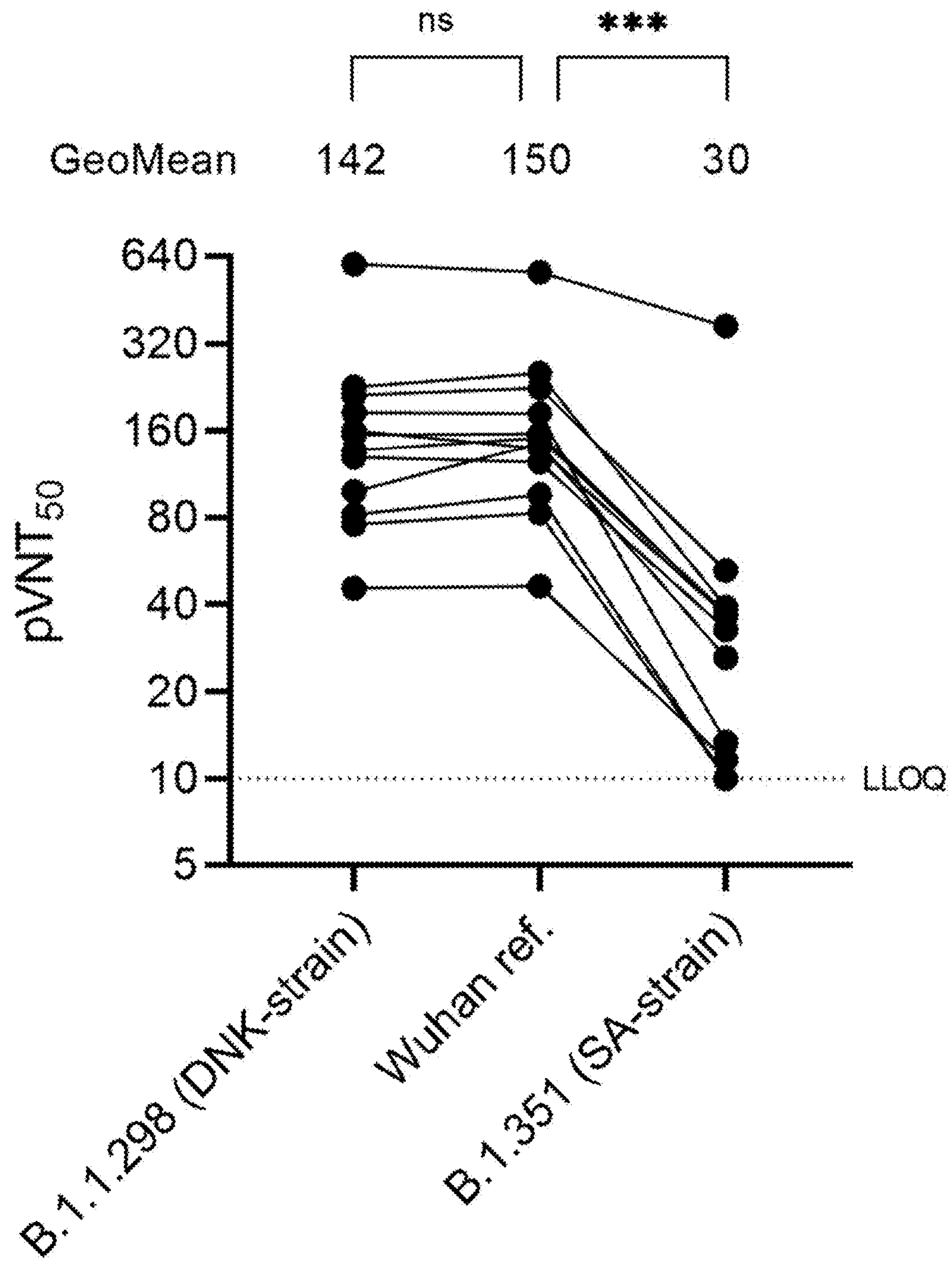

FIG. 127. 50% pseudovirus neutralization titers (pVNT50) of 12 sera from BNT162b2 vaccine recipients against VSV-SARS-CoV-2-S pseudovirus bearing the Wuhan Hu-1 reference, lineage B.1.1.298 or lineage B.1.351 spike protein. N=12 sera from younger adults immunized with 30 μg BNT162b2 drawn at either day 29 or day 43 (7 or 21 days after dose 2) were tested. Geometric mean titers are indicated. Statistical significance of the difference between the neutralization of the Wuhan Hu-1 reference pseudovirus and either the lineage B.1.1.298 or the lineage B.1.351 pseudovirus was calculated by a Wilcoxon matched-pairs signed rank test. Two-tailed p-values are reported. ns, not significant;***, P<0.001; LLOQ, lower limit of quantification.

Figure 128:
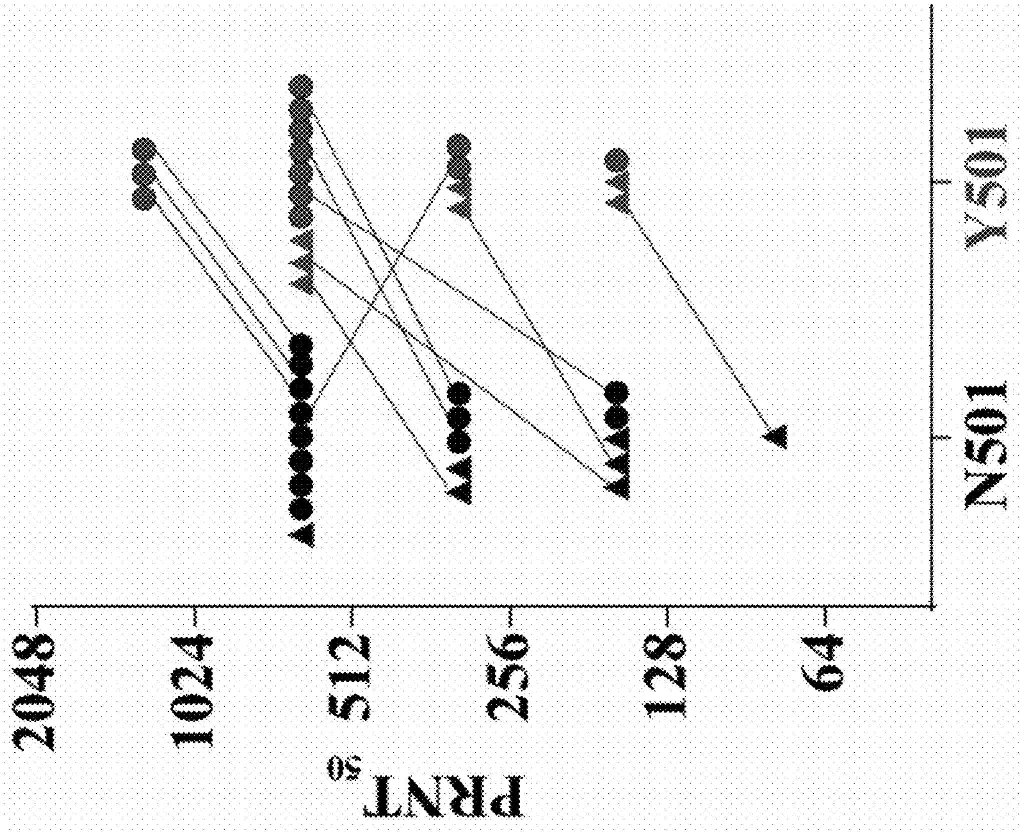

FIG. 128. 50% plaque reduction neutralization titers of 20 sera from BNT162b2 vaccine recipients against N501 and Y501 SARS-CoV-2. Seven sera (indicated by triangles) were drawn 2 weeks after the second dose of vaccine; 13 sera (indicated by circles) were drawn 4 weeks after the second dose.

Figure 129:
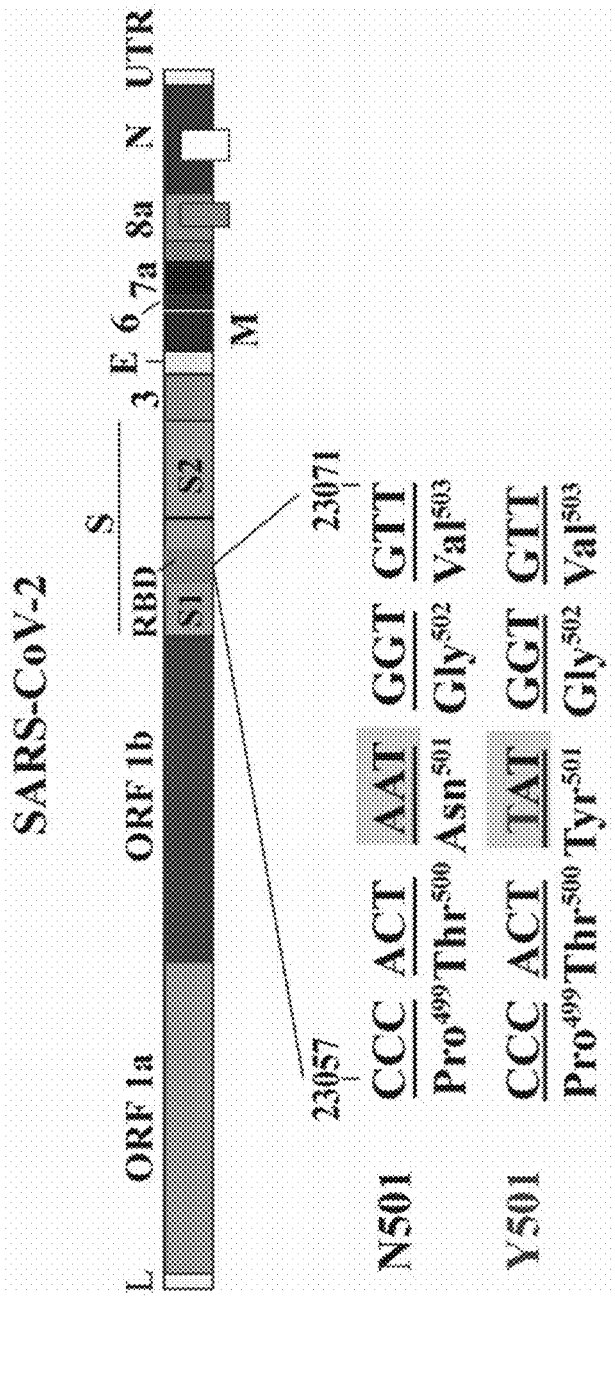

FIG. 129. Diagram of the N501Y substitution. L—leader sequence; ORF—open reading frame; RBD—receptor binding domain; S—spike glycoprotein; S1—N-terminal furin cleavage fragment of S; S2—C-terminal furin cleavage fragment of S; E—envelope protein; M —membrane protein; N—nucleoprotein; UTR—untranslated region.

Figure 130:
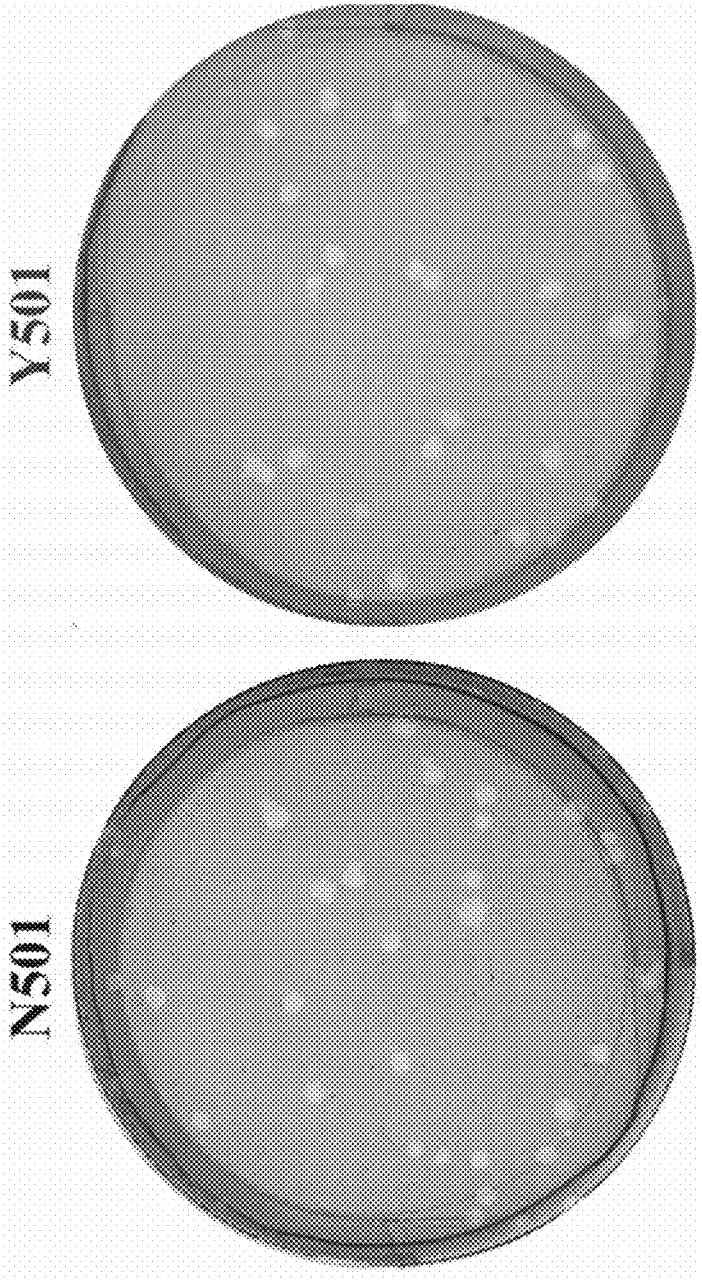

FIG. 130. Plaque morphologies of N501 and Y501 SARS-CoV-2 on Vero E6 cells.

Figure 131:
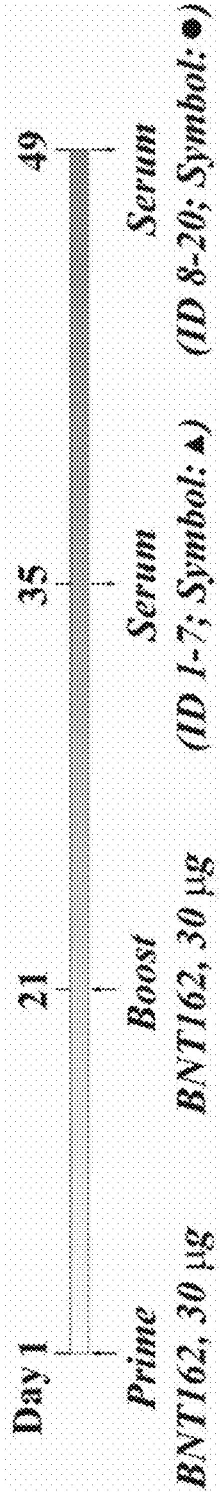

FIG. 131. Scheme of the BNT162 vaccination and serum sampling.

Figure 132:
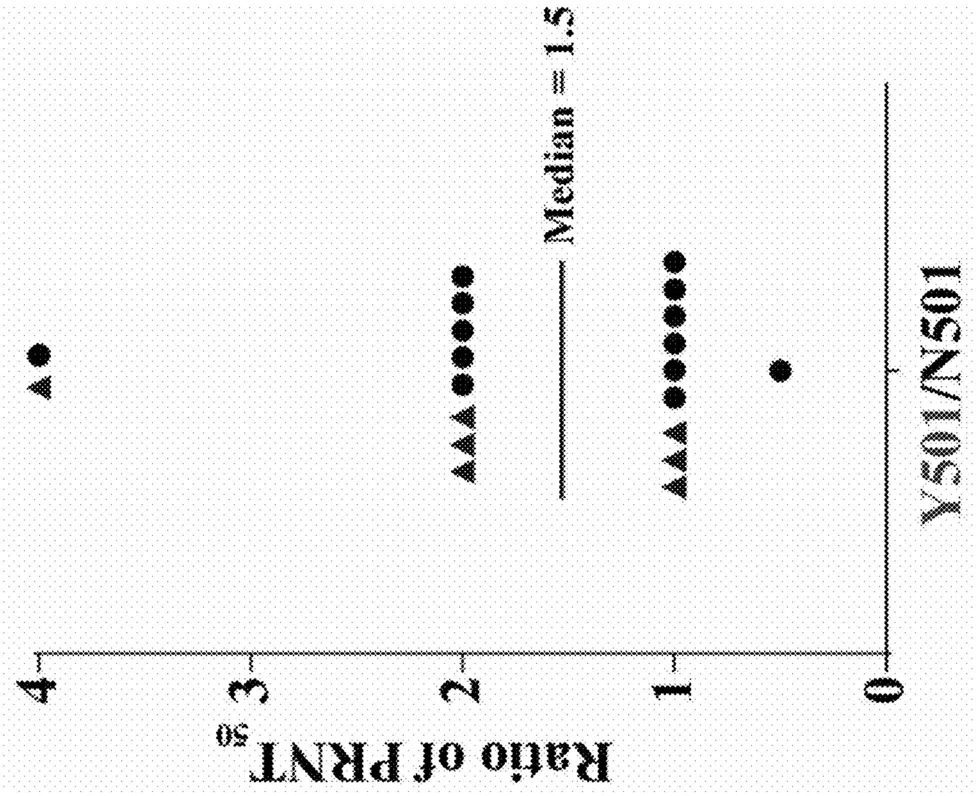

FIG. 132. Plot of the ratio of $PRNT_{50}$ between Y501 and N501 viruses. Triangles represent sera drawn two weeks after the second dose; circles represent sera drawn four weeks after the second dose.

Figure 133:
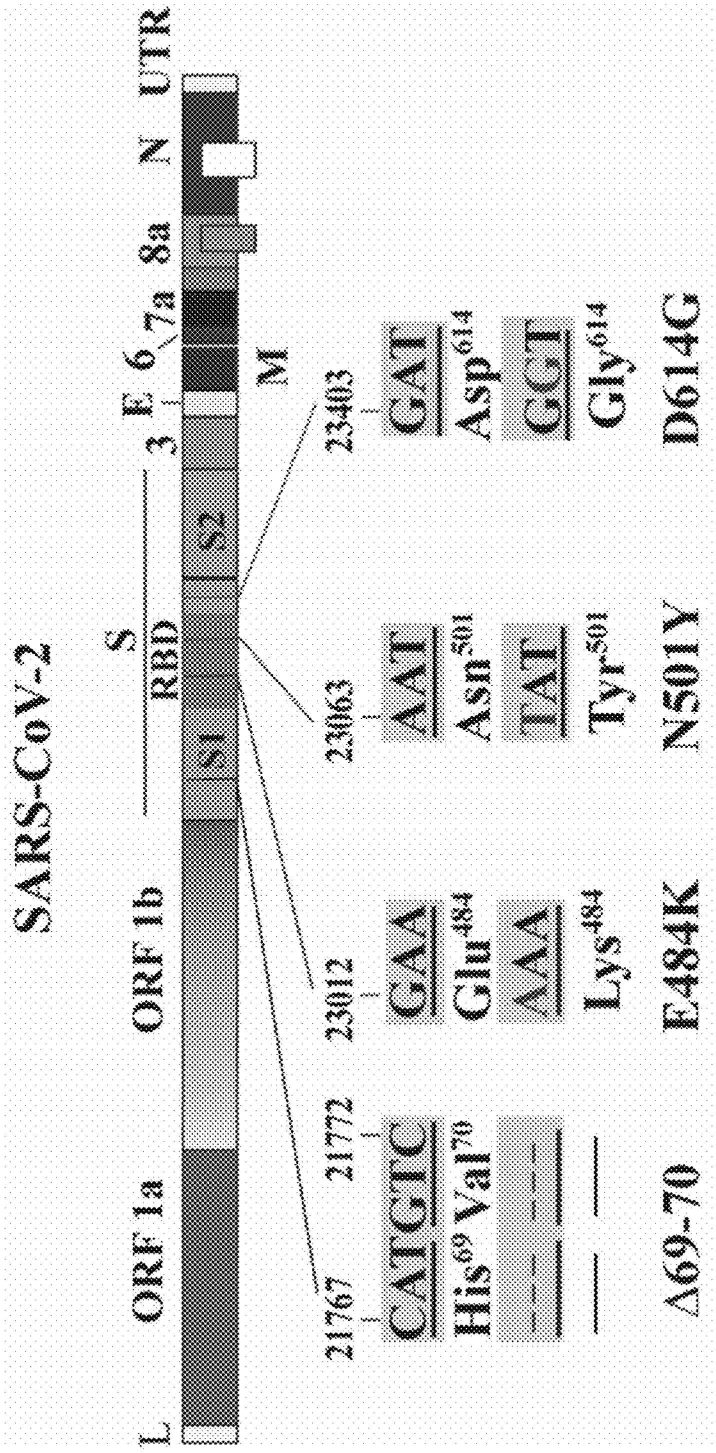

FIG. 133. Engineered mutations. Nucleotide and amino acid positions are indicated. Deletions are depicted by dotted lines. Mutant nucleotides are in red. L, leader sequence; ORF, open reading frame; RBD, receptor binding domain; S, spike glycoprotein; S1, N-terminal furin cleavage fragment of S; S2, C-terminal furin cleavage fragment of S; E, envelope protein; M, membrane protein; N, nucleoprotein; UTR, untranslated region.

Figure 134:
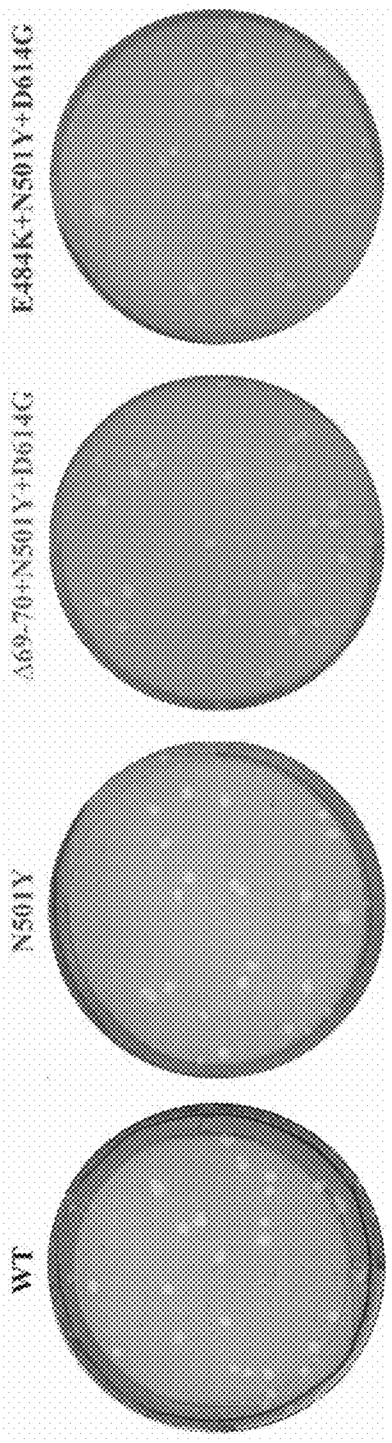

FIG. 134. Plaque morphologies of WT (USA-WA1/2020), mutant N501Y, Δ69/70+N501Y+D614G, and E484K+N501Y+D614G SARS-CoV-2s on Vero E6 cells.

Figure 135:
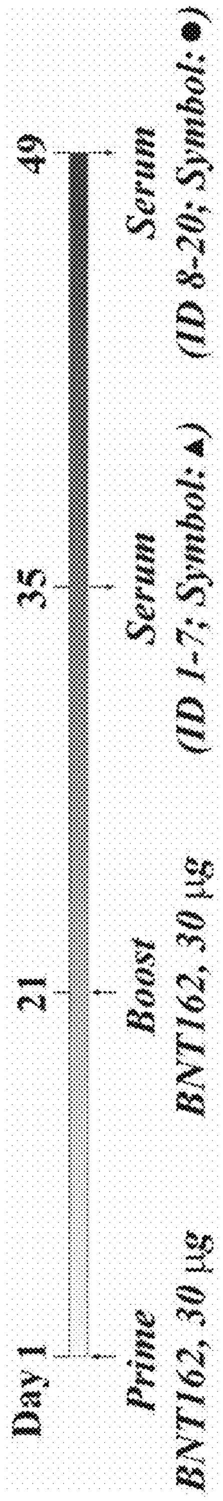

FIG. 135. Scheme of the BNT162 vaccination and serum sampling.

Figure 136:
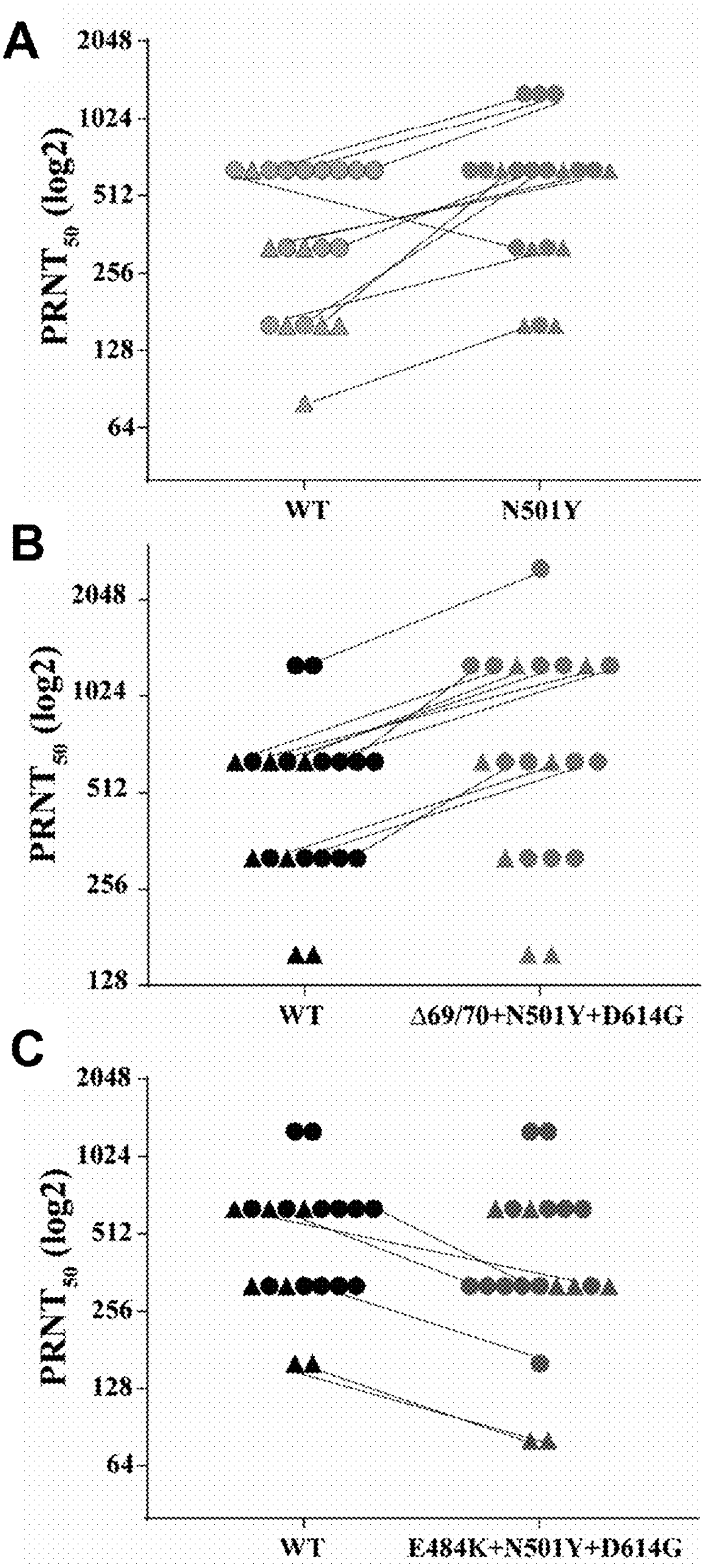

FIG. 136. $PRNT_{50}$s of twenty BNT162b2-vaccinated human sera against wild-type (WT) and mutant SARS-CoV-2. (A) WT (USA-WA1/2020) and mutant N501Y. (B) WT and Δ69/70+N501Y+D614G. (C) WT and E484K+N501Y+D614G. Seven (triangles) and thirteen (circles) sera were drawn 2 and 4 weeks after the second dose of vaccination, respectively. Sera with different $PRNT_{50}$s against WT and mutant viruses are connected by lines. Results in (A) were from one experiment; results in (B) and (C) were from another set of experiments. Each data point is the average of duplicate assay results.

Figure 137:
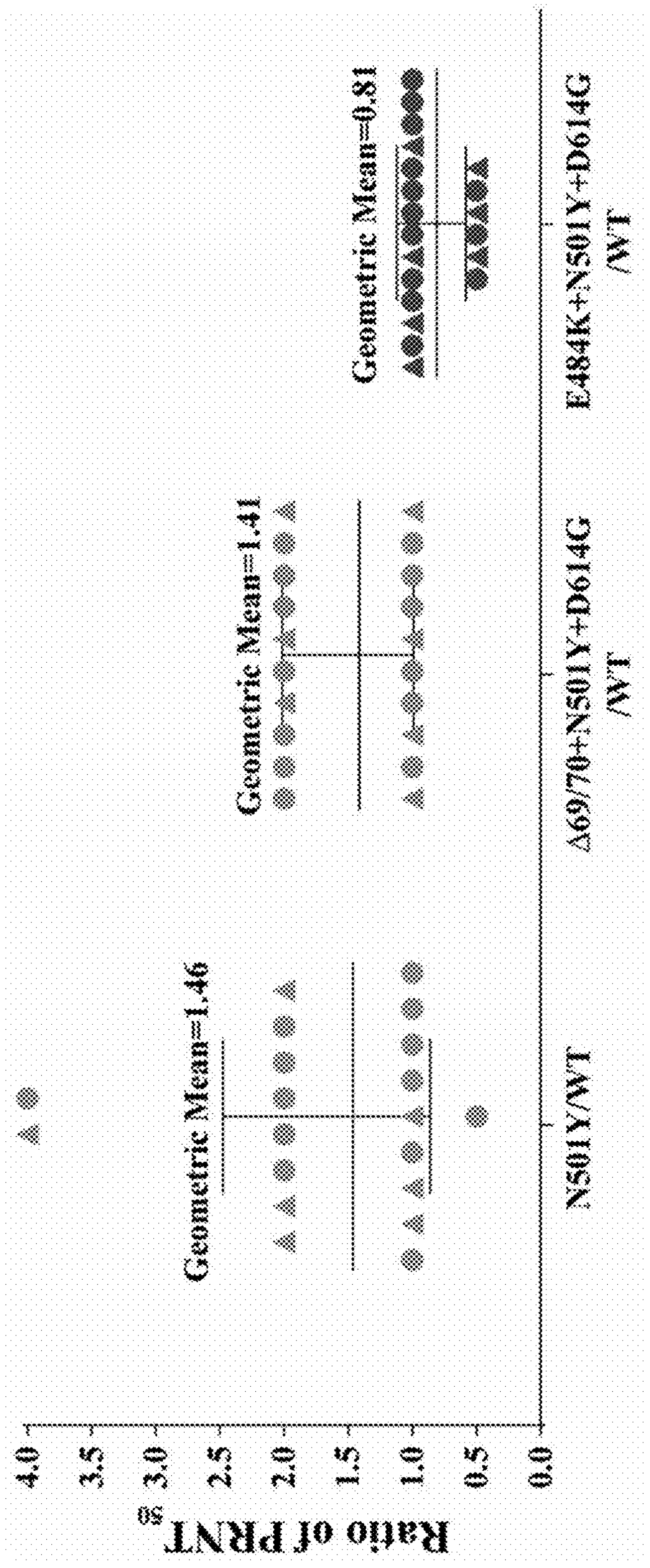

FIG. 137. Ratios of neutralization GMTs against mutant viruses to GMTs against WT virus. Triangles represent sera drawn two weeks after the second dose of vaccination; circles represent sera drawn four weeks after the second dose of vaccination.

Figure 138:
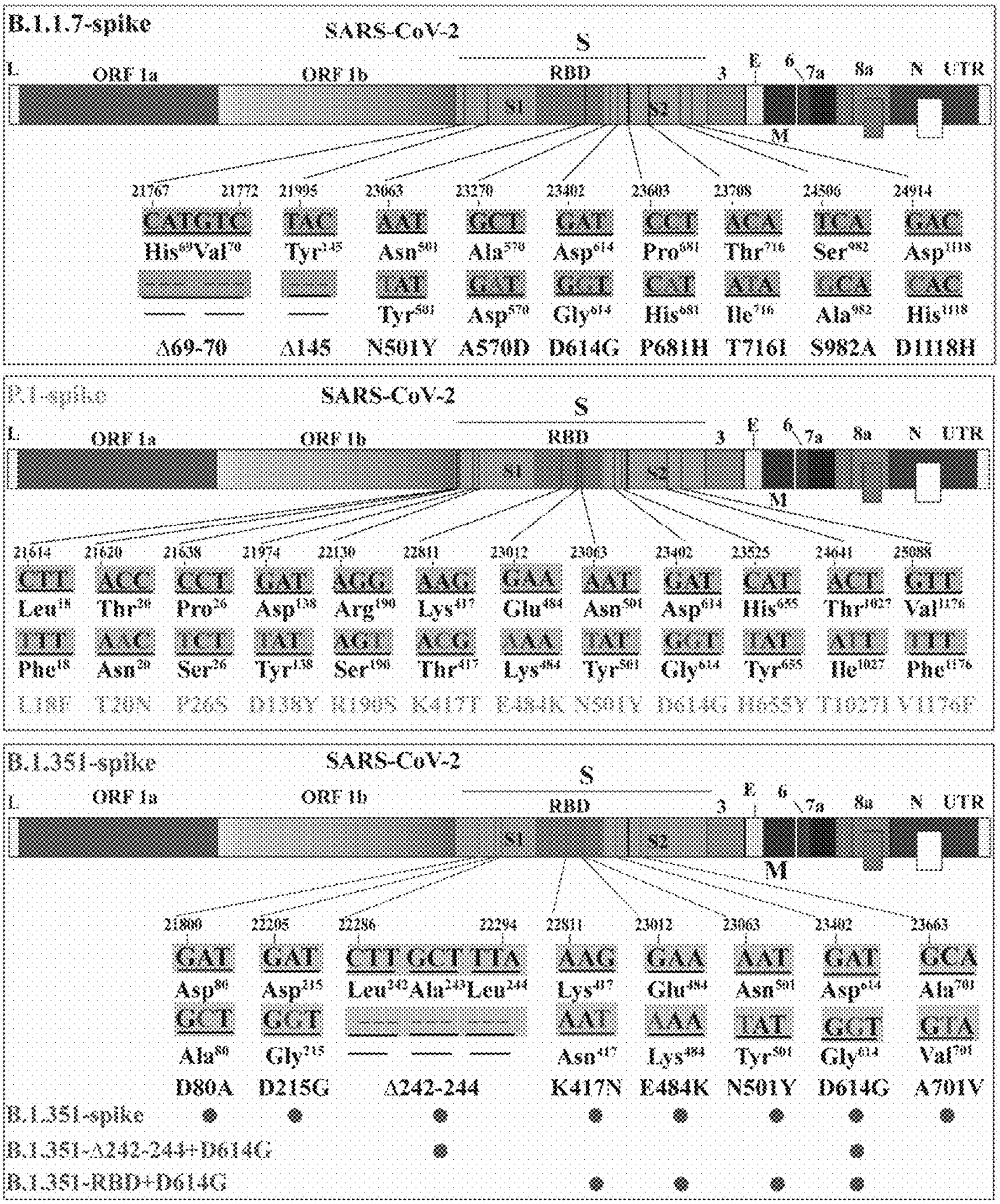

FIG. 138. Diagram of engineered spike substitutions and deletions. The genome and sequence of clinical isolate USA-WA1/2020 are used as the wild-type virus in this study. Mutations from the United Kingdom B.1.1.7, Brazilian P.1, and South African B.1.351 lineages are presented. Deletions are indicated by dotted lines. Mutated nucleotides are in red. Nucleotide and amino acid positions are indicated. L—leader sequence; ORF—open reading frame; RBD—receptor binding domain; S—spike glycoprotein; S1—N-terminal furin cleavage fragment of S; S2—C-terminal furin cleavage fragment of S; E—envelope protein; M —membrane protein; N—nucleoprotein; UTR—untranslated region.

Figure 139:
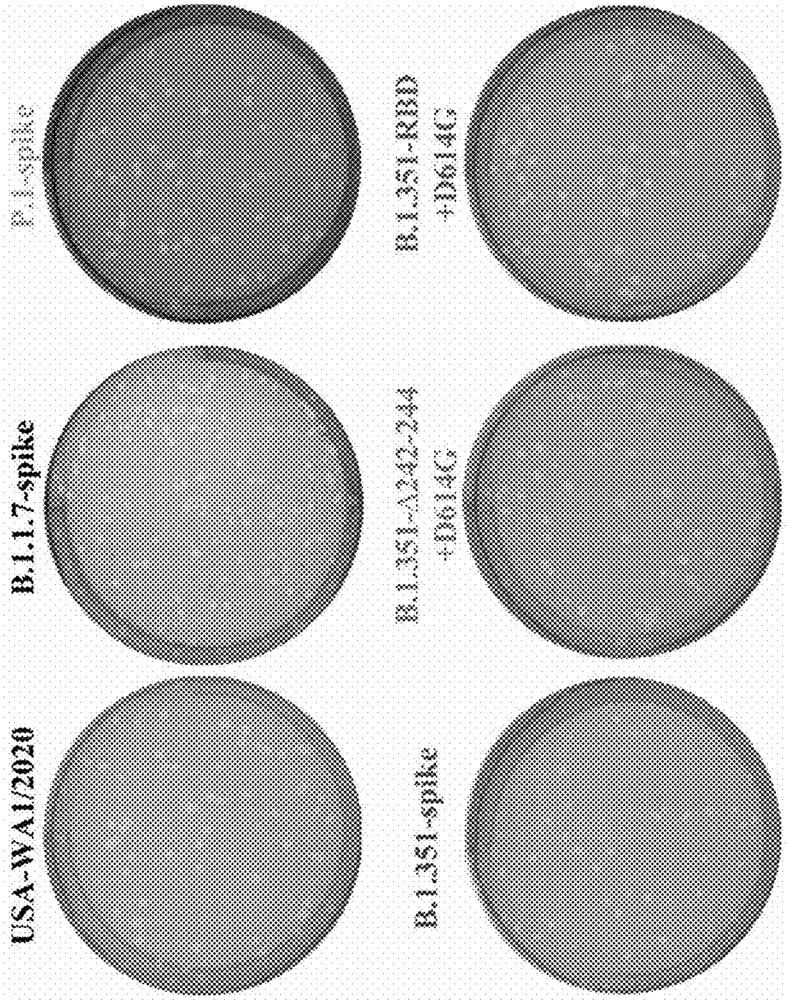

FIG. 139. Plaque morphologies of USA-WA1/2020 and mutant SARS-CoV-2's. The plaque assays were performed on Vero E6 cells in 6-well plates.

Figure 140:
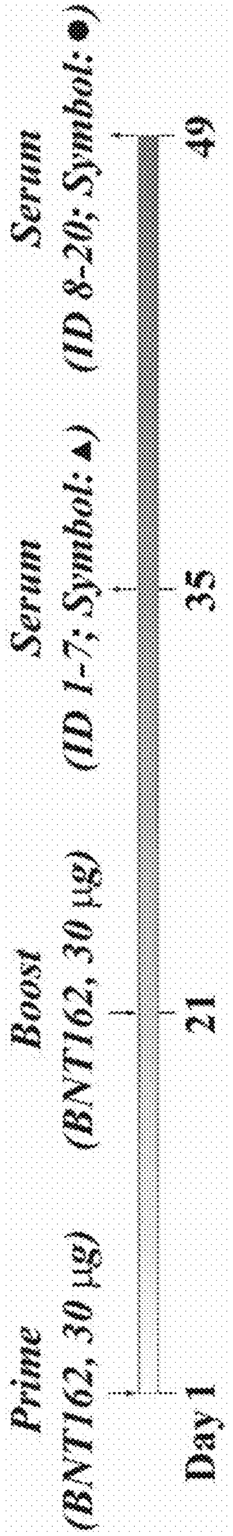

FIG. 140. Scheme of BNT162 immunization and serum collection.

Figure 141:
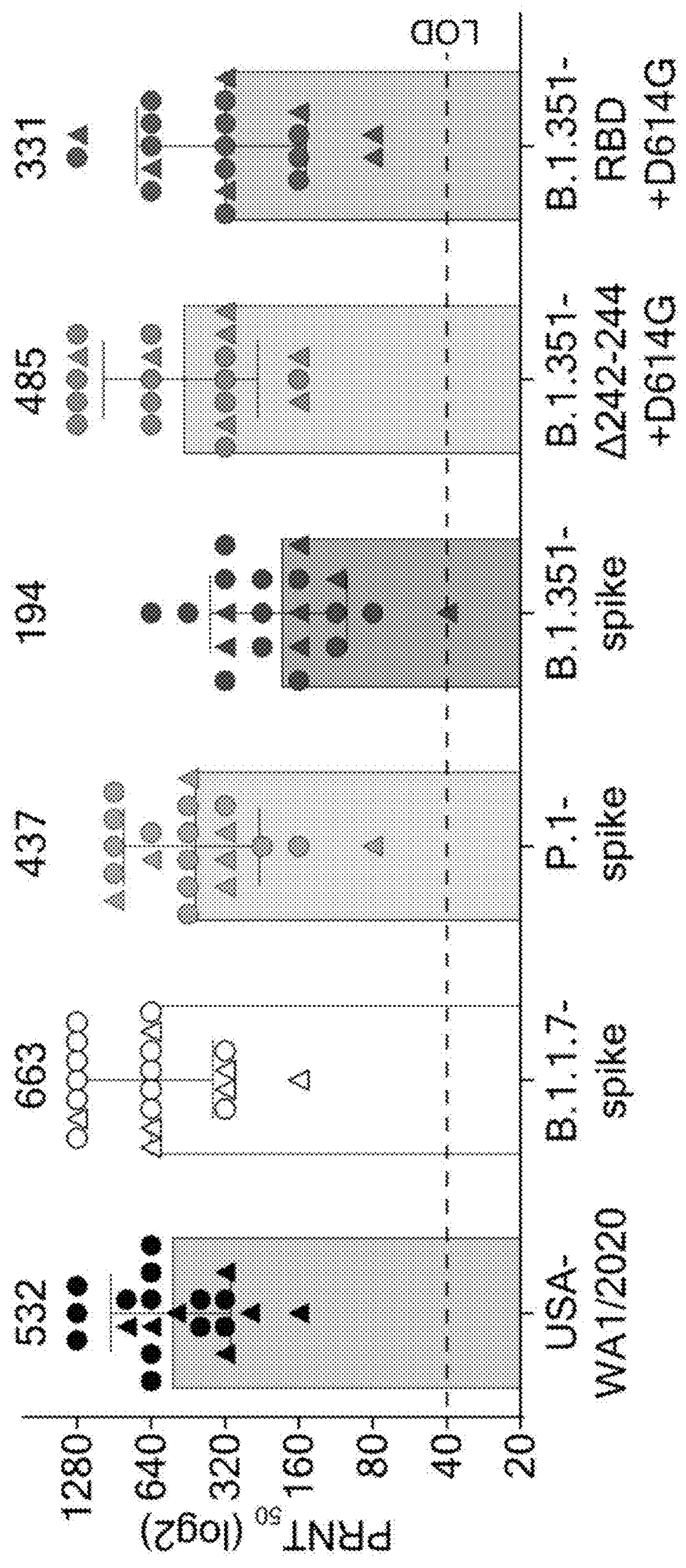

FIG. 141. Serum Neutralization of Variant Strains of SARS-CoV-2 after the Second Dose of BNT162b2 Vaccine. Shown are the results of 50% plaque reduction neutralization testing (PRNT50) with the use of 20 samples obtained from 15 trial participants 2 weeks (circles) or 4 weeks (triangles) after the administration of the second dose of the BNT162b2 vaccine. The mutant viruses were obtained by engineering the full set of mutations in the B.1.1.7, P.1., or B.1.351 lineages or subsets of the S gene mutations in the B.1.351 lineage (B.1.351-Δ242-244+D614G and B.1.351-RBD-D614G) into USA-WA1/2020. Each data point represents the geometric mean $PRNT_{50}$ obtained with a serum sample against the indicated virus, including data from repeat experiments, as detailed in Table 31. The data for USA-WA1/2020 are from three experiments; for B.1.1.7-spike, B.1.351-Δ242-244+D614G, and B.1.351-RBD-D614G viruses from one experiment each; and for P.1-spike and B.1.351-spike viruses from two experiments each. In each experiment, the neutralization titer was determined in duplicate assays, and the geometric mean was taken. LOD: limit of detection.

Figure 142:
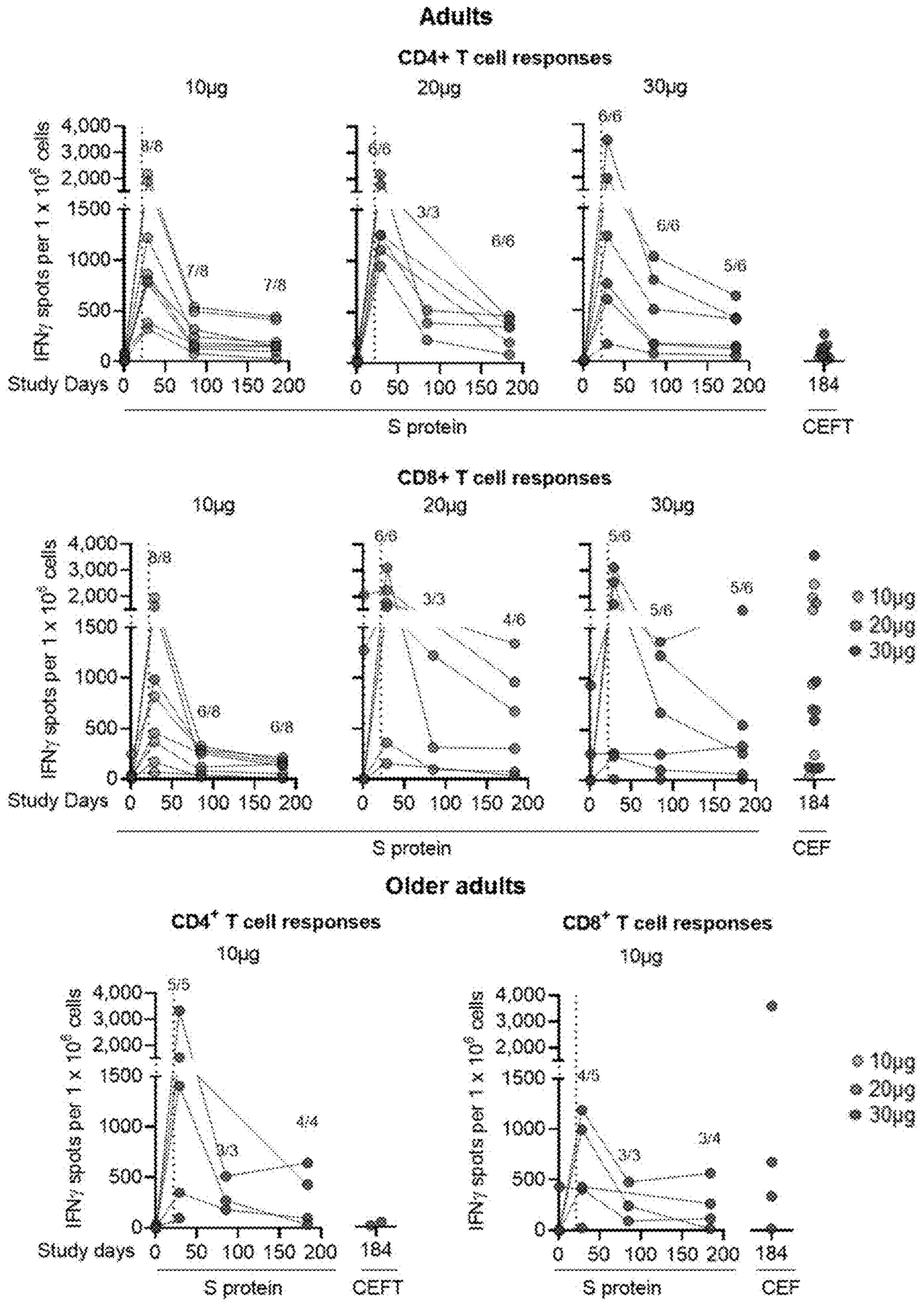

FIG. 142. Durability of BNT162b2-induced T cell responses.

PBMCs obtained on Day 1 (pre-prime), Day 29, Day 85, and Day 184 (7 days, 9 and 23 weeks post-boost, respectively), were analyzed in ex vivo IFNγ ELISpot (for details see GA-RB-022-01A). Common pathogen T-cell epitope pools CEF (CMV, EBV, and influenza virus HLA class I epitopes) and CEFT (CMV, EBV, influenza virus, and tetanus toxoid HLA class II epitopes) served to assess general T-cell reactivity, cell culture medium served as negative control. Each dot represents the sum of normalized mean spot count from duplicate wells stimulated with two peptide pools corresponding to the full-length wt S protein for one study subject, after subtraction of the medium-only control. Ratios above post-vaccination data points are the number of subjects with detectable $CD4^+$ or $CD8^+$ T-cell responses within the total number of tested subjects per dose cohort and time-point.

Figure 143:
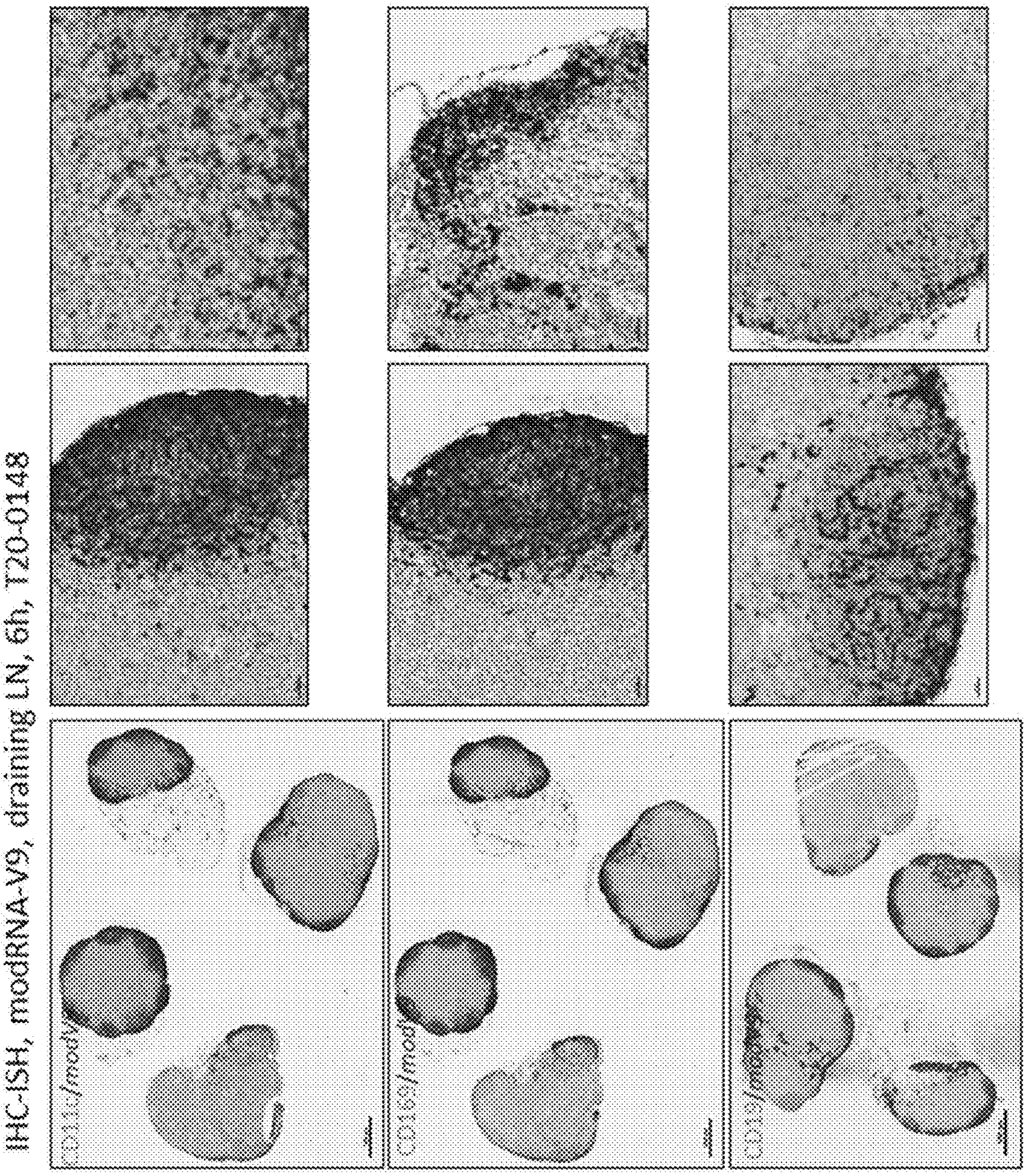

FIG. 143. A specific vaccine mRNA signal (red) is detected in the LN 6h post injection using modV9 probe in dual IHC-ISH assay. Vaccine is mostly localized to subcapsular sinus (LN in 9 and 5 positions) and B cell follicles (LN in 12 and 1 positions). Dendritic cells are visualized by CD11c staining (turquoise, upper images) and only some of them uptake the vaccine. Majority of CD169+ macrophages (subcapsular sinus macrophages, turquoise, middle images) are positive for the vaccine. B cells (CD19+, turquoise, lower images) are the second major population showing vaccine signal.

Figure 144:
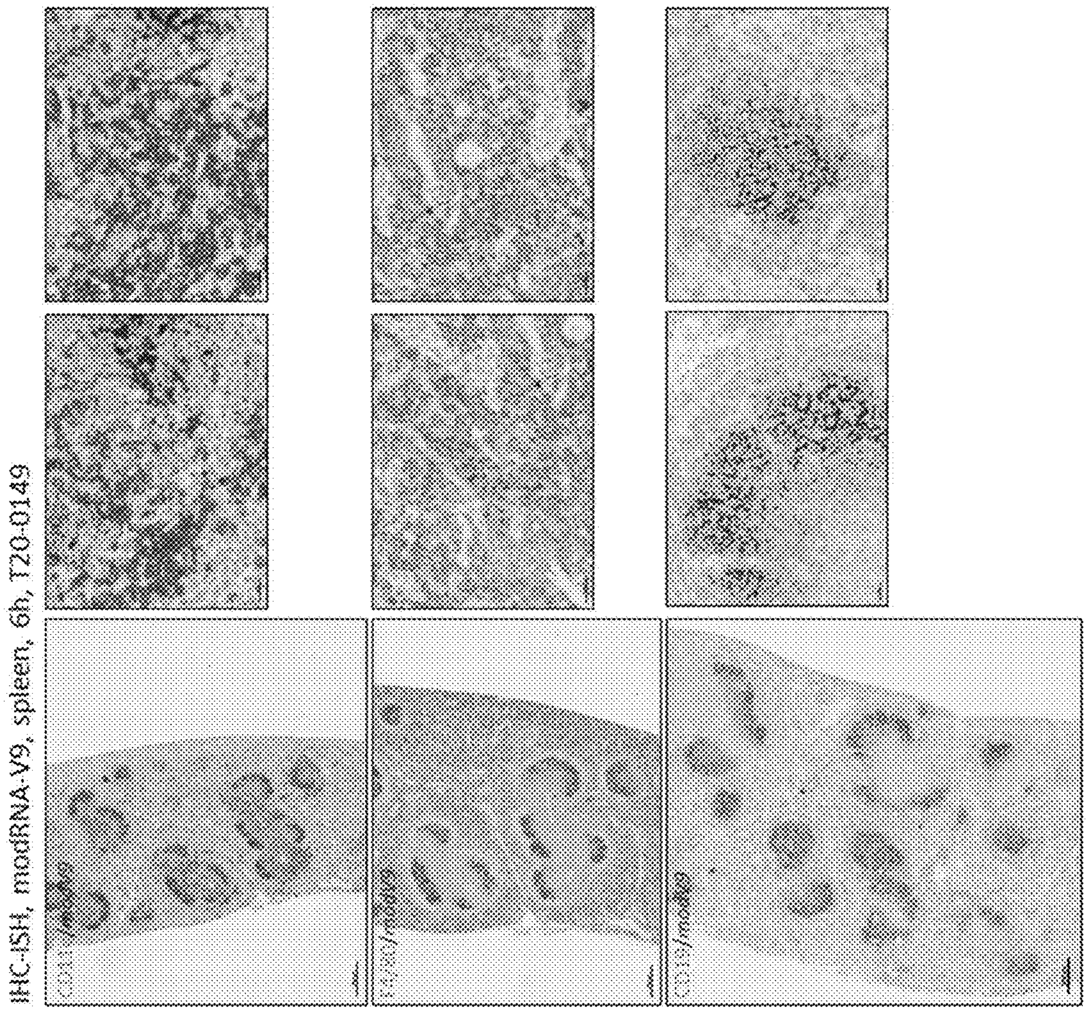

FIG. 144. A specific vaccine mRNA signal (red) is detected in the spleen 6h post injection using modV9 probe in dual IHC-ISH assay. Majority of the vaccine signal is detected in the white pulp. Dendritic cells are visualized by CD11c staining (turquoise, upper images) and only some of them uptake the vaccine. A small portion of F4/80+ macrophages (turquoise, middle images) uptake the vaccine. B cells (CD19+, turquoise, lower images) are the major population showing the vaccine signal.

Figure 145:
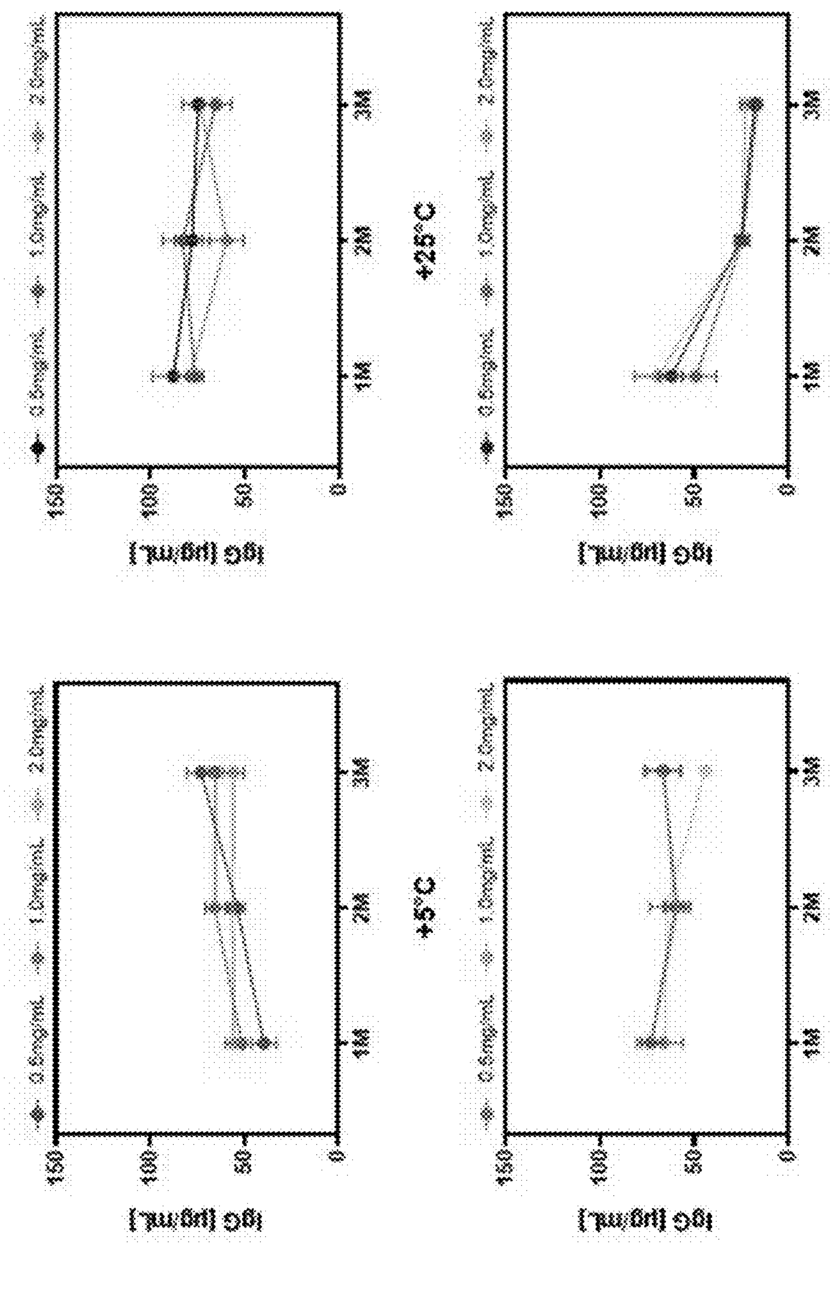

FIG. 145. Exemplary Stability Data. Exemplary data from certain stability studies (see, for example, Example 42, are shown for a BNT162b2 LNP preparation at indicated concentrations and temperature conditions, as assessed by ELISA characterizing antibodies reactive to S1 spike protein.

DESCRIPTION OF THE SEQUENCES

The following table provides a listing of certain sequences referenced herein.

TABLE 1

| DESCRIPTION OF THE SEQUENCES | | |
|---|---|---|
| SEQ ID NO: | Description | SEQUENCE |
| Antigenic S protein sequences | | |
| 1 | S protein (amino acid) | MFVFLVLLPLVSSQCVNLTTRTQLPPAYTNSFTRGVYYPDKVFRSSVLHSTQDLFLPFFSNVTWFHAIHVSGTNGTKRFDNP<br>VLPFNDGVYFASTEKSNIIRGWIFGTTLDSKTQSLLIVNNATNVVIKVCEFQFCNDPFLGVYYHKNNKSWMESEFRVYSSAN<br>NCTFEYVSQPFLMDLEGKQGNFKNLREFVFKNIDGYFKIYSKHTPINLVRDLPQGFSALEPLVDLPIGINITRFQTLLALHR<br>SYLTPGDSSSGWTAGAAAYYVGYLQPRTFLLKYNENGTITDAVDCALDPLSETKCTLKSFTVEKGIYQTSNFRVQPTESIVR<br>FPNITNLCPFGEVFNATRFASVYAWNRKRISNCVADYSVLYNSASFSTFKCYGVSPTKLNDLCFTNVYADSFVIRGDEVRQI<br>APGQTGKIADYNYKLPDDFTGCVIAWNSNNLDSKVGGNYNYLYRLFRKSNLKPFERDISTEIYQAGSTPCNGVEGFNCYFPL<br>QSYGFQPTNGVGYQPYRVVVLSFELLHAPATVCGPKKSTNLVKNKCVNFNFNGLTGTGVLTESNKKFLPFQQFGRDIADTTD<br>AVRDPQTLEILDITPCSFGGVSVITPGTNTSNQVAVLYQDVNCTEVPVAIHADQLTPTWRVYSTGSNVFQTRAGCLIGAEHV<br>NNSYECDIPIGAGICASYQTQTNSPRRARSVASQSIIAYTMSLGAENSVAYSNNSIAIPTNFTISVTTEILPVSMTKTSVDC<br>TMYICGDSTECSNLLLQYGSFCTQLNRALTGIAVEQDKNTQEVFAQVKQIYKTPPIKDFGGFNFSQILPDPSKPSKRSFIED<br>LLFNKVTLADAGFIKQYGDCLGDIAARDLICAQKFNGLTVLPPLLTDEMIAQYTSALLAGTITSGWTFGAGAALQIPFAMQM<br>AYRFNGIGVTQNVLYENQKLIANQFNSAIGKIQDSLSSTASALGKLQDVVNQNAQALNTLVKQLSSNFGAISSVLNDILSRL<br>DKVEAEVQIDRLITGRLQSLQTYVTQQLIRAAEIRASANLAATKMSECVLGQSKRVDFCGKGYHLMSFPQSAPHGVVFLHVT<br>YVPAQEKNFTTAPAICHDGKAHFPREGVFVSNGTHWFVTQRNFYEPQIITTDNTFVSGNCDVVIGIVNNTVYDPLQPELDSF<br>KEELDKYFKNHTSPDVDLGDISGINASVVNIQKEIDRLNEVAKNLNESLIDLQELGKYEQYIKWPWYIWLGFIAGLIAIVMV<br>TIMLCCMTSCCSCLKGCCSCGSCCKFDEDDSEPVLKGVKLHYT |
| 2 | S protein (CDS) | auguuuguguuucuugugcugcugccucuugugucuucucagugugugaauuugacaacaagaacacagcugccaccagcuu<br>auacaaauucuuuuaccagaggaguguauuauccugauaaaguguuuagaucuucugugcugcacagcacacaggaccuguu<br>ucugccauuuuuuagcaaugugacaugguuucaugcaauucaugugucuggaacaaauggaacaaaaagauuugauaauccu<br>gugcugccuuuuaaugauggaguguauuuugcuucaacagaaaagucaaauauuauuagaggauggauuuuuggaacaacac<br>uggauucuaaaacacagucucugcugauugugaauaaugcaacaaaugguggauuaaagugugugaauuucaguuuuguaa<br>ugauccuuuucugggaguguauuaucacaaaaauaauaaaucuuggauggaaucugaauuuagaguguauuccucugcaaau<br>aauuguacauuugaauaugugucucagccuuuucugauggaucuggaaggaaaacagggcaauuuaaaaaucugagagaau<br>uuguguuuaaaaauauugauggauauuuuaaaauuuauucuaaacacacaccaauuaauuuagugagagaucugccucaggg<br>auuuucugcucuggaaccucugguggaucugccaauuggcauuaauauuacaagauuucagacacugcuggcucugcacaga<br>ucuuaucugacaccuggagauucuucuucuggauggacagccggagcugcagcuuauuaugugggcuaucugcagccaagaa<br>cauuucugcugaaauauaaugaaaauggaacaauuacagaugcuguggauugugcucuggauccucugucugaaacaaaaug<br>uacauuaaaaucuuuuacaguggaaaaaggcauuuaucagacaucuaauuuuagagugcagccaacagaaucuauugugaga<br>uuuccaaauauuacaaaucuguguccauuuggagaaguguuuaaugcaacaagauuugcaucuguguaugcauggaauagaa<br>aaagaauuucuaauuguguggcugauuauucugugcuguauaauagugcuucuuuuuccacauuuaaauguuauggagugc<br>uccaacaaaauuaaaugauuuauguuuuacaaauguguaugcugauucuuuugugaucagaggugaugaagugagacagauu<br>gcccccggacagacaggaaaaauugcugauuacaauuacaaacugccugaugauuuuacaggaugugugauugcuuggaauu<br>cuaauaauuuagauucuaaaguggaggaaauuacaauuaucuguacagacuguuuagaaaaucaaaucugaaaccuuuuga<br>aagagauauuucaacagaaauuuaucaggcuggaucaacaccuuguaauggaguggaaggauuuaauuguuauuuuccauua<br>cagagcuauggauuucagccaaccaauggugugggauaucagccauauagagugguggugcugucuuuugaacugcugcaug<br>caccugcaacagugugugggaccuaaaaaaucuacaaauuuagugaaaaauaaaugugugaauuuuaauuuuaauggauuaac<br>aggaacaggagugcugacagaaucuaauaaaaaauuucugccuuuucagcaguuuggcagagauauugcagauaccacagau<br>gcagugagagauccucagacauuagaaauucuggauauuacaccuuguucuuuugggggugugucugugauuacaccuggaa<br>caaauacaucuaaucagguggcugugcuguaucaggaugugaauuguacagaagugccaguggcaauucaugcagaucagcu<br>gacaccaacauggagaguguauucuacaggaucuaauguguuucagacaagagcaggaugucugauuggagcagaacaugug<br>aauaauucuuaugaaugugauauuccaauuggagcaggcauuugugcaucuuaucagacacagacaaauuccccaaggagag<br>caagaucuguggcaucucagucuauuauugcauacaccaugucucugggagcagaaaauucuguggcauauucuaauaauuc<br>uauugcuauuccaacaaauuuuaccauuucugugacaacagaaauuuuaccugugucuaugacaaaaacaucuguggauugu<br>accauguacauuuguggagauucuacagaauguucuaaucugcugcugcaguauggaucuuuuuguacacagcugaauagag<br>cuuuaacaggaauugcuguggaacaggauaaaaauacacaggaaguguuugcucaggugaaacagauuuacaaaacaccacc<br>aauuaaagauuuuggaggauuuaauuuuagccagauucugccugauccuucuaaaccuucuaaaagaucuuuuauugaagau<br>cugcuguuuaauaaagugacacuggcagaugcaggauuuauuaaacaguauggagauugccuggugauauugcugcaagag<br>aucugauuugugcucagaaauuuaauggacugacagugcugccuccucugcugacagaugaaaugauugcucaguacacauc<br>ugcuuuacuggcuggaacaauuacaagcggauggacauuuggagcuggagcugcucugcagauuccuuuugcaaugcagaug<br>gcuuacagauuuaauggaauuggagugacacagaauguguuauaugaaaaucagaaacugauugcaaaucaguuuaauucug<br>caauuggcaaaauucaggauucucugucuucuacagcuucugcucugggaaaacugcaggaugguggaaucagaaugcaca<br>ggcacugaauacucuggugaaacagcugucuagcaauuuuggggcaauuucuucugugcugaaugauauucugucuagacug<br>gauaaaguggaagcugaagugcagauugauagacugaucacaggaagacugcagucucugcagacuuaugugacacagcagc<br>ugauuagagcugcugaaauuagagcuucugcuaaucuggcugcuacaaaaaugucugaaugugugcugggacagucaaaaag<br>aguggauuuuuguggaaaaggauaucaucugaugucuuuuccacagucugcuccacauggagugguguuuuuacaugugaca<br>uaugugccagcacaggaaaagaauuuuaccacagcaccagcaauuugucaugauggaaaagcacauuuuccaagagaaggag<br>uguuugugucuaauggaacacauugguuugugacacagagaaauuuuuaugaaccucagauuauuacaacagauaauacauu<br>ugugucaggaaauugugaugguggugauuggaauugugaauaauacaguguaugauccacugcagccagaacuggauucuuuu<br>aaagaagaacuggauaaauauuuuaaaaaucacacaucuccugauguggauuuaggagauauuucuggaaucaaugcaucug<br>uggugaauauucagaaagaaauugauagacugaaugaaguggccaaaaaucugaaugaaucucugauugaucugcaggaacu<br>uggaaaauaugaacaguacauuaaauggccuugguacauuuggcuuggauuuauugcaggauuaauugcaauugugauggug<br>acaauuauguuauguuguaugacaucauguuguucuuguuuaaaaggauguuguucuuguggaagcuguuguaaauuugaug<br>aagaugauucugaaccuguguuaaaaggagugaaauugcauuacaca |
| 3 | S protein RBD (amino acid)(V05) | MFVFLVLLPLVSSQCVVRFPNITNLCPFGEVFNATRFASVYAWNRKRISNCVADYSVLYNSASFSTFKCYGVSPTKLNDLCF<br>TNVYADSFVIRGDEVRQIAPGQTGKIADYNYKLPDDFTGCVIAWNSNNLDSKVGGNYNYLYRLFRKSNLKPFERDISTEIYQ<br>AGSTPCNGVEGFNCYFPLQSYGFQPTNGVGYQPYRVVVLSFELLHAPATVCGPK |
| 4 | S protein RBD (CDS)(V05) | auguuuguguuucuugugcugcugccucuugugucuucucagugugugggugagauuuccaaauauuacaaaucuguguccau<br>uuggagaaguguuuaaugcaacaagauuugcaucuguguaugcauggaauagaaaaagaauuucuaauuguguggcugauua<br>uucugugcuguauaauagugcuucuuuuuccacauuuaaauguuauggagugucuccaacaaaauuaaaugauuuauguuuu |

TABLE 1-continued

DESCRIPTION OF THE SEQUENCES

| SEQ ID NO: | Description | SEQUENCE |
|---|---|---|
| | | acaaauguguaugcugauucuuuugugaucagaggugaugaagugagacagauugcccccggacagacaggaaaaauugcug<br>auuacaauuacaaacugccugaugauuuuacaggaugugugauugcuuggaauucuaauaauuuagauucuaaagugggagg<br>aaauuacaauuaucuguacagacuguuuagaaaaucaaaucugaaaccuuuugaaagagauauuucaacagaaauuuaucag<br>gcuggaucaacaccuuguaauggaguggaaggauuuaauuguuauuuuccauuacagagcuauggauuucagccaaccaaug<br>gugugggauaucagccauauagagugguggugcugucuuuugaacugcugcaugcaccugcaacaguguguggaccuaaa |
| 5 | S protein RBD/<br>Fibritin (amino<br>acid)(V05) | MFVFLVLLPLVSSQCVVRFPNITNLCPFGEVFNATRFASVYAWNRKRISNCVADYSVLYNSASFSTFKCYGVSPTKLNDLCF<br>TNVYADSFVIRGDEVRQIAPGQTGKIADYNYKLPDDFTGCVIAWNSNNLDSKVGGNYNYLYRLFRKSNLKPFERDISTEIYQ<br>AGSTPCNGVEGFNCYFPLQSYGFQPTNGVGYQPYRVVVLSFELLHAPATVCGPKGSPGSGSGSGYIPEAPRDGQAYVRKDGE<br>WVLLSTFLGRSLEVLFQGPG |
| 6 | S protein RBD/<br>Fibritin (CDS)<br>(V05) | auguuuguguuucuugugcugcugccucuugugucuucucagugugugguggagauuuccaaauauuacaaaucuguguccau<br>uuggagaaguguuuaaugcaacaagauuugcaucuguguaugcauggaauagaaaaagaauuucuaauuguguggcugauua<br>uucugugcuguauaauagugcuucuuuuuccacauuuaaauguuauggagugucuccaacaaaauuaaaugauuuauguuuu<br>acaaauguguaugcugauucuuuugugaucagaggugaugaagugagacagauugcccccggacagacaggaaaaauugcug<br>auuacaauuacaaacugccugaugauuuuacaggaugugugauugcuuggaauucuaauaauuuagauucuaaagugggagg<br>aaauuacaauuaucuguacagacuguuuagaaaaucaaaucugaaaccuuuugaaagagauauuucaacagaaauuuaucag<br>gcuggaucaacaccuuguaauggaguggaaggauuuaauuguuauuuuccauuacagagcuauggauuucagccaaccaaug<br>gugugggauaucagccauauagagugguggugcugucuuuugaacugcugcaugcaccugcaacaguguguggaccuaaagg<br>cucccccggcuccggcuccggaucugguuauauuccugaagcuccaagagaugggcaagcuuacguucguaaagauggcgaa<br>uggguauuacuuucuaccuuuuuaggccggucccuggaggugcuguuccagggccccggc |
| 7 | S protein PP<br>(amino acid)<br>(V08/V09) | MFVFLVLLPLVSSQCVNLTTRTQLPPAYTNSFTRGVYYPDKVFRSSVLHSTQDLFLPFFSNVTWFHAIHVSGTNGTKRFDNP<br>VLPFNDGVYFASTEKSNIIRGWIFGTTLDSKTQSLLIVNNATNVVIKVCEFQFCNDPFLGVYYHKNNKSWMESEFRVYSSAN<br>NCTFEYVSQPFLMDLEGKQGNFKNLREFVFKNIDGYFKIYSKHTPINLVRDLPQGFSALEPLVDLPIGINITRFQTLLALHR<br>SYLTPGDSSSGWTAGAAAYYVGYLQPRTFLLKYNENGTITDAVDCALDPLSETKCTLKSFTVEKGIYQTSNFRVQPTESIVR<br>FPNITNLCPFGEVFNATRFASVYAWNRKRISNCVADYSVLYNSASFSTFKCYGVSPTKLNDLCFTNVYADSFVIRGDEVRQI<br>APGQTGKIADYNYKLPDDFTGCVIAWNSNNLDSKVGGNYNYLYRLFRKSNLKPFERDISTEIYQAGSTPCNGVEGFNCYFPL<br>QSYGFQPTNGVGYQPYRVVVLSFELLHAPATVCGPKKSTNLVKNKCVNFNFNGLTGTGVLTESNKKFLPFQQFGRDIADTTD<br>AVRDPQTLEILDITPCSFGGVSVITPGTNTSNQVAVLYQDVNCTEVPVAIHADQLTPTWRVYSTGSNVFQTRAGCLIGAEHV<br>NNSYECDIPIGAGICASYQTQTNSPRRARSVASQSIIAYTMSLGAENSVAYSNNSIAIPTNFTISVTTEILPVSMTKTSVDC<br>TMYICGDSTECSNLLLQYGSFCTQLNRALTGIAVEQDKNTQEVFAQVKQIYKTPPIKDFGGFNFSQILPDPSKPSKRSFIED<br>LLFNKVTLADAGFIKQYGDCLGDIAARDLICAQKFNGLTVLPPLLTDEMIAQYTSALLAGTITSGWTFGAGAALQIPFAMQM<br>AYRFNGIGVTQNVLYENQKLIANQFNSAIGKIQDSLSSTASALGKLQDVVNQNAQALNTLVKQLSSNFGAISSVLNDILSRL<br>DPPEAEVQIDRLITGRLQSLQTYVTQQLIRAAEIRASANLAATKMSECVLGQSKRVDFCGKGYHLMSFPQSAPHGVVFLHVT<br>YVPAQEKNFTTAPAICHDGKAHFPREGVFVSNGTHWFVTQRNFYEPQIITTDNTFVSGNCDVVIGIVNNTVYDPLQPELDSF<br>KEELDKYFKNHTSPDVDLGDISGINASVVNIQKEIDRLNEVAKNLNESLIDLQELGKYEQYIKWPWYIWLGFIAGLIAIVMV<br>TIMLCCMTSCCSCLKGCCSCGSCCKFDEDDSEPVLKGVKLHYT |
| 8 | S protein PP<br>(CDS)(V08) | auguuuguguuucuugugcugcugccucuugugucuucucagugugugaauuugacaacaagaacacagcugccaccagcuu<br>auacaaauucuuuuaccagaggaguguauuauccugauaaaguguuuagaucuucugugcugcacagcacacaggaccuguu<br>ucugccauuuuuuagcaaugugacaugguuucaugcaauucaugugucuggaacaaauggaacaaaaagauuugauaauccu<br>gugcugccuuuuaaugauggaguguauuuugcuucaacagaaaagucaaauauuauuagaggauggauuuuuggaacaacac<br>uggauucuaaaacacagucucugcugauugugaauaaugcaacaaaugguggugauuaaagugugugaauuucaguuuuguaa<br>ugauccuuuucugggaguguauuaucacaaaaauaauaaaucuuggauggaaucugaauuuagaguguauuccucugcaaau<br>aauuguacauuugaauaugugucucagccuuuucugauggaucuggaaggaaaacagggcaauuuuaaaaaucugagagaau<br>uuguguuuaaaaauauugauggauauuuuaaaauuuauucuaaacacacaccaauuaauuuagugagagaucugccucaggg<br>auuuucugcucuggaaccucugguggaucugccaauuggcauuaauauuacaagauuucagacacugcuggcucugcacaga<br>ucuuaucugacaccuggagauucuucuucuggauggacagccggagcugcagcuuauuaugugggcuaucugcagccaagaa<br>cauuucugcugaaauauaaugaaaauggaacaauuacagaugcuguggauugugcucuggauccucugucugaaacaaaaug<br>uacauuaaaaucuuuuacaguggaaaaaggcauuuaucagacaucuaauuuuagagugcagccaacagaaucuauugugaga<br>uuuccaaauauuacaaaucugugucccauuuggagaaguguuuaaugcaacaagauuugcaucuguguaugcauggaauagaa<br>aaagaauuucuaauuguguggcugauuauucugugcuguauaauagugcuucuuuuuccacauuuaaauguuauggagugu c<br>uccaacaaaauuaaaugauuuauguuuuacaaauguguaugcugauucuuuugugaucagaggugaugaagugagacagauu<br>gcccccggacagacaggaaaaauugcugauuacaauuacaaacugccugaugauuuuacaggaugugugauugcuuggaauu<br>cuaauaauuuagauucuaaagugggaggaaauuacaauuaucuguacagacuguuuagaaaaucaaaucugaaaccuuuuga<br>aagagauauuucaacagaaauuuaucaggcuggaucaacaccuuguaauggaguggaaggauuuaauuguuauuuuccauua<br>cagagcuauggauuucagccaaccaauggugugggauaucagccauauagagugguggugcugucuuuugaacugcugcaug<br>caccugcaacaguguguggaccuaaaaaaucuacaaauuuagugaaaaauaaaugugugaauuuuaauuuuaauggauuaac<br>aggaacaggagugcugacagaaucuaauaaaaaauuucugccuuuucagcaguuuggcagagauauugcagauaccacagau<br>gcagugagagauccucagacauuagaaauucuggauauuacaccuuguucuuuuggggugugucugugauuacaccuggaa<br>caaauacaucuaaucagguggcugugcuguaucaggaugugaauuguacagaagugccaguggcaauucaugcagaucagcu<br>gacaccaacauggagaguguauucuacaggaucuaauguguuucagacaagagcaggaugucugauuggagcagaacaugug<br>aauaauucuuaugaaugugauauuccaauuggagcaggcauuugugcaucuuaucagacacagacaaauuccccaaggagag<br>caagaucuguggcaucucagucuauuauugcauacaccaugucucugggagcagaaaauucuguggcauauucuaauaauuc<br>uauugcuauuccaacaaauuuuaccauuucugugacaacagaaauuuuaccugugucuaugacaaaaacaucuguggauugu<br>accauguacauuuguggagauucuacagaauguucuaaucugcugcugcaguauggaucuuuuuguacacagcugaauagag<br>cuuuaacaggaauugcuguggaacaggauaaaaauacacaggaaguguuugcucaggugaaacagauuuacaaaacaccacc<br>aauuaaagauuuuggaggauuuaauuuuagccagauucugccugauccuucuaaaccuucuaaaagaucuuuuauugaagau<br>cugcuguuuaauaaagugacacuggcagaugcaggauuuauuaaacaguauggagauugccuggguggauauugcugcaagag<br>aucugauuugugcucagaaauuuaauggacugacagugcugccucucugcugacagaugaaaugauugcucaguacacauc<br>ugcuuuacuggcuggaacaauuacaagcggauggacauuuggagcuggagcugcucugcagauuccuuuugcaaugcagaug<br>gcuuacagauuuaauggaauuggagugacacagaauguguuauaugaaaaucagaaacugauugcaaaucaguuuaauucug<br>caauuggcaaaauucaggauucucugucuucuacagcuucugcucugggaaaacugcaggauguggugaaucagaaugcaca |

TABLE 1-continued

DESCRIPTION OF THE SEQUENCES

| SEQ ID NO: | Description | SEQUENCE |
|---|---|---|
| | | ggcacugaauacucuggugaaacagcugucuagcaauuuuggggcaauuucuucugugcugaaugauauucugucuagacug<br>gauccucccugaagcugaagugcagauugauagacugaucacaggaagacugcagucucugcagacuuaugugacacagcagc<br>ugauuagagcugcugaaauuagagcuucugcuaaucuggcugcuacaaaaaugucugaaugugugcugggacagucaaaaag<br>aguggauuuuuguggaaaaggauaucaucugaugucuuuuccacagucugcuccacauggaguggguguuuuuacaugugaca<br>uaugugccagcacaggaaaagaauuuuaccacagcaccagcaauuugucaugauggaaaagcacauuuuccaagagaaggag<br>uguuugugucuaauggaacacauugguuugugacacagagaaauuuuuaugaaccucagauuauuacaacagauaauacauu<br>ugugucaggaaauugugauguggugauuggaauugugaauaauacaguguaugauccacugcagccagaacuggauucuuuu<br>aaagaagaacuggauaaauauuuuaaaaaucacacaucuccugauguggauuuaggagauauuucuggaaucaaugcaucug<br>uggugaauauucagaaagaaauugauagacugaaugaaguggccaaaaaucugaaugaaucucugauugaucugcaggaacu<br>uggaaaauaugaacaguacauuaaauggccuugguacauuuggcuuggauuuauugcaggauuaauugcaauugugauggug<br>acaauuauguuauguuguaugacaucauguuguucuuguuuaaaaggauguuguucuuguggaagcuguuguaaauuugaug<br>aagaugauucugaaccuguguuaaaaggagugaaauugcauuacaca |
| 9 | S protein PP (CDS)(V09) | auguucguguuccuggugcugcugccucugguguccagccagugugugaaccugaccaccagaacacagcugccuccagccu<br>acaccaacagcuuuaccagaggcguguacuaccccgacaagguguucagauccagcgugcugcacucuacccaggaccuguu<br>ccugccuuucuucagcaacgugaccugguuccacgccauccacguguccggcaccaauggcaccaagagauucgacaacccc<br>gugcugcccuucaacgacgggguguacuuugccagcaccgagaaguccaacaucaucagaggcuggaucuucggcaccacac<br>uggacagcaagacccagagccugcugaucgugaacaacgccaccaacgugguaucaucaaagugugcgaguuccaguucugcaa<br>cgaccccuuccugggcgucuacuaccacaagaacaacaagagcuggauggaaagcgaguuccggguguacagcagcgccaac<br>aacugcaccuucgaguacgugucccagccuuuccugauggaccuggaaggcaagcagggcaacuucaagaaccugcgcgagu<br>ucguguuuaagaacaucgacggcuacuucaagaucuacagcaagcacaccccuaucaaccucgugcgggaucugccucaggg<br>cuucucugcucuggaaccccugguggaucugcccaucggcaucaacaucacccgguuucagacacugcuggcccugcacaga<br>agcuaccugacaccuggcgauagcagcagcggauggacagcuggugccgccgcuuacuaugugggcuaccugcagccuagaa<br>ccuuccugcugaaguacaacgagaacggcaccaucaccgacgccguggauugugcucuggauccucugagcgagacaaagug<br>cacccugaaguccuucaccguggaaaagggcaucuaccagaccagcaacuuccgggugcagcccaccgaauccaucgugcgg<br>uuccccaauaucaccaaucugugcccccuucggcgagguguucaaugccaccagauucgccucuguguacgccuggaaccgga<br>agcggaucagcaauugcguggccgacuacuccgugcuguacaacuccgccagcuucagcaccuucaagugcuacggcguguc<br>cccuaccaagcugaacgaccugugcuucacaaacguguacgccgacagcuucgugauccggggagaugaagugcggcagauu<br>gccccuggacagacaggcaagaucgccgacuacaacuacaagcugcccgacgacuucaccggcugugugauugccuggaaca<br>gcaacaaccuggacuccaaagucggcggcaacuacaauuaccuguaccggcuguuccggaaguccaaucugaagcccuucga<br>gcgggacaucuccaccgagaucuaucaggccggcagcaccccuuguaacggcguggaaggcuucaacugcuacuucccacug<br>caguccuacggcuuucagcccacaaauggcgugggcuaucagcccuacagagugguggugcugagcuucgaacugcugcaug<br>ccccugccacagugugcggcccuaagaaaagcaccaaucucgugaagaacaaaugcgugaacuucaacuucaacggccugac<br>cggcaccggcgugcugacagagagcaacaagaaguuccugccauuccagcaguuuggccgggauaucgccgauaccacagac<br>gccguuagagauccccagacacuggaaauccuggacaucaccccuugcagcuucggcggagugucugugaucaccccuggca<br>ccaacaccagcaaucagguggcagugcuguaccaggacgugaacuguaccgaagugcccguggccauucacgccgaucagcu<br>gacaccuacauggcggguguacuccaccggcagcaauguguuucagaccagagccggcugucugaucggagccgagcacgug<br>aacaauagcuacgagugcgacaucccccaucggcgcuggaaucugcgccagcuaccagacacagacaaacagcccucggagag<br>ccagaagcguggccagccagagcaucauugccuacacaaugucucugggcgccgagaacagcguggccuacuccaacaacuc<br>uaucgcuaucccccaccaacuucaccaucagcgugaccacagagauccugccugugucaugaccaagaccagcguggacugc<br>accauguacaucugcggcgauuccaccgagugcuccaaccugcugcugcaguacggcagcuucugcacccagcugaauagag<br>cccugacagggaucgccguggaacaggacaagaacacccaagagguguucgcccaagugaagcagaucuacaagaccccucc<br>uaucaaggacuucggcggcuucaauuucagccagauucugcccgauccuagcaagcccagcaagcggagcuucaucgaggac<br>cugcuguucaacaaagugacacuggccgacgccggcuucaucaagcaguauggcgauugucugggcgacauugccgccaggg<br>aucugauuugcgcccagaaguuuaacggacugacagugcugccuccucugcugaccgaugagaugaucgcccaguacacauc<br>ugcccugcuggccggcacaaucacaagcggcuggacauuuggagcaggcgccgcucugcagaucccccuuugcuaugcagaug<br>gccuaccgguucaacggcaucggagugacccagaaugugcuguacgagaaccagaagcugaucgccaaccaguucaacagcg<br>ccaucggcaagauccaggacagccugagcagcacagcaagcgcccugggaaagcugcaggacguggucaaccagaaugccca<br>ggcacugaacacccuggucaagcagcuguccuccaacuucggcgccaucagcucugugcugaacgauauccugagcagacug<br>gacccuccugaggccgaggugcagaucgacagacugaucacaggcagacugcagagccuccagacauacgugacccagcagc<br>ugaucagagccgccgagauuagagccucugccaaucuggccgccaccaagaugucugagugugugcugggccagagcaagag<br>aguggacuuuugcggcaagggcuaccaccugaugagcuucccucagucugccccucacggcgugguguuucugcacgugaca<br>uaugugcccgcucaagagaagaauuucaccaccgcuccagccaucugccacgacggcaaagcccacuuuccuagagaaggcg<br>uguucguguccaacggcacccauugguucgugacacagcggaacuucuacgagccccagaucaucaccaccgacaacaccuu<br>cgugucuggcaacugcgacgucgugaucggcauugugaacaauaccguguacgacccucugcagcccgagcuggacagcuuc<br>aaagaggaacuggacaaguacuuuaagaaccacacaagccccgacguggaccugggcgauaucagcggaaucaaugccagcg<br>ucgugaacauccagaaagagaucgaccggcugaacgagguggccaagaaucugaacgagagccugaucgaccugcaagaacu<br>ggggaaguacgagcaguacaucaaguggcccugguacaucuggcugggcuuuaucgccggacugauugccaucgugauggu c<br>acaaucaugcuguguugcaugaccagcugcuguagcugccugaagggcuguuguagcuguggcagcugcugcaaguucgacg<br>aggacgauucugagcccgugcugaagggcgugaaacugcacuacaca |

Foldon

| SEQ ID NO: | Description | SEQUENCE |
|---|---|---|
| 10 | Foldon (amino acid) | GSGYIPEAPRDGQAYVRKDGEWVLLSTFLGRSLEVLFQGPG |
| 11 | Foldon (CDS) | ggaucugguuauauuccugaagcuccaagagaugggcaagcuuacguucguaaagauggcgaaugggguauuacuuucuaccu<br>uuuuaggccggucccuggaggugcuguuccagggccccggc |

TABLE 1-continued

DESCRIPTION OF THE SEQUENCES

| SEQ ID NO: | Description | SEQUENCE |
|---|---|---|
| | | 5′-UTR (hAg-Kozak) |
| 12 | 5′-UTR | AACUAGUAUUCUUCUGGUCCCCACAGACUCAGAGAGAACCCGCCACC |
| | | 3′-UTR (FI element) |
| 13 | 3′-UTR | CUGGUACUGCAUGCACGCAAUGCUAGCUGCCCCUUUCCCGUCCUGGGUACCCCGAGUCUCCCCCGACCUCGGGUCCCAGGUA UGCUCCCACCUCCACCUGCCCCACUCACCACCUCUGCUAGUUCCAGACACCUCCCAAGCACGCAGCAAUGCAGCUCAAAACG CUUAGCCUAGCCACACCCCCACGGGAAACAGCAGUGAUUAACCUUUAGCAAUAAACGAAAGUUUAACUAAGCUAUACUAACC CCAGGGUUGGUCAAUUUCGUGCCAGCCACACC |
| | | A30L70 |
| 14 | A30L70 | AAAAAAAAAAAAAAAAAAAAAAAAAAAAAAGCAUAUGACUAAAAAAAAAAAAAAAAAAAAAAAAAAAAAAAAAAAAAAAA AAAAAAAAAAAAAAAAAAAAAAAAAAAAAA |

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientificterms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of" or "consisting essentially of". Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

Terms such as "reduce", "decrease", "inhibit" or "impair" as used herein relate to an overall reduction or the ability to cause an overall reduction, preferably of at least 5%, at least 10%, at least 20%, at least 50%, at least 75% or even more, in the level. These terms include a complete or essentially complete inhibition, i.e., a reduction to zero or essentially to zero. Terms such as "increase", "enhance" or "exceed" preferably relate to an increase or enhancement by at least 10%, at least 20%, at least 30%, at least 40%, at least 50%, at least 80%, at least 100%, at least 200%, at least 500%, or even more.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 150 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, antigens for vaccination and immunostimulants such as cytokines.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" herein is meant an amino acid sequence that differs from a parent amino acid sequence by virtue of at least one amino acid modification. The parent amino acid sequence may be a naturally occurring or wild type (WT) amino acid sequence, or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" herein is meant an amino acid sequence that is found in nature, including allelic variations. A wild type amino acid sequence, peptide or protein has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5. "Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1,−2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence. Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to antigens or antigenic sequences, one particular function is one or more immunogenic activities displayed by the amino acid sequence from which the fragment or variant is derived. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., inducing an immune response. In one embodiment, the modifications in the amino acid sequence of the parent molecule or sequence do not significantly affect or alter the characteristics of the molecule or sequence. In different embodiments, the function of the functional fragment or functional variant may be reduced but still significantly present, e.g., immunogenicity of the functional variant may be at least 50%, at least 60%, at least 70%, at least 80%, or at least 90% of the parent molecule or sequence. However, in other embodiments, immunogenicity of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens suitable for use herein may be altered such that they vary in sequence from the naturally occurring or native sequences from which they were derived, while retaining the desirable activity of the native sequences.

As used herein, an "instructional material" or "instructions" includes a publication, a recording, a diagram, or any other medium of expression which can be used to communicate the usefulness of the compositions and methods of the invention. The instructional material of the kit of the invention may, for example, be affixed to a container which contains the compositions of the invention or be shipped together with a container which contains the compositions. Alternatively, the instructional material may be shipped separately from the container with the intention that the instructional material and the compositions be used cooperatively by the recipient.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

"Physiological pH" as used herein refers to a pH of about 7.5.

The term "genetic modification" or simply "modification" includes the transfection of cells with nucleic acid. The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, nucleic acid encoding antigen is transiently transfected into cells. RNA can be transfected into cells to transiently express its coded protein.

The term "seroconversion" includes a ≥4-fold rise from before vaccination to 1-month post Dose 2.

Coronavirus

Coronaviruses are enveloped, positive-sense, single-stranded RNA ((+) ssRNA) viruses. They have the largest genomes (26-32 kb) among known RNA viruses and are phylogenetically divided into four genera (α, β, γ, and δ), with betacoronaviruses further subdivided into four lineages (A, B, C, and D). Coronaviruses infect a wide range of avian and mammalian species, including humans. Some human coronaviruses generally cause mild respiratory diseases, although severity can be greater in infants, the elderly, and the immunocompromised. Middle East respiratory syndrome coronavirus (MERS-CoV) and severe acute respiratory syndrome coronavirus (SARS-CoV), belonging to betacoronavirus lineages C and B, respectively, are highly pathogenic. Both viruses emerged into the human population from animal reservoirs within the last 15 years and caused outbreaks with high case-fatality rates. The outbreak of severe acute respiratory syndrome coronavirus-2 (SARS-CoV-2) that causes atypical pneumonia (coronavirus disease 2019; COVID-19) has raged in China since mid-December 2019, and has developed to be a public health emergency of international concern. SARS-CoV-2 (MN908947.3) belongs to betacoronavirus lineage B. It has at least 70% sequence similarity to SARS-CoV.

In general, coronaviruses have four structural proteins, namely, envelope (E), membrane (M), nucleocapsid (N), and spike (S). The E and M proteins have important functions in the viral assembly, and the N protein is necessary for viral RNA synthesis. The critical glycoprotein S is responsible for virus binding and entry into target cells. The S protein is synthesized as a single-chain inactive precursor that is cleaved by furin-like host proteases in the producing cell into two noncovalently associated subunits, S1 and S2. The S1 subunit contains the receptor-binding domain (RBD), which recognizes the host-cell receptor. The S2 subunit contains the fusion peptide, two heptad repeats, and a transmembrane domain, all of which are required to mediate fusion of the viral and host-cell membranes by undergoing a large conformational rearrangement. The S1 and S2 subunits trimerize to form a large prefusion spike.

The S precursor protein of SARS-CoV-2 can be proteolytically cleaved into S1 (685 aa) and S2 (588 aa) subunits. The S1 subunit consists of the receptor-binding domain (RBD), which mediates virus entry into sensitive cells through the host angiotensin-converting enzyme 2 (ACE2) receptor.

Antigen

The present invention comprises the use of RNA encoding an amino acid sequence comprising SARS-CoV-2 S protein, an immunogenic variant thereof, or an immunogenic fragment of the SARS-CoV-2 S protein or the immunogenic variant thereof. Thus, the RNA encodes a peptide or protein comprising at least an epitope SARS-CoV-2 S protein or an immunogenic variant thereof for inducing an immune response against coronavirus S protein, in particular SARS-CoV-2 S protein in a subject. The amino acid sequence comprising SARS-CoV-2 S protein, an immunogenic variant thereof, or an immunogenic fragment of the SARS-CoV-2 S protein or the immunogenic variant thereof (i.e., the antigenic peptide or protein) is also designated herein as "vaccine antigen", "peptide and protein antigen", "antigen molecule" or simply "antigen". The SARS-CoV-2 S protein, an immunogenic variant thereof, or an immunogenic fragment of the SARS-CoV-2 S protein or the immunogenic variant thereof is also designated herein as "antigenic peptide or protein" or "antigenic sequence".

SARS-CoV-2 coronavirus full length spike (S) protein consist of 1273 amino acids (see SEQ ID NO: 1). In specific embodiments, full length spike (S) protein according to SEQ ID NO: 1 is modified in such a way that the prototypical prefusion conformation is stabilized. Stabilization of the prefusion conformation may be obtained by introducing two consecutive proline substitutions at AS residues 986 and 987 in the full length spike protein. Specifically, spike (S) protein stabilized protein variants are obtained in a way that the amino acid residue at position 986 is exchanged to proline and the amino acid residue at position 987 is also exchanged to proline. In one embodiment, a SARS-CoV-2 S protein variant comprises the amino acid sequence shown in SEQ ID NO: 7.

In one embodiment, the vaccine antigen described herein comprises, consists essentially of or consists of a spike protein (S) of SARS-CoV-2, a variant thereof, or a fragment thereof.

In one embodiment, a vaccine antigen comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7. In one embodiment, a vaccine antigen comprises the amino acid sequence of amino acids 17 to 1273 of SEQ ID NO: 1 or 7.

In one embodiment, RNA encoding a vaccine antigen (i) comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) encodes an amino acid sequence comprising the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7. In one embodiment, RNA encoding a vaccine antigen (i) comprises the nucleotide sequence of nucleotides 49 to 3819 of SEQ ID NO: 2, 8 or 9; and/or (ii) encodes an amino acid sequence comprising the amino acid sequence of amino acids 17 to 1273 of SEQ ID NO: 1 or 7.

In one embodiment, the vaccine antigen comprises, consists essentially of or consists of SARS-CoV-2 spike S1 fragment (S1) (the S1 subunit of a spike protein (S) of SARS-CoV-2), a variant thereof, or a fragment thereof.

In one embodiment, a vaccine antigen comprises the amino acid sequence of amino acids 17 to 683 of SEQ ID NO: 1, an amino acid sequence having at least 99%, 98%, 97%, 96%, 95%, 90%, 85%, or 80% identity to the amino acid sequence of amino acids 17 to 683 of SEQ ID NO: 1, or an immunogenic fragment of the amino acid sequence of amino acids 17 to 683 of SEQ ID NO: 1, or the amino acid sequence having at least 99%, 98%, 97%, 96%, 95%, 90%, 85%, or 80% identity to the amino acid sequence of amino acids 17 to 683 of SEQ ID NO: 1. In one embodiment, a vaccine antigen comprises the amino acid sequence of amino acids 17 to 683 of SEQ ID NO: 1.

In one embodiment, RNA encoding a vaccine antigen (i) comprises the nucleotide sequence of nucleotides 49 to 2049 of SEQ ID NO: 2, 8 or 9, a nucleotide sequence having at least 99%, 98%, 97%, 96%, 95%, 90%, 85%, or 80% identity to the nucleotide sequence of nucleotides 49 to 2049 of SEQ ID NO: 2, 8 or 9, or a fragment of the nucleotide sequence of nucleotides 49 to 2049 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2049 of SEQ ID NO: 2, 8 or 9; and/or (ii) encodes an amino acid sequence comprising the amino acid sequence of amino acids 17 to 683 of SEQ ID NO: 1, an amino acid sequence having at least 99%, 98%, 97%, 96%, 95%, 90%, 85%, or 80% identity to the amino acid sequence of amino acids 17 to 683 of SEQ ID NO: 1, or an immunogenic fragment of the amino acid sequence of amino acids 17 to 683 of SEQ ID NO: 1, or the amino acid sequence having at least 99%, 98%, 97%, 96%, 95%, 90%, 85%, or 80% identity to the amino acid sequence of amino acids 17 to 683 of SEQ ID NO: 1. In one embodiment, RNA encoding a vaccine antigen (i) comprises the nucleotide sequence of nucleotides 49 to 2049 of SEQ ID NO: 2, 8 or 9; and/or (ii) encodes an amino acid sequence comprising the amino acid sequence of amino acids 17 to 683 of SEQ ID NO: 1.

In one embodiment, a vaccine antigen comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1. In one embodiment, a vaccine antigen comprises the amino acid sequence of amino acids 17 to 685 of SEQ ID NO: 1.

In one embodiment, RNA encoding a vaccine antigen (i) comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) encodes an amino acid sequence comprising the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1. In one embodiment, RNA encoding a vaccine antigen (i) comprises the nucleotide sequence of nucleotides 49 to 2055 of SEQ ID NO: 2, 8 or 9; and/or (ii) encodes an amino acid sequence comprising the amino acid sequence of amino acids 17 to 685 of SEQ ID NO: 1.

In one embodiment, the vaccine antigen comprises, consists essentially of or consists of the receptor binding domain (RBD) of the S1 subunit of a spike protein (S) of SARS-CoV-2, a variant thereof, or a fragment thereof. The amino acid sequence of amino acids 327 to 528 of SEQ ID NO: 1, a variant thereof, or a fragment thereof is also referred to herein as “RBD” or “RBD domain”.

In one embodiment, a vaccine antigen comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1. In one embodiment, a vaccine antigen comprises the amino acid sequence of amino acids 327 to 528 of SEQ ID NO: 1.

In one embodiment, RNA encoding a vaccine antigen (i) comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) encodes an amino acid sequence comprising the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1. In one embodiment, RNA encoding a vaccine antigen (i) comprises the nucleotide sequence of nucleotides 979 to 1584 of SEQ ID NO: 2, 8 or 9; and/or (ii) encodes an amino acid sequence comprising the amino acid sequence of amino acids 327 to 528 of SEQ ID NO: 1.

According to certain embodiments, a signal peptide is fused, either directly or through a linker, to a SARS-CoV-2 S protein, a variant thereof, or a fragment thereof, i.e., the antigenic peptide or protein. Accordingly, in one embodiment, a signal peptide is fused to the above described amino acid sequences derived from SARS-CoV-2 S protein or immunogenic fragments thereof (antigenic peptides or proteins) comprised by the vaccine antigens described above.

Such signal peptides are sequences, which typically exhibit a length of about 15 to 30 amino acids and are preferably located at the N-terminus of the antigenic peptide or protein, without being limited thereto. Signal peptides as defined herein preferably allow the transport of the antigenic peptide or protein as encoded by the RNA into a defined cellular compartment, preferably the cell surface, the endoplasmic reticulum (ER) or the endosomal-lysosomal compartment. In one embodiment, the signal peptide sequence as defined herein includes, without being limited thereto, the signal peptide sequence of SARS-CoV-2 S protein, in particular a sequence comprising the amino acid sequence of amino acids 1 to 16 or 1 to 19 of SEQ ID NO: 1 or a functional variant thereof.

In one embodiment, a signal sequence comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1. In one embodiment, a signal sequence comprises the amino acid sequence of amino acids 1 to 16 of SEQ ID NO: 1.

In one embodiment, RNA encoding a signal sequence (i) comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) encodes an amino acid sequence comprising the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1. In one embodiment, RNA encoding a signal sequence (i) comprises the nucleotide sequence of nucleotides 1 to 48 of SEQ ID NO: 2, 8 or 9; and/or (ii) encodes an amino acid sequence comprising the amino acid sequence of amino acids 1 to 16 of SEQ ID NO: 1.

In one embodiment, a signal sequence comprises the amino acid sequence of amino acids 1 to 19 of SEQ ID NO: 1, an amino acid sequence having at least 99%, 98%, 97%, 96%, 95%, 90%, 85%, or 80% identity to the amino acid sequence of amino acids 1 to 19 of SEQ ID NO: 1, or a functional fragment of the amino acid sequence of amino acids 1 to 19 of SEQ ID NO: 1, or the amino acid sequence having at least 99%, 98%, 97%, 96%, 95%, 90%, 85%, or 80% identity to the amino acid sequence of amino acids 1 to 19 of SEQ ID NO: 1. In one embodiment, a signal sequence comprises the amino acid sequence of amino acids 1 to 19 of SEQ ID NO: 1.

In one embodiment, RNA encoding a signal sequence (i) comprises the nucleotide sequence of nucleotides 1 to 57 of SEQ ID NO: 2, 8 or 9, a nucleotide sequence having at least 99%, 98%, 97%, 96%, 95%, 90%, 85%, or 80% identity to the nucleotide sequence of nucleotides 1 to 57 of SEQ ID NO: 2, 8 or 9, or a fragment of the nucleotide sequence of nucleotides 1 to 57 of SEQ ID NO: 2, 8 or 9, or the nucleotide sequence having at least 99%, 98%, 97%, 96%, 95%, 90%, 85%, or 80% identity to the nucleotide sequence of nucleotides 1 to 57 of SEQ ID NO: 2, 8 or 9; and/or (ii) encodes an amino acid sequence comprising the amino acid sequence of amino acids 1 to 19 of SEQ ID NO: 1, an amino acid sequence having at least 99%, 98%, 97%, 96%, 95%, 90%, 85%, or 80% identity to the amino acid sequence of amino acids 1 to 19 of SEQ ID NO: 1, or a functional fragment of the amino acid sequence of amino acids 1 to 19 of SEQ ID NO: 1, or the amino acid sequence having at least 99%, 98%, 97%, 96%, 95%, 90%, 85%, or 80% identity to the amino acid sequence of amino acids 1 to 19 of SEQ ID NO: 1. In one embodiment, RNA encoding a signal sequence (i) comprises the nucleotide sequence of nucleotides 1 to 57 of SEQ ID NO: 2, 8 or 9; and/or (ii) encodes an amino acid sequence comprising the amino acid sequence of amino acids 1 to 19 of SEQ ID NO: 1.

The signal peptide sequence as defined herein further includes, without being limited thereto, the signal peptide sequence of an immunoglobulin, e.g., the signal peptide sequence of an immunoglobulin heavy chain variable region, wherein the immunoglobulin may be human immunoglobulin. In particular, the signal peptide sequence as defined herein includes a sequence comprising the amino acid sequence of amino acids 1 to 22 of SEQ ID NO: 31 or a functional variant thereof.

In one embodiment, a signal sequence comprises the amino acid sequence of amino acids 1 to 22 of SEQ ID NO: 31, an amino acid sequence having at least 99%, 98%, 97%, 96%, 95%, 90%, 85%, or 80% identity to the amino acid sequence of amino acids 1 to 22 of SEQ ID NO: 31, or a functional fragment of the amino acid sequence of amino acids 1 to 22 of SEQ ID NO: 31, or the amino acid sequence having at least 99%, 98%, 97%, 96%, 95%, 90%, 85%, or 80% identity to the amino acid sequence of amino acids 1 to 22 of SEQ ID NO: 31. In one embodiment, a signal sequence comprises the amino acid sequence of amino acids 1 to 22 of SEQ ID NO: 31.

In one embodiment, RNA encoding a signal sequence (i) comprises the nucleotide sequence of nucleotides 54 to 119 of SEQ ID NO: 32, a nucleotide sequence having at least 99%, 98%, 97%, 96%, 95%, 90%, 85%, or 80% identity to the nucleotide sequence of nucleotides 54 to 119 of SEQ ID NO: 32, or a fragment of the nucleotide sequence of nucleotides 54 to 119 of SEQ ID NO: 32, or the nucleotide sequence having at least 99%, 98%, 97%, 96%, 95%, 90%, 85%, or 80% identity to the nucleotide sequence of nucleotides 54 to 119 of SEQ ID NO: 32; and/or (ii) encodes an amino acid sequence comprising the amino acid sequence of amino acids 1 to 22 of SEQ ID NO: 31, an amino acid sequence having at least 99%, 98%, 97%, 96%, 95%, 90%, 85%, or 80% identity to the amino acid sequence of amino acids 1 to 22 of SEQ ID NO: 31, or a functional fragment of the amino acid sequence of amino acids 1 to 22 of SEQ ID NO: 31, or the amino acid sequence having at least 99%, 98%, 97%, 96%, 95%, 90%, 85%, or 80% identity to the amino acid sequence of amino acids 1 to 22 of SEQ ID NO: 31. In one embodiment, RNA encoding a signal sequence (i) comprises the nucleotide sequence of nucleotides 54 to 119 of SEQ ID NO: 32; and/or (ii) encodes an amino acid sequence comprising the amino acid sequence of amino acids 1 to 22 of SEQ ID NO: 31.

Such signal peptides are preferably used in order to promote secretion of the encoded antigenic peptide or protein. More preferably, a signal peptide as defined herein is fused to an encoded antigenic peptide or protein as defined herein.

Accordingly, in particularly preferred embodiments, the RNA described herein comprises at least one coding region encoding an antigenic peptide or protein and a signal peptide, said signal peptide preferably being fused to the antigenic peptide or protein, more preferably to the N-terminus of the antigenic peptide or protein as described herein.

In one embodiment, a vaccine antigen comprises the amino acid sequence of SEQ ID NO: 1 or 7, an amino acid sequence having at least 99%, 98%, 97%, 96%, 95%, 90%, 85%, or 80% identity to the amino acid sequence of SEQ ID NO: 1 or 7, or an immunogenic fragment of the amino acid sequence of SEQ ID NO: 1 or 7, or the amino acid sequence having at least 99%, 98%, 97%, 96%, 95%, 90%, 85%, or 80% identity to the amino acid sequence of SEQ ID NO: 1 or 7. In one embodiment, a vaccine antigen comprises the amino acid sequence of SEQ ID NO: 1 or 7.

In one embodiment, RNA encoding a vaccine antigen (i) comprises the nucleotide sequence of SEQ ID NO: 2, 8 or 9, a nucleotide sequence having at least 99%, 98%, 97%, 96%, 95%, 90%, 85%, or 80% identity to the nucleotide sequence of SEQ ID NO: 2, 8 or 9, or a fragment of the nucleotide sequence of SEQ ID NO: 2, 8 or 9, or the nucleotide sequence having at least 99%, 98%, 97%, 96%, 95%, 90%, 85%, or 80% identity to the nucleotide sequence of SEQ ID NO: 2, 8 or 9; and/or (ii) encodes an amino acid sequence comprising the amino acid sequence of SEQ ID NO: 1 or 7, an amino acid sequence having at least 99%, 98%, 97%, 96%, 95%, 90%, 85%, or 80% identity to the amino acid sequence of SEQ ID NO: 1 or 7, or an immunogenic fragment of the amino acid sequence of SEQ ID NO: 1 or 7, or the amino acid sequence having at least 99%, 98%, 97%, 96%, 95%, 90%, 85%, or 80% identity to the amino acid sequence of SEQ ID NO: 1 or 7. In one embodiment, RNA encoding a vaccine antigen (i) comprises the nucleotide sequence of SEQ ID NO: 2, 8 or 9; and/or (ii) encodes an amino acid sequence comprising the amino acid sequence of SEQ ID NO: 1 or 7.

In one embodiment, a vaccine antigen comprises the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, a vaccine antigen comprises the amino acid sequence of SEQ ID NO: 7.

In one embodiment, RNA encoding a vaccine antigen (i) comprises the nucleotide sequence of SEQ ID NO: 15, 16, 19, 20, 24, or 25, a nucleotide sequence having at least 99%, 98%, 97%, 96%, 95%, 90%, 85%, or 80% identity to the nucleotide sequence of SEQ ID NO: 15, 16, 19, 20, 24, or 25, or a fragment of the nucleotide sequence of SEQ ID NO: 15, 16, 19, 20, 24, or 25, or the nucleotide sequence having at least 99%, 98%, 97%, 96%, 95%, 90%, 85%, or 80% identity to the nucleotide sequence of SEQ ID NO: 15, 16, 19, 20, 24, or 25; and/or (ii) encodes an amino acid sequence comprising the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, RNA encoding a vaccine antigen (i) comprises the nucleotide sequence of SEQ ID NO: 15, 16, 19, 20, 24, or 25; and/or (ii) encodes an amino acid sequence comprising the amino acid sequence of SEQ ID NO: 7.

In one embodiment, a vaccine antigen comprises the amino acid sequence of amino acids 1 to 683 of SEQ ID NO: 1, an amino acid sequence having at least 99%, 98%, 97%, 96%, 95%, 90%, 85%, or 80% identity to the amino acid sequence of amino acids 1 to 683 of SEQ ID NO: 1, or an immunogenic fragment of the amino acid sequence of amino acids 1 to 683 of SEQ ID NO: 1, or the amino acid sequence having at least 99%, 98%, 97%, 96%, 95%, 90%, 85%, or 80% identity to the amino acid sequence of amino acids 1 to 683 of SEQ ID NO: 1. In one embodiment, a vaccine antigen comprises the amino acid sequence of amino acids 1 to 683 of SEQ ID NO: 1.

In one embodiment, RNA encoding a vaccine antigen (i) comprises the nucleotide sequence of nucleotides 1 to 2049 of SEQ ID NO: 2, 8 or 9, a nucleotide sequence having at least 99%, 98%, 97%, 96%, 95%, 90%, 85%, or 80% identity to the nucleotide sequence of nucleotides 1 to 2049 of SEQ ID NO: 2, 8 or 9, or a fragment of the nucleotide sequence of nucleotides 1 to 2049 of SEQ ID NO: 2, 8 or 9, or the nucleotide sequence having at least 99%, 98%, 97%, 96%, 95%, 90%, 85%, or 80% identity to the nucleotide sequence of nucleotides 1 to 2049 of SEQ ID NO: 2, 8 or 9; and/or (ii) encodes an amino acid sequence comprising the amino acid sequence of amino acids 1 to 683 of SEQ ID NO: 1, an amino acid sequence having at least 99%, 98%, 97%, 96%, 95%, 90%, 85%, or 80% identity to the amino acid sequence of amino acids 1 to 683 of SEQ ID NO: 1, or an immunogenic fragment of the amino acid sequence of amino acids 1 to 683 of SEQ ID NO: 1, or the amino acid sequence having at least 99%, 98%, 97%, 96%, 95%, 90%, 85%, or 80% identity to the amino acid sequence of amino acids 1 to 683 of SEQ ID NO: 1. In one embodiment, RNA encoding a vaccine antigen (i) comprises the nucleotide sequence of nucleotides 1 to 2049 of SEQ ID NO: 2, 8 or 9; and/or (ii) encodes an amino acid sequence comprising the amino acid sequence of amino acids 1 to 683 of SEQ ID NO: 1.

In one embodiment, a vaccine antigen comprises the amino acid sequence of amino acids 1 to 685 of SEQ ID NO: 1, an amino acid sequence having at least 99%, 98%, 97%, 96%, 95%, 90%, 85%, or 80% identity to the amino acid sequence of amino acids 1 to 685 of SEQ ID NO: 1, or an immunogenic fragment of the amino acid sequence of amino acids 1 to 685 of SEQ ID NO: 1, or the amino acid sequence having at least 99%, 98%, 97%, 96%, 95%, 90%, 85%, or 80% identity to the amino acid sequence of amino acids 1 to 685 of SEQ ID NO: 1. In one embodiment, a vaccine antigen comprises the amino acid sequence of amino acids 1 to 685 of SEQ ID NO: 1.

In one embodiment, RNA encoding a vaccine antigen (i) comprises the nucleotide sequence of nucleotides 1 to 2055 of SEQ ID NO: 2, 8 or 9, a nucleotide sequence having at least 99%, 98%, 97%, 96%, 95%, 90%, 85%, or 80% identity to the nucleotide sequence of nucleotides 1 to 2055 of SEQ ID NO: 2, 8 or 9, or a fragment of the nucleotide sequence of nucleotides 1 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 1 to 2055 of SEQ ID NO: 2, 8 or 9; and/or (ii) encodes an amino acid sequence comprising the amino acid sequence of amino acids 1 to 685 of SEQ ID NO: 1, an amino acid sequence having at least 99%, 98%, 97%, 96%, 95%, 90%, 85%, or 80% identity to the amino acid sequence of amino acids 1 to 685 of SEQ ID NO: 1, or an immunogenic fragment of the amino acid sequence of amino acids 1 to 685 of SEQ ID NO: 1, or the amino acid sequence having at least 99%, 98%, 97%, 96%, 95%, 90%, 85%, or 80% identity to the amino acid sequence of amino acids 1 to 685 of SEQ ID NO: 1. In one embodiment, RNA encoding a vaccine antigen (i) comprises the nucleotide sequence of nucleotides 1 to 2055 of SEQ ID NO: 2, 8 or 9; and/or (ii) encodes an amino acid sequence comprising the amino acid sequence of amino acids 1 to 685 of SEQ ID NO: 1.

In one embodiment, a vaccine antigen comprises the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, a vaccine antigen comprises the amino acid sequence of SEQ ID NO: 3.

In one embodiment, RNA encoding a vaccine antigen (i) comprises the nucleotide sequence of SEQ ID NO: 4, a nucleotide sequence having at least 99%, 98%, 97%, 96%, 95%, 90%, 85%, or 80% identity to the nucleotide sequence of SEQ ID NO: 4, or a fragment of the nucleotide sequence of SEQ ID NO: 4, or the nucleotide sequence having at least 99%, 98%, 97%, 96%, 95%, 90%, 85%, or 80% identity to the nucleotide sequence of SEQ ID NO: 4; and/or (ii) encodes an amino acid sequence comprising the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, RNA encoding a vaccine antigen (i) comprises the nucleotide sequence of SEQ ID NO: 4; and/or (ii) encodes an amino acid sequence comprising the amino acid sequence of SEQ ID NO: 3.

In one embodiment, a vaccine antigen comprises the amino acid sequence of amino acids 1 to 221 of SEQ ID NO: 29, an amino acid sequence having at least 99%, 98%, 97%, 96%, 95%, 90%, 85%, or 80% identity to the amino acid sequence of amino acids 1 to 221 of SEQ ID NO: 29, or an immunogenic fragment of the amino acid sequence of amino acids 1 to 221 of SEQ ID NO: 29, or the amino acid sequence having at least 99%, 98%, 97%, 96%, 95%, 90%, 85%, or 80% identity to the amino acid sequence of amino acids 1 to 221 of SEQ ID NO: 29. In one embodiment, a vaccine antigen comprises the amino acid sequence of amino acids 1 to 221 of SEQ ID NO: 29.

In one embodiment, RNA encoding a vaccine antigen (i) comprises the nucleotide sequence of nucleotides 54 to 716 of SEQ ID NO: 30, a nucleotide sequence having at least 99%, 98%, 97%, 96%, 95%, 90%, 85%, or 80% identity to the nucleotide sequence of nucleotides 54 to 716 of SEQ ID NO: 30, or a fragment of the nucleotide sequence of nucleotides 54 to 716 of SEQ ID NO: 30, or the nucleotide sequence having at least 99%, 98%, 97%, 96%, 95%, 90%, 85%, or 80% identity to the nucleotide sequence of nucleotides 54 to 716 of SEQ ID NO: 30; and/or (ii) encodes an amino acid sequence comprising the amino acid sequence of amino acids 1 to 221 of SEQ ID NO: 29, an amino acid sequence having at least 99%, 98%, 97%, 96%, 95%, 90%, 85%, or 80% identity to the amino acid sequence of amino acids 1 to 221 of SEQ ID NO: 29, or an immunogenic fragment of the amino acid sequence of amino acids 1 to 221 of SEQ ID NO: 29, or the amino acid sequence having at least 99%, 98%, 97%, 96%, 95%, 90%, 85%, or 80% identity to the amino acid sequence of amino acids 1 to 221 of SEQ ID NO: 29. In one embodiment, RNA encoding a vaccine antigen (i) comprises the nucleotide sequence of nucleotides 54 to 716 of SEQ ID NO: 30; and/or (ii) encodes an amino acid sequence comprising the amino acid sequence of amino acids 1 to 221 of SEQ ID NO: 29.

In one embodiment, a vaccine antigen comprises the amino acid sequence of amino acids 1 to 224 of SEQ ID NO: 31, an amino acid sequence having at least 99%, 98%, 97%, 96%, 95%, 90%, 85%, or 80% identity to the amino acid sequence of amino acids 1 to 224 of SEQ ID NO: 31, or an immunogenic fragment of the amino acid sequence of amino acids 1 to 224 of SEQ ID NO: 31, or the amino acid sequence having at least 99%, 98%, 97%, 96%, 95%, 90%, 85%, or 80% identity to the amino acid sequence of amino acids 1 to 224 of SEQ ID NO: 31. In one embodiment, a vaccine antigen comprises the amino acid sequence of amino acids 1 to 224 of SEQ ID NO: 31.

In one embodiment, RNA encoding a vaccine antigen (i) comprises the nucleotide sequence of nucleotides 54 to 725 of SEQ ID NO: 32, a nucleotide sequence having at least 99%, 98%, 97%, 96%, 95%, 90%, 85%, or 80% identity to the nucleotide sequence of nucleotides 54 to 725 of SEQ ID NO: 32, or a fragment of the nucleotide sequence of nucleotides 54 to 725 of SEQ ID NO: 32, or the nucleotide sequence having at least 99%, 98%, 97%, 96%, 95%, 90%, 85%, or 80% identity to the nucleotide sequence of nucleotides 54 to 725 of SEQ ID NO: 32; and/or (ii) encodes an amino acid sequence comprising the amino acid sequence of amino acids 1 to 224 of SEQ ID NO: 31, an amino acid sequence having at least 99%, 98%, 97%, 96%, 95%, 90%, 85%, or 80% identity to the amino acid sequence of amino acids 1 to 224 of SEQ ID NO: 31, or an immunogenic fragment of the amino acid sequence of amino acids 1 to 224 of SEQ ID NO: 31, or the amino acid sequence having at least 99%, 98%, 97%, 96%, 95%, 90%, 85%, or 80% identity to the amino acid sequence of amino acids 1 to 224 of SEQ ID NO: 31. In one embodiment, RNA encoding a vaccine antigen (i) comprises the nucleotide sequence of nucleotides 54 to 725 of SEQ ID NO: 32; and/or (ii) encodes an amino acid sequence comprising the amino acid sequence of amino acids 1 to 224 of SEQ ID NO: 31.

According to certain embodiments, a trimerization domain is fused, either directly or through a linker, e.g., a glycine/serine linker, to a SARS-CoV-2 S protein, a variant thereof, or a fragment thereof, i.e., the antigenic peptide or protein. Accordingly, in one embodiment, a trimerization domain is fused to the above described amino acid sequences derived from SARS-CoV-2 S protein or immunogenic fragments thereof (antigenic peptides or proteins) comprised by the vaccine antigens described above (which may optionally be fused to a signal peptide as described above).

Such trimerization domains are preferably located at the C-terminus of the antigenic peptide or protein, without being limited thereto. Trimerization domains as defined herein preferably allow the trimerization of the antigenic peptide or protein as encoded by the RNA. Examples of trimerization domains as defined herein include, without being limited thereto, foldon, the natural trimerization domain of T4 fibritin. The C-terminal domain of T4 fibritin (foldon) is obligatory for the formation of the fibritin trimer structure and can be used as an artificial trimerization domain. In one embodiment, the trimerization domain as defined herein includes, without being limited thereto, a sequence comprising the amino acid sequence of amino acids 3 to 29 of SEQ ID NO: 10 or a functional variant thereof. In one embodiment, the trimerization domain as defined herein includes, without being limited thereto, a sequence comprising the amino acid sequence of SEQ ID NO: 10 or a functional variant thereof.

In one embodiment, a trimerization domain comprises the amino acid sequence of amino acids 3 to 29 of SEQ ID NO: 10, an amino acid sequence having at least 99%, 98%, 97%, 96%, 95%, 90%, 85%, or 80% identity to the amino acid sequence of amino acids 3 to 29 of SEQ ID NO: 10, or a functional fragment of the amino acid sequence of amino acids 3 to 29 of SEQ ID NO: 10, or the amino acid sequence having at least 99%, 98%, 97%, 96%, 95%, 90%, 85%, or 80% identity to the amino acid sequence of amino acids 3 to 29 of SEQ ID NO: 10. In one embodiment, a trimerization domain comprises the amino acid sequence of amino acids 3 to 29 of SEQ ID NO: 10.

In one embodiment, RNA encoding a trimerization domain (i) comprises the nucleotide sequence of nucleotides 7 to 87 of SEQ ID NO: 11, a nucleotide sequence having at least 99%, 98%, 97%, 96%, 95%, 90%, 85%, or 80% identity to the nucleotide sequence of nucleotides 7 to 87 of SEQ ID NO: 11, or a fragment of the nucleotide sequence of nucleotides 7 to 87 of SEQ ID NO: 11, or the nucleotide sequence having at least 99%, 98%, 97%, 96%, 95%, 90%, 85%, or 80% identity to the nucleotide sequence of nucleotides 7 to 87 of SEQ ID NO: 11; and/or (ii) encodes an amino acid sequence comprising the amino acid sequence of amino acids 3 to 29 of SEQ ID NO: 10, an amino acid sequence having at least 99%, 98%, 97%, 96%, 95%, 90%, 85%, or 80% identity to the amino acid sequence of amino acids 3 to 29 of SEQ ID NO: 10, or a functional fragment of the amino acid sequence of amino acids 3 to 29 of SEQ ID NO: 10, or the amino acid sequence having at least 99%, 98%, 97%, 96%, 95%, 90%, 85%, or 80% identity to the amino acid sequence of amino acids 3 to 29 of SEQ ID NO: 10. In one embodiment, RNA encoding a trimerization domain (i) comprises the nucleotide sequence of nucleotides 7 to 87 of SEQ ID NO: 11; and/or (ii) encodes an amino acid sequence comprising the amino acid sequence of amino acids 3 to 29 of SEQ ID NO: 10.

In one embodiment, a trimerization domain comprises the amino acid sequence SEQ ID NO: 10, an amino acid sequence having at least 99%, 98%, 97%, 96%, 95%, 90%, 85%, or 80% identity to the amino acid sequence of SEQ ID NO: 10, or a functional fragment of the amino acid sequence of SEQ ID NO: 10, or the amino acid sequence having at least 99%, 98%, 97%, 96%, 95%, 90%, 85%, or 80% identity to the amino acid sequence of SEQ ID NO: 10. In one embodiment, a trimerization domain comprises the amino acid sequence of SEQ ID NO: 10.

In one embodiment, RNA encoding a trimerization domain (i) comprises the nucleotide sequence of SEQ ID NO: 11, a nucleotide sequence having at least 99%, 98%, 97%, 96%, 95%, 90%, 85%, or 80% identity to the nucleotide sequence of SEQ ID NO: 11, or a fragment of the nucleotide sequence of SEQ ID NO: 11, or the nucleotide sequence having at least 99%, 98%, 97%, 96%, 95%, 90%, 85%, or 80% identity to the nucleotide sequence of SEQ ID NO: 11; and/or (ii) encodes an amino acid sequence comprising the amino acid sequence of SEQ ID NO: 10, an amino acid sequence having at least 99%, 98%, 97%, 96%, 95%, 90%, 85%, or 80% identity to the amino acid sequence of SEQ ID NO: 10, or a functional fragment of the amino acid sequence of SEQ ID NO: 10, or the amino acid sequence having at least 99%, 98%, 97%, 96%, 95%, 90%, 85%, or 80% identity to the amino acid sequence of SEQ ID NO: 10. In one embodiment, RNA encoding a trimerization domain (i) comprises the nucleotide sequence of SEQ ID NO: 11; and/or (ii) encodes an amino acid sequence comprising the amino acid sequence of SEQ ID NO: 10.

Such trimerization domains are preferably used in order to promote trimerization of the encoded antigenic peptide or protein. More preferably, a trimerization domain as defined herein is fused to an antigenic peptide or protein as defined herein.

Accordingly, in particularly preferred embodiments, the RNA described herein comprises at least one coding region encoding an antigenic peptide or protein and a trimerization domain as defined herein, said trimerization domain preferably being fused to the antigenic peptide or protein, more preferably to the C-terminus of the antigenic peptide or protein.

In one embodiment, a vaccine antigen comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, a vaccine antigen comprises the amino acid sequence of SEQ ID NO: 5.

In one embodiment, RNA encoding a vaccine antigen (i) comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) encodes an amino acid sequence comprising the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, RNA encoding a vaccine antigen (i) comprises the nucleotide sequence of SEQ ID NO: 6; and/or (ii) encodes an amino acid sequence comprising the amino acid sequence of SEQ ID NO: 5.

In one embodiment, RNA encoding a vaccine antigen (i) comprises the nucleotide sequence of SEQ ID NO: 17, 21, or 26, a nucleotide sequence having at least 99%, 98%, 97%, 96%, 95%, 90%, 85%, or 80% identity to the nucleotide sequence of SEQ ID NO: 17, 21, or 26, or a fragment of the nucleotide sequence of SEQ ID NO: 17, 21, or 26, or the nucleotide sequence having at least 99%, 98%, 97%, 96%, 95%, 90%, 85%, or 80% identity to the nucleotide sequence of SEQ ID NO: 17, 21, or 26; and/or (ii) encodes an amino acid sequence comprising the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, RNA encoding a vaccine antigen (i) comprises the nucleotide sequence of SEQ ID NO: 17, 21, or 26; and/or (ii) encodes an amino acid sequence comprising the amino acid sequence of SEQ ID NO: 5.

In one embodiment, a vaccine antigen comprises the amino acid sequence of SEQ ID NO: 18, an amino acid sequence having at least 99%, 98%, 97%, 96%, 95%, 90%, 85%, or 80% identity to the amino acid sequence of SEQ ID NO: 18, or an immunogenic fragment of the amino acid sequence of SEQ ID NO: 18, or the amino acid sequence having at least 99%, 98%, 97%, 96%, 95%, 90%, 85%, or 80% identity to the amino acid sequence of SEQ ID NO: 18. In one embodiment, a vaccine antigen comprises the amino acid sequence of SEQ ID NO: 18.

In one embodiment, a vaccine antigen comprises the amino acid sequence of amino acids 1 to 257 of SEQ ID NO: 29, an amino acid sequence having at least 99%, 98%, 97%, 96%, 95%, 90%, 85%, or 80% identity to the amino acid sequence of amino acids 1 to 257 of SEQ ID NO: 29, or an immunogenic fragment of the amino acid sequence of amino acids 1 to 257 of SEQ ID NO: 29, or the amino acid sequence having at least 99%, 98%, 97%, 96%, 95%, 90%, 85%, or 80% identity to the amino acid sequence of amino acids 1 to 257 of SEQ ID NO: 29. In one embodiment, a vaccine antigen comprises the amino acid sequence of amino acids 1 to 257 of SEQ ID NO: 29.

In one embodiment, RNA encoding a vaccine antigen (i) comprises the nucleotide sequence of nucleotides 54 to 824 of SEQ ID NO: 30, a nucleotide sequence having at least 99%, 98%, 97%, 96%, 95%, 90%, 85%, or 80% identity to the nucleotide sequence of nucleotides 54 to 824 of SEQ ID NO: 30, or a fragment of the nucleotide sequence of nucleotides 54 to 824 of SEQ ID NO: 30, or the nucleotide sequence having at least 99%, 98%, 97%, 96%, 95%, 90%, 85%, or 80% identity to the nucleotide sequence of nucleotides 54 to 824 of SEQ ID NO: 30; and/or (ii) encodes an amino acid sequence comprising the amino acid sequence of amino acids 1 to 257 of SEQ ID NO: 29, an amino acid sequence having at least 99%, 98%, 97%, 96%, 95%, 90%, 85%, or 80% identity to the amino acid sequence of amino acids 1 to 257 of SEQ ID NO: 29, or an immunogenic fragment of the amino acid sequence of amino acids 1 to 257 of SEQ ID NO: 29, or the amino acid sequence having at least 99%, 98%, 97%, 96%, 95%, 90%, 85%, or 80% identity to the amino acid sequence of amino acids 1 to 257 of SEQ ID NO: 29. In one embodiment, RNA encoding a vaccine antigen (i) comprises the nucleotide sequence of nucleotides 54 to 824 of SEQ ID NO: 30; and/or (ii) encodes an amino acid sequence comprising the amino acid sequence of amino acids 1 to 257 of SEQ ID NO: 29.

In one embodiment, a vaccine antigen comprises the amino acid sequence of amino acids 1 to 260 of SEQ ID NO: 31, an amino acid sequence having at least 99%, 98%, 97%, 96%, 95%, 90%, 85%, or 80% identity to the amino acid sequence of amino acids 1 to 260 of SEQ ID NO: 31, or an immunogenic fragment of the amino acid sequence of amino acids 1 to 260 of SEQ ID NO: 31, or the amino acid sequence having at least 99%, 98%, 97%, 96%, 95%, 90%, 85%, or 80% identity to the amino acid sequence of amino acids 1 to 260 of SEQ ID NO: 31. In one embodiment, a vaccine antigen comprises the amino acid sequence of amino acids 1 to 260 of SEQ ID NO: 31.

In one embodiment, RNA encoding a vaccine antigen (i) comprises the nucleotide sequence of nucleotides 54 to 833 of SEQ ID NO: 32, a nucleotide sequence having at least 99%, 98%, 97%, 96%, 95%, 90%, 85%, or 80% identity to the nucleotide sequence of nucleotides 54 to 833 of SEQ ID NO: 32, or a fragment of the nucleotide sequence of nucleotides 54 to 833 of SEQ ID NO: 32, or the nucleotide sequence having at least 99%, 98%, 97%, 96%, 95%, 90%, 85%, or 80% identity to the nucleotide sequence of nucleotides 54 to 833 of SEQ ID NO: 32; and/or (ii) encodes an amino acid sequence comprising the amino acid sequence of amino acids 1 to 260 of SEQ ID NO: 31, an amino acid sequence having at least 99%, 98%, 97%, 96%, 95%, 90%, 85%, or 80% identity to the amino acid sequence of amino acids 1 to 260 of SEQ ID NO: 31, or an immunogenic fragment of the amino acid sequence of amino acids 1 to 260 of SEQ ID NO: 31, or the amino acid sequence having at least 99%, 98%, 97%, 96%, 95%, 90%, 85%, or 80% identity to the amino acid sequence of amino acids 1 to 260 of SEQ ID NO: 31. In one embodiment, RNA encoding a vaccine antigen (i) comprises the nucleotide sequence of nucleotides 54 to 833 of SEQ ID NO: 32; and/or (ii) encodes an amino acid sequence comprising the amino acid sequence of amino acids 1 to 260 of SEQ ID NO: 31.

In one embodiment, a vaccine antigen comprises the amino acid sequence of amino acids 20 to 257 of SEQ ID NO: 29, an amino acid sequence having at least 99%, 98%, 97%, 96%, 95%, 90%, 85%, or 80% identity to the amino acid sequence of amino acids 20 to 257 of SEQ ID NO: 29, or an immunogenic fragment of the amino acid sequence of amino acids 20 to 257 of SEQ ID NO: 29, or the amino acid sequence having at least 99%, 98%, 97%, 96%, 95%, 90%, 85%, or 80% identity to the amino acid sequence of amino acids 20 to 257 of SEQ ID NO: 29. In one embodiment, a vaccine antigen comprises the amino acid sequence of amino acids 20 to 257 of SEQ ID NO: 29.

In one embodiment, RNA encoding a vaccine antigen (i) comprises the nucleotide sequence of nucleotides 111 to 824 of SEQ ID NO: 30, a nucleotide sequence having at least 99%, 98%, 97%, 96%, 95%, 90%, 85%, or 80% identity to the nucleotide sequence of nucleotides 111 to 824 of SEQ ID NO: 30, or a fragment of the nucleotide sequence of nucleotides 111 to 824 of SEQ ID NO: 30, or the nucleotide sequence having at least 99%, 98%, 97%, 96%, 95%, 90%, 85%, or 80% identity to the nucleotide sequence of nucleotides 111 to 824 of SEQ ID NO: 30; and/or (ii) encodes an amino acid sequence comprising the amino acid sequence of amino acids 20 to 257 of SEQ ID NO: 29, an amino acid sequence having at least 99%, 98%, 97%, 96%, 95%, 90%, 85%, or 80% identity to the amino acid sequence of amino acids 20 to 257 of SEQ ID NO: 29, or an immunogenic fragment of the amino acid sequence of amino acids 20 to 257 of SEQ ID NO: 29, or the amino acid sequence having at least 99%, 98%, 97%, 96%, 95%, 90%, 85%, or 80% identity to the amino acid sequence of amino acids 20 to 257 of SEQ ID NO: 29. In one embodiment, RNA encoding a vaccine antigen (i) comprises the nucleotide sequence of nucleotides 111 to 824 of SEQ ID NO: 30; and/or (ii) encodes an amino acid sequence comprising the amino acid sequence of amino acids 20 to 257 of SEQ ID NO: 29.

In one embodiment, a vaccine antigen comprises the amino acid sequence of amino acids 23 to 260 of SEQ ID NO: 31, an amino acid sequence having at least 99%, 98%, 97%, 96%, 95%, 90%, 85%, or 80% identity to the amino acid sequence of amino acids 23 to 260 of SEQ ID NO: 31, or an immunogenic fragment of the amino acid sequence of amino acids 23 to 260 of SEQ ID NO: 31, or the amino acid sequence having at least 99%, 98%, 97%, 96%, 95%, 90%, 85%, or 80% identity to the amino acid sequence of amino acids 23 to 260 of SEQ ID NO: 31. In one embodiment, a vaccine antigen comprises the amino acid sequence of amino acids 23 to 260 of SEQ ID NO: 31.

In one embodiment, RNA encoding a vaccine antigen (i) comprises the nucleotide sequence of nucleotides 120 to 833 of SEQ ID NO: 32, a nucleotide sequence having at least 99%, 98%, 97%, 96%, 95%, 90%, 85%, or 80% identity to the nucleotide sequence of nucleotides 120 to 833 of SEQ ID NO: 32, or a fragment of the nucleotide sequence of nucleotides 120 to 833 of SEQ ID NO: 32, or the nucleotide sequence having at least 99%, 98%, 97%, 96%, 95%, 90%, 85%, or 80% identity to the nucleotide sequence of nucleotides 120 to 833 of SEQ ID NO: 32; and/or (ii) encodes an amino acid sequence comprising the amino acid sequence of amino acids 23 to 260 of SEQ ID NO: 31, an amino acid sequence having at least 99%, 98%, 97%, 96%, 95%, 90%, 85%, or 80% identity to the amino acid sequence of amino acids 23 to 260 of SEQ ID NO: 31, or an immunogenic fragment of the amino acid sequence of amino acids 23 to 260 of SEQ ID NO: 31, or the amino acid sequence having at least 99%, 98%, 97%, 96%, 95%, 90%, 85%, or 80% identity to the amino acid sequence of amino acids 23 to 260 of SEQ ID NO: 31. In one embodiment, RNA encoding a vaccine antigen (i) comprises the nucleotide sequence of nucleotides 120 to 833 of SEQ ID NO: 32; and/or (ii) encodes an amino acid sequence comprising the amino acid sequence of amino acids 23 to 260 of SEQ ID NO: 31.

According to certain embodiments, a transmembrane domain domain is fused, either directly or through a linker, e.g., a glycine/serine linker, to a SARS-CoV-2 S protein, a variant thereof, or a fragment thereof, i.e., the antigenic peptide or protein. Accordingly, in one embodiment, a transmembrane domain is fused to the above described amino acid sequences derived from SARS-CoV-2 S protein or immunogenic fragments thereof (antigenic peptides or proteins) comprised by the vaccine antigens described above (which may optionally be fused to a signal peptide and/or trimerization domain as described above).

Such transmembrane domains are preferably located at the C-terminus of the antigenic peptide or protein, without being limited thereto. Preferably, such transmembrane domains are located at the C-terminus of the trimerization domain, if present, without being limited thereto. In one embodiment, a trimerization domain is present between the SARS-CoV-2 S protein, a variant thereof, or a fragment thereof, i.e., the antigenic peptide or protein, and the transmembrane domain.

Transmembrane domains as defined herein preferably allow the anchoring into a cellular membrane of the antigenic peptide or protein as encoded by the RNA.

In one embodiment, the transmembrane domain sequence as defined herein includes, without being limited thereto, the transmembrane domain sequence of SARS-CoV-2 S protein, in particular a sequence comprising the amino acid sequence of amino acids 1207 to 1254 of SEQ ID NO: 1 or a functional variant thereof.

In one embodiment, a transmembrane domain sequence comprises the amino acid sequence of amino acids 1207 to 1254 of SEQ ID NO: 1, an amino acid sequence having at least 99%, 98%, 97%, 96%, 95%, 90%, 85%, or 80% identity to the amino acid sequence of amino acids 1207 to 1254 of SEQ ID NO: 1, or a functional fragment of the amino acid sequence of amino acids 1207 to 1254 of SEQ ID NO: 1, or the amino acid sequence having at least 99%, 98%, 97%, 96%, 95%, 90%, 85%, or 80% identity to the amino acid sequence of amino acids 1207 to 1254 of SEQ ID NO: 1. In one embodiment, a transmembrane domain sequence comprises the amino acid sequence of amino acids 1207 to 1254 of SEQ ID NO: 1.

In one embodiment, RNA encoding a transmembrane domain sequence (i) comprises the nucleotide sequence of nucleotides 3619 to 3762 of SEQ ID NO: 2, 8 or 9, a nucleotide sequence having at least 99%, 98%, 97%, 96%, 95%, 90%, 85%, or 80% identity to the nucleotide sequence of nucleotides 3619 to 3762 of SEQ ID NO: 2, 8 or 9, or a fragment of the nucleotide sequence of nucleotides 3619 to 3762 of SEQ ID NO: 2, 8 or 9, or the nucleotide sequence having at least 99%, 98%, 97%, 96%, 95%, 90%, 85%, or 80% identity to the nucleotide sequence of nucleotides 3619 to 3762 of SEQ ID NO: 2, 8 or 9; and/or (ii) encodes an amino acid sequence comprising the amino acid sequence of amino acids 1207 to 1254 of SEQ ID NO: 1, an amino acid sequence having at least 99%, 98%, 97%, 96%, 95%, 90%, 85%, or 80% identity to the amino acid sequence of amino acids 1207 to 1254 of SEQ ID NO: 1, or a functional fragment of the amino acid sequence of amino acids 1207 to 1254 of SEQ ID NO: 1, or the amino acid sequence having at least 99%, 98%, 97%, 96%, 95%, 90%, 85%, or 80% identity to the amino acid sequence of amino acids 1207 to 1254 of SEQ ID NO: 1. In one embodiment, RNA encoding a transmembrane domain sequence (i) comprises the nucleotide sequence of nucleotides 3619 to 3762 of SEQ ID NO: 2, 8 or 9; and/or (ii) encodes an amino acid sequence comprising the amino acid sequence of amino acids 1207 to 1254 of SEQ ID NO: 1.

In one embodiment, a vaccine antigen comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29. In one embodiment, a vaccine antigen comprises the amino acid sequence of amino acids 1 to 311 of SEQ ID NO: 29.

In one embodiment, RNA encoding a vaccine antigen (i) comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) encodes an amino acid sequence comprising the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29. In one embodiment, RNA encoding a vaccine antigen (i) comprises the nucleotide sequence of nucleotides 54 to 986 of SEQ ID NO: 30; and/or (ii) encodes an amino acid sequence comprising the amino acid sequence of amino acids 1 to 311 of SEQ ID NO: 29.

In one embodiment, a vaccine antigen comprises the amino acid sequence of amino acids 1 to 314 of SEQ ID NO: 31, an amino acid sequence having at least 99%, 98%, 97%, 96%, 95%, 90%, 85%, or 80% identity to the amino acid sequence of amino acids 1 to 314 of SEQ ID NO: 31, or an immunogenic fragment of the amino acid sequence of amino acids 1 to 314 of SEQ ID NO: 31, or the amino acid sequence having at least 99%, 98%, 97%, 96%, 95%, 90%, 85%, or 80% identity to the amino acid sequence of amino acids 1 to 314 of SEQ ID NO: 31. In one embodiment, a vaccine antigen comprises the amino acid sequence of amino acids 1 to 314 of SEQ ID NO: 31.

In one embodiment, RNA encoding a vaccine antigen (i) comprises the nucleotide sequence of nucleotides 54 to 995 of SEQ ID NO: 32, a nucleotide sequence having at least 99%, 98%, 97%, 96%, 95%, 90%, 85%, or 80% identity to the nucleotide sequence of nucleotides 54 to 995 of SEQ ID NO: 32, or a fragment of the nucleotide sequence of nucleotides 54 to 995 of SEQ ID NO: 32, or the nucleotide sequence having at least 99%, 98%, 97%, 96%, 95%, 90%, 85%, or 80% identity to the nucleotide sequence of nucleotides 54 to 995 of SEQ ID NO: 32; and/or (ii) encodes an amino acid sequence comprising the amino acid sequence of amino acids 1 to 314 of SEQ ID NO: 31, an amino acid sequence having at least 99%, 98%, 97%, 96%, 95%, 90%, 85%, or 80% identity to the amino acid sequence of amino acids 1 to 314 of SEQ ID NO: 31, or an immunogenic fragment of the amino acid sequence of amino acids 1 to 314 of SEQ ID NO: 31, or the amino acid sequence having at least 99%, 98%, 97%, 96%, 95%, 90%, 85%, or 80% identity to the amino acid sequence of amino acids 1 to 314 of SEQ ID NO: 31. In one embodiment, RNA encoding a vaccine antigen (i) comprises the nucleotide sequence of nucleotides 54 to 995 of SEQ ID NO: 32; and/or (ii) encodes an amino acid sequence comprising the amino acid sequence of amino acids 1 to 314 of SEQ ID NO: 31.

In one embodiment, a vaccine antigen comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29. In one embodiment, a vaccine antigen comprises the amino acid sequence of amino acids 20 to 311 of SEQ ID NO: 29.

In one embodiment, RNA encoding a vaccine antigen (i) comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) encodes an amino acid sequence comprising the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29.

In one embodiment, RNA encoding a vaccine antigen (i) comprises the nucleotide sequence of nucleotides 111 to 986 of SEQ ID NO: 30; and/or (ii) encodes an amino acid sequence comprising the amino acid sequence of amino acids 20 to 311 of SEQ ID NO: 29.

In one embodiment, a vaccine antigen comprises the amino acid sequence of amino acids 23 to 314 of SEQ ID NO: 31, an amino acid sequence having at least 99%, 98%, 97%, 96%, 95%, 90%, 85%, or 80% identity to the amino acid sequence of amino acids 23 to 314 of SEQ ID NO: 31, or an immunogenic fragment of the amino acid sequence of amino acids 23 to 314 of SEQ ID NO: 31, or the amino acid sequence having at least 99%, 98%, 97%, 96%, 95%, 90%, 85%, or 80% identity to the amino acid sequence of amino acids 23 to 314 of SEQ ID NO: 31. In one embodiment, a vaccine antigen comprises the amino acid sequence of amino acids 23 to 314 of SEQ ID NO: 31.

In one embodiment, RNA encoding a vaccine antigen (i) comprises the nucleotide sequence of nucleotides 120 to 995 of SEQ ID NO: 32, a nucleotide sequence having at least 99%, 98%, 97%, 96%, 95%, 90%, 85%, or 80% identity to the nucleotide sequence of nucleotides 120 to 995 of SEQ ID NO: 32, or a fragment of the nucleotide sequence of nucleotides 120 to 995 of SEQ ID NO: 32, or the nucleotide sequence having at least 99%, 98%, 97%, 96%, 95%, 90%, 85%, or 80% identity to the nucleotide sequence of nucleotides 120 to 995 of SEQ ID NO: 32; and/or (ii) encodes an amino acid sequence comprising the amino acid sequence of amino acids 23 to 314 of SEQ ID NO: 31, an amino acid sequence having at least 99%, 98%, 97%, 96%, 95%, 90%, 85%, or 80% identity to the amino acid sequence of amino acids 23 to 314 of SEQ ID NO: 31, or an immunogenic fragment of the amino acid sequence of amino acids 23 to 314 of SEQ ID NO: 31, or the amino acid sequence having at least 99%, 98%, 97%, 96%, 95%, 90%, 85%, or 80% identity to the amino acid sequence of amino acids 23 to 314 of SEQ ID NO: 31.

In one embodiment, RNA encoding a vaccine antigen (i) comprises the nucleotide sequence of nucleotides 120 to 995 of SEQ ID NO: 32; and/or (ii) encodes an amino acid sequence comprising the amino acid sequence of amino acids 23 to 314 of SEQ ID NO: 31.

In one embodiment, RNA encoding a vaccine antigen (i) comprises the nucleotide sequence of SEQ ID NO: 30, a nucleotide sequence having at least 99%, 98%, 97%, 96%, 95%, 90%, 85%, or 80% identity to the nucleotide sequence of SEQ ID NO: 30, or a fragment of the nucleotide sequence of SEQ ID NO: 30, or the nucleotide sequence having at least 99%, 98%, 97%, 96%, 95%, 90%, 85%, or 80% identity to the nucleotide sequence of SEQ ID NO: 30; and/or (ii) encodes an amino acid sequence comprising the amino acid sequence of SEQ ID NO: 29, an amino acid sequence having at least 99%, 98%, 97%, 96%, 95%, 90%, 85%, or 80% identity to the amino acid sequence of SEQ ID NO: 29, or an immunogenic fragment of the amino acid sequence of SEQ ID NO: 29, or the amino acid sequence having at least 99%, 98%, 97%, 96%, 95%, 90%, 85%, or 80% identity to the amino acid sequence of SEQ ID NO: 29. In one embodiment, RNA encoding a vaccine antigen (i) comprises the nucleotide sequence of SEQ ID NO: 30; and/or (ii) encodes an amino acid sequence comprising the amino acid sequence of SEQ ID NO: 29.

In one embodiment, RNA encoding a vaccine antigen (i) comprises the nucleotide sequence of SEQ ID NO: 32, a nucleotide sequence having at least 99%, 98%, 97%, 96%, 95%, 90%, 85%, or 80% identity to the nucleotide sequence of SEQ ID NO: 32, or a fragment of the nucleotide sequence of SEQ ID NO: 32, or the nucleotide sequence having at least 99%, 98%, 97%, 96%, 95%, 90%, 85%, or 80% identity to the nucleotide sequence of SEQ ID NO: 32; and/or (ii) encodes an amino acid sequence comprising the amino acid sequence of SEQ ID NO: 31, an amino acid sequence having at least 99%, 98%, 97%, 96%, 95%, 90%, 85%, or 80% identity to the amino acid sequence of SEQ ID NO: 31, or an immunogenic fragment of the amino acid sequence of SEQ ID NO: 31, or the amino acid sequence having at least 99%, 98%, 97%, 96%, 95%, 90%, 85%, or 80% identity to the amino acid sequence of SEQ ID NO: 31. In one embodiment, RNA encoding a vaccine antigen (i) comprises the nucleotide sequence of SEQ ID NO: 32; and/or (ii) encodes an amino acid sequence comprising the amino acid sequence of SEQ ID NO: 31.

In one embodiment, a vaccine antigen comprises the amino acid sequence of SEQ ID NO: 28, an amino acid sequence having at least 99%, 98%, 97%, 96%, 95%, 90%, 85%, or 80% identity to the amino acid sequence of SEQ ID NO: 28, or an immunogenic fragment of the amino acid sequence of SEQ ID NO: 28, or the amino acid sequence having at least 99%, 98%, 97%, 96%, 95%, 90%, 85%, or 80% identity to the amino acid sequence of SEQ ID NO: 28. In one embodiment, a vaccine antigen comprises the amino acid sequence of SEQ ID NO: 28.

In one embodiment, RNA encoding a vaccine antigen (i) comprises the nucleotide sequence of SEQ ID NO: 27, a nucleotide sequence having at least 99%, 98%, 97%, 96%, 95%, 90%, 85%, or 80% identity to the nucleotide sequence of SEQ ID NO: 27, or a fragment of the nucleotide sequence of SEQ ID NO: 27, or the nucleotide sequence having at least 99%, 98%, 97%, 96%, 95%, 90%, 85%, or 80% identity to the nucleotide sequence of SEQ ID NO: 27; and/or (ii) encodes an amino acid sequence comprising the amino acid sequence of SEQ ID NO: 28, an amino acid sequence having at least 99%, 98%, 97%, 96%, 95%, 90%, 85%, or 80% identity to the amino acid sequence of SEQ ID NO: 28, or an immunogenic fragment of the amino acid sequence of SEQ ID NO: 28, or the amino acid sequence having at least 99%, 98%, 97%, 96%, 95%, 90%, 85%, or 80% identity to the amino acid sequence of SEQ ID NO: 28. In one embodiment, RNA encoding a vaccine antigen (i) comprises the nucleotide sequence of SEQ ID NO: 27; and/or (ii) encodes an amino acid sequence comprising the amino acid sequence of SEQ ID NO: 28.

In one embodiment, the vaccine antigens described above comprise a contiguous sequence of SARS-CoV-2 coronavirus spike (S) protein that consists of or essentially consists of the above described amino acid sequences derived from SARS-CoV-2 S protein or immunogenic fragments thereof (antigenic peptides or proteins) comprised by the vaccine antigens described above. In one embodiment, the vaccine antigens described above comprise a contiguous sequence of SARS-CoV-2 coronavirus spike (S) protein of no more than 220 amino acids, 215 amino acids, 210 amino acids, or 205 amino acids.

In one embodiment, RNA encoding a vaccine antigen is nucleoside modified messenger RNA (modRNA) described herein as BNT162b1 (RBP020.3), BNT162b2 (RBP020.1 or RBP020.2). In one embodiment, RNA encoding a vaccine antigen is nucleoside modified messenger RNA (modRNA) described herein as RBP020.2.

In one embodiment, RNA encoding a vaccine antigen is nucleoside modified messenger RNA (modRNA) and (i) comprises the nucleotide sequence of SEQ ID NO: 21, a nucleotide sequence having at least 99%, 98%, 97%, 96%, 95%, 90%, 85%, or 80% identity to the nucleotide sequence of SEQ ID NO: 21, and/or (ii) encodes an amino acid sequence comprising the amino acid sequence of SEQ ID NO: 5, or an amino acid sequence having at least 99%, 98%, 97%, 96%, 95%, 90%, 85%, or 80% identity to the amino acid sequence of SEQ ID NO: 5. In one embodiment, RNA encoding a vaccine antigen is nucleoside modified messenger RNA (modRNA) and (i) comprises the nucleotide sequence of SEQ ID NO: 21; and/or (ii) encodes an amino acid sequence comprising the amino acid sequence of SEQ ID NO: 5.

In one embodiment, RNA encoding a vaccine antigen is nucleoside modified messenger RNA (modRNA) and (i) comprises the nucleotide sequence of SEQ ID NO: 19, or 20, a nucleotide sequence having at least 99%, 98%, 97%, 96%, 95%, 90%, 85%, or 80% identity to the nucleotide sequence of SEQ ID NO: 19, or 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA encoding a vaccine antigen is nucleoside modified messenger RNA (modRNA) and (i) comprises the nucleotide sequence of SEQ ID NO: 19, or 20; and/or (ii) encodes an amino acid sequence comprising the amino acid sequence of SEQ ID NO: 7.

In one embodiment, RNA encoding a vaccine antigen is nucleoside modified messenger RNA (modRNA) and (i) comprises the nucleotide sequence of SEQ ID NO: 20, a nucleotide sequence having at least 99%, 98%, 97%, 96%, 95%, 90%, 85%, or 80% identity to the nucleotide sequence of SEQ ID NO: 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA encoding a vaccine antigen is nucleoside modified messenger RNA (modRNA) and (i) comprises the nucleotide sequence of SEQ ID NO: 20; and/or (ii) encodes an amino acid sequence comprising the amino acid sequence of SEQ ID NO: 7.

As used herein, the term "vaccine" refers to a composition that induces an immune response upon inoculation into a subject. In some embodiments, the induced immune response provides protective immunity.

In one embodiment, the RNA encoding the antigen molecule is expressed in cells of the subject to provide the antigen molecule. In one embodiment, expression of the antigen molecule is at the cell surface or into the extracellular space. In one embodiment, the antigen molecule is presented in the context of MHC. In one embodiment, the RNA encoding the antigen molecule is transiently expressed in cells of the subject. In one embodiment, after administration of the RNA encoding the antigen molecule, in particular after intramuscular administration of the RNA encoding the antigen molecule, expression of the RNA encoding the antigen molecule in muscle occurs. In one embodiment, after administration of the RNA encoding the antigen molecule, expression of the RNA encoding the antigen molecule in spleen occurs. In one embodiment, after administration of the RNA encoding the antigen molecule, expression of the RNA encoding the antigen molecule in antigen presenting cells, preferably professional antigen presenting cells occurs. In one embodiment, the antigen presenting cells are selected from the group consisting of dendritic cells, macrophages and B cells. In one embodiment, after administration of the RNA encoding the antigen molecule, no or essentially no expression of the RNA encoding the antigen molecule in lung and/or liver occurs. In one embodiment, after administration of the RNA encoding the antigen molecule, expression of the RNA encoding the antigen molecule in spleen is at least 5-fold the amount of expression in lung.

In some embodiments, the methods and agents, e.g., mRNA compositions, described herein following administration, in particular following intramuscular administration, to a subject result in delivery of the RNA encoding a vaccine antigen to lymph nodes and/or spleen. In some embodiments, RNA encoding a vaccine antigen is detectable in lymph nodes and/or spleen 6 hours or later following administration and preferably up to 6 days or longer. In some embodiments, the methods and agents, e.g., mRNA compositions, described herein following administration, in particular following intramuscular administration, to a subject result in delivery of the RNA encoding a vaccine antigen to B cell follicles, subcapsular sinus, and/or T cell zone, in particular B cell follicles and/or subcapsular sinus of lymph nodes. In some embodiments, the methods and agents, e.g., mRNA compositions, described herein following administration, in particular following intramuscular administration, to a subject result in delivery of the RNA encoding a vaccine antigen to B cells (CD19+), subcapsular sinus macrophages (CD169+) and/or dendritic cells (CD11c+) in the T cell zone and intermediary sinus of lymph nodes, in particular to B cells (CD19+) and/or subcapsular sinus macrophages (CD169+) of lymph nodes.

In some embodiments, the methods and agents, e.g., mRNA compositions, described herein following administration, in particular following intramuscular administration, to a subject result in delivery of the RNA encoding a vaccine antigen to white pulp of spleen. In some embodiments, the methods and agents, e.g., mRNA compositions, described herein following administration, in particular following intramuscular administration, to a subject result in delivery of the RNA encoding a vaccine antigen to B cells, DCs (CD11c+), in particular those surrounding the B cells, and/or mcrophages of spleen, in particular to B cells and/or DCs (CD11c+).

In one embodiment, the vaccine antigen is expressed in lymph node and/or spleen, in particular in the cells of lymph node and/or spleen described above.

The peptide and protein antigens suitable for use according to the disclosure typically include a peptide or protein comprising an epitope of SARS-CoV-2 S protein or a functional variant thereof for inducing an immune response. The peptide or protein or epitope may be derived from a target antigen, i.e. the antigen against which an immune response is to be elicited. For example, the peptide or protein antigen or the epitope contained within the peptide or protein antigen may be a target antigen or a fragment orvariant of a target antigen. The target antigen may be a coronavirus S protein, in particular SARS-CoV-2 S protein.

The antigen molecule or a procession product thereof, e.g., a fragment thereof, may bind to an antigen receptor such as a BCR or TCR carried by immune effector cells, or to antibodies. A peptide and protein antigen which is provided to a subject according to the invention by administering RNA encoding the peptide and protein antigen, i.e., a vaccine antigen, preferably results in the induction of an immune response, e.g., a humoral and/or cellular immune response in the subject being provided the peptide or protein antigen. Said immune response is preferably directed against a target antigen, in particular coronavirus S protein, in particular SARS-CoV-2 S protein. Thus, a vaccine antigen may comprise the target antigen, a variant thereof, or a fragment thereof. In one embodiment, such fragment or variant is immunologically equivalent to the target antigen. In the context of the present disclosure, the term "fragment of an antigen" or "variant of an antigen" means an agent which results in the induction of an immune response which immune response targets the antigen, i.e. a target antigen. Thus, the vaccine antigen may correspond to or may comprise the target antigen, may correspond to or may comprise a fragment of the target antigen or may correspond to or may comprise an antigen which is homologous to the target antigen or a fragment thereof. Thus, according to the disclosure, a vaccine antigen may comprise an immunogenic fragment of a target antigen or an amino acid sequence being homologous to an immunogenic fragment of a target antigen. An "immunogenic fragment of an antigen" according to the disclosure preferably relates to a fragment of an antigen which is capable of inducing an immune response against the target antigen. The vaccine antigen may be a recombinant antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject induces an immune reaction having a specificity of reacting with the reference amino acid sequence.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which immune effector cells are stimulated by an antigen, proliferate, and the specific immune effector cell recognizing said antigen is amplified. Preferably, clonal expansion leads to differentiation of the immune effector cells.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a procession product thereof such as a T-cell epitope is in one embodiment bound by a T- or B-cell receptor, or by an immunoglobulin molecule such as an antibody. Accordingly, an antigen or a procession product thereof may react specifically with antibodies or T lymphocytes (T cells). In one embodiment, an antigen is a viral antigen, such as a coronavirus S protein, e.g., SARS-CoV-2 S protein, and an epitope is derived from such antigen.

The term "viral antigen" refers to any viral component having antigenic properties, i.e. being able to provoke an immune response in an individual. The viral antigen may be coronavirus S protein, e.g., SARS-CoV-2 S protein.

The term "expressed on the cell surface" or "associated with the cell surface" means that a molecule such as an antigen is associated with and located at the plasma membrane of a cell, wherein at least a part of the molecule faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells. The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The term "epitope" refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 8 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class MHC/peptide complexes, the binding peptides are typically about 10 to about 25 amino acids long and are in particular about 13 to about 18 amino acids long, whereas longer and shorter peptides may be effective.

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to the peptide or protein.

In one embodiment, vaccine antigen is recognized by an immune effector cell. Preferably, the vaccine antigen if recognized by an immune effector cell is able to induce in the presence of appropriate co-stimulatory signals, stimulation, priming and/or expansion of the immune effector cell carrying an antigen receptor recognizing the vaccine antigen. In the context of the embodiments of the present invention, the vaccine antigen is preferably presented or present on the surface of a cell, preferably an antigen presenting cell. In one embodiment, an antigen is presented by a diseased cell such as a virus-infected cell. In one embodiment, an antigen receptor is a TCR which binds to an epitope of an antigen presented in the context of MHC. In one embodiment, binding of a TCR when expressed by T cells and/or present on T cells to an antigen presented by cells such as antigen presenting cells results in stimulation, priming and/or expansion of said T cells. In one embodiment, binding of a TCR when expressed byT cells and/or present on T cells to an antigen presented on diseased cells results in cytolysis and/or apoptosis of the diseased cells, wherein said T cells preferably release cytotoxic factors, e.g. perforins and granzymes.

In one embodiment, an antigen receptor is an antibody or B cell receptor which binds to an epitope in an antigen. In one embodiment, an antibody or B cell receptor binds to native epitopes of an antigen.

Nucleic Acids

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a polynucleotide is preferably isolated.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. In one embodiment of all aspects of the invention, the RNA encoding the vaccine antigen is expressed in cells such as antigen presenting cells of the subject treated to provide the vaccine antigen.

The nucleic acids described herein may be recombinant and/or isolated molecules. In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA. In certain embodiments of the present disclosure, the RNA is "replicon RNA" or simply a "replicon", in particular "self-replicating RNA" or "self-amplifying RNA". In one particularly preferred embodiment, the replicon or self-replicating RNA is derived from or comprises elements derived from a ssRNA virus, in particular a positive-stranded ssRNA virus such as an alphavirus. Alphaviruses are typical representatives of positive-stranded RNA viruses. Alphaviruses replicate in the cytoplasm of infected cells (for review of the alphaviral life cycle see José et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In one embodiment, the RNA described herein may have modified nucleosides. In some embodiments, the RNA comprises a modified nucleoside in place of at least one (e.g., every) uridine.

The term "uracil," as used herein, describes one of the nucleobases that can occur in the nucleic acid of RNA. The structure of uracil is:

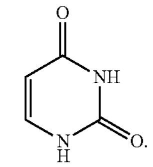

The term "uridine," as used herein, describes one of the nucleosides that can occur in RNA. The structure of uridine is:

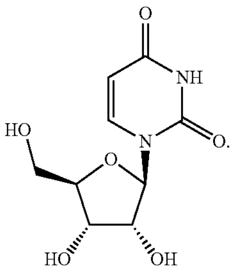 [SMILES: O=c1ccn([C@@H]2O[C@H](CO)[C@@H](O)[C@H]2O)c(=O)[nH]1]

UTP (uridine 5'-triphosphate) has the following structure:

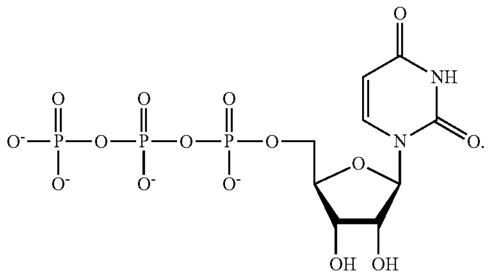

Pseudo-UTP (pseudouridine 5'-triphosphate) has the following structure:

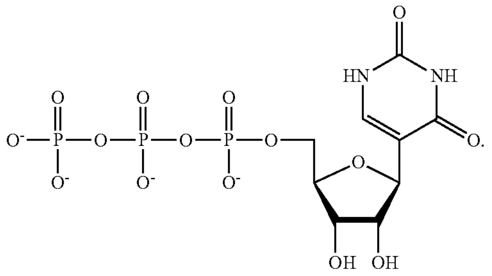

"Pseudouridine" is one example of a modified nucleoside that is an isomer of uridine, where the uracil is attached to the pentose ring via a carbon-carbon bond instead of a nitrogen-carbon glycosidic bond.

Another exemplary modified nucleoside is N1-methyl-pseudouridine (m1ψ), which has the structure:

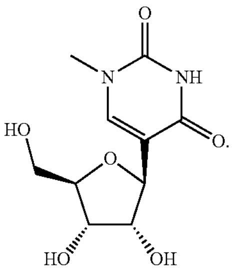 [SMILES: Cn1cc([C@@H]2O[C@H](CO)[C@@H](O)[C@H]2O)c(=O)[nH]c1=O]

N1-methyl-pseudo-UTP has the following structure:

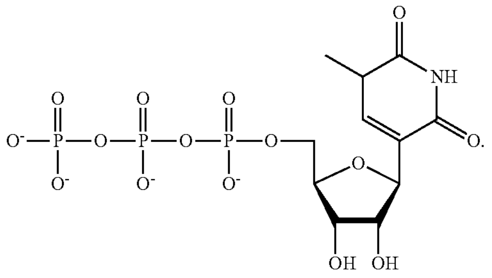

Another exemplary modified nucleoside is 5-methyl-uridine (m5U), which has the structure:

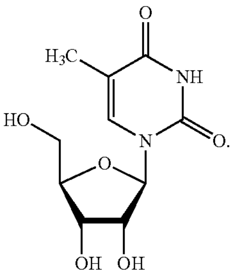

In some embodiments, one or more uridine in the RNA described herein is replaced by a modified nucleoside. In some embodiments, the modified nucleoside is a modified uridine.

In some embodiments, RNA comprises a modified nucleoside in place of at least one uridine.

In some embodiments, RNA comprises a modified nucleoside in place of each uridine.

In some embodiments, the modified nucleoside is independently selected from pseudouridine ($\psi$), N1-methyl-pseudouridine (m1$\psi$), and 5-methyl-uridine (m5U). In some embodiments, the modified nucleoside comprises pseudouridine ($\psi$). In some embodiments, the modified nucleoside comprises N1-methyl-pseudouridine (m1$\psi$). In some embodiments, the modified nucleoside comprises 5-methyl-uridine (m5U). In some embodiments, RNA may comprise more than one type of modified nucleoside, and the modified nucleosides are independently selected from pseudouridine ($\psi$), N1-methyl-pseudouridine (m1$\psi$), and 5-methyl-uridine (m5U). In some embodiments, the modified nucleosides comprise pseudouridine ($\psi$) and N1-methyl-pseudouridine (m1$\psi$). In some embodiments, the modified nucleosides comprise pseudouridine ($\psi$) and 5-methyl-uridine (m5U). In some embodiments, the modified nucleosides comprise N1-methyl-pseudouridine (m1$\psi$) and 5-methyl-uridine (m5U). In some embodiments, the modified nucleosides comprise pseudouridine ($\psi$), N1-methyl-pseudouridine (m1$\psi$), and 5-methyl-uridine (m5U).

In some embodiments, the modified nucleoside replacing one or more, e.g., all, uridine in the RNA may be any one or more of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($tm^5U$), 1-taurinomethyl-pseudouridine, 5-taurinomethyl-2-thio-uridine(tm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), $\alpha$-thio-uridine, 2'-O-methyl-uridine (Um), 5,2'-O-dimethyl-uridine ($m^5Um$), 2'-O-methyl-pseudouridine ($\psi m$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

In one embodiment, the RNA comprises other modified nucleosides or comprises further modified nucleosides, e.g., modified cytidine. For example, in one embodiment, in the RNA 5-methylcytidine is substituted partially or completely, preferably completely, for cytidine. In one embodiment, the RNA comprises 5-methylcytidine and one or more selected from pseudouridine ($\psi$), N1-methyl-pseudouridine (m1$\psi$), and 5-methyl-uridine (m5U). In one embodiment, the RNA comprises 5-methylcytidine and N1-methyl-pseudouridine (m1$\psi$). In some embodiments, the RNA comprises 5-methylcytidine in place of each cytidine and N1-methyl-pseudouridine (m1$\psi$) in place of each uridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes. In some embodiments, the building block cap for RNA is $m_2^{7,3'-O}Gppp(m_1^{2'-O})ApG$ (also sometimes referred to as $m_2^{7,3'-O}G(5')ppp(5')m^{2'-O}ApG$), which has the following structure:

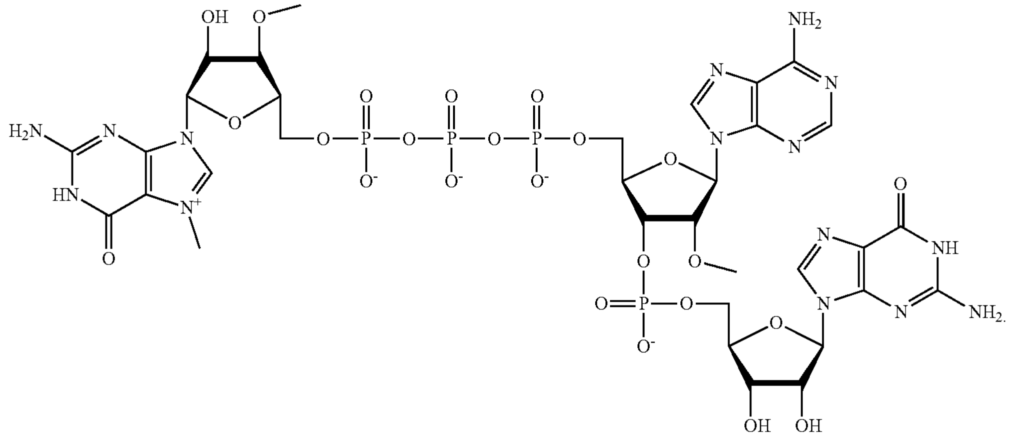
Below is an exemplary Cap1 RNA, which comprises RNA and $m_2{}^{7,3'\text{-}O}G(5')ppp(5')m^{2'\text{-}O}ApG$:
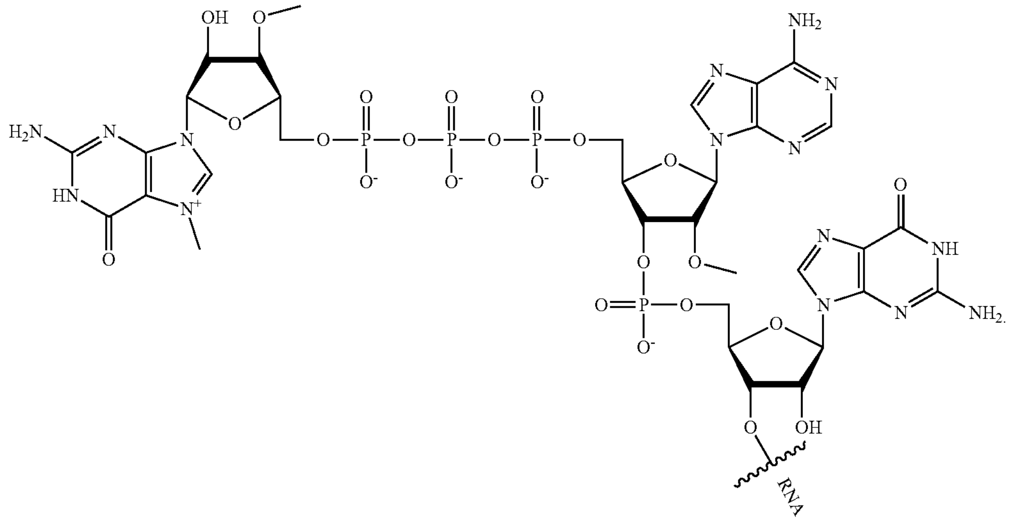
Below is another exemplary Cap1 RNA (no cap analog):
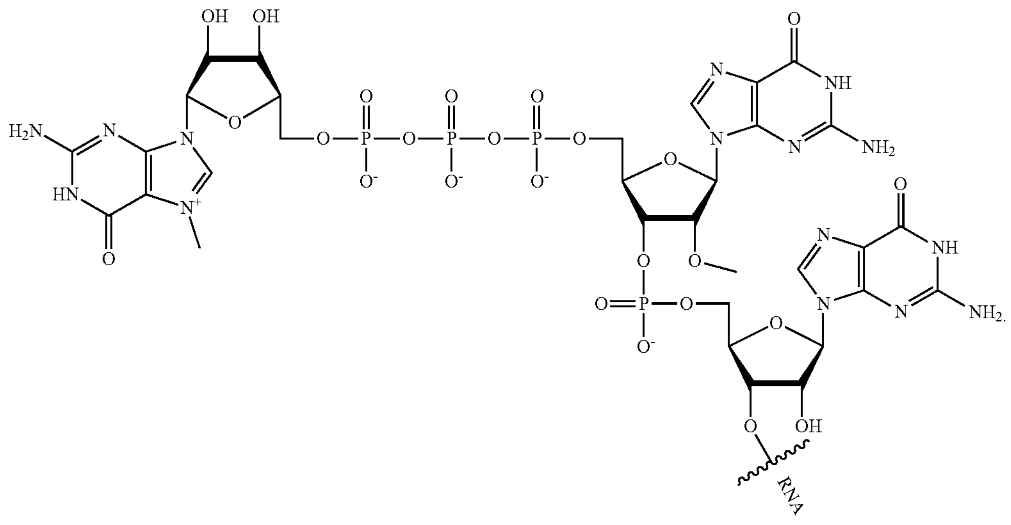

In some embodiments, the RNA is modified with "Cap0" structures using, in one embodiment, the cap analog anti-reverse cap (ARCA Cap ($m_2^{7,3'-O}$ G(5')ppp(5')G)) with the structure:
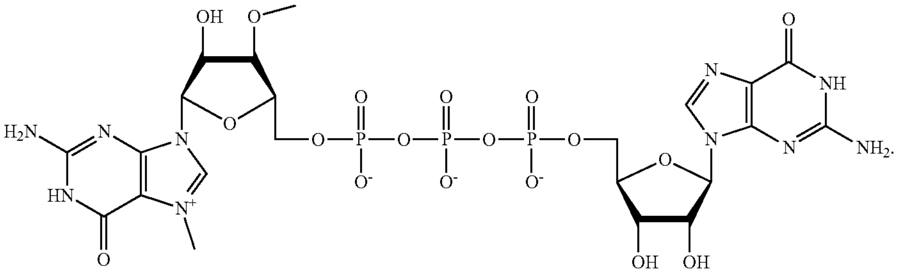
Below is an exemplary Cap0 RNA comprising RNA and $m_2^{7,3'O}$ G(5')ppp(5')G:
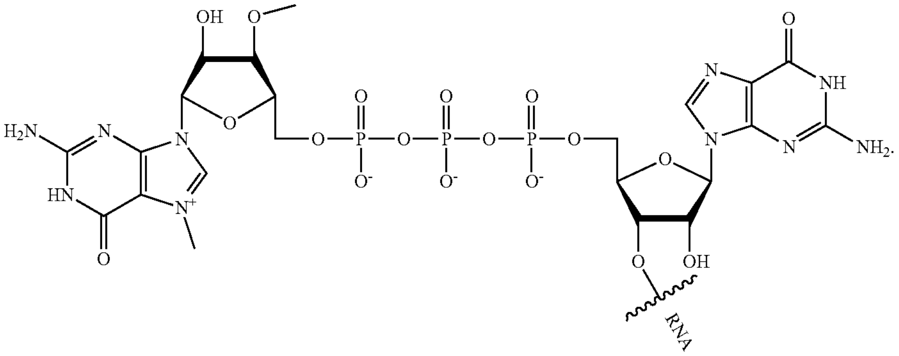
In some embodiments, the "Cap0" structures are generated using the cap analog Beta-S-ARCA ($m_2^{7,2'O}$ G(5')ppSp (5')G) with the structure:
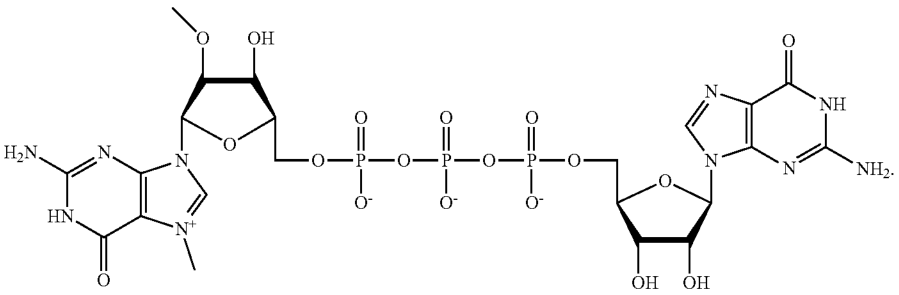

Below is an exemplary Cap0 RNA comprising Beta-S-ARCA ($m_2^{7,2'O}G(5')ppSp(5')G$) and RNA:

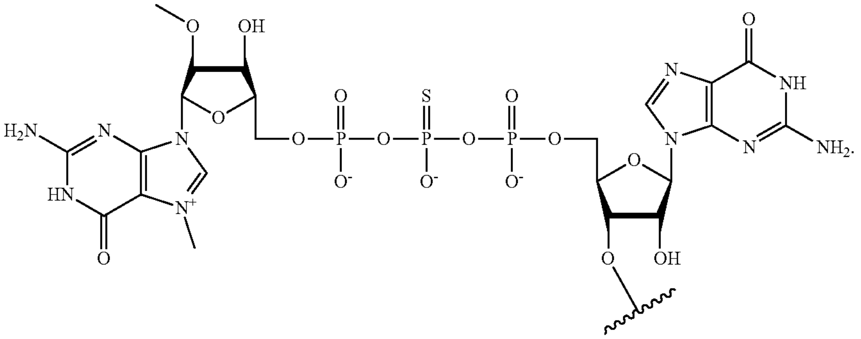

RNA

The "D1" diastereomer of beta-S-ARCA or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time (cf., WO 2011/015347, herein incorporated by reference).

A particularly preferred cap is beta-S-ARCA(D1) ($m_2^{7,2'-O}GppSpG$) or $m_2^{7,3'-O}$ Gppp($m_1^{2'-O}$)ApG. In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, RNA comprises a 5'-UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In some embodiments, RNA comprises a 3'-UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

A particularly preferred 5'-UTR comprises the nucleotide sequence of SEQ ID NO: 12. A particularly preferred 3'-UTR comprises the nucleotide sequence of SEQ ID NO: 13.

In some embodiments, the RNA according to the present disclosure comprises a 3'-poly(A) sequence.

As used herein, the term "poly(A) sequence" or "poly-A tail" refers to an uninterrupted or interrupted sequence of adenylate residues which is typically located at the 3'-end of an RNA molecule. Poly(A) sequences are known to those of skill in the art and may follow the 3'-UTR in the RNAs described herein. An uninterrupted poly(A) sequence is characterized by consecutive adenylate residues. In nature, an uninterrupted poly(A) sequence is typical. RNAs disclosed herein can have a poly(A) sequence attached to the free 3'-end of the RNA by a template-independent RNA polymerase after transcription or a poly(A) sequence encoded by DNA and transcribed by a template-dependent RNA polymerase.

It has been demonstrated that a poly(A) sequence of about 120 Å nucleotides has a beneficial influence on the levels of RNA in transfected eukaryotic cells, as well as on the levels of protein that is translated from an open reading frame that is present upstream (5') of the poly(A) sequence (Holtkamp et al., 2006, Blood, vol. 108, pp. 4009-4017).

The poly(A) sequence may be of any length. In some embodiments, a poly(A) sequence comprises, essentially consists of, or consists of at least 20, at least 30, at least 40, at least 80, or at least 100 and up to 500, up to 400, up to 300, up to 200, or up to 150 Å nucleotides, and, in particular, about 120 A nucleotides. In this context, "essentially consists of" means that most nucleotides in the poly(A) sequence, typically at least 75%, at least 80%, at least 85%, at least 90%, at least 95%, at least 96%, at least 97%, at least 98%, or at least 99% by number of nucleotides in the poly(A) sequence are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly(A) sequence, i.e., 100% by number of nucleotides in the poly(A) sequence, are A nucleotides. The term "A nucleotide" or "A" refers to adenylate.

In some embodiments, a poly(A) sequence is attached during RNA transcription, e.g., during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present invention. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. Consequently, in some embodiments, the poly(A) sequence contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly(A) sequence at its 3'-end, i.e., the poly(A) sequence is not masked or followed at its 3'-end by a nucleotide other than A.

In some embodiments, the poly(A) sequence may comprise at least 20, at least 30, at least 40, at least 80, or at least 100 and up to 500, up to 400, up to 300, up to 200, or up to 150 nucleotides. In some embodiments, the poly(A) sequence may essentially consist of at least 20, at least 30, at least 40, at least 80, or at least 100 and up to 500, up to 400, up to 300, up to 200, or up to 150 nucleotides. In some embodiments, the poly(A) sequence may consist of at least 20, at least 30, at least 40, at least 80, or at least 100 and up to 500, up to 400, up to 300, up to 200, or up to 150 nucleotides. In some embodiments, the poly(A) sequence comprises at least 100 nucleotides. In some embodiments, the poly(A) sequence comprises about 150 nucleotides. In some embodiments, the poly(A) sequence comprises about 120 nucleotides.

In some embodiments, RNA comprises a poly(A) sequence comprising the nucleotide sequence of SEQ ID NO: 14, or a nucleotide sequence having at least 99%, 98%, 97%, 96%, 95%, 90%, 85%, or 80% identity to the nucleotide sequence of SEQ ID NO: 14. A particularly preferred poly(A) sequence comprises comprises the nucleotide sequence of SEQ ID NO: 14.

According to the disclosure, vaccine antigen is preferably administered as single-stranded, 5'-capped mRNA that is translated into the respective protein upon entering cells of a subject being administered the RNA. Preferably, the RNA contains structural elements optimized for maximal efficacy of the RNA with respect to stability and translational efficiency (5'-cap, 5'-UTR, 3'-UTR, poly(A) sequence).

In one embodiment, beta-S-ARCA(D1) is utilized as specific capping structure at the 5'-end of the RNA. In one embodiment, $m_2^{7,3'-O}$ Gppp($m_1^{2'-O}$)ApG is utilized as specific capping structure at the 5'-end of the RNA. In one embodiment, the 5'-UTR sequence is derived from the human alpha-globin mRNA and optionally has an optimized 'Kozak sequence' to increase translational efficiency. In one embodiment, a combination of two sequence elements (FI element) derived from the "amino terminal enhancer of split" (AES) mRNA (called F) and the mitochondrial encoded 12S ribosomal RNA (called I) are placed between the coding sequence and the poly(A) sequence to assure higher maximum protein levels and prolonged persistence of the mRNA. In one embodiment, two re-iterated 3'-UTRs derived from the human beta-globin mRNA are placed between the coding sequence and the poly(A) sequence to assure higher maximum protein levels and prolonged persistence of the mRNA. In one embodiment, a poly(A) sequence measuring 110 nucleotides in length, consisting of a stretch of 30 adenosine residues, followed by a 10 nucleotide linker sequence and another 70 adenosine residues is used. This poly(A) sequence was designed to enhance RNA stability and translational efficiency.

In one embodiment of all aspects of the invention, RNA encoding a vaccine antigen is expressed in cells of the subject treated to provide the vaccine antigen. In one embodiment of all aspects of the invention, the RNA is transiently expressed in cells of the subject. In one embodiment of all aspects of the invention, the RNA is in vitro transcribed RNA. In one embodiment of all aspects of the invention, expression of the vaccine antigen is at the cell surface. In one embodiment of all aspects of the invention, the vaccine antigen is expressed and presented in the context of MHC. In one embodiment of all aspects of the invention, expression of the vaccine antigen is into the extracellular space, i.e., the vaccine antigen is secreted.

In the context of the present disclosure, the term "transcription" relates to a process, wherein the genetic code in a DNA sequence is transcribed into RNA. Subsequently, the RNA may be translated into peptide or protein.

According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

With respect to RNA, the term "expression" or "translation" relates to the process in the ribosomes of a cell by which a strand of mRNA directs the assembly of a sequence of amino acids to make a peptide or protein.

In one embodiment, after administration of the RNA described herein, e.g., formulated as RNA lipid particles, at least a portion of the RNA is delivered to a target cell. In one embodiment, at least a portion of the RNA is delivered to the cytosol of the target cell. In one embodiment, the RNA is translated by the target cell to produce the peptide or protein it enodes. In one embodiment, the target cell is a spleen cell. In one embodiment, the target cell is an antigen presenting cell such as a professional antigen presenting cell in the spleen. In one embodiment, the target cell is a dendritic cell or macrophage. RNA particles such as RNA lipid particles described herein may be used for delivering RNA to such target cell. Accordingly, the present disclosure also relates to a method for delivering RNA to a target cell in a subject comprising the administration of the RNA particles described herein to the subject. In one embodiment, the RNA is delivered to the cytosol of the target cell. In one embodiment, the RNA is translated by the target cell to produce the peptide or protein encoded by the RNA.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

In one embodiment, the RNA encoding vaccine antigen to be administered according to the invention is non-immunogenic. RNA encoding immunostimulant may be administered according to the invention to provide an adjuvant effect. The RNA encoding immunostimulant may be standard RNA or non-immunogenic RNA.

The term "non-immunogenic RNA" as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic, i.e., than would have been induced by standard RNA (stdRNA). In one preferred embodiment, non-immunogenic RNA, which is also termed modified RNA (modRNA) herein, is rendered non-immunogenic by incorporating modified nucleosides suppressing RNA-mediated activation of innate immune receptors into the RNA and removing double-stranded RNA (dsRNA).

For rendering the non-immunogenic RNA non-immunogenic by the incorporation of modified nucleosides, any modified nucleoside may be used as long as it lowers or suppresses immunogenicity of the RNA. Particularly preferred are modified nucleosides that suppress RNA-mediated activation of innate immune receptors. In one embodiment, the modified nucleosides comprises a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($tm^5U$), 1-taurinomethyl-pseudouridine, 5-taurinomethyl-2-thio-uridine(tm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3$ $\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine ($\psi m$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine ($\psi$), N1-methyl-pseudouridine ($m1\psi$) or 5-methyl-uridine (m5U), in particular N1-methyl-pseudouridine.

In one embodiment, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines.

During synthesis of mRNA by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaselll that specifically hydrolyzes dsRNA but not ssRNA, thereby eliminating dsRNA contaminants from IVT RNA preparations can be used. Furthermore, dsRNA can be separated from ssRNA by using a cellulose material. In one embodiment, an RNA preparation is contacted with a cellulose material and the ssRNA is separated from the cellulose material under conditions which allow binding of dsRNA to the cellulose material and do not allow binding of ssRNA to the cellulose material.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

In one embodiment, the removal of dsRNA from non-immunogenic RNA comprises a removal of dsRNA such that less than 10%, less than 5%, less than 4%, less than 3%, less than 2%, less than 1%, less than 0.5%, less than 0.3%, or less than 0.1% of the RNA in the non-immunogenic RNA composition is dsRNA. In one embodiment, the non-immunogenic RNA is free or essentially free of dsRNA. In some embodiments, the non-immunogenic RNA composition comprises a purified preparation of single-stranded nucleoside modified RNA. For example, in some embodiments, the purified preparation of single-stranded nucleoside modified RNA is substantially free of double stranded RNA (dsRNA). In some embodiments, the purified preparation is at least 90%, at least 91%, at least 92%, at least 93%, at least 94%, at least 95%, at least 96%, at least 97%, at least 98%, at least 99%, at least 99.5%, or at least 99.9% single stranded nucleoside modified RNA, relative to all other nucleic acid molecules (DNA, dsRNA, etc.).

In one embodiment, the non-immunogenic RNA is translated in a cell more efficiently than standard RNA with the same sequence. In one embodiment, translation is enhanced by a factor of 2-fold relative to its unmodified counterpart. In one embodiment, translation is enhanced by a 3-fold factor. In one embodiment, translation is enhanced by a 4-fold factor. In one embodiment, translation is enhanced by a 5-fold factor. In one embodiment, translation is enhanced by a 6-fold factor. In one embodiment, translation is enhanced by a 7-fold factor. In one embodiment, translation is enhanced by an 8-fold factor. In one embodiment, translation is enhanced by a 9-fold factor. In one embodiment, translation is enhanced by a 10-fold factor. In one embodiment, translation is enhanced by a 15-fold factor. In one embodiment, translation is enhanced by a 20-fold factor. In one embodiment, translation is enhanced by a 50-fold factor. In one embodiment, translation is enhanced by a 100-fold factor. In one embodiment, translation is enhanced by a 200-fold factor. In one embodiment, translation is enhanced by a 500-fold factor. In one embodiment, translation is enhanced by a 1000-fold factor. In one embodiment, translation is enhanced by a 2000-fold factor. In one embodiment, the factor is 10-1000-fold. In one embodiment, the factor is 10-100-fold. In one embodiment, the factor is 10-200-fold. In one embodiment, the factor is 10-300-fold. In one embodiment, the factor is 10-500-fold. In one embodiment, the factor is 20-1000-fold. In one embodiment, the factor is 30-1000-fold. In one embodiment, the factor is 50-1000-fold. In one embodiment, the factor is 100-1000-fold. In one embodiment, the factor is 200-1000-fold. In one embodiment, translation is enhanced by any other significant amount or range of amounts.

In one embodiment, the non-immunogenic RNA exhibits significantly less innate immunogenicity than standard RNA with the same sequence. In one embodiment, the non-immunogenic RNA exhibits an innate immune response that is 2-fold less than its unmodified counterpart. In one embodiment, innate immunogenicity is reduced by a 3-fold factor. In one embodiment, innate immunogenicity is reduced by a 4-fold factor. In one embodiment, innate immunogenicity is reduced by a 5-fold factor. In one embodiment, innate immunogenicity is reduced by a 6-fold factor. In one embodiment, innate immunogenicity is reduced by a 7-fold factor. In one embodiment, innate immunogenicity is reduced by a 8-fold factor. In one embodiment, innate immunogenicity is reduced by a 9-fold factor. In one embodiment, innate immunogenicity is reduced by a 10-fold factor. In one embodiment, innate immunogenicity is reduced by a 15-fold factor. In one embodiment, innate immunogenicity is reduced by a 20-fold factor. In one embodiment, innate immunogenicity is reduced by a 50-fold factor. In one embodiment, innate immunogenicity is reduced by a 100-fold factor. In one embodiment, innate immunogenicity is reduced by a 200-fold factor. In one embodiment, innate immunogenicity is reduced by a 500-fold factor. In one embodiment, innate immunogenicity is reduced by a 1000-fold factor. In one embodiment, innate immunogenicity is reduced by a 2000-fold factor.

The term "exhibits significantly less innate immunogenicity" refers to a detectable decrease in innate immunogenicity. In one embodiment, the term refers to a decrease such that an effective amount of the non-immunogenic RNA can be administered without triggering a detectable innate immune response. In one embodiment, the term refers to a decrease such that the non-immunogenic RNA can be repeatedly administered without eliciting an innate immune response sufficient to detectably reduce production of the protein encoded by the non-immunogenic RNA. In one embodiment, the decrease is such that the non-immunogenic RNA can be repeatedly administered without eliciting an innate immune response sufficient to eliminate detectable production of the protein encoded by the non-immunogenic RNA.

"Immunogenicity" is the ability of a foreign substance, such as RNA, to provoke an immune response in the body of a human or other animal. The innate immune system is the component of the immune system that is relatively unspecific and immediate. It is one of two main components of the vertebrate immune system, along with the adaptive immune system. As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked," "fused", or "fusion" are used interchangeably. These terms refer to the joining together of two or more elements or components or domains.

Codon-Optimization/Increase in G/C Content

In some embodiment, the amino acid sequence comprising a SARS-CoV-2 S protein, an immunogenic variant thereof, or an immunogenic fragment of the SARS-CoV-2 S protein or the immunogenic variant thereof described herein is encoded by a coding sequence which is codon-optimized and/or the G/C content of which is increased compared to wild type coding sequence. This also includes embodiments, wherein one or more sequence regions of the coding sequence are codon-optimized and/or increased in the G/C content compared to the corresponding sequence regions of the wild type coding sequence. In one embodiment, the codon-optimization and/or the increase in the G/C content preferably does not change the sequence of the encoded amino acid sequence.

The term "codon-optimized" refers to the alteration of codons in the coding region of a nucleic acid molecule to reflect the typical codon usage of a host organism without preferably altering the amino acid sequence encoded by the nucleic acid molecule. Within the context of the present invention, coding regions are preferably codon-optimized for optimal expression in a subject to be treated using the RNA molecules described herein. Codon-optimization is based on the finding that the translation efficiency is also determined by a different frequency in the occurrence of tRNAs in cells. Thus, the sequence of RNA may be modified such that codons for which frequently occurring tRNAs are available are inserted in place of "rare codons".

In some embodiments of the invention, the guanosine/cytosine (G/C) content of the coding region of the RNA described herein is increased compared to the G/C content of the corresponding coding sequence of the wild type RNA, wherein the amino acid sequence encoded by the RNA is preferably not modified compared to the amino acid sequence encoded by the wild type RNA. This modification of the RNA sequence is based on the fact that the sequence of any RNA region to be translated is important for efficient translation of that mRNA. Sequences having an increased G (guanosine)/C (cytosine) content are more stable than sequences having an increased A (adenosine)/U (uracil) content. In respect to the fact that several codons code for one and the same amino acid (so-called degeneration of the genetic code), the most favourable codons for the stability can be determined (so-called alternative codon usage). Depending on the amino acid to be encoded by the RNA, there are various possibilities for modification of the RNA sequence, compared to its wild type sequence. In particular, codons which contain A and/or U nucleotides can be modified by substituting these codons by other codons, which code for the same amino acids but contain no A and/or U or contain a lower content of A and/or U nucleotides.

In various embodiments, the G/C content of the coding region of the RNA described herein is increased by at least 10%, at least 20%, at least 30%, at least 40%, at least 50%, at least 55%, or even more compared to the G/C content of the coding region of the wild type RNA.

Embodiments of Administered RNAs

In some embodiments, compositions or medical preparations described herein comprise RNA encoding an amino acid sequence comprising SARS-CoV-2 S protein, an immunogenic variant thereof, or an immunogenic fragment of the SARS-CoV-2 S protein or the immunogenic variant thereof. Likewise, methods described herein comprise administration of such RNA.

The active platform for use herein is based on an antigen-coding RNA vaccine to induce robust neutralising antibodies and accompanying/concomitant T cell response to achieve protective immunization with preferably minimal vaccine doses. The RNA administered is preferably in-vitro transcribed RNA.

Three different RNA platforms are particularly preferred, namely non-modified uridine containing mRNA (uRNA), nucleoside modified mRNA (modRNA) and self-amplifying RNA (saRNA). In one particularly preferred embodiment, the RNA is in vitro transcribed RNA.

As described herein, embodiments of each of these platforms are assessed herein (see, for example Example 2), representing a novel and powerful approach to and system for rapid vaccine development. This described approach and system achieved remarkable and efficient success, enabling development of an effective clinical candidate within several months of provision of antigen (e.g., SARS-CoV-2 S1 protein and/or RBD thereof) sequence (as described herein, relevant sequence information (e.g., GenBank: MN908947.3) became available in January 2020). Insights and advantages embodied in this described approach and system include, for example, ability to directly compare one or more features of different strategies to achieve rapid, efficient, and effective development. Among other things, the present disclosure encompasses insights that identify the source of a problem with more typical strategies for vaccine development. Moreover, findings included herein establish a variety of advantages and benefits, particularly in rapid vaccine development and notably of special benefit in a pandemic.

As described herein, in some embodiments, vaccine candidates are assessed for titer of antibodies induced in a model organism (e.g., mouse; see e.g., Example 2) directed to an encoded antigen (e.g., S1 protein) or portion thereof (e.g., RBD). In some embodiments, vaccine candidates are assessed for pseudoviral neutralization (see e.g., Example 2) activity of induced antibodies. In some embodiments, vaccine candidates are characterized for nature of T cell response induced (e.g., $T_H1$ vs $T_H2$ character; see, e.g., Example 4). In some embodiments, vaccine candidates are assessed in more than one model organism (see. E.g., Examples 2, Example 4, etc)

In the following, embodiments of these three different RNA platforms are described, wherein certain terms used when describing elements thereof have the following meanings:

S1S2 protein/S1S2 RBD: Sequences encoding the respective antigen of SARS-CoV-2.

nsP1, nsP2, nsP3, and nsP4: Wildtype sequences encoding the Venezuelan equine encephalitis virus (VEEV) RNA-dependent RNA polymerase replicase and a subgenomic promotor plus conserved sequence elements supporting replication and translation.

virUTR: Viral untranslated region encoding parts of the subgenomic promotor as well as replication and translation supporting sequence elements.

hAg-Kozak: 5'-UTR sequence of the human alpha-globin mRNA with an optimized 'Kozak sequence' to increase translational efficiency.

Sec: Sec corresponds to the intrinsic S1S2 protein secretory signal peptide (sec), which guides translocation of the nascent polypeptide chain into the endoplasmatic reticulum.

Glycine-serine linker (GS): Sequences coding for short linker peptides predominantly consisting of the amino acids glycine (G) and serine (S), as commonly used for fusion proteins.

Fibritin: Partial sequence of T4 fibritin (foldon), used as artificial trimerization domain.

TM: TM sequence corresponds to the transmembrane part of the S1S2 protein.

FI element: The 3'-UTR is a combination of two sequence elements derived from the "amino terminal enhancer of split" (AES) mRNA (called F) and the mitochondrial encoded 12S ribosomal RNA (called I). These were identified by an ex vivo selection process for sequences that confer RNA stability and augment total protein expression.

A30L70: A poly(A)-tail measuring 110 nucleotides in length, consisting of a stretch of 30 adenosine residues, followed by a 10 nucleotide linker sequence and another 70 adenosine residues designed to enhance RNA stability and translational efficiency in dendritic cells.

In general, vaccine RNA described herein may comprise, from 5' to 3', one of the following structures:

Cap-5'-UTR-Vaccine Antigen-Encoding Sequence-3'-UTR-Poly(A)

or beta-S-ARCA(D1)-hAg-Kozak-Vaccine Antigen-Encoding Sequence-FI-A30L70.

In general, a vaccine antigen described herein may comprise, from N-terminus to C-terminus, one of the following structures:

Signal Sequence-RBD-Trimerization Domain or

Signal Sequence-RBD-Trimerization Domain-Transmembrane Domain.

RBD and Trimerization Domain may be separated by a linker, in particular a GS linker such as a linker having the amino acid sequence GSPGSGSGS (SEQ ID NO: 33). Trimerization Domain and Transmembrane Domain may be separated by a linker, in particular a GS linker such as a linker having the amino acid sequence GSGSGS (SEQ ID NO: 34).

Signal Sequence may be a signal sequence as described herein. RBD may be a RBD domain as described herein. Trimerization Domain may be a trimerization domain as described herein. Transmembrane Domain may be a transmembrane domain as described herein.

In one embodiment,

Signal sequence comprises the amino acid sequence of amino acids 1 to 16 or 1 to 19 of SEQ ID NO: 1 or the amino acid sequence of amino acids 1 to 22 of SEQ ID NO: 31, or an amino acid sequence having at least 99%, 98%, 97%, 96%, 95%, 90%, 85%, or 80% identity to this amino acid sequence, RBD comprises the amino acid sequence of amino acids 327 to 528 of SEQ ID NO: 1, or an amino acid sequence having at least 99%, 98%, 97%, 96%, 95%, 90%, 85%, or 80% identity to this amino acid sequence, Trimerization Domain comprises the amino acid sequence of amino acids 3 to 29 of SEQ ID NO: 10 or the amino acid sequence of SEQ ID NO: 10, or an amino acid sequence having at least 99%, 98%, 97%, 96%, 95%, 90%, 85%, or 80% identity to this amino acid sequence; and Transmembrane Domain comprises the amino acid sequence of amino acids 1207 to 1254 of SEQ ID NO: 1, or an amino acid sequence having at least 99%, 98%, 97%, 96%, 95%, 90%, 85%, or 80% identity to this amino acid sequence.

In one embodiment,

Signal sequence comprises the amino acid sequence of amino acids 1 to 16 or 1 to 19 of SEQ ID NO: 1 or the amino acid sequence of amino acids 1 to 22 of SEQ ID NO: 31, RBD comprises the amino acid sequence of amino acids 327 to 528 of SEQ ID NO: 1, Trimerization Domain comprises the amino acid sequence of amino acids 3 to 29 of SEQ ID NO: 10 or the amino acid sequence of SEQ ID NO: 10; and Transmembrane Domain comprises the amino acid sequence of amino acids 1207 to 1254 of SEQ ID NO: 1.

The above described RNA or RNA encoding the above described vaccine antigen may be non-modified uridine containing mRNA (uRNA), nucleoside modified mRNA (modRNA) or self-amplifying RNA (saRNA). In one embodiment, the above described RNA or RNA encoding the above described vaccine antigen is nucleoside modified mRNA (modRNA).

Non-Modified Uridine Messenger RNA (uRNA)

The active principle of the non-modified messenger RNA (uRNA) drug substance is a single-stranded mRNA that is translated upon entering a cell. In addition to the sequence encoding the coronavirus vaccine antigen (i.e. open reading frame), each uRNA preferably contains common structural elements optimized for maximal efficacy of the RNA with respect to stability and translational efficiency (5'-cap, 5'-UTR, 3'-UTR, poly(A)-tail). The preferred 5' cap structure is beta-S-ARCA(D1) ($m_2^{7,2'-O}$GppSpG). The preferred 5'-UTR and 3'-UTR comprise the nucleotide sequence of SEQ ID NO: 12 and the nucleotide sequence of SEQ ID NO: 13, respectively. The preferred poly(A)-tail comprises the sequence of SEQ ID NO: 14.

Different embodiment of this platform are as follows:

RBL063.1 (SEQ ID NO: 15; SEQ ID NO: 7)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

RBL063.2 (SEQ ID NO: 16; SEQ ID NO: 7)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

BNT162a1; RBL063.3 (SEQ ID NO: 17; SEQ ID NO: 5)

Structure beta-S-ARCA(D1)-hAg-Kozak-RBD-GS-Fibritin-FI-A30L70

Encoded antigen Viral spike protein (S protein) of the SARS-CoV-2 (partial sequence, Receptor Binding Domain (RBD) of S1S2 protein)

FIG. 19 schematizes the general structure of the antigen-encoding RNAs.

Nucleotide Sequence of RBL063.1 (SEQ ID NO: 15; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40         50  52
GGGCGAACUA GUAUUCUUCU GGUCCCCACA GACUCAGAGA GAACCCGCCA CC
                           hAg-Kozak

        62         72         82         92        102        112
AUGUUUGUGU UUCUUGUGCU GCUGCCUCUU GUGUCUUCUC AGUGUGUGGU UUUGACAACA
  M  F  V   F  L  V   L  L  P  L   V  S  S   Q  C  V   N  L  T  T
                           S protein

       122        132        142        152        162        172
AGAACACAGC UGCCACCAGC UUAUACAAAU UCUUUUACCA GAGGAGUGUA UUAUCCUGAU
  R  T  Q   L  P  P   A  Y  T  N   S  F  T   R  G  V   Y  Y  P  D
                           S protein

       182        192        202        212        222        232
AAAGUGUUUA GAUCUUCUGU GCUGCACAGC ACACAGGACC UGUUUCUGCC AUUUUUUAGC
  K  V  F   R  S  S   V  L  H  S   T  Q  D   L  F  L   P  F  F  S
                           S protein

       242        252        262        272        282        292
AAUGUGACAU GGUUUCAUGC AAUUCAUGUG UCUGGAACAA AUGGAACAAA AAGAUUUGAU
  N  V  T   W  F  H   A  I  H  V   S  G  T   N  G  T   K  R  F  D
                           S protein
```

-continued

```
       302        312        322        332        342        352
AAUCCUGUGC UGCCUUUUAA UGAUGGAGUG UAUUUUGCUU CAACAGAAAA GUCAAAUAUU
 N  P  V   L  P  F   N  D  G  V   Y  F  A   S  T  E   K  S  N  I
                              S protein

       362        372        382        392        402        412
AUUAGAGGAU GGAUUUUUGG AACAACACUG GAUUCUAAAA CACAGUCUCU GCUGAUUGUG
 I  R  G   W  I  F   G  T  T  L   D  S  K   T  Q  S   L  L  I  V
                              S protein

       422        432        442        452        462        472
AAUAAUGCAA CAAAUGUGGU GAUUAAAGUG UGUGAAUUUC AGUUUUGUAA UGAUCCUUUU
 N  N  A   T  N  V   V  I  K  V   C  E  F   Q  F  C   N  D  P  F
                              S protein

       482        492        502        512        522        532
CUGGGAGUGU AUUAUCACAA AAAUAAUAAA UCUUGGAUGG AAUCUGAAUU UAGAGUGUAU
 L  G  V   Y  Y  H   K  N  N  K   S  W  M   E  S  E   F  R  V  Y
                              S protein

       542        552        562        572        582        592
UCCUCUGCAA AUAAUUGUAC AUUUGAAUAU GUGUCUCAGC CUUUUCUGAU GGAUCUGGAA
 S  S  A   N  N  C   T  F  E  Y   V  S  Q   P  F  L   M  D  L  E
                              S protein

       602        612        622        632        642        652
GGAAAACAGG GCAAUUUUAA AAAUCUGAGA GAAUUUGUGU UUAAAAAUAU UGAUGGAUAU
 G  K  Q   G  N  F   K  N  L  R   E  F  V   F  K  N   I  D  G  Y
                              S protein

       662        672        682        692        702        712
UUUAAAAUUU AUUCUAAACA CACACCAAUU AAUUUAGUGA GAGAUCUGCC UCAGGGAUUU
 F  K  I   Y  S  K   H  T  P  I   N  L  V   R  D  L   P  Q  G  F
                              S protein

       722        732        742        752        762        772
UCUGCUCUGG AACCUCUGGU GGAUCUGCCA AUUGGCAUUA AUAUUACAAG AUUUCAGACA
 S  A  L   E  P  L   V  D  L  P   I  G  I   N  I  T   R  F  Q  T
                              S protein

       782        792        802        812        822        832
CUGCUGGCUC UGCACAGAUC UUAUCUGACA CCUGGAGAUU CUUCUUCUGG AUGGACAGCC
 L  L  A   L  H  R   S  Y  L  T   P  G  D   S  S  S   G  W  T  A
                              S protein

       842        852        862        872        882        892
GGAGCUGCAG CUUAUUAUGU GGGCUAUCUG CAGCCAAGAA CAUUUCUGCU GAAAUAUAAU
 G  A  A   A  Y  Y   V  G  Y  L   Q  P  R   T  F  L   L  K  Y  N
                              S protein

       902        912        922        932        942        952
GAAAAUGGAA CAAUUACAGA UGCUGUGGAU UGUGCUCUGG AUCCUCUGUC UGAAACAAAA
 E  N  G   T  I  T   D  A  V  D   C  A  L   D  P  L   S  E  T  K
                              S protein

       962        972        982        992       1002       1012
UGUACAUUAA AAUCUUUUAC AGUGGAAAAA GGCAUUUAUC AGACAUCUAA UUUUAGAGUG
 C  T  L   K  S  F   T  V  E  K   G  I  Y   Q  T  S   N  F  R  V
                              S protein

      1022       1032       1042       1052       1062       1072
CAGCCAACAG AAUCUAUUGU GAGAUUUCCA AAUAUUACAA AUCUGUGUCC AUUUGGAGAA
 Q  P  T   E  S  I   V  R  F  P   N  I  T   N  L  C   P  F  G  E
                              S protein

      1082       1092       1102       1112       1122       1132
GUGUUUAAUG CAACAAGAUU UGCAUCUGUG UAUGCAUGGA AUAGAAAAAG AAUUUCUAAU
 V  F  N   A  T  R   F  A  S  V   Y  A  W   N  R  K   R  I  S  N
                              S protein

      1142       1152       1162       1172       1182       1192
UGUGUGGCUG AUUAUUCUGU GCUGUAUAAU AGUGCUUCUU UUUCCACAUU UAAAUGUUAU
 C  V  A   D  Y  S   V  L  Y  N   S  A  S   F  S  T   F  K  C  Y
                              S protein

      1202       1212       1222       1232       1242       1252
GGAGUGUCUC CAACAAAAUU AAAUGAUUUA UGUUUUACAA AUGUGUAUGC UGAUUCUUUU
 G  V  S   P  T  K   L  N  D  L   C  F  T   N  V  Y   A  D  S  F
                              S protein
```

-continued

```
     1262        1272        1282        1292        1302        1312
GUGAUCAGAG GUGAUGAAGU GAGACAGAUU GCCCCCGGAC AGACAGGAAA AAUUGCUGAU
 V  I  R   G  D  E   V  R  Q  I   A  P  G   Q  T  G   K  I  A  D
                              S protein

     1322        1332        1342        1352        1362        1372
UACAAUUACA AACUGCCUGA UGAUUUUACA GGAUGUGUGA UUGCUUGGAA UUCUAAUAAU
 Y  N  Y   K  L  P   D  D  F  T   G  C  V   I  A  W   N  S  N  N
                              S protein

     1382        1392        1402        1412        1422        1432
UUAGAUUCUA AAGUGGGAGG AAAUUACAAU UAUCUGUACA GACUGUUUAG AAAAUCAAAU
 L  D  S   K  V  G   G  N  Y  N   Y  L  Y   R  L  F   R  K  S  N
                              S protein

     1442        1452        1462        1472        1482        1492
CUGAAACCUU UUGAAAGAGA UAUUUCAACA GAAAUUUAUC AGGCUGGAUC AACACCUUGU
 L  K  P   F  E  R   D  I  S  T   E  I  Y   Q  A  G   S  T  P  C
                              S protein

     1502        1512        1522        1532        1542        1552
AAUGGAGUGG AAGGAUUUAA UUGUUAUUUU CCAUUACAGA GCUAUGGAUU UCAGCCAACC
 N  G  V   E  G  F   N  C  Y  F   P  L  Q   S  Y  G   F  Q  P  T
                              S protein

     1562        1572        1582        1592        1602        1612
AAUGGUGUGG GAUAUCAGCC AUAUAGAGUG GUGGUGCUGU CUUUUGAACU GCUGCAUGCA
 N  G  V   G  Y  Q   P  Y  R  V   V  V  L   S  F  E   L  L  H  A
                              S protein

     1622        1632        1642        1652        1662        1672
CCUGCAACAG UGUGUGGACC UAAAAAAUCU ACAAAUUUAG UGAAAAAUAA AUGUGUGAAU
 P  A  T   V  C  G   P  K  K  S   T  N  L   V  K  N   K  C  V  N
                              S protein

     1682        1692        1702        1712        1722        1732
UUUAAUUUUA AUGGAUUAAC AGGAACAGGA GUGCUGACAG AAUCUAAUAA AAAAUUUCUG
 F  N  F   N  G  L   T  G  T  G   V  L  T   E  S  N   K  K  F  L
                              S protein

     1742        1752        1762        1772        1782        1792
CCUUUUCAGC AGUUUGGCAG AGAUAUUGCA GAUACCACAG AUGCAGUGAG AGAUCCUCAG
 P  F  Q   Q  F  G   R  D  I  A   D  T  T   D  A  V   R  D  P  Q
                              S protein

     1802        1812        1822        1832        1842        1852
ACAUUAGAAA UUCUGGAUAU UACACCUUGU UCUUUUGGGG GUGUGUCUGU GAUUACACCU
 T  L  E   I  L  D   I  T  P  C   S  F  G   G  V  S   V  I  T  P
                              S protein

     1862        1872        1882        1892        1902        1912
GGAACAAAUA CAUCUAAUCA GGUGGCUGUG CUGUAUCAGG AUGUGAAUUG UACAGAAGUG
 G  T  N   T  S  N   Q  V  A  V   L  Y  Q   D  V  N   C  T  E  V
                              S protein

     1922        1932        1942        1952        1962        1972
CCAGUGGCAA UUCAUGCAGA UCAGCUGACA CCAACAUGGA GAGUGUAUUC UACAGGAUCU
 P  V  A   T  H  A   D  Q  L  T   P  T  W   R  V  Y   S  T  G  S
                              S protein

     1982        1992        2002        2012        2022        2032
AAUGUGUUUC AGACAAGAGC AGGAUGUCUG AUUGGAGCAG AACAUGUGAA UAAUUCUUAU
 N  V  F   Q  T  R   A  G  C  L   I  G  A   E  H  V   N  N  S  Y
                              S protein

     2042        2052        2062        2072        2082        2092
GAAUGUGAUA UUCCAAUUGG AGCAGGCAUU UGUGCAUCUU AUCAGACACA GACAAAUUCC
 E  C  D   I  P  T   G  A  G  I   C  A  S   Y  Q  T   Q  T  N  S
                              S protein

     2102        2112        2122        2132        2142        2152
CCAAGGAGAG CAAGAUCUGU GGCAUCUCAG UCUAUUAUUG CAUACACCAU GUCUCUGGGA
 P  R  R   A  R  S   V  A  S  Q   S  I  T   A  Y  T   M  S  L  G
                              S protein

     2162        2172        2182        2192        2202        2212
GCAGAAAAUU CUGUGGCAUA UUCUAAUAAU UCUAUUGCUA UUCCAACAAA UUUUACCAUU
 A  E  N   S  V  A   Y  S  N  N   S  T  A   I  P  T   N  E  T  T
                              S protein
```

-continued

```
      2222       2232       2242       2252       2262       2272
UCUGUGACAA CAGAAAUUUU ACCUGUGUCU AUGACAAAAA CAUCUGUGGA UUGUACCAUG
  S  V  T   T  E  T   L  P  V  S   M  T  K   T  S  V   D  C  T  M
                            S protein

      2282       2292       2302       2312       2322       2332
UACAUUUGUG GAGAUUCUAC AGAAUGUUCU AAUCUGCUGC UGCAGUAUGG AUCUUUUUGU
  Y  I  C   G  D  S   T  E  C  S   N  L  L   L  Q  Y   G  S  F  C
                            S protein

      2342       2352       2362       2372       2382       2392
ACACAGCUGA AUAGAGCUUU AACAGGAAUU GCUGUGGAAC AGGAUAAAAA UACACAGGAA
  T  Q  L   N  R  A   L  T  G  I   A  V  E   Q  D  K   N  T  Q  E
                            S protein

      2402       2412       2422       2432       2442       2452
GUGUUUGCUC AGGUGAAACA GAUUUACAAA ACACCACCAA UUAAAGAUUU UGGAGGAUUU
  V  F  A   Q  V  K   Q  I  Y  K   T  P  P   I  K  D   F  G  G  F
                            S protein

      2462       2472       2482       2492       2502       2512
AAUUUUAGCC AGAUUCUGCC UGAUCCUUCU AAACCUUCUA AAAGAUCUUU UAUUGAAGAU
  N  F  S   Q  I  L   P  D  P  S   K  P  S   K  R  S   F  I  E  D
                            S protein

      2522       2532       2542       2552       2562       2572
CUGCUGUUUA AUAAAGUGAC ACUGGCAGAU GCAGGAUUUA UUAAACAGUA UGGAGAUUGC
  L  L  F   N  K  V   T  L  A  D   A  G  F   I  K  Q   Y  G  D  C
                            S protein

      2582       2592       2602       2612       2622       2632
CUGGGUGAUA UUGCUGCAAG AGAUCUGAUU UGUGCUCAGA AAUUUAAUGG ACUGACAGUG
  L  G  D   I  A  A   R  D  L  I   C  A  Q   K  F  N   G  L  T  V
                            S protein

      2642       2652       2662       2672       2682       2692
CUGCCUCCUC UGCUGACAGA UGAAAUGAUU GCUCAGUACA CAUCUGCUUU ACUGGCUGGA
  L  P  P   L  L  T   D  E  M  I   A  Q  Y   T  S  A   L  L  A  G
                            S protein

      2702       2712       2722       2732       2742       2752
ACAAUUACAA GCGGAUGGAC AUUUGGAGCU GGAGCUGCUC UGCAGAUUCC UUUUGCAAUG
  T  I  T   S  G  W   T  F  G  A   G  A  A   L  Q  I   P  F  A  M
                            S protein

      2762       2772       2782       2792       2802       2812
CAGAUGGCUU ACAGAUUUAA UGGAAUUGGA GUGACACAGA AUGUGUUAUA UGAAAAUCAG
  Q  M  A   Y  R  F   N  G  I  G   V  T  Q   N  V  L   Y  E  N  Q
                            S protein

      2822       2832       2842       2852       2862       2872
AAACUGAUUG CAAAUCAGUU UAAUUCUGCA AUUGGCAAAA UUCAGGAUUC UCUGUCUUCU
  K  L  I   A  N  Q   F  N  S  A   I  G  K   I  Q  D   S  L  S  S
                            S protein

      2882       2892       2902       2912       2922       2932
ACAGCUUCUG CUCUGGGAAA ACUGCAGGAU GUGGUGAAUC AGAAUGCACA GGCACUGAAU
  T  A  S   A  L  G   K  L  Q  D   V  V  N   Q  N  A   Q  A  L  N
                            S protein

      2942       2952       2962       2972       2982       2992
ACUCUGGUGA AACAGCUGUC UAGCAAUUUU GGGGCAAUUU CUUCUGUGCU GAAUGAUAUU
  T  L  V   K  Q  L   S  S  N  F   G  A  I   S  S  V   L  N  D  I
                            S protein

      3002       3012       3022       3032       3042       3052
CUGUCUAGAC UGGAUCCUCC UGAAGCUGAA GUGCAGAUUG AUAGACUGAU CACAGGAAGA
  L  S  R   L  D  P   P  E  A  E   V  Q  I   D  R  L   I  T  G  R
                            S protein

      3062       3072       3082       3092       3102       3112
CUGCAGUCUC UGCAGACUUA UGUGACACAG CAGCUGAUUA GAGCUGCUGA AAUUAGAGCU
  L  Q  S   L  Q  T   Y  V  T  Q   Q  L  I   R  A  A   E  I  R  A
                            S protein

      3122       3132       3142       3152       3162       3172
UCUGCUAAUC UGGCUGCUAC AAAAAUGUCU GAAUGUGUGC UGGGACAGUC AAAAAGAGUG
  S  A  N   L  A  A   T  K  M  S   E  C  V   L  G  Q   S  K  R  V
                            S protein
```

-continued

```
     3182       3192       3202       3212       3222       3232
GAUUUUUGUG GAAAAGGAUA UCAUCUGAUG UCUUUUCCAC AGUCUGCUCC ACAUGGAGUG
  D  F  C   G  K  G   Y  H  L  M   S  F  P   Q  S  A   P  H  G  V
                                S protein

     3242       3252       3262       3272       3282       3292
GUGUUUUUAC AUGUGACAUA UGUGCCAGCA CAGGAAAAGA AUUUUACCAC AGCACCAGCA
  V  F  L   H  V  T   Y  V  P  A   Q  E  K   N  F  T   T  A  P  A
                                S protein

     3302       3312       3322       3332       3342       3352
AUUUGUCAUG AUGGAAAAGC ACAUUUUCCA AGAGAAGGAG UGUUUGUGUC UAAUGGAACA
  I  C  H   D  G  K   A  H  F  P   R  E  G   V  F  V   S  N  G  T
                                S protein

     3362       3372       3382       3392       3402       3412
CAUUGGUUUG UGACACAGAG AAAUUUUUAU GAACCUCAGA UUAUUACAAC AGAUAAUACA
  H  W  F   V  T  Q   R  N  F  Y   E  P  Q   I  I  T   T  D  N  T
                                S protein

     3422       3432       3442       3452       3462       3472
UUUGUGUCAG GAAAUUGUGA UGUGGUGAUU GGAAUUGUGA AUAAUACAGU GUAUGAUCCA
  F  V  S   G  N  C   D  V  V  I   G  I  V   N  N  T   V  Y  D  P
                                S protein

     3482       3492       3502       3512       3522       3532
CUGCAGCCAG AACUGGAUUC UUUUAAAGAA GAACUGGAUA AAUAUUUUAA AAAUCACACA
  L  Q  P   E  L  D   S  F  K  E   E  L  D   K  Y  F   K  N  H  T
                                S protein

     3542       3552       3562       3572       3582       3592
UCUCCUGAUG UGGAUUUAGG AGAUAUUUCU GGAAUCAAUG CAUCUGUGGU GAAUAUUCAG
  S  P  D   V  D  L   G  D  I  S   G  I  N   A  S  V   V  N  I  Q
                                S protein

     3602       3612       3622       3632       3642       3652
AAAGAAAUUG AUAGACUGAA UGAAGUGGCC AAAAAUCUGA AUGAAUCUCU GAUUGAUCUG
  K  E  I   D  R  L   N  E  V  A   K  N  L   N  E  S   L  I  D  L
                                S protein

     3662       3672       3682       3692       3702       3712
CAGGAACUUG GAAAAUAUGA ACAGUACAUU AAAUGGCCUU GGUACAUUUG GCUUGGAUUU
  Q  E  L   G  K  Y   E  Q  Y  I   K  W  P   W  Y  I   W  L  G  F
                                S protein

     3722       3732       3742       3752       3762       3772
AUUGCAGGAU UAAUUGCAAU UGUGAUGGUG ACAAUUAUGU UAUGUUGUAU GACAUCAUGU
  I  A  G   L  I  A   I  V  M  V   T  I  M   L  C  C   M  T  S  C
                                S protein

     3782       3792       3802       3812       3822       3832
UGUUCUUGUU UAAAAGGAUG UUGUUCUUGU GGAAGCUGUU GUAAAUUUGA UGAAGAUGAU
  C  S  C   L  K  G   C  C  S  C   G  S  C   C  K  F   D  E  D  D
                                S protein

     3842       3852       3862       3872   3877
UCUGAACCUG UGUUAAAAGG AGUGAAAUUG CAUUACACAU GAUGA
  S  E  P   V  L  K   G  V  K  L   H  Y  T   *  *
                                S protein

     3887       3897       3907       3917       3927       3937
CUCGAGCUGG UACUGCAUGC ACGCAAUGCU AGCUGCCCCU UUCCCGUCCU GGGUACCCCG
                               FI element

     3947       3957       3967       3977       3987       3997
AGUCUCCCCC GACCUCGGGU CCCAGGUAUG CUCCCACCUC CACCUGCCCC ACUCACCACC
                               FI element

     4007       4017       4027       4037       4047       4057
UCUGCUAGUU CCAGACACCU CCCAAGCACG CAGCAAUGCA GCUCAAAACG CUUAGCCUAG
                               FI element

     4067       4077       4087       4097       4107       4117
CCACACCCCC ACGGGAAACA GCAGUGAUUA ACCUUUAGCA AUAAACGAAA GUUUAACUAA
                               FI element

     4127       4137       4147       4157       4167  4172
GCUAUACUAA CCCCAGGGUU GGUCAAUUUC GUGCCAGCCA CACCGCGGCC CUAGC
                               FI element
```

-continued

```
      4182       4192       4202       4212       4222       4232
AAAAAAAAAA AAAAAAAAAA AAAAAAAAAA GCAUAUGACU AAAAAAAAAA AAAAAAAAAA
                                 Poly(A)

      4242       4252       4262       4272       4282
AAAAAAAAAA AAAAAAAAAA AAAAAAAAAA AAAAAAAAAA AAAAAAAAAA
                                 Poly(A)
```

Nucleotide Sequence of RBL063.2 (SEQ ID NO: 16; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40         50  52
GGGCGAACUA GUAUUCUUCU GGUCCCCACA GACUCAGAGA GAACCCGCCA CC
                     hAg-Kozak

        62         72         82         92        102        112
AUGUUCGUGU UCCUGGUGCU GCUGCCUCUG GUGUCCAGCC AGUGUGUGAA CCUGACCACC
  M  F  V   F  L  V   L  L  P  L   V  S  S   Q  C  V   N  L  T  T
                     S protein

       122        132        142        152        162        172
AGAACACAGC UGCCUCCAGC CUACACCAAC AGCUUUACCA GAGGCGUGUA CUACCCCGAC
  R  T  Q   L  P  P   A  Y  T  N   S  F  T   R  G  V   Y  Y  P  D
                     S protein

       182        192        202        212        222        232
AAGGUGUUCA GAUCCAGCGU GCUGCACUCU ACCCAGGACC UGUUCCUGCC UUUCUUCAGC
  K  V  F   R  S  S   V  L  H  S   T  Q  D   L  F  L   P  F  F  S
                     S protein

       242        252        262        272        282        292
AACGUGACCU GGUUCCACGC CAUCCACGUG UCCGGCACCA AUGGCACCAA GAGAUUCGAC
  N  V  T   W  F  H   A  I  H  V   S  G  T   N  G  T   K  R  F  D
                     S protein

       302        312        322        332        342        352
AACCCCGUGC UGCCCUUCAA CGACGGGGUG UACUUUGCCA GCACCGAGAA GUCCAACAUC
  N  P  V   L  P  F   N  D  G  V   Y  F  A   S  T  E   K  S  N  I
                     S protein

       362        372        382        392        402        412
AUCAGAGGCU GGAUCUUCGG CACCACACUG GACAGCAAGA CCCAGAGCCU GCUGAUCGUG
  I  R  G   W  I  F   G  T  T  L   D  S  K   T  Q  S   L  L  I  V
                     S protein

       422        432        442        452        462        472
AACAACGCCA CCAACGUGGU CAUCAAAGUG UGCGAGUUCC AGUUCUGCAA CGACCCCUUC
  N  N  A   T  N  V   V  I  K  V   C  E  F   Q  F  C   N  D  P  F
                     S protein

       482        492        502        512        522        532
CUGGGCGUCU ACUACCACAA GAACAACAAG AGCUGGAUGG AAAGCGAGUU CCGGGUGUAC
  L  G  V   Y  Y  H   K  N  N  K   S  W  M   E  S  E   F  R  V  Y
                     S protein

       542        552        562        572        582        592
AGCAGCGCCA ACAACUGCAC CUUCGAGUAC GUGUCCCAGC CUUUCCUGAU GGACCUGGAA
  S  S  A   N  N  C   T  F  E  Y   V  S  Q   P  F  L   M  D  L  E
                     S protein

       602        612        622        632        642        652
GGCAAGCAGG GCAACUUCAA GAACCUGCGC GAGUUCGUGU UUAAGAACAU CGACGGCUAC
  G  K  Q   G  N  F   K  N  L  R   E  F  V   F  K  N   I  D  G  Y
                     S protein

       662        672        682        692        702        712
UUCAAGAUCU ACAGCAAGCA CACCCCUAUC AACCUCGUGC GGGAUCUGCC UCAGGGCUUC
  F  K  I   Y  S  K   H  T  P  I   N  L  V   R  D  L   P  Q  G  F
                     S protein

       722        732        742        752        762        772
UCUGCUCUGG AACCCCUGGU GGAUCUGCCC AUCGGCAUCA ACAUCACCCG GUUUCAGACA
  S  A  L   E  P  L   V  D  L  P   I  G  I   N  I  T   R  F  Q  T
                     S protein
```

-continued

```
        782        792        802        812        822        832
CUGCUGGCCC UGCACAGAAG CUACCUGACA CCUGGCGAUA GCAGCAGCGG AUGGACAGCU
  L  L  A   L  H  R   S  Y  L  T   P  G  D   S  S  S   G  W  T  A
                              S protein

        842        852        862        872        882        892
GGUGCCGCCG CUUACUAUGU GGGCUACCUG CAGCCUAGAA CCUUCCUGCU GAAGUACAAC
  G  A  A   A  Y  Y   V  G  Y  L   Q  P  R   T  F  L   L  K  Y  N
                              S protein

        902        912        922        932        942        952
GAGAACGGCA CCAUCACCGA CGCCGUGGAU UGUGCUCUGG AUCCUCUGAG CGAGACAAAG
  E  N  G   T  I  T   D  A  V  D   C  A  L   D  P  L   S  E  T  K
                              S protein

        962        972        982        992       1002       1012
UGCACCCUGA AGUCCUUCAC CGUGGAAAAG GGCAUCUACC AGACCAGCAA CUUCCGGGUG
  C  T  L   K  S  F   T  V  E  K   G  I  Y   Q  T  S   N  F  R  V
                              S protein

       1022       1032       1042       1052       1062       1072
CAGCCCACCG AAUCCAUCGU GCGGUUCCCC AAUAUCACCA AUCUGUGCCC CUUCGGCGAG
  Q  P  T   E  S  I   V  R  F  P   N  I  T   N  L  C   P  F  G  E
                              S protein

       1082       1092       1102       1112       1122       1132
GUGUUCAAUG CCACCAGAUU CGCCUCUGUG UACGCCUGGA ACCGGAAGCG GAUCAGCAAU
  V  F  N   A  T  R   F  A  S  V   Y  A  W   N  R  K   R  I  S  N
                              S protein

       1142       1152       1162       1172       1182       1192
UGCGUGGCCG ACUACUCCGU GCUGUACAAC UCCGCCAGCU UCAGCACCUU CAAGUGCUAC
  C  V  A   D  Y  S   V  L  Y  N   S  A  S   F  S  T   F  K  C  Y
                              S protein

       1202       1212       1222       1232       1242       1252
GGCGUGUCCC CUACCAAGCU GAACGACCUG UGCUUCACAA ACGUGUACGC CGACAGCUUC
  G  V  S   P  T  K   L  N  D  L   C  F  T   N  V  Y   A  D  S  F
                              S protein

       1262       1272       1282       1292       1302       1312
GUGAUCCGGG GAGAUGAAGU GCGGCAGAUU GCCCCUGGAC AGACAGGCAA GAUCGCCGAC
  V  I  R   G  D  E   V  R  Q  I   A  P  G   Q  T  G   K  I  A  D
                              S protein

       1322       1332       1342       1352       1362       1372
UACAACUACA AGCUGCCCGA CGACUUCACC GGCUGUGUGA UUGCCUGGAA CAGCAACAAC
  Y  N  Y   K  L  P   D  D  F  T   G  C  V   I  A  W   N  S  N  N
                              S protein

       1382       1392       1402       1412       1422       1432
CUGGACUCCA AAGUCGGCGG CAACUACAAU UACCUGUACC GGCUGUUCCG GAAGUCCAAU
  L  D  S   K  V  G   G  N  Y  N   Y  L  Y   R  L  F   R  K  S  N
                              S protein

       1442       1452       1462       1472       1482       1492
CUGAAGCCCU UCGAGCGGGA CAUCUCCACC GAGAUCUAUC AGGCCGGCAG CACCCCUUGU
  L  K  P   F  E  R   D  I  S  T   E  I  Y   Q  A  G   S  T  P  C
                              S protein

       1502       1512       1522       1532       1542       1552
AACGGCGUGG AAGGCUUCAA CUGCUACUUC CCACUGCAGU CCUACGGCUU UCAGCCCACA
  N  G  V   E  G  F   N  C  Y  F   P  L  Q   S  Y  G   F  Q  P  T
                              S protein

       1562       1572       1582       1592       1602       1612
AAUGGCGUGG GCUAUCAGCC CUACAGAGUG GUGGUGCUGA GCUUCGAACU GCUGCAUGCC
  N  G  V   G  Y  Q   P  Y  R  V   V  V  L   S  F  E   L  L  H  A
                              S protein

       1622       1632       1642       1652       1662       1672
CCUGCCACAG UGUGCGGCCC UAAGAAAAGC ACCAAUCUCG UGAAGAACAA AUGCGUGAAC
  P  A  T   V  C  G   P  K  K  S   T  N  L   V  K  N   K  C  V  N
                              S protein

       1682       1692       1702       1712       1722       1732
UUCAACUUCA ACGGCCUGAC CGGCACCGGC GUGCUGACAG AGAGCAACAA GAAGUUCCUG
  F  N  F   N  G  L   T  G  T  G   V  L  T   E  S  N   K  K  F  L
                              S protein
```

-continued

```
     1742       1752       1762       1772       1782       1792
CCAUUCCAGC AGUUUGGCCG GGAUAUCGCC GAUACCACAG ACGCCGUUAG AGAUCCCCAG
  P  F  Q   Q  F  G   R  D  I  A   D  T  T   D  A  V   R  D  P  Q
                               S protein

     1802       1812       1822       1832       1842       1852
ACACUGGAAA UCCUGGACAU CACCCCUUGC AGCUUCGGCG GAGUGUCUGU GAUCACCCCU
  T  L  E   I  L  D   I  T  P  C   S  F  G   G  V  S   V  I  T  P
                               S protein

     1862       1872       1882       1892       1902       1912
GGCACCAACA CCAGCAAUCA GGUGGCAGUG CUGUACCAGG ACGUGAACUG UACCGAAGUG
  G  T  N   T  S  N   Q  V  A  V   L  Y  Q   D  V  N   C  T  E  V
                               S protein

     1922       1932       1942       1952       1962       1972
CCCGUGGCCA UUCACGCCGA UCAGCUGACA CCUACAUGGC GGGUGUACUC CACCGGCAGC
  P  V  A   T  H  A   D  Q  L  T   P  T  W   R  V  Y   S  T  G  S
                               S protein

     1982       1992       2002       2012       2022       2032
AAUGUGUUUC AGACCAGAGC CGGCUGUCUG AUCGGAGCCG AGCACGUGAA CAAUAGCUAC
  N  V  F   Q  T  R   A  G  C  L   I  G  A   E  H  V   N  N  S  Y
                               S protein

     2042       2052       2062       2072       2082       2092
GAGUGCGACA UCCCCAUCGG CGCUGGAAUC UGCGCCAGCU ACCAGACACA GACAAACAGC
  E  C  D   I  P  T   G  A  G  I   C  A  S   Y  Q  T   Q  T  N  S
                               S protein

     2102       2112       2122       2132       2142       2152
CCUCGGAGAG CCAGAAGCGU GGCCAGCCAG AGCAUCAUUG CCUACACAAU GUCUCUGGGC
  P  R  R   A  R  S   V  A  S  Q   S  I  T   A  Y  T   M  S  L  G
                               S protein

     2162       2172       2182       2192       2202       2212
GCCGAGAACA GCGUGGCCUA CUCCAACAAC UCUAUCGCUA UCCCCACCAA CUUCACCAUC
  A  E  N   S  V  A   Y  S  N  N   S  T  A   I  P  T   N  E  T  T
                               S protein

     2222       2232       2242       2252       2262       2272
AGCGUGACCA CAGAGAUCCU GCCUGUGUCC AUGACCAAGA CCAGCGUGGA CUGCACCAUG
  S  V  T   T  E  T   L  P  V  S   M  T  K   T  S  V   D  C  T  M
                               S protein

     2282       2292       2302       2312       2322       2332
UACAUCUGCG GCGAUUCCAC CGAGUGCUCC AACCUGCUGC UGCAGUACGG CAGCUUCUGC
  Y  I  C   G  D  S   T  E  C  S   N  L  L   L  Q  Y   G  S  F  C
                               S protein

     2342       2352       2362       2372       2382       2392
ACCCAGCUGA AUAGAGCCCU GACAGGGAUC GCCGUGGAAC AGGACAAGAA CACCCAAGAG
  T  Q  L   N  R  A   L  T  G  I   A  V  E   Q  D  K   N  T  Q  E
                               S protein

     2402       2412       2422       2432       2442       2452
GUGUUCGCCC AAGUGAAGCA GAUCUACAAG ACCCCUCCUA UCAAGGACUU CGGCGGCUUC
  V  F  A   Q  V  K   Q  I  Y  K   T  P  P   I  K  D   F  G  G  F
                               S protein

     2462       2472       2482       2492       2502       2512
AAUUUCAGCC AGAUUCUGCC CGAUCCUAGC AAGCCCAGCA AGCGGAGCUU CAUCGAGGAC
  N  F  S   Q  I  L   P  D  P  S   K  P  S   K  R  S   F  I  E  D
                               S protein

     2522       2532       2542       2552       2562       2572
CUGCUGUUCA ACAAAGUGAC ACUGGCCGAC GCCGGCUUCA UCAAGCAGUA UGGCGAUUGU
  L  L  F   N  K  V   T  L  A  D   A  G  F   I  K  Q   Y  G  D  C
                               S protein

     2582       2592       2602       2612       2622       2632
CUGGGCGACA UUGCCGCCAG GGAUCUGAUU UGCGCCCAGA AGUUUAACGG ACUGACAGUG
  L  G  D   I  A  A   R  D  L  I   C  A  Q   K  F  N   G  L  T  V
                               S protein

     2642       2652       2662       2672       2682       2692
CUGCCUCCUC UGCUGACCGA UGAGAUGAUC GCCCAGUACA CAUCUGCCCU GCUGGCCGGC
  L  P  P   L  L  T   D  E  M  I   A  Q  Y   T  S  A   L  L  A  G
                               S protein
```

-continued

```
      2702       2712       2722       2732       2742       2752
ACAAUCACAA GCGGCUGGAC AUUUGGAGCA GGCGCCGCUC UGCAGAUCCC CUUUGCUAUG
  T  I  T   S  G  W   T  F  G  A   G  A  A   L  Q  I   P  F  A  M
                              S protein

      2762       2772       2782       2792       2802       2812
CAGAUGGCCU ACCGGUUCAA CGGCAUCGGA GUGACCCAGA AUGUGCUGUA CGAGAACCAG
  Q  M  A   Y  R  F   N  G  I  G   V  T  Q   N  V  L   Y  E  N  Q
                              S protein

      2822       2832       2842       2852       2862       2872
AAGCUGAUCG CCAACCAGUU CAACAGCGCC AUCGGCAAGA UCCAGGACAG CCUGAGCAGC
  K  L  I   A  N  Q   F  N  S  A   I  G  K   I  Q  D   S  L  S  S
                              S protein

      2882       2892       2902       2912       2922       2932
ACAGCAAGCG CCCUGGGAAA GCUGCAGGAC GUGGUCAACC AGAAUGCCCA GGCACUGAAC
  T  A  S   A  L  G   K  L  Q  D   V  V  N   Q  N  A   Q  A  L  N
                              S protein

      2942       2952       2962       2972       2982       2992
ACCCUGGUCA AGCAGCUGUC CUCCAACUUC GGCGCCAUCA GCUCUGUGCU GAACGAUAUC
  T  L  V   K  Q  L   S  S  N  F   G  A  I   S  S  V   L  N  D  I
                              S protein

      3002       3012       3022       3032       3042       3052
CUGAGCAGAC UGGACUC TGAGGCCGAG GUGCAGAUCG ACAGACUGAU CACAGGCAGA
  L  S  R   L  D  P   P  E  A  E   V  Q  I   D  R  L   I  T  G  R
                              S protein

      3062       3072       3082       3092       3102       3112
CUGCAGAGCC UCCAGACAUA CGUGACCCAG CAGCUGAUCA GAGCCGCCGA GAUUAGAGCC
  L  Q  S   L  Q  T   Y  V  T  Q   Q  L  I   R  A  A   E  I  R  A
                              S protein

      3122       3132       3142       3152       3162       3172
UCUGCCAAUC UGGCCGCCAC CAAGAUGUCU GAGUGUGUGC UGGGCCAGAG CAAGAGAGUG
  S  A  N   L  A  A   T  K  M  S   E  C  V   L  G  Q   S  K  R  V
                              S protein

      3182       3192       3202       3212       3222       3232
GACUUUUGCG GCAAGGGCUA CCACCUGAUG AGCUUCCCUC AGUCUGCCCC UCACGGCGUG
  D  F  C   G  K  G   Y  H  L  M   S  F  P   Q  S  A   P  H  G  V
                              S protein

      3242       3252       3262       3272       3282       3292
GUGUUUCUGC ACGUGACAUA UGUGCCCGCU CAAGAGAAGA AUUUCACCAC CGCUCCAGCC
  V  F  L   H  V  T   Y  V  P  A   Q  E  K   N  F  T   T  A  P  A
                              S protein

      3302       3312       3322       3332       3342       3352
AUCUGCCACG ACGGCAAAGC CCACUUUCCU AGAGAAGGCG UGUUCGUGUC CAACGGCACC
  I  C  H   D  G  K   A  H  F  P   R  E  G   V  F  V   S  N  G  T
                              S protein

      3362       3372       3382       3392       3402       3412
CAUUGGUUCG UGACACAGCG GAACUUCUAC GAGCCCCAGA UCAUCACCAC CGACAACACC
  H  W  F   V  T  Q   R  N  F  Y   E  P  Q   I  I  T   T  D  N  T
                              S protein

      3422       3432       3442       3452       3462       3472
UUCGUGUCUG GCAACUGCGA CGUCGUGAUC GGCAUUGUGA ACAAUACCGU GUACGACCCU
  F  V  S   G  N  C   D  V  V  I   G  I  V   N  N  T   V  Y  D  P
                              S protein

      3482       3492       3502       3512       3522       3532
CUGCAGCCCG AGCUGGACAG CUUCAAAGAG GAACUGGACA AGUACUUUAA GAACCACACA
  L  Q  P   E  L  D   S  F  K  E   E  L  D   K  Y  F   K  N  H  T
                              S protein

      3542       3552       3562       3572       3582       3592
AGCCCCGACG UGGACCUGGG CGAUAUCAGC GGAAUCAAUG CCAGCGUCGU GAACAUCCAG
  S  P  D   V  D  L   G  D  I  S   G  I  N   A  S  V   V  N  I  Q
                              S protein

      3602       3612       3622       3632       3642       3652
AAAGAGAUCG ACCGGCUGAA CGAGGUGGCC AAGAAUCUGA ACGAGAGCCU GAUCGACCUG
  K  E  I   D  R  L   N  E  V  A   K  N  L   N  E  S   L  I  D  L
                              S protein
```

-continued

```
      3662        3672        3682        3692        3702        3712
CAAGAACUGG GGAAGUACGA GCAGUACAUC AAGUGGCCCU GGUACAUCUG GCUGGGCUUU
  Q  E  L   G  K  Y   E  Q  Y  I   K  W  P   W  Y  I   W  L  G  F
                              S protein

      3722        3732        3742        3752        3762        3772
AUCGCCGGAC UGAUUGCCAU CGUGAUGGUC ACAAUCAUGC UGUGUUGCAU GACCAGCUGC
  I  A  G   L  I  A   I  V  M  V   T  I  M   L  C  C   M  T  S  C
                              S protein

      3782        3792        3802        3812        3822        3832
UGUAGCUGCC UGAAGGGCUG UUGUAGCUGU GGCAGCUGCU GCAAGUUCGA CGAGGACGAU
  C  S  C   L  K  G   C  C  S  C   G  S  C   C  K  F   D  E  D  D
                              S protein

      3842        3852        3862        3872   3877
UCUGAGCCCG UGCUGAAGGG CGUGAAACUG CACUACACAU GAUGA
  S  E  P   V  L  K   G  V  K  L   H  Y  T   *  *
                              S protein

      3887        3897        3907        3917        3927        3937
CUCGAGCUGG UACUGCAUGC ACGCAAUGCU AGCUGCCCCU UUCCCGUCCU GGGUACCCCG
                              FI element

      3947        3957        3967        3977        3987        3997
AGUCUCCCCC GACCUCGGGU CCCAGGUAUG CUCCCACCUC CACCUGCCCC ACUCACCACC
                              FI element

      4007        4017        4027        4037        4047        4057
UCUGCUAGUU CCAGACACCU CCCAAGCACG CAGCAAUGCA GCUCAAAACG CUUAGCCUAG
                              FI element

      4067        4077        4087        4097        4107        4117
CCACACCCCC ACGGGAAACA GCAGUGAUUA ACCUUUAGCA AUAAACGAAA GUUUAACUAA
                              FI element

      4127        4137        4147        4157        4167  4172
GCUAUACUAA CCCCAGGGUU GGUCAAUUUC GUGCCAGCCA CACCGCGGCC GCAUGAAUAC
                              FI element

      4182        4192        4202        4212        4222        4232
AAAAAAAAAA AAAAAAAAAA AAAAAAAAAA GCAUAUGACU AAAAAAAAAA AAAAAAAAAA
                                Poly(A)

      4242        4252        4262        4272        4282
AAAAAAAAAA AAAAAAAAAA AAAAAAAAAA AAAAAAAAAA AAAAAAAAAA
                                Poly(A)
```

Nucleotide Sequence of RBL063.3 (SEQ ID NO: 17; SEQ ID NO: 5)

Nucleotide sequence is shown with individual sequence elements as indicated in bold letters. In addition, the sequence of the translated protein is shown in italic letters below the coding nucleotide sequence (*=stop codon).

```
        10          20          30          40          50  52
GGGCGAACUA GUAUUCUUCU GGUCCCCACA GACUCAGAGA GAACCCGCCA CC
                            hAg-Kozak

        62          72          82          92         102         112
AUGUUUGUGU UUCUUGUGCU GCUGCCUCUU GUGUCUUCUC AGUGUGUGGU GAGAUUUCCA
  M  F  V   F  L  V   L  L  P  L   V  S  S   Q  C  V   V  R  F  P
                          RBD (S protein)

       122         132         142         152         162         172
AAUAUUACAA AUCUGUGUCC AUUUGGAGAA GUGUUUAAUG CAACAAGAUU UGCAUCUGUG
  N  I  T   N  L  C   P  F  G  E   V  F  N   A  T  R   F  A  S  V
                          RBD (S protein)

       182         192         202         212         222         232
UAUGCAUGGA AUAGAAAAAG AAUUUCUAAU UGUGUGGCUG AUUAUUCUGU GCUGUAUAAU
  Y  A  W   N  R  K   R  I  S  N   C  V  A   D  Y  S   V  L  Y  N
                          RBD (S protein)

       242         252         262         272         282         292
AGUGCUUCUU UUUCCACAUU UAAAUGUUAU GGAGUGUCUC CAACAAAAUU AAAUGAUUUA
  S  A  S   F  S  T   F  K  C  Y   G  V  S   P  T  K   L  N  D  L
                          RBD (S protein)
```

-continued

```
       302        312        322        332        342        352
UGUUUUACAA AUGUGUAUGC UGAUUCUUUU GUGAUCAGAG GUGAUGAAGU GAGACAGAUU
  C  F  T   N  V  Y   A  D  S  F   V  I  R   G  D  E   V  R  Q  I
                              RBD (S protein)

       362        372        382        392        402        412
GCCCCCGGAC AGACAGGAAA AAUUGCUGAU UACAAUUACA AACUGCCUGA UGAUUUUACA
  A  P  G   Q  T  G   K  I  A  D   Y  N  Y   K  L  P   D  D  F  T
                              RBD (S protein)

       422        432        442        452        462        472
GGAUGUGUGA UUGCUUGGAA UUCUAAUAAU UUAGAUUCUA AAGUGGGAGG AAAUUACAAU
  G  C  V   I  A  W   N  S  N  N   L  D  S   K  V  G   G  N  Y  N
                              RBD (S protein)

       482        492        502        512        522        532
UAUCUGUACA GACUGUUUAG AAAAUCAAAU CUGAAACCUU UUGAAAGAGA UAUUUCAACA
  Y  L  Y   R  L  F   R  K  S  N   L  K  P   F  E  R   D  I  S  T
                              RBD (S protein)

       542        552        562        572        582        592
GAAAUUUAUC AGGCUGGAUC AACACCUUGU AAUGGAGUGG AAGGAUUUAA UUGUUAUUUU
  E  I  Y   Q  A  G   S  T  P  C   N  G  V   E  G  F   N  C  Y  F
                              RBD (S protein)

       602        612        622        632        642        652
CCAUUACAGA GCUAUGGAUU UCAGCCAACC AAUGGUGUGG GAUAUCAGCC AUAUAGAGUG
  P  L  Q   S  Y  G   F  Q  P  T   N  G  V   G  Y  Q   P  Y  R  V
                              RBD (S protein)

       662        672        682        692        702  706
GUGGUGCUGU CUUUUGAACU GCUGCAUGCA CCUGCAACAG UGUGUGGACC UAAA
  V  V  L   S  F  E   L  L  H  A   P  A  T   V  C  G   P  K
                              RBD (S protein)

       716        726     733
GGCUCCCCCG GCUCCGGCUC CGGAUCU
  G  S  P   G  S  G   S  G  S
                 GS linker

       743        753        763        773        783        793
GGUUAUAUUC CUGAAGCUCC AAGAGAUGGG CAAGCUUACG UUCGUAAAGA UGGCGAAUGG
  G  Y  I   P  E  A   P  R  D  G   Q  A  Y   V  R  K   D  G  E  W
                                  fibritin

       803        813        823        833        843        853
GUAUUACUUU CUACCUUUUU AGGCCGGUCC CUGGAGGUGC UGUUCCAGGG CCCCGGCUGA
  V  L  L   S  T  F   L  G  R  S   L  E  V   L  F  Q   G  P  G  *
                                  fibritin

 856
UGA
  *
fibritin

       866        876        886        896        906        916
CUCGAGCUGG UACUGCAUGC ACGCAAUGCU AGCUGCCCCU UUCCCGUCCU GGGUACCCCG
                                FI element

       926        936        946        956        966        976
AGUCUCCCCC GACCUCGGGU CCCAGGUAUG CUCCCACCUC CACCUGCCCC ACUCACCACC
                                FI element

        986        996       1006       1016       1026       1036
UCUGCUAGUU CCAGACACCU CCCAAGCACG CAGCAAUGCA GCUCAAAACG CUUAGCCUAG
                                FI element

      1046       1056       1066       1076       1086       1096
CCACACCCCC ACGGGAAACA GCAGUGAUUA ACCUUUAGCA AUAAACGAAA GUUUAACUAA
                                FI element

      1106       1116       1126       1136       1146   1151
GCUAUACUAA CCCCAGGGUU GGUCAAUUUC GUGCCAGCCA CACCCUGGAC CUAGC
                                FI element

      1161       1171       1181       1191       1201       1211
AAAAAAAAAA AAAAAAAAAA AAAAAAAAAA GCAUAUGACU AAAAAAAAAA AAAAAAAAAA
                                  Poly(A)
```

-continued

```
     1221       1231       1241       1251       1261
AAAAAAAAAA AAAAAAAAAA AAAAAAAAAA AAAAAAAAAA AAAAAAAAAA
```

Nucleoside Modified Messenger RNA (modRNA)

The active principle of the nucleoside modified messenger RNA (modRNA) drug substance is as well a single-stranded mRNA that is translated upon entering a cell. In addition to the sequence encoding the coronavirus vaccine antigen (i.e. open reading frame), each modRNA contains common structural elements optimized for maximal efficacy of the RNA as the uRNA (5'-cap, 5'-UTR, 3'-UTR, poly(A)-tail). Compared to the uRNA, modRNA contains 1-methyl-pseudouridine instead of uridine. The preferred 5' cap structure is $m_2^{7,3'-O}Gppp(m_1^{2'-O})ApG$. The preferred 5'-UTR and 3'-UTR comprise the nucleotide sequence of SEQ ID NO: 12 and the nucleotide sequence of SEQ ID NO: 13, respectively. The preferred poly(A)-tail comprises the sequence of SEQ ID NO: 14. An additional purification step is applied for modRNA to reduce dsRNA contaminants generated during the in vitro transcription reaction.

Different embodiment of this platform are as follows:

BNT162b2; RBP020.1 (SEQ ID NO: 19; SEQ ID NO: 7)

Structure $m_2^{7,3'-O}Gppp(m_1^{2'-O})ApG$)-hAg-Kozak-S1S2-PP-FI-A30L70

Encoded antigen Viral spike protein (S1S2 protein) of the SARS-CoV-2 (S1S2 full-length protein, sequence variant)

BNT162b2; RBP020.2 (SEQ ID NO: 20; SEQ ID NO: 7)

Structure $m_2^{7,3'-O}Gppp(m_1^{2'-O})ApG$)-hAg-Kozak-S1S2-PP-F1-A30L70

Encoded antigen Viral spike protein (S1S2 protein) of the SARS-CoV-2 (S1S2 full-length protein, sequence variant)

BNT162b1; RBP020.3 (SEQ ID NO: 21; SEQ ID NO: 5)

Structure $m_2^{7,3'-O}Gppp(m_1^{2'-O})ApG$)-hAg-Kozak-RBD-GS-Fibritin-FI-A30L70

Encoded antigen Viral spike protein (S1S2 protein) of the SARS-CoV-2 (partial sequence, Receptor Binding Domain (RBD) of S1S2 protein fused to fibritin)

FIG. 20 schematizes the general structure of the antigen-encoding RNAs.

Nucleotide Sequence of RBP020.1 (SEQ ID NO: 19; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40         50  53
AGAAUAAACU AGUAUUCUUC UGGUCCCCAC AGACUCAGAG AGAACCCGCC ACC
                           hAg-Kozak

        63         73         83         93        103        113
AUGUUUGUGU UUCUUGUGCU GCUGCCUCUU GUGUCUUCUC AGUGUGUGAA UUUGACAACA
  M  F  V   F  L  V   L  L  P  L   V  S  S   Q  C  V   N  L  T  T
                              S protein

       123        133        143        153        163        173
AGAACACAGC UGCCACCAGC UUAUACAAAU UCUUUUACCA GAGGAGUGUA UUAUCCUGAU
  R  T  Q   L  P  P   A  Y  T  N   S  F  T   R  G  V   Y  Y  P  D
                              S protein

       183        193        203        213        223        233
AAAGUGUUUA GAUCUUCUGU GCUGCACAGC ACACAGGACC UGUUUCUGCC AUUUUUUAGC
  K  V  F   R  S  S   V  L  H  S   T  Q  D   L  F  L   P  F  F  S
                              S protein

       243        253        263        273        283        293
AAUGUGACAU GGUUUCAUGC AAUUCAUGUG UCUGGAACAA AUGGAACAAA AAGAUUUGAU
  N  V  T   W  F  H   A  I  H  V   S  G  T   N  G  T   K  R  F  D
                              S protein

       303        313        323        333        343        353
AAUCCUGUGC UGCCUUUUAA UGAUGGAGUG UAUUUUGCUU CAACAGAAAA GUCAAAUAUU
  N  P  V   L  P  F   N  D  G  V   Y  F  A   S  T  E   K  S  N  I
                              S protein

       363        373        383        393        403        413
AUUAGAGGAU GGAUUUUUGG AACAACACUG GAUUCUAAAA CACAGUCUCU GCUGAUUGUG
  I  R  G   W  I  F   G  T  T  L   D  S  K   T  Q  S   L  L  I  V
                              S protein

       423        433        443        453        463        473
AAUAAUGCAA CAAAUGUGGU GAUUAAAGUG UGUGAAUUUC AGUUUUGUAA UGAUCCUUUU
  N  N  A   T  N  V   V  I  K  V   C  E  F   Q  F  C   N  D  P  F
                              S protein

       483        493        503        513        523        533
CUGGGAGUGU AUUAUCACAA AAAUAAUAAA UCUUGGAUGG AAUCUGAAUU UAGAGUGUAU
  L  G  V   Y  Y  H   K  N  N  K   S  W  M   E  S  E   F  R  V  Y
                              S protein
```

-continued

```
        543        553        563        573        583        593
UCCUCUGCAA AUAAUUGUAC AUUUGAAUAU GUGUCUCAGC CUUUUCUGAU GGAUCUGGAA
  S  S  A   N  N  C   T  F  E  Y   V  S  Q   P  F  L   M  D  L  E
                                S protein

        603        613        622        633        643        653
GGAAAACAGG GCAAUUUUAA AAAUCUGAGA GAAUUUGUGU UUAAAAAUAU UGAUGGAUAU
  G  K  Q   G  N  F   K  N  L  R   E  F  V   F  K  N   I  D  G  Y
                                S protein

        663        673        683        693        703        713
UUUAAAAUUU AUUCUAAACA CACACCAAUU AAUUUAGUGA GAGAUCUGCC UCAGGGAUUU
  F  K  I   Y  S  K   H  T  P  I   N  L  V   R  D  L   P  Q  G  F
                                S protein

        723        733        743        753        763        773
UCUGCUCUGG AACCUCUGGU GGAUCUGCCA AUUGGCAUUA AUAUUACAAG AUUUCAGACA
  S  A  L   E  P  L   V  D  L  P   I  G  I   N  I  T   R  F  Q  T
                                S protein

        783        793        803        813        823        833
CUGCUGGCUC UGCACAGAUC UUAUCUGACA CCUGGAGAUU CUUCUUCUGG AUGGACAGCC
  L  L  A   L  H  R   S  Y  L  T   P  G  D   S  S  S   G  W  T  A
                                S protein

        843        853        863        873        883        893
GGAGCUGCAG CUUAUUAUGU GGGCUAUCUG CAGCCAAGAA CAUUUCUGCU GAAAUAUAAU
  G  A  A   A  Y  Y   V  G  Y  L   Q  P  R   T  F  L   L  K  Y  N
                                S protein

        903        913        923        933        943        953
GAAAAUGGAA CAAUUACAGA UGCUGUGGAU UGUGCUCUGG AUCCUCUGUC UGAAACAAAA
  E  N  G   T  I  T   D  A  V  D   C  A  L   D  P  L   S  E  T  K
                                S protein

        963        973        983        993       1003       1013
UGUACAUUAA AAUCUUUUAC AGUGGAAAAA GGCAUUUAUC AGACAUCUAA UUUUAGAGUG
  C  T  L   K  S  F   T  V  E  K   G  I  Y   Q  T  S   N  F  R  V
                                S protein

       1023       1033       1043       1053       1063       1073
CAGCCAACAG AAUCUAUUGU GAGAUUUCCA AAUAUUACAA AUCUGUGUCC AUUUGGAGAA
  Q  P  T   E  S  I   V  R  F  P   N  I  T   N  L  C   P  F  G  E
                                S protein

       1083       1093       1103       1113       1123       1133
GUGUUUAAUG CAACAAGAUU UGCAUCUGUG UAUGCAUGGA AUAGAAAAAG AAUUUCUAAU
  V  F  N   A  T  R   F  A  S  V   Y  A  W   N  R  K   R  I  S  N
                                S protein

       1143       1153       1163       1173       1183       1193
UGUGUGGCUG AUUAUUCUGU GCUGUAUAAU AGUGCUUCUU UUUCCACAUU UAAAUGUUAU
  C  V  A   D  Y  S   V  L  Y  N   S  A  S   F  S  T   F  K  C  Y
                                S protein

       1203       1213       1223       1233       1243       1253
GGAGUGUCUC CAACAAAAUU AAAUGAUUUA UGUUUUACAA AUGUGUAUGC UGAUUCUUUU
  G  V  S   P  T  K   L  N  D  L   C  F  T   N  V  Y   A  D  S  F
                                S protein

       1263       1273       1283       1293       1303       1313
GUGAUCAGAG GUGAUGAAGU GAGACAGAUU GCCCCCGGAC AGACAGGAAA AAUUGCUGAU
  V  I  R   G  D  E   V  R  Q  I   A  P  G   Q  T  G   K  I  A  D
                                S protein

       1323       1333       1343       1353       1363       1373
UACAAUUACA AACUGCCUGA UGAUUUUACA GGAUGUGUGA UUGCUUGGAA UUCUAAUAAU
  Y  N  Y   K  L  P   D  D  F  T   G  C  V   I  A  W   N  S  N  N
                                S protein

       1383       1393       1403       1413       1423       1433
UUAGAUUCUA AAGUGGGAGG AAAUUACAAU UAUCUGUACA GACUGUUUAG AAAAUCAAAU
  L  D  S   K  V  G   G  N  Y  N   Y  L  Y   R  L  F   R  K  S  N
                                S protein

       1443       1453       1463       1473       1483       1493
CUGAAACCUU UUGAAAGAGA UAUUUCAACA GAAAUUUAUC AGGCUGGAUC AACACCUUGU
  L  K  P   F  E  R   D  I  S  T   E  I  Y   Q  A  G   S  T  P  C
                                S protein
```

-continued

```
       1503        1513        1523        1533        1543        1553
AAUGGAGUGG AAGGAUUUAA UUGUUAUUUU CCAUUACAGA GCUAUGGAUU UCAGCCAACC
  N  G  V   E  G  F   N  C  Y  F   P  L  Q   S  Y  G   E  Q  P  T
                             S protein

       1563        1573        1583        1593        1603        1613
AAUGGUGUGG GAUAUCAGCC AUAUAGAGUG GUGGUGCUGU CUUUUGAACU GCUGCAUGCA
  N  G  V   G  Y  Q   P  Y  R  V   V  V  L   S  F  E   L  L  H  A
                             S protein

       1623        1633        1643        1653        1663        1673
CCUGCAACAG UGUGUGGACC UAAAAAAUCU ACAAAUUUAG UGAAAAAUAA AUGUGUGAAU
  P  A  T   V  C  G   P  K  K  S   T  N  L   V  K  N   K  C  V  N
                             S protein

       1683        1693        1703        1713        1723        1733
UUUAAUUUUA AUGGAUUAAC AGGAACAGGA GUGCUGACAG AAUCUAAUAA AAAAUUUCUG
  F  N  F   N  G  L   T  G  T  G   V  L  T   E  S  N   K  K  F  L
                             S protein

       1743        1753        1763        1773        1783        1793
CCUUUUCAGC AGUUUGGCAG AGAUAUUGCA GAUACCACAG AUGCAGUGAG AGAUCCUCAG
  P  F  Q   Q  F  G   R  D  I  A   D  T  T   D  A  V   R  D  P  Q
                             S protein

       1803        1813        1823        1833        1843        1853
ACAUUAGAAA UUCUGGAUAU UACACCUUGU UCUUUUGGGG GUGUGUCUGU GAUUACACCU
  T  L  E   I  L  D   I  T  P  C   S  F  G   G  V  S   V  I  T  P
                             S protein

       1863        1873        1883        1893        1903        1913
GGAACAAAUA CAUCUAAUCA GGUGGCUGUG CUGUAUCAGG AUGUGAAUUG UACAGAAGUG
  G  T  N   T  S  N   Q  V  A  V   L  Y  Q   D  V  N   C  T  E  V
                             S protein

       1923        1933        1943        1953        1963        1973
CCAGUGGCAA UUCAUGCAGA UCAGCUGACA CCAACAUGGA GAGUGUAUUC UACAGGAUCU
  P  V  A   I  H  A   D  Q  L  T   P  T  W   R  V  Y   S  T  G  S
                             S protein

       1983        1993        2003        2013        2023       2033
AAUGUGUUUC AGACAAGAGC AGGAUGUCUG AUUGGAGCAG AACAUGUGAA UAAUUCUUAU
  N  V  F   Q  T  R   A  G  C  L   I  G  A   E  H  V   N  N  S  Y
                             S protein

       2043        2053        2063        2073        2083        2093
GAAUGUGAUA UUCCAAUUGG AGCAGGCAUU UGUGCAUCUU AUCAGACACA GACAAAUUCC
  E  C  D   I  P  T   G  A  G  I   C  A  S   Y  Q  T   Q  T  N  S
                             S protein

       2103        2113        2123        2133        2143        2153
CCAAGGAGAG CAAGAUCUGU GGCAUCUCAG UCUAUUAUUG CAUACACCAU GUCUCUGGGA
  P  R  R   A  R  S   V  A  S  Q   S  I  T   A  Y  T   M  S  L  G
                             S protein

       2163        2173        2183        2193        2203        2213
GCAGAAAAUU CUGUGGCAUA UUCUAAUAAU UCUAUUGCUA UUCCAACAAA UUUUACCAUU
  A  E  N   S  V  A   Y  S  N  N   S  T  A   I  P  T   N  F  T  I
                             S protein

       2223        2233        2243        2253        2263        2273
UCUGUGACAA CAGAAAUUUU ACCUGUGUCU AUGACAAAAA CAUCUGUGGA UUGUACCAUG
  S  V  T   T  E  T   L  P  V  S   M  T  K   T  S  V   D  C  T  M
                             S protein

       2283        2293        2303        2313        2323        2333
UACAUUUGUG GAGAUUCUAC AGAAUGUUCU AAUCUGCUGC UGCAGUAUGG AUCUUUUUGU
  Y  I  C   G  D  S   T  E  C  S   N  L  L   L  Q  Y   G  S  F  C
                             S protein

       2343        2353        2363        2373        2383        2393
ACACAGCUGA AUAGAGCUUU AACAGGAAUU GCUGUGGAAC AGGAUAAAAA UACACAGGAA
  T  Q  L   N  R  A   L  T  G  I   A  V  E   Q  D  K   N  T  Q  E
                             S protein

       2403        2413        2423        2433        2443        2453
GUGUUUGCUC AGGUGAAACA GAUUUACAAA ACACCACCAA UUAAAGAUUU UGGAGGAUUU
  V  F  A   Q  V  K   Q  T  Y  K   T  P  P   I  K  D   F  G  G  F
                             S protein
```

-continued

```
      2463       2473       2483       2493       2503       2513
AAUUUUAGCC AGAUUCUGCC UGAUCCUUCU AAACCUUCUA AAAGAUCUUU UAUUGAAGAU
 N  F  S   Q  I  L   P  D  P  S   K  P  S   K  R  S   F  I  E  D
                                S protein

      2523       2533       2543       2553       2563       2573
CUGCUGUUUA AUAAAGUGAC ACUGGCAGAU GCAGGAUUUA UUAAACAGUA UGGAGAUUGC
 L  L  F   N  K  V   T  L  A  D   A  G  F   I  K  Q   Y  G  D  C
                                S protein

      2583       2593       2603       2613       2623       2633
CUGGGUGAUA UUGCUGCAAG AGAUCUGAUU UGUGCUCAGA AAUUUAAUGG ACUGACAGUG
 L  G  D   I  A  A   R  D  L  I   C  A  Q   K  E  N   G  L  T  V
                                S protein

      2643       2653       2663       2673       2683       2693
CUGCCUCCUC UGCUGACAGA UGAAAUGAUU GCUCAGUACA CAUCUGCUUU ACUGGCUGGA
 L  P  P   L  L  T   D  E  M  I   A  Q  Y   T  S  A   L  L  A  G
                                S protein

      2703       2713       2723       2733       2743       2753
ACAAUUACAA GCGGAUGGAC AUUUGGAGCU GGAGCUGCUC UGCAGAUUCC UUUUGCAAUG
 T  I  T   S  G  W   T  F  G  A   G  A  A   L  Q  I   P  E  A  M
                                S protein

      2763       2773       2783       2793       2803       2813
CAGAUGGCUU ACAGAUUUAA UGGAAUUGGA GUGACACAGA AUGUGUUAUA UGAAAAUCAG
 Q  M  A   Y  R  F   N  G  I  G   V  T  Q   N  V  L   Y  E  N  Q
                                S protein

      2823       2833       2843       2853       2863       2873
AAACUGAUUG CAAAUCAGUU UAAUUCUGCA AUUGGCAAAA UUCAGGAUUC UCUGUCUUCU
 K  L  I   A  N  Q   E  N  S  A   I  G  K   I  Q  D   S  L  S  S
                                S protein

      2883       2893       2903       2913       2923       2933
ACAGCUUCUG CUCUGGGAAA ACUGCAGGAU GUGGUGAAUC AGAAUGCACA GGCACUGAAU
 T  A  S   A  L  G   K  L  Q  D   V  V  N   Q  N  A   Q  A  L  N
                                S protein

      2943       2953       2963       2973       2983       2993
ACUCUGGUGA AACAGCUGUC UAGCAAUUUU GGGGCAAUUU CUUCUGUGCU GAAUGAUAUU
 T  L  V   K  Q  L   S  S  N  F   G  A  I   S  S  V   L  N  D  I
                                S protein

      3003       3013       3023       3033       3043       3053
CUGUCUAGAC UGGAUCCUCC UGAAGCUGAA GUGCAGAUUG AUAGACUGAU CACAGGAAGA
 L  S  R   L  D  P   P  E  A  E   V  Q  I   D  R  L   I  T  G  R
                                S protein

      3063       3073       3083       3093       3103       3113
CUGCAGUCUC UGCAGACUUA UGUGACACAG CAGCUGAUUA GAGCUGCUGA AAUUAGAGCU
 L  Q  S   L  Q  T   Y  V  T  Q   Q  L  I   R  A  A   E  I  R  A
                                S protein

      3123       3133       3143       3153       3163       3173
UCUGCUAAUC UGGCUGCUAC AAAAAUGUCU GAAUGUGUGC UGGGACAGUC AAAAAGAGUG
 S  A  N   L  A  A   T  K  M  S   E  C  V   L  G  Q   S  K  R  V
                                S protein

      3183       3193       3203       3213       3223       3233
GAUUUUUGUG GAAAAGGAUA UCAUCUGAUG UCUUUUCCAC AGUCUGCUCC ACAUGGAGUG
 D  E  C   G  K  G   Y  H  L  M   S  E  P   Q  S  A   P  H  G  V
                                S protein

      3243       3253       3263       3273       3283       3293
GUGUUUUUAC AUGUGACAUA UGUGCCAGCA CAGGAAAAGA AUUUUACCAC AGCACCAGCA
 V  F  L   H  V  T   Y  V  P  A   Q  E  K   N  F  T   T  A  P  A
                                S protein

      3303       3313       3323       3333       3343       3353
AUUUGUCAUG AUGGAAAAGC ACAUUUUCCA AGAGAAGGAG UGUUUGUGUC UAAUGGAACA
 I  C  H   D  G  K   A  H  F  P   R  E  G   V  F  V   S  N  G  T
                                S protein

      3363       3373       3383       3393       3403       3413
CAUUGGUUUG UGACACAGAG AAAUUUUUAU GAACCUCAGA UUAUUACAAC AGAUAAUACA
 H  W  F   V  T  Q   R  N  F  Y   E  P  Q   I  T  T   T  D  N  T
                                S protein
```

-continued

```
      3423       3433       3443       3453       3463       3473
UUUGUGUCAG GAAAUUGUGA UGUGGUGAUU GGAAUUGUGA AUAAUACAGU GUAUGAUCCA
  F  V  S   G  N  C   D  V  V  I   G  I  V   N  N  T   V  Y  D  P
                              S protein

      3483       3493       3503       3513       3523       3533
CUGCAGCCAG AACUGGAUUC UUUUAAAGAA GAACUGGAUA AAUAUUUUAA AAAUCACACA
  L  Q  P   E  L  D   S  F  K  E   E  L  D   K  Y  F   K  N  H  T
                              S protein

      3543       3553       3563       3573       3583       3593
UCUCCUGAUG UGGAUUUAGG AGAUAUUUCU GGAAUCAAUG CAUCUGUGGU GAAUAUUCAG
  S  P  D   V  D  L   G  D  I  S   G  I  N   A  S  V   V  N  I  Q
                              S protein

      3603       3613       3623       3633       3643       3653
AAAGAAAUUG AUAGACUGAA UGAAGUGGCC AAAAAUCUGA AUGAAUCUCU GAUUGAUCUG
  K  E  I   D  R  L   N  E  V  A   K  N  L   N  E  S   L  I  D  L
                              S protein

      3663       3673       3683       3693       3703       3713
CAGGAACUUG GAAAAUAUGA ACAGUACAUU AAAUGGCCUU GGUACAUUUG GCUUGGAUUU
  Q  E  L   G  K  Y   E  Q  Y  I   K  W  P   W  Y  I   W  L  G  F
                              S protein

      3723       3733       3743       3753       3763       3773
AUUGCAGGAU UAAUUGCAAU UGUGAUGGUG ACAAUUAUGU UAUGUUGUAU GACAUCAUGU
  I  A  G   L  I  A   I  V  M  V   T  I  M   L  C  C   M  T  S  C
                              S protein

      3783       3793       3803       3813       3823       3833
UGUUCUUGUU UAAAAGGAUG UUGUUCUUGU GGAAGCUGUU GUAAAUUUGA UGAAGAUGAU
  C  S  C   L  K  G   C  C  S  C   G  S  C   C  K  F   D  E  D  D
                              S protein

      3843       3853       3863       3873  3878
UCUGAACCUG UGUUAAAAGG AGUGAAAUUG CAUUACACAU GAUGA
  S  E  P   V  L  K   G  V  K  L   H  Y  T   *  *
                              S protein

      3888       3898       3908       3918       3928       3938
CUCGAGCUGG UACUGCAUGC ACGCAAUGCU AGCUGCCCCU UUCCCGUCCU GGGUACCCCG
                             FI element

      3948       3958       3968       3978       3988       3998
AGUCUCCCCC GACCUCGGGU CCCAGGUAUG CUCCCACCUC CACCUGCCCC ACUCACCACC
                             FI element

      4008       4018       4028       4038       4048       4058
UCUGCUAGUU CCAGACACCU CCCAAGCACG CAGCAAUGCA GCUCAAAACG CUUAGCCUAG
                             FI element

      4068       4078       4088       4098       4108       4118
CCACACCCCC ACGGGAAACA GCAGUGAUUA ACCUUUAGCA AUAAACGAAA GUUUAACUAA
                             FI element

      4128       4138       4148       4158       4168  4173
GCUAUACUAA CCCCAGGGUU GGUCAAUUUC GUGCCAGCCA CACCCUGGAG CUAGC
                             FI element

      4183       4193       4203       4213       4223       4233
AAAAAAAAAA AAAAAAAAAA AAAAAAAAAA GCAUAUGACU AAAAAAAAAA AAAAAAAAAA
                               Poly(A)

      4243       4253       4263       4273       4283
AAAAAAAAAA AAAAAAAAAA AAAAAAAAAA AAAAAAAAAA AAAAAAAAAA
                               Poly(A)
```

Nucleotide Sequence of RBP020.2 (SEQ ID NO: 20; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40         50  53
AGAAUAAACU AGUAUUCUUC UGGUCCCCAC AGACUCAGAG AGAACCCGCC ACC
                            hAg-Kozak

        63         73         83         93        103        113
AUGUUCGUGU UCCUGGUGCU GCUGCCUCUG GUGUCCAGCC AGUGUGUGAA CCUGACCACC
  M  F  V   F  L  V   L  L  P  L   V  S  S   Q  C  V   N  L  T  T
                           S protein

       123        133        143        153        163        173
AGAACACAGC UGCCUCCAGC CUACACCAAC AGCUUUACCA GAGGCGUGUA CUACCCCGAC
  R  T  Q   L  P  P   A  Y  T  N   S  F  T   R  G  V   Y  Y  P  D
                            S protein

       183        193        203        213        223        233
AAGGUGUUCA GAUCCAGCGU GCUGCACUCU ACCCAGGACC UGUUCCUGCC UUUCUUCAGC
  K  V  F   R  S  S   V  L  H  S   T  Q  D   L  F  L   P  F  F  S
                            S protein

       243        253        263        273        283        293
AACGUGACCU GGUUCCACGC CAUCCACGUG UCCGGCACCA AUGGCACCAA GAGAUUCGAC
  N  V  T   W  F  H   A  I  H  V   S  G  T   N  G  T   K  R  F  D
                            S protein

       303        313        323        333        343        353
AACCCCGUGC UGCCCUUCAA CGACGGGGUG UACUUUGCCA GCACCGAGAA GUCCAACAUC
  N  P  V   L  P  F   N  D  G  V   Y  F  A   S  T  E   K  S  N  I
                            S protein

       363        373        383        393        403        413
AUCAGAGGCU GGAUCUUCGG CACCACACUG GACAGCAAGA CCCAGAGCCU GCUGAUCGUG
  I  R  G   W  I  F   G  T  T  L   D  S  K   T  Q  S   L  L  I  V
                            S protein

       423        433        443        453        463        473
AACAACGCCA CCAACGUGGU CAUCAAAGUG UGCGAGUUCC AGUUCUGCAA CGACCCCUUC
  N  N  A   T  N  V   V  I  K  V   C  E  F   Q  F  C   N  D  P  F
                            S protein

       483        493        503        513        523        533
CUGGGCGUCU ACUACCACAA GAACAACAAG AGCUGGAUGG AAAGCGAGUU CCGGGUGUAC
  L  G  V   Y  Y  H   K  N  N  K   S  W  M   E  S  E   F  R  V  Y
                            S protein

       543        553        563        573        583        593
AGCAGCGCCA ACAACUGCAC CUUCGAGUAC GUGUCCCAGC CUUUCCUGAU GGACCUGGAA
  S  S  A   N  N  C   T  F  E  Y   V  S  Q   P  F  L   M  D  L  E
                            S protein

       603        613        623        633        643        653
GGCAAGCAGG GCAACUUCAA GAACCUGCGC GAGUUCGUGU UUAAGAACAU CGACGGCUAC
  G  K  Q   G  N  F   K  N  L  R   E  F  V   F  K  N   I  D  G  Y
                            S protein

       663        673        683        693        703        713
UUCAAGAUCU ACAGCAAGCA CACCCCUAUC AACCUCGUGC GGGAUCUGCC UCAGGGCUUC
  F  K  I   Y  S  K   H  T  P  I   N  L  V   R  D  L   P  Q  G  F
                            S protein

       723        733        743        753        763        773
UCUGCUCUGG AACCCCUGGU GGAUCUGCCC AUCGGCAUCA ACAUCACCCG GUUUCAGACA
  S  A  L   E  P  L   V  D  L  P   I  G  I   N  I  T   R  F  Q  T
                            S protein

       783        793        803        813        823        833
CUGCUGGCCC UGCACAGAAG CUACCUGACA CCUGGCGAUA GCAGCAGCGG AUGGACAGCU
  L  L  A   L  H  R   S  Y  L  T   P  G  D   S  S  S   G  W  T  A
                            S protein

       843        853        863        873        883        893
GGUGCCGCCG CUUACUAUGU GGGCUACCUG CAGCCUAGAA CCUUCCUGCU GAAGUACAAC
  G  A  A   A  Y  Y   V  G  Y  L   Q  P  R   T  F  L   L  K  Y  N
                            S protein
```

-continued

```
       903        913        923        933        943        953
GAGAACGGCA CCAUCACCGA CGCCGUGGAU UGUGCUCUGG AUCCUCUGAG CGAGACAAAG
  E  N  G   T  I  T   D  A  V  D   C  A  L   D  P  L   S  E  T  K
                              S protein

       963        973        983        993       1003       1013
UGCACCCUGA AGUCCUUCAC CGUGGAAAAG GGCAUCUACC AGACCAGCAA CUUCCGGGUG
  C  T  L   K  S  F   T  V  E  K   G  I  Y   Q  T  S   N  F  R  V
                              S protein

      1023       1033       1043       1053       1063       1073
CAGCCCACCG AAUCCAUCGU GCGGUUCCCC AAUAUCACCA AUCUGUGCCC CUUCGGCGAG
  Q  P  T   E  S  I   V  R  F  P   N  I  T   N  L  C   P  F  G  E
                              S protein

      1083       1093       1103       1113       1123       1133
GUGUUCAAUG CCACCAGAUU CGCCUCUGUG UACGCCUGGA ACCGGAAGCG GAUCAGCAAU
  V  F  N   A  T  R   F  A  S  V   Y  A  W   N  R  K   R  I  S  N
                              S protein

      1143       1153       1163       1173       1183       1193
UGCGUGGCCG ACUACUCCGU GCUGUACAAC UCCGCCAGCU UCAGCACCUU CAAGUGCUAC
  C  V  A   D  Y  S   V  L  Y  N   S  A  S   F  S  T   F  K  C  Y
                              S protein

      1203       1213       1223       1233       1243       1253
GGCGUGUCCC CUACCAAGCU GAACGACCUG UGCUUCACAA ACGUGUACGC CGACAGCUUC
  G  V  S   P  T  K   L  N  D  L   C  F  T   N  V  Y   A  D  S  F
                              S protein

      1263       1273       1283       1293       1303       1313
GUGAUCCGGG GAGAUGAAGU GCGGCAGAUU GCCCCUGGAC AGACAGGCAA GAUCGCCGAC
  V  I  R   G  D  E   V  R  Q  I   A  P  G   Q  T  G   K  I  A  D
                              S protein

      1323       1333       1343       1353       1363       1373
UACAACUACA AGCUGCCCGA CGACUUCACC GGCUGUGUGA UUGCCUGGAA CAGCAACAAC
  Y  N  Y   K  L  P   D  D  F  T   G  C  V   I  A  W   N  S  N  N
                              S protein

      1383       1393       1403       1413       1423       1433
CUGGACUCCA AAGUCGGCGG CAACUACAAU UACCUGUACC GGCUGUUCCG GAAGUCCAAU
  L  D  S   K  V  G   G  N  Y  N   Y  L  Y   R  L  F   R  K  S  N
                              S protein

      1443       1453       1463       1473       1483       1493
CUGAAGCCCU UCGAGCGGGA CAUCUCCACC GAGAUCUAUC AGGCCGGCAG CACCCCUUGU
  L  K  P   F  E  R   D  I  S  T   E  I  Y   Q  A  G   S  T  P  C
                              S protein

      1503       1513       1523       1533       1543       1553
AACGGCGUGG AAGGCUUCAA CUGCUACUUC CCACUGCAGU CCUACGGCUU UCAGCCCACA
  N  G  V   E  G  F   N  C  Y  F   P  L  Q   S  Y  G   E  Q  P  T
                              S protein

      1563       1573       1583       1593       1603       1613
AAUGGCGUGG GCUAUCAGCC CUACAGAGUG GUGGUGCUGA GCUUCGAACU GCUGCAUGCC
  N  G  V   G  Y  Q   P  Y  R  V   V  V  L   S  F  E   L  L  H  A
                              S protein

      1623       1633       1643       1653       1663       1673
CCUGCCACAG UGUGCGGCCC UAAGAAAAGC ACCAAUCUCG UGAAGAACAA AUGCGUGAAC
  P  A  T   V  C  G   P  K  K  S   T  N  L   V  K  N   K  C  V  N
                              S protein

      1683       1693       1703       1713       1723       1733
UUCAACUUCA ACGGCCUGAC CGGCACCGGC GUGCUGACAG AGAGCAACAA GAAGUUCCUG
  F  N  F   N  G  L   T  G  T  G   V  L  T   E  S  N   K  K  F  L
                              S protein

      1743       1753       1763       1773       1783       1793
CCAUUCCAGC AGUUUGGCCG GGAUAUCGCC GAUACCACAG ACGCCGUUAG AGAUCCCCAG
  P  F  Q   Q  F  G   R  D  I  A   D  T  T   D  A  V   R  D  P  Q
                              S protein

      1803       1813       1823       1833       1843       1853
ACACUGGAAA UCCUGGACAU CACCCCUUGC AGCUUCGGCG GAGUGUCUGU GAUCACCCCU
  T  L  E   I  L  D   I  T  P  C   S  F  G   G  V  S   V  I  T  P
                              S protein
```

-continued

```
      1863        1873        1883        1893        1903        1913
GGCACCAACA CCAGCAAUCA GGUGGCAGUG CUGUACCAGG ACGUGAACUG UACCGAAGUG
  G  T  N   T  S  N   Q  V  A  V  L  Y  Q   D  V  N   C  T  E  V
                              S protein

      1923        1933        1943        1953        1963        1973
CCCGUGGCCA UUCACGCCGA UCAGCUGACA CCUACAUGGC GGGUGUACUC CACCGGCAGC
  P  V  A   I  H  A   D  Q  L  T   P  T  W   R  V  Y   S  T  G  S
                              S protein

      1983        1993        2003        2013        2023        2033
AAUGUGUUUC AGACCAGAGC CGGCUGUCUG AUCGGAGCCG AGCACGUGAA CAAUAGCUAC
  N  V  F   Q  T  R   A  G  C  L   I  G  A   E  H  V   N  N  S  Y
                              S protein

      2043        2053        2063        2073        2083        2093
GAGUGCGACA UCCCCAUCGG CGCUGGAAUC UGCGCCAGCU ACCAGACACA GACAAACAGC
  E  C  D   I  P  T   G  A  G  I   C  A  S   Y  Q  T   Q  T  N  S
                              S protein

      2103        2113        2123        2133        2143        2153
CCUCGGAGAG CCAGAAGCGU GGCCAGCCAG AGCAUCAUUG CCUACACAAU GUCUCUGGGC
  P  R  R   A  R  S   V  A  S  Q   S  I  T   A  Y  T   M  S  L  G
                              S protein

      2163        2173        2183        2193        2203        2213
GCCGAGAACA GCGUGGCCUA CUCCAACAAC UCUAUCGCUA UCCCCACCAA CUUCACCAUC
  A  E  N   S  V  A   Y  S  N  N   S  T  A   I  P  T   N  F  T  I
                              S protein

      2223        2233        2243        2253        2263        2273
AGCGUGACCA CAGAGAUCCU GCCUGUGUCC AUGACCAAGA CCAGCGUGGA CUGCACCAUG
  S  V  T   T  E  T   L  P  V  S   M  T  K   T  S  V   D  C  T  M
                              S protein

      2283        2293        2303        2313        2323        2333
UACAUCUGCG GCGAUUCCAC CGAGUGCUCC AACCUGCUGC UGCAGUACGG CAGCUUCUGC
  Y  I  C   G  D  S   T  E  C  S   N  L  L   L  Q  Y   G  S  F  C
                              S protein

      2343        2353        2363        2373        2383        2393
ACCCAGCUGA AUAGAGCCCU GACAGGGAUC GCCGUGGAAC AGGACAAGAA CACCCAAGAG
  T  Q  L   N  R  A   L  T  G  I   A  V  E   Q  D  K   N  T  Q  E
                              S protein

      2403        2413        2423        2433        2443        2453
GUGUUCGCCC AAGUGAAGCA GAUCUACAAG ACCCCUCCUA UCAAGGACUU CGGCGGCUUC
  V  F  A   Q  V  K   Q  T  Y  K   T  P  P   I  K  D   F  G  G  F
                              S protein

      2463        2473        2483        2493        2503        2513
AAUUUCAGCC AGAUUCUGCC CGAUCCUAGC AAGCCCAGCA AGCGGAGCUU CAUCGAGGAC
  N  F  S   Q  I  L   P  D  P  S   K  P  S   K  R  S   F  I  E  D
                              S protein

      2523        2533        2543        2553        2563        2573
CUGCUGUUCA ACAAAGUGAC ACUGGCCGAC GCCGGCUUCA UCAAGCAGUA UGGCGAUUGU
  L  L  F   N  K  V   T  L  A  D   A  G  F   I  K  Q   Y  G  D  C
                              S protein

      2583        2593        2603        2613        2623        2633
CUGGGCGACA UUGCCGCCAG GGAUCUGAUU UGCGCCCAGA AGUUUAACGG ACUGACAGUG
  L  G  D   I  A  A   R  D  L  I   C  A  Q   K  E  N   G  L  T  V
                              S protein

      2643        2653        2663        2673        2683        2693
CUGCCUCCUC UGCUGACCGA UGAGAUGAUC GCCCAGUACA CAUCUGCCCU GCUGGCCGGC
  L  P  P   L  L  T   D  E  M  I   A  Q  Y   T  S  A   L  L  A  G
                              S protein

      2703        2713        2723        2733        2743        2753
ACAAUCACAA GCGGCUGGAC AUUUGGAGCA GGCGCCGCUC UGCAGAUCCC CUUUGCUAUG
  T  I  T   S  G  W   T  F  G  A   G  A  A   L  Q  I   P  E  A  M
                              S protein

      2763        2773        2783        2793        2803        2813
CAGAUGGCCU ACCGGUUCAA CGGCAUCGGA GUGACCCAGA AUGUGCUGUA CGAGAACCAG
  Q  M  A   Y  R  F   N  G  I  G   V  T  Q   N  V  L   Y  E  N  Q
                              S protein
```

-continued

```
      2823       2833       2843       2853       2863       2873
AAGCUGAUCG CCAACCAGUU CAACAGCGCC AUCGGCAAGA UCCAGGACAG CCUGAGCAGC
  K  L  I   A  N  Q   E  N  S  A   I  G  K   I  Q  D   S  L  S  S
                               S protein

      2883       2893       2903       2913       2923       2933
ACAGCAAGCG CCCUGGGAAA GCUGCAGGAC GUGGUCAACC AGAAUGCCCA GGCACUGAAC
  T  A  S   A  L  G   K  L  Q  D   V  V  N   Q  N  A   Q  A  L  N
                               S protein

      2943       2953       2963       2973       2983       2993
ACCCUGGUCA AGCAGCUGUC CUCCAACUUC GGCGCCAUCA GCUCUGUGCU GAACGAUAUC
  T  L  V   K  Q  L   S  S  N  F   G  A  I   S  S  V   L  N  D  I
                               S protein

      3003       3013       3023       3033       3043       3053
CUGAGCAGAC UGGACCCUCC UGAGGCCGAG GUGCAGAUCG ACAGACUGAU CACAGGCAGA
  L  S  R   L  I  D   P  E  A  E   V  Q  I   D  R  L   I  T  G  R
                               S protein

      3063       3073       3083       3093       3103       3113
CUGCAGAGCC UCCAGACAUA CGUGACCCAG CAGCUGAUCA GAGCCGCCGA GAUUAGAGCC
  L  Q  S   L  Q  T   Y  V  T  Q   Q  L  I   R  A  A   E  I  R  A
                               S protein

      3123       3133       3143       3153       3163       3173
UCUGCCAAUC UGGCCGCCAC CAAGAUGUCU GAGUGUGUGC UGGGCCAGAG CAAGAGAGUG
  S  A  N   L  A  A   T  K  M  S   E  C  V   L  G  Q   S  K  R  V
                               S protein

      3183       3193       3203       3213       3223       3233
GACUUUUGCG GCAAGGGCUA CCACCUGAUG AGCUUCCCUC AGUCUGCCCC UCACGGCGUG
  D  E  C   G  K  G   Y  H  L  M   S  E  P   Q  S  A   P  H  G  V
                               S protein

      3243       3253       3263       3273       3283       3293
GUGUUUCUGC ACGUGACAUA UGUGCCCGCU CAAGAGAAGA AUUUCACCAC CGCUCCAGCC
  V  F  L   H  V  T   Y  V  P  A   Q  E  K   N  F  T   T  A  P  A
                               S protein

      3303       3313       3323       3333       3343       3353
AUCUGCCACG ACGGCAAAGC CCACUUUCCU AGAGAAGGCG UGUUCGUGUC CAACGGCACC
  I  C  H   D  G  K   A  H  F  P   R  E  G   V  F  V   S  N  G  T
                               S protein

      3363       3373       3383       3393       3403       3413
CAUUGGUUCG UGACACAGCG GAACUUCUAC GAGCCCCAGA UCAUCACCAC CGACAACACC
  H  W  F   V  T  Q   R  N  F  Y   E  P  Q   I  T  T   T  D  N  T
                               S protein

      3423       3433       3443       3453       3463       3473
UUCGUGUCUG GCAACUGCGA CGUCGUGAUC GGCAUUGUGA ACAAUACCGU GUACGACCCU
  F  V  S   G  N  C   D  V  V  I   G  I  V   N  N  T   V  Y  D  P
                               S protein

      3483       3493       3503       3513       3523       3533
CUGCAGCCCG AGCUGGACAG CUUCAAAGAG GAACUGGACA AGUACUUUAA GAACCACACA
  L  Q  P   E  L  D   S  F  K  E   E  L  D   K  Y  F   K  N  H  T
                               S protein

      3543       3553       3563       3573       3583       3593
AGCCCCGACG UGGACCUGGG CGAUAUCAGC GGAAUCAAUG CCAGCGUCGU GAACAUCCAG
  S  P  D   V  D  L   G  D  I  S   G  I  N   A  S  V   V  N  I  Q
                               S protein

      3603       3613       3623       3633       3643       3653
AAAGAGAUCG ACCGGCUGAA CGAGGUGGCC AAGAAUCUGA ACGAGAGCCU GAUCGACCUG
  K  E  I   D  R  L   N  E  V  A   K  N  L   N  E  S   L  I  D  L
                               S protein

      3663       3673       3683       3693       3703       3713
CAAGAACUGG GGAAGUACGA GCAGUACAUC AAGUGGCCCU GGUACAUCUG GCUGGGCUUU
  Q  E  L   G  K  Y   E  Q  Y  I   K  W  P   W  Y  I   W  L  G  F
                               S protein

      3723       3733       3743       3753       3763       3773
AUCGCCGGAC UGAUUGCCAU CGUGAUGGUC ACAAUCAUGC UGUGUUGCAU GACCAGCUGC
  I  A  G   L  I  A   I  V  M  V   T  I  M   L  C  C   M  T  S  C
                               S protein
```

-continued

```
      3783       3793       3803       3813       3823       3833
UGUAGCUGCC UGAAGGGCUG UUGUAGCUGU GGCAGCUGCU GCAAGUUCGA CGAGGACGAU
  C  S  C   L  K  G   C  C  S  C   G  S  C   C  K  F   D  E  D  D
                         S protein

      3843       3853       3863       3873  3878
UCUGAGCCCG UGCUGAAGGG CGUGAAACUG CACUACACAU GAUGA
  S  E  P   V  L  K   G  V  K  L   H  Y  T   *  *
                         S protein

      3888       3898       3908       3918       3928       3938
CUCGAGCUGG UACUGCAUGC ACGCAAUGCU AGCUGCCCCU UUCCCGUCCU GGGUACCCCG
                        FI element

      3948       3958       3968       3978       3988       3998
AGUCUCCCCC GACCUCGGGU CCCAGGUAUG CUCCCACCUC CACCUGCCCC ACUCACCACC
                        FI element

      4008       4018       4028       4038       4048       4058
UCUGCUAGUU CCAGACACCU CCCAAGCACG CAGCAAUGCA GCUCAAAACG CUUAGCCUAG
                        FI element

      4068       4078       4088       4098       4108       4118
CCACACCCCC ACGGGAAACA GCAGUGAUUA ACCUUUAGCA AUAAACGAAA GUUUAACUAA
                        FI element

      4128       4138       4148       4158       4168  4173
GCUAUACUAA CCCCAGGGUU GGUCAAUUUC GUGCCAGCCA CACCCUGGAG CUAGC
                        FI element

      4183       4193       4203       4213       4223       4233
AAAAAAAAAA AAAAAAAAAA AAAAAAAAAA GCAUAUGACU AAAAAAAAAA AAAAAAAAAA
                          Poly(A)

      4243       4253       4263       4273       4283
AAAAAAAAAA AAAAAAAAAA AAAAAAAAAA AAAAAAAAAA AAAAAAAAAA
                          Poly(A)
```

Nucleotide Sequence of RBP020.3 (SEQ ID NO: 21; SEQ ID NO: 5)

Nucleotide sequence is shown with individual sequence elements as indicated in bold letters. In addition, the sequence of the translated protein is shown in italic letters below the coding nucleotide sequence (*=stop codon).

```
        10         20         30         40         50  53
AGAAUAAACU AGUAUUCUUC UGGUCCCCAC AGACUCAGAG AGAACCCGCC ACC
                         hAg-Kozak

        63         73         83         93        103        113
AUGUUUGUGU UUCUUGUGCU GCUGCCUCUU GUGUCUUCUC AGUGUGUGGU GAGAUUUCCA
  M  F  V   F  L  V   L  L  P  L   V  S  S   Q  C  V   V  R  F  P
                      RBD (S protein)

       123        133        143        153        163        173
AAUAUUACAA AUCUGUGUCC AUUUGGAGAA GUGUUUAAUG CAACAAGAUU UGCAUCUGUG
  N  I  T   N  L  C   P  F  G  E   V  F  N   A  T  R   F  A  S  V
                      RBD (S protein)

       183        193        203        213        223        233
UAUGCAUGGA AUAGAAAAAG AAUUUCUAAU UGUGUGGCUG AUUAUUCUGU GCUGUAUAAU
  Y  A  W   N  R  K   R  I  S  N   C  V  A   D  Y  S   V  L  Y  N
                      RBD (S protein)

       243        253        263        273        283        293
AGUGCUUCUU UUUCCACAUU UAAAUGUUAU GGAGUGUCUC CAACAAAAUU AAAUGAUUUA
  S  A  S   F  S  T   F  K  C  Y   G  V  S   P  T  K   L  N  D  L
                      RBD (S protein)

       303        313        323        333        343        353
UGUUUUACAA AUGUGUAUGC UGAUUCUUUU GUGAUCAGAG GUGAUGAAGU GAGACAGAUU
  C  F  T   N  V  Y   A  D  S  F   V  I  R   G  D  E   V  R  Q  I
                      RBD (S protein)

       363        373        383        393        403        413
GCCCCCGGAC AGACAGGAAA AAUUGCUGAU UACAAUUACA AACUGCCUGA UGAUUUUACA
  A  P  G   Q  T  G   K  I  A  D   Y  N  Y   K  L  P   D  D  F  T
                      RBD (S protein)
```

-continued

```
       423        433        443        453        463        473
GGAUGUGUGA UUGCUUGGAA UUCUAAUAAU UUAGAUUCUA AAGUGGGAGG AAAUUACAAU
  G  C  V   I  A  W   N  S  N   N  L  D  S   K  V  G   G  N  Y  N
                              RBD (S protein)

       483        493        503        513        523        533
UAUCUGUACA GACUGUUUAG AAAAUCAAAU CUGAAACCUU UUGAAAGAGA UAUUUCAACA
  Y  L  Y   R  L  F   R  K  S  N   L  K  P   F  E  R   D  I  S  T
                              RBD (S protein)

       543        553        563        573        583        593
GAAAUUUAUC AGGCUGGAUC AACACCUUGU AAUGGAGUGG AAGGAUUUAA UUGUUAUUUU
  E  I  Y   Q  A  G   S  T  P  C   N  G  V   E  G  F   N  C  Y  F
                              RBD (S protein)

       603        613        623        633        643        653
CCAUUACAGA GCUAUGGAUU UCAGCCAACC AAUGGUGUGG GAUAUCAGCC AUAUAGAGUG
  P  L  Q   S  Y  G   F  Q  P  T   N  G  V   G  Y  Q   P  Y  R  V
                              RBD (S protein)

       663        673        683        693        703  707
GUGGUGCUGU CUUUUGAACU GCUGCAUGCA CCUGCAACAG UGUGUGGACC UAAA
  V  V  L   S  F  E   L  L  H  A   P  A  T   V  C  G   P  K
                              RBD (S protein)

       717        727      734
GGCUCCCCCG GCUCCGGCUC CGGAUCU
  G  S  P   G  S  G   S  G  S
         GS linker

       744        754        764        774        784        794
GGUUAUAUUC CUGAAGCUCC AAGAGAUGGG CAAGCUUACG UUCGUAAAGA UGGCGAAUGG
  G  Y  I   P  E  A   P  R  D  G   Q  A  Y   V  R  K   D  G  E  W
                                 fibritin

       804        814        824        834        844        854
GUAUUACUUU CUACCUUUUU AGGCCGGUCC CUGGAGGUGC UGUUCCAGGG CCCCGGCUGA
  V  L  L   S  T  F   L  G  R  S   L  E  V   L  F  Q   G  P  G  *
                                 fibritin

857
UGA
  *
fibritin

       867        877        887        897        907        917
CUCGAGCUGG UACUGCAUGC ACGCAAUGCU AGCUGCCCCU UUCCCGUCCU GGGUACCCCG
                                FI element

       927        937        947        957        967        977
AGUCUCCCCC GACCUCGGGU CCCAGGUAUG CUCCCACCUC CACCUGCCCC ACUCACCACC
                                FI element

       987        997       1007       1017       1027       1037
UCUGCUAGUU CCAGACACCU CCCAAGCACG CAGCAAUGCA GCUCAAAACG CUUAGCCUAG
                                FI element

      1047       1057       1067       1077       1087       1097
CCACACCCCC ACGGGAAACA GCAGUGAUUA ACCUUUAGCA AUAAACGAAA GUUUAACUAA
                                FI element

      1107       1117       1127       1137       1147  1152
GCUAUACUAA CCCCAGGGUU GGUCAAUUUC GUGCCAGCCA CACCCUGGAG CUAGC
                                FI element

      1162       1172       1182       1192       1202       1212
AAAAAAAAAA AAAAAAAAAA AAAAAAAAAA GCAUAUGACU AAAAAAAAAA AAAAAAAAAA
                                 Poly(A)

      1222       1232       1242       1252       1262
AAAAAAAAAA AAAAAAAAAA AAAAAAAAAA AAAAAAAAAA AAAAAAAAAA
                                 Poly(A)
```

Further embodiments of the nucleoside modified messenger RNA (modRNA) platform are as follows:

BNT162b3c (SEQ ID NO: 29; SEQ ID NO: 30)

Structure $m_2^{7,3'-O}$Gppp($m_1^{2'-O}$)ApG-hAg-Kozak-RBD-GS-Fibritin-GS-TM-FI-A30L70

Encoded antigen Viral spike protein (S1S2 protein) of the SARS-CoV-2 (partial sequence, Receptor Binding Domain (RBD) of S1S2 protein fused to Fibritin fused to Transmembrane Domain™ of S1S2 protein); intrinsic S1S2 protein secretory signal peptide (aa 1-19) at the N-terminus of the antigen sequence

```
agaauaaacu aguauucuuc uggucccac agacucagag agaacccgcc acc aug       56
                                                         Met
                                                         1

uuu gug uuu cuu gug cug cug ccu cuu gug ucu ucu cag ugu gug aau      104
Phe Val Phe Leu Val Leu Leu Pro Leu Val Ser Ser Gln Cys Val Asn
            5                   10                  15

uug aca gug aga uuu cca aau auu aca aau cug ugu cca uuu gga gaa      152
Leu Thr Val Arg Phe Pro Asn Ile Thr Asn Leu Cys Pro Phe Gly Glu
        20                  25                  30

gug uuu aau gca aca aga uuu gca ucu gug uau gca ugg aau aga aaa      200
Val Phe Asn Ala Thr Arg Phe Ala Ser Val Tyr Ala Trp Asn Arg Lys
    35                  40                  45

aga auu ucu aau ugu gug gcu gau uau ucu gug cug uau aau agu gcu      248
Arg Ile Ser Asn Cys Val Ala Asp Tyr Ser Val Leu Tyr Asn Ser Ala
50                  55                  60                  65

ucu uuu ucc aca uuu aaa ugu uau gga gug ucu cca aca aaa uua aau      296
Ser Phe Ser Thr Phe Lys Cys Tyr Gly Val Ser Pro Thr Lys Leu Asn
                70                  75                  80

gau uua ugu uuu aca aau gug uau gcu gau ucu uuu gug auc aga ggu      344
Asp Leu Cys Phe Thr Asn Val Tyr Ala Asp Ser Phe Val Ile Arg Gly
            85                  90                  95

gau gaa gug aga cag auu gcc ccc gga cag aca gga aaa auu gcu gau      392
Asp Glu Val Arg Gln Ile Ala Pro Gly Gln Thr Gly Lys Ile Ala Asp
        100                 105                 110

uac aau uac aaa cug ccu gau gau uuu aca gga ugu gug auu gcu ugg      440
Tyr Asn Tyr Lys Leu Pro Asp Asp Phe Thr Gly Cys Val Ile Ala Trp
    115                 120                 125

aau ucu aau aau uua gau ucu aaa gug gga gga aau uac aau uau cug      488
Asn Ser Asn Asn Leu Asp Ser Lys Val Gly Gly Asn Tyr Asn Tyr Leu
130                 135                 140                 145

uac aga cug uuu aga aaa uca aau cug aaa ccu uuu gaa aga gau auu      536
Tyr Arg Leu Phe Arg Lys Ser Asn Leu Lys Pro Phe Glu Arg Asp Ile
                150                 155                 160

uca aca gaa auu uau cag gcu gga uca aca ccu ugu aau gga gug gaa      584
Ser Thr Glu Ile Tyr Gln Ala Gly Ser Thr Pro Cys Asn Gly Val Glu
            165                 170                 175

gga uuu aau ugu uau uuu cca uua cag agc uau gga uuu cag cca acc      632
Gly Phe Asn Cys Tyr Phe Pro Leu Gln Ser Tyr Gly Phe Gln Pro Thr
        180                 185                 190

aau ggu gug gga uau cag cca uau aga gug gug gug cug ucu uuu gaa      680
Asn Gly Val Gly Tyr Gln Pro Tyr Arg Val Val Val Leu Ser Phe Glu
    195                 200                 205

cug cug cau gca ccu gca aca gug ugu gga ccu aaa ggc ucc ccc ggc      728
Leu Leu His Ala Pro Ala Thr Val Cys Gly Pro Lys Gly Ser Pro Gly
210                 215                 220                 225

ucc ggc ucc gga ucu ggu uau auu ccu gaa gcu cca aga gau ggg caa      776
Ser Gly Ser Gly Ser Gly Tyr Ile Pro Glu Ala Pro Arg Asp Gly Gln
                230                 235                 240

gcu uac guu cgu aaa gau ggc gaa ugg gua uua cuu ucu acc uuu uua      824
Ala Tyr Val Arg Lys Asp Gly Glu Trp Val Leu Leu Ser Thr Phe Leu
            245                 250                 255

gga agc ggc agc gga ucu gaa cag uac auu aaa ugg ccu ugg uac auu      872
Gly Ser Gly Ser Gly Ser Glu Gln Tyr Ile Lys Trp Pro Trp Tyr Ile
        260                 265                 270

ugg cuu gga uuu auu gca gga uua auu gca auu gug aug gug aca auu      920
Trp Leu Gly Phe Ile Ala Gly Leu Ile Ala Ile Val Met Val Thr Ile
    275                 280                 285

aug uua ugu ugu aug aca uca ugu ugu ucu ugu uua aaa gga ugu ugu      968
Met Leu Cys Cys Met Thr Ser Cys Cys Ser Cys Leu Lys Gly Cys Cys
290                 295                 300                 305
```

-continued

```
ucu ugu gga agc ugu ugu uga ugacucgagc ugguacugca ugcacgcaau        1019
Ser Cys Gly Ser Cys Cys
                310

gcuagcugcc ccuuucccgu ccuggguacc ccgagucucc cccgaccucg ggucccaggu   1079

augcucccac cuccaccugc cccacucacc accucugcua guuccagaca ccucccaagc   1139

acgcagcaau gcagcucaaa acgcuuagcc uagccacacc cccacgggaa acagcaguga   1199

uuaaccuuua gcaauaaacg aaaguuuaac uaagcuauac uaaccccagg guuggucaau   1259

uucgugccag ccacacccug gagcuagcaa aaaaaaaaaa aaaaaaaaaa aaaaaaaagc   1319

auaugacuaa aaaaaaaaaa aaaaaaaaaa aaaaaaaaaa aaaaaaaaaa aaaaaaaaaa   1379

aaaaaaaaaa aaaaaaaa                                                 1397
```

BNT162b3d (SEQ ID NO: 31; SEQ ID NO: 32)

Structure $m_2^{7,3'-O}$ Gppp($m_1^{2'-O}$)ApG-hAg-Kozak-RBD-GS-Fibritin-GS-TM-F1-A30L70 Encoded antigen Viral spike protein (S1S2 protein) of the SARS-CoV-2 (partial sequence, Receptor Binding Domain (RBD) of S1S2 protein fused to Fibritin fused to Transmembrane Domain™ of S1S2 protein); immunoglobulin secretory signal peptide (aa 1-22) at the N-terminus of the antigen sequence

```
agaauaaacu aguauucuuc ugguccccac agacucagag agaacccgcc acc aug       56
                                                            Met
                                                            1

gau ugg auu ugg aga auc cug uuc cuc gug gga gcc gcu aca gga gcc      104
Asp Trp Ile Trp Arg Ile Leu Phe Leu Val Gly Ala Ala Thr Gly Ala
            5                   10                  15

cac ucc cag aug cag gug aga uuu cca aau auu aca aau cug ugu cca      152
His Ser Gln Met Gln Val Arg Phe Pro Asn Ile Thr Asn Leu Cys Pro
        20                  25                  30

uuu gga gaa gug uuu aau gca aca aga uuu gca ucu gug uau gca ugg      200
Phe Gly Glu Val Phe Asn Ala Thr Arg Phe Ala Ser Val Tyr Ala Trp
    35                  40                  45

aau aga aaa aga auu ucu aau ugu gug gcu gau uau ucu gug cug uau      248
Asn Arg Lys Arg Ile Ser Asn Cys Val Ala Asp Tyr Ser Val Leu Tyr
50                  55                  60                  65

aau agu gcu ucu uuu ucc aca uuu aaa ugu uau gga gug ucu cca aca      296
Asn Ser Ala Ser Phe Ser Thr Phe Lys Cys Tyr Gly Val Ser Pro Thr
                70                  75                  80

aaa uua aau gau uua ugu uuu aca aau gug uau gcu gau ucu uuu gug      344
Lys Leu Asn Asp Leu Cys Phe Thr Asn Val Tyr Ala Asp Ser Phe Val
            85                  90                  95

auc aga ggu gau gaa gug aga cag auu gcc ccc gga cag aca gga aaa      392
Ile Arg Gly Asp Glu Val Arg Gln Ile Ala Pro Gly Gln Thr Gly Lys
        100                 105                 110

auu gcu gau uac aau uac aaa cug ccu gau gau uuu aca gga ugu gug      440
Ile Ala Asp Tyr Asn Tyr Lys Leu Pro Asp Asp Phe Thr Gly Cys Val
    115                 120                 125

auu gcu ugg aau ucu aau aau uua gau ucu aaa gug gga gga aau uac      488
Ile Ala Trp Asn Ser Asn Asn Leu Asp Ser Lys Val Gly Gly Asn Tyr
130                 135                 140                 145

aau uau cug uac aga cug uuu aga aaa uca aau cug aaa ccu uuu gaa      536
Asn Tyr Leu Tyr Arg Leu Phe Arg Lys Ser Asn Leu Lys Pro Phe Glu
                150                 155                 160

aga gau auu uca aca gaa auu uau cag gcu gga uca aca ccu ugu aau      584
Arg Asp Ile Ser Thr Glu Ile Tyr Gln Ala Gly Ser Thr Pro Cys Asn
            165                 170                 175

gga gug gaa gga uuu aau ugu uau uuu cca uua cag agc uau gga uuu      632
Gly Val Glu Gly Phe Asn Cys Tyr Phe Pro Leu Gln Ser Tyr Gly Phe
        180                 185                 190
```

-continued

```
cag cca acc aau ggu gug gga uau cag cca uau aga gug gug gug cug      680
Gln Pro Thr Asn Gly Val Gly Tyr Gln Pro Tyr Arg Val Val Val Leu
    195                 200                 205

ucu uuu gaa cug cug cau gca ccu gca aca gug ugu gga ccu aaa ggc      728
Ser Phe Glu Leu Leu His Ala Pro Ala Thr Val Cys Gly Pro Lys Gly
210                 215                 220                 225

ucc ccc ggc ucc ggc ucc gga ucu ggu uau auu ccu gaa gcu cca aga      776
Ser Pro Gly Ser Gly Ser Gly Ser Gly Tyr Ile Pro Glu Ala Pro Arg
                230                 235                 240

gau ggg caa gcu uac guu cgu aaa gau ggc gaa ugg gua uua cuu ucu      824
Asp Gly Gln Ala Tyr Val Arg Lys Asp Gly Glu Trp Val Leu Leu Ser
            245                 250                 255

acc uuu uua gga agc ggc agc gga ucu gaa cag uac auu aaa ugg ccu      872
Thr Phe Leu Gly Ser Gly Ser Gly Ser Glu Gln Tyr Ile Lys Trp Pro
        260                 265                 270

ugg uac auu ugg cuu gga uuu auu gca gga uua auu gca auu gug aug      920
Trp Tyr Ile Trp Leu Gly Phe Ile Ala Gly Leu Ile Ala Ile Val Met
    275                 280                 285

gug aca auu aug uua ugu ugu aug aca uca ugu ugu ucu ugu uua aaa      968
Val Thr Ile Met Leu Cys Cys Met Thr Ser Cys Cys Ser Cys Leu Lys
290                 295                 300                 305

gga ugu ugu ucu ugu gga agc ugu ugu uga ugacucgagc ugguacugca       1018
Gly Cys Cys Ser Cys Gly Ser Cys Cys
                310

ugcacgcaau gcuagcugcc ccuuucccgu ccuggguacc ccgagucucc cccgaccucg   1078

ggucccaggu augcucccac cuccaccugc cccacucacc accucugcua guuccagaca   1138

ccucccaagc acgcagcaau gcagcucaaa acgcuuagcc uagccacacc cccacgggaa   1198

acagcaguga uuaaccuuua gcaauaaacg aaaguuuaac uaagcuauac uaaccccagg   1258

guuggucaau uucgugccag ccacacccug gagcuagcaa aaaaaaaaaa aaaaaaaaaa   1318

aaaaaaaagc auaugacuaa aaaaaaaaaa aaaaaaaaaa aaaaaaaaaa aaaaaaaaaa   1378

aaaaaaaaaa aaaaaaaaaa aaaaaaaa                                      1406
```

Self-Amplifying RNA (saRNA)

The active principle of the self-amplifying mRNA (saRNA) drug substance is a single-stranded RNA, which self-amplifies upon entering a cell, and the coronavirus vaccine antigen is translated thereafter. In contrast to uRNA and modRNA that preferably code for a single protein, the coding region of saRNA contains two open reading frames (ORFs). The 5'-ORF encodes the RNA-dependent RNA polymerase such as Venezuelan equine encephalitis virus (VEEV) RNA-dependent RNA polymerase (replicase). The replicase ORF is followed 3' by a subgenomic promoter and a second ORF encoding the antigen. Furthermore, saRNA UTRs contain 5' and 3' conserved sequence elements (CSEs) required for self-amplification. The saRNA contains common structural elements optimized for maximal efficacy of the RNA as the uRNA (5'-cap, 5'-UTR, 3'-UTR, poly(A)-tail). The saRNA preferably contains uridine. The preferred 5' cap structure is beta-S-ARCA(D1) ($m_2^{7,2'-O}$GppSpG).

Cytoplasmic delivery of saRNA initiates an alphavirus-like life cycle. However, the saRNA does not encode for alphaviral structural proteins that are required for genome packaging or cell entry, therefore generation of replication competent viral particles is very unlikely to not possible. Replication does not involve any intermediate steps that generate DNA. The use/uptake of saRNA therefore poses no risk of genomic integration or other permanent genetic modification within the target cell. Furthermore, the saRNA itself prevents its persistent replication by effectively activating innate immune response via recognition of dsRNA intermediates.

Different embodiment of this platform are as follows:

RBS004.1 (SEQ ID NO: 24; SEQ ID NO: 7)

Structure beta-S-ARCA(D1)-replicase-S1S2-PP-FI-A30L70

Encoded antigen Viral spike protein (S protein) of the SARS-CoV-2 (S1S2 full-length protein, sequence variant)

RBS004.2 (SEQ ID NO: 25; SEQ ID NO: 7)

Structure beta-S-ARCA(D1)-replicase-S1S2-PP-FI-A30L70

Encoded antigen Viral spike protein (S protein) of the SARS-CoV-2 (S1S2 full-length protein, sequence variant)

BNT162c1; RBS004.3 (SEQ ID NO: 26; SEQ ID NO: 5)

Structure beta-S-ARCA(D1)-replicase-RBD-GS-Fibritin-FI-A30L70

Encoded antigen Viral spike protein (S protein) of the SARS-CoV-2 (partial sequence, Receptor Binding Domain (RBD) of S1S2 protein)

RBS004.4 (SEQ ID NO: 27; SEQ ID NO: 28)

Structure beta-S-ARCA(D1)-replicase-RBD-GS-Fibritin-TM-FI-A30L70

Encoded antigen Viral spike protein (S protein) of the SARS-CoV-2 (partial sequence, Receptor Binding Domain (RBD) of S1S2 protein)

FIG. 21 schematizes the general structure of the antigen-encoding RNAs.

Nucleotide Sequence of RBS004.1 (SEQ ID NO: 24; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40    45
GAUGGGCGGC GCAUGAGAGA AGCCCAGACC AAUUACCUAC CCAAA
                                5' UTR

        55         65         75         85         95        105
AUGGAGAAAG UUCACGUUGA CAUCGAGGAA GACAGCCCAU UCCUCAGAGC UUUGCAGCGG
  M  E  K   V  H  V   D  I  E  E   D  S  P   F  L  R   A  L  Q  R
                                 nsp1

       115        125        135        145        155        165
AGCUUCCCGC AGUUUGAGGU AGAAGCCAAG CAGGUCACUG AUAAUGACCA UGCUAAUGCC
  S  F  P   Q  F  E   V  E  A  K   Q  V  T   D  N  D   H  A  N  A
                                 nsp1

       175        185        195        205        215        225
AGAGCGUUUU CGCAUCUGGC UUCAAAACUG AUCGAAACGG AGGUGGACCC AUCCGACACG
  R  A  F   S  H  L   A  S  K  L   I  E  T   E  V  D   P  S  D  T
                                 nsp1

       235        245        255        265        275        285
AUCCUUGACA UUGGAAGUGC GCCCGCCCGC AGAAUGUAUU CUAAGCACAA GUAUCAUUGU
  I  L  D   I  G  S   A  P  A  R   R  M  Y   S  K  H   K  Y  H  C
                                 nsp1

       295        305        315        325        335        345
AUCUGUCCGA UGAGAUGUGC GGAAGAUCCG GACAGAUUGU AUAAGUAUGC AACUAAGCUG
  I  C  P   M  R  C   A  E  D  P   D  R  L   Y  K  Y   A  T  K  L
                                 nsp1

       355        365        375        385        395        405
AAGAAAAACU GUAAGGAAAU AACUGAUAAG GAAUUGGACA AGAAAAUGAA GGAGCUCGCC
  K  K  N   C  K  E   I  T  D  K   E  L  D   K  K  M   K  E  L  A
                                 nsp1

       415        425        435        445        455        465
GCCGUCAUGA GCGACCCUGA CCUGGAAACU GAGACUAUGU GCCUCCACGA CGACGAGUCG
  A  V  M   S  D  P   D  L  E  T   E  T  M   C  L  H   D  D  E  S
                                 nsp1

       475        485        495        505        515        525
UGUCGCUACG AAGGGCAAGU CGCUGUUUAC CAGGAUGUAU ACGCGGUUGA CGGACCGACA
  C  R  Y   E  G  Q   V  A  V  Y   Q  D  V   Y  A  V   D  G  P  T
                                 nsp1

       535        545        555        565        575        585
AGUCUCUAUC ACCAAGCCAA UAAGGGAGUU AGAGUCGCCU ACUGGAUAGG CUUUGACACC
  S  L  Y   H  Q  A   N  K  G  V   R  V  A   Y  W  I   G  F  D  T
                                 nsp1

       595        605        615        625        635        645
ACCCCUUUUA UGUUUAAGAA CUUGGCUGGA GCAUAUCCAU CAUACUCUAC CAACUGGGCC
  T  P  F   M  F  K   N  L  A  G   A  Y  P   S  Y  S   T  N  W  A
                                 nsp1

       655        665        675        685        695        705
GACGAAACCG UGUUAACGGC UCGUAACAUA GGCCUAUGCA GCUCUGACGU UAUGGAGCGG
  D  E  T   V  L  T   A  R  N  I   G  L  C   S  S  D   V  M  E  R
                                 nsp1

       715        725        735        745        755        765
UCACGUAGAG GGAUGUCCAU UCUUAGAAAG AAGUAUUUGA AACCAUCCAA CAAUGUUCUA
  S  R  R   G  M  S   I  L  R  K   K  Y  L   K  P  S   N  N  V  L
                                 nsp1

       775        785        795        805        815        825
UUCUCUGUUG GCUCGACCAU CUACCACGAA AAGAGGGACU UACUGAGGAG CUGGCACCUG
  F  S  V   G  S  T   I  Y  H  E   K  R  D   L  L  R   S  W  H  L
                                 nsp1

       835        845        855        865        875        885
CCGUCUGUAU UUCACUUACG UGGCAAGCAA AAUUACACAU GUCGGUGUGA GACUAUAGUU
  P  S  V   F  H  L   R  G  K  Q   N  Y  T   C  R  C   E  T  I  V
                                 nsp1
```

-continued

```
       895        905        915        925        935        945
AGUUGCGACG GGUACGUCGU UAAAAGAAUA GCUAUCAGUC CAGGCCUGUA UGGGAAGCCU
  S  C  D   G  Y  V   V  K  R  I   A  I  S   P  G  L   Y  G  K  P
                                 nsp1

       955        965        975        985        995       1005
UCAGGCUAUG CUGCUACGAU GCACCGCGAG GGAUUCUUGU GCUGCAAAGU GACAGACACA
  S  G  Y   A  A  T   M  H  R  E   G  F  L   C  C  K   V  T  D  T
                                 nsp1

      1015       1025       1035       1045       1055       1065
UUGAACGGGG AGAGGGUCUC UUUUCCCGUG UGCACGUAUG UGCCAGCUAC AUUGUGUGAC
  L  N  G   E  R  V   S  F  P  V   C  T  Y   V  P  A   T  L  C  D
                                 nsp1

      1075       1085       1095       1105       1115       1125
CAAAUGACUG GCAUACUGGC AACAGAUGUC AGUGCGGACG ACGCGCAAAA ACUGCUGGUU
  Q  M  T   G  I  L   A  T  D  V   S  A  D   D  A  Q   K  L  L  V
                                 nsp1

      1135       1145       1155       1165       1175       1185
GGGCUCAACC AGCGUAUAGU CGUCAACGGU CGCACCCAGA GAAACACCAA UACCAUGAAA
  G  L  N   Q  R  I   V  V  N  G   R  T  Q   R  N  T   N  T  M  K
                                 nsp1

      1195       1205       1215       1225       1235       1245
AAUUACCUUU UGCCCGUAGU GGCCCAGGCA UUUGCUAGGU GGGCAAAGGA AUAUAAGGAA
  N  Y  L   L  P  V   V  A  Q  A   F  A  R   W  A  K   E  Y  K  E
                                 nsp1

      1255       1265       1275       1285       1295       1305
GAUCAAGAAG AUGAAAGGCC ACUAGGACUA CGAGAUAGAC AGUUAGUCAU GGGGUGUUGU
  D  Q  E   D  E  R   P  L  G  L   R  D  R   Q  L  V   M  G  C  C
                                 nsp1

      1315       1325       1335       1345       1355       1365
UGGGCUUUUA GAAGGCACAA GAUAACAUCU AUUUAUAAGC GCCCGGAUAC CCAAACCAUC
  W  A  F   R  R  H   K  I  T  S   I  Y  K   R  P  D   T  Q  T  I
                                 nsp1

      1375       1385       1395       1405       1415       1425
AUCAAAGUGA ACAGCGAUUU CCACUCAUUC GUGCUGCCCA GGAUAGGCAG UAACACAUUG
  I  K  V   N  S  D   F  H  S  F   V  L  P   R  I  G   S  N  T  L
                                 nsp1

      1435       1445       1455       1465       1475       1485
GAGAUCGGGC UGAGAACAAG AAUCAGGAAA AUGUUAGAGG AGCACAAGGA GCCGUCACCU
  E  I  G   L  R  T   R  I  R  K   M  L  E   E  H  K   E  P  S  P
                                 nsp1

      1495       1505       1515       1525       1535       1545
CUCAUUACCG CCGAGGACGU ACAAGAAGCU AAGUGCGCAG CCGAUGAGGC UAAGGAGGUG
  L  I  T   A  E  D   V  Q  E  A   K  C  A   A  D  E   A  K  E  V
                                 nsp1

      1555       1565       1575       1585       1595       1605
CGUGAAGCCG AGGAGUUGCG CGCAGCUCUA CCACCUUUGG CAGCUGAUGU UGAGGAGCCC
  R  E  A   E  E  L   R  A  A  L   P  P  L   A  A  D   V  E  E  P
                                 nsp1

      1615       1625       1635       1645  1650
ACUCUGGAAG CCGAUGUCGA CUUGAUGUUA CAAGAGGCUG GGGCC
  T  L  E   A  D  V   D  L  M  L   Q  E  A   G  A
                                 nsp1

      1660       1670       1680       1690       1700       1710
GGCUCAGUGG AGACACCUCG UGGCUUGAUA AAGGUUACCA GCUACGCUGG CGAGGACAAG
  G  S  V   E  T  P   R  G  L  I   K  V  T   S  Y  A   G  E  D  K
                                 nsp2

      1720       1730       1740       1750       1760       1770
AUCGGCUCUU ACGCUGUGCU UUCUCCGCAG GCUGUACUCA AGAGUGAAAA AUUAUCUUGC
  I  G  S   Y  A  V   L  S  P  Q   A  V  L   K  S  E   K  L  S  C
                                 nsp2

      1780       1790       1800       1810       1820       1830
AUCCACCCUC UCGCUGAACA AGUCAUAGUG AUAACACACU CUGGCCGAAA AGGGCGUUAU
  I  H  P   L  A  E   Q  V  I  V   I  T  H   S  G  R   K  G  R  Y
                                 nsp2
```

-continued

```
      1840       1850       1860       1870       1880       1890
GCCGUGGAAC CAUACCAUGG UAAAGUAGUG GUGCCAGAGG GACAUGCAAU ACCCGUCCAG
  A  V  E   P  Y  H   G  K  V  V   V  P  E   G  H  A   I  P  V  Q
                                nsp2

      1900       1910       1920       1930       1940       1950
GACUUUCAAG CUCUGAGUGA AAGUGCCACC AUUGUGUACA ACGAACGUGA GUUCGUAAAC
  D  F  Q   A  L  S   E  S  A  T   I  V  Y   N  E  R   E  F  V  N
                                nsp2

      1960       1970       1980       1990       2000       2010
AGGUACCUGC ACCAUAUUGC CACACAUGGA GGAGCGCUGA ACACUGAUGA AGAAUAUUAC
  R  Y  L   H  H  I   A  T  H  G   G  A  L   N  T  D   E  E  Y  Y
                                nsp2

      2020       2030       2040       2050       2060       2070
AAAACUGUCA AGCCCAGCGA GCACGACGGC GAAUACCUGU ACGACAUCGA CAGGAAACAG
  K  T  V   K  P  S   E  H  D  G   E  Y  L   Y  D  I   D  R  K  Q
                                nsp2

      2080       2090       2100       2110       2120       2130
UGCGUCAAGA AAGAGCUAGU CACUGGGCUA GGGCUCACAG GCGAGCUGGU CGAUCCUCCC
  C  V  K   K  E  L   V  T  G  L   G  L  T   G  E  L   V  D  P  P
                                nsp2

      2140       2150       2160       2170       2180       2190
UUCCAUGAAU UCGCCUACGA GAGUCUGAGA ACACGACCAG CCGCUCCUUA CCAAGUACCA
  F  H  E   F  A  Y   E  S  L  R   T  R  P   A  A  P   Y  Q  V  P
                                nsp2

      2200       2210       2220       2230       2240       2250
ACCAUAGGGG UGUAUGGCGU GCCAGGAUCA GGCAAGUCUG GCAUCAUUAA AAGCGCAGUC
  T  I  G   V  Y  G   V  P  G  S   G  K  S   G  I  I   K  S  A  V
                                nsp2

      2260       2270       2280       2290       2300       2310
ACCAAAAAAG AUCUAGUGGU GAGCGCCAAG AAAGAAAACU GUGCAGAAAU UAUAAGGGAC
  T  K  K   D  L  V   V  S  A  K   K  E  N   C  A  E   I  I  R  D
                                nsp2

      2320       2330       2340       2350       2360       2370
GUCAAGAAAA UGAAAGGGCU GGACGUCAAU GCCAGAACUG UGGACUCAGU GCUCUUGAAU
  V  K  K   M  K  G   L  D  V  N   A  R  T   V  D  S   V  L  L  N
                                nsp2

      2380       2390       2400       2410       2420       2430
GGAUGCAAAC ACCCCGUAGA GACCCUGUAU AUUGACGAGG CUUUUGCUUG UCAUGCAGGU
  G  C  K   H  P  V   E  T  L  Y   I  D  E   A  F  A   C  H  A  G
                                nsp2

      2440       2450       2460       2470       2480       2490
ACUCUCAGAG CGCUCAUAGC CAUUAUAAGA CCUAAAAAGG CAGUGCUCUG CGGAGAUCCC
  T  L  R   A  L  I   A  I  I  R   P  K  K   A  V  L   C  G  D  P
                                nsp2

      2500       2510       2520       2530       2540       2550
AAACAGUGCG GUUUUUUUAA CAUGAUGUGC CUGAAAGUGC AUUUUAACCA CGAGAUUUGC
  K  Q  C   G  F  F   N  M  M  C   L  K  V   H  F  N   H  E  I  C
                                nsp2

      2560       2570       2580       2590       2600       2610
ACACAAGUCU UCCACAAAAG CAUCUCUCGC CGUUGCACUA AAUCUGUGAC UUCGGUCGUC
  T  Q  V   F  H  K   S  I  S  R   R  C  T   K  S  V   T  S  V  V
                                nsp2

      2620       2630       2640       2650       2660       2670
UCAACCUUGU UUUACGACAA AAAAAUGAGA ACGACGAAUC CGAAAGAGAC UAAGAUUGUG
  S  T  L   F  Y  D   K  K  M  R   T  T  N   P  K  E   T  K  I  V
                                nsp2

      2680       2690       2700       2710       2720       2730
AUUGACACUA CCGGCAGUAC CAAACCUAAG CAGGACGAUC UCAUUCUCAC UUGUUUCAGA
  I  D  T   T  G  S   T  K  P  K   Q  D  D   L  I  L   T  C  F  R
                                nsp2

      2740       2750       2760       2770       2780       2790
GGGUGGGUGA AGCAGUUGCA AAUAGAUUAC AAAGGCAACG AAAUAAUGAC GGCAGCUGCC
  G  W  V   K  Q  L   Q  I  D  Y   K  G  N   E  I  M   T  A  A  A
                                nsp2
```

-continued

```
      2800       2810       2820       2830       2840       2850
UCUCAAGGGC UGACCCGUAA AGGUGUGUAU GCCGUUCGGU ACAAGGUGAA UGAAAAUCCU
  S  Q  G   L  T  R   K  G  V  Y   A  V  R   Y  K  V   N  E  N  P
                                nsp2

      2860       2870       2880       2890       2900       2910
CUGUACGCAC CCACCUCAGA ACAUGUGAAC GUCCUACUGA CCCGCACGGA GGACCGCAUC
  L  Y  A   P  T  S   E  H  V  N   V  L  L   T  R  T   E  D  R  I
                                nsp2

      2920       2930       2940       2950       2960       2970
GUGUGGAAAA CACUAGCCGG CGACCCAUGG AUAAAAACAC UGACUGCCAA GUACCCUGGG
  V  W  K   T  L  A   G  D  P  W   I  K  T   L  T  A   K  Y  P  G
                                nsp2

      2980       2990       3000       3010       3020       3030
AAUUUCACUG CCACGAUAGA GGAGUGGCAA GCAGAGCAUG AUGCCAUCAU GAGGCACAUC
  N  F  T   A  T  I   E  E  W  Q   A  E  H   D  A  I   M  R  H  I
                                nsp2

      3040       3050       3060       3070       3080       3090
UUGGAGAGAC CGGACCCUAC CGACGUCUUC CAGAAUAAGG CAAACGUGUG UUGGGCCAAG
  L  E  R   P  D  P   T  D  V  F   Q  N  K   A  N  V   C  W  A  K
                                nsp2

      3100       3110       3120       3130       3140       3150
GCUUUAGUGC CGGUGCUGAA GACCGCUGGC AUAGACAUGA CCACUGAACA AUGGAACACU
  A  L  V   P  V  L   K  T  A  G   I  D  M   T  T  E   Q  W  N  T
                                nsp2

      3160       3170       3180       3190       3200       3210
GUGGAUUAUU UUGAAACGGA CAAAGCUCAC UCAGCAGAGA UAGUAUUGAA CCAACUAUGC
  V  D  Y   F  E  T   D  K  A  H   S  A  E   I  V  L   N  Q  L  C
                                nsp2

      3220       3230       3240       3250       3260       3270
GUGAGGUUCU UUGGACUCGA UCUGGACUCC GGUCUAUUUU CUGCACCCAC UGUUCCGUUA
  V  R  F   F  G  L   D  L  D  S   G  L  F   S  A  P   T  V  P  L
                                nsp2

      3280       3290       3300       3310       3320       3330
UCCAUUAGGA AUAAUCACUG GGAUAACUCC CCGUCGCCUA ACAUGUACGG GCUGAAUAAA
  S  I  R   N  N  H   W  D  N  S   P  S  P   N  M  Y   G  L  N  K
                                nsp2

      3340       3350       3360       3370       3380       3390
GAAGUGGUCC GUCAGCUCUC UCGCAGGUAC CCACAACUGC CUCGGGCAGU UGCCACUGGU
  E  V  V   R  Q  L   S  R  R  Y   P  Q  L   P  R  A   V  A  T  G
                                nsp2

      3400       3410       3420       3430       3440       3450
AGAGUCUAUG ACAUGAACAC UGGUACACUG CGCAAUUAUG AUCCGCGCAU AAACCUAGUA
  R  V  Y   D  M  N   T  G  T  L   R  N  Y   D  P  R   I  N  L  V
                                nsp2

      3460       3470       3480       3490       3500       3510
CCUGUAAACA GAAGACUGCC UCAUGCUUUA GUCCUCCACC AUAAUGAACA CCCACAGAGU
  P  V  N   R  R  L   P  H  A  L   V  L  H   H  N  E   H  P  Q  S
                                nsp2

      3520       3530       3540       3550       3560       3570
GACUUUUCUU CAUUCGUCAG CAAAUUGAAG GGCAGAACUG UCCUGGUGGU CGGGGAAAAG
  D  F  S   S  F  V   S  K  L  K   G  R  T   V  L  V   V  G  E  K
                                nsp2

      3580       3590       3600       3610       3620       3630
UUGUCCGUCC CAGGCAAAAU GGUUGACUGG UUGUCAGACC GGCCUGAGGC UACCUUCAGA
  L  S  V   P  G  K   M  V  D  W   L  S  D   R  P  E   A  T  F  R
                                nsp2

      3640       3650       3660       3670       3680       3690
GCUCGGCUGG AUUUAGGCAU CCCAGGUGAU GUGCCCAAAU AUGACAUAAU AUUUGUUAAU
  A  R  L   D  L  G   I  P  G  D   V  P  K   Y  D  I   I  F  V  N
                                nsp2

      3700       3710       3720       3730       3740       3750
GUGAGGACCC CAUAUAAAUA CCAUCACUAU CAGCAGUGUG AAGACCAUGC CAUUAAGCUA
  V  R  T   P  Y  K   Y  H  H  Y   Q  Q  C   E  D  H   A  I  K  L
                                nsp2
```

-continued

```
      3760       3770       3780       3790       3800       3810
AGCAUGUUGA CCAAGAAAGC AUGUCUGCAU CUGAAUCCCG GCGGAACCUG UGUCAGCAUA
  S  M  L   T  K  K   A  C  L  H   L  N  P   G  G  T   C  V  S  I
                               nsp2

      3820       3830       3840       3850       3860       3870
GGUUAUGGUU ACGCUGACAG GGCCAGCGAA AGCAUCAUUG GUGCUAUAGC GCGGCAGUUC
  G  Y  G   Y  A  D   R  A  S  E   S  I  I   G  A  I   A  R  Q  F
                               nsp2

      3880       3890       3900       3910       3920       3930
AAGUUUUCCC GAGUAUGCAA ACCGAAAUCC UCACUUGAGG AGACGGAAGU UCUGUUUGUA
  K  F  S   R  V  C   K  P  K  S   S  L  E   E  T  E   V  L  F  V
                               nsp2

      3940       3950       3960       3970       3980       3990
UUCAUUGGGU ACGAUCGCAA GGCCCGUACG CACAAUCCUU ACAAGCUAUC AUCAACCUUG
  F  I  G   Y  D  R   K  A  R  T   H  N  P   Y  K  L   S  S  T  L
                               nsp2

      4000       4010       4020       4030 4032
ACCAACAUUU AUACAGGUUC CAGACUCCAC GAAGCCGGAU GU
  T  N  I   Y  T  G   S  R  L  H   E  A  G   C
                               nsp2

      4042       4052       4062       4072       4082       4092
GCACCCUCAU AUCAUGUGGU GCGAGGGGAU AUUGCCACGG CCACCGAAGG AGUGAUUAUA
  A  P  S   Y  H  V   V  R  G  D   I  A  T   A  T  E   G  V  I  I
                               nsp3

      4102       4112       4122       4132       4142       4152
AAUGCUGCUA ACAGCAAAGG ACAACCUGGC GGAGGGGUGU GCGGAGCGCU GUAUAAGAAA
  N  A  A   N  S  K   G  Q  P  G   G  G  V   C  G  A   L  Y  K  K
                               nsp3

      4162       4172       4182       4192       4202       4212
UUCCCGGAAA GUUUCGAUUU ACAGCCGAUC GAAGUAGGAA AAGCGCGACU GGUCAAAGGU
  F  P  E   S  F  D   L  Q  P  I   E  V  G   K  A  R   L  V  K  G
                               nsp3

      4222       4232       4242       4252       4262       4272
GCAGCUAAAC AUAUCAUUCA UGCCGUAGGA CCAAACUUCA ACAAAGUUUC GGAGGUUGAA
  A  A  K   H  I  I   H  A  V  G   P  N  F   N  K  V   S  E  V  E
                               nsp3

      4282       4292       4302       4312       4322       4332
GGUGACAAAC AGUUGGCAGA GGCUUAUGAG UCCAUCGCUA AGAUUGUCAA CGAUAACAAU
  G  D  K   Q  L  A   E  A  Y  E   S  I  A   K  I  V   N  D  N  N
                               nsp3

      4342       4352       4362       4372       4382       4392
UACAAGUCAG UAGCGAUUCC ACUGUUGUCC ACCGGCAUCU UUUCCGGGAA CAAAGAUCGA
  Y  K  S   V  A  I   P  L  L  S   T  G  I   F  S  G   N  K  D  R
                               nsp3

      4402       4412       4422       4432       4442       4452
CUAACCCAAU CAUUGAACCA UUUGCUGACA GCUUUAGACA CCACUGAUGC AGAUGUAGCC
  L  T  Q   S  L  N   H  L  L  T   A  L  D   T  T  D   A  D  V  A
                               nsp3

      4462       4472       4482       4492       4502       4512
AUAUACUGCA GGGACAAGAA AUGGGAAAUG ACUCUCAAGG AAGCAGUGGC UAGGAGAGAA
  I  Y  C   R  D  K   K  W  E  M   T  L  K   E  A  V   A  R  R  E
                               nsp3

      4522       4532       4542       4552       4562       4572
GCAGUGGAGG AGAUAUGCAU AUCCGACGAU UCUUCAGUGA CAGAACCUGA UGCAGAGCUG
  A  V  E   E  I  C   I  S  D  D   S  S  V   T  E  P   D  A  E  L
                               nsp3

      4582       4592       4602       4612       4622       4632
GUGAGGGUGC AUCCCAAGAG UUCUUUGGCU GGAAGGAAGG GCUACAGCAC AAGCGAUGGC
  V  R  V   H  P  K   S  S  L  A   G  R  K   G  Y  S   T  S  D  G
                               nsp3

      4642       4652       4662       4672       4682       4692
AAAACUUUCU CAUAUUUGGA AGGGACCAAG UUUCACCAGG CGGCCAAGGA UAUAGCAGAA
  K  T  F   S  Y  L   E  G  T  K   F  H  Q   A  A  K   D  I  A  E
                               nsp3
```

-continued

```
      4702       4712       4722       4732       4742       4752
AUUAAUGCCA UGUGGCCCGU UGCAACGGAG GCCAAUGAGC AGGUAUGCAU GUAUAUCCUC
  I  N  A   M  W  P   V  A  T  E   A  N  E   Q  V  C   M  Y  I  L
                                 nsp3

      4762       4772       4782       4792       4802       4812
GGAGAAAGCA UGAGCAGUAU UAGGUCGAAA UGCCCCGUCG AGGAGUCGGA AGCCUCCACA
  G  E  S   M  S  S   I  R  S  K   C  P  V   E  E  S   E  A  S  T
                                 nsp3

      4822       4832       4842       4852       4862       4872
CCACCUAGCA CGCUGCCUUG CUUGUGCAUC CAUGCCAUGA CUCCAGAAAG AGUACAGCGC
  P  P  S   T  L  P   C  L  C  I   H  A  M   T  P  E   R  V  Q  R
                                 nsp3

      4882       4892       4902       4912       4922       4932
CUAAAAGCCU CACGUCCAGA ACAAAUUACU GUGUGCUCAU CCUUUCCAUU GCCGAAGUAU
  L  K  A   S  R  P   E  Q  I  T   V  C  S   S  E  P   L  P  K  Y
                                 nsp3

      4942       4952       4962       4972       4982       4992
AGAAUCACUG GUGUGCAGAA GAUCCAAUGC UCCCAGCCUA UAUUGUUCUC ACCGAAAGUG
  R  I  T   G  V  Q   K  I  Q  C   S  Q  P   I  L  F   S  P  K  V
                                 nsp3

      5002       5012       5022       5032       5042       5052
CCUGCGUAUA UUCAUCCAAG GAAGUAUCUC GUGGAAACAC CACCGGUAGA CGAGACUCCG
  P  A  Y   I  H  P   R  K  Y  L   V  E  T   P  P  V   D  E  T  P
                                 nsp3

      5062       5072       5082       5092       5102       5112
GAGCCAUCGG CAGAGAACCA AUCCACAGAG GGGACACCUG AACAACCACC ACUUAUAACC
  E  P  S   A  E  N   Q  S  T  E   G  T  P   E  Q  P   P  L  I  T
                                 nsp3

      5122       5132       5142       5152       5162       5172
GAGGAUGAGA CCAGGACUAG AACGCCUGAG CCGAUCAUCA UCGAAGAAGA AGAAGAAGAU
  E  D  E   T  R  T   R  T  P  E   P  I  I   I  E  E   E  E  E  D
                                 nsp3

      5182       5192       5202       5212       5222       5232
AGCAUAAGUU UGCUGUCAGA UGGCCCGACC CACCAGGUGC UGCAAGUCGA GGCAGACAUU
  S  I  S   L  L  S   D  G  P  T   H  Q  V   L  Q  V   E  A  D  I
                                 nsp3

      5242       5252       5262       5272       5282       5292
CACGGGCCGC CCUCUGUAUC UAGCUCAUCC UGGUCCAUUC CUCAUGCAUC CGACUUUGAU
  H  G  P   P  S  V   S  S  S  S   W  S  I   P  H  A   S  D  E  D
                                 nsp3

      5302       5312       5322       5332       5342       5352
GUGGACAGUU UAUCCAUACU UGACACCCUG GAGGGAGCUA GCGUGACCAG CGGGGCAACG
  V  D  S   L  S  I   L  D  T  L   E  G  A   S  V  T   S  G  A  T
                                 nsp3

      5362       5372       5382       5392       5402       5412
UCAGCCGAGA CUAACUCUUA CUUCGCAAAG AGUAUGGAGU UUCUGGCGCG ACCGGUGCCU
  S  A  E   T  N  S   Y  F  A  K   S  M  E   F  L  A   R  P  V  P
                                 nsp3

      5422       5432       5442       5452       5462       5472
GCGCCUCGAA CAGUAUUCAG GAACCCUCCA CAUCCCGCUC CGCGCACAAG AACACCGUCA
  A  P  R   T  V  F   R  N  P  P   H  P  A   P  R  T   R  T  P  S
                                 nsp3

      5482       5492       5502       5512       5522       5532
CUUGCACCCA GCAGGGCCUG CUCCAGAACC AGCCUAGUUU CCACCCCGCC AGGCGUGAAU
  L  A  P   S  R  A   C  S  R  T   S  L  V   S  T  P   P  G  V  N
                                 nsp3

      5542       5552       5562       5572       5582       5592
AGGGUGAUCA CUAGAGAGGA GCUCGAAGCG CUUACCCCGU CACGCACUCC UAGCAGGUCG
  R  V  I   T  R  E   E  L  E  A   L  T  P   S  R  T   P  S  R  S
                                 nsp3

      5602       5612       5622       5632       5642       5652
GUCUCCAGAA CCAGCCUGGU CUCCAACCCG CCAGGCGUAA AUAGGGUGAU UACAAGAGAG
  V  S  R   T  S  L   V  S  N  P   P  G  V   N  R  V   I  T  R  E
                                 nsp3
```

-continued

```
       5662        5672        5682        5692        5702 5703
GAGUUUGAGG CGUUCGUAGC ACAACAACAA UGACGGUUUG AUGCGGGUGC A
  E  F  E   A  F  V   A  Q  Q  Q   *  R  F   D  A  G   A
                                   nsp3

       5713        5723        5733        5743        5753        5763
UACAUCUUUU CCUCCGACAC CGGUCAAGGG CAUUUACAAC AAAAAUCAGU AAGGCAAACG
  Y  I  F   S  S  D   T  G  Q  G   H  L  Q   Q  K  S   V  R  Q  T
                                   nsp4

       5773        5783        5793        5803        5813        5823
GUGCUAUCCG AAGUGGUGUU GGAGAGGACC GAAUUGGAGA UUUCGUAUGC CCCGCGCCUC
  V  L  S   E  V  V   L  E  R  T   E  L  E   I  S  Y   A  P  R  L
                                   nsp4

       5833        5843        5853        5863        5873        5883
GACCAAGAAA AAGAAGAAUU ACUACGCAAG AAAUUACAGU UAAAUCCCAC ACCUGCUAAC
  D  Q  E   K  E  E   L  L  R  K   K  L  Q   L  N  P   T  P  A  N
                                   nsp4

       5893        5903        5913        5923        5933        5943
AGAAGCAGAU ACCAGUCCAG GAAGGUGGAG AACAUGAAAG CCAUAACAGC UAGACGUAUU
  R  S  R   Y  Q  S   R  K  V  E   N  M  K   A  I  T   A  R  R  I
                                   nsp4

       5953        5963        5973        5983        5993        6003
CUGCAAGGCC UAGGGCAUUA UUUGAAGGCA GAAGGAAAAG UGGAGUGCUA CCGAACCCUG
  L  Q  G   L  G  H   Y  L  K  A   E  G  K   V  E  C   Y  R  T  L
                                   nsp4

       6013        6023        6033        6043        6053        6063
CAUCCUGUUC CUUUGUAUUC AUCUAGUGUG AACCGUGCCU UUUCAAGCCC CAAGGUCGCA
  H  P  V   P  L  Y   S  S  S  V   N  R  A   F  S  S   P  K  V  A
                                   nsp4

       6073        6083        6093        6103        6113        6123
GUGGAAGCCU GUAACGCCAU GUUGAAAGAG AACUUUCCGA CUGUGGCUUC UUACUGUAUU
  V  E  A   C  N  A   M  L  K  E   N  F  P   T  V  A   S  Y  C  I
                                   nsp4

       6133        6143       6153         6163        6173        6183
AUUCCAGAGU ACGAUGCCUA UUUGGACAUG GUUGACGGAG CUUCAUGCUG CUUAGACACU
  I  P  E   Y  D  A   Y  L  D  M   V  D  G   A  S  C   C  L  D  T
                                   nsp4

       6193        6203        6213        6223        6233        6243
GCCAGUUUUU GCCCUGCAAA GCUGCGCAGC UUUCCAAAGA AACACUCCUA UUUGGAACCC
  A  S  F   C  P  A   K  L  R  S   F  P  K   K  H  S   Y  L  E  P
                                   nsp4

       6253        6263        6273        6283        6293        6303
ACAAUACGAU CGGCAGUGCC UUCAGCGAUC CAGAACACGC UCCAGAACGU CCUGGCAGCU
  T  I  R   S  A  V   P  S  A  I   Q  N  T   L  Q  N   V  L  A  A
                                   nsp4

       6313        6323        6333        6343        6353        6363
GCCACAAAAA GAAAUUGCAA UGUCACGCAA AUGAGAGAAU UGCCCGUAUU GGAUUCGGCG
  A  T  K   R  N  C   N  V  T  Q   M  R  E   L  P  V   L  D  S  A
                                   nsp4

       6373        6383        6393        6403        6413        6423
GCCUUUAAUG UGGAAUGCUU CAAGAAAUAU GCGUGUAAUA AUGAAUAUUG GGAAACGUUU
  A  F  N   V  E  C   F  K  K  Y   A  C  N   N  E  Y   W  E  T  F
                                   nsp4

       6433        6443        6453        6463        6473        6483
AAAGAAAACC CCAUCAGGCU UACUGAAGAA AACGUGGUAA AUUACAUUAC CAAAUUAAAA
  K  E  N   P  I  R   L  T  E  E   N  V  V   N  Y  I   T  K  L  K
                                   nsp4

       6493        6503        6513        6523        6533        6543
GGACCAAAAG CUGCUGCUCU UUUUGCGAAG ACACAUAAUU UGAAUAUGUU GCAGGACAUA
  G  P  K   A  A  A   L  F  A  K   T  H  N   L  N  M   L  Q  D  I
                                   nsp4

       6553        6563        6573        6583        6593        6603
CCAAUGGACA GGUUUGUAAU GGACUUAAAG AGAGACGUGA AAGUGACUCC AGGAACAAAA
  P  M  D   R  F  V   M  D  L  K   R  D  V   K  V  T   P  G  T  K
                                   nsp4
```

-continued

```
      6613       6623       6633       6643       6653       6663
CAUACUGAAG AACGGCCCAA GGUACAGGUG AUCCAGGCUG CCGAUCCGCU AGCAACAGCG
  H  T  E   E  R  P   K  V  Q  V   I  Q  A   A  D  P   L  A  T  A
                                 nsp4

      6673       6683       6693       6703       6713       6723
UAUCUGUGCG GAAUCCACCG AGAGCUGGUU AGGAGAUUAA AUGCGGUCCU GCUUCCGAAC
  Y  L  C   G  I  H   R  E  L  V   R  R  L   N  A  V   L  L  P  N
                                 nsp4

      6733       6743       6753       6763       6773       6783
AUUCAUACAC UGUUUGAUAU GUCGGCUGAA GACUUUGACG CUAUUAUAGC CGAGCACUUC
  I  H  T   L  F  D   M  S  A  E   D  F  D   A  I  I   A  E  H  F
                                 nsp4

      6793       6803       6813       6823       6833       6843
CAGCCUGGGG AUUGUGUUCU GGAAACUGAC AUCGCGUCGU UUGAUAAAAG UGAGGACGAC
  Q  P  G   D  C  V   L  E  T  D   I  A  S   F  D  K   S  E  D  D
                                 nsp4

      6853       6863       6873       6883       6893       6903
GCCAUGGCUC UGACCGCGUU AAUGAUUCUG GAAGACUUAG GUGUGGACGC AGAGCUGUUG
  A  M  A   L  T  A   L  M  I  L   E  D  L   G  V  D   A  E  L  L
                                 nsp4

      6913       6923       6933       6943       6953       6963
ACGCUGAUUG AGGCGGCUUU CGGCGAAAUU UCAUCAAUAC AUUUGCCCAC UAAAACUAAA
  T  L  I   E  A  A   F  G  E  I   S  S  I   H  L  P   T  K  T  K
                                 nsp4

      6973       6983       6993       7003       7013       7023
UUUAAAUUCG GAGCCAUGAU GAAAUCUGGA AUGUUCCUCA CACUGUUUGU GAACACAGUC
  F  K  F   G  A  M   M  K  S  G   M  F  L   T  L  F   V  N  T  V
                                 nsp4

      7033       7043       7053       7063       7073       7083
AUUAACAUUG UAAUCGCAAG CAGAGUGUUG AGAGAACGGC UAACCGGAUC ACCAUGUGCA
  I  N  I   V  I  A   S  R  V  L   R  E  R   L  T  G   S  P  C  A
                                 nsp4

      7093       7103       7113       7123       7133       7143
GCAUUCAUUG GAGAUGACAA UAUCGUGAAA GGAGUCAAAU CGGACAAAUU AAUGGCAGAC
  A  F  I   G  D  D   N  I  V  K   G  V  K   S  D  K   L  M  A  D
                                 nsp4

      7153       7163       7173       7183       7193       7203
AGGUGCGCCA CCUGGUUGAA UAUGGAAGUC AAGAUUAUAG AUGCUGUGGU GGGCGAGAAA
  R  C  A   T  W  L   N  M  E  V   K  I  I   D  A  V   V  G  E  K
                                 nsp4

      7213       7223       7233       7243       7253       7263
GCGCCUUAUU UCUGUGGAGG GUUUAUUUUG UGUGACUCCG UGACCGGCAC AGCGUGCCGU
  A  P  Y   F  C  G   G  F  I  L   C  D  S   V  T  G   T  A  C  R
                                 nsp4

      7273       7283       7293       7303       7313       7323
GUGGCAGACC CCCUAAAAAG GCUGUUUAAG CUAGGCAAAC CUCUGGCAGC AGACGAUGAA
  V  A  D   P  L  K   R  L  F  K   L  G  K   P  L  A   A  D  D  E
                                 nsp4

      7333       7343       7353       7363       7373       7383
CAUGAUGAUG ACAGGAGAAG GGCAUUGCAU GAGGAGUCAA CACGCUGGAA CCGAGUGGGU
  H  D  D   D  R  R   R  A  L  H   E  E  S   T  R  W   N  R  V  G
                                 nsp4

      7393       7403       7413       7423       7433       7443
AUUCUUUCAG AGCUGUGCAA GGCAGUAGAA UCAAGGUAUG AAACCGUAGG AACUUCCAUC
  I  L  S   E  L  C   K  A  V  E   S  R  Y   E  T  V   G  T  S  I
                                 nsp4

      7453       7463       7473       7483       7493       7503
AUAGUUAUGG CCAUGACUAC UCUAGCUAGC AGUGUUAAAU CAUUCAGCUA CCUGAGAGGG
  I  V  M   A  M  T   T  L  A  S   S  V  K   S  F  S   Y  L  R  G
                                 nsp4

      7513       7523          7527
GCCCCUAUAA CUCUCUACGG CUAA
  A  P  I   T  L  Y   G  *
             nsp4
```

-continued

```
       7537        7547        7557        7567        7568
CCUGAAUGGA CUACGACAUA GUCUAGUCCG CCAAGACUAG U
                          virUTR

       7578        7588        7598        7608        7618        7628
AUGUUUGUGU UUCUUGUGCU GCUGCCUCUU GUGUCUUCUC AGUGUGUGGU UUUGACAACA
  M  F  V   F  L  V   L  L  P  L   V  S  S   Q  C  V   N  L  T  T
                         S protein

       7638        7648        7658        7668        7678        7688
AGAACACAGC UGCCACCAGC UUAUACAAAU UCUUUUACCA GAGGAGUGUA UUAUCCUGAU
  R  T  Q   L  P  P   A  Y  T  N   S  F  T   R  G  V   Y  Y  P  D
                         S protein

       7698        7708        7718        7728        7738        7748
AAAGUGUUUA GAUCUUCUGU GCUGCACAGC ACACAGGACC UGUUUCUGCC AUUUUUUAGC
  K  V  F   R  S  S   V  L  H  S   T  Q  D   L  F  L   P  F  F  S
                         S protein

       7758        7768        7778        7788        7798        7808
AAUGUGACAU GGUUUCAUGC AAUUCAUGUG UCUGGAACAA AUGGAACAAA AAGAUUUGAU
  N  V  T   W  F  H   A  I  H  V   S  G  T   N  G  T   K  R  F  D
                         S protein

       7818        7828        7838        7848        7858        7868
AAUCCUGUGC UGCCUUUUAA UGAUGGAGUG UAUUUUGCUU CAACAGAAAA GUCAAAUAUU
  N  P  V   L  P  F   N  D  G  V   Y  F  A   S  T  E   K  S  N  I
                         S protein

       7878        7888        7898        7908        7918        7928
AUUAGAGGAU GGAUUUUUGG AACAACACUG GAUUCUAAAA CACAGUCUCU GCUGAUUGUG
  I  R  G   W  I  F   G  T  T  L   D  S  K   T  Q  S   L  L  I  V
                         S protein

       7938        7948        7958        7968        7978        7988
AAUAAUGCAA CAAAUGUGGU GAUUAAAGUG UGUGAAUUUC AGUUUUGUAA UGAUCCUUUU
  N  N  A   T  N  V   V  I  K  V   C  E  F   Q  F  C   N  D  P  F
                         S protein

       7998        8008        8018        8028        8038        8048
CUGGGAGUGU AUUAUCACAA AAAUAAUAAA UCUUGGAUGG AAUCUGAAUU UAGAGUGUAU
  L  G  V   Y  Y  H   K  N  N  K   S  W  M   E  S  E   F  R  V  Y
                         S protein

       8058        8068        8078        8088        8098        8108
UCCUCUGCAA AUAAUUGUAC AUUUGAAUAU GUGUCUCAGC CUUUUCUGAU GGAUCUGGAA
  S  S  A   N  N  C   T  F  E  Y   V  S  Q   P  F  L   M  D  L  E
                         S protein

       8118        8128        8138        8148        8158        8168
GGAAAACAGG GCAAUUUUAA AAAUCUGAGA GAAUUUGUGU UUAAAAAUAU UGAUGGAUAU
  G  K  Q   G  N  F   K  N  L  R   E  F  V   F  K  N   I  D  G  Y
                         S protein

       8178        8188        8198        8208        8218        8228
UUUAAAAUUU AUUCUAAACA CACACCAAUU AAUUUAGUGA GAGAUCUGCC UCAGGGAUUU
  F  K  I   Y  S  K   H  T  P  I   N  L  V   R  D  L   P  Q  G  F
                         S protein

       8238        8248        8258        8268        8278        8288
UCUGCUCUGG AACCUCUGGU GGAUCUGCCA AUUGGCAUUA AUAUUACAAG AUUUCAGACA
  S  A  L   E  P  L   V  D  L  P   I  G  I   N  I  T   R  F  Q  T
                         S protein

       8298        8308        8318        8328        8338        8348
CUGCUGGCUC UGCACAGAUC UUAUCUGACA CCUGGAGAUU CUUCUUCUGG AUGGACAGCC
  L  L  A   L  H  R   S  Y  L  T   P  G  D   S  S  S   G  W  T  A
                         S protein

       8358        8368        8378        8388        8398        8408
GGAGCUGCAG CUUAUUAUGU GGGCUAUCUG CAGCCAAGAA CAUUUCUGCU GAAAUAUAAU
  G  A  A   A  Y  Y   V  G  Y  L   Q  P  R   T  F  L   L  K  Y  N
                         S protein

       8418        8428        8438        8448        8458        8468
GAAAAUGGAA CAAUUACAGA UGCUGUGGAU UGUGCUCUGG AUCCUCUGUC UGAAACAAAA
  E  N  G   T  I  T   D  A  V  D   C  A  L   D  P  L   S  E  T  K
                         S protein

       8478        8488        8498        8508        8518        8528
UGUACAUUAA AAUCUUUUAC AGUGGAAAAA GGCAUUUAUC AGACAUCUAA UUUUAGAGUG
```

-continued

```
 C  T  L   K  S  F   T  V  E   K  G  I   Y  Q  T   S  N  F   R  V
                              S protein

       8538       8548       8558       8568       8578       8588
CAGCCAACAG AAUCUAUUGU GAGAUUUCCA AAUAUUACAA AUCUGUGUCC AUUUGGAGAA
 Q  P  T   E  S  I   V  R  F   P  N  I   T  N  L   C  P  F   G  E
                              S protein

       8598       8608       8618       8628       8638       8648
GUGUUUAAUG CAACAAGAUU UGCAUCUGUG UAUGCAUGGA AUAGAAAAAG AAUUUCUAAU
 V  F  N   A  T  R   F  A  S   V  Y  A   W  N  R   K  R  I   S  N
                              S protein

       8658       8668       8678       8688       8698       8708
UGUGUGGCUG AUUAUUCUGU GCUGUAUAAU AGUGCUUCUU UUUCCACAUU UAAAUGUUAU
 C  V  A   D  Y  S   V  L  Y   N  S  A   S  F  S   T  F  K   C  Y
                              S protein

       8718       8728       8738       8748       8758       8768
GGAGUGUCUC CAACAAAAUU AAAUGAUUUA UGUUUUACAA AUGUGUAUGC UGAUUCUUUU
 G  V  S   P  T  K   L  N  D   L  C  F   T  N  V   Y  A  D   S  F
                              S protein

       8778       8788       8798       8808       8818       8828
GUGAUCAGAG GUGAUGAAGU GAGACAGAUU GCCCCCGGAC AGACAGGAAA AAUUGCUGAU
 V  I  R   G  D  E   V  R  Q   I  A  P   G  Q  T   G  K  I   A  D
                              S protein

       8838       8848       8858       8868       8878       8888
UACAAUUACA AACUGCCUGA UGAUUUUACA GGAUGUGUGA UUGCUUGGAA UUCUAAUAAU
 Y  N  Y   K  L  P   D  D  F   T  G  C   V  I  A   W  N  S   N  N
                              S protein

       8898       8908       8918       8928       8938       8948
UUAGAUUCUA AAGUGGGAGG AAAUUACAAU UAUCUGUACA GACUGUUUAG AAAAUCAAAU
 L  D  S   K  V  G   G  N  Y   N  Y  L   Y  R  L   F  R  K   S  N
                              S protein

       8958       8968       8978       8988       8998       9008
CUGAAACCUU UUGAAAGAGA UAUUUCAACA GAAAUUUAUC AGGCUGGAUC AACACCUUGU
 L  K  P   F  E  R   D  I  S   T  E  I   Y  Q  A   G  S  T   P  C
                              S protein

       9018       9028       9038       9048       9058       9068
AAUGGAGUGG AAGGAUUUAA UUGUUAUUUU CCAUUACAGA GCUAUGGAUU UCAGCCAACC
 N  G  V   E  G  F   N  C  Y   F  P  L   Q  S  Y   G  F  Q   P  T
                              S protein

       9078       9088       9098       9108       9118       9128
AAUGGUGUGG GAUAUCAGCC AUAUAGAGUG GUGGUGCUGU CUUUUGAACU GCUGCAUGCA
 N  G  V   G  Y  Q   P  Y  R   V  V  V   L  S  F   E  L  L   H  A
                              S protein

       9138       9148       9158       9168       9178       9188
CCUGCAACAG UGUGUGGACC UAAAAAAUCU ACAAAUUUAG UGAAAAAUAA AUGUGUGAAU
 P  A  T   V  C  G   P  K  K   S  T  N   L  V  K   N  K  C   V  N
                              S protein

       9198       9208       9218       9228       9238       9248
UUUAAUUUUA AUGGAUUAAC AGGAACAGGA GUGCUGACAG AAUCUAAUAA AAAAUUUCUG
 F  N  F   N  G  L   T  G  T   G  V  L   T  E  S   N  K  K   F  L
                              S protein

       9258       9268       9278       9288       9298       9308
CCUUUUCAGC AGUUUGGCAG AGAUAUUGCA GAUACCACAG AUGCAGUGAG AGAUCCUCAG
 P  F  Q   Q  F  G   R  D  I   A  D  T   T  D  A   V  R  D   P  Q
                              S protein

       9318       9328       9338       9348       9358       9368
ACAUUAGAAA UUCUGGAUAU UACACCUUGU UCUUUUGGGG GUGUGUCUGU GAUUACACCU
 T  L  E   I  L  D   I  T  P   C  S  F   G  G  V   S  V  I   T  P
                              S protein

       9378       9388       9398       9408       9418       9428
GGAACAAAUA CAUCUAAUCA GGUGGCUGUG CUGUAUCAGG AUGUGAAUUG UACAGAAGUG
 G  T  N   T  S  N   Q  V  A   V  L  Y   Q  D  V   N  C  T   E  V
                              S protein
```

-continued

```
      9438       9448       9458       9468       9478       9488
CCAGUGGCAA UUCAUGCAGA UCAGCUGACA CCAACAUGGA GAGUGUAUUC UACAGGAUCU
  P  V  A   T  H  A   D  Q  L  T   P  T  W   R  V  Y   S  T  G  S
                          S protein

      9498       9508       9518       9528       9538       9548
AAUGUGUUUC AGACAAGAGC AGGAUGUCUG AUUGGAGCAG AACAUGUGAA UAAUUCUUAU
  N  V  F   Q  T  R   A  G  C  L   I  G  A   E  H  V   N  N  S  Y
                          S protein

      9558       9568       9578       9588       9598       9608
GAAUGUGAUA UUCCAAUUGG AGCAGGCAUU UGUGCAUCUU AUCAGACACA GACAAAUUCC
  E  C  D   I  P  T   G  A  G  I   C  A  S   Y  Q  T   Q  T  N  S
                          S protein

      9618       9628       9638       9648       9658       9668
CCAAGGAGAG CAAGAUCUGU GGCAUCUCAG UCUAUUAUUG CAUACACCAU GUCUCUGGGA
  P  R  R   A  R  S   V  A  S  Q   S  I  T   A  Y  T   M  S  L  G
                          S protein

      9678       9688       9698       9708       9718       9728
GCAGAAAAUU CUGUGGCAUA UUCUAAUAAU UCUAUUGCUA UUCCAACAAA UUUUACCAUU
  A  E  N   S  V  A   Y  S  N  N   S  T  A   I  P  T   N  E  T  T
                          S protein

      9738       9748       9758       9768       9778       9788
UCUGUGACAA CAGAAAUUUU ACCUGUGUCU AUGACAAAAA CAUCUGUGGA UUGUACCAUG
  S  V  T   T  E  T   L  P  V  S   M  T  K   T  S  V   D  C  T  M
                          S protein

      9798       9808       9818       9828       9838       9848
UACAUUUGUG GAGAUUCUAC AGAAUGUUCU AAUCUGCUGC UGCAGUAUGG AUCUUUUUGU
  Y  I  C   G  D  S   T  E  C  S   N  L  L   L  Q  Y   G  S  F  C
                          S protein

      9858       9868       9878       9888       9898       9908
ACACAGCUGA AUAGAGCUUU AACAGGAAUU GCUGUGGAAC AGGAUAAAAA UACACAGGAA
  T  Q  L   N  R  A   L  T  G  I   A  V  E   Q  D  K   N  T  Q  E
                          S protein

      9918       9928       9938       9948       9958       9968
GUGUUUGCUC AGGUGAAACA GAUUUACAAA ACACCACCAA UUAAAGAUUU UGGAGGAUUU
  V  F  A   Q  V  K   Q  I  Y  K   T  P  P   I  K  D   F  G  G  F
                          S protein

      9978       9988       9998      10008      10018      10028
AAUUUUAGCC AGAUUCUGCC UGAUCCUUCU AAACCUUCUA AAAGAUCUUU UAUUGAAGAU
  N  F  S   Q  I  L   P  D  P  S   K  P  S   K  R  S   F  I  E  D
                          S protein

     10038      10048      10058      10068      10078      10088
CUGCUGUUUA AUAAAGUGAC ACUGGCAGAU GCAGGAUUUA UUAAACAGUA UGGAGAUUGC
  L  L  F   N  K  V   T  L  A  D   A  G  F   I  K  Q   Y  G  D  C
                          S protein

     10098      10108      10118      10128      10138      10148
CUGGGUGAUA UUGCUGCAAG AGAUCUGAUU UGUGCUCAGA AAUUUAAUGG ACUGACAGUG
  L  G  D   I  A  A   R  D  L  I   C  A  Q   K  F  N   G  L  T  V
                          S protein

     10158      10168      10178      10188      10198      10208
CUGCCUCCUC UGCUGACAGA UGAAAUGAUU GCUCAGUACA CAUCUGCUUU ACUGGCUGGA
  L  P  P   L  L  T   D  E  M  I   A  Q  Y   T  S  A   L  L  A  G
                          S protein

     10218      10228      10238      10248      10258      10268
ACAAUUACAA GCGGAUGGAC AUUUGGAGCU GGAGCUGCUC UGCAGAUUCC UUUUGCAAUG
  T  I  T   S  G  W   T  F  G  A   G  A  A   L  Q  I   P  F  A  M
                          S protein

     10278      10288      10298      10308      10318      10328
CAGAUGGCUU ACAGAUUUAA UGGAAUUGGA GUGACACAGA AUGUGUUAUA UGAAAAUCAG
  Q  M  A   Y  R  F   N  G  I  G   V  T  Q   N  V  L   Y  E  N  Q
                          S protein

     10338      10348      10358      10368      10378      10388
AAACUGAUUG CAAAUCAGUU UAAUUCUGCA AUUGGCAAAA UUCAGGAUUC UCUGUCUUCU
  K  L  I   A  N  Q   F  N  S  A   I  G  K   I  Q  D   S  L  S  S
                          S protein
```

-continued

```
     10398      10408      10418      10428      10438      10448
ACAGCUUCUG CUCUGGGAAA ACUGCAGGAU GUGGUGAAUC AGAAUGCACA GGCACUGAAU
 T  A  S   A  L  G   K  L  Q  D   V  V  N   Q  N  A   Q  A  L  N
                               S protein

     10458      10468      10478      10488      10498      10508
ACUCUGGUGA AACAGCUGUC UAGCAAUUUU GGGGCAAUUU CUUCUGUGCU GAAUGAUAUU
 T  L  V   K  Q  L   S  S  N  F   G  A  I   S  S  V   L  N  D  I
                               S protein

     10518      10528      10538      10548      10558      10568
CUGUCUAGAC UGGAUCCUCC TGAAGCUGAA GUGCAGAUUG AUAGACUGAU CACAGGAAGA
 L  S  R   L  D  P   P  E  A  E   V  Q  I   D  R  L   I  T  G  R
                               S protein

     10578      10588      10598      10608      10618      10628
CUGCAGUCUC UGCAGACUUA UGUGACACAG CAGCUGAUUA GAGCUGCUGA AAUUAGAGCU
 L  Q  S   L  Q  T   Y  V  T  Q   Q  L  I   R  A  A   E  I  R  A
                               S protein

     10638      10648      10658      10668      10678      10688
UCUGCUAAUC UGGCUGCUAC AAAAAUGUCU GAAUGUGUGC UGGGACAGUC AAAAAGAGUG
 S  A  N   L  A  A   T  K  M  S   E  C  V   L  G  Q   S  K  R  V
                               S protein

     10698      10708      10718      10728      10738      10748
GAUUUUUGUG GAAAAGGAUA UCAUCUGAUG UCUUUUCCAC AGUCUGCUCC ACAUGGAGUG
 D  F  C   G  K  G   Y  H  L  M   S  F  P   Q  S  A   P  H  G  V
                               S protein

     10758      10768      10778      10788      10798      10808
GUGUUUUUAC AUGUGACAUA UGUGCCAGCA CAGGAAAAGA AUUUUACCAC AGCACCAGCA
 V  F  L   H  V  T   Y  V  P  A   Q  E  K   N  F  T   T  A  P  A
                               S protein

     10818      10828      10838      10848      10858      10868
AUUUGUCAUG AUGGAAAAGC ACAUUUUCCA AGAGAAGGAG UGUUUGUGUC UAAUGGAACA
 I  C  H   D  G  K   A  H  F  P   R  E  G   V  F  V   S  N  G  T
                               S protein

     10878      10888      10898      10908      10918      10928
CAUUGGUUUG UGACACAGAG AAAUUUUUAU GAACCUCAGA UUAUUACAAC AGAUAAUACA
 H  W  F   V  T  Q   R  N  F  Y   E  P  Q   I  I  T   T  D  N  T
                               S protein

     10938      10948      10958      10968      10978      10988
UUUGUGUCAG GAAAUUGUGA UGUGGUGAUU GGAAUUGUGA AUAAUACAGU GUAUGAUCCA
 F  V  S   G  N  C   D  V  V  I   G  I  V   N  N  T   V  Y  D  P
                               S protein

     10998      11008      11018      11028      11038      11048
CUGCAGCCAG AACUGGAUUC UUUUAAAGAA GAACUGGAUA AAUAUUUUAA AAAUCACACA
 L  Q  P   E  L  D   S  F  K  E   E  L  D   K  Y  F   K  N  H  T
                               S protein

     11058      11068      11078      11088      11098      11108
UCUCCUGAUG UGGAUUUAGG AGAUAUUUCU GGAAUCAAUG CAUCUGUGGU GAAUAUUCAG
 S  P  D   V  D  L   G  D  I  S   G  I  N   A  S  V   V  N  I  Q
                               S protein

     11118      11128      11138      11148      11158      11168
AAAGAAAUUG AUAGACUGAA UGAAGUGGCC AAAAAUCUGA AUGAAUCUCU GAUUGAUCUG
 K  E  I   D  R  L   N  E  V  A   K  N  L   N  E  S   L  I  D  L
                               S protein

     11178      11188      11198      11208      11218      11228
CAGGAACUUG GAAAAUAUGA ACAGUACAUU AAAUGGCCUU GGUACAUUUG GCUUGGAUUU
 Q  E  L   G  K  Y   E  Q  Y  I   K  W  P   W  Y  I   W  L  G  F
                               S protein

     11238      11248      11258      11268      11278      11288
AUUGCAGGAU UAAUUGCAAU UGUGAUGGUG ACAAUUAUGU UAUGUUGUAU GACAUCAUGU
 I  A  G   L  I  A   I  V  M  V   T  I  M   L  C  C   M  T  S  C
                               S protein

     11298      11308      11318      11328      11338      11348
UGUUCUUGUU UAAAAGGAUG UUGUUCUUGU GGAAGCUGUU GUAAAUUUGA UGAAGAUGAU
 C  S  C   L  K  G   C  C  S  C   G  S  C   C  K  F   D  E  D  D
                               S protein
```

-continued

```
     11358      11368      11378      11388  11393
UCUGAACCUG UGUUAAAAGG AGUGAAAUUG CAUUACACAU GAUGA
  S  E  P   V  L  K   G  V  K  L   H  Y  T   *  *
                          S protein

     11403      11413      11423      11433      11443      11453
CUCGAGCUGG UACUGCAUGC ACGCAAUGCU AGCUGCCCCU UUCCCGUCCU GGGUACCCCG
                          FI element

     11463      11473      11483      11493      11503      11513
AGUCUCCCCC GACCUCGGGU CCCAGGUAUG CUCCCACCUC CACCUGCCCC ACUCACCACC
                          FI element

     11523      11533      11543      11553      11563      11573
UCUGCUAGUU CCAGACACCU CCCAAGCACG CAGCAAUGCA GCUCAAAACG CUUAGCCUAG
                          FI element

     11583      11593      11603      11613      11623      11633
CCACACCCCC ACGGGAAACA GCAGUGAUUA ACCUUUAGCA AUAAACGAAA GUUUAACUAA
                          FI element

     11643      11653      11663      11673      11683      11693
GCUAUACUAA CCCCAGGGUU GGUCAAUUUC GUGCCAGCCA CACCGCGGCC GCAUGAAUAC
                          FI element

     11703      11713      11723      11733      11743      11753
AGCAGCAAUU GGCAAGCUGC UUACAUAGAA CUCGCGGCGA UUGGCAUGCC GCCUUAAAAU
                          FI element

     11763      11773      11783      11793      11803      11807
UUUUAUUUUA UUUUUUCUUU UCUUUUCCGA AUCGGAUUUU GUUUUUAAUA UUUC
                          FI element

     11817      11827      11837      11847      11857      11867
AAAAAAAAAA AAAAAAAAAA AAAAAAAAAA GCAUAUGACU AAAAAAAAAA AAAAAAAAAA
                            Poly(A)

     11877      11887      11897      11907      11917
AAAAAAAAAA AAAAAAAAAA AAAAAAAAAA AAAAAAAAAA AAAAAAAAAA
                            Poly(A)
```

Nucleotide Sequence of RBS004.2 (SEQ ID NO: 25; SEQ ID NO: 7)

Nucleotide sequence is shown with individual sequence elements as indicated in bold letters. In addition, the sequence of the translated protein is shown in italic letters below the coding nucleotide sequence (*=stop codon).

```
        10         20         30         40    45
GAUGGGCGGC GCAUGAGAGA AGCCCAGACC AAUUACCUAC CCAAA
                           5' UTR

        55         65         75         85         95        105
AUGGAGAAAG UUCACGUUGA CAUCGAGGAA GACAGCCCAU UCCUCAGAGC UUUGCAGCGG
  M  E  K   V  H  V   D  I  E  E   D  S  P   F  L  R   A  L  Q  R
                             nsp1

       115        125        135        145        155        165
AGCUUCCCGC AGUUUGAGGU AGAAGCCAAG CAGGUCACUG AUAAUGACCA UGCUAAUGCC
  S  F  P   Q  F  E   V  E  A  K   Q  V  T   D  N  D   H  A  N  A
                             nsp1

       175        185        195        205        215        225
AGAGCGUUUU CGCAUCUGGC UUCAAAACUG AUCGAAACGG AGGUGGACCC AUCCGACACG
  R  A  F   S  H  L   A  S  K  L   I  E  T   E  V  D   P  S  D  T
                             nsp1

       235        245        255        265        275        285
AUCCUUGACA UUGGAAGUGC GCCCGCCCGC AGAAUGUAUU CUAAGCACAA GUAUCAUUGU
  I  L  D   I  G  S   A  P  A  R   R  M  Y   S  K  H   K  Y  H  C
                             nsp1

       295        305        315        325        335        345
AUCUGUCCGA UGAGAUGUGC GGAAGAUCCG GACAGAUUGU AUAAGUAUGC AACUAAGCUG
  I  C  P   M  R  C   A  E  D  P   D  R  L   Y  K  Y   A  T  K  L
                             nsp1
```

-continued

```
        355        365        375        385        395        405
AAGAAAAACU GUAAGGAAAU AACUGAUAAG GAAUUGGACA AGAAAAUGAA GGAGCUCGCC
 K  K  N   C  K  E   I  T  D  K   E  L  D   K  K  M   K  E  L  A
                                nsp1

        415        425        435        445        455        465
GCCGUCAUGA GCGACCCUGA CCUGGAAACU GAGACUAUGU GCCUCCACGA CGACGAGUCG
 A  V  M   S  D  P   D  L  E  T   E  T  M   C  L  H   D  D  E  S
                                nsp1

        475        485        495        505        515        525
UGUCGCUACG AAGGGCAAGU CGCUGUUUAC CAGGAUGUAU ACGCGGUUGA CGGACCGACA
 C  R  Y   E  G  Q   V  A  V  Y   Q  D  V   Y  A  V   D  G  P  T
                                nsp1

        535        545        555        565        575        585
AGUCUCUAUC ACCAAGCCAA UAAGGGAGUU AGAGUCGCCU ACUGGAUAGG CUUUGACACC
 S  L  Y   H  Q  A   N  K  G  V   R  V  A   Y  W  I   G  F  D  T
                                nsp1

        595        605        615        625        635        645
ACCCCUUUUA UGUUUAAGAA CUUGGCUGGA GCAUAUCCAU CAUACUCUAC CAACUGGGCC
 T  P  F   M  F  K   N  L  A  G   A  Y  P   S  Y  S   T  N  W  A
                                nsp1

        655        665        675        685        695        705
GACGAAACCG UGUUAACGGC UCGUAACAUA GGCCUAUGCA GCUCUGACGU UAUGGAGCGG
 D  E  T   V  L  T   A  R  N  I   G  L  C   S  S  D   V  M  E  R
                                nsp1

        715        725        735        745        755        765
UCACGUAGAG GGAUGUCCAU UCUUAGAAAG AAGUAUUUGA AACCAUCCAA CAAUGUUCUA
 S  R  R   G  M  S   I  L  R  K   K  Y  L   K  P  S   N  N  V  L
                                nsp1

        775        785        795        805        815        825
UUCUCUGUUG GCUCGACCAU CUACCACGAA AAGAGGGACU UACUGAGGAG CUGGCACCUG
 F  S  V   G  S  T   I  Y  H  E   K  R  D   L  L  R   S  W  H  L
                                nsp1

        835        845        855        865        875        885
CCGUCUGUAU UUCACUUACG UGGCAAGCAA AAUUACACAU GUCGGUGUGA GACUAUAGUU
 P  S  V   F  H  L   R  G  K  Q   N  Y  T   C  R  C   E  T  I  V
                                nsp1

        895        905        915        925        935        945
AGUUGCGACG GGUACGUCGU UAAAAGAAUA GCUAUCAGUC CAGGCCUGUA UGGGAAGCCU
 S  C  D   G  Y  V   V  K  R  I   A  I  S   P  G  L   Y  G  K  P
                                nsp1

        955        965        975        985        995       1005
UCAGGCUAUG CUGCUACGAU GCACCGCGAG GGAUUCUUGU GCUGCAAAGU GACAGACACA
 S  G  Y   A  A  T   M  H  R  E   G  F  L   C  C  K   V  T  D  T
                                nsp1

       1015       1025       1035       1045       1055       1065
UUGAACGGGG AGAGGGUCUC UUUUCCCGUG UGCACGUAUG UGCCAGCUAC AUUGUGUGAC
 L  N  G   E  R  V   S  F  P  V   C  T  Y   V  P  A   T  L  C  D
                                nsp1

       1075       1085       1095       1105       1115       1125
CAAAUGACUG GCAUACUGGC AACAGAUGUC AGUGCGGACG ACGCGCAAAA ACUGCUGGUU
 Q  M  T   G  I  L   A  T  D  V   S  A  D   D  A  Q   K  L  L  V
                                nsp1

       1135       1145       1155       1165       1175       1185
GGGCUCAACC AGCGUAUAGU CGUCAACGGU CGCACCCAGA GAAACACCAA UACCAUGAAA
 G  L  N   Q  R  I   V  V  N  G   R  T  Q   R  N  T   N  T  M  K
                                nsp1

       1195       1205       1215       1225       1235       1245
AAUUACCUUU UGCCCGUAGU GGCCCAGGCA UUUGCUAGGU GGGCAAAGGA AUAUAAGGAA
 N  Y  L   L  P  V   V  A  Q  A   F  A  R   W  A  K   E  Y  K  E
                                nsp1

       1255       1265       1275       1285       1295       1305
GAUCAAGAAG AUGAAAGGCC ACUAGGACUA CGAGAUAGAC AGUUAGUCAU GGGGUGUUGU
 D  Q  E   D  E  R   P  L  G  L   R  D  R   Q  L  V   M  G  C  C
                                nsp1
```

-continued

```
      1315       1325       1335       1345       1355       1365
UGGGCUUUUA GAAGGCACAA GAUAACAUCU AUUUAUAAGC GCCCGGAUAC CCAAACCAUC
  W  A  F   R  R  H   K  I  T  S   I  Y  K   R  P  D   T  Q  T  I
                                nsp1

      1375       1385       1395       1405       1415       1425
AUCAAAGUGA ACAGCGAUUU CCACUCAUUC GUGCUGCCCA GGAUAGGCAG UAACACAUUG
  I  K  V   N  S  D   F  H  S  F   V  L  P   R  I  G   S  N  T  L
                                nsp1

      1435       1445       1455       1465       1475       1485
GAGAUCGGGC UGAGAACAAG AAUCAGGAAA AUGUUAGAGG AGCACAAGGA GCCGUCACCU
  E  I  G   L  R  T   R  I  R  K   M  L  E   E  H  K   E  P  S  P
                                nsp1

      1495       1505       1515       1525       1535       1545
CUCAUUACCG CCGAGGACGU ACAAGAAGCU AAGUGCGCAG CCGAUGAGGC UAAGGAGGUG
  L  I  T   A  E  D   V  Q  E  A   K  C  A   A  D  E   A  K  E  V
                                nsp1

      1555       1565       1575       1585       1595       1605
CGUGAAGCCG AGGAGUUGCG CGCAGCUCUA CCACCUUUGG CAGCUGAUGU UGAGGAGCCC
  R  E  A   E  E  L   R  A  A  L   P  P  L   A  A  D   V  E  E  P
                                nsp1

      1615       1625       1635       1645  1650
ACUCUGGAAG CCGAUGUCGA CUUGAUGUUA CAAGAGGCUG GGGCC
  T  L  E   A  D  V   D  L  M  L   Q  E  A   G  A
                                nsp1

      1660       1670       1680       1690       1700       1710
GGCUCAGUGG AGACACCUCG UGGCUUGAUA AAGGUUACCA GCUACGCUGG CGAGGACAAG
  G  S  V   E  T  P   R  G  L  I   K  V  T   S  Y  A   G  E  D  K
                                nsp2

      1720       1730       1740       1750       1760       1770
AUCGGCUCUU ACGCUGUGCU UUCUCCGCAG GCUGUACUCA AGAGUGAAAA AUUAUCUUGC
  I  G  S   Y  A  V   L  S  P  Q   A  V  L   K  S  E   K  L  S  C
                                nsp2

      1780       1790       1800       1810       1820       1830
AUCCACCCUC UCGCUGAACA AGUCAUAGUG AUAACACACU CUGGCCGAAA AGGGCGUUAU
  I  H  P   L  A  E   Q  V  I  V   I  T  H   S  G  R   K  G  R  Y
                                nsp2

      1840       1850       1860       1870       1880       1890
GCCGUGGAAC CAUACCAUGG UAAAGUAGUG GUGCCAGAGG GACAUGCAAU ACCCGUCCAG
  A  V  E   P  Y  H   G  K  V  V   V  P  E   G  H  A   I  P  V  Q
                                nsp2

      1900       1910       1920       1930       1940       1950
GACUUUCAAG CUCUGAGUGA AAGUGCCACC AUUGUGUACA ACGAACGUGA GUUCGUAAAC
  D  F  Q   A  L  S   E  S  A  T   I  V  Y   N  E  R   E  F  V  N
                                nsp2

      1960       1970       1980       1990       2000       2010
AGGUACCUGC ACCAUAUUGC CACACAUGGA GGAGCGCUGA ACACUGAUGA AGAAUAUUAC
  R  Y  L   H  H  I   A  T  H  G   G  A  L   N  T  D   E  E  Y  Y
                                nsp2

      2020       2030       2040       2050       2060       2070
AAAACUGUCA AGCCCAGCGA GCACGACGGC GAAUACCUGU ACGACAUCGA CAGGAAACAG
  K  T  V   K  P  S   E  H  D  G   E  Y  L   Y  D  I   D  R  K  Q
                                nsp2

      2080       2090       2100       2110       2120       2130
UGCGUCAAGA AAGAGCUAGU CACUGGGCUA GGGCUCACAG GCGAGCUGGU CGAUCCUCCC
  C  V  K   K  E  L   V  T  G  L   G  L  T   G  E  L   V  D  P  P
                                nsp2

      2140       2150       2160       2170       2180       2190
UUCCAUGAAU UCGCCUACGA GAGUCUGAGA ACACGACCAG CCGCUCCUUA CCAAGUACCA
  F  H  E   F  A  Y   E  S  L  R   T  R  P   A  A  P   Y  Q  V  P
                                nsp2

      2200       2210       2220       2230       2240       2250
ACCAUAGGGG UGUAUGGCGU GCCAGGAUCA GGCAAGUCUG GCAUCAUUAA AAGCGCAGUC
  T  I  G   V  Y  G   V  P  G  S   G  K  S   G  I  I   K  S  A  V
                                nsp2
```

-continued

```
      2260       2270       2280       2290       2300       2310
ACCAAAAAAG AUCUAGUGGU GAGCGCCAAG AAAGAAAACU GUGCAGAAAU UAUAAGGGAC
 T  K  K   D  L  V   V  S  A  K   K  E  N   C  A  E   I  I  R  D
                                nsp2

      2320       2330       2340       2350       2360       2370
GUCAAGAAAA UGAAAGGGCU GGACGUCAAU GCCAGAACUG UGGACUCAGU GCUCUUGAAU
 V  K  K   M  K  G   L  D  V  N   A  R  T   V  D  S   V  L  L  N
                                nsp2

      2380       2390       2400       2410       2420       2430
GGAUGCAAAC ACCCCGUAGA GACCCUGUAU AUUGACGAGG CUUUUGCUUG UCAUGCAGGU
 G  C  K   H  P  V   E  T  L  Y   I  D  E   A  F  A   C  H  A  G
                                nsp2

      2440       2450       2460       2470       2480       2490
ACUCUCAGAG CGCUCAUAGC CAUUAUAAGA CCUAAAAAGG CAGUGCUCUG CGGAGAUCCC
 T  L  R   A  L  I   A  I  I  R   P  K  K   A  V  L   C  G  D  P
                                nsp2

      2500       2510       2520       2530       2540       2550
AAACAGUGCG GUUUUUUUAA CAUGAUGUGC CUGAAAGUGC AUUUUAACCA CGAGAUUUGC
 K  Q  C   G  F  F   N  M  M  C   L  K  V   H  F  N   H  E  I  C
                                nsp2

      2560       2570       2580       2590       2600       2610
ACACAAGUCU UCCACAAAAG CAUCUCUCGC CGUUGCACUA AAUCUGUGAC UUCGGUCGUC
 T  Q  V   F  H  K   S  I  S  R   R  C  T   K  S  V   T  S  V  V
                                nsp2

      2620       2630       2640       2650       2660       2670
UCAACCUUGU UUUACGACAA AAAAAUGAGA ACGACGAAUC CGAAAGAGAC UAAGAUUGUG
 S  T  L   F  Y  D   K  K  M  R   T  T  N   P  K  E   T  K  I  V
                                nsp2

      2680       2690       2700       2710       2720       2730
AUUGACACUA CCGGCAGUAC CAAACCUAAG CAGGACGAUC UCAUUCUCAC UUGUUUCAGA
 I  D  T   T  G  S   T  K  P  K   Q  D  D   L  I  L   T  C  F  R
                                nsp2

      2740       2750       2760       2770       2780       2790
GGGUGGGUGA AGCAGUUGCA AAUAGAUUAC AAAGGCAACG AAAUAAUGAC GGCAGCUGCC
 G  W  V   K  Q  L   Q  I  D  Y   K  G  N   E  I  M   T  A  A  A
                                nsp2

      2800       2810       2820       2830       2840       2850
UCUCAAGGGC UGACCCGUAA AGGUGUGUAU GCCGUUCGGU ACAAGGUGAA UGAAAAUCCU
 S  Q  G   L  T  R   K  G  V  Y   A  V  R   Y  K  V   N  E  N  P
                                nsp2

      2860       2870       2880       2890       2900       2910
CUGUACGCAC CCACCUCAGA ACAUGUGAAC GUCCUACUGA CCCGCACGGA GGACCGCAUC
 L  Y  A   P  T  S   E  H  V  N   V  L  L   T  R  T   E  D  R  I
                                nsp2

      2920       2930       2940       2950       2960       2970
GUGUGGAAAA CACUAGCCGG CGACCCAUGG AUAAAAACAC UGACUGCCAA GUACCCUGGG
 V  W  K   T  L  A   G  D  P  W   I  K  T   L  T  A   K  Y  P  G
                                nsp2

      2980       2990       3000       3010       3020       3030
AAUUUCACUG CCACGAUAGA GGAGUGGCAA GCAGAGCAUG AUGCCAUCAU GAGGCACAUC
 N  F  T   A  T  I   E  E  W  Q   A  E  H   D  A  I   M  R  H  I
                                nsp2

      3040       3050       3060       3070       3080       3090
UUGGAGAGAC CGGACCCUAC CGACGUCUUC CAGAAUAAGG CAAACGUGUG UUGGGCCAAG
 L  E  R   P  D  P   T  D  V  F   Q  N  K   A  N  V   C  W  A  K
                                nsp2

      3100       3110       3120       3130       3140       3150
GCUUUAGUGC CGGUGCUGAA GACCGCUGGC AUAGACAUGA CCACUGAACA AUGGAACACU
 A  L  V   P  V  L   K  T  A  G   I  D  M   T  T  E   Q  W  N  T
                                nsp2

      3160       3170       3180       3190       3200       3210
GUGGAUUAUU UUGAAACGGA CAAAGCUCAC UCAGCAGAGA UAGUAUUGAA CCAACUAUGC
 V  D  Y   F  E  T   D  K  A  H   S  A  E   I  V  L   N  Q  L  C
                                nsp2
```

-continued 3220 3230 3240 3250 3260 3270
GUGAGGUUCU UUGGACUCGA UCUGGACUCC GGUCUAUUUU CUGCACCCAC UGUUCCGUUA
V R F F G L D L D S G L F S A P T V P L
nsp2

3280 3290 3300 3310 3320 3330
UCCAUUAGGA AUAAUCACUG GGAUAACUCC CCGUCGCCUA ACAUGUACGG GCUGAAUAAA
S I R N N H W D N S P S P N M Y G L N K
nsp2

3340 3350 3360 3370 3380 3390
GAAGUGGUCC GUCAGCUCUC UCGCAGGUAC CCACAACUGC CUCGGGCAGU UGCCACUGGU
E V V R Q L S R R Y P Q L P R A V A T G
nsp2

3400 3410 3420 3430 3440 3450
AGAGUCUAUG ACAUGAACAC UGGUACACUG CGCAAUUAUG AUCCGCGCAU AAACCUAGUA
R V Y D M N T G T L R N Y D P R I N L V
nsp2

3460 3470 3480 3490 3500 3510
CCUGUAAACA GAAGACUGCC UCAUGCUUUA GUCCUCCACC AUAAUGAACA CCCACAGAGU
P V N R R L P H A L V L H H N E H P Q S
nsp2

3520 3530 3540 3550 3560 3570
GACUUUUCUU CAUUCGUCAG CAAAUUGAAG GGCAGAACUG UCCUGGUGGU CGGGGAAAAG
D F S S F V S K L K G R T V L V V G E K
nsp2

3580 3590 3600 3610 3620 3630
UUGUCCGUCC CAGGCAAAAU GGUUGACUGG UUGUCAGACC GGCCUGAGGC UACCUUCAGA
L S V P G K M V D W L S D R P E A T F R
nsp2

3640 3650 3660 3670 3680 3690
GCUCGGCUGG AUUUAGGCAU CCCAGGUGAU GUGCCCAAAU AUGACAUAAU AUUUGUUAAU
A R L D L G I P G D V P K Y D I I F V N
nsp2

3700 3710 3720 3730 3740 3750
GUGAGGACCC CAUAUAAAUA CCAUCACUAU CAGCAGUGUG AAGACCAUGC CAUUAAGCUA
V R T P Y K Y H H Y Q Q C E D H A I K L
nsp2

3760 3770 3780 3790 3800 3810
AGCAUGUUGA CCAAGAAAGC AUGUCUGCAU CUGAAUCCCG GCGGAACCUG UGUCAGCAUA
S M L T K K A C L H L N P G G T C V S I
nsp2

3820 3830 3840 3850 3860 3870
GGUUAUGGUU ACGCUGACAG GGCCAGCGAA AGCAUCAUUG GUGCUAUAGC GCGGCAGUUC
G Y G Y A D R A S E S I I G A I A R Q F
nsp2

3880 3890 3900 3910 3920 3930
AAGUUUUCCC GAGUAUGCAA ACCGAAAUCC UCACUUGAGG AGACGGAAGU UCUGUUUGUA
K F S R V C K P K S S L E E T E V L F V
nsp2

3940 3950 3960 3970 3980 3990
UUCAUUGGGU ACGAUCGCAA GGCCCGUACG CACAAUCCUU ACAAGCUAUC AUCAACCUUG
F I G Y D R K A R T H N P Y K L S S T L
nsp2

4000 4010 4020 4030 4032
ACCAACAUUU AUACAGGUUC CAGACUCCAC GAAGCCGGAU GU
T N I Y T G S R L H E A G C
nsp2

4042 4052 4062 4072 4082 4092
GCACCCUCAU AUCAUGUGGU GCGAGGGGAU AUUGCCACGG CCACCGAAGG AGUGAUUAUA
A P S Y H V V R G D I A T A T E G V I I
nsp3

4102 4112 4122 4132 4142 4152
AAUGCUGCUA ACAGCAAAGG ACAACCUGGC GGAGGGGUGU GCGGAGCGCU GUAUAAGAAA
N A A N S K G Q P G G G V C G A L Y K K
nsp3

-continued

```
      4162        4172        4182        4192        4202        4212
UUCCCGGAAA GUUUCGAUUU ACAGCCGAUC GAAGUAGGAA AAGCGCGACU GGUCAAAGGU
  F  P  E   S  F  D   L  Q  P  I   E  V  G   K  A  R   L  V  K  G
                                nsp3

      4222        4232        4242        4252        4262        4272
GCAGCUAAAC AUAUCAUUCA UGCCGUAGGA CCAAACUUCA ACAAAGUUUC GGAGGUUGAA
  A  A  K   H  I  I   H  A  V  G   P  N  F   N  K  V   S  E  V  E
                                nsp3

      4282        4292        4302        4312        4322        4332
GGUGACAAAC AGUUGGCAGA GGCUUAUGAG UCCAUCGCUA AGAUUGUCAA CGAUAACAAU
  G  D  K   Q  L  A   E  A  Y  E   S  I  A   K  I  V   N  D  N  N
                                nsp3

      4342        4352        4362        4372        4382        4392
UACAAGUCAG UAGCGAUUCC ACUGUUGUCC ACCGGCAUCU UUUCCGGGAA CAAAGAUCGA
  Y  K  S   V  A  I   P  L  L  S   T  G  I   F  S  G   N  K  D  R
                                nsp3

      4402        4412        4422        4432        4442        4452
CUAACCCAAU CAUUGAACCA UUUGCUGACA GCUUUAGACA CCACUGAUGC AGAUGUAGCC
  L  T  Q   S  L  N   H  L  L  T   A  L  D   T  T  D   A  D  V  A
                                nsp3

      4462        4472        4482        4492        4502        4512
AUAUACUGCA GGGACAAGAA AUGGGAAAUG ACUCUCAAGG AAGCAGUGGC UAGGAGAGAA
  I  Y  C   R  D  K   K  W  E  M   T  L  K   E  A  V   A  R  R  E
                                nsp3

      4522        4532        4542        4552        4562        4572
GCAGUGGAGG AGAUAUGCAU AUCCGACGAU UCUUCAGUGA CAGAACCUGA UGCAGAGCUG
  A  V  E   E  I  C   I  S  D  D   S  S  V   T  E  P   D  A  E  L
                                nsp3

      4582        4592        4602        4612        4622        4632
GUGAGGGUGC AUCCCAAGAG UUCUUUGGCU GGAAGGAAGG GCUACAGCAC AAGCGAUGGC
  V  R  V   H  P  K   S  S  L  A   G  R  K   G  Y  S   T  S  D  G
                                nsp3

      4642        4652        4662        4672        4682        4692
AAAACUUUCU CAUAUUUGGA AGGGACCAAG UUUCACCAGG CGGCCAAGGA UAUAGCAGAA
  K  T  F   S  Y  L   E  G  T  K   F  H  Q   A  A  K   D  I  A  E
                                nsp3

      4702        4712        4722        4732        4742        4752
AUUAAUGCCA UGUGGCCCGU UGCAACGGAG GCCAAUGAGC AGGUAUGCAU GUAUAUCCUC
  I  N  A   M  W  P   V  A  T  E   A  N  E   Q  V  C   M  Y  I  L
                                nsp3

      4762        4772        4782        4792        4802        4812
GGAGAAAGCA UGAGCAGUAU UAGGUCGAAA UGCCCCGUCG AGGAGUCGGA AGCCUCCACA
  G  E  S   M  S  S   I  R  S  K   C  P  V   E  E  S   E  A  S  T
                                nsp3

      4822        4832        4842        4852        4862        4872
CCACCUAGCA CGCUGCCUUG CUUGUGCAUC CAUGCCAUGA CUCCAGAAAG AGUACAGCGC
  P  P  S   T  L  P   C  L  C  I   H  A  M   T  P  E   R  V  Q  R
                                nsp3

      4882        4892        4902        4912        4922        4932
CUAAAAGCCU CACGUCCAGA ACAAAUUACU GUGUGCUCAU CCUUUCCAUU GCCGAAGUAU
  L  K  A   S  R  P   E  Q  I  T   V  C  S   S  E  P   L  P  K  Y
                                nsp3

      4942        4952        4962        4972        4982        4992
AGAAUCACUG GUGUGCAGAA GAUCCAAUGC UCCCAGCCUA UAUUGUUCUC ACCGAAAGUG
  R  I  T   G  V  Q   K  I  Q  C   S  Q  P   I  L  F   S  P  K  V
                                nsp3

      5002        5012        5022        5032        5042        5052
CCUGCGUAUA UUCAUCCAAG GAAGUAUCUC GUGGAAACAC CACCGGUAGA CGAGACUCCG
  P  A  Y   I  H  P   R  K  Y  L   V  E  T   P  P  V   D  E  T  P
                                nsp3

      5062        5072        5082        5092        5102        5112
GAGCCAUCGG CAGAGAACCA AUCCACAGAG GGGACACCUG AACAACCACC ACUUAUAACC
  E  P  S   A  E  N   Q  S  T  E   G  T  P   E  Q  P   P  L  I  T
                                nsp3
```

-continued

```
       5122       5132       5142       5152       5162       5172
GAGGAUGAGA CCAGGACUAG AACGCCUGAG CCGAUCAUCA UCGAAGAAGA AGAAGAAGAU
  E  D  E   T  R  T   R  T  P  E   P  I  I   I  E  E   E  E  E  D
                                 nsp3

       5182       5192       5202       5212       5222       5232
AGCAUAAGUU UGCUGUCAGA UGGCCCGACC CACCAGGUGC UGCAAGUCGA GGCAGACAUU
  S  I  S   L  L  S   D  G  P  T   H  Q  V   L  Q  V   E  A  D  I
                                 nsp3

       5242       5252       5262       5272       5282       5292
CACGGGCCGC CCUCUGUAUC UAGCUCAUCC UGGUCCAUUC CUCAUGCAUC CGACUUUGAU
  H  G  P   P  S  V   S  S  S  S   W  S  I   P  H  A   S  D  E  D
                                 nsp3

       5302       5312       5322       5332       5342       5352
GUGGACAGUU UAUCCAUACU UGACACCCUG GAGGGAGCUA GCGUGACCAG CGGGGCAACG
  V  D  S   L  S  I   L  D  T  L   E  G  A   S  V  T   S  G  A  T
                                 nsp3

       5362       5372       5382       5392       5402       5412
UCAGCCGAGA CUAACUCUUA CUUCGCAAAG AGUAUGGAGU UUCUGGCGCG ACCGGUGCCU
  S  A  E   T  N  S   Y  F  A  K   S  M  E   F  L  A   R  P  V  P
                                 nsp3

       5422       5432       5442       5452       5462       5472
GCGCCUCGAA CAGUAUUCAG GAACCCUCCA CAUCCCGCUC CGCGCACAAG AACACCGUCA
  A  P  R   T  V  F   R  N  P  P   H  P  A   P  R  T   R  T  P  S
                                 nsp3

       5482       5492       5502       5512       5522       5532
CUUGCACCCA GCAGGGCCUG CUCCAGAACC AGCCUAGUUU CCACCCCGCC AGGCGUGAAU
  L  A  P   S  R  A   C  S  R  T   S  L  V   S  T  P   P  G  V  N
                                 nsp3

       5542       5552       5562       5572       5582       5592
AGGGUGAUCA CUAGAGAGGA GCUCGAAGCG CUUACCCCGU CACGCACUCC UAGCAGGUCG
  R  V  I   T  R  E   E  L  E  A   L  T  P   S  R  T   P  S  R  S
                                 nsp3

       5602       5612       5622       5632       5642       5652
GUCUCCAGAA CCAGCCUGGU CUCCAACCCG CCAGGCGUAA AUAGGGUGAU UACAAGAGAG
  V  S  R   T  S  L   V  S  N  P   P  G  V   N  R  V   I  T  R  E
                                 nsp3

       5662       5672       5682       5692       5702 5703
GAGUUUGAGG CGUUCGUAGC ACAACAACAA UGACGGUUUG AUGCGGGUGC A
  E  F  E   A  F  V   A  Q  Q  Q   *  R  F   D  A  G   A
                                 nsp3

       5713       5723       5733       5743       5753       5763
UACAUCUUUU CCUCCGACAC CGGUCAAGGG CAUUUACAAC AAAAAUCAGU AAGGCAAACG
  Y  I  F   S  S  D   T  G  Q  G   H  L  Q   Q  K  S   V  R  Q  T
                                 nsp4

       5773       5783       5793       5803       5813       5823
GUGCUAUCCG AAGUGGUGUU GGAGAGGACC GAAUUGGAGA UUUCGUAUGC CCCGCGCCUC
  V  L  S   E  V  V   L  E  R  T   E  L  E   I  S  Y   A  P  R  L
                                 nsp4

       5833       5843       5853       5863       5873       5883
GACCAAGAAA AAGAAGAAUU ACUACGCAAG AAAUUACAGU UAAAUCCCAC ACCUGCUAAC
  D  Q  E   K  E  E   L  L  R  K   K  L  Q   L  N  P   T  P  A  N
                                 nsp4

       5893       5903       5913       5923       5933       5943
AGAAGCAGAU ACCAGUCCAG GAAGGUGGAG AACAUGAAAG CCAUAACAGC UAGACGUAUU
  R  S  R   Y  Q  S   R  K  V  E   N  M  K   A  I  T   A  R  R  I
                                 nsp4

       5953       5963       5973       5983       5993       6003
CUGCAAGGCC UAGGGCAUUA UUUGAAGGCA GAAGGAAAAG UGGAGUGCUA CCGAACCCUG
  L  Q  G   L  G  H   Y  L  K  A   E  G  K   V  E  C   Y  R  T  L
                                 nsp4

       6013       6023       6033       6043       6053       6063
CAUCCUGUUC CUUUGUAUUC AUCUAGUGUG AACCGUGCCU UUUCAAGCCC CAAGGUCGCA
  H  P  V   P  L  Y   S  S  S  V   N  R  A   F  S  S   P  K  V  A
                                 nsp4
```

-continued

```
      6073       6083       6093       6103       6113       6123
GUGGAAGCCU GUAACGCCAU GUUGAAAGAG AACUUUCCGA CUGUGGCUUC UUACUGUAUU
  V  E  A   C  N  A   M  L  K  E   N  F  P   T  V  A   S  Y  C  I
                                nsp4

      6133       6143       6153       6163       6173       6183
AUUCCAGAGU ACGAUGCCUA UUUGGACAUG GUUGACGGAG CUUCAUGCUG CUUAGACACU
  I  P  E   Y  D  A   Y  L  D  M   V  D  G   A  S  C   C  L  D  T
                                nsp4

      6193       6203       6213       6223       6233       6243
GCCAGUUUUU GCCCUGCAAA GCUGCGCAGC UUUCCAAAGA AACACUCCUA UUUGGAACCC
  A  S  F   C  P  A   K  L  R  S   F  P  K   K  H  S   Y  L  E  P
                                nsp4

      6253       6263       6273       6283       6293       6303
ACAAUACGAU CGGCAGUGCC UUCAGCGAUC CAGAACACGC UCCAGAACGU CCUGGCAGCU
  T  I  R   S  A  V   P  S  A  I   Q  N  T   L  Q  N   V  L  A  A
                                nsp4

      6313       6323       6333       6343       6353       6363
GCCACAAAAA GAAAUUGCAA UGUCACGCAA AUGAGAGAAU UGCCCGUAUU GGAUUCGGCG
  A  T  K   R  N  C   N  V  T  Q   M  R  E   L  P  V   L  D  S  A
                                nsp4

      6373       6383       6393       6403       6413       6423
GCCUUUAAUG UGGAAUGCUU CAAGAAAUAU GCGUGUAAUA AUGAAUAUUG GGAAACGUUU
  A  F  N   V  E  C   F  K  K  Y   A  C  N   N  E  Y   W  E  T  F
                                nsp4

      6433       6443       6453       6463       6473       6483
AAAGAAAACC CCAUCAGGCU UACUGAAGAA AACGUGGUAA AUUACAUUAC CAAAUUAAAA
  K  E  N   P  I  R   L  T  E  E   N  V  V   N  Y  I   T  K  L  K
                                nsp4

      6493       6503       6513       6523       6533       6543
GGACCAAAAG CUGCUGCUCU UUUUGCGAAG ACACAUAAUU UGAAUAUGUU GCAGGACAUA
  G  P  K   A  A  A   L  F  A  K   T  H  N   L  N  M   L  Q  D  I
                                nsp4

      6553       6563       6573       6583       6593       6603
CCAAUGGACA GGUUUGUAAU GGACUUAAAG AGAGACGUGA AAGUGACUCC AGGAACAAAA
  P  M  D   R  F  V   M  D  L  K   R  D  V   K  V  T   P  G  T  K
                                nsp4

      6613       6623       6633       6643       6653       6663
CAUACUGAAG AACGGCCCAA GGUACAGGUG AUCCAGGCUG CCGAUCCGCU AGCAACAGCG
  H  T  E   E  R  P   K  V  Q  V   I  Q  A   A  D  P   L  A  T  A
                                nsp4

      6673       6683       6693       6703       6713       6723
UAUCUGUGCG GAAUCCACCG AGAGCUGGUU AGGAGAUUAA AUGCGGUCCU GCUUCCGAAC
  Y  L  C   G  I  H   R  E  L  V   R  R  L   N  A  V   L  L  P  N
                                nsp4

      6733       6743       6753       6763       6773       6783
AUUCAUACAC UGUUUGAUAU GUCGGCUGAA GACUUUGACG CUAUUAUAGC CGAGCACUUC
  I  H  T   L  F  D   M  S  A  E   D  F  D   A  I  I   A  E  H  F
                                nsp4

      6793       6803       6813       6823       6833       6843
CAGCCUGGGG AUUGUGUUCU GGAAACUGAC AUCGCGUCGU UUGAUAAAAG UGAGGACGAC
  Q  P  G   D  C  V   L  E  T  D   I  A  S   F  D  K   S  E  D  D
                                nsp4

      6853       6863       6873       6883       6893       6903
GCCAUGGCUC UGACCGCGUU AAUGAUUCUG GAAGACUUAG GUGUGGACGC AGAGCUGUUG
  A  M  A   L  T  A   L  M  I  L   E  D  L   G  V  D   A  E  L  L
                                nsp4

      6913       6923       6933       6943       6953       6963
ACGCUGAUUG AGGCGGCUUU CGGCGAAAUU UCAUCAAUAC AUUUGCCCAC UAAAACUAAA
  T  L  I   E  A  A   F  G  E  I   S  S  I   H  L  P   T  K  T  K
                                nsp4

      6973       6983       6993       7003       7013       7023
UUUAAAUUCG GAGCCAUGAU GAAAUCUGGA AUGUUCCUCA CACUGUUUGU GAACACAGUC
  F  K  F   G  A  M   M  K  S  G   M  F  L   T  L  F   V  N  T  V
                                nsp4
```

-continued

```
      7033       7043       7053       7063       7073       7083
AUUAACAUUG UAAUCGCAAG CAGAGUGUUG AGAGAACGGC UAACCGGAUC ACCAUGUGCA
  I  N  I   V  I  A   S  R  V  L   R  E  R   L  T  G   S  P  C  A
                                  nsp4

      7093       7103       7113       7123       7133       7143
GCAUUCAUUG GAGAUGACAA UAUCGUGAAA GGAGUCAAAU CGGACAAAUU AAUGGCAGAC
  A  F  I   G  D  D   N  I  V  K   G  V  K   S  D  K   L  M  A  D
                                  nsp4

      7153       7163       7173       7183       7193       7203
AGGUGCGCCA CCUGGUUGAA UAUGGAAGUC AAGAUUAUAG AUGCUGUGGU GGGCGAGAAA
  R  C  A   T  W  L   N  M  E  V   K  I  I   D  A  V   V  G  E  K
                                  nsp4

      7213       7223       7233       7243       7253       7263
GCGCCUUAUU UCUGUGGAGG GUUUAUUUUG UGUGACUCCG UGACCGGCAC AGCGUGCCGU
  A  P  Y   F  C  G   G  F  I  L   C  D  S   V  T  G   T  A  C  R
                                  nsp4

      7273       7283       7293       7303       7313       7323
GUGGCAGACC CCCUAAAAAG GCUGUUUAAG CUAGGCAAAC CUCUGGCAGC AGACGAUGAA
  V  A  D   P  L  K   R  L  F  K   L  G  K   P  L  A   A  D  D  E
                                  nsp4

      7333       7343       7353       7363       7373       7383
CAUGAUGAUG ACAGGAGAAG GGCAUUGCAU GAGGAGUCAA CACGCUGGAA CCGAGUGGGU
  H  D  D   D  R  R   R  A  L  H   E  E  S   T  R  W   N  R  V  G
                                  nsp4

      7393       7403       7413       7423       7433       7443
AUUCUUUCAG AGCUGUGCAA GGCAGUAGAA UCAAGGUAUG AAACCGUAGG AACUUCCAUC
  I  L  S   E  L  C   K  A  V  E   S  R  Y   E  T  V   G  T  S  I
                                  nsp4

      7453       7463       7473       7483       7493       7503
AUAGUUAUGG CCAUGACUAC UCUAGCUAGC AGUGUUAAAU CAUUCAGCUA CCUGAGAGGG
  I  V  M   A  M  T   T  L  A  S   S  V  K   S  F  S   Y  L  R  G
                                  nsp4

      7513       7523        7527
GCCCCUAUAA CUCUCUACGG CUAA
  A  P  I   T  L  Y   G  *
                                  nsp4

      7537       7547       7557       7567 7568
CCUGAAUGGA CUACGACAUA GUCUAGUCCG CCAAGACUAG U
                                virUTR

      7578       7588       7598       7608       7618       7628
AUGUUCGUGU UCCUGGUGCU GCUGCCUCUG GUGUCCAGCC AGUGUGUGAA CCUGACCACC
  M  F  V   F  L  V   L  L  P  L   V  S  S   Q  C  V   N  L  T  T
                              S protein

      7638       7648       7658       7668       7678       7688
AGAACACAGC UGCCUCCAGC CUACACCAAC AGCUUUACCA GAGGCGUGUA CUACCCCGAC
  R  T  Q   L  P  P   A  Y  T  N   S  F  T   R  G  V   Y  Y  P  D
                              S protein

      7698       7708       7718       7728       7738       7748
AAGGUGUUCA GAUCCAGCGU GCUGCACUCU ACCCAGGACC UGUUCCUGCC UUUCUUCAGC
  K  V  F   R  S  S   V  L  H  S   T  Q  D   L  F  L   P  F  F  S
                              S protein

      7758       7768       7778       7788       7798       7808
AACGUGACCU GGUUCCACGC CAUCCACGUG UCCGGCACCA AUGGCACCAA GAGAUUCGAC
  N  V  T   W  F  H   A  I  H  V   S  G  T   N  G  T   K  R  F  D
                              S protein

      7818       7828       7838       7848       7858       7868
AACCCCGUGC UGCCCUUCAA CGACGGGGUG UACUUUGCCA GCACCGAGAA GUCCAACAUC
  N  P  V   L  P  F   N  D  G  V   Y  F  A   S  T  E   K  S  N  I
                              S protein

      7878       7888       7898       7908       7918       7928
AUCAGAGGCU GGAUCUUCGG CACCACACUG GACAGCAAGA CCCAGAGCCU GCUGAUCGUG
  I  R  G   W  I  F   G  T  T  L   D  S  K   T  Q  S   L  L  I  V
                              S protein
```

-continued

```
       7938       7948       7958       7968       7978       7988
AACAACGCCA CCAACGUGGU CAUCAAAGUG UGCGAGUUCC AGUUCUGCAA CGACCCCUUC
  N  N  A   T  N  V   V  I  K  V   C  E  F   Q  F  C   N  D  P  F
                             S protein

       7998       8008       8018       8028       8038       8048
CUGGGCGUCU ACUACCACAA GAACAACAAG AGCUGGAUGG AAAGCGAGUU CCGGGUGUAC
  L  G  V   Y  Y  H   K  N  N  K   S  W  M   E  S  E   F  R  V  Y
                             S protein

       8058       8068       8078       8088       8098       8108
AGCAGCGCCA ACAACUGCAC CUUCGAGUAC GUGUCCCAGC CUUUCCUGAU GGACCUGGAA
  S  S  A   N  N  C   T  F  E  Y   V  S  Q   P  F  L   M  D  L  E
                             S protein

       8118       8128       8138       8148       8158       8168
GGCAAGCAGG GCAACUUCAA GAACCUGCGC GAGUUCGUGU UUAAGAACAU CGACGGCUAC
  G  K  Q   G  N  F   K  N  L  R   E  F  V   F  K  N   I  D  G  Y
                             S protein

       8178       8188       8198       8208       8218       8228
UUCAAGAUCU ACAGCAAGCA CACCCCUAUC AACCUCGUGC GGGAUCUGCC UCAGGGCUUC
  F  K  I   Y  S  K   H  T  P  I   N  L  V   R  D  L   P  Q  G  F
                             S protein

       8238       8248       8258       8268       8278       8288
UCUGCUCUGG AACCCCUGGU GGAUCUGCCC AUCGGCAUCA ACAUCACCCG GUUUCAGACA
  S  A  L   E  P  L   V  D  L  P   I  G  I   N  I  T   R  F  Q  T
                             S protein

       8298       8308       8318       8328       8338       8348
CUGCUGGCCC UGCACAGAAG CUACCUGACA CCUGGCGAUA GCAGCAGCGG AUGGACAGCU
  L  L  A   L  H  R   S  Y  L  T   P  G  D   S  S  S   G  W  T  A
                             S protein

       8358       8368       8378       8388       8398       8408
GGUGCCGCCG CUUACUAUGU GGGCUACCUG CAGCCUAGAA CCUUCCUGCU GAAGUACAAC
  G  A  A   A  Y  Y   V  G  Y  L   Q  P  R   T  F  L   L  K  Y  N
                             S protein

       8418       8428       8438       8448       8458       8468
GAGAACGGCA CCAUCACCGA CGCCGUGGAU UGUGCUCUGG AUCCUCUGAG CGAGACAAAG
  E  N  G   T  I  T   D  A  V  D   C  A  L   D  P  L   S  E  T  K
                             S protein

       8478       8488       8498       8508       8518       8528
UGCACCCUGA AGUCCUUCAC CGUGGAAAAG GGCAUCUACC AGACCAGCAA CUUCCGGGUG
  C  T  L   K  S  F   T  V  E  K   G  I  Y   Q  T  S   N  F  R  V
                             S protein

       8538       8548       8558       8568       8578       8588
CAGCCCACCG AAUCCAUCGU GCGGUUCCCC AAUAUCACCA AUCUGUGCCC CUUCGGCGAG
  Q  P  T   E  S  I   V  R  F  P   N  I  T   N  L  C   P  F  G  E
                             S protein

       8598       8608       8618       8628       8638       8648
GUGUUCAAUG CCACCAGAUU CGCCUCUGUG UACGCCUGGA ACCGGAAGCG GAUCAGCAAU
  V  F  N   A  T  R   F  A  S  V   Y  A  W   N  R  K   R  I  S  N
                             S protein

       8658       8668       8678       8688       8698       8708
UGCGUGGCCG ACUACUCCGU GCUGUACAAC UCCGCCAGCU UCAGCACCUU CAAGUGCUAC
  C  V  A   D  Y  S   V  L  Y  N   S  A  S   F  S  T   F  K  C  Y
                             S protein

       8718       8728       8738       8748       8758       8768
GGCGUGUCCC CUACCAAGCU GAACGACCUG UGCUUCACAA ACGUGUACGC CGACAGCUUC
  G  V  S   P  T  K   L  N  D  L   C  F  T   N  V  Y   A  D  S  F
                             S protein

       8778       8788       8798       8808       8818       8828
GUGAUCCGGG GAGAUGAAGU GCGGCAGAUU GCCCCUGGAC AGACAGGCAA GAUCGCCGAC
  V  I  R   G  D  E   V  R  Q  I   A  P  G   Q  T  G   K  I  A  D
                             S protein

       8838       8848       8858       8868       8878       8888
UACAACUACA AGCUGCCCGA CGACUUCACC GGCUGUGUGA UUGCCUGGAA CAGCAACAAC
  Y  N  Y   K  L  P   D  D  F  T   G  C  V   I  A  W   N  S  N  N
                             S protein
```

-continued

```
       8898       8908       8918       8928       8938       8948
CUGGACUCCA AAGUCGGCGG CAACUACAAU UACCUGUACC GGCUGUUCCG GAAGUCCAAU
  L  D  S   K  V  G   G  N  Y  N  Y  L  Y   R  L  F   R  K  S  N
                           S protein

       8958       8968       8978       8988       8998       9008
CUGAAGCCCU UCGAGCGGGA CAUCUCCACC GAGAUCUAUC AGGCCGGCAG CACCCCUUGU
  L  K  P   F  E  R   D  I  S  T  E  I  Y   Q  A  G   S  T  P  C
                           S protein

       9018       9028       9038       9048       9058       9068
AACGGCGUGG AAGGCUUCAA CUGCUACUUC CCACUGCAGU CCUACGGCUU UCAGCCCACA
  N  G  V   E  G  F   N  C  Y  F  P  L  Q   S  Y  G   F  Q  P  T
                           S protein

       9078       9088       9098       9108       9118       9128
AAUGGCGUGG GCUAUCAGCC CUACAGAGUG GUGGUGCUGA GCUUCGAACU GCUGCAUGCC
  N  G  V   G  Y  Q   P  Y  R  V  V  V  L   S  F  E   L  L  H  A
                           S protein

       9138       9148       9158       9168       9178       9188
CCUGCCACAG UGUGCGGCCC UAAGAAAAGC ACCAAUCUCG UGAAGAACAA AUGCGUGAAC
  P  A  T   V  C  G   P  K  K  S  T  N  L   V  K  N   K  C  V  N
                           S protein

       9198       9208       9218       9228       9238       9248
UUCAACUUCA ACGGCCUGAC CGGCACCGGC GUGCUGACAG AGAGCAACAA GAAGUUCCUG
  F  N  F   N  G  L   T  G  T  G  V  L  T   E  S  N   K  K  F  L
                           S protein

       9258       9268       9278       9288       9298       9308
CCAUUCCAGC AGUUUGGCCG GGAUAUCGCC GAUACCACAG ACGCCGUUAG AGAUCCCCAG
  P  F  Q   Q  F  G   R  D  I  A  D  T  T   D  A  V   R  D  P  Q
                           S protein

       9318       9328       9338       9348       9358       9368
ACACUGGAAA UCCUGGACAU CACCCCUUGC AGCUUCGGCG GAGUGUCUGU GAUCACCCCU
  T  L  E   I  L  D   I  T  P  C  S  F  G   G  V  S   V  I  T  P
                           S protein

       9378       9388       9398       9408       9418       9428
GGCACCAACA CCAGCAAUCA GGUGGCAGUG CUGUACCAGG ACGUGAACUG UACCGAAGUG
  G  T  N   T  S  N   Q  V  A  V  L  Y  Q   D  V  N   C  T  E  V
                           S protein

       9438       9448       9458       9468       9478       9488
CCCGUGGCCA UUCACGCCGA UCAGCUGACA CCUACAUGGC GGGUGUACUC CACCGGCAGC
  P  V  A   T  H  A   D  Q  L  T  P  T  W   R  V  Y   S  T  G  S
                           S protein

       9498       9508       9518       9528       9538       9548
AAUGUGUUUC AGACCAGAGC CGGCUGUCUG AUCGGAGCCG AGCACGUGAA CAAUAGCUAC
  N  V  F   Q  T  R   A  G  C  L  I  G  A   E  H  V   N  N  S  Y
                           S protein

       9558       9568       9578       9588       9598       9608
GAGUGCGACA UCCCCAUCGG CGCUGGAAUC UGCGCCAGCU ACCAGACACA GACAAACAGC
  E  C  D   I  P  T   G  A  G  I  C  A  S   Y  Q  T   Q  T  N  S
                           S protein

       9618       9628       9638       9648       9658       9668
CCUCGGAGAG CCAGAAGCGU GGCCAGCCAG AGCAUCAUUG CCUACACAAU GUCUCUGGGC
  P  R  R   A  R  S   V  A  S  Q  S  I  T   A  Y  T   M  S  L  G
                           S protein

       9678       9688       9698       9708       9718       9728
GCCGAGAACA GCGUGGCCUA CUCCAACAAC UCUAUCGCUA UCCCCACCAA CUUCACCAUC
  A  E  N   S  V  A   Y  S  N  N  S  T  A   I  P  T   N  E  T  T
                           S protein

       9738       9748       9758       9768       9778       9788
AGCGUGACCA CAGAGAUCCU GCCUGUGUCC AUGACCAAGA CCAGCGUGGA CUGCACCAUG
  S  V  T   T  E  T   L  P  V  S  M  T  K   T  S  V   D  C  T  M
                           S protein

       9798       9808       9818       9828       9838       9848
UACAUCUGCG GCGAUUCCAC CGAGUGCUCC AACCUGCUGC UGCAGUACGG CAGCUUCUGC
  Y  I  C   G  D  S   T  E  C  S  N  L  L   L  Q  Y   G  S  F  C
                           S protein
```

-continued

```
       9858       9868       9878       9888       9898       9908
ACCCAGCUGA AUAGAGCCCU GACAGGGAUC GCCGUGGAAC AGGACAAGAA CACCCAAGAG
  T  Q  L   N  R  A   L  T  G  I   A  V  E   Q  D  K   N  T  Q  E
                           S protein

       9918       9928       9938       9948       9958       9968
GUGUUCGCCC AAGUGAAGCA GAUCUACAAG ACCCCUCCUA UCAAGGACUU CGGCGGCUUC
  V  F  A   Q  V  K   Q  I  Y  K   T  P  P   I  K  D   F  G  G  F
                           S protein

       9978       9988       9998      10008      10018      10028
AAUUUCAGCC AGAUUCUGCC CGAUCCUAGC AAGCCCAGCA AGCGGAGCUU CAUCGAGGAC
  N  F  S   Q  I  L   P  D  P  S   K  P  S   K  R  S   F  I  E  D
                           S protein

      10038      10048      10058      10068      10078      10088
CUGCUGUUCA ACAAAGUGAC ACUGGCCGAC GCCGGCUUCA UCAAGCAGUA UGGCGAUUGU
  L  L  F   N  K  V   T  L  A  D   A  G  F   I  K  Q   Y  G  D  C
                           S protein

      10098      10108      10118      10128      10138      10148
CUGGGCGACA UUGCCGCCAG GGAUCUGAUU UGCGCCCAGA AGUUUAACGG ACUGACAGUG
  L  G  D   I  A  A   R  D  L  I   C  A  Q   K  F  N   G  L  T  V
                           S protein

      10158      10168      10178      10188      10198      10208
CUGCCUCCUC UGCUGACCGA UGAGAUGAUC GCCCAGUACA CAUCUGCCCU GCUGGCCGGC
  L  P  P   L  L  T   D  E  M  I   A  Q  Y   T  S  A   L  L  A  G
                           S protein

      10218      10228      10238      10248      10258      10268
ACAAUCACAA GCGGCUGGAC AUUUGGAGCA GGCGCCGCUC UGCAGAUCCC CUUUGCUAUG
  T  I  T   S  G  W   T  F  G  A   G  A  A   L  Q  I   P  F  A  M
                           S protein

      10278      10288      10298      10308      10318      10328
CAGAUGGCCU ACCGGUUCAA CGGCAUCGGA GUGACCCAGA AUGUGCUGUA CGAGAACCAG
  Q  M  A   Y  R  F   N  G  I  G   V  T  Q   N  V  L   Y  E  N  Q
                           S protein

      10338      10348      10358      10368      10378      10388
AAGCUGAUCG CCAACCAGUU CAACAGCGCC AUCGGCAAGA UCCAGGACAG CCUGAGCAGC
  K  L  I   A  N  Q   F  N  S  A   I  G  K   I  Q  D   S  L  S  S
                           S protein

      10398      10408      10418      10428      10438      10448
ACAGCAAGCG CCCUGGGAAA GCUGCAGGAC GUGGUCAACC AGAAUGCCCA GGCACUGAAC
  T  A  S   A  L  G   K  L  Q  D   V  V  N   Q  N  A   Q  A  L  N
                           S protein

      10458      10468      10478      10488      10498      10508
ACCCUGGUCA AGCAGCUGUC CUCCAACUUC GGCGCCAUCA GCUCUGUGCU GAACGAUAUC
  T  L  V   K  Q  L   S  S  N  F   G  A  I   S  S  V   L  N  D  I
                           S protein

      10518      10528      10538      10548      10558      10568
CUGAGCAGAC UGGACTC TGAGGCCGAG GUGCAGAUCG ACAGACUGAU CACAGGCAGA
  L  S  R   L  D  P   P  E  A  E   V  Q  I   D  R  L   I  T  G  R
                           S protein

      10578      10588      10598      10608      10618      10628
CUGCAGAGCC UCCAGACAUA CGUGACCCAG CAGCUGAUCA GAGCCGCCGA GAUUAGAGCC
  L  Q  S   L  Q  T   Y  V  T  Q   Q  L  I   R  A  A   E  I  R  A
                           S protein

      10638      10648      10658      10668      10678      10688
UCUGCCAAUC UGGCCGCCAC CAAGAUGUCU GAGUGUGUGC UGGGCCAGAG CAAGAGAGUG
  S  A  N   L  A  A   T  K  M  S   E  C  V   L  G  Q   S  K  R  V
                           S protein

      10698      10708      10718      10728      10738      10748
GACUUUUGCG GCAAGGGCUA CCACCUGAUG AGCUUCCCUC AGUCUGCCCC UCACGGCGUG
  D  F  C   G  K  G   Y  H  L  M   S  F  P   Q  S  A   P  H  G  V
                           S protein

      10758      10768      10778      10788      10798      10808
GUGUUUCUGC ACGUGACAUA UGUGCCCGCU CAAGAGAAGA AUUUCACCAC CGCUCCAGCC
  V  F  L   H  V  T   Y  V  P  A   Q  E  K   N  F  T   T  A  P  A
                           S protein
```

-continued

```
     10818       10828       10838       10848       10858       10868
AUCUGCCACG ACGGCAAAGC CCACUUUCCU AGAGAAGGCG UGUUCGUGUC CAACGGCACC
  I  C  H   D  G  K   A  H  F  P   R  E  G   V  F  V   S  N  G  T
                              S protein

     10878       10888       10898       10908       10918       10928
CAUUGGUUCG UGACACAGCG GAACUUCUAC GAGCCCCAGA UCAUCACCAC CGACAACACC
  H  W  F   V  T  Q   R  N  F  Y   E  P  Q   I  I  T   T  D  N  T
                              S protein

     10938       10948       10958       10968       10978       10988
UUCGUGUCUG GCAACUGCGA CGUCGUGAUC GGCAUUGUGA ACAAUACCGU GUACGACCCU
  F  V  S   G  N  C   D  V  V  I   G  I  V   N  N  T   V  Y  D  P
                              S protein

     10998       11008       11018       11028       11038       11048
CUGCAGCCCG AGCUGGACAG CUUCAAAGAG GAACUGGACA AGUACUUUAA GAACCACACA
  L  Q  P   E  L  D   S  F  K  E   E  L  D   K  Y  F   K  N  H  T
                              S protein

     11058       11068       11078       11088       11098       11108
AGCCCCGACG UGGACCUGGG CGAUAUCAGC GGAAUCAAUG CCAGCGUCGU GAACAUCCAG
  S  P  D   V  D  L   G  D  I  S   G  I  N   A  S  V   V  N  I  Q
                              S protein

     11118       11128       11138       11148       11158       11168
AAAGAGAUCG ACCGGCUGAA CGAGGUGGCC AAGAAUCUGA ACGAGAGCCU GAUCGACCUG
  K  E  I   D  R  L   N  E  V  A   K  N  L   N  E  S   L  I  D  L
                              S protein

     11178       11188       11198       11208       11218       11228
CAAGAACUGG GGAAGUACGA GCAGUACAUC AAGUGGCCCU GGUACAUCUG GCUGGGCUUU
  Q  E  L   G  K  Y   E  Q  Y  I   K  W  P   W  Y  I   W  L  G  F
                              S protein

     11238       11248       11258       11268       11278       11288
AUCGCCGGAC UGAUUGCCAU CGUGAUGGUC ACAAUCAUGC UGUGUUGCAU GACCAGCUGC
  I  A  G   L  I  A   I  V  M  V   T  I  M   L  C  C   M  T  S  C
                              S protein

     11298       11308       11318       11328       11338       11348
UGUAGCUGCC UGAAGGGCUG UUGUAGCUGU GGCAGCUGCU GCAAGUUCGA CGAGGACGAU
  C  S  C   L  K  G   C  C  S  C   G  S  C   C  K  F   D  E  D  D
                              S protein

     11358       11368       11378       11388 11393
UCUGAGCCCG UGCUGAAGGG CGUGAAACUG CACUACACAU GAUGA
  S  E  P   V  L  K   G  V  K  L   H  Y  T   *  *
                              S protein

     11403       11413       11423       11433       11443       11453
CUCGAGCUGG UACUGCAUGC ACGCAAUGCU AGCUGCCCCU UUCCCGUCCU GGGUACCCCG
                             FI element

     11463       11473       11483       11493       11503       11513
AGUCUCCCCC GACCUCGGGU CCCAGGUAUG CUCCCACCUC CACCUGCCCC ACUCACCACC
                             FI element

     11523       11533       11543       11553       11563       11573
UCUGCUAGUU CCAGACACCU CCCAAGCACG CAGCAAUGCA GCUCAAAACG CUUAGCCUAG
                             FI element

     11583       11593       11603       11613       11623       11633
CCACACCCCC ACGGGAAACA GCAGUGAUUA ACCUUUAGCA AUAAACGAAA GUUUAACUAA
                             FI element

     11643       11653       11663       11673       11683       11693
GCUAUACUAA CCCCAGGGUU GGUCAAUUUC GUGCCAGCCA CACCGCGGCC GCAUGAAUAC
                             FI element

     11703       11713       11723       11733       11743       11753
AGCAGCAAUU GGCAAGCUGC UUACAUAGAA CUCGCGGCGA UUGGCAUGCC GCCUUAAAAU
                             FI element

     11763       11773       11783       11793       11803       11807
UUUUAUUUUA UUUUUUCUUU UCUUUUCCGA AUCGGAUUUU GUUUUUAAUA UUUC
                             FI element

     11817       11827       11837       11847       11857       11867
AAAAAAAAAA AAAAAAAAAA AAAAAAAAAA GCAUAUGACU AAAAAAAAAA AAAAAAAAAA
                              Poly(A)
```

-continued

```
      11877      11887      11897      11907      11917
AAAAAAAAAA AAAAAAAAAA AAAAAAAAAA AAAAAAAAAA AAAAAAAAAA
                                Poly(A)
```

Nucleotide Sequence of RBS004.3 (SEQ ID NO: 26; SEQ ID NO: 5)

Nucleotide sequence is shown with individual sequence elements as indicated in bold letters. In addition, the sequence of the translated protein is shown in italic letters below the coding nucleotide sequence (*=stop codon).

```
        10         20         30         40    45
GAUGGGCGGC GCAUGAGAGA AGCCCAGACC AAUUACCUAC CCAAA
                              5' UTR

        55         65         75         85         95        105
AUGGAGAAAG UUCACGUUGA CAUCGAGGAA GACAGCCCAU UCCUCAGAGC UUUGCAGCGG
 M  E  K   V  H  V   D  I  E  E   D  S  P   F  L  R   A  L  Q  R
                               nsp1

       115        125        135        145        155        165
AGCUUCCCGC AGUUUGAGGU AGAAGCCAAG CAGGUCACUG AUAAUGACCA UGCUAAUGCC
 S  F  P   Q  F  E   V  E  A  K   Q  V  T   D  N  D   H  A  N  A
                               nsp1

       175        185        195        205        215        225
AGAGCGUUUU CGCAUCUGGC UUCAAAACUG AUCGAAACGG AGGUGGACCC AUCCGACACG
 R  A  F   S  H  L   A  S  K  L   I  E  T   E  V  D   P  S  D  T
                               nsp1

       235        245        255        265        275        285
AUCCUUGACA UUGGAAGUGC GCCCGCCCGC AGAAUGUAUU CUAAGCACAA GUAUCAUUGU
 I  L  D   I  G  S   A  P  A  R   R  M  Y   S  K  H   K  Y  H  C
                               nsp1

       295        305        315        325        335        345
AUCUGUCCGA UGAGAUGUGC GGAAGAUCCG GACAGAUUGU AUAAGUAUGC AACUAAGCUG
 I  C  P   M  R  C   A  E  D  P   D  R  L   Y  K  Y   A  T  K  L
                               nsp1

       355        365        375        385        395        405
AAGAAAAACU GUAAGGAAAU AACUGAUAAG GAAUUGGACA AGAAAAUGAA GGAGCUCGCC
 K  K  N   C  K  E   I  T  D  K   E  L  D   K  K  M   K  E  L  A
                               nsp1

       415        425        435        445        455        465
GCCGUCAUGA GCGACCCUGA CCUGGAAACU GAGACUAUGU GCCUCCACGA CGACGAGUCG
 A  V  M   S  D  P   D  L  E  T   E  T  M   C  L  H   D  D  E  S
                               nsp1

       475        485        495        505        515        525
UGUCGCUACG AAGGGCAAGU CGCUGUUUAC CAGGAUGUAU ACGCGGUUGA CGGACCGACA
 C  R  Y   E  G  Q   V  A  V  Y   Q  D  V   Y  A  V   D  G  P  T
                               nsp1

       535        545        555        565        575        585
AGUCUCUAUC ACCAAGCCAA UAAGGGAGUU AGAGUCGCCU ACUGGAUAGG CUUUGACACC
 S  L  Y   H  Q  A   N  K  G  V   R  V  A   Y  W  I   G  F  D  T
                               nsp1

       595        605        615        625        635        645
ACCCCUUUUA UGUUUAAGAA CUUGGCUGGA GCAUAUCCAU CAUACUCUAC CAACUGGGCC
 T  P  F   M  F  K   N  L  A  G   A  Y  P   S  Y  S   T  N  W  A
                               nsp1

       655        665        675        685        695        705
GACGAAACCG UGUUAACGGC UCGUAACAUA GGCCUAUGCA GCUCUGACGU UAUGGAGCGG
 D  E  T   V  L  T   A  R  N  I   G  L  C   S  S  D   V  M  E  R
                               nsp1

       715        725        735        745        755        765
UCACGUAGAG GGAUGUCCAU UCUUAGAAAG AAGUAUUUGA AACCAUCCAA CAAUGUUCUA
 S  R  R   G  M  S   I  L  R  K   K  Y  L   K  P  S   N  N  V  L
                               nsp1
```

-continued

```
       775       785       795       805       815       825
UUCUCUGUUG GCUCGACCAU CUACCACGAA AAGAGGGACU UACUGAGGAG CUGGCACCUG
  F  S  V   G  S  T   I  Y  H  E   K  R  D   L  L  R   S  W  H  L
                          nsp1

       835       845       855       865       875       885
CCGUCUGUAU UUCACUUACG UGGCAAGCAA AAUUACACAU GUCGGUGUGA GACUAUAGUU
  P  S  V   F  H  L   R  G  K  Q   N  Y  T   C  R  C   E  T  I  V
                          nsp1

       895       905       915       925       935       945
AGUUGCGACG GGUACGUCGU UAAAAGAAUA GCUAUCAGUC CAGGCCUGUA UGGGAAGCCU
  S  C  D   G  Y  V   V  K  R  I   A  I  S   P  G  L   Y  G  K  P
                          nsp1

       955       965       975       985       995      1005
UCAGGCUAUG CUGCUACGAU GCACCGCGAG GGAUUCUUGU GCUGCAAAGU GACAGACACA
  S  G  Y   A  A  T   M  H  R  E   G  F  L   C  C  K   V  T  D  T
                          nsp1

      1015      1025      1035      1045      1055      1065
UUGAACGGGG AGAGGGUCUC UUUUCCCGUG UGCACGUAUG UGCCAGCUAC AUUGUGUGAC
  L  N  G   E  R  V   S  F  P  V   C  T  Y   V  P  A   T  L  C  D
                          nsp1

      1075      1085      1095      1105      1115      1125
CAAAUGACUG GCAUACUGGC AACAGAUGUC AGUGCGGACG ACGCGCAAAA ACUGCUGGUU
  Q  M  T   G  I  L   A  T  D  V   S  A  D   D  A  Q   K  L  L  V
                          nsp1

      1135      1145      1155      1165      1175      1185
GGGCUCAACC AGCGUAUAGU CGUCAACGGU CGCACCCAGA GAAACACCAA UACCAUGAAA
  G  L  N   Q  R  I   V  V  N  G   R  T  Q   R  N  T   N  T  M  K
                          nsp1

      1195      1205      1215      1225      1235      1245
AAUUACCUUU UGCCCGUAGU GGCCCAGGCA UUUGCUAGGU GGGCAAAGGA AUAUAAGGAA
  N  Y  L   L  P  V   V  A  Q  A   F  A  R   W  A  K   E  Y  K  E
                          nsp1

      1255      1265      1275      1285      1295      1305
GAUCAAGAAG AUGAAAGGCC ACUAGGACUA CGAGAUAGAC AGUUAGUCAU GGGGUGUUGU
  D  Q  E   D  E  R   P  L  G  L   R  D  R   Q  L  V   M  G  C  C
                          nsp1

      1315      1325      1335      1345      1355      1365
UGGGCUUUUA GAAGGCACAA GAUAACAUCU AUUUAUAAGC GCCCGGAUAC CCAAACCAUC
  W  A  F   R  R  H   K  I  T  S   I  Y  K   R  P  D   T  Q  T  I
                          nsp1

      1375      1385      1395      1405      1415      1425
AUCAAAGUGA ACAGCGAUUU CCACUCAUUC GUGCUGCCCA GGAUAGGCAG UAACACAUUG
  I  K  V   N  S  D   F  H  S  F   V  L  P   R  I  G   S  N  T  L
                          nsp1

      1435      1445      1455      1465      1475      1485
GAGAUCGGGC UGAGAACAAG AAUCAGGAAA AUGUUAGAGG AGCACAAGGA GCCGUCACCU
  E  I  G   L  R  T   R  I  R  K   M  L  E   E  H  K   E  P  S  P
                          nsp1

      1495      1505      1515      1525      1535      1545
CUCAUUACCG CCGAGGACGU ACAAGAAGCU AAGUGCGCAG CCGAUGAGGC UAAGGAGGUG
  L  I  T   A  E  D   V  Q  E  A   K  C  A   A  D  E   A  K  E  V
                          nsp1

      1555      1565      1575      1585      1595      1605
CGUGAAGCCG AGGAGUUGCG CGCAGCUCUA CCACCUUUGG CAGCUGAUGU UGAGGAGCCC
  R  E  A   E  E  L   R  A  A  L   P  P  L   A  A  D   V  E  E  P
                          nsp1

      1615      1625      1635      1645  1650
ACUCUGGAAG CCGAUGUCGA CUUGAUGUUA CAAGAGGCUG GGGCC
  T  L  E   A  D  V   D  L  M  L   Q  E  A   G  A
                          nsp1

      1660      1670      1680      1690      1700      1710
GGCUCAGUGG AGACACCUCG UGGCUUGAUA AAGGUUACCA GCUACGCUGG CGAGGACAAG
  G  S  V   E  T  P   R  G  L  I   K  V  T   S  Y  A   G  E  D  K
                          nsp2
```

-continued

```
      1720       1730       1740       1750       1760       1770
AUCGGCUCUU ACGCUGUGCU UUCUCCGCAG GCUGUACUCA AGAGUGAAAA AUUAUCUUGC
  I  G  S   Y  A  V   L  S  P  Q   A  V  L   K  S  E   K  L  S  C
                                nsp2

      1780       1790       1800       1810       1820       1830
AUCCACCCUC UCGCUGAACA AGUCAUAGUG AUAACACACU CUGGCCGAAA AGGGCGUUAU
  I  H  P   L  A  E   Q  V  I  V   I  T  H   S  G  R   K  G  R  Y
                                nsp2

      1840       1850       1860       1870       1880       1890
GCCGUGGAAC CAUACCAUGG UAAAGUAGUG GUGCCAGAGG GACAUGCAAU ACCCGUCCAG
  A  V  E   P  Y  H   G  K  V  V   V  P  E   G  H  A   I  P  V  Q
                                nsp2

      1900       1910       1920       1930       1940       1950
GACUUUCAAG CUCUGAGUGA AAGUGCCACC AUUGUGUACA ACGAACGUGA GUUCGUAAAC
  D  F  Q   A  L  S   E  S  A  T   I  V  Y   N  E  R   E  F  V  N
                                nsp2

      1960       1970       1980       1990       2000       2010
AGGUACCUGC ACCAUAUUGC CACACAUGGA GGAGCGCUGA ACACUGAUGA AGAAUAUUAC
  R  Y  L   H  H  I   A  T  H  G   G  A  L   N  T  D   E  E  Y  Y
                                nsp2

      2020       2030       2040       2050       2060       2070
AAAACUGUCA AGCCCAGCGA GCACGACGGC GAAUACCUGU ACGACAUCGA CAGGAAACAG
  K  T  V   K  P  S   E  H  D  G   E  Y  L   Y  D  I   D  R  K  Q
                                nsp2

      2080       2090       2100       2110       2120       2130
UGCGUCAAGA AAGAGCUAGU CACUGGGCUA GGGCUCACAG GCGAGCUGGU CGAUCCUCCC
  C  V  K   K  E  L   V  T  G  L   G  L  T   G  E  L   V  D  P  P
                                nsp2

      2140       2150       2160       2170       2180       2190
UUCCAUGAAU UCGCCUACGA GAGUCUGAGA ACACGACCAG CCGCUCCUUA CCAAGUACCA
  F  H  E   F  A  Y   E  S  L  R   T  R  P   A  A  P   Y  Q  V  P
                                nsp2

      2200       2210       2220       2230       2240       2250
ACCAUAGGGG UGUAUGGCGU GCCAGGAUCA GGCAAGUCUG GCAUCAUUAA AAGCGCAGUC
  T  I  G   V  Y  G   V  P  G  S   G  K  S   G  I  I   K  S  A  V
                                nsp2

      2260       2270       2280       2290       2300       2310
ACCAAAAAAG AUCUAGUGGU GAGCGCCAAG AAAGAAAACU GUGCAGAAAU UAUAAGGGAC
  T  K  K   D  L  V   V  S  A  K   K  E  N   C  A  E   I  I  R  D
                                nsp2

      2320       2330       2340       2350       2360       2370
GUCAAGAAAA UGAAAGGGCU GGACGUCAAU GCCAGAACUG UGGACUCAGU GCUCUUGAAU
  V  K  K   M  K  G   L  D  V  N   A  R  T   V  D  S   V  L  L  N
                                nsp2

      2380       2390       2400       2410       2420       2430
GGAUGCAAAC ACCCCGUAGA GACCCUGUAU AUUGACGAGG CUUUUGCUUG UCAUGCAGGU
  G  C  K   H  P  V   E  T  L  Y   I  D  E   A  F  A   C  H  A  G
                                nsp2

      2440       2450       2460       2470       2480       2490
ACUCUCAGAG CGCUCAUAGC CAUUAUAAGA CCUAAAAAGG CAGUGCUCUG CGGAGAUCCC
  T  L  R   A  L  I   A  I  I  R   P  K  K   A  V  L   C  G  D  P
                                nsp2

      2500       2510       2520       2530       2540       2550
AAACAGUGCG GUUUUUUUAA CAUGAUGUGC CUGAAAGUGC AUUUUAACCA CGAGAUUUGC
  K  Q  C   G  F  F   N  M  M  C   L  K  V   H  F  N   H  E  I  C
                                nsp2

      2560       2570       2580       2590       2600       2610
ACACAAGUCU UCCACAAAAG CAUCUCUCGC CGUUGCACUA AAUCUGUGAC UUCGGUCGUC
  T  Q  V   F  H  K   S  I  S  R   R  C  T   K  S  V   T  S  V  V
                                nsp2

      2620       2630       2640       2650       2660       2670
UCAACCUUGU UUUACGACAA AAAAAUGAGA ACGACGAAUC CGAAAGAGAC UAAGAUUGUG
  S  T  L   F  Y  D   K  K  M  R   T  T  N   P  K  E   T  K  I  V
                                nsp2
```

-continued

```
       2680       2690       2700       2710       2720       2730
AUUGACACUA CCGGCAGUAC CAAACCUAAG CAGGACGAUC UCAUUCUCAC UUGUUUCAGA
  I  D  T   T  G  S   T  K  P  K  Q  D  D   L  I  L   T  C  F  R
                               nsp2

       2740       2750       2760       2770       2780       2790
GGGUGGGUGA AGCAGUUGCA AAUAGAUUAC AAAGGCAACG AAAUAAUGAC GGCAGCUGCC
  G  W  V   K  Q  L   Q  I  D  Y   K  G  N   E  I  M   T  A  A  A
                               nsp2

       2800       2810       2820       2830       2840       2850
UCUCAAGGGC UGACCCGUAA AGGUGUGUAU GCCGUUCGGU ACAAGGUGAA UGAAAAUCCU
  S  Q  G   L  T  R   K  G  V  Y   A  V  R   Y  K  V   N  E  N  P
                               nsp2

       2860       2870       2880       2890       2900       2910
CUGUACGCAC CCACCUCAGA ACAUGUGAAC GUCCUACUGA CCCGCACGGA GGACCGCAUC
  L  Y  A   P  T  S   E  H  V  N   V  L  L   T  R  T   E  D  R  I
                               nsp2

       2920       2930       2940       2950       2960       2970
GUGUGGAAAA CACUAGCCGG CGACCCAUGG AUAAAAACAC UGACUGCCAA GUACCCUGGG
  V  W  K   T  L  A   G  D  P  W   I  K  T   L  T  A   K  Y  P  G
                               nsp2

       2980       2990       3000       3010       3020       3030
AAUUUCACUG CCACGAUAGA GGAGUGGCAA GCAGAGCAUG AUGCCAUCAU GAGGCACAUC
  N  F  T   A  T  I   E  E  W  Q   A  E  H   D  A  I   M  R  H  I
                               nsp2

       3040       3050       3060       3070       3080       3090
UUGGAGAGAC CGGACCCUAC CGACGUCUUC CAGAAUAAGG CAAACGUGUG UUGGGCCAAG
  L  E  R   P  D  P   T  D  V  F   Q  N  K   A  N  V   C  W  A  K
                               nsp2

       3100       3110       3120       3130       3140       3150
GCUUUAGUGC CGGUGCUGAA GACCGCUGGC AUAGACAUGA CCACUGAACA AUGGAACACU
  A  L  V   P  V  L   K  T  A  G   I  D  M   T  T  E   Q  W  N  T
                               nsp2

       3160       3170       3180       3190       3200       3210
GUGGAUUAUU UUGAAACGGA CAAAGCUCAC UCAGCAGAGA UAGUAUUGAA CCAACUAUGC
  V  D  Y   F  E  T   D  K  A  H   S  A  E   I  V  L   N  Q  L  C
                               nsp2

       3220       3230       3240       3250       3260       3270
GUGAGGUUCU UUGGACUCGA UCUGGACUCC GGUCUAUUUU CUGCACCCAC UGUUCCGUUA
  V  R  F   F  G  L   D  L  D  S   G  L  F   S  A  P   T  V  P  L
                               nsp2

       3280       3290       3300       3310       3320       3330
UCCAUUAGGA AUAAUCACUG GGAUAACUCC CCGUCGCCUA ACAUGUACGG GCUGAAUAAA
  S  I  R   N  N  H   W  D  N  S   P  S  P   N  M  Y   G  L  N  K
                               nsp2

       3340       3350       3360       3370       3380       3390
GAAGUGGUCC GUCAGCUCUC UCGCAGGUAC CCACAACUGC CUCGGGCAGU UGCCACUGGU
  E  V  V   R  Q  L   S  R  R  Y   P  Q  L   P  R  A   V  A  T  G
                               nsp2

       3400       3410       3420       3430       3440       3450
AGAGUCUAUG ACAUGAACAC UGGUACACUG CGCAAUUAUG AUCCGCGCAU AAACCUAGUA
  R  V  Y   D  M  N   T  G  T  L   R  N  Y   D  P  R   I  N  L  V
                               nsp2

       3460       3470       3480       3490       3500       3510
CCUGUAAACA GAAGACUGCC UCAUGCUUUA GUCCUCCACC AUAAUGAACA CCCACAGAGU
  P  V  N   R  R  L   P  H  A  L   V  L  H   H  N  E   H  P  Q  S
                               nsp2

       3520       3530       3540       3550       3560       3570
GACUUUUCUU CAUUCGUCAG CAAAUUGAAG GGCAGAACUG UCCUGGUGGU CGGGGAAAAG
  D  F  S   S  F  V   S  K  L  K   G  R  T   V  L  V   V  G  E  K
                               nsp2

       3580       3590       3600       3610       3620       3630
UUGUCCGUCC CAGGCAAAAU GGUUGACUGG UUGUCAGACC GGCCUGAGGC UACCUUCAGA
  L  S  V   P  G  K   M  V  D  W   L  S  D   R  P  E   A  T  F  R
                               nsp2
```

-continued

```
      3640       3650       3660       3670       3680       3690
GCUCGGCUGG AUUUAGGCAU CCCAGGUGAU GUGCCCAAAU AUGACAUAAU AUUUGUUAAU
  A  R  L   D  L  G   I  P  G   D  V  P   K  Y  D  I   I  F  V  N
                           nsp2

      3700       3710       3720       3730       3740       3750
GUGAGGACCC CAUAUAAAUA CCAUCACUAU CAGCAGUGUG AAGACCAUGC CAUUAAGCUA
  V  R  T   P  Y  K   Y  H  H  Y   Q  Q  C   E  D  H   A  I  K  L
                           nsp2

      3760       3770       3780       3790       3800       3810
AGCAUGUUGA CCAAGAAAGC AUGUCUGCAU CUGAAUCCCG GCGGAACCUG UGUCAGCAUA
  S  M  L   T  K  K   A  C  L  H   L  N  P   G  G  T   C  V  S  I
                           nsp2

      3820       3830       3840       3850       3860       3870
GGUUAUGGUU ACGCUGACAG GGCCAGCGAA AGCAUCAUUG GUGCUAUAGC GCGGCAGUUC
  G  Y  G   Y  A  D   R  A  S  E   S  I  I   G  A  I   A  R  Q  F
                           nsp2

      3880       3890       3900       3910       3920       3930
AAGUUUUCCC GAGUAUGCAA ACCGAAAUCC UCACUUGAGG AGACGGAAGU UCUGUUUGUA
  K  F  S   R  V  C   K  P  K  S   S  L  E   E  T  E   V  L  F  V
                           nsp2

      3940       3950       3960       3970       3980       3990
UUCAUUGGGU ACGAUCGCAA GGCCCGUACG CACAAUCCUU ACAAGCUAUC AUCAACCUUG
  F  I  G   Y  D  R   K  A  R  T   H  N  P   Y  K  L   S  S  T  L
                           nsp2

      4000       4010       4020       4030 4032
ACCAACAUUU AUACAGGUUC CAGACUCCAC GAAGCCGGAU GU
  T  N  I   Y  T  G   S  R  L  H   E  A  G   C
                           nsp2

      4042       4052       4062       4072       4082       4092
GCACCCUCAU AUCAUGUGGU GCGAGGGGAU AUUGCCACGG CCACCGAAGG AGUGAUUAUA
  A  P  S   Y  H  V   V  R  G  D   I  A  T   A  T  E   G  V  I  I
                           nsp3

      4102       4112       4122       4132       4142       4152
AAUGCUGCUA ACAGCAAAGG ACAACCUGGC GGAGGGGUGU GCGGAGCGCU GUAUAAGAAA
  N  A  A   N  S  K   G  Q  P  G   G  G  V   C  G  A   L  Y  K  K
                           nsp3

      4162       4172       4182       4192       4202       4212
UUCCCGGAAA GUUUCGAUUU ACAGCCGAUC GAAGUAGGAA AAGCGCGACU GGUCAAAGGU
  F  P  E   S  F  D   L  Q  P  I   E  V  G   K  A  R   L  V  K  G
                           nsp3

      4222       4232       4242       4252       4262       4272
GCAGCUAAAC AUAUCAUUCA UGCCGUAGGA CCAAACUUCA ACAAAGUUUC GGAGGUUGAA
  A  A  K   H  I  I   H  A  V  G   P  N  F   N  K  V   S  E  V  E
                           nsp3

      4282       4292       4302       4312       4322       4332
GGUGACAAAC AGUUGGCAGA GGCUUAUGAG UCCAUCGCUA AGAUUGUCAA CGAUAACAAU
  G  D  K   Q  L  A   E  A  Y  E   S  I  A   K  I  V   N  D  N  N
                           nsp3

      4342       4352       4362       4372       4382       4392
UACAAGUCAG UAGCGAUUCC ACUGUUGUCC ACCGGCAUCU UUUCCGGGAA CAAAGAUCGA
  Y  K  S   V  A  I   P  L  L  S   T  G  I   F  S  G   N  K  D  R
                           nsp3

      4402       4412       4422       4432       4442       4452
CUAACCCAAU CAUUGAACCA UUUGCUGACA GCUUUAGACA CCACUGAUGC AGAUGUAGCC
  L  T  Q   S  L  N   H  L  L  T   A  L  D   T  T  D   A  D  V  A
                           nsp3

      4462       4472       4482       4492       4502       4512
AUAUACUGCA GGGACAAGAA AUGGGAAAUG ACUCUCAAGG AAGCAGUGGC UAGGAGAGAA
  I  Y  C   R  D  K   K  W  E  M   T  L  K   E  A  V   A  R  R  E
                           nsp3

      4522       4532       4542       4552       4562       4572
GCAGUGGAGG AGAUAUGCAU AUCCGACGAU UCUUCAGUGA CAGAACCUGA UGCAGAGCUG
  A  V  E   E  I  C   I  S  D  D   S  S  V   T  E  P   D  A  E  L
                           nsp3
```

-continued

```
        4582        4592        4602        4612        4622        4632
GUGAGGGUGC AUCCCAAGAG UUCUUUGGCU GGAAGGAAGG GCUACAGCAC AAGCGAUGGC
  V  R  V   H  P  K   S  S  L  A   G  R  K   G  Y  S   T  S  D  G
                                 nsp3

        4642        4652        4662        4672        4682        4692
AAAACUUUCU CAUAUUUGGA AGGGACCAAG UUUCACCAGG CGGCCAAGGA UAUAGCAGAA
  K  T  F   S  Y  L   E  G  T  K   F  H  Q   A  A  K   D  I  A  E
                                 nsp3

        4702        4712        4722        4732        4742        4752
AUUAAUGCCA UGUGGCCCGU UGCAACGGAG GCCAAUGAGC AGGUAUGCAU GUAUAUCCUC
  I  N  A   M  W  P   V  A  T  E   A  N  E   Q  V  C   M  Y  I  L
                                 nsp3

        4762        4772        4782        4792        4802        4812
GGAGAAAGCA UGAGCAGUAU UAGGUCGAAA UGCCCCGUCG AGGAGUCGGA AGCCUCCACA
  G  E  S   M  S  S   I  R  S  K   C  P  V   E  E  S   E  A  S  T
                                 nsp3

        4822        4832        4842        4852        4862        4872
CCACCUAGCA CGCUGCCUUG CUUGUGCAUC CAUGCCAUGA CUCCAGAAAG AGUACAGCGC
  P  P  S   T  L  P   C  L  C  I   H  A  M   T  P  E   R  V  Q  R
                                 nsp3

        4882        4892        4902        4912        4922        4932
CUAAAAGCCU CACGUCCAGA ACAAAUUACU GUGUGCUCAU CCUUUCCAUU GCCGAAGUAU
  L  K  A   S  R  P   E  Q  I  T   V  C  S   S  E  P   L  P  K  Y
                                 nsp3

        4942        4952        4962        4972        4982        4992
AGAAUCACUG GUGUGCAGAA GAUCCAAUGC UCCCAGCCUA UAUUGUUCUC ACCGAAAGUG
  R  I  T   G  V  Q   K  I  Q  C   S  Q  P   I  L  F   S  P  K  V
                                 nsp3

        5002        5012        5022        5032        5042        5052
CCUGCGUAUA UUCAUCCAAG GAAGUAUCUC GUGGAAACAC CACCGGUAGA CGAGACUCCG
  P  A  Y   I  H  P   R  K  Y  L   V  E  T   P  P  V   D  E  T  P
                                 nsp3

        5062        5072        5082        5092        5102        5112
GAGCCAUCGG CAGAGAACCA AUCCACAGAG GGGACACCUG AACAACCACC ACUUAUAACC
  E  P  S   A  E  N   Q  S  T  E   G  T  P   E  Q  P   P  L  I  T
                                 nsp3

        5122        5132        5142        5152        5162        5172
GAGGAUGAGA CCAGGACUAG AACGCCUGAG CCGAUCAUCA UCGAAGAAGA AGAAGAAGAU
  E  D  E   T  R  T   R  T  P  E   P  I  I   I  E  E   E  E  E  D
                                 nsp3

        5182        5192        5202        5212        5222        5232
AGCAUAAGUU UGCUGUCAGA UGGCCCGACC CACCAGGUGC UGCAAGUCGA GGCAGACAUU
  S  I  S   L  L  S   D  G  P  T   H  Q  V   L  Q  V   E  A  D  I
                                 nsp3

        5242        5252        5262        5272        5282        5292
CACGGGCCGC CCUCUGUAUC UAGCUCAUCC UGGUCCAUUC CUCAUGCAUC CGACUUUGAU
  H  G  P   P  S  V   S  S  S  S   W  S  I   P  H  A   S  D  E  D
                                 nsp3

        5302        5312        5322        5332        5342        5352
GUGGACAGUU UAUCCAUACU UGACACCCUG GAGGGAGCUA GCGUGACCAG CGGGGCAACG
  V  D  S   L  S  I   L  D  T  L   E  G  A   S  V  T   S  G  A  T
                                 nsp3

        5362        5372        5382        5392        5402        5412
UCAGCCGAGA CUAACUCUUA CUUCGCAAAG AGUAUGGAGU UUCUGGCGCG ACCGGUGCCU
  S  A  E   T  N  S   Y  F  A  K   S  M  E   F  L  A   R  P  V  P
                                 nsp3

        5422        5432        5442        5452        5462        5472
GCGCCUCGAA CAGUAUUCAG GAACCCUCCA CAUCCCGCUC CGCGCACAAG AACACCGUCA
  A  P  R   T  V  F   R  N  P  P   H  P  A   P  R  T   R  T  P  S
                                 nsp3

        5482        5492        5502        5512        5522        5532
CUUGCACCCA GCAGGGCCUG CUCCAGAACC AGCCUAGUUU CCACCCCGCC AGGCGUGAAU
  L  A  P   S  R  A   C  S  R  T   S  L  V   S  T  P   P  G  V  N
                                 nsp3
```

-continued

```
      5542        5552        5562        5572        5582        5592
AGGGUGAUCA CUAGAGAGGA GCUCGAAGCG CUUACCCCGU CACGCACUCC UAGCAGGUCG
  R  V  I   T  R  E   E  L  E  A   L  T  P   S  R  T   P  S  R  S
                                 nsp3

      5602        5612        5622        5632        5642        5652
GUCUCCAGAA CCAGCCUGGU CUCCAACCCG CCAGGCGUAA AUAGGGUGAU UACAAGAGAG
  V  S  R   T  S  L   V  S  N  P   P  G  V   N  R  V   I  T  R  E
                                 nsp3

      5662        5672        5682        5692        5702 5703
GAGUUUGAGG CGUUCGUAGC ACAACAACAA UGACGGUUUG AUGCGGGUGC A
  E  F  E   A  F  V   A  Q  Q  Q   *  R  F   D  A  G   A
                                 nsp3

      5713        5723        5733        5743        5753        5763
UACAUCUUUU CCUCCGACAC CGGUCAAGGG CAUUUACAAC AAAAAUCAGU AAGGCAAACG
  Y  I  F   S  S  D   T  G  Q  G   H  L  Q   Q  K  S   V  R  Q  T
                                 nsp4

      5773        5783        5793        5803        5813        5823
GUGCUAUCCG AAGUGGUGUU GGAGAGGACC GAAUUGGAGA UUUCGUAUGC CCCGCGCCUC
  V  L  S   E  V  V   L  E  R  T   E  L  E   I  S  Y   A  P  R  L
                                 nsp4

      5833        5843        5853        5863        5873        5883
GACCAAGAAA AAGAAGAAUU ACUACGCAAG AAAUUACAGU UAAAUCCCAC ACCUGCUAAC
  D  Q  E   K  E  E   L  L  R  K   K  L  Q   L  N  P   T  P  A  N
                                 nsp4

      5893        5903        5913        5923        5933        5943
AGAAGCAGAU ACCAGUCCAG GAAGGUGGAG AACAUGAAAG CCAUAACAGC UAGACGUAUU
  R  S  R   Y  Q  S   R  K  V  E   N  M  K   A  I  T   A  R  R  I
                                 nsp4

      5953        5963        5973        5983        5993        6003
CUGCAAGGCC UAGGGCAUUA UUUGAAGGCA GAAGGAAAAG UGGAGUGCUA CCGAACCCUG
  L  Q  G   L  G  H   Y  L  K  A   E  G  K   V  E  C   Y  R  T  L
                                 nsp4

      6013        6023        6033        6043        6053        6063
CAUCCUGUUC CUUUGUAUUC AUCUAGUGUG AACCGUGCCU UUUCAAGCCC CAAGGUCGCA
  H  P  V   P  L  Y   S  S  S  V   N  R  A   F  S  S   P  K  V  A
                                 nsp4

      6073        6083        6093        6103        6113        6123
GUGGAAGCCU GUAACGCCAU GUUGAAAGAG AACUUUCCGA CUGUGGCUUC UUACUGUAUU
  V  E  A   C  N  A   M  L  K  E   N  F  P   T  V  A   S  Y  C  I
                                 nsp4

      6133        6143       6153         6163        6173        6183
AUUCCAGAGU ACGAUGCCUA UUUGGACAUG GUUGACGGAG CUUCAUGCUG CUUAGACACU
  I  P  E   Y  D  A   Y  L  D  M   V  D  G   A  S  C   C  L  D  T
                                 nsp4

      6193        6203        6213        6223        6233        6243
GCCAGUUUUU GCCCUGCAAA GCUGCGCAGC UUUCCAAAGA AACACUCCUA UUUGGAACCC
  A  S  F   C  P  A   K  L  R  S   F  P  K   K  H  S   Y  L  E  P
                                 nsp4

      6253        6263        6273        6283        6293        6303
ACAAUACGAU CGGCAGUGCC UUCAGCGAUC CAGAACACGC UCCAGAACGU CCUGGCAGCU
  T  I  R   S  A  V   P  S  A  I   Q  N  T   L  Q  N   V  L  A  A
                                 nsp4

      6313        6323        6333        6343        6353        6363
GCCACAAAAA GAAAUUGCAA UGUCACGCAA AUGAGAGAAU UGCCCGUAUU GGAUUCGGCG
  A  T  K   R  N  C   N  V  T  Q   M  R  E   L  P  V   L  D  S  A
                                 nsp4

      6373        6383        6393        6403        6413        6423
GCCUUUAAUG UGGAAUGCUU CAAGAAAUAU GCGUGUAAUA AUGAAUAUUG GGAAACGUUU
  A  F  N   V  E  C   F  K  K  Y   A  C  N   N  E  Y   W  E  T  F
                                 nsp4

      6433        6443        6453        6463        6473        6483
AAAGAAAACC CCAUCAGGCU UACUGAAGAA AACGUGGUAA AUUACAUUAC CAAAUUAAAA
  K  E  N   P  I  R   L  T  E  E   N  V  V   N  Y  I   T  K  L  K
                                 nsp4
```

-continued

```
      6493       6503       6513       6523       6533       6543
GGACCAAAAG CUGCUGCUCU UUUUGCGAAG ACACAUAAUU UGAAUAUGUU GCAGGACAUA
 G  P  K   A  A  A   L  F  A  K   T  H  N   L  N  M   L  Q  D  I
                            nsp4

      6553       6563       6573       6583       6593       6603
CCAAUGGACA GGUUUGUAAU GGACUUAAAG AGAGACGUGA AAGUGACUCC AGGAACAAAA
 P  M  D   R  F  V   M  D  L  K   R  D  V   K  V  T   P  G  T  K
                            nsp4

      6613       6623       6633       6643       6653       6663
CAUACUGAAG AACGGCCCAA GGUACAGGUG AUCCAGGCUG CCGAUCCGCU AGCAACAGCG
 H  T  E   E  R  P   K  V  Q  V   I  Q  A   A  D  P   L  A  T  A
                            nsp4

      6673       6683       6693       6703       6713       6723
UAUCUGUGCG GAAUCCACCG AGAGCUGGUU AGGAGAUUAA AUGCGGUCCU GCUUCCGAAC
 Y  L  C   G  I  H   R  E  L  V   R  R  L   N  A  V   L  L  P  N
                            nsp4

      6733       6743       6753       6763       6773       6783
AUUCAUACAC UGUUUGAUAU GUCGGCUGAA GACUUUGACG CUAUUAUAGC CGAGCACUUC
 I  H  T   L  F  D   M  S  A  E   D  F  D   A  I  I   A  E  H  F
                            nsp4

      6793       6803       6813       6823       6833       6843
CAGCCUGGGG AUUGUGUUCU GGAAACUGAC AUCGCGUCGU UUGAUAAAAG UGAGGACGAC
 Q  P  G   D  C  V   L  E  T  D   I  A  S   F  D  K   S  E  D  D
                            nsp4

      6853       6863       6873       6883       6893       6903
GCCAUGGCUC UGACCGCGUU AAUGAUUCUG GAAGACUUAG GUGUGGACGC AGAGCUGUUG
 A  M  A   L  T  A   L  M  I  L   E  D  L   G  V  D   A  E  L  L
                            nsp4

      6913       6923       6933       6943       6953       6963
ACGCUGAUUG AGGCGGCUUU CGGCGAAAUU UCAUCAAUAC AUUUGCCCAC UAAAACUAAA
 T  L  I   E  A  A   F  G  E  I   S  S  I   H  L  P   T  K  T  K
                            nsp4

      6973       6983       6993       7003       7013       7023
UUUAAAUUCG GAGCCAUGAU GAAAUCUGGA AUGUUCCUCA CACUGUUUGU GAACACAGUC
 F  K  F   G  A  M   M  K  S  G   M  F  L   T  L  F   V  N  T  V
                            nsp4

      7033       7043       7053       7063       7073       7083
AUUAACAUUG UAAUCGCAAG CAGAGUGUUG AGAGAACGGC UAACCGGAUC ACCAUGUGCA
 I  N  I   V  I  A   S  R  V  L   R  E  R   L  T  G   S  P  C  A
                            nsp4

      7093       7103       7113       7123       7133       7143
GCAUUCAUUG GAGAUGACAA UAUCGUGAAA GGAGUCAAAU CGGACAAAUU AAUGGCAGAC
 A  F  I   G  D  D   N  I  V  K   G  V  K   S  D  K   L  M  A  D
                            nsp4

      7153       7163       7173       7183       7193       7203
AGGUGCGCCA CCUGGUUGAA UAUGGAAGUC AAGAUUAUAG AUGCUGUGGU GGGCGAGAAA
 R  C  A   T  W  L   N  M  E  V   K  I  I   D  A  V   V  G  E  K
                            nsp4

      7213       7223       7233       7243       7253       7263
GCGCCUUAUU UCUGUGGAGG GUUUAUUUUG UGUGACUCCG UGACCGGCAC AGCGUGCCGU
 A  P  Y   F  C  G   G  F  I  L   C  D  S   V  T  G   T  A  C  R
                            nsp4

      7273       7283       7293       7303       7313       7323
GUGGCAGACC CCCUAAAAAG GCUGUUUAAG CUAGGCAAAC CUCUGGCAGC AGACGAUGAA
 V  A  D   P  L  K   R  L  F  K   L  G  K   P  L  A   A  D  D  E
                            nsp4

      7333       7343       7353       7363       7373       7383
CAUGAUGAUG ACAGGAGAAG GGCAUUGCAU GAGGAGUCAA CACGCUGGAA CCGAGUGGGU
 H  D  D   D  R  R   R  A  L  H   E  E  S   T  R  W   N  R  V  G
                            nsp4

      7393       7403       7413       7423       7433       7443
AUUCUUUCAG AGCUGUGCAA GGCAGUAGAA UCAAGGUAUG AAACCGUAGG AACUUCCAUC
 I  L  S   E  L  C   K  A  V  E   S  R  Y   E  T  V   G  T  S  I
                            nsp4
```

-continued

```
     7453       7463       7473       7483       7493       7503
AUAGUUAUGG CCAUGACUAC UCUAGCUAGC AGUGUUAAAU CAUUCAGCUA CCUGAGAGGG
  I  V  M   A  M  T   T  L  A  S   S  V  K   S  F  S   Y  L  R  G
                                nsp4

     7513       7523   7527
GCCCCUAUAA CUCUCUACGG CUAA
  A  P  I   T  L  Y  G  *
             nsp4

     7537       7547       7557       7567 7568
CCUGAAUGGA CUACGACAUA GUCUAGUCCG CCAAGACUAG U
                                virUTR

     7578       7588       7598       7608       7618       7628
AUGUUUGUGU UUCUUGUGCU GCUGCCUCUU GUGUCUUCUC AGUGUGUGGU GAGAUUUCCA
  M  F  V   F  L  V   L  L  P  L   V  S  S   Q  C  V   V  R  F  P
                            RBD (S protein)

     7638       7648       7658       7668       7678       7688
AAUAUUACAA AUCUGUGUCC AUUUGGAGAA GUGUUUAAUG CAACAAGAUU UGCAUCUGUG
  N  I  T   N  L  C   P  F  G  E   V  F  N   A  T  R   F  A  S  V
                            RBD (S protein)

     7698       7708       7718       7728       7738       7748
UAUGCAUGGA AUAGAAAAAG AAUUUCUAAU UGUGUGGCUG AUUAUUCUGU GCUGUAUAAU
  Y  A  W   N  R  K   R  I  S  N   C  V  A   D  Y  S   V  L  Y  N
                            RBD (S protein)

     7758       7768       7778       7788       7798       7808
AGUGCUUCUU UUUCCACAUU UAAAUGUUAU GGAGUGUCUC CAACAAAAUU AAAUGAUUUA
  S  A  S   F  S  T   F  K  C  Y   G  V  S   P  T  K   L  N  D  L
                            RBD (S protein)

     7818       7828       7838       7848       7858       7868
UGUUUUACAA AUGUGUAUGC UGAUUCUUUU GUGAUCAGAG GUGAUGAAGU GAGACAGAUU
  C  F  T   N  V  Y   A  D  S  F   V  I  R   G  D  E   V  R  Q  I
                            RBD (S protein)

     7878       7888       7898       7908       7918       7928
GCCCCCGGAC AGACAGGAAA AAUUGCUGAU UACAAUUACA AACUGCCUGA UGAUUUUACA
  A  P  G   Q  T  G   K  I  A  D   Y  N  Y   K  L  P   D  D  F  T
                            RBD (S protein)

     7938       7948       7958       7968       7978       7988
GGAUGUGUGA UUGCUUGGAA UUCUAAUAAU UUAGAUUCUA AAGUGGGAGG AAAUUACAAU
  G  C  V   I  A  W   N  S  N  N   L  D  S   K  V  G   G  N  Y  N
                            RBD (S protein)

     7998       8008       8018       8028       8038       8048
UAUCUGUACA GACUGUUUAG AAAAUCAAAU CUGAAACCUU UUGAAAGAGA UAUUUCAACA
  Y  L  Y   R  L  F   R  K  S  N   L  K  P   F  E  R   D  I  S  T
                            RBD (S protein)

     8058       8068       8078       8088       8098       8108
GAAAUUUAUC AGGCUGGAUC AACACCUUGU AAUGGAGUGG AAGGAUUUAA UUGUUAUUUU
  E  I  Y   Q  A  G   S  T  P  C   N  G  V   E  G  F   N  C  Y  F
                            RBD (S protein)

     8118       8128       8138       8148       8158       8168
CCAUUACAGA GCUAUGGAUU UCAGCCAACC AAUGGUGUGG GAUAUCAGCC AUAUAGAGUG
  P  L  Q   S  Y  G   F  Q  P  T   N  G  V   G  Y  Q   P  Y  R  V
                            RBD (S protein)

     8178       8188       8198       8208       8218  8222
GUGGUGCUGU CUUUUGAACU GCUGCAUGCA CCUGCAACAG UGUGUGGACC UAAA
  V  V  L   S  F  E   L  L  H  A   P  A  T   V  C  G   P  K
                            RBD (S protein)

     8232       8242   8249
GGCUCCCCCG GCUCCGGCUC CGGAUCU
  G  S  P   G  S  G   S  G  S
             GS linker

     8259       8269       8279       8289       8299       8309
GGUUAUAUUC CUGAAGCUCC AAGAGAUGGG CAAGCUUACG UUCGUAAAGA UGGCGAAUGG
  G  Y  I   P  E  A   P  R  D  G   Q  A  Y   V  R  K   D  G  E  W
                               fibritin

     8319       8329       8339       8349       8359       8369
GUAUUACUUU CUACCUUUUU AGGCCGGUCC CUGGAGGUGC UGUUCCAGGG CCCCGGCUGA
```

-continued

```
 V  L  L   S  T  F   L  G  R   S  L  E   V  L  F   Q  G  P   G  *
                              fibritin

  8372
UGA
  *
fibritin

      8382       8392       8402       8412       8422       8432
CUCGAGCUGG UACUGCAUGC ACGCAAUGCU AGCUGCCCCU UUCCCGUCCU GGGUACCCCG
                            FI element

      8442       8452       8462       8472       8482       8492
AGUCUCCCCC GACCUCGGGU CCCAGGUAUG CUCCCACCUC CACCUGCCCC ACUCACCACC
                            FI element

      8502       8512       8522       8532       8542       8552
UCUGCUAGUU CCAGACACCU CCCAAGCACG CAGCAAUGCA GCUCAAAACG CUUAGCCUAG
                            FI element

      8562       8572       8582       8592       8602       8612
CCACACCCCC ACGGGAAACA GCAGUGAUUA ACCUUUAGCA AUAAACGAAA GUUUAACUAA
                            FI element

      8622       8632       8642       8652       8662       8672
GCUAUACUAA CCCCAGGGUU GGUCAAUUUC GUGCCAGCCA CACCGCGGCC GCAUGAAUAC
                            FI element

      8682       8692       8702       8712       8722       8732
AGCAGCAAUU GGCAAGCUGC UUACAUAGAA CUCGCGGCGA UUGGCAUGCC GCCUUAAAAU
                            FI element

      8742       8752       8762       8772       8782  8786
UUUUAUUUUA UUUUUUCUUU UCUUUUCCGA AUCGGAUUUU GUUUUUAAUA UUUC
                            FI element

      8796       8806       8816       8826       8836       8846
AAAAAAAAAA AAAAAAAAAA AAAAAAAAAA GCAUAUGACU AAAAAAAAAA AAAAAAAAAA
                              Poly(A)

      8856       8866       8876       8886       8896
AAAAAAAAAA AAAAAAAAAA AAAAAAAAAA AAAAAAAAAA AAAAAAAAAA
                              Poly(A)
```

Nucleotide Sequence of RBS004.4 (SEQ ID NO: 27; SEQ ID NO: 28)

Nucleotide sequence is shown with individual sequence elements as indicated in bold letters. In addition, the sequence of the translated protein is shown in italic letters below the coding nucleotide sequence (*=stop codon).

```
        10         20         30         40     45
GAUGGGCGGC GCAUGAGAGA AGCCCAGACC AAUUACCUAC CCAAA
                              5' UTR

        55         65         75         85         95        105
AUGGAGAAAG UUCACGUUGA CAUCGAGGAA GACAGCCCAU UCCUCAGAGC UUUGCAGCGG
  M  E  K   V  H  V   D  I  E   E  D  S   P  F  L   R  A  L   Q  R
                              nsp1

       115        125        135        145        155        165
AGCUUCCCGC AGUUUGAGGU AGAAGCCAAG CAGGUCACUG AUAAUGACCA UGCUAAUGCC
  S  F  P   Q  F  E   V  E  A   K  Q  V   T  D  N   D  H  A   N  A
                              nsp1

       175        185        195        205        215        225
AGAGCGUUUU CGCAUCUGGC UUCAAAACUG AUCGAAACGG AGGUGGACCC AUCCGACACG
  R  A  F   S  H  L   A  S  K   L  I  E   T  E  V   D  P  S   D  T
                              nsp1

       235        245        255        265        275        285
AUCCUUGACA UUGGAAGUGC GCCCGCCCGC AGAAUGUAUU CUAAGCACAA GUAUCAUUGU
  I  L  D   I  G  S   A  P  A   R  R  M   Y  S  K   H  K  Y   H  C
                              nsp1
```

-continued

```
       295        305        315        325        335        345
AUCUGUCCGA UGAGAUGUGC GGAAGAUCCG GACAGAUUGU AUAAGUAUGC AACUAAGCUG
  I  C  P   M  R  C   A  E  D  P   D  R  L   Y  K  Y   A  T  K  L
                                 nsp1

       355        365        375        385        395        405
AAGAAAAACU GUAAGGAAAU AACUGAUAAG GAAUUGGACA AGAAAAUGAA GGAGCUCGCC
  K  K  N   C  K  E   I  T  D  K   E  L  D   K  K  M   K  E  L  A
                                 nsp1

       415        425        435        445        455        465
GCCGUCAUGA GCGACCCUGA CCUGGAAACU GAGACUAUGU GCCUCCACGA CGACGAGUCG
  A  V  M   S  D  P   D  L  E  T   E  T  M   C  L  H   D  D  E  S
                                 nsp1

       475        485        495        505        515        525
UGUCGCUACG AAGGGCAAGU CGCUGUUUAC CAGGAUGUAU ACGCGGUUGA CGGACCGACA
  C  R  Y   E  G  Q   V  A  V  Y   Q  D  V   Y  A  V   D  G  P  T
                                 nsp1

       535        545        555        565        575        585
AGUCUCUAUC ACCAAGCCAA UAAGGGAGUU AGAGUCGCCU ACUGGAUAGG CUUUGACACC
  S  L  Y   H  Q  A   N  K  G  V   R  V  A   Y  W  I   G  F  D  T
                                 nsp1

       595        605        615        625        635        645
ACCCCUUUUA UGUUUAAGAA CUUGGCUGGA GCAUAUCCAU CAUACUCUAC CAACUGGGCC
  T  P  F   M  F  K   N  L  A  G   A  Y  P   S  Y  S   T  N  W  A
                                 nsp1

       655        665        675        685        695        705
GACGAAACCG UGUUAACGGC UCGUAACAUA GGCCUAUGCA GCUCUGACGU UAUGGAGCGG
  D  E  T   V  L  T   A  R  N  I   G  L  C   S  S  D   V  M  E  R
                                 nsp1

       715        725        735        745        755        765
UCACGUAGAG GGAUGUCCAU UCUUAGAAAG AAGUAUUUGA AACCAUCCAA CAAUGUUCUA
  S  R  R   G  M  S   I  L  R  K   K  Y  L   K  P  S   N  N  V  L
                                 nsp1

       775        785        795        805        815        825
UUCUCUGUUG GCUCGACCAU CUACCACGAA AAGAGGGACU UACUGAGGAG CUGGCACCUG
  F  S  V   G  S  T   I  Y  H  E   K  R  D   L  L  R   S  W  H  L
                                 nsp1

       835        845        855        865        875        885
CCGUCUGUAU UUCACUUACG UGGCAAGCAA AAUUACACAU GUCGGUGUGA GACUAUAGUU
  P  S  V   F  H  L   R  G  K  Q   N  Y  T   C  R  C   E  T  I  V
                                 nsp1

       895        905        915        925        935        945
AGUUGCGACG GGUACGUCGU UAAAAGAAUA GCUAUCAGUC CAGGCCUGUA UGGGAAGCCU
  S  C  D   G  Y  V   V  K  R  I   A  I  S   P  G  L   Y  G  K  P
                                 nsp1

       955        965        975        985        995       1005
UCAGGCUAUG CUGCUACGAU GCACCGCGAG GGAUUCUUGU GCUGCAAAGU GACAGACACA
  S  G  Y   A  A  T   M  H  R  E   G  E  L   C  C  K   V  T  D  T
                                 nsp1

      1015       1025       1035       1045       1055       1065
UUGAACGGGG AGAGGGUCUC UUUUCCCGUG UGCACGUAUG UGCCAGCUAC AUUGUGUGAC
  L  N  G   E  R  V   S  F  P  V   C  T  Y   V  P  A   T  L  C  D
                                 nsp1

      1075       1085       1095       1105       1115       1125
CAAAUGACUG GCAUACUGGC AACAGAUGUC AGUGCGGACG ACGCGCAAAA ACUGCUGGUU
  Q  M  T   G  I  L   A  T  D  V   S  A  D   D  A  Q   K  L  L  V
                                 nsp1

      1135       1145       1155       1165       1175       1185
GGGCUCAACC AGCGUAUAGU CGUCAACGGU CGCACCCAGA GAAACACCAA UACCAUGAAA
  G  L  N   Q  R  I   V  V  N  G   R  T  Q   R  N  T   N  T  M  K
                                 nsp1

      1195       1205       1215       1225       1235       1245
AAUUACCUUU UGCCCGUAGU GGCCCAGGCA UUUGCUAGGU GGGCAAAGGA AUAUAAGGAA
  N  Y  L   L  P  V   V  A  Q  A   F  A  R   W  A  K   E  Y  K  E
                                 nsp1
```

-continued

```
      1255       1265       1275       1285       1295       1305
GAUCAAGAAG AUGAAAGGCC ACUAGGACUA CGAGAUAGAC AGUUAGUCAU GGGGUGUUGU
  D  Q  E   D  E  R   P  L  G  L   R  D  R   Q  L  V   M  G  C  C
                          nsp1

      1315       1325       1335       1345       1355       1365
UGGGCUUUUA GAAGGCACAA GAUAACAUCU AUUUAUAAGC GCCCGGAUAC CCAAACCAUC
  W  A  F   R  R  H   K  I  T  S   I  Y  K   R  P  D   T  Q  T  I
                          nsp1

      1375       1385       1395       1405       1415       1425
AUCAAAGUGA ACAGCGAUUU CCACUCAUUC GUGCUGCCCA GGAUAGGCAG UAACACAUUG
  I  K  V   N  S  D   F  H  S  F   V  L  P   R  I  G   S  N  T  L
                          nsp1

      1435       1445       1455       1465       1475       1485
GAGAUCGGGC UGAGAACAAG AAUCAGGAAA AUGUUAGAGG AGCACAAGGA GCCGUCACCU
  E  I  G   L  R  T   R  I  R  K   M  L  E   E  H  K   E  P  S  P
                          nsp1

      1495       1505       1515       1525       1535       1545
CUCAUUACCG CCGAGGACGU ACAAGAAGCU AAGUGCGCAG CCGAUGAGGC UAAGGAGGUG
  L  I  T   A  E  D   V  Q  E  A   K  C  A   A  D  E   A  K  E  V
                          nsp1

      1555       1565       1575       1585       1595       1605
CGUGAAGCCG AGGAGUUGCG CGCAGCUCUA CCACCUUUGG CAGCUGAUGU UGAGGAGCCC
  R  E  A   E  E  L   R  A  A  L   P  P  L   A  A  D   V  E  E  P
                          nsp1

      1615       1625       1635       1645  1650
ACUCUGGAAG CCGAUGUCGA CUUGAUGUUA CAAGAGGCUG GGGCC
  T  L  E   A  D  V   D  L  M  L   Q  E  A   G  A
                          nsp1

      1660       1670       1680       1690       1700       1710
GGCUCAGUGG AGACACCUCG UGGCUUGAUA AAGGUUACCA GCUACGCUGG CGAGGACAAG
  G  S  V   E  T  P   R  G  L  I   K  V  T   S  Y  A   G  E  D  K
                          nsp2

      1720       1730       1740       1750       1760       1770
AUCGGCUCUU ACGCUGUGCU UUCUCCGCAG GCUGUACUCA AGAGUGAAAA AUUAUCUUGC
  I  G  S   Y  A  V   L  S  P  Q   A  V  L   K  S  E   K  L  S  C
                          nsp2

      1780       1790       1800       1810       1820       1830
AUCCACCCUC UCGCUGAACA AGUCAUAGUG AUAACACACU CUGGCCGAAA AGGGCGUUAU
  I  H  P   L  A  E   Q  V  I  V   I  T  H   S  G  R   K  G  R  Y
                          nsp2

      1840       1850       1860       1870       1880       1890
GCCGUGGAAC CAUACCAUGG UAAAGUAGUG GUGCCAGAGG GACAUGCAAU ACCCGUCCAG
  A  V  E   P  Y  H   G  K  V  V   V  P  E   G  H  A   I  P  V  Q
                          nsp2

      1900       1910       1920       1930       1940       1950
GACUUUCAAG CUCUGAGUGA AAGUGCCACC AUUGUGUACA ACGAACGUGA GUUCGUAAAC
  D  F  Q   A  L  S   E  S  A  T   I  V  Y   N  E  R   E  F  V  N
                          nsp2

      1960       1970       1980       1990       2000       2010
AGGUACCUGC ACCAUAUUGC CACACAUGGA GGAGCGCUGA ACACUGAUGA AGAAUAUUAC
  R  Y  L   H  H  I   A  T  H  G   G  A  L   N  T  D   E  E  Y  Y
                          nsp2

      2020       2030       2040       2050       2060       2070
AAAACUGUCA AGCCCAGCGA GCACGACGGC GAAUACCUGU ACGACAUCGA CAGGAAACAG
  K  T  V   K  P  S   E  H  D  G   E  Y  L   Y  D  I   D  R  K  Q
                          nsp2

      2080       2090       2100       2110       2120       2130
UGCGUCAAGA AAGAGCUAGU CACUGGGCUA GGGCUCACAG GCGAGCUGGU CGAUCCUCCC
  C  V  K   K  E  L   V  T  G  L   G  L  T   G  E  L   V  D  P  P
                          nsp2

      2140       2150       2160       2170       2180       2190
UUCCAUGAAU UCGCCUACGA GAGUCUGAGA ACACGACCAG CCGCUCCUUA CCAAGUACCA
  F  H  E   F  A  Y   E  S  L  R   T  R  P   A  A  P   Y  Q  V  P
                          nsp2
```

-continued

```
        2200       2210       2220       2230       2240       2250
ACCAUAGGGG UGUAUGGCGU GCCAGGAUCA GGCAAGUCUG GCAUCAUUAA AAGCGCAGUC
  T  I  G   V  Y  G   V  P  G  S   G  K  S   G  I  I   K  S  A  V
                             nsp2

        2260       2270       2280       2290       2300       2310
ACCAAAAAAG AUCUAGUGGU GAGCGCCAAG AAAGAAAACU GUGCAGAAAU UAUAAGGGAC
  T  K  K   D  L  V   V  S  A  K   K  E  N   C  A  E   I  I  R  D
                             nsp2

        2320       2330       2340       2350       2360       2370
GUCAAGAAAA UGAAAGGGCU GGACGUCAAU GCCAGAACUG UGGACUCAGU GCUCUUGAAU
  V  K  K   M  K  G   L  D  V  N   A  R  T   V  D  S   V  L  L  N
                             nsp2

        2380       2390       2400       2410       2420       2430
GGAUGCAAAC ACCCCGUAGA GACCCUGUAU AUUGACGAGG CUUUUGCUUG UCAUGCAGGU
  G  C  K   H  P  V   E  T  L  Y   I  D  E   A  F  A   C  H  A  G
                             nsp2

        2440       2450       2460       2470       2480       2490
ACUCUCAGAG CGCUCAUAGC CAUUAUAAGA CCUAAAAAGG CAGUGCUCUG CGGAGAUCCC
  T  L  R   A  L  I   A  I  I  R   P  K  K   A  V  L   C  G  D  P
                             nsp2

        2500       2510       2520       2530       2540       2550
AAACAGUGCG GUUUUUUUAA CAUGAUGUGC CUGAAAGUGC AUUUUAACCA CGAGAUUUGC
  K  Q  C   G  E  F   N  M  M  C   L  K  V   H  F  N   H  E  I  C
                             nsp2

        2560       2570       2580       2590       2600       2610
ACACAAGUCU UCCACAAAAG CAUCUCUCGC CGUUGCACUA AAUCUGUGAC UUCGGUCGUC
  T  Q  V   F  H  K   S  I  S  R   R  C  T   K  S  V   T  S  V  V
                             nsp2

        2620       2630       2640       2650       2660       2670
UCAACCUUGU UUUACGACAA AAAAAUGAGA ACGACGAAUC CGAAAGAGAC UAAGAUUGUG
  S  T  L   F  Y  D   K  K  M  R   T  T  N   P  K  E   T  K  I  V
                             nsp2

        2680       2690       2700       2710       2720       2730
AUUGACACUA CCGGCAGUAC CAAACCUAAG CAGGACGAUC UCAUUCUCAC UUGUUUCAGA
  I  D  T   T  G  S   T  K  P  K   Q  D  D   L  I  L   T  C  F  R
                             nsp2

        2740       2750       2760       2770       2780       2790
GGGUGGGUGA AGCAGUUGCA AAUAGAUUAC AAAGGCAACG AAAUAAUGAC GGCAGCUGCC
  G  W  V   K  Q  L   Q  I  D  Y   K  G  N   E  I  M   T  A  A  A
                             nsp2

        2800       2810       2820       2830       2840       2850
UCUCAAGGGC UGACCCGUAA AGGUGUGUAU GCCGUUCGGU ACAAGGUGAA UGAAAAUCCU
  S  Q  G   L  T  R   K  G  V  Y   A  V  R   Y  K  V   N  E  N  P
                             nsp2

        2860       2870       2880       2890       2900       2910
CUGUACGCAC CCACCUCAGA ACAUGUGAAC GUCCUACUGA CCCGCACGGA GGACCGCAUC
  L  Y  A   P  T  S   E  H  V  N   V  L  L   T  R  T   E  D  R  I
                             nsp2

        2920       2930       2940       2950       2960       2970
GUGUGGAAAA CACUAGCCGG CGACCCAUGG AUAAAAACAC UGACUGCCAA GUACCCUGGG
  V  W  K   T  L  A   G  D  P  W   I  K  T   L  T  A   K  Y  P  G
                             nsp2

        2980       2990       3000       3010       3020       3030
AAUUUCACUG CCACGAUAGA GGAGUGGCAA GCAGAGCAUG AUGCCAUCAU GAGGCACAUC
  N  F  T   A  T  I   E  E  W  Q   A  E  H   D  A  I   M  R  H  I
                             nsp2

        3040       3050       3060       3070       3080       3090
UUGGAGAGAC CGGACCCUAC CGACGUCUUC CAGAAUAAGG CAAACGUGUG UUGGGCCAAG
  L  E  R   P  D  P   T  D  V  F   Q  N  K   A  N  V   C  W  A  K
                             nsp2

        3100       3110       3120       3130       3140       3150
GCUUUAGUGC CGGUGCUGAA GACCGCUGGC AUAGACAUGA CCACUGAACA AUGGAACACU
  A  L  V   P  V  L   K  T  A  G   I  D  M   T  T  E   Q  W  N  T
                             nsp2
```

-continued

```
      3160       3170       3180       3190       3200       3210
GUGGAUUAUU UUGAAACGGA CAAAGCUCAC UCAGCAGAGA UAGUAUUGAA CCAACUAUGC
  V  D  Y   F  E  T   D  K  A  H   S  A  E   I  V  L   N  Q  L  C
                              nsp2

      3220       3230       3240       3250       3260       3270
GUGAGGUUCU UUGGACUCGA UCUGGACUCC GGUCUAUUUU CUGCACCCAC UGUUCCGUUA
  V  R  F   F  G  L   D  L  D  S   G  L  F   S  A  P   T  V  P  L
                              nsp2

      3280       3290       3300       3310       3320       3330
UCCAUUAGGA AUAAUCACUG GGAUAACUCC CCGUCGCCUA ACAUGUACGG GCUGAAUAAA
  S  I  R   N  N  H   W  D  N  S   P  S  P   N  M  Y   G  L  N  K
                              nsp2

      3340       3350       3360       3370       3380       3390
GAAGUGGUCC GUCAGCUCUC UCGCAGGUAC CCACAACUGC CUCGGGCAGU UGCCACUGGU
  E  V  V   R  Q  L   S  R  R  Y   P  Q  L   P  R  A   V  A  T  G
                              nsp2

      3400       3410       3420       3430       3440       3450
AGAGUCUAUG ACAUGAACAC UGGUACACUG CGCAAUUAUG AUCCGCGCAU AAACCUAGUA
  R  V  Y   D  M  N   T  G  T  L   R  N  Y   D  P  R   I  N  L  V
                              nsp2

      3460       3470       3480       3490       3500       3510
CCUGUAAACA GAAGACUGCC UCAUGCUUUA GUCCUCCACC AUAAUGAACA CCCACAGAGU
  P  V  N   R  R  L   P  H  A  L   V  L  H   H  N  E   H  P  Q  S
                              nsp2

      3520       3530       3540       3550       3560       3570
GACUUUUCUU CAUUCGUCAG CAAAUUGAAG GGCAGAACUG UCCUGGUGGU CGGGGAAAAG
  D  F  S   S  F  V   S  K  L  K   G  R  T   V  L  V   V  G  E  K
                              nsp2

      3580       3590       3600       3610       3620       3630
UUGUCCGUCC CAGGCAAAAU GGUUGACUGG UUGUCAGACC GGCCUGAGGC UACCUUCAGA
  L  S  V   P  G  K   M  V  D  W   L  S  D   R  P  E   A  T  F  R
                              nsp2

      3640       3650       3660       3670       3680       3690
GCUCGGCUGG AUUUAGGCAU CCCAGGUGAU GUGCCCAAAU AUGACAUAAU AUUUGUUAAU
  A  R  L   D  L  G   I  P  G  D   V  P  K   Y  D  I   I  F  V  N
                              nsp2

      3700       3710       3720       3730       3740       3750
GUGAGGACCC CAUAUAAAUA CCAUCACUAU CAGCAGUGUG AAGACCAUGC CAUUAAGCUA
  V  R  T   P  Y  K   Y  H  H  Y   Q  Q  C   E  D  H   A  I  K  L
                              nsp2

      3760       3770       3780       3790       3800       3810
AGCAUGUUGA CCAAGAAAGC AUGUCUGCAU CUGAAUCCCG GCGGAACCUG UGUCAGCAUA
  S  M  L   T  K  K   A  C  L  H   L  N  P   G  G  T   C  V  S  I
                              nsp2

      3820       3830       3840       3850       3860       3870
GGUUAUGGUU ACGCUGACAG GGCCAGCGAA AGCAUCAUUG GUGCUAUAGC GCGGCAGUUC
  G  Y  G   Y  A  D   R  A  S  E   S  I  T   G  A  T   A  R  Q  F
                              nsp2

      3880       3890       3900       3910       3920       3930
AAGUUUUCCC GAGUAUGCAA ACCGAAAUCC UCACUUGAGG AGACGGAAGU UCUGUUUGUA
  K  F  S   R  V  C   K  P  K  S   S  L  E   E  T  E   V  L  F  V
                              nsp2

      3940       3950       3960       3970       3980       3990
UUCAUUGGGU ACGAUCGCAA GGCCCGUACG CACAAUCCUU ACAAGCUAUC AUCAACCUUG
  F  I  G   Y  D  R   K  A  R  T   H  N  P   Y  K  L   S  S  T  L
                              nsp2

      4000       4010       4020       4030 4032
ACCAACAUUU AUACAGGUUC CAGACUCCAC GAAGCCGGAU GU
  T  N  I   Y  T  G   S  R  L  H   E  A  G   C
                              nsp2

      4042       4052       4062       4072       4082       4092
GCACCCUCAU AUCAUGUGGU GCGAGGGGAU AUUGCCACGG CCACCGAAGG AGUGAUUAUA
  A  P  S   Y  H  V   V  R  G  D   I  A  T   A  T  E   G  V  I  I
                              nsp3
```

-continued

```
      4102       4112       4122       4132       4142       4152
AAUGCUGCUA ACAGCAAAGG ACAACCUGGC GGAGGGGUGU GCGGAGCGCU GUAUAAGAAA
  N  A  A   N  S  K   G  Q  P  G   G  G  V   C  G  A   L  Y  K  K
                              nsp3

      4162       4172       4182       4192       4202       4212
UUCCCGGAAA GUUUCGAUUU ACAGCCGAUC GAAGUAGGAA AAGCGCGACU GGUCAAAGGU
  F  P  E   S  F  D   L  Q  P  I   E  V  G   K  A  R   L  V  K  G
                              nsp3

      4222       4232       4242       4252       4262       4272
GCAGCUAAAC AUAUCAUUCA UGCCGUAGGA CCAAACUUCA ACAAAGUUUC GGAGGUUGAA
  A  A  K   H  I  I   H  A  V  G   P  N  F   N  K  V   S  E  V  E
                              nsp3

      4282       4292       4302       4312       4322       4332
GGUGACAAAC AGUUGGCAGA GGCUUAUGAG UCCAUCGCUA AGAUUGUCAA CGAUAACAAU
  G  D  K   Q  L  A   E  A  Y  E   S  I  A   K  I  V   N  D  N  N
                              nsp3

      4342       4352       4362       4372       4382       4392
UACAAGUCAG UAGCGAUUCC ACUGUUGUCC ACCGGCAUCU UUUCCGGGAA CAAAGAUCGA
  Y  K  S   V  A  I   P  L  L  S   T  G  I   F  S  G   N  K  D  R
                              nsp3

      4402       4412       4422       4432       4442       4452
CUAACCCAAU CAUUGAACCA UUUGCUGACA GCUUUAGACA CCACUGAUGC AGAUGUAGCC
  L  T  Q   S  L  N   H  L  L  T   A  L  D   T  T  D   A  D  V  A
                              nsp3

      4462       4472       4482       4492       4502       4512
AUAUACUGCA GGGACAAGAA AUGGGAAAUG ACUCUCAAGG AAGCAGUGGC UAGGAGAGAA
  I  Y  C   R  D  K   K  W  E  M   T  L  K   E  A  V   A  R  R  E
                              nsp3

      4522       4532       4542       4552       4562       4572
GCAGUGGAGG AGAUAUGCAU AUCCGACGAU UCUUCAGUGA CAGAACCUGA UGCAGAGCUG
  A  V  E   E  I  C   I  S  D  D   S  S  V   T  E  P   D  A  E  L
                              nsp3

      4582       4592       4602       4612       4622       4632
GUGAGGGUGC AUCCCAAGAG UUCUUUGGCU GGAAGGAAGG GCUACAGCAC AAGCGAUGGC
  V  R  V   H  P  K   S  S  L  A   G  R  K   G  Y  S   T  S  D  G
                              nsp3

      4642       4652       4662       4672       4682       4692
AAAACUUUCU CAUAUUUGGA AGGGACCAAG UUUCACCAGG CGGCCAAGGA UAUAGCAGAA
  K  T  F   S  Y  L   E  G  T  K   F  H  Q   A  A  K   D  I  A  E
                              nsp3

      4702       4712       4722       4732       4742       4752
AUUAAUGCCA UGUGGCCCGU UGCAACGGAG GCCAAUGAGC AGGUAUGCAU GUAUAUCCUC
  I  N  A   M  W  P   V  A  T  E   A  N  E   Q  V  C   M  Y  I  L
                              nsp3

      4762       4772       4782       4792       4802       4812
GGAGAAAGCA UGAGCAGUAU UAGGUCGAAA UGCCCCGUCG AGGAGUCGGA AGCCUCCACA
  G  E  S   M  S  S   I  R  S  K   C  P  V   E  E  S   E  A  S  T
                              nsp3

      4822       4832       4842       4852       4862       4872
CCACCUAGCA CGCUGCCUUG CUUGUGCAUC CAUGCCAUGA CUCCAGAAAG AGUACAGCGC
  P  P  S   T  L  P   C  L  C  I   H  A  M   T  P  E   R  V  Q  R
                              nsp3

      4882       4892       4902       4912       4922       4932
CUAAAAGCCU CACGUCCAGA ACAAAUUACU GUGUGCUCAU CCUUUCCAUU GCCGAAGUAU
  L  K  A   S  R  P   E  Q  I  T   V  C  S   S  E  P   L  P  K  Y
                              nsp3

      4942       4952       4962       4972       4982       4992
AGAAUCACUG GUGUGCAGAA GAUCCAAUGC UCCCAGCCUA UAUUGUUCUC ACCGAAAGUG
  R  I  T   G  V  Q   K  I  Q  C   S  Q  P   I  L  F   S  P  K  V
                              nsp3

      5002       5012       5022       5032       5042       5052
CCUGCGUAUA UUCAUCCAAG GAAGUAUCUC GUGGAAACAC CACCGGUAGA CGAGACUCCG
  P  A  Y   I  H  P   R  K  Y  L   V  E  T   P  P  V   D  E  T  P
                              nsp3
```

-continued

```
      5062       5072       5082       5092       5102       5112
GAGCCAUCGG CAGAGAACCA AUCCACAGAG GGGACACCUG AACAACCACC ACUUAUAACC
  E  P  S   A  E  N   Q  S  T  E   G  T  P   E  Q  P   P  L  I  T
                              nsp3

      5122       5132       5142       5152       5162       5172
GAGGAUGAGA CCAGGACUAG AACGCCUGAG CCGAUCAUCA UCGAAGAAGA AGAAGAAGAU
  E  D  E   T  R  T   R  T  P  E   P  I  I   I  E  E   E  E  E  D
                              nsp3

      5182       5192       5202       5212       5222       5232
AGCAUAAGUU UGCUGUCAGA UGGCCCGACC CACCAGGUGC UGCAAGUCGA GGCAGACAUU
  S  I  S   L  L  S   D  G  P  T   H  Q  V   L  Q  V   E  A  D  I
                              nsp3

      5242       5252       5262       5272       5282       5292
CACGGGCCGC CCUCUGUAUC UAGCUCAUCC UGGUCCAUUC CUCAUGCAUC CGACUUUGAU
  H  G  P   P  S  V   S  S  S  S   W  S  I   P  H  A   S  D  F  D
                              nsp3

      5302       5312       5322       5332       5342       5352
GUGGACAGUU UAUCCAUACU UGACACCCUG GAGGGAGCUA GCGUGACCAG CGGGGCAACG
  V  D  S   L  S  I   L  D  T  L   E  G  A   S  V  T   S  G  A  T
                              nsp3

      5362       5372       5382       5392       5402       5412
UCAGCCGAGA CUAACUCUUA CUUCGCAAAG AGUAUGGAGU UUCUGGCGCG ACCGGUGCCU
  S  A  E   T  N  S   Y  F  A  K   S  M  E   F  L  A   R  P  V  P
                              nsp3

      5422       5432       5442       5452       5462       5472
GCGCCUCGAA CAGUAUUCAG GAACCCUCCA CAUCCCGCUC CGCGCACAAG AACACCGUCA
  A  P  R   T  V  F   R  N  P  P   H  P  A   P  R  T   R  T  P  S
                              nsp3

      5482       5492       5502       5512       5522       5532
CUUGCACCCA GCAGGGCCUG CUCCAGAACC AGCCUAGUUU CCACCCCGCC AGGCGUGAAU
  L  A  P   S  R  A   C  S  R  T   S  L  V   S  T  P   P  G  V  N
                              nsp3

      5542       5552       5562       5572       5582       5592
AGGGUGAUCA CUAGAGAGGA GCUCGAAGCG CUUACCCCGU CACGCACUCC UAGCAGGUCG
  R  V  I   T  R  E   E  L  E  A   L  T  P   S  R  T   P  S  R  S
                              nsp3

      5602       5612       5622       5632       5642       5652
GUCUCCAGAA CCAGCCUGGU CUCCAACCCG CCAGGCGUAA AUAGGGUGAU UACAAGAGAG
  V  S  R   T  S  L   V  S  N  P   P  G  V   N  R  V   I  T  R  E
                              nsp3

      5662       5672       5682       5692       5702 5703
GAGUUUGAGG CGUUCGUAGC ACAACAACAA UGACGGUUUG AUGCGGGUGC A
  E  F  E   A  F  V   A  Q  Q  Q   *  R  F   D  A  G   A
                              nsp3

      5713       5723       5733       5743       5753       5763
UACAUCUUUU CCUCCGACAC CGGUCAAGGG CAUUUACAAC AAAAAUCAGU AAGGCAAACG
  Y  I  F   S  S  D   T  G  Q  G   H  L  Q   Q  K  S   V  R  Q  T
                              nsp4

      5773       5783       5793       5803       5813       5823
GUGCUAUCCG AAGUGGUGUU GGAGAGGACC GAAUUGGAGA UUUCGUAUGC CCCGCGCCUC
  V  L  S   E  V  V   L  E  R  T   E  L  E   I  S  Y   A  P  R  L
                              nsp4

      5833       5843       5853       5863       5873       5883
GACCAAGAAA AAGAAGAAUU ACUACGCAAG AAAUUACAGU UAAAUCCCAC ACCUGCUAAC
  D  Q  E   K  E  E   L  L  R  K   K  L  Q   L  N  P   T  P  A  N
                              nsp4

      5893       5903       5913       5923       5933       5943
AGAAGCAGAU ACCAGUCCAG GAAGGUGGAG AACAUGAAAG CCAUAACAGC UAGACGUAUU
  R  S  R   Y  Q  S   R  K  V  E   N  M  K   A  I  T   A  R  R  I
                              nsp4

      5953       5963       5973       5983       5993       6003
CUGCAAGGCC UAGGGCAUUA UUUGAAGGCA GAAGGAAAAG UGGAGUGCUA CCGAACCCUG
  L  Q  G   L  G  H   Y  L  K  A   E  G  K   V  E  C   Y  R  T  L
                              nsp4
```

-continued

```
      6013       6023       6033       6043       6053       6063
CAUCCUGUUC CUUUGUAUUC AUCUAGUGUG AACCGUGCCU UUUCAAGCCC CAAGGUCGCA
  H  P  V   P  L  Y   S  S  S  V   N  R  A   F  S  S   P  K  V  A
                               nsp4

      6073       6083       6093       6103       6113       6123
GUGGAAGCCU GUAACGCCAU GUUGAAAGAG AACUUUCCGA CUGUGGCUUC UUACUGUAUU
  V  E  A   C  N  A   M  L  K  E   N  F  P   T  V  A   S  Y  C  I
                               nsp4

      6133       6143       6153       6163       6173       6183
AUUCCAGAGU ACGAUGCCUA UUUGGACAUG GUUGACGGAG CUUCAUGCUG CUUAGACACU
  I  P  E   Y  D  A   Y  L  D  M   V  D  G   A  S  C   C  L  D  T
                               nsp4

      6193       6203       6213       6223       6233       6243
GCCAGUUUUU GCCCUGCAAA GCUGCGCAGC UUUCCAAAGA AACACUCCUA UUUGGAACCC
  A  S  F   C  P  A   K  L  R  S   F  P  K   K  H  S   Y  L  E  P
                               nsp4

      6253       6263       6273       6283       6293       6303
ACAAUACGAU CGGCAGUGCC UUCAGCGAUC CAGAACACGC UCCAGAACGU CCUGGCAGCU
  T  I  R   S  A  V   P  S  A  I   Q  N  T   L  Q  N   V  L  A  A
                               nsp4

      6313       6323       6333       6343       6353       6363
GCCACAAAAA GAAAUUGCAA UGUCACGCAA AUGAGAGAAU UGCCCGUAUU GGAUUCGGCG
  A  T  K   R  N  C   N  V  T  Q   M  R  E   L  P  V   L  D  S  A
                               nsp4

      6373       6383       6393       6403       6413       6423
GCCUUUAAUG UGGAAUGCUU CAAGAAAUAU GCGUGUAAUA AUGAAUAUUG GGAAACGUUU
  A  F  N   V  E  C   F  K  K  Y   A  C  N   N  E  Y   W  E  T  F
                               nsp4

      6433       6443       6453       6463       6473       6483
AAAGAAAACC CCAUCAGGCU UACUGAAGAA AACGUGGUAA AUUACAUUAC CAAAUUAAAA
  K  E  N   P  I  R   L  T  E  E   N  V  V   N  Y  I   T  K  L  K
                               nsp4

      6493       6503       6513       6523       6533       6543
GGACCAAAAG CUGCUGCUCU UUUUGCGAAG ACACAUAAUU UGAAUAUGUU GCAGGACAUA
  G  P  K   A  A  A   L  F  A  K   T  H  N   L  N  M   L  Q  D  I
                               nsp4

      6553       6563       6573       6583       6593       6603
CCAAUGGACA GGUUUGUAAU GGACUUAAAG AGAGACGUGA AAGUGACUCC AGGAACAAAA
  P  M  D   R  F  V   M  D  L  K   R  D  V   K  V  T   P  G  T  K
                               nsp4

      6613       6623       6633       6643       6653       6663
CAUACUGAAG AACGGCCCAA GGUACAGGUG AUCCAGGCUG CCGAUCCGCU AGCAACAGCG
  H  T  E   E  R  P   K  V  Q  V   I  Q  A   A  D  P   L  A  T  A
                               nsp4

      6673       6683       6693       6703       6713       6723
UAUCUGUGCG GAAUCCACCG AGAGCUGGUU AGGAGAUUAA AUGCGGUCCU GCUUCCGAAC
  Y  L  C   G  I  H   R  E  L  V   R  R  L   N  A  V   L  L  P  N
                               nsp4

      6733       6743       6753       6763       6773       6783
AUUCAUACAC UGUUUGAUAU GUCGGCUGAA GACUUUGACG CUAUUAUAGC CGAGCACUUC
  I  H  T   L  E  D   M  S  A  E   D  F  D   A  I  I   A  E  H  F
                               nsp4

      6793       6803       6813       6823       6833       6843
CAGCCUGGGG AUUGUGUUCU GGAAACUGAC AUCGCGUCGU UUGAUAAAAG UGAGGACGAC
  Q  P  G   D  C  V   L  E  T  D   I  A  S   F  D  K   S  E  D  D
                               nsp4

      6853       6863       6873       6883       6893       6903
GCCAUGGCUC UGACCGCGUU AAUGAUUCUG GAAGACUUAG GUGUGGACGC AGAGCUGUUG
  A  M  A   L  T  A   L  M  I  L   E  D  L   G  V  D   A  E  L  L
                               nsp4

      6913       6923       6933       6943       6953       6963
ACGCUGAUUG AGGCGGCUUU CGGCGAAAUU UCAUCAAUAC AUUUGCCCAC UAAAACUAAA
  T  L  I   E  A  A   F  G  E  I   S  S  I   H  L  P   T  K  T  K
                               nsp4
```

-continued

```
      6973        6983        6993        7003        7013        7023
UUUAAAUUCG GAGCCAUGAU GAAAUCUGGA AUGUUCCUCA CACUGUUUGU GAACACAGUC
  F  K  F   G  A  M   M  K  S  G   M  F  L   T  L  F   V  N  T  V
                              nsp4

      7033        7043        7053        7063        7073        7083
AUUAACAUUG UAAUCGCAAG CAGAGUGUUG AGAGAACGGC UAACCGGAUC ACCAUGUGCA
  I  N  I   V  I  A   S  R  V  L   R  E  R   L  T  G   S  P  C  A
                              nsp4

      7093        7103        7113        7123        7133        7143
GCAUUCAUUG GAGAUGACAA UAUCGUGAAA GGAGUCAAAU CGGACAAAUU AAUGGCAGAC
  A  F  I   G  D  D   N  I  V  K   G  V  K   S  D  K   L  M  A  D
                              nsp4

      7153        7163        7173        7183        7193        7203
AGGUGCGCCA CCUGGUUGAA UAUGGAAGUC AAGAUUAUAG AUGCUGUGGU GGGCGAGAAA
  R  C  A   T  W  L   N  M  E  V   K  I  I   D  A  V   V  G  E  K
                              nsp4

      7213        7223        7233        7243        7253        7263
GCGCCUUAUU UCUGUGGAGG GUUUAUUUUG UGUGACUCCG UGACCGGCAC AGCGUGCCGU
  A  P  Y   F  C  G   G  F  I  L   C  D  S   V  T  G   T  A  C  R
                              nsp4

      7273        7283        7293        7303        7313        7323
GUGGCAGACC CCCUAAAAAG GCUGUUUAAG CUAGGCAAAC CUCUGGCAGC AGACGAUGAA
  V  A  D   P  L  K   R  L  F  K   L  G  K   P  L  A   A  D  D  E
                              nsp4

      7333        7343        7353        7363        7373        7383
CAUGAUGAUG ACAGGAGAAG GGCAUUGCAU GAGGAGUCAA CACGCUGGAA CCGAGUGGGU
  H  D  D   D  R  R   R  A  L  H   E  E  S   T  R  W   N  R  V  G
                              nsp4

      7393        7403        7413        7423        7433        7443
AUUCUUUCAG AGCUGUGCAA GGCAGUAGAA UCAAGGUAUG AAACCGUAGG AACUUCCAUC
  I  L  S   E  L  C   K  A  V  E   S  R  Y   E  T  V   G  T  S  I
                              nsp4

      7453        7463        7473        7483        7493        7503
AUAGUUAUGG CCAUGACUAC UCUAGCUAGC AGUGUUAAAU CAUUCAGCUA CCUGAGAGGG
  I  V  M   A  M  T   T  L  A  S   S  V  K   S  F  S   Y  L  R  G
                              nsp4

      7513        7523    7527
GCCCCUAUAA CUCUCUACGG CUAA
  A  P  I   T  L  Y   G  *
              nsp4

      7537        7547        7557        7567 7568
CCUGAAUGGA CUACGACAUA GUCUAGUCCG CCAAGACUAG U
                             virUTR

      7578        7588        7598       7608        7618        7628
AUGUUUGUGU UUCUUGUGCU GCUGCCUCUU GUGUCUUCUC AGUGUGUGGU GAGAUUUCCA
  M  F  V   F  L  V   L  L  P  L   V  S  S   Q  C  V   V  R  F  P
                          RBD (S protein)

      7638        7648        7658        7668        7678        7688
AAUAUUACAA AUCUGUGUCC AUUUGGAGAA GUGUUUAAUG CAACAAGAUU UGCAUCUGUG
  N  I  T   N  L  C   P  F  G  E   V  F  N   A  T  R   F  A  S  V
                          RBD (S protein)

      7698        7708        7718        7728        7738        7748
UAUGCAUGGA AUAGAAAAAG AAUUUCUAAU UGUGUGGCUG AUUAUUCUGU GCUGUAUAAU
  Y  A  W   N  R  K   R  I  S  N   C  V  A   D  Y  S   V  L  Y  N
                          RBD (S protein)

      7758        7768        7778        7788        7798        7808
AGUGCUUCUU UUUCCACAUU UAAAUGUUAU GGAGUGUCUC CAACAAAAUU AAAUGAUUUA
  S  A  S   F  S  T   F  K  C  Y   G  V  S   P  T  K   L  N  D  L
                          RBD (S protein)

      7818        7828        7838        7848        7858        7868
UGUUUUACAA AUGUGUAUGC UGAUUCUUUU GUGAUCAGAG GUGAUGAAGU GAGACAGAUU
  C  F  T   N  V  Y   A  D  S  F   V  I  R   G  D  E   V  R  Q  I
                          RBD (S protein)

      7878        7888        7898        7908        7918        7928
GCCCCCGGAC AGACAGGAAA AAUUGCUGAU UACAAUUACA AACUGCCUGA UGAUUUUACA
```

-continued

```
 A  P  G   Q  T  G   K  I  A  D   Y  N  Y   K  L  P   D  D  F  T
                           RBD (S protein)

      7938       7948       7958       7968       7978       7988
GGAUGUGUGA UUGCUUGGAA UUCUAAUAAU UUAGAUUCUA AAGUGGGAGG AAAUUACAAU
 G  C  V   I  A  W   N  S  N  N   L  D  S   K  V  G   G  N  Y  N
                           RBD (S protein)

      7998       8008       8018       8028       8038       8048
UAUCUGUACA GACUGUUUAG AAAAUCAAAU CUGAAACCUU UUGAAAGAGA UAUUUCAACA
 Y  L  Y   R  L  F   R  K  S  N   L  K  P   F  E  R   D  I  S  T
                           RBD (S protein)

      8058       8068       8078       8088       8098       8108
GAAAUUUAUC AGGCUGGAUC AACACCUUGU AAUGGAGUGG AAGGAUUUAA UUGUUAUUUU
 E  I  Y   Q  A  G   S  T  P  C   N  G  V   E  G  F   N  C  Y  F
                           RBD (S protein)

      8118       8128       8138       8148       8158       8168
CCAUUACAGA GCUAUGGAUU UCAGCCAACC AAUGGUGUGG GAUAUCAGCC AUAUAGAGUG
 P  L  Q   S  Y  G   F  Q  P  T   N  G  V   G  Y  Q   P  Y  R  V
                           RBD (S protein)

      8178       8188       8198       8208       8218    8222
GUGGUGCUGU CUUUUGAACU GCUGCAUGCA CCUGCAACAG UGUGUGGACC UAAA
 V  V  L   S  F  E   L  L  H  A   P  A  T   V  C  G   P  K
                           RBD (S protein)

      8232       8242    8249
GGCUCCCCCG GCUCCGGCUC CGGAUCU
 G  S  P   G  S  G   S  G  S
        GS linker

      8259       8269       8279       8289       8299       8309
GGUUAUAUUC CUGAAGCUCC AAGAGAUGGG CAAGCUUACG UUCGUAAAGA UGGCGAAUGG
 G  Y  I   P  E  A   P  R  D  G   Q  A  Y   V  R  K   D  G  E  W
                              fibritin

      8319       8329 8330
GUAUUACUUU CUACCUUUUU A
 V  L  L   S  T  F   L
       fibritin

      8340    8345
GGAAGCGGCA GCGGA
 G  S  G   S  G
   GS linker

      8355       8365       8375       8385       8395       8405
UCUGAACAGU ACAUUAAAUG GCCUUGGUAC AUUUGGCUUG GAUUUAUUGC AGGAUUAAUU
 S  E  Q   Y  I  K   W  P  W  Y   I  W  L   G  F  I   A  G  L  I
                                 TM

      8415       8425       8435       8445       8455       8465
GCAAUUGUGA UGGUGACAAU UAUGUUAUGU UGUAUGACAU CAUGUUGUUC UUGUUUAAAA
 A  I  V   M  V  T   I  M  L  C   C  M  T   S  C  C   S  C  L  K
                                 TM

      8475       8485       8495       8505       8515       8525
GGAUGUUGUU CUUGUGGAAG CUGUUGUAAA UUUGAUGAAG AUGAUUCUGA ACCUGUGUUA
 G  C  C   S  C  G   S  C  C  K   F  D  E   D  D  S   E  P  V  L
                                 TM

      8535       8545       8555
AAAGGAGUGA AAUUGCAUUA CACAUGAUGA
 K  G  V   K  L  H   Y  T  *  *
              TM

      8565       8575       8585       8595       8605       8615
CUCGAGCUGG UACUGCAUGC ACGCAAUGCU AGCUGCCCCU UUCCCGUCCU GGGUACCCCG
                             FI element
```

-continued

```
      8625       8635       8645       8655       8665       8675
AGUCUCCCCC GACCUCGGGU CCCAGGUAUG CUCCCACCUC CACCUGCCCC ACUCACCACC
                          FI element

      8685       8695       8705       8715       8725       8735
UCUGCUAGUU CCAGACACCU CCCAAGCACG CAGCAAUGCA GCUCAAAACG CUUAGCCUAG
                          FI element

      8745       8755       8765       8775       8785       8795
CCACACCCCC ACGGGAAACA GCAGUGAUUA ACCUUUAGCA AUAAACGAAA GUUUAACUAA
                          FI element

      8805       8815       8825       8835       8845       8855
GCUAUACUAA CCCCAGGGUU GGUCAAUUUC GUGCCAGCCA CACCGCGGCC GCAUGAAUAC
                          FI element

      8865       8875       8885       8895       8905       8915
AGCAGCAAUU GGCAAGCUGC UUACAUAGAA CUCGCGGCGA UUGGCAUGCC GCCUUAAAAU
                          FI element

      8925       8935       8945       8955       8965    8969
UUUUAUUUUA UUUUUUCUUU UCUUUUCCGA AUCGGAUUUU GUUUUUAAUA UUUC
                          FI element

      8979      8989       8999       9009       9019       9029
AAAAAAAAAA AAAAAAAAAA AAAAAAAAAA GCAUAUGACU AAAAAAAAAA AAAAAAAAAA
                            Poly(A)

      9039       9049       9059       9069       9079
AAAAAAAAAA AAAAAAAAAA AAAAAAAAAA AAAAAAAAAA AAAAAAAAAA
                            Poly(A)
```

In some embodiments, vaccine RNA described herein comprises a nucleotide sequence selected from the group consisting of SEQ ID NO: 15, 16, 17, 19, 20, 21, 24, 25, 26, 27, 30, and 32. A particularly preferred vaccine RNA described herein comprises a nucleotide sequence selected from the group consisting of SEQ ID NO: 15, 17, 19, 21, 25, 26, 30, and 32 such as selected from the group consisting of SEQ ID NO: 17, 19, 21, 26, 30, and 32.

RNA described herein is preferably formulated in lipid nanoparticles (LNP). In one embodiment, the LNP comprise a cationic lipid, a neutral lipid, a steroid, a polymer conjugated lipid; and the RNA. In one embodiment, the cationic lipid is ALC-0315, the neutral lipid is DSPC, the steroid is cholesterol, and the polymer conjugated lipid is ALC-0159. The preferred mode of administration is intramuscular administration, more preferably in aqueous cryoprotectant buffer for intramuscular administration. The drug product is a preferably a preservative-free, sterile dispersion of RNA formulated in lipid nanoparticles (LNP) in aqueous cryoprotectant buffer for intramuscular administration.

In different embodiments, the drug product comprises the components shown below, preferably at the proportions or concentrations shown below:

| Component | Function | Proportion (mol %) |
|---|---|---|
| ALC-0315 [1] | Functional lipid | 47.5 |
| ALC-0159 [2] | Functional lipid | 1.8 |
| DSPC [3] | Structural lipid | 10.0 |
| Cholesterol, synthetic | Structural lipid | 40.7 |

-continued

| Component | Function | Concentration (mg/mL) |
|---|---|---|
| Drug Substance | Active | 0.5 |
| ALC-0315 [1] | Functional lipid | 7.17 |
| ALC-0159 [2] | Functional lipid | 0.89 |
| DSPC [3] | Structural lipid | 1.56 |
| Cholesterol, synthetic | Structural lipid | 3.1 |
| Sucrose | Cryoprotectant | 102.69 |
| NaCl | Buffer | 6.0 |
| KCl | Buffer | 0.15 |
| $Na_2HPO_4$ | Buffer | 1.08 |
| $KH_2PO_4$ | Buffer | 0.18 |
| Water for injection | Solvent/Vehicle | q.s. |

| Component | Function | Concentration (mg/mL) |
|---|---|---|
| Drug Substance | Active | 1.0 |
| ALC-0315 [1] | Functional lipid | 13.56 |
| ALC-0159 [2] | Functional lipid | 1.77 |
| DSPC [3] | Structural lipid | 3.11 |
| Cholesterol, synthetic | Structural lipid | 6.20 |
| Sucrose | Cryoprotectant | 102.69 |
| NaCl | Buffer | 6.0 |
| KCl | Buffer | 0.15 |
| $Na_2HPO_4$ | Buffer | 1.08 |
| $KH_2PO_4$ | Buffer | 0.15 |
| Water for injection | Solvent/Vehicle | q.s. |

[1] ALC-0315 = ((4-hydroxybutyl)azanediyl)bis(hexane-6,1-diyl)bis(2-hexyldecanoate)/6-[N-6-(2-hexyldecanoyloxy)hexyl-N-(4-hydroxybutyl)amino]hexyl 2-hexyldecanoate

[2] ALC-0159 = 2-[(polyethylene glycol)-2000]-N,N-ditetradecylacetamide/2-[2-(ω{u)-methoxy (polyethyleneglycol2000) ethoxy]-N,N-ditetradecylacetamide

[3] DSPC = 1,2-Distearoyl-sn-glycero-3-phosphocholine q.s. = quantum satis (as much as may suffice)

ALC-0315:

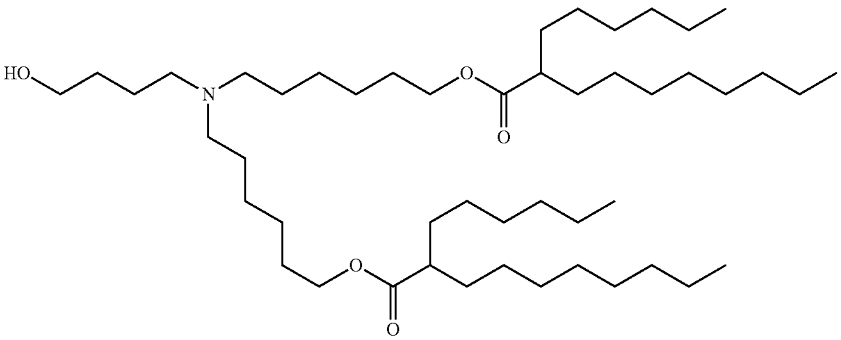 [SMILES: CCCCCCCCC(CCCCCC)C(=O)OCCCCCCN(CCCCO)CCCCCCOC(=O)C(CCCCCC)CCCCCCCC]

ALC-0159:

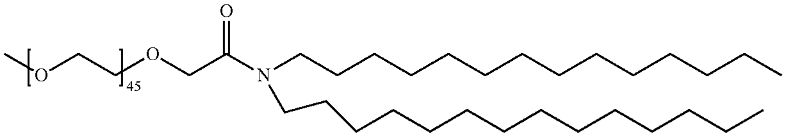

DSPC:

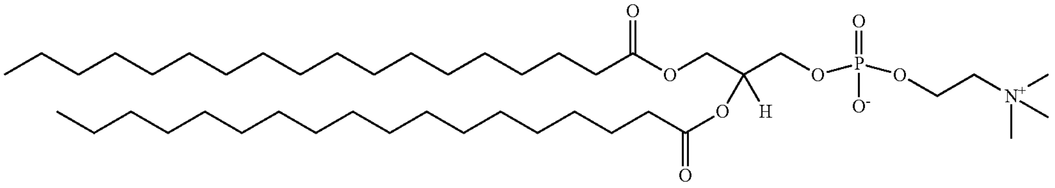 [SMILES: CCCCCCCCCCCCCCCCCC(=O)OCC(COP(=O)([O-])OCC[N+](C)(C)C)OC(=O)CCCCCCCCCCCCCCCCC]

Cholesterol:

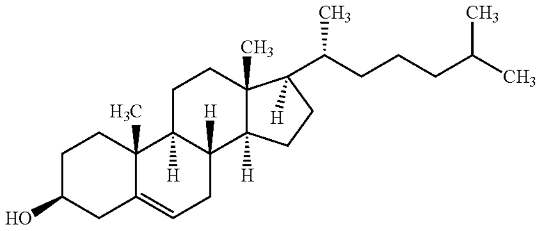

In one embodiment, the ratio of mRNA to total lipid (N/P) is between 6.0 and 6.5 such as about 6.0 or about 6.3.

Nucleic Acid Containing Particles

Nucleic acids described herein such as RNA encoding a vaccine antigen may be administered formulated as particles.

In the context of the present disclosure, the term "particle" relates to a structured entity formed by molecules or molecule complexes. In one embodiment, the term "particle" relates to a micro- or nano-sized structure, such as a micro- or nano-sized compact structure dispersed in a medium. In one embodiment, a particle is a nucleic acid containing particle such as a particle comprising DNA, RNA or a mixture thereof.

Electrostatic interactions between positively charged molecules such as polymers and lipids and negatively charged nucleic acid are involved in particle formation. This results in complexation and spontaneous formation of nucleic acid particles. In one embodiment, a nucleic acid particle is a nanoparticle.

As used in the present disclosure, "nanoparticle" refers to a particle having an average diameter suitable for parenteral administration.

A "nucleic acid particle" can be used to deliver nucleic acid to a target site of interest (e.g., cell, tissue, organ, and the like). A nucleic acid particle may be formed from at least one cationic or cationically ionizable lipid or lipid-like material, at least one cationic polymer such as protamine, or a mixture thereof and nucleic acid. Nucleic acid particles include lipid nanoparticle (LNP)-based and lipoplex (LPX)-based formulations.

Without intending to be bound by any theory, it is believed that the cationic or cationically ionizable lipid or lipid-like material and/or the cationic polymer combine together with the nucleic acid to form aggregates, and this aggregation results in colloidally stable particles.

In one embodiment, particles described herein further comprise at least one lipid or lipid-like material other than a cationic or cationically ionizable lipid or lipid-like material, at least one polymer other than a cationic polymer, or a mixture thereof In some embodiments, nucleic acid particles comprise more than one type of nucleic acid molecules, where the molecular parameters of the nucleic acid molecules may be similar or different from each other, like with respect to molar mass or fundamental structural elements such as molecular architecture, capping, coding regions or other features, Nucleic acid particles described herein may have an average diameter that in one embodiment ranges from about 30 nm to about 1000 nm, from about 50 nm to about 800 nm, from about 70 nm to about 600 nm, from about 90 nm to about 400 nm, or from about 100 nm to about 300 nm.

Nucleic acid particles described herein may exhibit a polydispersity index less than about 0.5, less than about 0.4, less than about 0.3, or about 0.2 or less. By way of example, the nucleic acid particles can exhibit a polydispersity index in a range of about 0.1 to about 0.3 or about 0.2 to about 0.3.

With respect to RNA lipid particles, the N/P ratio gives the ratio of the nitrogen groups in the lipid to the number of phosphate groups in the RNA. It is correlated to the charge ratio, as the nitrogen atoms (depending on the pH) are usually positively charged and the phosphate groups are negatively charged. The N/P ratio, where a charge equilibrium exists, depends on the pH. Lipid formulations are frequently formed at N/P ratios larger than four up to twelve, because positively charged nanoparticles are considered favorable for transfection. In that case, RNA is considered to be completely bound to nanoparticles.

Nucleic acid particles described herein can be prepared using a wide range of methods that may involve obtaining a colloid from at least one cationic or cationically ionizable lipid or lipid-like material and/or at least one cationic polymer and mixing the colloid with nucleic acid to obtain nucleic acid particles.

The term "colloid" as used herein relates to a type of homogeneous mixture in which dispersed particles do not settle out. The insoluble particles in the mixture are microscopic, with particle sizes between 1 and 1000 nanometers. The mixture may be termed a colloid or a colloidal suspension. Sometimes the term "colloid" only refers to the particles in the mixture and not the entire suspension.

For the preparation of colloids comprising at least one cationic or cationically ionizable lipid or lipid-like material and/or at least one cationic polymer methods are applicable herein that are conventionally used for preparing liposomal vesicles and are appropriately adapted. The most commonly used methods for preparing liposomal vesicles share the following fundamental stages: (i) lipids dissolution in organic solvents, (ii) drying of the resultant solution, and (iii) hydration of dried lipid (using various aqueous media).

In the film hydration method, lipids are firstly dissolved in a suitable organic solvent, and dried down to yield a thin film at the bottom of the flask. The obtained lipid film is hydrated using an appropriate aqueous medium to produce a liposomal dispersion. Furthermore, an additional downsizing step may be included.

Reverse phase evaporation is an alternative method to the film hydration for preparing liposomal vesicles that involves formation of a water-in-oil emulsion between an aqueous phase and an organic phase containing lipids. A brief sonication of this mixture is required for system homogenization. The removal of the organic phase under reduced pressure yields a milky gel that turns subsequently into a liposomal suspension.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion. Using the ethanol injection technique, such colloidal liposome dispersion is, in one embodiment, formed as follows: an ethanol solution comprising lipids, such as cationic lipids and additional lipids, is injected into an aqueous solution under stirring. In one embodiment, the RNA lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

Other methods having organic solvent free characteristics may also be used according to the present disclosure for preparing a colloid.

LNPs typically comprise four components: ionizable cationic lipids, neutral lipids such as phospholipids, a steroid such as cholesterol, and a polymer conjugated lipid such as polyethylene glycol (PEG)-lipids. Each component is responsible for payload protection, and enables effective intracellular delivery. LNPs may be prepared by mixing lipids dissolved in ethanol rapidly with nucleic acid in an aqueous buffer.

The term "average diameter" refers to the mean hydrodynamic diameter of particles as measured by dynamic laser light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

Different types of nucleic acid containing particles have been described previously to be suitable for delivery of nucleic acid in particulate form (e.g. Kaczmarek, J. C. et al., 2017, Genome Medicine 9, 60). For non-viral nucleic acid delivery vehicles, nanoparticle encapsulation of nucleic acid physically protects nucleic acid from degradation and, depending on the specific chemistry, can aid in cellular uptake and endosomal escape.

The present disclosure describes particles comprising nucleic acid, at least one cationic or cationically ionizable lipid or lipid-like material, and/or at least one cationic polymer which associate with nucleic acid to form nucleic acid particles and compositions comprising such particles. The nucleic acid particles may comprise nucleic acid which is complexed in different forms by non-covalent interactions to the particle. The particles described herein are not viral particles, in particular infectious viral particles, i.e., they are not able to virally infect cells.

Suitable cationic or cationically ionizable lipids or lipid-like materials and cationic polymers are those that form nucleic acid particles and are included by the term "particle forming components" or "particle forming agents". The term "particle forming components" or "particle forming agents" relates to any components which associate with nucleic acid to form nucleic acid particles. Such components include any component which can be part of nucleic acid particles.

Cationic Polymer

Given their high degree of chemical flexibility, polymers are commonly used materials for nanoparticle-based delivery. Typically, cationic polymers are used to electrostatically condense the negatively charged nucleic acid into nanoparticles. These positively charged groups often consist of amines that change their state of protonation in the pH range between 5.5 and 7.5, thought to lead to an ion imbalance that results in endosomal rupture. Polymers such as poly-L-lysine, polyamidoamine, protamine and polyethyleneimine, as well as naturally occurring polymers such as chitosan have all been applied to nucleic acid delivery and are suitable as cationic polymers herein. In addition, some investigators have synthesized polymers specifically for nucleic acid delivery. Poly(β-amino esters), in particular, have gained widespread use in nucleic acid delivery owing to their ease of synthesis and biodegradability. Such synthetic polymers are also suitable as cationic polymers herein.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties such as those described herein.

If more than one type of repeat unit is present within the polymer, then the polymer is said to be a "copolymer." It is to be understood that the polymer being employed herein can be a copolymer. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body.

In certain embodiments, polymer may be protamine or polyalkyleneimine, in particular protamine.

The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the disclosure, the term "protamine" as used herein is meant to comprise any protamine amino acid sequence obtained or derived from natural or biological sources including fragments thereof and multimeric forms of said amino acid sequence or fragment thereof as well as (synthesized) polypeptides which are artificial and specifically designed for specific purposes and cannot be isolated from native or biological sources.

In one embodiment, the polyalkyleneimine comprises polyethylenimine and/or polypropylenimine, preferably polyethyleneimine. A preferred polyalkyleneimine is polyethyleneimine (PEI). The average molecular weight of PEI is preferably $0.75.10^2$ to 107 Da, preferably 1000 to 105 Da, more preferably 10000 to 40000 Da, more preferably 15000 to 30000 Da, even more preferably 20000 to 25000 Da.

Preferred according to the disclosure is linear polyalkyleneimine such as linear polyethyleneimine (PEI).

Cationic polymers (including polycationic polymers) contemplated for use herein include any cationic polymers which are able to electrostatically bind nucleic acid. In one embodiment, cationic polymers contemplated for use herein include any cationic polymers with which nucleic acid can be associated, e.g. by forming complexes with the nucleic acid or forming vesicles in which the nucleic acid is enclosed or encapsulated.

Particles described herein may also comprise polymers other than cationic polymers, i.e., non-cationic polymers and/or anionic polymers. Collectively, anionic and neutral polymers are referred to herein as non-cationic polymers.

Lipid and Lipid-Like Material

The terms "lipid" and "lipid-like material" are broadly defined herein as molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually poorly soluble in water. In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). The hydrophilic groups may comprise polar and/or charged groups and include carbohydrates, phosphate, carboxylic, sulfate, amino, sulfhydryl, nitro, hydroxyl, and other like groups.

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as sterol-containing metabolites such as cholesterol.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides. Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

The glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

According to the disclosure, lipids and lipid-like materials may be cationic, anionic or neutral. Neutral lipids or lipid-like materials exist in an uncharged or neutral zwitterionic form at a selected pH.

Cationic or Cationically Ionizable Lipids or Lipid-Like Materials

The nucleic acid particles described herein may comprise at least one cationic or cationically ionizable lipid or lipid-like material as particle forming agent. Cationic or cationically ionizable lipids or lipid-like materials contemplated for use herein include any cationic or cationically ionizable lipids or lipid-like materials which are able to electrostatically bind nucleic acid. In one embodiment, cationic or cationically ionizable lipids or lipid-like materials contemplated for use herein can be associated with nucleic acid, e.g. by forming complexes with the nucleic acid or forming vesicles in which the nucleic acid is enclosed or encapsulated.

As used herein, a "cationic lipid" or "cationic lipid-like material" refers to a lipid or lipid-like material having a net positive charge. Cationic lipids or lipid-like materials bind negatively charged nucleic acid by electrostatic interaction. Generally, cationic lipids possess a lipophilic moiety, such as a sterol, an acyl chain, a diacyl or more acyl chains, and the head group of the lipid typically carries the positive charge.

In certain embodiments, a cationic lipid or lipid-like material has a net positive charge only at certain pH, in particular acidic pH, while it has preferably no net positive charge, preferably has no charge, i.e., it is neutral, at a different, preferably higher pH such as physiological pH. This ionizable behavior is thought to enhance efficacy through helping with endosomal escape and reducing toxicity as compared with particles that remain cationic at physiological pH. For purposes of the present disclosure, such "cationically ionizable" lipids or lipid-like materials are comprised by the term "cationic lipid or lipid-like material" unless contradicted by the circumstances.

In one embodiment, the cationic or cationically ionizable lipid or lipid-like material comprises a head group which includes at least one nitrogen atom (N) which is positive charged or capable of being protonated.

Examples of cationic lipids include, but are not limited to 1,2-dioleoyl-3-trimethylammonium propane (DOTAP); N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-1-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis(tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis(dodecyloxy)-1-propanaminium bromide (GAP-DLRIE), (±)-N-(3-aminopropyl)-N,N-dimethyl-2,3-bis(tetradecyloxy)-1-propanaminium bromide (GAP-DMRIE), N-(2-Aminoethyl)-N,N-dimethyl-2,3-bis(tetradecyloxy)-1-propanaminium bromide (βAE-DMRIE), N-(4-carboxybenzyl)-N,N-dimethyl-2,3-bis(oleoyloxy)propan-1-aminium (DOBAQ), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl)amino]butylcarboxamido)ethyl]-3,4-di[oleyloxy]-benzamide (MVL5), 1,2-dioleoyl-sn-glycero-3-ethylphosphocholine (DOEPC), 2,3-bis(dodecyloxy)-N-(2-hydroxyethyl)-N,N-dimethylpropan-1-amonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl)dioctanoate (ATX), N,N-dimethyl-2,3-bis(dodecyloxy)propan-1-amine (DLDMA), N,N-dimethyl-2,3-bis(tetradecyloxy)propan-1-amine (DMDMA), Di((Z)-non-2-en-1-yl)-9-((4-(dimethylaminobutanoyl)oxy)heptadecanedioate (L319), N-Dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethylamino)propionamide (lipidoid $98N_{12}$-5), 1-[2-[bis(2-hydroxydodecyl)amino]ethyl-[2-[4-[2-[bis(2 hydroxydodecyl)amino]ethyl]piperazin-1-yl]ethyl]amino]dodecan-2-ol (lipidoid C12-200).

In some embodiments, the cationic lipid may comprise from about 10 mol % to about 100 mol %, about 20 mol % to about 100 mol %, about 30 mol % to about 100 mol %, about 40 mol % to about 100 mol %, or about 50 mol % to about 100 mol % of the total lipid present in the particle.

Additional Lipids or Lipid-Like Materials

Particles described herein may also comprise lipids or lipid-like materials other than cationic or cationically ionizable lipids or lipid-like materials, i.e., non-cationic lipids or lipid-like materials (including non-cationically ionizable lipids or lipid-like materials). Collectively, anionic and neutral lipids or lipid-like materials are referred to herein as non-cationic lipids or lipid-like materials. Optimizing the formulation of nucleic acid particles by addition of other hydrophobic moieties, such as cholesterol and lipids, in addition to an ionizable/cationic lipid or lipid-like material may enhance particle stability and efficacy of nucleic acid delivery. An additional lipid or lipid-like material may be incorporated which may or may not affect the overall charge of the nucleic acid particles. In certain embodiments, the additional lipid or lipid-like material is a non-cationic lipid or lipid-like material. The non-cationic lipid may comprise, e.g., one or more anionic lipids and/or neutral lipids. As used herein, an "anionic lipid" refers to any lipid that is negatively charged at a selected pH. As used herein, a "neutral lipid" refers to any of a number of lipid species that exist either in an uncharged or neutral zwitterionic form at a selected pH. In preferred embodiments, the additional lipid comprises one of the following neutral lipid components: (1) a phospholipid, (2) cholesterol or a derivative thereof; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoyl-phosphatidylethanolamine (DMPE), dilauroyl-phosphatidylethanolamine (DLPE), diphytanoyl-phosphatidylethanolamine (DPyPE), and further phosphatidylethanolamine lipids with different hydrophobic chains.

In certain preferred embodiments, the additional lipid is DSPC or DSPC and cholesterol.

In certain embodiments, the nucleic acid particles include both a cationic lipid and an additional lipid.

In one embodiment, particles described herein include a polymer conjugated lipid such as a pegylated lipid. The term "pegylated lipid" refers to a molecule comprising both a lipid portion and a polyethylene glycol portion. Pegylated lipids are known in the art.

Without wishing to be bound by theory, the amount of the at least one cationic lipid compared to the amount of the at least one additional lipid may affect important nucleic acid particle characteristics, such as charge, particle size, stability, tissue selectivity, and bioactivity of the nucleic acid. Accordingly, in some embodiments, the molar ratio of the at least one cationic lipid to the at least one additional lipid is from about 10:0 to about 1:9, about 4:1 to about 1:2, or about 3:1 to about 1:1.

In some embodiments, the non-cationic lipid, in particular neutral lipid, (e.g., one or more phospholipids and/or cholesterol) may comprise from about 0 mol % to about 90 mol %, from about 0 mol % to about 80 mol %, from about 0 mol % to about 70 mol %, from about 0 mol % to about 60 mol %, or from about 0 mol % to about 50 mol %, of the total lipid present in the particle.

Lipoplex Particles

In certain embodiments of the present disclosure, the RNA described herein may be present in RNA lipoplex particles.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The RNA lipoplex particles and compositions comprising RNA lipoplex particles described herein are useful for delivery of RNA to a target tissue after parenteral administration, in particular after intravenous administration. The RNA lipoplex particles may be prepared using liposomes that may be obtained by injecting a solution of the lipids in ethanol into water or a suitable aqueous phase. In one embodiment, the aqueous phase has an acidic pH. In one embodiment, the aqueous phase comprises acetic acid, e.g., in an amount of about 5 mM. Liposomes may be used for preparing RNA lipoplex particles by mixing the liposomes with RNA. In one embodiment, the liposomes and RNA lipoplex particles comprise at least one cationic lipid and at least one additional lipid. In one embodiment, the at least one cationic lipid comprises 1,2-di-O-octadecenyl-3-trimethylammonium propane (DOTMA) and/or 1,2-dioleoyl-3-trimethylammonium-propane (DOTAP). In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC). In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

Lipid Nanoparticles (LNPs)

In one embodiment, nucleic acid such as RNA described herein is administered in the form of lipid nanoparticles (LNPs). The LNP may comprise any lipid capable of forming a particle to which the one or more nucleic acid molecules are attached, or in which the one or more nucleic acid molecules are encapsulated.

In one embodiment, the LNP comprises one or more cationic lipids, and one or more stabilizing lipids. Stabilizing lipids include neutral lipids and pegylated lipids.

In one embodiment, the LNP comprises a cationic lipid, a neutral lipid, a steroid, a polymer conjugated lipid; and the RNA, encapsulated within or associated with the lipid nanoparticle.

In one embodiment, the LNP comprises from 40 to 55 mol percent, from 40 to 50 mol percent, from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, from 47 to 48 mol percent, or from 47.2 to 47.8 mol percent of the cationic lipid. In one embodiment, the LNP comprises about 47.0, 47.1, 47.2, 47.3, 47.4, 47.5, 47.6, 47.7, 47.8, 47.9 or 48.0 mol percent of the cationic lipid.

In one embodiment, the neutral lipid is present in a concentration ranging from 5 to 15 mol percent, from 7 to 13 mol percent, or from 9 to 11 mol percent. In one embodiment, the neutral lipid is present in a concentration of about 9.5, 10 or 10.5 mol percent.

In one embodiment, the steroid is present in a concentration ranging from 30 to 50 mol percent, from 35 to 45 mol percent or from 38 to 43 mol percent. In one embodiment, the steroid is present in a concentration of about 40, 41, 42, 43, 44, 45 or 46 mol percent.

In one embodiment, the LNP comprises from 1 to 10 mol percent, from 1 to 5 mol percent, or from 1 to 2.5 mol percent of the polymer conjugated lipid.

In one embodiment, the LNP comprises from 40 to 50 mol percent a cationic lipid; from 5 to 15 mol percent of a neutral lipid; from 35 to 45 mol percent of a steroid; from 1 to 10 mol percent of a polymer conjugated lipid; and the RNA, encapsulated within or associated with the lipid nanoparticle.

In one embodiment, the mol percent is determined based on total mol of lipid present in the lipid nanoparticle.

In one embodiment, the neutral lipid is selected from the group consisting of DSPC, DPPC, DMPC, DOPC, POPC, DOPE, DOPG, DPPG, POPE, DPPE, DMPE, DSPE, and SM. In one embodiment, the neutral lipid is selected from the group consisting of DSPC, DPPC, DMPC, DOPC, POPC, DOPE and SM. In one embodiment, the neutral lipid is DSPC.

In one embodiment, the steroid is cholesterol.

In one embodiment, the polymer conjugated lipid is a pegylated lipid. In one embodiment, the pegylated lipid has the following structure:

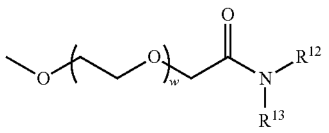

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60. In one embodiment, $R^{12}$ and $R^{13}$ are each independently straight, saturated alkyl chains containing from 12 to 16 carbon atoms. In one embodiment, w has a mean value ranging from 40 to 55.

In one embodiment, the average w is about 45. In one embodiment, $R^{12}$ and $R^{13}$ are each independently a straight, saturated alkyl chain containing about 14 carbon atoms, and w has a mean value of about 45.

In one embodiment, the pegylated lipid is DMG-PEG 2000, e.g., having the following structure:

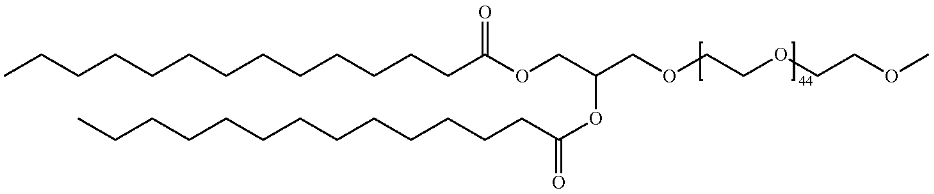

In some embodiments, the cationic lipid component of the LNPs has the structure of Formula (III):

(III)

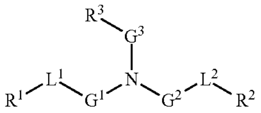

or a pharmaceutically acceptable salt, tautomer, prodrug or stereoisomer thereof, wherein: one of L1 or $L^2$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O—, and the other of $L^1$ or $L^2$ is —O(C═O)—, —(C═O)O—, —C(═O)—, —O—, —S(O)X—, —S—S—, —C(═O)S—, SC(═O)—, —$NR^a$C(═O)—, —C(═O)NR—, $NR^a$C(═O)NR—, —OC(═O)$NR^a$— or —$NR^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)$OR^4$, —OC(═O)$R^4$ or —$NR^5$C(═O)$R^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following structures (IIIA) or (IIIB):

(IIIA)

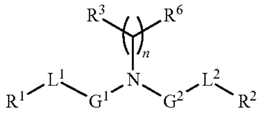 or (IIIB)

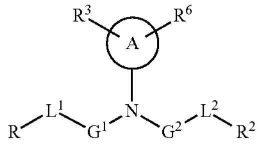

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

(IIIC)

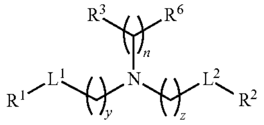 or (IIID)

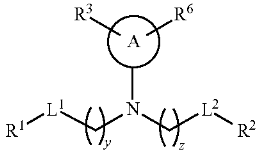

wherein y and z are each independently integers ranging from 1 to 12.

In any of the foregoing embodiments of Formula (III), one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of $L^1$ and $L^2$ is —(C═O)O—.

In some different embodiments of Formula (III), the lipid has one of the following structures (IIIE) or (IIIF):

(IIIE)

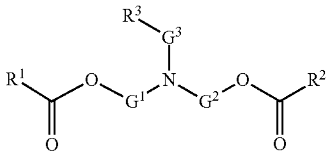 or (IIIF)

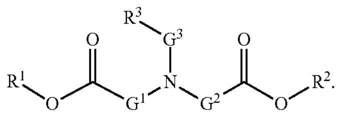

In some of the foregoing embodiments of Formula (III), the lipid has one of the following structures (IIIG), (IIIH), (IIII), or (IIIJ):

(IIIG)

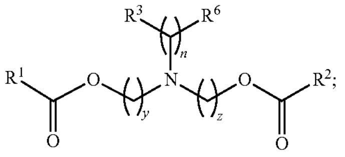

(IIIH)

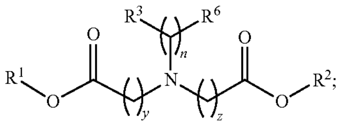

(IIII)

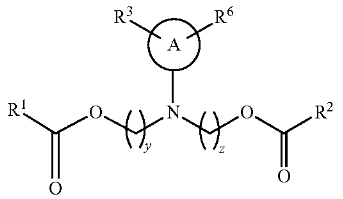 or (IIIJ)

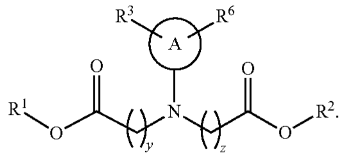

In some of the foregoing embodiments of Formula (III), n is an integer ranging from 2 to 12, for example from 2 to 8 or from 2 to 4. For example, in some embodiments, n is 3, 4, 5 or 6.

In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

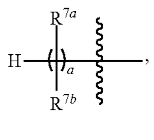

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

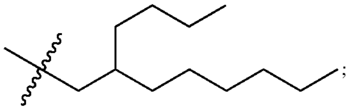
;

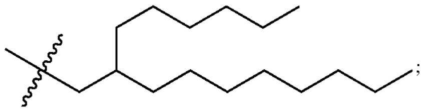
;

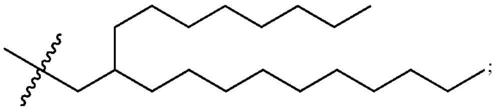
;

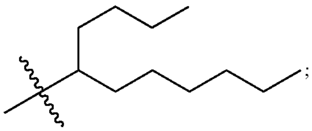
;

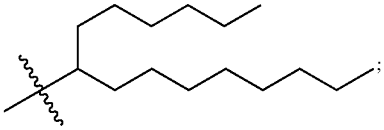
;

-continued

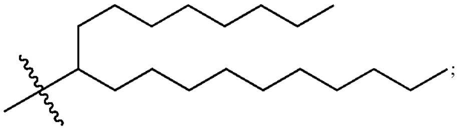
;

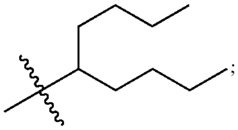
;

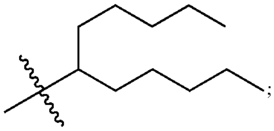
;

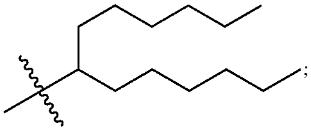
;

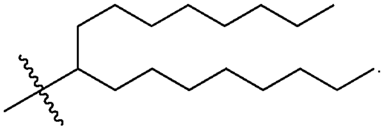
.

In some of the foregoing embodiments of Formula (III), $R^3$ is OH, CN, —C(=O)OR$^4$, —OC(=O)R$^4$ or —NHC(=O)R$^4$. In some embodiments, $R^4$ is methyl or ethyl.

In various different embodiments, the cationic lipid of Formula (III) has one of the structures set forth in the table below.

Representative Compounds of Formula (III).

| No. | Structure |
|---|---|
| III-1 | 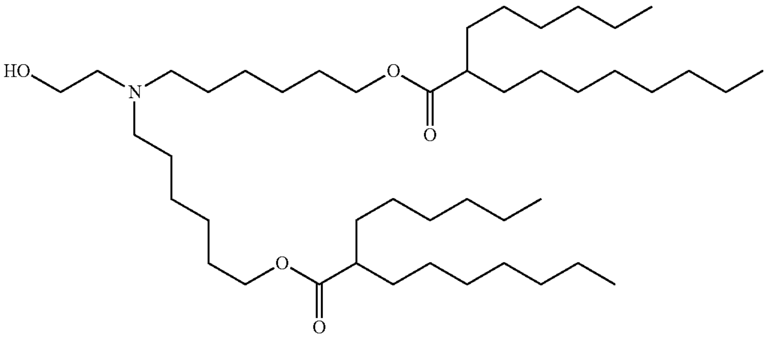 [SMILES: CCCCCCCCC(CCCCCC)C(=O)OCCCCCCN(CCO)CCCCCCOC(=O)C(CCCCCC)CCCCCCC] |

-continued
| No. | Structure |
|---|---|
| III-2 | 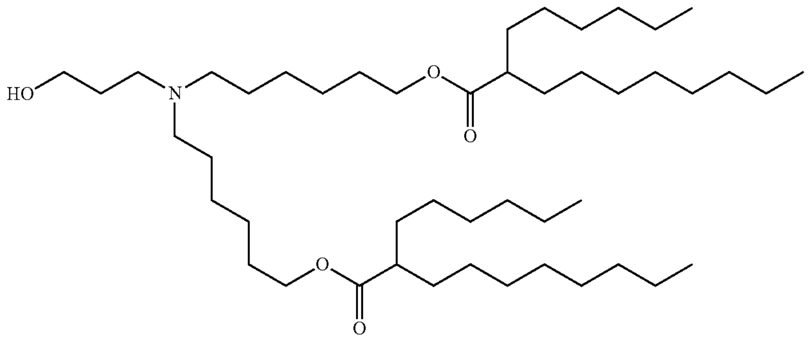 [SMILES: CCCCCCCCC(CCCCCC)C(=O)OCCCCCCN(CCCO)CCCCCCOC(=O)C(CCCCCC)CCCCCCCC] |
| III-3 | 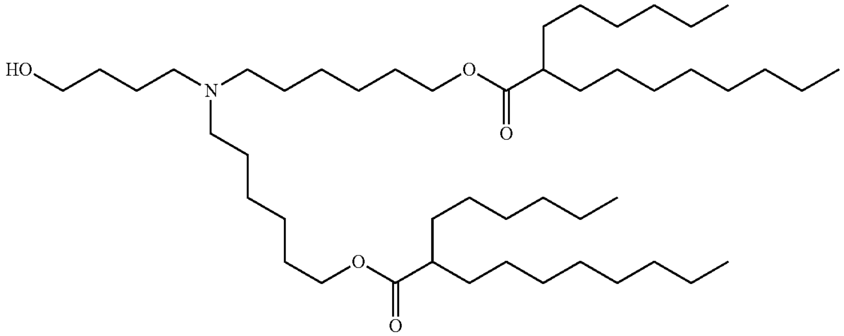 [SMILES: CCCCCCCCC(CCCCCC)C(=O)OCCCCCCN(CCCCO)CCCCCCOC(=O)C(CCCCCC)CCCCCCCC] |
| III-4 | 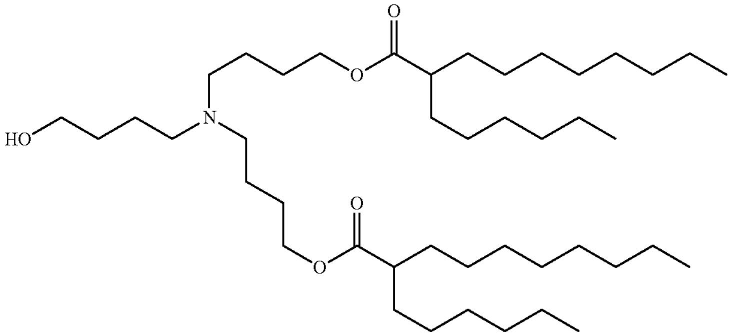 [SMILES: CCCCCCCCC(CCCCCC)C(=O)OCCCCN(CCCCO)CCCCOC(=O)C(CCCCCC)CCCCCCCC] |
| III-5 | 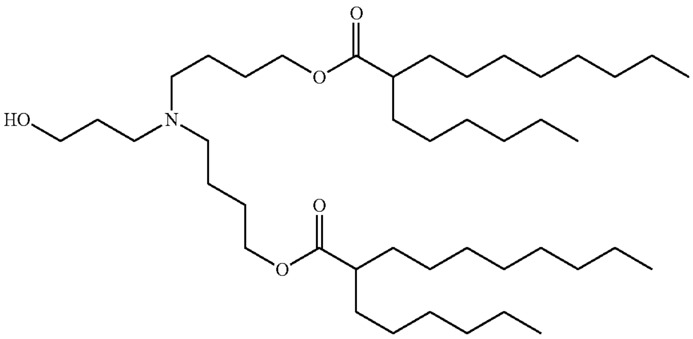 [SMILES: CCCCCCCCC(CCCCCC)C(=O)OCCCCN(CCCO)CCCCOC(=O)C(CCCCCC)CCCCCCCC] |

-continued
| No. | Structure |
|---|---|
| III-6 | 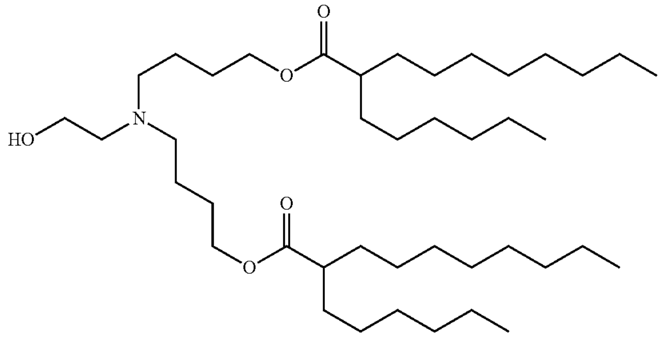 [SMILES: CCCCCCCCC(CCCCCC)C(=O)OCCCCN(CCO)CCCCOC(=O)C(CCCCCC)CCCCCCCC] |
| III-7 | 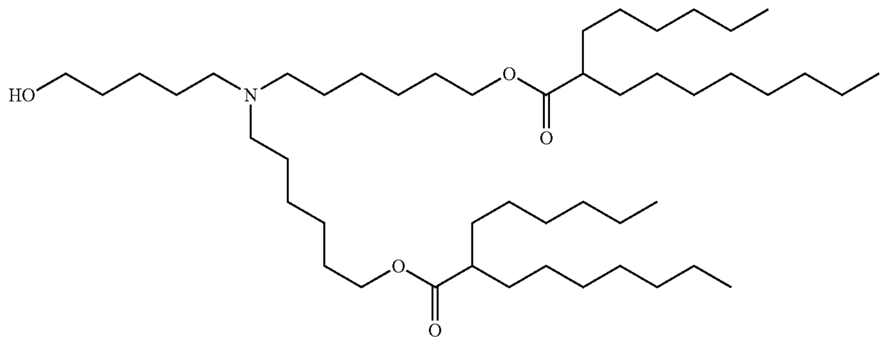 [SMILES: CCCCCCCCC(CCCCCC)C(=O)OCCCCCCN(CCCCCO)CCCCCCOC(=O)C(CCCCCC)CCCCCCC] |
| III-8 | 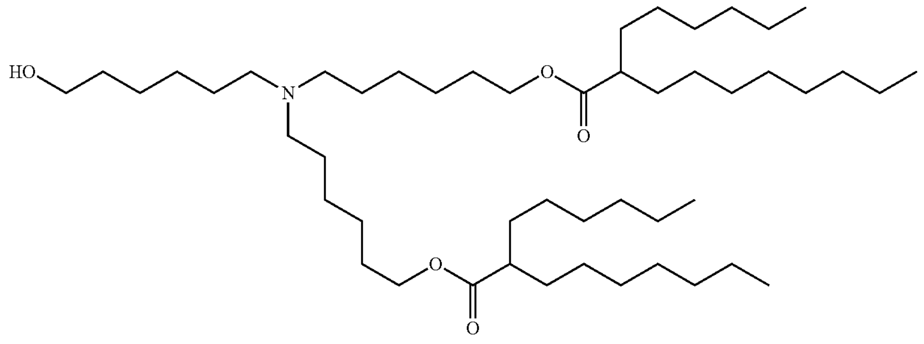 [SMILES: CCCCCCCCC(CCCCCC)C(=O)OCCCCCCN(CCCCCCO)CCCCCCOC(=O)C(CCCCCC)CCCCCCC] |
| III-9 | 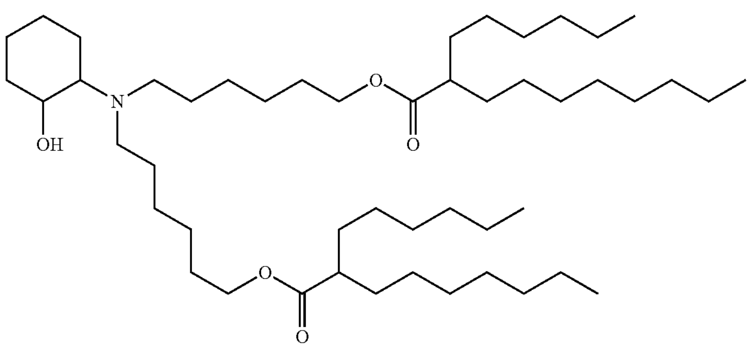 [SMILES: CCCCCCCCC(CCCCCC)C(=O)OCCCCCCN(CCCCCCOC(=O)C(CCCCCC)CCCCCCC)C1CCCCC1O] |

-continued
| No. | Structure |
| --- | --- |
| III-10 | 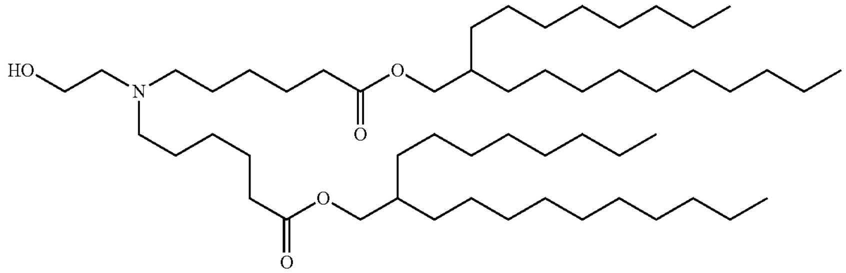 [SMILES: CCCCCCCCCCC(CCCCCCCC)COC(=O)CCCCCN(CCO)CCCCCC(=O)OCC(CCCCCCCC)CCCCCCCCCC] |
| III-11 | 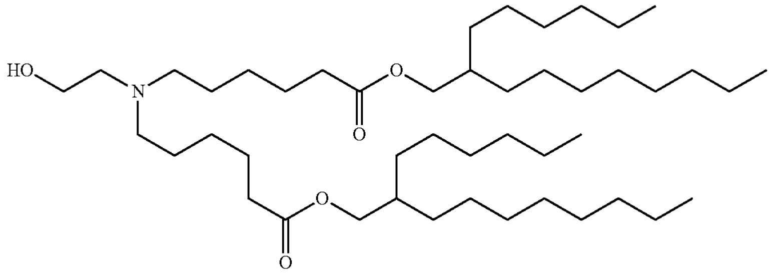 [SMILES: CCCCCCCCC(CCCCCC)COC(=O)CCCCCN(CCO)CCCCCC(=O)OCC(CCCCCC)CCCCCCCC] |
| III-12 | 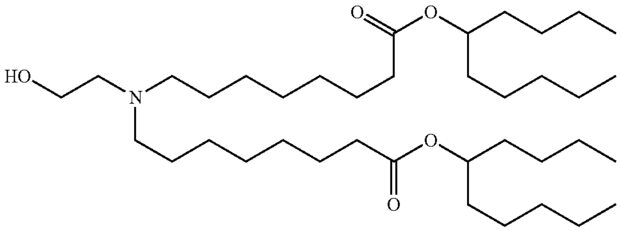 [SMILES: CCCCCC(CCCC)OC(=O)CCCCCCCN(CCO)CCCCCCCC(=O)OC(CCCC)CCCCC] |
| III-13 | 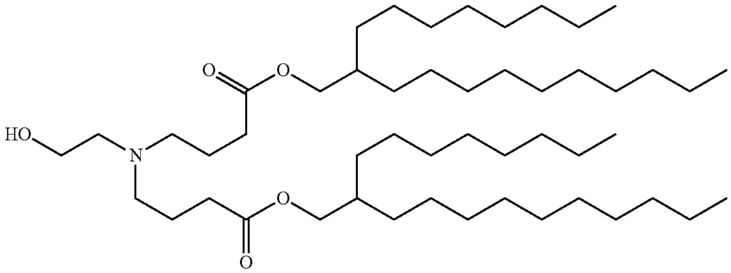 [SMILES: CCCCCCCCCCC(CCCCCCCC)COC(=O)CCCN(CCO)CCCC(=O)OCC(CCCCCCCC)CCCCCCCCCC] |
| III-14 | 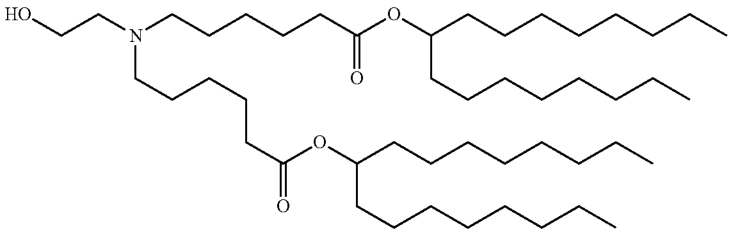 [SMILES: CCCCCCCCC(CCCCCCCC)OC(=O)CCCCCN(CCO)CCCCCC(=O)OC(CCCCCCCC)CCCCCCCC] |
| III-15 | 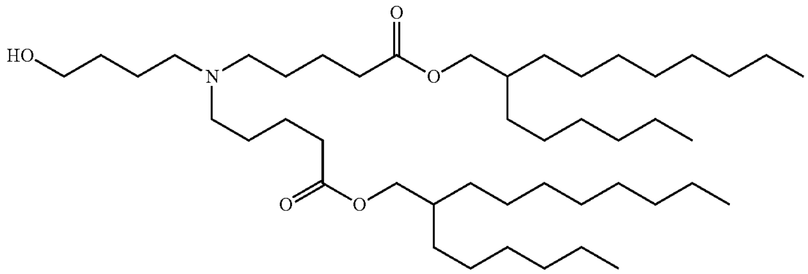 [SMILES: CCCCCCCCC(CCCCCC)COC(=O)CCCCN(CCCCO)CCCCC(=O)OCC(CCCCCC)CCCCCCCC] |

-continued
| No. | Structure |
|---|---|
| III-16 | 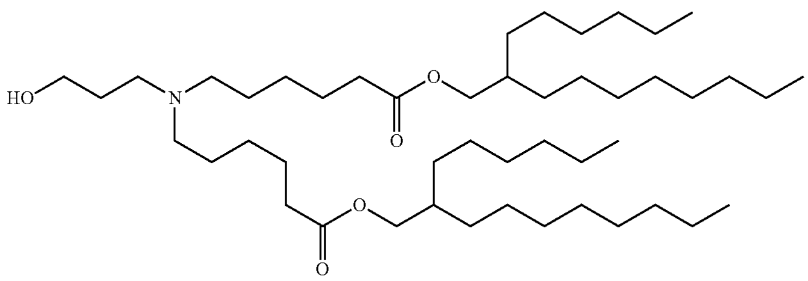 [SMILES: CCCCCCCCC(CCCCCC)COC(=O)CCCCCN(CCCO)CCCCCC(=O)OCC(CCCCCC)CCCCCCCC] |
| III-17 | 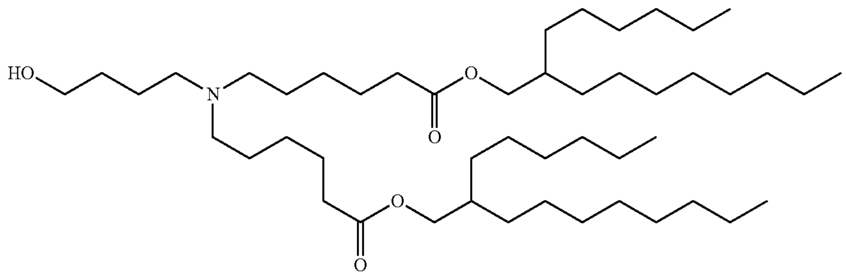 [SMILES: CCCCCCCCC(CCCCCC)COC(=O)CCCCCN(CCCCO)CCCCCC(=O)OCC(CCCCCC)CCCCCCCC] |
| III-18 | 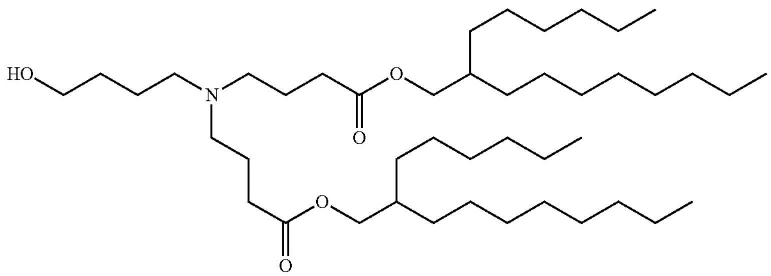 [SMILES: CCCCCCCCC(CCCCCC)COC(=O)CCCN(CCCCO)CCCC(=O)OCC(CCCCCC)CCCCCCCC] |
| III-19 | 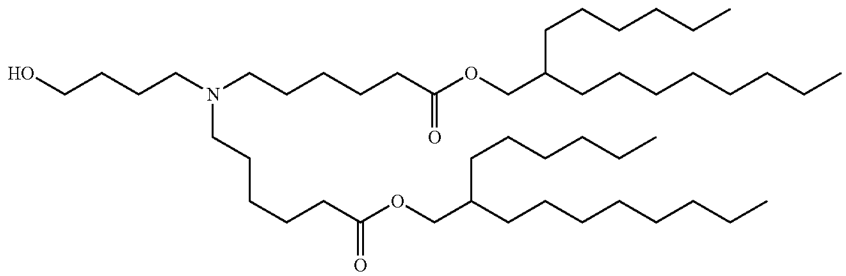 [SMILES: CCCCCCCCC(CCCCCC)COC(=O)CCCCCN(CCCCO)CCCCCC(=O)OCC(CCCCCC)CCCCCCCC] |
| III-20 | 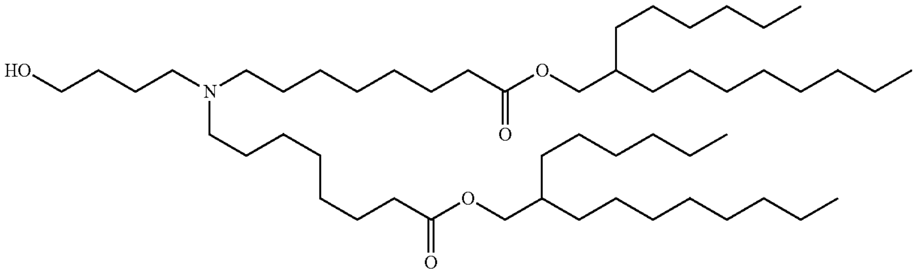 [SMILES: CCCCCCCCC(CCCCCC)COC(=O)CCCCCCCN(CCCCO)CCCCCCCC(=O)OCC(CCCCCC)CCCCCCCC] |

-continued
| No. | Structure |
|---|---|
| III-21 | 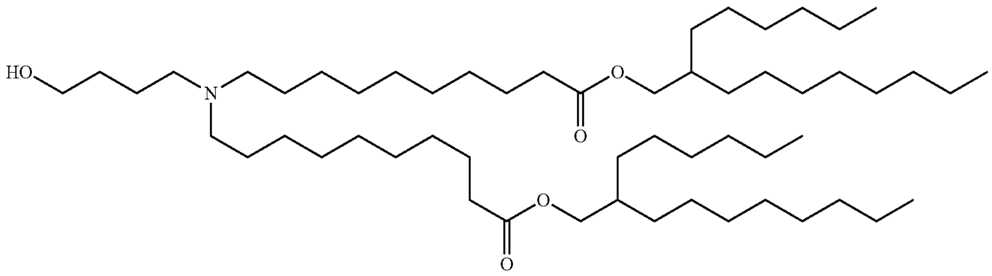 [SMILES: CCCCCCCCC(CCCCCC)COC(=O)CCCCCCCCCN(CCCCO)CCCCCCCCCC(=O)OCC(CCCCCC)CCCCCCCC] |
| III-22 | 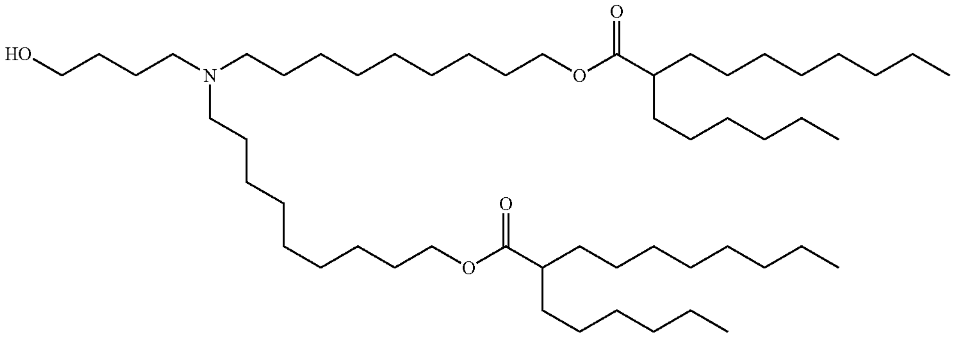 [SMILES: CCCCCCCCC(CCCCCC)C(=O)OCCCCCCCCCN(CCCCO)CCCCCCCCCOC(=O)C(CCCCCC)CCCCCCCC] |
| III-23 | 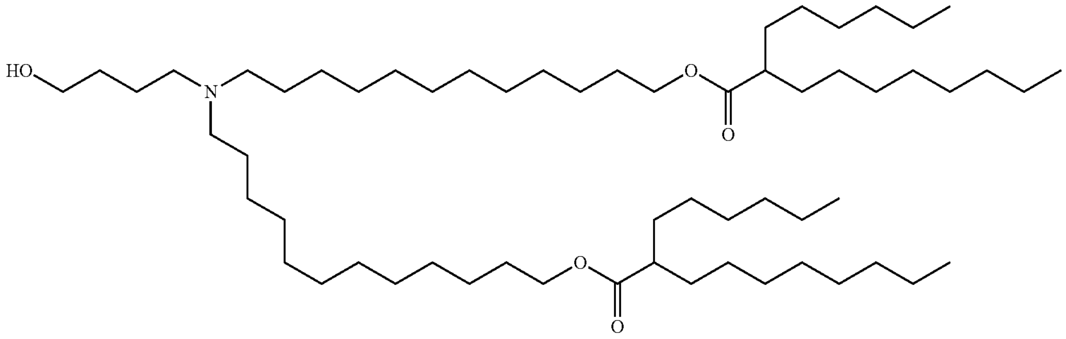 [SMILES: CCCCCCCCC(CCCCCC)C(=O)OCCCCCCCCCCCCN(CCCCO)CCCCCCCCCCCCOC(=O)C(CCCCCC)CCCCCCCC] |
| III-24 | 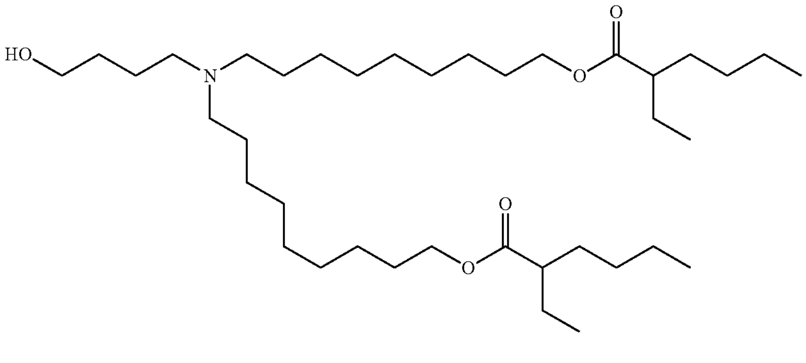 [SMILES: CCCCC(CC)C(=O)OCCCCCCCCCN(CCCCO)CCCCCCCCCOC(=O)C(CC)CCCC] |

-continued
| No. | Structure |
|---|---|
| III-25 | 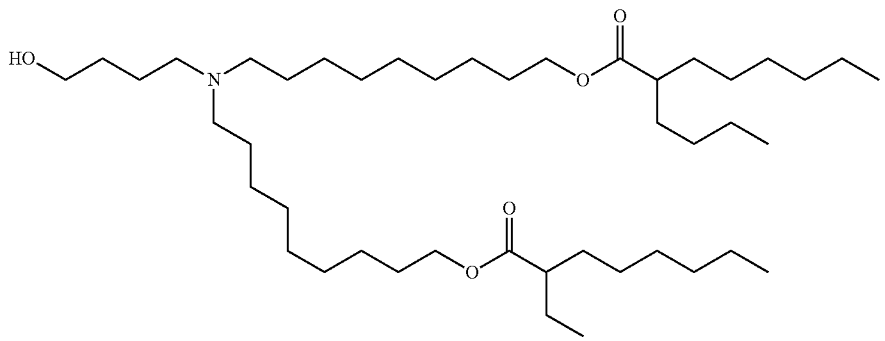 [SMILES: CCCCCCC(CC)C(=O)OCCCCCCCCCN(CCCCO)CCCCCCCCCOC(=O)C(CCCC)CCCCCC] |
| III-26 | 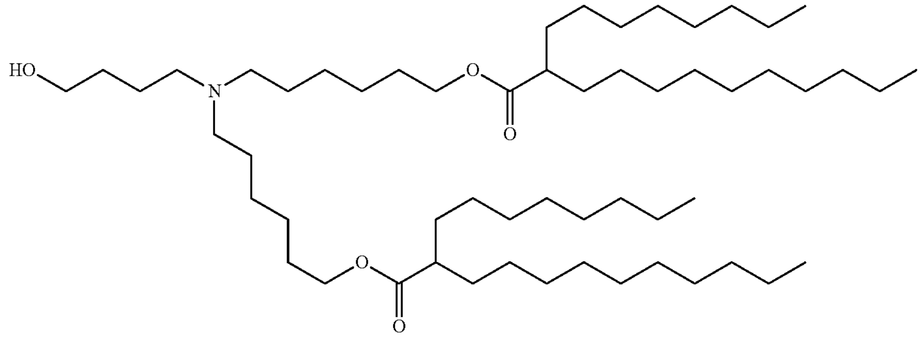 [SMILES: CCCCCCCCCCC(CCCCCCCC)C(=O)OCCCCCCN(CCCCO)CCCCCCOC(=O)C(CCCCCCCC)CCCCCCCCCC] |
| III-27 | 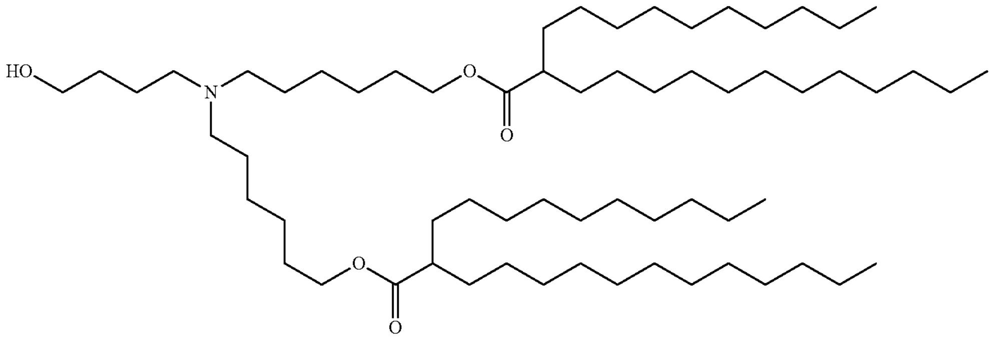 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| III-28 | 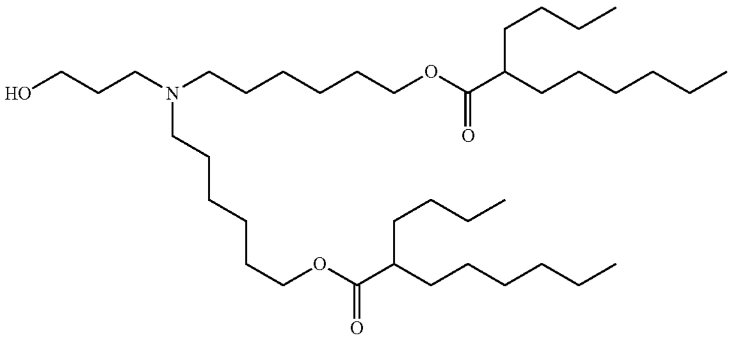 [SMILES: CCCCCCC(CCCC)C(=O)OCCCCCCN(CCCO)CCCCCCOC(=O)C(CCCC)CCCCCC] |

-continued
| No. | Structure |
|---|---|
| III-29 | 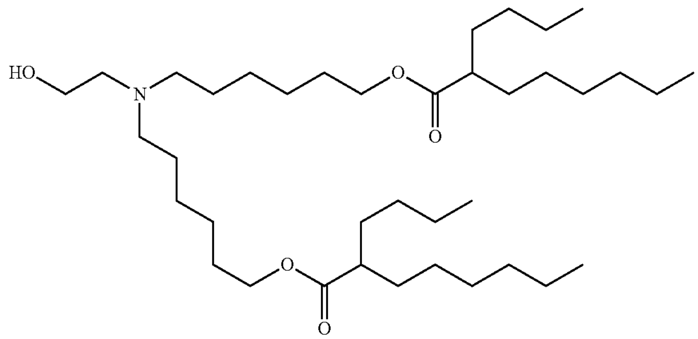 [SMILES: CCCCCCC(CCCC)C(=O)OCCCCCCN(CCO)CCCCCCOC(=O)C(CCCC)CCCCCC] |
| III-30 | 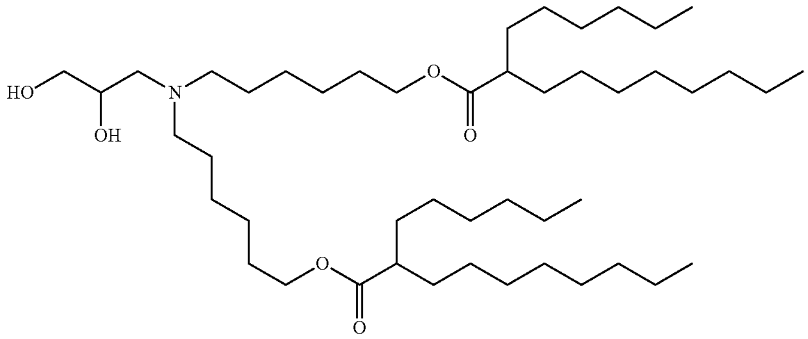 [SMILES: CCCCCCCCC(CCCCCC)C(=O)OCCCCCCN(CCCCCCOC(=O)C(CCCCCC)CCCCCCCC)CC(O)CO] |
| III-31 | 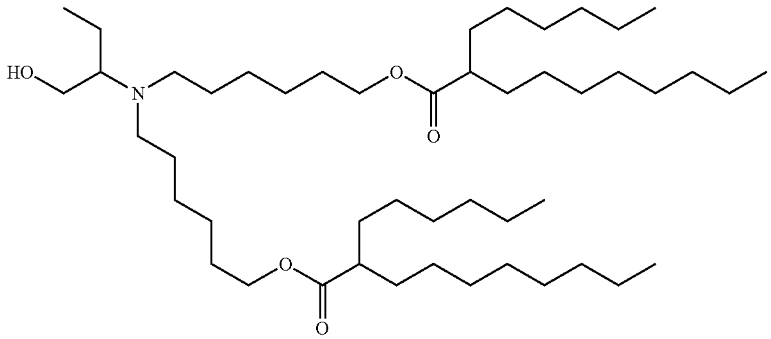 [SMILES: CCCCCCCCC(CCCCCC)C(=O)OCCCCCCN(CCCCCCOC(=O)C(CCCCCC)CCCCCCCC)C(CC)CO] |
| III-32 | 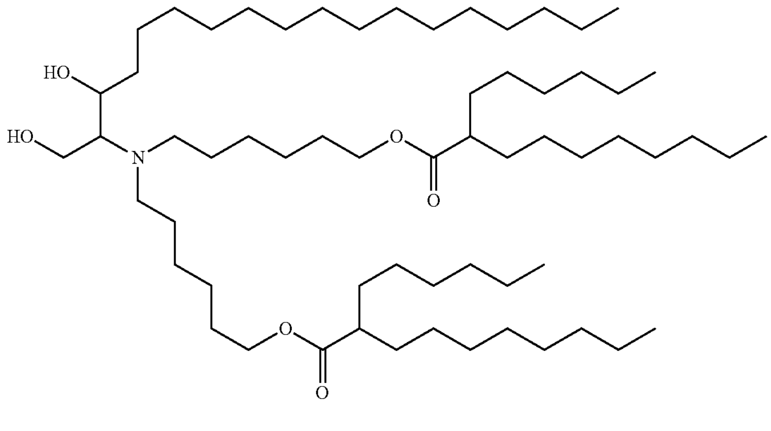 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |

-continued

| No. | Structure |
|---|---|
| III-33 | 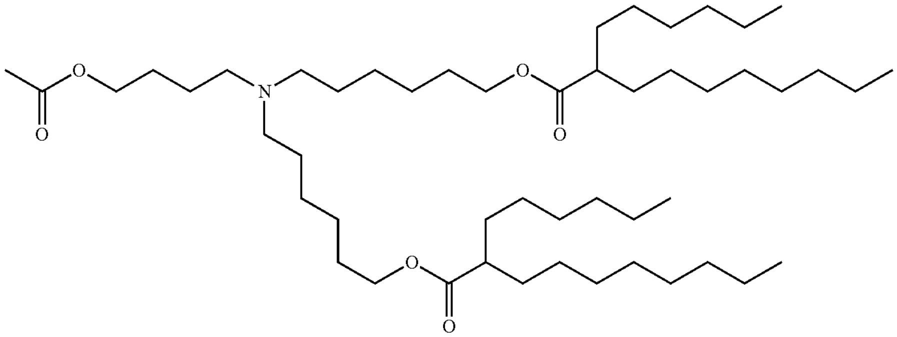 |
| III-34 | 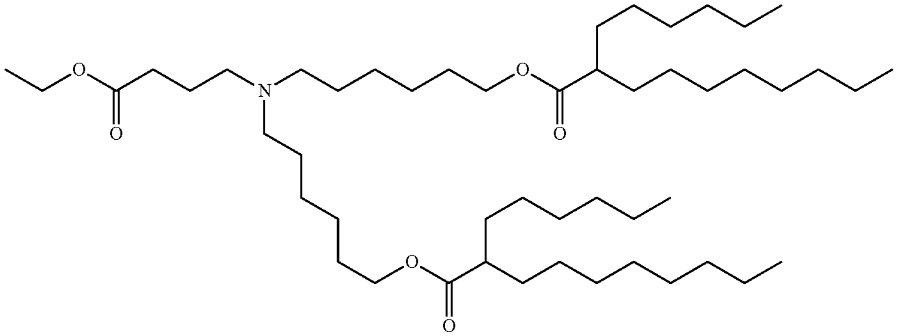 [SMILES: CCCCCCCCC(CCCCCC)C(=O)OCCCCCCN(CCCCCCOC(=O)C(CCCCCC)CCCCCCCC)CCCC(=O)OCC] |
| III-35 | 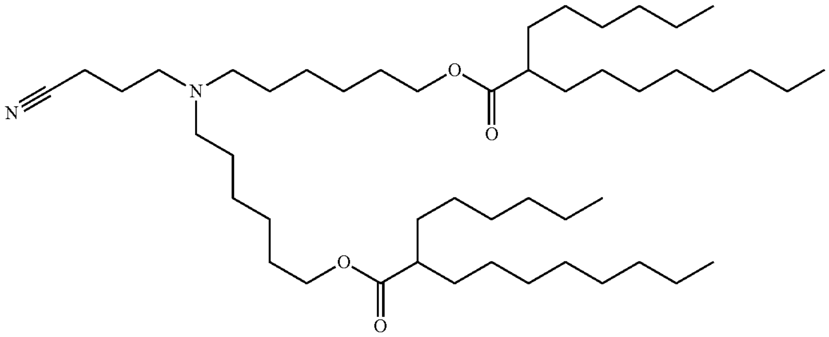 [SMILES: CCCCCCCCC(CCCCCC)C(=O)OCCCCCCN(CCCC#N)CCCCCCOC(=O)C(CCCCCC)CCCCCCCC] |
| III-36 | 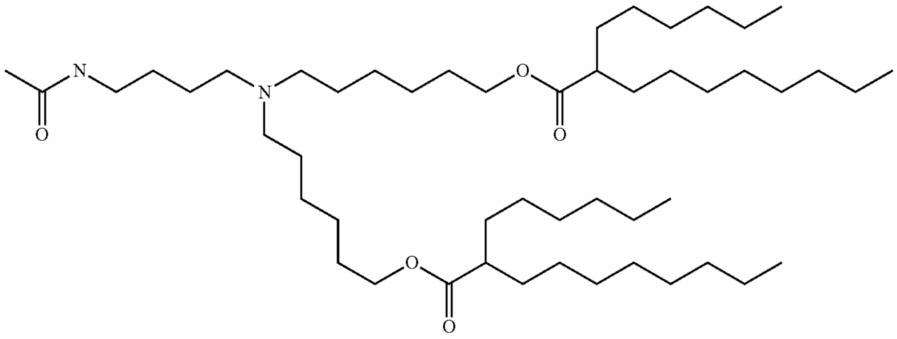 [SMILES: CCCCCCCCC(CCCCCC)C(=O)OCCCCCCN(CCCCCCOC(=O)C(CCCCCC)CCCCCCCC)CCCCNC(C)=O] |

In some embodiments, the LNP comprises a lipid of Formula (III), RNA, a neutral lipid, a steroid and a pegylated lipid. In some embodiments, the lipid of Formula (III) is compound 111-3. In some embodiments, the neutral lipid is DSPC. In some embodiments, the steroid is cholesterol. In some embodiments, the pegylated lipid is ALC-0159.

In some embodiments, the cationic lipid is present in the LNP in an amount from about 40 to about 50 mole percent. In one embodiment, the neutral lipid is present in the LNP in an amount from about 5 to about 15 mole percent. In one embodiment, the steroid is present in the LNP in an amount from about 35 to about 45 mole percent. In one embodiment, the pegylated lipid is present in the LNP in an amount from about 1 to about 10 mole percent.

In some embodiments, the LNP comprises compound 111-3 in an amount from about 40 to about 50 mole percent, DSPC in an amount from about 5 to about 15 mole percent, cholesterol in an amount from about 35 to about 45 mole percent, and ALC-0159 in an amount from about 1 to about 10 mole percent.

In some embodiments, the LNP comprises compound 111-3 in an amount of about 47.5 mole percent, DSPC in an amount of about 10 mole percent, cholesterol in an amount of about 40.7 mole percent, and ALC-0159 in an amount of about 1.8 mole percent.

In various different embodiments, the cationic lipid has one of the structures set forth in the table below.

| No. | Structure |
|---|---|
| A | 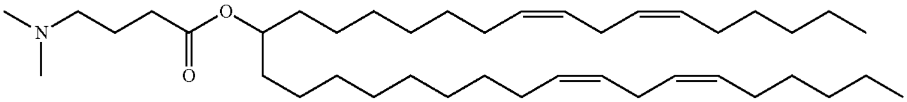 [SMILES: CCCCC/C=C\C/C=C\CCCCCCCCC(CCCCCC/C=C\C/C=C\CCCCC)OC(=O)CCCN(C)C] |
| B | 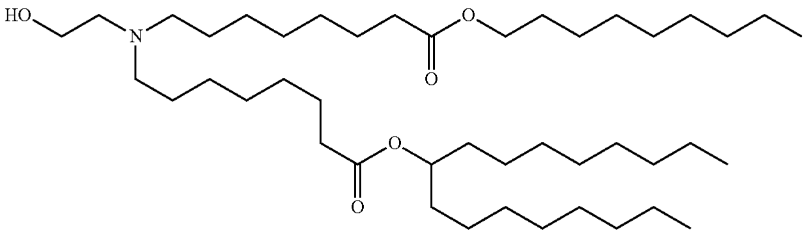 [SMILES: CCCCCCCCCOC(=O)CCCCCCCN(CCO)CCCCCCCC(=O)OC(CCCCCCCC)CCCCCCCC] |
| C | 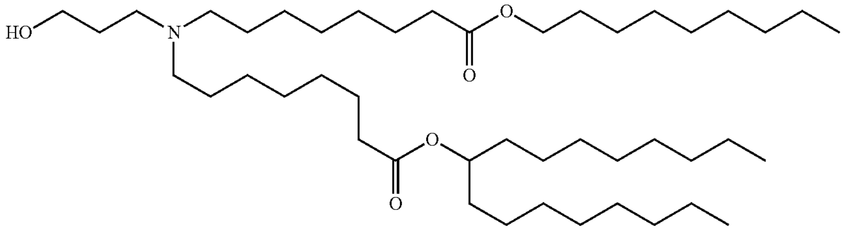 [SMILES: CCCCCCCCCOC(=O)CCCCCCCN(CCCO)CCCCCCCC(=O)OC(CCCCCCCC)CCCCCCCC] |
| D | 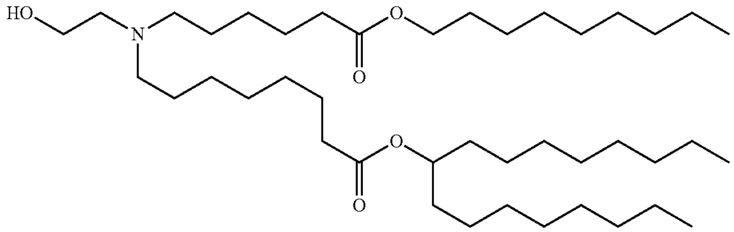 [SMILES: CCCCCCCCCOC(=O)CCCCCN(CCO)CCCCCCCC(=O)OC(CCCCCCCC)CCCCCCCC] |
| E | 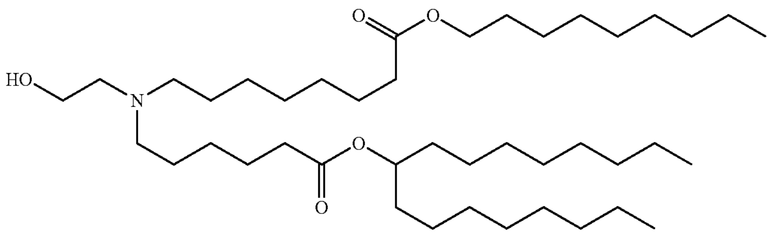 [SMILES: CCCCCCCCCOC(=O)CCCCCCCN(CCO)CCCCCC(=O)OC(CCCCCCCC)CCCCCCCC] |
| F | 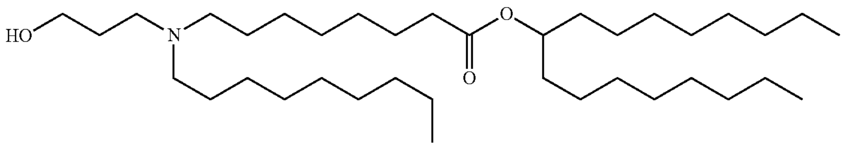 [SMILES: CCCCCCCCCN(CCCO)CCCCCCCC(=O)OC(CCCCCCCC)CCCCCCCC] |

In some embodiments, the LNP comprises a cationic lipid shown in the above table, e.g., a cationic lipid of Formula (B) or Formula (D), in particular a cationic lipid of Formula (D), RNA, a neutral lipid, a steroid and a pegylated lipid. In some embodiments, the neutral lipid is DSPC.

In some embodiments, the steroid is cholesterol. In some embodiments, the pegylated lipid is DMG-PEG 2000.

In one embodiment, the LNP comprises a cationic lipid that is an ionizable lipid-like material (lipidoid). In one embodiment, the cationic lipid has the following structure:

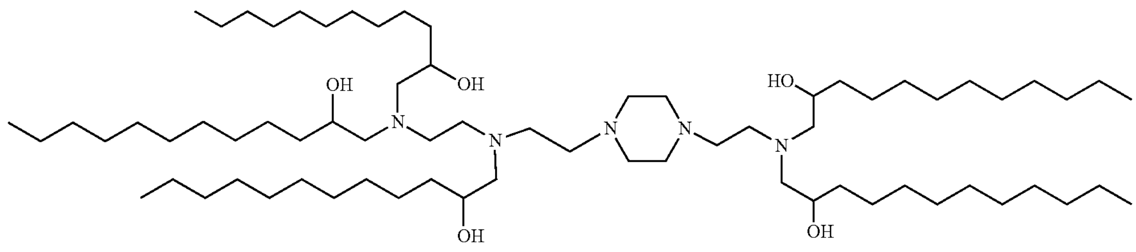 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]

The N/P value is preferably at least about 4. In some embodiments, the N/P value ranges from 4 to 20, 4 to 12, 4 to 10, 4 to 8, or 5 to 7. In one embodiment, the N/P value is about 6. LNP described herein may have an average diameter that in one embodiment ranges from about 30 nm to about 200 nm, or from about 60 nm to about 120 nm.

RNA Targeting

Some aspects of the disclosure involve the targeted delivery of the RNA disclosed herein (e.g., RNA encoding vaccine antigens and/or immunostimulants).

In one embodiment, the disclosure involves targeting lung. Targeting lung is in particular preferred if the RNA administered is RNA encoding vaccine antigen. RNA may be delivered to lung, for example, by administering the RNA which may be formulated as particles as described herein, e.g., lipid particles, by inhalation.

In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding vaccine antigen.

In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naïve lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2, or about 1.6:2 to about 1:2, or about 1.6:2 to about 1.1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0. Immunostimulants may be provided to a subject by administering to the subject RNA encoding an immunostimulant in a formulation for preferential delivery of RNA to liver or liver tissue. The delivery of RNA to such target organ or tissue is preferred, in particular, if it is desired to express large amounts of the immunostimulant and/or if systemic presence of the immunostimulant, in particular in significant amounts, is desired or required.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

For in vivo delivery of RNA to the liver, a drug delivery system may be used to transport the RNA into the liver by preventing its degradation. For example, polyplex nanomicelles consisting of a poly(ethylene glycol) (PEG)-coated surface and an mRNA-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

Examples of suitable immunostimulants for targeting liver are cytokines involved in T cell proliferation and/or maintenance. Examples of suitable cytokines include IL2 or IL7, fragments and variants thereof, and fusion proteins of these cytokines, fragments and variants, such as extended-PK cytokines.

In another embodiment, RNA encoding an immunostimulant may be administered in a formulation for preferential delivery of RNA to the lymphatic system, in particular secondary lymphoid organs, more specifically spleen. The delivery of an immunostimulant to such target tissue is preferred, in particular, if presence of the immunostimulant in this organ or tissue is desired (e.g., for inducing an immune response, in particular in case immunostimulants such as cytokines are required during T-cell priming or for activation of resident immune cells), while it is not desired that the immunostimulant is present systemically, in particular in significant amounts (e.g., because the immunostimulant has systemic toxicity).

Examples of suitable immunostimulants are cytokines involved in T cell priming. Examples of suitable cytokines include IL12, IL15, IFN-α, or IFN-β, fragments and variants thereof, and fusion proteins of these cytokines, fragments and variants, such as extended-PK cytokines.

Immunostimulants

In one embodiment, the RNA encoding vaccine antigen may be non-immunogenic. In this and other embodiments, the RNA encoding vaccine antigen may be co-administered with an immunostimulant or RNA encoding an immunostimulant. The methods and agents described herein are particularly effective if the immunostimulant is attached to a pharmacokinetic modifying group (hereafter referred to as "extended-pharmacokinetic (PK)" immunostimulant). The methods and agents described herein are particularly effective if the immunostimulant is administered in the form of RNA encoding an immunostimulant. In one embodiment, said RNA is targeted to the liver for systemic availability. Liver cells can be efficiently transfected and are able to produce large amounts of protein.

An "immunostimulant" is any substance that stimulates the immune system by inducing activation or increasing activity of any of the immune system's components, in particular immune effector cells. The immunostimulant may be pro-inflammatory.

According to one aspect, the immunostimulant is a cytokine or a variant thereof. Examples of cytokines include interferons, such as interferon-alpha (IFN-α) or interferon-gamma (IFN-γ), interleukins, such as IL2, IL7, IL12, IL15 and IL23, colony stimulating factors, such as M-CSF and GM-CSF, and tumor necrosis factor. According to another aspect, the immunostimulant includes an adjuvant-type immunostimulatory agent such as APC Toll-like Receptor agonists or costimulatory/cell adhesion membrane proteins. Examples of Toll-like Receptor agonists include costimulatory/adhesion proteins such as CD80, CD86, and ICAM-1.

Cytokines are a category of small proteins (~5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

According to the disclosure, a cytokine may be a naturally occurring cytokine or a functional fragment or variant thereof. A cytokine may be human cytokine and may be derived from any vertebrate, especially any mammal. One particularly preferred cytokine is interferon-α.

Interferons

Interferons (IFNs) are a group of signaling proteins made and released by host cells in response to the presence of several pathogens, such as viruses, bacteria, parasites, and also tumor cells. In a typical scenario, a virus-infected cell will release interferons causing nearby cells to heighten their anti-viral defenses.

Based on the type of receptor through which they signal, interferons are typically divided among three classes: type I interferon, type II interferon, and type III interferon.

All type I interferons bind to a specific cell surface receptor complex known as the IFN-α/β receptor (IFNAR) that consists of IFNAR1 and IFNAR2 chains.

The type I interferons present in humans are IFNα, IFNβ, IFNε, IFNκ and IFNω. In general, type I interferons are produced when the body recognizes a virus that has invaded it. They are produced by fibroblasts and monocytes. Once released, type I interferons bind to specific receptors on target cells, which leads to expression of proteins that will prevent the virus from producing and replicating its RNA and DNA.

The IFNα proteins are produced mainly by plasmacytoid dendritic cells (pDCs). They are mainly involved in innate immunity against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9.

The IFNβ proteins are produced in large quantities by fibroblasts. They have antiviral activity that is involved mainly in innate immune response. Two types of IFNβ have been described, IFNβ1 and IFNβ3. The natural and recombinant forms of IFNβ1 have antiviral, antibacterial, and anticancer properties.

Type II interferon (IFNγ in humans) is also known as immune interferon and is activated by IL12. Furthermore, type II interferons are released by cytotoxic T cells and T helper cells.

Type III interferons signal through a receptor complex consisting of IL10R2 (also called CRF2-4) and IFNLR1 (also called CRF2-12). Although discovered more recently than type I and type II IFNs, recent information demonstrates the importance of type III IFNs in some types of virus or fungal infections.

In general, type I and II interferons are responsible for regulating and activating the immune response.

According to the disclosure, a type I interferon is preferably IFNα or IFNβ, more preferably IFNα.

According to the disclosure, an interferon may be a naturally occurring interferon or a functional fragment or variant thereof. An interferon may be human interferon and may be derived from any vertebrate, especially any mammal.

Interleukins

Interleukins (ILs) are a group of cytokines (secreted proteins and signal molecules) that can be divided into four major groups based on distinguishing structural features. However, their amino acid sequence similarity is rather weak (typically 15-25% identity). The human genome encodes more than 50 interleukins and related proteins.

According to the disclosure, an interleukin may be a naturally occurring interleukin or a functional fragment or variant thereof. An interleukin may be human interleukin and may be derived from any vertebrate, especially any mammal.

Extended-PK Group

Immunostimulant polypeptides described herein can be prepared as fusion or chimeric polypeptides that include an immunostimulant portion and a heterologous polypeptide (i.e., a polypeptide that is not an immunostimulant). The immunostimulant may be fused to an extended-PK group, which increases circulation half-life. Non-limiting examples of extended-PK groups are described infra. It should be understood that other PK groups that increase the circulation half-life of immunostimulants such as cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK" immunostimulant refers to an immunostimulant moiety in combination with an extended-PK group. In one embodiment, the extended-PK immunostimulant is a fusion protein in which an immunostimulant moiety is linked or fused to an extended-PK group.

In certain embodiments, the serum half-life of an extended-PK immunostimulant is increased relative to the immunostimulant alone (i.e., the immunostimulant not fused to an extended-PK group). In certain embodiments, the serum half-life of the extended-PK immunostimulant is at least 20, 40, 60, 80, 100, 120, 150, 180, 200, 400, 600, 800, or 1000% longer relative to the serum half-life of the immunostimulant alone. In certain embodiments, the serum half-life of the extended-PK immunostimulant is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the immunostimulant alone. In certain embodiments, the serum half-life of the extended-PK immunostimulant is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

As used herein, "half-life" refers to the time taken for the serum or plasma concentration of a compound such as a peptide or protein to reduce by 50%, in vivo, for example due to degradation and/or clearance or sequestration by natural mechanisms. An extended-PK immunostimulant suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular an immunostimulant. The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver, that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In one embodiment, the different therapeutic proteins are both cytokines.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term "Fc region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, US2014/0220017, and US2017/0145062, which are herein incorporated by reference in their entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK immunostimulant, suitable for use according to the disclosure, can employ one or more peptide linkers. As used herein, the term "peptide linker" refers to a peptide or polypeptide sequence which connects two or more domains (e.g., the extended-PK moiety and an immunostimulant moiety) in a linear amino acid sequence of a polypeptide chain. For example, peptide linkers may be used to connect an immunostimulant moiety to a HSA domain.

Linkers suitable for fusing the extended-PK group to e.g. an immunostimulant are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In addition to, or in place of, the heterologous polypeptides described above, an immunostimulant polypeptide described herein can contain sequences encoding a "marker" or "reporter". Examples of marker or reporter genes include β-lactamase, chloramphenicol acetyltransferase (CAT), adenosine deaminase (ADA), aminoglycoside phosphotransferase, dihydrofolate reductase (DHFR), hygromycin-B-hosphotransferase (HPH), thymidine kinase (TK), β-galactosidase, and xanthine guanine phosphoribosyltransferase (XGPRT).

Pharmaceutical Compositions

The agents described herein may be administered in pharmaceutical compositions or medicaments and may be administered in the form of any suitable pharmaceutical composition.

In one embodiment, the pharmaceutical composition described herein is an immunogenic composition for inducing an immune response against coronavirus in a subject. For example, in one embodiment, the immunogenic composition is a vaccine.

In one embodiment of all aspects of the invention, the components described herein such as RNA encoding a vaccine antigen may be administered in a pharmaceutical composition which may comprise a pharmaceutically acceptable carrier and may optionally comprise one or more adjuvants, stabilizers etc. In one embodiment, the pharmaceutical composition is for therapeutic or prophylactic treatments, e.g., for use in treating or preventing a coronavirus infection.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation". The term "pharmaceutically acceptable" refers to the non-toxicity of a material which does not interact with the action of the active component of the pharmaceutical composition. The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal. The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical composition is formulated for intramuscular administration. In another embodiment, the pharmaceutical composition is formulated for systemic administration, e.g., for intravenous administration.

The term "co-administering" as used herein means a process whereby different compounds or compositions (e.g., RNA encoding an antigen and RNA encoding an immunostimulant) are administered to the same patient. The different compounds or compositions may be administered simultaneously, at essentially the same time, or sequentially.

The pharmaceutical compositions and products described herein may be provided as a frozen concentrate for solution for injection, e.g., at a concentration of 0.50 mg/mL. In one embodiment, for preparation of solution for injection, a drug product is thawed and diluted with isotonic sodium chloride solution (e.g., 0.9% NaCl, saline), e.g., by a one-step dilution process. In some embodiments, bacteriostatic sodium chloride solution (e.g., 0.9% NaCl, saline) cannot be used as a diluent. In some embodiments, a diluted drug product is an off-white suspension. The concentration of the final solution for injection varies depending on the respective dose level to be administered.

In one embodiment, administration is performed within 6 h after begin of preparation due to the risk of microbial contamination and considering the multiple-dose approach of the preparation process. In one embodiment, in this period of 6 h, two conditions are allowed: room temperature for preparation, handling and transfer as well as 2 to 8° C. for storage. Compositions described herein may be shipped and/or stored under temperature-controlled conditions, e.g., temperature conditions of about 4-5° C. or below, about −20° C. or below, −70° C.±10° C. (e.g., −80° C. to −60° C.), e.g., utilizing a cooling system (e.g., that may be or include dry ice) to maintain the desired temperature. In one embodiment, compositions described herein are shipped in temperature-controlled thermal shippers. Such shippers may contain a GPS-enabled thermal sensor to track the location and temperature of each shipment. The compositions can be stored by refilling with, e.g., dry ice.

Treatments

The present invention provides methods and agents for inducing an adaptive immune response against coronavirus in a subject comprising administering an effective amount of a composition comprising RNA encoding a coronavirus vaccine antigen described herein.

In one embodiment, the methods and agents described herein provide immunity in a subject to coronavirus, coronavirus infection, or to a disease or disorder associated with coronavirus. The present invention thus provides methods and agents for treating or preventing the infection, disease, or disorder associated with coronavirus.

In one embodiment, the methods and agents described herein are administered to a subject having an infection, disease, or disorder associated with coronavirus. In one embodiment, the methods and agents described herein are administered to a subject at risk for developing the infection, disease, or disorder associated with coronavirus. For example, the methods and agents described herein may be administered to a subject who is at risk for being in contact with coronavirus. In one embodiment, the methods and agents described herein are administered to a subject who lives in, traveled to, or is expected to travel to a geographic region in which coronavirus is prevalent. In one embodiment, the methods and agents described herein are administered to a subject who is in contact with or expected to be in contact with another person who lives in, traveled to, or is expected to travel to a geographic region in which coronavirus is prevalent. In one embodiment, the methods and agents described herein are administered to a subject who has knowingly been exposed to coronavirus through their occupation, or other contact. In one embodiment, a coronavirus is SARS-CoV-2. In some embodiments, methods and agents described herein are administered to a subject with evidence of prior exposure to and/or infection with SARS-CoV-2 and/or an antigen or epitope thereof or cross-reactive therewith. For example, in some embodiments, methods and agents described herein are administered to a subject in whom antibodies, B cells, and/or T cells reactive with one or more epitopes of a SARS-CoV-2 spike protein are detectable and/or have been detected.

For a composition to be useful as a vaccine, the composition must induce an immune response against the coronavirus antigen in a cell, tissue or subject (e.g., a human). In some embodiments, the composition induces an immune response against the coronavirus antigen in a cell, tissue or subject (e.g., a human). In some instances, the vaccine induces a protective immune response in a mammal. The therapeutic compounds or compositions of the invention may be administered prophylactically (i.e., to prevent a disease or disorder) or therapeutically (i.e., to treat a disease or disorder) to subjects suffering from, or at risk of (or susceptible to) developing a disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term “prevent” encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The present disclosure reports various characterization of provided compositions (see, e.g., Example 2; see also Examples thereafter) and furthermore establishes parameters for vaccines effective in humans.

In some embodiments, administration of an immunogenic composition or vaccine of the present invention may be performed by single administration or boosted by multiple administrations.

In some embodiments, an amount the RNA described herein from 0.1 μg to 300 μg, 0.5 μg to 200 μg, or 1 μg to 100 μg, such as about 1 μg, about 3 μg, about 10 μg, about 30 μg, about 50 μg, or about 100 μg may be administered per dose. In one embodiment, the invention envisions administration of a single dose. In one embodiment, the invention envisions administration of a priming dose followed by one or more booster doses. The booster dose or the first booster dose may be administered 7 to 28 days or 14 to 24 days following administration of the priming dose.

In some embodiments, an amount of the RNA described herein of 60 μg or lower, 50 μg or lower, 40 μg or lower, 30 μg or lower, 20 μg or lower, 10 μg or lower, 5 μg or lower, 2.5 μg or lower, or 1 μg or lower may be administered per dose.

In some embodiments, an amount of the RNA described herein of at least 0.25 μg, at least 0.5 μg, at least 1 μg, at least 2 μg, at least 3 μg, at least 4 μg, at least 5 μg, at least 10 μg, at least 20 μg, at least 30 μg, or at least 40 μg may be administered per dose.

In some embodiments, an amount of the RNA described herein of 0.25 μg to 60 μg, 0.5 μg to 55 μg, 1 μg to 50 μg, 5 μg to 40 μg, or 10 μg to 30 μg may be administered per dose.

In one embodiment, an amount of the RNA described herein of about 30 μg is administered per dose. In one embodiment, at least two of such doses are administered. For example, a second dose may be administered about 21 days following administration of the first dose. In some embodiments, the efficacy of the RNA vaccine described herein (e.g., administered in two doses, wherein a second dose may be administered about 21 days following administration of the first dose, and administered, for example, in an amount of about 30 μg per dose) is at least 70%, at least 80%, at least 90, or at least 95% beginning 7 days after administration of the second dose (e.g., beginning 28 days after administration of the first dose if a second dose is administered 21 days following administration of the first dose). In some embodiments, such efficacy is observed in populations of age of at least 50, at least 55, at least 60, at least 65, at least 70, or older. In some embodiments, the efficacy of the RNA vaccine described herein (e.g., administered in two doses, wherein a second dose may be administered about 21 days following administration of the first dose, and administered, for example, in an amount of about 30 μg per dose) beginning 7 days after administration of the second dose (e.g., beginning 28 days after administration of the first dose if a second dose is administered 21 days following administration of the first dose) in populations of age of at least 65, such as 65 to 80, 65 to 75, or 65 to 70, is at least 90%, at least 91%, at least 92%, at least 93%, at least 94%, or at least 95%. Such efficacy may be observed over time periods of up to 1 month, 2 months, 3 months, 6 months or even longer.

In one embodiment, vaccine efficacy is defined as the percent reduction in the number of subjects with evidence of infection (vaccinated subjects vs. non-vaccinated subjects).

In one embodiment, efficacy is assessed through surveillance for potential cases of COVID-19. If, at any time, a patient develops acute respiratory illness, for the purposes herein, the patient can be considered to potentially have COVID-19 illness. The assessments can include a nasal (midturbinate) swab, which may be tested using a reverse transcription-polymerase chain reaction (RT-PCR) test to detect SARS-CoV-2. In addition, clinical information and results from local standard-of-care tests can be assessed.

In some embodiments, efficacy assessments may utilize a definition of SARS-CoV-2-related cases wherein:

Confirmed COVID-19: presence of at least 1 of the following symptoms and SARS-CoV-2 NAAT (nucleic acid amplification-based test) positive during, or within 4 days before or after, the symptomatic period: fever; new or increased cough; new or increased shortness of breath; chills; new or increased muscle pain; new loss of taste or smell; sore throat; diarrhea; vomiting.

Alternatively or additionally, in some embodiments, efficacy assessments may utilize a definition of SARS-CoV-2-related cases wherein one or more of the following additional symptoms defined by the CDC can be considered: fatigue; headache; nasal congestion or runny nose; nausea.

In some embodiments, efficacy assessments may utilize a definition of SARS-CoV-2-related severe cases Confirmed severe COVID-19: confirmed COVID-19 and presence of at least 1 of the following: clinical signs at rest indicative of severe systemic illness (e.g., RR 30 breaths per minute, HR≥125 beats per minute, $SpO_2 \leq 93\%$ on room air at sea level, or $PaO_2/FiO_2 < 300$ mm Hg); respiratory failure (which can be defined as needing high-flow oxygen, noninvasive ventilation, mechanical ventilation, or ECMO); evidence of shock (e.g., SBP<90 mm Hg, DBP<60 mm Hg, or requiring vasopressors); significant acute renal, hepatic, or neurologic dysfunction; admission to an ICU; death.

Alternatively or additionally, in some embodiments a serological definition can be used for patients without clinical presentation of COVID-19: e.g., confirmed seroconversion to SARS-CoV-2 without confirmed COVID-19: e.g., positive N-binding antibody result in a patient with a prior negative N-binding antibody result.

In some embodiments, any or all of the following assays can be performed on serum samples: SARS-CoV-2 neutralization assay; S1-binding IgG level assay; RBD-binding IgG level assay; N-binding antibody assay.

In one embodiment, methods and agents described herein are administered to a paediatric population. In various embodiments, the paediatric population comprises or consists of subjects under 18 years, e.g., 5 to less than 18 years of age, 12 to less than 18 years of age, 16 to less than 18 years of age, 12 to less than 16 years of age, or 5 to less than 12 years of age. In various embodiments, the paediatric population comprises or consists of subjects under 5 years, e.g., 2 to less than 5 years of age, 12 to less than 24 months of age, 7 to less than 12 months of age, or less than 6 months of age.

In one embodiment, the paediatric population comprises or consists of subjects 12 to less than 18 years of age including subjects 16 to less than 18 years of age and/or subjects 12 to less than 16 years of age. In this embodiment, treatments may comprise 2 vaccinations 21 days apart, wherein, in one embodiment, the vaccine is administered in an amount of 30 μg RNA per dose, e.g., by intramuscular administration.

In one embodiment, the paediatric population comprises or consists of subjects 5 to less than 18 years of age including subjects 12 to less than 18 years of age and/or subjects 5 to less than 12 years of age. In this embodiment, treatments may comprise 2 vaccinations 21 days apart, wherein, in various embodiments, the vaccine is administered in an amount of 10 μg, 20 μg, or 30 μg RNA per dose, e.g., by intramuscular administration.

In one embodiment, the paediatric population comprises or consists of subjects less than 5 years of age including subjects 2 to less than 5 years of age, subjects 12 to less than 24 months of age, subjects 7 to less than 12 months of age, subjects 6 to less than 12 months of age and/or subjects less than 6 months of age. In this embodiment, treatments may comprise 2 vaccinations, e.g., 21 to 42 days apart, e.g., 21 days apart, wherein, in various embodiments, the vaccine is administered in an amount of 10 μg, 20 μg, or 30 μg RNA per dose, e.g., by intramuscular administration.

In some embodiments, efficacy for mRNA compositions described in pediatric populations (e.g., described herein) may be assessed by various metrics described herein (including, e.g., but not limited to COVID-19 incidence per 1000 person-years in subjects with no serological or virological evidence of past SARS-CoV-2 infection; geometric mean ratio (GMR) of SARS CoV-2 neutralizing titers measured, e.g., 7 days after a second dose; etc.) In some embodiments, pediatric populations described herein (e.g., from 12 to less than 16 years of age) may be monitored for occurrence of multisystem inflammatory syndrome (MIS) (e.g., inflammation in different body parts such as, e.g., heart, lung, kidneys, brain, skin, eyes, and/or gastrointestinal organs), after administration of an RNA composition (e.g., mRNA) described herein. Exemplary symptoms of MIS in children may include, but are not limited to fever, abdominal pain, vomiting, diarrhea, neck pain, rash, bloodshot eyes, feeling extra tried, and combinations thereof.

In one embodiment, RNA administered as described above is nucleoside modified messenger RNA (modRNA) described herein as BNT162b1 (RBP020.3), BNT162b2 (RBP020.1 or RBP020.2). In one embodiment, RNA administered as described above is nucleoside modified messenger RNA (modRNA) described herein as RBP020.2.

In one embodiment, RNA administered as described above is nucleoside modified messenger RNA (modRNA) and (i) comprises the nucleotide sequence of SEQ ID NO: 21, a nucleotide sequence having at least 99%, 98%, 97%, 96%, 95%, 90%, 85%, or 80% identity to the nucleotide sequence of SEQ ID NO: 21, and/or (ii) encodes an amino acid sequence comprising the amino acid sequence of SEQ ID NO: 5, or an amino acid sequence having at least 99%, 98%, 97%, 96%, 95%, 90%, 85%, or 80% identity to the amino acid sequence of SEQ ID NO: 5. In one embodiment, RNA administered as described above is nucleoside modified messenger RNA (modRNA) and (i) comprises the nucleotide sequence of SEQ ID NO: 21; and/or (ii) encodes an amino acid sequence comprising the amino acid sequence of SEQ ID NO: 5.

In one embodiment, RNA administered as described above is nucleoside modified messenger RNA (modRNA) and (i) comprises the nucleotide sequence of SEQ ID NO: 19, or 20, a nucleotide sequence having at least 99%, 98%, 97%, 96%, 95%, 90%, 85%, or 80% identity to the nucleotide sequence of SEQ ID NO: 19, or 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA administered as described above is nucleoside modified messenger RNA (modRNA) and (i) comprises the nucleotide sequence of SEQ ID NO: 19, or 20; and/or (ii) encodes an amino acid sequence comprising the amino acid sequence of SEQ ID NO: 7.

In one embodiment, RNA administered as described above is nucleoside modified messenger RNA (modRNA) and (i) comprises the nucleotide sequence of SEQ ID NO: 20, a nucleotide sequence having at least 99%, 98%, 97%, 96%, 95%, 90%, 85%, or 80% identity to the nucleotide sequence of SEQ ID NO: 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA administered as described above is nucleoside modified messenger RNA (modRNA) and (i) comprises the nucleotide sequence of SEQ ID NO: 20; and/or (ii) encodes an amino acid sequence comprising the amino acid sequence of SEQ ID NO: 7.

In one embodiment, RNA administered is nucleoside modified messenger RNA (modRNA), (i) comprises the nucleotide sequence of SEQ ID NO: 20; and/or (ii) encodes an amino acid sequence comprising the amino acid sequence of SEQ ID NO: 7, and is administered in an amount of about 30 μg per dose. In one embodiment, at least two of such doses are administered. For example, a second dose may be administered about 21 days following administration of the first dose.

In some embodiments, populations to be treated with RNA described herein comprise, essentially consist of, or consist of subjects of age of at least 50, at least 55, at least 60, or at least 65. In some embodiments, populations to be treated with RNA described herein comprise, essentially consist of, or consist of subjects of age of between 55 to 90, 60 to 85, or 65 to 85.

In some embodiments, the period of time between the doses administered is at least 7 days, at least 14 days, or at least 21 days. In some embodiments, the period of time between the doses administered is between 7 days and 28 days such as between 14 days and 23 days. In some embodiments, no more than 5 doses, no more than 4 doses, or no more than 3 doses of the RNA described herein may be administered to a subject.

In some embodiments, the methods and agents described herein are administered (in a regimen, e.g., at a dose, frequency of doses and/or number of doses) such that adverse events (AE), i.e., any unwanted medical occurrence in a patient, e.g., any unfavourable and unintended sign, symptom, or disease associated with the use of a medicinal product, whether or not related to the medicinal product, are mild or moderate in intensity. In some embodiments, the methods and agents described herein are administered such that adverse events (AE) can be managed with interventions such as treatment with, e.g., paracetamol or other drugs that provide analgesic, antipyretic (fever-reducing) and/or anti-inflammatory effects, e.g., nonsteroidal anti-inflammatory drugs (NSAIDs), e.g., aspirin, ibuprofen, and naproxen. Paracetamol or "acetaminophen" which is not classified as a NSAID exerts weak anti-inflammatory effects and can be administered as analgesic according to the invention. In some embodiments, the methods and agents described herein provide a neutralizing effect in a subject to coronavirus, coronavirus infection, or to a disease or disorder associated with coronavirus.

In some embodiments, the methods and agents described herein following administration to a subject induce an immune response that blocks or neutralizes coronavirus in the subject. In some embodiments, the methods and agents described herein following administration to a subject induce the generation of antibodies such as IgG antibodies that block or neutralize coronavirus in the subject. In some embodiments, the methods and agents described herein following administration to a subject induce an immune response that blocks or neutralizes coronavirus S protein binding to ACE2 in the subject. In some embodiments, the methods and agents described herein following administration to a subject induce the generation of antibodies that block or neutralize coronavirus S protein binding to ACE2 in the subject.

In some embodiments, the methods and agents described herein following administration to a subject induce geometric mean concentrations (GMCs) of RBD domain-binding antibodies such as IgG antibodies of at least 500 U/ml, 1000 U/ml, 2000 U/ml, 3000 U/ml, 4000 U/ml, 5000 U/ml, 10000 U/ml, 15000 U/ml, 20000 U/ml, 25000 U/ml, 30000 U/ml or even higher.

In some embodiments, the elevated GMCs of RBD domain-binding antibodies persist for at least 14 days, 21 days, 28 days, 1 month, 3 months, 6 months, 12 months or even longer.

In some embodiments, the methods and agents described herein following administration to a subject induce geometric mean titers (GMTs) of neutralizing antibodies such as IgG antibodies of at least 100 U/ml, 200 U/ml, 300 U/ml, 400 U/ml, 500 U/ml, 1000 U/ml, 1500 U/ml, or even higher. In some embodiments, the elevated GMTs of neutralizing antibodies persist for at least 14 days, 21 days, 28 days, 1 month, 3 months, 6 months, 12 months or even longer.

As used herein, the term "neutralization" refers to an event in which binding agents such as antibodies bind to a biological active site of a virus such as a receptor binding protein, thereby inhibiting the viral infection of cells. As used herein, the term "neutralization" with respect to coronavirus, in particular coronavirus S protein, refers to an event in which binding agents such as antibodies bind to the RBD domain of the S protein, thereby inhibiting the viral infection of cells. In particular, the term "neutralization" refers to an event in which binding agents eliminate or significantly reduce virulence (e.g. ability of infecting cells) of viruses of interest.

The type of immune response generated in response to an antigenic challenge can generally be distinguished by the subset of T helper (Th) cells involved in the response. Immune responses can be broadly divided into two types: Th1 and Th2. Th1 immune activation is optimized for intracellular infections such as viruses, whereas Th2 immune responses are optimized for humoral (antibody) responses. Th1 cells produce interleukin 2 (IL-2), tumor necrosis factor (TNFα) and interferon gamma (IFNγ). Th2 cells produce IL-4, IL-5, IL-6, IL-9, IL-10 and IL-13. Th1 immune activation is the most highly desired in many clinical situations. Vaccine compositions specialized in eliciting Th2 or humoral immune responses are generally not effective against most viral diseases.

In some embodiments, the methods and agents described herein following administration to a subject induce or promote a Th1-mediated immune response in the subject. In some embodiments, the methods and agents described herein following administration to a subject induce or promote a cytokine profile that is typical for a Th1-mediated immune response in the subject. In some embodiments, the methods and agents described herein following administration to a subject induce or promote the production of interleukin 2 (IL-2), tumor necrosis factor (TNFα) and/or interferon gamma (IFNγ) in the subject. In some embodiments, the methods and agents described herein following administration to a subject induce or promote the production of interleukin 2 (IL-2) and interferon gamma (IFNγ) in the subject. In some embodiments, the methods and agents described herein following administration to a subject do not induce or promote a Th2-mediated immune response in the subject, or induce or promote a Th2-mediated immune response in the subject to a significant lower extent compared to the induction or promotion of a Th1-mediated immune response. In some embodiments, the methods and agents described herein following administration to a subject do not induce or promote a cytokine profile that is typical for a Th2-mediated immune response in the subject, or induce or promote a cytokine profile that is typical for a Th2-mediated immune response in the subject to a significant lower extent compared to the induction or promotion of a cytokine profile that is typical for a Th1-mediated immune response. In some embodiments, the methods and agents described herein following administration to a subject do not induce or promote the production of IL-4, IL-5, IL-6, IL-9, IL-10 and/or IL-13, or induce or promote the production of IL-4, IL-5, IL-6, IL-9, IL-10 and/or IL-13 in the subject to a significant lower extent compared to the induction or promotion of interleukin 2 (IL-2), tumor necrosis factor (TNFα) and/or interferon gamma (IFNγ) in the subject. In some embodiments, the methods and agents described herein following administration to a subject do not induce or promote the production of IL-4, or induce or promote the production of IL-4 in the subject to a significant lower extent compared to the induction or promotion of interleukin 2 (IL-2) and interferon gamma (IFNγ) in the subject.

In some embodiments, the methods and agents described herein following administration to a subject induce an antibody response, in particular a neutralizing antibody response, in the subject that targets a panel of different S protein variants such as SARS-CoV-2 S protein variants, in particular naturally occurring S protein variants. In some embodiments, the panel of different S protein variants comprises at least 5, at least 10, at least 15, or even more S protein variants. In some embodiments, such S protein variants comprise variants having amino acid modifications in the RBD domain and/or variants having amino acid modifications outside the RBD domain. In one embodiment, such S protein variant comprises SARS-CoV-2 S protein or a naturally occurring variant thereof wherein the amino acid corresponding to position 321 (Q) in SEQ ID NO: 1 is S. In one embodiment, such S protein variant comprises SARS-CoV-2 S protein or a naturally occurring variant thereof wherein the amino acid corresponding to position 321 (Q) in SEQ ID NO: 1 is L. In one embodiment, such S protein variant comprises SARS-CoV-2 S protein or a naturally occurring variant thereof wherein the amino acid corresponding to position 341 (V) in SEQ ID NO: 1 is I. In one embodiment, such S protein variant comprises SARS-CoV-2 S protein or a naturally occurring variant thereof wherein the amino acid corresponding to position 348 (A) in SEQ ID NO: 1 is T. In one embodiment, such S protein variant comprises SARS-CoV-2 S protein or a naturally occurring variant thereof wherein the amino acid corresponding to position 354 (N) in SEQ ID NO: 1 is D. In one embodiment, such S protein variant comprises SARS-CoV-2 S protein or a naturally occurring variant thereof wherein the amino acid corresponding to position 359 (S) in SEQ ID NO: 1 is N. In one embodiment, such S protein variant comprises SARS-CoV-2 S protein or a naturally occurring variant thereof wherein the amino acid corresponding to position 367 (V) in SEQ ID NO: 1 is F. In one embodiment, such S protein variant comprises SARS-CoV-2 S protein or a naturally occurring variant thereof wherein the amino acid corresponding to position 378 (K) in SEQ ID NO: 1 is S. In one embodiment, such S protein variant comprises SARS-CoV-2 S protein or a naturally occurring variant thereof wherein the amino acid corresponding to position 378 (K) in SEQ ID NO: 1 is R. In one embodiment, such S protein variant comprises SARS-CoV-2 S protein or a naturally occurring variant thereof wherein the amino acid corresponding to position 408 (R) in SEQ ID NO: 1 is I. In one embodiment, such S protein variant comprises SARS-CoV-2 S protein or a naturally occurring variant thereof wherein the amino acid corresponding to position 409 (Q) in SEQ ID NO: 1 is E. In one embodiment, such S protein variant comprises SARS-CoV-2 S protein or a naturally occurring variant thereof wherein the amino acid corresponding to position 435 (A) in SEQ ID NO: 1 is S. In one embodiment, such S protein variant comprises SARS-CoV-2 S protein or a naturally occurring variant thereof wherein the amino acid corresponding to position 439 (N) in SEQ ID NO: 1 is K. In one embodiment, such S protein variant comprises SARS-CoV-2 S protein or a naturally occurring variant thereof wherein the amino acid corresponding to position 458 (K) in SEQ ID NO: 1 is R. In one embodiment, such S protein variant comprises SARS-CoV-2 S protein or a naturally occurring variant thereof wherein the amino acid corresponding to position 472 (I) in SEQ ID NO: 1 is V. In one embodiment, such S protein variant comprises SARS-CoV-2 S protein or a naturally occurring variant thereof wherein the amino acid corresponding to position 476 (G) in SEQ ID NO: 1 is S. In one embodiment, such S protein variant comprises SARS-CoV-2 S protein or a naturally occurring variant thereof wherein the amino acid corresponding to position 477 (S) in SEQ ID NO: 1 is N. In one embodiment, such S protein variant comprises SARS-CoV-2 S protein or a naturally occurring variant thereof wherein the amino acid corresponding to position 483 (V) in SEQ ID NO: 1 is A. In one embodiment, such S protein variant comprises SARS-CoV-2 S protein or a naturally occurring variant thereof wherein the amino acid corresponding to position 508 (Y) in SEQ ID NO: 1 is H. In one embodiment, such S protein variant comprises SARS-CoV-2 S protein or a naturally occurring variant thereof wherein the amino acid corresponding to position 519 (H) in SEQ ID NO: 1 is P. In one embodiment, such S protein variant comprises SARS-CoV-2 S protein or a naturally occurring variant thereof wherein the amino acid corresponding to position 614 (D) in SEQ ID NO: 1 is G.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 501(N) in SEQ ID NO: 1. In one embodiment, the amino acid corresponding to position 501 (N) in SEQ ID NO: 1 is Y.

Said S protein variant comprising a mutation at a position corresponding to position 501 (N) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 484 (E), 701 (A), 18 (L), 246 (R), 417 (K), 242 (L), 243 (A), and 244 (L). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D->G mutation at a position corresponding to position 614 in SEQ ID NO: 1. In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a deletion at a position corresponding to positions 69 (H) and 70 (V) in SEQ ID NO: 1.

In some embodiments, a S protein variant comprising a deletion at a position corresponding to positions 69 (H) and 70 (V) in SEQ ID NO: 1 may comprise one or more further mutations. Such one or more further mutations may be selected from mutations at positions corresponding to the following positions in SEQ ID NO: 1: 144 (Y), 501 (N), 570 (A), 614 (D), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (I), 1147 (S), and 1229 (M). In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets “Cluster 5”.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, Y453F, I692V, M1229I, and optionally S1147L.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 614 (D) in SEQ ID NO: 1. In one embodiment, the amino acid corresponding to position 614 (D) in SEQ ID NO: 1 is G.

In some embodiments, a S protein variant comprising a mutation at a position corresponding to position 614 (D) in SEQ ID NO: 1 may comprise one or more further mutations.

Such one or more further mutations may be selected from mutations at positions corresponding to the following positions in SEQ ID NO: 1: 69 (H), 70 (V), 144 (Y), 501 (N), 570 (A), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (I), 1147 (S), and 1229 (M). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, D614G and A701V, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N) and 614 (D) in SEQ ID NO: 1. In one embodiment, the amino acid corresponding to position 501 (N) in SEQ ID NO: 1 is Y and the amino acid corresponding to position 614 (D) in SEQ ID NO: 1 is G.

In some embodiments, a S protein variant comprising a mutation at positions corresponding to positions 501(N) and 614 (D) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (I), 1147 (S), and 1229 (M). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 681(P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, D614G and A701V, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 484 (E) in SEQ ID NO: 1. In one embodiment, the amino acid corresponding to position 484 (E) in SEQ ID NO: 1 is K.

In some embodiments, a S protein variant comprising a mutation at a position corresponding to position 484 (E) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (I), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D->G mutation at a position corresponding to position 614 in SEQ ID NO: 1. In some embodiments, the methods and agents described herein following administration to a subject induce an antibody response, in particular a neutralizing antibody response, in the subject that targets "B.1.1.28".

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N) and 484 (E) in SEQ ID NO: 1. In one embodiment, the amino acid corresponding to position 501 (N) in SEQ ID NO: 1 is Y and the amino acid corresponding to position 484 (E) in SEQ ID NO: 1 is K.

In some embodiments, a S protein variant comprising a mutation at positions corresponding to positions 501 (N) and 484 (E) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (I), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D->G mutation at a position corresponding to position 614 in SEQ ID NO: 1.

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N), 484 (E) and 614 (D) in SEQ ID NO: 1. In one embodiment, the amino acid corresponding to position 501 (N) in SEQ ID NO: 1 is Y, the amino acid corresponding to position 484 (E) in SEQ ID NO: 1 is K and the amino acid corresponding to position 614 (D) in SEQ ID NO: 1 is G.

In some embodiments, a S protein variant comprising a mutation at positions corresponding to positions 501 (N), 484 (E) and 614 (D) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (I), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and D614G, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a deletion at a position corresponding to positions 242 (L), 243 (A) and 244 (L) in SEQ ID NO: 1.

In some embodiments, a S protein variant comprising a deletion at a position corresponding to positions 242 (L), 243 (A) and 244 (L) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 484 (E), 701 (A), 18 (L), 246 (R), 417 (K), 453 (Y), 692 (I), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V and deletion 242-244, and optionally: L18F, R246I, and K417N. Said S protein variant may also comprise a D->G mutation at a position corresponding to position 614 in SEQ ID NO: 1. In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 417 (K) in SEQ ID NO: 1. In one embodiment, the amino acid corresponding to position 417 (K) in SEQ ID NO: 1 is N. In one embodiment, the amino acid corresponding to position 417 (K) in SEQ ID NO: 1 is T.

In some embodiments, a S protein variant comprising a mutation at a position corresponding to position 417 (K) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 484 (E), 701 (A), 18 (L), 246 (R), 242 (L), 243 (A), 244 (L), 453 (Y), 692 (I), 1147 (S), 1229 (M), 20 (T), 26 (P), 138 (D), 190 (R), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and K417N, and optionally: L18F, R246I, and deletion 242-244. Said S protein variant may also comprise a D->G mutation at a position corresponding to position 614 in SEQ ID NO: 1. In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 417 (K) and 484 (E) and/or 501 (N) in SEQ ID NO: 1. In one embodiment, the amino acid corresponding to position 417 (K) in SEQ ID NO: 1 is N, and the amino acid corresponding to position 484 (E) in SEQ ID NO: 1 is K and/or the amino acid corresponding to position 501 (N) in SEQ ID NO: 1 is Y. In one embodiment, the amino acid corresponding to position 417 (K) in SEQ ID NO: 1 is T, and the amino acid corresponding to position 484 (E) in SEQ ID NO: 1 is K and/or the amino acid corresponding to position 501 (N) in SEQ ID NO: 1 is Y.

In some embodiments, a S protein variant comprising a mutation at positions corresponding to positions 417 (K) and 484 (E) and/or 501 (N) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 701 (A), 18 (L), 246 (R), 242 (L), 243 (A), 244 (L), 453 (Y), 692 (1), 1147 (S), 1229 (M), 20 (T), 26 (P), 138 (D), 190 (R), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is 1. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is 1. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is 1. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and K417N and optionally: L18F, R246I, and deletion 242-244. Said S protein variant may also comprise a D->G mutation at a position corresponding to position 614 in SEQ ID NO: 1.

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

The term "amino acid corresponding to position . . . " as used herein refers to an amino acid position number corresponding to an amino acid position number in SARS-CoV-2 S protein, in particular the amino acid sequence shown in SEQ ID NO: 1. Corresponding amino acid positions in other coronavirus S protein variants such as SARS-CoV-2 S protein variants may be found by alignment with SARS-CoV-2 S protein, in particular the amino acid sequence shown in SEQ ID NO: 1. It is considered well-known in the art how to align a sequence or segment in a sequence and thereby determine the corresponding position in a sequence to an amino acid position according to the present invention. Standard sequence alignment programs such as ALIGN, ClustalW or similar, typically at default settings may be used.

In some embodiments, the panel of different S protein variants to which an antibody response is targeted comprises at least 5, at least 10, at least 15, or even more S protein variants selected from the group consisting of the Q321S, V341I, A348T, N354D, S359N, V367F, K378S, R408I, Q409E, A435S, K458R, I472V, G476S, V483A, Y508H, H519P and D614G variants described above. In some embodiments, the panel of different S protein variants to which an antibody response is targeted comprises all S protein variants from the group consisting of the Q321S, V341I, A348T, N354D, S359N, V367F, K378S, R408I, Q409E, A435S, K458R, I472V, G476S, V483A, Y508H, H519P and D614G variants described above.

In some embodiments, the panel of different S protein variants to which an antibody response is targeted comprises at least 5, at least 10, at least 15, or even more S protein variants selected from the group consisting of the Q321L, V341I, A348T, N354D, S359N, V367F, K378R, R408I, Q409E, A435S, N439K, K458R, I472V, G476S, S477N, V483A, Y508H, H519P and D614G variants described above. In some embodiments, the panel of different S protein variants to which an antibody response is targeted comprises all S protein variants from the group consisting of the Q321L, V341I, A348T, N354D, S359N, V367F, K378R, R408I, Q409E, A435S, N439K, K458R, I472V, G476S, S477N, V483A, Y508H, H519P and D614G variants described above.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises one or more of the mutations described herein for S protein variants such as SARS-CoV-2 S protein variants, in particular naturally occurring S protein variants. In one embodiment, a SARS-CoV-2 S protein, an immunogenic variant thereof, or an immunogenic fragment of the SARS-CoV-2 S protein or the immunogenic variant thereof, e.g., as encoded by the RNA described herein, comprises a mutation at a position corresponding to position 501 (N) in SEQ ID NO: 1. In one embodiment, the amino acid corresponding to position 501 (N) in SEQ ID NO: 1 is Y. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises one or more mutations, such as all mutations, of a SARS-CoV-2 S protein of a SARS-CoV-2 variant selected from the group consisting of VOC-202012/01, 501.V2, Cluster 5 and B.1.1.248. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1. In some embodiments, the methods and agents, e.g., mRNA compositions, described herein following administration to a subject induce a cell-mediated immune response (e.g., CD4+ and/or CD8+ T cell response). In some embodiments, T cells are induced that recognize one or more eptiopes (e.g., MHC class I-restricted epitopes) selected from the group consisting of LPFNDGVYF (SEQ ID NO: 47), GVYFASTEK (SEQ ID NO: 52), YLQPRTFLL (SEQ ID NO: 40), QPTESIVRF (SEQ ID NO: 45), CVADYSVLY (SEQ ID NO: 53), KCYGVSPTK (SEQ ID NO: 54), NYNYLYRLF (SEQ ID NO: 43), FQPTNGVGY (SEQ ID NO: 55), IPFAMQMAY (SEQ ID NO: 46), RLQSLQTYV (SEQ ID NO: 41), GTHWFVTQR (SEQ ID NO: 56), VYDPLQPEL (SEQ ID NO: 57), QYIKWPWYI (SEQ ID NO: 42), and KWPWYIWLGF (SEQ ID NO: 44). In one embodiment, T cells are induced that recognize the eptiope YLQPRTFLL (SEQ ID NO: 40). In one embodiment, T cells are induced that recognize the eptiope NYNYLYRLF (SEQ ID NO: 43). In one embodiment, T cells are induced that recognize the eptiope QYIKWPWYI (SEQ ID NO: 42). In one embodiment, T cells are induced that recognize the eptiope KCYGVSPTK (SEQ ID NO: 54). In one embodiment, T cells are induced that recognize the eptiope RLQSLQTYV (SEQ ID NO: 41). In some embodiments, the methods and agents, e.g., mRNA compositions, described herein are administered according to a regimen which achieves such induction of T cells.

In some embodiments, the methods and agents, e.g., mRNA compositions, described herein following administration to a subject induce a cell-mediated immune response (e.g., CD4+ and/or CD8+ T cell response) that is detectable 15 weeks or later, 16 weeks or later, 17 weeks or later, 18 weeks or later, 19 weeks or later, 20 weeks or later, 21 weeks or later, 22 weeks or later, 23 weeks or later, 24 weeks or later or 25 weeks or later after administration, e.g., using two doses of the RNA described herein (wherein the second dose may be administered about 21 days following administration of the first dose). In some embodiments, the methods and agents, e.g., mRNA compositions, described herein are administered according to a regimen which achieves such induction of a cell-mediated immune response.

In one embodiment, vaccination against Coronavirus described herein, e.g., using RNA described herein which may be administered in the amounts and regimens described herein, e.g., at two doses of 30 μg per dose e.g. administered 21 days apart, may be repeated after a certain period of time, e.g., once it is observed that protection against Coronavirus infection diminishes, using the same or a different vaccine as used for the first vaccination. Such certain period of time may be at least 6 months, 1 year, two years etc. In one embodiment, the same RNA as used for the first vaccination is used for the second or further vaccination, however, at a lower dose or a lower frequency of administration. For example, the first vaccination may comprise vaccination using a dose of about 30 μg per dose, wherein in one embodiment, at least two of such doses are administered, (for example, a second dose may be administered about 21 days following administration of the first dose) and the second or further vaccination may comprise vaccination using a dose of less than about 30 μg per dose, wherein in one embodiment, only one of such doses is administered. In one embodiment, a different RNA as used for the first vaccination is used for the second or further vaccination, e.g., BNT162b2 is used for the first vaccination and BNT162B1 or BNT162b3 is used for the second or further vaccination.

In one embodiment, the vaccination regimen comprises a first vaccination using at least two doses of the RNA described herein, e.g., two doses of the RNA described herein (wherein the second dose may be administered about 21 days following administration of the first dose), and a second vaccination using a single dose or multiple doses, e.g., two doses, of the RNA described herein. In various embodiments, the second vaccination is administered 3 to 24 months, 6 to 18 months, 6 to 12 months, or 5 to 7 months after administration of the first vaccination, e.g., after the initial two-dose regimen. The amount of RNA used in each dose of the second vaccination may be equal or different to the amount of RNA used in each dose of the first vaccination. In one embodiment, the amount of RNA used in each dose of the second vaccination is equal to the amount of RNA used in each dose of the first vaccination. In one embodiment, the amount of RNA used in each dose of the second vaccination and the amount of RNA used in each dose of the first vaccination is about 30 μg per dose. In one embodiment, the same RNA as used for the first vaccination is used for the second vaccination. In one embodiment, the RNA used for the first vaccination and for the second vaccination is BNT162b2. In one embodiment, a different RNA as used for the first vaccination is used for the second vaccination. In one embodiment, the RNA used for the first vaccination is BNT162b2 and the RNA used for the second vaccination is RNA encoding a SARS-CoV-2 S protein of a SARS-CoV-2 variant strain, e.g., a strain discussed herein. In one embodiment, the RNA used for the first vaccination is BNT162b2 and the RNA used for the second vaccination is RNA encoding a SARS-CoV-2 S protein of a SARS-CoV-2 variant strain that is prevalent or rapidly spreading at the time of the second vaccination. In one embodiment, the RNA used for the first vaccination is BNT162b2 and the RNA used for the second vaccination is RNA encoding a SARS-CoV-2 S protein, an immunogenic variant thereof, or an immunogenic fragment of the SARS-CoV-2 S protein or the immunogenic variant thereof comprising one or more of the mutations described herein for S protein variants such as SARS-CoV-2 S protein variants, in particular naturally occurring S protein variants. In one embodiment, the RNA used for the first vaccination is BNT162b2 and the RNA used for the second vaccination is RNA encoding a SARS-CoV-2 S protein, an immunogenic variant thereof, or an immunogenic fragment of the SARS-CoV-2 S protein or the immunogenic variant thereof comprising one or more mutations, such as all mutations, of a SARS-CoV-2 S protein of a SARS-CoV-2 variant selected from the group consisting of VOC-202012/01, 501.V2, Cluster 5 and B.1.1.248. In one embodiment, the RNA used for the first vaccination encodes a polypeptide comprising an amino acid sequence with proline residue substitutions at positions 986 and 987 of SEQ ID NO:1 and the RNA used for the second vaccination is RNA encoding a polypeptide comprising an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with proline residue substitutions at positions 986 and 987 of SEQ ID NO:1 administered about 6 to 12 months after administration of the first vaccination, i.e., after the initial two-dose regimen. In one embodiment, each RNA dose comprises 30 μg RNA.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1 administered about 6 to 12 months after administration of the first vaccination, i.e., after the initial two-dose regimen. In one embodiment, each RNA dose comprises 30 μg RNA.

In one embodiment, the second vaccination results in a boosting of the immune response. In one embodiment, the RNA described herein is co-administered with other vaccines. In some embodiments, an RNA composition described herein is co-administered with an influenza vaccine. In some embodiments, an RNA composition provided herein and other injectable vaccine(s) are administered at different times. In some embodiments, an RNA composition provided herein is administered at the same time as other injectable vaccine(s). In some such embodiments, an RNA composition provided herein and at least one another injectable vaccine(s) are administered at different injection sites. In some embodiments, an RNA composition provided herein is not mixed with any other vaccine in the same syringe. In some embodiments, an RNA composition provided herein is not combined with other coronavirus vaccines as part of vaccination against coronavirus, e.g., SARS-CoV-2.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder but may or may not have the disease or disorder. In many embodiments, the individual is a human being. Unless otherwise stated, the terms "individual" and "subject" do not denote a particular age, and thus encompass adults, elderlies, children, and newborns. In some embodiments, the term "subject" includes humans of age of at least 50, at least 55, at least 60, at least 65, at least 70, or older. In some embodiments, the term "subject" includes humans of age of at least 65, such as 65 to 80, 65 to 75, or 65 to 70. In embodiments of the present disclosure, the "individual" or "subject" is a "patient".

The term "patient" means an individual or subject for treatment, in particular a diseased individual or subject.

In one embodiment of the disclosure, the aim is to provide an immune response against coronavirus, and to prevent or treat coronavirus infection.

A pharmaceutical composition comprising RNA encoding a peptide or protein comprising an epitope may be administered to a subject to elicit an immune response against an antigen comprising said epitope in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. The immune system is divided into a more primitive innate immune system, and acquired or adaptive immune system of vertebrates, each of which contains humoral and cellular components.

"Cell-mediated immunity", "cellular immunity", "cellular immune response", or similar terms are meant to include a cellular response directed to cells characterized by expression of an antigen, in particular characterized by presentation of an antigen with class I or class II MHC. The cellular response relates to immune effector cells, in particular to cells called T cells or T lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as virus-infected cells, preventing the production of more diseased cells.

An immune effector cell includes any cell which is responsive to vaccine antigen. Such responsiveness includes activation, differentiation, proliferation, survival and/or indication of one or more immune effector functions. The cells include, in particular, cells with lytic potential, in particular lymphoid cells, and are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells.

The term "effector functions" in the context of the present invention includes any functions mediated by components of the immune system that result, for example, in the neutralization of a pathogenic agent such as a virus and/or in the killing of diseased cells such as virus-infected cells. In one embodiment, the effector functions in the context of the present invention are T cell mediated effector functions. Such functions comprise in the case of a helper T cell ($CD4^+$ T cell) the release of cytokines and/or the activation of $CD8^+$ lymphocytes (CTLs) and/or B cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term “immune effector cell” or “immunoreactive cell” in the context of the present invention relates to a cell which exerts effector functions during an immune reaction. An “immune effector cell” in one embodiment is capable of binding an antigen such as an antigen presented in the context of MHC on a cell or expressed on the surface of a cell and mediating an immune response. For example, immune effector cells comprise T cells (cytotoxic T cells, helper T cells, tumor infiltrating T cells), B cells, natural killer cells, neutrophils, macrophages, and dendritic cells. Preferably, in the context of the present invention, “immune effector cells” are T cells, preferably $CD4^+$ and/or $CD8^+$ T cells, most preferably $CD8^+$ T cells. According to the invention, the term “immune effector cell” also includes a cell which can mature into an immune cell (such as T cell, in particular T helper cell, or cytolytic T cell) with suitable stimulation. Immune effector cells comprise $CD34^+$ hematopoietic stem cells, immature and mature T cells and immature and mature B cells. The differentiation of T cell precursors into a cytolytic T cell, when exposed to an antigen, is similar to clonal selection of the immune system.

A “lymphoid cell” is a cell which is capable of producing an immune response such as a cellular immune response, or a precursor cell of such cell, and includes lymphocytes, preferably T lymphocytes, lymphoblasts, and plasma cells. A lymphoid cell may be an immune effector cell as described herein. A preferred lymphoid cell is a T cell.

The terms “T cell” and “T lymphocyte” are used interchangeably herein and include T helper cells ($CD4^+$ T cells) and cytotoxic T cells (CTLs, $CD8^+$ T cells) which comprise cytolytic T cells. The term “antigen-specific T cell” or similar terms relate to a T cell which recognizes the antigen to which the T cell is targeted and preferably exerts effector functions of T cells. T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function. T helper cells assist other white blood cells in immunologic processes, including maturation of B cells into plasma cells and activation of cytotoxic T cells and macrophages, among other functions. These cells are also known as $CD4^+$ T cells because they express the CD4 glycoprotein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as $CD8^+$ T cells since they express the CD8 glycoprotein on their surface. These cells recognize their targets by binding to antigen associated with MHC class I, which is present on the surface of nearly every cell of the body. A majority of T cells have a T cell receptor (TCR) existing as a complex of several proteins. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

“Humoral immunity” or “humoral immune response” is the aspect of immunity that is mediated by macromolecules found in extracellular fluids such as secreted antibodies, complement proteins, and certain antimicrobial peptides. It contrasts with cell-mediated immunity. Its aspects involving antibodies are often called antibody-mediated immunity. Humoral immunity refers to antibody production and the accessory processes that accompany it, including: Th2 activation and cytokine production, germinal center formation and isotype switching, affinity maturation and memory cell generation. It also refers to the effector functions of antibodies, which include pathogen neutralization, classical complement activation, and opsonin promotion of phagocytosis and pathogen elimination.

In humoral immune response, first the B cells mature in the bone marrow and gain B-cell receptors (BCR's) which are displayed in large number on the cell surface. These membrane-bound protein complexes have antibodies which are specific for antigen detection. Each B cell has a unique antibody that binds with an antigen. The mature B cells migrate from the bone marrow to the lymph nodes or other lymphatic organs, where they begin to encounter pathogens. When a B cell encounters an antigen, the antigen is bound to the receptor and taken inside the B cell by endocytosis. The antigen is processed and presented on the B cell's surface again by MHC-II proteins. The B cell waits for a helper T cell (TH) to bind to the complex. This binding will activate the TH cell, which then releases cytokines that induce B cells to divide rapidly, making thousands of identical clones of the B cell. These daughter cells either become plasma cells or memory cells. The memory B cells remain inactive here; later when these memory B cells encounter the same antigen due to reinfection, they divide and form plasma cells. On the other hand, the plasma cells produce a large number of antibodies which are released free into the circulatory system. These antibodies will encounter antigens and bind with them. This will either interfere with the chemical interaction between host and foreign cells, or they may form bridges between their antigenic sites hindering their proper functioning, or their presence will attract macrophages or killer cells to attack and phagocytose them.

The term “antibody” includes an immunoglobulin comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody binds, preferably specifically binds with an antigen.

Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

An "antibody heavy chain", as used herein, refers to the larger of the two types of polypeptide chains present in antibody molecules in their naturally occurring conformations.

An "antibody light chain", as used herein, refers to the smaller of the two types of polypeptide chains present in antibody molecules in their naturally occurring conformations, K and A light chains refer to the two major antibody light chain isotypes.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" refers to any disease which implicates an antigen, e.g. a disease which is characterized by the presence of an antigen. The disease involving an antigen can be an infectious disease. As mentioned above, the antigen may be a disease-associated antigen, such as a viral antigen. In one embodiment, a disease involving an antigen is a disease involving cells expressing an antigen, preferably on the cell surface.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. *chlamydia* or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

CERTAIN EXEMPLARY EMBODIMENTS

1. A method of immunizing against SARS-CoV-2, the method comprising steps of:

administering a composition comprising a lipid nanoparticle encapsulated mRNA that encodes at least an epitope of a SARS-CoV-2-encoded polypeptide, according to a regimen established to achieve detectable antibody titer against the epitope in serum within 7 days, which regimen comprises administration of at least one dose of the composition.

2. The method of embodiment 1, wherein the regimen comprises administration of at least two doses of the composition.

3. The method of embodiment 1, wherein the regimen consists of administration of two doses of the composition.

4. The method of embodiment 2 or embodiment 3, wherein the first dose is a different amount that one or more subsequent doses.

5. The method of embodiment 1 or embodiment 4, wherein the first dose is administered a period of time before the subsequent dose, which period of time is at least 1 week, 1 month, 2 months, 3 months, 6 months, 1 year, 2 years, 3 years or more.

6. The method of any one of embodiments 1-6, wherein the regimen has been established to have an incidence of adverse events below 60% when administered to a relevant population of adults. 7. The method of embodiment 6, wherein the regimen has been established not to elicit local injection site reactions above moderate severity with an incidence greater than about 1 in 75.

8. The method of any one of embodiments 1-7, wherein each dose is no more than 60 ug or lower, including, e.g., no more than 50 ug, no more than 40 ug, no more than 30 ug, no more than 20 ug, no more than 10 ug, no more than 5 ug, no more than 2.5 ug, no more than 1 ug.

9. The method of any one of embodiments 1-8, wherein each dose is at least 1 ug or higher, including, e.g., at least 2 ug, at least 5 ug, at least 10 ug, at least 20 ug, at least 30 ug, at least 40 ug, or more.

10. A method comprising administering to a subject a composition comprising a lipid nanoparticle encapsulated mRNA, wherein the mRNA encodes an amino acid sequence comprising SARS-COV2 S protein or a fragment thereof, wherein the composition is administered in an effective amount to induce in the subject a SARS-COV-2 S-protein specific immune response, wherein the effective amount is sufficient to provide sterilizing immunity in the subject at an at least 2-fold (including, e.g., at least 3-fold, at least 4-fold, at least 5-fold) lower dose relative to a reference composition (e.g., a reference RNA vaccine or composition).

11. A method comprising administering to a subject a composition comprising a lipid nanoparticle encapsulated mRNA, wherein the mRNA encodes an amino acid sequence comprising SARS-COV2 S protein or a fragment thereof, wherein the composition is administered in an effective amount to reduce viral load in the subject by at least 80%, relative to a control, at 2 days or more (including, e.g., 3 days, 4 days, 5 days, 6 days, 7 days, 8 days, 9 days, or more) following exposure to SARS-COV2, wherein the control is the viral load in a subject administered a reference composition (e.g., a reference RNA vaccine or composition).

12. A method comprising administering to a subject a composition comprising a lipid nanoparticle encapsulated mRNA, wherein the mRNA encodes an amino acid sequence comprising SARS-COV2 S protein or a fragment thereof, wherein the composition is administered in an effective amount to induce in the subject a SARS-COV-2 S-protein specific immune response, wherein efficacy of the RNA vaccine is at least 80% relative to unvaccinated control subjects.

13. The method of any one of embodiments 10-12, wherein the effective amount is sufficient to produce detectable levels of SARS-COV-2 S protein or a fragment thereof as measured in serum of the subject at 1-72 hours post administration.

14. The method of any one of embodiments 10-12, wherein the effective amount is sufficient to produce a 1,000-10,000 neutralization titer produced by neutralizing antibody against the SARS-COV-2 S protein as measured in serum of the subject at 1-72 hours post administration.

15. The method of any one of embodiments 10-14, wherein an anti-SARS-COV-2 S protein antibody titer produced in the subject is increased by at least 1 log relative to a control, wherein the control is an anti-SARS-COV-2 S protein antibody titer produced in a subject who has not been administered a vaccine against SARS-COV-2.

16. The method of any one of embodiments 10-15, wherein the anti-SARS-COV-2 S protein antibody titer produced in the subject is increased at least 2 times relative to a control, wherein the control is an anti-SARS-COV-2 S protein antibody titer produced in a subject who has not been administered a vaccine against SARS-COV-2.

17. The method of any one of embodiments 1-16, wherein the administering is performed by intramuscular injection.

18. An immunogenic composition comprising a lipid nanoparticle encapsulated RNA (e.g., mRNA) that encodes at least an epitope of a SARS-CoV-2-encoded polypeptide, which vaccine composition has been established to achieve detectable antibody titer against the epitope in serum within 7 days after administration to a population of adult human subjects according to a regimen that includes administration of at least one dose of the vaccine composition.

19. The immunogenic composition of embodiment 18, wherein at least 80% of the uridines in the RNA have a chemical modification.

20. The immunogenic composition of embodiment 18 or 19, wherein 100% of the uridines in the RNA have a chemical modification.

21. The immunogenic composition of any one of embodiments 18-20, wherein the 5' terminal cap is 7mG(5')ppp(5') NlmpNp.

22. The immunogenic composition of any one of embodiments 18-21, wherein the lipid nanoparticles in the composition comprise a cationic lipid, a PEG-modified lipid, a sterol and a non-cationic lipid.

23. The immunogenic composition of any one of embodiments 18-22, wherein lipid nanoparticles in the composition comprise a molar ratio of about 20-60% cationic lipid, 0.5-15% PEG-modified lipid, 25-55% sterol, and 5-25% non-cationic lipid.

24. The immunogenic composition of embodiment 22 or 23, wherein the cationic lipid is an ionizable cationic lipid, the non-cationic lipid is a neutral lipid, and the sterol is a cholesterol.

25. The immunogenic composition of any one of embodiments 22 or 23, wherein the cationic lipid is selected from the group consisting of 2,2-dilinoleyl-4-dimethylamino-ethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate.

26. The immunogenic composition of any one of embodiments 18-25, wherein the RNA comprises a 5' terminal cap and a chemical modification, and the RNA is formulated or is to be formulated as an lipid nanoparticle.

27. The immunogenic composition of any one of embodiments 18-26, wherein the SARS-CoV-2 S protein, an immunogenic variant thereof, or an immunogenic fragment of the SARS-CoV-2 S protein or the immunogenic variant thereof is linked to a signal peptide.

28. The immunogenic composition of embodiment 27, wherein the signal peptide is selected from the group consisting of: a HulgGk signal peptide (METPAQLLFLLLL-WLPDTTG (SEQ ID NO: 36)); an IgE heavy chain epsilon-1signal peptide (MDWTWILFLVAAATRVHS (SEQ ID NO: 37)); a Japanese encephalitis PRM signal sequence (MLGSNSGQRVVFTILLLLVAPAYS (SEQ ID NO: 38)) and a VSVg protein signal sequence (MKCLLYLAFL-FIGVNCA (SEQ ID NO: 39)).

29. A method for eliciting an immune response in a subject by activating T cells in vivo, comprising administering to the subject a composition comprising a lipid nanoparticle encapsulated modified nucleoside mRNA, wherein the mRNA encodes an amino acid sequence comprising SARS-COV2 S protein or a fragment thereof, thereby activating T cells in vivo against infection by SARS-COV2 in the subject.

30. A method for eliciting an immune response against SARS-COV-2 in a subject, comprising administering to the subject a composition comprising a lipid nanoparticle encapsulated modified nucleoside mRNA, wherein the mRNA encodes an amino acid sequence comprising SARS-COV2 S protein or a fragment thereof, wherein the composition elicits an increased production of the SARS-COV2 polypeptide or fragment thereof production, as compared to a composition comprising a corresponding unmodified mRNA.

31. A method for eliciting an immune response against SARS-COV-2 in a subject, comprising administering to the subject a composition comprising a lipid nanoparticle encapsulated modified nucleoside mRNA, wherein the mRNA encodes an amino acid sequence comprising SARS-COV2 S protein or a fragment thereof, wherein the composition elicits increased antibody titers, as compared to a composition comprising a corresponding unmodified mRNA.

32. A method for eliciting an immune response against SARS-COV-2 in a subject, comprising administering at least one dose to the subject a composition comprising a lipid nanoparticle encapsulated modified nucleoside mRNA, wherein the mRNA encodes an amino acid sequence comprising SARS-COV2 S protein or a fragment thereof, wherein the composition elicits increased antibody titers in the subject at least 7 days after the first dose, as compared to the antibody titers against SARS-COV-2 prior to administration of the composition.

33. A method for eliciting an immune response against SARS-COV-2 in a subject, comprising administering at least one dose to the subject a composition comprising a lipid nanoparticle encapsulated modified nucleoside mRNA, wherein the mRNA encodes an amino acid sequence comprising SARS-COV2 S protein or a fragment thereof, wherein the composition elicits increased antibody titers in the subject at least 7 days after the first dose, as compared to a composition comprising a corresponding unmodified mRNA.

34. The method according to any one of embodiments 29-33, wherein the mRNA is present at a purity of 90% or greater.

35. The method according to any one of embodiments 29-34, wherein the composition does not further comprise a unmodified RNA encoding SARS-COV2 S protein or a fragment thereof.

36. The method according to any one of embodiments 29-35, wherein the composition is administered at least 2 times, the first and second administrations being at least 7 days apart.

37. The method according to any one of embodiments 29-36, wherein the subject is at risk for a SARS-CoV-2 infection.

38. The method according to any one of embodiments 29-37, wherein the subject is undergoing treatment for cardiovascular disease.

39. The method according to any one of embodiments 29-37, wherein the subject is undergoing treatment for diabetes.

40. The method according to any one of embodiments 29-37, wherein the subject is undergoing treatment for chronic cardiopulmonary disease.

41. The method according to any one of embodiments 29-37, wherein the subject is undergoing treatment for chronic renal disease.

42. The method according to any one of embodiments 29-41, wherein the immune response is sustained for at least about 30 days.

43. The method according to any one of embodiments 29-42, wherein the immune response is sustained for at least about 60 days.

44. The method according to any one of embodiments 29-43, wherein the immune response is sustained for at least about 180 days.

45. The method according to any one of embodiments 29-44, wherein the immune response comprises virus neutralizing titer.

46. The method according to any one of embodiments 29-45, wherein the subject is at least 18 years of age.

47. The method according to any one of embodiments 29-46, wherein the dose comprises 100 ug or less of mRNA.

48. The method according to any one of embodiments 29-47, wherein the dose comprises less than 100 ug of mRNA and the composition elicits an immune response that is greater than the immune response elicited by a composition comprising at least 100 ug of mRNA.

49. The method according to any one of embodiments 29-48, wherein the dose comprises about 30 ug of mRNA.

50. The method according to any one of embodiments 29-49, wherein the immune response comprises antibodies against the receptor binding domain of the S protein of SARS-CoV-2.

51. The method according to any one of embodiments 29-50, wherein the immune response comprises RBD-binding IgG.

52. The method according to any one of embodiments 29-50, wherein the SARS-CoV-2 S protein or a fragment thereof comprises a receptor binding domain.

53. A kit comprising a) a composition comprising a lipid nanoparticle encapsulated mRNA; and b) a temperature monitoring system.

54. The kit according to embodiment 53, wherein the temperature monitoring system comprises a temperature sensor and a display, wherein when the temperature monitoring system displays or warns when the temperature of the composition attains a temperature above about −80° C.

55. The kit according to embodiment 53, wherein the temperature monitoring system comprises a temperature sensor and a display, wherein when the temperature monitoring system displays or warns when the temperature of the composition attains a temperature above about −60° C.

56. A kit comprising a) a composition comprising a lipid nanoparticle encapsulated mRNA; and b) a light sensor.

57. The kit according to embodiment 56, wherein the light sensor comprises a photosensitive element configured to react to exposure to light, resulting in a change in a material property of the photosensitive element.

58. The method according to any one of embodiments 29-35, wherein the composition is administered at least 2 times, the first and second administrations being at least 14 days apart.

59. The method according to any one of embodiments 29-35, wherein the composition is administered at least 2 times, the first and second administrations being at least 21 days apart.

60. The method according to any one of embodiments 29-48, wherein the dose comprises about 10 ug of mRNA.

61. The method according to any one of embodiments 29-35, wherein the composition is administered at least 2 times, the first and second administrations being at least 28 days apart.

62. The method according to any one of embodiments 29-35, wherein the mRNA encodes any one of the amino acid sequences SEQ ID NO: 3, SEQ ID NO: 5, and SEQ ID NO: 7.

63. An immunogenic composition comprising a messenger ribonucleic acid (mRNA) polynucleotide comprising an open reading frame encoding a polypeptide that comprises a receptor-binding portion of a SARs-CoV-2 S protein formulated in at least one lipid nanoparticle comprising a cationic lipid, in an effective amount to induce an immune response in a subject administered at least one dose of the immunogenic composition, wherein the isolated mRNA polynucleotide is not self-replicating RNA.

64. The immunogenic composition of embodiment 63, wherein the lipid nanoparticle further comprises any one of a non-cationic lipid, sterol, and PEG-modified lipid.

65. The immunogenic composition of embodiment 63, comprising an isolated messenger ribonucleic acid (mRNA) polynucleotide comprising an open reading frame encoding a polypeptide that comprises a receptor-binding portion of a SARs-CoV-2 S protein; formulated in at least one lipid nanoparticle that comprises a molar ratio of 20-60% ionizable cationic lipid, 5-25% non-cationic lipid, 25-55% sterol, and 0.5-15% PEG-modified lipid, in an effective amount to induce an immune response in a subject administered at least one dose of the immunogenic composition, wherein the isolated mRNA polynucleotide is not self-replicating RNA.

66. The immunogenic composition of embodiment 63, wherein the polypeptide does not comprise the complete S protein.

67. The immunogenic composition of embodiment 63, wherein the polypeptide comprises the receptor binding domain (RBD) of a SARs-CoV-2 S protein.

68. The immunogenic composition of embodiment 63, wherein the polypeptide comprises SEQ ID NO: 5.

69. The immunogenic composition of embodiment 63, wherein the polypeptide comprises SEQ ID NO: 29 or 31.

70. The immunogenic composition of embodiment 63, wherein the polypeptide comprises SEQ ID NO: 3.

71. The immunogenic composition of embodiment 63, wherein the polypeptide comprises SEQ ID NO: 7.

72. The immunogenic composition of any one of embodiments 63-71, wherein the isolated mRNA polynucleotide further comprises a 5' terminal cap, 7mG(5')ppp(5')NlmpNp.

73. The immunogenic composition of any one of embodiments 63-72, wherein at least 80% of the uracil in the open reading frame have a chemical modification selected from N1-methyl-pseudouridine or N1-ethyl-pseudouridine.

74. The immunogenic composition of any one of embodiments 63-73, wherein the chemical modification is in the 5-position of the uracil.

75. The immunogenic composition of any one of embodiments 63-74, wherein the efficacy of the immunogenic composition in vaccinated subjects is at least 60%, relative to unvaccinated subjects, following a single dose of the immunogenic composition.

76. The immunogenic composition of embodiment 75, wherein the efficacy of the immunogenic composition in vaccinated subjects is at least 70%, relative to unvaccinated subjects, following a single dose of the immunogenic composition.

77. The immunogenic composition of embodiment 75, wherein the efficacy of the immunogenic composition in vaccinated subjects is at least 80%, relative to unvaccinated subjects, following a single dose of the immunogenic composition.

78. The immunogenic composition of embodiment 75, wherein the efficacy of the immunogenic composition in vaccinated subjects is at least 90%, relative to unvaccinated subjects, following a single dose of the immunogenic composition.

79. The immunogenic composition of any one of embodiments 63-78, wherein the effective amount is sufficient to produce detectable levels of a polypeptide that comprises a receptor-binding portion of a SARS-CoV-2 S protein as measured in serum of a subject vaccinated with at least one dose of the immunogenic composition at 1-72 hours post administration.

80. The immunogenic composition of any one of embodiments 63-79, wherein the effective amount is sufficient to produce a 1,000-10,000 neutralization titer produced by neutralizing antibody against the antigenic polypeptide that comprises a receptor-binding portion of a SARS-CoV-2 S protein as measured in serum of a subject vaccinated with at least one dose of the immunogenic composition at 1-72 hours post administration.

81. The immunogenic composition of embodiment 80, wherein the 1,000-10,000 neutralization titer is produced in the absence of antibody-dependent enhancement (ADE) of a SARS-CoV-2-associated disease.

82. The immunogenic composition of any one of embodiments 63-81, wherein the effective amount does not induce the immunogenic composition-associated enhanced respiratory disease (ERD).

83. The immunogenic composition of any one of embodiments 63-82, wherein the effective amount reduces the amount of SARS-CoV-2 viral RNA in a lung of the subject after infection with a SARS-CoV-2 virus, as compared to the amount of SARS-CoV-2 viral RNA in a lung of an unvaccinated subject after infection with a SARS-CoV-2 virus.

84. The immunogenic composition of any one of embodiments 63-82, wherein the effective amount reduces the amount of SARS-CoV-2 viral RNA in a lung of the subject at least 3 days after infection with a SARS-CoV-2 virus, as compared to the amount of SARS-CoV-2 viral RNA in a lung of the subject 3 days after infection with a SARS-CoV-2 virus.

85. The immunogenic composition of any one of embodiments 63-82, wherein the effective amount reduces the amount of SARS-CoV-2 viral RNA in a nasal swab sample of the subject after infection with a SARS-CoV-2 virus, as compared to the amount of SARS-CoV-2 viral RNA in a nasal swab sample of an unvaccinated subject after infection with a SARS-CoV-2 virus.

86. The immunogenic composition of any one of embodiments 63-82, wherein the effective amount does not increase the amount of SARS-CoV-2 viral RNA in a nasal swab sample of the subject 3 days after infection with a SARS-CoV-2 virus, as compared to the amount of SARS-CoV-2 viral RNA in a nasal swab sample of the subject 1 day after infection with a SARS-CoV-2 virus.

87. The immunogenic composition of any one of embodiments 63-87, wherein an anti-SARS-CoV-2 antibody titer produced in a subject vaccinated with at least one dose of the immunogenic composition is increased by at least 1 log relative to a control, wherein the control is an anti-SARS-CoV-2 antibody titer produced in a subject who has not been administered an immunogenic composition against SARS-CoV-2.

88. The immunogenic composition of any one of embodiments 63-87, wherein an anti-SARS-CoV-2 antibody titer produced in a subject vaccinated with at least one dose of the immunogenic composition is increased at least 2 times relative to a control, wherein the control is an anti-SARS-CoV-2 antibody titer produced in a subject who has not been administered an immunogenic composition against SARS-CoV-2.

89. The immunogenic composition of any one of embodiments 63-88, wherein the effective amount is a total dose of 2 μg-100 μg.

90. The immunogenic composition of embodiment 89, wherein the effective amount is a total dose of 100 μg.

91. The immunogenic composition of embodiment 89, wherein the effective amount is a total dose of 20 μg-50 μg.

92. The immunogenic composition of embodiment 89, wherein the effective amount is a total dose of 10 μg-30 μg.

93. The immunogenic composition of embodiment 89, wherein the effective amount is a total dose of 10 μg.

94. The immunogenic composition of embodiment 89, wherein the effective amount is a total dose of 20 μg.

95. The immunogenic composition of embodiment 89, wherein the effective amount is a total dose of 30 μg.

96. The immunogenic composition of any one of embodiments 63-95, wherein the composition is formulated in a single-dose vial.

97. The immunogenic composition of any one of embodiments 63-95, wherein the composition is formulated in a multi-dose vial.

98. The immunogenic composition of any one of embodiments 63-97, wherein intramuscular administration of the effective amount of the immunogenic composition to a subject induces a neutralizing antibody titer in a subject.

99. The immunogenic composition of embodiment 98, wherein the neutralizing antibody titer is sufficient to reduce viral infection of B cells by at least 50% relative to a neutralizing antibody titer of an unvaccinated control subject or relative to a neutralizing antibody titer of a subject vaccinated with a live attenuated viral vaccine, an inactivated viral vaccine, or a protein subunit viral vaccine.

100. The immunogenic composition of embodiment 98 or 99, wherein the neutralizing antibody titer is induced in the subject following fewer than three doses of the immunogenic composition.

101. The immunogenic composition of any one of embodiments 98-100, wherein the neutralizing antibody titer and/or a T cell immune response is sufficient to reduce the rate of asymptomatic viral infection relative to the neutralizing antibody titer of unvaccinated control subjects.

102. The immunogenic composition of any one of embodiments 98-101, wherein the neutralizing antibody titer and/or a T cell immune response is sufficient to prevent viral latency in the subject.

103. The immunogenic composition of any one of embodiments 98-102, wherein the neutralizing antibody titer is sufficient to block fusion of virus with epithelial cells and/or B cells of the subject.

104. The immunogenic composition of any one of embodiments 63-103, wherein intramuscular administration of the effective amount of the immunogenic composition to a subject induces a T cell immune response in the subject.

105. The immunogenic composition of embodiment 104, wherein the T cell immune response comprises a $CD4^+$ T cell immune response and/or a $CD8^+$ T cell immune response.

106. The immunogenic composition of any one of embodiments 63-105, wherein the encoded polypeptide is presented on the surface of cells of the subject.

107. A method comprising administering to a subject an immunogenic composition of any one of embodiments 63-106, wherein the immunogenic composition is administered to the subject in an effective amount to induce an immune response in the subject.

108. The method of embodiment 107, wherein the immune response is induced against a SARs-CoV-2 virus having a mutation in the RBD, as compared to SEQ ID NO: 5.

109. The method of embodiment 107, wherein the immune response is induced against a SARs-CoV-2 virus having a mutation in the spike protein, as compared to SEQ ID NO: 1.

110. The method of embodiment 108 or 109, wherein the immune response is induced against a SARs-CoV-2 virus having any one of the following mutations in the RBD: Q321L, V341I, A348T, N354D, S359N, V367F, K378R, R408I, Q409E, A435S, N439K, K458R, I472V, G476S, S477N, V483A, Y508H, and H519P, as compared to SEQ ID NO: 1.

111. The method of embodiment 109, wherein the immune response is induced against a SARs-CoV-2 virus having a D614G mutation in the spike protein, as compared to SEQ ID NO: 1.

112. The method of embodiment 107, wherein the immunogenic composition is administered to the subject annually.

113. An RNA, optionally complexed by a (poly)cationic polymer, polyplex(es), protein(s) or peptide(s), which RNA: (a) comprises an open reading frame encoding a polypeptide that comprises a receptor-binding-portion of a SARS-CoV-2 S protein; and (b) is suitable for intracellular expression of the polypeptide.

114. The RNA of embodiment 113, wherein the polypeptide does not comprise the complete S protein.

115. The RNA of embodiment 113 or 114, wherein the RNA further comprises a 5' terminal cap, 7mG(5')ppp(5')NlmpNp.

116. The RNA of any one of embodiments 113-115, wherein at least 80% of the uracil in the open reading frame have a chemical modification selected from N1-methyl-pseudouridine or N1-ethyl-pseudouridine.

117. The RNA of any one of embodiments 113-116, wherein the chemical modification is in the 5-position of the uracil.

118. The RNA of any one of embodiments 113-117 for use in inducing an immune response in humans or vaccinating humans.

119. The RNA for use of embodiment 118, wherein the humans comprise humans known to have been exposed to SARS-CoV-2.

120. The RNA for use of embodiment 118, wherein the humans comprise humans known to have been infected by SARS-CoV-2.

121. The RNA for use of embodiment 118, wherein the humans comprise humans not known to have been exposed to SARS-CoV-2.

122. Use of the RNA of any one of embodiments 113-117 for vaccinating humans.

123. The use of embodiment 122, wherein the humans comprise humans known to have been exposed to SARS-CoV-2.

124. The use of embodiment 122, wherein the humans comprise humans known to have been infected by SARS-CoV-2.

125. The use of embodiment 122, wherein the humans comprise humans not known to have been exposed to SARS-CoV-2.

126. A single-dose formulation comprising the immunogenic composition of any one of embodiments 63-106.

127. A multi-dose formulation comprising the immunogenic composition of any one of embodiments 63-106 in one vial.

128. The formulation according to embodiment 126, comprising at least 2 doses per vial.

129. The formulation according to embodiment 126, comprising a total of 2-12 doses per vial.

130. The formulation according to any one of embodiments 126-129, wherein each dose is equal in volume.

131. The formulation according to any one of embodiments 126-130, wherein each formulation comprises a total volume of 1-3 mL in the vial.

132. The formulation according to any one of embodiments 126-131, wherein the immunogenic composition is frozen.

133. A pre-filled vaccine delivery device comprising the immunogenic composition of any one of embodiments 63-106.

Further certain exemplary embodiments:

1. A composition or medical preparation comprising RNA encoding an amino acid sequence comprising a SARS-CoV-2 S protein, an immunogenic variant thereof, or an immunogenic fragment of the SARS-CoV-2 S protein or the immunogenic variant thereof.

2. The composition or medical preparation of embodiment 1, wherein an immunogenic fragment of the SARS-CoV-2 S protein comprises the S1 subunit of the SARS-CoV-2 S protein, or the receptor binding domain (RBD) of the S1 subunit of the SARS-CoV-2 S protein.

3. The composition or medical preparation of embodiments 1 or 2, wherein the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

4. The composition or medical preparation of any one of embodiments 1 to 3, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

5. The composition or medical preparation of any one of embodiments 1 to 4, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

6. The composition or medical preparation of any one of embodiments 1 to 5, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

7. The composition or medical preparation of any one of embodiments 1 to 6, wherein the amino acid sequence comprising a SARS-CoV-2 S protein, an immunogenic variant thereof, or an immunogenic fragment of the SARS-CoV-2 S protein or the immunogenic variant thereof comprises a secretory signal peptide.

8. The composition or medical preparation of embodiment 7, wherein the secretory signal peptide is fused, preferably N-terminally, to a SARS-CoV-2 S protein, an immunogenic variant thereof, or an immunogenic fragment of the SARS-CoV-2 S protein or the immunogenic variant thereof.

9. The composition or medical preparation of embodiment 7 or 8, wherein (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

10. The composition or medical preparation of any one of embodiments 1 to 9, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

11. The composition or medical preparation of any one of embodiments 1 to 10, wherein the RNA comprises a modified nucleoside in place of uridine.

12. The composition or medical preparation of embodiment 11, wherein the modified nucleoside is selected from pseudouridine (ψ), N1-methyl-pseudouridine (m1ψ), and 5-methyl-uridine (m5U).

13. The composition or medical preparation of any one of embodiments 1 to 12, wherein the RNA comprises a 5' cap.

14. The composition or medical preparation of any one of embodiments 1 to 13, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

15. The composition or medical preparation of any one of embodiments 1 to 14, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

16. The composition or medical preparation of any one of embodiments 1 to 15, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

17. The composition or medical preparation of embodiment 16, wherein the poly-A sequence comprises at least 100 nucleotides.

18. The composition or medical preparation of embodiment 16 or 17, wherein the poly-A sequence comprises or consists of the nucleotide sequence of SEQ ID NO: 14.

19. The composition or medical preparation of any one of embodiments 1 to 18, wherein the RNA is formulated or is to be formulated as a liquid, a solid, or a combination thereof.

20. The composition or medical preparation of any one of embodiments 1 to 19, wherein the RNA is formulated or is to be formulated for injection.

21. The composition or medical preparation of any one of embodiments 1 to 20, wherein the RNA is formulated or is to be formulated for intramuscular administration.

22. The composition or medical preparation of any one of embodiments 1 to 21, wherein the RNA is formulated or is to be formulated as particles.

23. The composition or medical preparation of embodiment 22, wherein the particles are lipid nanoparticles (LNP) or lipoplex (LPX) particles.

24. The composition or medical preparation of embodiment 23, wherein the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

25. The composition or medical preparation of embodiment 23, wherein the RNA lipoplex particles are obtainable by mixing the RNA with liposomes.

26. The composition or medical preparation of any one of embodiments 1 to 25, wherein the RNA is mRNA or saRNA.

27. The composition or medical preparation of any one of embodiments 1 to 26, which is a pharmaceutical composition.

28. The composition or medical preparation of any one of embodiments 1 to 27, which is a vaccine.

29. The composition or medical preparation of embodiment 27 or 28, wherein the pharmaceutical composition further comprises one or more pharmaceutically acceptable carriers, diluents and/or excipients.

30. The composition or medical preparation of any one of embodiments 1 to 26, which is a kit.

31. The composition or medical preparation of embodiment 30, wherein the RNA and optionally the particle forming components are in separate vials.

32. The composition or medical preparation of embodiment 30 or 31, further comprising instructions for use of the composition or medical preparation for inducing an immune response against coronavirus in a subject.

33. The composition or medical preparation of any one of embodiments 1 to 32 for pharmaceutical use.

34. The composition or medical preparation of embodiment 33, wherein the pharmaceutical use comprises inducing an immune response against coronavirus in a subject.

35. The composition or medical preparation of embodiment 33 or 34, wherein the pharmaceutical use comprises a therapeutic or prophylactic treatment of a coronavirus infection.

36. The composition or medical preparation of any one of embodiments 1 to 35, which is for administration to a human.

37. The composition or medical preparation of any one of embodiments 32 to 36, wherein the coronavirus is a betacoronavirus.

38. The composition or medical preparation of any one of embodiments 32 to 37, wherein the coronavirus is a sarbecovirus.

39. The composition or medical preparation of any one of embodiments 32 to 38, wherein the coronavirus is SARS-CoV-2.

40. A method of inducing an immune response against coronavirus in a subject comprising administering to the subject a composition comprising RNA encoding an amino acid sequence comprising a SARS-CoV-2 S protein, an immunogenic variant thereof, or an immunogenic fragment of the SARS-CoV-2 S protein or the immunogenic variant thereof.

41. The method of embodiment 40, wherein an immunogenic fragment of the SARS-CoV-2 S protein comprises the S1 subunit of the SARS-CoV-2 S protein, or the receptor binding domain (RBD) of the S1 subunit of the SARS-CoV-2 S protein.

42. The method of any one of embodiments 40 or 41, wherein the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

43. The method of any one of embodiments 40 to 42, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

44. The method of any one of embodiments 40 to 43, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

45. The method of any one of embodiments 40 to 44, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

46. The method of any one of embodiments 40 to 45, wherein the amino acid sequence comprising a SARS-CoV-2 S protein, an immunogenic variant thereof, or an immunogenic fragment of the SARS-CoV-2 S protein or the immunogenic variant thereof comprises a secretory signal peptide.

47. The method of embodiment 46, wherein the secretory signal peptide is fused, preferably N-terminally, to a SARS-CoV-2 S protein, an immunogenic variant thereof, or an immunogenic fragment of the SARS-CoV-2 S protein or the immunogenic variant thereof.

48. The method of embodiment 46 or 47, wherein (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1. 49. The method of any one of embodiments 40 to 48, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

50. The method of any one of embodiments 40 to 49, wherein the RNA comprises a modified nucleoside in place of uridine.

51. The method of embodiment 50, wherein the modified nucleoside is selected from pseudouridine (ψ), N1-methyl-pseudouridine (m1ψ), and 5-methyl-uridine (m5U).

52. The method of any one of embodiments 40 to 51, wherein the RNA comprises a cap.

53. The method of any one of embodiments 40 to 52, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

54. The method of any one of embodiments 40 to 53, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

55. The method of any one of embodiments 40 to 54, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

56. The method of embodiment 55, wherein the poly-A sequence comprises at least 100 nucleotides.

57. The method of embodiment 55 or 56, wherein the poly-A sequence comprises or consists of the nucleotide sequence of SEQ ID NO: 14.

58. The method of any one of embodiments 40 to 57, wherein the RNA is formulated as a liquid, a solid, or a combination thereof.

59. The method of any one of embodiments 40 to 58, wherein the RNA is administered by injection.

60. The method of any one of embodiments 40 to 59, wherein the RNA is administered by intramuscular administration.

61. The method of any one of embodiments 40 to 60, wherein the RNA is formulated as particles.

62. The method of embodiment 61, wherein the particles are lipid nanoparticles (LNP) or lipoplex (LPX) particles.

63. The method of embodiment 62, wherein the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

64. The method of any one of embodiment 62, wherein the RNA lipoplex particles are obtainable by mixing the RNA with liposomes.

65. The composition or medical preparation of any one of embodiments 40 to 64, wherein the RNA is mRNA or saRNA.

66. The method of any one of embodiments 40 to 65, which is a method for vaccination against coronavirus.

67. The method of any one of embodiments 40 to 66, which is a method for therapeutic or prophylactic treatment of a coronavirus infection.

68. The method of any one of embodiments 40 to 67, wherein the subject is a human.

69. The method of any one of embodiments 40 to 68, wherein the coronavirus is a betacoronavirus.

70. The method of any one of embodiments 40 to 69, wherein the coronavirus is a sarbecovirus.

71. The method of any one of embodiments 40 to 70, wherein the coronavirus is SARS-CoV-2.

72. The method of any one of embodiments 40 to 71, wherein the composition is a composition of any one of embodiments 1 to 39.

73. A composition or medical preparation of any one of embodiments 1 to 39 for use in a method of any one of embodiments 40 to 72.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: In Vivo Immunogenicity Using Influenza Hemagglutinin (Ha) as a Model Antigen The potency of the RNA platforms to be used for the coronavirus vaccine described herein has been tested by performing extensive immunogenicity and virus challenge studies using Influenza HA as a model antigen. The studies investigated the induction of antibody responses determined with antigen specific enzyme-linked immunosorbent assay (ELISA) test and functional studies applying virus-neutralization (VNT) assays. One study evaluated the potency of the LNP formulation using a modRNA-LNP vaccine that encodes Influenza HA. Mice were injected IM with 1 μg on days 0 ad 28 with an LNP-formulated Influenza HA modRNA. On days 14, 28 and 49 blood samples were taken, and tested for immunogenicity. The analysis showed a high antibody immune response, resulting in very high titers of antigen-specific IgG in serum and high viral-neutralization activity (FIG. 3). Moreover, strong Th1 CD4 and CD8 T cell responses (FIG. 4) were induced by the modRNA vaccine.

Example 2: Immunogenicity Studies for Coronavirus Vaccine Candidates

Primary pharmacodynamics studies were performed in BALB/c mice to test the immunogenicity of the vaccine candidates shown in the following table.

TABLE 2

Vaccine candidates

| Vaccine | mRNA type | Vaccine encoded antigen |
|---|---|---|
| BNT162a1 | uRNA | RBD (Receptor Binding Domain) of SARS-CoV-2 Spike protein (S protein) |
| BNT162b1 | modRNA | RBD (Receptor Binding Domain) of SARS-CoV-2 Spike protein (S protein) |
| BNT162b2 | modRNA | Modified version of SARS-CoV-2 Spike protein (S protein) |
| BNT162c1 | saRNA | RBD (Receptor Binding Domain) of SARS-CoV-2 Spike protein (S protein) |

Thus, as can be seen, embodiments of multiple formats were assessed in parallel. This described approach and system achieved remarkable and efficient success, enabling development of an effective clinical candidate within several months of provision of antigen (e.g., SARS-CoV-2 S1 protein and/or RBD thereof) sequence (as described herein, relevant sequence information (e.g., GenBank: MN908947.3) became available in January 2020) In the study, four groups of each eight female BALB/c mice were immunized once with the animal trial material at three different doses, or with buffer (control group; see Table 3). While the clinical trial material will be diluted in saline, the animal trial material was diluted in PBS including 300 mM sucrose. As this is the storage buffer of the material itself, the test items are representative for the vaccine that will be used in the planned clinical trials. Immunizations were given IM using a dose volume of 20 μL.

TABLE 3

Study design

| Group No | No of animals | Vaccine dose | Immunization Day | Dose volume [μL]/route | Blood collection Day | End of in-life phase |
|---|---|---|---|---|---|---|
| 1 | 8 | buffer | 0 | 20/IM | 7, 14, 21 | 28 |
| 2 | 8 | Low | 0 | 20/IM | 7, 14, 21 | 28 |
| 3 | 8 | Medium | 0 | 20/IM | 7, 14, 21 | 28 |
| 4 | 8 | High | 0 | 20/IM | 7, 14, 21 | 28 |

Blood of immunized animals was collected on days 7, 14, 21 and 28, and analyzed for the antibody immune response by ELISA and pseudovirus-based neutralization assay (pVNT).

SARS-CoV-2-S specific antibody responses directed against the recombinant S1 subunit or the RBD were detected by ELISA. In brief, high protein-binding 96-well plates (MaxiSorp ELISA plates, VWR International GmbH, Cat. No. 7341284) were coated with 100 ng recombinant S1 subunit (Sino Biological Inc., Cat. No. 40591-V08H) or RBD (Sino Biological Inc., Cat. No. 40592-V02H) per well in 100 μL coating buffer (50 mM sodium carbonate-bicarbonate buffer, pH9.6) overnight at 4° C. Plates were washed three times with 300 μL/well 1× phosphate-buffered saline (PBS, VWR International GmbH, Cat. No. 0780-10L) supplemented with 0.01% Tween 20 (Carl Roth GmbH & Co. KG, Cat. No. 9127.1) and blocked with 250 μL/well 1× Casein Blocking Buffer (Sigma-Aldrich GmbH, Cat No. B6429-500 ml) for 1 hour at 37° C. on a microplate shaker. Plates were again washed three times with 300 μL/well 1×PBS supplemented with 0.01% Tween 20 and incubated with mouse serum samples diluted in 1× Casein Blocking Buffer for 1 hour at 37° C. on a microplate shaker. Plates were washed three times with 300 μL/well 1×PBS supplemented with 0.01% Tween 20 and subsequently incubated with Peroxidase-conjugated goat anti-mouse secondary antibody (Jackson ImmunoResearch Ltd., Cat. No. 115-036-071; diluted 1:7500 in 1× Casein Blocking Buffer) for 45 minutes at 37° C. on a microplate shaker. Plates were washed three times with 300 μL/well 1×PBS supplemented with 0.01% Tween 20 and 100 μL/well TMB substrate (Biotrend Chemiekalien GmbH, Cat. No. 4380A) was added. Plates were incubated for 8 min at room temperature and the reaction stopped by addition of 100 μL 25% sulphuric acid (VWR International GmbH, Cat. No. 1007161000). Plates were read on a microplate reader and the recorded absorbance at 450 nm corrected by subtracting the reference absorbance at 620 nM.

Functional antibody responses to the vaccine candidates were detected by pVNT. The pVNT uses a replication-deficient vesicular stomatitis virus (VSV) that lacks the genetic information for the VSV envelope glycoprotein G but contains an open-reading frame (ORF) for green fluorescent protein (GFP). VSV/SARS-CoV-2 pseudovirus was generated according to a published protocol (Hoffmann et al., Cell, 2020; PMID 32142651). The pseudotype virus bears the SARS-CoV-2 S protein, which mediates cell entry. Therefore, the pseudovirus can be inactivated by neutralizing antibodies that bind SARS-CoV-2 S. This inactivation can be analyzed via in vitro methods.

In brief, $4\times10^4$ Vero 76 cells (ATCC® CRL-1587™) per well were seeded in a 96-well plate (Greiner Bio-One GmbH, Cat. No. 655160) in 150 μL/well DMEM (Thermo Fisher Scientific, Cat. No. 61965059) supplemented with 10% fetal bovine serum (FBS, Sigma-Aldrich GmbH, Cat. No. F7524). Cells were incubated for 4 to 6 hours at 37° C. and 7.5% $CO_2$. Meanwhile, mouse serum samples were diluted 1:6 up to 1:768 in DMEM/10% FBS in two-fold dilution steps. Diluted serum samples were combined with an equal volume of titrated and pre-diluted VSV/SARS CoV-2 pseudovirus supernatant, resulting in a serum dilution ranging from 1:12 up to 1:1536. The pseudovirus/serum dilution mix was incubated for 5 min at RT on a microplate shaker at 750 rpm with an additional 5 min incubation at RT without agitation. 50 μL/well pseudovirus/serum dilution mix was added to the seeded Vero-76 cells with the applied pseudovirus volume per well corresponding to 200 infectious units (IU). Each dilution of serum samples was tested in duplicate wells. Cells were incubated for 16 to 24 hours at 37° C. and 7.5% $CO_2$. Vero 76 cells incubated with pseudovirus in the absence of mouse sera were used as positive controls. Vero 76 cells incubated without pseudovirus were used as negative controls. After the incubation, the cell culture plates were removed from the incubator, placed in an IncuCyte Live Cell Analysis system (Essen Bioscience) and incubated for 30 min prior to the analysis. Whole well scanning for brightfield and GFP fluorescence was performed using a 4× objective. To calculate the neutralizing titer, infected GFP-positive cell number per well was compared with the pseudovirus positive control. Mean values of the pseudovirus positive control multiplied by 0.5 represent the pseudovirus neutralization 50% (pVN50). Serum samples with mean values below this cut-off exhibit >50% virus neutralization activity, respectively.

Immunogenicity study of BNT162a1 (RBL063.3)

To dissect the potency of the LNP-formulated uRNA vaccine coding for BNT162a1, BALB/c mice were immunized IM once as outlined in Table 3. The immunogenicity of the RNA vaccine will be investigated by focusing on the antibody immune response.

ELISA data 7, 14, 21 and 28 d after the first immunization show an early, dose-dependent immune activation against the S1 protein and the receptor binding domain (FIG. 5).

Immunogenicity Study of BNT162b1 (RBP020.3)

To dissect the potency of the LNP-formulated modRNA vaccine coding for BNT162b1, BALB/c mice were immunized IM once as outlined in Table 3. The immunogenicity of the RNA vaccine will be investigated by focusing on the antibody immune response.

ELISA data 7, 14, 21 and 28 d after the first immunization show an early, dose-dependent immune activation against the S1 protein and the receptor binding domain (FIG. 6). Sera obtained 14, 21, and 28 d after immunization show high SARS-CoV-2 pseudovirus neutralization, especially sera from mice immunized with 1 or 5 μg BNT162b1 and correlating with the strong increase of IgG antibody titers (FIG. 7).

Immunogenicity Study of BNT162c1 (RBS004.3)

To dissect the potency of the LNP-formulated saRNA vaccine coding for BNT162c1, BALB/c mice were immunized IM once as outlined in Table 3. The immunogenicity of the RNA vaccine will be investigated by focusing on the antibody immune response.

ELISA data 7, 14 and 21 d after the first immunization show an early, dose-dependent immune activation against the S1 protein and the receptor binding domain (FIG. 8). Sera obtained 14, and 21 d after immunization show dose-dependent SARS-CoV-2 pseudovirus neutralization activity (FIG. 9).

Immunogenicity study of LNP-formulated uRNA encoding the viral S protein-V8 (SEQ ID NO: 7, 8) (RBL063.1)

To dissect the potency of the LNP-formulated uRNA vaccine coding for the viral S protein-V8 (RBL063.1), BALB/c mice were immunized IM once as outlined in Table 3. The immunogenicity of the RNA vaccine will be investigated by focusing on the antibody immune response. ELISA data 7, 14, 21 and 28 d after the first immunization are available that show an early, dose-dependent immune activation against the S1 protein and the receptor binding domain (FIG. 10). Sera obtained 14, 21 and 28 d after immunization show dose-dependent SARS-CoV-2 pseudovirus neutralization activity (FIG. 11).

Immunogenicity Study of BNT162b2 (RBP020.1)

To dissect the potency of the vaccine BNT162b2 (RBP020.1), the immunogenicity of the construct was investigated. For this purpose, a dose titration study in BALB/c mice was initiated where the immune response will be analyzed focusing on the antibody immune response.

ELISA data 7, 14, and 21 d after the first immunization are available that show an early, dose-dependent immune activation against the S1 protein and the receptor binding domain (FIG. 12). Sera obtained 14, and 21 d after immunization show dose-dependent SARS-CoV-2 pseudovirus neutralization activity (FIG. 13).

Immunogenicity Study of the LNP-Formulated saRNA Encoding the Viral S Protein-V9 (SEQ ID NO: 7, 9) (RBS004.2)

To dissect the potency of the LNP-formulated saRNA vaccine coding for V9, BALB/c mice were immunized IM once as outlined in Table 3. The immunogenicity of the RNA vaccine will be investigated by focusing on the antibody immune response.

ELISA data 7, 14, and 21 d after the first immunization are available that show an early, dose-dependent immune activation against the S1 protein and the receptor binding domain (FIG. 14). Sera obtained 14, and 21 d after immunization show dose-dependent SARS-CoV-2 pseudovirus neutralization activity (FIG. 15).

The above data demonstrate an immune response for both the RBD with a trimerization domain ("V5") and the mutated full-length S protein ("V8"/"V9") in vivo in all tested platforms (including the vaccines BNT162a1, BNT162b1, BNT162b2, and BNT162c1). The antibody immune response was already seen at very early time points by ELISA (i.e., at 7 d post-immunization) Importantly, induced antibodies were able to efficiently neutralize SARS-COV-2 pseudovirus infection in vitro. Also, the induction of an antibody response using a very low immunization dose of 0.2 ag/mouse when using the modRNA platform (BNT162b1, BNT162b2) as well as the saRNA platform (BNT162c1) indicates a high potency of the vaccine candidates.

In mice, BNT162b2 induced a higher antigen-specific titer compared to BNT162b1 encoded with the identical RNA platform. As expected, the immunogenicity in mice against the antigens differs between the RNA platforms. In mice, the most immunogenic platform based on antigen-specific antibody induction is the modRNA followed by saRNA. The uRNA platform induces the lowest antigen-specific antibody titer.

Example 3: Selection of Formulation

The LNP delivery system was in general developed to effectively and safely deliver therapeutic nucleic acids into the cytosol of various cell types after local administration in vivo. The early formulation work was performed with several promising LNP formulations and surrogate RNA coding for luciferase. The aim of the experiments was to correlate the effect of different ionizable cationic lipids on the efficacy of RNA delivery by LNPs in vivo. Formulations were compared in terms of RNA encapsulation efficiency, apparent pKa, LNP size and polydispersity. Among the screened cationic lipids, ALC-0315 exhibited suitable physical characteristics regarding particle size, homogeneity, and RNA encapsulation efficiency.

Based on this the ALC-0315/DSPC/CHOL/ALC-0159 prototype was submitted for in vivo screening. The results presented in FIG. 16 summarize the in vivo testing of two independent pilot batches using luciferase (Luc) RNA. The results demonstrate improved potency of the ALC-0315 prototype as compared to an internal benchmark (ALC-0218). On the basis of these studies, ALC-0315 was identified as a highly potent cationic lipid and brought forward for further product development studies.

The formulation screening procedure described above involves intravenous administration resulting in delivery primarily to the liver. The mechanism of LNP uptake into hepatocytes is driven by binding of endogenous apolipoproteins to the LNP followed by receptor-mediated endocytosis e.g. through low density lipoprotein receptors. In order to investigate whether the same mechanism is involved for an intramuscular administration, Luc RNA containing LNPs comprising ALC-0315 were injected intravenously (0.3 mg/kg) and intramuscularly (0.2 mg/kg) into ApoE knockout mice in the presence or absence of recombinant human ApoE3. As control, wild-type C57Bl/6 mice were also treated by the different routes of administration. RNA-LNP were pre-incubated with recombinant human ApoE3 (1 mg encapsulated mRNA with 1 mg ApoE3) for 1 hour at room temperature (RT) prior to administration. Luc expression was monitored at 4, 24, 72 and 96 hours post administration (FIG. 17).

When mice were administered intravenously, Luc expression was detected in the wild-type C57Bl/6 mice. In the ApoE knockout mice Luc expression was significantly reduced however when preincubated with exogenous ApoE the expression of Luc was recovered to similar expression levels as wild-type mice (FIG. 18).

In vivo Luc expression experiments using mouse models showed, that similar mechanisms are involved in the uptake of RNA-LNP in case of intramuscular administration as for intravenous administration, and this is not only true for hepatocytes but also for the cells local to the administration site.

In vivo experiments after intramuscular administration of the final ALC-0315/DSPC/CHOL/ALC-0159, confirmed minimal drainage with regards to biodistribution, immunogenicity (vaccine activity) and tolerability.

Example 4: Immunogenicity Studies for Coronavirus Vaccine Candidates

Functional cellular immune responses to the vaccine candidates were detected by ELISpot assay using the IFN-γ ELISpot$^{PLUS}$ kit (Mabtech, Cat. No. 3321-4APT-2). In brief, spleens were removed from animals after sacrifice at day 28 after vaccination. Spleens were mechanically dissociated using the plunger of a syringe and a 70 μM cell strainer (Greiner Bio-One GmbH, Cat. No. 542070). Splenocytes were washed with an excess volume of DPBS (Thermo Fisher Scientific, Cat. No. 14190-094) followed by centrifugation at 300×g for 6 min at RT and discarding the supernatants. Erythrocytes were then lysed with erythrocyte lysis buffer (154 mM $NH_4Cl$, 10 mM $KHCO_3$, 0.1 mM EDTA) for 5 min at RT. The reaction was stopped with an excess volume of DPBS. After another washing step, cells were resuspended in RPMI 1640 medium (Gibco, Cat. no. 61870-010) supplemented with 10% FBS, 1% MEM Non-Essential Amino Acids Solution (Gibco, Cat. No. 11140-035), 1% sodium pyruvate (Gibco, Cat. No. 11360-039), 0.5% penicillin/streptomycin (Gibco, Cat. No. 15140-122), passed through a 70 μm cell mesh again and counted. CD8+ or CD4+ T cells were isolated from splenocyte cell suspensions using CD8a or CD4 MACS® MicroBeads (Miltenyi Biotec, Cat. No. 130-117-044 and 130-117-043) according to the manufacturer's instructions. In parallel, 96-well ELISpot plates were washed with PBS and blocked with medium (RPMI 1640 medium supplemented with 10% FBS, 1% MEM Non-Essential Amino Acids Solution, 1% sodium pyruvate, 0.5% penicillin/streptomycinmedium) for at least 30 min at 37° C. $1\times10^5$ CD8+ or CD4+ T cells in 100 μL medium were subsequently re-stimulated by addition of 50 μL peptide solution (irrelevant control peptide AH1 (2 μg/mL; sequence: SPSYVYHQF (SEQ ID NO: 35)), PepMix™ SARS-CoV-2 S-RBD (0.025 μg/mL per peptide; JPT, customized) or PepMix™ SARS-CoV-2 Spike Glycoprotein (0.1 μg/mL per peptide; JPT, Cat. No. PM-WCPV-S-2) and 50 μL of autologous bone marrow-derived dendritic cells in the IFN-γ ELISpot assay. Each condition was tested in duplicate. Plates were incubated overnight in a 37° C. humidified incubator with 5% $CO_2$ and after approximately 18 h, cells were removed from the plates. IFN-γ spots were detected according to the manufacturer's protocol. After plate drying for 2-3 h under the laminar flow, an ELISpot plate reader (ImmunoSpot® S6 Core Analyzer, CTL) was used to count and analyze spot numbers per well.

In addition to ELISpot assay, Luminex analyses were conducted to inform about the $T_H1$ or $T_H2$ nature of the detected T cell response. $5\times10^5$ splenocytes in 100 μL RPMI 1640 medium supplemented with 10% FBS, 1% MEM Non-Essential Amino Acids Solution, 1% sodium pyruvate, 0.5% penicillin/streptomycinmedium were transferred to a 96-well flat bottom cell culture plate. 100 μL irrelevant control peptide AH1 (2 μg/mL; sequence: SPSYVYHQF (SEQ ID NO: 35)), or PepMix™ SARS-CoV-2 Spike Glycoprotein (0.1 μg/mL per peptide; JPT, Cat. No. PM-WCPV-S-2) were added. The plates were incubated for 48 hours and supernatant thereafter was harvested for cytokine profiling. Cytokine concentrations in supernatants of the re-stimulated splenocytes were determined using a bead-based $T_H1/T_H2$ ProcartaPlex immunoassay (Thermo Fisher Scientific, Cat. No. EPX110-20820-901) according to the manufacturer's instructions. Fluorescence was measured with the Bioplex200 System (Biorad) and analyzed with ProcartaPlex Analyst 1.0 software (Thermo Fisher Scientific). The following analytes were measured: IFN-γ; IL-12p70; IL-13; IL-1 beta; IL-2; IL-4; IL-5; IL-6; TNF alpha; GM-CSF; IL-18.

For immunophenotyping, flow cytometry analysis was performed. Briefly, erythrocytes from 50 μL freshly drawn blood were lysed with ACK lysing buffer (Gibco) and cells were stained with fixable viability dye (eBioscience) and anti-CXCR5 (rat IgG2a) antibody in the presence of Fc block (both BD Bioscience) in flow buffer (DPBS (Gibco) supplemented with 2% FCS, 2 mM EDTA (both Sigma) and 0.01% sodium azide (Morphisto) for 20 minutes at room temperature. After staining with anti-rat IgG2a biotin in flow buffer for 20 minutes at 2-8° C., cells were stained extracellularly with antibodies against CD3, CD4, CD8a, CD38, CD44, PD-1, ICOS, CD62L, CXCR5, CD19 and streptavidin in Brilliant Stain Buffer Plus (BD Bioscience) diluted in flow buffer for 20 minutes at 2-8° C. Cells were fixed with 2% RotiHistofix (Roth) for 15 minutes at room temperature. Cells were resuspended in Perm buffer (FoxP3/Transcription Factor Staining Buffer Set, eBioscience) and incubated over night at 2-8° C. Permeabilized cells were intracellularly treated with Fc block for 10 minutes at 2-8° C. and stained with T-bet and GATA (BD Bioscience) antibodies for 30 minutes at 2-8° C. Cells were resuspended in flow buffer and acquired on a BD Symphony A3 flow cytometer (BD Bioscience) and analyzed with FlowJo 10.6.2.

For mouse B cell subtyping in draining lymph nodes, $2.5\times10^5$ lymph node cells were treated with Fc block for 15 minutes and stained extracellularly with antibodies against CD19, CD45R/B220, IgD, CD138, IgM, CD38, CD95/FAS, IgG1, IgG2a, CD73, GR-1, F4/80, CD4, CD8 in Brilliant Stain Buffer (BD Bioscience) for 20 minutes at 2-8° C. Cells were fixed with 2% RotiHistofix and incubated over night at 2-8° C.

Immunogenicity Study of BNT162b1 (RBP020.3)

To dissect the potency of the LNP-formulated modRNA vaccine coding for BNT162b1, BALB/c mice were immunized IM once as outlined in Table 3. The immunogenicity of the RNA vaccine was investigated by focusing on the cellular immune response.

After stimulation with an S protein- or RBD-specific peptide pool, but not after stimulation with irrelevant peptide AH1, both $CD4^+$ and $CD8^+$ T cells displayed IFN-γ responses in the IFN-γ ELISpot assay (FIG. 22). In Luminex analysis, cytokine production after peptide stimulation was confirmed for analytes that indicate a $T_H1$-driven immune response (FIG. 23).

Immunophenotyping analysis of blood 7 days after immunization (FIG. 24) revealed a significant increase in circulating T follicular helper cells (Tfh) and activated T cells. At day 12 after immunization, draining lymph nodes from immunized BALB/c mice were dissected and B cell subpopulation analysis was performed (FIG. 25). A significant increase in B cells was found in lymph nodes with detectable numbers of plasma cells, class switched B cells and IgG1 or IgG2a positive germinal center B cells. Both in blood and draining lymph node, an activation and maturation of the adaptive immune response was confirmed.

Immunogenicity Study of the LNP-Formulated modRNA Encoding the Viral P2-S Protein V8 (RBP020.1)

To dissect the potency of the LNP-formulated modRNA vaccine coding for RBP020.1, BALB/c mice were immunized IM once as outlined in Table 3. The immunogenicity of the RNA vaccine was investigated by focusing on the cellular immune response.

After stimulation with an S protein-specific peptide pool, but not after stimulation with irrelevant peptide AH1, both CD4+ and CD8+ T cells displayed IFN-γ responses in the IFN-γ ELISpot assay (FIG. 26). In Luminex analysis, cytokine production after peptide stimulation was confirmed for analytes that indicate a $T_H1$-driven immune response (FIG. 27).

Immunogenicity Study of the LNP-Formulated saRNA Encoding the Viral P2-S Protein V9 (RBS004.2)

To dissect the potency of the LNP-formulated saRNA vaccine coding for RBS004.2, BALB/c mice were immunized IM once as outlined in Table 3. The immunogenicity of the RNA vaccine was investigated by focusing on the cellular immune response.

After stimulation with an S protein-specific peptide pool, but not after stimulation with irrelevant peptide AH1, both CD4+ and CD8+ T cells displayed IFN-γ responses in the IFN-γ ELISpot assay (FIG. 28). In Luminex analysis, cytokine production after peptide stimulation was confirmed for analytes that indicate a $T_H1$-driven immune response (FIG. 29).

Immunogenicity Study of BNT162b3 Variants BNT162b3c and BNT162b3d

To get an idea about the potential potency of transmembrane-anchored RBD-based vaccine antigens (Schematic in FIG. 30; BNT162b3c (1) and BNT162b3d (2)), BALB/c mice were immunized IM once with 4 μg LNP-C12 formulated mRNA or with buffer as control. The non-clinical LNP-C12 formulated mRNAs were used as surrogate for the BNT162b3 variants BNT162b3c and BNT162b3d. The immunogenicity of the RNA vaccine was investigated by focusing on the antibody immune response.

ELISA data 6, 14 and 21 d after the first immunization show an early, dose-dependent immune activation against the S1 protein and the receptor binding domain (FIG. 31). Sera obtained 6, 14 and 21 d after immunization show high SARS-CoV-2 pseudovirus neutralization, correlating with the increase of IgG antibody titers (FIG. 32).

Example 5: Immunogenicity Studies for Coronavirus Vaccine Candidates in Non-Human Primates (NHP)

Six *Rhesus macaques* per group were immunized IM with 30 or 100 μg of BNT162b1 or with buffer on days 0 and 21. By 14 days after the first dose, antibodies that bound a recombinant S1 were readily detectable, and levels of S1-binding antibodies exceeded the upper limit of quantification of the assay (10,000 U/mL) by day 28. For comparison, S1-binding antibodies of 62 human COVID-19 convalescent sera, obtained after the onset of symptoms were analyzed. All timepoints throughout the two NHP groups significantly exceeded the mean of the human COVID-19 convalescent sera of 422 U/mL (FIG. 33(A)). The VNT geometric mean titers (GMTs) of sera from *Rhesus macaques* immunized with either dose level of BNT162b1 were detectable by 14 days after a single immunization and reached a geometric mean of 768 (30 μg dose level) or 1,714 (100 μg) by day 28 (FIG. 33(B)). The neutralization GMTs were 282 (30 μg) and 975 (100 μg) on day 35 (14 days after the boost) (FIG. 33(B)). Flow cytometry analysis of $CD4^+$ T cells from blood samples stimulated with a S peptide mix on day 42 revealed significant secretion of the $T_H1$ cytokines IFNγ, IL-2 and TNFα. Additionally, IL-21 secretion was significantly increased. IL-21 is known to play a critical role in B cell activation, expansion and plasma cell generation as well as the generation of Tfh. In contrast, no significant amounts of the $T_H2$ cytokine IL-4 were detected (FIG. 33(C)). In summary and in alignment to the results obtained in mice, BNT162b1 induced a high antibody immune with an early affinity maturation coming with a $T_H1$ biased immune response.

In summary, we demonstrate that the methyl-nucleoside m1ω-modified mRNA encoding the trimeric receptor binding domain from the SARS-CoV-2 S protein is protective in non-human primates.

Example 6: Phase 1/2 Study to Describe the Safety, Tolerability, and Immunogenicity of a COVID-19 RNA Vaccine Candidate (BNT162b1) in Healthy Adults 18 to 55 Years of Age We report safety, tolerability, and immunogenicity from a placebo-controlled, observer-blinded dose escalation trial among healthy adults randomized to receive 2 doses of 10 μg, 30 μg, or 100 μg of BNT162b1, a lipid nanoparticle (LNP)-formulated, nucleoside-modified, mRNA vaccine candidate that encodes trimerized SARS-CoV-2 spike glycoprotein RBD antigen. Local reactions and systemic events were dose-dependent, generally mild to moderate, and transient. RBD-binding IgG concentrations and SARS-CoV-2 neutralizing titers increased with dose level and after a second dose. Geometric mean neutralizing titers reached 1.8- to 2.8-fold that of a COVID-19 convalescent human serum panel.

The BNT162b1 vaccine candidate now being tested clinically incorporates nucleoside 1-methyl-pseudouridine modified RNA (modRNA) and encodes the receptor binding domain of the SARS-CoV-2 spike, a key target of neutralizing antibodies. The RBD antigen expressed by BNT162b1 is modified by the addition of a T4 fibritin-derived “foldon” trimerization domain to increase its immunogenicity. This RNA vaccine candidate is being tested in parallel in coordinated studies in Germany and in the US. Here, we present data obtained in the US study.

Methods

Study design and participants: This Phase 1/2, randomized, placebo-controlled, observer-blinded trial was conducted in the United States to assess the safety, tolerability, and immunogenicity of ascending dose levels of various BNT162 mRNA vaccine candidates. Assessment of three dose levels (10, 30, or 100 μg) of the BNT162b1 candidate was conducted at two sites in the United States. This study utilized a sentinel cohort design with progression and dose escalation taking place after review of data from the sentinel cohort at each dose level. Healthy men and nonpregnant women 18 to 55 years of age were enrolled. Key exclusion criteria included individuals with known infection with human immunodeficiency virus, hepatitis C virus, or hepatitis B virus; immunocompromised individuals and those with a history of autoimmune disease; those with increased risk for severe COVID-19; previous clinical or microbiological diagnosis of COVID-19; receipt of medications intended to prevent COVID-19; previous vaccination with any coronavirus vaccine; and a SARS-CoV-2 NAAT-positive nasal swab within 24 hours before study vaccination.

The final protocol and informed consent document were approved by institutional review boards for each of the investigational centers participating in this study, and this study was conducted in compliance with all International Council for Harmonisation (ICH) Good Clinical Practice (GCP) guidelines and the ethical principles of the Declaration of Helsinki. A signed and dated informed consent was required before any study-specific activity was performed.

Endpoints: The study's primary endpoints included: the proportion of participants reporting prompted local reactions, systemic events, and use of antipyretic and/or pain medication within 7 days after vaccination, AEs through 1 month after the last dose, and SAEs through 6 months after vaccination, and the proportion of sentinel cohort participants with clinical laboratory abnormalities 1 week after vaccination and grading shifts in laboratory assessments between baseline and 1 and 7 days after Dose 1 and between Dose 2 and 7 days after Dose 2. Secondary endpoints included: SARS-CoV-2 neutralizing geometric mean titers (GMTs); SARS-CoV-2 S1—binding IgG and RBD-binding IgG geometric mean concentrations (GMCs) 7 and 21 days after Dose 1 and 7 and 14 days after Dose 2; geometric mean fold rise (GMFR), ≥4-fold rise from baseline and geometric mean ratio (GMR) of SARS-CoV-2 serum neutralizing GMTs to SARS-CoV-2-antigen binding antibody GMCs at each time point.

Procedures: Study participants were randomly assigned to a vaccine group using an interactive web-based response technology system with each group comprising 15 participants (12 active vaccine recipients and 3 placebo recipients). Participants received two 0.5-mL doses of either BNT162b1 or placebo, administered by intramuscular injection into the deltoid muscle.

BNT162b1 incorporates a Good Manufacturing Process (GMP)-grade mRNA drug substance that encodes the trimerized SARS-CoV-2 spike glycoprotein RBD antigen. The mRNA is formulated with lipids as the mRNA-LNP drug product. The vaccine was supplied as a buffered-liquid solution for IM injection and was stored at −80° C. The placebo was a sterile saline solution for injection (0.9% sodium chloride injection, in a 0.5-mL dose).

Safety assessments for all participants included 4-hour observation after vaccination (for the first 5 participants vaccinated in each sentinel group, and a 30-minute observation (for the remainder of participants) for immediate AEs. The safety assessments also included self-reporting of prompted local reactions (redness, swelling, and pain at the injection site), systemic events (fever, fatigue, headache, chills, vomiting, diarrhea, muscle pain, and joint pain), and the use of antipyretic and/or pain medication in an electronic diary (e-diary) for 7 days after vaccination, reporting of unprompted AEs through 1 month after vaccination and SAEs through 6 months after the last vaccination. Hematology and chemistry assessments were conducted at screening, 1 and 7 days after Dose 1, and 7 days after Dose 2.

The protocol specified safety stopping rules for all sentinel-cohort participants. Both an internal review committee (IRC) and an external data monitoring committee (EDMC) reviewed all safety data.

Immunogenicity testing: 50 mL of blood was collected for immunogenicity assessments (SARS-CoV-2 serum neutralization assay, SARS-CoV-2 S1-specific IgG direct Luminex immunoassay, SARS-CoV-2 RBD-specific IgG direct Luminex immunoassay and nonvaccine antigen (NVA) Ig direct Luminex immunoassay) before each study vaccination, at 7 and 21 days after Dose 1 and at 7, 14, 1 month and 6 months after Dose 2.

The SARS-CoV-2 neutralization assay used a previously described strain of SARS-CoV-2 (USA_WA1/2020) that had been rescued by reverse genetics and engineered by the insertion of an mNeonGreen (mNG) gene into open reading frame 7 of the viral genome. This reporter virus generates similar plaque morphologies and indistinguishable growth curves from wild-type virus. Serial dilutions of heat inactivated sera were incubated with the reporter virus for 1 hour at 37° C. before inoculating Vero E6 cell monolayers. Infected foci were detected by fluorescence between 16-24 hours after inoculation by the addition of Hoechst 33342 Solution and counted with a Cytation 7 Cell Imaging Multi-Mode Reader.

Statistical analysis: The sample size for the sentinel cohort of the study was not based on statistical hypothesis testing. The primary safety objective was evaluated by descriptive summary statistics for local reactions, systemic events, abnormal hematology and chemistry laboratory parameters, and AEs and SAEs for each vaccine group. A 3-tier approach was used to summarize AEs. The secondary immunogenicity objectives were descriptively summarized at the various time points.

Results

Between 4 May 2020 and 19 Jun. 2020, 76 subjects were screened, and 45 participants were randomized and vaccinated. Twelve participants per dose level (10 μg, 30 μg, or 100 μg) were vaccinated with BNT162b1 on Days 0 and 21, and 9 participants received placebo (FIG. 34). The study population consisted of healthy male and nonpregnant female participants, 18 to 55 years of age with a mean age of 35.4 years (minimum 19 and maximum 54 years). Overall, 51.1% of participants were male and 48.9% were female. Most participants were white (82.2%) and non-Hispanic/non-Latino (93.3%).

Safety and Tolerability

In the 7 days after either vaccination, pain at the injection site was the most frequently local reaction, reported by 58.3% (7/12) in the 10 μg and 100.0% (12/12 each) in the 30 μg and 100 μg BNT162b1 groups and by 22.2% (2/9) of placebo recipients after Dose 1 and by 83.3% and 100.0% of BNT162b1 recipients at the 10 μg and 30 μg dose levels, respectively, after Dose 2. All local reactions were mild or moderate in severity except for one report of severe pain following Dose 1 of 100 μg BNT162b1.

The most common systemic events reported in the 7 days after vaccination were mild to moderate fatigue and headache in both BNT162b1 and placebo recipients. Systemic events increased with dose level and were reported in a greater number of subjects after the second dose (10 μg and 30 μg groups). Following Dose 1, fever ≥38.0° C. was reported by 50.0% (6/12) of BNT162b1 recipients in the 100 ag group and 8.3% (1/12) of participants each in the 10 μg and 30 μg groups. Following Dose 2, 8.3% (1/12) of participants in the 10 μg group and 75.0% (9/12) of participants in the 30 μg group reported fever ≥38.0° C. No Grade 4 systemic events or fever were reported. (FIGS. 35 & 36). Most local reactions and systemic events peaked by Day 2 after vaccination and resolved by Day 7. Based on the reactogenicity profile, participants who received an initial 100 μg dose did not receive a second vaccination.

Adverse events were reported by 50.0% (6/12) of participants who received 10 μg or 30 μg of BNT162b1, by 58.3% (7/12) of those who received 100 μg of BNT162b1, and by 11.1% (1/9) of placebo recipients. Two participants reported a severe AE, one at the 30 μg dose level (Grade 3 pyrexia 2 days after vaccination) and one at the 100 μg dose level (sleep disturbance 1 day after vaccination). Related AEs were reported by 25% (3/12) to 50% (6/12) of BNT162b1 recipients and by 11.1% (1/6) of those who received placebo. No serious adverse events were reported.

No Grade 1 or greater change in routine clinical laboratory values or laboratory abnormalities were observed for most subjects after either of the BNT162b1 vaccinations. The most notable changes were decreases in lymphocyte count in 8.3% (1/12), 45.5% (5/11), and 50.0% (6/12) of participants who received 10 μg, 30 μg, or 100 μg, respectively, of BNT162b1. One participant each at the 10 μg (8.3%) and 30 μg (9.1%) dose levels and 4 participants at the 100 μg dose level (33.3%) had Grade 3 decreases in lymphocytes. These hematological changes, which were noted in blood drawn 1-3 days after Dose 1, returned to normal 6-8 days after vaccination. None of the changes in laboratory values after vaccination were associated with clinical findings. In addition, Grade 2 neutropenia was noted 6-9 days after the second dose of 10 μg or 30 μg BNT162b1, in 1 participant each. The neutrophil count was not repeated for these two subjects however they continue be followed in the study and no adverse events or clinical manifestation of neutropenia have been reported to date.

Immunogenicity

RBD-binding IgG concentrations and SARS-CoV-2 neutralizing titers were assessed in sera drawn at baseline and at 7 and 21 days after the first dose and 7 days (Day 28) after the second dose of BNT162b1 (FIG. 37(A)). By 21 days after the first dose (for all three dose levels), geometric mean concentrations (GMCs) of RBD-binding IgG were 534-1,778 units/mL, compared to 602 units/mL for a panel of COVID-19 convalescent human sera. By 7 days after the second dose (for the 10 μg and 30 μg dose levels) RBD-binding IgG GMCs had increased to 4,813-30,207 units/mL. Because the participants who received a first dose of 100 μg BNT162b1 did not receive a second dose, the development of the antibody response without a second dose could not be evaluated, and there was no further increase in RBD-binding antibody concentration beyond 21 days after the first dose among participants in this dosing group. Highly elevated RBD-binding antibody concentrations persisted to Day 35 (two weeks after the second dose) in the participants who received 10 μg and 30 μg dose levels of BNT162b1.

Modest increases in SARS-CoV-2 neutralizing geometric mean titers (GMTs) were observed 21 days after Dose 1(FIG. 37(B)). Substantially greater serum neutralizing GMTs were achieved 7 days after participants received a second 10 μg or 30 μg dose, reaching 168-267, compared to 94 for the COVID-19 convalescent serum panel.

DISCUSSION

The RNA-based vaccine candidate BNT162b1 was safe and well tolerated. All dose levels exhibited a tolerability and safety profile consistent with those previously observed for mRNA-based vaccines. A clear dose level response was observed after Doses 1 and 2 in adults 18-55 years of age. Reactogenicity was generally higher after the second dose, but symptoms resolved within a few days after presentation. Based on the tolerability profile of the first dose at the 100 μg dose level, participants randomized to the 100 μg group did not receive a second vaccination. Transient decreases in lymphocytes (Grades 1-3) were observed within a few days after vaccination; however, lymphocyte counts returned to baseline within 6-8 days in all participants. These laboratory abnormalities were not associated with clinical findings. Lymphopenia following vaccination is most likely explained by transient migration of lymphocytes into the tissues.

Robust immunogenicity was observed after vaccination with BNT162b1. RBD-binding IgG concentrations were detected at Day 21 and substantially increased 7 days after the booster dose given at Day 21. After the first dose, the RBD-binding IgG GMCs in vaccinated participants (10 μg dose level) were similar to those observed in a panel of 38 sera from COVID-19 convalescing humans obtained 20-40 days after the onset of symptoms and at least 14 days after the start of asymptomatic convalescence. In sera drawn from the 30 μg and 100 μg dose level cohorts, GMCs were substantially higher than in the convalescent serum panel. After the booster vaccinations (Dose 2) with 10 μg or 30 μg BNT162b1, the RBD-binding IgG GMCs were 8.0-fold to 50-fold higher than the convalescent serum panel GMC.

Sera from vaccinated participants were also tested in the SARS-CoV-2 neutralization assay. Neutralization titers were measurable at Day 21 for all dose levels. At Day 28 (7 days after the booster dose), substantial SARS-CoV-2 neutralization titers were observed. The virus neutralizing GMTs after the 10 μg and 30 μg booster vaccinations (Dose 2) were, respectively, 1.8-fold and 2.8-fold higher than the neutralizing GMT of the convalescent serum panel. As the 100 μg dose level cohort was not boosted, no corresponding data for immunogenicity after a second vaccination are available.

These clinical findings for the BNT162b1 vaccine candidate are very encouraging and provide strong evidence supporting accelerated development and at-risk manufacturing to maximize the opportunity for the soonest availability of a prophylactic vaccine to prevent COVID-19.

Example 7: Concurrent Antibody and, T Cell and Cytokine Responses Elicited by a COVID-19 RNA Vaccine In this example, we present characterisation of antibody and T cell responses after BNT162b1 vaccination from a non-randomized open-label phase I/II trial in healthy adults, 18-55 years of age. Two doses, of 1 μg, 10 μg, 30 μg and 50 μg of BNT162b1 administered 21 days apart elicited concomitant antibody, and robust $CD4^+$ and $CD8^+$ T cell responses. All subjects exhibited strong antibody responses with IgG concentrations significantly above those observed in COVID-19 convalescent human sera. Day 43 SARS-CoV-2 serum neutralising geometric mean titers were in the range of 0.7-fold (1 μg) to 3.3-fold (50 μg) compared to those of a panel of COVID-19 convalescent human sera, and were broadly active against diverse SARS-CoV-2 spike variants. Interferon (IFN)γ, an immune stimulatory cytokine with anti-viral properties, was produced by a high frequency of RBD-antigen specific $CD8^+$ T and numerous $CD4^+$ T cells. IL-12p70, which reinforces a $T_H1$ immune cell profile, was detected in RBD-stimulated immune cells. The robust RBD-specific antibody, T-cell and favorable cytokine responses by the BNT162b1 mRNA vaccine suggests a potential for multiple beneficial protective mechanisms against COVID-19.

Materials and Methods

Clinical Trial Design

Study BNT162-01 (NCT04380701—Germany trial) is an ongoing, first-in-human, Phase I/II, open-label dose-finding clinical trial to assess the safety, tolerability, and immunogenicity of ascending dose levels of various intramuscularly administered BNT162 mRNA vaccine candidates. Healthy men and non-pregnant women 18 to 55 years (amended to add 56-85 of age) of age are eligible. Key exclusion criteria included previous clinical or microbiological diagnosis of COVID-19; receipt of medications to prevent COVID-19; previous vaccination with any coronavirus vaccine; a positive serological test for SARS-CoV-2 IgM and/or IgG at the screening visit; and a SARS-CoV-2 NAAT-positive nasal swab within 24 hours before study vaccination; those with increased risk for severe COVID-19; immunocompromised individuals, those with known infection with HIV, hepatitis C virus, or hepatitis B virus and those with a history of autoimmune disease. The primary endpoints of the study are safety and immunogenicity.

In the part of the study reported here five dose levels (1 μg, 10 μg, 30 μg, 50 μg or 60 μg) of the BNT162b1 candidate were assessed at one site in Germany with 12 healthy volunteers per dose level in a dose escalation and de-escalation design. Sentinel dosing was performed in each dose-escalation cohort. Progression in that cohort and dose escalation required data review by a safety review committee. Subjects received a BNT162b1 prime dose on day 1, and a boost dose on day 22±2. Serum for antibody assays was obtained on day 1 (pre-prime), 8±1 (post-prime), 22±2 (pre-boost), 29±3 and 43±4 (post-boost). PBMCs for T cell studies were obtained on day 1 (pre-prime) and 29±3 (post-boost). One subject of the 10 μg, and one subject of the 50 μg dose cohort left the study prior to the boost immunisation due to withdrawal of consent and private reasons.

The presented data comprise the BNT162b1-immunised cohorts only and are based on a preliminary analysis with a data extraction date of Jul. 13, 2020, focused on analysis of vaccine-induced immunogenicity (secondary endpoint) descriptively summarised at the various time points. All participants with data available were included in the immunogenicity analyses.

The trial was carried out in Germany in accordance with the Declaration of Helsinki and Good Clinical Practice Guidelines and with approval by an independent ethics committee (Ethik-Kommission of the Landessrztekammer Baden-Wurttemberg, Stuttgart, Germany) and the competent regulatory authority (Paul-Ehrlich Institute, Langen, Germany). All subjects provided written informed consent.

Manufacturing of RNA

BNT162b1 incorporates a Good Manufacturing Practice (GMP)-grade mRNA drug substance that encodes the trimerized SARS-CoV-2 spike glycoprotein RBD antigen. The RNA is generated from a DNA template by in vitro transcription in the presence of 1-methylpseudouridine-5'-triphosphate (m1YTP; Thermo Fisher Scientific) instead of uridine-5'-triphosphate (UTP). Capping is performed co-transcriptionally using a trinucleotide cap 1 analogue (($m_2^{7,3'-O}$)Gppp($m^{2'-O}$)ApG; TriLink). The antigen-encoding RNA contains sequence elements that increase RNA stability and translation efficiency in human dendritic cells (Holtkamp, S. et al., Blood 108, 4009-4017 (2006); Orlandini von Niessen, A. G. et al., Mol. Ther. 27, 824-836 (2019)). The mRNA is formulated with lipids to obtain the RNA-LNP drug product. The vaccine was transported and supplied as a buffered-liquid solution for IM injection and was stored at −80° C.

Proteins and Peptides

A pool of 15-mer peptides overlapping by 11 aa and covering the whole sequence of the BNT162b1-encoded SARS-CoV-2 RBD, was used for ex vivo stimulation of PBMCs for flow cytometry, IFNγ ELISpot and cytokine profiling. CEF (CMV, EBV, influenza virus; HLA class I epitope peptide pool) and CEFT (CMV, EBV, influenza virus, tetanus toxoid; HLA class II epitope peptide pool) (both JPT Peptide Technologies) were used as controls for general T-cell reactivity.

Human Convalescent Sera and PBMC Panel

Human SARS-CoV-2 infection/COVID-19 convalescent sera (n=38) were drawn from subjects 18-83 years of age at least 14 days after PCR-confirmed diagnosis and at a time when the subjects were asymptomatic. Serum donors had symptomatic infections (n=35), or had been hospitalized (n=1). Sera were obtained from Sanguine Biosciences (Sherman Oaks, Calif.), the MT Group (Van Nuys, Calif.) and Pfizer Occupational Health and Wellness (Pearl River, N.Y.). Human SARS-CoV-2 infection/COVID-19 convalescent PBMC samples (n=6) were collected from subjects 41-79 years of age 45-59 days after PCR-confirmed diagnosis when subjects were asymptomatic. PBMC donors had asymptomatic/mild infections (n=4; clinical score 1 and 2) or had been hospitalized (n=2; clinical score 4 and 5). Blood samples were obtained from the Frankfurt University Hospital (Germany).

Cell Culture and Primary Cell Isolation

Vero cells (ATCC CCL-81) and Vero E6 cells (ATCC CRL-1586) were cultured in Dulbecco's modified Eagle's medium (DMEM) with GlutaMAX™ (Gibco) supplemented with 10% fetal bovine serum (FBS) (Sigma-Aldrich). Cell lines were tested for *mycoplasma* contamination after receipt and before expansion and cryopreservation. Peripheral blood mononuclear cells (PBMCs) were isolated by Ficoll-Hypaque (Amersham Biosciences) density gradient centrifugation and cryopreserved prior to subsequent analysis.

RBD Binding IgG Antibody Assay

A recombinant SARS-CoV-2 RBD containing a C-terminal Avitag™ (Acro Biosystems) was bound to streptavidin-coated Luminex microspheres. Heat-inactivated subject sera were diluted 1:500, 1:5,000, and 1:50,000. Following an overnight incubation at 2-8° C. while shaking, plates were washed in a solution containing 0.05% Tween-20. A secondary fluorescently labelled goat anti-human polyclonal antibody (Jackson Labs) was added for 90 minutes at room temperature while shaking, before plates were washed once more in a solution containing 0.05% Tween-20. Data were captured as median fluorescent intensities (MFIs) using a Luminex reader and converted to U/mL antibody concentrations using a reference standard curve with arbitrary assigned concentrations of 100 U/mL and accounting for the serum dilution factor. Three dilutions are used to increase the likelihood that at least one result for any sample will fall within the useable range of the standard curve. Assay results were reported in U/mL of IgG. The final assay results are expressed as the geometric mean concentration of all sample dilutions that produced a valid assay result within the assay range.

SARS-CoV-2 Neutralisation Assay

The neutralisation assay used a previously described strain of SARS-CoV-2 (USA_WA1/2020) that had been rescued by reverse genetics and engineered by the insertion of an mNeonGreen (mNG) gene into open reading frame 7 of the viral genome (Xie, X. et al., Cell Host Microbe 27, 841-848.e3 (2020)). This reporter virus generates similar plaque morphologies and indistinguishable growth curves from wild-type virus. Viral master stocks ($2\times10^7$ PFU/mL) were grown in Vero E6 cells as previously described (Xie, X. et al., Cell Host Microbe 27, 841-848.e3 (2020)). Serial dilutions of heat-inactivated sera were incubated with the reporter virus ($2\times10^4$ PFU per well for a final multiplicity of infection (MOI) of 0.5 to yield approximately a 10-30% infection rate of the Vero monolayer) for 1 hour at 37° C. before inoculating Vero CCL81 cell monolayers (targeted to have 8,000 to 15,000 cells per well) in 96-well plates to allow accurate quantification of infected cells. Total cell counts per well were enumerated by nuclear stain (Hoechst 33342) and fluorescent virally infected foci were detected 16-24 hours after inoculation with a Cytation 7 Cell Imaging Multi-Mode Reader (Biotek) with Gen5 Image Prime version 3.09. Titers were calculated in GraphPad Prism version 8.4.2 by generating a 4-parameter (4PL) logistical fit of the percent neutralisation at each serial serum dilution. The 50% neutralisation titre ($VNT_{50}$) was reported as the interpolated reciprocal of the dilution yielding a 50% reduction in fluorescent viral foci.

VSV-SARS-CoV-2 Spike Variant Pseudovirus Neutralisation Assay

VSV-SARS-CoV-2-S pseudoparticle generation and neutralisation assays were performed as previously described (Baum, A. et al., Science, eabd0831 (2020). doi:10.1126/science.abd0831). Briefly, human codon optimized SARS-CoV-2 spike (GenBank: MN908947.3) was synthesised (Genscript) and cloned into an expression plasmid. SARS-CoV-2 complete genome sequences were downloaded from GISAID Nucleotide database (www.gisaid.org) (last accessed 24 Aug. 2020). Sequences were curated and genetic diversity of the Spike-encoding gene was assessed across high quality genome sequences using custom pipelines. Amino acid substitutions were cloned into the spike expression plasmid using site-directed mutagenesis. HEK293T cells (ATCC CRL-3216) were seeded (culture medium: DMEM high glucose (Life Technologies) supplemented with 10% heat-inactivated fetal bovine serum (FBS; Life Technologies) and Penicillin/Streptomycin/L-Glutamine (Life Technologies)) and transfected the following day with spike expression plasmid using Lipofectamine LTX (Life Technologies) following the manufacturer's protocol. At 24 hours post-transfection at 37° C., cells were infected with the VSVΔG:mNeon/VSV-G virus diluted in Opti-MEM (Life Technologies) at a multiplicity of infection of 1. Cells were incubated 1 hour at 37° C., washed to remove residual input virus and overlaid with infection medium (DMEM high glucose supplemented with 0.7% Low IgG BSA (Sigma), sodium pyruvate (Life Technologies) and 0.5% Gentamicin (Life Technologies)). After 24 hours at 37° C., the supernatant containing VSV-SARS-CoV-2-S pseudoparticles was collected, centrifuged at 3000×g for 5 minutes to clarify and stored at −80° C. until further use.

For pseudovirus neutralisation assays, Vero cells (ATCC CCL-81) were seeded in 96-well plates in culture medium and allowed to reach approximately 85% confluence before use in the assay (24 hours later). Sera were serially diluted 1:2 in infection medium starting with a 1:40 dilution. VSV-SARS-CoV-2-S pseudoparticles were diluted 1:1 in infection medium for a fluorescent focus unit (ffu) count in the assay of ~1000. Serum dilutions were mixed 1:1 with pseudoparticles for 30 minutes at room temperature prior to addition to Vero cells and incubation at 37° C. for 24 hours. Supernatants were removed and replaced with PBS (Gibco), and fluorescent foci were quantified using the SpectraMax i3 plate reader with MiniMax imaging cytometer (Molecular Devices). Neutralisation titers were calculated in GraphPad Prism version 8.4.2 by generating a 4-parameter logistical (4PL) fit of the percent neutralisation at each serial serum dilution. The 50% pseudovirus neutralisation titre ($pVNT_{50}$)

was reported as the interpolated reciprocal of the dilution yielding a 50% reduction in fluorescent viral foci.

IFNγ ELISpot.

IFNγ ELISpot analysis was performed ex vivo (without further in vitro culturing for expansion) using PBMCs depleted of $CD4^+$ and enriched for $CD8^+$ T cells ($CD8^+$ effectors), or depleted of $CD8^+$ and enriched for $CD4^+$ T cells ($CD4^+$ effectors). Tests were performed in duplicate and with a positive control (anti-CD3 monoclonal antibody CD3-2 (1:1,000; Mabtech)). Multiscreen filter plates (Merck Millipore) pre-coated with IFNγ-specific antibodies (ELISpotPro kit, Mabtech) were washed with PBS and blocked with X-VIVO 15 medium (Lonza) containing 2% human serum albumin (CSL-Behring) for 1-5 hours. Per well, $3.3\times10^5$ effector cells were stimulated for 16-20 hours with an overlapping peptide pool representing the vaccine-encoded RBD. Bound IFNγ was visualized using a secondary antibody directly conjugated with alkaline phosphatase followed by incubation with BCIP/NBT substrate (ELISpotPro kit, Mabtech). Plates were scanned using an AID Classic Robot ELISPOT Reader and analysed by ImmunoCapture V6.3 (Cellular Technology Limited) or AID ELISPOT 7.0 software (AID Autoimmun Diagnostika). Spot counts were displayed as mean values of each duplicate. T-cell responses stimulated by peptides were compared to effectors incubated with medium only as negative control using an in-house ELISpot data analysis tool (EDA), based on two statistical tests (distribution-free resampling) according to Moodie et al. (Moodie, Z., et al., J. Immunol. Methods 315, 121-32 (2006); Moodie, Z. et al., Cancer Immunol. Immunother. 59, 1489-501 (2010)), to provide sensitivity while maintaining control over false positives.

To account for varying sample quality reflected in the number of spots in response to anti-CD3 antibody stimulation, a normalisation method was applied to enable direct comparison of spot counts/strength of response between individuals. This dependency was modelled in a log-linear fashion with a Bayesian model including a noise component (unpublished). For a robust normalization, each normalisation was sampled 1000 times from the model and the median taken as normalized spot count value. Likelihood of the model: $\log \lambda_E = \alpha \log \lambda_P + \log \beta_j + \sigma\varepsilon$, where $\lambda_E$ is the normalized spot count of the sample, $\alpha$ is a stable factor (normally distributed) common among all positive controls $\lambda_p$, $\beta_j$ a sample j specific component (normally distributed) and $\sigma\varepsilon$ is the noise component, of which $\sigma$ is Cauchy distributed and $\varepsilon$ is Student's-t distributed. $\beta_j$ ensures that each sample is treated as a different batch.

Flow Cytometry

Cytokine-producing T cells were identified by intracellular cytokine staining. PBMCs thawed and rested for 4 hours in OpTmizer medium supplemented with 2 μg/mL DNAseI (Roche), were restimulated with a peptide pool representing the vaccine-encoded SARS-CoV-2 RBD (2 μg/mL/peptide; JPT Peptide Technologies) in the presence of GolgiPlug (BD) for 18 hours at 37° C. Controls were treated with DMSO-containing medium. Cells were stained for viability and surface markers in flow buffer ((DPBS (Gibco) supplemented with 2% FCS (Biochrom), 2 mM EDTA (Sigma-Aldrich)) for 20 minutes at 4° C. Afterwards, samples were fixed and permeabilized using the Cytofix/Cytoperm kit according to manufacturer's instructions (BD Biosciences). Intracellular staining was performed in Perm/Wash buffer for 30 minutes at 4° C. Samples were acquired on a FACS VERSE instrument (BD Biosciences) and analysed with FlowJo software version 10.5.3 (FlowJo LLC, BD Biosciences). RBD-specific cytokine production was corrected for background by subtraction of values obtained with DMSO-containing medium. Negative values were set to zero. Cytokine production in FIG. 42(B) was calculated by summing up the fractions of all $CD4^+$ T cells positive for either IFNγ, IL-2 or IL-4, setting this sum to 100% and calculating the fraction of each specific cytokine-producing subset thereof.

Cytokine Profiling

Human PBMCs were restimulated for 48 hours with SARS-CoV-2 RBD peptide pool (2 μg/mL final concentration per peptide). Stimulation with DMSO-containing medium served as negative controls. Concentrations of TNF, IL-1β and IL-12p70 in supernatants were determined using a bead-based, 11-plex $T_H1/T_H2$ human ProcartaPlex immunoassay (Thermo Fisher Scientific) according to the manufacturer's instructions. Fluorescence was measured with a Bioplex200 system (Bio-Rad) and analysed with ProcartaPlex Analyst 1.0 software (Thermo Fisher Scientific). RBD-specific cytokine production was corrected for background by subtraction of values obtained with DMSO-containing medium. Negative values were set to zero.

Results

Study Design and Analysis Set

Between Apr. 23 2020 and May 22 2020, 60 subjects were vaccinated with BNT162b1. Twelve participants per 1 μg, 10 μg, 30 μg, and 50 μg dose levels received a first dose on day 1 and were boosted on day 22, and 12 participants received a 60 μg prime dose on Day 1 only (FIG. 43). The study population consisted of healthy males and non-pregnant females with a mean age of 41 years (range 19 to 55 years) with equal gender distribution. Most participants were Caucasian (96.7%) with one African American and one Asian subject (1.7% each). Preliminary data analysis was focused on immunogenicity (Table 4).

TABLE 4

Subject disposition and analysis sets.

| BNT162b1 | | | Antibody analysis | | | | | T-cell analysis | |
|---|---|---|---|---|---|---|---|---|---|
| Cohort | Prime | Boost | Day 1 | Day 8 ± 1 | Day 22 ± 2 | Day 29 ± 3 | Day 43 ± 4 | Day 1 | Day 29 ± 3 |
| 1 μg | 12 | 12 | 12 | 12 | 12 | 12 | 12 | 8 | 8 |
| 10 μg | 12 | 11 | 12 | 12 | 12 | 11 | 11 (10) | 10 (6) | 10 (6) |
| 30 μg | 12 | 12 | 12 | 12 | 12 | 12 | 12 (10) | 10 (7) | 10 (7) |
| 50 μg | 12 | 11 | 12 | 12 | 12 | 11 | 6 | 8 (5) | 8 (5) |
| 60 μg | 12 | N/A | 12 | 12 | 11 | 12 | N/A | N/A | N/A |

Antibody analysis: Values indicated number of subjects for which virus neutralisation assay was performed. Values in parentheses indicate number of subjects for which RBD binding IgG antibody assay was performed.
T-cell analysis: Values indicated number of subjects for which IFNγ ELISpot was performed. Values in parentheses indicate number of subjects for which flow cytometry was performed.
N/A: Samples not yet available.

Briefly, no serious adverse events (SAE), no unexpected toxicities, and no withdrawals due to related AEs were observed. Most reported solicited AEs were signs and symptoms of vaccine reactogenicity, typically with onset within the first 24 hours post immunisation, such as systemic, and injection site reactions, chiefly symptoms of pain and tenderness (FIG. 44). Symptomatology was mostly mild or moderate in intensity with occasional severe (Grade 3) AEs such as fever, chills, headache, muscle and joint pain, and injection site reactions. All AEs resolved spontaneously, mostly within 24 hours of onset and could be managed with simple measures (e.g. paracetamol). Based on the reactogenicity reported after the first dose, participants who had received an initial 60 μg dose did not receive a second 60 μg dose. Whereas no relevant change in routine clinical laboratory values occurred after BNT162b1 vaccination, a transient increase of the inflammatory marker C-reactive protein (CRP) and temporary reduction of blood lymphocyte counts were observed in a dose-dependent manner in vaccinated subjects (FIG. 45). Based on our previous clinical experience with RNA vaccines, the latter is likely attributable to innate immune stimulation-related transient redistribution of lymphocytes (Kamphuis, E., et al., Blood 108, 3253-61 (2006)).

Vaccine-Induced Antibody Response

RBD-binding IgG concentrations and SARS-CoV-2 neutralising titers were assessed at baseline, 7 and 21 days after the BNT162b1 prime dose (days 8 and 22), and 7 and 21 days after the boost dose (days 29 and 43), except for the 60 μg cohort, which received prime only (FIG. 39).

All subjects including those who received the 1 μg dose showed a strong, dose-dependent vaccine-induced antibody response. Twenty-one days after the priming dose (for the four dose levels ranging from 1-50 μg), geometric mean concentrations (GMCs) of RBD-binding IgG were dose dependently about 265-1,672 U/mL (FIG. 39). Seven days after the boosting dose (day 29) RBD-binding IgG GMCs in subjects treated with 1-50 μg BNT162b1 strongly increased dose-dependently to about 2,015-25,006 U/mL. At day 43 (21 days after boost), RBD-binding antibody GMCs were in the range of about 3,920-22,700 U/mL in BNT162b1 vaccinated individuals as compared to about 602 U/mL measured in a panel of sera from 38 SARS-CoV-2 infection convalescent patients (18-83 years of age) drawn at least 14 days after PCR-confirmed diagnosis. In the 60 μg dose cohort with prime dose only, RBD-binding IgG GMCs were about 1,058 U/mL by day 29 indicating the necessity of the second dose for boosting the antibody titer.

SARS-CoV-2 neutralising antibody geometric mean titers (GMTs) increased modestly in a dose-dependent manner 21 days after the priming dose (FIG. 40(A)). Substantially higher serum neutralizing GMTs were achieved 7 days after the boost dose, reaching about 36 (1 μg dose level), about 158 (10 μg dose level), about 308 (30 μg dose level), and about 578 (50 μg dose level), compared to about 94 for the convalescent serum panel. On day 43 (21 days after the boost), depending on the dose level, the neutralising antibody GMT were further increased to about 62 (1 μg dose), were relatively stable at about 126 (10 μg dose), or decreased slightly to about 157 (30 μg dose), and about 309 (50 μg dose). Neutralising antibody GMTs were strongly correlated with RBD-binding IgG GMC (FIG. 40(B)). In summary, neutralising antibody titers were largely in the range of those previously reported in the US study with BNT162b1.

Further, by 7 days after the second dose, sera of vaccinated subjects displayed broad neutralising activity across a panel of seventeen SARS-CoV-2 spike variants identified in publicly available SARS-CoV-2 sequences, including sixteen RBD mutants (Baum, A. et al., Science, eabd0831 (2020). doi:10.1126/science.abd0831) and the dominant spike variant D614G (Baum, A. et al., Science, eabd0831 (2020). doi:10.1126/science.abd0831) (FIG. 40(C)).

Vaccine-Induced T Cell Responses $CD4^+$ and $CD8^+$ T cell responses in BNT162b1 immunized subjects were characterized prior to prime vaccination (day 1) and on day 29 after prime (7 days after boost vaccination) using direct ex vivo IFNγ ELISPOT with PBMCs from 36 subjects across the 1 μg to 50 μg dose cohorts (FIG. 41). In this assay, $CD4^+$ or $CD8^+$ T cell effectors were stimulated overnight with overlapping peptides representing the full-length sequence of the vaccine-encoded RBD. Of 36 subjects, 34 (94.4%, including all subjects treated with ≥10 μg BNT162b1) mounted RBD-specific $CD4^+$ T cell responses. The magnitude varied between individuals with the strongest CD4 T cell responses being more than 10-fold of the memory responses observed against a panel of cytomegalovirus (CMV), Epstein Barr virus (EBV), influenza virus and tetanus toxoid-derived immuno-dominant peptides in the same subjects (FIG. 41(A-C)). No $CD4^+$ T cell responses were detectable at baseline, except for one subject with a low number of preexisting RBD-reactive $CD4^+$ T cells, which increased significantly after vaccination (normalized mean spot count from 63 to 1,519, in the 50 μg dose cohort). The strength of RBD-specific $CD4^+$ T cell responses correlated positively with both RBD-binding IgG and with SARS-CoV-2 neutralising antibody titers (FIG. 41(D), FIG. 46(A)), in line with the concept of intramolecular help (Sette, A. et al., Immunity 28, 847-58 (2008)). The two subjects lacking $CD4^+$ response had no detectable $VNT_{50}$ titers either (FIG. 41(D)).

Vaccine-induced $CD8^+$ T cell responses, some strong ones were mounted by the majority of subjects (29/36, 80.6%) (FIG. 41(A)) and were quite comparable with memory responses against CMV, EBV, Influenza virus and tetanus toxoid in the same subjects (FIG. 41(B, C)). The strength of RBD-specific $CD8^+$ T cell responses correlated positively with vaccine-induced $CD4^+$ T cell responses but did not significantly correlate with SARS-CoV-2 neutralizing antibody titers (FIG. 46(B, C)).

Of note, although at 1 μg BNT162b1 the immunogenicity rate was lower (6/8 responding subjects), the magnitude of vaccine-induced $CD4^+$ and $CD8^+$ T cells in some subjects was almost as high as with 50 μg BNT162b1 (FIG. 41(A)). To assess functionality and polarization of RBD-specific T cells, cytokines secreted in response to stimulation with the vaccine antigen were determined by intracellular staining (ICS) with IFNγ, IL-2 and IL-4 specific antibodies in pre- and post-vaccination PBMCs of 18 BNT162b1 immunised subjects. RBD-specific $CD4^+$ T cells secreted IFNγ, IL-2, or both, but did not secrete IL-4 (FIG. 42(A-C)). Similarly, a fraction of RBD-specific $IFN\gamma^+CD8^+$ T cells also secreted IL-2.

The mean fraction of RBD-specific T cells within total circulating T cells obtained by BNT162b1 vaccination was substantially higher than that observed in six subjects recovered from COVID-19. Frequency of RBD-specific $IFN\gamma^+$ $CD8^+$ T cells reached up to several percent of total peripheral blood $CD8^+$ T cells (FIG. 42(C)). Analysis of supernatants of PBMCs stimulated ex vivo with overlapping RBD peptides from a subgroup of five vaccinated subjects showed cognate release of proinflammatory cytokines TNF, IL-1β and IL-12p70 (FIG. 42(D)).

In summary, these findings indicate that BNT162b1 induces functional and proinflammatory $CD4^+$/$CD8^+$ T cell responses in almost all subjects, with $T_H1$ polarized helper response.

DISCUSSION

We observed concurrent production of neutralising antibodies, activation of virus-specific $CD4^+$ and $CD8^+$ T cells, and robust release of immune-modulatory cytokines such as IFNγ, which represents a coordinated immune response to counter a viral intrusion (for review Vabret, N. et al., Immunity 52, 910-941 (2020)). IFNγ represents a key cytokine for several anti-viral responses. Indeed, patients with IFNγ gene polymorphism related to impaired IFNγ activity have been shown to display 5-fold increased susceptibility to SARS (Chong, W. P. et al., BMC Infect. Dis. 6, 82 (2006)). Also, IFNγ acts in synergy with type I interferons to inhibit replication of SARS-CoV-2 (Sainz, B., et al., Virology 329, 11-7 (2004)). The robust production of IFNγ from $CD8^+$ T cells indicates a favourable immune response with both anti-viral and immune-augmenting properties.

Importantly, the detection of IFNγ, IL-2 and IL-12p70 but not IL-4 indicates a favorable $T_H1$ profile and the absence of a potentially deleterious $T_H2$ immune response. $CD4^+$ and $CD8^+$ T cells may confer long lasting immunity against corona viruses as indicated in SARS-CoV-1 survivors, where $CD8^+$ T-cell immunity persisted for 6-11 years (Vabret, N. et al., Immunity 52, 910-941 (2020); Ng, O.-W. et al., Vaccine 34, 2008-14 (2016)).

Some cases of asymptomatic virus exposure have been associated with cellular immune response without seroconversion indicating that SARS-Cov-2 specific T cells could be relevant in disease control even in the absence of neutralising antibodies (Gallais, F. et al. (2020). doi:medRxiv: 10.1101/2020.06.21.20132449). Almost all vaccinated volunteers mounted RBD-specific T cell responses detected with an ex vivo ELISpot assay, which was performed without prior expansion of T cells that captures only high-magnitude T cell responses. Although the strength of the T-cell responses varied considerably between subjects, we observed no clear dose dependency of the T-cell response strength in the dose range of 1 μg to 50 μg, indicating that stimulation and robust expansion of T cells might be accomplished at the lowest mRNA-encoded immunogen levels.

The study confirms the dose-dependency of RBD-binding IgG and neutralisation responses, reproduces our previous findings for 10 and 30 μg dose levels in the US trial, and shows that neutralising antibody titers are further increased by a prime/boost regimen at 50 μg.

A notable observation is that two injections of BNT162b1 at a dose level as low as 1 μg are capable of inducing RBD-binding IgG levels higher than those observed in convalescent sera, and serum neutralising antibody titers that are still increasing up to day 43. Considering that the magnitude of a protective neutralising antibody titer is not known, and given the substantial T-cell responses we observed for some subjects in the 1 μg cohort may hold the promise that a considerable fraction of individuals may benefit even from this lowest tested dose level.

A purely RBD-directed immunity might be considered prone to escape of the virus by single amino acid changes in this small domain. However, neutralisation of 17 pseudotyped viruses, 16 of which enter cells using a spike with a different RBD variant found in circulating strains and one of which uses the dominant spike variant D614G, alleviates this potential concern.

Example 8: Summary of Safety and Immunogenicity Data from Stage 1 of COVID-19 Vaccine BNT162

This example provides additional safety and immunogenicity data for the BNT162b1 and BNT162b2 vaccine candidates. These safety and tolerability data, as well as immunoglobulin G (IgG) binding and severe acute respiratory syndrome coronavirus 2 (SARS-CoV-2) neutralization titer data, are coming from US participants in a Stage 1 US Study of these vaccine candidates.

For BNT162b1, the following is observed:

For 10 μg to 30 μg dose levels, reactogenicity (particularly systemic events) increases with increasing dose level in 18 to 55-year-old and 65 to 85-year-old participants. Reactogenicity (particularly systemic events) increased after Dose 2 compared to Dose 1.

For BNT162b2, the following is observed:

Dose level- and dose number-dependent increases in reactogenicity were minimal to modest in either age group. Based on all available data, the reactogenicity profile observed with BNT162b2 (and particularly SEQ ID NO:20) is quite favorable.

The immunogenicity data presented herein, focusing on SARS-CoV-2 neutralizing responses post-dose 2, allow to conclude the following:

For BNT162b1 at Day 28 (7 days post-dose 2):

Neutralizing antibody responses elicited after immunization with 10 μg and 30 μg dosages (where data are available in both age groups) are higher in adults 18 to 55 years of age compared to the 65 to 85-year-old group. In the 65 to 85 year old group, neutralizing antibody responses after 20 μg and 30 μg dosages were similar, although numerically higher at the 20 μg dose level.

For BNT162b2 (particularly, SEQ ID NO:20) at Day 28 (7 days post-dose 2):

Neutralizing antibody responses after the 20 μg dosage (where data are available in both age groups) were higher in the 18 to 55 year old group compared to the 65 to 85-year-old group. In the 18 to 55 year-old group, neutralizing antibody responses were higher after receiving 20 μg compared to 10 μg dose levels. The S1 IgG binding antibody data in FIG. 56, and comparisons of post-dose 1 responses across dose levels that are highest at the 30 μg dose level, suggest that neutralizing antibody levels will likely also be higher for the 30 μg dose level post-dose 2, as levels of binding antibody correlate well with neutralizing antibody levels. In the 65 to 85 year old group, neutralizing antibody responses after 20 μg and 30 μg doses were higher at the 30 μg dose level.

The data overall show similar neutralizing antibody responses post-dose 2 between BNT162b1 and BNT162b2.

Safety and Tolerability of BNT162b1

18-55 Years of Age Groups

Safety data are available for this age group through post-dose 2 for all dose levels, except for 20 μg, which for now has partial data available through post-dose 2 (and 100 μg where a second dose has not been administered at the recommendation of the Internal Review Committee (IRC)). Local reactions are shown in FIG. 48. Systemic events are shown in FIG. 49.

Immunogenicity of BNT162b1

65-85 Years of Age Groups

Immunogenicity data are available for this age group through post-dose 2 for all dose levels. RBD-binding IgG geometric mean concentrations (GMCs) are shown in FIG. 50. SARS-CoV-2 neutralizing geometric mean titers (GMTs) are shown in FIG. 51.

Safety and Tolerability of BNT162b2

18-55 Years of Age Groups

Safety data are available for this age group through post-dose 2 for all dose levels. Local reactions are shown in FIG. 52. Systemic events are shown in FIG. 53.

65-85 Years of Age Groups

Safety data are available for this age group through post-dose 2 for all dose levels, however, the data for the 10 μg dose level are only partial. Local reactions are shown in FIG. 54. Systemic events are shown in FIG. 55.

Immunogenicity of BNT162b2

18-55 Years of Age Groups

Immunogenicity data are available for this age group through post-dose 1 for the 30 μg dose level and post-dose 2 for the 10 μg and 20 μg dose levels. S1-binding IgG GMCs are shown in FIG. 56. SARS-CoV-2 neutralizing GMTs are shown in FIG. 57.

65-85 Years of Age Groups

Immunogenicity data are available for this age group through post-dose 2 for the 20 μg and 30 μg dose levels. S1-binding IgG GMCs are shown in FIG. 58. SARS-CoV-2 neutralizing GMTs are shown in FIG. 59.

Conclusions

The local tolerability profiles of BNT162b1 and BNT162b2 (and particularly SEQ ID NO:20) and the immune response data are similar between the 2 candidates. BNT162b2 (particularly SEQ ID NO:20) may show a favorable systemic reactogenicity profile (particularly in the 65 to 85-year-old group). When selecting the dose level for BNT162b2 (particularly SEQ ID NO:20), the SARS-CoV-2 neutralizing antibody response level in the 65 to 85-year-old group could be of weight to maximize the neutralizing antibody responses in this age group, which is at highest risk of severe disease. Comparing the neutralizing antibody levels in the 20 μg and 30 μg older adult cohorts in this study, the 30 μg dose level showed higher neutralizing antibody levels than those in the 20 μg cohort (FIG. 59). In comparison to the neutralizing antibody level of a human convalescent serum panel (HCS) with a GMT of 94, the GMT at the 30 μg dose level was 1.6 times the GMT of the HCS; the GMT at the 20 μg dose level was 0.9 times the GMT of HCS. Thus, both showed neutralizing antibody titres at least comparable to that of the human convalescent serum panel. The 38 human SARS-CoV-2 infection/COVID-19 convalescent sera were drawn from participants 18 to 83 years of age, at least 14 days after PCR-confirmed diagnosis, and at a time when participants were asymptomatic. The serum donors predominantly had symptomatic infections (35/38), and one had been hospitalized. The sera were obtained from Sanguine Biosciences (Sherman Oaks, Calif.), the MT Group (Van Nuys, Calif.), and Pfizer Occupational Health and Wellness (Pearl River, N.Y.). In addition, S1-IgG antibody binding concentrations in both older (FIG. 58, post-dose 2) and younger (FIG. 56, post-dose 1) adult cohorts also favored the selection of the 30 μg dose level. Preliminary human T cell data that are being generated in a German trial with BNT162b2 are confirming the robust $CD4^+$ and $CD8^+$ expected for the RNA platform. With these considerations, it is proposed to use BNT162b2 (particularly SEQ ID NO:20) at the 30 μg dose level to proceed into Phase 2b/3 because this dose and construct provides the optimum combination of a favorable reactogenicity profile and a robust immune response, likely to afford protection against COVID-19 in younger and older adults.

Example 9: Immunology of COVID-19 Vaccine BNT162

To support progression to Phase 2/3 in adults 18-85 years of age, provided herein are nonclinical and clinical data summarizing the T cell response following BNT162b2 immunization in mice and in humans enrolled in a trial with BNT162. The following immunogenicity data are provided:

1. Preliminary and unaudited mouse immunogenicity data: IFNγ ELISpot (FIG. 60), intracellular cytokine staining, and Luminex quantification of cytokines produced following BNT162b2 immunization.

2. From a German trial (BNT162-01): IFNγ ELISpot (FIG. 61, FIG. 62, FIG. 63) for BNT162b2 at the 10 μg dose level in 18-55 year old participants before the first dose and 7 days after dose 2.

T Cell Responses for BNT162b2 in Mice

Four groups of eight female BALB/c mice were immunized on day 0 with doses of 0.2 μg, 1 μg or 5 μg per animal BNT162b2 (particularly SEQ ID NO:20), or with the buffer alone (control group), by intramuscular (IM) injection. On days 12 and 28, spleens were collected for splenocyte isolation and analysis of T-cell responses using IFNγ ELISpot assays. Luminex assays and intracellular cytokine staining (ICS) were performed to assess cytokine responses. A high fraction of splenocytes of both CD4+ and CD8+ T-cell phenotypes isolated from BNT162b2-immunized mice on days 12 and 28 after immunization, when re-stimulated ex vivo with a full-length S peptide mix, exerted a strong antigen-specific IFNγ- and IL-2-response in ELISpot and flow cytometry assays (FIGS. 60(A and B)). Splenocytes harvested on day 28 and stimulated with the full-length S peptide pool produced high levels of the $T_H1$ cytokines IL-2 and IFNγ with correspondingly minimal levels of the $T_H2$ cytokines IL-4, IL-5, and IL-13 in multiplex immunoassays (FIG. 60(C)).

T Cell Responses in Humans for BNT162b2 from German Study

To evaluate the T cell phenotype elicited by immunization of humans with BNT162b2 (particularly SEQ ID NO:20), IFNγ ELISpot was performed on peripheral blood mononuclear cells (PBMCs) obtained from participants in a German study.

IFNγ ELISpot

Vaccine-elicited T cell responses were determined using CD4- or CD8-depleted PBMCs obtained from subjects prior to dose 1 and on day 29 (7 days after dose 2). IFNγ ELISpot data were generated for 5 subjects immunized with 10 μg of BNT162b2 (particularly SEQ ID NO:20) at day 1 and 22. Post-vaccination spike-specific ex vivo CD4+ and CD8+ T cell responses were detected in 5/5 (100%) subjects, respectively. All responses were minimal or undetectable in the prevaccination samples. The responses are considered vaccine induced (FIG. 61, FIG. 62, FIG. 63).

The BNT162b2 vaccine-elicited, antigen specific CD8+ and CD4+ T cell responses stimulated by S peptide pool 1 (N-terminal portion of the spike, which includes the receptor binding domain [RBD]) and S peptide pool 2 (C-terminal portion of the spike) were comparable to or higher than the memory responses in the same subjects against CMV, EBV, influenza virus, and tetanus toxoid (FIG. 63).

Conclusions

These data for the BNT162b2 vaccine candidate confirm prior results obtained in preclinical models and in humans immunized with modRNA (nucleoside-modified) platforms. The data indicate that modRNA elicits substantial Th1-type $CD4^+$ and $CD8^+$ T cell responses.

Example 10: A Trimeric SARS-CoV-2 Receptor-Binding Domain RNA Vaccine is Highly Immunogenic and Protective in Non-Human Primates Here, we report the design and non-clinical development of the BNT162b1 vaccine candidate. We demonstrate that nucleoside-modified mRNA encoding a structurally stable, trimerised receptor-binding domain (RBD) of SARS-CoV-2, encapsulated in lipid nanoparticles (LNP) for effective intramuscular delivery, elicits strong antibody and $T_H1$-dominated cellular immune responses in mice. Immunisation of mice with single doses of BNT162b1 elicited substantial dose level-dependent increases in pseudovirus neutralisation titers and strong IFNγ-positive $CD4^+$ and $CD8^+$ T-cell responses. Prime-boost vaccination of *Rhesus macaques* with BNT162b1 elicited authentic SARS-CoV-2 neutralising geometric mean titers, 2.6 to 6.0 times those of a SARS-CoV-2 convalescent human serum panel. Upon SARS-CoV-2 infectious challenge, the immunised macaques had either no or more transient presence of viral RNA in the nose and lungs than did non-immunised control macaques.

Materials and Methods

Ethics Statement.

All mouse studies were performed at BioNTech SE, and protocols were approved by the local authorities (local welfare committee), conducted according to FELASA recommendations and in compliance with the German Animal Welfare Act and Directive 2010/63/EU. Only animals with an unobjectionable health status were selected for testing procedures.

Immunisations for the non-human primate (NHP) study were performed at the University of Louisiana at Lafayette-New Iberia Research Center (NIRC), which is accredited by the Association for Assessment and Accreditation of Laboratory Animal Care (AAALAC, Animal Assurance #: 000452). The work was in accordance with USDA Animal Welfare Act and Regulations and the NIH Guidelines for Research Involving Recombinant DNA Molecules, and Biosafety in Microbiological and Biomedical Laboratories. All procedures performed on these animals were in accordance with regulations and established guidelines and were reviewed and approved by an Institutional Animal Care and Use Committee or through an ethical review process. Infectious SARS-CoV-2 challenge for the NHP study was performed at the Southwest National Primate Research Center. Animal husbandry followed standards recommended by AAALAC International and the NIH Guide for the Care of Use of Laboratory Animals. This study was approved by the Texas Biomedical Research Institute Animal Care and Use Committee.

Protein and Peptide Reagents.

A purified recombinant SARS-CoV-2 RBD fusion with a mouse IgG1 constant region was used as a target for Western Blot and tagged with a human Fc-tag (both Sino Biological) was used in ELISA to detect SARS-CoV-2 S-specific IgG. A purified recombinant RBD with a histidine tag (Sino Biological) was used for surface plasmon resonance (SPR) spectroscopy. An overlapping 15-mer peptide pool of the S protein was used for ELISpot, cytokine profiling and intracellular cytokine staining. A peptide control (SPSYVYHQF (SEQ ID NO: 35), derived from gp70 AH-1 (Slansky, J. E. et al., Immunity 13, 529-538, 2000)) was used as control for ELISpot assays. All peptides were obtained from JPT Peptide Technologies.

Human Convalescent Sera.

Human COVID-19 convalescent sera (n=38) were drawn from donors 18-83 years of age at least 14 days after PCR-confirmed diagnosis and at a time when the participants were asymptomatic. Serum donors had symptomatic infections (35/38), or had had been hospitalised (1/38). Sera were obtained from Sanguine Biosciences (Sherman Oaks, Calif.), the MT group (Van Nuys, Calif.) and Pfizer Occupational Health and Wellness (Pearl River, N.Y.).

Cell Culture.

Human embryonic kidney (HEK)293T/17 and Vero-76 cells (both ATCC) were cultured in Dulbecco's modified Eagle's medium (DMEM) with GlutaMAX™ (Gibco) supplemented with 10% fetal bovine serum (Sigma-Aldrich). Cell lines were tested for *mycoplasma* contamination after receipt, before expansion and cryopreservation. Vero E6 and Vero CCL81 (both ATCC) cells were cultured in DMEM (Gibco) containing 2% HyClone fetal bovine serum and 100 U/mL *penicillium*/streptomycin (Gibco). Expi293F™ cells were grown in Expi293™ media and transiently transfected using ExpiFectamine™293 (all from Thermo Fisher Scientific).

Manufacturing of In Vitro Transcribed RNA.

To generate the template for RNA synthesis, a DNA fragment encoding a fusion protein composed of the signal peptide (SP, amino acids 1-16), the SARS-CoV-2 S RBD (GenBank: MN908947) and a T4 fibritintrimerisation motif ('foldon'), was cloned into a starting plasmid vector with backbone sequence elements for improved RNA stability and translational efficiency (Orlandini von Niessen, A. G. et al., Mol Ther 27, 824-836; 2019; Holtkamp, S. et al., Blood 108, 4009-4017, 2006). Non-coding backbone elements included the regions from the T7 promoter to the 5' and 3' UTR plus a poly(A) tail (100 nucleotides) interrupted by a linker (A30LA70, 10 nucleotides). The DNA was purified, spectrophotometrically quantified, and in vitro transcribed by T7 RNA polymerase in the presence of a trinucleotide cap1 analogue ($(m_2^{7,3'-O})Gppp(m^{2'-O})ApG$; TriLink) and of N1-methylpseudouridine-5'-triphosphate (m1ψTP; Thermo Fisher Scientific) instead of uridine-5'-triphosphate (UTP) (Grudzien-Nogalska, E. et al., Methods in molecular biology (Clifton, N.J.) 969, 55-72, 2013). RNA was purified using magnetic particles (Berensmeier, S., Appl. Microbiol. Biotechnol. 73, 495-504, 2006), integrity assessed by microfluidic capillary electrophoresis (Agilent Fragment Analyser), and concentration, pH, osmolality, endotoxin level and bioburden determined.

Lipid-Nanoparticle Formulation of the RNA.

Purified RNA was formulated into LNPs using an ethanolic lipid mixture ofionisable cationic lipid and transferred into an aqueous buffer system via diafiltration to yield an LNP composition similar to one previously described (Maier, M. A. et al., Molecular therapy: the journal of the American Society of Gene Therapy 21, 1570-1578, 2013). BNT162b1 was stored at −70° C. at a concentration of 0.5 mg/mL.

mRNA Transfection.

HEK293T/17 cells were transfected with transfection reagent-mixed BNT162b1 RNA or BNT162b1 by incubation for 18 hours. Non-LNP formulated mRNA (1 μg for Western blot and flow cytometry, 2.5 μg for immunofluorescence) was diluted in Opti-MEM medium (Thermo Fisher Scientific) and mixed with the transfection reagents according to the manufacturer's instructions (RiboJuice, Merck Millipore).

Western Blot Analysis.

A lysate of BNT162b1 RNA transfected HEK293T/17 cells was analysed by denaturing SDS-PAGE with 10% Mini-Protean TGX precast polyacrylamide gels (Bio-Rad) and Western blot. Transfer to a nitrocellulose membrane (Carl Roth) was performed using a semi-dry transfer system (Trans-Blot Turbo Transfer System, Bio-Rad). Blotted proteins were detected with a primary rabbit polyclonal antibody elicited by a recombinant S1 fragment of the SARS-CoV S (SinoBiological) and a secondary anti-rabbit horse raddish peroxidase (HRP)-conjugated antibody (Sigma Aldrich). Blots were developed with SuperSignal West Femto chemiluminescent substrate (Thermo Fisher Scientific) and imaged with a Bio-Rad ChemiDoc system using the Image Lab software version 5.0.

Immunofluorescence.

Transfected HEK293T/17 cells were fixed in 4% paraformaledehyde (PFA) and permeabilised in phosphate-buffered saline (PBS)/0.2% Triton X-100. Free binding sites were blocked and cells incubated with a rabbit polyclonal antibody recognising the S1 Subunit (SinoBiological) and anti-rabbit IgG secondary antibody (Jackson ImmunoResearch), or labelled Concanavalin A (Invitrogen). DNA was stained with Hoechst (Life Technologies). Images were acquired with a Leica SP8 confocal microscope.

Flow Cytometry.

Transfected HEK293T/17 cells were stained with Fixable Viability Dye (eBioscience). After fixation (Fixation Buffer, Biolegend), cells were permeabilised (Perm Buffer, eBioscience) and stained with a monoclonal SARS-CoV-2 spike S1 antibody (SinoBiological). Cells were acquired on a FACSCanto II flow cytometer (BD Biosciences) using BD FACSDiva software version 8.0.1 and analysed by FlowJo software version 10.6.2 (FlowJo LLC, BD Biosciences).

For mouse T-cell analysis in peripheral blood, erythrocytes from 50 μL freshly drawn blood were lysed (ACK lysing buffer, Gibco), and cells were stained with Fixable Viability Dye (eBioscience) and primary antibodies in the presence of Fc block in flow buffer (DPBS [Gibco] supplemented with 2% FCS, 2 mM EDTA [both Sigma] and 0.01% sodium azide [Morphisto]). After staining with secondary biotin-coupled antibodies in flow buffer, cells were stained extracellularly against surface markers with directly labelled antibodies and streptavidin in Brilliant Stain Buffer Plus (BD Bioscience) diluted in flow buffer. Cells were fixed with 2% RotiHistofix (Carl Roth) and permeabilised (Perm Buffer, FoxP3/Transcription Factor Staining Buffer Set, eBioscience) overnight. Permeabilised cells were intracellularly treated with Fc block and stained with antibodies against transcription factors in Perm Buffer.

For mouse T-cell analysis in lymphoid tissues, $1\times10^6$ lymph node and $4\times10^6$ spleen cells were stained for viability and extracellular antigens with directly labelled antibodies. Cells were washed in 2% RotiHistofix and fixed (Fix/Perm Buffer, FoxP3/Transcription Factor Staining Buffer Set, eBioscience) overnight. Intracellular staining was performed as described for blood T-cell staining. For mouse B-cell subtyping in lymphoid tissues, $2.5\times10^1$ lymph node and $1\times10^6$ spleen cells were treated with Fc block, stained for viability and extracellular antigens as described for blood T-cell staining and fixed with 2% RotiHistofix overnight. For mouse intracellular cytokine staining in T cells, $1\times10^6$ lymph node and $4\times10^6$ spleen cells were ex vivo restimulated with 0.2 μg/mL final concentration per peptide of full-length S peptide mix in the presence of GolgiStop and GolgiPlug (both BD Bioscience) for 5 hours. Cells were stained for viability and extracellular antigens as described for lymphoid T-cell staining. Cells were fixed with 2% RotiHistofix and permeabilised overnight. Intracellular staining was performed as described for blood T-cell staining.

Mouse cells were acquired on a BD Symphony A3 or BD Celesta (B-cell subtyping) flow cytometer (BD Bioscience) using BD FACSDiva software version 9.1 or 8.0.1.1, respectively, and analysed with FlowJo 10.6 (FlowJo LLC, BD Biosciences).

Protein Expression and Purification.

To express the RBD-foldon encoded by BNT162b1 for biochemical and structural analysis, DNA corresponding to the RNA coding sequence was cloned into the pMCG1309 vector. A plasmid encoding amino acids 1-615 of human ACE2 with C-terminal His-10 and Avi tags was generated for transient expression of the ACE2 peptidase domain (ACE2 PD) in Expi293F cells. The ACE2/$B^0$ AT1 complex was produced by co-expression of two plasmids in Expi293F cells, one of them encoding ACE2 amino acids 1-17 followed by haemagglutinin and Strep II tags and ACE2 amino acids 18-805, and the other containing a methionine followed by a FLAG tag and amino acids 2-634 of human $B^0$AT1.

Secreted ACE2 PD was isolated from conditioned cell culture medium using Nickel Excel resin (GE Healthcare) followed by gel filtration chromatography on a Superdex200 10/30 column (GE Healthcare) in PBS. Approximately 5 mg of purified ACE2 PD was covalently attached per 1 mL of 4% beaded agarose by amine coupling using AminoLink Plus resin (Thermo Fisher Scientific). The RBD-trimer was purified from conditioned medium by affinity capture with the ACE2 PD crosslinked agarose and was eluted from the resin with 3 M $MgCl_2$. Following dialysis, the protein was concentrated and purified by gel filtration using a Superdex200 10/300 column in HEPES-buffered saline (HBS) with 10% glycerol. Purification of the ACE2/$B^0$ AT1 complex was based on the procedure described previously (Yan, R. et al., Science (New York, N.Y.) 367, 1444-1448, 2020). To form the ACE2/$B^0$ AT1/RBD-trimer complex, ACE2/$B^0$ AT1 aliquots were combined with purified RBD-foldon diluted in ACE2/$B^0$AT1 size exclusion chromatography buffer (25 mM Tris pH 8.0, 150 mM NaCl, 0.02% glyco diosgenin) for a 3:1 molar ratio of RBD-trimers to ACE2 protomers. After incubation at 4° C. for 30 minutes, the sample was concentrated and resolved on a Superose 6 Increase 10/300 GL column. Peak fractions containing the complex were pooled and concentrated.

Surface Plasmon Resonance Spectroscopy.

Binding kinetics of murine RBD-specific serum IgGs was determined using a Biacore T200 device (Cytiva) with HBS-EP running buffer (BR100669, Cytiva) at 25° C. Carboxyl groups on the CM5 sensor chip matrix were activated with a mixture of 1-ethyl-3-(3-dimethylaminopropyl) carbodiimidehydrochloride (EDC) and N-hydroxysuccinimide (NHS) to form active esters for the reaction with amine groups. Anti-mouse-Fc-antibody (Jackson ImmunoResearch) was diluted in 10 mM sodium acetate buffer pH 5 (30 μg/mL) for covalent coupling to immobilisation level of ~10,000 response units (RU). Free N-hydroxysuccinimide esters on the sensor surface were deactivated with ethanolamine.

Mouse serum was diluted 1:50 in HBS-EP buffer and applied at 10 μL/min for 30 seconds to the active flow cell for capture by immobilised antibody, while the reference flow cell was treated with buffer. Binding analysis of captured murine IgG antibodies to RBD-His (Sino Biological Inc.) was performed using a multi-cycle kinetic method with concentrations ranging from 1.5625 to 50 nM. An association period of 180 seconds was followed by a dissociation period of 600 seconds with a constant flow rate of 40 μL/min and a final regeneration step. Binding kinetics were calculated using a global kinetic fit model (1:1 Langmuir, Biacore T200 Evaluation Software Version 3.1, Cytiva).

Biolayer Interferometry.

Binding of RBD-foldon to the ACE2-PD was measured by biolayer interferometry on an Octet RED384 (FortéBio) in a buffer composed of 10 mM HEPES pH 7.5, 150 mM NaCl and 1 mM EDTA at 25° C. Avi-tagged human ACE2 PD was immobilised on streptavidin-coated sensors. Binding data were collected for 10 minutes of association and 15 minutes of dissociation for a concentration series of RBD-trimer. Data were reference-subtracted and fit to a 1:1 binding model with $R^2$ value greater than 0.96 to determine kinetics and affinity of binding, using Octet Data Analysis Software v10.0 (FortéBio). The dissociation rate of interaction ($k_d$) was slower than the limit of measurement of the instrument, and the binding affinity ($K_D$) was estimated using an assumed dissociation rate $k_d$ of $1\times10^{-6}$ $s^{-1}$.

Electron Microscopy of Negatively Stained Samples.

Purified RBD-trimer protein in 4 μL was applied to a glow-discharged copper grid overlaid with formvar and amorphous carbon (Ted Pella). Staining was performed with Nano-W organotungstate stain (Nanoprobes) according to the manufacturer's protocol, and the sample imaged using an FEI TF-20 microscope operating at 200 kV, with a magnification of 62,000× and defocus of −2.5 μm. Micrographs were contrast transfer function (CTF)-corrected in RELION using CTFFIND-4.1 (Rohou, A. & Grigorieff, N., Journal of structural biology 192, 216-221, 2015). A small manually picked dataset was used to generate 2D references for auto-picking. The resulting particle set was subjected to 2D classification in RELION 3.0.6 (Zivanov, J. et al., eLife 7; 10.7554/eLife.42166 (2018)).

Cryo-Electron Microscopy.

Purified ACE2/$B^0$ AT1/RBD-trimer complex at 6 mg/mL in 4 μL was applied to gold Quantifoil R1.2/1.3 200 mesh grids glow discharged in residual air for 30 seconds at 20 mA using a Pelco Easiglow. The sample was blotted using a Vitrobot Mark IV for 5 seconds with a force of −3 before being plunged into liquid ethane cooled by liquid nitrogen. In total, 7,455 micrographs were collected from a single grid on a Titan Krios operating at 300 keV equipped with a Gatan K2 Summit direct electron detector in super-resolution mode at a magnification of 165,000×, for a magnified pixel size of 0.435 Å at the specimen level. Data were collected over a defocus range of −1.2 to −3.4 μm with a total electron dose of 52.06 $e^-/Å^2$ fractionated into 40 frames over a 6-second exposure for 1.30 $e^-/Å^2$/frame. Initial motion correction was performed in Warp (Tegunov, D. & Cramer, P., Nature methods 16, 1146-1152, 2019), during which super-resolution data were binned to give a pixel size of 0.87 Å. Corrected micrographs were imported into RELION 3.1-beta (Zivanov, J. et al., eLife 7; 10.7554/eLife.42166 (2018)) for CTF estimation with CTFFIND-4.1 (Rohou, A. & Grigorieff, N., Journal of structural biology 192, 216-221, 2015). Particles were picked using the LaPlacian-of-Gaussian particle picking algorithm as implemented in RELION and extracted with a box size of 450 pixels. References obtained by 2D classification were used for a second round of reference-based auto-picking, yielding a dataset of 715,356 particles. Particle heterogeneity was filtered out with 2D and 3D classification with a mask size of 280 nm to filter out the non-ACE2-bound RBD copies in each RBD-trimer, yielding a set of 87,487 particles, which refined to 3.73 Å with $C_2$ symmetry. Refinement after subtraction of micelle and $B^0$ AT1 density from the particles yielded an improved map of 3.24 Å. The atomic model from PDB ID 6M17 (Yan, R. et al., Science (New York, N.Y.) 367, 1444-1448, 2020) was rigid-body fitted into the 3.24 Å density, then flexibly fitted to the density using real-space refinement in Phenix (Adams, P. D. et al., Acta crystallographica. Section D, Biological crystallography 66, 213-221, 2010) alternating with manual building in Coot (Emsley, P. et al., Acta crystallographica. Section D, Biological crystallography 66, 486-501, 2010). The microscope was operated for image acquisition using SerialEM software version 3.8.0 beta (Mastronarde, D. N., Journal of structural biology 152, 36-51, 2005). Biolayer interferometry data was collected with Octet Data Acquisition software version 10.0.0.87 and processing was performed using ForteBio Data Analysis software version 10.0.

Immunisation.

Mice. Female BALB/c mice (Janvier; 8-12 weeks) were randomly allocated to groups. BNT162b1 was diluted in PBS, 300 mM sucrose or saline (0.9% NaCl) and injected IM into the gastrocnemius muscle at a volume of 20 μL under isoflurane anaesthesia.

*Rhesus macaques* (*Macaca* mulatta). Male *Rhesus macaques* (2-4 years) were randomly assigned to receive either BNT162b1 or saline placebo control in 0.5 mL volume administered by IM injection in the left quadriceps muscle on Days 0 and 21. Blood for serum and PBMCs was collected in compliance with animal protocol 2017-8725-023 approved by the NIRC Institutional Animal Care and Use Committee. Animals were anesthetised with ketamine HCl (10 mg/kg; IM) during blood collection and immunisation, and monitored for adequate sedation.

SARS-CoV-2 Challenge of *Rhesus Macaques*.

The SARS-CoV-2 inoculum was obtained from a stock of $2.1\times10^6$ PFU/mL previously prepared at Texas Biomedical Research Institute (San Antonio, Tex.), aliquoted into single use vials, and stored at −70° C. The working virus stock was generated from two passages of the SARS-CoV-2 USA-WA1/2020 isolate (a $4^{th}$ passage seed stock purchased from BEI Resources; NR-52281) in Vero E6 cells. The virus was confirmed to be SARS-CoV-2 by deep sequencing and identical to the published sequence (GenBank accession number MN985325.1).

BNT162b1-immunised (n=6) and age-matched saline control-immunised (n=6) male *rhesus macaques* (control) were challenged with $1\times10^6$ plaque forming units of SARS-CoV-2 USA-WA1/2020 isolate, split equally between the intranasal (IN; 0.2 mL) and intratracheal (IT; 0.2 mL) routes as previously described (Singh, D. K. et al., SARS-CoV-2 infection leads to acute infection with dynamic cellular and inflammatory flux in the lung that varies across nonhuman primate species, 2020). The challenge was performed 41 to 48 days after the second immunisation. A separate sentinel group of non-immunised age- and sex-matched animals (n=3) received only DMEM supplemented with 10% FCS IN (0.2 mL) and IT (0.2 mL). Approximately two weeks prior to challenge, animals were moved to the Animal Biosafety Level 3 (ABSL-3) facility at Southwest National Primate Research Center (SNPRC; San Antonio, Tex.). Animals were monitored regularly by a board-certified veterinary clinician for rectal body temperature, weight and physical examination. Specimen collection was performed under tiletamine zolazepam (Telazol) anaesthesia as described (Singh, D. K. et al., SARS-CoV-2 infection leads to acute infection with dynamic cellular and inflammatory flux in the lung that varies across nonhuman primate species, 2020). Nasal swabs were collected from macaques at 0, 1, 3, and 6 days after inoculation to assess viral titers. Bronchoalveolar lavage (BAL) was performed the week before challenge and at Days 3 and 6 post-inoculation by instilling four times 20 mL of saline. These washings were pooled, aliquoted and stored frozen at −70° C.

Reverse-Transcription Quantitative Polymerase Chain Reaction.

To detect and quantify SARS-CoV-2, viral RNA was extracted from nasal swabs and BAL specimens as previously described (Mehra, S. et al., The Journal of infectious diseases 207, 1115-1127, 2013; Gautam, U. S. et al., Proceedings of the National Academy of Sciences of the United States of America 115, E62-E71; 2018; Joosten, S. A. et al., PLoS pathogens 6, e1000782, 2010) and tested by RT-qPCR as previously described (Singh, D. K. et al., SARS-CoV-2 infection leads to acute infection with dynamic cellular and inflammatory flux in the lung that varies across nonhuman primate species, 2020). Briefly, 10 μg yeast tRNA and $1 \times 10^3$ PFU of MS2 phage (*Escherichia coli* bacteriophage MS2, ATCC) were added to each thawed sample, and RNA extraction performed using the NucleoMag Pathogen kit (Macherey-Nagel). The SARS-CoV-2 RT-qPCR was performed on extracted RNA using a CDC-developed 2019-nCoV_N1 assay on a QuantStudio 3 instrument (Applied Biosystems). The cut-off for positivity (limit of detection, LOD) was established at 10 gene equivalents (GE) per reaction (800 GE/mL). Samples were tested in duplicate. On day 6, one BAL specimen from the control group and one day 1 nasal swab from the BNT162b1-immunised group had, on repeated measurements, viral RNA levels on either side of the LLOD. These specimens were categorised as indeterminate and excluded from the graphs and the analysis.

Tissue Preparation.

Mice. Peripheral blood was collected from the retroorbital venous plexus or vena facialis under isoflurane anaesthesia. Blood was centrifuged for 5 minutes at 16.000× g, and the serum was immediately used for downstream assays or stored at −20° C. Spleen single-cell suspensions were prepared in PBS by mashing tissue against the surface of a 70 μm cell strainer (BD Falcon) using the plunger of a 3-mL syringe (BD Biosciences). Erythrocytes were removed by hypotonic lysis. Popliteal, inguinal and iliac lymph nodes were pooled, cut into pieces, digested with collagenase D (1 mg/mL; Roche) and passed through cell strainers. *Rhesus macaques* (*Macaca* mulatta). Blood for serum and PBMCs was collected in compliance with animal protocol 2017-8725-023 approved by the NIRC Institutional Animal Care and Use Committee.

RBD-Binding IgG Antibody Assay.

For mouse sera, MaxiSorp plates (Thermo Fisher Scientific) were coated with recombinant RBD (100 ng/100 μL) in sodium carbonate buffer, and bound IgG was detected using an HRP-conjugated secondary antibody and TMB substrate (Biotrend). Data collection was performed using a BioTek Epoch reader and Gen5 software version 3.0.9. For concentration analysis, the signal of the specific samples was correlated to a standard curve of an isotype control. For *Rhesus macaque* and human sera, a recombinant SARS-CoV-2 RBD containing a C-terminal Avitag™ (Acro Biosystems) was bound to streptavidin-coated Luminex microspheres. Bound *Rhesus macaque* or human anti-RBD antibodies present in the serum were detected with a fluorescently labelled goat anti-human polyclonal secondary antibody (Jackson ImmunoResearch). Data were captured as median fluorescent intensities (MFIs) using a Bioplex200 system (Bio-Rad) and converted to U/mL antibody concentrations using a reference standard curve consisting of 5 pooled human COVID-19 convalescent serum samples (obtained >14 days PCR diagnosis), diluted in antibody depleted human serum, with arbitrary assigned concentrations of 100 U/mL and accounting for the serum dilution factor.

VSV-SARS-CoV-2 Spike Variant Pseudovirus Neutralisation.

A recombinant replication-deficient vesicular stomatitis virus (VSV) vector that encodes GFP instead of VSV-G (VSVAG-GFP) was pseudotyped with SARS-CoV-2 S protein according to published pseudotyping protocols (Berger Rentsch, M. & Zimmer, G., PLoS ONE 6, e25858, 2011; Lester, S. et al., Access Microbiology 1, 20290, 2019). In brief, HEK293T/17 monolayers transfected to express SARS-CoV-2 S truncated of the C-terminal cytoplasmic 19 amino acids (SARS-CoV-2-S-CΔ19) were inoculated with VSVAG-GFP vector. After incubation for 1 hour at 37° C., the inoculum was removed and cells were washed with PBS before medium supplemented with anti-VSV-G antibody (clone 8G5F11, Kerafast Inc.) was added to neutralise residual input virus. VSV/SARS-CoV-2 pseudovirus-containing medium was harvested 20 hours after inoculation, 0.2 μm filtered and stored at −80° C.

Vero-76 cells were seeded in 96-well plates. Serial dilutions of mouse serum samples were prepared and pre-incubated for 10 minutes at room temperature with VSV/SARS-CoV-2 pseudovirus suspension ($4.8 \times 10^3$ infectious units [IU]/mL) before transferring the mix to Vero-76 cells. Inoculated Vero-76 cells were incubated for 20 hours at 37° C. Plates were placed in an IncuCyte Live Cell Analysis system (Sartorius) and incubated for 30 minutes prior to the analysis (IncuCyte 2019B Rev2 software). Whole well scanning for brightfield and GFP fluorescence was performed using a 4× objective. The 50% pseudovirus neutralisation titre ($pVNT_{50}$) was reported as the reciprocal of the first serum dilution yielding a 50% reduction in GFP-positive infected cell number per well compared to the mean of the no serum pseudovirus positive control. Each serum sample dilution was tested in duplicates.

SARS-CoV-2 Neutralisation by Human Convalescent and *Rhesus macaque* Sera.

The SARS-CoV-2 neutralisation assay used a previously described strain of SARS-CoV-2 (USA_WA1/2020) that had been rescued by reverse genetics and engineered by the insertion of an mNeonGreen (mNG) gene into open reading frame 7 of the viral genome (Xie, X. et al., Cell host & microbe 27, 841-848.e3, 2020). This reporter virus generates similar plaque morphologies and indistinguishable growth curves from wild-type virus. Viral master stocks were grown in Vero E6 cells as previously described (Lester, S. et al., Access Microbiology 1, 20290, 2019). When testing human convalescent serum specimens, the fluorescent neutralisation assay produced comparable results as the conventional plaque reduction neutralisation assay. Serial dilutions of heat-inactivated sera were incubated with the reporter virus ($2 \times 10^4$ PFU per well) to yield approximately a 10-30% infection rate of the Vero CCL81 monolayer) for 1 hour at 37° C. before inoculating Vero CCL81 cell monolayers (targeted to have 8,000 to 15,000 cells per well) in 96-well plates to allow accurate quantification of infected cells. Total cell counts per well were enumerated by nuclear stain (Hoechst 33342) and fluorescent virally infected foci were detected 16-24 hours after inoculation with a Cytation 7 Cell Imaging Multi-Mode Reader (Biotek) with Gen5 Image Prime version 3.09. Titers were calculated in GraphPad Prism version 8.4.2 by generating a 4-parameter (4PL) logistical fit of the percent neutralisation at each serial serum dilution. The 50% neutralisation titre ($VNT_{50}$) was reported as the interpolated reciprocal of the dilution yielding a 50% reduction in fluorescent viral foci.

IFNγ ELISpot.

ELISpot assays were performed with mouse IFNγ ELISpot$^{PLUS}$ kits according to the manufacturer's instructions (Mabtech). A total of $5\times10^5$ splenocytes was ex vivo were restimulated with the full-length S peptide mix (0.1 μg/mL final concentration per peptide, JPT) or controls (gp70-AH1 [SPSYVYHQF (SEQ ID NO: 35)] (Slansky, J. E. et al., Immunity 13, 529-538, 2000), JPT, 4 μg/mL; Concanavalin A (ConA), Sigma, 2 μg/mL). Streptavidin-ALP and BCIP/NBT-plus substrate were added, and spots counted using an ELISpot plate reader (ImmunoSpot® S6 Core Analyzer, CTL). Spot numbers were evaluated using ImmunoCapture Image Aquision Software V7.0 and ImmunoSpot 7.0.17.0 Professional. For T-cell subtyping, $CD8^+$ T cells were isolated from splenocyte suspensions using MACS MicroBeads (CD8a [Ly-2], Miltenyi Biotec) according to the manufacturer's instructions. The flow-through served as a source of $CD4^+$ T cells. $CD8^+$ or $CD4^+$ T cells were subsequently restimulated with syngeneic bone marrow-derived dendritic cells loaded with full-length S peptide mix (0.1 μg/mL final concentration per peptide) or medium as control. Purity of isolated T-cell subsets was determined by flow cytometry to calculate spot counts per $1\times10^5$ $CD8^+$ or $CD4^+$ T cells.

Cytokine Profiling.

Mouse splenocytes were re-stimulated for 48 hours with full-length S peptide mix (0.2 μg/mL final concentration per peptide) or medium only. Concentrations of IFNγ, IL-2, IL-4 and IL-5 in supernatants were determined using a bead-based, 11-plex $T_H1/T_H2$ mouse ProcartaPlex multiplex immunoassay (Thermo Fisher Scientific) according to the manufacturer's instructions. Fluorescence was measured with a Bioplex200 system (Bio-Rad) and analysed with ProcartaPlex Analyst 1.0 software (Thermo Fisher Scientific).

Statistics and Reproducibility.

No statistical methods were used to predetermine group and samples sizes (n). All experiments were performed once. P-values reported for RT-qPCR analysis were determined by categorical analysis for binomial response (undetectable viral RNA after challenge as success, measurable viral RNA after challenge as failure) with logit link to treatment and day effects using PROC GENMOD from SAS© 9.4. Samples from post challenge days (Days 3 and 6 for BAL; Days 1, 3 and 6 for nasal swab) were included in the analysis. Indeterminate results were excluded from this analysis. All remaining analyses were carried out using GraphPad Prism 8.4.

Results

We designed a SARS-CoV-2 vaccine named BNT162b1, which is composed of an LNP-encapsulated N1-methyl-pseudouridine (m1ψ) nucleoside-modified mRNA that encodes the RBD fused at its C-terminus to the natural trimerisation domain (foldon) of T4 fibritin (Meier, S. et al., Journal of molecular biology 344, 1051-1069, 2004) (FIG. 64*a*). The SARS-CoV-2 S signal peptide (SP) enables ER translocation and secretion of the trimeric RBD. The m1ψ-modification of the RNA dampens innate immune sensing and, together with optimized non-coding sequence elements, increases RNA translation in vivo (Orlandini von Niessen, A. G. et al., Mol Ther 27, 824-836, 2019; Karikó, K. et al., Molecular therapy: the journal of the American Society of Gene Therapy 16, 1833-1840, 2008).

BNT162b1 RNA in vitro transcribed by T7 polymerase from a plasmid DNA template had a single, sharp peak microfluidic capillary electrophoresis profile, consistent with its calculated length of 1262 nucleotides, indicating purity and integrity (data not shown). Western blot analysis of a lysate of BNT162b1 RNA-transfected HEK293T/17 cells demonstrated that the RBD was expressed from the RNA and had an apparent molecular weight consistent with its calculated weight of 29.46 kDa (data not shown). Protein expression and endoplasmic reticulum localisation on the secretory pathway in transfected cells were confirmed by flow cytometry and immunofluorescence microscopy, respectively (data not shown).

For structural characterization, the trimerised RBD was expressed from a DNA sequence corresponding to the coding sequence of BNT162b1 RNA in Expi293F cells and purified by affinity capture with the ACE2 peptidase domain immobilized on agarose beads. The trimerised RBD bound to the human ACE2 peptidase domain (PD) with high affinity (5 pM $K_D$), which is approximately 1,000-fold the reported $K_D$ of 5.09 nM for monomeric RBD and consistent with the avidity effect of multimeric binding (data not shown). The trimeric valency of the RBD-foldon and its flexibility were visualized by electron microscopy (EM) of negatively stained specimens, which revealed a range of conformations (FIG. 64*b*). Although the flexibility of the RBD-foldon precluded direct structural analysis at high resolution, the RBD domains could be immobilized by binding to a complex of ACE2 and the $B^0$ AT1 neutral amino acid transporter, which ACE2 chaperones, when that complex was in the previously reported closed conformation (Yan, R. et al., Science (New York, N.Y.) 367, 1444-1448, 2020). The size and symmetry of the RBD-foldon/ACE2/$B^0$ AT1 ternary complex aided image reconstruction by electron cryomicroscopy (cryoEM), and the structure of the RBD domains in the complex was determined to 3.24 Å resolution (FIG. 64*c*). One copy of the RBD was resolved for each bound trimer. The binding interface between the resolved RBD and the ACE2 extracellular domain was fitted to a previously reported structure and showed good agreement (He, Y. et al., Biochemical and Biophysical Research Communications 324, 773-781, 2004; Yi, C. et al., Cellular & molecular immunology; 10.1038/s41423-020-0458-z, 2020). The high affinity binding to ACE2 and well-resolved structure in complex with ACE2 demonstrate that the recombinant RBD-foldon authentically presents the ACE2 binding site targeted by many SARS-CoV-2 neutralising antibodies (Brouwer, P. J. M. et al., Science (New York, N.Y.); 10.1126/science.abc5902 (2020); Zost, S. J. et al., Nature medicine; 10.1038/s41591-020-0998-x (2020)).

BNT162b1-elicited B- and T-cell immune responses were characterised in a series of experiments in BALB/c mice after a single intramuscular (IM) immunisation with 0.2, 1, or 5 μg BNT162b1 or with buffer alone. RBD-specific serum IgG developed quickly at all dose levels in a dose-dependent manner and plateaued around day 21 (at 1.63±0.13 mg/mL for the 5 μg dose level; FIG. 65*a*). Vaccine-elicited IgG had high RBD-binding affinity (geometric mean $K_D$ 48.0 pM) with high on-rate (geometric mean $k_{on}$ $1.72\times10^6$/Ms) and low off-rate (geometric mean $K_{off}$ $8.27\times10^{-5}$/s; FIG. 65*b*). SARS-CoV-2 neutralising activity in mouse serum was measured by a vesicular stomatitis virus (VSV)-based SARS-CoV-2 pseudovirus neutralisation assay. Mean 50% pseudovirus neutralisation titers ($pVNT_{50}$) increased steadily after immunisation to 102, 192, and 1,056 on day 28 for the 0.2, 1, and 5 μg dose levels, respectively (FIG. 65*c*).

A high fraction of splenocytes of both $CD4^+$ and $CD8^+$ T-cell phenotypes isolated from BNT162b1-immunised mice on days 12 and 28 after immunisation, when re-stimulated ex vivo with a full-length S peptide mix, exerted a strong antigen-specific IFNγ-response in ELISpot assays (FIG. 65*d*). Full-length S peptide-stimulated bulk splenocytes and $CD4^+$ and $CD8^+$ subsets also show high IFNγ production at day 12 and significant IL-2 responses but much lower IL-4 responses in flow cytometric cytokine release analyses, indicating a $T_H1$ phenotype response (FIG. 65*e*). The $T_H1$ phenotype persists, with total splenocytes harvested on day 28 and stimulated with the full-length S peptide pool producing high levels of IL-2 and IFNγ but undetectable amounts of the $T_H2$ cytokines IL-4 and IL-5 in multiplex immunoassays (FIG. 65*f*). In draining lymph nodes (dLN) and spleens obtained 12 days after immunisation of mice with BNT162b1 or buffer, much higher numbers of B cells (including plasma cells, class switched IgG1- and IgG2a-positive B cells, and germinal center B cells) were observed in the samples from mice that received BNT162b1 (data not shown). In blood obtained 7 days after immunisation, the number of circulating B cells was lower than in buffer-immunised mice, most likely due to B-cell homing to lymphoid compartments (data not shown). dLNs from BNT162b1-immunised mice also displayed an elevation in T-cell counts, particularly numbers of T follicular helper ($T_{FH}$) cells, including subsets with ICOS upregulation, which are known to play an essential role in the formation of germinal centers (Hutloff, A., Oncotarget 6, 21785-21786, 2015) (data not shown). BNT162b1-induced elevation of $T_{FH}$ cells was also detected in the spleen and blood (data not shown). In aggregate, these data indicate a strong and concurrent induction of SARS-CoV-2 S-specific neutralising antibody titers and a $T_H1$-driven T-cell response by BNT162b1. Intramuscularly administered BNT162b1 appears to be delivered to dLNs as immune-educated sites for proficient vaccine priming, with migration of lymphocytes from the blood to lymphoid tissues to participate in the vaccine response.

The immunogenicity of BNT162b1 was next tested in 2-4 year old male *Rhesus macaques*. Groups of six were immunised IM with 30 or 100 μg of BNT162b1 or with saline control on Days 0 and 21. RBD-binding IgG was readily detectable by Day 14 after a single immunisation, and levels increased further through Day 21, when the boosting dose was given (FIG. 66*a*). Seven days after the second immunisation (Day 28), the geometric mean RBD-binding IgG concentrations (GMCs) were 20,962 units (U)/mL (30 μg dose level) and 48,575 U/mL (100 μg dose level). For comparison, the RBD-binding IgG GMC of a panel of 38 SARS-CoV-2 convalescent human sera was 602 U/mL, substantially lower than the GMC of the immunised *Rhesus macaques* after one or two doses. Fifty percent neutralisation titers ($VNT_{50}$), measured by an authentic SARS-CoV-2 neutralisation assay (Muruato, A. E. et al., bioRxiv: the preprint server for biology; 10.1101/2020.05.21.109546, 2020), were detectable in *rhesus* sera by Day 14 after a single immunisation and reached geometric mean titers (GMTs) of 768 (30 μg dose level) or 1,714 (100 μg dose level) 7 days after the boost (Day 28, FIG. 66*b*). Robust neutralisation GMTs of 247 for 30 μg and 564 for 100 μg dose levels persisted to at least Day 42 (most recent time point tested). For comparison, the 50% neutralisation GMT of the human convalescent serum panel was 93.6.

The groups of *Rhesus macaques* (n=6) that had received two immunisations with 100 μg BNT162b1 or buffer control were challenged 41 to 48 days after the second immunisation with $1\times10^6$ plaque forming units of SARS-CoV-2 (strain USA-WA1/2020), split equally between the intranasal and intratracheal routes, as previously described (Singh, D. K. et al. SARS-CoV-2 infection leads to acute infection with dynamic cellular and inflammatory flux in the lung that varies across nonhuman primate species, 2020). Three non-immunised, age-matched, male *Rhesus macaques* (sentinel) were mock-challenged with cell culture medium. At the time of challenge, SARS-CoV-2 neutralising titers ranged from 208 to 1,185 in the BNT162b1-immunised animals and were undetectable in animals from the control-immunised and sentinel groups.

SARS-CoV-2 RNA was measured in bronchoalveolar lavage (BAL) and nasal swab samples by reverse-transcription quantitative polymerase chain reaction (RT-qPCR). All BAL and nasal swab samples obtained before the infectious challenge and all those obtained from sentinel animals lacked detectable SARS-CoV-2 RNA (FIG. 67). Three days after SARS-CoV-2 challenge, viral RNA was detected in BAL fluid from 5/6 control-immunised and 2/6 BNT162b1-immunised animals (FIG. 67*a*). By 6 days after challenge, all six BNT162b1-immunised macaques had undetectable viral RNA in their lungs; of the control-immunised macaques, three had a high level of viral RNA in BAL fluid, two had cleared, and one had an indeterminate RT-qPCR result. At the time of necropsy (7-23 days after challenge), no viral RNA was detectable in BAL fluid from any animal. After SARS-CoV-2 challenge, viral RNA was detected in nasal swabs of the control-immunised group at each time point: two animals at Day 1, three animals at Days 3 and 6 after challenge (FIG. 67*b*), and two animals at the time of necropsy (not shown). In BNT162b1-immunised animals, all nasal swabs were negative or indeterminate at Day 1, and all were negative at Day 3 and at the time of necropsy; at Day 6, swabs from two were positive, indicating a more transient course of viral RNA detection compared to non-immunised *Rhesus macaques*. The difference in the proportion of animals with detectable viral RNA between BNT162b1-immunised animals and control-immunised animals is statistically significant (p=0.0037 for BAL, and 0.0212 for nasal swab). None of the challenged animals showed clinical or radiographic signs of significant illness, indicating that the 2-4 years old male *Rhesus* challenge model is primarily an infection model for SARS-CoV-2, not a COVID-19 disease model.

DISCUSSION

We demonstrate that BNT162b1, an LNP-formulated m1ψ nucleoside-modified mRNA encoding the trimeric RBD antigen, is highly immunogenic in mice and *Rhesus macaques* and limits infection in *Rhesus macaques* challenged with infectious SARS-CoV-2. The RBD-foldon coding sequence directs the expression of a flexible, trimeric protein that binds ACE2 with high affinity and has a structurally intact ACE2 receptor binding site. One key finding is that in mice, a single sub-microgram immunisation rapidly induces high neutralising antibody titers that are in the range or above recently reported SARS-CoV-2 vaccine candidates (van Doremalen, N. et al., bioRxiv: the preprint server for biology; 10.1101/2020.05.13.093195 (2020); Corbett, K. S. et al., bioRxiv: the preprint server for biology; 10.1101/2020.06.11.145920 (2020)). The strong $CD4^+$ and stronger $CD8^+$ T-cell responses, both skewing towards a $T_H1$-bias, and $T_{FH}$ generation may imply a strong protection capacity induced by the vaccine candidate (Pardi, N. et al., The Journal of Experimental Medicine 215, 1571-1588, 2018). Proliferation of $T_{FH}$ in germinal centres is integral for generation of an adaptive B-cell response. In humans, $T_{FH}$ occurring in the circulation after vaccination were correlated with a high frequency of antigen-specific antibodies (Farooq, F. et al., Scientific reports 6, 27944, 2016). Immunisation with BNT162b1 triggered redistribution of B cells and $T_{FH}$ cells from the blood to lymphoid tissues, where antigen presentation occurs.

Another significant finding is that in *Rhesus macaques* two doses of m1ψ nucleoside-modified mRNA encoding the trimeric SARS-CoV-2 S RBD-foldon elicited SARS-CoV-2 neutralising GMTs 8.2 to 18.2-fold the GMT of a SARS-CoV-2 convalescent human serum panel. Results in nonhuman primates confirm the vaccine's high potency and ability to protect against SARS-CoV-2 challenge in a preclinical model of acute SARS-CoV-2 infection.

Example 11: A RNA Vaccine Encoding the Prefusion-Stable SARS-CoV-2 S is Highly Immunogenic in Mice and Non Human Primates Here, we report a SARS-CoV-2 infectious challenge of immunised macaques with BNT162b2 vaccine.

Materials and Methods

Manufacturing of In Vitro Transcribed RNA.

To generate the template for RNA synthesis, a DNA fragment encoding the full-length SARS-CoV-2 S protein (GenBank: MN908947), with amino acid exchanges K986P and V987P, was cloned into a starting plasmid vector with backbone sequence elements for improved RNA stability and translational efficiency (Orlandini von Niessen, A. G. et al., Mol Ther 27, 824-836, 2019; Holtkamp, S. et al., Blood 108, 4009-4017, 2006). Non-coding backbone elements included the regions from the T7 promoter to the 5' and 3' UTR plus a poly(A) tail (100 nucleotides) interrupted by a linker (A30LA70, 10 nucleotides). The DNA was purified, spectrophotometrically quantified, and in vitro transcribed by T7 RNA polymerase in the presence of a trinucleotide cap1 analogue (($m_2^{7,3'-O}$)Gppp($m^{2'-O}$)ApG; TriLink) and of $N^1$-methylpseudouridine-5'-triphosphate (m1ψTP; Thermo Fisher Scientific) instead of uridine-5'-triphosphate (UTP) (Grudzien-Nogalska, E. et al., Methods in molecular biology (Clifton, N.J.) 969, 55-72, 2013). RNA was purified using magnetic particles (Berensmeier, S., Appl. Microbiol. Biotechnol. 73, 495-504, 2006), integrity assessed by microfluidic capillary electrophoresis (Agilent Fragment Analyser), and concentration, pH, osmolality, endotoxin level and bioburden determined.

Lipid-Nanoparticle Formulation of the RNA.

Purified RNA was formulated into LNPs using an ethanolic lipid mixture ofionisable cationic lipid and transferred into an aqueous buffer system via diafiltration to yield an LNP composition similar to one previously described (Maier, M. A. et al., Molecular therapy: the journal of the American Society of Gene Therapy 21, 1570-1578, 2013). BNT162b2 was stored at −70° C. at a concentration of 0.5 mg/mL.

Immunisation.

Male *Rhesus macaques* (2-4 years) were randomly assigned to receive either BNT162b2 or saline placebo control in 0.5 mL volume administered by IM injection in the left quadriceps muscle on Days 0 and 21. Blood for serum and PBMCs was collected in compliance with animal protocol 2017-8725-023 approved by the NIRC Institutional Animal Care and Use Committee. Animals were anesthetised with ketamine HCl (10 mg/kg; IM) during blood collection and immunisation, and monitored for adequate sedation.

SARS-CoV-2 Challenge of *Rhesus Macaques.*

The SARS-CoV-2 inoculum was obtained from a stock of $2.1\times10^6$ PFU/mL previously prepared at Texas Biomedical Research Institute (San Antonio, Tex.), aliquoted into single use vials, and stored at −70° C. The working virus stock was generated from two passages of the SARS-CoV-2 USA-WA1/2020 isolate (a $4^{th}$ passage seed stock purchased from BEI Resources; NR-52281) in Vero E6 cells. The virus was confirmed to be SARS-CoV-2 by deep sequencing and identical to the published sequence (GenBank accession number MN985325.1).

BNT162b2-immunised (n=6) and age-matched saline control-immunised (n=6) male *rhesus macaques* (control) were challenged with $1\times10^6$ plaque forming units of SARS-CoV-2 USA-WA1/2020 isolate, split equally between the intranasal (IN; 0.2 mL) and intratracheal (IT; 0.2 mL) routes as previously described (Singh, D. K. et al. SARS-CoV-2 infection leads to acute infection with dynamic cellular and inflammatory flux in the lung that varies across nonhuman primate species (2020)). The challenge was performed 41 to 48 days after the second immunisation. A separate sentinel group of non-immunised age- and sex-matched animals (n=3) received only DMEM supplemented with 10% FCS IN (0.2 mL) and IT (0.2 mL).

Approximately two weeks prior to challenge, animals were moved to the ABSL-3 facility at Southwest National Primate Research Center (SNPRC; San Antonio, Tex.). Animals were monitored regularly by a board-certified veterinary clinician for rectal body temperature, weight and physical examination. Specimen collection was performed under tiletamine zolazepam (Telazol) anaesthesia as described (Singh, D. K. et al. SARS-CoV-2 infection leads to acute infection with dynamic cellular and inflammatory flux in the lung that varies across nonhuman primate species (2020)). Nasal swabs were collected from macaques at 0, 1, 3, and 6 days after inoculation to assess viral titers. Bronchoalveolar lavage (BAL) was performed the week before challenge and at Days 3 and 6 post-inoculation by instilling four times 20 mL of saline. These washings were pooled, aliquoted and stored frozen at −70° C.

Reverse-Transcription Quantitative Polymerase Chain Reaction.

SARS-CoV-2 was detected and quantified in NHP essentially as described above in Example 10.

Results

Results showed COVID-19 mRNA Vaccine BNT162b2 was immunogenic eliciting IgG responses after a single dose which were boosted by a second dose. These also showed a dose-response. At 30 μg BNT162, the neutralizing geometric mean titre was compared to that seen in covalescent plasma from human patients with SARS CoV-2 and found to be ~8-fold higher with seven days after Dose of the higher dose of 100 μg giving a higher excess of ~18-fold and remaining 3.3-times higher than this benchmark five weeks after the last immunization. In monkeys the response was also characterised as Th1-dominant with IFN-γ and IL-2, but no IL-4 response. CD4 and CD8 positive cellular responses were also observed in monkeys too. Such cellular immune response was characterized as a strongly Th1-biased CD4+ T cell response with a concurrent interferon-γ (IFN-γ)+ CD8+ T cell response.

The groups of *Rhesus macaques* (n=6) that had received two immunisations with 100 μg BNT162b2 or buffer control were challenged 41 to 48 days after the second immunisation with $1\times10^6$ plaque forming units of SARS-CoV-2 (strain USA-WA1/2020), split equally between the intranasal and intratracheal routes, as previously described (Singh, D. K. et al. SARS-CoV-2 infection leads to acute infection with dynamic cellular and inflammatory flux in the lung that varies across nonhuman primate species, 2020). Three non-immunised, age-matched, male *Rhesus macaques* (sentinel) were mock-challenged with cell culture medium. At the time of challenge, SARS-CoV-2 neutralising titers ranged from 204 to 938 in the BNT162b2-immunised animals and were undetectable in animals from the control-immunised and sentinel groups.

SARS-CoV-2 RNA was measured in bronchoalveolar lavage (BAL) and nasal swab samples by reverse-transcription quantitative polymerase chain reaction (RT-qPCR). All BAL and nasal swab samples obtained before the infectious challenge and all those obtained from sentinel animals lacked detectable SARS-CoV-2 RNA (FIG. 68). Three days after SARS-CoV-2 challenge, viral RNA was detected in BAL fluid from 5/6 control-immunised and 2/6 BNT162b2-immunised animals (FIG. 68). By 6 days after challenge, all six BNT162b2-immunised macaques had undetectable viral RNA in their lungs; of the control-immunised macaques, three had a high level of viral RNA in BAL fluid, two had cleared, and one had an indeterminate RT-qPCR result. After SARS-CoV-2 challenge, viral RNA was detected in nasal swabs of the control-immunised group at each time point: two animals at Day 1, three animals at Days 3 and 6 after challenge (FIG. 68). In BNT162b2-immunised animals, all nasal swabs were negative at Day 3 and at Day 6.

In lung tissues, control monkeys had evidence of pulmonary disease indicated by their increased scores on computed tomography scans with a suggestion of recovery in that scores at day 10 were less than those at day 3; in contrast, the monkeys given COVID-19 mRNA Vaccine BNT162b2 had lower scores. Microscopic analysis of lung tissues showed that lung inflammation was similar between control and BNT162b2-immunized monkeys, and there was no evidence of enhanced respiratory disease.

DISCUSSION

Results in nonhuman primates confirm the potency and ability of BNT162b2, an LNP-formulated m1ψ nucleoside-modified mRNA encoding the S antigen captured in a prefusion conformation, to protect against SARS-CoV-2 challenge in a preclinical model of acute SARS-CoV-2 infection.

Example 12: Storage, Shipping and Dose Preparation

This example illustrates storage, shipping and dose preparation of a multi-dose vial of BNT162b2 concentrate for injection.

Figure 69:
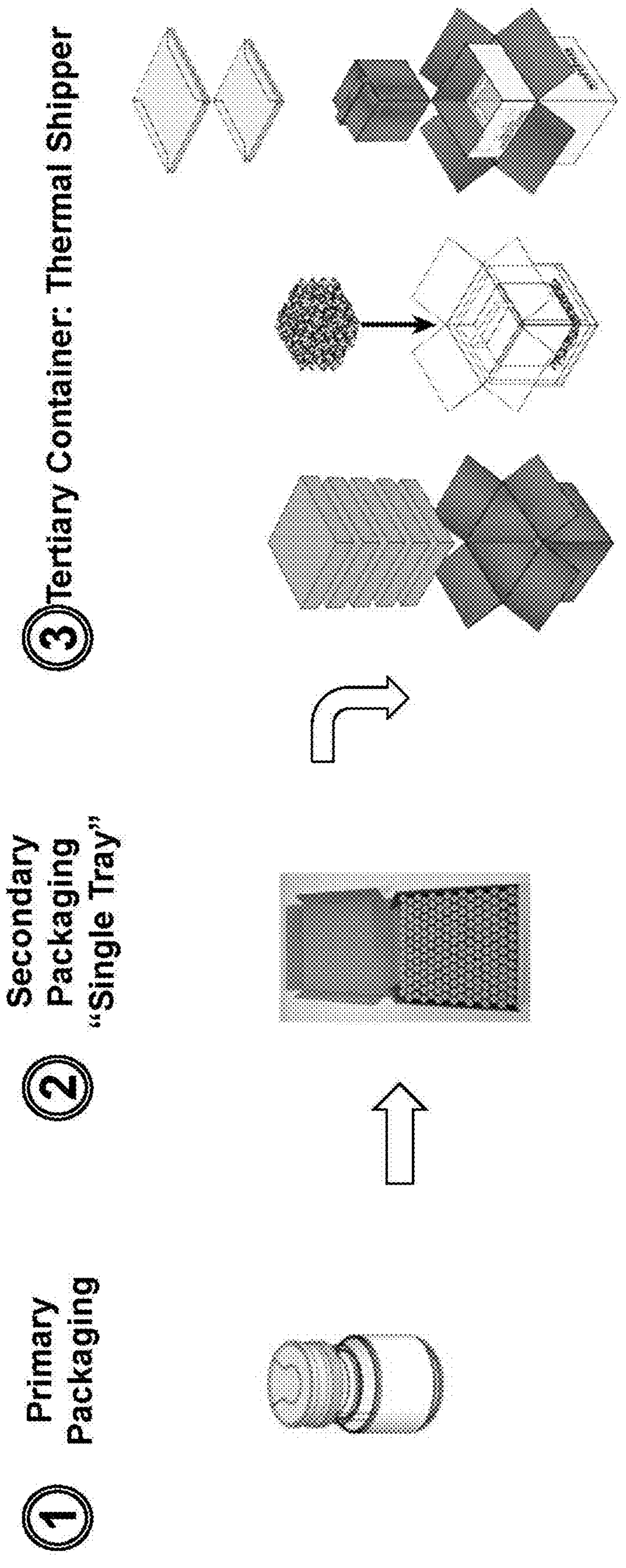

As shown in FIG. 69, at the stage of primary packing, 2 ml type 1 glass, preservative-free, multi-dose vial (MDV) is used, wherein the MDV has 0.45 ml frozen liquid drug product and there are 5 doses per vial. At the stage of secondary packing, a single tray holds 195 vials, such as 975 doses per tray. The tray (white box) dimensions are 229×229×40 mm. At the stage of teriary packing, a minimum of 1 tray (975 doses) (or up to 5 trays (max 4875 doses)) is stacked in a payload carton. The payload carton is submerged in 23 Kg of dry ice pellets (10 mm-16 mm pellets). The thermal shipper dimensions are as follows: internal dimensions: 245 mm×245 mm×241 mm; external dimensions: 400 mm×400 mm×560 mm. The total weight of the thermal shipper is ~35 Kg.

Figure 70:

Different sizes of Ultra-Low Temperature (ULT) freezers are available in the market. FIG. 70 shows an example for a small volume storage (about 90 litres; about 30K doses (left)) and for a large volume storage (about 500 litres; about 200K doses (right)). Thermal shipper keeps ULT (e.g., −90° C. to −60° C.) up to 10 days if stored at 15° C. to 25° C. temperatures without opening and such storage period of time can be extended further by consistently refilling to the top of the container with dry ice. Upon receipt and after opening, the box should be replenished with dry ice within 24 hours (23 Kg of dry ice pellets (10 mm-16 mm pellets). Thermal shipper should be re-iced every 5 days. It is recommended that the thermal shipper is opened not more than twice a day. Thermal shipper should be closed within 1 minute (or less) after opening. The vaccine can be stored at 2° C. to 8° C. up to 2 days or at room temperature for no more than 2 hours after thawing. Post-dilution in use period is 6 hours.

Figure 71:
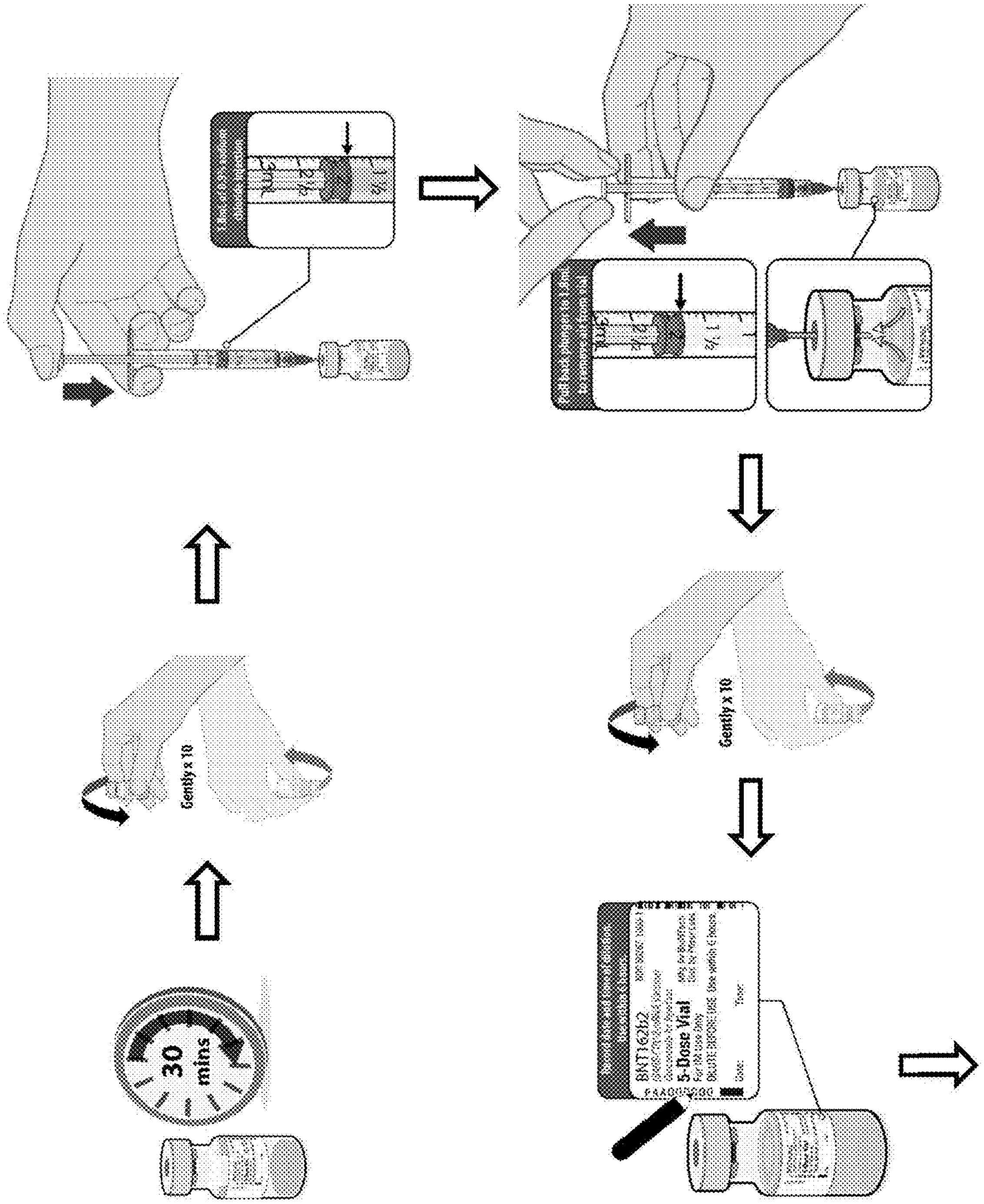
Figure 71:
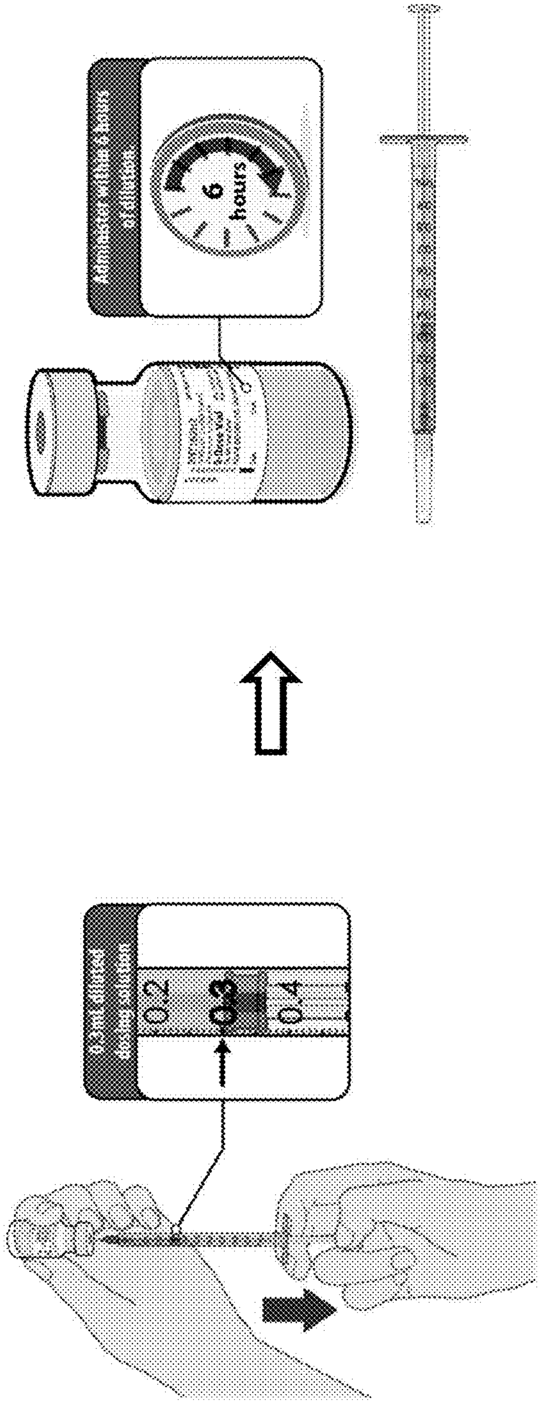

FIG. 71 shows an exemplary dose preparation for a BNT162b2 5-dose vial which contains a frozen concentrated solution that is preservative-free and must be thawed and diluted prior to administration. The preparation steps are as follows:

Remove a 5-dose vial of BNT162b2 concentrate for injection from its carton in frozen storage and allow to thaw for approximately 30 minutes at room temperature (e.g., up to 25° C.). In some embodiments, such a multi-dose vial of BNT162b2 may be thawed and stored in a refrigerator (e.g., 2° C.-8° C.), for example, for up to 5 days. Vials thawed at room temperature must be diluted within 2 hours or transferred to a refrigerator. Undiluted vials may be stored for up to 48 hours in the refrigerator. Do not refreeze thawed vials. During storage, minimize exposure to room light, and avoid exposure to direct sunlight and ultraviolet light. Thawed vials can be handled in room light conditions.

After thawing and prior to use, ensure the vial is equilibrated to room temperature, and invert gently 10 times to mix. Do not shake.

Using aseptic technique, cleanse the vial stopper with a single-use antiseptic swab, then dilute the thawed vial of BNT162b2 by adding 1.8 mL of 0.9% Sodium Chloride Injection, USP into the vial. Needles 21 gauge or narrower needles are recommended. However, those skill in the art will understand that in some embodiments, wider needeles may be used. For example, in some embodiments, needles 20, 19, 18, 17, 16, 15 or wider needles may be used.

You may feel some pressure in the vial as you add the diluent. Ensure vial pressure is equalized by withdrawing 1.8 mL air into the empty diluent syringe before removing the needle from the vial.

Gently invert the diluted vial 10 times to mix. Do not shake.

Record the date and time of dilution in the appropriate place on the BNT162b2 vial label. Expiry is 6 hours from the time of dilution. Diluted multi-dose vials are stored between 2° C. and 25° C. Do not freeze. Discard if frozen.

Using aseptic technique, cleanse the vial stopper with a single-use antiseptic swab, and draw up 0.3 mL of the diluted dosing solution into a new sterile dosing syringe with a needle appropriate for intramuscular injection. Adjustments to remove air bubbles should be done with the needle still in the vial to avoid loss of dosing solution. It is recommended to use the same needle to withdraw and administer the dose whenever possible. If a second needle is required for administration, pull back on the syringe plunger until a small amount of air enters the syringe prior to removing the first needle to avoid loss of dosing solution during the needle change. Take care when priming the administration needle to prevent any loss of dose. For each additional dose, use a new sterile syringe and needle and ensure the vial stopper is cleansed with antiseptic before each withdrawal. Prepared syringes should be administered immediately. If they cannot be administered immediately, they must be administered within 6 hours of the initial vial dilution. Before administration, ensure a final injection volume in the syringe of 0.3 mL.

Example 13: Vaccine Candidate Against COVID-19 Achieved Success in First Interim Analysis from Phase 3 Study The Phase 3 clinical trial of BNT162b2 has enrolled more than 43,000 participants to date, almost 39,000 of whom have received a second dose of the vaccine candidate as of Nov. 8, 2020. Approximately 42% of global participants and 30% of U.S. participants have racially (e.g., including White, Black or African American, American Indian or Alaska native, Asian, native Hawaiian or other Pacific Islander, multiracial) and ethnically (e.g., including Hispanic/Latino and non-Hispanic/non-Latino) diverse backgrounds. The trial is continuing to enroll and is expected to continue through the final analysis when a total of 164 confirmed COVID-19 cases have accrued.

Vaccine candidate BNT162b2 achieved success in First Interim Analysis from Phase 3 Study. The vaccine candidate was found to be more than 90% effective in preventing COVID-19 in participants without evidence of prior SARS-CoV-2 infection in the first interim efficacy analysis. Analysis evaluated 94 confirmed cases of COVID-19 in trial participants. No serious safety concerns have been observed.

A set of results from the Phase 3 COVID-19 vaccine trial, assembled by Nov. 4, 2020, provides evidence of the ability of BNT162b2 to prevent COVID-19. The case split between vaccinated individuals and those who received the placebo indicates a vaccine efficacy rate above 90%, at 7 days after the second dose. In particular, early analysis of the results showed that individuals who received two injections of the vaccine three weeks apart experienced more than 90% fewer cases of symptomatic COVID-19 than those who received a placebo. This confirms that protection is achieved 28 days after the initiation of the vaccination, which consists of a 2-dose schedule.

Preliminary such data includes the following tables:

TABLE 5

Vaccine Efficacy - First COVID-19 Occurrence From 7 Days After Dose 2 - Subjects Without Evidence of Infection Prior to 7 Days After Dose 2 - Evaluable Efficacy Population (7 Days) - Interim Analysis 1.

| | Vaccine Group (as Randomized) | | | | | | |
|---|---|---|---|---|---|---|---|
| | | BNT162b2 (30 μg) ($N^a$ = 16061) | | Placebo ($N^a$ = 16218) | | | |
| Efficacy Endpoint | $n1^b$ | Surveillance $Time^c$ ($n2^d$) | $n1^b$ | Surveillance $Time^c$ ($n2^d$) | VE (%) | (95% $CI^e$) | Pr (VE >30% \| data)$^f$ |
| First COVID-19 occurrence from 7 days after Dose 2 | 4 | 1.72161 (15899) | 90 | 1.73212 (16010) | 95.5 | (88.8, 98.4) | >0.9999 |

Abbreviations:

N-binding = SARS-CoV-2 nucleoprotein-binding;

NAAT = nucleic acid amplification test;

SARS-CoV-2 = severe acute respiratory syndrome coronavirus 2;

VE = vaccine efficacy.

Note:

Subjects who had no serological or virological evidence (prior to 7 days after receipt of the last dose) of past SARS-CoV-2 infection (ie, N-binding antibody [serum] negative at Visit 1 and SARS-CoV-2 not detected by NAAT [nasal swab] at Visits 1 and 2), and had negative NAAT at any unscheduled visit prior to 7 days after Dose 2 were included in the analysis.

Note:

Data from subjects who are not confirmed 7 days post dose 2 cases are included in the analysis to comprehensively show all data reported and/or contribute to the total surveillance time calculation but may be subject to change with additional follow-up.

a. N =number of subjects in the specified group.

b. n1 =Number of subjects meeting the endpoint definition.

c. Total surveillance time in 1000 person-years for the given endpoint across all subjects within each group at risk for the endpoint. Time period for
COVID-19 case accrual is from 7 days after Dose 2 to the end of the surveillance period.

d. n2 = Number of subjects at risk for the endpoint.

e. Credible interval for VE was calculated using a beta-binomial model adjusted for surveillance time.

f. Posterior probability (Pr) was calculated using a beta-binomial model adjusted for surveillance time. This probability must be at least 99.5% at the interim analysis in order to conclude that the vaccine is efficacious.

Note:

Data from subjects who are not confirmed 7 days post dose 2 cases are included in the analysis to comprehensively show all data reported and/or contribute to the total surveillance time calculation but may be subject to change with additional follow-up.

a. N = number of subjects in the specified group.

b. n = Number of subjects meeting the endpoint definition.

Example 14: Efficacy and Immunogenicity Evaluation

Efficacy Results

Vaccine efficacy of BNT162b2 against COVID-19 among participants without evidence of past SARS-CoV-2 infection was demonstrated at the first interim analysis conducted after accrual of at least 62 cases following the protocol and SAP. The primary efficacy results presented in this section are from that interim analysis.

Only the vaccine efficacy of BNT162b2 for the first primary efficacy endpoint (COVID-19 incidence based on central laboratory or locally confirmed NAAT in participants without serological or virological evidence of past SARS-CoV-2 infection prior to 7 days after receipt of the second dose) is analyzed and presented at this interim analysis.

First Primary Efficacy Endpoint

Among participants included in the evaluable efficacy population, 32,279 participants (16,061 in BNT162b2 group and 16,218 in placebo group) did not have evidence of infection with SARS-CoV-2 through 7 days after the second dose. There were 4 COVID-19 cases in the BNT162b2 group compared to 90 COVID-19 cases reported in the placebo group. These data give an estimated vaccine efficacy of 95.5% for BNT162b2. The posterior probability of >99.99% met the prespecified interim analysis success criterion of >99.5% (Table 7). The 95% credible interval for the vaccine efficacy was 88.8% to 98.4%, indicating that given the current observed data there is a 95% probability that the true VE lies in this interval. Also, note that the posterior probability that true VE>86.0% is 99.5% and VE>88.8% is 97.5%.

TABLE 7

Vaccine Efficacy - First COVID-19 Occurrence From 7 Days After Dose 2 - Subjects Without Evidence of Infection Prior to 7 Days After Dose 2 - Evaluable Efficacy Population (7 Days) - Interim Analysis 1

| | Vaccine Group (as Randomized) | | | | | | |
|---|---|---|---|---|---|---|---|
| | BNT162b2 (30 μg) (N[a] = 16061) | | Placebo (N[a] = 16218) | | | | |
| Efficacy Endpoint | n1[b] | Surveillance Time[c] (n2[d]) | n1[b] | Surveillance Time[c] (n2[d]) | VE (%) | (95% CI[e]) | Pr (VE >30% $\mid$ data)[f] |
| First COVID-19 occurrence from 7 days after Dose 2 | 4 | 1.722 (15899) | 90 | 1.732 (16010) | 95.5 | (88.8, 98.4) | >0.9999 |

Abbreviations:
N-binding = SARS-CoV-2 nucleoprotein-binding;
NAAT = nucleic acid amplification test;
SARS-CoV-2 = severe acute respiratory syndrome coronavirus 2;
VE = vaccine efficacy.

Note: Subjects who had no serological or virological evidence (prior to 7 days after receipt of the last dose) of past SARS-CoV-2 infection (ie, N-binding antibody [serum] negative at Visit 1 and SARS-CoV-2 not detected by NAAT [nasal swab] at Visits 1 and 2), and had negative NAAT at any unscheduled visit prior to 7 days after Dose 2 were included in the analysis.

Note: Data from subjects who are not confirmed 7 days post dose 2 cases are included in the analysis to comprehensively show all data reported and/or contribute to the total surveillance time calculation but may be subject to change with additional follow-up.

a. N = number of subjects in the specified group.

b. n1 = Number of subjects meeting the endpoint definition.

c. Total surveillance time in 1000 person-years for the given endpoint across all subjects within each group at risk for the endpoint. Time period for COVID-19 case accrual is from 7 days after Dose 2 to the end of the surveillance period.

d. n2 = Number of subjects at risk for the endpoint.

e. Credible interval for VE was calculated using a beta-binomial model adjusted for surveillance time.

f. Posterior probability (Pr) was calculated using a beta-binomial model adjusted for surveillance time. This probability must be at least 99.5% at the interim analysis in order to conclude that the vaccine is efficacious.

The vaccine efficacy of BNT162b2 for the same primary efficacy endpoint based on the all-available efficacy population was 95.7%, with 4 and 93 cases in the BNT162b2 and placebo groups, respectively.

No clinically meaningful differences in VE by subgroup were observed by age group, country, ethnicity, sex, or race in the in the Dose 2 evaluable efficacy population, with VE estimates that ranged from 91.2% to 100.0% (Table 8).

TABLE 8

Vaccine Efficacy - First COVID-19 Occurrence From 7 Days After Dose 2, by Subgroup - Subjects Without Evidence of Infection Prior to 7 Days After Dose 2 - Evaluable Efficacy Population (7 Days) - Interim Analysis 1

| | Vaccine Group (as Randomized) | | | | | |
|---|---|---|---|---|---|---|
| | BNT162b2 (30 μg) (N[a] = 16061) | | Placebo (N[a] = 16218) | | | |
| Efficacy Endpoint Subgroup | n1[b] | Surveillance Time[c] (n2[d]) | n1[b] | Surveillance Time[c] (n2[d]) | VE (%) | (95% CI[e]) |
| First COVID-19 occurrence from 7 days after Dose 2 | | | | | | |
| Overall | 4 | 1.722 (15899) | 90 | 1.732 (16010) | 95.5 | (88.1, 98.8) |

TABLE 8-continued

Vaccine Efficacy - First COVID-19 Occurrence From 7 Days After Dose 2, by Subgroup - Subjects Without Evidence of Infection Prior to 7 Days After Dose 2 - Evaluable Efficacy Population (7 Days) - Interim Analysis 1

| | Vaccine Group (as Randomized) | | | | | |
|---|---|---|---|---|---|---|
| | BNT162b2 (30 μg) ($N^a$ = 16061) | | Placebo ($N^a$ = 16218) | | | |
| Efficacy Endpoint Subgroup | n1[b] | Surveillance Time[c] (n2[d]) | n1[b] | Surveillance Time[c] (n2[d]) | VE (%) | (95% CI[e]) |
| Age group (years) | | | | | | |
| 16 to 55 | 2 | 0.954 (8994) | 67 | 0.959 (9040) | 97.0 | (88.7, 99.6) |
| >55 | 2 | 0.767 (6905) | 23 | 0.773 (6970) | 91.2 | (64.6, 99.0) |
| Sex | | | | | | |
| Male | 2 | 0.874 (8115) | 38 | 0.865 (8029) | 94.8 | (79.8, 99.4) |
| Female | 2 | 0.848 (7784) | 52 | 0.867 (7981) | 96.1 | (85.1, 99.5) |
| Race | | | | | | |
| White | 4 | 1.477 (13399) | 85 | 1.491 (13530) | 95.3 | (87.4, 98.7) |
| Black or African American | 0 | 0.124 (1263) | 4 | 0.124 (1277) | 100.0 | (−51.8, 100.0) |
| All others[f] | 0 | 0.121 (1237) | 1 | 0.118 (1203) | 100.0 | (−3690.1, 100.0) |
| Ethnicity | | | | | | |
| Hispanic/Latino | 1 | 0.464 (4389) | 34 | 0.459 (4342) | 97.1 | (82.7, 99.9) |
| Non-Hispanic/non-Latino | 3 | 1.247 (11418) | 56 | 1.262 (11570) | 94.6 | (83.3, 98.9) |
| Country | | | | | | |
| Argentina | 0 | 0.271 (2436) | 28 | 0.266 (2402) | 100.0 | (86.2, 100.0) |
| Brazil | 0 | 0.087 (878) | 2 | 0.087 (879) | 100.0 | (−432.5, 100.0) |
| USA | 4 | 1.360 (12384) | 60 | 1.376 (12530) | 93.3 | (81.8, 98.2) |

Abbreviations:

N-binding = SARS-CoV-2 nucleoprotein-binding;

NAAT = nucleic acid amplification test;

SARS-CoV-2 = severe acute respiratory syndrome coronavirus 2;

VE = vaccine efficacy.

Note: Subjects who had no serological or virological evidence (prior to 7 days after receipt of the last dose) of past SARS-CoV-2 infection (ie, N-binding antibody [serum] negative at Visit 1 and SARS-CoV-2 not detected by NAAT [nasal swab] at Visits 1 and 2), and had negative NAAT at any unscheduled visit prior to 7 days after Dose 2 were included in the analysis.

Note: Data from subjects who are not confirmed 7 days post dose 2 cases are included in the analysis to comprehensively show all data reported and/or contribute to the total surveillance time calculation but may be subject to change with additional follow-up.

a. N = number of subjects in the specified group.

b. n1 = Number of subjects meeting the endpoint definition.

c. Total surveillance time in 1000 person-years for the given endpoint across all subjects within each group at risk for the endpoint. Time period for COVID-19 case accrual is from 7 days after Dose 2 to the end of the surveillance period.

d. n2 = Number of subjects at risk for the endpoint.

e. Confidence interval (CI) for VE is derived based on the Clopper and Pearson method adjusted to the surveillance time.

f. American Indian or Alaska native, Asian, Native Hawaiian or other Pacific Islander, multiracial, not reported race categories are presented as “All others”.

Severe COVID-19 Cases

Severe COVID-19 cases were reported in a total of 7 participants in Phase 3, all in the placebo group, as of the data cutoff date of 4 Nov. 2020 for the first interim analysis (Table 9). Five of these cases were reported between Dose 1 and Dose 2, none were reported less than 7 days after Dose 2, and 2 cases were reported at least 7 days after Dose 2.

TABLE 9

Severe COVID-19 Occurrence After Dose 1-Dose 1
All-Available Efficacy Population-Interim Analysis 1

| | Vaccine Group (as Randomized) | |
|---|---|---|
| Efficacy Endpoint | BNT162b2 (30 μg) ($N^a$ = 21617) $n^b$ | Placebo ($N^a$ = 21633) $n^b$ |
| Severe COV1D-19 occurrence after Dose 1 | 0 | 7 |

Note:
Data from subjects who are not confirmed 7 days post dose 2 cases are included in the analysis to comprehensively show all data reported and/or contribute to the total surveillance time calculation but may be subject to change with additional follow-up.
[a]N = number of subjects in the specified group.
[b]n = Number of subjects meeting the endpoint definition Efficacy Conclusions The first primary efficacy objective met success criteria. BNT162b2 achieved vaccine efficacy of 95.5% with a 2-sided 95% credible interval of 88.8% to 98.4% among participants without evidence of infection up to 7 days after Dose 2, and a >99.99% posterior probability for the true vaccine efficacy greater than 30% conditioning on available data.

All 7 severe COVID-19 cases (after Dose 1) were observed in the placebo group, as of the interim analysis cutoff date.

Immunogenicity Results

Phase 1

This Phase 1 interim Clinical Study Report (CSR) presents immunogenicity results for both adult age groups up to 1 month after Dose 2 for the BNT162b1 and BNT162b2 vaccine candidates at the 10-μg, 20-μg, and 30-μg dose levels, and up to 7 weeks after Dose 1 of BNT162b1 at the 100-μg dose level (younger age group only).

Results for the 7 days after Dose 1 time point are only analyzed and presented in the younger age group (18 to 55 years of age) for 10 μg and 30 μg BNT162b1.

SARS-CoV-2 Neutralizing Titers—Phase 1

GMTs

Overall, for both the BNT162b1 and the BNT162b2 recipients in both age groups, SARS-CoV-2 50% neutralizing GMTs modestly increased by Day 21 after Dose 1 and were substantially increased 7 days after Dose 2. Generally, GMTs in the older age group tended to be somewhat lower than the GMTs in the younger age group at most time points for both BNT162b1 and BNT162b2 recipients.

BNT162b1

Figure 72:
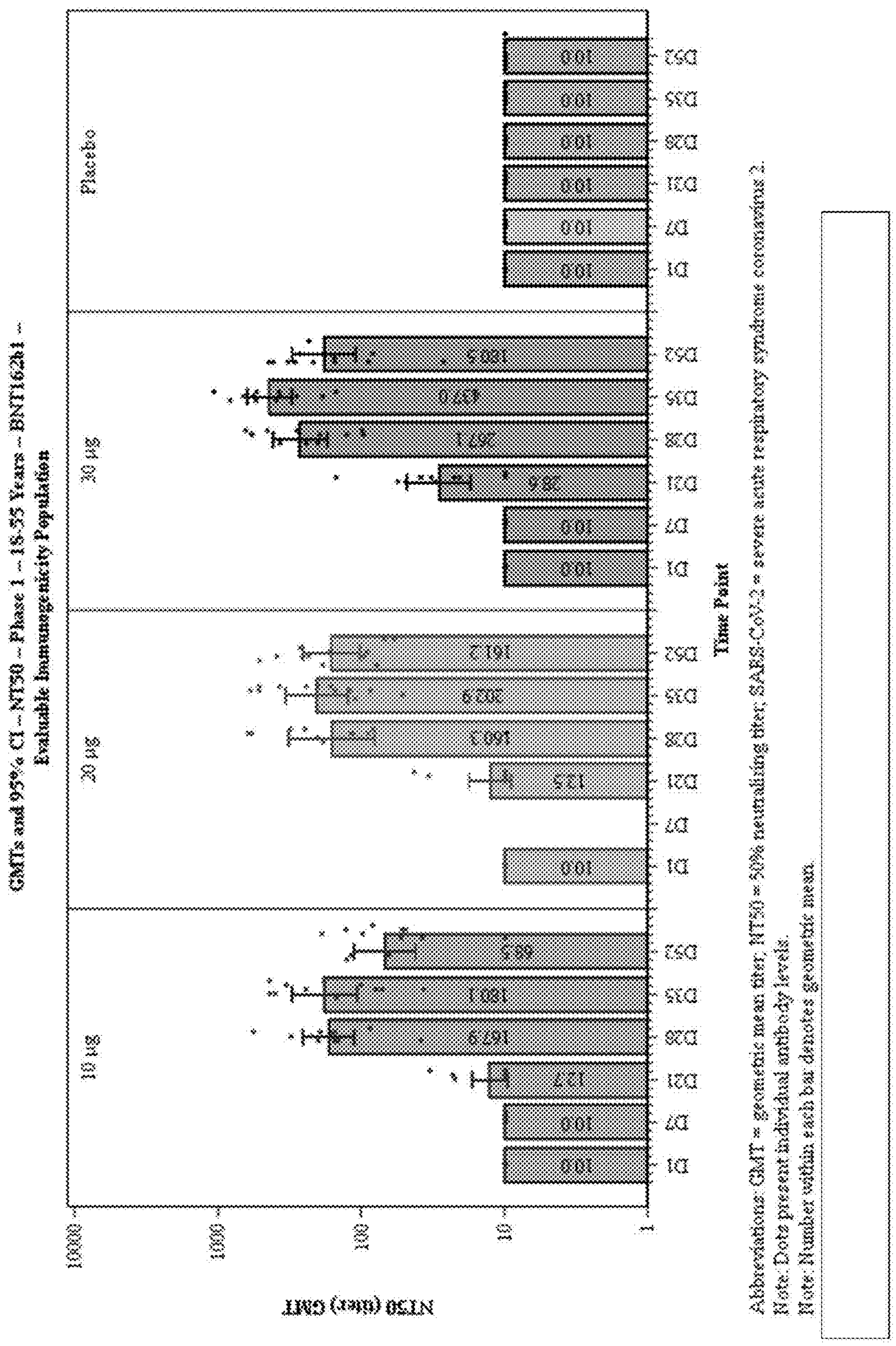

In the younger age group, SARS-CoV-2 50% neutralizing GMTs modestly increased by Day 21 after Dose 1 and were substantially increased 7 days after Dose 2 (Day 28) of BNT162b1, with higher GMTs observed in the 30-μg dose group compared to the 10-μg and 20-μg dose groups (FIG. 72). GMTs increased at 14 days after Dose 2 (Day 35) for all dose groups, and although GMTs decreased at 1 month after Dose 2 (Day 52), the Day 52 GMTs remained substantially higher than those at the earlier time points after Dose 1.

Figure 73:
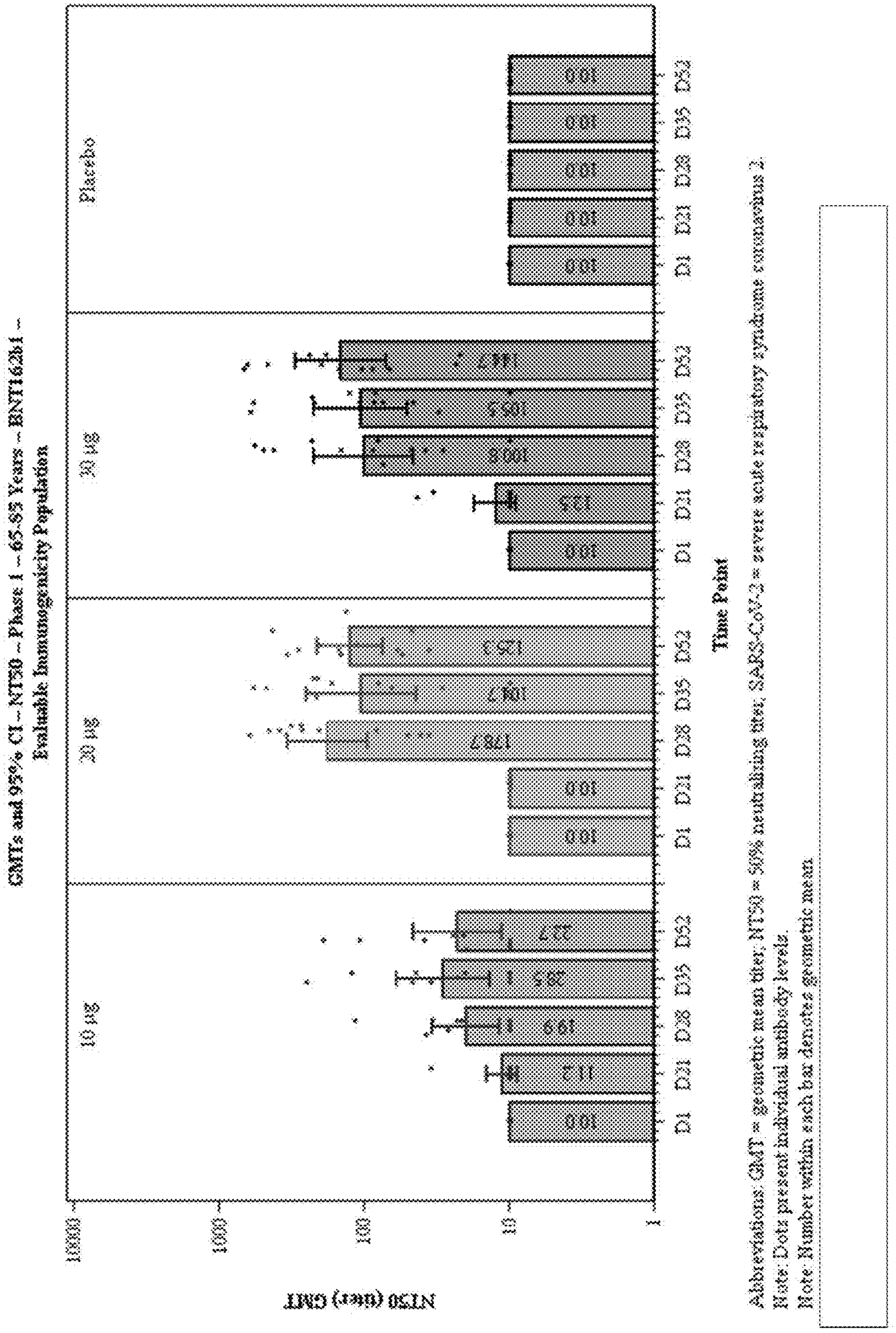

In the 100-μg dose group, SARS-CoV-2 50% neutralizing GMTs modestly increased by Day 21 after Dose 1 of BNT162b1 and decreased to a near baseline value by Day 52. Generally similar trends were observed in the older age group, with higher GMTs observed in the 20-μg and 30-μg dose groups of BNT162b1 compared to the 10-μg dose group (FIG. 73).

Similar trends were observed for the SARS-CoV-2 90% neutralizing GMTs.

Results for the all-available immunogenicity population in the younger age and older age groups were similar to those observed for the evaluable immunogenicity population.

RCDCs of SARS-CoV-2 50% and 90% neutralizing titers after BNT162b1 for the younger and older age groups show that the majority of participants responded by 7 days after Dose 2 of BNT162b1.

BNT162b2

Figure 74:
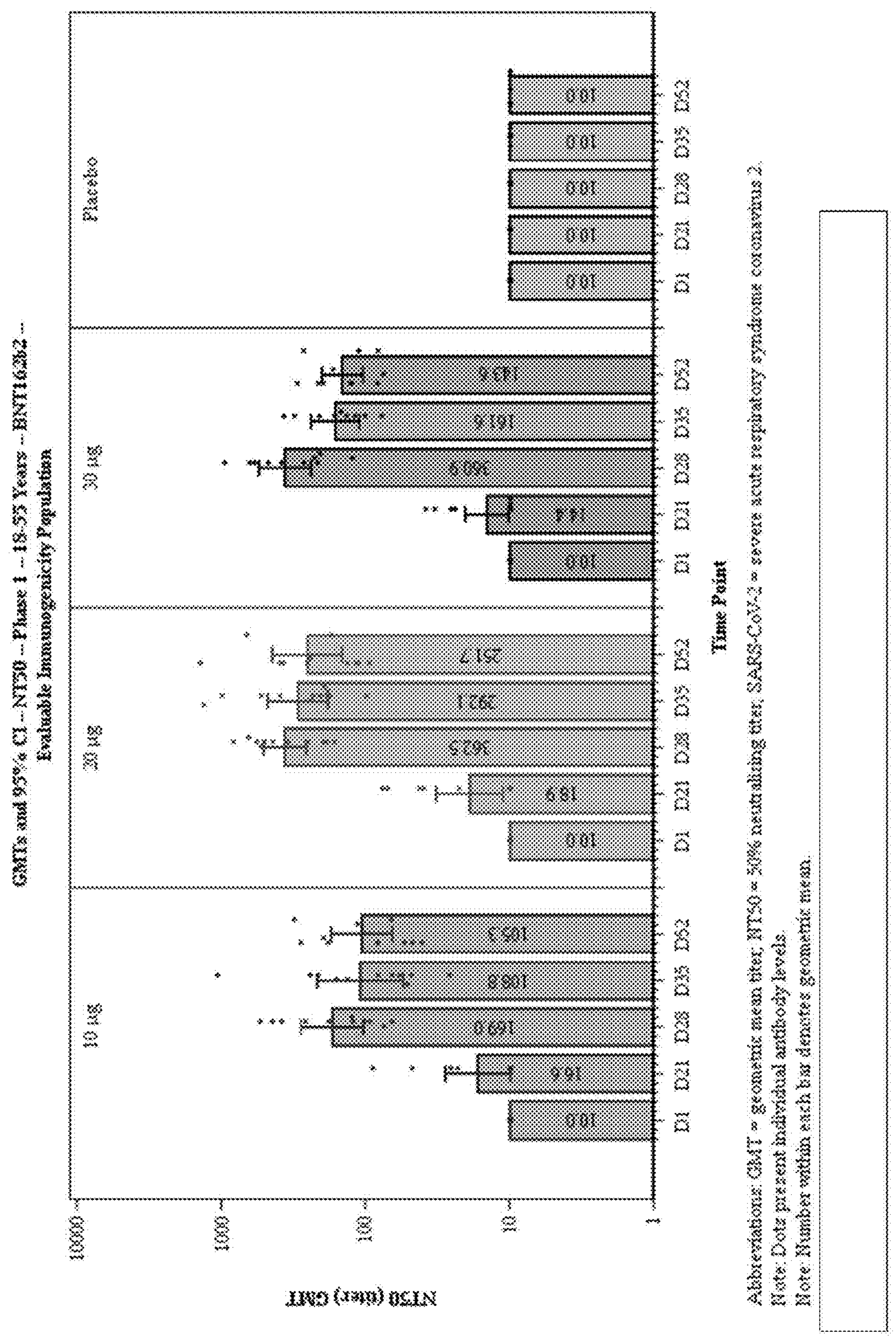
Figure 75:
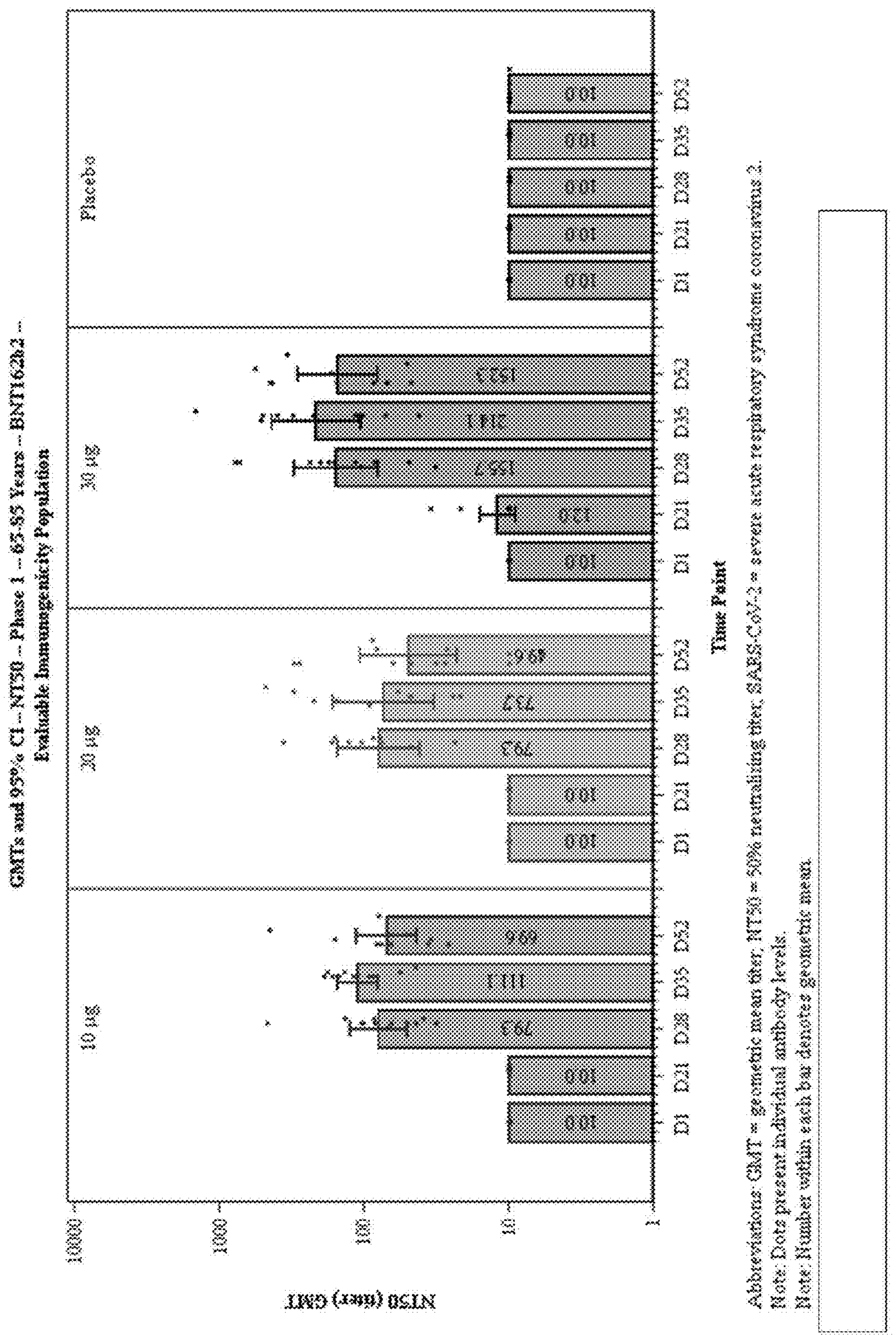

In the younger age group, SARS-CoV-2 50% neutralizing GMTs increased by Day 21 after Dose 1 and were substantially increased 7 days after Dose 2 (Day 28) of BNT162b2, with higher GMTs observed in the 20-μg and 30-μg dose groups compared to the 10-μg dose group (FIG. 74). The GMTs decreased at 14 days after Dose 2 (Day 35) and 1 month after Dose 2 (Day 52) of BNT162b2; however, the GMTs remained substantially higher than those at the earlier time points after Dose 1. Similar trends were generally observed in the older age group, with higher GMTs observed in the 30-μg dose groups compared to the 20-μg and 10-μg dose groups (FIG. 75). SARS-CoV-2 50% neutralizing GMTs were increased 7 days after Dose 2 and were similar in the 10-μg and 20-μg dose groups and higher in the 30-μg dose group. At 1 month after Dose 2, GMTs remained substantially higher than those at the earlier time points after Dose 1. In the older age group, SARS-CoV-2 50% neutralizing GMTs were generally lower than the GMTs in the younger age group. Similar trends were observed for the SARS-CoV-2 90% neutralizing GMTs.

Results for the all-available immunogenicity population in the younger and older age groups were similar to those observed for the evaluable immunogenicity population. RCDCs of SARS-CoV-2 50% and 90% neutralizing titers for the younger and older age groups show that the majority of participants responded by 7 days after Dose 2 of BNT162b2.

GMFRs

Overall, for both the BNT162b1 and the BNT162b2 recipients, and in both age groups, GMFRs of SARS-CoV-2 50% neutralizing titers from before vaccination to 7 days after Dose 2 (Day 28) were substantially higher compared to the respective GMFRs after Dose 1. GMFRs in the older age group were generally lower than the those in the younger age group for both BNT162b1 and BNT162b2 recipients.

BNT162b1

In the younger age group, GMFRs of SARS-CoV-2 50% neutralizing titers from before vaccination to 7 days after Dose 2 (Day 28) of BNT162b1 were substantially high compared to GMFRs at earlier time points after Dose 1 of BNT162b1 in all dose groups, with GMFRs being highest in the 30-μg dose group. At 1 month after Dose 2, the GMFRs remained higher than those at the earlier time points after Dose 1.

In the 100-μg dose group, the GMFRs of SARS-CoV-2 50% neutralizing titers were not substantially increased through Day 52 after Dose 1 of BNT162b1.

In the older age group, GMFRs of SARS-CoV-2 50% neutralizing titers from before vaccination to 7 days after Dose 2 (Day 28) of BNT162b1 were substantially high compared to GMFRs at the earlier time point after Dose 1 of BNT162b1 in the 20-µg and 30-µg dose groups with GMFRs being highest in the 20-µg dose group. The GMFRs remained high in the 20-µg and 30-µg dose groups at 1 month after Dose 2 (Day 52) of BNT162b1 compared to GMFRs at the earlier time point after Dose 1.

Similar trends were observed for GMFRs of SARS-CoV-2 90% neutralizing titers in the younger age group and older age group.

Results for the all-available immunogenicity population in the younger age and older age groups were similar to those observed for the evaluable immunogenicity population.

BNT162b2

In the younger age group, GMFRs of SARS-CoV-2 50% neutralizing titers from before vaccination to 7 days after Dose 2 (Day 28) of BNT162b2 were substantially high compared to GMFRs at the earlier time point after Dose 1 of BNT162b2 for all dose groups, with GMFRs being similar and highest in the 20-µg and 30-µg dose groups. GMFRs remained high through 1 month after Dose 2 of BNT162b2 compared to GMFRs 21 days after Dose 1 of BNT162b2.

In the older age group, GMFRs of SARS-CoV-2 50% neutralizing titers from before vaccination to 7 days after Dose 2 (Day 28) of BNT162b2 were substantially high compared to GMFRs at the earlier time point after Dose 1 of BNT162b2 in all dose groups, with GMFRs being highest in the 30-µg dose group. GMFRs remained high through 1 month after Dose 2 of BNT162b2 compared to GMFRs at 21 days after Dose 1 of BNT162b2.

Similar trends were observed for GMFRs of SARS-CoV-2 90% neutralizing titers in the younger and older age groups.

Results for the all-available immunogenicity population in the younger and older age groups were similar to those observed for the evaluable immunogenicity population.

Number (%) of Participants Achieving a ≥4-Fold Rise

Overall, for both the BNT162b1 and the BNT162b2 recipients, and in both age groups, most participants achieved a ≥4-fold rise in SARS-CoV-2 50% neutralizing titers from before vaccination to 7 days after Dose 2, except in the older participants in the 10-µg BNT162b1 dose group.

BNT162b1

In the younger age group, from before vaccination to 21 days after Dose 1 of BNT162b1, no participants in the 10-µg dose group and ≤3 participants in the 20-µg and the 30-µg dose groups achieved a ≥4-fold rise in SARS-CoV-2 50% neutralizing titers. From before vaccination to both 7 days and 1 month after Dose 2 of BNT162b1 most or all participants in the 10-µg, 20-µg, and 30-µg dose groups achieved a ≥4-fold rise in SARS-CoV-2 50% neutralizing titers.

In the older age group, from before vaccination to 21 days after Dose 1 of BNT162b1, only 1 participant in the 30-µg dose group achieved a ≥4-fold rise in SARS-CoV-2 50% neutralizing titers. From before vaccination to both 7 days and 1 month after Dose 2 of BNT162b1, ≤2 participants in the 10-µg group and 9 to 11 participants in the 20-µg and 30-µg dose groups achieved a ≥4-fold rise in SARS-CoV-2 50% neutralizing titers.

Results for the all-available immunogenicity population in the younger and older age groups were similar to those observed for the evaluable immunogenicity population.

BNT162b2

In the younger age group, from before vaccination to 21 days after Dose 1 of BNT162b2, 2 (18.2%) participants in the 10-µg dose group, 3 (25.0%) participants in the 20-µg dose group, and none in the 30-µg group achieved a ≥4-fold rise in SARS-CoV-2 50% neutralizing titers. From before vaccination to 7 days after Dose 2 of BNT162b2, all participants achieved a ≥4-fold rise in SARS-CoV-2 50% neutralizing titers, which was maintained through 1 month after Dose 2 of BNT162b2.

In the older age group, from before vaccination to 21 days after Dose 1 of BNT162b2, no participants achieved a ≥4-fold rise in SARS-CoV-2 50% neutralizing titers in any dose group. From before vaccination to 7 days after Dose 2 of BNT162b2, 10 (83.3%), 9 (81.8%), and 10 (90.9%) participants achieved a ≥4-fold rise in SARS-CoV-2 50% neutralizing titers in the 10-µg, 20-µg, and 30-µg dose groups, respectively. From before vaccination to 1 month after Dose 2 of BNT162b2, 9 (75.0%), 6 (54.5%), and 11 (100.0%) participants achieved a ≥4-fold rise in SARS-CoV-2 50% neutralizing titers in the 10-µg, 20-µg, and 30-µg dose groups, respectively.

Results for the all-available immunogenicity population in the younger and older age groups were similar to those observed for the evaluable immunogenicity population.

SARS-CoV-2 Antigen-Specific Binding Antibody Levels—Phase 1

Vaccine candidate BNT162b1 encodes for the RBD of SARS-CoV-2. RBD-binding IgG responses for each dose level and age group for this candidate are described in this section. RBD-binding IgG levels were also assessed for candidate BNT62b2 which encodes the P2 S of SARS-CoV-2.

Vaccine candidate BNT162b2 encodes for the P2 S of SARS-CoV-2. S1-binding IgG responses for each dose level and age group for this candidate are described in this section. S1-binding IgG levels were also assessed for candidate BNT62b1 which encodes the RBD of SARS-CoV-2.

GMCs

Overall, for both the BNT162b1 and the BNT162b2 recipients, and in both age groups, RBD- and S1-binding GMCs increased substantially by Day 21 after Dose 1 and were further increased 7 days after Dose 2. Responses were maintained through Day 52. GMCs in the older age group were generally lower than the GMCs in the younger age group, with the exception of Day 28 in the 20-µg BNT162b1 dose group for both RBD- and S1-binding IgG levels.

BNT162b1

Figure 76:
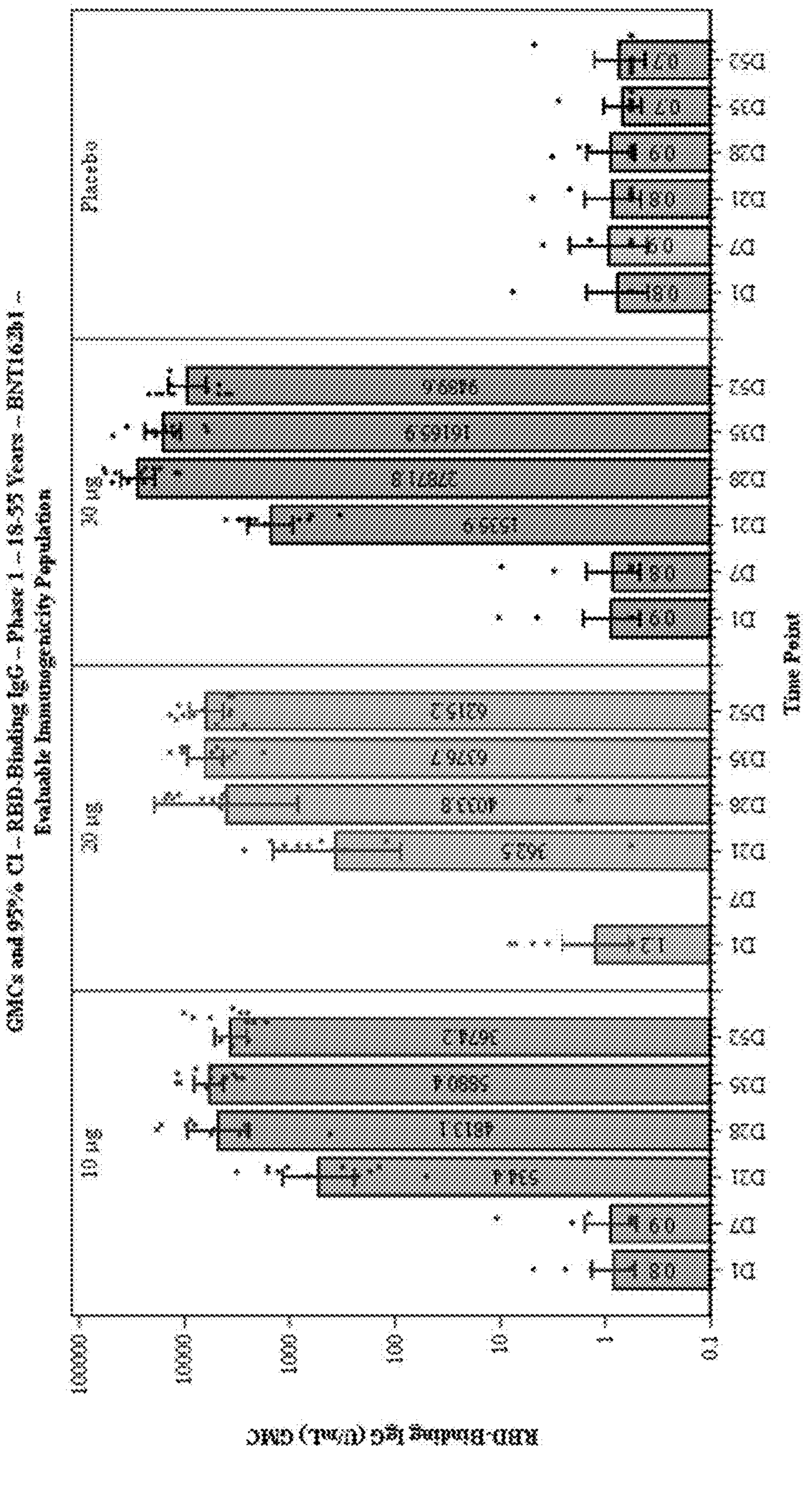

In the younger age group, RBD-binding GMCs increased substantially by Day 21 after Dose 1 of BNT162b1 and further increased 7 days after Dose 2 (Day 28) of BNT162b1, with higher GMCs observed in the 30-µg dose group compared to the 10-µg and 20-µg dose groups (FIG. 76). At 1 month after Dose 2 (Day 52), the GMCs remained substantially higher than at the earlier time points after Dose 1.

In the 100-µg BNT162b1 group, the RBD-binding GMC increased substantially by 21 days after BNT162b1 and remained higher through Day 52 compared to the Day 7 GMC.

Figure 77:
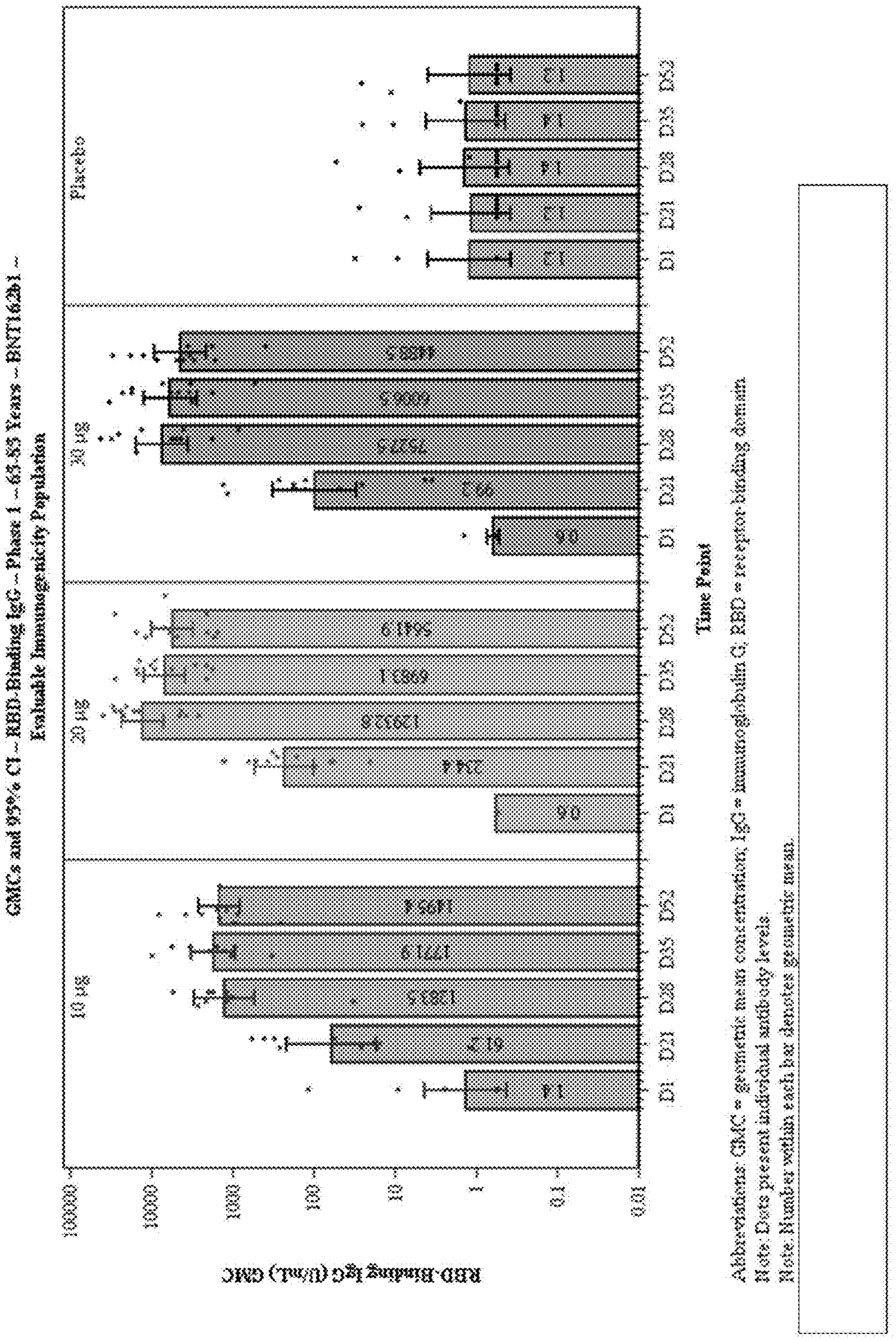

In the older age group, RBD-binding GMCs increased substantially by Day 21 after Dose 1 of BNT162b1 and further increased 7 days after Dose 2 (Day 28) of BNT162b1, with higher GMCs observed in the 20-µg and 30-µg dose groups compared to the 10-µg group (FIG. 77). At 1 month after Dose 2 (Day 52), the GMCs remained substantially higher than at the earlier time point after Dose 1.

S1-binding IgG GMC results for BNT162b1 were similar to those observed for RBD-binding IgG GMCs in the younger (FIG. 78) and older age groups (FIG. 79), and in the 100-μg BNT162b1 group.

Results for the all-available immunogenicity population in the younger and older age groups were similar to those observed for the evaluable immunogenicity population. RCDCs of RBD- and S1-binding IgG levels show that the majority of participants responded by 21 days after Dose 1 of BNT162b1.

BNT162b2

Figure 80:
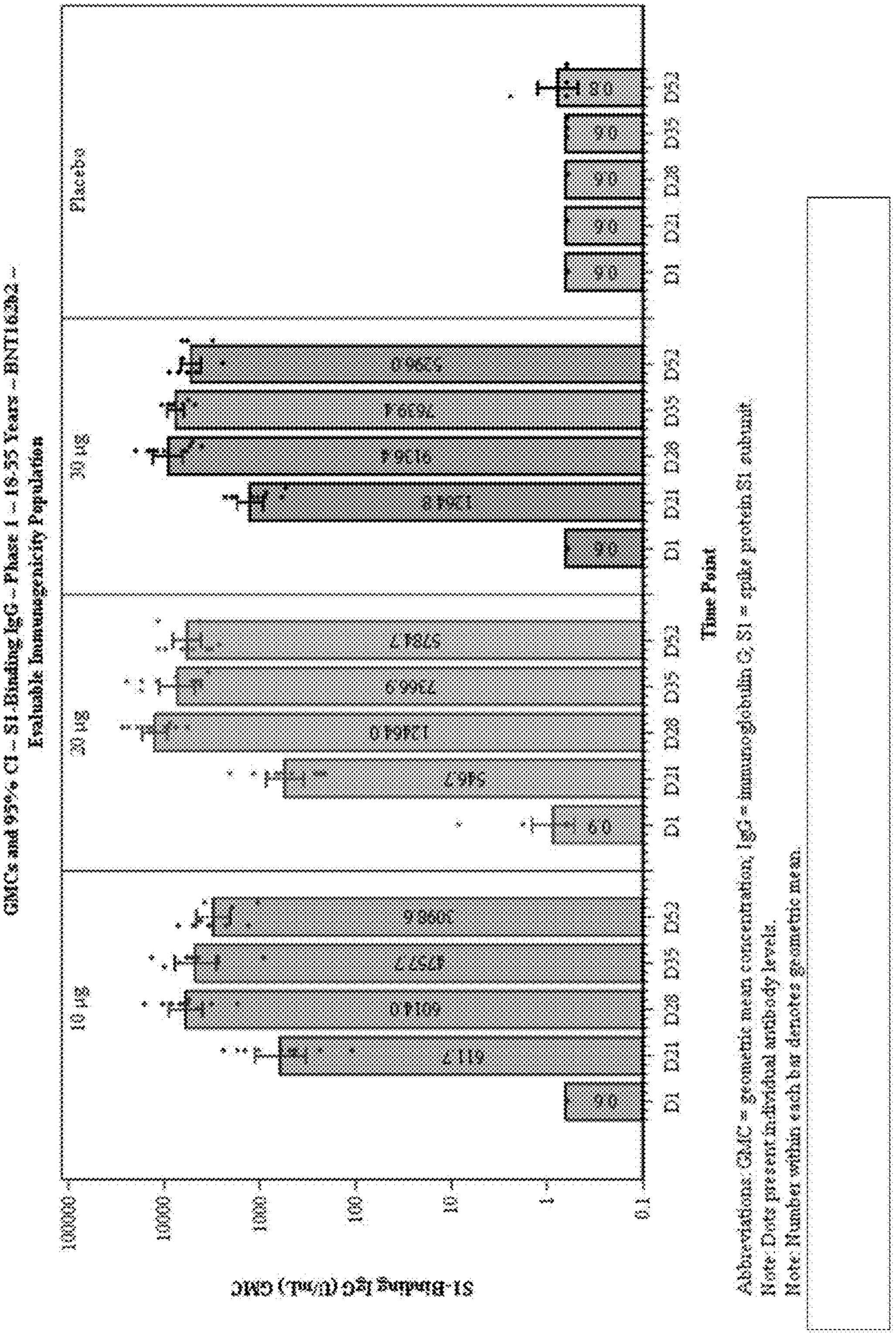
Figure 81:
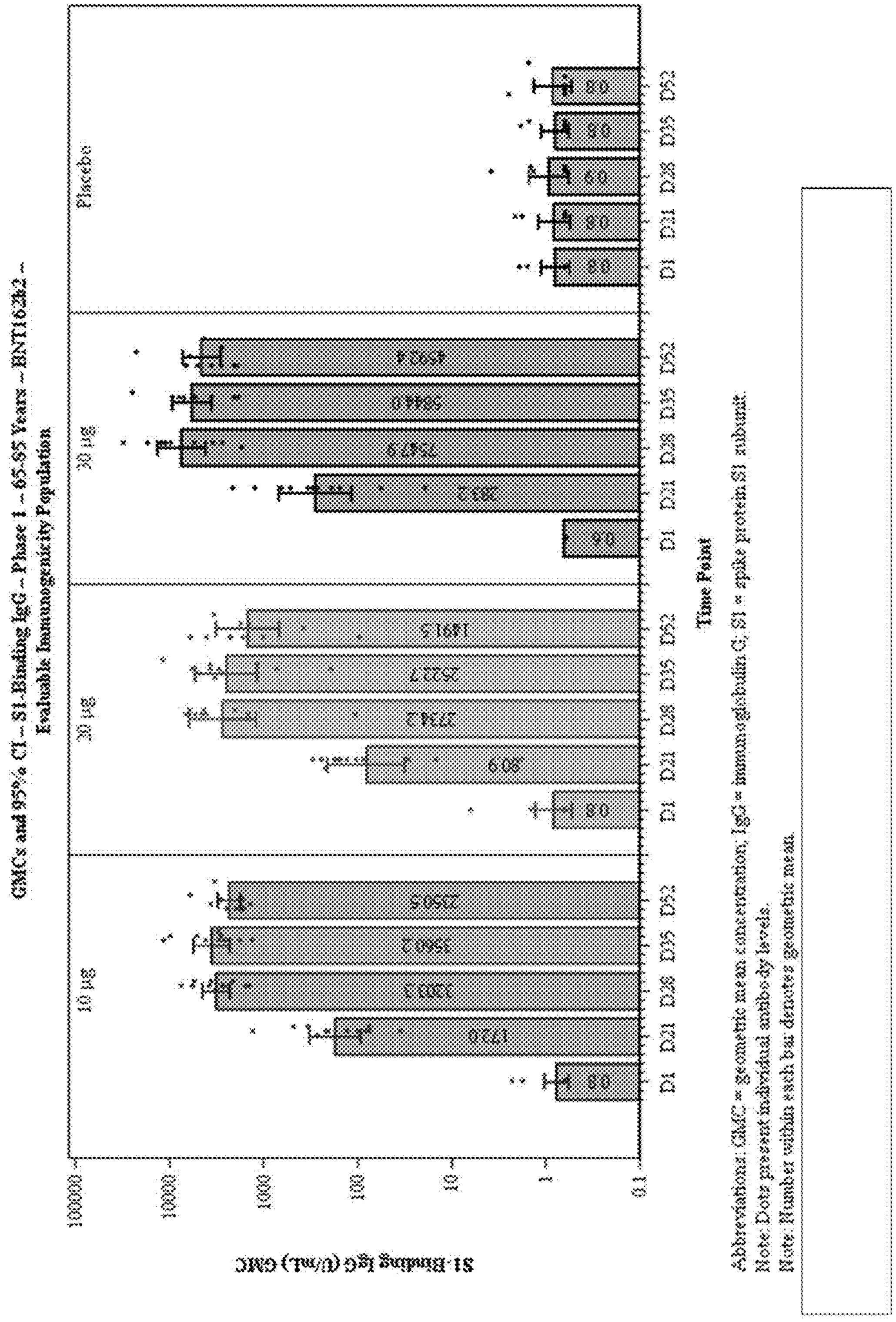
Figure 82:
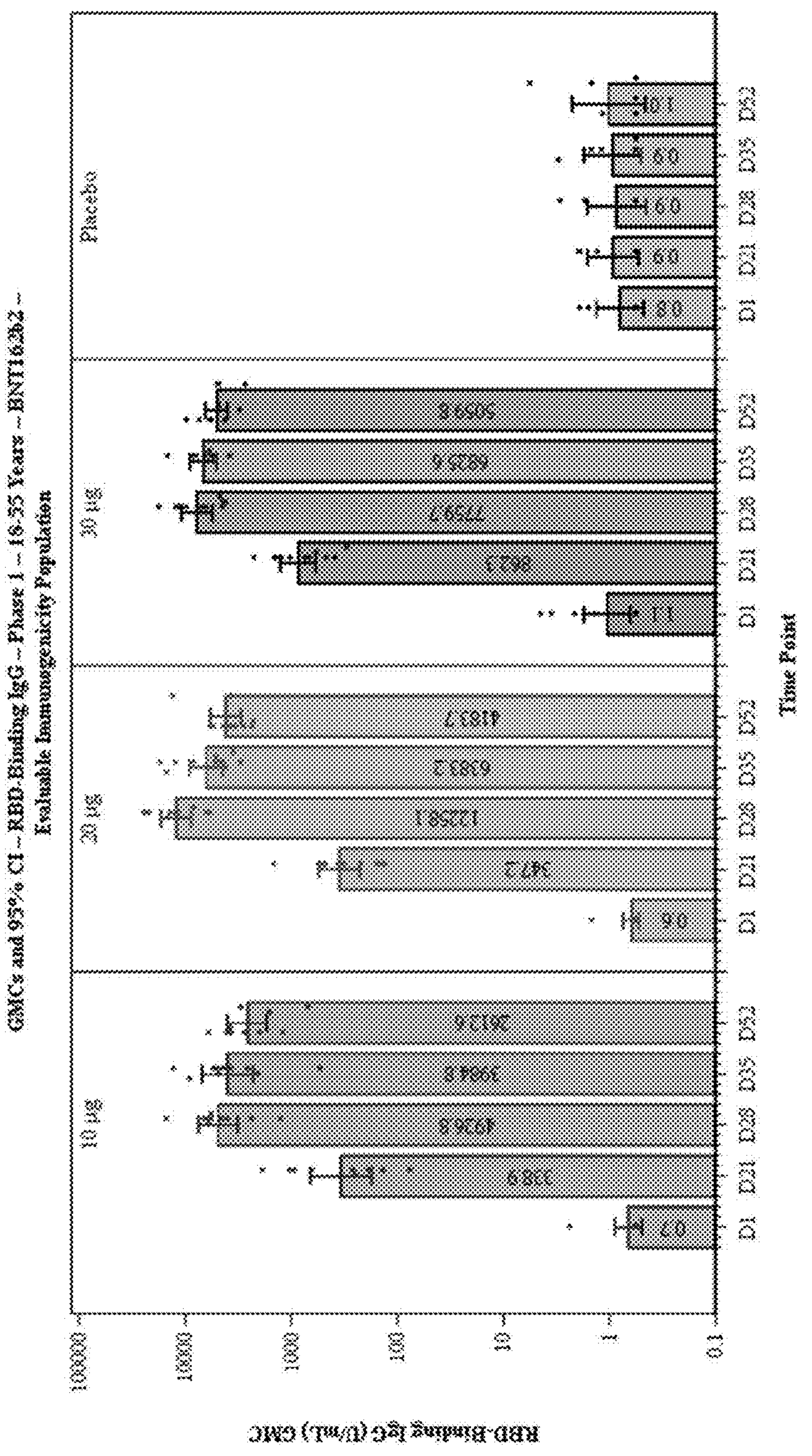

In the younger age group, S1-binding GMCs increased substantially by Day 21 after Dose 1 of BNT162b2 and were substantially increased by 7 days after Dose 2 (Day 28) of BNT162b2, with higher GMCs observed in the 20-μg and 30-μg dose groups compared to the 10-μg dose group (FIG. 80). At 1 month after Dose 2 (Day 52), the GMCs remained substantially higher than at the earlier time point after Dose 1. Similar trends were observed in the older age group, with higher S1-binding GMCs observed in the 30-μg dose group compared to the 10-μg and 20-μg dose groups (FIG. 81).

Figure 83:
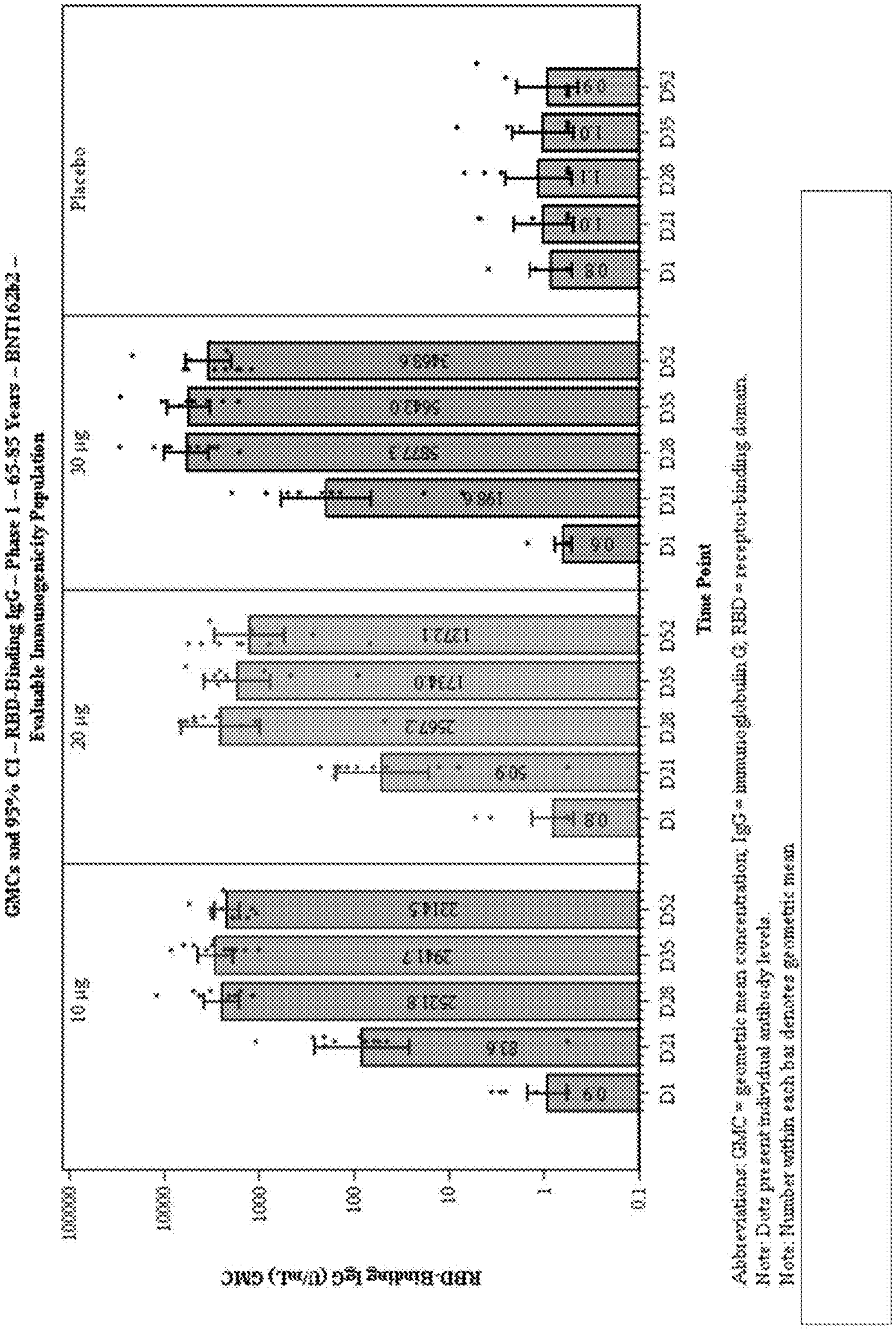

RBD-binding IgG GMC results for BNT162b2 were similar to those observed for S1-binding IgG GMCs in the younger (FIG. 82) and older age groups (FIG. 83). Results for the all-available immunogenicity population in the younger and older age groups were similar to those observed for the evaluable immunogenicity population. RCDCs of RBD- and S1-binding IgG levels after BNT162b2 show that the majority of participants responded by 21 days after Dose 1 of BNT162b2.

GMFRs

Overall, for the BNT162b1 and the BNT162b2 recipients, and in both age groups, GMFRs of RBD-binding IgG levels and GMFRs of S1-binding IgG levels were substantially high from before vaccination to 21 days after Dose 1, with greater GMFRs observed from before vaccination to 7 days after Dose 2.

BNT162b1

GMFRs of RBD-binding IgG levels were substantially high from before vaccination to Day 21 (before Dose 2) after Dose 1 of BNT162b1, with greater GMFRs observed from before vaccination to 7 days after Dose 2 (Day 28) of BNT162b1 in both the younger and older age groups, for the 10-μg, 20-μg, and 30-μg dose groups. GMFRs remained substantially high in the 10-μg, 20-μg, and 30-μg BNT162b1 groups from before vaccination to 1 month after Dose 2 compared to the earlier time points after Dose 1 for both age groups.

In the 100-μg BNT162b1 group, GMFR of RBD-binding IgG levels was substantially high from before vaccination by 21 days after BNT162b1 and remained higher through Day 52 compared to the Day 7 GMFR.

Similar trends were observed for GMFRs of S1-binding IgG levels for BNT162b1. Results for the all-available immunogenicity population in the younger age and older age groups were similar to those observed for the evaluable immunogenicity population.

BNT162b2

GMFRs of S1-binding IgG levels were substantially high from before vaccination to Day 21 (before Dose 2) after Dose 1 of BNT162b2, with greater GMFRs observed from before vaccination to 7 days after Dose 2 (Day 28) of BNT162b2 in both the younger and older age groups, for the 10-μg, 20-μg, and 30-μg dose groups. GMFRs remained substantially high in all BNT162b2 groups from before vaccination to 1 month after Dose 2 compared to the earlier time point after Dose 1 for both age groups. Similar trends were observed for GMFRs of RBD-binding IgG levels for BNT162b2. Results for the all-available immunogenicity population in the younger and older age groups were similar to those observed for the evaluable immunogenicity population.

Number (%) of Participants Achieving a ≥4-Fold Rise

Overall, for the BNT162b1 and the BNT162b2 recipients, and in both age groups, all participants achieved a ≥4-fold rise in S1- and RBD-binding IgG levels from before vaccination to 7 days after Dose 2, with the exception of 1 participant in the younger 20-μg BNT162b1 group.

BNT162b1

In the younger age group, from before vaccination to 21 days following Dose 1 of BNT162b1, all participants (except 1 in the 20-μg dose group) across all dose groups achieved a ≥4-fold rise in RBD-binding IgG levels. All participants in the 20-μg dose group achieved a ≥4-fold rise in RBD-binding IgG levels from before vaccination to 14 days after Dose 2 (Day 35).

In the older age group, from before vaccination to 21 days following Dose 1 of BNT162b1, all participants in the 20-μg and 30-μg dose groups and 8 (72.7%) participants in the 10-μg dose group achieved a ≥4-fold rise in RBD-binding IgG levels. All participants in the 10-μg dose group achieved a ≥4-fold rise in RBD-binding IgG levels from before vaccination to 7 days after Dose 2 (Day 28).

Similar trends were generally observed for participants achieving a ≥4-fold rise in S1-binding IgG levels for BNT162b1.

Results for the all-available immunogenicity population in the younger and older age groups were similar to those observed for the evaluable immunogenicity population.

BNT162b2

In the younger age group, from before vaccination to 21 days following Dose 1 of BNT162b2, all participants in each dose group achieved a ≥4-fold rise in S1-binding IgG levels.

In the older age group, from before vaccination to 21 days following Dose 1 of BNT162b2, all participants in the 10-μg, and 30-μg dose groups and 11 (91.7%) participants in the 20-μg dose group achieved a ≥4-fold rise in S1-binding IgG levels. All participants in the 20-μg dose group achieved a ≥4-fold rise in S1-binding IgG levels from before vaccination to 7 days after Dose 2 (Day 28).

Similar trends were generally observed for participants achieving a ≥4-fold rise in RBD-binding IgG levels for BNT162b2.

Results for the all-available immunogenicity population were similar to those observed for the evaluable immunogenicity population in the younger and older age groups.

GMRs of SARS-CoV-2-Neutralizing Titers to SARS-CoV-2 Antigen-Specific Binding Antibody Levels Overall, for BNT162b1 and BNT162b2 recipients, GMRs of SARS-CoV-2 50% neutralizing titers to RBD- or S1-binding IgG levels show a more robust RBD- or S1-binding levels relative to neutralizing titers, which were similar within each age group.

BNT162b1

At 21 days after Dose 1 at 10 μg, 20 μg, or 30 μg, GMRs of SARS-CoV-2 50% neutralizing titers to RBD-binding IgG levels were ≤0.035 in the younger age group and ≤0.183 in the older age group. At 14 days after Dose 2, the GMRs were ≤0.032 in the younger age group and 0.018 in the older age group.

For the 100-μg dose group, the GMR was 0.018 at 21 days after Dose 1 and 0.014 at 35 days after Dose 1.

GMRs of SARS-CoV-2 50% neutralizing titers to S1-binding IgG levels were similar to GMRs of SARS- CoV-2 50% neutralizing titers to RBD-binding IgG levels in the younger and older age groups after BNT162b1.

Results for the all-available immunogenicity population in the younger and older age groups were similar to those observed for the evaluable immunogenicity population.

BNT162b2

At 21 days after Dose 1, GMRs of SARS-CoV-2 50% neutralizing titers to S1-binding IgG levels were ≤0.035 in the younger age group and ≤0.124 in the older age group. At 14 days after Dose 2, the GMRs were ≤0.040 in the younger age group and ≤0.037 in the older age group.

Results for the all-available immunogenicity population in the younger and older age groups were similar to those observed for the evaluable immunogenicity population.

Evaluating BNT162b1 and BNT162b2 GMRs

In the younger age group at 21 days after Dose 1, GMRs of SARS-CoV-2 50% neutralizing titers to RBD-binding IgG levels were ≤0.035 after BNT162b1 and ≤0.054 after BNT162b2. At 14 days after Dose 2, the GMRs were ≤0.032 after BNT162b1 and ≤0.046 after BNT162b2.

In the older age group at 21 days after Dose 1, GMRs of SARS-CoV-2 50% neutralizing titers to RBD-binding IgG levels were ≤0.183 after BNT162b1 and ≤0.196 after BNT162b2. At 14 days after Dose 2, the GMRs were ≤0.018 after BNT162b1 and ≤0.043 after BNT162b2.

In the younger age group at 21 days after Dose 1, GMRs of SARS-CoV-2 50% neutralizing titers to S1-binding IgG levels were ≤0.061 after BNT162b1 and ≤0.035 after BNT162b2. At 14 days after Dose 2, the GMRs were ≤0.035 after BNT162b1 and ≤0.040 after BNT162b2.

In the older age group at 21 days after Dose 1, GMRs of SARS-CoV-2 50% neutralizing titers to S1-binding IgG levels were ≤0.328 after BNT162b1 and ≤0.124 after BNT162b2. At 14 days after Dose 2, the GMRs were ≤0.022 after BNT162b1 and ≤0.037 after BNT162b2.

Phase 1 Summary of Immunogenicity Results Evaluating BNT162b1 and BNT162b2

In general, a modest neutralizing immune response was observed in both the younger and older age groups after the first dose. A much more robust immune response was observed 7 days after the second dose of either BNT162b1 or BNT162b2 at all dose levels in both the younger and older age groups. Antibody levels at the last time point tested were still substantially above those at baseline.

In the younger age group:

At 7 days after Dose 2, SARS-CoV-2 50% neutralizing GMTs in the 20-μg and 30-μg dose groups were higher for BNT162b2 recipients than for BNT162b1 recipients. The GMTs were similar in the 10-μg dose group for both recipients. At 1 month after Dose 2 (Day 52), GMTs remained substantially higher than those at the earlier time points after Dose 1 for both BNT162b1 and BNT162b2 recipients.

From before vaccination to 7 days after Dose 2, GMFRs of SARS-CoV-2 50% neutralizing titers were substantially high for BNT162b1 and BNT162b2 recipients at the 30 μg dose level.

From before vaccination to 7 days after Dose 2, all participants at the 30-μg dose level who received BNT162b1 or BNT162b2 achieved a ≥4-fold rise in SARS CoV-2 50% neutralizing titers.

In the older age group:

At 7 days after Dose 2, SARS-CoV-2 50% neutralizing GMT in the 30-μg dose group was higher for BNT162b2 recipients than for BNT162b1 recipients. At 1 month after Dose 2 (Day 52), the SARS-CoV-2 50% neutralizing GMTs in the 30-μg dose group were similar for both BNT162b1 and BNT162b2 recipients.

From before vaccination to 7 days after Dose 2, the GMFR of SARS-CoV-2 50% neutralizing titers were substantially high for BNT162b1 and BNT162b2 recipients at the 30-μg dose level.

From before vaccination to 7 days after Dose 2, most participants who received BNT162b1 or BNT162b2 at the 30-μg dose level achieved a ≥4-fold rise in SARS-CoV-2 50% neutralizing titers.

Phase 1 Immunogenicity Conclusions

Both BNT162b1 and BNT162b2 elicited robust SARS-CoV-2 neutralizing antibody response 7 days after Dose 2 in younger and older adults, based on GMTs, GMFRs, proportions of participants achieving a ≥4-fold rise in neutralizing titers, and RCDCs. Neutralizing antibody response was maintained through Day 52 and was similar for the candidates within the corresponding age and dose groups.

Both BNT162b1 and BNT162b2 elicited substantial rises in antigen binding IgG levels 7 days after Dose 2, based on GMCs, GMFRs, and proportions of participants achieving a ≥4-fold rise in IgG-antigen specific binding. Responses were maintained through Day 52.

In the 100-μg dose group, SARS-CoV-2 neutralizing antibody response modestly increased by 3 weeks after Dose 1 of BNT162b1, but neutralizing antibody response returned to levels similar to baseline by 7 weeks after Dose 1.

These data support the need for a 2-dose vaccination series.

Phase 2

Immunogenicity is an exploratory endpoint for the Phase 2 part of the study.

Phase 3

Immunogenicity is a secondary (12 to 15 year olds compared with 16 to 25 year olds) and an exploratory endpoint for the Phase 3 part of the study.

Example 15: Safety Evaluation

In this interim CSR, all participants in Phase 1 and the first 6610 participants in Phase 2/3 (360 participants from Phase 2 included) used an e-diary for reporting local reactions and systemic events. A total of 1125 participants in Phase 2/3 were identified as baseline SARS-CoV-2 positive, defined as having a positive N-binding antibody test result or positive nucleic acid amplification test (NAAT) result on the day of Dose 1; of these, 545 received BNT162b2 and 580 received placebo.

Phase 1

Safety data are available up through the date cutoff date (24 Aug. 2020) and are summarized at various time points relative to Dose 1 or Dose 2. Safety results for Phase 1 vaccine candidates BNT162b1 and BNT162b2 for both adult age groups are presented up to 1 month after Dose 2 (or data cutoff date) at the 10-μg, 20-μg, and 30-μg dose levels. Safety results for BNT162b1 at the 100-μg dose level in the younger age group are presented up to 3 weeks after Dose 1 or to before Dose 2 based on the data cutoff date. Note that the group of participants 18 to 55 years of age who received 100 μg BNT162b1 did not receive a second dose of 100 μg BNT162b2 per IRC decision.

Local Reactions—Phase 1

Overall, for both the BNT162b1 and the BNT162b2 recipients, and in both age groups, pain at the injection site was the most frequent local reaction. Redness and swelling occurred less frequently in the BNT162b2 group and in the BNT162b1 group. In both the BNT162b1 and BNT162b2 groups, the frequency of local reactions was lower in the older age group compared to the younger age group, and there was a trend of a higher frequency of local reactions with increased dose.

BNT162b1

Figure 84:
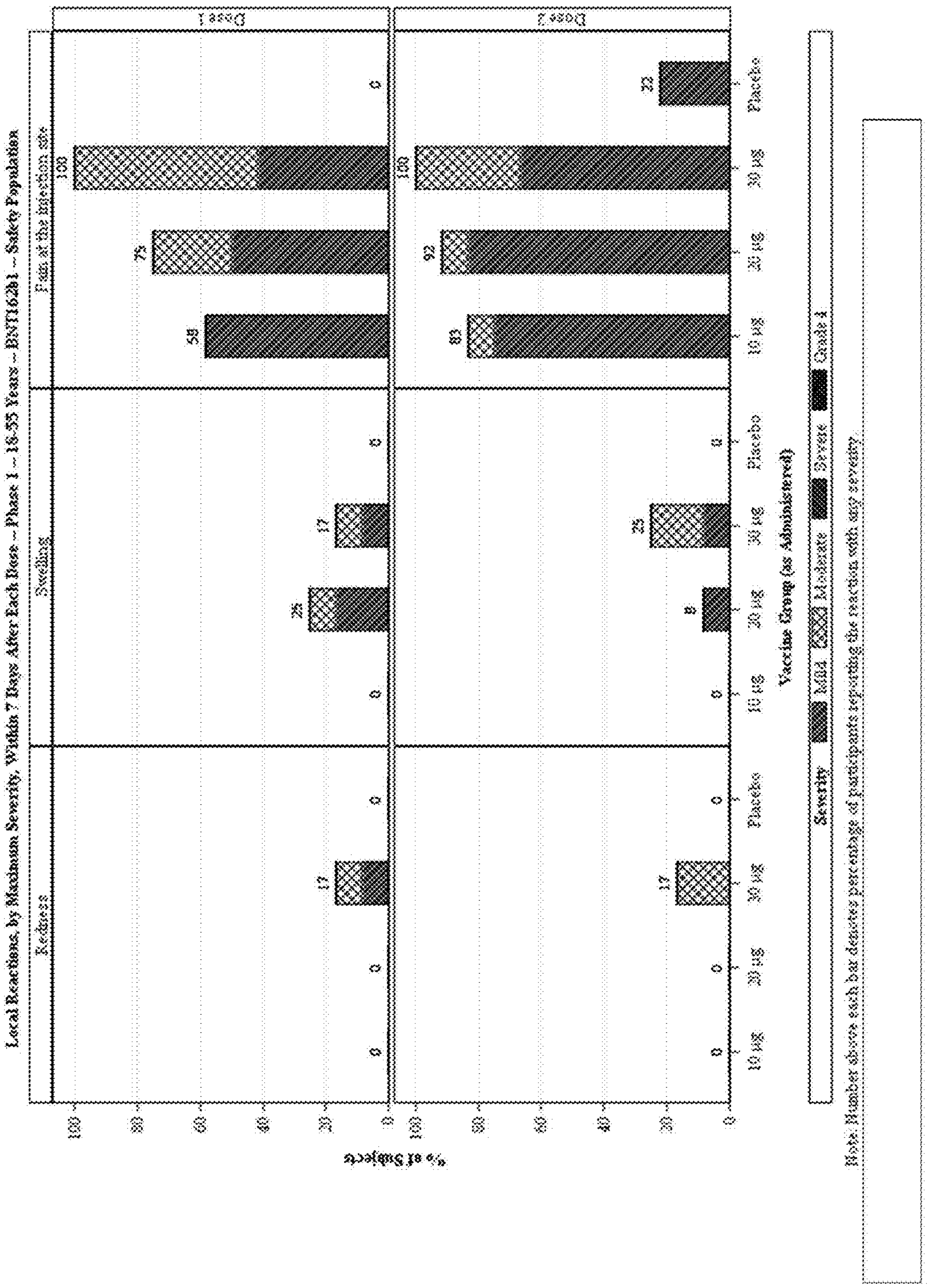

In the younger age group, pain at the injection site was the most frequently reported local reaction within 7 days after Dose 1 of BNT162b1. As dose level increased from 10 μg to 30 μg, increasing frequencies of pain at the injection site (58.3% to 100.0%, 7 and 12 participants, respectively) were observed compared to none in the placebo group (FIG. 84). Redness was reported in 2 (16.7%) participants in the 30-μg dose group, and swelling was reported in 3 (25.0%) participants in the 20-μg dose group and 2 (16.7%) participants in the 30-μg dose group. In the 100-μg dose group, pain at the injection site (12 [100.0%] participants), swelling (5 [41.7%] participants), and redness (4 [33.3%] participants) were reported, and 1 [8.3%] participant had severe injection site pain (note: per IRC decision, Dose 2 was later administered to participants at the 10-μg dose level).

Within 7 days after Dose 2 of BNT162b1 in the younger age group, pain at the injection site remained the most frequently reported local reaction reaching 12 (100.0%) participants with the 30-μg dose group compared to the placebo group (2 [22.2%] participants), while the proportions of participants with redness (2 [16.7%] participants) and swelling (3 [25.0%] participants) were highest in the 30-μg dose group (FIG. 84). No redness or swelling was reported in the placebo group.

Figure 85:
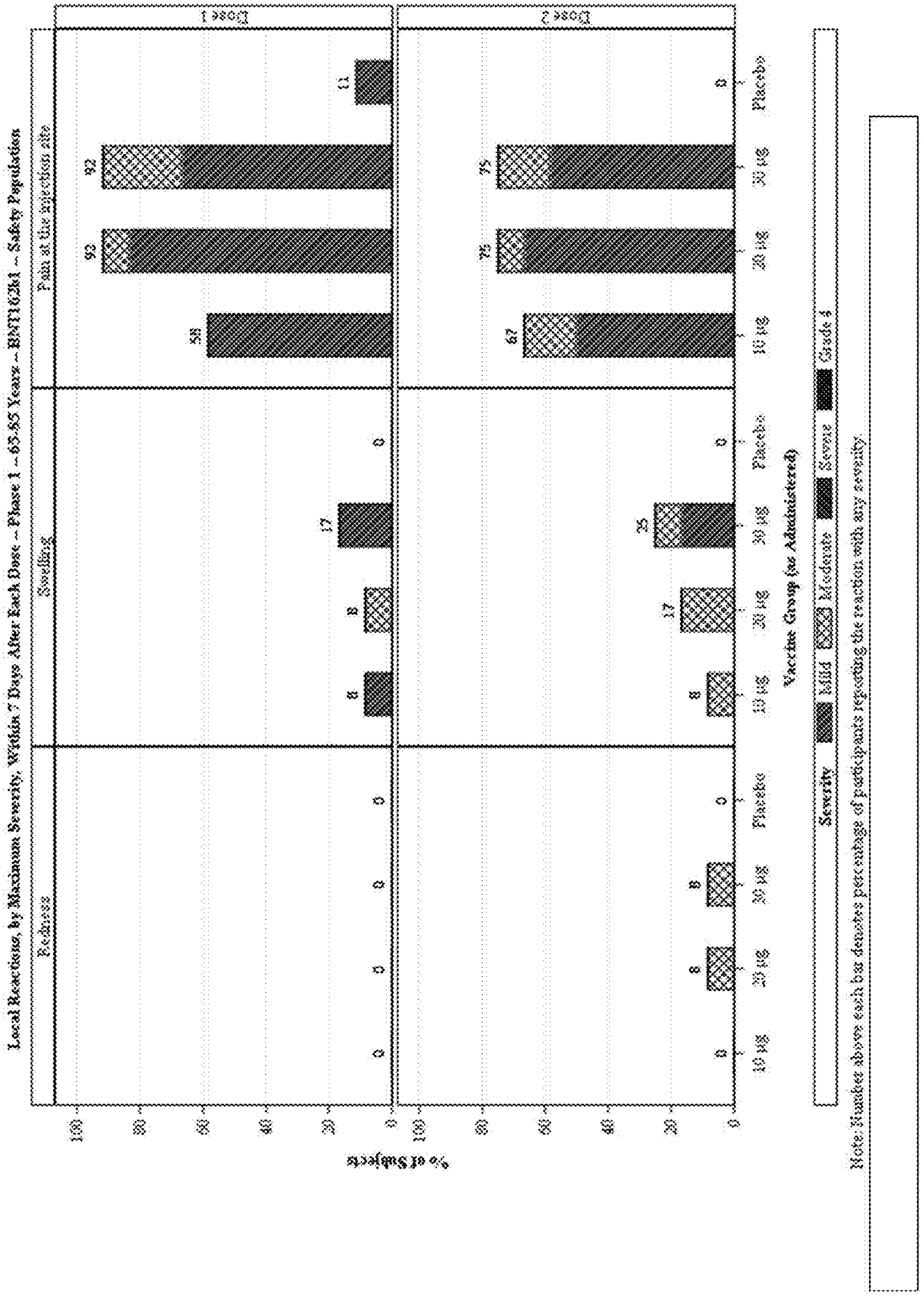

In the older age group, pain at the injection site was the most frequently reported local reaction within 7 days after Dose 1 of BNT162b1 in both the 20-μg and 30-μg dose groups (11 [91.7%] participants each) compared to the placebo group (1 [11.1%] participant) (FIG. 85). No redness was reported, and the maximal frequency of swelling (2 [16.7%] participants) was in the 30-μg group. No redness or swelling was reported in the placebo group.

Within 7 days after Dose 2 of BNT162b1 in the older age group, pain at the injection site was the most frequently reported local reaction in both the 20-μg and 30-μg dose groups (9 [75.0%] participants each). The frequency of swelling (3 [25.0%] participants) was maximal at 30 μg, while redness (1 [8.3%] participant each) was reported in the 20-μg and 30-μg dose groups. No redness or swelling was reported in the placebo group.

After the first and second dose and in both age groups, the majority of local reactions were mild or moderate in severity, and no Grade 4 local reactions were reported. Overall, for BNT162b1 recipients and in both age groups, pain at the injection site was the most frequent local reaction (58.3% to 100.0%), and redness (0% to 16.7%) and swelling (0% to 25.0%) occurred at a lower frequency. Notably, the frequency of local reactions was lower in the older age group compared to the younger age group, and there was a trend of a higher frequency of local reactions with increased dose.

In the younger age group, pain at the injection site had median onset day of Day 1.0 (day of vaccination) after either dose of BNT162b1 across doses 10 μg to 30 μg and after Dose 1 of BNT162b1 100 μg. Median onset day for redness and swelling was between Day 1.0 and Day 3.0 in all dose groups.

In the older age group, pain at the injection site had median onset day of Day 1.0 (day of vaccination) after Dose 1 of BNT162b1 across all dose groups and after Dose 2 for the 20-μg and 30-μg dose groups (median onset day was on Day 1.5 in the 10-μg dose group after Dose 2). With the exception of redness on Day 4 (20-μg dose group) and Day 5 (30-μg dose group) in 1 participant each after Dose 2, all other local reactions of redness or swelling reported had median onset day between Day 1.0 and Day 3.0 for all dose groups.

Local reactions resolved with median durations between 1.0 and 4.0 days in the younger age group and older age group across dose levels.

BNT162b2

Figure 86:
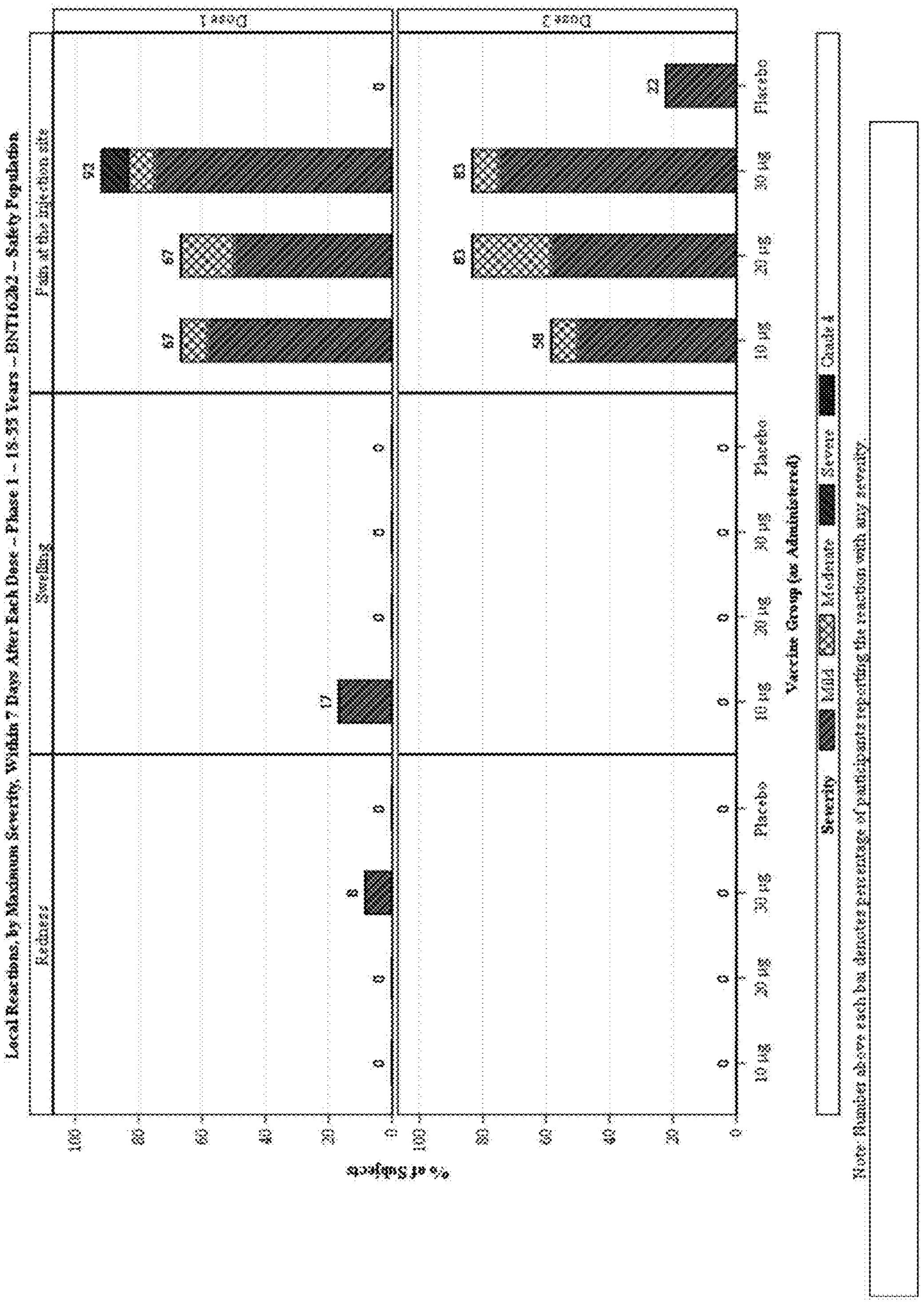

In the younger age group, pain at the injection site was the most frequently reported local reaction within 7 days after Dose 1, which was maximal in the 30-μg dose group (11 [91.7%] participants) (FIG. 86). One [8.3%] participant had severe injection site pain after Dose 1 of 30 μg. Most participants did not report swelling and redness. After Dose 2, pain at the injection site remained the most frequently reported local reaction (83.3%, 10 participants in each) in the 20-μg and 30-μg dose groups compared to the placebo group (2 [22.2%] participants). No participants reported redness and swelling for any dose group including placebo.

Figure 87:
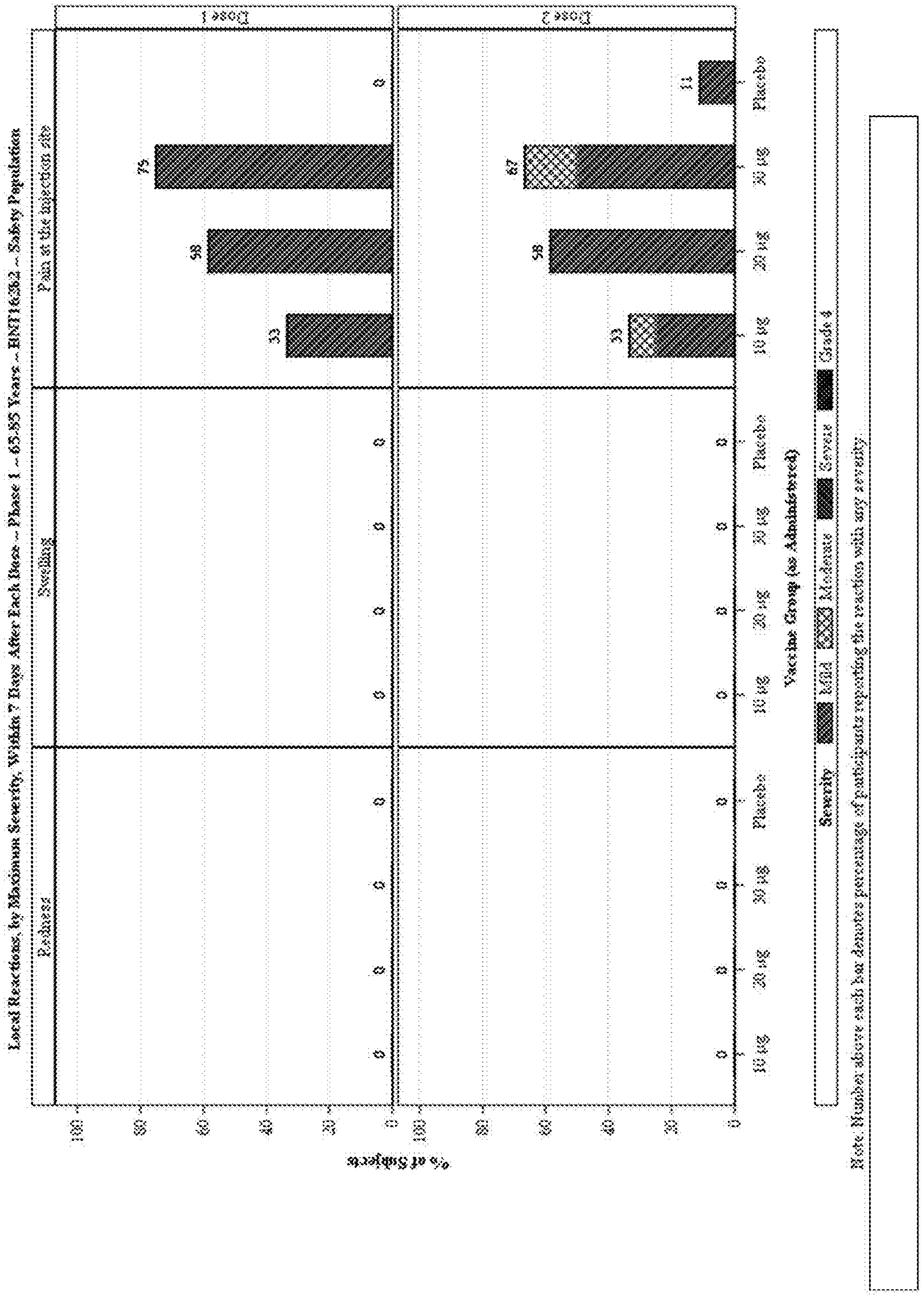

In the older age group, pain at the injection site was reported within 7 days after Dose 1 of BNT162b2 in all dose groups and was maximal in the 30-μg dose group (75.0%, 9 participants), while no redness and swelling was reported in any group (FIG. 87). Local reactions were not reported in the placebo group. After Dose 2, pain at the injection site (8 [66.7%] participants) was reported in the 30-μg group compared to the placebo group (9 [11.1%] participants); no participants who received BNT162b2 or placebo reported redness and swelling.

After the first and second dose and in both age groups, the majority of local reactions were mild or moderate in severity, and no Grade 4 local reactions were reported. Overall, for BNT162b2 recipients and in both age groups, pain at the injection site was the most frequent local reaction (33.3% to 91.7%), and redness (0% to 8.3%) and swelling (0% to 16.7%) were infrequent. The frequency of local reactions was lower in the older age group compared to the younger age group, and there was a trend of a higher frequency of local reactions with increased dose.

In the younger age group, median onset day for local reactions occurred between Day 1.0 (day of vaccination) to Day 2.0 after any dose of BNT162b2 across any dose level. In the older age group, median onset day for local reactions occurred between Day 1.0 (day of vaccination) to Day 2.0 after any dose of BNT162b2 across any dose level. Local reactions generally resolved with median durations between 1.0 to 2.0 days in the younger and older age groups across dose levels.

Systemic Events—Phase 1

Overall, within 7 days after Dose 1, fatigue was generally the most frequently reported systemic event in the both the younger and older BNT162b1 groups and in the older BNT162b2 group; while headache and fatigue were most frequently reported in the younger BNT162b2 dose group. Overall, within 7 days after Dose 2, headache was the most frequently reported systemic event in the both the younger and older BNT162b1 groups and fatigue was the most frequently reported systemic event in the both the younger and older BNT162b2 groups. Chills was generally reported at a higher frequency after Dose 2 and at a higher frequency in the BNT162b1 group than in the BNT162b2 group. Fever was reported more frequently in the younger BNT162b1 group after Dose 2 than in the older BNT162b2 group. For both the BNT162b1 and the BNT162b2 recipients, after the first and second dose and in both age groups, the majority of systemic events were mild or moderate in severity, and no Grade 4 systemic events were reported.

BNT162b1

In the younger age group, fatigue was the most frequently reported systemic event within 7 days after Dose 1 of BNT162b1, reported by 4 (33.3%), 8 (66.7%), and 6 (50.0%) participants in the 10-μg, 20-μg, and 30-μg dose groups, respectively (FIG. 88), compared to the placebo group (2 [22.2%] participants). Headache (6 [50.0%] participants) and chills (7 [58.3%] participants) were reported in the 30-μg dose group, and 1 (8.1%) participant reported fever in each group through 30 μg. In the placebo group, headache (1 [11.1%]) participant) was reported and none reported fever or chills. In the 100-μg dose group, higher frequencies were reported compared to the 30-μg dose group: fatigue (10 [83.3%] participants), headache (9 [75.0%] participants), chills (10 [83.3%] participants), and fever (6 [50.0%] participants).

Within 7 days after Dose 2 of BNT162b1 in the younger age group, headache was the most frequently reported systemic event, reported by all 12 (100.0%) participants in the 30-μg dose group compared to none in the placebo group, while fatigue and chills were reported by 10 (83.3% participants) and 8 (66.7%) participants in the 30-μg dose group, respectively. Fever was reported in 17% and 75% of participants in the 20-μg and 30-μg dose groups, respectively. In the placebo group, 2 (22.2%) participants reported fatigue, and none reported fever and chills.

In the older age group, fatigue was the most frequently reported systemic event within 7 days after Dose 1 of BNT162b1, with 7 (58.3%) and 6 (50.0)% of participants reporting fatigue in the 20-μg and 30-μg dose groups, respectively (FIG. 89), compared to 4 (44.4%) participants in the placebo group. Headache (6 [50.0%] participants) and chills (2 [16.7%] participants) were reported in the 30-μg dose group, and fever (3 [25.0%] participants) was reported only in the 30-μg dose group. In the placebo group, chills (2 [22.2%] participants) was reported and none reported headache or fever. One participant each reported severe muscle pain (20-μg dose group) and severe fatigue (30-μg dose group) (the former was pain related to onset of herpes zoster).

Within 7 days after Dose 2 of BNT162b1 in the older age group, headache was the most frequent systemic event reported in both the 20-μg and 30-μg dose groups (9 [75.0%] participants each) compared to the placebo group (1 [11.1%] participant). Chills was reported in 7 (58.3%) and 4 (33.3%) participants at the 20-μg and 30-μg dose groups, respectively. Fever was reported in 6 (50.0%) participants in the 20-μg dose group and in 4 (33.3%) participants in the 30-μg dose group, with 1 participant reporting fever >38.9° C. to 40.0° C. In the placebo group, fatigue (2 [22.2%] participants) was reported and none reported fever and chills.

After the first and second dose and in both age groups, the majority of systemic events were mild or moderate in severity, and no Grade 4 systemic events were reported. In the older age group, prompted systemic events after each dose were milder and less frequent than those observed in the younger age group.

Systemic events had the highest frequency and/or severity with the 100-μg dose group after Dose 1. Use of antipyretic/pain medication also increased with increasing dose level and number of doses in both age groups. For these reasons, the IRC decided that the younger age group participants should not receive a second dose of 100 μg of BNT162b1.

In the younger age group, median onset day for most systemic events after either dose of BNT162b1 across doses 10 μg to 30 μg and after Dose 1 of BNT162b1 100 μg was between Day 1.0 and Day 2.0. Most systemic events generally resolved with median durations between 1.0 to 2.0 days. For fatigue, median duration after Dose 1 was 4.0 days in the 10-μg dose group compared with 2.0 days in the 30-μg dose group. In the older age group, median onset day for most systemic events after either dose of BNT162b1, and across any dose group, was between Day 1.0 and Day 3.5. Most systemic events generally resolved with median durations between 1.0 to 3.0 days.

BNT162b2

Figure 90:
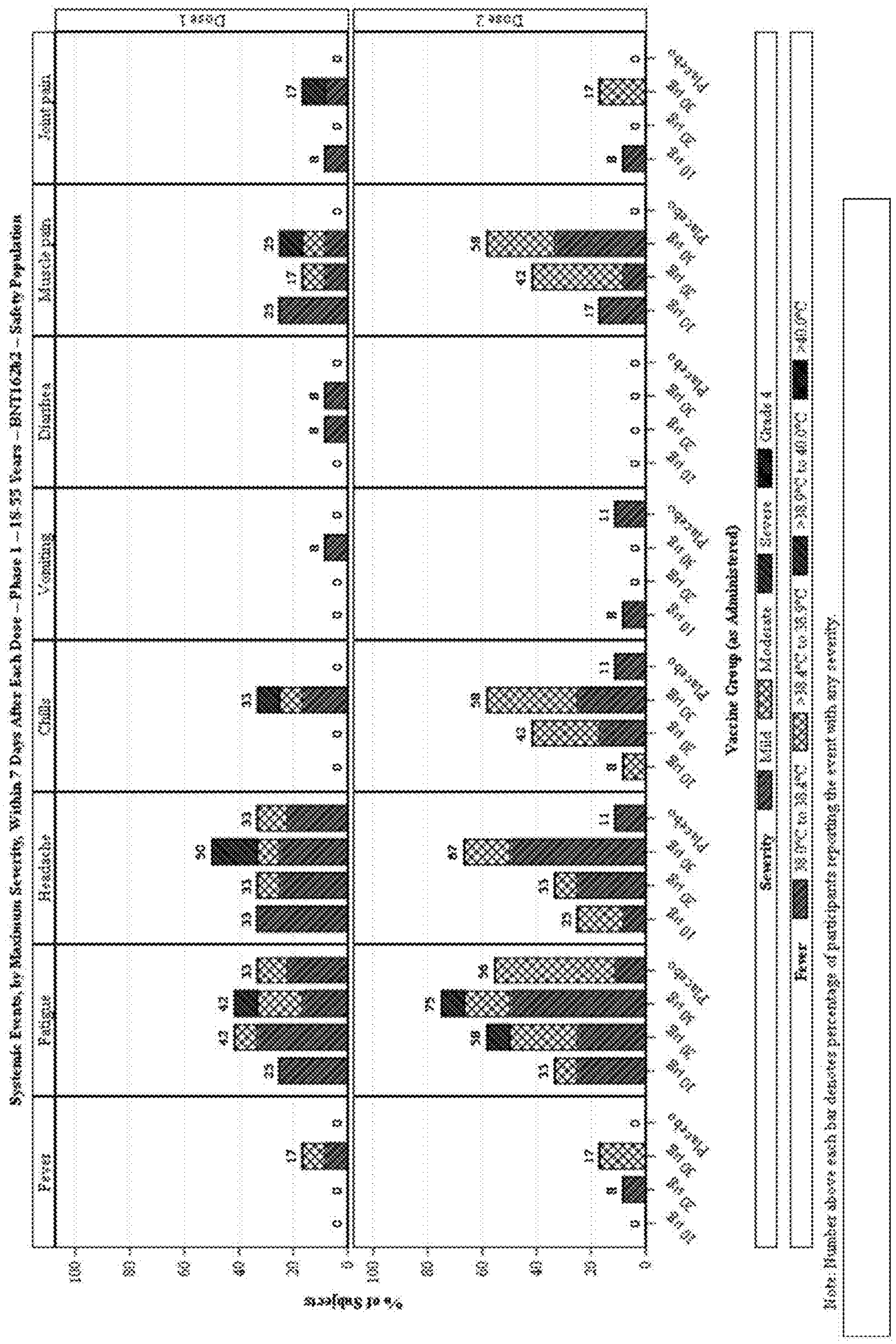

In the younger age group, headache (4 [33.3%] to 6 [50.0%] participants) and fatigue (3 [25.0%] to 5 [41.7%] participants) were the most frequently reported systemic events within 7 days after Dose 1 of BNT162b2 compared to the placebo group (3 [33.3%] participants each) (FIG. 90). Fever (2 [16.7%] participants) and chills (4 [33.3%] participants) were reported only in the 30-μg dose group. One participant in the 30-μg group with a prior history of migraine reported a severe migraine headache on Day 7 after Dose 1.

Within 7 days after Dose 2 of BNT162b2 in the younger age group, fatigue was the most frequently reported systemic event in the 20-μg and 30-μg dose groups (7 [58.3%] and 9 [75.0%] participants, respectively) compared to the placebo group (5 [55.6%] participants). Headache (8 [66.7%] participants), chills (7 [58.3%] participants), and muscle pain (7 [58.3%] participants), and fever (2 [16.7%] participants) were reported in the 30-μg dose group. Of these events, fatigue (5 [55.6%] participants), headache (1 [11.1%] participant), and chills (1 [11.1%] participant) were reported in the placebo group, and none were reported for muscle pain.

Figure 91:
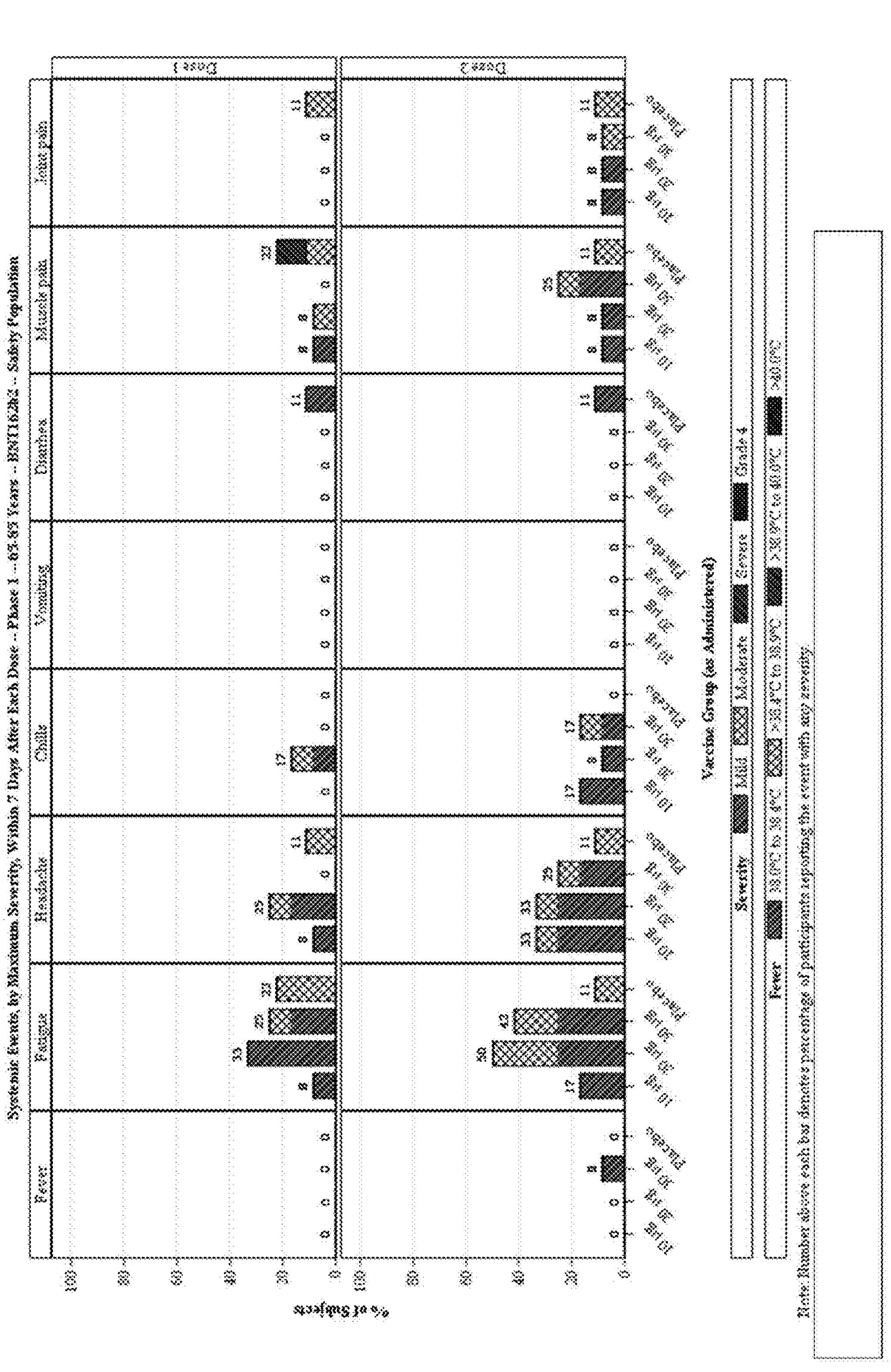

In the older age group, the most frequently reported systemic event within 7 days after Dose 1 of BNT162b2 was fatigue in the 20-μg and at 30-μg dose groups (4 [33.3%]and 3 [25.0%] participants, respectively) compared to the placebo group (2 [22.2%] participants) (FIG. 91). Headache (3 [25.0%] participants), chills (2 [16.7%] participants), and muscle pain (1 [8.3%] participant) were maximal in the 20-μg dose group. Of these events, only headache (1 [11.1%] participant) and muscle pain (2 [22.2%] participants) were reported in the placebo group. Fever was not reported. Within 7 days after Dose 2 of BNT162b2 in the older age group, fatigue remained the most frequent systemic event in the 20-μg and 30-μg dose groups (6 [50.0%] and 5 [41.7%] participants, respectively), compared to the placebo group (1 [11.1%] participant). Headache was reported in the 20-μg and 30-μg dose groups (4 [33.3%] and 3 [25.0%] participants, respectively), while muscle pain and chills were reported in the 30-μg dose group (3 [25.0%] and 2 [16.7%] participants, respectively). Fever (1 [8.3%] participant) was reported in the 30-μg dose group. Of these events, headache and muscle pain were reported in the placebo group (1 [11.1%] participant each).

After the first and second dose and in both age groups, the majority of systemic events were mild or moderate in severity, and no Grade 4 systemic events were reported. In the younger age group, median onset day for most systemic events after either dose of BNT162b2, and across any dose group, was between Day 1.0 and Day 4.0. Most systemic events generally resolved with median durations between 1.0 to 2.5 days. In the older age group, median onset day for any systemic event after either dose of BNT162b2, and across any dose level, was between Day 1.5 and Day 2.0, except for systemic events in the 10-μg dose group after Dose 1, which had a median onset day of Day 5.5. Most systemic events generally resolved with median durations between 1.0 to 3.0 days.

Adverse Events—Phase 1

Summary of Adverse Events—Phase 1

All AEs from Dose 1 through the data cutoff date of 24 Aug. 2020 were included in the summary for all dose levels for each vaccine candidate and age group other than BNT162b1 100-μg group for which AEs from Dose 1 to before Dose 2 were summarized.

Overall, fewer participants reported at least 1 AE after Dose 1 in the older BNT162b2 group (8.3% to 25.0%) compared to the younger (41.7% to 50.0%) and older (25.0% to 58.3%) BNT162b1 groups and the younger BNT162b2 group (33.3% to 41.7%).

BNT162b1

In the younger age group, 5 (41.7%) to 6 (50%) participants reported at least 1 AE after Dose 1 of BNT162b1 up to 30 μg, compared to 2 (22.2%) participants in the placebo group. Related AEs increased with increasing BNT162b1 dose level (25.0% to 50.0%); six (50%) participants reported at least 1 related AE in the 30-μg dose group. One (8.3%) participant reported a severe AE (pyrexia) in the 30-μg dose group.

In the 100-μg dose group, 8 (66.7%) participants reported at least 1 AE after Dose 1 to before Dose 2 of BNT162b1, compared to 1 (33.3%) participant in the placebo group. Six (50.0%) participants had at least 1 related AE, and 1 (8.3%) participant reported a severe AE (sleep disorder).

In the older group, 3 (25.0%) participants (30-μg dose group) and 7 (58.3%) participants each (10-μg and 20-μg dose groups) reported at least 1 AE after Dose 1 of BNT162b1, compared to 4 (44.4%) participants in the placebo group. Two (16.7%) to 4 (33.3%) participants reported at least 1 related AE, with the highest frequency in the 20-μg dose group. One participant each reported a severe AE in the 20-μg (herpes zoster) and 30-μg (fatigue) dose groups.

No SAEs, AEs leading to withdrawals, or deaths were reported in either age group.

BNT162b2

In the younger age group, 4 (33.3%) to 5 (41.7%) participants reported at least 1 AE after Dose 1 of BNT162b2, compared to 2 (22.2%) participants in the placebo group.

Two (16.7%) to 4 (33.3%) participants reported at least 1 related AE, with the highest frequency in the 20-μg dose group. One participant reported a severe AE (migraine) in the 30-μg dose group.

In the older group, 1 (8.3%) to 3 (25.0%) participants reported at least 1 AE after Dose 1 of BNT162b2, compared to 2 (22.2%) participants in the placebo group. Only 1 (8.3%) participant reported at least 1 related AE (20-μg dose group). One participant each reported a severe AE in the 30-μg dose group (muscle spasms) and placebo group (radiculopathy).

No SAEs, AEs leading to withdrawals, or deaths were reported in either age group.

Analysis of Adverse Events—Phase 1

Adverse Events by System Organ Class and Preferred Term—Phase 1

AE by SOC and PT summaries in this section included AEs from Dose 1 to 1 month after Dose 2 for all groups other than BNT162b1 100-ug group for which AEs from Dose 1 to 3 weeks after Dose 1 or from Dose 1 to before Dose 2 were summarized.

General disorders and administration site conditions was the most commonly reported SOC in the older BNT162b1 group and the younger BNT162b2 group. The most commonly reported SOC was gastrointestinal disorders in the younger BNT162b1 group and nervous system disorders in the older BNT162b2 group. Generally, most PTs were reported by 2 participants per dose group.

BNT162b1

In the younger age group, from Dose 1 to 1 month after Dose 2 of BNT162b1, gastrointestinal disorders was the most commonly reported SOC (2 [16.7%] participants each dose group) in the BNT162b1 groups up to 30 μg. In the 20-μg dose group only, paraesthesia (3 [25.0%]) was the most common AE by PT. All other AEs were reported by 2 participants per dose group, including those in the placebo group. In the 100-μg dose group, from Dose 1 to 3 weeks after Dose 1 of BNT162b1, psychiatric disorders was the most commonly reported SOC (3 [25.0%] participants), and sleep disorder (3 [25%] participants) was the most common AE by PT. All other AEs were reported by ≤2 participants, including those in the placebo group.

In the older age group, from Dose 1 to 1 month after Dose 2 of BNT162b1, general disorders and administration site conditions was the most commonly reported SOC in the BNT162b1 groups, reported in a total of 6 participants: 1 (8.3%) participant in the 10-μg dose group, 2 (16.7%) participants in the 20-μg dose group, and 3 (25.0%) participants in the 30-μg dose group. Any AEs by PT were reported by no more than 1 participant per dose group.

BNT162b2

In the younger age group, general disorders and administration site conditions was the most commonly reported SOC. These events included injection site pain and injection site erythema. Any AEs by PT were reported by no more than 1 participant per dose group.

In the older age group, nervous system disorders was the most commonly reported SOC, reported in 1 participant each in the 30-μg group (sciatica) and the placebo group (radiculopathy). Any AEs by PT were reported by no more than 1 participant per dose group.

Related Adverse Events—Phase 1

Overall, general disorders and administration site conditions was the most commonly reported SOC for the younger and older BNT162b1 groups and the younger BNT162b2 group. In the older BNT162b2 group, nausea, reported in 1 (8.3%) participant, was the only related AE.

BNT162b1

In the younger age group, general disorders and administration site conditions was the most commonly reported SOC (injection site pain, pyrexia, chills, fatigue, and injection site swelling). Two (16.7%) participants each in the 30-μg dose group reported related AEs of tachycardia and pyrexia. All other related AEs were reported by 2 participants per dose group.

In the 100-μg BNT162b1 group, psychiatric disorders were the most commonly reported SOC. Three (25.0%) participants reported sleep disorder as their psychiatric disorder. All other related AEs were reported by 2 participants each.

In the older age group, general disorders and administration site conditions was the most commonly reported SOC (fatigue, injection site bruising, injection site pain, and peripheral swelling). Any related AEs by PT were reported by no more than 1 participant per dose group.

BNT162b2

In the younger age group, general disorders and administration site conditions was the most commonly reported SOC (injection site pain and injection site erythema). Any related AEs by PT were reported by no more than 1 participant per dose group, including those in the placebo group.

In the older age group, only 1 (8.3%) participant reported a related AE of nausea in the 20-μg dose group.

Immediate Adverse Events—Phase 1

BNT162b1

In the younger age group, 1 participant reported an immediate AE of paraesthesia after Dose 1 of 20 μg BNT162b1. In the 100-μg group, no participants reported an immediate AE after Dose 1.

In the older age group, 1 participant reported an immediate AE of eye paraesthesia after Dose 1 of 10 μg BNT162b1.

There were no participants in either age group who reported any immediate AEs after Dose 2 of BNT162b1.

BNT162b2

In the younger age group, after Dose 1 of BNT162b2, there were 3 participants who reported an immediate AE: injection site erythema (10-μg dose group), ageusia (20-μg dose group), and injection site pain (30-μg dose group). After Dose 2 of BNT162b2, there was 1 participant who reported an immediate AE of taste disorder (20-μg dose group).

There were no participants in the older age group who reported any immediate AE after any dose of BNT162b2.

Severe Adverse Events—Phase 1

BNT162b1

In the younger age group, there was 1 participant who reported a severe AE of pyrexia (102.4° F.) 2 days after Dose 2 (30-μg dose group) and 1 participant who reported a severe AE of sleep disorder 1 day after Dose 1 (100-μg dose group). Both AEs were determined by the investigator to be related to study intervention.

In the older age group, 2 participants reported a severe AE: herpes zoster which occurred 2 days after Dose 1 (20-μg dose group, considered unrelated to BNT162b1) and fatigue 1 day after Dose 2 (30-μg dose group, considered related to BNT162b1).

BNT162b2

In the younger age group, 1 participant with a history of migraines reported a severe migraine 7 days after Dose 1 (30-μg dose group, considered unrelated). In the older age group, 2 participants reported a severe AE: muscle spasms 2 days after Dose 2 (30-μg dose group, considered unrelated to BNT162b2) and radiculopathy 3 days after Dose 1 (placebo), considered unrelated to study intervention.

Deaths, Serious Adverse Events, Safety-Related Participant Withdrawals, and Other Significant Adverse Events—Phase 1

Deaths—Phase 1

There were no Phase 1 participants who died through the data cutoff date of 24 Aug. 2020 in this interim CSR.

Serious Adverse Events—Phase 1

There were no Phase 1 participants who reported any SAEs during the period covered in this interim CSR.

Safety-Related Participant Withdrawals—Phase 1

There were no Phase 1 participants with any AEs leading to withdrawal from the study through the data cutoff date of 24 Aug. 2020 in this interim CSR.

Other Significant Adverse Events—Phase 1

AEs of special interest were not defined for Phase 1 of this study.

Other Safety Assessments—Phase 1

Severe COVID-19 Illness—Phase 1

There were no COVID-19 cases reported in the Phase 1 participants through the data cutoff date of 24 Aug. 2020.

Pregnancy—Phase 1

Pregnancy was not reported in any Phase 1 participants through the data cutoff date of 24 Aug. 2020.

Analysis and Discussion of Deaths, Serious Adverse Events, Safety-Related Participant Withdrawals, and Other Significant Adverse Events—Phase 1

During the period covered in this interim CSR, there were no SAEs, AEs leading to withdrawals, or deaths reported in either age group.

Clinical Laboratory Evaluation—Phase 1

Overall, 1 to 3 days after Dose 1, there were transient decreases in lymphocytes (<0.8×LLN), which returned to normal by 6 to 8 days after Dose 1, in the younger and older BNT162b1 and BNT162b2 groups. Most shifts were from normal or Grade 1 to Grade 1, 2, or 3 decrease in lymphocyte counts, which returned to normal by 6 to 8 days after Dose 1, and were observed in all age and dose groups. Shifts from normal to Grade 1 (younger BNT162b1 group) or Grade 2 (older BNT162b2 group) neutrophil decrease were also observed but were infrequent.

Overall, other clinical chemistry abnormalities reported or shifts of laboratory results were infrequent. The incidence of decreased lymphocyte counts was lower for BNT162b2 recipients compared with BNT162b1 recipients. None of the laboratory abnormalities were associated with clinical findings.

BNT162b1

In the younger age group, laboratory abnormalities of transient decreases in lymphocytes (<0.8×LLN) were observed in 1 (8.3%), 4 (33.3%), and 6 (54.5%) of participants 1 to 3 days after Dose 1 of BNT162b1 10 μg, 20 μg, or 30 μg, respectively, which returned to normal by 6 to 8 days after Dose 1. A shift from normal to Grade 3 decrease in lymphocyte counts was observed in 1 participant each in the 10-μg and 30-μg dose groups and 2 (16.7%) participants the 20-μg dose group. No Grade 3 decrease in lymphocyte counts was observed by 6 to 8 days after Dose 1. After Dose 1, a shift from normal to Grade 2 neutrophil decrease was observed in 1 (11.1%) participant in the placebo group, which was not observed by 19 to 23 days after Dose 1. At 6 to 8 days after Dose 2, a shift in neutrophil decrease was observed in 1 participant each in the 10-μg dose group (Grade 1 to Grade 2) and in the 30-μg dose group (normal to Grade 2). Both participants had a shift to Grade 1 at the unplanned visit approximately 1 month after Dose 2.

In the 100-μg BNT162b1 group, laboratory abnormalities of transient decreases in lymphocytes (<0.8×LLN) were observed in 9 (75.0%) participants 1 to 3 days after Dose 1, which returned to normal by 6 to 8 days after Dose 1. A shift from normal to Grade 3 decrease in lymphocyte counts was observed in 4 (33.3%) participants 1 to 3 days after Dose 1, which returned to normal by 6 to 8 days after Dose 1. A shift from normal to Grade 1 neutrophil decrease was observed in 3 (25.0%) participants at 6 to 8 days after Dose 1, which returned to normal by 19 to 23 days after Dose 1. In the older age group, laboratory abnormalities of transient decreases in lymphocytes (<0.8×LLN) were also observed in 1 (8.3%), 3 (25.0%), and 2 (16.7%) participants 1 to 3 days after Dose 1 of BNT162b1 10 μg, 20 μg, or 30 μg, respectively, which returned to normal by 6 to 8 days after Dose 1. At 1 to 3 days after Dose 1 of BNT162b1, shifts from normal to Grade 3 or Grade 4 decrease in lymphocyte counts were observed in 1 (8.3%) participant each in the 30-μg and 10-μg dose groups, respectively, and both returned to normal by 6 to 8 days after Dose 1.

Overall, other clinical chemistry abnormalities reported or shifts of laboratory results were infrequent. None of the abnormalities were associated with clinical findings.

BNT162b2

In the younger age group, laboratory abnormalities of transient decreases in lymphocytes (<0.8×LLN) were observed in 1 (8.3%) participant each 1 to 3 days after Dose 1 of BNT162b2 in the 20-μg and 30-μg dose groups, which returned to normal by 6 to 8 days after Dose 1. At 1 to 3 days after Dose 1 of BNT162b2, shifts from normal to Grade 1 decrease in lymphocyte counts were observed in 3 (25.0%), 2 (16.7%), and 4 (33.3%) participants in the 10-μg, 20-μg, and 30-μg dose groups, respectively, and shifts from normal to Grade 2 decrease in lymphocyte counts were observed in 1 (8.3%) participant each in the 20-μg and 30-μg dose groups. By 6 to 8 days after Dose 1, no Grade 2 or Grade 3 decrease in lymphocyte counts were observed.

In the older age group, laboratory abnormalities of transient decreases in lymphocytes (<0.8×LLN) were also observed in 1 (8.3%) participant each 1 to 3 days after Dose 1 of BNT162b2 across all dose levels, which returned to normal by 6 to 8 days after Dose 1. A shift from normal to Grade 3 (10-μg dose group) and a Grade 1 to Grade 3 (30-μg dose group) decrease in lymphocyte counts was observed in 1 (8.3%) participant each after Dose 1. A shift from normal to Grade 2 neutrophil decrease was observed in 2 (16.7%) participants in the 20-μg dose group at 1 to 3 days after Dose 1, and no shifts to Grade 2 were observed by 6 to 8 days after Dose 1. A shift from normal to Grade 2 neutrophil decrease was observed in 1 (8.3%) participant in the 10-μg dose group at 6 to 8 days after Dose 1. By 19 to 23 days after Dose 1, no shifts to Grade 2 neutrophil decrease were observed for any dose group.

Overall, other clinical chemistry abnormalities reported or shifts of laboratory results were infrequent. The incidence of decreased lymphocyte counts was lower for BNT162b2 recipients compared with BNT162b1 recipients. None of the laboratory abnormalities were associated with clinical findings.

Physical Examination Findings—Phase 1

Overall, there were fewer abnormalities noted during physical examinations after BNT162b2 than after BNT162b1 in both age groups. Abnormalities were generally observed 1 to 3 days after Dose 1 and most were of the extremities, musculoskeletal system, or skin.

BNT162b1

In the younger age group, there were no abnormalities noted during baseline physical examinations. Overall, after randomization, most abnormalities were observed 1 to 3 days after Dose 1 of 10 μg, 20 μg, or 30 μg BNT162b1 (9 [20.0%] participants) and 6 to 8 days after Dose 2 (7 [15.6%] participants). In the 30-μg dose group, a maximum of 6 (50.0%) participants had abnormalities 1 to 3 days after Dose 1, and most abnormalities were of the extremities.

In the 100-μg dose group, only 1 (8.3%) participant had an abnormality at baseline. From Dose 1 to 3 weeks after Dose 1, 9 (75.0%) participants had abnormalities 1 to 3 days after BNT162b1, and most abnormalities were of the extremities.

In the older age group, there were 5 (11.1%) participants with abnormalities noted during baseline physical examinations, with 2 participants in any dose group. Overall, after randomization, most abnormalities were observed 1 to 3 days after Dose 1 of BNT162b1 (15 [33.3%] participants). In the 20-μg and 30-μg dose groups, 6 (50.0%) and 4 (33.3%) participants had abnormalities 1 to 3 days after Dose 1, and most abnormalities involved either the musculoskeletal system or extremities.

There were no clinically important findings from physical examinations.

BNT162b2

In the younger age group, there were 5 (11.1%) participants with abnormalities noted during baseline physical examinations, with 2 participants in any dose group. Overall, after randomization, most abnormalities were observed 1 to 3 days after Dose 1 of 10 μg, 20 μg, or 30 μg BNT162b2 (5 [11.1%] participants) and 6 to 8 days after Dose 2 (4 [8.9%] participants), with most being abnormalities of the extremities or skin. In the older age group, there was 1 (8.3%) participant in the 30-μg dose group with an abnormality noted during the baseline physical examination. After randomization, ≤2 participants in any dose group overall had an abnormality in physical examination during any visit window.

There were no clinically important findings from physical examinations at baseline.

Phase 1 Summary of Safety Results Evaluating BNT162b1 and BNT162b2

Overall, reactogenicity events were well tolerated and short-lived (median durations 1.0 to 4.0 days). All participants returned to receive their second dose. All AEs as a result of reactogenicity events resolved without sequelae.

For local reactions in both age groups, pain at the injection site (58.3% to 100.0%), redness (0% to 16.7%), and swelling (0% to 25.0%) were reported for BNT162b1 recipients, which were more frequent than for BNT162b2 recipients: pain at the injection site (33.3% to 91.7%), redness (0% to 8.3%), and swelling (0% to 16.7%). In general, frequencies of local reactions were observed to be higher with increased dose level.

The frequency of local reactions was lower in the older age group compared to the younger age group. The frequency of pain at the injection site, the most frequently reported local reaction, was lower in the older age groups after 30 μg BNT162b1 (91.7% and 75.0%) and after 30 μg of BNT162b2 (75.0% and 66.7% for Dose 1 and Dose 2, respectively), compared to the younger age groups after 30 μg of BNT162b1 (100.0% for both Dose 1 and Dose 2) and 30 μg of BNT162b2 (91.7% and 83.3% for Dose 1 and Dose 2, respectively).

BNT162b2 recipients in the older age group reported lower frequencies of local reactions compared with BNT162b1 recipients in the older age group. In the older 30-μg BNT162b2 group, pain at the injection site was lower after Dose 1 (75.0%) and Dose 2 (66.7%) than in the older 30-μg BNT162b1 group after Dose 1 (91.7%) and Dose 2 (75.0%).

Common systemic events in both age groups after either Dose 1 or Dose 2 included fatigue (16.7% to 83.3%), headache (25.0% to 100%), chills (8.3% to 66.7%), fever (0% to 75.0%), and muscle pain (8.3% to 75.0%) for BNT162b1 recipients up to 30 μg, which were more frequent than BNT162b2 recipients up to 30 μg: fatigue (8.3% to 75.0%), headache (0% to 66.7%), chills (0% to 58.3%), fever (0% to 16.7%), and muscle pain (0% to 58.3%). In general, frequencies of systemic events were observed to be higher with increased dose level.

The frequency of systemic events was lower in the older age group compared to the younger age group. The frequency of fatigue was lower in the older age groups after 30 μg of BNT162b1 (50.0% and 66.7%) and after 30 μg of BNT162b2 (25.0% and 41.7% for Dose 1 and Dose 2, respectively), compared to the younger age groups after 30

μg of BNT162b1 (50.0% and 83.3%) and after 30 μg of BNT162b2 (41.7% and 75.0%) for Dose 1 and Dose 2, respectively.

BNT162b2 recipients in the older age group reported lower frequencies of systemic events compared with BNT162b1 recipients in the older age group. The frequency of fatigue was lower in the older 30-μg BNT162b2 group (25.0% and 41.7% for Dose 1 and Dose 2, respectively) than in the older 30-μg BNT162b1 group (50.0% and 66.7% for Dose 1 and Dose 2, respectively).

Most AEs were mild or moderate in severity. Most related AEs were similar to the solicited reactogenicity events reported in the e-diary. Few severe AE were reported but were considered not related to study intervention.

There were no SAEs, deaths, or discontinuations because of AEs.

Transient decrease in lymphocytes were observed in all age and dose groups 1 to 3 days after Dose 1, which resolved by 6 to 8 days after Dose 1.

There were no clinically important findings from physical examinations.

BNT162b2 demonstrated a favorable reactogenicity and safety profile compared with BNT162b1, contributing to the selection of BNT162b2 for Phase 2/3 development.

Phase 1 Safety Conclusions

All doses tested for BNT162b1 and BNT162b2 (10 μg, 20 μg, and 30 μg) were safe and well tolerated except for BNT162b1 at 100 μg, which was discontinued after the first dose due to the reactogenicity profile.

Reactogenicity was generally higher after Dose 2 than Dose 1.

The frequency of local and systemic reactogenicity was generally lower for BNT162b2 compared to BNT162b1 especially after the second dose.

Reactogenicity events after each dose for both BNT162b1 and BNT162b2 in older adults were milder and less frequent than those observed in younger adults. The majority of reactogenicity events were mild or moderate in severity.

Most AEs were mild or moderate. There were no SAEs or discontinuations because of AEs.

Overall, fewer AEs were experienced by participants who received BNT162b2 compared with those who received BNT162b1, with the least number of participants experiencing AEs in the BNT162b2 older age group. Few severe AEs in the older age group after BNT162b2 were observed, and all were considered unrelated to study intervention.

Clinical laboratory evaluations showed a transient decrease in lymphocytes that was observed in all age and dose groups after Dose 1, which resolved within a few days, were not associated with any other clinical sequelae, and were not considered clinically relevant.

BNT162b2 at 30 μg was selected to proceed into the Phase 2/3 portion of the study because this dose and construct provided the optimum combination of a favorable reactogenicity profile and a robust immune response.

Phase 2

Safety data are available up to the data cutoff date (2 Sep. 2020) and are summarized up to the data cutoff date for the 360 participants in Phase 2. All participants in Phase 2 used an e-diary for reporting local reactions and systemic events.

Local Reactions—Phase 2

After the first and second dose of BNT162b2 and in both age groups, the majority of local reactions were mild or moderate in severity, and no Grade 4 (potentially life-threatening) local reactions were reported.

In the BNT162b2 group, pain at the injection site was reported more frequently in the younger age group (FIG. 92) than in the older age group (FIG. 93), and frequency was similar after Dose 1 compared with Dose 2 of BNT162b2 in the younger age group (85.2% vs. 80.2%, respectively) and in the older age group (70.7% vs. 72.5%, respectively). In the placebo group, pain at the injection site was reported at similar frequencies (7.8% to 10.2%) in the younger and older age groups after Dose 1 and Dose 2.

In the BNT162b2 group, redness and swelling were similar in the younger and older age group after Dose 1. After Dose 2, the frequency of redness and swelling was slightly higher in the older age group (7.7% and 12.1%, respectively) than in the younger age group (3.5% and 3.5%, respectively). In the placebo group, only 1 participant in the older age group reported redness after Dose 1, and no swelling was reported.

One participant in the BNT162b2 group (older age group) reported severe injection site pain after Dose 1, and 1 participant in the younger age group reported severe injection site pain after Dose 2. One participant in the BNT162b2 group (older age group) reported severe redness after Dose 2.

Overall, across age groups, pain at the injection site was the most frequent local reaction and did not increase after Dose 2, and redness and swelling were generally similar in frequency after Dose 1 and Dose 2.

Across age groups, local reactions for the BNT162b2 group after either dose had a median onset day between Day 1.0 and Day 3.0 (Day 1.0 was the day of vaccination), and ranges were generally similar in the younger and older age groups. Across age groups, after either dose of BNT162b2, local reactions resolved after a median duration of 1.0 to 3.0 days, which was generally similar in the younger and older age groups.

Systemic Events—Phase 2

In the BNT162b2 group, systemic events were generally reported more frequently and were of higher severity in the younger group (FIG. 94) compared with the older group (FIG. 95), with frequencies and severity increasing with number of doses (Dose 1 vs Dose 2). Vomiting and diarrhea were exceptions with vomiting infrequent and similar in both age groups and vomiting and diarrhea similar after each dose. Frequencies of systemic events in the younger and older BNT162b2 groups (Dose 1 vs Dose 2) are listed below:

fatigue: younger group (50.0% vs 59.3%) compared to older group (35.9% vs 52.7%)

headache: younger group (31.8% vs 51.2%) compared to older group (27.2% vs 36.3%)

muscle pain: younger group (23.9% vs 45.3%) compared to older group (14.1% vs 28.6%)

chills: younger group (9.1% vs 40.7%) compared to older group (7.6% vs 20.9%)

joint pain: younger group (9.1% vs 17.4%) compared to older group (4.3% vs 16.5%)

fever: younger group (3.4% vs 17.4%) compared to older group (0.0% vs 11.0%).

vomiting: similar in both age groups and after either dose.

diarrhea: reported less frequently in the older group and was similar after each dose.

Figure 94:
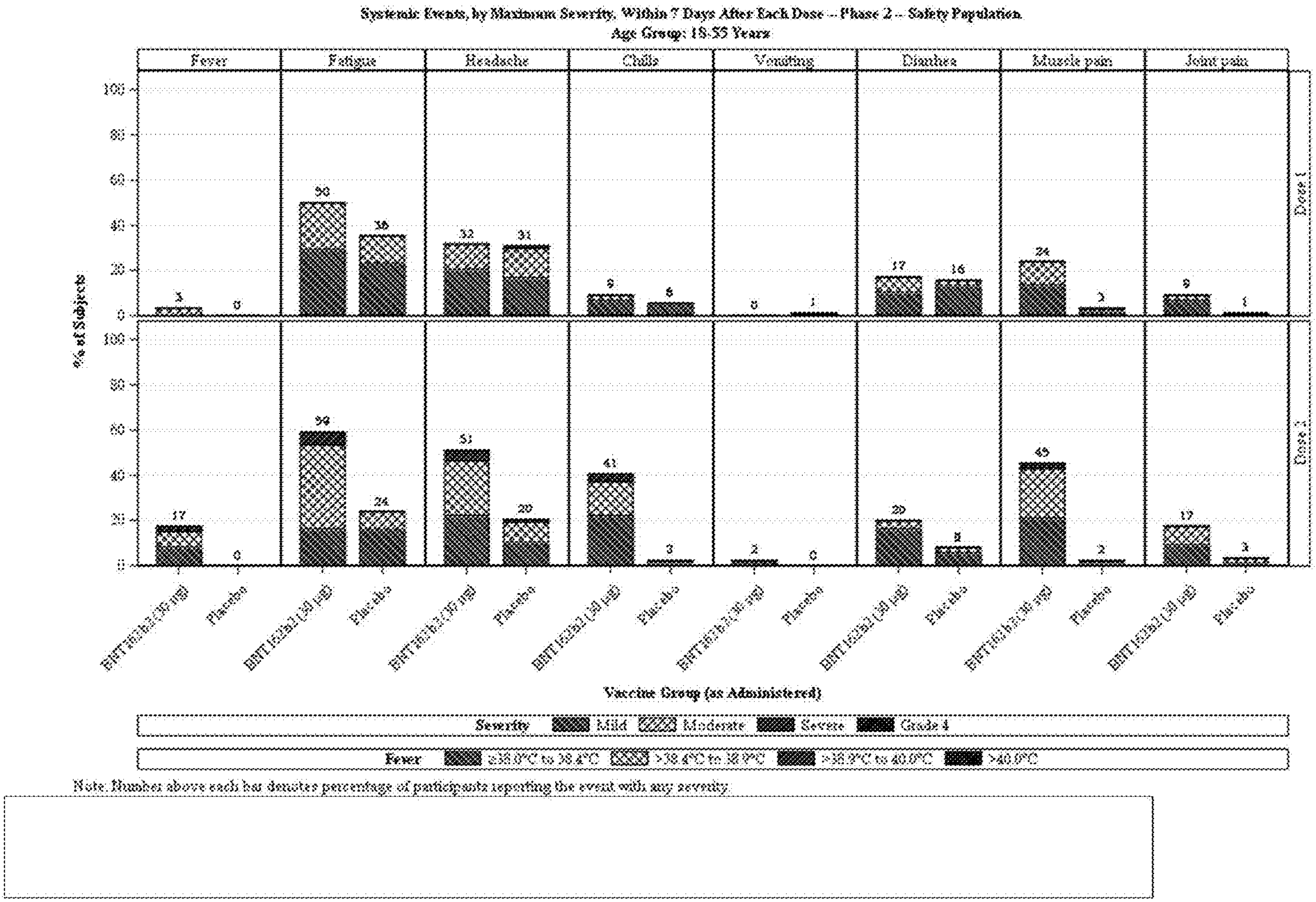
Figure 95:
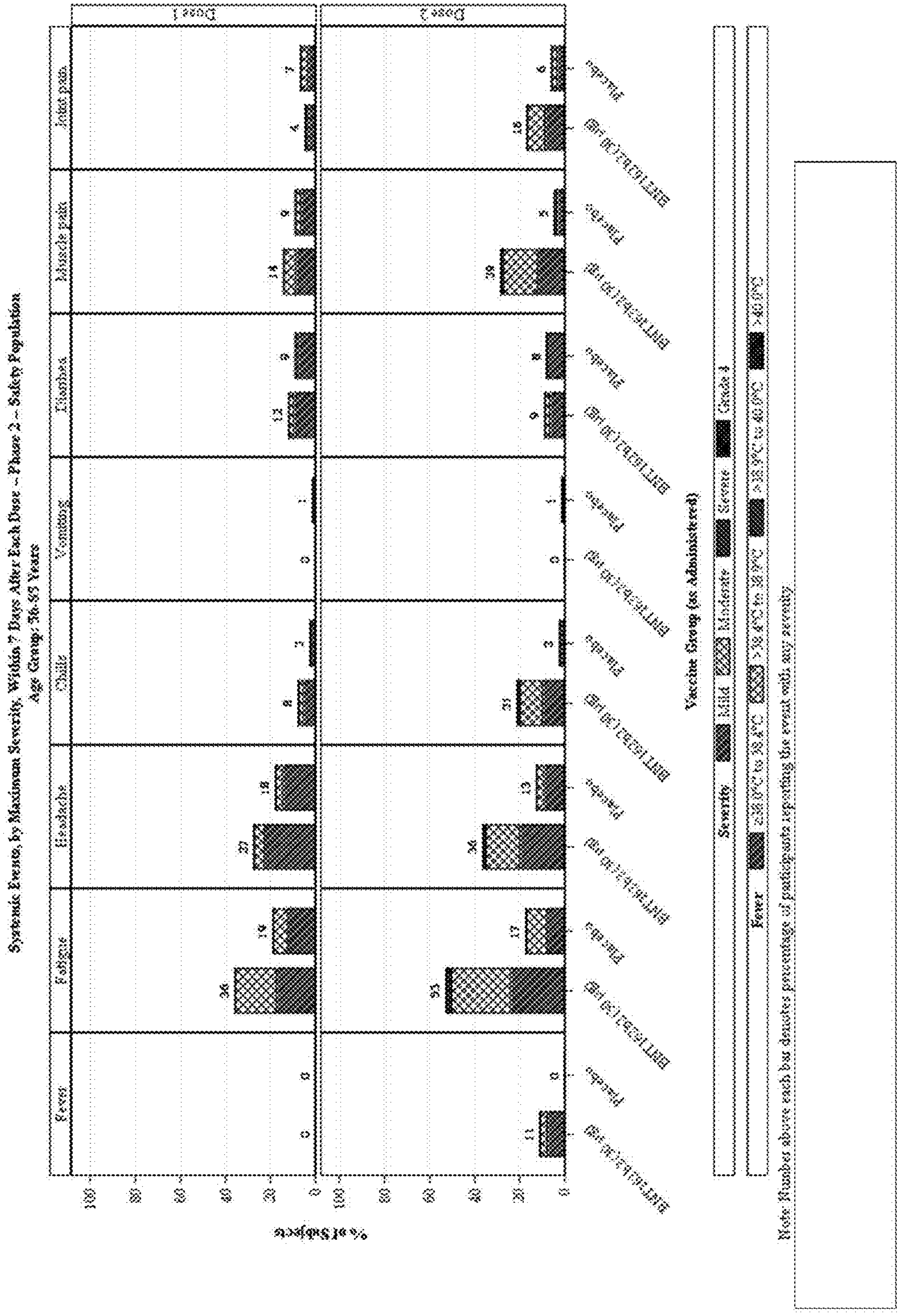

Systemic events were generally reported less frequently in the placebo group than in the BNT162b2 group, for both age groups and doses, with some exceptions. In the younger age group, fever, headache, chills, vomiting, and diarrhea after Dose 1, and vomiting after Dose 2 were reported at similar frequencies in both the placebo and BNT162b2 groups (FIG. 94). In the older age group, vomiting, diarrhea, muscle pain, and joint pain after Dose 1, and vomiting and diarrhea after Dose 2 were reported at similar frequencies in the placebo and BNT162b2 groups (FIG. 95).

Use of antipyretic/pain medication was slightly less frequent in the older age group after both doses but increased in both age groups overall after Dose 2 as compared with after Dose 1. Use of antipyretic/pain medication was less frequent in the placebo group than in the BNT162b2 group.

After the first and second dose and in both age groups, the majority of systemic events were mild or moderate in severity, and no Grade 4 (potentially life-threatening) systemic events were reported. Across age groups, severe systemic events were only reported after Dose 2 of BNT162b2 overall and included fever (1.1%), fatigue (4.0%), headache (2.8%), chills (2.3%), and muscle pain (1.7%).

Across age groups, systemic events after both doses of BNT162b2 had a median onset day between Day 2.0 to Day 3.0 (Day 1.0 was the day of vaccination), and ranges were similar in the younger and older age groups. Across age groups, systemic events for this group after either dose resolved with a median duration of 1 day, which was similar in the younger and older age groups. There was no clear difference in the durations of systemic events that occurred after Dose 1 compared to those that occurred after Dose 2.

Adverse Events—Phase 2

Summary of Adverse Events—Phase 2

The number of participants who reported at least 1 AE was similar in the BNT162b2 group compared with the placebo group, which was generally similar in the 2 vaccine groups in the younger and older age groups (Table 10 and Table 11, respectively).

Two severe events were reported for 2 participants in the BNT162b2 younger age group: myalgia (AE) and gastric adenocarcinoma (SAE) The SAE of gastric adenocarcinoma occurred 23 days after receiving Dose 1. Both events were assessed by the investigator as not related to study intervention.

From 7 days after Dose 2 to the data cutoff date (2 Sep. 2020), no additional participants reported any AE.

TABLE 10

Number (%) of Subjects Reporting at Least 1 Adverse Event From Dose 1 to 7 Days After Dose 2, by Age Group-Phase 2-Safety Population Age Group: 18-55 Years

| | Vaccine Group (as Administered) | |
|---|---|---|
| Adverse Event | BNT162b2 (30 μg) ($N^a$ = 88) $n^b$ (%) | Placebo ($N^a$ = 90) $n^b$ ( %) |
| Any event | 8 (9.1) | 10 (11.1) |
| Related[c] | 3 (3.4) | 6 (6.7) |
| Severe | 2 (2.3) | 0 |
| Life-threatening | 0 | 0 |
| Any serious adverse event | 1 (1.1) | 0 |
| Related[c] | 0 | 0 |
| Severe | 1 (1.1) | 0 |
| Life-threatening | 0 | 0 |
| Any adverse event leading to withdrawal | 1 (1.1) | 0 |
| Related[c] | 0 | 0 |
| Severe | 1 (1.1) | 0 |
| Life-threatening | 0 | 0 |
| Death | 0 | 0 |

[a]N = number of subjects in the specified group. This value is the denominator for the percentage calculations.
[b]n = Number of subjects reporting at least 1 occurrence of the specified adverse event category. For "any event", n = the number of subjects reporting at least 1 occurrence of any adverse event.
[c]Assessed by the investigator as related to investigational product.

TABLE 11

Number (%) of Subjects Reporting at Least 1 Adverse Event From Dose 1 to 7 Days After Dose 2, by Age Group-Phase 2-Safety Population Age Group: 56-85 Years

| | Vaccine Group (as Administered) | |
|---|---|---|
| Adverse Event | BNT162b2 (30 μg) ($N^a$ = 92) $n^b$ (%) | Placebo ($N^a$ = 90) $n^b$ (%) |
| Any event | 4 (4.3) | 8 (8.9) |
| Related[c] | 2 (2.2) | 2 (2.2) |
| Severe | 0 | 0 |
| Life-threatening | 0 | 0 |
| Any serious adverse event | 0 | 0 |
| Related[c] | 0 | 0 |
| Severe | 0 | 0 |
| Life-threatening | 0 | 0 |
| Any adverse event leading to withdrawal | 0 | 0 |
| Related[c] | 0 | 0 |
| Severe | 0 | 0 |
| Life-threatening | 0 | 0 |
| Death | 0 | 0 |

[a]N = number of subjects in the specified group. This value is the denominator for the percentage calculations.
[b]n = Number of subjects reporting at least 1 occurrence of the specified adverse event category. For "any event", n = the number of subjects reporting at least 1 occurrence of any adverse event.
[c]Assessed by the investigator as related to investigational product.

Analysis of Adverse Events—Phase 2

Adverse Events by System Organ Class and Preferred Term—Phase 2

Table 12 presents the number of participants who reported at least 1 AE from Dose 1 to 7 days after Dose 2 by SOC and PT.

The number of participants who reported at least 1 AE was similar in the BNT162b2 group compared to the placebo group from Dose 1 to 7 days after Dose 2.

In the younger age group, 8 (9.1%) and 10 (11.1%) participants reported at least 1 AE in the BNT162b2 group and the placebo group, respectively. In the older age group, 4 (4.3%) and 8 (8.9%) participants reported at least 1 AE in the BNT162b2 group and the placebo group, respectively.

Overall, most AEs reported up to 7 days after Dose 2 were in the SOCs of gastrointestinal disorders (3 [1.7%] in the BNT162b2 group and 2 [1.1%] in the placebo group), general disorders and administration site conditions (3 [1.7%] in the BNT162b2 group and 7 [3.9%] in the placebo group), and musculoskeletal and connective tissue disorders (3 [1.7%] in the BNT162b2 group and 1 [0.6%] in the placebo group).

The most frequently reported AE by PT was injection site pain (3 [3.4%]) in the younger BNT162b2 group, which all occurred on the day of vaccination with Dose 1 during the reporting period for local reactions. Two events resolved within 3 days, and 1 event resolved 11 days later. All other AEs by PT were reported in 2 participants in each vaccine group.

One participant in the older BNT162b2 group had an AE of contusion in the upper left arm deltoid region, which was assessed by the investigator as related to study intervention.

TABLE 12

Number (%) of Subjects Reporting at Least 1 Adverse Event From Dose 1 to 7 Days After Dose 2, by System Organ Class and Preferred Term - Phase 2 - Safety Population

| | Vaccine Group (as Administered) | | | | | | | |
|---|---|---|---|---|---|---|---|---|
| | BNT162b2 (30 μg) | | | | | | Placebo | |
| | 18-55 Years ($N^a$ = 88) | | 56-85 Years ($N^a$ = 92) | | 18-85 Years ($N^a$ = 180) | | 18-85 Years ($N^a$ = 180) | |
| System Organ Class Preferred Term | $n^b$ (%) | (95% $CI^c$) | $n^b$ (%) | (95% $CI^c$) | $n^b$ (%) | (95% $CI^c$) | $n^b$ (%) | (95% $CI^c$) |
| Any event | 8 (9.1) | (4.0, 17.1) | 4 (4.3) | (1.2, 10.8) | 12 (6.7) | (3.5, 11.4) | 18 (10.0) | (6.0, 15.3) |
| BLOOD AND LYMPHATIC SYSTEM DISORDERS | 1 (1.1) | (0.0, 6.2) | 0 | (0.0, 3.9) | 1 (0.6) | (0.0, 3.1) | 0 | (0.0, 2.0) |
| Lymphadenopathy | 1 (1.1) | (0.0, 6.2) | 0 | (0.0, 3.9) | 1 (0.6) | (0.0, 3.1) | 0 | (0.0, 2.0) |
| GASTROINTESTINAL DISORDERS | 1 (1.1) | (0.0, 6.2) | 2 (2.2) | (0.3, 7.6) | 3 (1.7) | (0.3, 4.8) | 2 (1.1) | (0.1, 4.0) |
| Diarrhoea | 1 (1.1) | (0.0, 6.2) | 1 (1.1) | (0.0, 5.9) | 2 (1.1) | (0.1, 4.0) | 1 (0.6) | (0.0, 3.1) |
| Odynophagia | 0 | (0.0, 4.1) | 1 (1.1) | (0.0, 5.9) | 1 (0.6) | (0.0, 3.1) | 0 | (0.0, 2.0) |
| Tongue discomfort | 0 | (0.0, 4.1) | 0 | (0.0, 3.9) | 0 | (0.0, 2.0) | 1 (0.6) | (0.0, 3.1) |
| GENERAL DISORDERS AND ADMINISTRATION SITE CONDITIONS | 3 (3.4) | (0.7, 9.6) | 0 | (0.0, 3.9) | 3 (1.7) | (0.3, 4.8) | 7 (3.9) | (1.6, 7.8) |
| Injection site erythema | 1 (1.1) | (0.0, 6.2) | 0 | (0.0, 3.9) | 1 (0.6) | (0.0, 3.1) | 2 (1.1) | (0.1, 4.0) |
| Injection site pain | 3 (3.4) | (0.7, 9.6) | 0 | (0.0, 3.9) | 3 (1.7) | (0.3, 4.8) | 0 | (0.0, 2.0) |
| Fatigue | 0 | (0.0, 4.1) | 0 | (0.0, 3.9) | 0 | (0.0, 2.0) | 2 (1.1) | (0.1, 4.0) |
| Chills | 0 | (0.0, 4.1) | 0 | (0.0, 3.9) | 0 | (0.0, 2.0) | 1 (0.6) | (0.0, 3.1) |
| Injection site discolouration | 0 | (0.0, 4.1) | 0 | (0.0, 3.9) | 0 | (0.0, 2.0) | 1 (0.6) | (0.0, 3.1) |
| Injection site swelling | 0 | (0.0, 4.1) | 0 | (0.0, 3.9) | 0 | (0.0, 2.0) | 1 (0.6) | (0.0, 3.1) |
| INFECTIONS AND INFESTATIONS | 0 | (0.0, 4.1) | 0 | (0.0, 3.9) | 0 | (0.0, 2.0) | 1 (0.6) | (0.0, 3.1) |
| Vulvovaginal mycotic infection | 0 | (0.0, 4.1) | 0 | (0.0, 3.9) | 0 | (0.0, 2.0) | 1 (0.6) | (0.0, 3.1) |
| INJURY, POISONING AND PROCEDURAL COMPLICATIONS | 0 | (0.0, 4.1) | 1 (1.1) | (0.0, 5.9) | 1 (0.6) | (0.0, 3.1) | 3 (1.7) | (0.3, 4.8) |
| Contusion | 0 | (0.0, 4.1) | 1 (1.1) | (0.0, 5.9) | 1 (0.6) | (0.0, 3.1) | 1 (0.6) | (0.0, 3.1) |
| Fall | 0 | (0.0, 4.1) | 0 | (0.0, 3.9) | 0 | (0.0, 2.0) | 1 (0.6) | (0.0, 3.1) |
| Muscle rupture | 0 | (0.0, 4.1) | 0 | (0.0, 3.9) | 0 | (0.0, 2.0) | 1 (0.6) | (0.0, 3.1) |
| Tendon rupture | 0 | (0.0, 4.1) | 0 | (0.0, 3.9) | 0 | (0.0, 2.0) | 1 (0.6) | (0.0, 3.1) |
| INVESTIGATIONS | 0 | (0.0, 4.1) | 0 | (0.0, 3.9) | 0 | (0.0, 2.0) | 1 (0.6) | (0.0, 3.1) |
| White blood cell count increased | 0 | (0.0, 4.1) | 0 | (0.0, 3.9) | 0 | (0.0, 2.0) | 1 (0.6) | (0.0, 3.1) |
| MUSCULOSKELETAL AND CONNECTIVE TISSUE DISORDERS | 2 (2.3) | (0.3, 8.0) | 1 (1.1) | (0.0, 5.9) | 3 (1.7) | (0.3, 4.8) | 1 (0.6) | (0.0, 3.1) |
| Myalgia | 1 (1.1) | (0.0, 6.2) | 0 | (0.0, 3.9) | 1 (0.6) | (0.0, 3.1) | 1 (0.6) | (0.0, 3.1) |
| Arthralgia | 1 (1.1) | (0.0, 6.2) | 0 | (0.0, 3.9) | 1 (0.6) | (0.0, 3.1) | 0 | (0.0, 2.0) |
| Neck pain | 0 | (0.0, 4.1) | 1 (1.1) | (0.0, 5.9) | 1 (0.6) | (0.0, 3.1) | 0 | (0.0, 2.0) |
| NEOPLASMS BENIGN, MALIGNANT AND UNSPECIFIED (INCL CYSTS AND POLYPS) | 1 (1.1) | (0.0, 6.2) | 0 | (0.0, 3.9) | 1 (0.6) | (0.0, 3.1) | 0 | (0.0, 2.0) |
| Adenocarcinoma gastric | 1 (1.1) | (0.0, 6.2) | 0 | (0.0, 3.9) | 1 (0.6) | (0.0, 3.1) | 0 | (0.0, 2.0) |
| NERVOUS SYSTEM DISORDERS | 0 | (0.0, 4.1) | 0 | (0.0, 3.9) | 0 | (0.0, 2.0) | 1 (0.6) | (0.0, 3.1) |
| Headache | 0 | (0.0, 4.1) | 0 | (0.0, 3.9) | 0 | (0.0, 2.0) | 1 (0.6) | (0.0, 3.1) |
| RESPIRATORY, THORACIC AND MEDIASTINAL DISORDERS | 0 | (0.0, 4.1) | 0 | (0.0, 3.9) | 0 | (0.0, 2.0) | 2 (1.1) | (0.1, 4.0) |
| Orophalyngeal pain | 0 | (0.0, 4.1) | 0 | (0.0, 3.9) | 0 | (0.0, 2.0) | 1 (0.6) | (0.0, 3.1) |
| Productive cough | 0 | (0.0, 4.1) | 0 | (0.0, 3.9) | 0 | (0.0, 2.0) | 1 (0.6) | (0.0, 3.1) |
| Rhinorrhoea | 0 | (0.0, 4.1) | 0 | (0.0, 3.9) | 0 | (0.0, 2.0) | 1 (0.6) | (0.0, 3.1) |
| SKIN AND SUBCUTANEOUS TISSUE DISORDERS | 1 (1.1) | (0.0, 6.2) | 1 (1.1) | (0.0, 5.9) | 2 (1.1) | (0.1, 4.0) | 1 (0.6) | (0.0, 3.1) |
| Dermatitis | 0 | (0.0, 4.1) | 0 | (0.0, 3.9) | 0 | (0.0, 2.0) | 1 (0.6) | (0.0, 3.1) |
| Hangnail | 1 (1.1) | (0.0, 6.2) | 0 | (0.0, 3.9) | 1 (0.6) | (0.0, 3.1) | 0 | (0.0, 2.0) |
| Macule | 0 | (0.0, 4.1) | 1 (1.1) | (0.0, 5.9) | 1 (0.6) | (0.0, 3.1) | 0 | (0.0, 2.0) |
| Rash macular | 0 | (0.0, 4.1) | 0 | (0.0, 3.9) | 0 | (0.0, 2.0) | 1 (0.6) | (0.0, 3.1) |

Note: MedDRA (v23.0) coding dictionary applied.

a. N = number of subjects in the specified group. This value is the denominator for the percentage calculations.

b. n = Number of subjects reporting at least 1 occurrence of the specified event. For "any event", n = number of subjects reporting at least 1 occurrence of any event.

c. Exact 2-sided CI based on the Clopper and Pearson method.

Related Adverse Events by System Organ Class and Preferred Term—Phase 2

The number of participants with AEs assessed by the investigator as related to study intervention from Dose 1 to 7 days after Dose 2 were low in frequency and similar in the BNT162b2 group and placebo group. Within the BNT162b2 group, a similar proportion of participants in the young and old age groups reported related AEs. Most investigator-assessed related AEs were reactogenicity events in the SOC of general disorders and administration site conditions, and they were reported by a similar proportion of participants in the BNT162b2 group overall compared with the placebo group, with injection site pain being the PT reported most frequently and exclusively in the BNT162b2 younger age group.

Immediate Adverse Events—Phase 2

There were no immediate AEs after any dose of BNT162b2 30 μg or placebo.

Severe or Life-Threatening Adverse Events—Phase 2

Two participants (both in the BNT162b2 younger age group) reported severe events of myalgia (AE) and gastric adenocarcinoma (SAE). The participant who reported myalgia had scapular muscle pain, which began 2 days after Dose 2 and was ongoing at the time of the data cutoff. Both events were assessed by the investigator as not related to study intervention.

Deaths, Serious Adverse Events, Safety-Related Participant Withdrawals, and Other Significant Adverse Events—Phase 2

Deaths—Phase 2

There were no Phase 2 participants who died through the data cutoff date of 2 Sep. 2020 in this interim CSR.

Serious Adverse Events—Phase 2

One participant had an SAE from Dose 1 to 7 days after Dose 2 (Table 13). One participant, who was in the BNT162b2 younger age group, had an SAE of gastric adenocarcinoma 23 days after Dose 1, which was assessed by the investigator as not related to study intervention (Table 13). The SAE was ongoing at the time of the data cutoff, and the participant was withdrawn from the study because of the SAE.

From 7 days after Dose 2 to the data cutoff date (2 Sep. 2020), no additional participants reported any SAE.

Safety-Related Participant Withdrawals—Phase 2

The participant in the BNT162b2 younger age group who reported an SAE of gastric adenocarcinoma was discontinued from the study on Day 23 after Dose 1 of BNT162b2.

Narratives of Safety-Related Participant Withdrawals—Phase 2

A narrative for the Phase 2 participant who was withdrawn from the study because of an SAE through the data cutoff date (2 Sep. 2020) was provided.

Other Significant Adverse Events—Phase 2

AEs of special interest were not defined for Phase 2 of this study; however, targeted medical events were monitored throughout the study.

Analysis and Discussion of Deaths, Serious Adverse Events, Safety-Related Participant Withdrawals, and Other Significant Adverse Events—Phase 2

Up to the data cutoff date of 2 Sep. 2020, there was 1 participant in the younger age group (BNT162b2 group) withdrawn from the study because of an SAE of gastric adenocarcinoma, which was assessed by the investigator as not related to study intervention.

Phase 2 Safety Conclusions

Across age groups, local reactions were generally similar in frequency after each dose, and systemic events generally increased in frequency and severity after Dose 2 compared to Dose 1. Local and systemic reactogenicity events were well-tolerated and short-lived.

Reactogenicity events after each dose of BNT162b2 in older adults were generally milder and less frequent than those observed in younger adults. The majority of reactogenicity events were mild or moderate in severity. No Grade 4 events were reported.

AEs in participants were low in frequency, and most AEs were mild or moderate in severity. There were no SAEs or discontinuations because of AEs that were assessed as related by the investigator.

The reactogenicity and AE profile after BNT162b2 30 μg evaluated in 360 participants was consistent with the safety profile observed after BNT162b2 30 μg in Phase 1. BNT162b2 at 30 μg was safe and well tolerated up to 7 days after Dose 2.

TABLE 13

Number (%) of Subjects Reporting at Least 1 Serious Adverse Event From Dose 1 to 7 Days After Dose 2, by System Organ Class and Preferred Term - Phase 2 - Safety Population

| | Vaccine Group (as Administered) | | | | | | | |
|---|---|---|---|---|---|---|---|---|
| | BNT162b2 (30 μg) | | | | | | Placebo | |
| System Organ Class | 18-55 Years ($N^a$ = 88) | | 56-85 Years ($N^a$ = 92) | | 18-85 Years ($N^a$ = 180) | | 18-85 Years ($N^a$ = 180) | |
| Preferred Term | $n^b$ (%) | (95% $CI^c$) | $n^b$ (%) | (95% $CI^c$) | $n^b$ (%) | (95% $CI^c$) | $n^b$ (%) | (95% $CI^c$) |
| Any event | 1 (1.1) | (0.0, 6.2) | 0 | (0.0, 3.9) | 1 (0.6) | (0.0, 3.1) | 0 | (0.0, 2.0) |
| NEOPLASMS BENIGN, MALIGNANT AND UNSPECIFIED (INCL CYSTS AND POLYPS) | 1 (1.1) | (0.0, 6.2) | 0 | (0.0, 3.9) | 1 (0.6) | (0.0, 3.1) | 0 | (0.0, 2.0) |
| Adenocarcinoma gastric | 1 (1.1) | (0.0, 6.2) | 0 | (0.0, 3.9) | 1 (0.6) | (0.0, 3.1) | 0 | (0.0, 2.0) |

Note: MedDRA (v23.0) coding dictionary applied.

a. N = number of subjects in the specified group. This value is the denominator for the percentage calculations.

b. n = Number of subjects reporting at least 1 occurrence of the specified adverse event. For "any event", n = number of subjects reporting at least 1 occurrence of any adverse event.

c. Exact 2-sided CI based on the Clopper and Pearson method.

Phase 2/3

In this interim CSR, safety results for Phase 3 included 36,855 older adolescent and adult participants (16 to 91 years of age) up through the safety data cutoff date of 6 Oct. 2020. AE summaries included any AE reported, regardless of whether participants completed the visit at 1 month after Dose 2. The first 6610 adult participants (18 to 85 years of age, which included the 360 participants in Phase 2) used an e-diary for reporting local reactions and systemic events and had safety data summarized through at least 1 month after Dose 2.

During the Phase 2/3 portion of the study, a stopping rule for the theoretical concern of vaccine enhanced disease was to be triggered if the 1-sided probability of observing the same or more extreme adverse severe case split was 5% or less, given the same true incidence for vaccine and placebo recipients, and alert criteria were to be triggered if this probability was less than 11%. It is also noted that, with ~18,000 per arm, the study has >83% probability of detecting at least 1 adverse event.

Local Reactions—Phase 2/3

In the BNT162b2 group, pain at the injection site was reported more frequently in the younger age group (FIG. 96) than in the older age group (FIG. 97), and frequency was similar after Dose 1 compared with Dose 2 of BNT162b2 in the younger age group (85.3% vs. 79.5%, respectively) and in the older age group (71.7% vs. 66.6%, respectively). In the placebo group, pain at the injection site after Doses 1 and 2 was reported at slightly higher frequencies in the younger age group (13.8% and 11.9%, respectively) than in the older age group (8.8% and 7.7%, respectively).

In the BNT162b2 group, frequencies of redness and swelling were similar in the younger and older age group after Doses 1 and 2. Frequencies of redness were similar after Dose 1 compared with Dose 2 of BNT162b2 in the younger age group (4.3% vs 5.4%, respectively) and in the older age group (4.5% vs 6.6%, respectively). Frequencies of swelling were similar after Dose 1 compared with Dose 2 of BNT162b2 in the younger age group (5.5% vs 5.9%, respectively) and in the older age group (6.5% vs 7.0%, respectively). In the placebo group, redness and swelling were reported infrequently in the younger (0.8%) and older (1.3%) age groups after Doses 1 and 2. Overall, across age groups, pain at the injection site did not increase after Dose 2, and redness and swelling were generally similar in frequency after Dose 1 and Dose 2. Severe local reactions (0.8%) were reported infrequently in the BNT162b2 group after either dose overall but occurred more frequently in the younger group. After the first and second dose and in both age groups, the majority of local reactions were mild or moderate in severity, and no Grade 4 local reactions were reported.

Subgroup Analyses

No clinically meaningful differences in local reactions were observed by country, sex, race, or ethnicity.

Across age groups, local reactions for the BNT162b2 group after either dose had a median onset day between Day 1.0 and Day 3.0 (Day 1.0 was the day of vaccination), and ranges were similar in the younger and older age groups. Across age groups, local reactions for this group after either dose resolved with median durations between 1.0 to 2.0 days, which were similar in the younger and older age groups.

Systemic Events—Phase 2/3

Systemic events were generally increased in frequency and severity in the younger group (FIG. 98) compared with the older group (FIG. 99), with frequencies and severity increasing with number of doses (Dose 1 vs Dose 2) Vomiting and diarrhea were exceptions with vomiting reported similarly infrequently in both age groups and both vomiting and diarrhea similar after each dose. Frequencies of systemic events in the younger and older BNT162b2 groups (Dose 1 vs Dose 2) are listed below:

fatigue: younger group (49.0% vs 61.6%) compared to older group (34.3% vs 51.2%)

headache: younger group (42.9% vs 53.1%) compared to older group (25.4% vs 39.5%)

muscle pain: younger group (22.0% vs. 38.6%) compared to older group (14.0% vs 28.5%)

chills: younger group (14.4% vs 36.5%) compared to older group (6.2% vs 22.8%)

joint pain: younger group (10.9% vs 22.4%) compared to older group (8.3% vs 18.9%)

fever: younger group (3.7% vs 16.6%) compared to older group (1.4% vs 11.5%).

vomiting: similar in both age groups and after either dose.

diarrhea: reported less frequently in the older group and was similar after each dose.

Figure 98:
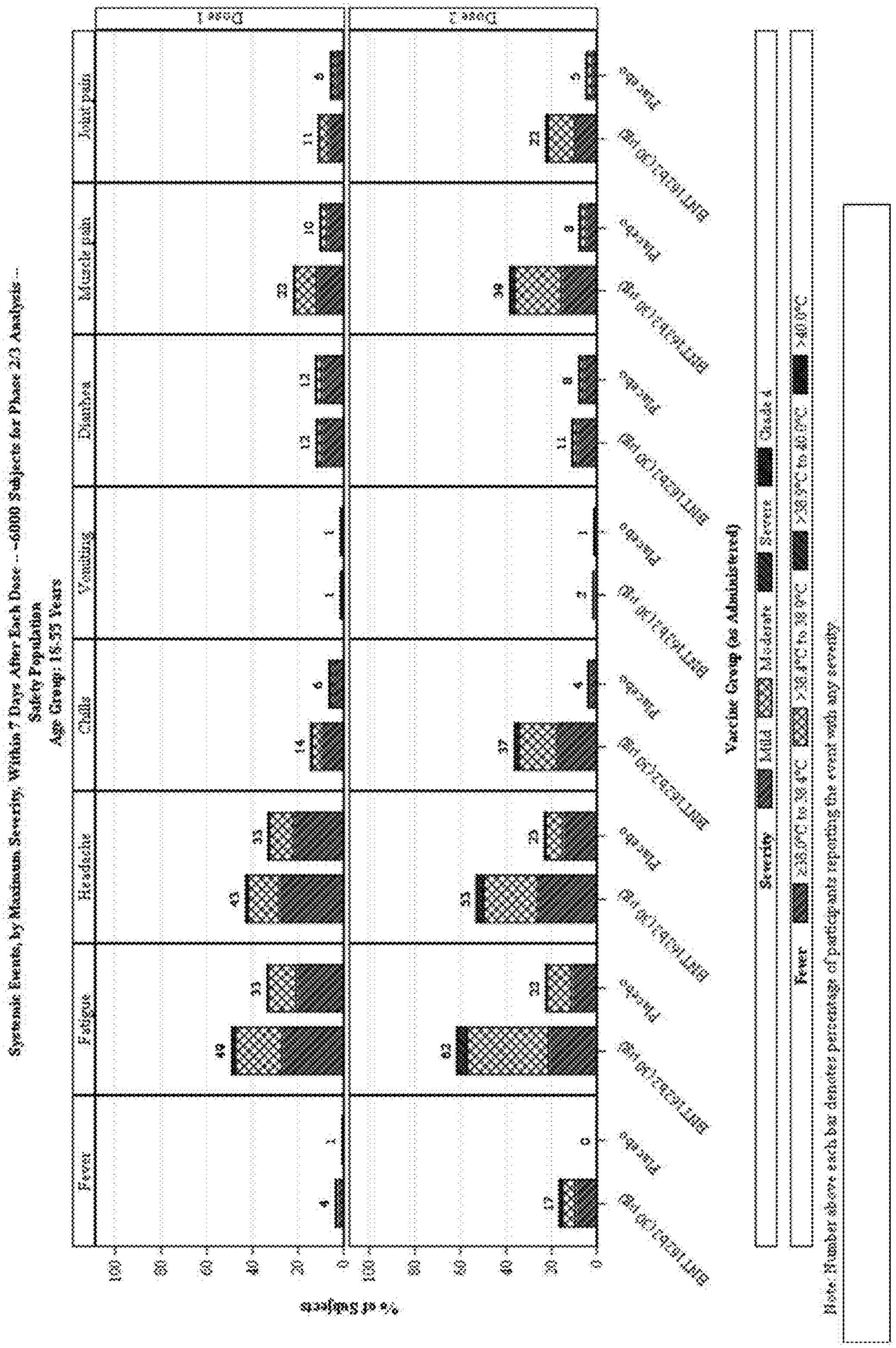
Figure 99:
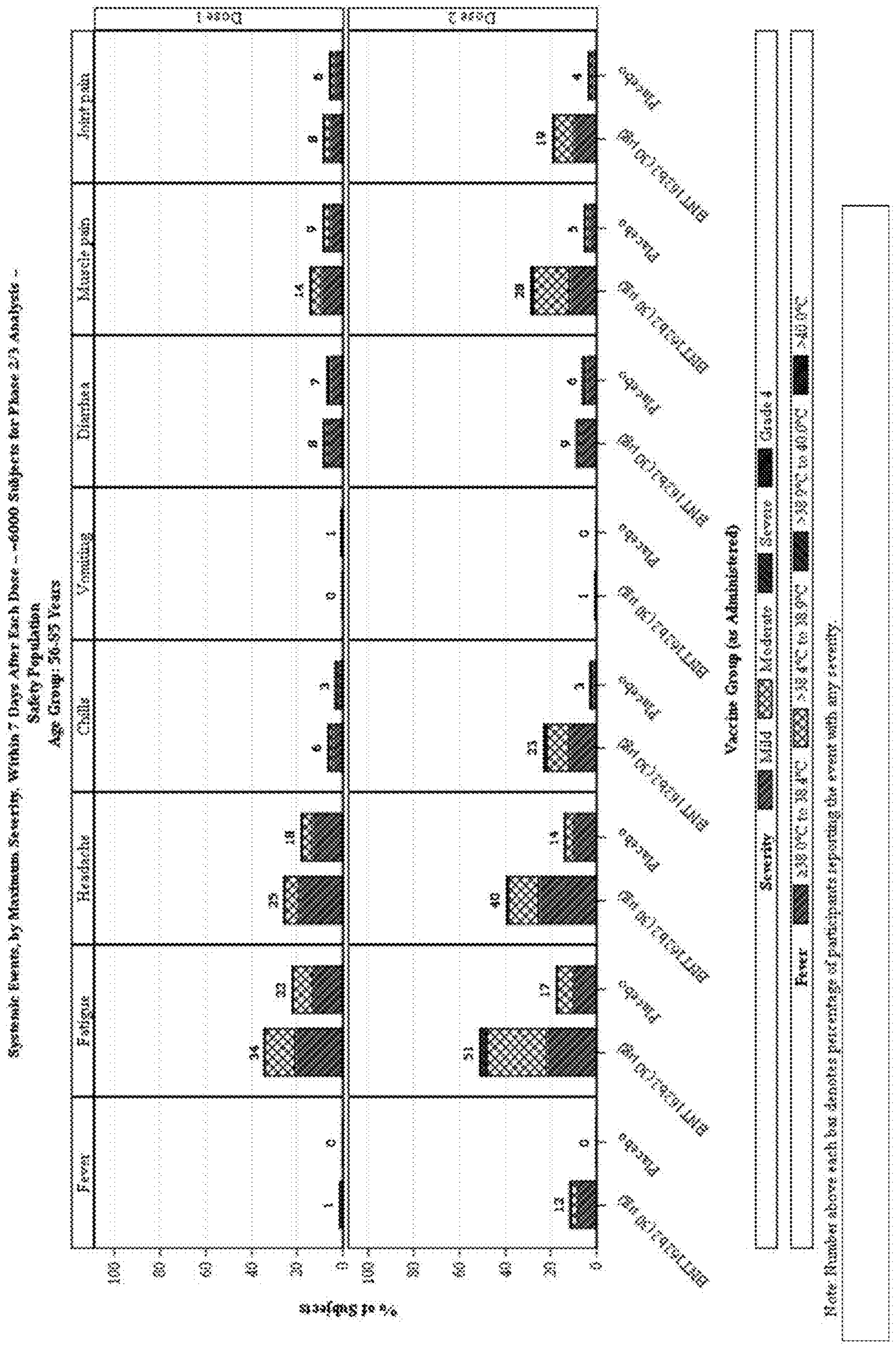

Systemic events were generally reported less frequently in the placebo group than in the BNT162b2 group, for both age groups and doses, with some exceptions. In the younger age group, fever and joint pain (after Dose 1) and vomiting and diarrhea (after Dose 1 and Dose 2) were reported at similar frequencies in the placebo group and the BNT162b2 group (FIG. 98). In the older age group, fever and joint pain (after Dose 1) and vomiting and diarrhea (after Dose 1 and Dose 2) were reported at similar frequencies in the placebo group and the BNT162b2 group (FIG. 99).

Use of antipyretic/pain medication was slightly less frequent in the older age group (20.1% to 37.4%) than in the younger age group (28.1% to 45.8%) after both doses, and medication use increased in both age groups after Dose 2 as compared with after Dose 1. Use of antipyretic/pain medication was less frequent in the placebo group than in the BNT162b2 group and was similar after Dose 1 and Dose 2 in the younger and older placebo groups (9.8% to 13.7%).

Severe systemic events across age groups after Dose 1 of BNT162b2 were generally lower in frequency than after Dose 2: fever (0.1% vs 0.8%), fatigue (0.8% vs 3.7%), headache (0.5% vs 1.9%), chills (0.2% vs 1.7%), muscle pain (0.3% vs. 1.6%), and joint pain (0.1% vs 0.6%). Diarrhea and vomiting frequencies were generally similar.

In the placebo group, severe fever was reported at a similar frequency (0.1%) after Dose 1 and Dose 2. One participant in the younger BNT162b2 group reported fever of 41.2° C. only on Day 2 after Dose 2 and was nonfebrile for all other days of the reporting period.

After the first and second dose and in both age groups, the majority of systemic events were mild or moderate in severity, and no Grade 4 (potentially life-threatening) systemic events were reported other than fever occurring only 1 day in 1 participant (41.2° C.) in the BNT162b2 group.

Subgroup Analyses

No clinically meaningful differences in systemic events were observed by country, ethnicity, sex, or race.

Across age groups, median onset day for most systemic events after either dose of BNT162b2 was Day 2.0 (Day 1.0 was the day of vaccination), and ranges were similar in the younger and older age groups. Across age groups, all systemic events resolved with median duration of 1.0 day, which was similar in the younger and older age groups.

Adverse Events—Phase 2/3

In this interim CSR, the first 6610 adult participants (which included the 360 participants in Phase 2) had safety data summarized through at least 1 month after Dose 2. AE summaries for all 36,855 participants up to the cutoff date (6 Oct. 2020) included any event reported, regardless of whether participants completed the visit at 1 month after Dose 2. At the time of the data cutoff date, there was a small percentage (0.7%) of participants with at least 1 uncoded term.

Summary of Adverse Events—Phase 2/3

First 6610 Participants—Phase 2/3

Table 14 presents a summary of the first 6610 participants reporting at least 1 AE from Dose 1 to 1 month after Dose 2.

The number of participants who reported at least 1 AE was similar in the BNT162b2 group as compared with the placebo group. Severe AEs, SAEs, and AEs leading to withdrawal were reported by 1.1%, 0.5%, and 0.2%, respectively, in both groups. In the younger and older age groups, the numbers of participants who reported at least 1 AE from Dose 1 to 1 month after Dose 2 were similar in the BNT162b2 group and the corresponding placebo group. Rates of related AEs, severe AEs, SAEs, and AEs leading to withdrawal in the younger and older age groups were also similar to the corresponding placebo group.

The first 6610 participants who reported at least 1 AE from Dose 1 to the data cutoff date in the BNT162b2 group and the placebo group were similar to those in the corresponding groups at 1 month after Dose 2 (Table 14). From 1 month after Dose 2 to the data cutoff date, 4 additional participants in the younger age group (3 in BNT162b2 and 1 in placebo) and 10 additional participants in the older age group (3 in BNT162b2 and 7 in placebo) reported at least 1 AE. There were no additional related AEs, severe AEs, SAEs, or AEs leading to withdrawal reported in either group.

TABLE 14

Number (%) of Subjects Reporting at Least 1 Adverse Event From Dose 1 to 1 Month After Dose 2-~6000 Subjects for Phase 2/3 Analysis-Safety Population

| | Vaccine Group (as Administered) | |
|---|---|---|
| Adverse Event | BNT162b2 (30 μg) ($N^a$ = 3314) $n^b$ (%) | Placebo ($N^a$ = 3296) $n^b$ (%) |
| Any event | 374 (11.3) | 316 (9.6) |
| Related[c] | 135 (4.1) | 68 (2.1) |
| Severe | 35 (1.1) | 19 (0.6) |
| Life-threatening | 4 (0.1) | 7 (0.2) |
| Any serious adverse event | 18 (0.5) | 17 (0.5) |
| Related[c] | 0 | 0 |
| Severe | 9 (0.3) | 8 (0.2) |
| Life-threatening | 4 (0.1) | 7 (0.2) |
| Any adverse event leading to withdrawal | 6 (0.2) | 5 (0.2) |
| Related[c] | 2 (0.1) | 1 (0.0) |
| Severe | 2 (0.1) | 1 (0.0) |
| Life-threatening | 1 (0.0) | 2 (0.1) |
| Death | 0 | 0 |

[a]N = number of subjects in the specified group. This value is the denominator for the percentage calculations.
[b]n = Number of subjects reporting at least 1 occurrence of the specified adverse event category. For "any event", n = the number of subjects reporting at least 1 occurrence of any adverse event.
[c]Assessed by the investigator as related to investigational product.

All Participants—Phase 2/3

From Dose 1 to the data cutoff date, the number of overall participants who reported at least 1 AE was higher in the BNT162b2 group as compared with the placebo group. Severe AEs, SAEs, and AEs leading to withdrawal were reported by 0.8%, 0.3%, and 0.1%, respectively, in both groups. Discontinuations due to related AEs were reported in 6 participants in the BNT162b2 group and 4 participants in the placebo group.

Three Phase 3 participants died: 1 participant in the BNT162b2 group and 2 participants in the placebo group. The participant in the BNT162b2 group who died experienced an SAE of arteriosclerosis which was assessed by the investigator as not related to study intervention.

In the younger age group, the number of participants who reported at least 1 AE was 1920 (18.1%) and 880 (8.3%) in the BNT162b2 and placebo groups, respectively. In the older age group, the number of participants who reported at least 1 AE was 1166 (14.9%) and 582 (7.4%) in the BNT162b2 and placebo groups, respectively.

Analysis of Adverse Events—Phase 2/3

Adverse Events by System Organ Class and Preferred Term—Phase 2/3

First 6610 Participants—Phase 2/3

There are no Tier 1 AEs identified for this program.

There were no Tier 2 AEs (defined as an event rate ≥1.0% in any vaccine group [PT level]) reported from Dose 1 to 1 month after Dose 2.

Most AEs reported up to 1 month after Dose 2 overall were reactogenicity and in the SOCs of general disorders and administration site conditions (81 [2.4%] in the BNT162b2 group and 57 [1.7%] in the placebo group), musculoskeletal and connective tissue disorders (81 [2.4%] in the BNT162b2 group and 56 [1.7%] in the placebo group), infections and infestations (56 [1.7%] in the BNT162b2 group and 48 [1.5%] in the placebo group), and gastrointestinal disorders (54 [1.6%] in the BNT162b2 group and 41 [1.2%] in the placebo group) (Table 15). In the younger BNT162b2 group, rates of AEs in these SOCs were: general disorders and administration site conditions (54 [3.0%]), musculoskeletal and connective tissue disorders (53 [3.0%]), infections and infestations (31 [1.7%]), and gastrointestinal disorders (32 [1.8%]). In the older BNT162b2 group, rates of AEs in these SOCs were: general disorders and administration site conditions (27 [1.8%]), musculoskeletal and connective tissue disorders (28 [1.8%]), infections and infestations (25 [1.6%]), and gastrointestinal disorders (22 [1.4%]).

In the BNT162b2 group, the most frequently reported AEs by PT overall were injection site pain (30 [0.9%]), headache (30 [0.9%]), and fatigue (27 [0.8%]) (Table 15), and during this time period (from Dose 1 to 1 month after Dose 2) most of these AEs were reported during the e-diary 1 week reporting period. The majority of these PTs were reported in the younger age group: headache (21[1.2%]), and fatigue (17 [1.0%]). Injection site pain was reported at a similar frequency in the younger (16 [0.9%]) and older (14 [0.9%]) age groups.

In the BNT162b2 group, there were 10 (0.3%) participants who reported an AE of lymphadenopathy: 6 in the younger age group and 4 in the older age group compared to none in the placebo group; 1 (0.1%) was male and 9 (0.5%) were females. AEs of lymphadenopathy occurred in the arm and neck region (in axillary, left axillary, left para clavicular, left supra clavicular, bilateral cervical, or unspecified lymph nodes). Most lymphadenopathy events were reported within 2 to 4 days after vaccination (2 events were reported 8 days after vaccination). Five of the events lasted 4 days, 3 events lasted between 12 to 16 days, and 2 events were ongoing at the time of the data cutoff date.

In the younger age group, an AE of angioedema 13 days after Dose 1 (both eyes) and hypersensitivity (allergy attack [no additional information available at the time of this report], unrelated to study intervention) were reported in 1 participant each (BNT162b2 group), and an AE of drug hypersensitivity (oral penicillin reaction) was reported in 1 participant (placebo). None of these events were assessed by the investigator as related to study intervention. Three participants in the younger BNT162b2 group reported appendicitis compared to 1 participant in the older placebo group with perforated appendicitis; all were assessed by the investigator as unrelated to study intervention.

TABLE 15

Number (%) of Subjects Reporting at Least 1 Adverse Event From Dose 1 to 1 Month After Dose 2, by System Organ Class and Preferred Term-~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Any event | 374 (11.3) | (10.2, 12.4) | 316 (9.6) | (8.6, 10.6) |
| BLOOD AND LYMPHATIC SYSTEM DISORDERS | 14 (0.4) | (0.2, 0.7) | 0 | (0.0, 0.1) |
| Lymphadenopathy | 10 (0.3) | (0.1, 0.6) | 0 | (0.0, 0.1) |
| Anaemia | 2 (0.1) | (0.0, 0.2) | 0 | (0.0, 0.1) |
| Iron deficiency anaemia | 1 (0.0) | (0.0, 0.2) | 0 | (0.0, 0.1) |
| Lymph node pain | 1 (0.0) | (0.0, 0.2) | 0 | (0.0, 0.1) |
| CARDIAC DISORDERS | 6 (0.2) | (0.1, 0.4) | 4 (0.1) | (0.0, 0.3) |
| Atrial fibrillation | 1 (0.0) | (0.0, 0.2) | 1 (0.0) | (0.0, 0.2) |
| Mitral valve incompetence | 0 | (0.0, 0.1) | 2 (0.1) | (0.0, 0.2) |
| Palpitations | 1 (0.0) | (0.0, 0.2) | 1 (0.0) | (0.0, 0.2) |
| Acute coronary syndrome | 0 | (0.0, 0.1) | 1 (0.0) | (0.0, 0.2) |
| Acute myocardial infarction | 0 | (0.0, 0.1) | 1 (0.0) | (0.0, 0.2) |
| Angina pectoris | 0 | (0.0, 0.1) | 1 (0.0) | (0.0, 0.2) |
| Angina unstable | 0 | (0.0, 0.1) | 1 (0.0) | (0.0, 0.2) |
| Atrial flutter | 0 | (0.0, 0.1) | 1 (0.0) | (0.0, 0.2) |
| Cardiac failure congestive | 1 (0.0) | (0.0, 0.2) | 0 | (0.0, 0.1) |
| Coronary artery disease | 1 (0.0) | (0.0, 0.2) | 0 | (0.0, 0.1) |
| Coronary artery dissection | 1 (0.0) | (0.0, 0.2) | 0 | (0.0, 0.1) |
| Coronary artery occlusion | 0 | (0.0, 0.1) | 1 (0.0) | (0.0, 0.2) |
| Left atrial enlargement | 0 | (0.0, 0.1) | 1 (0.0) | (0.0, 0.2) |
| Left ventricular hypertrophy | 0 | (0.0, 0.1) | 1 (0.0) | (0.0, 0.2) |
| Mitral valve prolapse | 0 | (0.0, 0.1) | 1 (0.0) | (0.0, 0.2) |
| Tachycardia | 1 (0.0) | (0.0, 0.2) | 0 | (0.0, 0.1) |
| CONGENITAL, FAMILIAL AND GENETIC DISORDERS | 1 (0.0) | (0.0, 0.2) | 0 | (0.0, 0.1) |
| Congenital cystic kidney disease | 1 (0.0) | (0.0, 0.2) | 0 | (0.0, 0.1) |
| EAR AND LABYRINTH DISORDERS | 7 (0.2) | (0.1, 0.4) | 6 (0.2) | (0.1, 0.4) |
| Vertigo | 2 (0.1) | (0.0, 0.2) | 2 (0.1) | (0.0, 0.2) |
| Vertigo positional | 1 (0.0) | (0.0, 0.2) | 2 (0.1) | (0.0, 0.2) |
| Ear discomfort | 2 (0.1) | (0.0, 0.2) | 0 | (0.0, 0.1) |
| Deafness unilateral | 1 (0.0) | (0.0, 0.2) | 0 | (0.0, 0.1) |
| Ear pain | 0 | (0.0, 0.1) | 1 (0.0) | (0.0, 0.2) |
| Tinnitus | 1 (0.0) | (0.0, 0.2) | 0 | (0.0, 0.1) |
| Tympanic membrane perforation | 0 | (0.0, 0.1) | 1 (0.0) | (0.0, 0.2) |
| ENDOCRINE DISORDERS | 2 (0.1) | (0.0, 0.2) | 0 | (0.0, 0.1) |
| Goitre | 1 (0.0) | (0.0, 0.2) | 0 | (0.0, 0.1) |
| Hypogonadism | 1 (0.0) | (0.0, 0.2) | 0 | (0.0, 0.1) |
| EYE DISORDERS | 8 (0.2) | (0.1, 0.5) | 6 (0.2) | (0.1, 0.4) |
| Cataract | 1 (0.0) | (0.0, 0.2) | 1 (0.0) | (0.0, 0.2) |
| Chalazion | 2 (0.1) | (0.0, 0.2) | 0 | (0.0, 0.1) |
| Vision blurred | 2 (0.1) | (0.0, 0.2) | 0 | (0.0, 0.1) |
| Blepharitis | 0 | (0.0, 0.1) | 1 (0.0) | (0.0, 0.2) |
| Conjunctival hyperaemia | 0 | (0.0, 0.1) | 1 (0.0) | (0.0, 0.2) |
| Dacryostenosis acquired | 0 | (0.0, 0.1) | 1 (0.0) | (0.0, 0.2) |
| Diplopia | 1 (0.0) | (0.0, 0.2) | 0 | (0.0, 0.1) |
| Eye pain | 1 (0.0) | (0.0, 0.2) | 0 | (0.0, 0.1) |
| Lacrimation increased | 0 | (0.0, 0.1) | 1 (0.0) | (0.0, 0.2) |
| Retinal detachment | 0 | (0.0, 0.1) | 1 (0.0) | (0.0, 0.2) |
| Vitreous detachment | 1 (0.0) | (0.0, 0.2) | 0 | (0.0, 0.1) |
| GASTROINTESTINAL DISORDERS | 54 (1.6) | (1.2, 2.1) | 41 (1.2) | (0.9, 1.7) |
| Diarrhoea | 17 (0.5) | (0.3, 0.8) | 15 (0.5) | (0.3, 0.7) |
| Nausea | 12 (0.4) | (0.2, 0.6) | 5 (0.2) | (0.0, 0.4) |
| Toothache | 5 (0.2) | (0.0, 0.4) | 2 (0.1) | (0.0, 0.2) |
| Vomiting | 4 (0.1) | (0.0, 0.3) | 3 (0.1) | (0.0, 0.3) |
| Abdominal pain | 3 (0.1) | (0.0, 0.3) | 1 (0.0) | (0.0, 0.2) |
| Constipation | 2 (0.1) | (0.0, 0.2) | 1 (0.0) | (0.0, 0.2) |
| Dyspepsia | 1 (0.0) | (0.0, 0.2) | 2 (0.1) | (0.0, 0.2) |
| Gastrooesophageal reflux disease | 0 | (0.0, 0.1) | 3 (0.1) | (0.0, 0.3) |
| Odynophagia | 1 (0.0) | (0.0, 0.2) | 2 (0.1) | (0.0, 0.2) |
| Dental caries | 1 (0.0) | (0.0, 0.2) | 1 (0.0) | (0.0, 0.2) |
| Inguinal hernia | 1 (0.0) | (0.0, 0.2) | 1 (0.0) | (0.0, 0.2) |

TABLE 15-continued

Number (%) of Subjects Reporting at Least 1 Adverse Event From Dose 1 to 1 Month After Dose 2, by System Organ Class and Preferred Term-~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Small intestinal obstruction | 0 | (0.0, 0.1) | 2 (0.1) | (0.0, 0.2) |
| Abdominal adhesions | 1 (0.0) | (0.0, 0.2) | 0 | (0.0, 0.1) |
| Abdominal pain upper | 1 (0.0) | (0.0, 0.2) | 0 | (0.0, 0.1) |
| Abdominal rigidity | 1 (0.0) | (0.0, 0.2) | 0 | (0.0, 0.1) |
| Angular cheilitis | 1 (0.0) | (0.0, 0.2) | 0 | (0.0, 0.1) |
| Colitis | 1 (0.0) | (0.0, 0.2) | 0 | (0.0, 0.1) |
| Diverticular perforation | 0 | (0.0, 0.1) | 1 (0.0) | (0.0, 0.2) |
| Faeces soft | 0 | (0.0, 0.1) | 1 (0.0) | (0.0, 0.2) |
| Gastric ulcer haemorrhage | 1 (0.0) | (0.0, 0.2) | 0 | (0.0, 0.1) |
| Gastrointestinal disorder | 1 (0.0) | (0.0, 0.2) | 0 | (0.0, 0.1) |
| Gingival discomfort | 0 | (0.0, 0.1) | 1 (0.0) | (0.0, 0.2) |
| Haematochezia | 1 (0.0) | (0.0, 0.2) | 0 | (0.0, 0.1) |
| Hiatus hernia | 1 (0.0) | (0.0, 0.2) | 0 | (0.0, 0.1) |
| Hypoaesthesia oral | 0 | (0.0, 0.1) | 1 (0.0) | (0.0, 0.2) |
| Intestinal obstruction | 0 | (0.0, 0.1) | 1 (0.0) | (0.0, 0.2) |
| Irritable bowel syndrome | 0 | (0.0, 0.1) | 1 (0.0) | (0.0, 0.2) |
| Mouth ulceration | 0 | (0.0, 0.1) | 1 (0.0) | (0.0, 0.2) |
| Parotid duct obstruction | 1 (0.0) | (0.0, 0.2) | 0 | (0.0, 0.1) |
| Rectal haemorrhage | 1 (0.0) | (0.0, 0.2) | 0 | (0.0, 0.1) |
| Salivary gland calculus | 0 | (0.0, 0.1) | 1 (0.0) | (0.0, 0.2) |
| Tongue discomfort | 0 | (0.0, 0.1) | 1 (0.0) | (0.0, 0.2) |
| Tongue ulceration | 1 (0.0) | (0.0, 0.2) | 0 | (0.0, 0.1) |
| GENERAL DISORDERS AND ADMINISTRATION SITE CONDITIONS | 81 (2.4) | (1.9, 3.0) | 57 (1.7) | (1.3, 2.2) |
| Fatigue | 27 (0.8) | (0.5, 1.2) | 17 (0.5) | (0.3, 0.8) |
| Injection site pain | 30 (0.9) | (0.6, 1.3) | 14 (0.4) | (0.2, 0.7) |
| Chills | 15 (0.5) | (0.3, 0.7) | 7 (0.2) | (0.1, 0.4) |
| Injection site erythema | 10 (0.3) | (0.1, 0.6) | 6 (0.2) | (0.1, 0.4) |
| Pyrexia | 13 (0.4) | (0.2, 0.7) | 2 (0.1) | (0.0, 0.2) |
| Injection site swelling | 4 (0.1) | (0.0, 0.3) | 4 (0.1) | (0.0, 0.3) |
| Pain | 4 (0.1) | (0.0, 0.3) | 3 (0.1) | (0.0, 0.3) |
| Malaise | 3 (0.1) | (0.0, 0.3) | 1 (0.0) | (0.0, 0.2) |
| Injection site bruising | 1 (0.0) | (0.0, 0.2) | 2 (0.1) | (0.0, 0.2) |
| Injection site reaction | 3 (0.1) | (0.0, 0.3) | 0 | (0.0, 0.1) |
| Asthenia | 1 (0.0) | (0.0, 0.2) | 1 (0.0) | (0.0, 0.2) |
| Injection site pruritus | 1 (0.0) | (0.0, 0.2) | 1 (0.0) | (0.0, 0.2) |
| Chest discomfort | 0 | (0.0, 0.1) | 1 (0.0) | (0.0, 0.2) |
| Chest pain | 0 | (0.0, 0.1) | 1 (0.0) | (0.0, 0.2) |
| Face oedema | 1 (0.0) | (0.0, 0.2) | 0 | (0.0, 0.1) |
| Inflammation | 1 (0.0) | (0.0, 0.2) | 0 | (0.0, 0.1) |
| Injection site discolouration | 0 | (0.0, 0.1) | 1 (0.0) | (0.0, 0.2) |
| Injection site discomfort | 0 | (0.0, 0.1) | 1 (0.0) | (0.0, 0.2) |
| Injection site hyperaesthesia | 1 (0.0) | (0.0, 0.2) | 0 | (0.0, 0.1) |
| Non-cardiac chest pain | 1 (0.0) | (0.0, 0.2) | 0 | (0.0, 0.1) |
| Swelling | 1 (0.0) | (0.0, 0.2) | 0 | (0.0, 0.1) |
| Unevaluable event | 0 | (0.0, 0.1) | 1 (0.0) | (0.0, 0.2) |
| Vaccination site nodule | 1 (0.0) | (0.0, 0.2) | 0 | (0.0, 0.1) |
| Vascular stent occlusion | 1 (0.0) | (0.0, 0.2) | 0 | (0.0, 0.1) |
| HEPATOBILIARY DISORDERS | 2 (0.1) | (0.0, 0.2) | 1 (0.0) | (0.0, 0.2) |
| Cholelithiasis | 2 (0.1) | (0.0, 0.2) | 0 | (0.0, 0.1) |
| Cholecystitis acute | 0 | (0.0, 0.1) | 1 (0.0) | (0.0, 0.2) |
| IMMUNE SYSTEM DISORDERS | 4 (0.1) | (0.0, 0.3) | 6 (0.2) | (0.1, 0.4) |
| Seasonal allergy | 1 (0.0) | (0.0, 0.2) | 3 (0.1) | (0.0, 0.3) |
| Food allergy | 1 (0.0) | (0.0, 0.2) | 1 (0.0) | (0.0, 0.2) |
| Allergy to vaccine | 0 | (0.0, 0.1) | 1 (0.0) | (0.0, 0.2) |
| Anaphylactic reaction | 1 (0.0) | (0.0, 0.2) | 0 | (0.0, 0.1) |
| Drug hypersensitivity | 0 | (0.0, 0.1) | 1 (0.0) | (0.0, 0.2) |
| Hypersensitivity | 1 (0.0) | (0.0, 0.2) | 0 | (0.0, 0.1) |
| Milk allergy | 0 | (0.0, 0.1) | 1 (0.0) | (0.0, 0.2) |
| INFECTIONS AND INFESTATIONS | 56 (1.7) | (1.3, 2.2) | 48 (1.5) | (1.1, 1.9) |
| Urinary tract infection | 10 (0.3) | (0.1, 0.6) | 7 (0.2) | (0.1, 0.4) |
| Sinusitis | 8 (0.2) | (0.1, 0.5) | 1 (0.0) | (0.0, 0.2) |
| Diverticulitis | 3 (0.1) | (0.0, 0.3) | 4 (0.1) | (0.0, 0.3) |
| Tooth infection | 2 (0.1) | (0.0, 0.2) | 3 (0.1) | (0.0, 0.3) |
| Otitis media | 0 | (0.0, 0.1) | 4 (0.1) | (0.0, 0.3) |
| Upper respiratory tract infection | 3 (0.1) | (0.0, 0.3) | 1 (0.0) | (0.0, 0.2) |
| Appendicitis | 3 (0.1) | (0.0, 0.3) | 0 | (0.0, 0.1) |
| Cellulitis | 1 (0.0) | (0.0, 0.2) | 2 (0.1) | (0.0, 0.2) |

TABLE 15-continued

Number (%) of Subjects Reporting at Least 1 Adverse Event From Dose 1 to 1 Month After Dose 2, by System Organ Class and Preferred Term--~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Ear infection | 2 (0.1) | (0.0, 0.2) | 1 (0.0) | (0.0, 0.2) |
| Herpes zoster | 2 (0.1) | (0.0, 0.2) | 1 (0.0) | (0.0, 0.2) |
| Pneumonia | 1 (0.0) | (0.0, 0.2) | 2 (0.1) | (0.0, 0.2) |
| Tonsillitis | 0 | (0.0, 0.1) | 3 (0.1) | (0.0, 0.3) |
| Conjunctivitis | 1 (0.0) | (0.0, 0.2) | 1 (0.0) | (0.0, 0.2) |
| Gastroenteritis | 0 | (0.0, 0.1) | 2 (0.1) | (0.0, 0.2) |
| Infected bite | 2 (0.1) | (0.0, 0.2) | 0 | (0.0, 0.1) |
| Otitis externa | 1 (0.0) | (0.0, 0.2) | 1 (0.0) | (0.0, 0.2) |
| Otitis media acute | 1 (0.0) | (0.0, 0.2) | 1 (0.0) | (0.0, 0.2) |
| Skin infection | 1 (0.0) | (0.0, 0.2) | 1 (0.0) | (0.0, 0.2) |
| Tooth abscess | 0 | (0.0, 0.1) | 2 (0.1) | (0.0, 0.2) |
| Acute sinusitis | 0 | (0.0, 0.1) | 1 (0.0) | (0.0, 0.2) |
| Appendicitis perforated | 0 | (0.0, 0.1) | 1 (0.0) | (0.0, 0.2) |
| Cystitis | 1 (0.0) | (0.0, 0.2) | 0 | (0.0, 0.1) |
| Dermatitis infected | 0 | (0.0, 0.1) | 1 (0.0) | (0.0, 0.2) |
| Eye infection | 1 (0.0) | (0.0, 0.2) | 0 | (0.0, 0.1) |
| Folliculitis | 1 (0.0) | (0.0, 0.2) | 0 | (0.0, 0.1) |
| Fungal infection | 1 (0.0) | (0.0, 0.2) | 0 | (0.0, 0.1) |
| Fungal skin infection | 0 | (0.0, 0.1) | 1 (0.0) | (0.0, 0.2) |
| Genital herpes | 0 | (0.0, 0.1) | 1 (0.0) | (0.0, 0.2) |
| Genital herpes simplex | 1 (0.0) | (0.0, 0.2) | 0 | (0.0, 0.1) |
| Gingivitis | 1 (0.0) | (0.0, 0.2) | 0 | (0.0, 0.1) |
| Hordeolum | 0 | (0.0, 0.1) | 1 (0.0) | (0.0, 0.2) |
| Kidney infection | 0 | (0.0, 0.1) | 1 (0.0) | (0.0, 0.2) |
| Lower respiratory tract infection | 1 (0.0) | (0.0, 0.2) | 0 | (0.0, 0.1) |
| Oral candidiasis | 1 (0.0) | (0.0, 0.2) | 0 | (0.0, 0.1) |
| Oral fungal infection | 0 | (0.0, 0.1) | 1 (0.0) | (0.0, 0.2) |
| Parotitis | 1 (0.0) | (0.0, 0.2) | 0 | (0.0, 0.1) |
| Peritoneal abscess | 1 (0.0) | (0.0, 0.2) | 0 | (0.0, 0.1) |
| Peritonitis | 0 | (0.0, 0.1) | 1 (0.0) | (0.0, 0.2) |
| Pharyngitis | 1 (0.0) | (0.0, 0.2) | 0 | (0.0, 0.1) |
| Pharyngitis streptococcal | 0 | (0.0, 0.1) | 1 (0.0) | (0.0, 0.2) |
| Respiratory tract infection viral | 1 (0.0) | (0.0, 0.2) | 0 | (0.0, 0.1) |
| Rhinitis | 1 (0.0) | (0.0, 0.2) | 0 | (0.0, 0.1) |
| Sepsis | 1 (0.0) | (0.0, 0.2) | 0 | (0.0, 0.1) |
| Skin bacterial infection | 0 | (0.0, 0.1) | 1 (0.0) | (0.0, 0.2) |
| Soft tissue infection | 1 (0.0) | (0.0, 0.2) | 0 | (0.0, 0.1) |
| Subcutaneous abscess | 0 | (0.0, 0.1) | 1 (0.0) | (0.0, 0.2) |
| Vulvovaginal candidiasis | 1 (0.0) | (0.0, 0.2) | 0 | (0.0, 0.1) |
| Vulvovaginal mycotic infection | 0 | (0.0, 0.1) | 1 (0.0) | (0.0, 0.2) |
| INJURY, POISONING AND PROCEDURAL COMPLICATIONS | 28 (0.8) | (0.6, 1.2) | 42 (1.3) | (0.9, 1.7) |
| Fall | 8 (0.2) | (0.1, 0.5) | 16 (0.5) | (0.3, 0.8) |
| Arthropod bite | 5 (0.2) | (0.0, 0.4) | 3 (0.1) | (0.0, 0.3) |
| Muscle strain | 4 (0.1) | (0.0, 0.3) | 3 (0.1) | (0.0, 0.3) |
| Contusion | 2 (0.1) | (0.0, 0.2) | 4 (0.1) | (0.0, 0.3) |
| Skin abrasion | 1 (0.0) | (0.0, 0.2) | 4 (0.1) | (0.0, 0.3) |
| Skin laceration | 0 | (0.0, 0.1) | 4 (0.1) | (0.0, 0.3) |
| Ankle fracture | 1 (0.0) | (0.0, 0.2) | 2 (0.1) | (0.0, 0.2) |
| Joint dislocation | 2 (0.1) | (0.0, 0.2) | 1 (0.0) | (0.0, 0.2) |
| Tooth fracture | 1 (0.0) | (0.0, 0.2) | 2 (0.1) | (0.0, 0.2) |
| Fibula fracture | 1 (0.0) | (0.0, 0.2) | 1 (0.0) | (0.0, 0.2) |
| Foot fracture | 1 (0.0) | (0.0, 0.2) | 1 (0.0) | (0.0, 0.2) |
| Joint injury | 1 (0.0) | (0.0, 0.2) | 1 (0.0) | (0.0, 0.2) |
| Ligament sprain | 1 (0.0) | (0.0, 0.2) | 1 (0.0) | (0.0, 0.2) |
| Limb injury | 0 | (0.0, 0.1) | 2 (0.1) | (0.0, 0.2) |
| Meniscus injury | 2 (0.1) | (0.0, 0.2) | 0 | (0.0, 0.1) |
| Muscle rupture | 0 | (0.0, 0.1) | 2 (0.1) | (0.0, 0.2) |
| Rib fracture | 1 (0.0) | (0.0, 0.2) | 1 (0.0) | (0.0, 0.2) |
| Bone contusion | 0 | (0.0, 0.1) | 1 (0.0) | (0.0, 0.2) |
| Chest injury | 0 | (0.0, 0.1) | 1 (0.0) | (0.0, 0.2) |
| Corneal abrasion | 0 | (0.0, 0.1) | 1 (0.0) | (0.0, 0.2) |
| Craniocerebral injury | 0 | (0.0, 0.1) | 1 (0.0) | (0.0, 0.2) |
| Forearm fracture | 0 | (0.0, 0.1) | 1 (0.0) | (0.0, 0.2) |
| Hand fracture | 1 (0.0) | (0.0, 0.2) | 0 | (0.0, 0.1) |
| Humerus fracture | 0 | (0.0, 0.1) | 1 (0.0) | (0.0, 0.2) |
| Lumbar vertebral fracture | 0 | (0.0, 0.1) | 1 (0.0) | (0.0, 0.2) |
| Muscle injury | 0 | (0.0, 0.1) | 1 (0.0) | (0.0, 0.2) |

TABLE 15-continued

Number (%) of Subjects Reporting at Least 1 Adverse Event From Dose 1 to 1 Month After Dose 2, by System Organ Class and Preferred Term--~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Postoperative ileus | 0 | (0.0, 0.1) | 1 (0.0) | (0.0, 0.2) |
| Procedural pain | 1 (0.0) | (0.0, 0.2) | 0 | (0.0, 0.1) |
| Radius fracture | 0 | (0.0, 0.1) | 1 (0.0) | (0.0, 0.2) |
| Road traffic accident | 1 (0.0) | (0.0, 0.2) | 0 | (0.0, 0.1) |
| Sunburn | 1 (0.0) | (0.0, 0.2) | 0 | (0.0, 0.1) |
| Tendon rupture | 0 | (0.0, 0.1) | 1 (0.0) | (0.0, 0.2) |
| Thermal burn | 1 (0.0) | (0.0, 0.2) | 0 | (0.0, 0.1) |
| INVESTIGATIONS | 9 (0.3) | (0.1, 0.5) | 4 (0.1) | (0.0, 0.3) |
| Body temperature increased | 2 (0.1) | (0.0, 0.2) | 1 (0.0) | (0.0, 0.2) |
| Blood glucose increased | 2 (0.1) | (0.0, 0.2) | 0 | (0.0, 0.1) |
| Blood cholesterol increased | 1 (0.0) | (0.0, 0.2) | 0 | (0.0, 0.1) |
| Blood pressure increased | 0 | (0.0, 0.1) | 1 (0.0) | (0.0, 0.2) |
| Blood triglycerides increased | 1 (0.0) | (0.0, 0.2) | 0 | (0.0, 0.1) |
| Cardiac stress test abnormal | 1 (0.0) | (0.0, 0.2) | 0 | (0.0, 0.1) |
| Electrocardiogram QT prolonged | 1 (0.0) | (0.0, 0.2) | 0 | (0.0, 0.1) |
| Heart rate increased | 0 | (0.0, 0.1) | 1 (0.0) | (0.0, 0.2) |
| Weight decreased | 1 (0.0) | (0.0, 0.2) | 0 | (0.0, 0.1) |
| White blood cell count increased | 0 | (0.0, 0.1) | 1 (0.0) | (0.0, 0.2) |
| METABOLISM AND NUTRITION DISORDERS | 12 (0.4) | (0.2, 0.6) | 7 (0.2) | (0.1, 0.4) |
| Decreased appetite | 3 (0.1) | (0.0, 0.3) | 0 | (0.0, 0.1) |
| Hypercholesterolaemia | 2 (0.1) | (0.0, 0.2) | 1 (0.0) | (0.0, 0.2) |
| Type 2 diabetes mellitus | 1 (0.0) | (0.0, 0.2) | 1 (0.0) | (0.0, 0.2) |
| Dehydration | 1 (0.0) | (0.0, 0.2) | 0 | (0.0, 0.1) |
| Diabetes mellitus inadequate control | 0 | (0.0, 0.1) | 1 (0.0) | (0.0, 0.2) |
| Dyslipidaemia | 1 (0.0) | (0.0, 0.2) | 0 | (0.0, 0.1) |
| Glucose tolerance impaired | 0 | (0.0, 0.1) | 1 (0.0) | (0.0, 0.2) |
| Hyperlipidaemia | 1 (0.0) | (0.0, 0.2) | 0 | (0.0, 0.1) |
| Hypertriglyceridaemia | 1 (0.0) | (0.0, 0.2) | 0 | (0.0, 0.1) |
| Hypoglycaemia | 0 | (0.0, 0.1) | 1 (0.0) | (0.0, 0.2) |
| Hypokalaemia | 1 (0.0) | (0.0, 0.2) | 0 | (0.0, 0.1) |
| Iron deficiency | 0 | (0.0, 0.1) | 1 (0.0) | (0.0, 0.2) |
| Obesity | 1 (0.0) | (0.0, 0.2) | 0 | (0.0, 0.1) |
| Vitamin D deficiency | 0 | (0.0, 0.1) | 1 (0.0) | (0.0, 0.2) |
| MUSCULOSKELETAL AND CONNECTIVE TISSUE DISORDERS | 81 (2.4) | (1.9, 3.0) | 56 (1.7) | (1.3, 2.2) |
| Arthralgia | 20 (0.6) | (0.4, 0.9) | 15 (0.5) | (0.3, 0.7) |
| Myalgia | 20 (0.6) | (0.4, 0.9) | 12 (0.4) | (0.2, 0.6) |
| Back pain | 8 (0.2) | (0.1, 0.5) | 8 (0.2) | (0.1, 0.5) |
| Pain in extremity | 10 (0.3) | (0.1, 0.6) | 4 (0.1) | (0.0, 0.3) |
| Neck pain | 5 (0.2) | (0.0, 0.4) | 5 (0.2) | (0.0, 0.4) |
| Muscle spasms | 4 (0.1) | (0.0, 0.3) | 2 (0.1) | (0.0, 0.2) |
| Musculoskeletal pain | 2 (0.1) | (0.0, 0.2) | 2 (0.1) | (0.0, 0.2) |
| Osteoarthritis | 3 (0.1) | (0.0, 0.3) | 1 (0.0) | (0.0, 0.2) |
| Tendonitis | 1 (0.0) | (0.0, 0.2) | 2 (0.1) | (0.0, 0.2) |
| Arthritis | 1 (0.0) | (0.0, 0.2) | 1 (0.0) | (0.0, 0.2) |
| Flank pain | 1 (0.0) | (0.0, 0.2) | 1 (0.0) | (0.0, 0.2) |
| Joint effusion | 2 (0.1) | (0.0, 0.2) | 0 | (0.0, 0.1) |
| Plantar fasciitis | 0 | (0.0, 0.1) | 2 (0.1) | (0.0, 0.2) |
| Bursitis | 1 (0.0) | (0.0, 0.2) | 0 | (0.0, 0.1) |
| Exostosis | 0 | (0.0, 0.1) | 1 (0.0) | (0.0, 0.2) |
| Limb discomfort | 1 (0.0) | (0.0, 0.2) | 0 | (0.0, 0.1) |
| Muscle twitching | 1 (0.0) | (0.0, 0.2) | 0 | (0.0, 0.1) |
| Muscular weakness | 1 (0.0) | (0.0, 0.2) | 0 | (0.0, 0.1) |
| Musculoskeletal discomfort | 1 (0.0) | (0.0, 0.2) | 0 | (0.0, 0.1) |
| Musculoskeletal stiffness | 0 | (0.0, 0.1) | 1 (0.0) | (0.0, 0.2) |
| Osteitis | 0 | (0.0, 0.1) | 1 (0.0) | (0.0, 0.2) |
| Osteopenia | 1 (0.0) | (0.0, 0.2) | 0 | (0.0, 0.1) |
| Pain in jaw | 1 (0.0) | (0.0, 0.2) | 0 | (0.0, 0.1) |
| Rotator cuff syndrome | 0 | (0.0, 0.1) | 1 (0.0) | (0.0, 0.2) |
| Tenosynovitis stenosans | 1 (0.0) | (0.0, 0.2) | 0 | (0.0, 0.1) |
| Torticollis | 1 (0.0) | (0.0, 0.2) | 0 | (0.0, 0.1) |
| NEOPLASMS BENIGN, MALIGNANT AND UNSPECIFIED (INCL CYSTS AND POLYPS) | 4 (0.1) | (0.0, 0.3) | 3 (0.1) | (0.0, 0.3) |
| Basal cell carcinoma | 1 (0.0) | (0.0, 0.2) | 1 (0.0) | (0.0, 0.2) |
| Adenocarcinoma gastric | 1 (0.0) | (0.0, 0.2) | 0 | (0.0, 0.1) |
| Breast cancer | 0 | (0.0, 0.1) | 1 (0.0) | (0.0, 0.2) |
| Seborrhoeic keratosis | 1 (0.0) | (0.0, 0.2) | 0 | (0.0, 0.1) |
| Uterine leiomyoma | 0 | (0.0, 0.1) | 1 (0.0) | (0.0, 0.2) |

TABLE 15-continued

Number (%) of Subjects Reporting at Least 1 Adverse Event From Dose 1 to 1 Month After Dose 2, by System Organ Class and Preferred Term-~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Vaginal neoplasm | 1 (0.0) | (0.0, 0.2) | 0 | (0.0, 0.1) |
| NERVOUS SYSTEM DISORDERS | 44 (1.3) | (1.0, 1.8) | 32 (1.0) | (0.7, 1.4) |
| Headache | 30 (0.9) | (0.6, 1.3) | 24 (0.7) | (0.5, 1.1) |
| Dizziness | 3 (0.1) | (0.0, 0.3) | 2 (0.1) | (0.0, 0.2) |
| Migraine | 3 (0.1) | (0.0, 0.3) | 1 (0.0) | (0.0, 0.2) |
| Paraesthesia | 3 (0.1) | (0.0, 0.3) | 1 (0.0) | (0.0, 0.2) |
| Syncope | 1 (0.0) | (0.0, 0.2) | 1 (0.0) | (0.0, 0.2) |
| Burning sensation | 0 | (0.0, 0.1) | 1 (0.0) | (0.0, 0.2) |
| Cervical radiculopathy | 1 (0.0) | (0.0, 0.2) | 0 | (0.0, 0.1) |
| Dysgeusia | 0 | (0.0, 0.1) | 1 (0.0) | (0.0, 0.2) |
| Hypoaesthesia | 0 | (0.0, 0.1) | 1 (0.0) | (0.0, 0.2) |
| Radiculopathy | 1 (0.0) | (0.0, 0.2) | 0 | (0.0, 0.1) |
| Sciatica | 1 (0.0) | (0.0, 0.2) | 0 | (0.0, 0.1) |
| Transient ischaemic attack | 1 (0.0) | (0.0, 0.2) | 0 | (0.0, 0.1) |
| Tremor | 1 (0.0) | (0.0, 0.2) | 0 | (0.0, 0.1) |
| PSYCHIATRIC DISORDERS | 13 (0.4) | (0.2, 0.7) | 13 (0.4) | (0.2, 0.7) |
| Anxiety | 4 (0.1) | (0.0, 0.3) | 4 (0.1) | (0.0, 0.3) |
| Depression | 2 (0.1) | (0.0, 0.2) | 2 (0.1) | (0.0, 0.2) |
| Anxiety disorder | 0 | (0.0, 0.1) | 2 (0.1) | (0.0, 0.2) |
| Irritability | 2 (0.1) | (0.0, 0.2) | 0 | (0.0, 0.1) |
| Mental status changes | 2 (0.1) | (0.0, 0.2) | 0 | (0.0, 0.1) |
| Bipolar-disorder | 0 | (0.0, 0.1) | 1 (0.0) | (0.0, 0.2) |
| Depressed mood | 0 | (0.0, 0.1) | 1 (0.0) | (0.0, 0.2) |
| Disorientation | 1 (0.0) | (0.0, 0.2) | 0 | (0.0, 0.1) |
| Gastrointestinal somatic symptom disorder | 0 | (0.0, 0.1) | 1 (0.0) | (0.0, 0.2) |
| Insomnia | 1 (0.0) | (0.0, 0.2) | 0 | (0.0, 0.1) |
| Mental disorder | 1 (0.0) | (0.0, 0.2) | 0 | (0.0, 0.1) |
| Mood swings | 0 | (0.0, 0.1) | 1 (0.0) | (0.0, 0.2) |
| Panic reaction | 0 | (0.0, 0.1) | 1 (0.0) | (0.0, 0.2) |
| Sleep disorder | 1 (0.0) | (0.0, 0.2) | 0 | (0.0, 0.1) |
| Suicidal ideation | 0 | (0.0, 0.1) | 1 (0.0) | (0.0, 0.2) |
| RENAL AND URINARY DISORDERS | 3 (0.1) | (0.0, 0.3) | 3 (0.1) | (0.0, 0.3) |
| Acute kidney injury | 1 (0.0) | (0.0, 0.2) | 0 | (0.0, 0.1) |
| Chronic kidney disease | 1 (0.0) | (0.0, 0.2) | 0 | (0.0, 0.1) |
| Dysuria | 1 (0.0) | (0.0, 0.2) | 0 | (0.0, 0.1) |
| Haematuria | 0 | (0.0, 0.1) | 1 (0.0) | (0.0, 0.2) |
| Nephrolithiasis | 0 | (0.0, 0.1) | 1 (0.0) | (0.0, 0.2) |
| Urinary retention | 0 | (0.0, 0.1) | 1 (0.0) | (0.0, 0.2) |
| REPRODUCTIVE SYSTEM AND BREAST DISORDERS | 4 (0.1) | (0.0, 0.3) | 2 (0.1) | (0.0, 0.2) |
| Dysmenorrhoea | 3 (0.1) | (0.0, 0.3) | 0 | (0.0, 0.1) |
| Cervical dysplasia | 1 (0.0) | (0.0, 0.2) | 0 | (0.0, 0.1) |
| Menorrhagia | 0 | (0.0, 0.1) | 1 (0.0) | (0.0, 0.2) |
| Prostatitis | 0 | (0.0, 0.1) | 1 (0.0) | (0.0, 0.2) |
| RESPIRATORY, THORACIC AND MEDIASTINAL DISORDERS | 21 (0.6) | (0.4, 1.0) | 26 (0.8) | (0.5, 1.2) |
| Oropharyngeal pain | 4 (0.1) | (0.0, 0.3) | 7 (0.2) | (0.1, 0.4) |
| Cough | 5 (0.2) | (0.0, 0.4) | 5 (0.2) | (0.0, 0.4) |
| Rhinitis allergic | 3 (0.1) | (0.0, 0.3) | 3 (0.1) | (0.0, 0.3) |
| Rhinorrhoea | 1 (0.0) | (0.0, 0.2) | 4 (0.1) | (0.0, 0.3) |
| Nasal congestion | 2 (0.1) | (0.0, 0.2) | 1 (0.0) | (0.0, 0.2) |
| Dyspnoea | 1 (0.0) | (0.0, 0.2) | 1 (0.0) | (0.0, 0.2) |
| Dyspnoea exertional | 1 (0.0) | (0.0, 0.2) | 1 (0.0) | (0.0, 0.2) |
| Upper-airway cough syndrome | 0 | (0.0, 0.1) | 2 (0.1) | (0.0, 0.2) |
| Acute respiratoly failure | 1 (0.0) | (0.0, 0.2) | 0 | (0.0, 0.1) |
| Allergic respiratory disease | 0 | (0.0, 0.1) | 1 (0.0) | (0.0, 0.2) |
| Asthma | 0 | (0.0, 0.1) | 1 (0.0) | (0.0, 0.2) |
| Bronchospasm | 1 (0.0) | (0.0, 0.2) | 0 | (0.0, 0.1) |
| Chronic obstructive pulmonary disease | 1 (0.0) | (0.0, 0.2) | 0 | (0.0, 0.1) |
| Productive cough | 0 | (0.0, 0.1) | 1 (0.0) | (0.0, 0.2) |
| Pulmonary embolism | 0 | (0.0, 0.1) | 1 (0.0) | (0.0, 0.2) |
| Sinus congestion | 0 | (0.0, 0.1) | 1 (0.0) | (0.0, 0.2) |
| Throat irritation | 1 (0.0) | (0.0, 0.2) | 0 | (0.0, 0.1) |
| SKIN AND SUBCUTANEOUS TISSUE DISORDERS | 32 (1.0) | (0.7, 1.4) | 19 (0.6) | (0.3, 0.9) |
| Dermatitis contact | 10 (0.3) | (0.1, 0.6) | 3 (0.1) | (0.0, 0.3) |
| Rash | 7 (0.2) | (0.1, 0.4) | 2 (0.1) | (0.0, 0.2) |
| Erythema | 3 (0.1) | (0.0, 0.3) | 1 (0.0) | (0.0, 0.2) |
| Urticaria | 2 (0.1) | (0.0, 0.2) | 2 (0.1) | (0.0, 0.2) |
| Dermatitis | 1 (0.0) | (0.0, 0.2) | 2 (0.1) | (0.0, 0.2) |

TABLE 15-continued

Number (%) of Subjects Reporting at Least 1 Adverse Event From Dose 1 to 1 Month After Dose 2, by System Organ Class and Preferred Term-~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Pruritus | 3 (0.1) | (0.0, 0.3) | 0 | (0.0, 0.1) |
| Hyperhidrosis | 0 | (0.0, 0.1) | 2 (0.1) | (0.0, 0.2) |
| Macule | 1 (0.0) | (0.0, 0.2) | 1 (0.0) | (0.0, 0.2) |
| Angioedema | 1 (0.0) | (0.0, 0.2) | 0 | (0.0, 0.1) |
| Dermatitis atopic | 0 | (0.0, 0.1) | 1 (0.0) | (0.0, 0.2) |
| Dermatitis bullous | 0 | (0.0, 0.1) | 1 (0.0) | (0.0, 0.2) |
| Drug eruption | 0 | (0.0, 0.1) | 1 (0.0) | (0.0, 0.2) |
| Ecchymosis | 0 | (0.0, 0.1) | 1 (0.0) | (0.0, 0.2) |
| Hangnail | 1 (0.0) | (0.0, 0.2) | 0 | (0.0, 0.1) |
| Papule | 1 (0.0) | (0.0, 0.2) | 0 | (0.0, 0.1) |
| Rash erythematous | 0 | (0.0, 0.1) | 1 (0.0) | (0.0, 0.2) |
| Rash maculo-papular | 0 | (0.0, 0.1) | 1 (0.0) | (0.0, 0.2) |
| Rosacea | 0 | (0.0, 0.1) | 1 (0.0) | (0.0, 0.2) |
| Skin discolouration | 1 (0.0) | (0.0, 0.2) | 0 | (0.0, 0.1) |
| Skin ulcer | 1 (0.0) | (0.0, 0.2) | 0 | (0.0, 0.1) |
| SURGICAL AND MEDICAL PROCEDURES | 5 (0.2) | (0.0, 0.4) | 4 (0.1) | (0.0, 0.3) |
| Dental care | 0 | (0.0, 0.1) | 1 (0.0) | (0.0, 0.2) |
| Dental operation | 0 | (0.0, 0.1) | 1 (0.0) | (0.0, 0.2) |
| Gingival operation | 1 (0.0) | (0.0, 0.2) | 0 | (0.0, 0.1) |
| Hip surgery | 1 (0.0) | (0.0, 0.2) | 0 | (0.0, 0.1) |
| Inguinal hernia repair | 1 (0.0) | (0.0, 0.2) | 0 | (0.0, 0.1) |
| Laryngeal operation | 0 | (0.0, 0.1) | 1 (0.0) | (0.0, 0.2) |
| Postoperative care | 1 (0.0) | (0.0, 0.2) | 0 | (0.0, 0.1) |
| Sclerotherapy | 1 (0.0) | (0.0, 0.2) | 0 | (0.0, 0.1) |
| Tooth extraction | 0 | (0.0, 0.1) | 1 (0.0) | (0.0, 0.2) |
| VASCULAR DISORDERS | 8 (0.2) | (0.1, 0.5) | 15 (0.5) | (0.3, 0.7) |
| Hypertension | 5 (0.2) | (0.0, 0.4) | 6 (0.2) | (0.1, 0.4) |
| Haematoma | 1 (0.0) | (0.0, 0.2) | 3 (0.1) | (0.0, 0.3) |
| Aortic aneurysm | 0 | (0.0, 0.1) | 1 (0.0) | (0.0, 0.2) |
| Deep vein thrombosis | 0 | (0.0, 0.1) | 1 (0.0) | (0.0, 0.2) |
| Essential hypertension | 1 (0.0) | (0.0, 0.2) | 0 | (0.0, 0.1) |
| Hypotension | 0 | (0.0, 0.1) | 1 (0.0) | (0.0, 0.2) |
| LYMPHOEDEMA | 0 | (0.0, 0.1) | 1 (0.0) | (0.0, 0.2) |
| Lymphorrhoea | 1 (0.0) | (0.0, 0.2) | 0 | (0.0, 0.1) |
| Orthostatic hypotension | 0 | (0.0, 0.1) | 1 (0.0) | (0.0, 0.2) |
| Raynaud's phenomenon | 0 | (0.0, 0.1) | 1 (0.0) | (0.0, 0.2) |

Note:
MedDRA (v23.0) coding dictionary applied.
[a]N = number of subjects in the specified group. This value is the denominator for the percentage calculations.
[b]n = Number of subjects reporting at least 1 occurrence of the specified event. For "any event", n = number of subjects reporting at least 1 occurrence of any event.
[c]Exact 2-sided CI based on the Clopper and Pearson method.

All Participants—Phase 2/3

For all 36,855 participants up to the data cutoff date, there were a total of 121 (0.7%) participants in the BNT162b2 group and 51 (0.3%) participants in the placebo group with at least 1 uncoded term. As a result, uncoded terms are also present in other AE tables summarized by SOC and PT.

From Dose 1 to the data cutoff date, the number of overall participants who reported at least 1 AE was higher in the BNT162b2 group (3086 [16.8%]) as compared with the placebo group (1462 [7.9%]). Most AEs reported in all participants from Dose 1 to the data cutoff date were reactogenicity and in the SOCs of general disorders and administration site conditions (1941 [10.5%] in the BNT162b2 group and 438 [2.4%] in the placebo group), musculoskeletal and connective tissue disorders (742 [4.0%] in the BNT162b2 group and 227 [1.2%] in the placebo group), and nervous system disorders (567 [3.1%] in the BNT162b2 group and 251 [1.4%] in the placebo group).

In the BNT162b2 group, the most frequently reported AEs by PT were injection site pain (1222 [6.6%]), pyrexia (504 [2.7%]), fatigue (481 [2.6%]), headache (470 [2.6%]), chills (458 [2.5%]), and myalgia (454 [2.5%]). The majority of these PTs were reported in the younger age group: injection site pain (787 [7.4%]), pyrexia (351 [3.3%]), fatigue (309 [2.9%]), headache (303 [2.9%]), chills (316 [3.0%]), and myalgia (304 [2.9%]). Beyond the first 6610 participants, events related to reactogenicity are no longer reported using an e-diary but are instead reported as AEs. Therefore, a post hoc analysis was conducted to evaluate if the imbalance in AEs observed in the overall participants from Dose 1 to the data cutoff date but not observed in the first 6610 participants from Dose 1 to 1 month after Dose 2 was attributed to reactogenicity events. The analysis examined the AEs reported within 7 days after each dose, which represented the reactogenicity reporting period. The time period was chosen because many AEs were reported in the SOCs of general disorders and administration site conditions, musculoskeletal and connective tissue disorders, and nervous system disorders, which contains AEs consistent with reactogenicity events, and could only be attributed to reactogenicity if they occurred during this time period as opposed to occurring up to a month from each dose.

From Dose 1 to 7 days after Dose 1 (as of the data cutoff date), 1494 (8.1%) participants reported at least 1 AE in the BNT162b2 group, which represented approximately half of the total number of the 3086 [16.8%] participants who reported at least 1 AE up to the data cutoff date. In the placebo group, 555 (3.0%) participants reported at least 1 AE from Dose 1 to 7 days after Dose 1, compared with the total number of 1462 (7.9%) participants who reported at least 1 AE up to the data cutoff date.

From Dose 2 to 7 days after Dose 2 (as of the data cutoff date), 1165 (6.3%) participants reported at least 1 AE in the BNT162b2 group, which represented approximately 38% of the total number of the 3086 [16.8%] participants who reported at least 1 AE up to the data cutoff date. From Dose 2 to 7 days after Dose 2, fewer participants reported AEs in the placebo group than the BNT162b2 group. In the placebo group, 268 (1.5%) participants reported at least 1 AE from Dose 2 to 7 days after Dose 2, compared with the total number of 1462 (7.9%) participants who reported at least 1 AE up to the data cutoff date.

AEs were reported from Dose 1 to 7 days after Dose 1 in the SOC of general disorders and administration site conditions (1127 [6.1%] in the BNT162b2 group and 251 [1.4%] in the placebo group), which represented more than half of the total number of participants reporting at least 1 AE in this SOC (1941 [10.5%] in the BNT162b2 group and 438 [2.4%] in the placebo group) up to the data cutoff date. Musculoskeletal and connective tissue disorders (252 [1.4%] in the BNT162b2 group and 76 [0.4%] in the placebo group) and nervous system disorders (220 [1.2%] in the BNT162b2 group and 115 [0.6%] in the placebo group) were also commonly reported, representing a smaller proportion of the total number of participants reporting AEs for these SOCs. In the BNT162b2 group, the most frequently reported AEs from Dose 1 to 7 days after Dose 1 by PT were injection site pain (881 [4.8%]), fatigue (231 [1.3%]), headache (181 [1.0%]), myalgia (147 [0.8%]), pyrexia (110 [0.6%]), and chills (100 [0.5%]). The majority of these PTs were reported in the younger age group: injection site pain (566 [5.3%]), fatigue (153 [1.4%]), headache (118 [1.1%]), myalgia (99 [0.9%]), pyrexia (82 [0.8%]), and chills (75 [0.7%]). Injection site pain reported from Dose 1 to 7 days after Dose 1 (881 [4.8%]) represented a large proportion of the total participants who reported AEs for this PT (1222 [6.6%]).

AEs were reported from Dose 2 to 7 days after Dose 2 in the SOCs of general disorders and administration site conditions (828 [4.5%] in the BNT162b2 group and 93 [0.5%] in the placebo group), musculoskeletal and connective tissue disorders (377 [2.0%] in the BNT162b2 group and 38 [0.2%] in the placebo group), and nervous system disorders (294 [1.6%] in the BNT162b2 group and 40 [0.2%] in the placebo group).

Musculoskeletal and connective tissue disorders and nervous system disorders reported from Dose 2 to 7 days after Dose 2 represented at least half of the total number of participants who reported at least 1 AE in these SOCs.

In the BNT162b2 group, the most frequently reported AEs from Dose 2 to 7 days after Dose 2 by PT were pyrexia (375 [2.0%]), chills (327 [1.8%]), injection site pain (313 [1.7%]), myalgia (282 [1.5%]), headache (258 [1.4%]), and fatigue (227 [1.2%]). The majority of these PTs were reported in the younger age group: pyrexia (251 [2.4%]), chills (216 [2.0%]), myalgia (185 [1.7%]), injection site pain (183 [1.7%]), headache (154 [1.5%]), and fatigue (134 [1.3%]). AEs for most of these PTs reported from Dose 2 to 7 days after Dose 2 represented at least half of the total number of participants who reported an AE for these PTs: pyrexia (504 [2.7%]), chills (458 [2.5%]), myalgia (454 [2.5%]), headache (470 [2.6%]), and fatigue (481 [2.6%]).

Overall, AEs reported from Dose 1 to 7 days after Dose 1 and from Dose 2 to 7 days after Dose 2 were largely attributable to reactogenicity events. This observation provides a reasonable explanation for the greater rates of AEs observed overall in the BNT162b2 group compared with the placebo group.

From Dose 1 to the data cutoff date, there were a total of 44 (0.2%) participants in the BNT162b2 group who reported an AE of lymphadenopathy, inclusive of those reported in the first 6610 participants (10 [0.3%]). Up to the data cutoff date, 34 additional participants in the BNT162b2 group and 4 additional participants in the placebo group reported an AE of lymphadenopathy. In the BNT162b2 group, lymphadenopathy was reported in 34 (0.3%) participants in the younger age group and 10 (0.1%) participants in the older age group compared to 4 (0.0%) in the placebo group (3 in the younger age group and 1 in the older age group). Lymphadenopathy occurred predominantly in the arm and neck region with most events reported in left axillary lymph node(s). Most lymphadenopathy events occurred after Dose 2, ≤3 days after Dose 1 or Dose 2, were Grade 1 or Grade 2 in severity, and 32 of 48 events were resolved by the data cutoff date. In 1 participant in the younger BNT162b2 age group, Grade 1 lymphadenopathy (swollen right axillary lymph nodes) was an immediate AE, which occurred after Dose 1 and was continuing at the data cutoff date.

In the younger age group, there was 1 participant each with an AE of suspected COVID-19 in the BNT162b2 (SAE) and placebo groups.

In the BNT162b2 group, 6 participants reported immunization reactions (vaccine reaction or systemic vaccine reaction [no additional information currently available at the time of this report]) assessed as related to study intervention. Three participants reported drug hypersensitivity in the BNT162b2 group in addition to the drug hypersensitivity in a participant in the placebo group. Drug hypersensitivity (allergic reaction) was assessed as related in 1 participant in the BNT162b2 group and drug hypersensitivity (drug allergy or allergic reaction to dipyrone) was assessed as unrelated to study intervention in 2 participants in the BNT162b2 group.

Nineteen (0.1%) participants in the BNT162b2 group (14 in the younger age group and 5 in the older age group reported at least 1 vaccine complication (most were descriptive of reactogenicity events) compared to none in the placebo group. All were assessed as related to the study intervention and included: post vaccination myalgia, fever, body aches, headache, chills, nausea, adverse reaction, arthralgia, fatigue, aches, muscle aches, malaise, and sore left shoulder. Most events were Grade 1, started within 3 days of vaccination, and lasted from 1 to 3 days.

In addition to the 4 participants with appendicitis (including 1 appendicitis perforated in the placebo group) in the first 6610 participants, there were an additional 3 participants with appendicitis (including 1 participant with appendicitis perforated) reported in the BNT162b2 group from Dose 1 through the data cutoff date for all participants. Therefore, a total of 6 participants in the BNT162b2 group reported appendicitis (including 1 appendicitis perforated) with 4 in the younger age group and 2 in the older age group, and 1 participant in the placebo group (older age group)

reported appendicitis (perforated). All events were severe or life-threatening and none were assessed as related to study intervention.

Related Adverse Events by System Organ Class and Preferred Term—Phase 2/3 First 6610 Participants—Phase 2/3

From Dose 1 to 1 month after Dose 2, 135 (4.1%) participants reported at least 1 AE assessed as related by the investigator in the BNT162b2 group, and 68 (2.1%) participants reported at least 1 related AE in the placebo group. Most related AEs were reactogenicity events and in the SOC of general disorders and administration site conditions (69 [2.1%] in the BNT162b2 group and 40 [1.2%] in the placebo group). The AEs of lymphadenopathy reported in 8 of 10 participants were assessed by the investigator as related to study intervention.

All Participants—Phase 2/3

From Dose 1 to the data cutoff date, 2303 (12.5%) participants in the BNT162b2 group and 593 (3.2%) participants in the placebo group reported at least 1 AE assessed as related by the investigator, inclusive of the related AEs for the first 6610 participants. Most related AEs were reactogenicity events and in the SOC of general disorders and administration site conditions (1869 [10.1%] in the BNT162b2 group and 365 [2.0%] in the placebo group).

The AEs of lymphadenopathy reported in 30 of 44 participants in the BNT162b2 group and 2 of 4 participants in the placebo group were assessed by the investigator as related to study intervention.

In the BNT162b2 group, based on all information currently available at the time of this report:

Six participants reported immunization reaction (vaccine reaction or systemic vaccine reaction) assessed as related to the study intervention. In most participants, immunization reactions occurred 1 or 2 days after Dose 2, lasted 2 or 3 days (1 participant was recovering at data cutoff date), and were Grade 1 or Grade 2 in severity. In 1 participant, immunization reactions (systemic vaccine reactions) occurred 2 days after Dose 1 (Grade 1) and lasted 2 days, and 1 day after Dose 2 (Grade 3) and lasted 4 days.

One participant reported an AE each of drug hypersensitivity (allergic reaction), urticaria (allergic reaction), and headache, which were all Grade 2 and assessed bythe investigator as related to study intervention. The AEs of drug hypersensitivity and urticaria both occurred within 1 day after Dose 1 and resolved that same day. The AE of headache occurred the following day after vaccination and lasted 4 days.

Immediate Adverse Events—Phase 2/3

First 6610 Participants—Phase 2/3

After Dose 1, ≤0.3% of participants reported immediate AEs. Most immediate AEs were in the SOC of general disorders and administration site conditions and were events related to injection site reactions (injection site pain, injection site erythema and injection site swelling).

After Dose 2, 0.1% of participants in each group reported immediate AEs. Most immediate AEs were in the SOC of general disorders and administration site conditions and were events related to injection site reactions (injection site pain, injection site hyperaesthesia, and injection site pruritus).

After either dose of BNT162b2, no participant reported an immediate allergic reaction to the vaccine.

All Participants—Phase 2/3

After Dose 1, 0.3% of participants in each group reported immediate AEs. Most immediate AEs were in the SOC of general disorders and administration site conditions and most events were related to injection site reactions with injection site pain most frequently reported (40 [0.2%] participants in the BNT162b2 group and 27 (0.1%) participants in the placebo group). One participant had an immediate AE of lymphadenopathy after Dose 1. All other immediate AEs were reported by 3 participants each in the BNT162b2 group.

After Dose 2, 0.1% of participants in each group reported immediate AEs. Most immediate AEs were in the SOC of general disorders and administration site conditions and most events were injection site reactions with injection site pain most frequently reported (10 [0.1%] participants in the BNT162b2 group and 7 [0.0%] participants in the placebo group). All other immediate AEs were reported by 2 participants each. After either dose of BNT162b2, no participant reported an immediate allergic reaction to the vaccine.

Severe or Life-Threatening Adverse Events—Phase 2/3

First 6610 Participants—Phase 2/3

From Dose 1 to 1 month after Dose 2, severe AEs reported were reported by 35 (1.1%) participants in the BNT162b2 group and 19 (0.6%) in the placebo group.

Four (0.1%) participants in the BNT162b2 group and 7 (0.2%) participants in the placebo group had at least 1 life-threatening AE from Dose 1 to 1 month after Dose 2.

None of these events were assessed by the investigator as related to study intervention.

In the BNT162b2 group:

One participant from Phase 2 had a severe event of gastric adenocarcinoma (SAE), which is discussed in a previous section.

Two participants had severe events of appendicitis: 1 event began 9 days after Dose 1 and the other event began 15 days after Dose 2 (SAEs) which were assessed by the investigator as not related to study intervention.

One participant had 2 life-threatening AEs of appendicitis and peritoneal abscess 7 days after Dose 1 (both SAEs); both events were assessed by the investigator as not related to study intervention.

One participant had 8 severe events: anemia, cardiac failure congestive, abdominal adhesions, sepsis, hypokalaemia, mental status changes, acute kidney injury, and acute respiratory failure (all SAEs). None of the events were assessed by the investigator as related to study intervention.

All Participants—Phase 2/3

Severe AEs reported up to the data cutoff date, inclusive of those discussed for the first 6610 participants, were reported by 142 [0.8%] participants in the BNT162b2 group and 70 (0.4%) in the placebo group. Additional events included:

Two participants in the BNT162b2 group had a severe event each of appendicitis: 1 event began 17 days after Dose 1 and the other event began 11 days after Dose 1 (SAE) which were assessed by the investigator as not related to study intervention.

One participant in the BNT162b2 group had a severe event of perforated appendicitis on the same day after Dose 1 (SAE) which was assessed by the investigator as not related to study intervention.

Nine participants (0.0%) in the BNT162b2 group and 12 (0.1%) participants in the placebo group had at least 1 life-threatening AE from Dose 1 to the data cutoff date, inclusive of those discussed for the first 6610 participants. None of these events were assessed by the investigator as related to study intervention.

Deaths, Serious Adverse Events, Safety-Related Participant Withdrawals, and Other Significant Adverse Events—Phase 2/3

Deaths—Phase 2/3

There were 3 Phase 3 participants (1 in the BNT162b2 group and 2 in the placebo group) who died through the data cutoff date of 6 Oct. 2020. None of these deaths were among the first 6610 participants (Table 14) and none were assessed by the investigator as related to study intervention.

One participant in the older BNT162b2 group experienced a Grade 4 SAE of arteriosclerosis 4 days after Dose 1 and died 15 days after Dose 1.

One participant in the younger placebo group experienced a Grade 4 SAE of unevaluable event (unknown of unknown origin [no additional information currently available at the time of this report) 8 days after Dose 1 and died the same day. One participant in the older placebo group experienced a Grade 4 SAE of hemorrhagic stroke 15 days after Dose 2 and died 35 days after Dose 2.

Death Narratives

Narratives for the participants who died through the data cutoff date (6 Oct. 2020) were provided.

Serious Adverse Events—Phase 2/3

First 6610 Participants—Phase 2/3

From Dose 1 to 1 month after Dose 2, the number of participants who reported at least 1 SAE was similar in the BNT162b2 group (18 (0.5%]) and in the placebo group (17 [0.5%]) (Table 16). None of the SAEs were assessed by the investigator as related to study intervention. Most PTs for SAEs were reported by only 1 participant (3 participants reported an SAE of appendicitis).

From Dose 1 to 1 month after Dose 2, the number of participants who reported at least 1 SAE in the younger and older age groups was similar.

In the BNT162b2 group:

Two participants had an SAE each of appendicitis: 1 event began 9 days after Dose 1 and the other event began 15 days after Dose 2.

One participant had an SAE each of appendicitis and peritoneal abscess 7 days after Dose 1, which was considered life-threatening. Both events lasted for 17 days.

One participant had 8 SAEs 17 days after Dose 1: anemia, cardiac failure congestive, abdominal adhesions, sepsis, hypokalaemia, mental status changes, acute kidney injury, and acute respiratory failure (all were severe). The SAEs of abdominal adhesions and acute respiratory failure lasted for 2 and 14 days, respectively. All other SAEs lasted for 19 days.

One participant had an SAE of anaphylactic reaction 9 days after Dose 2 as a result of a bee sting which was considered life threatening. The event resolved on the same day.

In the placebo group, 1 participant had an SAE each of appendicitis perforated and peritonitis 13 and 15 days after Dose 2, respectively (both severe). Both events lasted 4 and 5 days, respectively.

From 1 month after Dose 2 to the data cutoff date, no additional SAEs were reported for these first 6610 participants.

TABLE 16

Number (%) of Subjects Reporting at Least 1 Serious Adverse Event From Dose 1 to 1 Month After Dose 2, by System Organ Class and Preferred Term--~6000 Subjects for Phase 2/3 Analysis-Safety Population

| | Vaccine Group (as Administered) | | | |
|---|---|---|---|---|
| System Organ Class | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Any event | 18 (0.5) | (0.3, 0.9) | 17 (0.5) | (0.3, 0.8) |
| BLOOD AND LYMPHATIC SYSTEM DISORDERS | 1 (0.0) | (0.0, 0.2) | 0 | (0.0, 0.1) |
| Anaemia | 1 (0.0) | (0.0, 0.2) | 0 | (0.0, 0.1) |
| CARDIAC DISORDERS | 3 (0.1) | (0.0, 0.3) | 3 (0.1) | (0.0, 0.3) |
| Acute coronary syndrome | 0 | (0.0, 0.1) | 1 (0.0) | (0.0, 0.2) |
| Atrial fibrillation | 0 | (0.0, 0.1) | 1 (0.0) | (0.0, 0.2) |
| Cardiac failure congestive | 1 (0.0) | (0.0, 0.2) | 0 | (0.0, 0.1) |
| Coronary artery disease | 1 (0.0) | (0.0, 0.2) | 0 | (0.0, 0.1) |
| Coronary artery dissection | 1 (0.0) | (0.0, 0.2) | 0 | (0.0, 0.1) |
| Coronary artery occlusion | 0 | (0.0, 0.1) | 1 (0.0) | (0.0, 0.2) |
| EAR AND LABYRINTH DISORDERS | 1 (0.0) | (0.0, 0.2) | 0 | (0.0, 0.1) |
| Vertigo | 1 (0.0) | (0.0, 0.2) | 0 | (0.0, 0.1) |
| EYE DISORDERS | 1 (0.0) | (0.0, 0.2) | 0 | (0.0, 0.1) |
| Diplopia | 1 (0.0) | (0.0, 0.2) | 0 | (0.0, 0.1) |
| GASTROINTESTINAL DISORDERS | 3 (0.1) | (0.0, 0.3) | 3 (0.1) | (0.0, 0.3) |
| Abdominal adhesions | 1 (0.0) | (0.0, 0.2) | 0 | (0.0, 0.1) |
| Colitis | 1 (0.0) | (0.0, 0.2) | 0 | (0.0, 0.1) |
| Diarrhoea | 1 (0.0) | (0.0, 0.2) | 0 | (0.0, 0.1) |
| Diverticular perforation | 0 | (0.0, 0.1) | 1 (0.0) | (0.0, 0.2) |
| Intestinal obstruction | 0 | (0.0, 0.1) | 1 (0.0) | (0.0, 0.2) |
| Small intestinal obstruction | 0 | (0.0, 0.1) | 1 (0.0) | (0.0, 0.2) |
| GENERAL DISORDERS AND ADMINISTRATION SITE CONDITIONS | 2 (0.1) | (0.0, 0.2) | 1 (0.0) | (0.0, 0.2) |
| Chest pain | 0 | (0.0, 0.1) | 1 (0.0) | (0.0, 0.2) |
| Non-cardiac chest pain | 1 (0.0) | (0.0, 0.2) | 0 | (0.0, 0.1) |
| Unevaluable event | 0 | (0.0, 0.1) | 1 (0.0) | (0.0, 0.2) |
| Vascular stent occlusion | 1 (0.0) | (0.0, 0.2) | 0 | (0.0, 0.1) |
| HEPATOBILIARY DISORDERS | 2 (0.1) | (0.0, 0.2) | 1 (0.0) | (0.0, 0.2) |
| Cholelithiasis | 2 (0.1) | (0.0, 0.2) | 0 | (0.0, 0.1) |
| Cholecystitis acute | 0 | (0.0, 0.1) | 1 (0.0) | (0.0, 0.2) |
| IMMUNE SYSTEM DISORDERS | 1 (0.0) | (0.0, 0.2) | 0 | (0.0, 0.1) |
| Anaphylactic reaction | 1 (0.0) | (0.0, 0.2) | 0 | (0.0, 0.1) |

TABLE 16-continued

Number (%) of Subjects Reporting at Least 1 Serious Adverse Event From Dose 1 to 1 Month After Dose 2, by System Organ Class and Preferred Term--~6000 Subjects for Phase 2/3 Analysis-Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| INFECTIONS AND INFESTATIONS | 4 (0.1) | (0.0, 0.3) | 3 (0.1) | (0.0, 0.3) |
| Appendicitis | 3 (0.1) | (0.0, 0.3) | 0 | (0.0, 0.1) |
| Appendicitis perforated | 0 | (0.0, 0.1) | 1 (0.0) | (0.0, 0.2) |
| Peritoneal abscess | 1 (0.0) | (0.0, 0.2) | 0 | (0.0, 0.1) |
| Peritonitis | 0 | (0.0, 0.1) | 1 (0.0) | (0.0, 0.2) |
| Pneumonia | 0 | (0.0, 0.1) | 1 (0.0) | (0.0, 0.2) |
| Sepsis | 1 (0.0) | (0.0, 0.2) | 0 | (0.0, 0.1) |
| Urinary tract infection | 0 | (0.0, 0.1) | 1 (0.0) | (0.0, 0.2) |
| INJURY, POISONING AND PROCEDURAL COMPLICATIONS | 0 | (0.0, 0.1) | 2 (0.1) | (0.0, 0.2) |
| Forearm fracture | 0 | (0.0, 0.1) | 1 (0.0) | (0.0, 0.2) |
| Skin laceration | 0 | (0.0, 0.1) | 1 (0.0) | (0.0, 0.2) |
| INVESTIGATIONS | 1 (0.0) | (0.0, 0.2) | 0 | (0.0, 0.1) |
| Cardiac stress test abnormal | 1(0.0) | (0.0, 0.2) | 0 | (0.0, 0.1) |
| METABOLISM AND NUTRITION DISORDERS | 1 (0.0) | (0.0, 0.2) | 0 | (0.0, 0.1) |
| Hypokalaemia | 1 (0.0) | (0.0, 0.2) | 0 | (0.0, 0.1) |
| NEOPLASMS BENIGN, MALIGNANT AND UNSPECIFIED (INCL CYSTS AND POLYPS) | 2 (0.1) | (0.0, 0.2) | 1 (0.0) | (0.0, 0.2) |
| Adenocarcinoma gastric | 1 (0.0) | (0.0, 0.2) | 0 | (0.0, 0.1) |
| Breast cancer | 0 | (0.0, 0.1) | 1 (0.0) | (0.0, 0.2) |
| Vaginal neoplasm | 1 (0.0) | (0.0, 0.2) | 0 | (0.0, 0.1) |
| NERVOUS SYSTEM DISORDERS | 0 | (0.0, 0.1) | 1 (0.0) | (0.0, 0.2) |
| Syncope | 0 | (0.0, 0.1) | 1 (0.0) | (0.0, 0.2) |
| PSYCHIATRIC DISORDERS | 2 (0.1) | (0.0, 0.2) | 2 (0.1) | (0.0, 0.2) |
| Bipolar disorder | 0 | (0.0, 0.1) | 1 (0.0) | (0.0, 0.2) |
| Mental disorder | 1 (0.0) | (0.0, 0.2) | 0 | (0.0, 0.1) |
| Mental status changes | 1 (0.0) | (0.0, 0.2) | 0 | (0.0, 0.1) |
| Suicidal ideation | 0 | (0.0, 0.1) | 1 (0.0) | (0.0, 0.2) |
| RENAL AND URINARY DISORDERS | 1 (0.0) | (0.0, 0.2) | 0 | (0.0, 0.1) |
| Acute kidney injury | 1 (0.0) | (0.0, 0.2) | 0 | (0.0, 0.1) |
| RESPIRATORY, THORACIC AND MEDIASTINAL DISORDERS | 1 (0.0) | (0.0, 0.2) | 0 | (0.0, 0.1) |
| Acute respiratory failure | 1 (0.0) | (0.0, 0.2) | 0 | (0.0, 0.1) |
| VASCULAR DISORDERS | 0 | (0.0, 0.1) | 2 (0.1) | (0.0, 0.2) |
| Deep vein thrombosis | 0 | (0.0, 0.1) | 1 (0.0) | (0.0, 0.2) |
| Orthostatic hypotension | 0 | (0.0, 0.1) | 1 (0.0) | (0.0, 0.2) |

Note:
MedDRA (v23.0) coding dictionary applied.
[a]N = number of subjects in the specified group. This value is the denominator for the percentage calculations.
[b]n = Number of subjects reporting at least 1 occurrence of the specified event. For "any event", n = number of subjects reporting at least 1 occurrence of any event.
[c]Exact 2-sided CI based on the Clopper and Pearson method.

All Participants—Phase 2/3

From Dose 1 to the data cutoff date, inclusive of those discussed for the first 6610 participants, the number of participants who reported at least 1 SAE was similar in the BNT162b2 group (63 [0.3%]) and in the placebo group (49 [0.3%]) (Table 17). Additional events included:

In the BNT162b2 group, there were 2 participants in the younger age group with an SAE each assessed by the investigator as related to study intervention:

One participant had an SAE of lymphadenopathy (right axilla) 13 days after Dose 1, which was not resolved at the time of the data cutoff. The participant was a 48-year-old woman with a relevant medical history of eczema and topical crisaborole use who was administered BNT162b2 vaccine in the left deltoid and had right axillary pain and lymphadenopathy. She had no injuries to the right arm, no fever, and no history of a similar incident. Her WBC was normal with a normal lymphocyte count and a right axilla ultrasound showed 4 enlarged lymph nodes (largest 2.5×1.1×2.4 cm). A biopsy was performed and was reported to be normal and without markers for lymphoma or other cancer. A follow-up visit with oncology (and possible repeat ultrasound) was planned for 3 months time.

One participant had an SAE of shoulder injury related to vaccine administration (SIRVA, erroneously administered into or near the shoulder joint capsule) after Dose 2, which was recovering at the time of the data cutoff.

From Dose 1 to the data cutoff date, a total of 6 participants in the BNT162b2 group reported an SAE of appendicitis. Three of these SAEs of appendicitis occurred in the first 6610 participants. The 3 additional SAEs of appendicitis are described below along with other specified SAEs that were assessed as not related to study intervention in the BNT162b2 group:

Two participants had an SAE each of appendicitis: 1 event began 17 days after Dose 1 which lasted for 3 days (younger age group), and the other event began 11 days after Dose 1 which lasted 5 days (older age group).

One participant in the older age group had an SAE of appendicitis perforated on the same day after Dose 1, which was resolving at the time of the data cutoff.

One participant in the younger age group had an SAE of suspected COVID-19 on the same day after Dose 2, which lasted for 6 days. The nasal swab result was negative.

TABLE 17

Number (%) of Subjects Reporting at Least 1 Serious Adverse Event From Dose 1 to Data Cutoff Date (06OCT2020), by System Organ Class and Preferred Term - Phase 2/3 (All Participants) - Safety Population

| System Organ Class | Vaccine Group (as Administered) | | | |
|---|---|---|---|---|
| | BNT162b2 (30 μg) ($N^a$ = 18419) | | Placebo ($N^a$ = 18436) | |
| Preferred Term | $n^b$ (%) | (95% $CI^c$) | $n^b$ (%) | (95% $CI^c$) |
| Any event | 63 (0.3) | (0.3, 0.4) | 49 (0.3) | (0.2, 0.4) |
| BLOOD AND LYMPHATIC SYSTEM DISORDERS | 2 (0.0) | (0.0, 0.0) | 2 (0.0) | (0.0, 0.0) |
| Anaemia | 1 (0.0) | (0.0, 0.0) | 0 | (0.0, 0.0) |
| Leukocytosis | 0 | (0.0, 0.0) | 1 (0.0) | (0.0, 0.0) |
| Lymphadenopathy | 1 (0.0) | (0.0, 0.0) | 0 | (0.0, 0.0) |
| Neutropenia | 0 | (0.0, 0.0) | 1 (0.0) | (0.0, 0.0) |
| Thrombocytosis | 0 | (0.0, 0.0) | 1 (0.0) | (0.0, 0.0) |
| CARDIAC DISORDERS | 10 (0.1) | (0.0, 0.1) | 6 (0.0) | (0.0, 0.1) |
| Cardiac failure congestive | 2 (0.0) | (0.0, 0.0) | 1 (0.0) | (0.0, 0.0) |
| Acute coronary syndrome | 1 (0.0) | (0.0, 0.0) | 1 (0.0) | (0.0, 0.0) |
| Atrial fibrillation | 1 (0.0) | (0.0, 0.0) | 1 (0.0) | (0.0, 0.0) |
| Acute myocardial infarction | 1 (0.0) | (0.0, 0.0) | 0 | (0.0, 0.0) |
| Angina pectoris | 1 (0.0) | (0.0, 0.0) | 0 | (0.0, 0.0) |
| Arrhythmia | 0 | (0.0, 0.0) | 1 (0.0) | (0.0, 0.0) |
| Arrhythmia supraventricular | 1 (0.0) | (0.0, 0.0) | 0 | (0.0, 0.0) |
| Arteriospasm coronary | 0 | (0.0, 0.0) | 1 (0.0) | (0.0, 0.0) |
| Coronary artery disease | 1 (0.0) | (0.0, 0.0) | 0 | (0.0, 0.0) |
| Coronary artery dissection | 1 (0.0) | (0.0, 0.0) | 0 | (0.0, 0.0) |
| Coronary artery occlusion | 0 | (0.0, 0.0) | 1 (0.0) | (0.0, 0.0) |
| Myocardial infarction | 1 (0.0) | (0.0, 0.0) | 0 | (0.0, 0.0) |
| EAR AND LABYRINTH DISORDERS | 1 (0.0) | (0.0, 0.0) | 0 | (0.0, 0.0) |
| Vertigo | 1 (0.0) | (0.0, 0.0) | 0 | (0.0, 0.0) |
| EYE DISORDERS | 1 (0.0) | (0.0, 0.0) | 1 (0.0) | (0.0, 0.0) |
| Diplopia | 1 (0.0) | (0.0, 0.0) | 0 | (0.0, 0.0) |
| Retinal artery occlusion | 0 | (0.0, 0.0) | 1 (0.0) | (0.0, 0.0) |
| GASTROINTESTINAL DISORDERS | 7 (0.0) | (0.0, 0.1) | 5 (0.0) | (0.0, 0.1) |
| Small intestinal obstruction | 1 (0.0) | (0.0, 0.0) | 1 (0.0) | (0.0, 0.0) |
| Abdominal adhesions | 1 (0.0) | (0.0, 0.0) | 0 | (0.0, 0.0) |
| Colitis | 1 (0.0) | (0.0, 0.0) | 0 | (0.0, 0.0) |
| Diarrhoea | 1 (0.0) | (0.0, 0.0) | 0 | (0.0, 0.0) |
| Diverticular perforation | 0 | (0.0, 0.0) | 1 (0.0) | (0.0, 0.0) |
| Gastrointestinal haemorrhage | 1 (0.0) | (0.0, 0.0) | 0 | (0.0, 0.0) |
| Intestinal obstruction | 0 | (0.0, 0.0) | 1 (0.0) | (0.0, 0.0) |
| Obstructive pancreatitis | 1 (0.0) | (0.0, 0.0) | 0 | (0.0, 0.0) |
| Oesophageal food impaction | 0 | (0.0, 0.0) | 1 (0.0) | (0.0, 0.0) |
| Pancreatitis | 1 (0.0) | (0.0, 0.0) | 0 | (0.0, 0.0) |
| Salivary gland calculus | 0 | (0.0, 0.0) | 1 (0.0) | (0.0, 0.0) |
| GENERAL DISORDERS AND ADMINISTRATION SITE CONDITIONS | 3 (0.0) | (0.0, 0.0) | 3 (0.0) | (0.0, 0.0) |
| Unevaluable event | 0 | (0.0, 0.0) | 2 (0.0) | (0.0, 0.0) |
| Chest pain | 0 | (0.0, 0.0) | 1 (0.0) | (0.0, 0.0) |
| Influenza like illness | 0 | (0.0, 0.0) | 1 (0.0) | (0.0, 0.0) |
| Non-cardiac chest pain | 1 (0.0) | (0.0, 0.0) | 0 | (0.0, 0.0) |
| Shoulder injury related to vaccine administration | 1 (0.0) | (0.0, 0.0) | 0 | (0.0, 0.0) |
| Vascular stent occlusion | 1 (0.0) | (0.0, 0.0) | 0 | (0.0, 0.0) |
| HEPATOBILIARY DISORDERS | 3 (0.0) | (0.0, 0.0) | 2 (0.0) | (0.0, 0.0) |
| Cholecystitis acute | 0 | (0.0, 0.0) | 2 (0.0) | (0.0, 0.0) |
| Cholelithiasis | 2 (0.0) | (0.0, 0.0) | 0 | (0.0, 0.0) |
| Bile duct stone | 1 (0.0) | (0.0, 0.0) | 0 | (0.0, 0.0) |
| IMMUNE SYSTEM DISORDERS | 1 (0.0) | (0.0, 0.0) | 0 | (0.0, 0.0) |
| Anaphylactic reaction | 1 (0.0) | (0.0, 0.0) | 0 | (0.0, 0.0) |
| INFECTIONS AND INFESTATIONS | 15 (0.1) | (0.0, 0.1) | 9 (0.0) | (0.0, 0.1) |
| Appendicitis | 5 (0.0) | (0.0, 0.1) | 0 | (0.0, 0.0) |
| Pneumonia | 1 (0.0) | (0.0, 0.0) | 4 (0.0) | (0.0, 0.1) |
| Appendicitis perforated | 1 (0.0) | (0.0, 0.0) | 1 (0.0) | (0.0, 0.0) |
| Cellulitis | 1 (0.0) | (0.0, 0.0) | 1 (0.0) | (0.0, 0.0) |
| Diverticulitis | 2 (0.0) | (0.0, 0.0) | 0 | (0.0, 0.0) |
| Pyelonephritis | 2 (0.0) | (0.0, 0.0) | 0 | (0.0, 0.0) |
| Osteomyelitis | 0 | (0.0, 0.0) | 1 (0.0) | (0.0, 0.0) |
| Peritoneal abscess | 1 (0.0) | (0.0, 0.0) | 0 | (0.0, 0.0) |
| Peritonitis | 0 | (0.0, 0.0) | 1 (0.0) | (0.0, 0.0) |
| Pharyngitis streptococcal | 1 (0.0) | (0.0, 0.0) | 0 | (0.0, 0.0) |
| Sepsis | 1 (0.0) | (0.0, 0.0) | 0 | (0.0, 0.0) |
| Suspected COVID-19 | 1 (0.0) | (0.0, 0.0) | 0 | (0.0, 0.0) |

TABLE 17-continued

Number (%) of Subjects Reporting at Least 1
Serious Adverse Event From Dose 1 to Data Cutoff Date (06OCT2020), by
System Organ Class and Preferred Term - Phase 2/3 (All Participants) - Safety Population

| System Organ Class | Vaccine Group (as Administered) | | | |
|---|---|---|---|---|
| | BNT162b2 (30 μg) ($N^a$ = 18419) | | Placebo ($N^a$ = 18436) | |
| Preferred Term | $n^b$ (%) | (95% $CI^c$) | $n^b$ (%) | (95% $CI^c$) |
| Urinary tract infection | 0 | (0.0, 0.0) | 1 (0.0) | (0.0, 0.0) |
| Urosepsis | 0 | (0.0, 0.0) | 1 (0.0) | (0.0, 0.0) |
| INJURY, POISONING AND PROCEDURAL COMPLICATIONS | 2 (0.0) | (0.0, 0.0) | 2 (0.0) | (0.0, 0.0) |
| Forearm fracture | 0 | (0.0, 0.0) | 1 (0.0) | (0.0, 0.0) |
| Head injury | 1 (0.0) | (0.0, 0.0) | 0 | (0.0, 0.0) |
| Hip fracture | 1 (0.0) | (0.0, 0.0) | 0 | (0.0, 0.0) |
| Skin laceration | 0 | (0.0, 0.0) | 1 (0.0) | (0.0, 0.0) |
| INVESTIGATIONS | 1 (0.0) | (0.0, 0.0) | 1 (0.0) | (0.0, 0.0) |
| Cardiac stress test abnormal | 1 (0.0) | (0.0, 0.0) | 0 | (0.0, 0.0) |
| Hepatic enzyme increased | 0 | (0.0, 0.0) | 1 (0.0) | (0.0, 0.0) |
| METABOLISM AND NUTRITION DISORDERS | 3 (0.0) | (0.0, 0.0) | 1 (0.0) | (0.0, 0.0) |
| Fluid retention | 1 (0.0) | (0.0, 0.0) | 0 | (0.0, 0.0) |
| Hyperglycaemia | 1 (0.0) | (0.0, 0.0) | 0 | (0.0, 0.0) |
| Hypoglycaemia | 0 | (0.0, 0.0) | 1 (0.0) | (0.0, 0.0) |
| Hypokalaemia | 1 (0.0) | (0.0, 0.0) | 0 | (0.0, 0.0) |
| MUSCULOSKELETAL AND CONNECTIVE TISSUE DISORDERS | 1 (0.0) | (0.0, 0.0) | 2 (0.0) | (0.0, 0.0) |
| Musculoskeletal chest pain | 0 | (0.0, 0.0) | 1 (0.0) | (0.0, 0.0) |
| Osteoarthritis | 0 | (0.0, 0.0) | 1 (0.0) | (0.0, 0.0) |
| Osteochondritis | 1 (0.0) | (0.0, 0.0) | 0 | (0.0, 0.0) |
| NEOPLASMS BENIGN, MALIGNANT AND UNSPECIFIED (INCL CYSTS AND POLYPS) | 3 (0.0) | (0.0, 0.0) | 2 (0.0) | (0.0, 0.0) |
| Adenocarcinoma gastric | 1 (0.0) | (0.0, 0.0) | 0 | (0.0, 0.0) |
| Breast cancer | 0 | (0.0, 0.0) | 1 (0.0) | (0.0, 0.0) |
| Metastases to central nervous system | 1 (0.0) | (0.0, 0.0) | 0 | (0.0, 0.0) |
| Uterine leiomyoma | 0 | (0.0, 0.0) | 1 (0.0) | (0.0, 0.0) |
| Vaginal neoplasm | 1 (0.0) | (0.0, 0.0) | 0 | (0.0, 0.0) |
| NERVOUS SYSTEM DISORDERS | 5 (0.0) | (0.0, 0.1) | 7 (0.0) | (0.0, 0.1) |
| Syncope | 0 | (0.0, 0.0) | 3 (0.0) | (0.0, 0.0) |
| Subarachnoid haemorrhage | 2 (0.0) | (0.0, 0.0) | 0 | (0.0, 0.0) |
| Cerebrovascular accident | 0 | (0.0, 0.0) | 1 (0.0) | (0.0, 0.0) |
| Diplegia | 0 | (0.0, 0.0) | 1 (0.0) | (0.0, 0.0) |
| Haemorrhagic stroke | 0 | (0.0, 0.0) | 1 (0.0) | (0.0, 0.0) |
| Ischaemic stroke | 1 (0.0) | (0.0, 0.0) | 0 | (0.0, 0.0) |
| Loss of consciousness | 1 (0.0) | (0.0, 0.0) | 0 | (0.0, 0.0) |
| Paraesthesia | 0 | (0.0, 0.0) | 1 (0.0) | (0.0, 0.0) |
| Transient ischaemic attack | 1 (0.0) | (0.0, 0.0) | 0 | (0.0, 0.0) |
| PREGNANCY, PUERPERIUM AND PERINATAL CONDITIONS | 0 | (0.0, 0.0) | 3 (0.0) | (0.0, 0.0) |
| Pregnancy | 0 | (0.0, 0.0) | 2 (0.0) | (0.0, 0.0) |
| Abortion spontaneous incomplete | 0 | (0.0, 0.0) | 1 (0.0) | (0.0, 0.0) |
| PSYCHIATRIC DISORDERS | 3 (0.0) | (0.0, 0.0) | 3 (0.0) | (0.0, 0.0) |
| Suicidal ideation | 0 | (0.0, 0.0) | 2 (0.0) | (0.0, 0.0) |
| Bipolar disorder | 0 | (0.0, 0.0) | 1 (0.0) | (0.0, 0.0) |
| Mental disorder | 1 (0.0) | (0.0, 0.0) | 0 | (0.0, 0.0) |
| Mental status changes | 1 (0.0) | (0.0, 0.0) | 0 | (0.0, 0.0) |
| Psychotic disorder | 1 (0.0) | (0.0, 0.0) | 0 | (0.0, 0.0) |
| RENAL AND URINARY DISORDERS | 4 (0.0) | (0.0, 0.1) | 0 | (0.0, 0.0) |
| Nephrolithiasis | 2 (0.0) | (0.0, 0.0) | 0 | (0.0, 0.0) |
| Acute kidney injury | 1 (0.0) | (0.0, 0.0) | 0 | (0.0, 0.0) |
| Renal colic | 1 (0.0) | (0.0, 0.0) | 0 | (0.0, 0.0) |
| RESPIRATORY, THORACIC AND MEDIASTINAL DISORDERS | 2 (0.0) | (0.0, 0.0) | 1 (0.0) | (0.0, 0.0) |
| Acute respiratory failure | 1 (0.0) | (0.0, 0.0) | 0 | (0.0, 0.0) |
| Pneumonitis | 1 (0.0) | (0.0, 0.0) | 0 | (0.0, 0.0) |
| Pulmonary embolism | 0 | (0.0, 0.0) | 1 (0.0) | (0.0, 0.0) |
| SURGICAL AND MEDICAL PROCEDURES | 1 (0.0) | (0.0, 0.0) | 0 | (0.0, 0.0) |
| Breast conserving surgery | 1 (0.0) | (0.0, 0.0) | 0 | (0.0, 0.0) |
| UNCODED TERM | 3 (0.0) | (0.0, 0.0) | 1 (0.0) | (0.0, 0.0) |
| INVASIVE DUCTAL CARCINOMA STAGE 1B, LEFT BREAST@@ | 0 | (0.0, 0.0) | 1 (0.0) | (0.0, 0.0) |
| LEFT OVARIAN CYST, BENIGN TUMOR@@ | 1 (0.0) | (0.0, 0.0) | 0 | (0.0, 0.0) |
| MRSA INFECTION RIGHT STUMP@@ | 1 (0.0) | (0.0, 0.0) | 0 | (0.0, 0.0) |
| PROLAPSED UTERUS@@ | 1 (0.0) | (0.0, 0.0) | 0 | (0.0, 0.0) |
| STEMI: ST ELEVATION MYOCARDIAL INFARCTION@@ | 1 (0.0) | (0.0, 0.0) | 0 | (0.0, 0.0) |
| VASCULAR DISORDERS | 4 (0.0) | (0.0, 0.1) | 2 (0.0) | (0.0, 0.0) |
| Deep vein thrombosis | 1 (0.0) | (0.0, 0.0) | 1 (0.0) | (0.0, 0.0) |

TABLE 17-continued

Number (%) of Subjects Reporting at Least 1 Serious Adverse Event From Dose 1 to Data Cutoff Date (06OCT2020), by System Organ Class and Preferred Term - Phase 2/3 (All Participants) - Safety Population

| | Vaccine Group (as Administered) | | | |
|---|---|---|---|---|
| System Organ Class | BNT162b2 (30 μg) ($N^a$ = 18419) | | Placebo ($N^a$ = 18436) | |
| Preferred Term | $n^b$ (%) | (95% $CI^c$) | $n^b$ (%) | (95% $CI^c$) |
| Arteriosclerosis | 1 (0.0) | (0.0, 0.0) | 0 | (0.0, 0.0) |
| Hypertension | 1 (0.0) | (0.0, 0.0) | 0 | (0.0, 0.0) |
| Hypertensive urgency | 1 (0.0) | (0.0, 0.0) | 0 | (0.0, 0.0) |
| Orthostatic hypotension | 0 | (0.0, 0.0) | 1 (0.0) | (0.0, 0.0) |

Note:
MedDRA (v23.0) coding dictionary applied.
[a]N = number of subjects in the specified group. This value is the denominator for the percentage calculations.
[b]n = Number of subjects reporting at least 1 occurrence of the specified event. For "any event", n = number of subjects reporting at least 1 occurrence of any event.
[c]Exact 2-sided CI based on the Clopper and Pearson method.

Serious Adverse Event Narratives—Phase 2/3

Narratives for the Phase 3 participants who reported SAEs assessed as related to study intervention by the investigator who completed their visit at 1 month after Dose 2 and through the data cutoff date (6 Oct. 2020) were provided.

Safety-Related Participant Withdrawals—Phase 2/3

First 6610 Participants—Phase 2/3

From Dose 1 to 1 month after Dose 2, 6 (0.2%) participants in the BNT162b2 group and 5 (0.2%) participants in the placebo group were withdrawn because of AEs (Table 18), and no additional withdrawals were reported for these participants from 1 month after Dose 2 until the data cutoff date.

Withdrawals of interest in the BNT162b2 group:

Two participants were withdrawn because of AEs that were assessed by the investigator as related to study intervention. One participant in the younger age group had an AE of myalgia 8 days after Dose 1 which was recovering at the time of the data cutoff. One participant in the older age group had an AE of pruritus and an AE of tachycardia 2 days after Dose 1; both events had a duration of 1 day and both were severe.

Three participants each had an SAE and were withdrawn from the study: younger age group (gastric adenocarcinoma), and in the older age group (coronary artery disease and coronary artery dissection).

Withdrawals of Interest in the Placebo Group:

One participant (younger age group) was withdrawn because of an AE of allergy to vaccine (study intervention) and an AE of erythematous rash 2 days after Dose 1; both AEs resolved 18 days later, and both were assessed by the investigator as related to study intervention.

One participant in the older group had an SAE (coronary artery occlusion) assessed by the investigator as not related and was withdrawn from the study.

One participant in the older group was withdrawn from the study because of an AE of urticaria 10 days after Dose 1. The event resolved on the same day and was assessed by the investigator as not related to study intervention.

TABLE 18

Number (%) of Subjects Withdrawn Because of Adverse Events From Dose 1 to 1 Month After Dose 2, by System Organ Class and Preferred Term - ~6000 Subjects for Phase 2/3 Analysis - Safety Population

| | Vaccine Group (as Administered) | | | |
|---|---|---|---|---|
| System Organ Class | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Any event | 6 (0.2) | (0.1, 0.4) | 5 (0.2) | (0.0, 0.4) |
| CARDIAC DISORDERS | 3 (0.1) | (0.0, 0.3) | 2 (0.1) | (0.0, 0.2) |
| Atrial fibrillation | 0 | (0.0, 0.1) | 1 (0.0) | (0.0, 0.2) |
| Coronary artery disease | 1 (0.0) | (0.0, 0.2) | 0 | (0.0, 0.1) |
| Coronary artery dissection | 1 (0.0) | (0.0, 0.2) | 0 | (0.0, 0.1) |
| Coronary artery occlusion | 0 | (0.0, 0.1) | 1 (0.0) | (0.0, 0.2) |
| Left ventricular hypertrophy | 0 | (0.0, 0.1) | 1 (0.0) | (0.0, 0.2) |
| Tachycardia | 1 (0.0) | (0.0, 0.2) | 0 | (0.0, 0.1) |
| GASTROINTESTINAL DISORDERS | 0 | (0.0, 0.1) | 1 (0.0) | (0.0, 0.2) |
| Diverticular perforation | 0 | (0.0, 0.1) | 1 (0.0) | (0.0, 0.2) |
| IMMUNE SYSTEM DISORDERS | 0 | (0.0, 0.1) | 1 (0.0) | (0.0, 0.2) |
| Allergy to vaccine | 0 | (0.0, 0.1) | 1 (0.0) | (0.0, 0.2) |
| INJURY, POISONING AND PROCEDURAL COMPLICATIONS | 1 (0.0) | (0.0, 0.2) | 0 | (0.0, 0.1) |
| Ankle fracture | 1 (0.0) | (0.0, 0.2) | 0 | (0.0, 0.1) |

TABLE 18-continued

Number (%) of Subjects Withdrawn Because of Adverse Events From Dose 1 to 1 Month After Dose 2, by System Organ Class and Preferred Term - ~6000 Subjects for Phase 2/3 Analysis - Safety Population

| System Organ Class | Vaccine Group (as Administered) | | | |
|---|---|---|---|---|
| | BNT162b2 (30 μg) ($N^a$ = 3314) | | Placebo ($N^a$ = 3296) | |
| Preferred Term | $n^b$ (%) | (95% $CI^c$) | $n^b$ (%) | (95% $CI^c$) |
| Fall | 1 (0.0) | (0.0, 0.2) | 0 | (0.0, 0.1) |
| MUSCULOSKELETAL AND CONNECTIVE TISSUE DISORDERS | 2 (0.1) | (0.0, 0.2) | 0 | (0.0, 0.1) |
| Muscular weakness | 1 (0.0) | (0.0, 0.2) | 0 | (0.0, 0.1) |
| Myalgia | 1 (0.0) | (0.0, 0.2) | 0 | (0.0, 0.1) |
| NEOPLASMS BENIGN, MALIGNANT AND UNSPECIFIED (INCL CYSTS AND POLYPS) | 1 (0.0) | (0.0, 0.2) | 0 | (0.0, 0.1) |
| Adenocarcinoma gastric | 1 (0.0) | (0.0, 0.2) | 0 | (0.0, 0.1) |
| NERVOUS SYSTEM DISORDERS | 1 (0.0) | (0.0, 0.2) | 0 | (0.0, 0.1) |
| Transient ischaemic attack | 1 (0.0) | (0.0, 0.2) | 0 | (0.0, 0.1) |
| SKIN AND SUBCUTANEOUS TISSUE DISORDERS | 1 (0.0) | (0.0, 0.2) | 2 (0.1) | (0.0, 0.2) |
| Pruritus | 1 (0.0) | (0.0, 0.2) | 0 | (0.0, 0.1) |
| Rash erythematous | 0 | (0.0, 0.1) | 1 (0.0) | (0.0, 0.2) |
| Urticaria | 0 | (0.0, 0.1) | 1 (0.0) | (0.0, 0.2) |

Note:
MedDRA (v23.0) coding dictionary applied.
[a]N = number of subjects in the specified group. This value is the denominator for the percentage calculations.
[b]n = Number of subjects reporting at least 1 occurrence of the specified event. For "any event", n = number of subjects reporting at least 1 occurrence of any event.
[c]Exact 2-sided CI based on the Clopper and Pearson method.

All Participants—Phase 2/3

From Dose 1 to the data cutoff date, 18 (0.1%) participants in the BNT162b2 group and 14 (0.1%) participants in the placebo group were withdrawn because of AEs. In addition to withdrawals discussed for the first 6610 participants, other withdrawals included:

One participant in the younger BNT162b2 group had an SAE of lymphadenopathy (right axilla) 13 days after Dose 1 assessed by the investigator as related to study intervention and was withdrawn, which was not resolved at the time of the data cutoff.

Three participants in the younger age group (1 BNT162b2 and 2 placebo) became pregnant after Dose 1 and were withdrawn.

One participant in the younger placebo group had a positive pregnancy test (exposure during pregnancy) 39 days after Dose 1 and was withdrawn.

Narratives of Safety-Related Participant Withdrawals—Phase 2/3

Narratives for the Phase 2/3 participants with any AEs leading to withdrawal from the study through the data cutoff date (6 Oct. 2020) were provided.

Other Significant Adverse Events—Phase 2/3

AEs of special interest were not defined for Phase 2/3 of this study; however, targeted medical events were monitored throughout the study.

Other Safety Assessments—Phase 2/3

Severe COVID-19 Illness—Phase 2/3

At the time of the efficacy interim analysis cutoff date of 4 Nov. 2020, all 7 severe COVID-19 cases were reported in the placebo group.

Pregnancy—Phase 2/3

Pregnancy was reported in 5 Phase 3 participants through the data cutoff date of 6 Oct. 2020: in 1 participant in the BNT162b2 group and 4 participants in the placebo group. Incomplete spontaneous abortion occurred in 1 participant in the placebo group.

Narratives for pregnancy were provided.

Analysis and Discussion of Deaths, Serious Adverse Events, Safety-Related Participant Withdrawals, and Other Significant Adverse Events—Phase 2/3

Up to the data cutoff date of 6 Oct. 2020, the numbers of SAEs were similar in the BNT162b2 group (63 [0.3%]) and in the placebo group (49 [0.3%]). Two participants in the BNT162b2 group reported SAEs that were assessed by the investigator as related to study intervention.

Few participants in the BNT162b2 group (18 [0.1%]) and in the placebo group (14 [0.1%]) were withdrawn because of AEs.

There were 3 deaths (1 in the BNT162b2 group and 2 in the placebo group); none of the deaths were assessed by the investigator as related to study intervention.

Phase 2/3 Safety Conclusions

Across age groups, local reactions were generally similar in frequency after each dose, and systemic events generally increased in frequency and severity after Dose 2 compared to Dose 1. Local and systemic reactogenicity events were well-tolerated and short-lived (median durations of 1.0 to 2.0 days).

Reactogenicity events after each dose of BNT162b2 in older adults were generally milder and less frequent than those observed in younger adults. The majority of reactogenicity events were mild or moderate in severity. No Grade 4 events were reported other than fever in 1 participant in the BNT162b2 group that began 1 day after Dose 2 and lasted 1 day.

The reactogenicity and AE profile after BNT162b2 30 μg evaluated in 6610 participants was consistent with the safety profile observed after BNT162b2 30 μg in Phase 1 and Phase 2.

AEs were reported in 16.8% of participants in the BNT162b2 group, and most AEs were mild or moderate in severity. At the time of the data cutoff date, the number of participants with AEs in the BNT162b2 group was greater as compared with the placebo group (7.9%), which upon analysis, was attributed to reactogenicity events reported as AEs within 7 days after each dose.

At the time of the data cutoff date, there were 2 related SAEs in the BNT162b2 group (lymphadenopathy and shoulder injury related to vaccine administration (SIRVA, erroneously administered into or near the shoulder joint capsule), and there were 6 discontinuations because of related AEs. There was 1 death in the BNT162b2 group (arteriosclerosis) and 2 deaths in the placebo group that were assessed as not related to study intervention.

Overall, BNT162b2 at 30 μg was well tolerated when measured up to 1 month after Dose 2 following dosing regimen.

Example 16: Conclusion of Phase 3 Study of COVID-19 Vaccine, Meeting All Primary Efficacy Endpoints After conducting the final efficacy analysis in the ongoing Phase 3 study, the mRNA-based COVID-19 vaccine, BNT162b2, met all of the study's primary efficacy endpoints. Analysis of the data indicated a vaccine efficacy rate of 95% ($p<0.0001$) in participants without prior SARS-CoV-2 infection (first primary objective) and also in participants with and without prior SARS-CoV-2 infection (second primary objective), in each case measured from 28 days after the first dose, 7 days after the second dose. The first primary objective analysis is based on 170 cases of COVID-19 of which 162 cases of COVID-19 were observed in the placebo group versus 8 cases in the BNT162b2 group. Efficacy was consistent across age, gender, race and ethnicity demographics. The observed efficacy in adults over 65 years of age was over 94%.

There were 10 severe cases of COVID-19 observed in the trial, with nine of the cases occurring in the placebo group and one in the BNT162b2 vaccinated group. No serious safety concerns related to the vaccine were reported. A review of unblinded reactogenicity data from the final analysis which consisted of a randomized subset of at least 8,000 participants 18 years and older in the Phase 2/3 study demonstrated that the vaccine was well tolerated, with most solicited adverse events resolving shortly after vaccination. The only Grade 3 (severe) solicited adverse events greater than or equal to 2% in frequency after the first or second dose were fatigue at 3.8% and headache at 2.0% following dose 2. Consistent with earlier shared results, older adults tended to report fewer and milder solicited adverse events following vaccination. The local reactogenicity profile among SARS-CoV-2 positive participants was consistent with that of the overall reactogenicity subset; similarly, on comparison of AE data with that of the 'All subjects', there is no indication of a worse safety profile in baseline positive participants. Indeed, there is no indication of a worse safety profile in baseline positive participants; therefore, BNT162b2 can be used irrespective of COVID-19 history or SARS-CoV-2 serological status.

In addition, the safety milestone required by the U.S. Food and Drug Administration (FDA) for Emergency Use Authorization (EUA) has been achieved.

The results of this first global trial to reach the final efficacy analysis mark indicated that a high rate of protection against COVID-19 can be achieved very fast after the first 30 μg dose, underscoring the potential of BNT162 to provide early protection.

In summary:

- Primary efficacy analysis demonstrated BNT162b2 to be 95% effective against COVID-19 beginning 28 days after the first dose; 170 confirmed cases of COVID-19 were evaluated, with 162 observed in the placebo group versus 8 in the vaccine group
- Efficacy was consistent across age, gender, race and ethnicity demographics; observed efficacy in adults over 65 years of age was over 94%
- Safety data milestone required by U.S. Food and Drug Administration (FDA) for Emergency Use Authorization (EUA) has been achieved
- Data demonstrates vaccine was well tolerated across all populations with over 43,000 participants enrolled; no serious safety concerns observed; the only Grade 3 adverse event greater than 2% in frequency was fatigue at 3.8% and headache at 2.0%

Example 17: All Confirmed Cases of COVID-19 After Dose 1

A number of confirmed cases of COVID-19 are not captured in the analyses of the first primary endpoint for the evaluable efficacy population because they occurred less than 7 days after Dose 2, or because they occurred in participants who were excluded from the evaluable efficacy population or who had evidence of infection before or during the vaccination regimen.

All reports of COVID-19 with onset at any time after Dose 1 are accounted for in Table 19, which provides a summary of cases for all participants in the Dose 1 all-available efficacy (modified intention-to-treat) population, regardless of evidence of infection before or during the vaccination regimen. Among these participants, 50 cases of COVID-19 occurred after Dose 1 in the BNT162b2 group compared to 275 cases in the placebo group (Table 19). Notably, in the BNT162b2 group, most cases occurred before Dose 2. The estimated VE against confirmed COVID-19 occurring after Dose 1 was 82% (2-sided 95% Cl: 75.6%, 86.9%), with an estimated VE of 52.4% (2-sided 95% Cl: 29.5%, 68.4%) against confirmed COVID-19 occurring after Dose 1 but before Dose 2.

TABLE 19

COVID-19 Occurrence After Dose 1 - Dose 1 All-Available Efficacy Population

| Efficacy Endpoint | BNT162b2 (30 μg) ($N^a$ = 21669) $n^b$ | Placebo ($N^a$ = 21686) $n^b$ |
|---|---|---|
| COVID-19 occurrence after Dose 1 | 50 | 275 |
| After Dose 1 to before Dose 2 | 39 | 82 |
| Dose 2 to 7 days after Dose 2 | 2 | 21 |
| ≥7 days after Dose 2 | 9 | 172 |

[a]N = number of subjects in the specified group.
[b]n1 = Number of subjects meeting the endpoint definition.

Figure 100:
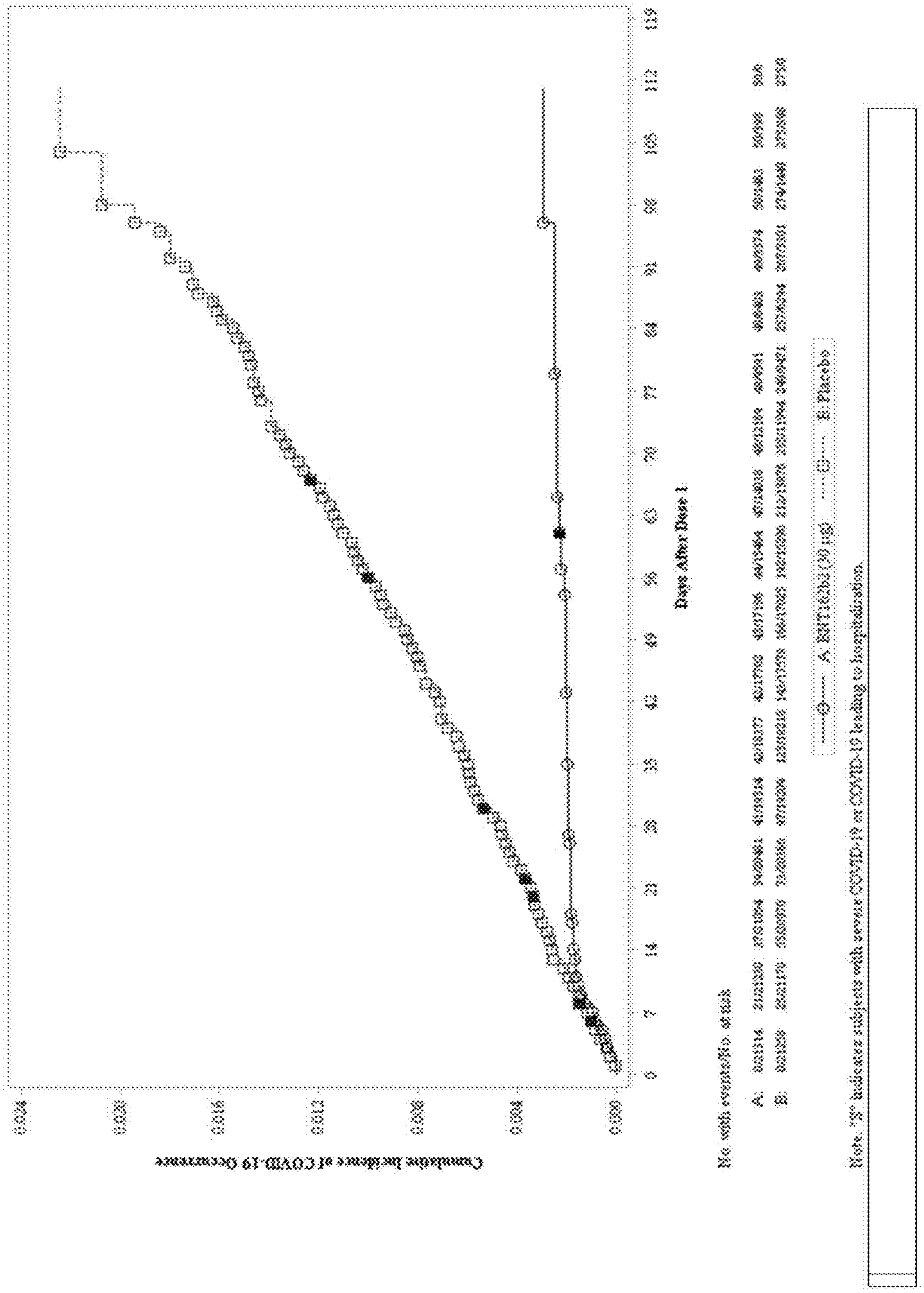

The early onset of protection is readily apparent in FIG. 100, which displays cumulative incidence for the first COVID-19 occurrence after Dose 1 among all vaccinated participants based on Dose 1 all-available efficacy (modified intention-to-treat) population. Disease onset appears to track together for BNT162b2 and placebo until approximately 14 days after Dose 1, at which point the curves diverge, with cases steadily accumulating in the placebo group, while remaining virtually flat in the BNT162b2 group.

The cumulative incidence of COVID-19 cases over time among placebo and vaccine recipients begins to diverge by 14 days after Dose 1, approximately 9 days after the estimated median incubation period of 5 days, indicating the early onset of a partially protective effect of immunization. In the interval between Dose 1 and Dose 2, the observed vaccine efficacy was 52%, and in the first 7 days after Dose 2, it was 91%, reaching full efficacy for COVID-19 with onset at least 7 days after Dose 2.

Example 18: Secondary Efficacy Results—Final Analysis

Vaccine Efficacy For COVID-19 Occurring Within 14 Days After Dose 2—Final Analysis Participants Without Evidence of Infection Before Vaccination For this efficacy endpoint, participants with positive or unknown NAAT results at any illness visit prior to 14 days after Dose 2 were not included in the evaluation for efficacy.

Among participants without evidence of SARS-CoV-2 infection before and during vaccination regimen, VE against confirmed COVID-19 occurring at least 14 days after Dose 2 was 94.2%, with 8 and 139 cases in the BNT162b2 and placebo groups respectively. The posterior probability of >99.99% for the true VE greater than 30% met the prespecified success criterion of >98.6% for this endpoint. The 95% credible interval for the vaccine efficacy was 88.7% to 97.2%, indicating that the true VE is at least 88.7% with a 97.5% probability given the available data.

Participants With or Without Evidence of Infection Before Vaccination

Among participants with or without evidence of SARS-CoV-2 infection before and during vaccination regimen, VE against confirmed COVID-19 occurring at least 14 days after Dose 2 was 94.4%, with 8 and 144 cases in the BNT162b2 and placebo groups respectively. The posterior probability of >99.99% for the true VE greater than 30% met the prespecified success criterion of >98.6% for this endpoint. The 95% credible interval for the vaccine efficacy was 89.1% to 97.3%, indicating that the true VE is at least 89.1% with a 97.5% probability given the available data.

Vaccine Efficacy for Severe COVID-19 Cases—Final Analysis

Efficacy Against Severe COVID-19 (≥7 Days After Dose 2)

Participants Without Evidence of Infection Before and During Vaccination Regimen For this efficacy endpoint, participants with positive or unknown NAAT results at any illness visit prior to 7 days after Dose 2 were not included in the evaluation for efficacy. Among participants without evidence of severe SARS-CoV-2 infection before and during vaccination regimen, the estimated VE against severe COVID-19 occurring at least 7 days after Dose 2 was 66.4%, with 1 and 3 cases in the BNT162b2 and placebo groups respectively. The posterior probability for the true vaccine efficacy greater than 30% is 74.29%, which did not meet the prespecified success criterion of >98.6% for this endpoint due to the small number of severe cases observed after Dose 2 in the study.

Participants With and Without Evidence of Infection Before and During Vaccination Regimen Among participants with or without evidence of severe SARS-CoV-2 infection prior to 7 days after Dose 2, VE against severe COVID-19 occurring at least 7 days after Dose 2 was 66.3%, with 1 and 3 cases in the BNT162b2 and placebo groups respectively. The posterior probability for the true vaccine efficacy greater than 30% is 74.19%.

All Confirmed Cases of Severe COVID-19 After Dose 1—All-Available Population

Among participants in the all-available efficacy population, 1 case of COVID-19 occurred after Dose 1 in the BNT162b2 group compared to 9 cases in the placebo group. The estimated VE against severe COVID-19 occurring after Dose 1 was 88.9% (2-sided 95% CI: 20.1%, 99.7%), with an estimated VE of 75.0% against severe COVID-19 occurring at least 7 days after Dose 2.

Efficacy Against Severe COVID-19 (≥14 Days After Dose 2)

Participants Without Evidence of Infection Before and During Vaccination Regimen (14 Days)—Severe Among participants without evidence of severe SARS-CoV-2 infection before and during vaccination regimen, the estimated VE against severe COVID-19 occurring at least 14 days after Dose 2 was 66.4%, with 1 and 3 cases in the BNT162b2 and placebo groups respectively. The posterior probability for the true vaccine efficacy greater than 30% is 74.32%.

Participants With or Without Evidence of Infection Before and During Vaccination Regimen (14 Days)—Severe Among participants with or without evidence of severe SARS-CoV-2 infection before and during vaccination phase, VE against severe COVID-19 occurring at least 14 days after Dose 2 was 66.3%, with 1 and 3 cases in the BNT162b2 and placebo groups respectively. The posterior probability for the true vaccine efficacy greater than 30% is 74.18%.

Vaccine Efficacy for COVID-19 Cases per CDC Definition—Final Analysis

Efficacy Against COVID-19 Based on CDC-Defined Symptoms (≥7 Days After Dose 2) Participants Without Evidence of Infection Before and During Vaccination Regimen—CDC Defined—7 Days Among participants without evidence of SARS-CoV-2 infection before and during vaccination regimen, VE against CDC-defined COVID-19 occurring at least 7 days after Dose 2 was 95.1% (2-sided 95% CI: 90.2%, 97.9%), with 8 and 165 cases in the BNT162b2 and placebo groups, respectively.

Participants With and Without Evidence of Infection Before and During Vaccination Regimen—CDC Defined—7 Days Among participants with and without evidence of SARS-CoV-2 infection before and during vaccination regimen, VE against CDC-defined COVID-19 occurring at least 7 days after Dose 2 was 94.7% (2-sided 95% CI: 89.8%-97.6%), with 9 and 172 cases in the BNT162b2 and placebo groups, respectively.

Efficacy Against COVID-19 Based on CDC-Defined Symptoms (≥14 Days After Dose 2)

Among participants without and with or without evidence of SARS-CoV-2 infection before and during vaccination regimen, VE against CDC-defined COVID-19 occurring at least 14 days after Dose 2 were similar to those occurring at least 7 days after Dose 2.

Example 19: Efficacy Conclusions—Final Analysis

In the final efficacy analysis, among participants without evidence of SARS-CoV-2 infection before and during vaccination regimen, VE against confirmed COVID-19 occurring at least 7 days after Dose 2 was 95.0%, with 8 COVID-19 cases in the BNT162b2 group compared to 162 COVID-19 cases in the placebo group. The 95% credible interval for the vaccine efficacy was 90.3% to 97.6%. For the second primary endpoint, VE against confirmed COVID-19 occurring at least 7 days after Dose 2 in participants with and without evidence of SARS-CoV-2 infection before and during vaccination regimen was 94.6%, with 9 and 169 cases in the BNT162b2 and placebo groups respectively.

The posterior probability of >99.99% for the true VE greater than 30% met the prespecified success criterion of >98.6% for this endpoint. The 95% credible interval for the vaccine efficacy was 89.9% to 97.3%, indicating that the true VE is at least 89.9% with a 97.5% probability given the available data Observed VE was very high for the first primary efficacy endpoint across subgroups of age, sex, race/ethnicity, and country, as VE was >93% in all subgroups, with the exception of "all others" race group (89.3% VE) and Brazil (87.7% VE).

A total of 10 cases of severe COVID-19 occurred after Dose 1, 1 in the BNT162b2 group, compared with 9 cases in the placebo group.

Among all participants (regardless of evidence of infection before or during the vaccination regimen) 50 cases of COVID-19 occurred after Dose 1 in the BNT162b2 group compared with 275 cases in the placebo group, indicating an estimated VE of 82% (95% CI: 75.6%, 86.9%) against confirmed COVID-19 occurring after Dose 1.

The early onset of protection is readily apparent from cumulative incidence curves, which show that disease onset tracks conjointly for BNT162b2 and placebo until approximately 14 days after Dose 1, at which point the curves diverge, with cases steadily accumulating in the placebo group, while remaining virtually flat after BNT162b2.

In conclusion, the final efficacy results show that BNT162b2 at 30 μg provided protection against COVID-19 in participants who had no evidence of prior infection with SARS-CoV-2, including across demographic subgroups, with severe cases observed predominantly in the placebo group.

Details of demographic populations assessed are presented below in Tables 20 and 21.

TABLE 20

Demographic Characteristics - ~38000 Subjects for Phase 2/3 Analysis - Safety Population

| | Vaccine Group (as Administered) | | |
|---|---|---|---|
| | BNT162b2 (30 μg) ($N^a$ = 18860) $n^b$ (%) | Placebo ($N^a$ = 18846) $n^b$ (%) | Total ($N^a$ = 37706) $n^b$ (%) |
| Sex | | | |
| Male | 9639 (51.1) | 9436 (50.1) | 19075 (50.6) |
| Female | 9221 (48.9) | 9410 (49.9) | 18631 (49.4) |
| Race | | | |
| White | 15636 (82.9) | 15630 (82.9) | 31266 (82.9) |
| Black or African American | 1729 (9.2) | 1763 (9.4) | 3492 (9.3) |
| American Indian or Alaska native | 102 (0.5) | 99 (0.5) | 201 (0.5) |
| Asian | 801 (4.2) | 807 (4.3) | 1608 (4.3) |
| Native Hawaiian or other Pacific Islander | 50 (0.3) | 26 (0.1) | 76 (0.2) |
| Multiracial | 449 (2.4) | 406 (2.2) | 855 (2.3) |
| Not reported | 93 (0.5) | 115 (0.6) | 208 (0.6) |
| Ethnicity | | | |
| Hispanic/ Latino | 5266 (27.9) | 5277 (28.0) | 10543 (28.0) |
| Non-Hispanic/ non-Latino | 13482 (71.5) | 13459 (71.4) | 26941 (71.5) |
| Not reported | 112 (0.6) | 110 (0.6) | 222 (0.6) |
| Country | | | |
| Argentina | 2883 (15.3) | 2881 (15.3) | 5764 (15.3) |
| Brazil | 1145 (6.1) | 1139 (6.0) | 2284 (6.1) |
| South Africa | 372 (2.0) | 372 (2.0) | 744 (2.0) |
| USA | 14460 (76.7) | 14454 (76.7) | 28914 (76.7) |
| Age group | | | |
| 16-55 Years | 10889 (57.7) | 10896 (57.8) | 21785 (57.8) |
| >55 Years | 7971 (42.3) | 7950 (42.2) | 15921 (42.2) |
| Age at vaccination (years) | | | |
| Mean (SD) | 50.5 (15.65) | 50.3 (15.72) | 50.4 (15.68) |
| Median | 52.0 | 52.0 | 52.0 |
| Min, max | (16, 89) | (16, 91) | (16, 91) |
| Body mass index (BMI) | | | |
| Underweight (<18.5 kg/$m^2$) | 201 (1.1) | 235 (1.2) | 436 (1.2) |
| Normal weight (>18.5 kg/$m^2$-24.9 kg/$m^2$) | 5517 (29.3) | 5460 (29.0) | 10977 (29.1) |
| Overweight (>25.0 kg/$m^2$-29.9 kg/$m^2$) | 6578 (34.9) | 6481 (34.4) | 13059 (34.6) |
| Obese (>30.0 kg/$m^2$) | 6556 (34.8) | 6662 (35.3) | 13218 (35.1) |
| Missing | 8 (0.0) | 8 (0.0) | 16 (0.0) |

Note:
HIV-positive subjects are included in this summary but not included in the analyses of the overall study objectives.
[a]N = number of subjects in the specified group, or the total sample. This value is the denominator for the percentage calculations.
[b]n = Number of subjects with the specified characteristic.

TABLE 21

Baseline Charlson Comorbidities - ~38000 Subjects for Phase 2/3 Analysis - Safety Population

| | Vaccine Group (as Administered) | | |
|---|---|---|---|
| Charlson Comorbidity Index Category | BNT162b2 (30 μg) ($N^a$ = 18860) $n^b$ (%) | Placebo ($N^a$ = 18846) $n^b$ (%) | Total ($N^a$ = 37706) $n^b$ (%) |
| Subjects with any Charlson comorbidity | 3934 (20.9) | 3809 (20.2) | 7743 (20.5) |
| AIDS/HIV | 59 (0.3) | 62 (0.3) | 121 (0.3) |
| Any Malignancy | 733 (3.9) | 662 (3.5) | 1395 (3.7) |
| Cerebrovascular Disease | 195 (1.0) | 166 (0.9) | 361 (1.0) |
| Chronic Pulmonary Disease | 1478 (7.8) | 1453 (7.7) | 2931 (7.8) |
| Congestive Heart Failure | 88 (0.5) | 83 (0.4) | 171 (0.5) |
| Dementia | 7 (0.0) | 11 (0.1) | 18 (0.0) |
| Diabetes With Chronic Complication | 99 (0.5) | 113 (0.6) | 212 (0.6) |
| Diabetes Without Chronic Complication | 1473 (7.8) | 1478 (7.8) | 2951 (7.8) |
| Hemiplegia or Paraplegia | 13 (0.1) | 21 (0.1) | 34 (0.1) |

TABLE 21-continued

| Baseline Charlson Comorbidities - ~38000 Subjects for Phase 2/3 Analysis - Safety Population | | | |
|---|---|---|---|
| | Vaccine Group (as Administered) | | |
| Charlson Comorbidity Index Category | BNT162b2 (30 μg) ($N^a$ = 18860) $n^b$ (%) | Placebo ($N^a$ = 18846) $n^b$ (%) | Total ($N^a$ = 37706) $n^b$ (%) |
| Leukemia | 12 (0.1) | 10 (0.1) | 22 (0.1) |
| Lymphoma | 22 (0.1) | 32 (0.2) | 54 (0.1) |
| Metastatic Solid Tumor | 4 (0.0) | 3 (0.0) | 7 (0.0) |
| Mild Liver Disease | 125 (0.7) | 89 (0.5) | 214 (0.6) |
| Moderate or Severe Liver Disease | 1 (0.0) | 2 (0.0) | 3 (0.0) |
| Myocardial Infarction | 194 (1.0) | 188 (1.0) | 382 (1.0) |
| Peptic Ulcer Disease | 52 (0.3) | 71 (0.4) | 123 (0.3) |
| Peripheral Vascular Disease | 124 (0.7) | 117 (0.6) | 241 (0.6) |
| Renal Disease | 123 (0.7) | 133 (0.7) | 256 (0.7) |
| Rheumatic Disease | 62 (0.3) | 56 (0.3) | 118 (0.3) |

Note:
MedDRA (v23.1) coding dictionary applied.
Note:
HIV-positive subjects are included in this summary but not included in the analyses of the overall study objectives.
[a]N = number of subjects in the specified group. This value is the denominator for the percentage calculations.
[b]n = Number of subjects with the specified characteristic. Subjects with multiple occurrences within each category are counted only once. For 'Subjects with any Charlson comorbidity', n = number of subjects reporting at least 1 occurrence of any Charlson comorbidity.

Example 20: Certain Observations Regarding Response of Young Adolescent Populations to Immunization with BNT162b2

In clinical trials described in Examples 13-19, the following were observed in younger adolescent populations.

Local Reactions in Younger Adolescents

Younger adolescents 12 to 15 years of age (N=100; 49 in the BNT162b2 group and 51 in the placebo group) contributed preliminary data to the reactogenicity subset and were analyzed separately. In this age group, pain at the injection site was the most frequently prompted local reaction in the BNT162b2 group, reported in 71.4% of participants compared to 17.6% in the placebo group after Dose 1. The incidence of pain was reduced in the BNT162b2 group and placebo group after Dose 2 (down to 58.7% vs 8.7%). Redness was reported in 1 participant in the BNT162b2 group after Dose 1 and in 2 participants after Dose 2, and in none in the placebo group after either dose. Swelling was reported in 2 participants in the BNT162b2 group after Dose 1 and in 3 participants after Dose 2, and in 1 in the placebo group after Dose 1 and none after Dose 2. Most local reactions were mild to moderate in severity. Two severe reactions were reported, both in the BNT162b2 group: severe redness and severe pain at the injection site.

Systemic Reactions in Younger Adolescents

Younger adolescents 12 to 15 years of age (N=100; 49 in the BNT162b2 group and 51 in the placebo group) contributed preliminary data to the reactogenicity subset and were analyzed separately. Most systemic events (other than vomiting and diarrhea, which had low incidences across groups) were reported at higher incidence in the BNT162b2 group than in the placebo group. However, there was no clear trend for increasing incidence or severity after Dose 1 compared to after Dose 2. In this age group, the most frequent prompted systemic events after Dose 1 compared to Dose 2 were (Dose 1 vs Dose 2):

fatigue: BNT162b2 (49.0% vs 50.0%) compared to placebo (25.5% vs 6.5%)

headache: BNT162b2 (42.9% vs 45.7%) compared to placebo (35.3% vs 21.7%)

muscle pain: BNT162b2 (22.4% vs 30.4%) compared to placebo (13.7% vs 4.3%)

chills: BNT162b2 (30.6% vs 28.3%) compared to placebo (7.8% vs 8.7%)

joint pain: BNT162b2 (12.2% vs 17.4%) compared to placebo (9.8% vs 6.5%)

fever: BNT162b2 (14.3% vs 19.6%) compared to placebo (0% vs 0%)

vomiting: reported at similar frequencies in both groups and similar after each dose diarrhea: reported at similar frequencies in both groups and similar after each dose.

Most systemic events in younger adolescents were mild to moderate in severity. Severe events were relatively infrequent in both groups, occurring in no more than 1 or 2 participants after either dose.

Antipyretic/pain medication use in the younger adolescent group was modestly increased after Dose 2 compared to Dose 1 (30.6% vs 41.3%) and was greater than use in the placebo group (9.8% vs 13%).

In summary, as observed in older age groups (e.g., greater than 16 years of age such as 16-85 years of age), reactogenicity was mostly mild to moderate and short-lived after dosing for younger adolescents 12 to 15 years of age, and the adverse event profile did not suggest any serious safety concerns.

Examples 21-24 below further confirm that neutralizing antibody responses and/or cell-mediated immune responses can be achieved with mRNA compositions described herein (including, e.g., BNT162b1 and BNT162b2) administered according to various dosing regimens described herein, including for example dosing regimens that involve administration of one or more doses lower than 30 ug, including, e.g., 20 ug, 10 ug, 3 ug, etc. Among other things, data provided in these Examples 21-24 further confirm induction of an immune response (e.g., as described herein) against SARS-CoV-2 upon administration of certain mRNA compositions described herein (including, e.g., BNT162b1 and BNT162b2) with one or more doses of 3 ug or above.

Those of ordinary skill in the art, reading the present disclosure, will appreciate that it demonstrates among other things, that administration of various mRNA compositions described herein can induce immune responses that include neutralizing antibodies against SARS-CoV-2; it furthermore confirms that certain such compositions (i.e., that induce neutralizing antibodies and/or that induce cell-mediated immune response such as T cell response) can induce protective immune responses that reduce SARS-CoV-2 infection and/or incidence of COVID19 sickness in organisms, specifically including primate organisms in which they have induced such neutralizing antibodies and/or cell-mediated immune response and furthermore including humans. In some embodiments, it also confirms that certain such compositions (e.g., described herein) do not significantly induce vaccine-mediated disease enhancement, for example, as evidenced by only one of the 10 cases of severe COVID-19 that were observed after a first dose. Indeed, the present disclosure documents that such compositions can effectively vaccinate humans (see, for example, clinical trial results included in Examples 13-19), for example, against severe COVID-19 disease.

Example 21: Immunogenicity Studies for Functional Antibody Responses

In clinical trials described in Example 7, the following were observed in healthy younger adults (18-55 years of age) and older adults (56-85 years of age) after BNT162b1 or BNT162b2 vaccination. Two doses, of 1 μg, 3 μg, 10 μg, 20 μg, or 30 μg were administered 21 days apart in younger adults. Two doses of 20 μg was administered 21 days apart in older adults. Functional antibody data for younger adult cohorts was determined up until Day 50 after an initial dose was administered for dose groups 1 μg and 3 μg, and up until Day 85 for dose groups 10, 20, and 30 μg. For BNT162b2-dosed older adults, data is available until Day 29 after an initial dose was administered.

For virus neutralizing antibody GMTs (neutralizing GMTs) and 95% confidence intervals for participants aged 18 to 55 years after dosing with BNT162b1, see FIG. 40.

For virus neutralizing antibody GMTs (neutralizing GMTs) and 95% confidence intervals for younger participants aged 18 to 55 yrs and older participants aged 56 to 85 yrs after dosing with BNT162b2, see FIG. 101 (50% neutralizing titer). Geometric means fold increase (GMFI) from baseline in functional antibody titer data are shown in FIG. 102 (BNT162b1) and FIG. 103 (BNT162b2).

Participants dosed with BNT162b1 showed a strong dose-dependent antibody response. On Day 22, at 21 days after dose 1, virus neutralising antibody GMTs had increased in a dose-dependent mannerforthe 1, 10, 30 and 50 μg dose groups. At Day 29 (7 days after Dose 2), neutralising GMTs showed a strong, dose level dependent booster response. In the single, 60 μg dose group, neutralising GMTs remained at a lower level, indicating a booster dose is necessary to increase functional antibody titers.

On Day 43 (21 days after Dose 2 of BNT162b1), neutralising GMTs decreased (with the exception of the 1 μg dose level). Day 43 virus neutralising GMTs were 0.7-fold (1 μg) to 3.6-fold (50 μg) those of a COVID-19 HCS panel.

The COVID-19 HCS panel is comprised of 38 human COVID-19 HCS sera drawn from individuals aged 18 to 85 yrs, at least 14 d after confirmed diagnosis, and at a time when the individuals were asymptomatic. The serum donors predominantly had symptomatic infections (35/38), and one had been hospitalized. The sera were obtained from Sanguine Biosciences (Sherman Oaks, Calif.), the MT Group (Van Nuys, Calif.), and Pfizer Occupational Health and Wellness (Pearl River, N.Y.).

Participants dosed with BNT162b2 showed a strong antibody response induced by BNT162b2. Virus neutralizing GMTs were detected at 21 days after Dose 1 (Day 22) and had increased substantially in younger participants (aged 18 to 55 years) immunized with ≥3 μg of BNT162b2, and older participants (aged 56-85 years) immunized with 20 μg BNT162b2 by 7 days after Dose 2 (Day 29). Day 29 virus neutralizing GMTs were comparable between the younger and odler adult 20 μg dose level cohorts. The lowest treated dose of 1 μg BNT162b2 elicited a minimal neutralising response in participants aged 18 to 55 years.

On Day 43 (21 days after Dose two of BNT162b2), virus neutralising GMTs in the younger adult cohorts decreased for the 3, 20, and 30 μg dose levels. Thereafter, neutralising GMTs in between Days 29 and 43, neutralizing GMTs remained stable up to Day 85 (63 days after Dose two) for younger adult dose groups 10, 20 and 30 μg and were 1.3-fold to 1.9-fold those of a COVID-19 HCS panel.

Seroconversion in this context is defined as a minimum of a 4-fold increase of antibody GMT as compared to baseline. The frequency of participants with seroconversion is shown in FIG. 104 (BNT162b1) and 105 (BNT162b2).

All participants dosed with Dose 1 at ≥30 μg BNT162b1 or BNT162b2 seroconverted either by 7 days or 21 days after Dose 2 (Day 29 or Day 43). All participants dosed with 30 μg BNT162b2 remained seropositive throughout the follow-up until Day 85.

Example 22: Immunogenicity Studies for Binding Antibody Concentrations

In clinical trials described in Example 7, the following were observed in healthy younger adults (18-55 years of age) and older adults (56-85 years of age) after BNT162b1 or BNT162b2 vaccination. Binding antibody concentration data is available up until Day 43 for BNT162b1-dosed younger participants aged 18 to 55 yrs dosed with 1, 10, 30, 50, or 60 μg on Days 1 (all dose levels) and 22 (all dose levels except 60 μg) (n=12 per group).

For BNT162b2-dosed participants, data is available for younger participants aged 18 to 55 yrs dosed with 1, 3, 10, 20, or 30 μg, and older participants aged 56 to 85 yrs dosed with 20 μg on Days 1 and 22 (n=12 per group). Binding antibody concentration data for younger participant dose groups is available up until Day 50 for dose groups 1 μg and 3 μg, and up until Day 85 for dose groups 10, 20, and 30 μg. For the BNT162b2-dosed older participants, data is available up until Day 29.

The fold increase from baseline in binding antibody concentrations after dosing with BNT162b1 and BNT162b2 are shown in FIG. 106 and FIG. 107, respectively. Participants dosed with BNT162b1 showed a strong dose-dependent antibody response against the SARS-CoV-2 spike (S) protein S1 subunit at Day 21 after Dose 1 (Day 22). At 7 days after Dose 2 (Day 29), S1-binding immunoglobulin (IgG) GMCs showed a strong, dose-dependent booster response. In the 60 μg dose group, which was only dosed once, S1-binding IgG GMCs remained at a lower level, indicating that a booster dose is necessary to increase antibody concentrations.

At 21 days after Dose 2 of BNT162b1 (Day 43), S1-binding IgG GMCs decreased (with exception of the 1 μg dose group), but were clearly above those of a COVID-19 HSC panel for all doses tested.

BNT162b2 dosed participants showed a strong BNT162b2-induced S1-binding IgG response at 21 days after Dose 1 (Day 22) with evidence of a dose-dependent response only between the 1 μg and 10 μg dose levels. S1-binding IgG GMCs showed a substantial boster response by 7 days after Dose 2 (Day 29). Day 29 S1-binding IgG GMCs were comparable between the younger and older participants at the 20 μg dose level.

Across all dose-level cohorts antibody levels decreased over time, but with S1-binding antibody GMCs well above that observed in a COVID-19 HCS panel at Day 85 (63 days after Dose 2; 10 to 30 μg dose level) (FIG. 107).

Almost all BNT162b1- and BNT162b2-immunized participants seroconverted with regard to the S1-binding antibody response as early as 21 days after Dose 1 (Day 22). Frequency of participants with seroconversion after dosing with BNT162b1 is shown in FIG. 108 and with BNT162b2 is shown in FIG. 109. Similar observations were made using only the RBD domain as the target antigen.

Example 23: Exemplary Cell-Mediated Immune Responses: SARS-CoV-2-Specific $CD4^+$ and $CD8^+$ T-Cell Responses In clinical trials described in Example 7, the following were observed in healthy younger adults (18-55 years of age) and older adults (56-85 years of age) after BNT162b1 or BNT162b2 vaccination. CD4+ and CD8+ T-cell response data were available from 97 study participants receiving BNT162b1, 70 younger participants at dose levels of 1, 3, 10, 20, 30, 50, or 60 μg (note: Dose 2 was not given in the 60 μg dose group), and 27 older participants at dose levels of 10, 20, or 30 μg, as well as 76 participants receiving BNT162b2 at dose levels of 1, 3, 10, 20, or 30 μg (47 younger participants), or 10, 20, or 30 μg (older participants).

BNT162b1 induced strong RBD-specific $CD4^+$ T-cell responses in the majority of participants given both dose one and dose two (86 of 88 [97.7%]), including all older participants (27 of 27 [100%]); $CD8^+$ responses were induced in 47 of 61 (77.0%) younger participants and in 21 of 27 (77.7%) of older participants. In contrast, T-cell responses were detected less often and were lower in magnitude in 9 younger participants who received only Dose 1 in the 60 μg dose group, indicating the importance of a booster dose BNT162b2 induced strong SARS-CoV-2 S protein-specific $CD4^+$ T-cell responses in all of the dosed younger or older participants (76 of 76 [100%]); $CD8^+$ T-cell responses were induced in 45/47 (95.7%) of younger participants and 24/29 (82.8%) older participants. Despite the slightly lower $CD8^+$ immunogenicity rate in older participants, the magnitude of the BNT162b2-induced responses was comparable to those induced in younger participants receiving 30 μg of BNT162b2. These T-cell responses were directed against different parts of the antigen including non-RBD sequences, indicating the induction of multi-epitopic responses by BNT162b2 in both age groups.

Dosing twice with BNT162b1 or BNT162b2 led to a substantial increase in incidence and magnitude of T-cell responses in both age groups, and across all dose levels for BNT162b1. While the magnitude of $CD4^+$ T-cell responses induced by BNT162b2 was also similar across different dose levels, the magnitude of $CD8^+$ T-cell responses was highest at the 30 μg dose level. The participants with the strongest $CD4^+$ T-cell responses had more than 10-fold of the memory responses observed in the same participants against immunodominant peptides from cytomegalovirus, Epstein Barr virus, influenza virus, and tetanus toxoid in the same participants. The same participants also had strong $CD8^+$ T-cell responses that were comparable to memory responses against the above mentioned viral antigens.

RBD- and S protein-specific $CD4^+$ T-cell responses observed after vaccination were induced de novo by BNT162b1 in 97.5% of participants and by BNT162b2 in 100% of participants. RBD- and S protein-specific $CD8^+$ T-cell responses observed after vaccination were induced de novo by BNT162b1 in 95.5% of participants and by BNT162b2 in 96.6% of participants.

Example 24: Exemplary Cell-Mediated Immune Responses: Functional and Pro-inflammatory $CD4^+/CD8^+$ T-Cell Responses In clinical trials described in Example 7, the following were observed in healthy younger adults (18-55 years of age) and older adults (56-85 years of age) after BNT162b1 or BNT162b2 vaccination. De novo induction of SARS-CoV-2 S protein or RBD protein directed T-cells was confirmed using intracellular cytokine staining (ICS). As described in Example 7 for BNT162b1, similar cell-mediated immune responses were also observed with BNT162b2 as described below.

For example, IFNγ-producing CD4+ and CD8+ T-cells against SARS-CoV-2 S protein or RBD were induced robustly by both BNT162b1 and BNT162b2. No clear dose dependency was observed for both BNT162b1 and BNT162b2. The cytokine responses elicited after dosing with either BNT162b1 or BNT162b2 in older participants was mostly identical in response pattern and intensity with that in younger participants.

BNT162b1 and BNT162 induced poly-functional and pro-inflammatory CD4+/CD8+ T-cell responses in almost all participants. The detection of interferon (IFN)γ, interleukin (IL)-2 but not IL-4 indicates a favorable Th1 profile and the absence of a potentially deleterious Th2 immune response.

Regarding BNT162b2, peripheral blood mononuclear cell (PBMC) fractions isolated from blood of study participants collected at baseline (pre-Dose 1) and 29±3 d after Dose 1 BNT162b2 were analyzed. This includes data for a total of 74 study participants:

Younger participants aged 18 to 55 yrs per dose group: 1 μg (n=8), 3 μg (n=9), 10 μg (n=10), 20 μg (n=9), 30 μg (n=10).

Older participants aged 56 to 85 yrs per dose group: 10 μg (n=11), 20 μg (n=8), 30 μg (n=9).

The functionality and polarization of vaccine-induced SARS-CoV-2 S-specific T cells were assessed by intracellular accumulation of cytokines IFN-gamma, IL-2, and IL-4 in response to stimulation with overlapping peptides representing the full-length sequence of the vaccine-encoded RBD and the wild-type SARS CoV-2 protein, respectively. As a control, PMBCs from 18 COVID-19 convalescent virologically confirmed patients were used.

Figure 110:
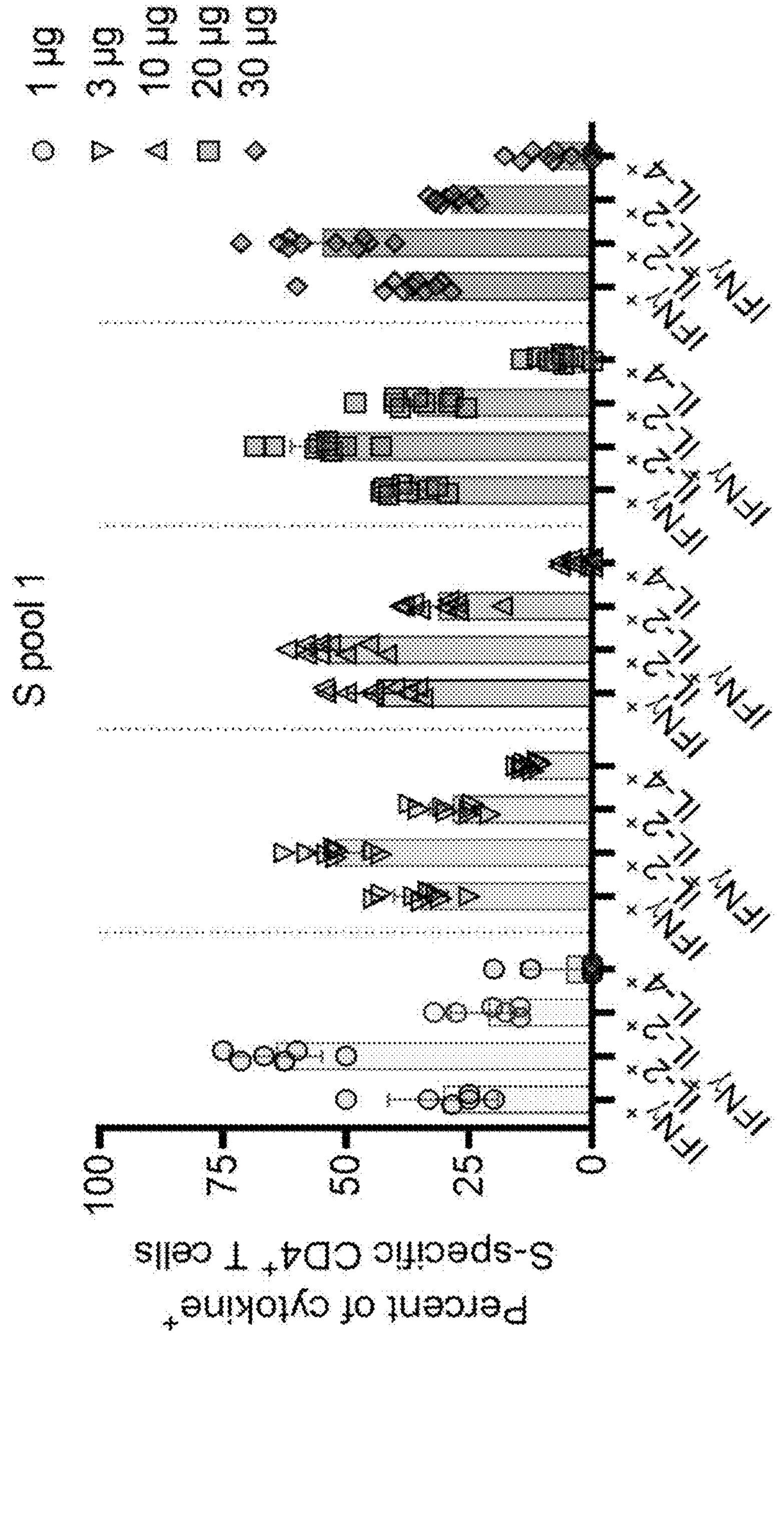

Two doses of BNT162b2 (dose range 1 to 30 μg), induced vaccine-specific T-cell responses in both age groups analyzed (FIGS. 110 and 111). Testing for SARS-CoV-2 S protein specific T-cell responses was performed with two different peptide pools, S pool 1 comprising overlapping peptides from the N-terminal region of the S protein (which is not equilvalent to structural domains) and S pool 2 comprising C-terminal regions of the S protein. S-specific $CD4^+$ T-cell responses analyzed in 74 participants dosed with BNT162b2 were characterized by a Th1 cytokine profile secreting IFN-gamma, or IL-2, or both.

Almost no Th2 cytokine IL-4 secreting T cells were detectable in response to S peptide sub-pool stimulations (mean fractions: 0.01% and 0.02% of antigen-specific circulating $CD4^+$ T cells in the 20 and 30 μg adult cohort, respectively; separate stimulation with S protein sub-pool 1 and sub-pool 2). S-specific $CD8^+$ T cells secreted IFNγ in 61 of the 74 analyzed participants (adults: 40 of 46 participants and older adults: 21 of 28 participants) and also IL-2 secreting $CD8^+$ T cells were detectable. Fractions of S-specific $IFN\gamma^+CD8^+$ T cells targeting the N-terminal domain of the S protein reached up to 1% of total peripheral blood $CD8^+$ T cells in the 20 and 30 μg younger participant dose groups and up to 2.4% in the 30 μg older participant dose group. Pre-existing $CD8^+$ T-cell responses against the C-terminal region of the S protein were detected in 17 of 74 dosed participants (range: 0.07 to 5.59% IFNγ-producing $CD8^+$ T cells). In 6 of 17 participants, these pre-existing responses were slightly amplified upon BNT162b2 dosing.

Overall, the mean fractions of S-specific $CD4^+$ and $CD8^+$ T cells were substantially higher (e.g., the S protein pool 1 IFNγ $CD8^+$ response of 30 μg dosed participants was 12.5-fold higher) than that observed in 18 patients who recovered from COVID-19. Importantly, for the clinically targeted 30 μg dose group, the cytokine responses elicited after vaccination with BNT162b2 in older participants was mostly identical in response pattern and intensity with that of the younger participants.

BNT162b2-induced T-cell responses, especially for $CD8^+$ T cells, were not limited to the RBD, and pronounced and strongT cell recognition of non-RBD regions of the S protein were observed.

BNT162b2 induced poly-functional and pro-inflammatory $CD4^+/CD8^+$ T-cell responses in almost all participants. The Th1 polarization of the helper response was characterized by a robust IFNγ/IL-2 and only minor IL-4 production upon antigen-specific (wild-type SARS-CoV-2 S protein peptide pools) re-stimulation.

Example 25: Certain T Cell Responses Induced by BNT162b2

In addition to Examples 23 and 24, which describe certain T cell responses induced by immunization with BNT162b2 as observed in the German trial (Study BNT162-01; NCT04380701), the present Example further demonstrates immunogenicity of prime-boost vaccination with 1, 10, 20 and 30 μg BNT162b2 in participants 19-55 years of age, including detailed characterisation of T cell responses, e.g., the first identification of epitopes recognised by CD8+ T cells induced by a COVID-19 vaccine described herein. Without wishing to be bound by any particular theory, it is noted that identity of epitopes to which a response is raised in a subject, and/or extent of response to particular epitope or combination of epitopes may impact one or more features (e.g., effectiveness and/or duration) of an immune response and/or of immune protection provided by an administered vaccine. In some embodiments, an administration regimen may involve one or more steps of monitoring one or more features of an immune response, including, for example, presence and/or level of response (e.g., of T cells and/or antibodies) that recognize one or more particular epitopes. In some embodiments, need for, timing of, and/or magnitude of a subsequent dose may be determined in light of such monitoring.

As further described below, the present Example demonstrates, in part, that the epitopes recognised by several BNT162b2-induced $CD8^+$ T cells when presented on frequent MHC alleles were identified using peptide MHC multimers; and that $CD8^+$ T cells were shown to be of the early-differentiated effector-memory phenotype, with single specificities reaching 0.01-3% of circulating $CD8^+$ T cells. Without wishing to be bound by any particular theory, it is noted that cells that exhibit "effector-memory" phenotype may provide longer term protection.

The present Example also documents that certain participants receiving BNT162b2 had pre-existing T cell responses. Thus, among other things, this example confirms that compositions as described herein, and particularly BNT162b2 may well be useful even in subjects who have already been exposed to one or more related viruses, including potentially the same virus—i.e., SARS-CoV-2 and/or to an antigen thereof or another antigen that shares one or more epitopes with SARS-CoV2 spike protein.

Prevalence and Magnitude of Vaccine-Induced T Cell Responses

T cell responses of 37 BNT162b2 immunised participants from whom sufficient peripheral blood mononuclear cells (PBMCs) were available were analysed pre-vaccination (day 1) and seven days after the booster dose (day 29) by direct ex vivo IFNγ enzyme-linked immunosorbent spot (ELISpot) assay (FIG. 112 and FIG. 113). One of ordinary skill in the art will understand that SARS-CoV-2 S protein is composed of a signal peptide (aa 1-13), the N-terminal S1 protease fragment (aa 14-685), and the C-terminal S2 protease fragment (aa 686-1273); and that S1 contains the RBD (aa 319-541), which binds to the host receptor, and that S2 mediates fusion between the viral envelope and cell membrane. To deconvolute reactivity against S protein, $CD4^+$ or $CD8^+$ T cell effectors were stimulated overnight with overlapping peptides representing different portions of the wild-type sequence of SARS-CoV-2 S, namely N-terminal pools 'S pool 1' (aa 1-643) and 'RBD' (aa 1-16 fused to aa 327-528 of S), and the C-terminal 'S pool 2' (aa 633-1273).

Seven days after the boost with BNT162b2 at any of the indicated doses, robustly expanded SARS-CoV-2 S-specific $CD4^+$ T-cells were detectable in all 37 participants (FIG. 112(A), FIG. 113(A)). In 34 of these participants, comparison to pre-vaccination PBMCs was possible. Thirty of the 34 subjects (88.2%) had de novo (not existent at baseline) $CD4^+$ T cell responses against both S pool 1 and S pool 2 of SARS-CoV-2. One participant had de novo response only against pool 2. The remaining three participants had de novo responses against S pool 1 and low numbers of pre-existing S pool 2-reactive $CD4^+$ T cells. In two of these three participants, the pre-existing responses against S pool 2 were amplified by vaccination (from 91 and 188 spots/$10^6$ cells pre-vaccination to 1391 and 965 spots after vaccination, respectively), whereas in one of the three participants, the pre-existing responses against S pool 2 remained stable (53 to 140 spots/$10^6$ cells). These data demonstrate that in 94.1% (32/34) of participants, two doses of BNT162b2 induce poly-epitopic $CD4^+$ T cell responses (de novo or amplified) directed against both N- and C-terminal portions of S and thus against epitopes outside the RBD (FIG. 113(B)).

Although for dose levels ≥10 μg the magnitude of $CD4^+$ T cell responses did not appear to be dose-dependent, it varied between individuals. In the strongest responders, the S-specific $CD4^+$ T cell responses were more than 10-fold of the individual memory responses to common viruses and recall antigens (those from cytomegalovirus, Epstein Barr virus, influenza virus and tetanus toxoid) (FIG. 112(B,C)).

Vaccine-induced S-specific $CD8^+$ T cell responses were detected in 34 of 37 vaccinated participants (91.9%). The majority were strong responses (FIG. 112(A), FIG. 113(A)) comparable to individual memory responses against cytomegalovirus (CMV), Epstein Barr virus (EBV) and influenza virus (FIG. 112(B,C)). De novo S—specific CD8+ T cell responses were induced in 33 participants, these were either directed against both (22 participants), or one of the S pools (S pool 1 in ten participants, and S pool 2 in two participants), indicating a preponderance of a poly-epitopic response including non-RBD S-specific T cells (FIG. 113 (B)). In seven participants, pre-existing $CD8^+$ T cell responses to S pool 2 were detected that were not further augmented by vaccination. Six out of these seven participants had a concurrent de novo response to pool 1 of S, which in strength did not differ significantly from those observed in individuals without pre-existing responses to S pool 2 (FIG. 113(C)). Of note, the strongest responses (higher than third quartile) against S pool 1 among the 34 participants with detectable $CD8^+$ T cell responses were observed in those without pre-existing S pool 2-specific responses.

The magnitude of S-specific $CD4^+$ T cell responses correlated positively with S1-binding IgG (FIG. 114(A)), and, in line with the concept of intramolecular help (e.g., a CD4 response to one eptiope in an antigen can support development of a CD8 response to an epitope in the same antigen), also with the strength of S-specific $CD8^+$ T cell responses (FIG. 114(B)). S-specific $CD8^+$ T cell responses also correlated positively with S1-binding IgG (FIG. 114(C)), indicating a convergent development of the humoral and cellular adaptive immunity.

Polarisation of Vaccine-Induced T Cell Responses

To assess functionality and polarisation of S-specific T cells, cytokines secreted in response to stimulation with S pool 1, S pool 2 and RBD pool were determined by intracellular staining (ICS) for IFNγ, IL-2 and IL-4 specific responses in pre- and post-vaccination PBMCs of 37 BNT162b2-immunised participants receiving different doses. A considerable fraction of vaccine-induced, S-specific $CD4^+$ T cells secreted IFNγ, IL-2, or both, while T cells secreting the $T_H2$ cytokine IL-4 were barely detectable (FIG. 115(A-C), FIG. 113(D-E)). Vaccine-induced S-specific $CD8^+$ T cells secreted predominantly IFNγ and lower levels of IL-2 in response to S pool 1 and S pool 2 stimulation. Fractions of $IFN\gamma^+CD8^+$ T cells specific to S pool 1 constituted up to about 1% of total peripheral blood $CD8^+$ T cells (FIG. 115(D)). Of note, several of the analysed participants (n=3 in the 20 μg dose cohort and n=3 in the 30 μg dose cohort) displayed pre-existing S pool 2 specific $CD8^+$ T cell responses, which in 5 out of the 6 participants were not further amplified after vaccination. A strong pre-existing S pool 2 specific $IFN\gamma^+CD4^+$ T cell response was detectable in one participant (20 μg dose cohort) (FIG. 115(C)).

In both assay systems, cytokine production of $CD4^+$ as well as $CD8^+$ T cells in response to peptide pools comprising the full SARS-CoV-2 S exceeded the responses against the RBD peptide pool, further confirming the poly-epitopic nature of T cell responses elicited by BNT162b2. The mean fraction of BNT162b2-induced S-specific $IFN\gamma^+$ or $IL\text{-}2^+$ $CD4^+$ and $CD8^+$ T cells within total circulating T cells was higher than that detected in eighteen control subjects who had recovered from COVID-19 (HCS) (FIG. 115(C,D)).

Epitope Specificity and Phenotype of $CD8^+$ T Cells Observed in Immunization with BNT162b2

$CD8^+$ T cell responses were characterised on the epitope level in three participants vaccinated with a 2-dose regimen with two doses (e.g., 10 μg/dose or 30 μg/dose) given 21 days apart.

Pre- and post-vaccination peripheral blood mononuclear cells (PBMCs) collected from the participants were stained with individualised peptide/MHC multimer staining cocktails for flow cytometry analysis. Twenty-three (4 for HLA-B*0702, 19 for HLA-A*2402), 14 (HLA-B*3501) and twenty-three (7 for HLA-B*4401, 16 for HLA-A*0201) diverse peptide/MHC allele pairs were used for participant 1, 2 and 3, respectively, thus probing a selected set of potential reactivities rather than comprehensively capturing the poly-epitopicT cell response. For each participant, de novo induced CD8+ T cell reactivities against multiple epitopes were identified adding up to a total of eight different epitope/MHC pairs spread across the full length of S protein (FIG. 116 (A, C)). The magnitude of epitope-specific T cell responses ranged between 0.01-3.09% of peripheral $CD8^+$ T cells and the most profound expansion was observed for HLA-A*0201 YLQPRTFLL (SEQ ID NO: 40) (3.09% $multimer^+$ of $CD8^+$), HLA-A*2402 QYIKWPWYI (SEQ ID NO: 42) (1.27% $multimer^+$ of $CD8^+$) and HLA-B*3501 QPTESIVRF (SEQ ID NO: 45) (0.17% $multimer^+$ of $CD8^+$). Comparison with the bulk $IFN\gamma^+CD8^+$ T cell response against full S protein in these individuals determined by ELISpot and intracellular staining (ICS) indicated that pMHC technology may be more useful to assess the true extent of the cellular immune response (FIG. 113(F)).

Phenotyping of the identified pMHC $multimer^+$ S antigen-experienced $CD8^+$ T cell specificities revealed an early differentiated effector memory phenotype characterized by low expression of CCR7 and CD45RA and high expression of the costimulatory molecules CD28 and CD27. $CD8^+$ T cells also expressed markers associated with cognate activation, such as CD38, HLA-DR and PD-1 (FIG. 116(B)).

DISCUSSION

Effectors of the adaptive immune system have complementary roles in the defense of viral infections. While neutralising antibodies are the first line of defense, CD8+ cytotoxic T lymphocytes (CTLs) contribute to virus clearance from intracellular compartments that are inaccessible to neutralising antibodies. Antigen-specific CD4+ T cells have immune orchestrating functions, including provision of cognate help to B cells and CD8+ T cells, support of memory generation, as well as indirect (e.g. via IFNγ) or direct (against MHC class II-expressing target cells) cytotoxic activity.

This Example shows that vaccination with BNT162b2 induces a coordinated immune response with SARS-CoV-2 S-specific neutralising antibodies (as described in other Examples), CD4+ T cells, CD8+ T cells, and immune-modulatory cytokines such as IFNγ. All participants vaccinated with BNT162b2 mounted de novo S-specific CD4+ T cell responses and almost 92% of participants mounted CD8+ T cell responses, as detected with an ex vivo ELISpot assay. The magnitude of the T cell responses varied inter-individually and showed no clear dose dependency. Even with the lowest dose of 1 μg BNT162b2, most of the vaccinated participants demonstrated robust expansion of CD4+ and CD8+ T cells. T cell responses were directed against RBD, S1 and S2 regions of S protein, indicating immune recognition of multiple independent MHC I and II epitopes.

Expression of IFNγ and IL-2 but only low levels of IL-4 in BNT162b2-induced CD4+ T cells indicated a TH1 profile and the absence of a potentially deleterious TH2 immune response.

While all CD8+ T cell responses against the S1 subunit of S protein were de novo and not detected at baseline, pre-existing immune responses against the S2 subunit were identified in several individuals. The S1 fragment has less sequence similarity to the corresponding seasonal coronavirus sequences than the S2 fragment does; without wishing to be bound by theory, it is proposed that this finding indicates that pre-existing cross-reactive CD8+ T cells may have been detected.

Peptide MHC (pMHC) multimer technology enabled the identification of S protein epitopes recognised by vaccine-induced $CD8^+$ T cells as well as direct quantification of the respective epitope-specific T cells. The cumulative T cell frequencies in each participant exceeded the overall T cell response measured in ELISpot and ICS assays, indicating that those assays underestimate the true magnitude of the poly-epitopic response. One of skill in the art will appreciate that single peptide analyses are known to yield higher T cell frequencies as compared to functional T cell assays that stimulate with peptide pools, with a multitude of immunogenic epitopes competing. A high proportion of induced $CD8^+$ T cells were early differentiated effector memory cells. This favourable phenotype has the potential to respond rapidly, but has a limited capacity to produce IFNγ, and thus is less likely to be detected in functional T cell assays. While epitopes in SARS-CoV-2 S against which infected individuals raise CD8+ T cells were identified and known in the art (see, e.g., Shomuradova et al., Immunity (2020) doi: 10.1016/j.immuni.2020.11.004; and Peng et al. Nat. Immunol. 21, 1336-1345 (2020)), the data presented herein is the first demonstration of epitopes recognised by COVID-19 vaccine-induced T cells. Of note, the immunodominant HLA-A*02:01 restricted peptide YLQPRTFLL (SEQ ID NO: 40) identified in this study has previously been described in convalescent COVID-19 patients. Id.

Materials and Methods

Proteins and Peptides.

Two pools of 15-mer peptides overlapping by 11 amino acids (aa) and together covering the whole sequence of wild-type SARS-CoV-2 S (S pool 1 featuring aa 1-643, S pool 2 featuring aa 633-1273) and one pool covering the SARS-CoV-2 RBD (aa 327-528) with the signal peptide of S (aa 1-16) fused to its N-terminus were used for ex vivo stimulation of PBMCs for flow cytometry and IFNγ ELISpot. CEF (CMV, EBV, influenza virus; human leukocyte antigen [HLA] class I epitope peptide pool) and CEFT (CMV, EBV, influenza virus, tetanus toxoid; HLA class II epitope peptide pool) were used as controls for general T-cell reactivity and to benchmark the magnitude of memory T cell responses. All peptides were obtained from JPT Peptide Technologies.

Human Convalescent Serum and PBMC Panel.

Human SARS-CoV-2 infection/COVID-19 convalescent sera (n=38) were drawn from donors 18-83 years of age at least 14 days after PCR-confirmed diagnosis and at a time when the participants were asymptomatic. The mean age of the donors was 45 years. Neutralising GMTs in subgroups of the donors were as follows: symptomatic infections, 90 (n=35); asymptomatic infections, 156 (n=3); hospitalized, 618 (n=1). Sera were obtained from Sanguine Biosciences (Sherman Oaks, Calif.), the MT Group (Van Nuys, Calif.) and Pfizer Occupational Health and Wellness (Pearl River, N.Y.). Human SARS-CoV-2 infection/COVID-19 convalescent PBMC samples (n=18) were collected from donors 22-79 years of age 30-62 days after PCR-confirmed diagnosis, when donors were asymptomatic. PBMC donors had asymptomatic or mild infections (n=16, clinical score 1 and 2) or had been hospitalized (n=2, clinical score 4 and 5). Blood samples were obtained from the Frankfurt University Hospital.

Primary Cell Isolation.

PBMCs were isolated by Ficoll-Paque™ PLUS (Cytiva) density gradient centrifugation and cryopreserved prior to analysis.

IFNγ ELISpot.

IFNγ ELISpot analysis was performed ex vivo (without further in vitro culturing for expansion) using PBMCs depleted of $CD4^+$ and enriched for $CD8^+$ T cells ($CD8^+$ effectors) or depleted of $CD8^+$ and enriched for $CD4^+$ T cells ($CD4^+$ effectors). Tests were performed in duplicate and with a positive control (anti-CD3 monoclonal antibody CD3-2 [1:1,000; Mabtech]). Multiscreen filter plates (Merck Millipore) pre-coated with IFNγ-specific antibodies (ELISpotPro kit, Mabtech) were washed with PBS and blocked with X-VIVO 15 medium (Lonza) containing 2% human serum albumin (CSL-Behring) for 1-5 hours. Per well, $3.3\times10^5$ effector cells were stimulated for 16-20 hours with three overlapping peptide pools representing different portions of the wild-type sequence of SARS-CoV-2 S (N-terminal pools S pool 1 [aa 1-643] and RBD [aa1-16 fused to aa 327-528], and the C-terminal S pool 2 [aa 633-1273]). Bound IFNγ was visualised using a secondary antibody directly conjugated with alkaline phosphatase followed by incubation with 5-bromo-4-chloro-3'-indolyl phosphate (BCIP)/nitro blue tetrazolium (NBT) substrate (ELISpotPro kit, Mabtech). Plates were scanned using an AID Classic Robot ELISPOT Reader and analysed by AID ELISPOT 7.0 software (AID Autoimmun Diagnostika). Spot counts were displayed as mean values of each duplicate. T-cell responses stimulated by peptides were compared to effectors incubated with medium only as a negative control using an in-house ELISpot data analysis tool (EDA), based on two statistical tests (distribution-free resampling), to provide sensitivity while maintaining control over false positives.

To account for varying sample quality reflected in the number of spots in response to anti-CD3 antibody stimulation, a normalisation method was applied, enabling direct comparison of spot counts and strength of response between individuals. This dependency was modelled in a log-linear fashion with a Bayesian model including a noise component (unpublished). For a robust normalization, each normalisation was sampled 1000 times from the model and the median taken as normalized spot count value. Likelihood of the model: $\log \lambda_E = \alpha \log_P + \log \beta_j + \sigma\varepsilon$, where $\lambda_E$ is the normalized spot count of the sample; α is a stable factor (normally distributed) common among all positive controls $\lambda_p$; $\beta_j$ is a sample j specific component (normally distributed); and σε is the noise component, of which σ is Cauchy distributed, and ε is Student's-t distributed. $\beta_j$ ensures that each sample is treated as a different batch.

Flow Cytometry.

Cytokine-producing T cells were identified by intracellular cytokine staining. PBMCs thawed and rested for 4 hours in OpTmizer medium supplemented with 2 μg/mL DNase I (Roche), were restimulated with different portions of the wild-type sequence of SARS-CoV-2 S in peptide pools described in the ELISpot section (2 μg/mL/peptide; JPT Peptide Technologies) in the presence of GolgiPlug (BD) for 18 hours at 37° C. Controls were treated with DMSO-containing medium. Cells were stained for viability and surface markers (CD3 BV421, 1:250; CD4 BV480, 1:50; CD8 BB515, 1:100; all BD Biosciences) in flow buffer (DPBS [Gibco] supplemented with 2% FBS [Biochrom], 2 mM ethylenediaminetetraacetic acid [EDTA; Sigma-Aldrich]) for 20 minutes at 4° C. Afterwards, samples were fixed and permeabilised using the Cytofix/Cytoperm kit according to manufacturer's instructions (BD Biosciences). Intracellular staining (CD3 BV421, 1:250; CD4 BV480, 1:50; CD8 BB515, 1:100; IFNγ PE-Cy7, 1:50 [for HCS]; IFNγ BB700, 1:250 [for participants]; IL-2 PE, 1:10; IL-4 APC, 1:500; all BD Biosciences) was performed in Perm/Wash buffer for 30 minutes at 4° C. Samples were acquired on a fluorescence-activated cell sorter (FACS) VERSE instrument (BD Biosciences) and analysed with FlowJo software version 10.6.2 (FlowJo LLC, BD Biosciences). S- and RBD-specific cytokine production was corrected for background by subtraction of values obtained with dimethyl sulfoxide (DMSO)-containing medium. Negative values were set to zero. Cytokine production in FIG. 116(B) was calculated by summing up the fractions of all $CD4^+$ T cells positive for either IFNγ, IL-2 or IL-4, setting this sum to 100% and calculating the fraction of each specific cytokine-producing subset thereof. Pseudocolor plot axes are in log 10 scale.

Peptide/MHC Multimer Staining.

In order to select MHC-class I epitopes for multimer analysis, a mass spectrometry-based binding and presentation predictor (e.g., as described in Abelin et al., Immunity 46, 315-326 (2017); and Poran et al., Genome Med. 12, 70 (2020)) was applied to 8-12 amino acid long peptide sequences from the Spike glycoprotein derived from the GenBank reference sequence for SARS-CoV-2 (accession: NC_045512.2, www.ncbi.nlm.nih.gov/nuccore/NC_045512) and paired with 18 MHC-class-I alleles with >5% frequency in the European population. Top predicted epitopes were identified by setting thresholds to the binding percent-rank (≤1%) and presentation scores ($\geq 10^{-22}$) and considered for synthesis of peptides of >90% purity. pMHC complexes were refolded with the easYmer technology (easYmer® kit, ImmuneAware Aps), and complex formation was validated in a bead-based flow cytometry assay according to the manufacturer's instructions. Combinatorial labeling was used for dissecting the antigen specificity of T cells utilizing two-color combinations of five different fluorescent labels to enable detection of up to ten different T cell populations per sample. For tetramerisation, streptavidin (SA)-fluorochrome conjugates were added: SA BV421, SA BV711, SA PE, SA PE-Cy7, SA APC (all BD Biosciences). For three BNT162b2 vaccinated participants, individualized pMHC multimer staining cocktails contained up to ten pMHC complexes, with each pMHC complex encoded by a unique two-color combination. PBMCs ($2\times10^6$) were stained ex vivo for 20 minutes at room temperature with each pMHC multimer cocktail at a final concentration of 4 nM in Brilliant Staining Buffer Plus (BSB Plus [BD Horizon™]). Surface and viability staining was carried out in flow buffer (DPBS [Gibco] with 2% FBS [Biochrom], 2 mM EDTA [Sigma-Aldrich]) supplemented with BSB Plus for 30 minutes at 4° C. (CD3 BUV395, 1:50; CD45RA BUV563, 1:200; CD27 BUV737, 1:200; CD8 BV480, 1:200; CD279 BV650, 1:20; CD197 BV786, 1:15; CD4 BB515, 1:50; CD28 BB700, 1:100; CD38 PE-CF594, 1:600; HLA-DR APC-R700, 1:150; all BD Biosciences; DUMP channel: CD14 APC-eFluor780, 1:100; CD16 APC-eFluor780, 1:100; CD19 APC-eFluor780, 1:100; fixable viability dye eFluor780, 1:1,667; all ThermoFisher Scientific). Cells were fixed for 15 minutes at 4° C. in 1× Stabilization Fixative (BD), acquired on a FACSymphony™ A3 flow cytometer (BD Biosciences) and analysed with FlowJo software version 10.6.2 (FlowJo LLC, BD Biosciences). $CD8^+$ T cell reactivities were considered positive, when a clustered population was observed that was labelled with only two pMHC multimer colors.

Example 26: Evidence Suggesting Possibility of Re-Infection

The primary endpoint was evaluated in individuals without prior evidence of COVID-19 disease, and very few cases of confirmed COVID-19 occurred among participants with evidence of infection prior to vaccination (although more cases occurred in the placebo group compared with the vaccine group). However, available data, while limited, as shown in Tables 22-23 suggest that previously infected individuals can be at risk of COVID-19 (i.e., reinfection) and could benefit from vaccination.

TABLE 22

Vaccine Efficacy - First COVID-19 Occurrence From 7 Days After Dose 2, by Test Status - Subjects With or Without Evidence of Infection Prior to 7 Days After Dose 2 - Evaluable Efficacy (7 Days) Population

| RT-PCR NP Swab Results and Serostatus: Time Points | Vaccine Group N[a] = 19965 Cases n1[b] surveillance time[c] (n2[d]) | Control Group N[a] = 20172 Cases n1[b] surveillance time[c] (n2[d]) | Vaccine Efficacy % (95% CI[e]) |
|---|---|---|---|
| Pre-dose 1 SARS-CoV-2 RT-PCR (NP swab) | | | |
| Positive | 0<br>0.013 (119) | 0<br>0.015 (137) | NE (NE, NE) |
| Negative | 9<br>2.301 (18259) | 166<br>2.314 (18410) | 94.5<br>(89.4, 97.6) |
| Unknown | 0<br>0.017 (181) | 3<br>0.016 (161) | 100.0<br>(−126.2, 100.0) |
| Pre-dose 2 SARS-CoV-2 RT-PCR (NP swab) | | | |
| Positive | 0<br>0.009 (83) | 1<br>0.012 (106) | 100<br>(−4916.4, 100.0) |
| Negative | 9<br>2.301 (18263) | 167<br>2.315 (18408) | 94.6<br>(89.5, 97.6) |
| Unknown | 0<br>0.022 (213) | 1<br>0.018 (194) | 100.0<br>(−3173.8, 100.0) |
| Subjects with negative RT-PCR pre-dose 1 and positive RT-PCR pre-dose 2 | | | |
| Subjects with documented COVID-19 symptoms between dose 1 and 2 | 0<br>0.000 (0) | 0<br>0.000 (1) | — |
| Subjects with no documented COVID-19 symptoms between dose 1 and 2 | 0<br>0.004 (44) | 1<br>0.006 (52) | — |
| Pre-dose 1 serostatus[f] | | | |
| Positive | 1<br>0.052 (488) | 1<br>0.056 (525) | −8.0<br>(−8378.1, 98.6) |

TABLE 22-continued

Vaccine Efficacy - First COVID-19 Occurrence From 7 Days After Dose 2, by Test Status - Subjects With or Without Evidence of Infection Prior to 7 Days After Dose 2 - Evaluable Efficacy (7 Days) Population

| RT-PCR NP Swab Results and Serostatus: Time Points | Vaccine Group $N^a$ = 19965 Cases n1[b] surveillance time[c] (n2[d]) | Control Group $N^a$ = 20172 Cases n1[b] surveillance time[c] (n2[d]) | Vaccine Efficacy % (95% CI[e]) |
|---|---|---|---|
| Negative | 8<br>2.255 (17823) | 167<br>2.260 (17894) | 95.2<br>(90.3, 98.0) |
| Unknown | 0<br>0.025 (248) | 1<br>0.030 (289) | 100.0<br>(−4527.0, 100.0) |
| 1-month post-dose 2 (Visit 3) serostatus* | | No data shown | |
| Positive | | | |
| Negative | | | |
| Subjects who seroconverted** between dose 1 and 1-month post-dose 2 | | No data shown | |
| Subjects with documented COVID-19 symptoms during time period | | | |
| Subjects with no documented COVID-19 symptoms during time period (protocol-defined vaccine efficacy against asymptomatic infection) | | | |

Abbreviations:
N-binding = SARS-CoV-2 nucleoprotein-binding; RT-PCR = reverse transcription-polymerase chain reaction; SARS-CoV-2 = severe acute respiratory syndrome coronavirus 2; VE = vaccine efficacy; NP = nasopharyngeal; NE = Not estimable.
[a]N = number of subjects in the specified group.
[b]n1 = Number of subjects meeting the endpoint definition.
[c]Total surveillance time in 1000 person-years for the given endpoint across all subjects within each group at risk for the endpoint. Time period for COVID-19 case accrual is from 7 days after Dose 2 to the end of the surveillance period.
[d]n2 = Number of subjects at risk for the endpoint.
[e]Confidence interval (CI) for VE is derived based on the Clopper and Pearson method adjusted for surveillance time.
[f]Based on N-binding test result.

TABLE 23

Vaccine Efficacy - First COVID-19 Occurrence From 7 Days After Dose 2, by Test Status - Subjects With or Without Evidence of Infection Prior to 7 Days After Dose 2 - All Available Efficacy Population

| RT-PCR NP Swab Results and Serostatus: Time Points | Vaccine Group $N^a$ = 20488 Cases n1[b] surveillance time[c] (n2[d]) | Control Group $N^a$ = 20459 Cases n1[b] surveillance time[c] (n2[d]) | Vaccine Efficacy % (95% CI[e]) |
|---|---|---|---|
| Pre-dose 1 SARS-CoV-2 RT-PCR (NP swab) | | | |
| Positive | 0<br>0.014 (122) | 0<br>0.015 (138) | NE (NE, NE) |
| Negative | 9<br>2.358 (18740) | 169<br>2.338 (18668) | 94.7<br>(89.7, 97.6) |
| Unknown | 0<br>0.018 (187) | 3<br>0.016 (165) | 100.0<br>(−125.3, 100.0) |
| Pre-dose 2 SARS-CoV-2 RT-PCR (NP swab) | | | |
| Positive | 0<br>0.010 (86) | 1<br>0.012 (107) | 100.0<br>(−4739.5, 100.0) |
| Negative | 9<br>2.357 (18743) | 170<br>2.339 (18660) | 94.7<br>(89.8, 97.6) |
| Unknown | 0<br>0.022 (220) | 1<br>0.019 (204) | 100.0<br>(−3290.7, 100.0) |
| Subjects with negative RT-PCR pre-dose 1 and positive RT-PCR pre-dose 2 | | | |
| Subjects with documented COVID-19 symptoms between dose 1 and 2 | 0<br>0.000 (0) | 0<br>0.000 (1) | — |

TABLE 23-continued

Vaccine Efficacy - First COVID-19 Occurrence From 7 Days After Dose 2, by Test Status - Subjects With or Without Evidence of Infection Prior to 7 Days After Dose 2 - All Available Efficacy Population

| RT-PCR NP Swab Results and Serostatus: Time Points | Vaccine Group $N^a$ = 20488 Cases n1[b] surveillance time[c] (n2[d]) | Control Group $N^a$ = 20459 Cases n1[b] surveillance time[c] (n2[d]) | Vaccine Efficacy % (95% CI[e]) |
|---|---|---|---|
| Subjects with no documented COVID-19 symptoms between dose 1 and 2 | 0<br>0.005 (47) | 1<br>0.006 (53) | — |
| Pre-dose 1 serostatus[f] | | | |
| Positive | 1<br>0.053 (500) | 1<br>0.057 (537) | −7.5<br>(−8335.1, 98.6) |
| Negative | 8<br>2.308 (18278) | 170<br>2.283 (18144) | 95.3<br>(90.6, 98.0) |
| Unknown | 0<br>0.028 (271) | 1<br>0.030 (290) | 100.0<br>(−4081.4, 100.0) |
| 1-month post-dose 2 (Visit 3) serostatus* | | No data shown | |
| Positive | | | |
| Negative | | | |
| Subjects who seroconverted** between dose 1 and 1-month post-dose 2 | | No data shown | |
| Subjects with documented COVID-19 symptoms during time period | | | |
| Subjects with no documented COVID-19 symptoms during time period (protocol-defined vaccine efficacy against asymptomatic infection) | | | |

Abbreviations:
N-binding = SARS-CoV-2 nucleoprotein-binding; RT-PCR = reverse transcription-polymerase chain reaction; SARS-CoV-2 = severe acute respiratory syndrome coronavirus 2; VE = vaccine efficacy; NP = nasopharyngeal; NE = Not estimable.
[a]N = number of subjects in the specified group.
[b]n1 = Number of subjects meeting the endpoint definition.
[c]Total surveillance time in 1000 person-years for the given endpoint across all subjects within each group at risk for the endpoint. Time period for COVID-19 case accrual is from 7 days after Dose 2 to the end of the surveillance period.
[d]n2 = Number of subjects at risk for the endpoint.
[e]Confidence interval (CI) for VE is derived based on the Clopper and Pearson method adjusted for surveillance time.
[f]Based on N-binding test result.

Example 27: Pharmacokinetics (PK) and Absorption, Distribution, Metabolism, and Excretion (ADME) Analysis of Certain Lipid Excipients The present Example describes various assessed characteristics (e.g., PK/ADME characteristics) of lipids used in a vaccine composition as described herein. Without wishing to be bound by any particular theory it is noted that such characteristics of lipid components may contribute to relevant features (e.g., distribution, expression, etc) of administered vaccines, including to efficacy generally and/or in particular circumstances (e.g., when administered according to particular regimens and/or to particular populations, etc).

Absorption

A single dose PK study of ALC-0315 and ALC-0319 following intravenous (IV) bolus injection of a nanparticle formulation in rats was conducted to assess the PK and metabolism of lipid excipients ALC-0315 and ALC-0159. This study used LNPs containing surrogate luciferase RNA, with the lipid composition being identical to BNT162b2, to investigate the in vivo disposition of ALC-0159 and ALC-0315.

Concentrations of ALC-0159 dropped approximately 8000- and >250-fold in plasma and liver, respectively, during this 2-week study. For ALC-0315, the elimination of the molecule from plasma and liver was slower, but concentrations fell approximately 7000- and 4-fold in two weeks for plasma and liver, respectively. Overall, the apparent terminal t½ in plasma and liver were similar in both tissues and were 2-3 and 6-8 days for ALC-0159 and ALC-0315, respectively. The apparent terminal t½ in plasma likely represents the re-distribution of the respective lipids from the tissues into which they have distributed as the LNP, back to plasma where they are eliminated.

Metabolism

In vitro metabolism of ALC-0315 and ALC-0159 was evaluated in blood, liver microsomes, S9 fractions, and hepatocytes from mice, rats, monkeys, and humans. In vivo metabolism was examined in rat plasma, urine, faeces, and liver samples from the PK study. Metabolism of ALC-0315 and ALC-0159 appears to occur relatively slowly in vitro and in vivo. ALC-0315 and ALC-0159 are apparently metabolised by hydrolytic metabolism of the ester and amide functionalities, respectively, and this hydrolytic metabolism is observed across the species evaluated.

Excretion

Excretion studies appeared to demonstrate that 50% of ALC-0159 was eliminated unchanged in faeces, and that metabolism played a role in the elimination of ALC-0315, as little to no unchanged material was detected in either urine or faeces. Investigations of urine, faeces and plasma from the rat PK study identified a series of ester cleavage products of ALC-0315. Without wishing to be bound by any particular theory, it is proposed that this likely represents the primary clearance mechanism acting on this molecule in vivo. In vitro, ALC-0159 was metabolized slowly by hydrolytic metabolism of the amide functionality.

Example 28: Distribution Analysis of Administered Vaccine Composition

In vivo biodistribution of COVID-19 mRNA Vaccine BNT162b2 was evaluated using mice as a model system and assessing luciferase expression as a surrogate reporter. Protein expression was demonstrated at the site of injection and to a lesser extent, and more transiently, in the liver after mice received an IM injection of RNA encoding luciferase in an LNP formulation like BNT162b2. Luciferase expression was identified at the injection site at 6 hours after injection and diminsihed to near near baseline levels by day 9. Expression in the liver was also present at 6 hours after injection and was not detected by 48 hours after injection. All other tissues than liver evaluated contain equal to or less than 1% of the dose.

Example 29: Repeat-Dose Toxicity Study of Various Dosing Regimens

A GLP-compliant repeat-dose study performed in rats to evaluate immunogenicity and toxicity of COVID-19 mRNA vaccines, including BNT162b2.

In certain studies, male and female Wistar Han rats were given a vaccine composition as described herein; compositions based on various RNA platforms (e.g., BNT162b2) were tested as IM injection(s) into the hind limb on three occasions each a week apart (dosing days 1, 8 and 15). Different doses (10, 30 and 100 μg) were tested; the lower doses were given as a single injection of 20-70 μl while the highest doses (100 μg) and controls were given as two injections (one in each hind limb) of 100 μl each. The control was phosphate buffered saline/300 mM sucrose, corresponding to the storage buffer of the vaccine product. Each group had 18 male and 18 female rats, assigned as 10 to the main study, 5 for recovery groups and 3 as additional animals for cytokine analyses. The recovery period was 3 weeks after the last dose. Necropsy was performed on study day 17, ~48 hours after the last dose and after the 3-week recovery period.

No unscheduled deaths were observed.

Dosing was considered well tolerated and did not present any signs of systemic toxicity; there was a slight increase in body temperature in the hours after dosing and some loss in body weight over the same period but these were not of a magnitude to be considered adverse.

Local inflammatory reactions were observed at the intramuscular injection site. Injection site changes noted were oedema, erythema, and induration, more severe and more frequent after the second and/or third doses compared to the first; however, these resolved prior to subsequent dosing and were fully recovered at the end of the 3-week recovery period.

Macroscopic findings at the injection sites included induration or thickening, occasionally accompanied by encrustation, which was noted for nearly all rats. This correlated microscopically with inflammation and variable fibrosis, oedema, and myofibre degeneration. Inflammation at the injection site was accompanied by elevations in circulating white blood cells and acute phase proteins (fibrinogen, alpha-2 macroglobulin, and alpha-1 acid glycoprotein).

Inflammation was occasionally evident extending into tissues adjacent to the injection site. There was enlargement of the draining (iliac) lymph nodes evident at the end of dosing. This correlated with increased cellularity of germinal centres and increased plasma cells in the draining (iliac) lymph node and is an anticipated immune response to the administered vaccine.

Enlargement of spleen and increased spleen weights correlated microscopically to increased haematopoiesis and increased haematopoiesis was also evident in the bone marrow. These findings are likely secondary to the immune/inflammatory responses to the vaccine.

At the end of the recovery period, injection sites were normal, clinical pathology findings and macroscopic observations had resolved and there was evidence of recovery of the injection site inflammation on microscopy.

Microscopic vacuolation of portal hepatocytes was present after the dosing phase. This observation was absent after the recovery period. There were no elevations in alanine aminotransferase (ALAT). There were elevations in gamma-glutamyltransferase (GGT) in all vaccinated rats, but there were no macroscopic or microscopic findings consistent with cholestasis or hepatobiliary injury to explain the increased gamma-GT activity which was completely resolved at the end of the 3-week recovery period. The vacuolation may be related to hepatic distribution of the pegylated lipids in the LNP. No changes were seen in serum cytokine concentrations. There were no effects noted on ophthalmological and auditory assessments, nor on external appearance or behaviour; in particular, gait was normal meaning that the changes seen did not affect the rats' mobility. No vaccine-related changes were seen in serum cytokine concentrations.

Testing for immunogenicity showed that COVID-19 mRNA Vaccines (including, e.g., BNT162b2 such as BNT162b2 v8) elicited a specific IgG antibody response to SARS CoV-2 spike protein directed against the S1 fragment and the receptor binding domain. A neutralizing antibody response was also observed with the vaccine in a pseudovirus neutralization assay.

Results from ELISA assays are shown in FIGS. 117 and 118 (from day 17 or day 10 as noted in the figures), in which the very top traces are those for COVID-19 mRNA Vaccine BNT162b2 and other traces are those for other COVID-19 mRNA vaccines using different constructs as described herein: similar results were shown for day 38 (not shown here). These translated into neutralising activity as seen in the VSV/SARS-CoV2-S pseudovirus neutralisation test using Vero 76 cells (FIG. 119): similar results were presented for day 38 (not shown here). Across the vaccines tested in this study those with a higher antigen-specific antibody titre also had a more pronounced virus neutralisation effect.

COVID-19 mRNA vaccines (e.g., BNT162b2) were well tolerated, and produced inflammatory changes at the injection sites and the draining lymph nodes, increased haematopoiesis in the bone marrow and spleen, and clinical pathology changes consistent with an immune response or inflammation in the injection sites. Those skilled in the art, reading the present disclosure, will appreciate that the findings in this Example can be considered typical of those expected with dosing of various mRNA constructs and/or lipid nanoparticles as described herein.

Example 30: Toxicity and Immunogenicity Study of Three-Dose Regimen

A study was performed to assess toxicity in rats given COVID-19 mRNA Vaccine (e.g., BNT162b2). This study was in compliance with Good Laboratory Practice.

Male and female Wistar Han rats were given BNT162b2 as an IM injection into the hind limb on three occasions, each a week apart (dosing days 1, 8 and 15). Necropsy was performed on study day 17, ~48 hours after the last dose, and after the 3-week recovery period. COVID-19 mRNA Vaccine BNT162b2 was supplied at 0.5 mg/ml and the dose volume was 60 μl, to give 30 μg per dose. Control rats received saline. Blood was taken at various points during the assessment, prior to and during dosing, and also during recovery, and antibody responses to vaccine components were assessed.

All rats given COVID-19 mRNA Vaccine (e.g., BNT162b2) survived to their scheduled necropsy: there were no changes noted in clinical signs or body weight changes noted. A reduction in food intake was noted on days 4 and 11 (to 0.83× controls) and there was an increase in mean body temperature post-dose on day 1 (up to 0.54° C.), day 8 (up to 0.98° C.), and day 15 (up to 1.03° C.) compared to controls.

At injection sites, there were instances of oedema and erythema on days 1 (maximum of slight oedema and very slight erythema), 8 (maximum of moderate oedema and very slight erythema) and 15 (maximum of moderate oedema and very slight erythema) which fully resolved and were not noted prior to dosing on days 8 and 15. Haematological tests showed higher white blood cells (up to 2.95× controls), primarily involving neutrophils (up to 6.80× controls), monocytes (up to 3.30× controls), and large unstained cells, LUC, (up to 13.2× controls) and slightly higher eosinophils and basophils on days 4 and 17. White blood cells were higher on day 17 as compared with day 4. There were transiently lower reticulocytes on day 4 (to 0.27× controls) in both sexes and higher reticulocytes on day 17 (up to 1.31× controls) in females only. Lower red blood cell mass parameters (to 0.90× controls) were present on days 4 and 17. There were lower A:G ratios (to 0.82×) on days 4 and 17. Higher fibrinogen was noted on day 17 (up to 2.49×) compared to controls, consistent with an acute phase response. The acute phase proteins alpha-1-acid glycoprotein (up to 39× on day 17) and alpha-2 macroglobulin (up to 71× on Day 17) were elevated on days 4 and 17 with higher concentrations in males. There were no changes urinalysis parameters.

At post-mortem there were higher absolute and relative spleen weights in vaccinated rats (up to 1.42× in males and to 1.62× in females). There were no other changes in organ weights. Macroscopic findings included enlarged draining lymph nodes and pale/dark firm injection sites in a minority of vaccinated rats. The dosing was tolerated without inducing any systemic toxicity with all changes consistent with an inflammatory response and immune activation: findings are consistent with those typically associated with dosing of lipid nanoparticle-encapsulated mRNA vaccines.

Example 31: Reproduction Toxicity

A study was performed to assess reproduction toxicity in female rats given COVID-19 mRNA vaccines, including BNT162b2. Female rats were given a COVID-19 mRNA vaccine (e.g., BNT162b2) twice before the start of mating and twice during gestation at a human clinical dose (e.g., 30 μg RNA/dosing day). The COVID-19 mRNA vaccine was administered intramuscularly (IM) to FO female Wistar rats 21 and 14 days before the start of mating (M-21 and M-14, respectively) and then on Gestation Day (GD) 9 and GD20, for a total of 4 doses. A subgroup was terminated at GD21 and another (litter) group was terminated at PostNatal Day (PND) 21. SARS-CoV-2 neutralizing antibody titers were found in the majority of females just prior to mating (M-14), in most females and foetuses at the end of gestation (GD21), and in most offspring at the end of lactation (PND21). There was transient reduced body weight gain and food consumption after each dose. No effects on the estrous cycle or fertility index were observed. While there was an increase (~2×) of pre-implantation loss (as compared to control), the pre-implantation loss percent observed in the vaccinated group was within historical control data range (5.1%-11.5%). Among foetuses (from a total of n=21 dams/litters), there was a very low incidence of gastroschisis, mouth/jaw malformations, right sided aortic arch, and/or cervical vertebrae abnormalities. Regarding skeletal findings, the exposed group had comparable to control group levels of presacral vertebral arches supernumerary lumbar ribs, supernumerary lumbar short ribs, caudal vertebrae number <5). There were no signs of adverse effects on the postnatal pups (terminated at PND21). This study shows that there is no significant adverse effects on fertility and early embryogenesis.

Example 32: Safety and Immunogenicity of the SARS-COV-2 BNT162b1 mRNA Vaccine in Younger and Older Chinese Adults: A Randomized, Placebo-Controlled, Observer-Blind Phase I Study The present Example reports initial results from a phase I trial testing BNT162b1 in 144 healthy Chinese participants. BNT162b1 encodes the SARS-CoV-2 spike glycoprotein receptor-binding domain (RBD) and is one of several RNA-based SARS-CoV-2 vaccine candidates described herein.

The present Example specifically reports on the observed safety profile, in which fever >39° C. was the only Grade 3 adverse event reported. Prime-boost vaccination with 10 μg or 30 μg BNT162b1 induced robust antibody and T-cell responses in both young (18 to 59 years of age) and older (65 to 85) Chinese adults. Both dose levels induced seroconversion after 41 d: Geometric mean titres of SARS-CoV-2 serum-neutralizing antibodies in younger participants in the 10 μg and 30 μg dose groups were 1.9 and 2.1 times that of convalescent sera from recovered COVID-19 patients; and in older participants 0.7 and 1.3 times. Interferon-γ T cell responses to RBD antigen challenge were significantly higher in participants receiving BNT162b1 than those in placebo group.

Increased reactogenicity as well as a more favorable vaccine-elicited virus-neutralizing response were associated with the 30 μg dose of BNT162b1 in both younger and older Chinese adults.

The safety and immunogenicity data provided in the present Example for BNT162b1, specifically with respect to vaccination of healthy, young and elderly Chinese participants, suggests that prime-boost vaccination with 10 μg and 30 μg dose levels of the BNT162b1 vaccine induces a strong humoral and cellular immunogenic response in both younger adults of 18 to 55 years of age and older adults of 65 to 85 years of age, with robust RBD-specific antibody and T-cell responses seen in in both younger and older participants, at least within 28 days following the prime-boost vaccination. Certain findings in this study further confirm aspects of the tolerability profile for BNT162b1, for example as also observed in American and German populations.

Methods

A randomized, placebo-controlled, observer-blind phase 1 trial was conducted in 144 healthy young adults, 18 to 59 years of age, and older adults 65 to 85 years of age in Taizhou, Jiangsu Province, China. Eligible participants were randomized to receive two doses, administered 21 days apart, of either BNT162b1 at a dose of 10 μg or 30 μg or placebo, administered as an intramuscular injection. Study participants, investigators, and laboratory staff were blinded to treatment administration. The primary safety endpoints were local reactions at injection site or systemic adverse reactions within 14 days after vaccination, and adverse events occurring up to 28 days after receiving the boost vaccination. The immunogenic endpoints of virus-neutralizing antibody, and antigen-specific binding antibodies and cellular immune responses elicited by vaccine were measured at predefined timepoints.

Results

Study Design and Analysis Set

A total of 296 adults aged between 18-55 years or 65-85 years were screened at Taizhou vaccine clinical research center in Jiangsu Province, in China. 144 eligible participants consented to participate in the trial and were randomized 1:1:1 to receive prime and boost doses of BNT162b1 at 10 μg or 30 μg, or two placebo doses 21 days apart. Following priming doses, two participants between the ages of 65 and 85 years had withdrawn from boost dose administration (one at 10 μg, one at 30 μg). The demographic characteristics of the participants are shown in Table 24. The mean age among the younger participants ranged from 37.9 to 42.0 years, and the mean age among the older participants ranged from 68.5 to 70.7 years in the treatment groups, with equal gender distribution across treatment groups. The medical history or existing underlying disorders of the participants were similar across treatment groups, with the exception of hypertension, which was noted in older participants at baseline.

Observed Safety and Tolerability Data

Within 14 days after completion of dosing, 21(88%) of the younger participants in the 10 μg BNT162b1 dose group and 24 (100%) of the younger participants in the 30 μg BNT162b1 dose group reported at least one solicited adverse reaction, versus 17% of the younger participants in the placebo group (Tables 25A-25B). Reactogenicity was dose level dependent and most evident in the 30 μg BNT162b1 dose group. The most common solicited adverse reactions reported were injection site pain, fever, headache, fatigue, malaise, joint pain, muscle pain chills. The adverse events were transient and either managed with simple standard of care management, or resolved spontaneously. Most of the reported adverse reactions were mild or moderate in severity, and resolved within the first seven days after each BNT162b1 dose. No injection site reactions were graded as severe (grade 3). All of the grade 3 systemic adverse reactions associated with the vaccination were fever, predominantly observed in the younger participants. One male participant in the older age group experienced an episodic Grade 3 fever accompanied by pain and pruritus at the injection site after administration of the prime BNT162b1 dose at 30 μg, and electively withdrew from boost vaccination administration.

No pre-specified trial-halting rules were met during the study. Only one serious adverse event was reported by a participant of 67 years of age (a humerus fracture caused by a car accident, preventing the participant from receiving the boost dose) which was considered as not related to the vaccine or study procedure. The overall frequencies of injection site adverse reactions post-vaccination were comparable after the BNT162b1 prime and boost doses. Some systematic adverse reactions such as fever, headache, fatigue, and malaise occurred more commonly after the BNT162b1 boost dose than after the prime dose in younger adults. In contrast to the younger participants, elderly participants did not present with increased reactogenicity after the BNT162b1 boost dose.

There were no changes reported in blood pressure and respiratory rates among the participants across different treatment groups before and after BNT162b1 administration. Transient increases of temperature and pulse rate 24 hours post-vaccination were noted in both younger and older participants, especially in the 30 μg dose group. The most common abnormalities in laboratory values from baseline were transient decreases in lymphocyte and platelet counts and increases in C-reaction protein. All laboratory abnormalities were self-limited and resolved in a short period of time without clinical manifestations. These data are consistent with certain findings reported in other populations (e.g., as described elsewhere herein).

Vaccine-Induced Antibody Responses

All participants were seronegative at baseline (day 1, pre-vaccination), and were monitored for seroconversion at days 8, 22, 29 and 43 by analyses of SARS-CoV-2 neutralizing antibodies and RBD and S1 protein binding antibodies. The BNT162b1 induced antibody responses in vaccinated participants were compared with a panel of human COVID-19 convalescent serum obtained at least 14 days after PCR-confirmed diagnosis from 28 COVID-19 patients. The highest neutralization titers were observed on day 43 (i.e., 21 days after the BNT162b1 boost dose), indicating a continuous uptrend in this group of Asian participants after day 29, which seems to further increase in this Asian population at day 43 among older participants as compared with reports in other populations, showing peak titres occurring earlier and subsequently subsiding in this subject population. On day 43, both 10 μg and 30 μg BNT162b1 dose levels induced significant virus-neutralizing antibody responses after the BNT162b1 prime dose which was boosted by the second BNT162b1 dose, with geometric mean titers (GMTs) of 232.9 (95% Cl 151.3 to 358.5) and 254.0 (184.6 to 349.4) in the younger participants, and 80.0 (49.2 to 130.2) and 160.0 (96.7 to 264.6) in the older participants in the 10 μg and 30 μg dose groups, respectively (FIG. 120). The virus-neutralizing responses of younger participants in the 10 μg and 30 μg dose groups were 1.9 and 2.1 times the GMT of a panel of the convalescent sera (GMT, 119.9; 95% Cl, 70.4 to 203.9). In the older participants, the corresponding ratios were 0.7 and 1.3 times in the 10 μg and 30 μg dose groups, respectively. All the younger recipients showed positive seroconversion on Day 43, and the seroconversion rate was 91% at the 10 μg dose and 96% at the 30 μg dose in the older recipients on Day 43, respectively. Participants who received the 30 μg dose appeared to have somewhat higher virus-neutralizing antibody responses than those received the 10 μg dose. However, the older participants between the ages of 65 and 85 generally showed a slower virus-neutralizing response and lower peak response than the younger participants between the ages 18 and 55.

Similarly, both doses of BNT162b1 induced high levels of S1- and RBD-binding IgG in the participants after the prime-boost regimen. The S1- and RBD-binding IgG levels after vaccination across all timepoints in the vaccine recipients were highly correlated with the neutralizing titers regardless of the age and dose groups, with a correlation coefficient of 0.85, and 0.79 ($p<0.0001$), respectively.

Vaccine-Induced T-Cell Responses

Vaccine-induced CD8+ T cell responses in individuals immunized with BNT162b1 were characterized before the priming vaccination (day 1), on day 29 (7 days after the boost vaccination) and on day 43 (21 days after the boost vaccination), using a direct ex vivo IFNγ enzyme-linked immunosorbent spot (ELISpot) assay with peripheral blood mononuclear cells (PBMCs). At day 29, specific IFN-γ ELISpot responses against the Sp1 peptide pool (covering RBD) were significantly higher in participants receiving BNT162b1 than those in placebo group (FIG. 121). Younger participants aged 18 to 55 years had average spot-forming cells of 227.5 (95% CI, 146.5 to 308.5) in those who had received 10 μg vaccinations, and 223.5 (181.2 to 265.9) in those who had received the 30 μg vaccinations per 105 PBMCs. In older participants aged 65 to 85 years, a slightly lower spot-forming cells with averages of 156.5 (84.1 to 229.0) and 171.9 (113.4 to 230.3) were noted post-vaccination across the two dose groups. At day 43, younger participants receiving the prime-boost BNT162b1 regimen tended to show a mild decrease in their S1-specific IFN-γ ELISpot response compared to that seen on day 29; no blood samples were collected at this time point from the older participants, as so this data is not available. No differences between the BNT162b1 and the placebo groups were observed for IFN-γ ELISpot responses to the Sp2 peptide pool (which does not include peptides of the RBD encoded by BNT162b1) and minor non-specific responses to CD8+ T cells were observed in both dose groups.

DISCUSSION

The trial described in this Example was conducted in China in parallel with other BNT162 vaccine candidates in multiple regions[14]. One focus of the study was to establish data with respect to safety and immunogenicity of mRNA vaccines in Asian populations. This Example reports a first evaluation of both the safety and immunogenicity profiles of such an mRNA vaccine in a Chinese population, and furthermore of younger and older Chinese populations.

This is a preliminary report for the clinical trial of the modified-RNA-based SARS-CoV-2 vaccine candidate BNT162b1, which encodes the SARS-CoV-2 RBD, administrated to a healthy adult Chinese population. BNT162b1, like BNT162b2 (modRNA encoding the S protein derived from the same nucleoside-modified platform) induces strong vaccine-induced antibody responses and strong T cell responses. Clinical safety and immunogenicity for both BNT162b1 and BNT162b2 candidates have been evaluated in healthy adults in both German (younger adults; BNT162-01) and American (younger adults and elderly adults aged 65 to 85 years; BNT162-02) populations. In younger adult groups, severe local reactogenicity AEs within 7 days were fewer in American study (BNT162-02) and the present study (BNT162-03) as compared with the German study (BNT162-01). Systemic reactogenicity AEs within 7 days were broadly similar across studies. Systemic AEs (independent of relatedness) within 28 days post Dose 2 were slightly higher in the BNT162-02 and BNT162-03 studies, as compared to the BNT162-01 study.

In older adult groups, severe local reactogenicity AEs within 7 days were similar across studies. Systemic reactogenicity AEs within 7 days were slightly lower in the BNT162-03 study, as compared to the BNT162-01 and the BNT162-02 studies. Systemic AEs (independent of relatedness) within 28 days post Dose 2 were slightly higher in the BNT162-03 study as compared to the BNT162-02 study, however the severe AEs were lower. In summary, comparative analyses of the BNT162b1 safety profile between the BNT162-01, BNT162-02 and BNT162-03 studies at 30 μg showed a generally comparable profile, and in the systemic reactogenicity/older population even a better safety profile in the Asian population vs non-Asian. Thus, findings reported here further complements and expands reporting of BNT162b1 and other RNA-based vaccine candidates from clinical trials conducted in Germany and the United States[7, 8, 15].

The rationale for this study was to evaluate whether intrinsic and extrinsic differences between German and Chinese population have any impact on tolerability or immune responses to this novel type of vaccine. The safety profile of the vaccine candidate BNT162b1 in healthy Chinese adults observed in our study appear to be better than that reported in other populations, in term of severe reactogenicity by local and systemic reactions[7,15]. Body habitus, endogenous antibody repertoire may have an influence. The reactogenicity of BNT162b1 was dose-dependent. Increased frequencies of adverse events were observed after administration of the boost vaccination compared with those after the prime vaccination, especially in the younger participants. Older adults had lower incidences of adverse reactions than the younger participants. Grade 3 fever was reported by 17% of the younger participants and 8% of the older participants receiving 30 μg dose, respectively. Nearly all severe fever reactions were transient and self-limiting. One participant had withdrawn from the boost vaccination due to the reactions afterthe prime dose administration, having episodic fever or cold intolerance with or without temperature record accompanied by the injection site pain, itching and pruritus, which lasted over two weeks and resolved after taking Hydrocortisone Butyrate ointment. Transient decreases in lymphocyte counts as pharmacodynamic markers were predominantly observed in the younger recipients at 30 μg dose level of BNT162b1, which was associated with the redistribution of lymphocytes into lymphoid tissues by innate immune stimulation[16].

Both doses of the vaccine candidate BNT162b1 were effective at eliciting specific humoral and cellular immune responses, with a clear boost effect of the second vaccination on antibody titers found in both younger and older adults. BNT162b1 administered at a 30 μg dose following a prime-boost regimen induced an optimal level of immune responses in terms of virus-neutralizing antibody to SARS-CoV-2, which was higher than those in a panel of human convalescent serum samples, regardless of age. The humoral response in the Chinese participants showed a unique temporal pattern and peaked at day 43 in both age groups. Although the number of participants was small, and methodological differences in measurements that may occur can influence observed results, the findings reported here suggest that there may be a populational difference in response to the vaccine.

Since the vaccine candidate BNT162b1 is a modified RNA vaccine encoding a trimeric version of the RBD, the vaccine recipients in the study reported in the present Example demonstrated significant T-cell responses specific to S1 peptide pool (containing 166 15-mer S1 peptides of from the human SARS-CoV-2 virus), but not to the S2 peptide pool. The results indicated the cellular responses elicited by BNT162b1 was antigen specific. By contrast, the vaccine candidate BNT162b2 spectrum was different from other RNA-based SARS-CoV-2 vaccine, inducing T-cell responses could recognize both S1 and S2 peptide pools[15]. Nevertheless, data showed BNT162b1 at the 30 μg dose was highly immunogenic capable of eliciting strong humoral and cell-mediated responses in healthy Chinese adults.

Those skilled in the art appreciate that small sample size and age restriction of 18 years and older may limit the conclusive rigor of findings observed in the present Example. Regardless, given that prophylactic RNA vaccines as described herein represent a novel approach to vaccination, safety assessments, including in particular populations (e.g., in children and adolescent populations) are particularly valuable. Also, although comparison of serum neutralizing responses elicited by the vaccine candidates described herein with that in human convalescent serum panels provides meaningful assessment of the vaccines, the level of serological immunity needed to protect against COVID-19 has not yet been rigorously established[17]. Those skilled in the art also recognize that the human convalescent serum panels that have been used in different trials are not standardized among laboratories, and thus may have a different distribution of patient characteristics and timepoints of collection, so that direct comparison of results (e.g., characterizing different vaccine candidates and/or characterizing vaccine candidates relative to different convalescent serum) may not be informative.

In summary, results described in the present Example confirmed the dose-dependency safety and good immunogenicity profile of the RNA-based SARS-CoV-2 vaccine candidate BNT162b1 and further expand the previous findings for BNT162b1 in the Germany and the United States trials[7, 8, 15]. Increased reactogenicity as well as a more favorable vaccine-elicited virus-neutralizing response were found associated with the 30 μg of the BNT162b1 in both younger and older adults. In contrast, another vaccine candidate BNT162b2 manufactured from same platform, showed a more favorable safety profile[8]. BNT162b1 encodes a relatively small RBD immunogen, which might induce a narrower spectrum of neutralizing antibodies that are less robust to potential antigenic drift of SARS-CoV-2, compared with BNT162b2, which encodes a full-length spike immunogen[18]. It is worth noting that the candidate BNT162b2 has been found to be more than 95% effective in preventing COVID-19 in participants, with no decreasing efficacy in those over 65 years of age[19].

Methods

Study Design and Participants

This randomized, placebo-controlled, observer-blind phase I trial was performed in healthy young adults between 18 and 59 years old, and older adults between 65 and 85 years of age, in Taizhou, Jiangsu Province, China. Participants were in overall good health established by medical history, physical examination, and laboratory tests at the screening visit. Both males and females were included and agreed to use contraception during the trial. We excluded participants that were pregnant or breast-feeding. Participants that tested positive for SARS-CoV-2 via a commercial rapid diagnostic kit for IgM/IgG antibody to SARS-CoV-2 (manufactured by Livzon diagnostics inc., Zhuhai, China), or via testing with a pharyngeal swab nucleic acid diagnostic test (manufactured by Fosun pharma, Shanghai, China) were excluded. Imaging features of COVID-19 present in a chest CT scan was a further exclusion criteria. Participants with serious cardiovascular disease or chronic conditions such as uncontrolled diabetes and hypertension, human immunodeficiency virus, hepatitis B and hepatitis C were excluded. Written informed consent was obtained from each participant before the start of the study.

The study was conducted in accordance with the Declaration of Helsinki and Good Clinical Practice. The trial protocol was reviewed and approved by the National Medical Products Administration, China, and the institutional review board of the Jiangsu Provincial Center of Disease Control and Prevention.

Randomization and Blinding

Eligible participants between 18 and 55 years of age were enrolled in the younger age group, and older participants aged greater than or equal to 65 years and less than or equal to 85 years were enrolled in the older age group. Participants were randomized in a ratio of 1:1:1 to receive the low-dose BNT126b1 or high-dose BNT126b1 or placebo. Participants were stratified by gender, using a Web-based interactive response technology (IRT) system. The blocked randomization list was generated by an independent statistician using SAS software (version 9.4).

Authorized unblinded pharmacists prepared the vaccines or placebo according to the allocation of participants through the IRT system, and nurses administrated the investigational products to participants. The unblinded staff had no further involvement in the trial, and were forbidden to disclosure allocation information to others. All other investigators, participants, laboratory staff and the sponsor remained blinded throughout the trial.

Vaccine and Vaccination

BNT162b1 as administered consisted of a Good Manufacturing Practice (GMP)-grade mRNA drug substance encoding the trimerized SARS-CoV-2 spike glycoprotein RBD antigen, formulated with lipids to obtain the RNA-LNP drug product. Vaccine was transported and supplied as a buffered-liquid solution for intramuscular injection, and stored at −80° C., e.g., as described herein.

The low-dose and high-dose BNT126b1 contained 10 μg and 30 μg active ingredient, respectively, and the placebo was a commercial saline solution. Each participant received a prime-boost dosing regimen of vaccine candidate BNT162b1 at either 10 μg/0.5 ml or at 30 μg/0.5 ml or placebo of 0.5 ml administered into the deltoid, 21 days apart.

Monitoring of Safety and Immunogenicity

Each participant was asked to remain at the study site for at least six hours post vaccine administration to donate blood samples prior to and 24 hours post prime vaccination and again prior to and 8 days post boost vaccination for laboratory testing. Vital signs including temperature, blood pressure, pulse, and respiratory rate were measured at baseline, and one hour, three hours and six hours post-vaccination. Any adverse events following the vaccination were documented by participants using diaries until day 28 post-administration of the boost dose. Younger group participants were enrolled and received the vaccination first. Enrollment of the older age group was launched following evaluation of the preliminary safety data of the younger age group for the first 14 days post-prime vaccination. Severity of adverse events and laboratory abnormal changes are graded with both the scale issued by the China State Food and Drug Administration[20] and the U.S. Food and Drug Administration (FDA)[21]. Serum and PBMCs were collected before the vaccination, at day 8 and/or day 22 after the boost dose, to facilitate measurement of specific IgG antibody responses to RBD and spike glycoprotein S1, neutralizing antibody to SARS-CoV-2, and T-cell responses. All reported adverse events were reviewed by investigators. Adverse events were categorized as either possibly, probably, or definitely related to the vaccine candidate.

Human Convalescent Sera

The neutralizing titer is the reciprocal of the highest sample dilution that protects at least 50% of cells from cytopathic effects. A panel of 24 convalescent human serum samples were obtained from donors 18 to 70 years of age (mean age, 45.8 years) who had recovered from SARS-CoV-2 infection; samples were obtained at least 14 days after a polymerase chain reaction-confirmed diagnosis and after symptom resolution. The disease severities of these patients varied from non-symptomatic (n=3, 13%), mild (n=8, 33%), moderate (n=10, 42%), or severe (n=3, 13%).

Neutralizing geometric mean titers (GMTs) in subgroups of the donors were as follows: 40 for the 3 donors with non-symptomatic infections; 91.9 for the 8 donors with mild infection; 160 for those with moderate infection; and 226.3 in the 3 donors with severe infection. Each serum sample in the panel was from a different donor. Thus, most of the serum samples were obtained from persons with moderate Covid-19. The convalescent serum samples were tested side by side as comparators with the serum samples obtained from participants in this trial.

ELISA

We assessed binding antibody responses against the SARS-CoV-2 RBD and S1 by using the enzyme-linked immunosorbent assay (ELISA).

Microneutralization Assay

We detected the SARS-CoV-2 specific neutralizing antibody in serum by microneutralization assay based on cytopathy observed in a biosafety level 3 laboratory (BSL-3) with SARS-CoV-2 virus strain BetaCoV/JS02/human/2020 (EPI_ISL_411952).

ELISpot

Specific T-cell responses against the peptides were assessed by using a commercial ex-vivo interferon-γ (INF-γ) enzyme-linked Immunospot (ELISpot) kit manufactured by Mabtech (Nacka Strand, Stockholm, Sweden)[22]. PBMCs were isolated from fresh blood samples, and stimulated with different overlapping peptide pools before the measurement. The S1 peptide pool, which covers the N-terminal half of SARS-CoV-2 spike, including the RBD, and the S2 peptide pool, which covers the C-terminal of SARS-CoV-2 spike, which does not include the RBD were used in this study[23]. A peptide pool consisting of 32 MHC class I restricted viral peptides from human Cytomegalovirus, Epstein-Barr virus and Influenza virus (CEF peptide pool), was used to stimulate CD8+ T cells to assess general T-cell reactivity (not specific to SARS-CoV-2[24].)

Outcomes

The primary and secondary objectives of this trial were to evaluate safety and immunogenicity of the candidate vaccine BNT162b1 in healthy Chinese adults. The primary endpoints for safety evaluation were the incidence of solicited local reactions at the injection site or systemic adverse reactions within 14 days post vaccination, and adverse events following the immunization until 28 days after receiving the boost dose. Any clinical laboratory abnormalities from baseline to 24 hours or 7 days after vaccination, and any serious adverse event (SAE) that occurred were also recorded. The secondary endpoints for immunogenicity were geometric mean titer (GMT), seroconversion rates, and fold increase of virus-neutralizing antibody, and ELISA IgG antibodies binding to S1 or RBD measured at days 8, 22 after each vaccination. Seroconversion is defined as an increase by a factor of four or more in antibody titer over the baseline, or the lower limit value if the baseline titer is below the limit of detection. The serum dilution for ELISA started at 1:100, while that for microneutralization assay started at 1:10.

Cellular immune responses in terms of the number of positive cells with interferon gamma (IFN-γ) secretion among PBMCs at a concentration of $1\times10^5$/well at day 8 and 22 after the boost dose were explored as an exploratory endpoint.

Statistical Analysis

The total sample size in this study was 144 participants, 24 participants of each age group was included in each treatment group. Based on an assumption of 8% of the adverse reaction occurrence post-vaccination, the probability of observation of at least one event in 24 participants in each dose group was 86.5%.

All randomized participants who received at least one dose of the investigational vaccine were included in the safety analysis. Safety endpoints were described as frequencies (%) with 95% confidence interval (CI) of the adverse reactions or events during the observation period. We compared the proportions of the participants with adverse reactions or events across the groups using Chi-square or Fisher exact. All participants who received at least one vaccination and had results of serologic measurements before or after vaccination were included in the immunogenicity analysis. The immunological endpoints were descriptively summarized at the specified time points, and compared across the groups, using ANOVA for log-transformed antibody titres, or Wilcoxon rank-sum test for non-normal data. The neutralising antibody responses of the participants in each dose group were compared with those of patients who had PCR-confirmed SARS-CoV-2 infection. Any serologic values below the lower limit of detection were set to half of the value (1:50 for ELISA and 1:5 for microneutralization assay), while the values above the highest dilution titer were assigned values of the highest dilution for calculation. Pearson correlation analysis of the RBD or S1 specific ELISA antibody and neutralising antibody was performed to assess the relationship between responses on different assays.

REFERENCES

1. Gudbjartsson, D. F., et al. Spread of SARS-CoV-2 in the Icelandic Population. *The New Englandjournal of medicine* 382, 2302-2315 (2020); see also WHO factsheet: covid19.who.int/.
2. Huang, C., et al. Clinical features of patients infected with 2019 novel coronavirus in Wuhan, China. *Lancet* (London, England) 395, 497-506 (2020).
3. Jackson, L. A., et al. An mRNA Vaccine against SARS-CoV-2—Preliminary Report. *The New England journal of medicine* 383, 1920-1931 (2020).
4. World Health Organization. DRAFT landscape of COVID-19 candidate vaccines—3 Nov. 2020. Vol. 2020 (2020).
5. Corbett, K. S., et al. SARS-CoV-2 mRNA vaccine design enabled by prototype pathogen preparedness. *Nature* 586, 567-571 (2020).
6. Anderson, E. J., et al. Safety and Immunogenicity of SARS-CoV-2 mRNA-1273 Vaccine in Older Adults. *The New England journal of medicine* (2020).
7. Mulligan, M. J., et al. Phase I/II study of COVID-19 RNA vaccine BNT162b1 in adults. *Nature* 586, 589-593 (2020).

8. Walsh, E. E., et al. Safety and Immunogenicity of Two RNA-Based Covid-19 Vaccine Candidates. *The New England journal of medicine* (2020).
9. Wrapp, D., et al. Cryo-EM structure of the 2019-nCoV spike in the prefusion conformation. *Science* (New York, N.Y.) 367, 1260-1263 (2020).
10. Güthe, S., et al. Very fast folding and association of a trimerization domain from bacteriophage T4 fibritin. *Journal of molecular biology* 337, 905-915 (2004).
11. Krammer, F. SARS-CoV-2 vaccines in development. *Nature* 586, 516-527 (2020).
12. O'Callaghan, K. P., Blatz, A. M. & Offit, P. A. Developing a SARS-CoV-2 Vaccine at Warp Speed. *Jama* 324, 437-438 (2020).
13. Poland, G. A., Ovsyannikova, I. G. & Kennedy, R. B. SARS-CoV-2 immunity: review and applications to phase 3 vaccine candidates. *Lancet* (London, England) 396, 1595-1606 (2020).
14. Deming, M. E., Michael, N. L., Robb, M., Cohen, M. S. & Neuzil, K. M. Accelerating Development of SARS-CoV-2 Vaccines—The Role for Controlled Human Infection Models. *The New England journal of medicine* 383, e63 (2020).
15. Sahin, U., et al. COVID-19 vaccine BNT162b1 elicits human antibody and T(H)1 T cell responses. *Nature* 586, 594-599 (2020).
16. Kamphuis, E., Junt, T., Waibler, Z., Forster, R. Kalinke, U. Type I interferons directly regulate lymphocyte recirculation and cause transient blood lymphopenia. Blood 108, 3253-61 (2006).
17. Hodgson, S. H., et al. What defines an efficacious COVID-19 vaccine? A review of the challenges assessing the clinical efficacy of vaccines against SARS-CoV-2. *The Lancet*. Infectious diseases (2020).
18. Lan, J., et al. Structure of the SARS-CoV-2 spike receptor-binding domain bound to the ACE2 receptor. *Nature* 581, 215-220 (2020).
19. Pfizer Inc. Pfizer and BioNTech Announce Vaccine Candidate Against COVID-19 Achieved Success in First Interim Analysis from Phase 3 Study. Vol. 2020 (2020).
20. Center For Drug Evaluation, NMPA. Guidances for grading adverse reactions in clinical trials of preventive vaccines. Vol. 2020 (2008).
21. US Food and Drug Administration. Toxicity Grading Scale for Healthy Adult and Adolescent Volunteers Enrolled in Preventive Vaccine Clinical Trials. Vol. 2020 (2007).
22. Slota, M., Lim, J. B., Dang, Y. & Disis, M. L. ELISpot for measuring human immune responses to vaccines. *Expert review of vaccines* 10, 299-306 (2011).
23. Buchan, S. A., et al. Effectiveness of Live Attenuated vs Inactivated Influenza Vaccines in Children During the 2012-2013 Through 2015-2016 Influenza Seasons in Alberta, Canada: A Canadian Immunization Research Network (CIRN) Study. *JAMA pediatrics* 172, e181514 (2018).
24. Victor, J. C., et al. Efficacy of a Russian-backbone live attenuated influenza vaccine among children in Senegal: a randomised, double-blind, placebo-controlled trial. *The Lancet. Global health* 4, e955-e965 (2016).

TABLE 24

Baseline characteristics of the participants, by age groups.

| | Younger participants aged 18-55 years | | | Older participants aged 65-85 years | | |
|---|---|---|---|---|---|---|
| Characteristic | 10 μg | 30 μg | Placebo | 10 μg | 30 μg | Placebo |
| No. of participants | 24 | 24 | 24 | 24 | 24 | 24 |
| Age, mean (SD), years | 37.9 (9.6) | 39.7 (9.0) | 42.0 (8.7) | 70.5 (5.0) | 68.5 (3.0) | 70.7 (4.4) |
| Sex (female) | 12 (50%) | 12 (50%) | 12 (50%) | 12 (50%) | 12 (50%) | 12 (50%) |
| Body-mass index, kg/$m^2$ | 24.7 (3.2) | 23.0 (2.7) | 24.3 (3.4) | 24.0 (3.0) | 24.8 (2.9) | 23.5 (2.5) |
| Medical history or existing disorder | | | | | | |
| Cardiac ischemia | 2 (8%) | 2 (8%) | 2 (8%) | 0 | 0 | 0 |
| Sinus bradycardia | 0 | 2 (8%) | 1 (4%) | 0 | 0 | 0 |
| Hyperuricemia | 3 (13%) | 1 (4%) | 1 (4%) | 3 (13%) | 2 (8%) | 2 (8%) |
| Nasopharyngitis | 2 (8%) | 0 | 0 | 0 | 0 | 0 |
| Blood uric acid increased | 2 (8%) | 1 (4%) | 1 (4%) | 0 | 0 | 0 |
| Hypertension | 3 (13%) | 0 | 1 (4%) | 12 (50%) | 9 (38%) | 7 (29%) |
| Diabetes | 0 | 0 | 0 | 1 (4%) | 2 (8%) | 1 (4%) |
| Gastric inflammation | 0 | 0 | 0 | 0 | 0 | 2 (8%) |
| Others* | 3 (13%) | 5 (21%) | 1 (4%) | 3 (13%) | 3 (13%) | 4 (17%) |

Data are mean (SD) or n (%).

*"Others" includes tonsillitis, helicobacter infection, human papilloma virus infection, periodontitis, electrocardiogram high voltage, lymphadenopathy, anemia, hepatic cyst, oropharyngeal discomfort, hyperthyroidism, noninfective gingivitis, hyperlipaemia, benign prostatic hyperplasia, prostatitis, blindness unilateral, cerebral infarct, limb injury, deformity of spine, calculus urinary and lymphadenopathy.

TABLE 25A

Solicited adverse reactions within 14 days post-vaccination, and unsolicited adverse reactions till day 43, by age groups.

| | Younger participants aged 18-55 years | | | | Older participants aged 65-85 years | | | |
|---|---|---|---|---|---|---|---|---|
| Adverse reactions | 10 μg (n = 24) | 30 μg (n = 24) | Placebo (n = 24) | P value | 10 μg (n = 24) | 30 μg (n = 24) | Placebo (n = 24) | P value |
| Solicited adverse reactions within 14 days | | | | | | | | |
| Any | 21 (88%) | 24 (100%) | 4 (17%) | <0.0001 | 21 (88%) | 23 (96%) | 2 (8%) | <0.0001 |
| Grade 3 | 3 (13%) | 9 (38%) | 0 | 0.0015 | 0 | 2 (8%) | 0 | 0.3239 |

TABLE 25A-continued

Solicited adverse reactions within 14 days post-vaccination, and unsolicited adverse reactions till day 43, by age groups.

| Adverse reactions | Younger participants aged 18-55 years 10 μg (n = 24) | 30 μg (n = 24) | Placebo (n = 24) | P value | Older participants aged 65-85 years 10 μg (n = 24) | 30 μg (n = 24) | Placebo (n = 24) | P value |
|---|---|---|---|---|---|---|---|---|
| Injection-site adverse reactions | | | | | | | | |
| Any | 21 (88%) | 24 (100%) | 2 (8%) | <0.0001 | 18 (75%) | 21 (88%) | 0 | <0.0001 |
| Grade 3 | 0 | 0 | 0 | — | 0 | 0 | 0 | — |
| Pain | 21 (88%) | 23 (96%) | 2 (8%) | <0.0001 | 16 (67%) | 21 (88%) | 0 | <0.0001 |
| Redness | 6 (25%) | 8 (33%) | 0 | 0.0059 | 3 (13%) | 4 (17%) | 0 | 0.1492 |
| Swelling | 5 (21%) | 7 (29%) | 0 | 0.0137 | 0 | 5 (21%) | 0 | 0.0091 |
| Induration | 0 | 3 (13%) | 0 | 0.1018 | 0 | 1 (4%) | 0 | 1.0000 |
| Systemic adverse reactions | | | | | | | | |
| Any | 17 (71%) | 22 (92%) | 3 (13%) | <0.0001 | 9 (38%) | 19 (79%) | 2 (8%) | <0.0001 |
| Grade 3 | 3 (13%) | 9 (38%) | 0 | 0.0015 | 0 | 2 (8%) | 0 | 0.3239 |
| Fever* | 14 (58%) | 21 (88%) | 1 (4%) | <0.0001 | 7 (29%) | 19 (79%) | 1 (4%) | <0.0001 |
| Grade 3 | 3 (13%) | 9 (38%) | 0 | 0.0015 | 0 | 2 (8%) | 0 | 0.3239 |
| Headache | 11 (46%) | 19 (79%) | 3 (13%) | <0.0001 | 1 (4%) | 2 (8%) | 0 | 0.7682 |
| Fatigue | 12 (50%) | 16 (67%) | 0 | <0.0001 | 3 (13%) | 8 (33%) | 0 | 0.0045 |
| Malaise | 8 (33%) | 9 (38%) | 0 | 0.0013 | 2 (8%) | 4 (17%) | 1 (4%) | 0.4858 |
| Joint pain | 4 (17%) | 10 (42%) | 1 (4%) | 0.0067 | 0 | 1 (4%) | 0 | 1.0000 |
| Muscle pain | 2 (8%) | 10 (42%) | 0 | <0.0001 | 0 | 1 (4%) | 0 | 1.0000 |
| Chills | 4 (17%) | 7 (29%) | 0 | 0.0118 | 1 (4%) | 4 (17%) | 0 | 0.1185 |
| Nausea | 3 (13%) | 3 (13%) | 0 | 0.2330 | 0 | 0 | 0 | — |
| Anorexia | 1 (4%) | 4 (17%) | 0 | 0.1185 | 0 | 3 (13%) | 1 (4%) | 0.3143 |
| Diarrhea | 2 (8%) | 1 (4%) | 1 (4%) | 1.0000 | 0 | 0 | 0 | 1.0000 |
| Vomiting | 0 | 2 (8%) | 0 | 0.3239 | 0 | 0 | 0 | — |

TABLE 25B (modified) Solicited adverse reactions within 14 days post-vaccination, and unsolicited adverse reactions until day 43, by age groups including "placebo-corrected" AE rates.

| Adverse reactions | Younger participants aged 18-55 years 10 μg (n = 24) | 10 μg (minus placebo-AEs) | 30 μg (n = 24) | 30 μg (minus placebo-AEs) | Placebo (n = 24) | P value | Older participants aged 65-85 years 10 μg (n = 24) | 10 μg (minus placebo-AEs) | 30 μg (n = 24) | 30 μg (minus placebo-AEs) | Placebo (n = 24) | P value |
|---|---|---|---|---|---|---|---|---|---|---|---|---|
| Solicited adverse reactions within 14 days | | | | | | | | | | | | |
| Any | 21 (88%) | 17 (71%) | 24 (100%) | 20 (83%) | 4 (17%) | <0.0001 | 21 (88%) | 19 (79%) | 23 (96%) | 21 (88%) | 2 (8%) | <0.0001 |
| Grade 3 | 3 (13%) | 3 (13%) | 9 (38%) | 9 (38%) | 0 | 0.0015 | 0 | 0 | 2 (8%) | 2 (8%) | 0 | 0.3239 |
| Injection site adverse reactions | | | | | | | | | | | | |
| Any | 21 (88%) | 19 (79%) | 24 (100%) | 22 (92%) | 2 (8%) | <0.0001 | 18 (75%) | 18 (75%) | 21 (88%) | 21 (88%) | 0 | <0.0001 |
| Grade 3 | 0 | 0 | 0 | 0 | 0 | — | 0 | 0 | 0 | 0 | 0 | — |
| Pain | 21 (88%) | 19 (79%) | 23 (96%) | 21 (88%) | 2 (8%) | <0.0001 | 16 (67%) | 16 (67%) | 21 (88%) | 21 (88%) | 0 | <0.0001 |
| Redness | 6 (25%) | 6 (25%) | 8 (33%) | 8 (33%) | 0 | 0.0059 | 3 (13%) | 3 (13%) | 4 (17%) | 4 (17%) | 0 | 0.1492 |
| Swelling | 5 (21%) | 5 (21%) | 7 (29%) | 7 (29%) | 0 | 0.0137 | 0 | 0 | 5 (21%) | 5 (21%) | 0 | 0.0091 |
| Induration | 0 | 0 | 3 (13%) | 3 (13%) | 0 | 0.1018 | 0 | 0 | 1 (4%) | 1 (4%) | 0 | 1.0000 |
| Systemic adverse reactions | | | | | | | | | | | | |
| Any | 17 (71%) | 14 (58%) | 22 (92%) | 19 (79%) | 3 (13%) | <0.0001 | 9 (38%) | 7 (29%) | 19 (79%) | 17 (71%) | 2 (8%) | <0.0001 |
| Grade 3 | 1 (4%) | 1 (4%) | 4 (17%) | 4 (17%) | 0 | 0.0015 | 0 | 0 | 2 (8%) | 2 (8%) | 0 | 0.3239 |
| Fever* | 14 (58%) | 13 (54%) | 21 (88%) | 20 (83%) | 1 (4%) | <0.0001 | 7 (29%) | 6 (25%) | 19 (79%) | 18 (75%) | 1 (4%) | <0.0001 |
| Grade 3 | 1 (4%) | 1 (4%) | 4 (17%) | 4 (17%) | 0 | 0.0015 | 0 | 0 | 2 (8%) | 2 (8%) | 0 | 0.3239 |
| Grade 3 by NMPA criteria | 3 (13%) | 3 (13%) | 9 (38%) | 9 (38%) | 0 | 0.0015 | 0 | 0 | 2 (8%) | 2 (8%) | 0 | 0.3239 |
| Headache | 11 (46%) | 8 (33%) | 19 (79%) | 16 (67%) | 3 (13%) | <0.0001 | 1 (4%) | 1 (4%) | 2 (8%) | 2 (8%) | 0 | 0.7682 |
| Fatigue | 12 (50%) | 12 (50%) | 16 (67%) | 16 (67%) | 0 | <0.0001 | 3 (13%) | 3 (13%) | 8 (33%) | 8 (33%) | 0 | 0.0045 |
| Malaise | 8 (33%) | 8 (33%) | 9 (38%) | 9 (38%) | 0 | 0.0013 | 2 (8%) | 1 (4%) | 4 (17%) | 3 (13%) | 1 (4%) | 0.4858 |
| Joint pain | 4 (17%) | 3 (13%) | 10 (42%) | 9 (38%) | 1 (4%) | 0.0067 | 0 | 0 | 1 (4%) | 1 (4%) | 0 | 1.0000 |
| Muscle pain | 2 (8%) | 2 (8%) | 10 (42%) | 10 (42%) | 0 | <0.0001 | 0 | 0 | 1 (4%) | 1 (4%) | 0 | 1.0000 |
| Chills | 4 (17%) | 4 (17%) | 7 (29%) | 7 (29%) | 0 | 0.0118 | 1 (4%) | 1 (4%) | 4 (17%) | 4 (17%) | 0 | 0.1185 |
| Nausea | 3 (13%) | 3 (13%) | 3 (13%) | 3 (13%) | 0 | 0.2330 | 0 | 0 | 0 | 0 | 0 | — |
| Anorexia | 1 (4%) | 1 (4%) | 4 (17%) | 4 (17%) | 0 | 0.1185 | 0 | −1 | 3 (13%) | 2 (8%) | 1 (4%) | 0.3143 |
| Diarrhea | 2 (8%) | 1 (4%) | 1 (4%) | 0 | 1 (4%) | 1.0000 | 0 | 0 | 0 | 0 | 0 | 1.0000 |
| Vomiting | 0 | 0 | 2 (8%) | 2 (8%) | 0 | 0.3239 | 0 | 0 | 0 | 0 | 0 | |

TABLE 25B-continued (modified) Solicited adverse reactions within 14 days post-vaccination, and unsolicited adverse reactions until day 43, by age groups including "placebo-corrected" AE rates.

| | Younger participants aged 18-55 years | | | | | | Older participants aged 65-85 years | | | | | |
|---|---|---|---|---|---|---|---|---|---|---|---|---|
| Adverse reactions | 10 µg (n = 24) | 10 µg (minus placebo-AEs) | 30 µg (n = 24) | 30 µg (minus placebo-AEs) | Placebo (n = 24) | P value | 10 µg (n = 24) | 10 µg (minus placebo-AEs) | 30 µg (n = 24) | 30 µg (minus placebo-AEs) | Placebo (n = 24) | P value |
| Unsolicited adverse reactions within 28 days | | | | | | | | | | | | |
| Any | 9 (38%) | 8 (33%) | 10 (42%) | 9 (38%) | 1 (4%) | 0.0046 | 4 (17%) | 2 (8%) | 9 (38%) | 7 (29%) | 2 (8%) | 0.0590 |
| Fever† | 0 | 0 | 0 | 0 | 0 | — | 0 | 0 | 1 (4%) | 1 (4%) | 0 | 1.0000 |
| Temperature intolerance | 2 (8%) | 2 (8%) | 6 (25%) | 6 (25%) | 0 | 0.0230 | 0 | 0 | 4 (17%) | 4 (17%) | 0 | — |
| Injection site discomfort | 3 (13%) | 3 (13%) | 4 (17%) | 4 (17%) | 0 | 0.1492 | 2 (8%) | 2 (8%) | 3 (13%) | 3 (13%) | 0 | 0.3580 |
| Injection site pruritus | 2 (8%) | 2 (8%) | 3 (13%) | 3 (13%) | 0 | 0.3580 | 0 | 0 | 1 (4%) | 1 (4%) | 0 | 1.0000 |
| Pain not at injection site | 1 (4%) | 1 (4%) | 1 (4%) | 1 (4%) | 0 | 1.0000 | 0 | 0 | 0 | 0 | 0 | — |
| Dizziness | 3 (13%) | 3 (13%) | 1 (4%) | 1 (4%) | 0 | 0.3142 | 0 | 0 | 3 (13%) | 3 (13%) | 0 | 0.1018 |
| Blood uric acid increased | 1 (4%) | 1 (4%) | 1 (4%) | 1 (4%) | 0 | 1.0000 | 2 (8%) | 0 | 1 (4%) | −1 | 2 (8%) | 1.0000 |

Data are shown as number of participants with event (%). Grade 3 was severe reaction (i.e., prevented activity).

SAEs = Serious adverse events.

A participant was only counted once in the specific reaction category, also with more than one episode of the adverse reaction. Only unsolicited adverse reactions reported by two or more participants were listed. * Those febrile participants were graded according to the guidelines of Food and Drug Administration (FDA), the United States. Fever was also graded according to the grading guidelines for adverse events in vaccine clinical trials, issued by the National Medical Products Administration (NMPA), China, which defines grade 3 fever as axillary temperature ≥38.5° C.

†One participant experienced grade 3 fever accompanied with pain, itching and pruritus at the injection site after the prime dose, and electively withdrew from the boost vaccination.

Example 33: Neutralization of SARS-CoV-2 Lineage B.1.1.7 Pseudovirus by BNT162b2 Vaccine-Elicited Sera In September 2020, the SARS-CoV-2 variant B.1.1.7 was detected in the United Kingdom, and it subsequently increased in prevalence, showed enhanced transmissibility, and spread to other countries and continents. B1.1.7 has a series of mutations in its spike protein: ΔH69/V70, ΔY144, N501Y, A570D, D614G, P681H, T716I, S982A, and D1118H. One of these, N501Y, was of particular concern because it is located in the receptor binding site; the spike with this mutation binds more tightly to its cellular receptor, ACE-2; and virus with this mutation has increased host range that includes mice. 19 pseudoviruses, each bearing a SARS-CoV-2 S with a different mutation found in circulating strains, were neutralized as efficiently as non-mutant pseudoviruses by BNT162b2-immune sera. The following study demonstrates that a virus with the full set of mutations in the UK variant spike is also neutralized efficiently by BNT162b2-immune sera.

We generated VSV-SARS-CoV-2-S pseudoviruses bearing the Wuhan reference strain or lineage B.1.1.7 strain spike protein. Sera of 16 participants in the previously reported trial (Sahin U. et al., medRxiv 2020.12.09.20245175; doi: doi.org/10.1101/2020.12.09.20245175), drawn from eight younger (18-55 yrs) and eight older adults (56-85 yrs) 21 days after the booster immunization with 30 µg BNT162b2, were tested for neutralization of SARS-CoV-2 Wuhan and lineage B.1.1.7 spike-pseudotyped VSV by a 50% pseudovirus neutralization assay ($pVNT_{50}$; FIG. 122). The ratio of the 50% neutralization GMT of the sera against the SARS-CoV-2 lineage B.1.1.7 spike-pseudotyped VSV to that against the Wuhan reference spike-pseudotyped VSV was 0.79, indicating no biologically significant difference in neutralization activity against the two pseudoviruses.

The preserved neutralization of pseudoviruses bearing the B.1.1.7 spike by BNT162b2-immune sera suggests that the UK variant viruses will not escape BNT162b2-mediated protection. Furthermore, since there is good concordance between pseudotype neutralization and SARS-CoV-2 neutralization assays, the use of a non-replicating pseudovirus system is not expected to be a potential limitation of the work.

Materials and Methods

VSV-SARS-CoV-2 S Variant Pseudovirus Generation

A recombinant replication-deficient vesicular stomatitis virus (VSV) vector that encodes green fluorescent protein (GFP) and luciferase instead of the VSV-glycoprotein (VSV-G) was pseudotyped with SARS-CoV-2 spike (S) derived from either the Wuhan reference strain (NCBI Ref: 43740568) or the variant of concern (VOC)-202012/01 (also known as SARS-CoV-2 lineage B.1.1.7) according to published pseudotyping protocols (FIG. 123) (PMID: 21998709). In brief, HEK293T/17 monolayers transfected to express SARS-CoV-2 S were inoculated with VSV-G complemented VSVΔG vector. After incubation for 1 h at 37° C., the inoculum was removed. Cells were washed with PBS before medium supplemented with anti-VSV-G antibody (clone 8G5F11, Kerafast Inc.) was added to neutralize residual VSV-G complemented input virus. VSV-SARS- CoV-2-S pseudotype-containing medium was harvested 20 h after inoculation, 0.2 μm filtered and stored at −80° C. Prior to use in the neutralization test, the pseudovirus batches were titrated on Vero 76 cells, and the percent infected cells determined by flow cytometry (FIG. 124). Individual titers were calculated in transducing units (TU) per mL. Production of the VSV-SARS-CoV-2-S pseudoviruses bearing the Wuhan reference strain or lineage B.1.1.7 strain spike protein yielded similar titers (Table 26).

TABLE 26

Titers of SARS-CoV-2 Wuhan reference strain and lineage B.1.1.7 spike-pseudotyped VSV in transducing units (TU) per mL.

| VSV pseudovirus bearing | Titer [TU/mL] |
|---|---|
| Wuhan strain SARS-CoV-2 S | $1.59 \times 10^5$ |
| Lineage B.1.1.7 SARS-CoV-2 S | $1.30 \times 10^5$ |

Serum Specimens and Neutralization Assay

The immunization and serum collection regimen is illustrated schematically in FIG. 125. For measuring neutralization titers, each serum was 2-fold serially diluted in culture medium with the first dilution of 1:20 (dilution range of 1:20 to 1:2560). VSV-SARS-CoV-2-S particles were diluted in culture medium to obtain 100 TU in the assay. Serum dilutions were mixed 1:1 with pseudovirus for 30 minutes at room temperature prior to addition to Vero 76 cell monolayers in 96-well plates and incubation at 37° C. for 24 hours. Supernatants were removed, and the cells were lysed with luciferase reagent (Promega). Luminescence was recorded, and neutralization titers were calculated in GraphPad Prism version 9 by generating a 4-parameter logistical (4PL) fit of the percent neutralization at each serial serum dilution. The 50% pseudovirus neutralisation titre ($pVNT_{50}$) was reported as the interpolated reciprocal of the dilution yielding a 50% reduction in luminescence. A table of the neutralization titers is provided (Table 27). The ratio for each serum of the $pVNT_{50}$ against SARS-CoV-2 lineage B.1.1.7 and the Wuhan reference strain spike-pseudotyped VSV is plotted in FIG. 126.

TABLE 27

$pVNT_{50}$ values of 16 BNT162b2 post-immunization sera against SARS-CoV-2 Wuhan reference strain spike-pseudotype and lineage B.1.1.7 spike-pseudotyped VSV.

| | $pVNT_{50}$ | | $pVNT_{50}$ ratio |
|---|---|---|---|
| Serum ID | Wuhan ref. | B.1.1.7 | (B.1.1.7/Wuhan ref.) |
| 1 | 160 | 161.2 | 1.01 |
| 2 | 114.1 | 85.8 | 0.75 |
| 3 | 223.2 | 128.6 | 0.58 |
| 4 | 193 | 268.4 | 1.39 |
| 5 | 111.9 | 64.3 | 0.57 |
| 6 | 128 | 99.1 | 0.77 |
| 7 | 278.1 | 226.8 | 0.82 |
| 8 | 203.6 | 185 | 0.91 |
| 9 | 94.9 | 58.4 | 0.62 |
| 10 | 209.7 | 126.8 | 0.60 |
| 11 | 50.8 | 41.7 | 0.82 |
| 12 | 241.3 | 486.1 | 2.01 |
| 13 | 174 | 84.8 | 0.49 |
| 14 | 292.5 | 136.7 | 0.47 |
| 15 | 186.7 | 121.6 | 0.65 |
| 16 | 86.3 | 116.2 | 1.35 |

Example 34: Exemplary Regimen for Administration of a SARS-CoV-2 RNA Vaccine in Pregnant Women The present Example describes an exemplary regimen for administration of a SARS-CoV-2 RNA vaccine described herein (specifically, in this Example, BNT162b2) in pregnant women (e.g., in healthy pregnant women 18 years of age and older).

Pregnant women are at risk for acquiring SARS-CoV-2 infection and COVID-19. Pregnancy may confer increased risk of severe COVID-19 because of physiological changes during pregnancy that can increase susceptibility to respiratory infections and subsequent rapid progression to respiratory failure. Additionally, pregnant women with COVID-19 have been reported to have higher rates of preterm birth, cesarean delivery, fetal distress, and infants requiring neonatal intensive care.

The present Example describes certain protocols in accordance with which BNT162b2 may be administered to pregnant women and/or to infants born from such pregnant women, and also describes certain assessments that may be performed and/or results that may be achieved. For example, this Example describes a study that will assess safety of BNT162b2 in pregnant women and their infants; it will also assess the immunogenicity of BNT162b2 in pregnant women, the transfer of antibody to their infants, and the kinetics of antibody transfer in the infant.

Among other things, the present Example describes a study that will assess the safety and tolerability of prophylactic BNT162b2 when administered to maternal participants 18 years of age or older vaccinated at 24 to 34 weeks' gestation. Without wishing to be bound by any particular theory, the present Example proposes that vaccination beginning within this time period may provide particular advantages. Recognizing that proposals ranging from vaccination at any time during pregnancy (see, for example, "Israel Recommends COVID Vaccination in All Stages of Pregnancy, Updating Guidelines" Haaretz Feb. 1, 2021) and others have proposed refraining from vaccinating during pregnancy (see, for example, WHO Strategic Advisory Group recommendation), the present Example describes a particular regimen in which pregnant mothers receive a first dose of vaccine between about 24 to about 34, or in some embodiments between about 27 to about 34 weeks of gestation, and a second dose about 21 days later, ideally prior to delivery of the baby.

Without wishing to be bound by any particular theory, the present Example proposes that vaccination according to this regimen may, for example, reduce risk to the fetus as may result, for example, from exposure to an immunized maternal immune response early in pregnancy. Furthermore, still without wishing to be bound by any particular theory, the present Example proposes that the provided vaccination schedule may provide particular benefits when at least two doses are administered prior to delivery of the baby. Among other things, the present Example proposes that a provided regimen may provide a particularly beneficial risk/benefit balance. Among other things, the present disclosure teaches that benefits that may be provided by immunization of pregnant mothers, and particularly by such immunization in accordance with a regimen described in the present Example, may impart immunity to the baby that, in some embodiments, may carry past delivery, this reducing need for immunization of the baby, at least for a period of days weeks, months, or years (e.g., 1, 2, 3, 4, 5, 6, 7, 8 weeks or more, or 1, 2, 3, 4, 5, 6, 7, 8, 9, 10, 11, 12, 13, 14, 15, 16, 17, 18, 19, 20, 21, 22, 23, 24 or more months, or 1, 2, 3, 4, or 5 years) post-delivery. Thus, in some embodiments, as noted herein, infants born of mothers vaccinated during pregnancy, e.g, according to a particular regimen as described herein, may not need further vaccination, or may need reduced vaccination (e.g., lower doses and/or smaller numbers of administrations—e.g., boosters —, and/or lower overall exposure over a given period of time), for a period of time (e.g., as noted herein) after birth.

For example, in maternal participants receiving at least 1 dose of study intervention from each vaccine group, the percentage of maternal participants reporting: (i) Local reactions for up to 7 days following each dose; (ii) Systemic events for up to 7 days following each dose (iii) AEs from Dose 1 through 1 month after Dose 2 (iv) SAEs from Dose 1 through 1 month after delivery will be assessed. Alternatively or additionally, in maternal participants complying with certain key protocol criteria (evaluable maternal participants) and no serological or virological evidence (up to 1 month after receipt of the second dose) of past SARS-CoV-2 infection: (v) GMR, estimated by the ratio of the geometric mean of SARS-CoV-2 neutralizing titers in pregnant women to those in nonpregnant women 1 month after Dose 2 may be assessed.

Still further alternatively or additionally, in maternal participants complying with the key protocol criteria (evaluable participants) and/or with without or without (e.g., separately for those with and those without, or independent of) serological or virological evidence (prior to 7 days after receipt of Dose 2) of past SARS-CoV-2 infection: (vi) 100×(1−IRR) [ratio of active vaccine to placebo] may be assessed.

Yet further alternatively or additionally, one or more of the following may be assessed:

- In maternal participants complying with the key protocol criteria (evaluable maternal participants) from each vaccine group: (a) GMCs/GMTs, at baseline (before Dose 1), 2 weeks after Dose 2, 1 month after Dose 2, and 6 months after delivery (b) GMFRs from baseline through 2 weeks after Dose 2, 1 month after Dose 2, and 6 months after delivery;
- In infants born to maternal participants receiving at least 1 dose of study intervention from each vaccine group, the percentage of infants with: (a) Specific birth outcomes (b) AEs from birth through 1 month of age (c) SAEs and AESIs (major congenital anomalies, developmental delay) through 6 months of age;
- In infants born to evaluable maternal participants from each vaccine group: (a) GMCs and GMFRs, at birth and 6 months after delivery;
- In maternal participants who received BNT162b2 (at initial randomization and at 1 month after delivery): (a) Incidence per 1000 person-years of follow-up;
- In maternal participants who received BNT162b2 at initial randomization and without evidence of prior SARS-CoV-2 infection: (a) Incidence per 1000 person-years of follow-up
- In each subset of evaluable maternal participants from each vaccine group with: (a) Confirmed COVID-19 (b) Confirmed severe COVID-19 (c) SARS-CoV-2 infection but no confirmed COVID-19 (d) GMCs/GMTs and GMFRs at baseline, 1 month after Dose 2, and 6 months after delivery;
- In evaluable maternal participants: (a) GMCs/GMTs at baseline and before Dose 2 (b) GMFRs from baseline to before Dose 2;
- In infants born to maternal participants from each vaccine group, based on the breastfeeding status: (a) GMCs and GMFRs, at birth and 6 months after delivery;
- In infants born to maternal participants receiving at least 1 dose of study intervention from each vaccine group, based on the breastfeeding status, the percentage of infants with:

(a) AEs from birth through 1 month of age (b) SAEs and AESIs (major congenital anomalies, developmental delay) through 6 months of age;

- In infants born to maternal participants from each vaccine group: (a) Incidence rate of infant participants with confirmed COVID-19;
- In infants born to maternal participants from each vaccine group: (a) Incidence rate of MIS-C.

In some embodiments, a first dose will be administered to pregnant women during their 27 to 34 weeks of gestation, followed by a second dose approximately 21 days later. In some embodiments, a first dose will be administered to pregnant women during their 24 to 34 weeks of gestation, followed by a second dose approximately 21 days later. In some embodiments, participant mothers are assessed for a period of time up to about 6, 7, 8, 9, 10, 12, 13, 14, 15, 16, 17, 18 months or more (e.g., after initiation of the study, after administration of the first dose, after administration of the second dose, and/or after birth of the infant).

Is some embodiments, an infant born to a mother to whom one or more (e.g., two) vaccine doses have been administered (e.g., to whom two doses were administered during gestation) is assessed for a period of time up to about 1, 2, 3, 4, 5, 6, 7, 8, 9, 10, 11, 12, 13, 14, 15, 16, 17, 18 months or more (e.g., after initiation of the study, after administration of the first dose, after administration of the second dose, and/or after birth of the infant).

In some embodiments, a dose will be 30 ug of BNT162b2 as described herein.

In some embodiments, assessment of vaccine performance are made in populations of pregnant women of any age, or within a particular age range (e.g., equal to or above 18 years of age). In some embodiments, assessment of vaccine performance are made in populations of women carrying singleton pregnancies.

In some embodiments, gestational age is assessed by one or more of last menstrual period, ultrasound examiniation, physical examination, and/or combinations thereof. In some embodiments, gestational age is determined by ultrasound. In some embodiments, gestational age is determined by consideration of two or more assessments (e.g., two or more ultrasounds performed at different times, such as in different trimesters, of the pregnancy).

In some embodiments, assessment of vaccine performance is made in populations characterized by one or more of: ultrasound examination performed at at least 18 weeks of pregnancy with no significant fetal abnormalities observed (e.g., upon assessment by a licensed investigator); documented negative HIV, syphilis, and/or HBV tests or combinations thereof; prepregnancy BMI of ≤40 $kg/m^2$.

In some embodiments, assessment of vaccine performance is made in populations that do not include subjects characterized by one or more of: suffering from a medical or psychiatric condition that may increase the risk of vaccination or otherwise, in the reasonable judgement of a licensed investigator make the subject inappropriate for receipt of the vaccine; prevopis clinical or micobiological diagnosis of COVID-19; history of severe adverse reaction associated with a vaccine and/or sever allergic reaction (e.g., anaphylaxis) to any component of the vaccine; known or suspected immunodeficiency; bleeding diathesis or condition associated with prolonged bleeding, gestational hypertension or preeclampsia-eclampsia, placental abnormality, polyhydramnios or oligohydramnios, significant bleeding or blood clotting disorder, gestational diabetes, one or more signs of premature labor with the current pregnancy or having ongoing intervention (medical/surgical) in the current pregnancy to prevent preterm birth, prior stillbirth or neonatal death, prior low birth weight or preterm delivery, prior history of at least 3 miscarriages, prior pregnancies numbering greater than 5, or previous infant with a known genetic disorder or major congenital anomaly, previous vaccination with any coronavirus vaccine, receipt of medications intended to prevent COVID-19, receipt of blood/plasma products or immunoglobulin from 60 days before administration of study intervention or planned receipt through delivery (with 1 exception, anti-D immunoglobulin (eg, RhoGAM), which can be given at anytime), current alcohol abuse or illicit drug use, participants who receive treatment with immunosuppressive therapy (including cytotoxic agents or systemic corticosteroids, eg, for cancer or an autoimmune disease, or planned receipt through the postvaccination blood draw), participation in other studies involving study intervention within 28 days prior to study entry and/or during study participation, previous participation in other studies involving study intervention containing LNPs, current febrile illness, current symptoms of COVID-19 infection, Receipt of any seasonal or pandemic influenza vaccine in the previous 14 days, anticipated receipt of any seasonal or pandemic influenza vaccine in the 7 days after study intervention administration, receipt of a tetanus-, diphtheria-, and/or pertussis-containing vaccine in the previous 14 days, anticipated receipt of a tetanus-, diphtheria-, and/or pertussis-containing vaccine in the 7 days after study intervention administration, receipt of short-term (<14 days) systemic corticosteroids less than 28 days prior to dosing (inhaled/nebulized, intra-articular, intrabursal, or topical (skin or eyes) corticosteroids are permitted).

In some embodiments, a mother vaccinated as described herein may be taking or may begin taking, for example, an antipyretic or other pain medication to treat symptoms associated with the vaccination. Alternatively or additionally, in some embodiments, a mother may be taking or may begin taking a medication required for treatment of a pre-existing stable condition and/or an inhaled, topical or localized injection of corticosteroids.

In some embodiments, a mother vaccinated as described herein may be given one or more antenatal corticosteroids, in particular if the pregnancy is at risk for preterm delivery. In some embodiments, the corticosteroid is a glucocorticoid. In some embodiments, the corticosteroid is betamethasone or progesterone, or a mixture thereof.

In some embodiments, vaccination as described in this Example reduces incidence of COVID-19 disease (and/or documented SARS-CoV-2 infection), or of severe COVID-19 disease, in mothers and/or infants born to them, for example relative to that observed in a comparable unvaccinated (e.g., having received placebo) population. In some embodiments, a mother is considered to have COVID-19 disease if least 1 of symptom of COVID-19 disease (fever; new or increased cough; new or increased shortness of breath; new or increased muscle pain; new loss of taste or smell; sore throat; diarrhea; vomiting; and/or in some embodiments fatigue, headache, nasal congestion or runny nose, nausea) is present and a SARS-CoV-2 NAAT-positive test is obtained during, or within 4 days before or after, the symptomatic period, either at the central laboratory or at a local testing facility (using an acceptable test). In some embodiments, a mother is considered to have severe COVID-19 disease if she has confirmed COVID-19 and one or more of the following is present:

Clinical signs at rest indicative of severe systemic illness (RR≥30 breaths/min, HR≥125 beats/min, SpO2≤93% on room air at sea level, or PaO2/FiO2<300 mm Hg);

Respiratory failure (defined as needing high-flow oxygen, noninvasive ventilation, mechanical ventilation, or ECMO);

Evidence of shock (SBP<90 mm Hg, DBP<60 mm Hg, or requiring vasopressors);

Significant acute renal, hepatic, or neurologic dysfunction*;

Admission to an ICU;

Death.

In some embodiments, an infant is considered to have COVID-19 disease if at least one symptom (fever, new or increased cough, new or increased shortness of breath, diarrhea, vomiting; and/or in some embodiments one or more of nasal congestion or runny nose, poor appetite or poor feeding, abdominal pain/colic) is present and a SARS-COV-2 NAAT-positive test result is obtained during, or within 4 days before or after, the symptomatic period, either at the central laboratory or at a local testing facility (using an acceptable test). In some embodiments, an infant is considered to have severe COVID-19 disease if she has confirmed COVID-19 and one or more of the following is present:

(i) Clinical signs at rest indicative of severe systemic illness:

RR (breaths/min): >50 from birth to 1 week of age, ≥40 from 1 week to 1 month of age, ≥34 from 1 month to 6 months of age;

HR (beats/min): >180;

SpO2≤92% on room air or >50% FiO2 to maintain ≥92%, or PaO2/FiO2<300 mm Hg24;

(ii) Respiratory failure (defined as needing high-flow oxygen including nasal CPaP/BiPaP, noninvasive ventilation, mechanical ventilation, or ECMO);

(iii) Evidence of shock or cardiac failure:

SBP (mm Hg) (<5th percentile for age):

+<65 from birth to 1 week of age, <75 from 1 week to 1 month of age, <100 from 1 month to 6 months of age;

OR

Requiring vasoactive drugs to maintain BP in the normal range;

(iv) Significant acute renal failure: serum creatinine >2 times ULN for age or 2-fold increase in baseline creatinine;

(v) Significant GI/hepatic failure: total bilirubin >4 mg/dL or ALT 2 times ULN for age;

(vi) Significant neurologic dysfunction: Glasgow Coma Scale score <11 or acute change in mental status with a decrease in Glasgow Coma Scale score ≥3 points from abnormal baseline;

(vii) Admission to an ICU;

(viii) Death.

In some embodiments, incidence of multisystem inflammatory syndrome is not significantly increased (e.g., relative to a comparable population whose mothers were not vaccinated, and/or who were not vaccinated according to a protocol as described herein) in infants whose mothers were vaccinated as described herein. In some embodiments, an infant is considered to have multisystem inflammatory syndrome if:

the infant presents with fever (≥38.0° C. for ≥24 hours or report of subjective fever lasting ≥24 hours); AND there is laboratory evidence of inflammation (based on local laboratory ranges) including, but not limited to, 1 or more of the following: an elevated CRP, ESR, fibrinogen, procalcitonin, D-dimer, ferritin, LDH, or IL-6, elevated neutrophils, reduced lymphocytes, and low albumin; AND there is evidence of clinically severe illness requiring hospitalization (definition as noted above for severe disease), with multisystem (2) organ involvement:

Cardiac (eg, shock, elevated troponin, elevated BNP, abnormal echocardiogram, arrhythmia);

Renal (eg, acute kidney injury or renal failure);

Respiratory (eg, pneumonia, ARDS, pulmonary embolism);

Hematologic (eg, elevated D-dimers, thrombophilia, or thrombocytopenia);

GI/hepatic (eg, elevated bilirubin, elevated liver enzymes, or diarrhea);

Dermatologic (eg, rash, mucocutaneous lesions);

Neurological (eg, CVA, aseptic meningitis, encephalopathy); AND there is no alternative plausible diagnoses; AND the infant is determined to be positive for current or recent SARS-CoV-2 infection by RT-PCR, serology, or antigen test; OR the infant has had COVID-19 exposure within the 4 weeks prior to the onset of symptoms.

In some embodiments, vaccination of mothers as described herein does not materially increase incidence of preterm delivery of infany morbidity.

In some embodiments, incidence of COVID-19 disease (and/or documented SARS-CoV-2 infection) in infants whose mothers were vaccinated as described herein is reduced relative to that of in facts whose mothers were not so vaccinated. In some embodiments, incidence of COVID-19 disease (and/or documented SARS-CoV-2 infection) in infants whose mothers were vaccinated as described herein is comparable to that of infants who were directly vaccinated after their delivery.

In some embodiments, vaccination as described herein achieves one or more of the following Primary or Secondary Outcome measures:

Primary Outcome Measures:

1. Percentage of maternal participants reporting: Local reactions

Pain at the injection site, redness, and swelling as self-reported on electronic diaries

[Time Frame: For 7 Days after Dose 1 and Dose 2]

2. Percentage of maternal participants reporting systemic events

Fever, fatigue, headache, chills, vomiting, diarrhea, new or worsened muscle pain, and new or worsened joint pain as self-reported on electronic diaries.

[Time Frame: For 7 days after Dose 1 and Dose 2]

3. Percentage of maternal participants reporting adverse events

As elicited by investigational site staff

[Time Frame: From Dose 1 through 1 month after Dose 2]

4. Percentage of maternal participants reporting serious adverse events

As elicited by investigational site staff

[Time Frame: From Dose 1 through 6 months after delivery]

5. Demonstrate non inferiority of immune response in pregnant women compared to nonpregnant female participants from the C4591001 study without evidence of past SARS-CoV-2 infection.

GMR, estimated by the ratio of the geometric mean of SARS CoV 2 neutralizing titers in pregnant women to those in nonpregnant female participants

[Time Frame: 1 month after Dose 2]

6. Demonstrate non inferiority of immune response in pregnant women compared to nonpregnant female participants from the C4591001 study with and without evidence of prior SARS-CoV-2 infection GMR, estimated by the ratio of the geometric mean of SARS CoV 2 neutralizing titers in pregnant women to those in nonpregnant female participants

[Time Frame: 1 month after Dose 2]

Secondary Outcome Measures:

7. Evaluate efficacy against confirmed COVID 19 in participants without evidence of infection prior to vaccination 1000 person years of follow-up

[Time Frame: 7 days after Dose 2]

8. Evaluate efficacy against confirmed COVID 19 in participants without evidence of prior infection.

1000 person years of follow-up

[Time Frame: 7 days after Dose 2]

Example 35: Neutralization of SARS-CoV-2 Lineage B.1.1.298 (Danish Strain; a.k.a., SARS-CoV-2/Hu/DK/CL-5/1 (Cluster 5)) and B.1.351 (South African Strain; a.k.a., 20H/501Y.V2 (501.V2)) Pseudovirus by BNT162b2 Vaccine-Elicited Human Sera Sera of 12 younger adult participants in the previously reported German phase 1/2 trial drawn at 7 or 21 days after the booster immunization with 30 μg BNT162b2, were tested for neutralization of SARS-CoV-2 Wuhan Hu-1 (reference), South African lineage B.1.351 (SA-strain), and Danish mink-related lineage B.1.1.298 (DNK-strain) spike protein pseudotyped VSV by a 50% neutralization assay (pVNT50). The SA-strain spike protein carries the following amino acid changes compared to the Wuhan reference: L18F, D80A, D215G, ΔL242-244, R246I, K417N, E484K, N501Y, D614G, A701V. The DNK-strain spike protein carries the following amino acid changes compared to the Wuhan reference: Y453F, D614G, I692V, M1229I.

BNT162b2-immune sera neutralized the DNK-strain pseudovirus almost as efficiently as the SARS-CoV-2 Wuhan Hu-1 pseudotyped reference. A decrease (5-fold) in neutralizing titers was measured against the SARS-CoV-2 lineage B.1.351 pseudovirus when comparing the titers to the Wuhan Hu-1 pseudotyped reference. Importantly, all tested BNT162b2-immune sera were still able to neutralize with no complete escape being noted (FIG. 127).

Materials and Methods:

A recombinant replication-deficient VSV vector that encodes green fluorescent protein (GFP) and luciferase (Luc) instead of the VSV-glycoprotein (VSV-G) was pseudotyped with Wuhan-Hu-1 isolate SARS-CoV-2 spike (S) (GenBank: QHD43416.1), a variant harbouring four mutations found in the S protein of the Danish mink-related lineage B.1.1.298 (Y453F, D614G, I692V, M1229I), or variants harbouring ten mutations (L18F, D80A, D215G, R246I, A242/243/244, K417N, E484K, N501Y, D614G, A701V) found in the South African lineage B.1.351 S protein according to published pseudotyping protocols. In brief, HEK293T/17 monolayers transfected to express the respective SARS-CoV-2 S truncated of the C-terminal cytoplasmic 19 amino acids (SARS-CoV-2-S(CΔ19)) were inoculated with VSVAG-GFP/Luc vector. After incubation for 1 h at 37° C., the inoculum was removed, and cells were washed with PBS before medium supplemented with anti-VSV-G antibody (clone 8G5F11, Kerafast) was added to neutralise residual input virus. VSV-SARS-CoV-2 pseudovirus-containing medium was collected 20 h after inoculation, 0.2-µm-filtered and stored at −80° C.

For pseudovirus neutralisation assays, 40,000 Vero 76 cells were seeded per 96-well. Sera were serially diluted 1:2 in culture medium starting with a 1:10 dilution (dilution range of 1:10 to 1:2,560). VSV-SARS-CoV-2-S pseudo particles were diluted in culture medium for a fluorescent focus unit (ffu) count in the assay of ~1,000 TU in the assay. Serum dilutions were mixed 1:1 with pseudovirus for 30 minutes at room temperature prior to addition to Vero 76 cell monolayers in 96-well plates and incubation at 37° C. for 24 hours. Supernatants were removed, and the cells were lysed with luciferase reagent (Promega). Luminescence was recorded, and neutralisation titers were calculated in GraphPad Prism version 9 by generating a 4-parameter logistical (4PL) fit of the percent neutralisation at each serial serum dilution. The 50% pseudovirus neutralisation titre (pVNT50) was reported as the interpolated reciprocal of the dilution yielding a 50% reduction in luminescence.

Example 36: Neutralization of N501Y Mutant SARS-CoV-2 by BNT162b2 Vaccine-Elicited Sera Rapidly spreading variants of SARS-CoV-2 have arisen in the United Kingdom and South Africa (Volz E. et al. Report 42-Transmission of SARS-CoV-2 Lineage B.1.1.7 in England: Insights from linking epidemiological and genetic data. www.imperial.ac.uk/mrc-global-infectious-disease-analysis/covid-19/report-42-sars-cov-2-variant/; Tegally H. et al. Emergence and rapid spread of a new severe acute respiratory syndrome-related coronavirus 2 (SARS-CoV-2) lineage with multiple spike mutations in South Afric. medRxiv 2020. doi.org/10.1101/2020.12.21.20248640). These variants have multiple mutations in their S glycoproteins, which are key targets of virus neutralizing antibodies. These rapidly spreading variants share the spike N501Y substitution. This mutation is of particular concern because it is located in the viral receptor binding site for cell entry, increases binding to the receptor (angiotensin converting enzyme 2), and enables the virus to expand its host range to infect mice (Gu H. et al. Adaptation of SARS-CoV-2 in BALB/c mice for testing vaccine efficacy. Science 2020; 369:1603-7; Chan K. K. et al. An engineered decoy receptor for SARS-CoV-2 broadly binds protein S sequence variants. Cold Spring Harbor Laboratory 2020.doi: 10.1101/2020.10.18.344622).

We generated an isogenic Y501 SARS-CoV-2 on the genetic background of the N501 clinical strain USA-WA1/2020, which also provided the genetic background of the BNT162b2-encoded spike antigen. Sera of 20 participants in the previously reported trial (Walsh E. E. et al. Safety and Immunogenicity of Two RNA-Based Covid-19 Vaccine Candidates. N Engl J Med 2020; Polack F. P. et al. Safety and efficacy of the BNT162b2 mRNA Covid-19 vaccine. N Eng. J Med 2020. DOI: 10.1056/NEJMoa2034577), drawn 2 or 4 weeks after immunization with two 30-µg doses of BNT162b2 spaced three weeks apart, were tested for neutralization of N501 and Y501 viruses by a 50% plaque reduction neutralization assay (PRNT$_{50}$; FIG. 128). The ratio of the 50% neutralization GMT of the sera against the Y501 virus to that against the N501 virus was 1.46, indicating no reduction in neutralization activity against the virus bearing the Y501 spike.

Materials and Methods
Construction of Isogenic Viruses

We prepared an isogenic pair of SARS-CoV-2 containing the N501 or Y501 spike protein (FIG. 129). The N501Y mutation was generated by an A-to-T substitution at nucleotide 23,063 of the viral genome using an infectious cDNA clone of clinical strain WA1 (2019-nCoV/USA_WA1/2020) (Xie X. et al. An Infectious cDNA Clone of SARS-CoV-2. Cell Host Microbe 2020; 27:841-8 e3). Following a previously reported mutagenesis protocol (Plante J. A. et al. Spike mutation D614G alters SARS-CoV-2 fitness. Nature 2020), we recovered N501 and Y501 viruses with titers of >10$^7$ plaque-forming units (PFU) per ml. The two viruses developed similar plaque morphologies on Vero E6 cells (FIG. 130).

Serum Specimens and Neutralization Assay

The immunization and serum collection regimen is illustrated schematically in FIG. 131. For measuring neutralization titers, each serum was 2-fold serially diluted in culture medium with the first dilution of 1:40 (dilution range of 1:40 to 1:1280). The diluted serum was incubated with 100 PFU of N501 or Y501 virus at 37° C. for 1 h, after which the serum-virus mixtures were inoculated onto Vero E6 cell monolayer in 6-well plates. A conventional (non-fluorescent) plaque reduction neutralization assay was performed to quantify the serum-mediated virus suppression as previously reported (Muruato A. E. et al. A high-throughput neutralizing antibody assay for COVID-19 diagnosis and vaccine evaluation. Nat Commun 2020; 11:4059). A minimal serum dilution that suppressed >50% of viral plaques is defined as PRNT$_{50}$. A table of the neutralization titers is provided (Table 28). The ratio for each serum of the PRNT$_{50}$ against N501 and Y501 virus is plotted in FIG. 132.

TABLE 28

PRNT$_{50}$ values of 20 BNT162b2 post-immunization sera against N501 and Y501 SARS-CoV-2.

| Serum ID | PRNT$_{50}$ N501 | PRNT$_{50}$ Y501 | PRNT$_{50}$ ratio (Y501/N501) |
|---|---|---|---|
| 1 | 160 | 640 | 4 |
| 2 | 160 | 320 | 2 |
| 3 | 320 | 640 | 2 |
| 4 | 80 | 160 | 2 |
| 5 | 160 | 160 | 1 |
| 6 | 320 | 320 | 1 |
| 7 | 640 | 640 | 1 |
| 8 | 160 | 160 | 1 |
| 9 | 640 | 640 | 1 |
| 10 | 640 | 1280 | 2 |
| 11 | 160 | 640 | 4 |
| 12 | 320 | 320 | 1 |
| 13 | 640 | 1280 | 2 |
| 14 | 640 | 320 | 0.5 |
| 15 | 320 | 640 | 2 |
| 16 | 320 | 640 | 2 |
| 17 | 640 | 640 | 1 |
| 18 | 640 | 1280 | 2 |
| 19 | 640 | 640 | 1 |
| 20 | 640 | 640 | 1 |

Example 37: Neutralization of Spike 69/70 Deletion, E484K, and N501Y SARS-CoV-2 by BNT162b2 Vaccine-Elicited Sera Rapidly spreading variants of SARS-CoV-2 have arisen in the United Kingdom (UK), South Africa (SA), and other regions (Volz E. et al. CMe. Report 42—Transmission of SARS-CoV-2 Lineage B.1.1.7 in England: Insights from linking epidemiological and genetic data. wwwimperialacuk/mrc-global-infectious-disease-analysis/covid-19/report-42-sars-cov-2-variant/2021; Tegally H. et al. e. Emergence and rapid spread of a new severe acute respiratory syndrome-related coronavirus 2 (SARS-CoV-2) lineage with multiple spike mutations in South Africa medRxiv 2020.:doi.org/10.1101/2020.12.21.20248640). These variants have multiple mutations in their spike glycoproteins, which are key targets of virus neutralizing antibodies. The emerged spike mutations have raised concerns of vaccine efficacy against these new strains. The goal of this study is to examine the effect of several key spike mutations from the UK and SA strains on BNT162b2 vaccine-elicited neutralization.

We engineered three SARS-CoV-2s containing key spike mutations from the newly emerged United Kingdom (UK) and South African (SA) variants: N501Y from UK and SA; 69/70-deletion+N501Y+D614G from UK; and E484K+N501Y+D614G from SA. Neutralization geometric mean titers (GMTs) of twenty BTN162b2-vaccinated human sera against the three mutant viruses were 0.81- to 1.46-fold of the GMTs against parental virus, indicating small mutational effects on neutralization by sera elicited by two BNT162b2 doses.

Using an infectious cDNA clone of SARS-CoV-2 (Xie X. et al. An Infectious cDNA Clone of SARS-CoV-2. Cell Host Microbe 2020; 27:841-8 e3), we engineered three spike mutant viruses on the genetic background of clinical strain USA-WA1/2020 (FIG. 133). (i) Mutant N501Y virus contains the N501Y mutation that is shared by both the UK and SA variants. This mutation is located in the viral receptor binding domain (RBD) for cell entry, increases binding to the receptor (angiotensin converting enzyme 2), and enables the virus to expand its host range to infect mice (Xie X. et al. An Infectious cDNA Clone of SARS-CoV-2. Cell Host Microbe 2020; 27:841-8 e3; Wrapp D. et al. Cryo-EM structure of the 2019-nCoV spike in the prefusion conformation. Science 2020; 367:1260-3). (ii) Mutant Δ69/70+N501Y+D614G virus contains two additional changes from the UK variants: amino acid 69 and 70 deletion (Δ69/70) and D614G substitution. Amino acids 69 and 70 are located in the N-terminal domain of the spike S1 fragment; deletion of these residues may allosterically change the conformation of spike (Wrapp D. et al. Cryo-EM structure of the 2019-nCoV spike in the prefusion conformation. Science 2020; 367: 1260-3). The D614G mutation is dominant in circulating strains around the world (Plante J A et al. Spike mutation D614G alters SARS-CoV-2 fitness. Nature 2020; Korber B. et al. Tracking Changes in SARS-CoV-2 Spike: Evidence that D614G Increases Infectivity of the COVID-19 Virus. Cell 2020). (iii) Mutant E484K+N501Y+D614G virus contains the E484K substitution, which is also located in the viral RBD. The E484K substitution alone confers resistance to several monoclonal antibodies (Ku Z. et al. Molecular determinants and mechanism for antibody cocktail preventing SARS-CoV-2 escape. Nat Commun 2021; 12:469; Baum A. et al. Antibody cocktail to SARS-CoV-2 spike protein prevents rapid mutational escape seen with individual antibodies. Science 2020; 369:1014-8). Compared with the wild-type USA-WA1/2020 strain, the three mutant viruses showed similar plaque morphologies on Vero E6 cells (FIG. 134).

We tested a panel of human sera from twenty participants in the previously reported clinical trial (Walsh E E et al. Safety and Immunogenicity of Two RNA-Based Covid-19 Vaccine Candidates. N Engl J Med 2020; Polack F P et al. Safety and Efficacy of the BNT162b2 mRNA Covid-19 Vaccine. N Engl J Med 2020), drawn 2 or 4 weeks after immunization with two 30-μg doses of BNT162b2 spaced three weeks apart (FIG. 135). Each serum was tested for neutralization of wild-type USA-WA1/2020 strain and the three mutant viruses by a 50% plaque reduction neutralization assay ($PRNT_{50}$; Tables 29 and 30).

TABLE 29

$PRNT_{50}$s of twenty BNT162b2 post-immunization sera against wild-type (USA-WA1/2020) and mutant N501Y SARS-CoV-2s

| | $PRNT_{50}$ | | $PRNT_{50}$ ratio |
|---|---|---|---|
| Serum ID | WT | N501Y | (N501Y/WT) |
| 1 | 160 | 640 | 4 |
| 2 | 160 | 320 | 2 |
| 3 | 320 | 640 | 2 |
| 4 | 80 | 160 | 2 |
| 5 | 160 | 160 | 1 |
| 6 | 320 | 320 | 1 |
| 7 | 640 | 640 | 1 |
| 8 | 160 | 160 | 1 |
| 9 | 640 | 640 | 1 |
| 10 | 640 | 1280 | 2 |
| 11 | 160 | 640 | 4 |
| 12 | 320 | 320 | 1 |
| 13 | 640 | 1280 | 2 |
| 14 | 640 | 320 | 0.5 |
| 15 | 320 | 640 | 2 |
| 16 | 320 | 640 | 2 |
| 17 | 640 | 640 | 1 |
| 18 | 640 | 1280 | 2 |
| 19 | 640 | 640 | 1 |
| 20 | 640 | 640 | 1 |

TABLE 30

$PRNT_{50}$s of twenty BNT162b2 post-immunization sera against wild-type (USA-WA1/2020), Δ69/70+N501Y+D614G, and E484K+N501Y+D614G SARS-CoV-2s

| | | $PRNT_{50}$ | | $PRNT_{50}$ ratio | |
|---|---|---|---|---|---|
| Serum ID | WT | Δ69/70+ N501Y+ D614G | E484K+ N501Y+ D614G | Δ69/70+ N501Y+ D614G/WT | E484K+ N501Y+ D614G/WT |
| 1 | 320 | 640 | 320 | 2 | 1 |
| 2 | 160 | 160 | 80 | 1 | 0.5 |
| 3 | 640 | 1280 | 640 | 2 | 1 |
| 4 | 160 | 160 | 80 | 1 | 0.5 |
| 5 | 320 | 320 | 320 | 1 | 1 |
| 6 | 640 | 640 | 640 | 1 | 1 |
| 7 | 640 | 1280 | 320 | 2 | 0.5 |
| 8 | 320 | 320 | 160 | 1 | 0.5 |
| 9 | 1280 | 1280 | 1280 | 1 | 1 |
| 10 | 640 | 1280 | 640 | 2 | 1 |
| 11 | 320 | 320 | 320 | 1 | 1 |
| 12 | 640 | 1280 | 320 | 2 | 0.5 |
| 13 | 1280 | 2560 | 1280 | 2 | 1 |
| 14 | 320 | 320 | 320 | 1 | 1 |
| 15 | 320 | 640 | 320 | 2 | 1 |
| 16 | 640 | 640 | 640 | 1 | 1 |
| 17 | 640 | 1280 | 640 | 2 | 1 |
| 18 | 320 | 640 | 320 | 2 | 1 |

TABLE 30-continued

PRNT$_{50}$s of twenty BNT162b2 post-immunization sera against wild-type (USA-WA1/2020), Δ69/70+N501Y+D614G, and E484K+N501Y+D614G SARS-CoV-2s

| | | PRNT$_{50}$ | | PRNT$_{50}$ ratio | |
|---|---|---|---|---|---|
| Serum ID | WT | Δ69/70+ N501Y+ D614G | E484K+ N501Y+ D614G | Δ69/70+ N501Y+ D614G/WT | E484K+ N501Y+ D614G/WT |
| 19 | 640 | 640 | 320 | 1 | 0.5 |
| 20 | 640 | 1280 | 640 | 2 | 1 |

All sera showed equivalent neutralization titers between the wild-type and mutant viruses, with differences of ≤4 fold (FIG. 136). Notably, ten out of the twenty sera had neutralization titers against mutant Δ69/70+N501Y+D614G virus that were twice their titers against the wild-type virus (FIG. 136*b*), whereas six out of the twenty sera had neutralization titers against mutant E484K+N501Y+D614G virus that were half their titers against the wild-type virus (FIG. 136*c*). The ratios of the neutralization GMTs of the sera against the N501Y, Δ69/70+N501Y+D614G, and E484K+N501Y+D614G viruses to their GMTs against the USA-WA1/2020 virus were 1.46, 1.41, and 0.81, respectively (FIG. 137).

Consistent with other recent reports of the neutralization of variant SARS-CoV-2 or corresponding pseudoviruses by convalescent or post-immunization sera (Wibmer C K et al. SARS-CoV-2 501Y.V2 escapes neutralization by South African COVID-19 donor plasma. bioRxiv 2021:doi: doi.org/10.1101/2021.01.18.427166; Wang Z. et al. mRNA vaccine-elicited antibodies to SARS-CoV-2 and circulating variants. bioRxiv 2021:doi: doi.org/10.1101/2021.01.15.426911), the neutralization GMT of the serum panel against the virus with three mutations from the SA variant (E484K+N501Y+D614G) was slightly lower than the neutralization GMTs against the N501Y virus or the virus with three mutations from the UK variant (Δ69/70+N501Y+D614G). However, the magnitude of the differences in neutralization GMTs against any of the viruses in this study was small, as compared to the 4-fold differences in hemagglutination-inhibition titers that have been used to signal potential need for a strain change in influenza vaccines (Smith D J et al. Mapping the antigenic and genetic evolution of influenza virus. Science 2004; 305:371-6).

Methods

Construction of isogenic viruses. Three recombinant SARS-CoV-2 mutants (N501Y, Δ69/70-N501Y+D614G, E484K+N501Y+D614G in spike protein) were prepared on the genetic background of an infectious cDNA clone derived from clinical strain WA1 (2019-nCoV/USA_WA1/2020) (Xie X. et al. An Infectious cDNA Clone of SARS-CoV-2. Cell Host Microbe 2020; 27:841-8 e3) by following the PCR-based mutagenesis protocol as reported previously (Plante J A et al. Spike mutation D614G alters SARS-CoV-2 fitness. Nature 2020). The full-length infectious cDNAs were in vitro ligated and used as templates to transcribe full-length viral RNA. Mutant viruses (PO) were recovered on day 2 from Vero E6 cells after electroporation of the in vitro RNA transcripts. P1 viruses were harvested as stocks by passaging the P0 virus once on Vero E6 cells. The titers of P1 viruses were determined by plaque assay on Vero E6 cells. The genome sequences of the P1 viruses were validated by Sanger sequencing. The detailed protocol was recently reported (Xie X. et al. Engineering SARS-CoV-2 using a reverse genetic system. Nature Protocols 2021: doi.org/10.1038/s41596-021-00491-8).

Serum specimens and neutralization assay. The immunization and serum collection regimen are illustrated schematically in FIG. 135. A conventional (non-fluorescent) plaque reduction neutralization assay was performed to quantify the serum-mediated virus suppression as previously reported (Muruato A E et al. A high-throughput neutralizing antibody assay for COVID-19 diagnosis and vaccine evaluation. Nat Commun 2020; 11:4059). Briefly, each serum was 2-fold serially diluted in culture medium with the first dilution of 1:40 (dilution range of 1:40 to 1:1280). The diluted sera were incubated with 100 plaque-forming units of wild-type or mutant viruses at 37° C. for 1 h, after which the serum-virus mixtures were inoculated onto Vero E6 cell monolayer in 6-well plates. After 1 h of infection at 37° C., 2 ml of 2% Seaplaque agar (Lonza) in Dulbecco's modified Eagle medium (DMEM) containing 2% fetal bovine serum (FBS) and 1% penicillin/streptomycin (P/S) was added to the cells. After 2 days of incubation, 2 ml of 2% Seaplaque agar (Lonza) in DMEM containing 2% FBS, 1% P/S and 0.01% neutral red (Sigma) were added on top of the first layer. After another 16 h of incubation at 37° C., plaque numbers were counted. The minimal serum dilution that inhibits 50% of plaque counts is defined as the 50% plaque reduction neutralization titer (PRNT$_{50}$). Each serum was tested in duplicates. The PRNT$_{50}$ assay was performed at the biosafety level-3 facility at the University of Texas Medical Branch.

Example 38: Neutralizing Activity of BNT162b2-Elicited Serum

New, highly transmissible SARS-CoV-2 variants that were first detected in the United Kingdom (B.1.1.7 lineage), South Africa (B.1.351 lineage), and Brazil (P.1 lineage) with mutations in the S gene are spreading globally. To analyze effects on neutralization elicited by BNT162b2, we engineered S mutations from each of the three new lineages into USA-WA1/2020, a relatively early isolate of the virus from January 2020 (FIG. 138). We subsequently produced five recombinant viruses. The first had all the mutations found in the S gene in the B.1.1.7 lineage (B.1.1.7-spike), the second had all the mutations found in the S gene in the P.1 lineage (P.1-spike), the third had all the mutations found in the S gene in the B.1.351 lineage (B.1.351-spike), the fourth had an N-terminal domain deletion found in the B.1.351 lineage and the globally dominant D614G substitution (B.1.351-Δ242-244+D614G), and the fifth had the three mutations from the B.1.351 lineage at the receptor-binding site (K417N, E484K, and N501Y) and a D614G substitution (B.1.351-RBD+D614G). The amino acid residues mutated in the B.1.351-RBD+D614G virus are also among those mutated in the P.1 lineage virus, though in the P.1 lineage virus, K417 is mutated to threonine rather than asparagine. All the mutant viruses yielded infectious viral titers exceeding 10 plaque-forming units per milliliter. The B.1.1.7-spike and B.1.351-spike virus formed plaques that were smaller than those of the other viruses (FIG. 139).

We performed 50% plaque reduction neutralization testing (PRNT$_{50}$) using 20 serum samples that had been obtained from 15 participants in the pivotal trial (Polack F P et al. Safety and efficacy of the BNT162b2 mRNA Covid-19 vaccine. N Engl J Med 2020; 383: 2603-15; Walsh E E et al. Safety and immunogenicity of two RNA-based Covid-19 vaccine candidates. N Engl J Med 2020; 383: 2439-50) 2 or 4 weeks after the administration of the second dose of 30 μg of BNT162b2 (which occurred 3 weeks after the first immunization) (FIG. 140). All the serum samples efficiently neutralized USA-WA1/2020 with almost all of them having titers higher than 1:40. Geometric mean neutralizing titers against USA-WA1/2020, B.1.1.7-spike, P.1-spike, B.1.351-spike, B.1.351-Δ242-244+D614G, and B.1.351-RBD+D614G viruses were 532, 663, 437, 194, 485, and 331, respectively (FIG. 141 and Table 31). Thus, as compared with neutralization of USA-WA1/2020, neutralization of B.1.1.7-spike and P.1-spike viruses was roughly equivalent, and neutralization of B.1.351-spike virus was still robust but ~2.7-fold lower. Our data are also consistent with lower neutralization titers against the virus with the full set of B.1.351-spike mutations than virus with either subset of mutations and suggest that mutations in the receptor-binding site (K417N, E484K, and N501Y) affect neutralization more than the 242-244 deletion in the N-terminal domain of the spike protein.

Because neutralization of the B.1.1.7-spike and P.1-spike viruses by BNT162b2-elicited sera is roughly equivalent to neutralization of USA-WA1/2020, the neutralization data provide strong support that BNT162b2 will continue to protect against the variants first detected in the UK or Brazil. Protection against B.1.351 lineage virus is also anticipated, given that, although neutralization titers against this variant are somewhat lower, they are still robust and much higher than the barely detectable titers observed after one dose of BNT162b2, when strong efficacy was already observed in the pivotal C4591001 efficacy trial (Polack F P et al. Safety and efficacy of the BNT162b2 mRNA Covid-19 vaccine. N Engl J Med 2020; 383:2603-15; Walsh E E et al. Safety and immunogenicity of two RNA-based Covid-19 vaccine candidates. N Engl J Med 2020; 383:2439-50; Sahin U et al. BNT162b2 induces SARS-CoV-2-neutralising antibodies and T cells in humans. Dec. 11, 2020 (www.-medrxiv.-org/-content/-10.-1101/-2020.-12.-09.-20245175v1). preprint.). In addition, T cell immunity may also be involved in protection (Liao M et al. Single-cell landscape of bronchoalveolar immune cells in patients with COVID-19. Nature Medicine 2020/), and BNT162b2 immunization elicits CD8+ T-cell responses that recognize multiple variants (Skelly D T et al. Vaccine-induced immunity provides more robust heterotypic immunity than natural infection to emerging SARS-CoV-2 variants of concern. Research Square 2021).

Materials and Methods

Construction of isogenic viruses. All recombinant SARS-CoV-2s with spike mutations (FIG. 138) were prepared on the genetic background of an infectious cDNA clone derived from clinical strain USA-WA1/2020 (Xie X et al. An Infectious cDNA Clone of SARS-CoV-2. Cell Host Microbe 2020; 27:841-8 e3). The mutations were introduced into the spike gene using a PCR-based mutagenesis protocol as reported previously (Plante J A et al. Spike mutation D614G alters SARS-CoV-2 fitness. Nature 2020. doi: 10.1038/s41586-020-2895-3; Xie X et al. Neutralization of SARS-CoV-2 spike 69/70 deletion, E484K and N501Y variants by BNT162b2 vaccine-elicited sera. Nat Med 2021. doi: 10.1038/s41591-021-01270-4). The full-length infectious cDNAs were ligated and used as templates to in vitro transcribe full-length viral RNAs. The original viral stocks (P0) were recovered from Vero E6 cells on day 2 post electroporation of the in vitro transcribed RNAs. The P0 viruses were propagated on Vero E6 cells for another round to produce P1 viruses for the neutralization assays. The titers of P1 viruses were measured by plaque assay on Vero E6 cells (FIG. 139). The complete spike sequences of the P1 viruses were confirmed by Sanger sequencing to have only the intended nucleotide changes from the USA-WA1/2020 sequence. A detailed protocol of the above experiments was recently reported (Xie X et al. Engineering SARS-CoV-2 using a reverse genetic system. Nature Protocols 2021: doi.org/10.1038/s41596-021-00491-8).

Serum specimens and neutralization assay. FIG. 140 illustrates the immunization and serum collection scheme. A conventional 50% plaque-reduction neutralization test ($PRNT_{50}$) was performed to quantify the serum-mediated virus suppression as previously reported (Muruato A E et al. A high-throughput neutralizing antibody assay for COVID-19 diagnosis and vaccine evaluation. Nat Commun 2020; 11:4059). Briefly, individual sera were 2-fold serially diluted in culture medium with a starting dilution of 1:40 (dilution range of 1:40 to 1:1280). The diluted sera were incubated with 100 PFU of USA-WA1/2020 or mutant SARS-CoV-2. After 1 h incubation at 37° C., the serum-virus mixtures were inoculated onto a monolayer of Vero E6 cells pre-seeded on 6-well plates on the previous day. A minimal serum dilution that suppressed >50% of viral plaques is defined as $PRNT_{50}$. The neutralization titers are presented in Table 31.

TABLE 31

$PRNT_{50}$'s of twenty BNT162b2 post-immunization sera against USA-WA1/2020 and mutant SARS-CoV-2.

| Serum | USA-WA1/2020 | | | | B.1.1.7- | P.1-spike | | | B.1.315-spike | | | B.1.351-Δ242-244 + | 3.1.351-RBD + |
|---|---|---|---|---|---|---|---|---|---|---|---|---|---|
| ID | Exp1 | Exp2 | Exp3 | GMT | spike | Exp1 | Exp2 | GMT | Exp1 | Exp2 | GMT | D614G | D614G |
| 1 | 320 | 320 | 320 | 320 | 640 | 320 | 320 | 320 | 160 | 160 | 160 | 320 | 320 |
| 2 | 160 | 160 | 160 | 160 | 160 | 80 | 80 | 80 | 40 | 40 | 40 | 160 | 80 |
| 3 | 640 | 640 | 640 | 640 | 640 | 640 | 640 | 640 | 320 | 320 | 320 | 640 | 640 |
| 4 | 160 | 320 | 320 | 254 | 320 | 320 | 320 | 320 | 80 | 160 | 113 | 160 | 80 |
| 5 | 320 | 320 | 320 | 320 | 640 | 320 | 320 | 320 | 160 | 160 | 160 | 320 | 320 |
| 6 | 320 | 640 | 640 | 508 | 320 | 640 | 320 | 453 | 160 | 160 | 160 | 320 | 160 |
| 7 | 1280 | 640 | 640 | 806 | 1280 | 640 | 1280 | 905 | 320 | 320 | 320 | 1280 | 1280 |
| 8 | 320 | 320 | 320 | 320 | 320 | 160 | 160 | 160 | 80 | 80 | 80 | 160 | 160 |
| 9 | 1280 | 1280 | 1280 | 1280 | 1280 | 1280 | 640 | 905 | 640 | 640 | 640 | 1280 | 1280 |
| 10 | 640 | 640 | 1280 | 806 | 1280 | 640 | 320 | 453 | 640 | 320 | 453 | 1280 | 640 |
| 11 | 320 | 320 | 320 | 320 | 640 | 320 | 320 | 320 | 80 | 160 | 113 | 320 | 160 |
| 12 | 640 | 640 | 640 | 640 | 640 | 640 | 320 | 453 | 160 | 160 | 160 | 320 | 320 |
| 13 | 1280 | 1280 | 1280 | 1280 | 1280 | 640 | 640 | 640 | 160 | 320 | 226 | 1280 | 640 |
| 14 | 320 | 320 | 640 | 403 | 320 | 320 | 160 | 226 | 160 | 80 | 113 | 320 | 160 |
| 15 | 640 | 640 | 640 | 640 | 640 | 1280 | 640 | 905 | 320 | 320 | 320 | 640 | 320 |
| 16 | 320 | 320 | 640 | 403 | 1280 | 640 | 320 | 453 | 160 | 320 | 226 | 640 | 320 |

TABLE 31-continued

PRNT$_{50}$'s of twenty BNT162b2 post-immunization sera against USA-WA1/2020 and mutant SARS-CoV-2.

| Serum | USA-WA1/2020 | | | | B.1.1.7- | P.1-spike | | | B.1.315-spike | | | B.1.351-Δ242-244 + | 3.1.351-RBD + |
|---|---|---|---|---|---|---|---|---|---|---|---|---|---|
| ID | Exp1 | Exp2 | Exp3 | GMT | spike | Exp1 | Exp2 | GMT | Exp1 | Exp2 | GMT | D614G | D614G |
| 17 | 1280 | 1280 | 1280 | 1280 | 1280 | 1280 | 640 | 905 | 320 | 320 | 320 | 1280 | 640 |
| 18 | 640 | 640 | 640 | 640 | 640 | 640 | 320 | 453 | 160 | 320 | 226 | 320 | 320 |
| 19 | 640 | 640 | 640 | 640 | 640 | 1280 | 640 | 905 | 320 | 320 | 320 | 640 | 640 |
| 20 | 640 | 640 | 640 | 640 | 1280 | 640 | 320 | 453 | 160 | 160 | 160 | 640 | 320 |
| †GMT | 502 | 520 | 577 | 532 | 663 | 520 | 368 | 437 | 184 | 204 | 194 | 485 | 331 |
| #95% CI | 371-680 | 401-674 | 443-751 | 409-693 | 497-884 | 372-726 | 275-491 | 325-589 | 133-255 | 151-276 | 144-261 | 345-681 | 228-480 |

*The data for USA-WA1/2020 are from three experiments; the data for B.1.1.7-spike, B.1.351-Δ242-244 + D614G, and B.1.351-RBD-D614G viruses are from one experiment each; and the data for P.1-spike and B.1.351-spike viruses are from two experiments. For each independent experiment, individual PRNT$_{50}$ value is the geometric mean of duplicate plaque assay results; no differences were observed between the duplicate assays.

†Geometric mean neutralizing titers.

#95% confidence interval (95% CI) for the GMT.

Example 39: Durability of BNT162b2-Induced CD4+ and CD8+ T-Cell Responses

In a subset of 24 subjects across dose levels 10 to 30 μg, samples collected at Day 85 and Day 184 (nine and 23 weeks post-boost, respectively) were analyzed in order to determine the durability of T-cell responses induced by BNT162b2. On Day 184 and after an initial contraction, both CD4$^+$ and CD8$^+$ T-cell responses were detectable in the majority of individuals, across the three dose levels tested. Kinetics of CD4$^+$ and CD8$^+$ responses observed in four older adult subjects vaccinated with 10 μg BNT162b2 were comparable to younger adult subjects, with S protein-specific CD4$^+$ T cells still detectable in all four subjects 23 weeks after boost vaccination. BNT162b2 induced CD4$^+$ and CD8$^+$ responses were either higher than or in the range of recall antigen memory responses (FIG. 142).

Example 40: MHC-I Binding Epitopes Recognized by CD8 T-Cells Induced by BNT162b2

Using MHC-class I multimer technology, several epitopes spread across the whole length of the S Protein and presented by a combination of common HLA-A and HLA-B alleles were identified to be recognized by CD8+ T-cells induced by BNT162-b2 (measured 7 days after the boost vaccination). Some peptide/HLA combinations were found in more than one subject.

TABLE 32

MHC-1 binding epitopes recognized by CD8 T-cells induced by BNT162b2

| HLA | Epitope | SEQ ID NO | Position in S Protein | Identified in No. Subjects |
|---|---|---|---|---|
| B35:01 | LPFNDGVYF | 47 | 84-92 | 1 |
| A03:01 | GVYFASTEK | 52 | 89-97 | 1 |
| A02:01 | YLQPRTFLL | 40 | 269-277 | 3 |
| B35:01 | QPTESIVRF | 45 | 321-329 | 1 |
| A26:01 | CVADYSVLY | 53 | 361-369 | 1 |
| B15:01 | CVADYSVLY | 53 | 361-369 | 1 |
| A03:01 | KCYGVSPTK | 54 | 378-386 | 2 |
| A24:02 | NYNYLYRLF | 43 | 448-456 | 3 |
| B15:01 | FQPTNGVGY | 55 | 497-505 | 1 |
| B35:01 | IPFAMQMAY | 46 | 896-904 | 1 |
| A02:01 | RLQSLQTYV | 41 | 1000-1008 | 2 |
| A68:01 | GTHWFVTQR | 56 | 1099-1108 | 1 |
| C04:01 | VYDPLQPEL | 57 | 1137-1145 | 1 |
| A24:02 | QYIKWPWYI | 42 | 1208-1216 | 3 |
| A24:02 | KWPWYIWLGF | 44 | 1211-1220 | 1 |

Example 41: Histological Findings Following Administration of BNT162b2

Classical chromogenic immunohistochemistry (IHC) and chromogenic dual IHC-ISH (in situ hybridization) experiments were performed to investigate biodistribution of BNT162b2 in mouse tissues 6h and 6d post-injection.

Protocol

After harvesting, tissue is fixed in 4% RotiHistofix overnight at 4° C. and embedded in paraffin wax after dehydration in Leica Tissue Processor. Chromogenic IHC is performed. Spike protein is detected with anti-Spike2 mouse monoclonal antibody (Genetex). Dual IHC-ISH assay is conducted according to a self-established protocol based on Document MK 51-149 from Advanced Cell Diagnostics using the company kits and reagents. BNT162b2 probe (modV9) for ISH is custom designed by Advanced Cell Diagnostics based on the sequence provided by TRON. IHC protocol for the immune cell markers CD11c (Cell Signaling), CD19 (Cell Signaling), CD169 (Thermo Fisher) and F4/80 (Cell Signaling) were in place at TRON and they are adapted to dual IHC-ISH assay for the project. Images are acquired using Vectra Polaris Multispectral Slide Scanner microscope (Akoya Bioscience) and analysed with PhenoChart software (Akoya Bioscience).

Results

As can be seen in FIG. 143, a specific vaccine mRNA signal (red) is detected in the lymph nodes (LN) 6h post injection using modV9 probe in dual IHC-ISH assay. Vaccine is mostly localized to subcapsular sinus (LN in 9 and 5 positions) and B cell follicles (LN in 12 and 1 positions). Dendritic cells are visualized by CD11c staining (turquoise, upper images) and only some of them uptake the vaccine. Majority of CD169+ macrophages (subcapsular sinus macrophages, turquoise, middle images) are positive for the vaccine. B cells (CD19+, turquoise, lower images) are the second major population showing vaccine signal.

A specific vaccine mRNA signal is still detectable in the LN 6d post injection using modV9 probe in dual IHC-ISH assay, albeit in very less amount (data not shown). Some CD11c+DCs and subcapsular sinus macrophages are positive for the vaccine. Most of the vaccine signal detected is in the B cells (CD19+).

As can be seen in FIG. 144, a specific vaccine mRNA signal (red) is detected in the spleen 6h post injection using modV9 probe in dual IHC-ISH assay. Majority of the vaccine signal is detected in the white pulp. Dendritic cells are visualized by CD11c staining (turquoise, upper images) and only some of them uptake the vaccine. A small portion of F4/80+ macrophages (turquoise, middle images) uptake the vaccine. B cells (CD19+, turquoise, lower images) are the major population showing the vaccine signal.

A specific vaccine mRNA signal is still detectable in the spleen 6d post injection using modV9 probe in dual IHC-ISH assay, albeit in very less amount (data not shown). The vaccine signal detected is solely in the B cells (CD19+). No DCs and macrophages show vaccine signal 6d post-injection.

After 6h, using mouse anti-S2 mouse monoclonal antibody, we detected a signal in the muscle, especially in some muscle fibers and in the connective tissue perimysium. In the LNs, we detected cells expressing Spike protein in the T cell zone (data not shown).

After 6d, using mouse anti-S2 mouse monoclonal antibody, no Spike expression is detectable in the muscle. On the contrary, LNs are full of cells expressing the vaccine (data not shown).

No nonspecific staining is detected with the S2 mouse monoclonal antibody in the chromogenic IHC experiments.

SUMMARY

A very strong vaccine signal is visible in the draining LNs and spleen 6h post-injection. In the LN, vaccine is mostly detected in B cell follicles and subcapsular sinus, with some signal also in the T cell zone. By dual IHC-ISH, we showed that indeed the B cells (CD19+) and subcapsular sinus macrophages (CD169+) are the major cells that uptake the vaccine. Dendritic cells (CD11c+) in the T cell zone and intermediary sinus also uptake the vaccine. After 6d, some vaccine mRNA is still visible in the draining LNs. The signal observed in the T-cell zone after 6d is in the dendritic cells (CD11c+). Some B cells and LN macrophages also still have some vaccine at that stage.

Analysis of the spleen harvested 6h post-injection showed that vaccine already reaches spleen within 6h, most probably via blood circulation. The signal is located white pulp, where B cells and T cells form the major population and antigen presentation to T cells occur in the white pulp. With dual IHC-ISH assay, we showed that majority of B cells uptake the vaccine. Many DCs (CD11c+) surrounding the B cells are also positive. After 6d, signal is restricted to B cells. IHC protocol is established to detect spike protein expression using anti-Spike S2 mouse monoclonal antibody on the cell pellets treated with/without the vaccine. A specific signal is detected only in the cells treated with BNT162b2. No nonspecific staining was visible in the naïve tissues tested. In the muscle, Spike expression is detected 6h post injection in the muscle fibers and in the connective tissue perimysium. After 6d, no staining is detectable in the muscle. On the contrary, the massive Spike expression is visible 6d post injection in LN, in particular in the T-cell zone.

Example 42: Stability Studies

Stability assessments of BNT162b2 formulations at various concentrations (e.g., 0.5 mg/mL, 1 mg/mL, and 2 mg/mL) have been performed, and have included assessments of compositions, stored at various temperatures (e.g., −70° C. [e.g., −70±10° C.], −20° C. [e.g., −20±5° C.], +5° C. [e.g., 5±3° C.], or +25° C. [e.g., 25±2° C.]) and/or for various periods of time (e.g., 0.5 months, 1 month, 2 months, 3 months, 4 months, and in certain cases one or more intervening time points (e.g., 1.5 months, 2.5 months, etc).

In exemplary studies, mice were injected (single leg) at day 0 with 20 uL of a relevant formulation. Blood was collected and serum generated at days 14, 21, and 28 after the administration; spleen were isolated at day 28.

ELISAs were performed to detect presence of antibodies in serum that bind to S1 protein, or specifically to the RBD domain. FIG. 145 presents exemplary S1 ELISA results obtained with 28-day serum from mice injected with indicated formulations that had been stored under indicated temperature conditions for indicated periods of time. As can be seen with reference to FIG. 145, all stored samples performed well, and reasonably comparably, after one (1) month of storage. After two (2) or three (3) months of storage, some decreased activity was observed for samples stored at +25° C., but samples stored at −70° C., −20° C., +5° C. maintained significant performance.

At some time points, one or more parameters such as appearance, RNA content, RNA integrity, RNA encapsulation, lipid content (overall and/or of individual components and/or ratios thereof), particle size, particle polydispersity index, in vitro expressability, etc) were assessed; additional or alternative parameters may be or have been assessed.

Exemplary observations include that storage at +25° C. is not recommended for periods of time longer than about 2 weeks, and preferably not more than about 1 week as, among other things, RNA integrity was observed to decrease significantly. It was also observed that, in at least some cases, significant ability to induce antibodies was maintained even when in vitro expressability was materially reduced. Change in polydispersity index, particularly after about 3 months of storage, or after about 4 months of storage, were observed to be greater for formulations stored at +5° C. or above than for those stored at lower temperatures.

We claim:

1. A pharmaceutical composition comprising an RNA comprising the nucleotide sequence of SEQ ID NO: 9 that includes modified uridines.

2. The composition of claim 1, wherein the RNA comprises a 5'-cap that is or comprises $m_2^{7,3'-O}Gppp(m_1^{2'-O})ApG$.

3. The composition of claim 1, wherein the RNA comprises a polyA sequence, wherein the polyA sequence comprises 30 adenine nucleotides followed by 70 adenine nucleotides, wherein the 30 adenine nucleotides and 70 adenine nucleotides are separated by a linker sequence.

4. The composition of claim 1, wherein the RNA comprises a 5'-UTR that is or comprises a modified human alpha-globin 5'-UTR.

5. The composition of claim 1, wherein the RNA comprises a 3'-UTR that is or comprises a first sequence from the amino terminal enhancer of split (AES) messenger RNA and a second sequence from the mitochondrial encoded 12S ribosomal RNA.

6. The composition of claim 1, wherein the nucleotide sequence includes modified uridines in place of all uridines.

7. The composition of claim 6, wherein the modified uridines are each N1-methyl-pseudouridine.

8. The composition of claim 1, wherein the RNA comprises: a 5' cap, a 5' UTR, a 3' UTR, and a polyA sequence.

9. The composition of claim 8, wherein the 5' cap is or comprises a cap1 structure.

10. The composition of claim 8, wherein the polyA sequence comprises at least 100 A nucleotides.

11. The composition of claim 10, wherein the polyA sequence is an interrupted sequence of A nucleotides.

12. The composition of claim 1, wherein the RNA is formulated in lipid nanoparticles comprising each of: (i) a cationically ionizable lipid; (ii) a neutral lipid; (iii) a sterol; and (iv) a lipid conjugate.

13. The composition of claim 12, further comprising at least one salt and/or a cryoprotectant.

14. The composition of claim 13, wherein the cryoprotectant is or comprises sucrose.

15. The composition of claim 12, wherein the composition is formulated for intramuscular administration.

16. The composition of claim 12, wherein the RNA is present in an amount within a range of about 1 μg to about 100 μg per dose in the composition.

17. The composition of claim 12, wherein the RNA is present in an amount of about 3 μg per dose in the composition.

18. The composition of claim 12, wherein the RNA is present in an amount of about 10 μg per dose in the composition.

19. The composition of claim 12, wherein the RNA is present in an amount of about 30 μg per dose in the composition.

20. A pharmaceutical composition comprising:

an RNA comprising a nucleotide sequence that includes modified uridines and encodes a SARS-CoV-2 Spike (S) polypeptide that is at least 95% identical to the polypeptide of SEQ ID NO: 7, and includes proline residues at positions 986 and 987 of SEQ ID NO: 7, wherein the RNA comprises a nucleotide sequence that is at least 95% identical to SEQ ID NO: 20.

21. The composition of claim 20, wherein the nucleotide sequence encodes a SARS-CoV-2 Spike (S) polypeptide comprising SEQ ID NO: 7.

22. The composition of claim 20, wherein the nucleotide sequence includes modified uridines in place of all uridines.

23. The composition of claim 22, wherein the modified uridines are each N1-methyl-pseudouridine.

24. The composition of claim 20, wherein the RNA comprises a 5' cap that is or comprises a cap1 structure.

25. The composition of claim 24, wherein the RNA comprises a 5'-cap that is or comprises $m_2^{7,3'-O}Gppp(m_1^{2'-O})$ ApG.

26. The composition of claim 20, wherein the RNA comprises a polyA sequence comprising at least 100 A nucleotides.

27. The composition of claim 26, wherein the polyA sequence comprises an interrupted sequence of A nucleotides.

28. The composition of claim 27, wherein the interrupted sequence comprises 30 adenine nucleotides followed by 70 adenine nucleotides, wherein the 30 adenine nucleotides and 70 adenine nucleotides are separated by a linker sequence.

29. The composition of claim 20, wherein the RNA comprises a 5'-UTR that is or comprises a modified human alpha-globin 5'-UTR.

30. The composition of claim 20, wherein the RNA comprises a 3'-UTR that is or comprises a first sequence from the amino terminal enhancer of split (AES) messenger RNA and a second sequence from the mitochondrial encoded 12S ribosomal RNA.

31. The composition of claim 20, wherein the nucleotide sequence that includes modified uridines and encodes a SARS-CoV-2 Spike (S) polypeptide is codon-optimized for human subjects.

32. The composition of claim 20, wherein the RNA is formulated in lipid nanoparticles comprising each of: (i) a cationically ionizable lipid; (ii) a neutral lipid; (iii) a sterol; and (iv) a lipid conjugate.

33. The composition of claim 32, further comprising at least one salt and/or a cryoprotectant.

34. The composition of claim 33, wherein the cryoprotectant is or comprises sucrose.

35. The composition of claim 32, wherein the composition is formulated for intramuscular administration.

36. The composition of claim 32, wherein the RNA is present in an amount within a range of about 1 μg to about 100 μg per dose in the composition.

37. The composition of claim 32, wherein the RNA is present in an amount of about 3 μg per dose in the composition.

38. The composition of claim 32, wherein the RNA is present in an amount of about 10 μg per dose in the composition.

39. The composition of claim 32, wherein the RNA is present in an amount of about 30 μg per dose in the composition.

40. The composition of claim 20, wherein the RNA comprises the nucleotide sequence of SEQ ID NO: 20.

41. The composition of claim 40, wherein the nucleotide sequence includes modified uridines in place of all uridines.

42. The composition of claim 41, wherein the modified uridines are each N1-methyl-pseudouridine.

43. The composition of claim 40, wherein the RNA comprises a 5'-cap that is or comprises a cap1 structure.

44. The composition of claim 40, wherein the RNA comprises a 5'-cap that is or comprises $m_2^{7,3'-O}Gppp(m\mathbf{1}_1^{2'-o})$ ApG.

45. The composition of claim 42, wherein the RNA comprises a 5'-cap that is or comprises $m_2^{7,3'-O}Gppp(m_1^{2'-O})$ ApG.

* * * * *

UNITED STATES PATENT AND TRADEMARK OFFICE

CERTIFICATE OF CORRECTION

PATENT NO. : 11,547,673 B1
APPLICATION NO. : 17/233396
DATED : January 10, 2023
INVENTOR(S) : Ugur Sahin et al.

It is certified that error appears in the above-identified patent and that said Letters Patent is hereby corrected as shown below:

In the Claims

Claim 20 (Column 643, Lines 11-12), replace “proline residues at positions 986 and 987 of SEQ ID NO: 7” with -- proline residues at positions corresponding to amino acids 986 and 987 of SEQ ID NO: 7 --

Claim 44 (Column 644, Lines 37-38), replace “$m_2^{7,3'-O}$Gppp($m1_1^{2'-O}$)ApG” with -- $m_2^{7,3'-O}$Gppp($m_1^{2'-O}$)ApG --

Signed and Sealed this
Twentieth Day of June, 2023

Katherine Kelly Vidal

Katherine Kelly Vidal
*Director of the United States Patent and Trademark Office*

SEQUENCE LISTING

```
<160> NUMBER OF SEQ ID NOS: 57

<210> SEQ ID NO 1
<211> LENGTH: 1273
<212> TYPE: PRT
<213> ORGANISM: Artificial Sequence
<220> FEATURE:
<223> OTHER INFORMATION: S protein

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30
```

-continued

```
Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445
```

```
Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
```

-continued

```
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

<210> SEQ ID NO 2
<211> LENGTH: 3819
<212> TYPE: RNA
<213> ORGANISM: Artificial Sequence
<220> FEATURE:
<223> OTHER INFORMATION: Coding Sequence

<400> SEQUENCE: 2
auguuugugu uucuugugcu gcugccucuu gugucuucuc agugugugaa uuugacaaca 60
agaacacagc ugccaccagc uuauacaaau ucuuuuacca gaggagugua uuauccugau 120
aaaguguuua gaucuucugu gcugcacagc acacaggacc uguuucugcc auuuuuuagc 180
aaugugacau gguuucaugc aauucaugug ucuggaacaa auggaacaaa aagauuugau 240
aauccugugc ugccuuuuaa ugauggagug uauuuugcuu caacagaaaa gucaaauauu 300
auuagaggau ggauuuuugg aacaacacug gauucuaaaa cacagucucu gcugauugug 360
aauaaugcaa caaauguggu gauuaaagug ugugaauuuc aguuuuguaa ugauccuuuu 420
cugggagugu auuaucacaa aaauaauaaa ucuuggaugg aaucugaauu uagaguguau 480
uccucugcaa auaauuguac auuugaauau gugucucagc cuuuucugau ggaucuggaa 540
ggaaaacagg gcaauuuuaa aaaucugaga gaauuugugu uuaaaaauau ugauggauau 600
uuuaaaauuu auucuaaaca cacaccaauu aauuuaguga gagaucugcc ucagggauuu 660
ucugcucugg aaccucuggu ggaucugcca auuggcauua auauuacaag auuucagaca 720
cugcuggcuc ugcacagauc uuaucugaca ccuggagauu cuucuucugg auggacagcc 780
ggagcugcag cuuauuaugu gggcuaucug cagccaagaa cauuucugcu gaaauauaau 840
gaaaauggaa caauuacaga ugcuguggau ugugcucugg auccucuguc ugaaacaaaa 900
uguacauuaa aaucuuuuac aguggaaaaa ggcauuuauc agacaucuaa uuuuagagug 960
cagccaacag aaucuauugu gagauuucca aauauuacaa aucuguguccc auuuggagaa 1020 guguuuaaug caacaagauu ugcaucugug uaugcaugga auagaaaaag aauuucuaau 1080
uguguggcug auuauucugu gcuguauaau agugcuucuu uuuccacauu uaaauguuau 1140
ggagugucuc caacaaaauu aaaugauuua uguuuuacaa auguguaugc ugauucuuuu 1200
gugaucagag gugaugaagu gagacagauu gcccccggac agacaggaaa aauugcugau 1260
uacaauuaca aacugccuga ugauuuuaca ggauguguga uugcuuggaa uucuaauaau 1320
uuagauucua aagugggagg aaauuacaau uaucuguaca gacuguuuag aaaaucaaau 1380
cugaaaccuu uugaaagaga uauuucaaca gaaauuuauc aggcuggauc aacaccuugu 1440
aauggagugg aaggauuuaa uuguuauuuu ccauuacaga gcuauggauu ucagccaacc 1500
aauggugugg gauaucagcc auauagagug guggugcugu cuuuugaacu gcugcaugca 1560
ccugcaacag uguguggacc uaaaaaaucu acaaauuuag ugaaaaauaa augugugaau 1620
uuuaauuuua auggauuaac aggaacagga gugcugacag aaucuaauaa aaaauuucug 1680
ccuuuucagc aguuuggcag agauauugca gauaccacag augcagugag agauccucag 1740
acauuagaaa uucuggauau uacaccuugu ucuuuugggg gugugucugu gauuacaccu 1800
ggaacaaaua caucuaauca gguggcugug cuguaucagg augugaauug uacagaagug 1860
ccaguggcaa uucaugcaga ucagcugaca ccaacaugga gaguguauuc uacaggaucu 1920
aauguguuuc agacaagagc aggaugucug auuggagcag aacaugugaa uaauucuuau 1980
gaaugugaua uuccaauugg agcaggcauu ugugcaucuu aucagacaca gacaaauucc 2040

```
ccaaggagag caagaucugu ggcaucucag ucuauuauug cauacaccau gucucuggga   2100

gcagaaaauu cuguggcaua uucuaauaau ucuauugcua uuccaacaaa uuuuaccauu   2160

ucugugacaa cagaaauuuu accuguguuu augacaaaaa caucugugga uuguaccaug   2220

uacauuugug gagauucuac agaauguucu aaucugcugc ugcaguaugg aucuuuuugu   2280

acacagcuga auagagcuuu aacaggaauu gcuguggaac aggauaaaaa uacacaggaa   2340

guguuugcuc aggugaaaca gauuuacaaa acaccaccaa uuaaagauuu uggaggauuu   2400

aauuuuagcc agauucugcc ugauccuucu aaaccuucua aaagaucuuu uauugaagau   2460

cugcuguuua auaaagugac acuggcagau gcaggauuua uuaaacagua uggagauugc   2520

cugggugaua uugcugcaag agaucugauu ugugcucaga aauuuaaugg acugacagug   2580

cugccuccuc ugcugacaga ugaaaugauu gcucaguaca caucugcuuu acuggcugga   2640

acaauuacaa gcggauggac auuuggagcu ggagcugcuc ugcagauucc uuuugcaaug   2700

cagauggcuu acagauuuaa uggaauugga gugacacaga auguguuaua ugaaaaucag   2760

aaacugauug caaaucaguu uaauucugca auuggcaaaa uucaggauuc ucugucuucu   2820

acagcuucug cucugggaaa acugcaggau guggugaauc agaaugcaca ggcacugaau   2880

acucugguga aacagcuguc uagcaauuuu ggggcaauuu cuucugugcu gaaugauauu   2940

cugucuagac uggauaaagu ggaagcugaa gugcagauug auagacugau cacaggaaga   3000

cugcagucuc ugcagacuua ugugacacag cagcugauua gagcugcuga aauuagagcu   3060

ucugcuaauc uggcugcuac aaaaaugucu gaaugugugc ugggacaguc aaaaagagug   3120

gauuuuugug gaaaaggaua ucaucugaug ucuuuuccac agucugcucc acauggagug   3180

guguuuuuac augugacaua ugugccagca caggaaaaga auuuuaccac agcaccagca   3240

auuugucaug auggaaaagc acauuuucca agagaaggag uguuuguguc uaauggaaca   3300

cauugguuug ugacacagag aaauuuuuau gaaccucaga uuauuacaac agauaauaca   3360

uuugugucag gaaauuguga uguggugauu ggaauuguga auaauacagu guaugaucca   3420

cugcagccag aacuggauuc uuuuaaagaa gaacuggaua aauauuuuaa aaaucacaca   3480

ucuccugaug uggauuuagg agauauuucu ggaaucaaug caucuguggu gaauauucag   3540

aaagaaauug auagacugaa ugaaguggcc aaaaaucuga augaaucucu gauugaucug   3600

caggaacuug gaaaauauga acaguacauu aaauggccuu gguacauuug gcuuggauuu   3660

auugcaggau uaauugcaau ugugauggug acaauuaugu uauguuguau gacaucaugu   3720

uguucuuguu uaaaaggaug uuguucuugu ggaagcuguu guaaauuuga ugaagaugau   3780

ucugaaccug uguuaaaagg agugaaauug cauuacaca                        3819
```

<210> SEQ ID NO 3
<211> LENGTH: 218
<212> TYPE: PRT
<213> ORGANISM: Artificial Sequence
<220> FEATURE:
<223> OTHER INFORMATION: S Protein RBD Fusion

<400> SEQUENCE: 3

```
Met Phe Val Phe Leu Val Leu Leu Pro Leu Val Ser Ser Gln Cys Val
1               5                   10                  15

Val Arg Phe Pro Asn Ile Thr Asn Leu Cys Pro Phe Gly Glu Val Phe
            20                  25                  30

Asn Ala Thr Arg Phe Ala Ser Val Tyr Ala Trp Asn Arg Lys Arg Ile
        35                  40                  45
```

```
Ser Asn Cys Val Ala Asp Tyr Ser Val Leu Tyr Asn Ser Ala Ser Phe
    50                  55                  60

Ser Thr Phe Lys Cys Tyr Gly Val Ser Pro Thr Lys Leu Asn Asp Leu
65                  70                  75                  80

Cys Phe Thr Asn Val Tyr Ala Asp Ser Phe Val Ile Arg Gly Asp Glu
                85                  90                  95

Val Arg Gln Ile Ala Pro Gly Gln Thr Gly Lys Ile Ala Asp Tyr Asn
            100                 105                 110

Tyr Lys Leu Pro Asp Asp Phe Thr Gly Cys Val Ile Ala Trp Asn Ser
        115                 120                 125

Asn Asn Leu Asp Ser Lys Val Gly Gly Asn Tyr Asn Tyr Leu Tyr Arg
    130                 135                 140

Leu Phe Arg Lys Ser Asn Leu Lys Pro Phe Glu Arg Asp Ile Ser Thr
145                 150                 155                 160

Glu Ile Tyr Gln Ala Gly Ser Thr Pro Cys Asn Gly Val Glu Gly Phe
                165                 170                 175

Asn Cys Tyr Phe Pro Leu Gln Ser Tyr Gly Phe Gln Pro Thr Asn Gly
            180                 185                 190

Val Gly Tyr Gln Pro Tyr Arg Val Val Val Leu Ser Phe Glu Leu Leu
        195                 200                 205

His Ala Pro Ala Thr Val Cys Gly Pro Lys
    210                 215
```

<210> SEQ ID NO 4
<211> LENGTH: 654
<212> TYPE: RNA
<213> ORGANISM: Artificial Sequence
<220> FEATURE:
<223> OTHER INFORMATION: Coding Sequence

<400> SEQUENCE: 4

```
auguuugugu uucuugugcu gcugccucuu gugucuucuc agugugugu gagauuucca      60

aauauuacaa aucugugucc auuuggagaa guguuuaaug caacaagauu ugcaucugug    120

uaugcaugga auagaaaaag aauuucuaau uguguggcug auuauucugu gcuguauaau    180

agugcuucuu uuuccacauu uaaauguuau ggagugucuc caacaaaauu aaaugauuua    240

uguuuuacaa auguguaugc ugauucuuuu gugaucagag gugaugaagu gagacagauu    300

gcccccggac agacaggaaa aauugcugau uacaauuaca aacugccuga ugauuuuaca    360

ggauguguga uugcuuggaa uucuaauaau uuagauucua aagugggagg aaauuacaau    420

uaucuguaca gacuguuuag aaaaucaaau cugaaaccuu uugaaagaga uauuucaaca    480

gaaauuuauc aggcuggauc aacaccuugu aauggagugg aaggauuuaa uuguuauuuu    540

ccauuacaga gcuauggauu ucagccaacc aauggugugg gauaucagcc auauagagug    600

guggugcugu cuuuugaacu gcugcaugca ccugcaacag ugugugggacc uaaa         654
```

<210> SEQ ID NO 5
<211> LENGTH: 266
<212> TYPE: PRT
<213> ORGANISM: Artificial Sequence
<220> FEATURE:
<223> OTHER INFORMATION: S Protein RBD Fusion

<400> SEQUENCE: 5

```
Met Phe Val Phe Leu Val Leu Leu Pro Leu Val Ser Ser Gln Cys Val
1               5                   10                  15

Val Arg Phe Pro Asn Ile Thr Asn Leu Cys Pro Phe Gly Glu Val Phe
```

```
            20                  25                  30

Asn Ala Thr Arg Phe Ala Ser Val Tyr Ala Trp Asn Arg Lys Arg Ile
        35                  40                  45

Ser Asn Cys Val Ala Asp Tyr Ser Val Leu Tyr Asn Ser Ala Ser Phe
    50                  55                  60

Ser Thr Phe Lys Cys Tyr Gly Val Ser Pro Thr Lys Leu Asn Asp Leu
65                  70                  75                  80

Cys Phe Thr Asn Val Tyr Ala Asp Ser Phe Val Ile Arg Gly Asp Glu
                85                  90                  95

Val Arg Gln Ile Ala Pro Gly Gln Thr Gly Lys Ile Ala Asp Tyr Asn
            100                 105                 110

Tyr Lys Leu Pro Asp Asp Phe Thr Gly Cys Val Ile Ala Trp Asn Ser
        115                 120                 125

Asn Asn Leu Asp Ser Lys Val Gly Gly Asn Tyr Asn Tyr Leu Tyr Arg
    130                 135                 140

Leu Phe Arg Lys Ser Asn Leu Lys Pro Phe Glu Arg Asp Ile Ser Thr
145                 150                 155                 160

Glu Ile Tyr Gln Ala Gly Ser Thr Pro Cys Asn Gly Val Glu Gly Phe
                165                 170                 175

Asn Cys Tyr Phe Pro Leu Gln Ser Tyr Gly Phe Gln Pro Thr Asn Gly
            180                 185                 190

Val Gly Tyr Gln Pro Tyr Arg Val Val Val Leu Ser Phe Glu Leu Leu
        195                 200                 205

His Ala Pro Ala Thr Val Cys Gly Pro Lys Gly Ser Pro Gly Ser Gly
    210                 215                 220

Ser Gly Ser Gly Tyr Ile Pro Glu Ala Pro Arg Asp Gly Gln Ala Tyr
225                 230                 235                 240

Val Arg Lys Asp Gly Glu Trp Val Leu Leu Ser Thr Phe Leu Gly Arg
                245                 250                 255

Ser Leu Glu Val Leu Phe Gln Gly Pro Gly
            260                 265
```

<210> SEQ ID NO 6
<211> LENGTH: 798
<212> TYPE: RNA
<213> ORGANISM: Artificial Sequence
<220> FEATURE:
<223> OTHER INFORMATION: Coding Sequence

<400> SEQUENCE: 6

```
auguuugugu uucuugugcu gcugccucuu gugucuucuc agugugugu gagauuucca      60

aauauuacaa aucugugucc auuuggagaa guguuuaaug caacaagauu ugcaucugug    120

uaugcaugga auagaaaaag aauuucuaau uguguggcug auuauucugu gcuguauaau    180

agugcuucuu uuuccacauu uaaauguuau ggagugucuc caacaaaauu aaaugauuua    240

uguuuuacaa auguguaugc ugauucuuuu gugaucagag gugaugaagu gagacagauu    300

gcccccggac agacaggaaa aauugcugau uacaauuaca aacugccuga ugauuuuaca    360

ggauguguga uugcuuggaa uucuaauaau uuagauucua aagugggagg aaauuacaau    420

uaucuguaca gacuguuuag aaaaucaaau cugaaaccuu uugaaagaga uauuucaaca    480

gaaauuuauc aggcuggauc aacaccuugu aauggagugg aaggauuuaa uuguuauuuu    540

ccauuacaga gcuauggauu ucagccaacc aauggugugg gauaucagcc auauagagug    600

guggugcugu cuuuugaacu gcugcaugca ccugcaacag uguguggacc uaaaggcucc    660
```

```
cccggcuccg gcuccggauc ugguuauauu ccugaagcuc caagagaugg gcaagcuuac     720

guucguaaag auggcgaaug gguauuacuu ucuaccuuuu uaggccgguc ccuggaggug     780

cuguuccagg gccccggc                                                   798


<210> SEQ ID NO 7
<211> LENGTH: 1273
<212> TYPE: PRT
<213> ORGANISM: Artificial Sequence
<220> FEATURE:
<223> OTHER INFORMATION: S Protein Variant

<400> SEQUENCE: 7

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
```

-continued

```
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170
```

-continued

```
Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 8
<211> LENGTH: 3819
<212> TYPE: RNA
<213> ORGANISM: Artificial Sequence
<220> FEATURE:
<223> OTHER INFORMATION: Coding Sequence

<400> SEQUENCE: 8

```
auguuugugu uucuugugcu gcugccucuu gugucuucuc agugugugaa uuugacaaca     60

agaacacagc ugccaccagc uuauacaaau ucuuuuacca gaggagugua uuauccugau    120

aaaguguuua gaucuucugu gcugcacagc acacaggacc uguuucugcc auuuuuuagc    180

aaugugacau gguuucaugc aauucaugug ucuggaacaa auggaacaaa aagauuugau    240

aauccugugc ugccuuuuaa ugauggagug uauuuugcuu caacagaaaa gucaaauauu    300

auuagaggau ggauuuuugg aacaacacug gauucuaaaa cacagucucu gcugauugug    360

aauaaugcaa caaauguggu gauuaaagug ugugaauuuc aguuuuguaa ugauccuuuu    420

cugggagugu auuaucacaa aaauaauaaa ucuuggaugg aaucugaauu uagaguguau    480

uccucugcaa auaauuguac auuugaauau gugucucagc cuuuucugau ggaucuggaa    540

ggaaaacagg gcaauuuuaa aaaucugaga gaauuugugu uuaaaaauau ugauggauau    600

uuuaaaauuu auucuaaaca cacaccaauu aauuuaguga gagaucugcc ucagggauuu    660

ucugcucugg aaccucuggu ggaucugcca auuggcauua auauuacaag auuucagaca    720

cugcuggcuc ugcacagauc uuaucugaca ccuggagauu cuucuucugg auggacagcc    780

ggagcugcag cuuauuaugu gggcuaucug cagccaagaa cauuucugcu gaaauauaau    840

gaaaauggaa caauuacaga ugcuguggau ugugcucugg auccucuguc ugaaacaaaa    900

uguacauuaa aaucuuuuac aguggaaaaa ggcauuuauc agacaucuaa uuuuagagug    960

cagccaacag aaucuauugu gagauuucca aauauuacaa aucuguguccc auuuggagaa   1020

guguuuaaug caacaagauu ugcaucugug uaugcaugga auagaaaaag aauuucuaau   1080

uguguggcug auuauucugu gcuguauaau agugcuucuu uuuccacauu uaaauguuau   1140

ggagugucuc caacaaaauu aaaugauuua uguuuuacaa auguguaugc ugauucuuuu   1200

gugaucagag gugaugaagu gagacagauu gcccccggac agacaggaaa aauugcugau   1260

uacaauuaca aacugccuga ugauuuuaca ggauguguga uugcuuggaa uucuaauaau   1320

uuagauucua aagugggagg aaauuacaau uaucuguaca gacuguuuag aaaaucaaau   1380

cugaaaccuu uugaaagaga uauuucaaca gaaauuuauc aggcuggauc aacaccuugu   1440
```

-continued

```
aauggagugg aaggauuuaa uuguuauuuu ccauuacaga gcuauggauu ucagccaacc   1500
aaugguguggg gauaucagcc auauagagug guggugcugu cuuuugaacu gcugcaugca   1560
ccugcaacag uguguggacc uaaaaaaucu acaaauuuag ugaaaaaauaa augugugaau   1620
uuuaauuuua auggauuaac aggaacagga gugcugacag aaucuaauaa aaaauuucug   1680
ccuuuucagc aguuuggcag agauauugca gauaccacag augcagugag agauccucag   1740
acauuagaaa uucuggauau uacaccuugu ucuuuugggg gugugucugu gauuacaccu   1800
ggaacaaaua caucuaauca gguggcugug cuguaucagg augugaauug uacagaagug   1860
ccaguggcaa uucaugcaga ucagcugaca ccaacaugga gaguguauuc uacaggaucu   1920
aauguguuuc agacaagagc aggaugucug auuggagcag aacaugugaa uaauucuuau   1980
gaaugugaua uuccaauugg agcaggcauu ugugcaucuu aucagacaca gacaaauucc   2040
ccaaggagag caagaucugu ggcaucucag ucuauuauug cauacaccau gucucuggga   2100
gcagaaaauu cuguggcaua uucuaauaau ucuauugcua uuccaacaaa uuuuaccauu   2160
ucugugacaa cagaaauuuu accugugucu augacaaaaa caucugugga uuguaccaug   2220
uacauuugug gagauucuac agaauguucu aaucugcugc ugcaguaugg aucuuuuugu   2280
acacagcuga auagagcuuu aacaggaauu gcuguggaac aggauaaaaa uacacaggaa   2340
guguuugcuc aggugaaaca gauuuacaaa acaccaccaa uuaaagauuu uggaggauuu   2400
aauuuuagcc agauucugcc ugauccuucu aaaccuucua aaagaucuuu uauugaagau   2460
cugcuguuua auaaagugac acuggcagau gcaggauuua uuaaacagua uggagauugc   2520
cugggugaua uugcugcaag agaucugauu ugugcucaga aauuuaaugg acugacagug   2580
cugccuccuc ugcugacaga ugaaaugauu gcucaguaca caucugcuuu acuggcugga   2640
acaauuacaa gcggauggac auuuggagcu ggagcugcuc ugcagauucc uuuugcaaug   2700
cagauggcuu acagauuuaa uggaauugga gugacacaga auguguuaua ugaaaaucag   2760
aaacugauug caaaucaguu uaauucugca auuggcaaaa uucaggauuc ucugucuucu   2820
acagcuucug cucugggaaa acugcaggau guggugaauc agaaugcaca ggcacugaau   2880
acucugguga aacagcuguc uagcaauuuu ggggcaauuu cuucugugcu gaaugauauu   2940
cugucuagac uggauccucc ugaagcugaa gugcagauug auagacugau cacaggaaga   3000
cugcagucuc ugcagacuua ugugacacag cagcugauua gagcugcuga aauuagagcu   3060
ucugcuaauc uggcugcuac aaaaaugucu gaaugugugc ugggacaguc aaaaagagug   3120
gauuuuugug gaaaaggaua ucaucugaug ucuuuuccac agucugcucc acauggagug   3180
guguuuuuac augugacaua ugugccagca caggaaaaga auuuuaccac agcaccagca   3240
auuugucaug auggaaaagc acauuuucca agagaaggag uguuugugc uaauggaaca   3300
cauugguuug ugacacagag aaauuuuuau gaaccucaga uuauuacaac agauaauaca   3360
uuugugucag gaaauuguga uguggugauu ggaauuguga auaauacagu guaugaucca   3420
cugcagccag aacuggauuc uuuuaaagaa gaacuggaua aauauuuuaa aaaucacaca   3480
ucuccugaug uggauuuagg agauauuucu ggaaucaaug caucuguggu gaauauucag   3540
aaagaaauug auagacugaa ugaaguggcc aaaaaucuga augaaucucu gauugaucug   3600
caggaacuug gaaaauauga acaguacauu aaauggccuu gguacauuug gcuuggauuu   3660
auugcaggau uaauugcaau ugugauggug acaauuaugu uauguuguau gacaucaugu   3720
uguucuuguu uaaaaggaug uuguucuugu ggaagcuguu guaaauuuga ugaagaugau   3780
```

-continued ucugaaccug uguuaaaagg agugaaauug cauuacaca 3819

<210> SEQ ID NO 9
<211> LENGTH: 3819
<212> TYPE: RNA
<213> ORGANISM: Artificial Sequence
<220> FEATURE:
<223> OTHER INFORMATION: Coding Sequence

<400> SEQUENCE: 9
auguucgugu uccuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac guguccuagc cuuuccugau ggaccuggaa 540
ggcaagcagg gcaacuucaa gaaccugcgc gaguucgugu uuaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcucugg auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcguguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380
cugaagcccu ucgagcggga caucuccacc gagaucuauc aggccggcag caccccuugu 1440
aacggcgugg aaggcuucaa cugcuacuuc ccacugcagu ccuacggcuu ucagcccaca 1500
aauggcgugg gcuaucagcc cuacagagug guggugcuga gcuucgaacu gcugcaugcc 1560
ccugccacag ugugcggccc uaagaaaagc accaaucucg ugaagaacaa augcgugaac 1620
uucaacuuca acggccugac cggcaccggc gugcugacag agagcaacaa gaaguuccug 1680
ccauuccagc aguuuggccg ggauaucgcc gauaccacag acgccguuag agaucccccag 1740 acacuggaaa uccuggacau caccccuugc agcuucggcg gagugucugu gaucaccccu 1800
ggcaccaaca ccagcaauca gguggcagug cuguaccagg acgugaacug uaccgaagug 1860
cccguggcca uucacgccga ucagcugaca ccuacauggc ggguguacuc caccggcagc 1920
aauguguuuc agaccagagc cggcugucug aucggagccg agcacgugaa caauagcuac 1980
gagugcgaca ucccccaucgg cgcuggaauc ugcgccagcu accagacaca gacaaacagc 2040

-continued

```
ccucggagag ccagaagcgu ggccagccag agcaucauug ccuacacaau gucucugggc   2100

gccgagaaca gcguggccua cuccaacaac ucuaucgcua uccccaccaa cuucaccauc   2160

agcgugacca cagagauccu gccugugucc augaccaaga ccagcgugga cugcaccaug   2220

uacaucugcg gcgauuccac cgagugcucc aaccugcugc ugcaguacgg cagcuucugc   2280

acccagcuga auagagcccu gacagggauc gccguggaac aggacaagaa cacccaagag   2340

guguucgccc aagugaagca gaucuacaag accccuccua ucaaggacuu cggcggcuuc   2400

aauuucagcc agauucugcc cgauccuagc aagcccagca agcggagcuu caucgaggac   2460

cugcuguuca acaaagugac acuggccgac gccggcuuca ucaagcagua uggcgauugu   2520

cugggcgaca uugccgccag ggaucugauu ugcgcccaga aguuuaacgg acugacagug   2580

cugccuccuc ugcugaccga ugagaugauc gcccaguaca caucugcccu gcuggccggc   2640

acaaucacaa gcggcuggac auuuggagca ggcgccgcuc ugcagauccc cuuugcuaug   2700

cagauggccu accgguucaa cggcaucgga gugacccaga augugcugua cgagaaccag   2760

aagcugaucg ccaaccaguu caacagcgcc aucggcaaga uccaggacag ccugagcagc   2820

acagcaagcg cccugggaaa gcugcaggac guggucaacc agaaugccca ggcacugaac   2880

acccugguca agcagcuguc cuccaacuuc ggcgccauca gcucugugcu gaacgauauc   2940

cugagcagac uggacccucc ugaggccgag gugcagaucg acagacugau cacaggcaga   3000

cugcagagcc uccagacaua cgugacccag cagcugauca gagccgccga gauuagagcc   3060

ucugccaauc uggccgccac caagauguca gagugugugc ugggccagag caagagagug   3120

gacuuuugcg gcaagggcua ccaccugaug agcuucccuc agucugcccc ucacggcgug   3180

guguuucugc acgugacaua ugugcccgcu caagagaaga auuucaccac cgcuccagcc   3240

aucugccacg acggcaaagc ccacuuuccu agagaaggcg uguucguguc caacggcacc   3300

cauugguucg ugacacagcg gaacuucuac gagccccaga ucaucaccac cgacaacacc   3360

uucgugucug gcaacugcga cgucgugauc ggcauuguga acaauaccgu guacgacccu   3420

cugcagcccg agcuggacag cuucaaagag gaacuggaca aguacuuuaa gaaccacaca   3480

agccccgacg uggaccuggg cgauaucagc ggaaucaaug ccagcgucgu gaacauccag   3540

aaagagaucg accggcugaa cgagguggcc aagaaucuga acgagagccu gaucgaccug   3600

caagaacugg ggaaguacga gcaguacauc aaguggcccu gguacaucug gcugggcuuu   3660

aucgccggac ugauugccau cgugauuggc acaaucaugc uguguugcau gaccagcugc   3720

uguagcugcc ugaagggcug uuguagcugu ggcagcugcu gcaaguucga cgaggacgau   3780

ucugagcccg ugcugaaggg cgugaaacug cacuacaca                          3819
```

<210> SEQ ID NO 10
<211> LENGTH: 41
<212> TYPE: PRT
<213> ORGANISM: Artificial Sequence
<220> FEATURE:
<223> OTHER INFORMATION: Foldon Sequence

<400> SEQUENCE: 10

```
Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu Gly Arg Ser
            20                  25                  30

Leu Glu Val Leu Phe Gln Gly Pro Gly
        35                  40
```

<210> SEQ ID NO 11
<211> LENGTH: 123
<212> TYPE: RNA
<213> ORGANISM: Artificial Sequence
<220> FEATURE:
<223> OTHER INFORMATION: Coding Sequence

<400> SEQUENCE: 11
ggaucugguu auauuccuga agcuccaaga gaugggcaag cuuacguucg uaaagauggc 60 gaaugggguau uacuuucuac cuuuuuaggc cggucccugg aggugcuguu ccagggcccc 120
ggc 123

<210> SEQ ID NO 12
<211> LENGTH: 47
<212> TYPE: RNA
<213> ORGANISM: Artificial Sequence
<220> FEATURE:
<223> OTHER INFORMATION: 5'-UTR

<400> SEQUENCE: 12
aacuaguauu cuucugg ucc ccacagacuc agagagaacc cgccacc 47

<210> SEQ ID NO 13
<211> LENGTH: 278
<212> TYPE: RNA
<213> ORGANISM: Artificial Sequence
<220> FEATURE:
<223> OTHER INFORMATION: 3'-UTR

<400> SEQUENCE: 13
cugguacugc augcacgcaa ugcuagcugc cccuuucccg uccuggguac cccgagucuc 60
ccccgaccuc gggucccagg uaugcuccca ccuccaccug ccccacucac caccucugcu 120
aguuccagac accucccaag cacgcagcaa ugcagcucaa aacgcuuagc cuagccacac 180
ccccacggga aacagcagug auuaaccuuu agcaauaaac gaaaguuuaa cuaagcuaua 240
cuaaccccag gguuggucaa uuucgugcca gccacacc 278

<210> SEQ ID NO 14
<211> LENGTH: 110
<212> TYPE: RNA
<213> ORGANISM: Artificial Sequence
<220> FEATURE:
<223> OTHER INFORMATION: A30L70

<400> SEQUENCE: 14
aaaaaaaaaa aaaaaaaaaa aaaaaaaaaa gcauaugacu aaaaaaaaaa aaaaaaaaaa 60
aaaaaaaaaa aaaaaaaaaa aaaaaaaaaa aaaaaaaaaa aaaaaaaaaa 110

<210> SEQ ID NO 15
<211> LENGTH: 4282
<212> TYPE: RNA
<213> ORGANISM: Artificial Sequence
<220> FEATURE:
<223> OTHER INFORMATION: RBL063.1

<400> SEQUENCE: 15
gggcgaacua guauucuucu gguccccaca gacucagaga gaacccgcca ccauguuugu 60
guuucuugug cugcugccuc uugugucuuc ucagugugug aauuugacaa caagaacaca 120
gcugccacca gcuuauacaa auucuuuuac cagaggagug uauuauccug auaaaguguu 180
uagaucuucu gugcugcaca gcacacagga ccuguuucug ccauuuuuua gcaaugugac 240
augguuucau gcaauucaug ugucuggaac aaauggaaca aaaagauuug auaauccugu 300
gcugccuuuu aaugauggag uguauuuugc uucaacagaa aagucaaaua uuauuagagg 360
auggauuuuu ggaacaacac uggauucuaa aacacagucu cugcugauug ugaauaaugc 420
aacaaaugug gugauuaaag ugugugaauu ucaguuuugu aaugauccuu uucugggagu 480
guauuaucac aaaaauaaua aaucuuggau ggaaucugaa uuuagagugu auuccucugc 540
aaauaauugu acauuugaau augugucuca gccuuuucug auggaucugg aaggaaaaca 600
gggcaauuuu aaaaaucuga gagaauuugu guuuaaaaau auugauggau auuuuaaaau 660
uuauucuaaa cacacaccaa uuaauuuagu gagagaucug ccucagggau uuucugcucu 720
ggaaccucug guggaucugc caauuggcau uaauauuaca agauuucaga cacugcuggc 780
ucugcacaga ucuuaucuga caccuggaga uucuucuucu ggauggacag ccggagcugc 840
agcuuauuau gugggcuauc ugcagccaag aacauuucug cugaaauaua augaaaaugg 900
aacaauuaca gaugcugugg auugugcucu ggauccucug ucugaaacaa aauguacauu 960
aaaaucuuuu acaguggaaa aaggcauuua ucagacaucu aauuuuagag ugcagccaac 1020
agaaucuauu gugagauuuc caaauauuac aaaucugugu ccauuuggag aaguguuuaa 1080
ugcaacaaga uuugcaucug uguaugcaug gaauagaaaa agaauuucua auuguguggc 1140
ugauuauucu gugcuguaua auagugcuuc uuuuuccaca uuuaaauguu auggagugucc 1200
uccaacaaaa uuaaaugauu uauguuuuac aaauguguau gcugauucuu uugugaucag 1260
aggugaugaa gugagacaga uugcccccgg acagacagga aaaauugcug auuacaauua 1320
caaacugccu gaugauuuua caggaugugu gauugcuugg aauucuaaua auuuagauuc 1380
uaaaguggga ggaaauuaca auuaucugua cagacuguuu agaaaaucaa aucugaaacc 1440
uuuugaaaga gauauuucaa cagaaauuua ucaggcugga ucaacaccuu guaauggagu 1500
ggaaggauuu aauuguuauu uuccauuaca gagcuaugga uuucagccaa ccaauggugu 1560
gggauaucag ccauauagag ugguggugcu gucuuuugaa cugcugcaug caccugcaac 1620
agugugugga ccuaaaaaau cuacaaauuu agugaaaaau aaauguguga auuuuaauuu 1680
uaauggauua acaggaacag gagugcugac agaaucuaau aaaaaauuuc ugccuuuuca 1740
gcaguuuggc agagauauug cagauaccac agaugcagug agagauccuc agacauuaga 1800
aauucuggau auuacaccuu guucuuuugg gggugugucu gugauuacac cuggaacaaa 1860
uacaucuaau cagguggcug ugcuguauca ggaugugaau uguacagaag ugccaguggc 1920
aauucaugca gaucagcuga caccaacaug gagaguguau ucuacaggau cuaauguguu 1980
ucagacaaga gcaggauguc ugauuggagc agaacaugug aauaauucuu augaauguga 2040
uauuccaauu ggagcaggca uuugugcauc uuaucagaca cagacaaauu ccccaaggag 2100
agcaagaucu guggcaucuc agucuauuau ugcauacacc augucucugg gagcagaaaa 2160
uucuguggca uauucuaaua auucuauugc uauuccaaca aauuuuacca uuucugugac 2220
aacagaaauu uuaccugugu cuaugacaaa aacaucugug gauuguacca uguacauuug 2280
uggagauucu acagaauguu cuaaucugcu gcugcaguau ggaucuuuuu guacacagcu 2340
gaauagagcu uuaacaggaa uugcugugga acaggauaaa aauacacagg aaguguuugc 2400
ucaggugaaa cagauuuaca aaacaccacc aauuaaagau uuuggaggau uuaauuuuag 2460
ccagauucug ccugauccuu cuaaaccuuc uaaaagaucu uuuauugaag aucugcuguu 2520
uaauaaagug acacuggcag augcaggauu uauuaaacag uauggagauu gccuggguga 2580

```
uauugcugca agagaucuga uuugugcuca gaaauuuaau ggacugacag ugcugccucc   2640

ucugcugaca gaugaaauga uugcucagua cacaucugcu uuacuggcug gaacaauuac   2700

aagcggaugg acauuuggag cuggagcugc ucugcagauu ccuuuugcaa ugcagauggc   2760

uuacagauuu aauggaauug gagugacaca gaauguguua uaugaaaauc agaaacugau   2820

ugcaaaucag uuuaauucug caauuggcaa aauucaggau ucucugucuu cuacagcuuc   2880

ugcucuggga aaacugcagg auguggugaa ucagaaugca caggcacuga auacucuggu   2940

gaaacagcug ucuagcaauu uuggggcaau uucuucugug cugaaugaua uucugucuag   3000

acuggauccu ccugaagcug aagugcagau ugauagacug aucacaggaa gacugcaguc   3060

ucugcagacu uaugugacac agcagcugau uagagcugcu gaaauuagag cuucugcuaa   3120

ucuggcugcu acaaaaaugu cugaaugugu gcugggacag ucaaaaagag uggauuuuug   3180

uggaaaagga uaucaucuga ugucuuuucc acagucugcu ccacauggag ugguguuuuu   3240

acaugugaca uaugugccag cacaggaaaa gaauuuuacc acagcaccag caauuuguca   3300

ugauggaaaa gcacauuuuc caagagaagg aguguuugug ucuaauggaa cacauugguu   3360

ugugacacag agaaauuuuu augaaccuca gauuauuaca acagauaaua cauuuguguc   3420

aggaaauugu gaugugguga uuggaauugu gaauaauaca guguaugauc cacugcagcc   3480

agaacuggau ucuuuuaaag aagaacugga uaaauauuuu aaaaaucaca caucuccuga   3540

uguggauuua ggagauauuu cuggaaucaa ugcaucugug gugaauauuc agaaagaaau   3600

ugauagacug aaugaagugg ccaaaaaucu gaaugaaucu cugauugauc ugcaggaacu   3660

uggaaaauau gaacaguaca uuaaauggcc uugguacauu uggcuuggau uuauugcagg   3720

auuaauugca auugugaugg ugacaauuau guuauguugu augacaucau guuguucuug   3780

uuuaaaagga uguuguucuu guggaagcug uuguaaauuu gaugaagaug auucugaacc   3840

uguguuaaaa ggagugaaau ugcauuacac augaugacuc gagcugguac ugcaugcacg   3900

caaugcuagc ugccccuuuc ccguccuggg uaccccgagu cucccccgac cucgggaccc   3960

agguaugcuc ccaccuccac cugccccacu caccaccucu gcuaguucca gacaccuccc   4020

aagcacgcag caaugcagcu caaaacgcuu agccuagcca cacccccacg ggaaacagca   4080

gugauuaacc uuuagcaaua aacgaaaguu uaacuaagcu auacuaaccc cagggguuggu  4140

caauuucgug ccagccacac ccuggagcua gcaaaaaaaa aaaaaaaaaa aaaaaaaaaa   4200

aagcauauga cuaaaaaaaa aaaaaaaaaa aaaaaaaaaa aaaaaaaaaa aaaaaaaaaa   4260

aaaaaaaaaa aaaaaaaaaa aa                                            4282
```

<210> SEQ ID NO 16
<211> LENGTH: 4282
<212> TYPE: RNA
<213> ORGANISM: Artificial Sequence
<220> FEATURE:
<223> OTHER INFORMATION: RBL063.2

<400> SEQUENCE: 16

```
gggcgaacua guauucuucu gguccccaca gacucagaga gaacccgcca ccauguucgu     60

guuccuggug cugcugccuc ugguguccag ccagugugug aaccugacca ccagaacaca    120

gcugccucca gccuacacca acagcuuuac cagaggcgug uacuaccccg acaaggugu    180

cagauccagc gugcugcacu cuacccagga ccuguuccug ccuuucuuca gcaacgugac    240

cugguuccac gccauccacg uguccggcac caauggcacc aagagauucg acaaccccgu    300
```

-continued

```
gcugcccuuc aacgacgggg uguacuuugc cagcaccgag aaguccaaca ucaucagagg    360
cuggaucuuc ggcaccacac uggacagcaa gacccagagc cugcugaucg ugaacaacgc    420
caccaacgug gucaucaaag ugugcgaguu ccaguucugc aacgaccccu uccugggcgu    480
cuacuaccac aagaacaaca agagcuggau ggaaagcgag uuccgggugu acagcagcgc    540
caacaacugc accuucgagu acgugucca gccuuuccug auggaccugg aaggcaagca     600
gggcaacuuc aagaaccugc gcgaguucgu guuuaagaac aucgacggcu acuucaagau    660
cuacagcaag cacaccccua ucaaccucgu gcgggaucug ccucagggcu ucucugcucu    720
ggaaccccug guggaucugc ccaucggcau caacaucacc cgguuucaga cacugcuggc    780
ccugcacaga agcuaccuga caccuggcga uagcagcagc ggauggacag cuggugccgc    840
cgcuuacuau gugggcuacc ugcagccuag aaccuuccug cugaaguaca acgagaacgg    900
caccaucacc gacgccgugg auugugcucu ggauccucug agcgagacaa agugcacccu    960
gaaguccuuc accguggaaa agggcaucua ccagaccagc aacuuccggg ugcagcccac   1020
cgaauccauc gugcgguucc ccaauaucac caaucugugc ccuucggcg aggguguucaa   1080
ugccaccaga uucgccucug uguacgccug gaaccggaag cggaucagca auugcguggc   1140
cgacuacucc gugcuguaca acuccgccag cuucagcacc uucaagugcu acggcguguc   1200
cccuaccaag cugaacgacc ugugcuucac aaacguguac gccgacagcu ucgugauccg   1260
gggagaugaa gugcggcaga uugccccugg acagacaggc aagaucgccg acuacaacua   1320
caagcugccc gacgacuuca ccggcugugu gauugccugg aacagcaaca accuggacuc   1380
caaagucggc ggcaacuaca auuaccugua ccggcuguuc cggaagucca aucugaagcc   1440
cuucgagcgg gacaucucca ccgagaucua ucaggccggc agcaccccuu guaacggcgu   1500
ggaaggcuuc aacugcuacu ucccacugca guccuacggc uuucagccca caaauggcgu   1560
gggcuaucag cccuacagag ugguggugcu gagcuucgaa cugcugcaug ccccugccac   1620
agugugcggc ccuaagaaaa gcaccaaucu cgugaagaac aaaugcguga acuucaacuu   1680
caacggccug accggcaccg gcgugcugac agagagcaac aagaaguucc ugccauucca   1740
gcaguuuggc cgggauaucg ccgauaccac agacgccguu agagaucccc agacacugga   1800
aauccuggac aucaccccuu gcagcuucgg cggagugucu gugaucaccc cuggcaccaa   1860
caccagcaau cagguggcag ugcuguacca ggacgugaac uguaccgaag ugcccguggc   1920
cauucacgcc gaucagcuga caccuacaug gcggguguac uccaccggca gcaauguguu   1980
ucagaccaga gccggcuguc ugaucggagc cgagcacgug aacaauagcu acgagugcga   2040
caucccauc ggcgcuggaa ucugcgccag cuaccagaca cagacaaaca gcccucggag    2100
agccagaagc guggccagcc agagcaucau ugccuacaca augucucugg gcgccgagaa   2160
cagcguggcc uacuccaaca acucuaucgc uauccccacc aacuucacca ucagcgugac   2220
cacagagauc cugccugugu ccaugaccaa gaccagcgug gacugcacca uguacaucug   2280
cggcgauucc accgagugcu ccaaccugcu gcugcaguac ggcagcuucu gcacccagcu   2340
gaauagagcc cugacaggga ucgccgugga acaggacaag aacacccaag agguguucgc   2400
ccaagugaag cagaucuaca agaccccucc uaucaaggac uucggcggcu ucaauuucag   2460
ccagauucug cccgauccua gcaagcccag caagcggagc uucaucgagg accugcuguu   2520
caacaaagug acacuggccg acgccggcuu caucaagcag uauggcgauu gucugggcga   2580
cauugccgcc agggaucuga uuugcgccca gaaguuuaac ggacugacag ugcugccucc   2640
ucugcugacc gaugagauga ucgcccagua cacaucugcc cugcuggccg gcacaaucac   2700
```

aagcggcugg acauuuggag caggcgccgc ucugcagauc cccuuugcua ugcagauggc 2760
cuaccgguuc aacggcaucg gagugaccca gaaugugcug uacgagaacc agaagcugau 2820
cgccaaccag uucaacagcg ccaucggcaa gauccaggac agccugagca gcacagcaag 2880
cgcccuggga aagcugcagg acguggucaa ccagaaugcc caggcacuga acacccuggu 2940
caagcagcug uccuccaacu ucggcgccau cagcucugug cugaacgaua uccugagcag 3000
acuggacccu ccugaggccg aggugcagau cgacagacug aucacaggca gacugcagag 3060
ccuccagaca uacgugaccc agcagcugau cagagccgcc gagauuagag ccucugccaa 3120
ucuggccgcc accaagaugu cugagugugu gcugggccag agcaagagag uggacuuuug 3180
cggcaagggc uaccaccuga ugagcuuccc ucagucugcc ccucacggcg ugguguuucu 3240
gcacgugaca uaugugcccg cucaagagaa gaauuucacc accgcuccag ccaucugcca 3300
cgacggcaaa gcccacuuuc cuagagaagg cguguucgug uccaacggca cccauugguu 3360
cgugacacag cggaacuucu acgagcccca gaucaucacc accgacaaca ccuucguguc 3420
uggcaacugc gacgucguga ucggcauugu gaacaauacc guguacgacc cucugcagcc 3480
cgagcuggac agcuucaaag aggaacugga caaguacuuu aagaaccaca caagccccga 3540
cguggaccug ggcgauauca gcggaaucaa ugccagcguc gugaacaucc agaaagagau 3600
cgaccggcug aacgaggugg ccaagaaucu gaacgagagc cugaucgacc ugcaagaacu 3660
ggggaaguac gagcaguaca ucaaguggcc cugguacauc uggcugggcu uuaucgccgg 3720
acugauugcc aucgugaugg ucacaaucau gcuguguugc augaccagcu gcuguagcug 3780
ccugaagggc uguuguagcu guggcagcug cugcaaguuc gacgaggacg auucugagcc 3840
cgugcugaag ggcgugaaac ugcacuacac augaugacuc gagcugguac ugcaugcacg 3900
caaugcuagc ugccccuuuc ccguccuggg uaccccgagu cucccccgac cucgggucccc 3960 agguaugcuc ccaccuccac cugccccacu caccaccucu gcuaguucca gacaccuccc 4020
aagcacgcag caaugcagcu caaaacgcuu agccuagcca cacccccacg ggaaacagca 4080
gugauuaacc uuuagcaaua aacgaaaguu uaacuaagcu auacuaaccc caggguuggu 4140
caauuucgug ccagccacac ccuggagcua gcaaaaaaaa aaaaaaaaaa aaaaaaaaaa 4200
aagcauauga cuaaaaaaaa aaaaaaaaaa aaaaaaaaaa aaaaaaaaaa aaaaaaaaaa 4260
aaaaaaaaaa aaaaaaaaaa aa 4282

<210> SEQ ID NO 17
<211> LENGTH: 1261
<212> TYPE: RNA
<213> ORGANISM: Artificial Sequence
<220> FEATURE:
<223> OTHER INFORMATION: RBL063.3

<400> SEQUENCE: 17
gggcgaacua guauucuucu gguccccaca gacucagaga gaacccgcca ccauguuugu 60
guuucuugug cugcugccuc uugugucuuc ucagugugug gugagauuuc caaauauuac 120
aaaucugugu ccauuuggag aaguguuuaa ugcaacaaga uuugcaucug uguaugcaug 180
gaauagaaaa agaauuucua auuguguggc ugauuauucu gugcuguaua auagugcuuc 240
uuuuuccaca uuuaaauguu auggaguguc uccaacaaaa uuaaaugauu uauguuuuac 300
aaauguguau gcugauucuu uugugaucag aggugaugaa gugagacaga uugcccccgg 360
acagacagga aaaauugcug auuacaauua caaacugccu gaugauuuua caggaugugu 420

-continued

```
gauugcuugg aauucuaaua auuuagauuc uaaaguggga ggaaauuaca auuaucugua    480

cagacuguuu agaaaaucaa aucugaaacc uuuugaaaga gauauuucaa cagaaauuua    540

ucaggcugga ucaacaccuu guaauggagu ggaaggauuu aauuguuauu uuccauuaca    600

gagcuaugga uuucagccaa ccaauggugu gggauaucag ccauauagag ugguggugcu    660

gucuuuugaa cugcugcaug caccugcaac agugugugga ccuaaaggcu cccccggcuc    720

cggcuccgga ucugguuaua uuccugaagc uccaagagau gggcaagcuu acguucguaa    780

agauggcgaa uggguauuac uuucuaccuu uuuaggccgg ucccuggagg ugcuguucca    840

gggccccggc ugaugacucg agcugguacu gcaugcacgc aaugcuagcu gccccuuucc    900

cguccugggu accccgaguc ucccccgacc ucggguccca gguaugcucc caccuccacc    960

ugccccacuc accaccucug cuaguuccag acaccuccca agcacgcagc aaugcagcuc   1020

aaaacgcuua gccuagccac acccccacgg gaaacagcag ugauuaaccu uuagcaauaa   1080

acgaaaguuu aacuaagcua uacuaacccc agguuggguc aauuucgugc cagccacacc   1140

cuggagcuag caaaaaaaaa aaaaaaaaaa aaaaaaaaaa agcauaugac uaaaaaaaaa   1200

aaaaaaaaaa aaaaaaaaaa aaaaaaaaaa aaaaaaaaaa aaaaaaaaaa aaaaaaaaaa   1260

a                                                                   1261
```

<210> SEQ ID NO 18
<211> LENGTH: 250
<212> TYPE: PRT
<213> ORGANISM: Artificial Sequence
<220> FEATURE:
<223> OTHER INFORMATION: S Protein RBD Fusion

<400> SEQUENCE: 18

```
Val Arg Phe Pro Asn Ile Thr Asn Leu Cys Pro Phe Gly Glu Val Phe
1               5                   10                  15

Asn Ala Thr Arg Phe Ala Ser Val Tyr Ala Trp Asn Arg Lys Arg Ile
            20                  25                  30

Ser Asn Cys Val Ala Asp Tyr Ser Val Leu Tyr Asn Ser Ala Ser Phe
        35                  40                  45

Ser Thr Phe Lys Cys Tyr Gly Val Ser Pro Thr Lys Leu Asn Asp Leu
    50                  55                  60

Cys Phe Thr Asn Val Tyr Ala Asp Ser Phe Val Ile Arg Gly Asp Glu
65                  70                  75                  80

Val Arg Gln Ile Ala Pro Gly Gln Thr Gly Lys Ile Ala Asp Tyr Asn
                85                  90                  95

Tyr Lys Leu Pro Asp Asp Phe Thr Gly Cys Val Ile Ala Trp Asn Ser
            100                 105                 110

Asn Asn Leu Asp Ser Lys Val Gly Gly Asn Tyr Asn Tyr Leu Tyr Arg
        115                 120                 125

Leu Phe Arg Lys Ser Asn Leu Lys Pro Phe Glu Arg Asp Ile Ser Thr
    130                 135                 140

Glu Ile Tyr Gln Ala Gly Ser Thr Pro Cys Asn Gly Val Glu Gly Phe
145                 150                 155                 160

Asn Cys Tyr Phe Pro Leu Gln Ser Tyr Gly Phe Gln Pro Thr Asn Gly
                165                 170                 175

Val Gly Tyr Gln Pro Tyr Arg Val Val Val Leu Ser Phe Glu Leu Leu
            180                 185                 190

His Ala Pro Ala Thr Val Cys Gly Pro Lys Gly Ser Pro Gly Ser Gly
        195                 200                 205
```

-continued

```
Ser Gly Ser Gly Tyr Ile Pro Glu Ala Pro Arg Asp Gly Gln Ala Tyr
    210                 215                 220

Val Arg Lys Asp Gly Glu Trp Val Leu Leu Ser Thr Phe Leu Gly Arg
225                 230                 235                 240

Ser Leu Glu Val Leu Phe Gln Gly Pro Gly
                245                 250


<210> SEQ ID NO 19
<211> LENGTH: 4283
<212> TYPE: RNA
<213> ORGANISM: Artificial Sequence
<220> FEATURE:
<223> OTHER INFORMATION: RBP020.1

<400> SEQUENCE: 19

agaauaaacu aguauucuuc uggucccac agacucagag agaacccgcc accauguuug     60

uguuucuugu gcugcugccu cuugugucuu cucagugugu gaauuugaca acaagaacac    120

agcugccacc agcuuauaca aauucuuuua ccagaggagu guauuauccu gauaaagugu    180

uuagaucuuc ugugcugcac agcacacagg accuguuucu gccauuuuuu agcaauguga    240

caugguuuca ugcaauucau gugucuggaa caaauggaac aaaaagauuu gauaauccug    300

ugcugccuuu uaaugaugga guguauuuug cuucaacaga aaagucaaau auuauuagag    360

gauggauuuu uggaacaaca cuggauucua aaacacaguc ucugcugauu gugaauaaug    420

caacaaaugu ggugauuaaa gugugugaau uucaguuuug uaaugauccu uuucugggag    480

uguauuauca caaaaauaau aaaucuugga uggaaucuga auuuagagug uauuccucug    540

caaauaauug uacauuugaa uaugugucuc agccuuuucu gauggaucug gaaggaaaac    600

agggcaauuu uaaaaaucug agagaauuug uguuuaaaaa uauugaugga uauuuuaaaa    660

uuuauucuaa acacacacca auuaauuuag ugagagaucu gccucaggga uuuucugcuc    720

uggaaccucu gguggaucug ccaauuggca uuaauauuac aagauuucag acacugcugg    780

cucugcacag aucuuaucug acaccuggag auucuucuuc uggauggaca gccggagcug    840

cagcuuauua ugugggcuau cugcagccaa gaacauuucu gcugaaauau aaugaaaaug    900

gaacaauuac agaugcugug gauugugcuc uggauccucu gucugaaaca aaauguacau    960

uaaaaucuuu uacaguggaa aaaggcauuu aucagacauc uaauuuuaga gugcagccaa   1020

cagaaucuau ugugagauuu ccaaauauua caaaucugug uccauuugga gaaguguuua   1080

augcaacaag auuugcaucu guguaugcau ggaauagaaa aagaauuucu aauugugugg   1140

cugauuauuc ugugcuguau aauagugcuu cuuuuuccac auuuaaaugu uauggagugu   1200

cuccaacaaa auuaaaugau uuauguuuua caaaugugua ugcugauucu uuugugauca   1260

gaggugauga agugagacag auugcccccg gacagacagg aaaaauugcu gauuacaauu   1320

acaaacugcc ugaugauuuu acaggaugug ugauugcuug gaauucuaau aauuuagauu   1380

cuaaaguggg aggaaauuac aauuaucugu acagacuguu uagaaaauca aaucugaaac   1440

cuuuugaaag agauauuuca acagaaauuu aucaggcugg aucaacaccu uguaauggag   1500

uggaaggauu uaauuguuau uuuccauuac agagcuaugg auuucagcca accaauggug   1560

ugggauauca gccauauaga gugguggugc ugucuuuuga acugcugcau gcaccugcaa   1620

cagugugugg accuaaaaaa ucuacaaauu uagugaaaaa uaaaugugug aauuuuaauu   1680

uuaauggauu aacaggaaca ggagugcuga cagaaucuaa uaaaaaauuu cugccuuuuc   1740

agcaguuugg cagagauauu gcagauacca cagaugcagu gagagauccu cagacauuag   1800
```

-continued

```
aaauucugga uauuacaccu uguucuuuug ggggugugu c ugugauuaca ccuggaacaa   1860
auacaucuaa ucagguggcu gugcuguauc aggaugugaa uuguacagaa gugccagugg   1920
caauucaugc agaucagcug acaccaacau ggagagugua uucuacagga ucuaaugugu   1980
uucagacaag agcaggaugu cugauuggag cagaacaugu gaauaauucu uaugaaugug   2040
auauuccaau uggagcaggc auuugugcau cuuaucagac acagacaaau uccccaagga   2100
gagcaagauc uguggcaucu cagucuauua uugcauacac caugucucug ggagcagaaa   2160
auucuguggc auauucuaau aauucuauug cuauuccaac aaauuuuacc auuucuguga   2220
caacagaaau uuuaccugug ucuaugacaa aaacaucugu ggauuguacc auguacauuu   2280
guggagauuc uacagaaugu ucuaaucugc ugcugcagua uggaucuuuu uguacacagc   2340
ugaauagagc uuuaacagga auugcugugg aacaggauaa aaauacacag gaaguguuug   2400
cucaggugaa acagauuuac aaaacaccac caauuaaaga uuuuggagga uuuaauuuua   2460
gccagauucu gccugauccu ucuaaaccuu cuaaaagauc uuuuauugaa gaucugcugu   2520
uuaauaaagu gacacuggca gaugcaggau uuauuaaaca guauggagau ugccugggug   2580
auauugcugc aagagaucug auuugugcuc agaaauuuaa uggacugaca gugcugccuc   2640
cucugcugac agaugaaaug auugcucagu acacaucugc uuuacuggcu ggaacaauua   2700
caagcggaug gacauuugga gcuggagcug cucugcagau uccuuuugca augcagaugg   2760
cuuacagauu uaauggaauu ggagugacac agaauguguu auaugaaaau cagaaacuga   2820
uugcaaauca guuuaauucu gcaauuggca aaauucagga uucucugucu ucuacagcuu   2880
cugcucuggg aaaacugcag gaugugguga aucagaaugc acaggcacug aauacucugg   2940
ugaaacagcu gucuagcaau uuuggggcaa uuucuucugu gcugaaugau auucugucua   3000
gacuggaucc uccugaagcu gaagugcaga uugauagacu gaucacagga agacugcagu   3060
cucugcagac uuaugugaca cagcagcuga uuagagcugc ugaaauuaga gcuucugcua   3120
aucuggcugc uacaaaaaug ucugaaugug ugcugggaca gucaaaaaga guggauuuuu   3180
guggaaaagg auaucaucug augucuuuuc cacagucugc uccacaugga gugguguuuu   3240
uacaugugac auaugugcca gcacaggaaa agaauuuuac cacagcacca gcaauuuguc   3300
augauggaaa agcacauuuu ccaagagaag gaguguuugu gucuaaugga acacauuggu   3360
uugugacaca gagaaauuuu uaugaaccuc agauuauuac aacagauaau acauuugugu   3420
caggaaauug ugauguggug auuggaauug ugaauaauac aguguaugau ccacugcagc   3480
cagaacugga uucuuuuaaa gaagaacugg auaaauauuu uaaaaaucac acaucuccug   3540
auguggauuu aggagauauu ucuggaauca augcaucugu ggugaauauu cagaaagaaa   3600
uugauagacu gaaugaagug gccaaaaauc ugaaugaauc ucugauugau cugcaggaac   3660
uuggaaaaua ugaacaguac auuaaauggc cuugguacau uuggcuugga uuuauugcag   3720
gauuaauugc aauugugaug gugacaauua uguuauguug uaugacauca uguuguucuu   3780
guuuaaaagg auguuguucu uguggaagcu guuguaaauu ugaugaagau gauucugaac   3840
cuguguuaaa aggagugaaa uugcauuaca caugaugacu cgagcuggua cugcaugcac   3900
gcaaugcuag cugccccuuu cccguccugg guaccccgag ucucccccga ccucgggucc   3960
cagguaugcu cccaccucca ccugccccac ucaccaccuc ugcuaguucc agacaccucc   4020
caagcacgca gcaaugcagc ucaaaacgcu uagccuagcc acacccccac gggaaacagc   4080
agugauuaac cuuuagcaau aaacgaaagu uuaacuaagc uauacuaacc ccaggguugg   4140
ucaauuucgu gccagccaca cccuggagcu agcaaaaaaa aaaaaaaaaa aaaaaaaaaa   4200
```

aaagcauaug acuaaaaaaa aaaaaaaaaa aaaaaaaaaa aaaaaaaaaa aaaaaaaaaa 4260
aaaaaaaaaa aaaaaaaaaa aaa 4283

<210> SEQ ID NO 20
<211> LENGTH: 4283
<212> TYPE: RNA
<213> ORGANISM: Artificial Sequence
<220> FEATURE:
<223> OTHER INFORMATION: RBP020.2

<400> SEQUENCE: 20
agaauaaacu aguauucuuc ugguccccac agacucagag agaacccgcc accauguucg 60
uguuccuggu gcugcugccu cuggugucca gccagugugu gaaccugacc accagaacac 120
agcugccucc agccuacacc aacagcuuua ccagaggcgu guacuacccc gacaaggugu 180
ucagauccag cgugcugcac ucuacccagg accuguuccu gccuuucuuc agcaacguga 240
ccugguucca cgccauccac guguccggca ccaauggcac caagagauuc gacaaccccg 300
ugcugcccuu caacgacggg guguacuuug ccagcaccga gaaguccaac aucaucagag 360
gcuggaucuu cggcaccaca cuggacagca agacccagag ccugcugauc gugaacaacg 420
ccaccaacgu ggucaucaaa gugugcgagu uccaguucug caacgacccc uuccugggcg 480
ucuacuacca caagaacaac aagagcugga uggaaagcga guuccgggug uacagcagcg 540
ccaacaacug caccuucgag uacguguccc agccuuuccu gauggaccug gaaggcaagc 600
agggcaacuu caagaaccug cgcgaguucg uguuuaagaa caucgacggc uacuucaaga 660
ucuacagcaa gcacaccccu aucaaccucg ugcgggaucu gccucagggc uucucugcuc 720
uggaaccccu gguggaucug cccaucggca ucaacaucac ccgguuucag acacugcugg 780
cccugcacag aagcuaccug acaccuggcg auagcagcag cggauggaca gcuggugccg 840
ccgcuuacua ugugggcuac cugcagccua gaaccuuccu gcugaaguac aacgagaacg 900
gcaccaucac cgacgccgug gauugugcuc uggauccucu gagcgagaca aagugcaccc 960
ugaaguccuu caccguggaa aagggcaucu accagaccag caacuuccgg gugcagccca 1020
ccgaauccau cgugcgguuc cccaauauca ccaaucugug ccccuucggc gagguguuca 1080
augccaccag auucgccucu guguacgccu ggaaccggaa gcggaucagc aauugcgugg 1140
ccgacuacuc cgugcuguac aacuccgcca gcuucagcac cuucaagugc uacggcgugu 1200
ccccuaccaa gcugaacgac cugugcuuca caaacgugua cgccgacagc uucgugaucc 1260
ggggagauga agugcggcag auugccccug gacagacagg caagaucgcc gacuacaacu 1320
acaagcugcc cgacgacuuc accggcugug ugauugccug gaacagcaac aaccuggacu 1380
ccaaagucgg cggcaacuac aauuaccugu accggcuguu ccggaagucc aaucugaagc 1440
ccuucgagcg ggacaucucc accgagaucu aucaggccgg cagcaccccu uguaacggcg 1500
uggaaggcuu caacugcuac uucccacugc aguccuacgg cuuucagccc acaaauggcg 1560
ugggcuauca gcccuacaga gugguggugc ugagcuucga acugcugcau gccccugcca 1620
cagugugcgg cccuaagaaa agcaccaauc ucgugaagaa caaaugcgug aacuucaacu 1680
ucaacggccu gaccggcacc ggcgugcuga cagagagcaa caagaaguuc cugccauucc 1740
agcaguuugg ccgggauauc gccgauacca cagacgccgu uagagauccc cagacacugg 1800
aaauccugga caucaccccu ugcagcuucg gcggaguguc ugugaucacc ccuggcacca 1860
acaccagcaa ucagguggca gugcuguacc aggacgugaa cuguaccgaa gugcccgugg 1920

-continued

```
ccauucacgc cgaucagcug acaccuacau ggcgggugua cuccaccggc agcaaugugu   1980
uucagaccag agccggcugu cugaucggag ccgagcacgu gaacaauagc uacgagugcg   2040
acaucccccau cggcgcugga aucugcgcca gcuaccagac acagacaaac agcccucgga   2100
gagccagaag cguggccagc cagagcauca uugccuacac aaugucucug ggcgccgaga   2160
acagcguggc cuacuccaac aacucuaucg cuaucccccac caacuucacc aucagcguga   2220
ccacagagau ccugccugug uccaugacca agaccagcgu ggacugcacc auguacaucu   2280
gcggcgauuc caccgagugc uccaaccugc ugcugcagua cggcagcuuc ugcacccagc   2340
ugaauagagc ccugacaggg aucgccgugg aacaggacaa gaacacccaa gagguguucg   2400
cccaagugaa gcagaucuac aagaccccuc cuaucaagga cuucggcggc uucaauuuca   2460
gccagauucu gcccgauccu agcaagccca gcaagcggag cuucaucgag gaccugcugu   2520
ucaacaaagu gacacuggcc gacgccggcu ucaucaagca guauggcgau ugucugggcg   2580
acauugccgc cagggaucug auuugcgccc agaaguuuaa cggacugaca gugcugccuc   2640
cucugcugac cgaugagaug aucgcccagu acacaucugc ccugcuggcc ggcacaauca   2700
caagcggcug gacauuugga gcaggcgccg cucugcagau ccccuuugcu augcagaugg   2760
ccuaccgguu caacggcauc ggagugaccc agaaugugcu guacgagaac cagaagcuga   2820
ucgccaacca guucaacagc gccaucggca agauccagga cagccugagc agcacagcaa   2880
gcgcccuggg aaagcugcag gacguggcuca accagaaugc ccaggcacug aacacccugg   2940
ucaagcagcu guccuccaac uucggcgcca ucagcucugu gcugaacgau auccugagca   3000
gacuggaccc uccugaggcc gaggugcaga ucgacagacu gaucacaggc agacugcaga   3060
gccuccagac auacgugacc cagcagcuga ucagagccgc cgagauuaga gccucugcca   3120
aucuggccgc caccaagaug ucugagugug ugcugggcca gagcaagaga guggacuuuu   3180
gcggcaaggg cuaccaccug augagcuucc cucagucugc cccucacggc guggguguuuc   3240
ugcacgugac auaugugccc gcucaagaga agaauuucac caccgcucca gccaucugcc   3300
acgacggcaa agcccacuuu ccuagagaag gcguguucgu guccaacggc acccauuggu   3360
ucgugacaca gcggaacuuc uacgagcccc agaucaucac caccgacaac accuucgugu   3420
cuggcaacug cgacgucgug aucggcauug ugaacaauac cguguacgac ccucugcagc   3480
ccgagcugga cagcuucaaa gaggaacugg acaaguacuu uaagaaccac acaagccccg   3540
acguggaccu gggcgauauc agcggaauca augccagcgu cgugaacauc cagaaagaga   3600
ucgaccggcu gaacgaggug gccaagaauc ugaacgagag ccugaucgac cugcaagaac   3660
uggggaagua cgagcaguac aucaaguggc ccugguacau cuggcugggc uuuaucgccg   3720
gacugauugc caucgugaug gucacaauca ugcuguguug caugaccagc ugcuguagcu   3780
gccugaaggg cuguuguagc uguggcagcu gcugcaaguu cgacgaggac gauucugagc   3840
ccgugcugaa gggcgugaaa cugcacuaca caugaugacu cgagcuggua cugcaugcac   3900
gcaaugcuag cugccccuuu cccguccugg guaccccgag ucucccccga ccucgggucc   3960
cagguaugcu cccaccucca ccugccccac ucaccaccuc ugcuaguucc agacaccucc   4020
caagcacgca gcaaugcagc ucaaaacgcu uagccuagcc acacccccac gggaaacagc   4080
agugauuaac cuuuagcaau aaacgaaagu uuaacuaagc uauacuaacc ccaggguugg   4140
ucaauuucgu gccagccaca cccuggagcu agcaaaaaaa aaaaaaaaaa aaaaaaaaaa   4200
aaagcauaug acuaaaaaaa aaaaaaaaaa aaaaaaaaaa aaaaaaaaaa aaaaaaaaaa   4260
aaaaaaaaaa aaaaaaaaaa aaa                                           4283
```

<210> SEQ ID NO 21
<211> LENGTH: 1262
<212> TYPE: RNA
<213> ORGANISM: Artificial Sequence
<220> FEATURE:
<223> OTHER INFORMATION: RBP020.3

<400> SEQUENCE: 21
agaauaaacu aguauucuuc ugguccccac agacucagag agaacccgcc accauguuug 60
uguuucuugu gcugcugccu cuugugucuu cucagugugu ggugagauuu ccaaauauua 120
caaaucugug uccauuugga gaaguguuua augcaacaag auuugcaucu guguaugcau 180
ggaauagaaa aagaauuucu aauuguguggg cugauuauuc ugugcuguau aauagugcuu 240
cuuuuuccac auuuaaaugu uauggagugu cuccaacaaa auuaaaugau uuauguuuua 300
caaaugugua ugcugauucu uuugugauca gaggugauga agugagacag auugccccccg 360 gacagacagg aaaaauugcu gauuacaauu acaaacugcc ugaugauuuu acaggaugug 420
ugauugcuug gaauucuaau aauuuagauu cuaaaguggg aggaaauuac aauuaucugu 480
acagacuguu uagaaaauca aaucugaaac cuuuugaaag agauauuuca acagaaauuu 540
aucaggcugg aucaacaccu uguaauggag uggaaggauu uaauuguuau uuuccauuac 600
agagcuaugg auuucagcca accaauggug ugggauauca gccauauaga gugguggugc 660
ugucuuuuga acugcugcau gcaccugcaa cagugugugg accuaaaggc ucccccggcu 720
ccggcuccgg aucugguuau auuccugaag cuccaagaga ugggcaagcu uacguucgua 780
aagauggcga augguauua cuuucuaccu uuuuaggccg gucccuggag gugcuguucc 840
agggccccgg cugaugacuc gagcugguac ugcaugcacg caaugcuagc ugccccuuuc 900
ccguccuggg uaccccgagu cucccccgac cucgggucccc agguaugcuc ccaccuccac 960
cugccccacu caccaccucu gcuaguucca gacaccuccc aagcacgcag caaugcagcu 1020
caaaacgcuu agccuagcca cacccccacg ggaaacagca gugauuaacc uuuagcaaua 1080
aacgaaaguu uaacuaagcu auacuaaccc cagguuuggu caauuucgug ccagccacac 1140
ccuggagcua gcaaaaaaaa aaaaaaaaaa aaaaaaaaaa aagcauauga cuaaaaaaaa 1200
aaaaaaaaaa aaaaaaaaaa aaaaaaaaaa aaaaaaaaaa aaaaaaaaaa aaaaaaaaaa 1260
aa 1262

<210> SEQ ID NO 22
<211> LENGTH: 1879
<212> TYPE: PRT
<213> ORGANISM: Artificial Sequence
<220> FEATURE:
<223> OTHER INFORMATION: Viral Protein

<400> SEQUENCE: 22

Met Glu Lys Val His Val Asp Ile Glu Glu Asp Ser Pro Phe Leu Arg
1 5 10 15

Ala Leu Gln Arg Ser Phe Pro Gln Phe Glu Val Glu Ala Lys Gln Val
20 25 30

Thr Asp Asn Asp His Ala Asn Ala Arg Ala Phe Ser His Leu Ala Ser
35 40 45

Lys Leu Ile Glu Thr Glu Val Asp Pro Ser Asp Thr Ile Leu Asp Ile
50 55 60

Gly Ser Ala Pro Ala Arg Arg Met Tyr Ser Lys His Lys Tyr His Cys
65 70 75 80

-continued

```
Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495
```

```
Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
```

```
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp  Pro Thr Asp Val Phe  Gln Asn Lys
        995                 1000                1005

Ala Asn  Val Cys Trp Ala Lys  Ala Leu Val Pro Val  Leu Lys Thr
    1010                1015                1020

Ala Gly  Ile Asp Met Thr Thr  Glu Gln Trp Asn Thr  Val Asp Tyr
    1025                1030                1035

Phe Glu  Thr Asp Lys Ala His  Ser Ala Glu Ile Val  Leu Asn Gln
    1040                1045                1050

Leu Cys  Val Arg Phe Phe Gly  Leu Asp Leu Asp Ser  Gly Leu Phe
    1055                1060                1065

Ser Ala  Pro Thr Val Pro Leu  Ser Ile Arg Asn Asn  His Trp Asp
    1070                1075                1080

Asn Ser  Pro Ser Pro Asn Met  Tyr Gly Leu Asn Lys  Glu Val Val
    1085                1090                1095

Arg Gln  Leu Ser Arg Arg Tyr  Pro Gln Leu Pro Arg  Ala Val Ala
    1100                1105                1110

Thr Gly  Arg Val Tyr Asp Met  Asn Thr Gly Thr Leu  Arg Asn Tyr
    1115                1120                1125

Asp Pro  Arg Ile Asn Leu Val  Pro Val Asn Arg Arg  Leu Pro His
    1130                1135                1140

Ala Leu  Val Leu His His Asn  Glu His Pro Gln Ser  Asp Phe Ser
    1145                1150                1155

Ser Phe  Val Ser Lys Leu Lys  Gly Arg Thr Val Leu  Val Val Gly
    1160                1165                1170

Glu Lys  Leu Ser Val Pro Gly  Lys Met Val Asp Trp  Leu Ser Asp
    1175                1180                1185

Arg Pro  Glu Ala Thr Phe Arg  Ala Arg Leu Asp Leu  Gly Ile Pro
    1190                1195                1200

Gly Asp  Val Pro Lys Tyr Asp  Ile Ile Phe Val Asn  Val Arg Thr
    1205                1210                1215

Pro Tyr  Lys Tyr His His Tyr  Gln Gln Cys Glu Asp  His Ala Ile
    1220                1225                1230

Lys Leu  Ser Met Leu Thr Lys  Lys Ala Cys Leu His  Leu Asn Pro
    1235                1240                1245

Gly Gly  Thr Cys Val Ser Ile  Gly Tyr Gly Tyr Ala  Asp Arg Ala
    1250                1255                1260

Ser Glu  Ser Ile Ile Gly Ala  Ile Ala Arg Gln Phe  Lys Phe Ser
    1265                1270                1275

Arg Val  Cys Lys Pro Lys Ser  Ser Leu Glu Glu Thr  Glu Val Leu
    1280                1285                1290

Phe Val  Phe Ile Gly Tyr Asp  Arg Lys Ala Arg Thr  His Asn Pro
    1295                1300                1305

Tyr Lys  Leu Ser Ser Thr Leu  Thr Asn Ile Tyr Thr  Gly Ser Arg
    1310                1315                1320
```

-continued

```
Leu His  Glu Ala Gly Cys Ala  Pro Ser Tyr His Val  Val Arg Gly
    1325                 1330                 1335

Asp Ile  Ala Thr Ala Thr Glu  Gly Val Ile Ile Asn  Ala Ala Asn
    1340                 1345                 1350

Ser Lys  Gly Gln Pro Gly Gly  Gly Val Cys Gly Ala  Leu Tyr Lys
    1355                 1360                 1365

Lys Phe  Pro Glu Ser Phe Asp  Leu Gln Pro Ile Glu  Val Gly Lys
    1370                 1375                 1380

Ala Arg  Leu Val Lys Gly Ala  Ala Lys His Ile Ile  His Ala Val
    1385                 1390                 1395

Gly Pro  Asn Phe Asn Lys Val  Ser Glu Val Glu Gly  Asp Lys Gln
    1400                 1405                 1410

Leu Ala  Glu Ala Tyr Glu Ser  Ile Ala Lys Ile Val  Asn Asp Asn
    1415                 1420                 1425

Asn Tyr  Lys Ser Val Ala Ile  Pro Leu Leu Ser Thr  Gly Ile Phe
    1430                 1435                 1440

Ser Gly  Asn Lys Asp Arg Leu  Thr Gln Ser Leu Asn  His Leu Leu
    1445                 1450                 1455

Thr Ala  Leu Asp Thr Thr Asp  Ala Asp Val Ala Ile  Tyr Cys Arg
    1460                 1465                 1470

Asp Lys  Lys Trp Glu Met Thr  Leu Lys Glu Ala Val  Ala Arg Arg
    1475                 1480                 1485

Glu Ala  Val Glu Glu Ile Cys  Ile Ser Asp Asp Ser  Ser Val Thr
    1490                 1495                 1500

Glu Pro  Asp Ala Glu Leu Val  Arg Val His Pro Lys  Ser Ser Leu
    1505                 1510                 1515

Ala Gly  Arg Lys Gly Tyr Ser  Thr Ser Asp Gly Lys  Thr Phe Ser
    1520                 1525                 1530

Tyr Leu  Glu Gly Thr Lys Phe  His Gln Ala Ala Lys  Asp Ile Ala
    1535                 1540                 1545

Glu Ile  Asn Ala Met Trp Pro  Val Ala Thr Glu Ala  Asn Glu Gln
    1550                 1555                 1560

Val Cys  Met Tyr Ile Leu Gly  Glu Ser Met Ser Ser  Ile Arg Ser
    1565                 1570                 1575

Lys Cys  Pro Val Glu Glu Ser  Glu Ala Ser Thr Pro  Pro Ser Thr
    1580                 1585                 1590

Leu Pro  Cys Leu Cys Ile His  Ala Met Thr Pro Glu  Arg Val Gln
    1595                 1600                 1605

Arg Leu  Lys Ala Ser Arg Pro  Glu Gln Ile Thr Val  Cys Ser Ser
    1610                 1615                 1620

Phe Pro  Leu Pro Lys Tyr Arg  Ile Thr Gly Val Gln  Lys Ile Gln
    1625                 1630                 1635

Cys Ser  Gln Pro Ile Leu Phe  Ser Pro Lys Val Pro  Ala Tyr Ile
    1640                 1645                 1650

His Pro  Arg Lys Tyr Leu Val  Glu Thr Pro Pro Val  Asp Glu Thr
    1655                 1660                 1665

Pro Glu  Pro Ser Ala Glu Asn  Gln Ser Thr Glu Gly  Thr Pro Glu
    1670                 1675                 1680

Gln Pro  Pro Leu Ile Thr Glu  Asp Glu Thr Arg Thr  Arg Thr Pro
    1685                 1690                 1695

Glu Pro  Ile Ile Ile Glu Glu  Glu Glu Glu Asp Ser  Ile Ser Leu
    1700                 1705                 1710
```

```
Leu Ser  Asp Gly Pro Thr His  Gln Val Leu Gln Val  Glu Ala Asp
    1715                 1720                 1725

Ile His  Gly Pro Pro Ser Val  Ser Ser Ser Ser Trp  Ser Ile Pro
    1730                 1735                 1740

His Ala  Ser Asp Phe Asp Val  Asp Ser Leu Ser Ile  Leu Asp Thr
    1745                 1750                 1755

Leu Glu  Gly Ala Ser Val Thr  Ser Gly Ala Thr Ser  Ala Glu Thr
    1760                 1765                 1770

Asn Ser  Tyr Phe Ala Lys Ser  Met Glu Phe Leu Ala  Arg Pro Val
    1775                 1780                 1785

Pro Ala  Pro Arg Thr Val Phe  Arg Asn Pro Pro His  Pro Ala Pro
    1790                 1795                 1800

Arg Thr  Arg Thr Pro Ser Leu  Ala Pro Ser Arg Ala  Cys Ser Arg
    1805                 1810                 1815

Thr Ser  Leu Val Ser Thr Pro  Pro Gly Val Asn Arg  Val Ile Thr
    1820                 1825                 1830

Arg Glu  Glu Leu Glu Ala Leu  Thr Pro Ser Arg Thr  Pro Ser Arg
    1835                 1840                 1845

Ser Val  Ser Arg Thr Ser Leu  Val Ser Asn Pro Pro  Gly Val Asn
    1850                 1855                 1860

Arg Val  Ile Thr Arg Glu Glu  Phe Glu Ala Phe Val  Ala Gln Gln
    1865                 1870                 1875

Gln


<210> SEQ ID NO 23
<211> LENGTH: 613
<212> TYPE: PRT
<213> ORGANISM: Artificial Sequence
<220> FEATURE:
<223> OTHER INFORMATION: Viral Protein

<400> SEQUENCE: 23

Arg Phe Asp Ala Gly Ala Tyr Ile Phe Ser Ser Asp Thr Gly Gln Gly
1               5                   10                  15

His Leu Gln Gln Lys Ser Val Arg Gln Thr Val Leu Ser Glu Val Val
            20                  25                  30

Leu Glu Arg Thr Glu Leu Glu Ile Ser Tyr Ala Pro Arg Leu Asp Gln
        35                  40                  45

Glu Lys Glu Glu Leu Leu Arg Lys Lys Leu Gln Leu Asn Pro Thr Pro
    50                  55                  60

Ala Asn Arg Ser Arg Tyr Gln Ser Arg Lys Val Glu Asn Met Lys Ala
65                  70                  75                  80

Ile Thr Ala Arg Arg Ile Leu Gln Gly Leu Gly His Tyr Leu Lys Ala
                85                  90                  95

Glu Gly Lys Val Glu Cys Tyr Arg Thr Leu His Pro Val Pro Leu Tyr
            100                 105                 110

Ser Ser Ser Val Asn Arg Ala Phe Ser Ser Pro Lys Val Ala Val Glu
        115                 120                 125

Ala Cys Asn Ala Met Leu Lys Glu Asn Phe Pro Thr Val Ala Ser Tyr
    130                 135                 140

Cys Ile Ile Pro Glu Tyr Asp Ala Tyr Leu Asp Met Val Asp Gly Ala
145                 150                 155                 160

Ser Cys Cys Leu Asp Thr Ala Ser Phe Cys Pro Ala Lys Leu Arg Ser
                165                 170                 175

Phe Pro Lys Lys His Ser Tyr Leu Glu Pro Thr Ile Arg Ser Ala Val
```

-continued

```
            180                 185                 190

Pro Ser Ala Ile Gln Asn Thr Leu Gln Asn Val Leu Ala Ala Ala Thr
        195                 200                 205

Lys Arg Asn Cys Asn Val Thr Gln Met Arg Glu Leu Pro Val Leu Asp
    210                 215                 220

Ser Ala Ala Phe Asn Val Glu Cys Phe Lys Lys Tyr Ala Cys Asn Asn
225                 230                 235                 240

Glu Tyr Trp Glu Thr Phe Lys Glu Asn Pro Ile Arg Leu Thr Glu Glu
                245                 250                 255

Asn Val Val Asn Tyr Ile Thr Lys Leu Lys Gly Pro Lys Ala Ala Ala
            260                 265                 270

Leu Phe Ala Lys Thr His Asn Leu Asn Met Leu Gln Asp Ile Pro Met
        275                 280                 285

Asp Arg Phe Val Met Asp Leu Lys Arg Asp Val Lys Val Thr Pro Gly
    290                 295                 300

Thr Lys His Thr Glu Glu Arg Pro Lys Val Gln Val Ile Gln Ala Ala
305                 310                 315                 320

Asp Pro Leu Ala Thr Ala Tyr Leu Cys Gly Ile His Arg Glu Leu Val
                325                 330                 335

Arg Arg Leu Asn Ala Val Leu Leu Pro Asn Ile His Thr Leu Phe Asp
            340                 345                 350

Met Ser Ala Glu Asp Phe Asp Ala Ile Ile Ala Glu His Phe Gln Pro
        355                 360                 365

Gly Asp Cys Val Leu Glu Thr Asp Ile Ala Ser Phe Asp Lys Ser Glu
    370                 375                 380

Asp Asp Ala Met Ala Leu Thr Ala Leu Met Ile Leu Glu Asp Leu Gly
385                 390                 395                 400

Val Asp Ala Glu Leu Leu Thr Leu Ile Glu Ala Ala Phe Gly Glu Ile
                405                 410                 415

Ser Ser Ile His Leu Pro Thr Lys Thr Lys Phe Lys Phe Gly Ala Met
            420                 425                 430

Met Lys Ser Gly Met Phe Leu Thr Leu Phe Val Asn Thr Val Ile Asn
        435                 440                 445

Ile Val Ile Ala Ser Arg Val Leu Arg Glu Arg Leu Thr Gly Ser Pro
    450                 455                 460

Cys Ala Ala Phe Ile Gly Asp Asp Asn Ile Val Lys Gly Val Lys Ser
465                 470                 475                 480

Asp Lys Leu Met Ala Asp Arg Cys Ala Thr Trp Leu Asn Met Glu Val
                485                 490                 495

Lys Ile Ile Asp Ala Val Val Gly Glu Lys Ala Pro Tyr Phe Cys Gly
            500                 505                 510

Gly Phe Ile Leu Cys Asp Ser Val Thr Gly Thr Ala Cys Arg Val Ala
        515                 520                 525

Asp Pro Leu Lys Arg Leu Phe Lys Leu Gly Lys Pro Leu Ala Ala Asp
    530                 535                 540

Asp Glu His Asp Asp Asp Arg Arg Arg Ala Leu His Glu Glu Ser Thr
545                 550                 555                 560

Arg Trp Asn Arg Val Gly Ile Leu Ser Glu Leu Cys Lys Ala Val Glu
                565                 570                 575

Ser Arg Tyr Glu Thr Val Gly Thr Ser Ile Ile Val Met Ala Met Thr
            580                 585                 590

Thr Leu Ala Ser Ser Val Lys Ser Phe Ser Tyr Leu Arg Gly Ala Pro
        595                 600                 605
```

Ile Thr Leu Tyr Gly
610

<210> SEQ ID NO 24
<211> LENGTH: 11917
<212> TYPE: RNA
<213> ORGANISM: Artificial Sequence
<220> FEATURE:
<223> OTHER INFORMATION: RBS004.1

<400> SEQUENCE: 24
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucauggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980

-continued

```
ggagcgcuga acacugauga agaauauuac aaaacuguca agcccagcga gcacgacggc   2040
gaauaccugu acgacaucga caggaaacag ugcgucaaga aagagcuagu cacugggcua   2100
gggcucacag gcgagcuggu cgauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga gggugggga agcaguugca aauagauuac   2760
aaaggcaacg aaauaaugac ggcagcugcc ucucaagggc ugacccguaa aggugugauu   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuaugguu acgcugacag ggccagcgaa   3840
agcaucauug gugcuauagc gcggcaguuc aaguuuuccc gaguaugcaa accgaaaucc   3900
ucacuugagg agacggaagu ucuguuugua uucauugggu acgaucgcaa ggcccguacg   3960
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aaguuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
```

-continued aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc uggugagggu gcaucccaag aguucuuugg cuggaaggaa gggcuacagc 4620
acaagcgaug gcaaaacuuu cucauauuug gaagggacca aguuucacca ggcggccaag 4680
gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaauc aguaaggcaa 5760
acggugcuau ccgaaguggu guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720

-continued

```
aacauucaua cacuguuuga uaugucggcu gaagacuuug acgcuauuau agccgagcac   6780
uuccagccug gggauugugu ucuggaaacu gacaucgcgu cguuugauaa aagugaggac   6840
gacgccaugg cucugaccgc guuaaugauu cuggaagacu uaggugugga cgcagagcug   6900
uugacgcuga uugaggcggc uuucggcgaa auuucaucaa uacauuugcc cacuaaaacu   6960
aaauuuaaau ucggagccau gaugaaaucu ggaauguucc ucacacuguu ugugaacaca   7020
gucauuaaca uuguaaucgc aagcagagug uugagagaac ggcuaaccgg aucaccaugu   7080
gcagcauuca uuggagauga caauaucgug aaaggaguca aaucggacaa auuaauggca   7140
gacaggugcg ccaccugguu gaauauggaa gucaagauua uagaugcugu ggugggcgag   7200
aaagcgccuu auuucugugg aggguuuauu uugugugacu ccgugaccgg cacagcgugc   7260
cguguggcag acccccuaaa aaggcuguuu aagcuaggca aaccucuggc agcagacgau   7320
gaacaugaug augacaggag aagggcauug caugaggagu caacacgcug gaaccgagug   7380
gguauucuuu cagagcugug caaggcagua gaaucaaggu augaaaccgu aggaacuucc   7440
aucauaguua uggccaugac uacucuagcu agcaguguua aaucauucag cuaccugaga   7500
ggggccccua uaacucucua cggcuaaccu gaauggacua cgacauaguc uaguccgcca   7560
agacuaguau guuuguguuu cuugugcugc ugccucuugu gucuucucag ugugugaauu   7620
ugacaacaag aacacagcug ccaccagcuu auacaaauuc uuuuaccaga ggaguguauu   7680
auccugauaa aguguuuaga ucuucugugc ugcacagcac acaggaccug uuucugccau   7740
uuuuuagcaa ugugacaugg uuucaugcaa uucauguguc uggaacaaau ggaacaaaaa   7800
gauuugauaa uccugugcug ccuuuuaaug auggagugua uuuugcuuca acagaaaagu   7860
caaauauuau uagaggaugg auuuuuggaa caacacugga uucuaaaaca cagucucugc   7920
ugauugugaa uaaugcaaca aaugugguga uuaaagugug ugaauuucag uuuuguaaug   7980
auccuuuucu gggaguguau uaucacaaaa auaauaaauc uuggauggaa ucugaauuua   8040
gaguguauuc cucugcaaau aauuguacau uugaauaugu gucucagccu uuucugaugg   8100
aucuggaagg aaaacagggc aauuuuaaaa aucugagaga auuuguguuu aaaaauauug   8160
auggauauuu uaaaauuuau ucuaaacaca caccaauuaa uuuagugaga gaucugccuc   8220
agggauuuuc ugcucuggaa ccucuggugg aucugccaau uggcauuaau auuacaagau   8280
uucagacacu gcuggcucug cacagaucuu aucugacacc uggagauucu ucuucuggau   8340
ggacagccgg agcugcagcu uauuaugugg gcuaucugca gccaagaaca uuucugcuga   8400
aauauaauga aaauggaaca auuacagaug cuguggauug ugcucuggau ccucugucug   8460
aaacaaaaug uacauuaaaa ucuuuuacag uggaaaaagg cauuuaucag acaucuaauu   8520
uuagagugca gccaacagaa ucuauuguga gauuuccaaa uauuacaaau cuguguccau   8580
uuggagaagu guuuaaugca acaagauuug caucugugua ugcauggaau agaaaaagaa   8640
uuucuaauug uguggcugau uauucugugc uguauaauag ugcuucuuuu uccacauuua   8700
aauguuaugg agugucucca acaaaauuaa augauuuaug uuuuacaaau guguaugcug   8760
auucuuuugu gaucagaggu gaugaaguga gacagauugc cccggacag acaggaaaaa   8820
uugcugauua caauuacaaa cugccugaug auuuuacagg augugugauu gcuuggaauu   8880
cuaauaauuu agauucuaaa gugggaggaa auuacaauua ucuguacaga cuguuuagaa   8940
aaucaaaucu gaaaccuuuu gaaagagaua uuucaacaga aauuuaucag gcuggaucaa   9000
caccuuguaa uggaguggaa ggauuuaauu guuauuuucc auuacagagc uauggauuuc   9060
```

-continued

```
agccaaccaa uggugugggga uaucagccau auagaguggu ggugcugucu uuugaacugc   9120
ugcaugcacc ugcaacagug uguggaccua aaaaaucuac aaauuuagug aaaaauaaau   9180
gugugaauuu uaauuuuaau ggauuaacag gaacaggagu gcugacagaa ucuaauaaaa   9240
aauuucugcc uuuucagcag uuuggcagag auauugcaga uaccacagau gcagugagag   9300
auccucagac auuagaaauu cuggauauua caccuuguuc uuuugggggu gugucuguga   9360
uuacaccugg aacaaauaca ucuaaucagg uggcugugcu guaucaggau gugaauugua   9420
cagaagugcc aguggcaauu caugcagauc agcugacacc aacauggaga guguauucua   9480
caggaucuaa uguguuucag acaagagcag gaugucugau uggagcagaa caugugaaua   9540
auucuuauga augugauauu ccaauuggag caggcauuug ugcaucuuau cagacacaga   9600
caaauucccc aaggagagca agaucugugg caucucaguc uauuauugca uacaccaugu   9660
cucugggagc agaaaauucu guggcauauu cuaauaauuc uauugcuauu ccaacaaauu   9720
uuaccauuuc ugugacaaca gaaauuuuac cugugucuau gacaaaaaca ucuguggauu   9780
guaccaugua cauuugugga gauucuacag aauguucuaa ucugcugcug caguauggau   9840
cuuuuuguac acagcugaau agagcuuuaa caggaauugc uguggaacag gauaaaaaua   9900
cacaggaagu guuugcucag gugaaacaga uuuacaaaac accaccaauu aaagauuuug   9960
gaggauuuaa uuuuagccag auucugccug auccuucuaa accuucuaaa agaucuuuua  10020
uugaagaucu gcuguuuaau aaagugacac uggcagaugc aggauuuauu aaacaguaug  10080
gagauugccu gggugauauu gcugcaagag aucugauuug ugcucagaaa uuuaauggac  10140
ugacagugcu gccuccucug cugacagaug aaaugauugc ucaguacaca ucugcuuuac  10200
uggcuggaac aauuacaagc ggauggacau uuggagcugg agcugcucug cagauuccuu  10260
uugcaaugca gauggcuuac agauuuaaug gaauuggagu gacacagaau guguuauaug  10320
aaaaucagaa acugauugca aaucaguuua auucugcaau uggcaaaauu caggauucuc  10380
ugucuucuac agcuucugcu cugggaaaac ugcaggaugu ggugaaucag aaugcacagg  10440
cacugaauac ucuggugaaa cagcugucua gcaauuuugg ggcaauuucu ucugugcuga  10500
augauauucu gucuagacug gauccuccug aagcugaagu gcagauugau agacugauca  10560
caggaagacu gcagucucug cagacuuaug ugacacagca gcugauuaga gcugcugaaa  10620
uuagagcuuc ugcuaaucug gcugcuacaa aaaugucuga augugugcug ggacagucaa  10680
aaagagugga uuuuugugga aaaggauauc aucugauguc uuuuccacag ucugcuccac  10740
auggaguggu guuuuuacau gugacauaug ugccagcaca ggaaaagaau uuuaccacag  10800
caccagcaau uugucaugau ggaaaagcac auuuuccaag agaaggagug uuugugucua  10860
auggaacaca uugguuugug acacagagaa auuuuuauga accucagauu auuacaacag  10920
auaauacauu ugugucagga aauugugaug uggugauugg aauugugaau aauacagugu  10980
augauccacu gcagccagaa cuggauucuu uuaaagaaga acuggauaaa uauuuuaaaa  11040
aucacacauc uccugaugug gauuuaggag auauuucugg aaucaaugca ucuguggugga  11100
auauucagaa agaaauugau agacugaaug aaguggccaa aaaucugaau gaaucucuga  11160
uugaucugca ggaacuugga aaauaugaac aguacauuaa auggccuugg uacauuuggc  11220
uuggauuuau ugcaggauua auugcaauug ugauggugac aauuauguua uguuguauga  11280
caucauguug uucuuguuua aaaggauguu guucuugugg aagcuguugu aaauuugaug  11340
aagaugauuc ugaaccugug uuaaaaggag ugaaauugca uuacacauga ugacucgagc  11400
ugguacugca ugcacgcaau gcuagcugcc ccuuucccgu ccuggguacc ccgagucucc  11460
```

cccgaccucg ggucccaggu augcucccac cuccaccugc cccacucacc accucugcua 11520
guuccagaca ccucccaagc acgcagcaau gcagcucaaa acgcuuagcc uagccacacc 11580
cccacgggaa acagcaguga uuaaccuuua gcaauaaacg aaaguuuaac uaagcuauac 11640
uaaccccagg guuggucaau uucgugccag ccacaccgcg gccgcaugaa uacagcagca 11700
auuggcaagc ugcuuacaua gaacucgcgg cgauuggcau gccgccuuaa aauuuuuauu 11760
uuauuuuuuc uuuucuuuuc cgaaucggau uuuguuuuua auauuucaaa aaaaaaaaaa 11820
aaaaaaaaaa aaaaaaagca uaugacuaaa aaaaaaaaaa aaaaaaaaaa aaaaaaaaaa 11880
aaaaaaaaaa aaaaaaaaaa aaaaaaaaaa aaaaaaa 11917

<210> SEQ ID NO 25
<211> LENGTH: 11917
<212> TYPE: RNA
<213> ORGANISM: Artificial Sequence
<220> FEATURE:
<223> OTHER INFORMATION: RBS004.2

<400> SEQUENCE: 25
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucauggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560

-continued

```
uugcgcgcag cucuaccacc uuuggcagcu gauguugagg agcccacucu ggaagccgau   1620
gucgacuuga uguuacaaga ggcuggggcc ggcucagugg agacaccucg uggcuugaua   1680
aagguuacca gcuacgcugg cgaggacaag aucggcucuu acgcugugcu uucuccgcag   1740
gcuguacuca agagugaaaa auuaucuugc auccacccuc ucgcugaaca agucauagug   1800
auaacacacu cuggccgaaa agggcguuau gccguggaac cauaccaugg uaaaguagug   1860
gugccagagg gacaugcaau acccguccag gacuuucaag cucugaguga aagugccacc   1920
auuguguaca acgaacguga guucguaaac agguaccugc accauauugc cacacaugga   1980
ggagcgcuga acacugauga agaauauuac aaaacuguca agcccagcga gcacgacggc   2040
gaauaccugu acgacaucga caggaaacag ugcgucaaga aagagcuagu cacugggcua   2100
gggcucacag gcgagcuggu cgauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga ggguggguga agcaguugca aauagauuac   2760
aaaggcaacg aaauaaugac ggcagcugcc ucucaagggc ugacccguaa aggugugguau   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuaugguu acgcugacag ggccagcgaa   3840
agcaucauug gugcuauagc gcggcaguuc aaguuuuccc gaguaugcaa accgaaaucc   3900
ucacuugagg agacggaagu ucuguuugua uucauugggu acgaucgcaa ggcccguacg   3960
```

```
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aaguuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
aacgauaaca auuacaaguc aguagcgauu ccacuguugu ccaccggcau cuuuuccggg   4380
aacaaagauc gacuaaccca aucauugaac cauuugcuga cagcuuuaga caccacugau   4440
gcagauguag ccauauacug cagggacaag aaaugggaaa ugacucucaa ggaagcagug   4500
gcuaggagag aagcagugga ggagauaugc auauccgacg auucuucagu gacagaaccu   4560
gaugcagagc uggugagggu gcaucccaag aguucuuugg cuggaaggaa gggcuacagc   4620
acaagcgaug gcaaaacuuu cucauauuug gaagggacca aguuucacca ggcggccaag   4680
gauauagcag aaauuaaugc cauguggccc guugcaacgg aggccaauga gcagguaugc   4740
auguauaucc ucggagaaag caugagcagu auuaggucga aaugccccgu cgaggagucg   4800
gaagccucca caccaccuag cacgcugccu ugcuugugca uccaugccau gacuccagaa   4860
agaguacagc gccuaaaagc cucacgucca gaacaaauua cugugugcuc auccuuucca   4920
uugccgaagu auagaaucac uggugugcag aagauccaau gcucccagcc uauauuguuc   4980
ucaccgaaag ugccugcgua uauucaucca aggaaguauc ucguggaaac accaccggua   5040
gacgagacuc cggagccauc ggcagagaac caauccacag aggggacacc ugaacaacca   5100
ccacuuauaa ccgaggauga gaccaggacu agaacgccug agccgaucau caucgaagaa   5160
gaagaagaag auagcauaag uuugcuguca gauggcccga cccaccaggu gcugcaaguc   5220
gaggcagaca uucacgggcc gcccucugua ucuagcucau ccugguccau uccucaugca   5280
uccgacuuug auguggacag uuuauccaua cuugacaccc uggagggagc uagcgugacc   5340
agcggggcaa cgucagccga gacuaacucu uacuucgcaa agaguaugga guuucuggcg   5400
cgaccggugc cugcgccucg aacaguauuc aggaacccuc cacaucccgc uccgcgcaca   5460
agaacaccgu cacuugcacc cagcagggcc ugcuccagaa ccagccuagu uuccaccccg   5520
ccaggcguga auagggugau cacuagagag gagcucgaag cgcuuacccc gucacgcacu   5580
ccuagcaggu cggucuccag aaccagccug gucuccaacc cgccaggcgu aaauagggug   5640
auuacaagag aggaguuuga ggcguucgua gcacaacaac aaugacgguu ugaugcgggu   5700
gcauacaucu uuuccuccga caccggucaa gggcauuuac aacaaaaauc aguaaggcaa   5760
acggugcuau ccgaaguggu guuggagagg accgaauugg agauuucgua ugccccgcgc   5820
cucgaccaag aaaaagaaga auuacuacgc aagaaauuac aguuaaaucc cacaccugcu   5880
aacagaagca gauaccaguc caggaaggug gagaacauga aagccauaac agcuagacgu   5940
auucugcaag gccuagggca uuauuugaag gcagaaggaa aaguggagug cuaccgaacc   6000
cugcauccug uuccuuugua uucaucuagu gugaaccgug ccuuuucaag ccccaagguc   6060
gcaguggaag ccuguaacgc cauguugaaa gagaacuuuc cgacuguggc uucuuacugu   6120
auuauuccag aguacgaugc cuauuuggac augguugacg gagcuucaug cugcuuagac   6180
acugccaguu uuugcccugc aaagcugcgc agcuuuccaa agaaacacuc cuauuuggaa   6240
cccacaauac gaucggcagu gccuucagcg auccagaaca cgcuccagaa cguccuggca   6300
```

-continued

```
gcugccacaa aaagaaauug caaugucacg caaaugagag aauugcccgu auuggauucg   6360
gcggccuuua auguggaaug cuucaagaaa uaugcgugua auaaugaaua uugggaaacg   6420
uuuaaagaaa accccaucag gcuuacugaa gaaaacgugg uaaauuacau uaccaaauua   6480
aaaggaccaa aagcugcugc ucuuuuugcg aagacacaua auuugaauau guugcaggac   6540
auaccaaugg acagguuugu aauggacuua aagagagacg ugaaagugac uccaggaaca   6600
aaacauacug aagaacggcc caagguacag gugauccagg cugccgaucc gcuagcaaca   6660
gcguaucugu gcggaaucca ccgagagcug guuaggagau uaaaugcggu ccugcuuccg   6720
aacauucaua cacuguuuga uaugucggcu gaagacuuug acgcuauuau agccgagcac   6780
uuccagccug ggauugugu ucuggaaacu gacaucgcgu cguuugauaa aagugaggac   6840
gacgccaugg cucugaccgc guuaaugauu cuggaagacu uaggugugga cgcagagcug   6900
uugacgcuga uugaggcggc uuucggcgaa auuucaucaa uacauuugcc cacuaaaacu   6960
aaauuuaaau ucggagccau gaugaaaucu ggaauguucc ucacacuguu ugugaacaca   7020
gucauuaaca uuguaaucgc aagcagagug uugagagaac ggcuaaccgg aucaccaugu   7080
gcagcauuca uuggagauga caauaucgug aaaggaguca aaucggacaa auuaauggca   7140
gacaggugcg ccaccugguu gaauauggaa gucaagauua uagaugcugu gguggggcgag   7200
aaagcgccuu auuucugugg aggguuuauu uugugugacu ccgugaccgg cacagcgugc   7260
cguguggcag acccccuaaa aaggcuguuu aagcuaggca aaccucuggc agcagacgau   7320
gaacaugaug augacaggag aagggcauug caugaggagu caacacgcug gaaccgagug   7380
gguauucuuu cagagcugug caaggcagua gaaucaaggu augaaaccgu aggaacuucc   7440
aucauaguua uggccaugac uacucuagcu agcaguguua aaucauucag cuaccugaga   7500
ggggccccua uaacucucua cggcuaaccu gaauggacua cgacauaguc uaguccgcca   7560
agacuaguau guucguguuc cuggugcugc ugccucuggu guccagccag ugugugaacc   7620
ugaccaccag aacacagcug ccuccagccu acaccaacag cuuuaccaga ggcguguacu   7680
accccgacaa ggguguucaga uccagcgugc ugcacucuac ccaggaccug uuccugccuu   7740
ucuucagcaa cgugaccugg uuccacgcca uccacguguc cggcaccaau ggcaccaaga   7800
gauucgacaa ccccgugcug cccuucaacg acggggugua cuuugccagc accgagaagu   7860
ccaacaucau cagaggcugg aucuucggca ccacacugga cagcaagacc cagagccugc   7920
ugaucgugaa caacgccacc aacgugguca ucaaagugug cgaguuccag uucugcaacg   7980
accccuuccu gggcgucuac uaccacaaga acaacaagag cuggauggaa agcgaguucc   8040
ggguguacag cagcgccaac aacugcaccu ucgaguacgu gucccagccu uuccugaugg   8100
accuggaagg caagcagggc aacuucaaga accugcgcga guucguguuu aagaacaucg   8160
acggcuacuu caagaucuac agcaagcaca ccccuaucaa ccucgugcgg gaucugccuc   8220
agggcuucuc ugcucuggaa ccccuggugg aucugcccau cggcaucaac aucacccggu   8280
uucagacacu gcuggcccug cacagaagcu accugacacc uggcgauagc agcagcggau   8340
ggacagcugg ugccgccgcu uacuaugugg gcuaccugca gccuagaacc uuccugcuga   8400
aguacaacga gaacggcacc aucaccgacg ccguggauug ugcucuggau ccucugagcg   8460
agacaaagug cacccugaag uccuucaccg uggaaaaggg caucuaccag accagcaacu   8520
uccgggugca gcccaccgaa uccaucgugc gguuccccaa uaucaccaau cugugccccu   8580
ucggcgaggu guucaaugcc accagauucg ccucugugua cgccuggaac cggaagcgga   8640
ucagcaauug cguggccgac uacuccgugc uguacaacuc cgccagcuuc agcaccuuca   8700
```

agugcuacgg cgugucccu accaagcuga acgaccugug cuucacaaac guguacgccg 8760
acagcuucgu gauccgggga gaugaagugc ggcagauugc cccuggacag acaggcaaga 8820
ucgccgacua caacuacaag cugcccgacg acuucaccgg cugugugauu gccuggaaca 8880
gcaacaaccu ggacuccaaa gucggcggca acuacaauua ccuguaccgg cuguuccgga 8940
aguccaaucu gaagcccuuc gagcgggaca ucuccaccga gaucuaucag gccggcagca 9000
ccccuuguaa cggcguggaa ggcuucaacu gcuacuuccc acugcagucc uacggcuuuc 9060
agcccacaaa uggcgugggc uaucagcccu acagaguggu ggugcugagc uucgaacugc 9120
ugcaugcccc ugccacagug ugcggcccua agaaaagcac caaucucgug aagaacaaau 9180
gcgugaacuu caacuucaac ggccugaccg gcaccggcgu gcugacagag agcaacaaga 9240
aguuccugcc auuccagcag uuuggccggg auaucgccga uaccacagac gccguuagag 9300
auccccagac acuggaaauc cuggacauca ccccuugcag cuucggcgga gugucuguga 9360
ucaccccugg caccaacacc agcaaucagg uggcagugcu guaccaggac gugaacugua 9420
ccgaagugcc cguggccauu cacgccgauc agcugacacc uacauggcgg guguacucca 9480
ccggcagcaa uguguuucag accagagccg gcugucugau cggagccgag cacgugaaca 9540
auagcuacga gugcgacauc cccaucggcg cuggaaucug cgccagcuac cagacacaga 9600
caaacagccc ucggagagcc agaagcgugg ccagccagag caucauugcc uacacaaugu 9660
cucugggcgc cgagaacagc guggccuacu ccaacaacuc uaucgcuauc cccaccaacu 9720
ucaccaucag cgugaccaca gagauccugc cuguguccau gaccaagacc agcgguggacu 9780
gcaccaugua caucugcggc gauuccaccg agugcuccaa ccugcugcug caguacggca 9840
gcuucugcac ccagcugaau agagcccuga cagggaucgc cguggaacag gacaagaaca 9900
cccaagaggu guucgcccaa gugaagcaga ucuacaagac cccuccuauc aaggacuucg 9960
gcggcuucaa uuucagccag auucugcccg auccuagcaa gcccagcaag cggagcuuca 10020
ucgaggaccu gcuguucaac aaagugacac uggccgacgc cggcuucauc aagcaguaug 10080
gcgauugucu gggcgacauu gccgccaggg aucugauuug cgcccagaag uuuaacggac 10140
ugacagugcu gccuccucug cugaccgaug agaugaucgc ccaguacaca ucugcccugc 10200
uggccggcac aaucacaagc ggcuggacau uuggagcagg cgccgcucug cagaucccccu 10260
uugcuaugca gauggccuac cgguucaacg gcaucggagu gacccagaau gugcuguacg 10320
agaaccagaa gcugaucgcc aaccaguuca acagcgccau cggcaagauc caggacagcc 10380
ugagcagcac agcaagcgcc cugggaaagc ugcaggacgu ggucaaccag aaugcccagg 10440
cacugaacac ccuggucaag cagcuguccu ccaacuucgg cgccaucagc ucugugcuga 10500
acgauauccu gagcagacug gacccuccug aggccgaggu gcagaucgac agacugauca 10560
caggcagacu gcagagccuc cagacauacg ugacccagca gcugaucaga gccgccgaga 10620
uuagagccuc ugccaaucug gccgccacca agaugucuga gugugugcug ggccagagca 10680
agagagugga cuuuugcggc aagggcuacc accugaugag cuucccucag ucugccccuc 10740
acggcguggu guuucugcac gugacauaug ugcccgcuca agagaagaau uucaccaccg 10800
cuccagccau cugccacgac ggcaaagccc acuuuccuag agaaggcgug uucgugucca 10860
acggcaccca uugguucgug acacagcgga acuucuacga gccccagauc aucaccaccg 10920
acaacaccuu cgugucuggc aacugcgacg ucgugaucgg cauugugaac aauaccgugu 10980
acgacccucu gcagcccgag cuggacagcu ucaaagagga acuggacaag uacuuuaaga 11040

```
accacacaag ccccgacgug gaccugggcg auaucagcgg aaucaaugcc agcgucguga  11100

acauccagaa agagaucgac cggcugaacg agguggccaa gaaucugaac gagagccuga  11160

ucgaccugca agaacugggg aaguacgagc aguacaucaa guggcccugg uacaucuggc  11220

ugggcuuuau cgccggacug auugccaucg ugauggucac aaucaugcug uguugcauga  11280

ccagcugcug uagcugccug aagggcuguu guagcugugg cagcugcugc aaguucgacg  11340

aggacgauuc ugagcccgug cugaagggcg ugaaacugca cuacacauga ugacucgagc  11400

ugguacugca ugcacgcaau gcuagcugcc ccuuucccgu ccuggguacc ccgagucucc  11460

cccgaccucg ggucccaggu augcucccac cuccaccugc ccccacucacc accucugcua  11520

guuccagaca ccucccaagc acgcagcaau gcagcucaaa acgcuuagcc uagccacacc  11580

cccacgggaa acagcaguga uuaaccuuua gcaauaaacg aaaguuuaac uaagcuauac  11640

uaaccccagg guuggucaau uucgugccag ccacaccgcg gccgcaugaa uacagcagca  11700

auuggcaagc ugcuuacaua gaacucgcgg cgauuggcau gccgccuuaa aauuuuuauu  11760

uuauuuuuuc uuuucuuuuc cgaaucggau uuuguuuuua auauuucaaa aaaaaaaaaa  11820

aaaaaaaaaa aaaaaaagca uaugacuaaa aaaaaaaaaa aaaaaaaaaa aaaaaaaaaa  11880

aaaaaaaaaa aaaaaaaaaa aaaaaaaaaa aaaaaaa                          11917
```

<210> SEQ ID NO 26
<211> LENGTH: 8896
<212> TYPE: RNA
<213> ORGANISM: Artificial Sequence
<220> FEATURE:
<223> OTHER INFORMATION: RBS004.3

<400> SEQUENCE: 26

```
gaugggcggc gcaugagaga agcccagacc aauuaccuac ccaaaaugga gaaaguucac     60

guugacaucg aggaagacag cccauuccuc agagcuuugc agcggagcuu cccgcaguuu    120

gagguagaag ccaagcaggu cacugauaau gaccaugcua augccagagc guuuucgcau    180

cuggcuucaa aacugaucga aacggaggug gacccauccg acacgauccu ugacauugga    240

agugcgcccg cccgcagaau guauucuaag cacaaguauc auuguaucug uccgaugaga    300

ugugcggaag auccggacag auuguauaag uaugcaacua agcugaagaa aaacuguaag    360

gaaauaacug auaaggaauu ggacaagaaa augaaggagc ucgccgccgu caugagcgac    420

ccugaccugg aaacugagac uaugugccuc cacgacgacg agucgugucg cuacgaaggg    480

caagucgcug uuuaccagga uguauacgcg guugacggac cgacaagucu cuaucaccaa    540

gccaauaagg gaguuagagu cgccuacugg auaggcuuug acaccacccc uuuuauguuu    600

aagaacuugg cuggagcaua uccaucauac ucuaccaacu gggccgacga aaccguguua    660

acggcucgua acauaggccu augcagcucu gacguuaugg agcggucacg uagagggaug    720

uccauucuua gaaagaagua uuugaaacca uccaacaaug uucuauucuc uguuggcucg    780

accaucuacc acgaaaagag ggacuuacug aggagcuggc accugccguc uguauuucac    840

uuacguggca agcaaaauua cacaugucgg ugugagacua uaguuaguug cgacggguac    900

gucguuaaaa gaauagcuau caguccaggc cuguauggga agccuucagg cuaugcugcu    960

acgaugcacc gcgagggauu cuugugcugc aaagugacag acacauugaa cggggagagg   1020

gucucuuuuc ccgugugcac guaugugcca gcuacauugu gugaccaaau gacuggcaua   1080

cuggcaacag augucagugc ggacgacgcg caaaaacugc ugguugggcu caaccagcgu   1140

auagucguca acggucgcac ccagagaaac accaauacca ugaaaaauua ccuuuugccc   1200
```

-continued

```
guaguggccc aggcauuugc uaggugggca aaggaauaua aggaagauca agaagaugaa   1260
aggccacuag gacuacgaga uagacaguua gucaugggu guuguugggc uuuuagaagg   1320
cacaagauaa caucuauuua uaagcgcccg gauacccaaa ccaucaucaa agugaacagc   1380
gauuuccacu cauucgugcu gcccaggaua ggcaguaaca cauuggagau cgggcugaga   1440
acaagaauca ggaaaauguu agaggagcac aaggagccgu caccucucau uaccgccgag   1500
gacguacaag aagcuaagug cgcagccgau gaggcuaagg aggugcguga agccgaggag   1560
uugcgcgcag cucuaccacc uuuggcagcu gauguugagg agcccacucu ggaagccgau   1620
gucgacuuga uguuacaaga ggcuggggcc ggcucagugg agacaccucg uggcuugaua   1680
aagguuacca gcuacgcugg cgaggacaag aucggcucuu acgcugugcu uucuccgcag   1740
gcuguacuca agagugaaaa auuaucuugc auccacccuc ucgcugaaca agucauagug   1800
auaacacacu cuggccgaaa agggcguuau gccguggaac cauaccaugg uaaaguagug   1860
gugccagagg gacaugcaau acccguccag gacuuucaag cucugaguga aagugccacc   1920
auuguguaca acgaacguga guucguaaac agguaccugc accauauugc cacacaugga   1980
ggagcgcuga acacugauga agaauauuac aaaacuguca agcccagcga gcacgacggc   2040
gaauaccugu acgacaucga caggaaacag ugcgucaaga aagagcuagu cacugggcua   2100
gggcucacag gcgagcuggu cgauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga gggugggguga agcaguugca aauagauuac   2760
aaaggcaacg aaauaaugac ggcagcugcc ucucaagggc ugacccguaa aggguguguau   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
```

```
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuaugguu acgcugacag ggccagcgaa   3840
agcaucauug gugcuauagc gcggcaguuc aaguuuuccc gaguaugcaa accgaaaucc   3900
ucacuugagg agacggaagu ucuguuugua uucauugggu acgaucgcaa ggcccguacg   3960
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aaguuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
aacgauaaca auuacaaguc aguagcgauu ccacuguugu ccaccggcau cuuuuccggg   4380
aacaaagauc gacuaaccca aucauugaac cauuugcuga cagcuuuaga caccacugau   4440
gcagauguag ccauauacug cagggacaag aaaugggaaa ugacucucaa ggaagcagug   4500
gcuaggagag aagcagugga ggagauaugc auauccgacg auucuucagu gacagaaccu   4560
gaugcagagc uggugagggu gcaucccaag aguucuuugg cuggaaggaa gggcuacagc   4620
acaagcgaug gcaaaacuuu cucauauuug gaagggacca aguuucacca ggcggccaag   4680
gauauagcag aaauuaaugc cauguggccc guugcaacgg aggccaauga gcagguaugc   4740
auguauaucc ucggagaaag caugagcagu auuaggucga aaugccccgu cgaggagucg   4800
gaagccucca caccaccuag cacgcugccu ugcuugugca uccaugccau gacuccagaa   4860
agaguacagc gccuaaaagc cucacgucca gaacaaauua cugugugcuc auccuuucca   4920
uugccgaagu auagaaucac uggugugcag aagauccaau gcucccagcc uauauuguuc   4980
ucaccgaaag ugccugcgua uauucaucca aggaaguauc ucguggaaac accaccggua   5040
gacgagacuc cggagccauc ggcagagaac caauccacag aggggacacc ugaacaacca   5100
ccacuuauaa ccgaggauga gaccaggacu agaacgccug agccgaucau caucgaagaa   5160
gaagaagaag auagcauaag uuugcuguca gauggcccga cccaccaggu gcugcaaguc   5220
gaggcagaca uucacgggcc gcccucugua ucuagcucau ccugguccau uccucaugca   5280
uccgacuuug auguggacag uuuauccaua cuugacaccc uggagggagc uagcgugacc   5340
agcggggcaa cgucagccga gacuaacucu uacuucgcaa agaguaugga guuucuggcg   5400
cgaccggugc cugcgccucg aacaguauuc aggaacccuc cacaucccgc uccgcgcaca   5460
agaacaccgu cacuugcacc cagcagggcc ugcuccagaa ccagccuagu uuccaccccg   5520
ccaggcguga auagggugau cacuagagag gagcucgaag cgcuuacccc gucacgcacu   5580
ccuagcaggu cggucuccag aaccagccug gucuccaacc cgccaggcgu aaauagggug   5640
auuacaagag aggaguuuga ggcguucgua gcacaacaac aaugacgguu ugaugcgggu   5700
gcauacaucu uuuccuccga caccggucaa gggcauuuac aacaaaaauc aguaaggcaa   5760
acggugcuau ccgaaguggu guuggagagg accgaauugg agauuucgua ugccccgcgc   5820
cucgaccaag aaaaagaaga auuacuacgc aagaaauuac aguuaaaucc cacaccugcu   5880
aacagaagca gauaccaguc caggaaggug gagaacauga aagccauaac agcuagacgu   5940
```

-continued auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug gggauugugu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu gguggcgag 7200
aaagcgccuu auuucugugg aggguuuauu uugugugacu ccgugaccgg cacagcgugc 7260
cgugugcag acccccuaaa aaggcuguuu aagcuaggca aaccucuggc agcagacgau 7320
gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guuuguguuu cuugugcugc ugccucuugu gucuucucag ugugugguga 7620
gauuuccaaa uauuacaaau cugugucccau uuggagaagu guuuaaugca acaagauuug 7680
caucugugua ugcauggaau agaaaaagaa uuucuaauug uguggcugau uauucugugc 7740
uguauaauag ugcuucuuuu uccacauuua aauguuaugg agugucucca acaaaauuaa 7800
augauuuaug uuuuacaaau guguaugcug auucuuuugu gaucagaggu gaugaaguga 7860
gacagauugc cccggacag acaggaaaaa uugcugauua caauuacaaa cugccugaug 7920
auuuuacagg augugugauu gcuuggaauu cuaauaauuu agauucuaaa gugggaggaa 7980
auuacaauua ucuguacaga cuguuuagaa aaucaaaucu gaaaccuuuu gaaagagaua 8040
uuucaacaga aauuuaucag gcuggaucaa caccuuguaa uggaguggaa ggauuuaauu 8100
guuauuuucc auuacagagc uauggauuuc agccaaccaa uggugugga uaucagccau 8160
auagaguggu ggugcugucu uuugaacugc ugcaugcacc ugcaacagug uguggaccua 8220
aaggcucccc cggcuccggc uccggaucug guuauauucc ugaagcucca agagaugggc 8280
aagcuuacgu ucguaaagau ggcgaauggg uauuacuuuc uaccuuuuua ggccggaccc 8340
uggaggugcu guuccagggc cccggcugau gacucgagcu gguacugcau gcacgcaaug 8400
cuagcugccc cuuucccguc cuggguaccc cgagucuccc ccgaccucgg gucccaggua 8460
ugcucccacc uccaccugcc ccacucacca ccucugcuag uuccagacac cucccaagca 8520
cgcagcaaug cagcucaaaa cgcuuagccu agccacaccc ccacgggaaa cagcagugau 8580
uaaccuuuag caauaaacga aaguuuaacu aagcuauacu aaccccaggg uuggucaauu 8640
ucgugccagc cacaccgcgg ccgcaugaau acagcagcaa uuggcaagcu gcuuacauag 8700
aacucgcggc gauuggcaug ccgccuuaaa auuuuuauuu uauuuuuucu uuucuuuucc 8760
gaaucggauu uuguuuuuaa uauuucaaaa aaaaaaaaaa aaaaaaaaaa aaaaaagcau 8820
augacuaaaa aaaaaaaaaa aaaaaaaaaa aaaaaaaaaa aaaaaaaaaa aaaaaaaaaa 8880
aaaaaaaaaa aaaaaa 8896

<210> SEQ ID NO 27
<211> LENGTH: 9079
<212> TYPE: RNA
<213> ORGANISM: Artificial Sequence
<220> FEATURE:
<223> OTHER INFORMATION: RBS004.4

<400> SEQUENCE: 27
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucauggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440

-continued

```
acaagaauca ggaaaauguu agaggagcac aaggagccgu caccucucau uaccgccgag   1500
gacguacaag aagcuaagug cgcagccgau gaggcuaagg aggugcguga agccgaggag   1560
uugcgcgcag cucuaccacc uuuggcagcu gauguugagg agcccacucu ggaagccgau   1620
gucgacuuga uguuacaaga ggcuggggcc ggcucagugg agacaccucg uggcuugaua   1680
aagguuacca gcuacgcugg cgaggacaag aucggcucuu acgcugugcu uucuccgcag   1740
gcuguacuca agagugaaaa auuaucuugc auccacccuc ucgcugaaca agucauagug   1800
auaacacacu cuggccgaaa agggcguuau gccguggaac cauaccaugg uaaaguagug   1860
gugccagagg gacaugcaau acccguccag gacuuucaag cucugaguga aagugccacc   1920
auuguguaca acgaacguga guucguaaac agguaccugc accauauugc cacacaugga   1980
ggagcgcuga acacugauga agaauauuac aaaacuguca agcccagcga gcacgacggc   2040
gaauaccugu acgacaucga caggaaacag ugcgucaaga aagagcuagu cacugggcua   2100
gggcucacag gcgagcuggu cgauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga ggguggguga agcaguugca aauagauuac   2760
aaaggcaacg aaauaaugac ggcagcugcc ucucaagggc ugacccguaa aggugugaau   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
```

-continued cugaaucccg gcggaaccug ugucagcaua gguuaugguu acgcugacag ggccagcgaa 3840
agcaucauug gugcuauagc gcggcaguuc aaguuuuccc gaguaugcaa accgaaaucc 3900
ucacuugagg agacggaagu ucuguuugua uucauugggu acgaucgcaa ggcccguacg 3960
cacaauccuu acaagcuauc aucaaccuug accaacauuu auacagguuc cagacuccac 4020
gaagccggau gugcacccuc auaucaugug gugcgagggg auauugccac ggccaccgaa 4080
ggagugauua uaaaugcugc uaacagcaaa ggacaaccug gcggaggggu gugcggagcg 4140
cuguauaaga aauucccgga aaguuucgau uuacagccga ucgaaguagg aaaagcgcga 4200
cuggucaaag gugcagcuaa acauaucauu caugccguag gaccaaacuu caacaaaguu 4260
ucggagguug aaggugacaa acaguuggca gaggcuuaug aguccaucgc uaagauuguc 4320
aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc uggugagggu gcaucccaag aguucuuugg cuggaaggaa gggcuacagc 4620
acaagcgaug gcaaaacuuu cucauauuug gaagggacca aguuucacca ggcggccaag 4680
gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaaauc aguaaggcaa 5760 acggugcuau ccgaaguggu guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180

-continued acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug gggauugugu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu ggugggcgag 7200
aaagcgccuu auuucugugg aggguuuauu uugugugacu ccgugaccgg cacagcgugc 7260
cguguggcag acccccuaaa aaggcuguuu aagcuaggca aaccucuggc agcagacgau 7320
gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guuuguguuu cuugugcugc ugccucuugu gucuucucag uguguggugu 7620
gauuuccaaa uauuacaaau cuguguccau uuggagaagu guuuaaugca acaagauuug 7680
caucugugua ugcauggaau agaaaaagaa uuucuaauug uguggcugau uauucugugc 7740
uguauaauag ugcuucuuuu uccacauuua aauguuaugg agugucucca acaaaauuaa 7800
augauuuaug uuuuacaaau guguaugcug auucuuuugu gaucagaggu gaugaaguga 7860
gacagauugc cccggacag acaggaaaaa uugcugauua caauuacaaa cugccugaug 7920
auuuuacagg augugugauu gcuuggaauu cuaauaauuu agauucuaaa gugggaggaa 7980
auuacaauua ucuguacaga cuguuuagaa aaucaaaucu gaaaccuuuu gaaagagaua 8040
uuucaacaga aauuuaucag gcuggaucaa caccuuguaa uggaguggaa ggauuuaauu 8100
guuauuuucc auuacagagc uauggauuuc agccaaccaa uggugugggga uaucagccau 8160
auagaguggu ggugcugucu uuugaacugc ugcaugcacc ugcaacagug uguggaccua 8220
aaggcucccc cggcuccggc uccggaucug guuauauucc ugaagcucca agagaugggc 8280
aagcuuacgu ucguaaagau ggcgaauggg uauuacuuuc uaccuuuuua ggaagcggca 8340
gcggaucuga acaguacauu aaauggccuu gguacauuug gcuuggauuu auugcaggau 8400
uaauugcaau ugugauggug acaauuaugu uauguuguau gacaucaugu uguucuuguu 8460
uaaaaggaug uuguucuugu ggaagcuguu guaaauuuga ugaagaugau ucugaaccug 8520

-continued uguuaaaagg agugaaauug cauuacacau gaugacucga gcugguacug caugcacgca 8580
augcuagcug ccccuuuccc guccugggua ccccgagucu cccccgaccu cgggucccag 8640
guaugcuccc accuccaccu gccccacuca ccaccucugc uaguuccaga caccucccaa 8700
gcacgcagca augcagcuca aaacgcuuag ccuagccaca cccccacggg aaacagcagu 8760
gauuaaccuu uagcaauaaa cgaaaguuua acuaagcuau acuaacccca ggguugguca 8820
auuucgugcc agccacaccg cggccgcaug aauacagcag caauuggcaa gcugcuuaca 8880
uagaacucgc ggcgauuggc augccgccuu aaaauuuuua uuuuauuuuu ucuuuucuuu 8940
uccgaaucgg auuuuguuuu uaauauuuca aaaaaaaaaa aaaaaaaaaa aaaaaaaaag 9000
cauaugacua aaaaaaaaaa aaaaaaaaaa aaaaaaaaaa aaaaaaaaaa aaaaaaaaaa 9060
aaaaaaaaaa aaaaaaaaa 9079

<210> SEQ ID NO 28
<211> LENGTH: 327
<212> TYPE: PRT
<213> ORGANISM: Artificial Sequence
<220> FEATURE:
<223> OTHER INFORMATION: Vaccine Antigen

<400> SEQUENCE: 28

Met Phe Val Phe Leu Val Leu Leu Pro Leu Val Ser Ser Gln Cys Val
1 5 10 15

Val Arg Phe Pro Asn Ile Thr Asn Leu Cys Pro Phe Gly Glu Val Phe
20 25 30

Asn Ala Thr Arg Phe Ala Ser Val Tyr Ala Trp Asn Arg Lys Arg Ile
35 40 45

Ser Asn Cys Val Ala Asp Tyr Ser Val Leu Tyr Asn Ser Ala Ser Phe
50 55 60

Ser Thr Phe Lys Cys Tyr Gly Val Ser Pro Thr Lys Leu Asn Asp Leu
65 70 75 80

Cys Phe Thr Asn Val Tyr Ala Asp Ser Phe Val Ile Arg Gly Asp Glu
85 90 95

Val Arg Gln Ile Ala Pro Gly Gln Thr Gly Lys Ile Ala Asp Tyr Asn
100 105 110

Tyr Lys Leu Pro Asp Asp Phe Thr Gly Cys Val Ile Ala Trp Asn Ser
115 120 125

Asn Asn Leu Asp Ser Lys Val Gly Gly Asn Tyr Asn Tyr Leu Tyr Arg
130 135 140

Leu Phe Arg Lys Ser Asn Leu Lys Pro Phe Glu Arg Asp Ile Ser Thr
145 150 155 160

Glu Ile Tyr Gln Ala Gly Ser Thr Pro Cys Asn Gly Val Glu Gly Phe
165 170 175

Asn Cys Tyr Phe Pro Leu Gln Ser Tyr Gly Phe Gln Pro Thr Asn Gly
180 185 190

Val Gly Tyr Gln Pro Tyr Arg Val Val Val Leu Ser Phe Glu Leu Leu
195 200 205

His Ala Pro Ala Thr Val Cys Gly Pro Lys Gly Ser Pro Gly Ser Gly
210 215 220

Ser Gly Ser Gly Tyr Ile Pro Glu Ala Pro Arg Asp Gly Gln Ala Tyr
225 230 235 240

Val Arg Lys Asp Gly Glu Trp Val Leu Leu Ser Thr Phe Leu Gly Ser
245 250 255

Gly Ser Gly Ser Glu Gln Tyr Ile Lys Trp Pro Trp Tyr Ile Trp Leu

```
            260                 265                 270

Gly Phe Ile Ala Gly Leu Ile Ala Ile Val Met Val Thr Ile Met Leu
        275                 280                 285

Cys Cys Met Thr Ser Cys Cys Ser Cys Leu Lys Gly Cys Cys Ser Cys
    290                 295                 300

Gly Ser Cys Cys Lys Phe Asp Glu Asp Asp Ser Glu Pro Val Leu Lys
305                 310                 315                 320

Gly Val Lys Leu His Tyr Thr
                325


<210> SEQ ID NO 29
<211> LENGTH: 311
<212> TYPE: PRT
<213> ORGANISM: Artificial Sequence
<220> FEATURE:
<223> OTHER INFORMATION: BNT162b3c

<400> SEQUENCE: 29

Met Phe Val Phe Leu Val Leu Leu Pro Leu Val Ser Ser Gln Cys Val
1               5                   10                  15

Asn Leu Thr Val Arg Phe Pro Asn Ile Thr Asn Leu Cys Pro Phe Gly
            20                  25                  30

Glu Val Phe Asn Ala Thr Arg Phe Ala Ser Val Tyr Ala Trp Asn Arg
        35                  40                  45

Lys Arg Ile Ser Asn Cys Val Ala Asp Tyr Ser Val Leu Tyr Asn Ser
    50                  55                  60

Ala Ser Phe Ser Thr Phe Lys Cys Tyr Gly Val Ser Pro Thr Lys Leu
65                  70                  75                  80

Asn Asp Leu Cys Phe Thr Asn Val Tyr Ala Asp Ser Phe Val Ile Arg
                85                  90                  95

Gly Asp Glu Val Arg Gln Ile Ala Pro Gly Gln Thr Gly Lys Ile Ala
            100                 105                 110

Asp Tyr Asn Tyr Lys Leu Pro Asp Asp Phe Thr Gly Cys Val Ile Ala
        115                 120                 125

Trp Asn Ser Asn Asn Leu Asp Ser Lys Val Gly Gly Asn Tyr Asn Tyr
    130                 135                 140

Leu Tyr Arg Leu Phe Arg Lys Ser Asn Leu Lys Pro Phe Glu Arg Asp
145                 150                 155                 160

Ile Ser Thr Glu Ile Tyr Gln Ala Gly Ser Thr Pro Cys Asn Gly Val
                165                 170                 175

Glu Gly Phe Asn Cys Tyr Phe Pro Leu Gln Ser Tyr Gly Phe Gln Pro
            180                 185                 190

Thr Asn Gly Val Gly Tyr Gln Pro Tyr Arg Val Val Val Leu Ser Phe
        195                 200                 205

Glu Leu Leu His Ala Pro Ala Thr Val Cys Gly Pro Lys Gly Ser Pro
    210                 215                 220

Gly Ser Gly Ser Gly Ser Gly Tyr Ile Pro Glu Ala Pro Arg Asp Gly
225                 230                 235                 240

Gln Ala Tyr Val Arg Lys Asp Gly Glu Trp Val Leu Leu Ser Thr Phe
                245                 250                 255

Leu Gly Ser Gly Ser Gly Ser Glu Gln Tyr Ile Lys Trp Pro Trp Tyr
            260                 265                 270

Ile Trp Leu Gly Phe Ile Ala Gly Leu Ile Ala Ile Val Met Val Thr
        275                 280                 285

Ile Met Leu Cys Cys Met Thr Ser Cys Cys Ser Cys Leu Lys Gly Cys
```

-continued 290 295 300

Cys Ser Cys Gly Ser Cys Cys
305 310

<210> SEQ ID NO 30
<211> LENGTH: 1397
<212> TYPE: RNA
<213> ORGANISM: Artificial Sequence
<220> FEATURE:
<223> OTHER INFORMATION: BNT162b3c

<400> SEQUENCE: 30
agaauaaacu aguauucuuc ugguccccac agacucagag agaacccgcc accauguuug 60
uguuucuugu gcugcugccu cuugugucuu cucagugugu gaauuugaca gugagauuuc 120
caaauauuac aaaucugugu ccauuuggag aaguguuuaa ugcaacaaga uuugcaucug 180
uguaugcaug gaauagaaaa agaauuucua auuguguggc ugauuauucu gugcuguaua 240
auagugcuuc uuuuuccaca uuuaaauguu auggaguguc uccaacaaaa uuaaaugauu 300
uauguuuuac aaauguguau gcugauucuu uugugaucag aggugaugaa gugagacaga 360
uugcccccgg acagacagga aaaauugcug auuacaauua caaacugccu gaugauuuua 420
caggaugugu gauugcuugg aauucuaaua auuuagauuc uaaaguggga ggaaauuaca 480
auuaucugua cagacuguuu agaaaaucaa aucugaaacc uuuugaaaga gauauuucaa 540
cagaaauuua ucaggcugga ucaacaccuu guaauggagu ggaaggauuu aauuguuauu 600
uuccauuaca gagcuaugga uuucagccaa ccaauggugu gggauaucag ccauauagag 660
ugguggugcu gucuuuugaa cugcugcaug caccugcaac agugugugga ccuaaaggcu 720
cccccggcuc cggcuccgga ucugguuaua uuccugaagc uccaagagau gggcaagcuu 780
acguucguaa agauggcgaa uggguauuac uuucuaccuu uuuaggaagc ggcagcggau 840
cugaacagua cauuaaaugg ccuugguaca uuuggcuugg auuuauugca ggauuaauug 900
caauugugau ggugacaauu auguuauguu guaugacauc auguuguucu uguuuaaaag 960
gauguuguuc uuguggaagc uguuguugau gacucgagcu gguacugcau gcacgcaaug 1020
cuagcugccc cuuucccguc cuggguaccc cgagucuccc ccgaccucgg gucccaggua 1080
ugcucccacc uccaccugcc ccacucacca ccucugcuag uuccagacac cucccaagca 1140
cgcagcaaug cagcucaaaa cgcuuagccu agccacaccc ccacgggaaa cagcagugau 1200
uaaccuuuag caauaaacga aaguuuaacu aagcuauacu aaccccaggg uuggucaauu 1260
ucgugccagc cacacccugg agcuagcaaa aaaaaaaaaa aaaaaaaaaa aaaaaaagca 1320
uaugacuaaa aaaaaaaaaa aaaaaaaaaa aaaaaaaaaa aaaaaaaaaa aaaaaaaaaa 1380
aaaaaaaaaa aaaaaaa 1397

<210> SEQ ID NO 31
<211> LENGTH: 314
<212> TYPE: PRT
<213> ORGANISM: Artificial Sequence
<220> FEATURE:
<223> OTHER INFORMATION: BNT162b3d

<400> SEQUENCE: 31

Met Asp Trp Ile Trp Arg Ile Leu Phe Leu Val Gly Ala Ala Thr Gly
1 5 10 15

Ala His Ser Gln Met Gln Val Arg Phe Pro Asn Ile Thr Asn Leu Cys
20 25 30

Pro Phe Gly Glu Val Phe Asn Ala Thr Arg Phe Ala Ser Val Tyr Ala
35 40 45

Trp Asn Arg Lys Arg Ile Ser Asn Cys Val Ala Asp Tyr Ser Val Leu
50 55 60

Tyr Asn Ser Ala Ser Phe Ser Thr Phe Lys Cys Tyr Gly Val Ser Pro
65 70 75 80

Thr Lys Leu Asn Asp Leu Cys Phe Thr Asn Val Tyr Ala Asp Ser Phe
85 90 95

Val Ile Arg Gly Asp Glu Val Arg Gln Ile Ala Pro Gly Gln Thr Gly
100 105 110

Lys Ile Ala Asp Tyr Asn Tyr Lys Leu Pro Asp Asp Phe Thr Gly Cys
115 120 125

Val Ile Ala Trp Asn Ser Asn Asn Leu Asp Ser Lys Val Gly Gly Asn
130 135 140

Tyr Asn Tyr Leu Tyr Arg Leu Phe Arg Lys Ser Asn Leu Lys Pro Phe
145 150 155 160

Glu Arg Asp Ile Ser Thr Glu Ile Tyr Gln Ala Gly Ser Thr Pro Cys
165 170 175

Asn Gly Val Glu Gly Phe Asn Cys Tyr Phe Pro Leu Gln Ser Tyr Gly
180 185 190

Phe Gln Pro Thr Asn Gly Val Gly Tyr Gln Pro Tyr Arg Val Val Val
195 200 205

Leu Ser Phe Glu Leu Leu His Ala Pro Ala Thr Val Cys Gly Pro Lys
210 215 220

Gly Ser Pro Gly Ser Gly Ser Gly Ser Gly Tyr Ile Pro Glu Ala Pro
225 230 235 240

Arg Asp Gly Gln Ala Tyr Val Arg Lys Asp Gly Glu Trp Val Leu Leu
245 250 255

Ser Thr Phe Leu Gly Ser Gly Ser Gly Ser Glu Gln Tyr Ile Lys Trp
260 265 270

Pro Trp Tyr Ile Trp Leu Gly Phe Ile Ala Gly Leu Ile Ala Ile Val
275 280 285

Met Val Thr Ile Met Leu Cys Cys Met Thr Ser Cys Cys Ser Cys Leu
290 295 300

Lys Gly Cys Cys Ser Cys Gly Ser Cys Cys
305 310

<210> SEQ ID NO 32
<211> LENGTH: 1406
<212> TYPE: RNA
<213> ORGANISM: Artificial Sequence
<220> FEATURE:
<223> OTHER INFORMATION: BNT162b3d

<400> SEQUENCE: 32
agaauaaacu aguauucuuc ugguccccac agacucagag agaacccgcc accauggauu 60
ggauuuggag aauccuguuc cucgugggag ccgcuacagg agcccacucc cagaugcagg 120
ugagauuucc aaauauuaca aaucugugucc cauuuggaga aguguuuaau gcaacaagau 180
uugcaucugu guaugcaugg aauagaaaaa gaauuucuaa uuguguggcu gauuauucug 240
ugcuguauaa uagugcuucu uuuuccacau uuaaauguua uggagugucu ccaacaaaau 300
uaaaugauuu auguuuuaca aauguguaug cugauucuuu ugugaucaga ggugaugaag 360
ugagacagau ugcccccgga cagacaggaa aaauugcuga uuacaauuac aaacugccug 420
augauuuuac aggaugugug auugcuugga auucuaauaa uuuagauucu aaagugggag 480

-continued

```
gaaauuacaa uuaucuguac agacuguuua gaaaaucaaa ucugaaaccu uuugaaagag    540

auauuucaac agaaauuuau caggcuggau caacaccuug uaauggagug gaaggauuua    600

auuguuauuu uccauuacag agcuauggau uucagccaac caaugguguug ggauaucagc   660

cauauagagu gguggugcug ucuuuugaac ugcugcaugc accugcaaca gugugugggac   720

cuaaaggcuc ccccggcucc ggcuccggau cugguuauau ucccugaagcu ccaagagaug   780

ggcaagcuua cguucguaaa gauggcgaau ggguauuacu uucuaccuuu uuaggaagcg    840

gcagcggauc ugaacaguac auuaaaaugc cuugguacau uuggcuugga uuuauugcag    900

gauuaauugc aauugugaug gugacaauua uguuuauguug uaugacauca uguuguucuu   960

guuuaaaagg auguuguucu uguggaagcu guuguugaug acucgagcug guacugcaug   1020

cacgcaaugc uagcugcccc uuucccgucc uggguacccc gagucucccc cgaccucggg   1080

ucccagguau gcucccaccu ccaccugccc cacucaccac cucugcuagu uccagacacc   1140

ucccaagcac gcagcaaugc agcucaaaac gcuuagccua gccacacccc cacgggaaac   1200

agcagugauu aaccuuuagc aauaaacgaa aguuuaacua agcuauacua accccagggu   1260

uggucaauuu cgugccagcc acacccugga gcuagcaaaa aaaaaaaaaa aaaaaaaaaa   1320

aaaaaagcau augacuaaaa aaaaaaaaaa aaaaaaaaaa aaaaaaaaaa aaaaaaaaaa   1380

aaaaaaaaaa aaaaaaaaaa aaaaaa                                         1406
```

<210> SEQ ID NO 33
<211> LENGTH: 9
<212> TYPE: PRT
<213> ORGANISM: Artificial Sequence
<220> FEATURE:
<223> OTHER INFORMATION: Linker

<400> SEQUENCE: 33

Gly Ser Pro Gly Ser Gly Ser Gly Ser
1               5

<210> SEQ ID NO 34
<211> LENGTH: 6
<212> TYPE: PRT
<213> ORGANISM: Artificial Sequence
<220> FEATURE:
<223> OTHER INFORMATION: Linker

<400> SEQUENCE: 34

Gly Ser Gly Ser Gly Ser
1               5

<210> SEQ ID NO 35
<211> LENGTH: 9
<212> TYPE: PRT
<213> ORGANISM: Artificial Sequence
<220> FEATURE:
<223> OTHER INFORMATION: AH1

<400> SEQUENCE: 35

Ser Pro Ser Tyr Val Tyr His Gln Phe
1               5

<210> SEQ ID NO 36
<211> LENGTH: 20
<212> TYPE: PRT
<213> ORGANISM: Artificial Sequence
<220> FEATURE:
<223> OTHER INFORMATION: HuIgGk signal peptide

<400> SEQUENCE: 36

Met Glu Thr Pro Ala Gln Leu Leu Phe Leu Leu Leu Leu Trp Leu Pro
1 5 10 15

Asp Thr Thr Gly
20

<210> SEQ ID NO 37
<211> LENGTH: 18
<212> TYPE: PRT
<213> ORGANISM: Artificial Sequence
<220> FEATURE:
<223> OTHER INFORMATION: IgE heavy chain epsilon-1signal peptide

<400> SEQUENCE: 37

Met Asp Trp Thr Trp Ile Leu Phe Leu Val Ala Ala Ala Thr Arg Val
1 5 10 15

His Ser

<210> SEQ ID NO 38
<211> LENGTH: 24
<212> TYPE: PRT
<213> ORGANISM: Artificial Sequence
<220> FEATURE:
<223> OTHER INFORMATION: Japanese encephalitis PRM signal sequence

<400> SEQUENCE: 38

Met Leu Gly Ser Asn Ser Gly Gln Arg Val Val Phe Thr Ile Leu Leu
1 5 10 15

Leu Leu Val Ala Pro Ala Tyr Ser
20

<210> SEQ ID NO 39
<211> LENGTH: 17
<212> TYPE: PRT
<213> ORGANISM: Artificial Sequence
<220> FEATURE:
<223> OTHER INFORMATION: VSVg protein signal sequence

<400> SEQUENCE: 39

Met Lys Cys Leu Leu Tyr Leu Ala Phe Leu Phe Ile Gly Val Asn Cys
1 5 10 15

Ala

<210> SEQ ID NO 40
<211> LENGTH: 9
<212> TYPE: PRT
<213> ORGANISM: Artificial Sequence
<220> FEATURE:
<223> OTHER INFORMATION: Epitope

<400> SEQUENCE: 40

Tyr Leu Gln Pro Arg Thr Phe Leu Leu
1 5

<210> SEQ ID NO 41
<211> LENGTH: 9
<212> TYPE: PRT
<213> ORGANISM: Artificial Sequence
<220> FEATURE:
<223> OTHER INFORMATION: Epitope

<400> SEQUENCE: 41

Arg Leu Gln Ser Leu Gln Thr Tyr Val 1 5

<210> SEQ ID NO 42
<211> LENGTH: 9
<212> TYPE: PRT
<213> ORGANISM: Artificial Sequence
<220> FEATURE:
<223> OTHER INFORMATION: Epitope

<400> SEQUENCE: 42

Gln Tyr Ile Lys Trp Pro Trp Tyr Ile
1 5

<210> SEQ ID NO 43
<211> LENGTH: 9
<212> TYPE: PRT
<213> ORGANISM: Artificial Sequence
<220> FEATURE:
<223> OTHER INFORMATION: Epitope

<400> SEQUENCE: 43

Asn Tyr Asn Tyr Leu Tyr Arg Leu Phe
1 5

<210> SEQ ID NO 44
<211> LENGTH: 10
<212> TYPE: PRT
<213> ORGANISM: Artificial Sequence
<220> FEATURE:
<223> OTHER INFORMATION: Epitope

<400> SEQUENCE: 44

Lys Trp Pro Trp Tyr Ile Trp Leu Gly Phe
1 5 10

<210> SEQ ID NO 45
<211> LENGTH: 9
<212> TYPE: PRT
<213> ORGANISM: Artificial Sequence
<220> FEATURE:
<223> OTHER INFORMATION: Epitope

<400> SEQUENCE: 45

Gln Pro Thr Glu Ser Ile Val Arg Phe
1 5

<210> SEQ ID NO 46
<211> LENGTH: 9
<212> TYPE: PRT
<213> ORGANISM: Artificial Sequence
<220> FEATURE:
<223> OTHER INFORMATION: Epitope

<400> SEQUENCE: 46

Ile Pro Phe Ala Met Gln Met Ala Tyr
1 5

<210> SEQ ID NO 47
<211> LENGTH: 9
<212> TYPE: PRT
<213> ORGANISM: Artificial Sequence
<220> FEATURE:
<223> OTHER INFORMATION: Epitope

<400> SEQUENCE: 47

Leu Pro Phe Asn Asp Gly Val Tyr Phe
1 5

<210> SEQ ID NO 48
<211> LENGTH: 15
<212> TYPE: DNA
<213> ORGANISM: Artificial Sequence
<220> FEATURE:
<223> OTHER INFORMATION: Nucleic acid fragment

<400> SEQUENCE: 48
cccactaatg gtgtt 15

<210> SEQ ID NO 49
<211> LENGTH: 5
<212> TYPE: PRT
<213> ORGANISM: Artificial Sequence
<220> FEATURE:
<223> OTHER INFORMATION: Protein fragment

<400> SEQUENCE: 49

Pro Thr Asn Gly Val
1 5

<210> SEQ ID NO 50
<211> LENGTH: 15
<212> TYPE: DNA
<213> ORGANISM: Artificial Sequence
<220> FEATURE:
<223> OTHER INFORMATION: Nucleic acid fragment

<400> SEQUENCE: 50
cccacttatg gtgtt 15

<210> SEQ ID NO 51
<211> LENGTH: 5
<212> TYPE: PRT
<213> ORGANISM: Artificial Sequence
<220> FEATURE:
<223> OTHER INFORMATION: Protein fragment

<400> SEQUENCE: 51

Pro Thr Tyr Gly Val
1 5

<210> SEQ ID NO 52
<211> LENGTH: 9
<212> TYPE: PRT
<213> ORGANISM: Artificial Sequence
<220> FEATURE:
<223> OTHER INFORMATION: Epitope

<400> SEQUENCE: 52

Gly Val Tyr Phe Ala Ser Thr Glu Lys
1 5

<210> SEQ ID NO 53
<211> LENGTH: 9
<212> TYPE: PRT
<213> ORGANISM: Artificial Sequence
<220> FEATURE:
<223> OTHER INFORMATION: Epitope

<400> SEQUENCE: 53

Cys Val Ala Asp Tyr Ser Val Leu Tyr
1 5

<210> SEQ ID NO 54

-continued

<211> LENGTH: 9
<212> TYPE: PRT
<213> ORGANISM: Artificial Sequence
<220> FEATURE:
<223> OTHER INFORMATION: Epitope

<400> SEQUENCE: 54

Lys Cys Tyr Gly Val Ser Pro Thr Lys
1 5

<210> SEQ ID NO 55
<211> LENGTH: 9
<212> TYPE: PRT
<213> ORGANISM: Artificial Sequence
<220> FEATURE:
<223> OTHER INFORMATION: Epitope

<400> SEQUENCE: 55

Phe Gln Pro Thr Asn Gly Val Gly Tyr
1 5

<210> SEQ ID NO 56
<211> LENGTH: 9
<212> TYPE: PRT
<213> ORGANISM: Artificial Sequence
<220> FEATURE:
<223> OTHER INFORMATION: Epitope

<400> SEQUENCE: 56

Gly Thr His Trp Phe Val Thr Gln Arg
1 5

<210> SEQ ID NO 57
<211> LENGTH: 9
<212> TYPE: PRT
<213> ORGANISM: Artificial Sequence
<220> FEATURE:
<223> OTHER INFORMATION: Epitope

<400> SEQUENCE: 57

Val Tyr Asp Pro Leu Gln Pro Glu Leu
1 5